US 7,723,380 B2

(12) United States Patent
Cannizzaro et al.

(10) Patent No.: US 7,723,380 B2
(45) Date of Patent: May 25, 2010

(54) ANTIVIRAL PROTEASE INHIBITORS

(75) Inventors: Carina E. Cannizzaro, Foster City, CA (US); James M. Chen, San Ramon, CA (US); Manoj C. Desai, Pleasant Hill, CA (US); Michael L. Mitchell, Hayward, CA (US); Sundaramoorthi Swaminathan, Burlingame, CA (US); Lianhong Xu, Palo Alto, CA (US); Zheng-Yu Yang, Palo Alto, CA (US)

(73) Assignee: Gilead Sciences, Inc., Foster City, CA (US)

( * ) Notice: Subject to any disclaimer, the term of this patent is extended or adjusted under 35 U.S.C. 154(b) by 35 days.

(21) Appl. No.: 11/880,069

(22) Filed: Jul. 19, 2007

(65) Prior Publication Data

US 2009/0105279 A1    Apr. 23, 2009

Related U.S. Application Data

(60) Provisional application No. 60/832,624, filed on Jul. 21, 2006.

(51) Int. Cl.
*A61K 31/343*     (2006.01)
*A61K 31/443*     (2006.01)
*A61K 31/427*     (2006.01)
*A61K 31/41*      (2006.01)
*A61K 31/4196*    (2006.01)
*C07D 493/02*     (2006.01)
*C07D 277/30*     (2006.01)
*C07D 249/08*     (2006.01)
*C07D 215/38*     (2006.01)
*C07D 257/04*     (2006.01)
*C07D 239/02*     (2006.01)

(52) U.S. Cl. .................. 514/469; 514/336; 514/461; 514/365; 514/256; 514/382; 514/383; 544/315; 544/225; 546/281.7; 546/284.1; 548/250; 548/202; 548/262.2

(58) Field of Classification Search .................. 514/336, 514/338, 469, 470, 461; 544/315, 225; 546/281.7, 546/284.1; 548/262.2, 250, 202; 549/59, 549/60, 464
See application file for complete search history.

(56) References Cited

U.S. PATENT DOCUMENTS

| | | | |
|---|---|---|---|
| 4,816,570 A | 3/1989 | Farquhar | |
| 4,968,788 A | 11/1990 | Farquhar | |
| 5,461,067 A | 10/1995 | Norbeck et al. | |
| 5,663,159 A | 9/1997 | Starrett, Jr. et al. | |
| 5,679,688 A | 10/1997 | Grobelny et al. | |
| 5,753,652 A | 5/1998 | Fassler et al. | |
| 5,792,756 A | 8/1998 | Starrett, Jr. et al. | |
| 5,849,911 A | 12/1998 | Fassler et al. | |
| 6,087,383 A | 7/2000 | Singh et al. | |
| 2004/0100960 A1 | 5/2004 | Mehta | |
| 2005/0159469 A1 | 7/2005 | Randolph et al. | |

FOREIGN PATENT DOCUMENTS

| | | |
|---|---|---|
| EP | 0 486 948 | 5/1992 |
| EP | 0 521 827 | 1/1993 |
| EP | 0 604 368 | 6/1994 |
| WO | WO-93/18006 | 9/1993 |
| WO | WO 94/14436 | 7/1994 |
| WO | WO-94/19332 | 9/1994 |
| WO | WO-95/07269 | 3/1995 |
| WO | WO-97/19055 | 5/1997 |
| WO | WO-97/40029 | 10/1997 |
| WO | WO-97/46514 | 12/1997 |
| WO | WO-98/03476 | 1/1998 |
| WO | WO-02/100410 | 12/2002 |
| WO | WO 02100410 A1 * | 12/2002 |
| WO | WO-03/078438 | 9/2003 |
| WO | WO-2005/061487 | 7/2005 |
| WO | WO 2005061487 A1 * | 7/2005 |

OTHER PUBLICATIONS

Cited ref_BMS-488043.*
Vippagunta et al., Advanced Drug Delivery Reviews, p. 1.*
Bold et al. "New Aza-Dipeptide Analogues as Potent and Orally Absorbed HIV-1 Protease Inhibitors: Candidates for Clinical Development."41:3387-3401;J Med Chem.,1998.
Bundgaard et al. "Design and Application of Prodrugs."pp. 113-191;Textbook of Drug Design and Development.,1991.
Farquhar et al. "Biologically Reversible Phosphate-Protective Groups."72:324-325;J Pharm Sci.,1983.
Paquette, Leo A. "Three-Membered Rings with One Hetero Atom."Chptr:1;Principals of Modern Heterocyclic Chemistry., 1968.
Paquette, Leo A. "The Four-Membered Heterocycles." Chptr:3;Principals of Modern Heterocyclic Chemistry., 1968.
Paquette, Leo A. "Furan, Pyrrole, and Thiophene."Chptr:4;Principals of Modern Heterocyclic Chemistry., 1968.

(Continued)

*Primary Examiner*—Yong Chu
(74) *Attorney, Agent, or Firm*—Cynthia H. Zhang

(57) ABSTRACT

The invention is related to compounds of Formula I:

$$\begin{array}{c}\text{Formula I}\end{array}$$

structure with substituents $R^1$, $R^2$, $OR^3$, $L^1$, $Ar^1$, $(L^2-Ar^2)_p$, $L^3$, $Ar^3$, $(L^4-Ar^4)_q$, $R^4$, $R^5$, $X$, $(R^6)_n$ or a pharmaceutically acceptable salt, solvate, ester, and/or phosphonate thereof, compositions containing such compounds, and therapeutic methods that include the administration of such compounds.

8 Claims, No Drawings

OTHER PUBLICATIONS

Paquette, Leo A. "The Azoles."Chptr:6;Principals of Modern Heterocyclic Chemistry., 1968.

Paquette, Leo A. "The Pyridine Group."Chptr:7;Principals of Modern Heterocyclic Chemistry., 1968.

Paquette, Leo A. "The Diazines and S-Triazine."Chptr:9;Principals of Modern Heterocyclic Chemistry., 1968.

Stuttgart, Georg Thieme "An Overview."p. 1-20; Protecting Groups., 1994.

Stuttgart, Georg Thieme "Hydroxyl Protecting Groups."p. 21-94;Protecting Groups.,1994.

Stuttgart, Georg Thieme "Diol Protecting Groups."p. 95-117;Protecting Groups.,1994.

Stuttgart, Georg Thieme "Carboxyl Protecting Groups."p. 118-154;Protecting Groups.,1994.

Stuttgart, Georg Thieme "Carbonyl Protecting Groups."p. 155-184;Protecting Groups., 1994.

Toth et al. "A simple, continuous fluorometric assay for HIV protease."36:544-550; Int. J. Peptide Protein Res.., 1990.

Weislow et al. "New Soluble-Formazan Assay for HIV-1 Cytopathic Effects: Application to High-Flux Screening of Synthetic . . . " 81(8):577-588; Natl. Cancer Inst., 1989.

* cited by examiner

ANTIVIRAL PROTEASE INHIBITORS

CROSS-REFERENCE TO RELATED APPLICATIONS

This application claims priority to U.S. Provisional Application Ser. No. 60/832,624, filed Jul. 21, 2006. The content of this provisional application is herein incorporated by reference in its entirety for all purposes.

FIELD OF THE INVENTION

This invention relates to novel HIV protease inhibitors, pharmaceutical compositions thereof, processes for making the novel HIV protease inhibitors, and methods for inhibiting and treating an HIV infection.

BACKGROUND OF THE INVENTION

In recent years, inhibitors of HIV protease have become an important class of therapeutic agents for inhibition and treatment of HIV infection in humans. HIV protease inhibitors are especially effective when administered in combination with other classes of HIV therapeutic agents, especially inhibitors of HIV reverse transcriptase, e.g. in "cocktails" of two or more HIV therapeutic agents.

On-going treatment of HIV-infected individuals with compounds that inhibit HIV protease has led to the development of mutant viruses that possess proteases that are resistant to the inhibitory effect of approved, commercially available HIV therapeutic agents currently in clinical use. Thus, to be effective, new HIV protease inhibitors must be effective not only against wild-type strains of HIV, but must also demonstrate efficacy against the newly emerging mutant strains that are resistant to the commercially available protease inhibitors. Accordingly, there continues to be a need for new HIV protease inhibitors, for example those targeting the HIV protease in both wild type and mutant strains of HIV.

SUMMARY OF THE INVENTION

Accordingly, in one embodiment, the present application provides novel HIV protease inhibitor compounds of Formula (I):

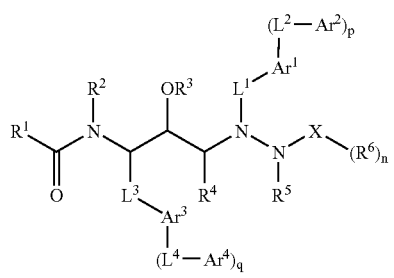

Formula I or a pharmaceutically acceptable salt, solvate, and/or ester thereof, wherein, X is H, alkyl, substituted alkyl, —C(O)—, —S(O)$_2$—, or —S(O)—;

n is 0 when X is H, alkyl, or substituted alkyl;

n is 1 when X is —C(O)—, —S(O)$_2$—, or —S(O)—;

$L^1$ and $L^3$ are alkylene;

$L^2$ and $L^4$ are independently selected from the group consisting of a covalent bond, —O—, —NH—, —O-alkylene-, and alkylene;

$Ar^1$, $Ar^2$, $Ar^3$, and $Ar^4$ are independently aryl, substituted aryl, heteroaryl, or substituted heteroaryl, wherein said substituted aryl or said substituted heteroaryl of $Ar^1$, $Ar^2$, $Ar^3$ and $Ar^4$ is independently substituted by one or more substituents selected from the group consisting of alkyl, substituted alkyl, haloalkyl, halo, nitro, cyano, hydroxy, amino, alkoxy, haloalkoxy, —NH-alkyl, —NH-(alkyl)$_2$, —NH-acyl, —N(alkyl)-acyl, —NR$^a$—S(O)$_2$—R$^b$, —C(O)—R$^c$, —S(O)$_2$R$^b$, —S(O)$_2$NHR$^a$, —C(O)—NH—R$^a$, —NR$^a$C(O)OR$^b$, —NR$^a$S(O)$_2$NR$^a$R$^b$, —C(O)OR$^a$, and -Z$^1$-alkylene-R$^7$;

$R^a$ is H, alkyl, or substituted alkyl;

$R^b$ is alkyl, aryl, or substituted aryl;

$R^7$ is aryl, heterocyclyl, substituted aryl, substituted heterocyclyl, -Z$^2$-L$^5$-R$^{7b}$, or O—PO$_3$R$^{7c}$R$^{7d}$;

$L^5$ is —C(O)—, —C(O)O—, —C(O)NR$^{7e}$—, —S(O$_2$)—, —S(O)—, —S(O$_2$)NR$^{7e}$—, or —S(O)NR$^{7e}$—;

$Z^1$ and $Z^2$ are independently O or NR$^{7a}$;

$R^{7a}$, $R^{7c}$, $R^{7d}$, and $R^{7e}$ are independently H, alkyl, or substituted alkyl;

$R^{7b}$ is alkyl, substituted alkyl, heterocyclyl, or substituted heterocyclyl;

p and q are independently 0 or 1;

$R^1$ is —NR$^{1a}$R$^{1b}$, —OR$^{1c}$, —C(R$^{1d}$R$^{1e}$)—NR$^{1f}$-L$^6$-R$^{1g}$, aryl, substituted aryl, heteroaryl, or substituted heteroaryl;

$R^{1a}$ is H, alkyl, or substituted alkyl;

$R^{1b}$ and $R^{1c}$ are independently selected from alkyl, substituted alkyl, aryl, substituted aryl, heterocyclyl, substituted heterocyclyl, arylalkyl, substituted arylalkyl, heterocyclyl alkyl, and substituted heterocyclyl alkyl, wherein said substituted arylalkyl is substituted on the aryl moiety and said substituted heterocyclyl alkyl is substituted on the heterocyclyl moiety;

$R^{1d}$ and $R^{1e}$ are independently selected from the group consisting of H, alkyl, and substituted alkyl; or $R^{1d}$ and $R^{1e}$ taken together with the carbon atom to which they are attached form a cycloalkyl, a substituted cycloalkyl, a non-aromatic heterocyclyl, or a substituted non-aromatic heterocyclyl;

$L^6$ is —C(O)—, —C(O)—O—, or —C(O)—NR$^{1h}$—, —S(O)$_2$—, —S(O)$_2$—O—, —S(O)$_2$—NR$^{1h}$—, —S(O)—, —S(O)—O—, or —S(O)—NR$^{1h}$—;

$R^{1f}$ and $R^{1h}$ are independently H, alkyl, or substituted alkyl;

$R^{1g}$ is alkyl or substituted alkyl;

$R^2$, $R^4$, and $R^5$ are each independently selected from the group consisting of H, alkyl, and substituted alkyl;

$R^3$ is selected from the group consisting of H, —CH$_2$—OC(O)—R$^{3a}$, —CH$_2$—OC(O)O—R$^{3a}$, —CH$_2$—O—PO$_3^{-2}$, —PO$_3^{-2}$, and —PO$_3$CH$_2$CF$_3^{-1}$;

$R^{3a}$ is H, alkyl, or substituted alkyl;

$R^6$ is selected from the group consisting of —OR$^{6a}$, —NR$^{6b}$R$^{6c}$, —C(R$^{6d}$R$^{6e}$)R$^{6f}$, alkyl, substituted alkyl, aryl, substituted aryl, heterocyclyl, and substituted heterocyclyl;

$R^{6a}$ and $R^{6b}$ are independently selected from the group consisting of alkyl, substituted alkyl, aryl, substituted aryl, heterocyclyl, substituted heterocyclyl, arylalkyl, substituted arylalkyl, heterocyclyl alkyl, substituted heterocyclyl alkyl, wherein said substituted arylalkyl is substituted on the aryl moiety and said substituted heterocyclyl alkyl is substituted on the heterocyclyl moiety;

$R^{6c}$ is H, alkyl, or substituted alkyl;

$R^{6d}$ and $R^{6e}$ are independently selected from the group consisting of H, alkyl, and substituted alkyl; or $R^{6d}$ and $R^{6e}$ taken together with the carbon atom to which they are attached form a cycloalkyl, a substituted cycloalkyl, a non-aromatic heterocyclyl, or a substituted non-aromatic heterocyclyl;

$R^{6f}$ is selected from the group consisting of heterocyclyl, substituted heterocyclyl, $-Z^3$-aryl, $-Z^3$-(substituted aryl), $-Z^3$-heteroaryl, $-Z^3$-(substituted heteroaryl), $-Z^3$-$L^7$-$R^{6f2}$, and $-Z^3$-$L^8$-$R^{6f3}$;

$Z^3$ is O or $NR^{6f1}$;

$L^7$ is selected from the group consisting of —C(O)—, —C(O)—O—, and —C(O)—$NR^{6f1}$—;

$L^8$ is selected from the group consisting of —S($O_2$)— or —S(O)—, —S($O_2$)—O—, and —S(O)—O—;

$R^{6f1}$ is H, alkyl, or substituted alkyl;

$R^{6f2}$ is alkyl, substituted alkyl, arylalkyl, substituted arylalkyl, heteroarylalkyl, substituted heteroarylalkyl, wherein said substituted arylalkyl is substituted on the aryl moiety and said substituted heteroarylalkyl is substituted on the heteroaryl moiety; and $R^{6f3}$ is alkyl, substituted alkyl, —O-alkyl, —O-(substituted alkyl), —NH-alkyl, —N(alkyl)$_2$, —NH-(substituted alkyl), or —N(substituted alkyl)$_2$; and with the following provisos:

(1) when X is —C(O)— and n is 1, then $R^1$ and $R^6$ are not both —CH($R^c$)—NH—C(O)—O—$R^d$, wherein $R^c$ is —C(CH$_3$)$_3$, —CH(CH$_3$)$_2$, or —CH(CH$_3$)CH$_2$CH$_3$ and $R^d$ is —CH$_3$ or —CH$_2$CH$_3$;

(2) when p and q are both 0, then Ar$^1$ and Ar$^3$ are not both phenyl or both fluorophenyl;

(3) when p and q are both 0; and Ar$^3$ is phenyl; then Ar$^1$ is not fluorophenyl, cyanophenyl, methoxyphenyl, hydroxyphenyl, tolyl, trifluoromethylphenyl, trimethoxyphenyl, or thienyl; and (4) when p and q are both 0; Ar$^3$ is phenyl; and $R^1$ is OR$^{1c}$; then $R^{1c}$ is not aryl methylene or heterocyclyl methylene.

In another embodiment, the present invention provides a pharmaceutical composition comprising a pharmaceutically acceptable carrier and a therapeutically effective amount of a compound of Formula I or pharmaceutically acceptable salt, solvate, and/or ester thereof.

In another embodiment, the present application provides a method for treating HIV infections which comprises administering to a patient in need of such treatment a therapeutically effective amount of at least one compound of Formula I, or a pharmaceutically acceptable salt, solvate, and/or ester thereof.

In another embodiment, the present application provides a method for treating HIV infections which comprises administering to a patient in need of such treatment a therapeutically effective combination of (a) one or more compounds of Formula I and (b) another therapeutic agent (e.g., one or more compounds selected from HIV reverse transcriptase inhibitors and HIV protease inhibitors).

In another embodiment, the present invention provides a method of treating HIV infection which comprises administering to a patient in need thereof a therapeutically effective amount of: (a) a compound of Formula (I); and, (b) at least one compound selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, non-nucleoside inhibitors of HCV, and CCR5 inhibitors.

In another embodiment, the present invention provides a kit or container comprising a compound of Formula (I) in an amount effective for use as a standard or reagent in a test or assay for determining the ability of a potential pharmaceutical compound to inhibit HIV protease and/or HIV growth.

DETAILED DESCRIPTION

Reference will now be made in detail to certain claims of the invention, examples of which are illustrated in the accompanying structures and formulas. While the invention will be described in conjunction with the enumerated claims, it will be understood that they are not intended the invention to those claims. On the contrary, the invention is intended to cover all alternatives, modifications, and equivalents, which may be included within the scope of the present invention as defined by the claims.

Definitions

Unless stated otherwise, the following terms and phrases as used herein are intended to have the following meanings:

When trade names are used herein, applicants intend to independently include the tradename product and the active pharmaceutical ingredient(s) of the tradename product.

As used herein, "a compound of the invention" or "a compound of formula (I)" means a compound of formula (I) or a pharmaceutically acceptable salt, solvate, or physiologically functional derivative thereof. Similarly, with respect to isolatable intermediates such as for example, compounds of formula (IX), the phrase "a compound of formula (number)" means a compound of that formula and pharmaceutically acceptable salts, solvates and physiologically functional derivatives thereof.

"Alkyl" is hydrocarbon containing normal, secondary, tertiary or cyclic carbon atoms. For example, an alkyl group can have 1 to 20 carbon atoms (i.e., $C_1$-$C_{20}$ alkyl), 1 to 10 carbon atoms (i.e., $C_1$-$C_{10}$ alkyl), or 1 to 6 carbon atoms (i.e., $C_1$-$C_6$ alkyl). Examples of suitable alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$, and octyl (—(CH$_2$)$_7$CH$_3$).

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of suitable alkoxy groups include, but are not limited to, methoxy (—O—$CH_3$ or —OMe), ethoxy (—$OCH_2CH_3$ or —OEt), t-butoxy (—O—$C(CH_3)_3$ or —OtBu) and the like.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), or 1 to 6 carbon atoms (i.e., $C_1$-$C_6$ alkyl). Examples of suitable haloalkyl groups include, but are not limited to, —$CF_3$, —$CHF_2$, —$CFH_2$, —$CH_2CF_3$, and the like.

"Alkenyl" is a hydrocarbon containing normal, secondary, tertiary or cyclic carbon atoms with at least one site of unsaturation, i.e. a carbon-carbon, $sp^2$ double bond. For example, an alkenyl group can have 2 to 20 carbon atoms (i.e., $C_2$-$C_{20}$ alkenyl), 2 to 12 carbon atoms (i.e., $C_2$-$C_{12}$ alkenyl), or 2 to 6 carbon atoms (i.e., $C_2$-$C_6$ alkenyl). Examples of suitable alkenyl groups include, but are not limited to, ethylene or vinyl (—CH=$CH_2$), allyl (—$CH_2$CH=$CH_2$), cyclopentenyl (—$C_5H_7$), and 5-hexenyl (—$CH_2CH_2CH_2CH_2$CH=$CH_2$).

"Alkynyl" is a hydrocarbon containing normal, secondary, tertiary or cyclic carbon atoms with at least one site of unsaturation, i.e. a carbon-carbon, sp triple bond. For example, an alkynyl group can have 2 to 20 carbon atoms (i.e., $C_2$-$C_{20}$ alkynyl), 2 to 12 carbon atoms (i.e., $C_2$-$C_{12}$ alkyne), or 2 to 6 carbon atoms (i.e., $C_2$-$C_6$ alkynyl). Examples of suitable alkynyl groups include, but are not limited to, acetylenic (—C≡CH), propargyl (—$CH_2$C≡CH), and the like.

"Alkylene" refers to a saturated, branched or straight chain or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene (—$CH_2$—), 1,1-ethyl (—CH($CH_3$)—), 1,2-ethyl (—$CH_2CH_2$—), 1,1-propyl (—CH($CH_2CH_3$)—), 1,2-propyl (—$CH_2$CH($CH_3$)—), 1,3-propyl (—$CH_2CH_2CH_2$—), 1,4-butyl (—$CH_2CH_2CH_2CH_2$—), and the like.

"Alkenylene" refers to an unsaturated, branched or straight chain or cyclic hydrocarbon radical having two monovalent radical centers derived by the removal of two hydrogen atoms from the same or two different carbon atoms of a parent alkene. For example, and alkenylene group can have 1 to 20 carbon atoms, 1 to 10 carbon atoms, or 1 to 6 carbon atoms. Typical alkenylene radicals include, but are not limited to, 1,2-ethylene (—CH=CH—).

"Alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 1 to 20 carbon atoms, 1 to 10 carbon atoms, or 1 to 6 carbon atoms. Typical alkynylene radicals include, but are not limited to, acetylene (—C≡C—), propargyl (—$CH_2$C≡C—), and 4-pentynyl (—$CH_2CH_2CH_2$C≡CH—).

"Aryl" means an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 12 carbon atoms. Typical aryl groups include, but are not limited to, radicals derived from benzene (e.g., phenyl), substituted benzene, naphthalene, anthracene, biphenyl, and the like.

"Arylalkyl" refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 6 to 20 carbon atoms, e.g., the alkyl moiety is 1 to 6 carbon atoms and the aryl moiety is 6 to 14 carbon atoms.

"Arylalkenyl" refers to an acyclic alkenyl radical in which one of the hydrogen atoms bonded to a carbon atom, typically a terminal or $sp^3$ carbon atom, but also an $sp^2$ carbon atom, is replaced with an aryl radical. The aryl portion of the arylalkenyl can include, for example, any of the aryl groups disclosed herein, and the alkenyl portion of the arylalkenyl can include, for example, any of the alkenyl groups disclosed herein. The arylalkenyl group can comprise 6 to 20 carbon atoms, e.g., the alkenyl moiety is 1 to 6 carbon atoms and the aryl moiety is 6 to 14 carbon atoms.

"Arylalkynyl" refers to an acyclic alkynyl radical in which one of the hydrogen atoms bonded to a carbon atom, typically a terminal or $sp^3$ carbon atom, but also an sp carbon atom, is replaced with an aryl radical. The aryl portion of the arylalkynyl can include, for example, any of the aryl groups disclosed herein, and the alkynyl portion of the arylalkynyl can include, for example, any of the alkynyl groups disclosed herein. The arylalkynyl group can comprise 6 to 20 carbon atoms, e.g., the alkynyl moiety is 1 to 6 carbon atoms and the aryl moiety is 6 to 14 carbon atoms.

The term "substituted" in reference to alkyl, alkylene, aryl, arylalkyl, heterocyclyl, etc., for example, "substituted alkyl", "substituted alkylene", "substituted aryl", "substituted arylalkyl", "substituted heterocyclyl", and "substituted carbocyclyl" means alkyl, alkylene, aryl, arylalkyl, heterocyclyl, carbocyclyl respectively, in which one or more hydrogen atoms are each independently replaced with a non-hydrogen substituent. Typical substituents include, but are not limited to, —X, —R, —O$^-$, =O, —OR, —SR, —S$^-$, —$NR_2$, —$NR_3$, =NR, —$CX_3$, —CN, —OCN, —SCN, —N=C=O, —NCS, —NO, —$NO_2$, =$N_2$, —$N_3$, NC(=O)R, —C(=O)R, —C(=O)NRR—S(=O)$_2$O$^-$, —S(=O)$_2$OH, —S(=O)$_2$R, —OS(=O)$_2$OR, —S(=O)$_2$NR, —S(=O)R, —OP(=O)O$_2$RR, —P(=O)O$_2$RR—P(=O)(O$^-$)$_2$, —P(=O)(OH)$_2$, —C(=O)R, —C(=O)X, —C(S)R, —C(O)OR, —C(O)O$^-$, —C(S)OR, —C(O)SR, —C(S)SR, —C(O)NRR, —C(S)NRR, —C(NR)NRR, where each X is independently a halogen: F, Cl, Br, or I; and each R is independently H, alkyl, aryl, arylalkyl, a heterocycle, or a protecting group or prodrug moiety. Alkylene, alkenylene, and alkynylene groups may also be similarly substituted.

"Bioavailability" is the degree to which the pharmaceutically active agent becomes available to the target tissue after the agent's introduction into the body. Enhancement of the bioavailability of a pharmaceutically active agent can provide a more efficient and effective treatment for patients because, for a given dose, more of the pharmaceutically active agent will be available at the targeted tissue sites.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —$OCH_3$, etc.), an amine (e.g., —$NHCH_3$—$N(CH_3)_2$, etc.), or a thioalkyl group (e.g., —$SCH_3$). If a non-terminal carbon atom of the alkyl group which is not attached to the parent molecule is replaced with a heteroatom (e.g., O, N, or S) and the resulting heteroalkyl groups are, respectively, an alkyl ether (e.g., —$CH_2CH_2$—O—$CH_3$, etc.), an alkyl amine (e.g., —CH$_2$NHCH$_3$, —CH$_2$N(CH$_3$)$_2$, etc.), or a thioalkyl ether (e.g., —CH$_2$—S—CH$_3$). If a terminal carbon atom of the alkyl group is replaced with a heteroatom (e.g., O, N, or S), the resulting heteroalkyl groups are, respectively, a hydroxyalkyl group (e.g., —CH$_2$CH$_2$—OH), an aminoalkyl group (e.g., —CH$_2$NH$_2$), or an alkyl thiol group (e.g., —CH$_2$CH$_2$—SH). A heteroalkyl group can have, for example, 1 to 20 carbon atoms, 1 to 10 carbon atoms, or 1 to 6 carbon atoms. A C$_1$-C$_6$ heteroalkyl group means a heteroalkyl group having 1 to 6 carbon atoms.

"Heterocycle" or "heterocyclyl" as used herein includes by way of example and not limitation those heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds A Series of Monographs* (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S). The terms "heterocycle" or "heterocyclyl" includes saturated rings, partially unsaturated rings, and aromatic rings (i.e., heteroaromatic rings). Substituted heterocyclyls include, for example, heterocyclic rings substituted with any of the substituents disclosed herein including carbonyl groups. A non-limiting example of a carbonyl substituted heterocyclyl is:

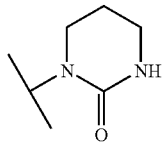

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

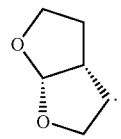

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Heterocyclylalkyl" refers to an acyclic alkyl radical in which one of the hydrogen atoms bonded to a carbon atom, typically a terminal or sp$^3$ carbon atom, is replaced with a heterocyclyl radical (i.e., a heterocyclyl-alkylene-moiety). Typical heterocyclyl alkyl groups include, but are not limited to heterocyclyl-CH$_2$—, 2-(heterocyclyl)ethan-1-yl, and the like, wherein the "heterocyclyl" portion includes any of the heterocyclyl groups described above, including those described in *Principles of Modern Heterocyclic Chemistry*. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. The heterocyclyl alkyl group comprises 6 to 20 carbon atoms, e.g., the alkyl portion of the arylalkyl group is 1 to 6 carbon atoms and the heterocyclyl moiety is 5 to 14 carbon atoms. Examples of heterocyclylalkyls include by way of example and not limitation 5-membered sulfur, oxygen, and/or nitrogen containing heterocycles such as thiazolylmethyl, 2-thiazolylethan-1-yl, imidazolylmethyl, oxazolylmethyl, thiadiazolylmethyl, etc., 6-membered sulfur, oxygen, and/or nitrogen containing heterocycles such as piperidinylmethyl, piperazinylmethyl, morpholinylmethyl, pyridinylmethyl, pyridizylmethyl, pyrimidylmethyl, pyrazinylmethyl, etc.

"Heterocyclylalkenyl" refers to an acyclic alkenyl radical in which one of the hydrogen atoms bonded to a carbon atom, typically a terminal or sp$^3$ carbon atom, but also a sp$^2$ carbon atom, is replaced with a heterocyclyl radical (i.e., a heterocyclyl-alkenylene-moiety). The heterocyclyl portion of the heterocyclyl alkenyl group includes any of the heterocyclyl groups described herein, including those described in *Prin-*

*ciples of Modern Heterocyclic Chemistry* and the alkenyl portion of the heterocyclyl alkenyl group includes any of the alkenyl groups disclosed herein. One skilled in the art will also understand that the heterocyclyl group can be attached to the alkenyl portion of the heterocyclyl alkenyl by means of a carbon-carbon bond or a carbon-heteroatom bond, with the proviso that the resulting group is chemically stable. The heterocyclyl alkenyl group comprises 6 to 20 carbon atoms, e.g., the alkenyl portion of the heterocyclyl alkenyl group is 1 to 6 carbon atoms and the heterocyclyl moiety is 5 to 14 carbon atoms.

"Heterocyclylalkynyl" refers to an acyclic alkynyl radical in which one of the hydrogen atoms bonded to a carbon atom, typically a terminal or $sp^3$ carbon atom, but also an sp carbon atom, is replaced with a heterocyclyl radical (i.e., a heterocyclyl-alkynylene-moiety). The heterocyclyl portion of the heterocyclyl alkynyl group includes any of the heterocyclyl groups described herein, including those described in *Principles of Modern Heterocyclic Chemistry*, and the alkynyl portion of the heterocyclyl alkynyl group includes any of the alkynyl groups disclosed herein. One skilled in the art will also understand that the heterocyclyl group can be attached to the alkynyl portion of the heterocyclyl alkynyl by means of a carbon-carbon bond or a carbon-heteroatom bond, with the proviso that the resulting group is chemically stable. The heterocyclyl alkynyl group comprises 6 to 20 carbon atoms, e.g., the alkynyl portion of the heterocyclyl alkynyl group is 1 to 6 carbon atoms and the heterocyclyl moiety is 5 to 14 carbon atoms.

"Heteroaryl" refers to an aromatic heterocyclyl having at least one heteroatom in the ring. Non-limiting examples of suitable heteroatoms which can be included in the aromatic ring include oxygen, sulfur, and nitrogen. Non-limiting examples of heteroaryl rings include all of those listed in the definition of "heterocyclyl", including pyridinyl, pyrrolyl, oxazolyl, indolyl, isoindolyl, purinyl, furanyl, thienyl, benzofuranyl, benzothiophenyl, carbazolyl, imidazolyl, thiazolyl, isoxazolyl, pyrazolyl, isothiazolyl, quinolyl, isoquinolyl, pyridazyl, pyrimidyl, pyrazyl, etc.

"Carbocycle" or "carbocyclyl" refers to a saturated, partially unsaturated or aromatic ring having 3 to 7 carbon atoms as a monocycle, 7 to 12 carbon atoms as a bicycle, and up to about 20 carbon atoms as a polycycle. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, and naphthyl.

"Arylheteroalkyl" refers to a heteroalkyl as defined herein, in which a hydrogen atom (which may be attached either to a carbon atom or a heteroatom) has been replaced with an aryl group as defined herein. The aryl groups may be bonded to a carbon atom of the heteroalkyl group, or to a heteroatom of the heteroalkyl group, provided that the resulting arylheteroalkyl group provides a chemically stable moiety. For example, an arylheteroalkyl group can have the general formulae -alkylene-O-aryl, -alkylene-O-alkylene-aryl, -alkylene-NH-aryl, -alkylene-NH-alkylene-aryl, -alkylene-S-aryl, -alkylene-S-alkylene-aryl, etc. In addition, any of the alkylene moieties in the general formulae above can be further substituted with any of the substituents defined or exemplified herein.

"Heteroarylalkyl" refers to an alkyl group, as defined herein, in which a hydrogen atom has been replaced with a heteroaryl group as defined herein. Non-limiting examples of heteroarylalkyl include —CH$_2$-pyridinyl, —CH$_2$-pyrrolyl, —CH$_2$-oxazolyl, —CH$_2$-indolyl, —CH$_2$-isoindolyl, —CH$_2$-purinyl, —CH$_2$-furanyl, —CH$_2$-thienyl, —CH$_2$-benzofuranyl, —CH$_2$-benzothiophenyl, —CH$_2$-carbazolyl, —CH$_2$-imidazolyl, —CH$_2$-thiazolyl, —CH$_2$-isoxazolyl, —CH$_2$-pyrazolyl, —CH$_2$-isothiazolyl, —CH$_2$-quinolyl, —CH$_2$-isoquinolyl, —CH$_2$-pyridazyl, —CH$_2$-pyrimidyl, —CH$_2$-pyrazyl, —CH(CH$_3$)-pyridinyl, —CH(CH$_3$)-pyrrolyl, —CH(CH$_3$)-oxazolyl, —CH(CH$_3$)-indolyl, —CH(CH$_3$)-isoindolyl, —CH(CH$_3$)-purinyl, —CH(CH$_3$)-furanyl, —CH(CH$_3$)-thienyl, —CH(CH$_3$)-benzofuranyl, —CH(CH$_3$)-benzothiophenyl, —CH(CH$_3$)-carbazolyl, —CH(CH$_3$)-imidazolyl, —CH(CH$_3$)-thiazolyl, —CH(CH$_3$)-isoxazolyl, —CH(CH$_3$)-pyrazolyl, —CH(CH$_3$)-isothiazolyl, —CH(CH$_3$)-quinolyl, —CH(CH$_3$)-isoquinolyl, —CH(CH$_3$)-pyridazyl, —CH(CH$_3$)-pyrimidyl, —CH(CH$_3$)-pyrazyl, etc.

The term "optionally substituted" in reference to a particular moiety of the compound of Formula I (e.g., an optionally substituted aryl group) refers to a moiety having 0, 1, 2, or more substituents.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

The term "heteroaryl," as used herein, refers to an aromatic five or six-membered ring where at least one atom is selected from the group consisting of N, O, and S, and the remaining atoms are carbon. The term "heteroaryl" also includes bicyclic systems where a heteroaryl ring is fused to a phenyl group, a monocyclic cycloalkyl group, as defined herein, a heterocycle group, as defined herein, or an additional heteroaryl group. The term "heteroaryl" also includes tricyclic systems where a bicyclic system is fused to a phenyl group, a monocyclic cycloalkyl group, as defined herein, a heterocycle group, as defined herein, or an additional heteroaryl group. The heteroaryl groups are connected to the parent molecular moiety through any substitutable carbon or nitrogen atom in the groups. Examples of heteroaryl groups include benzothienyl, benzoxazolyl, benzimidazolyl, benzoxadiazolyl, dibenzofuranyl, dihydrobenzothiazolyl, furanyl (furyl), imidazolyl, imidazopyridinyl, indazolyl, indolyl, isoindolyl, isoxazolyl, isoquinolinyl, isothiazolyl, oxadiazolyl, oxazolyl, thiazolyl, thienopyridinyl, thienyl, triazolyl, thiadiazolyl, tetrazolyl, pyridoimidazolyl, pyridyl, pyridazinyl, pyrimidinyl, pyrazinyl, pyrazolyl, pyrrolyl, quinolinyl, tetrahydroquinolinyl, tetrahydropyranyl and triazinyl. The heteroaryl groups of the present invention can be substituted or unsubstituted. In addition, the nitrogen heteroatoms can be optionally quaternized or oxidized to the N-oxide. Also, the nitrogen containing rings can be optionally N-protected.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York.

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

"Linker" or "link" refers to a chemical moiety comprising a covalent bond or a chain or group of atoms that covalently attaches a phosphonate group to a drug. Linkers include portions of substituents $A^1$ and $A^3$, which include moieties such as: repeating units of alkyloxy (e.g., polyethylenoxy, PEG, polymethyleneoxy) and alkylamino (e.g., polyethyleneamino, Jeffamine™); and diacid ester and amides including succinate, succinamide, diglycolate, malonate, and caproamide.

The terms "phosphonate" and "phosphonate group" include functional groups or moieties within a molecule that comprises a phosphorous that is 1) single-bonded to a carbon, 2) double-bonded to a heteroatom, 3) single-bonded to a heteroatom, and 4) single-bonded to another heteroatom, wherein each heteroatom can be the same or different. The terms "phosphonate" and "phosphonate group" also include functional groups or moieties that comprise a phosphorous in the same oxidation state as the phosphorous described above, as well as functional groups or moieties that comprise a prodrug moiety that can separate from a compound so that the compound retains a phosphorous having the characteristics described above. For example, the terms "phosphonate" and "phosphonate group" include phosphonic acid, phosphonic monoester, phosphonic diester, phosphonamidate, and phosphonthioate functional groups. In one specific embodiment of the invention, the terms "phosphonate" and "phosphonate group" include functional groups or moieties within a molecule that comprises a phosphorous that is 1) single-bonded to a carbon, 2) double-bonded to an oxygen, 3) single-bonded to an oxygen, and 4) single-bonded to another oxygen, as well as functional groups or moieties that comprise a prodrug moiety that can separate from a compound so that the compound retains a phosphorous having such characteristics. In another specific embodiment of the invention, the terms "phosphonate" and "phosphonate group" include functional groups or moieties within a molecule that comprises a phosphorous that is 1) single-bonded to a carbon, 2) double-bonded to an oxygen, 3) single-bonded to an oxygen or nitrogen, and 4) single-bonded to another oxygen or nitrogen, as well as functional groups or moieties that comprise a prodrug moiety that can separate from a compound so that the compound retains a phosphorous having such characteristics.

The term "prodrug" as used herein refers to any compound that when administered to a biological system generates the drug substance, i.e. active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically-active compound.

"Prodrug moiety" refers to a labile functional group which separates from the active compound during metabolism, systemically, inside a cell, by hydrolysis, enzymatic cleavage, or by some other process (Bundgaard, Hans, "Design and Application of Prodrugs" in *A Textbook of Drug Design and Development* (1991), P. Krogsgaard-Larsen and H. Bundgaard, Eds. Harwood Academic Publishers, pp. 113-191). Enzymes which are capable of an enzymatic activation mechanism with the phosphonate prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy. A prodrug moiety may include an active metabolite or drug itself.

Exemplary prodrug moieties include the hydrolytically sensitive or labile acyloxymethyl esters —CH$_2$OC(=O)R$^a$ and acyloxymethyl carbonates —CH$_2$OC(=O)OR$^a$ where R$^a$ is $C_1$-$C_6$ alkyl, $C_1$-$C_6$ substituted alkyl, $C_6$-$C_{20}$ aryl or $C_6$-$C_{20}$ substituted aryl. The acyloxyalkyl ester was first used as a prodrug strategy for carboxylic acids and then applied to phosphates and phosphonates by Farquhar et al. (1983) *J. Pharm. Sci.* 72: 324; also U.S. Pat. Nos. 4,816,570, 4,968, 788, 5,663,159 and 5,792,756. Subsequently, the acyloxyalkyl ester was used to deliver phosphonic acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the combinations of the invention. An exemplary acyloxymethyl ester is pivaloyloxymethoxy, (POM) —CH$_2$OC(=O)C(CH$_3$)$_3$. An exemplary acyloxymethyl carbonate prodrug moiety is pivaloyloxymethylcarbonate (POC)—CH$_2$OC(=O)OC(CH$_3$)$_3$.

The phosphonate group may be a phosphonate prodrug moiety. The prodrug moiety may be sensitive to hydrolysis, such as, but not limited to a pivaloyloxymethyl carbonate (POC) or POM group. Alternatively, the prodrug moiety may be sensitive to enzymatic potentiated cleavage, such as a lactate ester or a phosphonamidate-ester group.

One skilled in the art will recognize that substituents and other moieties of the compounds of Formula I should be selected in order to provide a compound which is sufficiently stable to provide a pharmaceutically useful compound which can be formulated into an acceptably stable pharmaceutical composition. Compounds of Formula I which have such stability are contemplated as falling within the scope of the present invention.

Protecting Groups

In the context of the present invention, protecting groups include prodrug moieties and chemical protecting groups.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. The PG groups do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis* Theodora W. Greene (John Wiley & Sons, Inc., New York, 1991, ISBN 0-471-62301-6) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below. Such groups include by way of example and not limitation, esters, amides, hydrazides, and the like.

Ether- and Ester-Forming Protecting Groups

Ester-forming groups include: (1) phosphonate ester-forming groups, such as phosphonamidate esters, phosphorothioate esters, phosphonate esters, and phosphon-bis-amidates; (2) carboxyl ester-forming groups, and (3) sulphur ester-forming groups, such as sulphonate, sulfate, and sulfinate.

Metabolites of the Compounds of the Invention

Also falling within the scope of this invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled (e.g., $C^{14}$ or $H^3$) compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no anti-infective activity of their own.

Compounds of Formula I

In one embodiment, the present application provides compounds according to Formula I, as described herein.

In another embodiment of the compounds of Formula I, X is —C(O)—, —S(O$_2$)—, or —S(O)—; and $R^3$ is H, or substituted alkyl.

In another embodiment of the compounds of Formula I, X is —C(O)— or —S(O$_2$)—; and $R^3$ is H.

In another embodiment of the compounds of Formula I, $R^2$ is H.

In another embodiment of the compounds of Formula I, $R^1$ is $OR^{1c}$; and $R^{1c}$ is alkyl, substituted alkyl, heterocyclyl, substituted heterocyclyl, heterocyclyl alkyl, or substituted heterocyclyl alkyl, wherein said substituted heterocyclyl alkyl is substituted on the heterocyclyl moiety, and said heterocyclyl is selected from the group consisting of: (i) a monocyclic 5- or 6-membered aromatic, nonaromatic dihydro, or nonaromatic tetrahydro heterocyclic ring having from 1 to 4 heteroatoms selected from N, O, and S; and (ii) a bi-cyclic 8-, 9-, or 10-membered aromatic, nonaromatic dihydro, or nonaromatic tetrahydro heterocyclic ring having from 1 to 6 heteroatoms selected from N, O, and S.

In another embodiment of the compounds of Formula I, $R^1$ is $OR^{1c}$; and $R^{1c}$ is methyl, ethyl, n-propyl, iso-propyl, n-butyl, iso-butyl, or tert-butyl.

In another embodiment of the compounds of Formula I, $R^1$ is $OR^{1c}$; and $R^{1c}$ is selected from the group consisting of

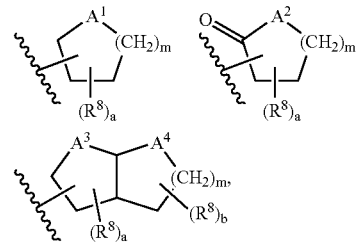

$A^1$, $A^2$, $A^3$, and $A^4$ are independently $NR^9$ or O; $R^8$ is alkyl, substituted alkyl, haloalkyl, substituted haloalkyl, hydroxyalkyl, substituted hydroxyalkyl, —O-(alkyl), or —O-(substituted alkyl); $R^9$ is H, alkyl, or substituted alkyl; m is 1 or 2; and a and b are independently 0, 1, or 2.

In another embodiment of the compounds of Formula I, $R^1$ is $OR^{1c}$; and $R^{1c}$ is selected from the group consisting of

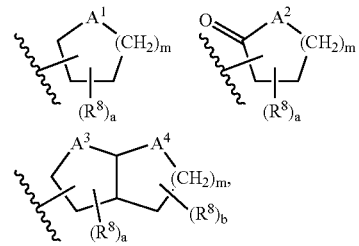

$A^1$, $A^2$, $A^3$, and $A^4$ are O; $R^8$ is alkyl, substituted alkyl, haloalkyl, substituted haloalkyl, hydroxyalkyl, substituted hydroxyalkyl, —O-(alkyl), or —O-(substituted alkyl); m is 1; and a and b are independently 0, 1, or 2.

In another embodiment of the compounds of Formula I, $R^1$ is $OR^{1c}$; and $R^{1c}$ is heterocyclyl having one of the following structures:

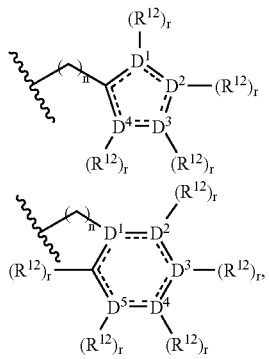

wherein $D^1$, $D^2$, $D^3$, $D^4$, and $D^5$ are independently selected from the group consisting of C, N, O, and S; n is 0 or 1; each $R^{12}$ is independently H, alkyl, or substituted alkyl, with the proviso that in each occurrence of $(R^{12})_r$, r is 0, 1, or 2, whereby carbon is tetravalent, nitrogen is trivalent, and sulfur and oxygen are divalent; and ==== is a single or double bond.

In another embodiment of the compounds of Formula I, $R^1$ is

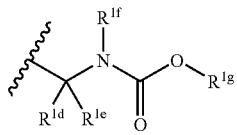

$R^{1d}$ and $R^{1e}$ are each independently selected from the group consisting of H, alkyl, and substituted alkyl; or $R^{1d}$ and $R^{1e}$ taken together with the carbon atom to which they are shown attached form a heterocyclyl or a substituted heterocyclyl, wherein said heterocyclyl or said substituted heterocyclyl is a 5- or 6-membered non-aromatic tetrahydro heterocyclic ring having from 1 to 3 heteroatoms selected from N, O, and S, $R^{1f}$ is H, alkyl, or substituted alkyl; and $R^{1g}$ is alkyl or substituted alkyl.

In another embodiment of the compounds of Formula I, $R^1$ is a 5- or 6-membered aryl, 5- or 6-membered substituted aryl, 5- or 6-membered heteroaryl, 5- or 6-membered substituted heteroaryl, 8- to 10-membered bi-cyclic heteroaryl, or 8- to 10-membered bi-cyclic substituted heteroaryl, wherein the substituted aryl or substituted heteroaryl is independently substituted with one or more substituents selected from the group consisting of alkyl, substituted alkyl, hydroxy, —O-alkyl, and —O-(substituted alkyl).

In another embodiment of the compounds of Formula I, $R^5$ is H.

In another embodiment of the compounds of Formula I, q is 0, $L^3$ is alkylene; $Ar^3$ is aryl, substituted aryl, heteroaryl, or substituted heteroaryl, wherein the substituted aryl or substituted heteroaryl of $Ar^3$ is substituted by one or more substituents selected from the group consisting of alkyl, substituted alkyl, hydroxy, alkoxy, haloalkoxy, —NH-alkyl, —NH-(alkyl)$_2$, —NH-acyl, —N(alkyl)-acyl, —NR$^a$—S(O)$_2$—R$^b$, —C(O)—R$^c$, —S(O)$_2$R$^b$, —S(O)$_2$NHR$^a$, —C(O)—NH—R$^a$, and —O-alkylene-R$^7$; $R^7$ is aryl, heterocyclyl, substituted aryl, substituted heterocyclyl, —NR$^{7a}$-L$^5$-R$^{7b}$, —O—PO$_3$R$^{7c}$R$^{7d}$, or a phosphonate group; $L^5$ is —C(O)—, —C(O)O—, —C(O)NR$^{7e}$—, —S(O)$_2$—, —S(O)—, —S(O)$_2$)NR$^{7e}$—, or —S(O)NR$^{7e}$—; $R^{7a}$, $R^{7c}$, $R^{7d}$, and $R^{7e}$ are independently H, alkyl, or substituted alkyl; $R^a$ is H, alkyl, or substituted alkyl; $R^b$ is alkyl, aryl, or substituted aryl; and $R^{7b}$ is alkyl or substituted alkyl.

In another embodiment of the compounds of Formula I, q is 0, -L$^3$-Ar$^3$ is

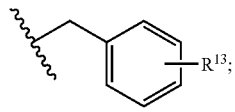

$R^{13}$ is H, alkyl, substituted alkyl, hydroxy, alkoxy; or $R^{13}$ is one of the following structures:

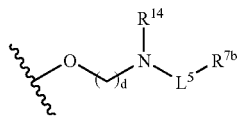

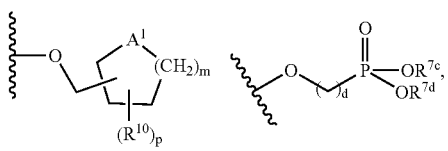

wherein $A^1$ is $NR^{14}$ or O; $R^{14}$ is H, alkyl, or substituted alkyl; $R^{10}$ is alkyl, substituted alkyl, haloalkyl, substituted haloalkyl, hydroxyalkyl, substituted hydroxyalkyl, alkoxyalkyl, or substituted alkoxyalkyl; m is 1 or 2; p is 0, 1, or 2; $L^5$ is —C(O)—, —C(O)—O—, or —S(O)$_2$—; $R^{7b}$ is alkyl, substituted alkyl, heteroaryl, or substituted heteroaryl; d is 1, 2, 3, or 4; and $R^{7c}$ and $R^{7d}$ are independently alkyl or substituted alkyl.

In another embodiment of the compounds of Formula I, $R^4$ is H. In another embodiment of the compounds of Formula I, p is 1; $L^1$ is alkylene; $L^2$ is a covalent bond; $Ar^1$ is aryl or substituted aryl; $Ar^3$ is heteroaryl or substituted heteroaryl;

wherein said substituted aryl or said substituted heteroaryl is substituted by one or more substituents selected from the group consisting of alkyl, substituted alkyl, haloalkyl, halo, nitro, cyano, hydroxy, amino, alkoxy, haloalkoxy, —NH-alkyl, —NH-(alkyl)$_2$, —NH-acyl, —N(alkyl)-acyl, —NR$^a$—S(O)$_2$—R$^b$, —C(O)—R$^c$, —S(O)$_2$R$^b$, —S(O)$_2$NHR$^a$, —C(O)—NH—R$^a$; $R^a$ is H, alkyl, or substituted alkyl; and $R^b$ is alkyl, aryl, or substituted aryl.

In another embodiment of the compounds of Formula I, p is 1; $L^1$ is alkylene;

—Ar$^1$-L$^2$-Ar$^2$ is

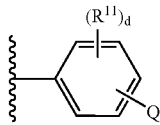

$R^{11}$ is H, alkyl, substituted alkyl, haloalkyl, substituted haloalkyl, hydroxyalkyl, substituted hydroxyalkyl, alkoxyalkyl, or substituted alkoxyalkyl; d is 1, 2, 3, or 4;

Q is a heterocyclyl having one of the following structures:

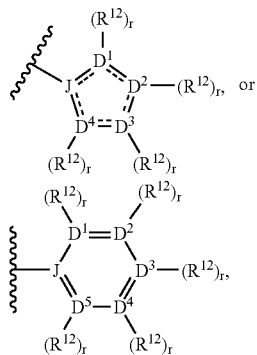

$D^1$, $D^2$, $D^3$, $D^4$, and $D^5$ are independently selected from the group consisting of C, N, O, and S; J is $CR^{12}$ or N; each $R^{12}$ is independently H, alkyl, or substituted alkyl, with the proviso that in each occurrence of $(R^{12})_r$, r is 0, 1, or 2, whereby carbon is tetravalent, nitrogen is trivalent, and sulfur and oxygen are divalent; and ----- is a single or double bond.

In another embodiment of the compounds of Formula I, p is 1; $L^1$ is alkylene; $Ar^1$-$L^2$-$Ar^2$ is

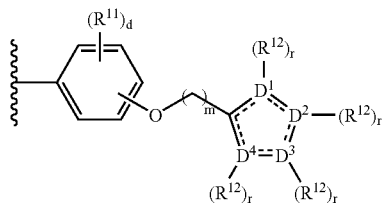

$D^1$, $D^2$, $D^3$, and $D^4$ are independently selected from the group consisting of C, N, O, and S; each $R^{12}$ is independently H, alkyl, or substituted alkyl, with the proviso that in each occurrence of $(R^{12})_r$, r is 0, 1, or 2, whereby carbon is tetravalent, nitrogen is trivalent, and sulfur and oxygen are divalent; and $R^{11}$ is H, alkyl, substituted alkyl, haloalkyl, substituted haloalkyl, hydroxyalkyl, substituted hydroxyalkyl, alkoxyalkyl, or substituted alkoxyalkyl; d is 1, 2, 3, or 4; m is 1 or 2; and ----- is a single or double bond.

In another embodiment of the compounds of Formula I, p is 1; $L^1$ is alkylene;

$Ar^1$-$L^2$-$Ar^2$ is

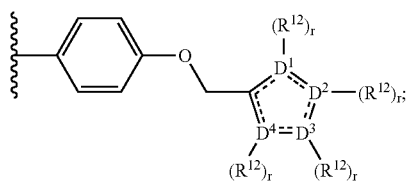

$D^1$, $D^2$, $D^3$, and $D^4$ are independently selected from the group consisting of C, N, O, and S; and each $R^{12}$ is independently H, alkyl, or substituted alkyl, with the proviso that in each occurrence of $(R^{12})_r$, r is 0, 1, or 2, whereby carbon is tetravalent, nitrogen is trivalent, and sulfur and oxygen are divalent.

In another embodiment of the compounds of Formula I, p is 0; $L^1$ is alkylene; $Ar^1$ is aryl, substituted aryl, heteroaryl, or substituted heteroaryl, wherein said substituted aryl or said substituted heteroaryl is substituted by one or more substituents selected from the group consisting of alkyl, substituted alkyl, hydroxy, alkoxy, —$NR^a$—$S(O)_2$—$R^b$, —$C(O)$—$R^c$, —$S(O)_2R^b$, —$S(O)_2NHR^a$, —$C(O)$—$NH$—$R^a$, and —O-alkylene-$R^7$; $R^7$ is aryl, heterocyclyl, substituted aryl, substituted heterocyclyl, —$NR^{7a}$-$L^5$-$R^{7b}$, —O—$PO_3R^{7c}R^{7d}$, a phosphonate group; $L^5$ is —$C(O)$—, —$C(O)O$—, —$C(O)NR^{7e}$, —$S(O_2)$—, —$S(O)$—, —$S(O_2)NR^{7e}$—, or —$S(O)NR^{7e}$—; $R^{7a}$, $R^{7c}$, $R^{7d}$, and $R^{7e}$ are independently H, alkyl, or substituted alkyl; $R^{7b}$ is alkyl or substituted alkyl; $R^a$ is H, alkyl, or substituted alkyl; and $R^b$ is alkyl, aryl, or substituted aryl.

In another embodiment of the compounds of Formula I, p is 0; q is 1; $L^1$ and $L^3$ are independently alkylene; $L^4$ is a covalent bond; $Ar^1$, $Ar^2$, $Ar^3$, and $Ar^4$ are independently aryl, substituted aryl, heteroaryl, or substituted heteroaryl; wherein said substituted aryl or said substituted heteroaryl is substituted by one or more substituents selected from the group consisting of alkyl, substituted alkyl, haloalkyl, hydroxy, alkoxy, and —O-alkylene-$R^7$; $R^7$ is aryl, heterocyclyl, substituted aryl, substituted heterocyclyl, —$NR^{7a}$-$L^5$-$R^{7b}$, —O—$PO_3R^{7c}R^{7d}$, or a phosphonates group; $L^5$ is —$C(O)$—, —$C(O)O$—, —$C(O)NR^{7e}$—, —$S(O_2)$—, —$S(O)$—, —$S(O_2)NR^{7e}$—, or —$S(O)NR^{7e}$—; $R^{7a}$, $R^{7c}$, $R^{7d}$, and $R^{7e}$ are independently H, alkyl, or substituted alkyl; and $R^{7b}$ is alkyl or substituted alkyl.

In another embodiment of the compounds of Formula I, p and q are both 0; $L^1$ and $L^3$ are independently alkylene; $Ar^1$ and $Ar^3$ are independently aryl or substituted aryl, wherein said substituted aryl is substituted by one or more substituents selected from the group consisting of alkoxy, haloalkoxy, —O-alkylene-$R^7$; and $R^7$ is aryl, substituted aryl, heteroaryl, or substituted heteroaryl; with the proviso that $Ar^1$ and $Ar^3$ are not both phenyl.

In another embodiment of the compounds of Formula I, $R^6$ is $OR^{6a}$, $R^{6a}$ is alkyl or selected from the group consisting of

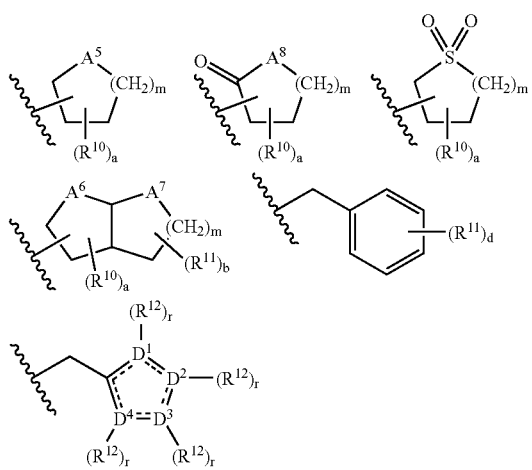

-continued

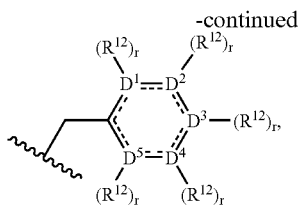

$A^5$ is $NR^{14}$ or O; $A^6$, $A^7$, and $A^8$ are independently $CR^{14}R^{15}$, $NR^{14}$, or O, with the proviso that at least one of $A^6$ and $A^7$ is $NR^{14}$, or O; $R^{10}$ and $R^{11}$ are independently H, alkyl, substituted alkyl, haloalkyl, substituted haloalkyl, hydroxyalkyl, substituted hydroxyalkyl, alkoxyalkyl, or substituted alkoxyalkyl; $R^{14}$ and $R^{15}$ are independently H, alkyl, or substituted alkyl; a and b are independently 0, 1, or 2; m is 1 or 2; $D^1$, $D^2$, $D^3$, $D^4$, and $D^5$ are independently selected from the group consisting of C, N, O, and S; each $R^{12}$ is independently H, alkyl, or substituted alkyl, with the proviso that in each occurrence of $(R^{12})_r$, r is 0, 1, or 2, whereby carbon is tetravalent, nitrogen is trivalent, and sulfur and oxygen are divalent; and ═══ is a single or double bond.

In another embodiment of the compounds of Formula I, $R^6$ is selected from the group consisting of

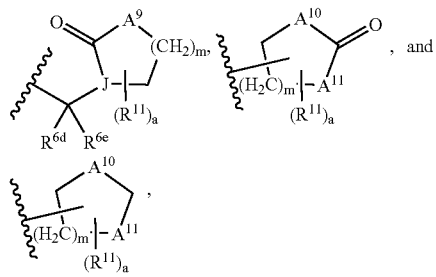

, and $R^{6d}$ and $R^{6e}$ are independently selected from the group consisting of H, alkyl, and substituted alkyl; $R^{11}$ is alkyl, substituted alkyl, haloalkyl, substituted haloalkyl, hydroxyalkyl, substituted hydroxyalkyl, alkoxyalkyl, or substituted alkoxyalkyl; $A^9$ is $CR^{14}R^{15}$, $NR^{14}$, or O; J is $CR^{14}R^{15}$ or N, with the proviso that $A^9$ and J are not both $CR^{14}R^{15}$; $R^{14}$ and $R^{15}$ are independently H, alkyl, or substituted alkyl; $A^{10}$ and $A^{11}$ are independently $CR^{14}R^{15}$, $NR^{14}$, S, or O, with the proviso that $A^{10}$ and $A^{11}$ are not both $CR^{14}R^{15}$; each $R^{14}$ and $R^{15}$ is independently H, alkyl, or substituted alkyl; m is 1 or 2; and a is 0, 1, or 2.

In another embodiment of the compounds of Formula I, $R^6$ is selected from a group consisting of

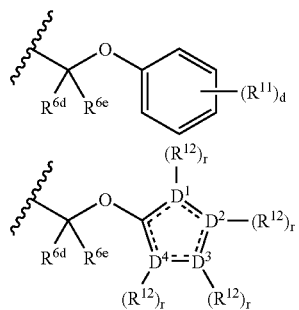

-continued

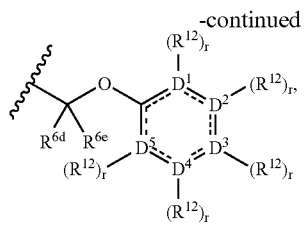

$R^{6d}$ and $R^{6e}$ are independently selected from the group consisting of H, alkyl, and substituted alkyl; $R^{11}$ is H, alkyl, substituted alkyl, haloalkyl, substituted haloalkyl, hydroxyalkyl, substituted hydroxyalkyl, alkoxyalkyl, or substituted alkoxyalkyl; d is 1, 2, 3, or 4; $D^1$, $D^2$, $D^3$, $D^4$, and $D^5$ are independently selected from the group consisting of C, N, O, and S; each $R^{12}$ is independently H, alkyl, or substituted alkyl, with the proviso that in each occurrence of $(R^{12})_r$, r is 0, 1, or 2, whereby carbon is tetravalent, nitrogen is trivalent, and sulfur and oxygen are divalent; and ═══ is a single or double bond.

In another embodiment of the compounds of Formula I, $R^6$ is

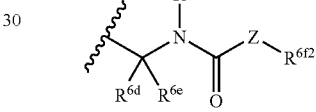

$R^{6d}$ and $R^{6e}$ are independently H, alkyl, haloalkyl, hydroxyalkyl, or alkoxy; or $R^{6d}$ and $R^{6e}$ are taken together to form a 5- or 6-membered non-aromatic tetrahydro heterocyclic ring; Z is —$NR^{14}$— or —O—; $R^{14}$ is H, alkyl, or substituted alkyl; $R^{6f1}$ is H, alkyl, or substituted alkyl; $R^{6f2}$ is alkyl, haloalkyl, hydroxyalkyl, or alkoxy.

In another embodiment of the compounds of Formula I, $R^6$ is

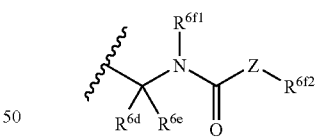

$R^{6d}$ and $R^{6e}$ are independently H, alkyl, haloalkyl, hydroxyalkyl, or alkoxy; or $R^{6d}$ and $R^{6e}$ are taken together to form a 5- or 6-membered non-aromatic tetrahydro heterocyclic ring; Z is —$NR^{14}$— or —O—; $R^{14}$ is H, alkyl, or substituted alkyl; $R^{6f1}$ is H, alkyl, or substituted alkyl; $R^{6f2}$ is

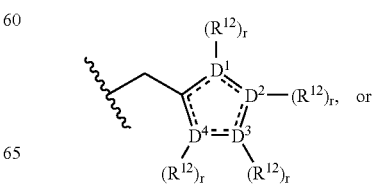

-continued

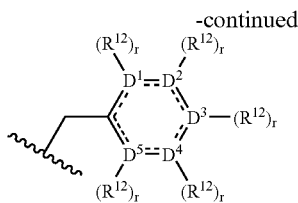

$D^1$, $D^2$, $D^3$, $D^4$, and $D^5$ are independently selected from the group consisting of C, N, O, and S; each $R^{12}$ is independently H, alkyl, or substituted alkyl, with the proviso that in each occurrence of $(R^{12})_r$, r is 0, 1, or 2, whereby carbon is tetravalent, nitrogen is trivalent, and sulfur and oxygen are divalent; and ---- is a single or double bond.

In another embodiment of the compounds of Formula I, $R^6$ is

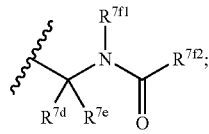

$R^{6d}$ and $R^{6e}$ are independently H, alkyl, haloalkyl, hydroxyalkyl, or alkoxy; $R^{6f1}$ is H, alkyl, or substituted alkyl; $R^{6f2}$ is alkyl, haloalkyl, hydroxyalkyl, or alkoxy.

In another embodiment of the compounds of Formula I, $R^6$ is

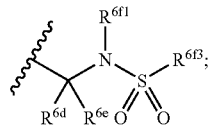

$R^{6d}$ and $R^{6e}$ are independently H, alkyl, haloalkyl, hydroxyalkyl, or alkoxy; $R^{6f1}$ is H, alkyl, or substituted alkyl; and $R^{6f3}$ is alkyl, substituted alkyl.

In another embodiment of the compounds of Formula I, X is $S(O_2)$ or $S(O)$; and $R^7$ is alkyl, substituted alkyl, aryl, substituted aryl, heterocyclyl, substituted heterocyclyl, wherein said heterocyclyl is selected from the group consisting of:

(i) a 5-membered aromatic, nonaromatic dihydro, or nonaromatic tetrahydro heterocyclic ring having from 1 to 4 heteroatoms selected from N, O, and S; and (ii) a 6-membered aromatic, nonaromatic dihydro, or nonaromatic tetrahydro heterocyclic ring having from 1 to 4 heteroatoms selected from N, O, and S.

In another embodiment of the compounds of Formula I, X is $S(O)_2$ and $R^7$ is methyl, ethyl, n-propyl, 2-propyl, n-butyl, 2-butyl, tert-butyl, and 2,2-dimethylpropyl In another embodiment of the compounds of Formula I, X is C(O); p is 1; q is 0; $L^1$ and $L^3$ are alkylene, $L^2$ is a covalent bond; $R^1$ is —C($R^{1d}R^{1e}$)—N$R^{1f}$-$L^6$-$R^{1g}$; $R^{1d}$ is alkyl; $R^{1e}$ is H; $R^{1f}$ is H; -$L^6$-$R^{1g}$ is —C(O)—O-alkyl; $R^6$ is —C($R^{6d}R^{6e}$)$R^{6f}$; $R^{6d}$ is alkyl; $R^{6e}$ is H; $R^{6f}$ is —NH—C(O)—O-alkyl; $Ar^3$ is -aryl-$Z^1$-alkylene-O—$PO_3R^{7c}R^{7d}$; and $Z^1$ is O or N$R^{7a}$; $R^{7a}$, $R^{7c}$, and $R^{7d}$ are independently H, alkyl, or substituted alkyl.

In another embodiment of the compounds of Formula I, X is C(O); p is 1; q is 0; $L^1$ and $L^3$ are alkylene; $L^2$ is a covalent bond; $R^1$ is —C($R^{1d}R^{1e}$)—N$R^{1f}$-$L^6$-$R^{1g}$; $R^{1d}$ is hydroxyalkyl; $R^{1e}$ is H; $R^{1f}$ is H; -$L^6$-$R^{1g}$ is —C(O)—O-alkyl; $R^6$ is —C($R^{6d}R^{6e}$)$R^{6f}$; and $R^{6d}$ is hydroxyalkyl; $R^{6e}$ is H; $R^{6f}$ is —NH—C(O)—O-alkyl.

In another embodiment of the compounds of Formula I, X is C(O); p and q are 0; $L^1$ and $L^3$ are alkylene; $Ar^3$ and $Ar^1$ are independently aryl or substituted aryl, wherein the substituted aryl contains one or more substituents selected from the group consisting of alkoxy, haloalkoxy, —O-alkylene-heterocyclyl, and —O-alkylene-(substituted heterocyclyl).

In another embodiment of the compounds of Formula I, X is C(O); p is 0; q is 1; $L^1$ and $L^3$ are alkylene; and $L^4$ is a covalent bond.

In another embodiment, the compounds of Formula I have one of the following structures:

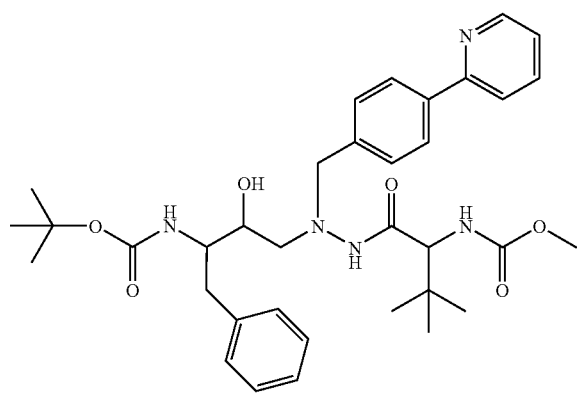

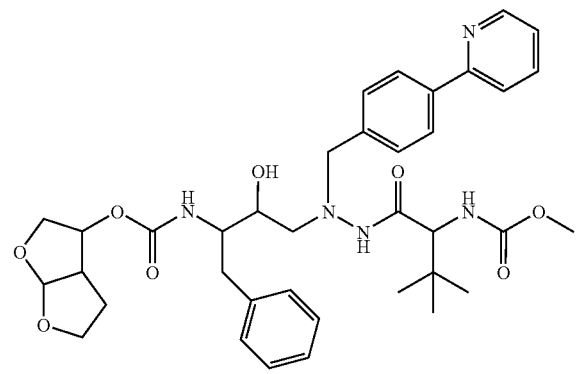

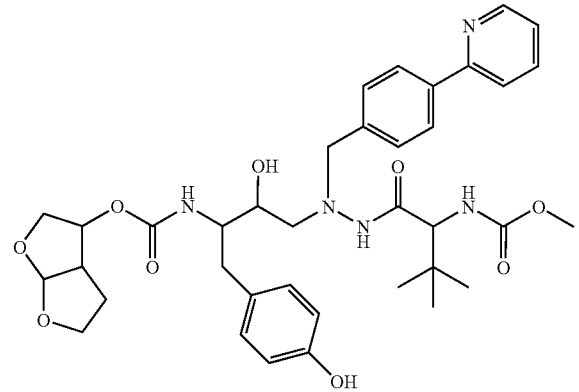

23
-continued
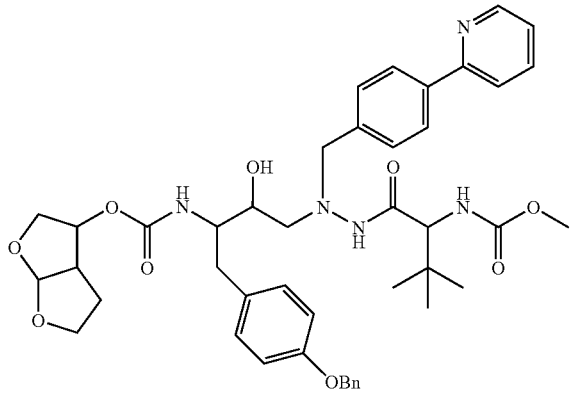
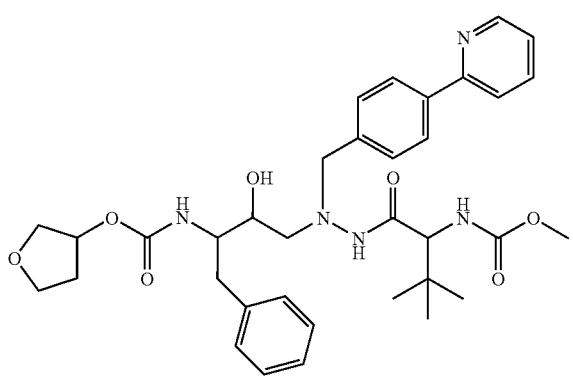
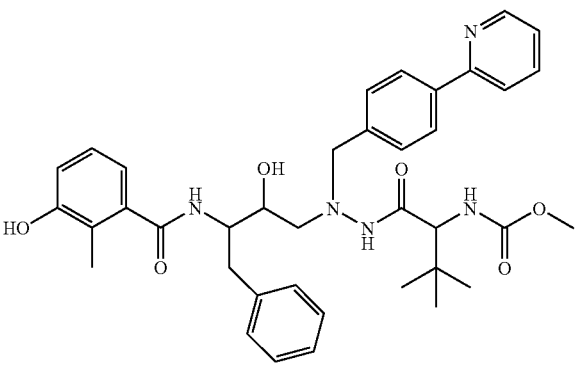
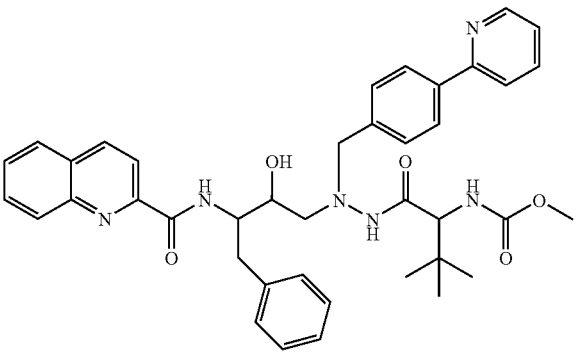
24
-continued
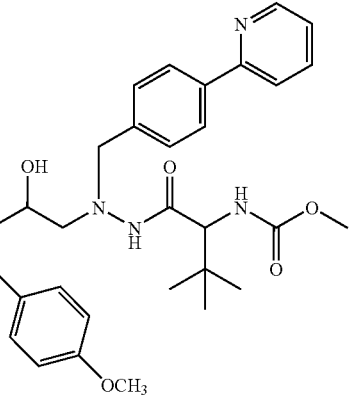
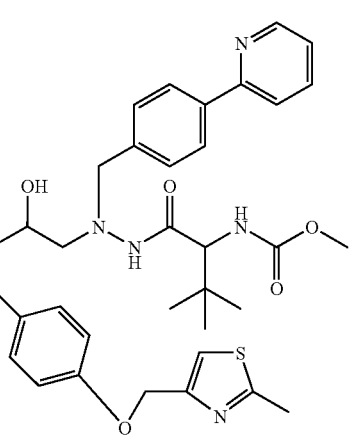
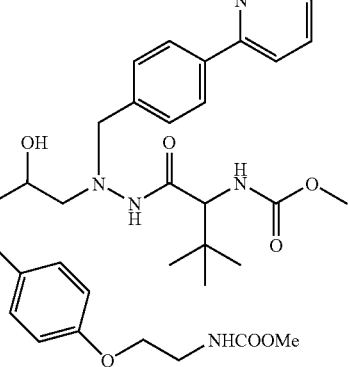

25
-continued
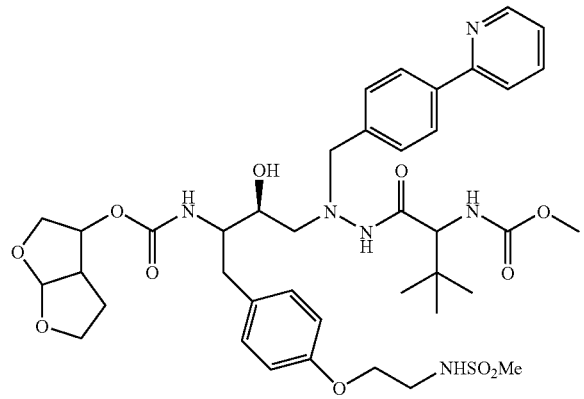
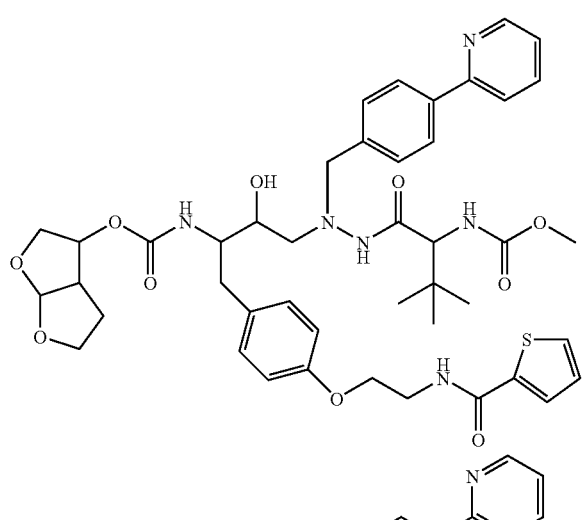
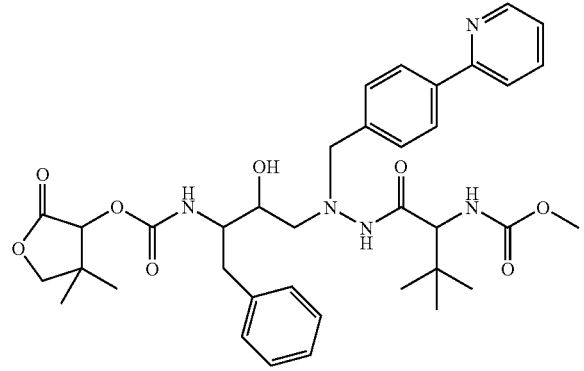
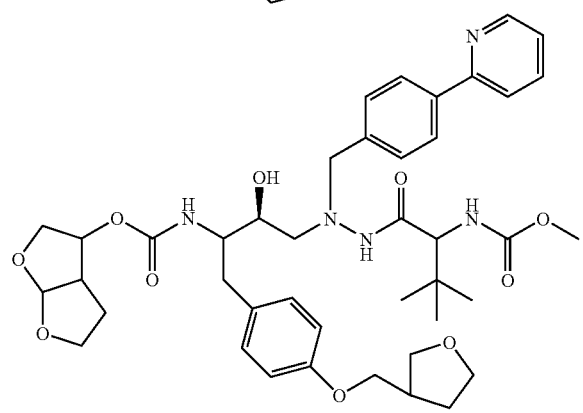
26
-continued
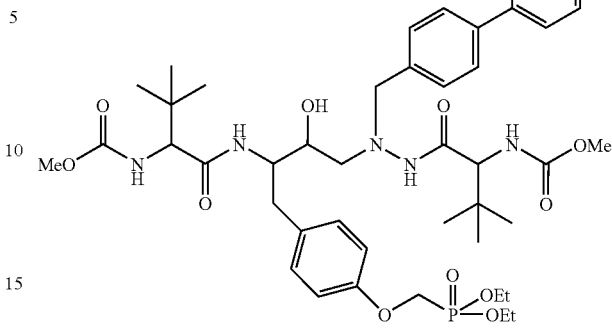
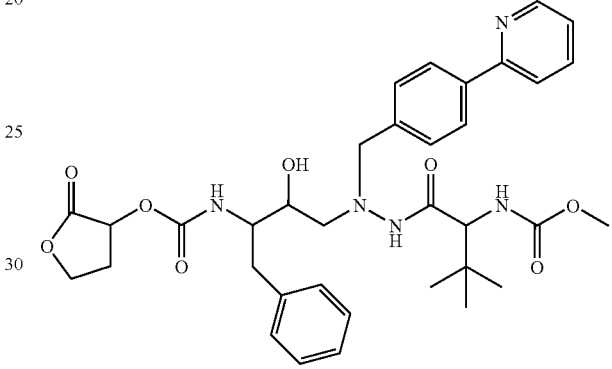
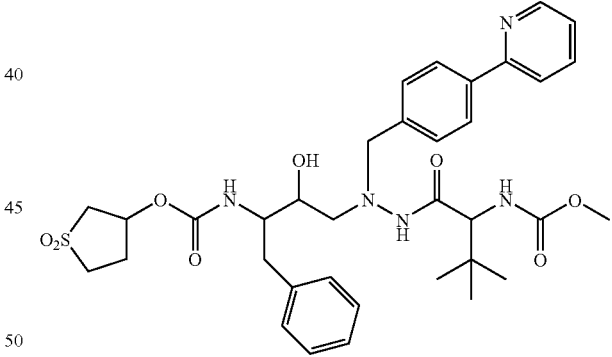
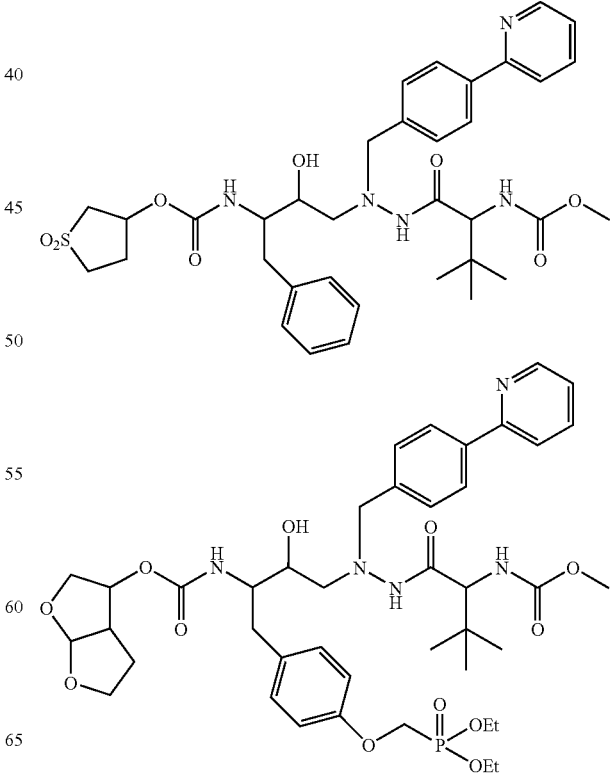

27
-continued
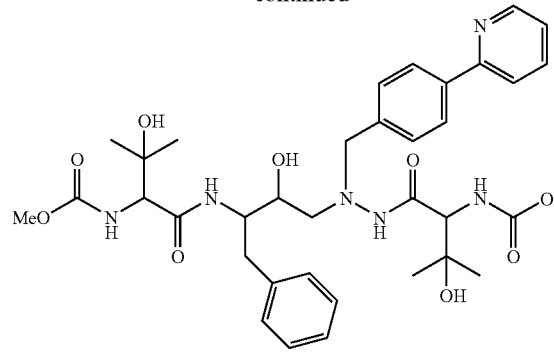
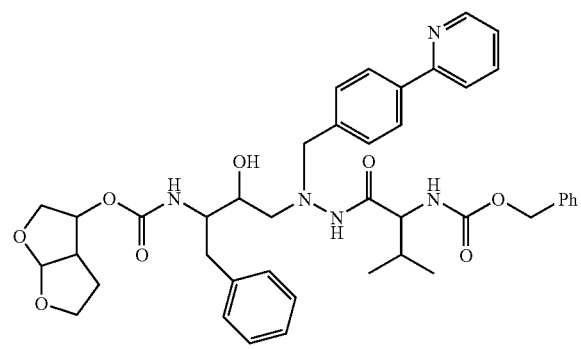
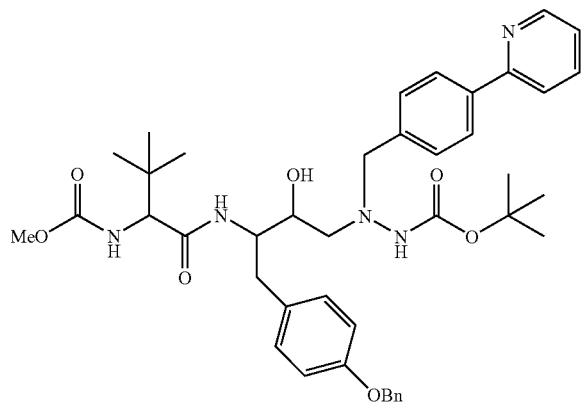
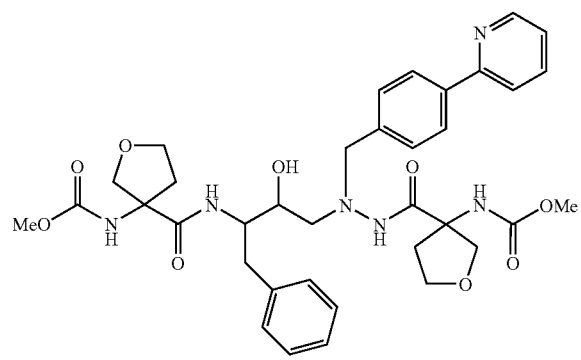
28
-continued
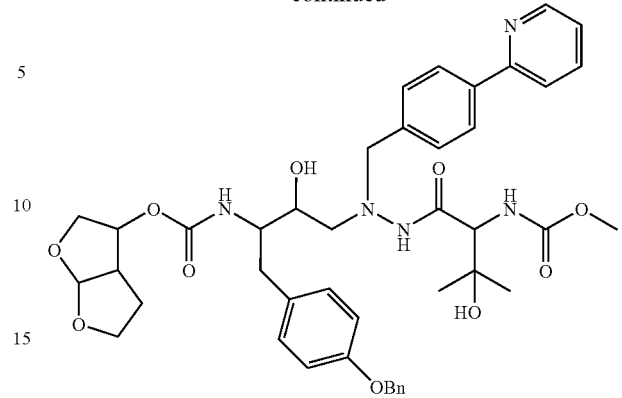
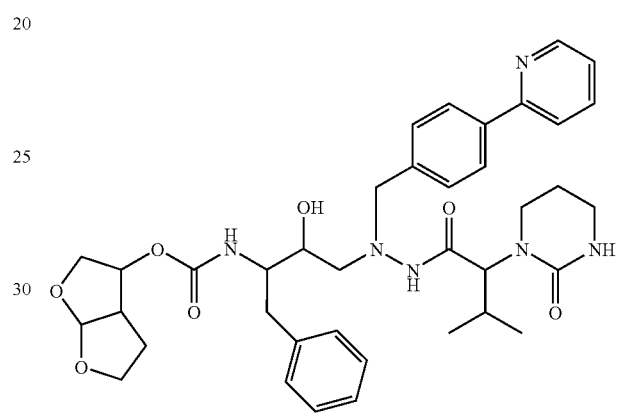
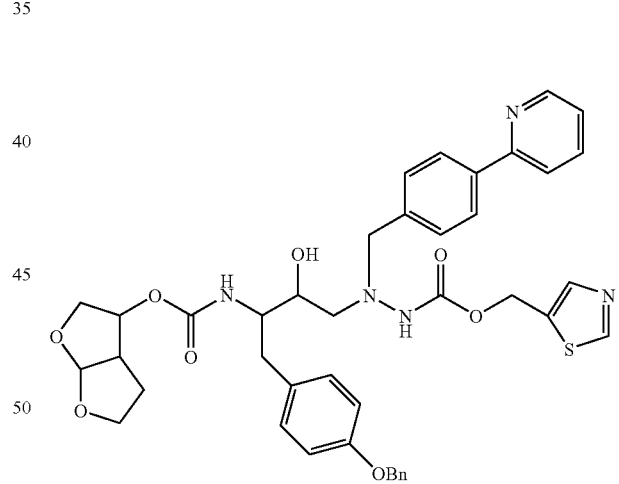
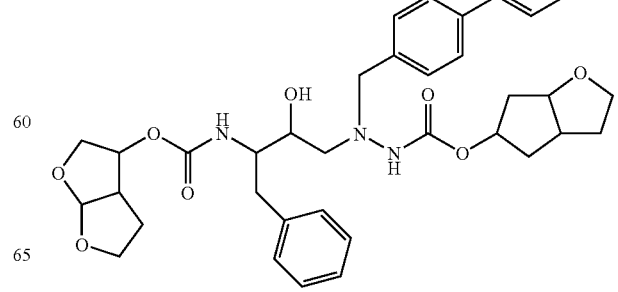

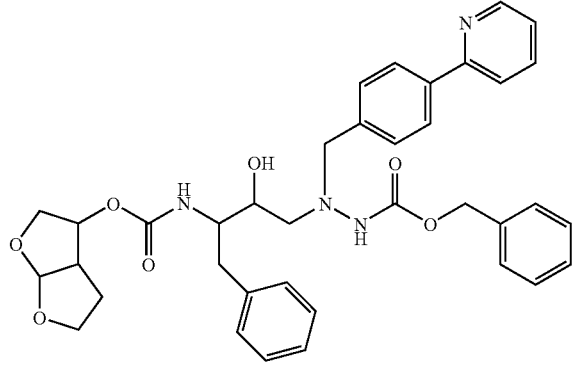
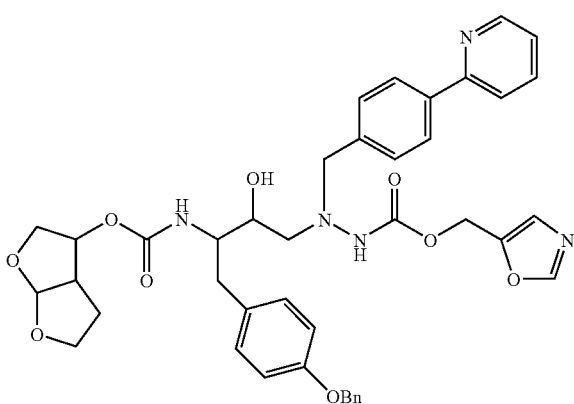
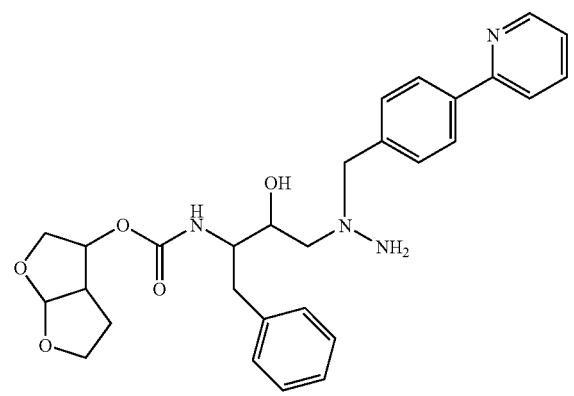
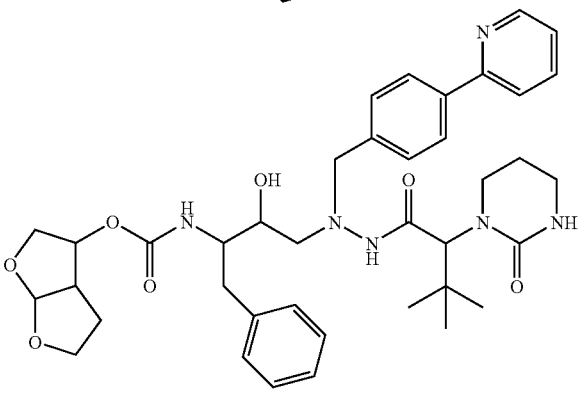
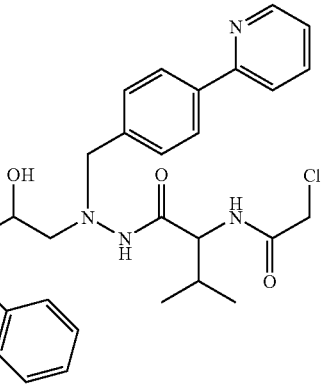
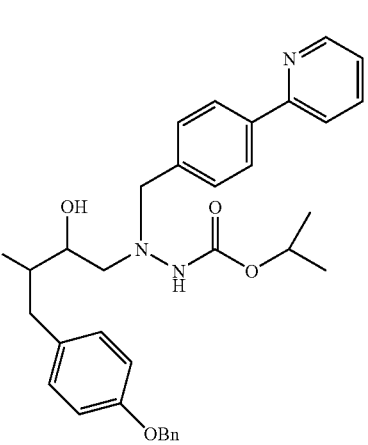
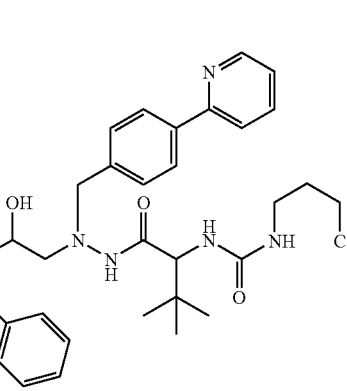
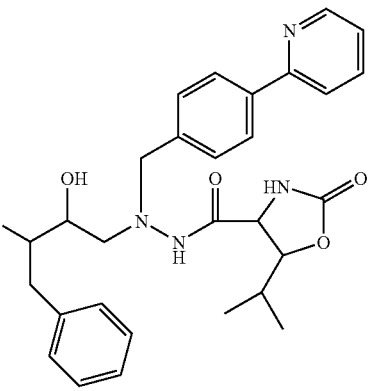

31
-continued
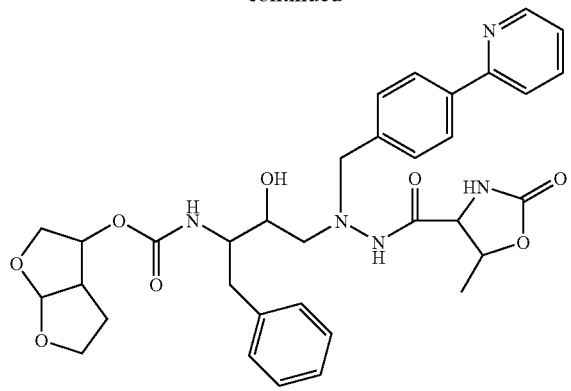
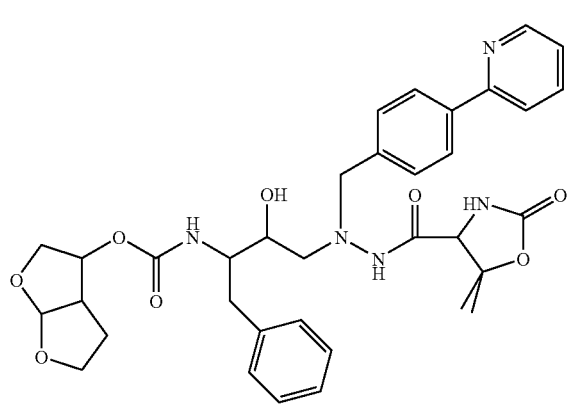
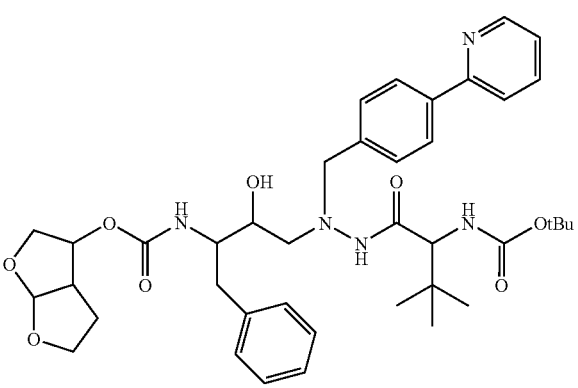
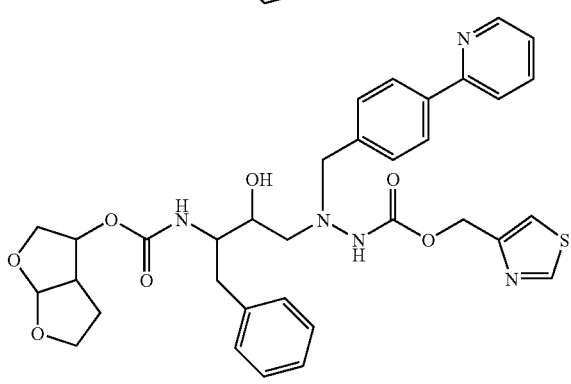
32
-continued
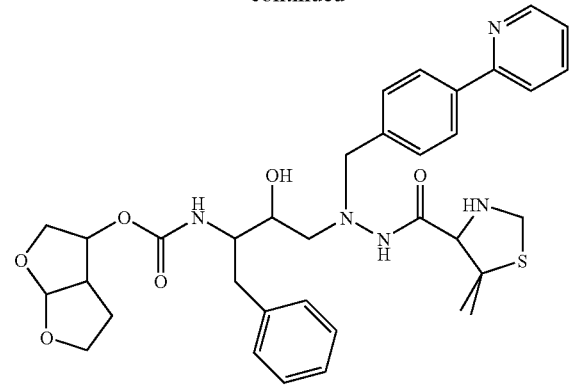
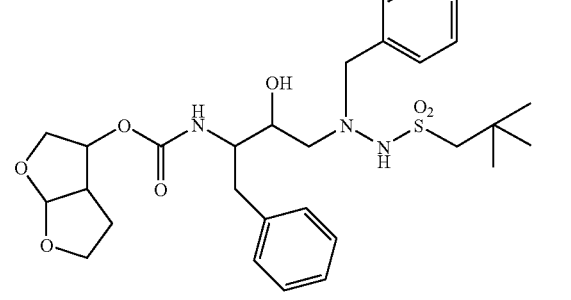
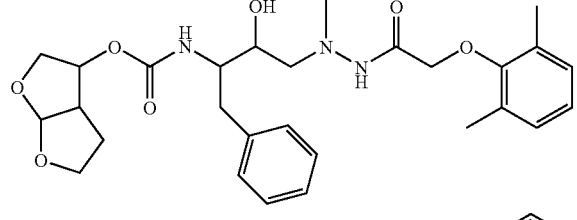
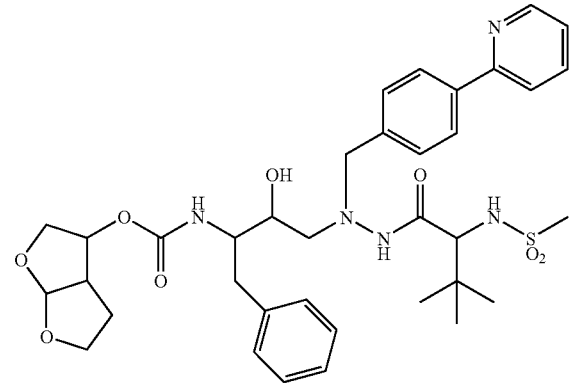

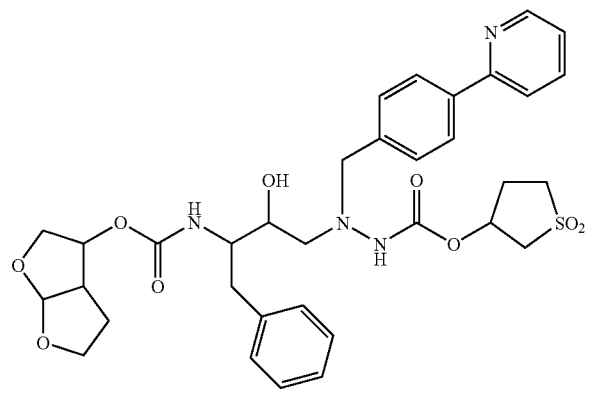
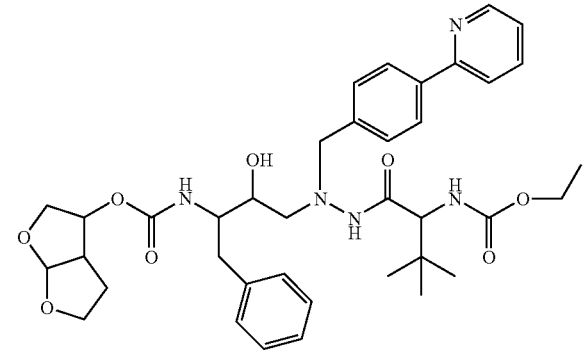
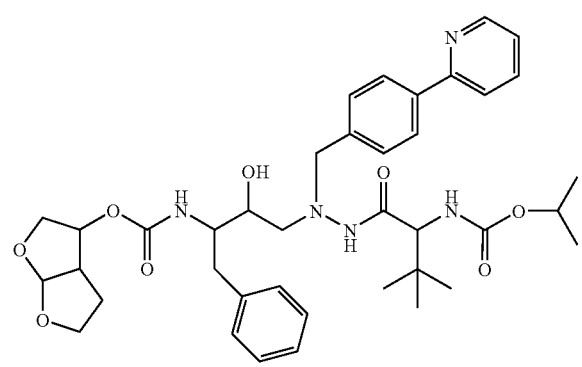
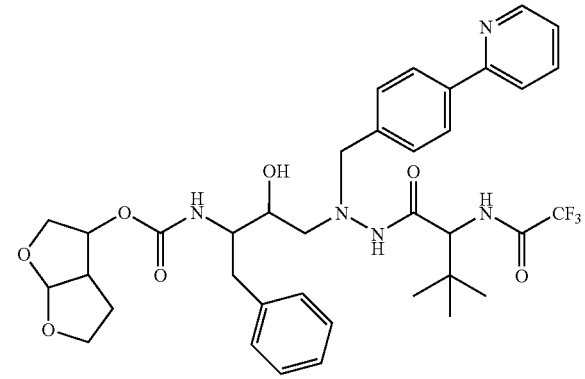
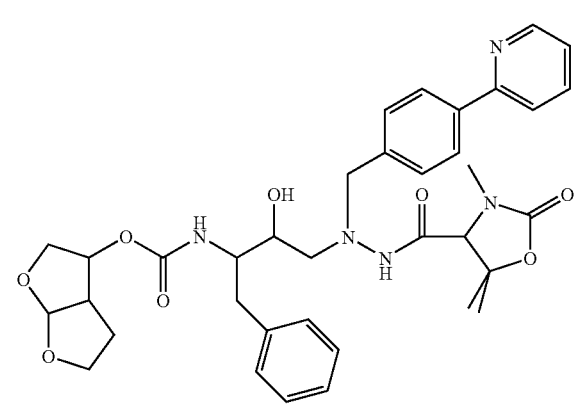
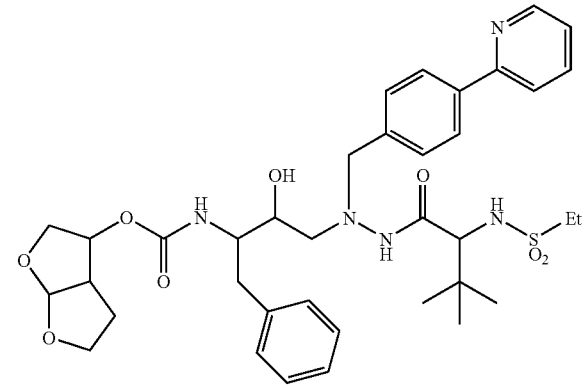
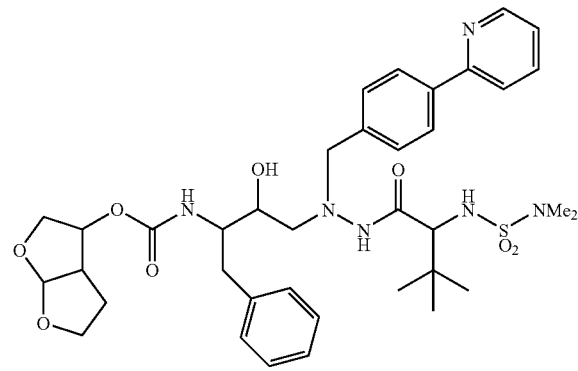
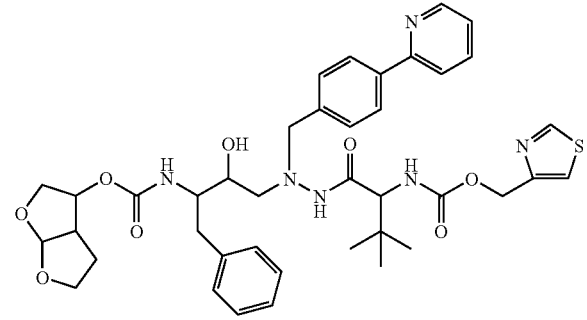

35
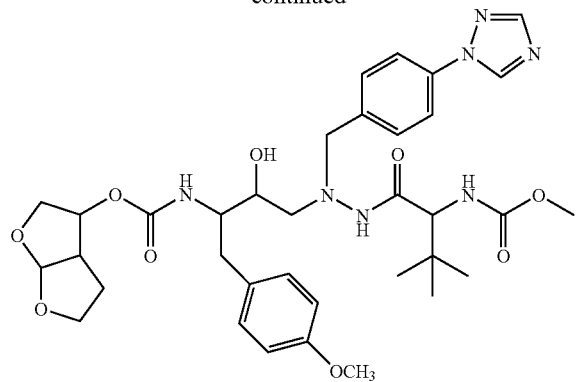
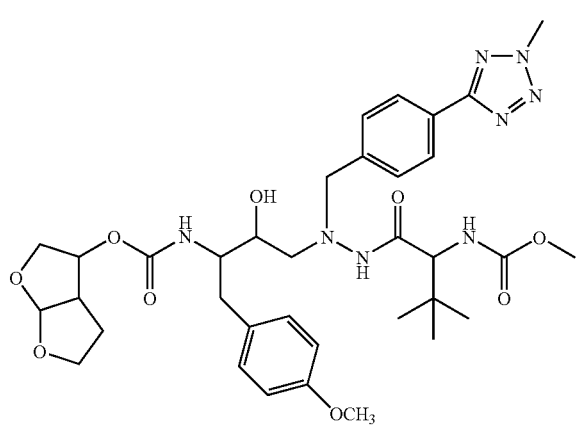
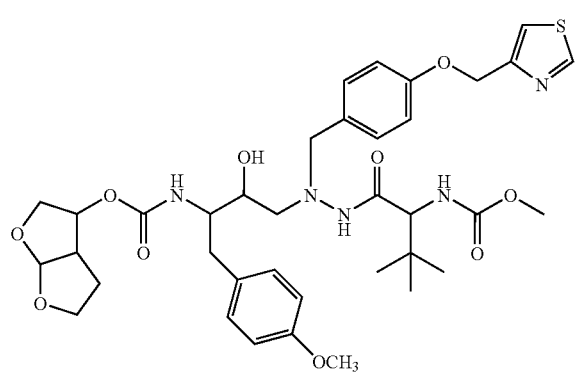
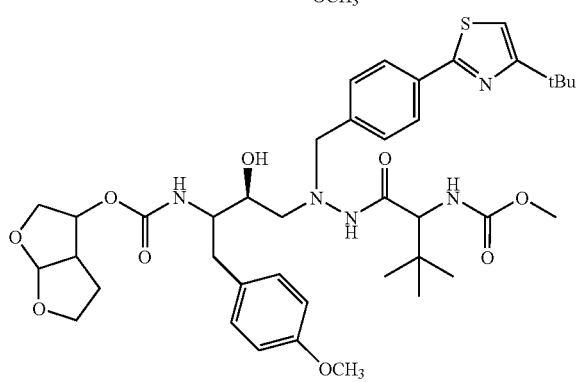
36
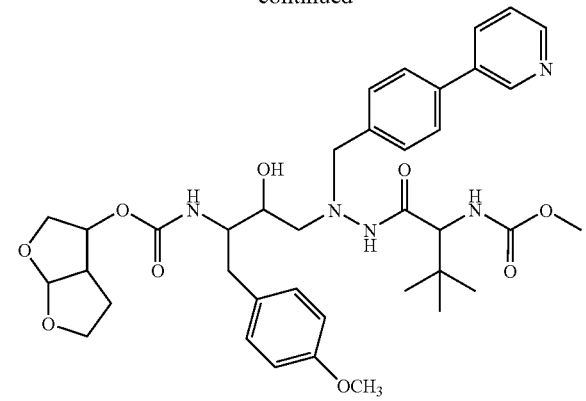
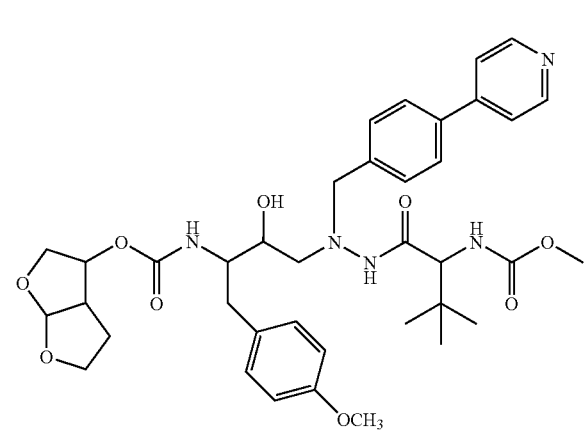
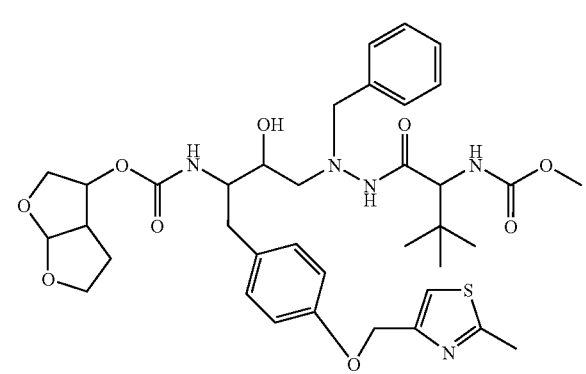
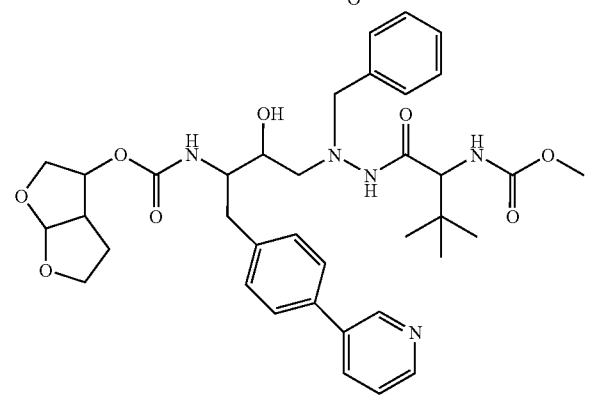

37
-continued
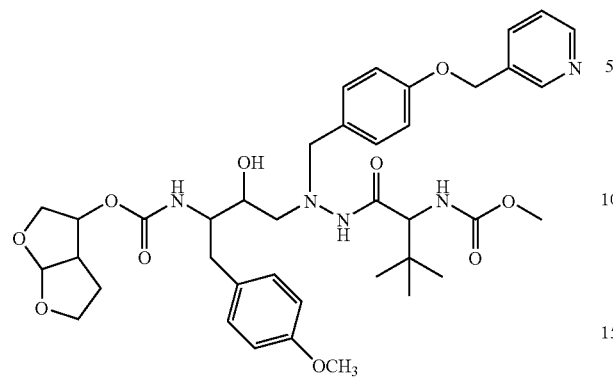
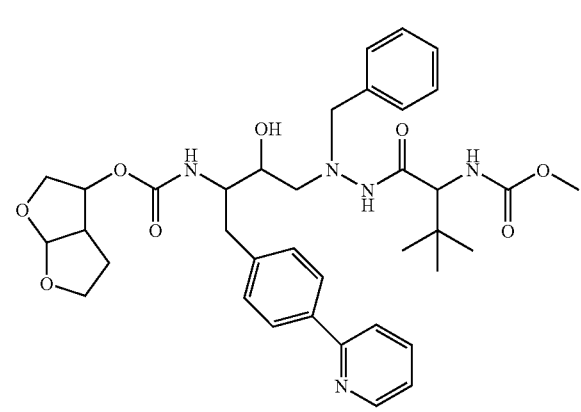
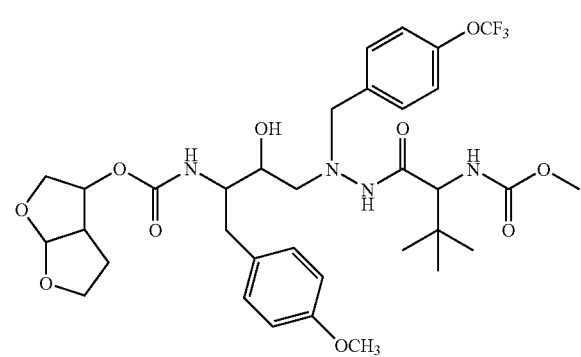
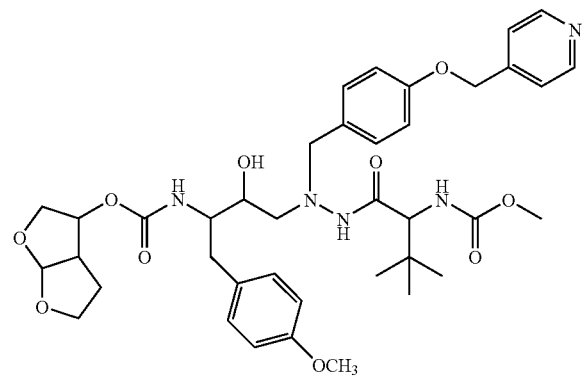
38
-continued
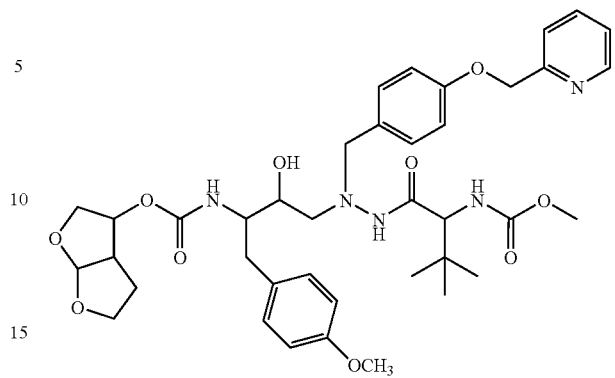
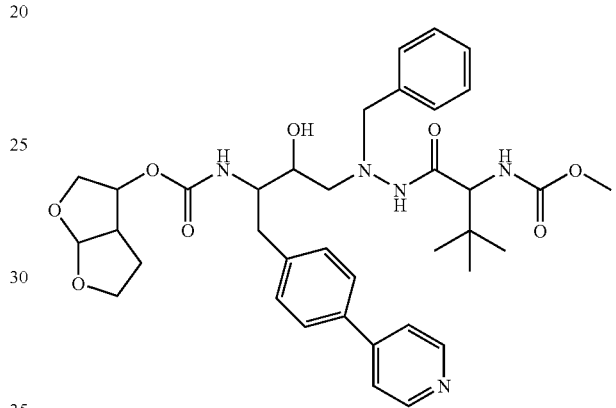
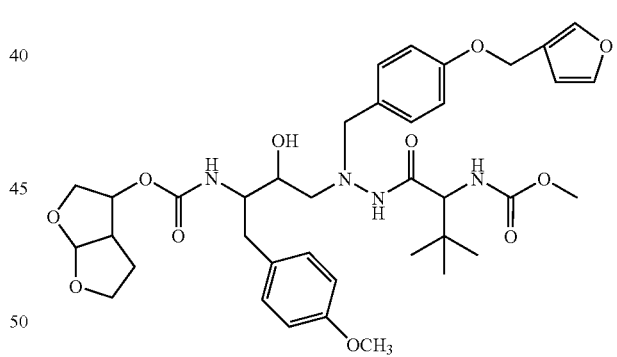
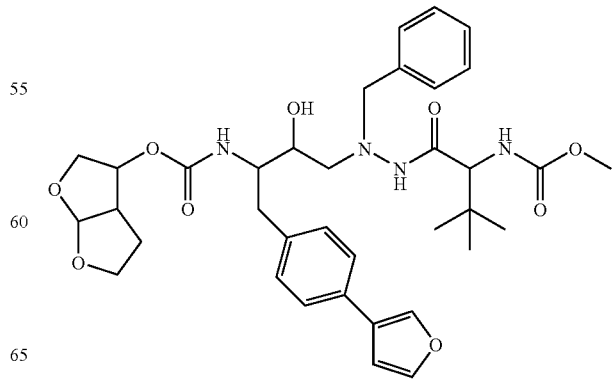

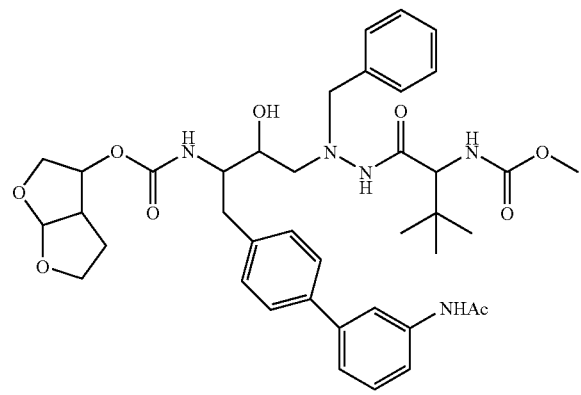
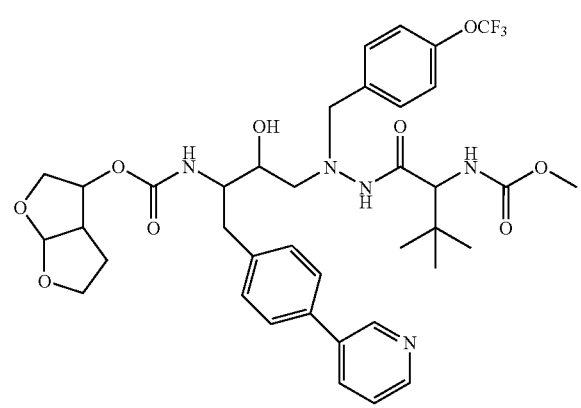
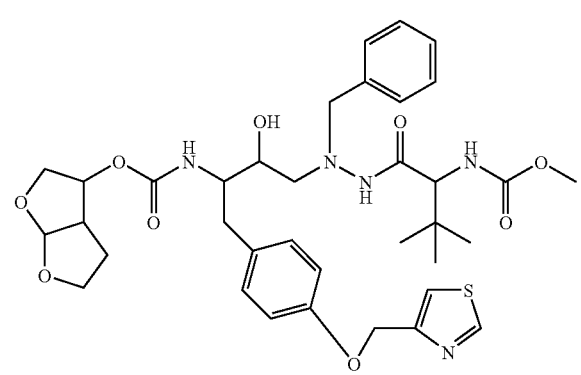
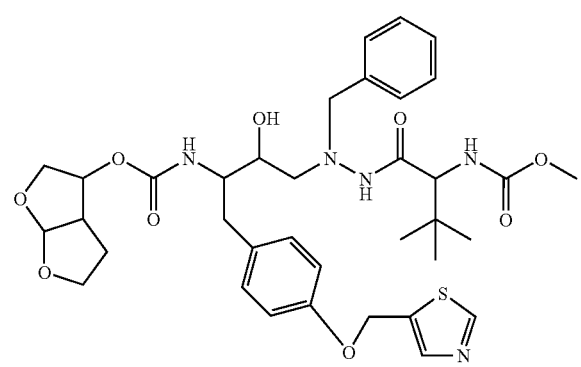
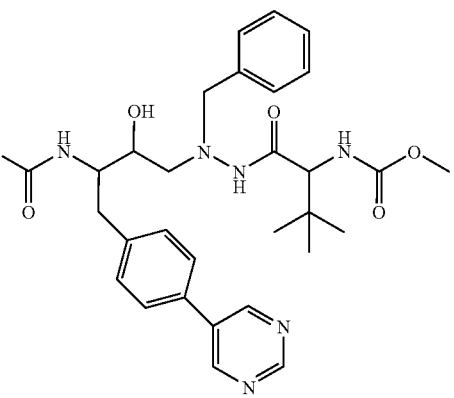
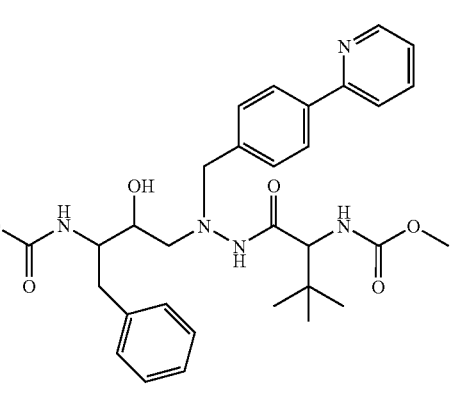
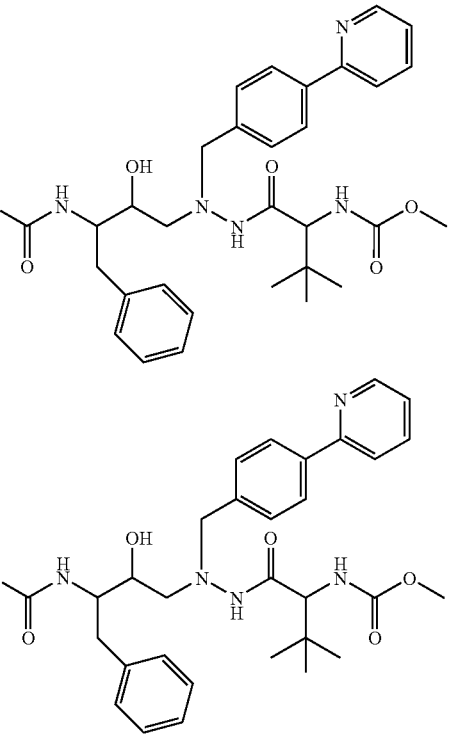

-continued
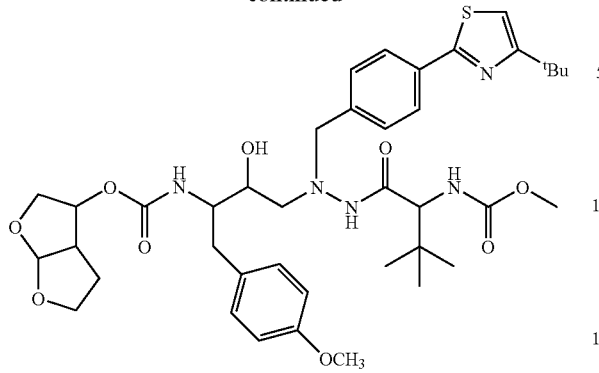
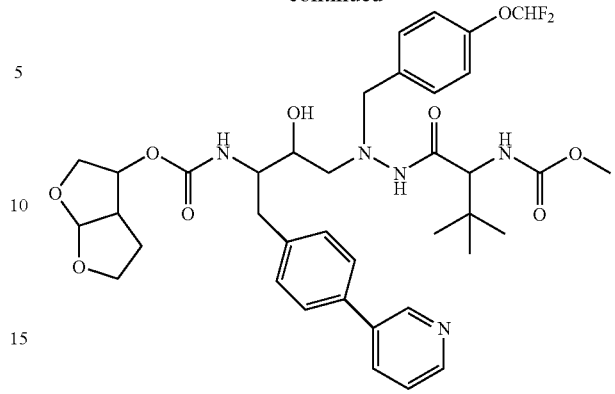
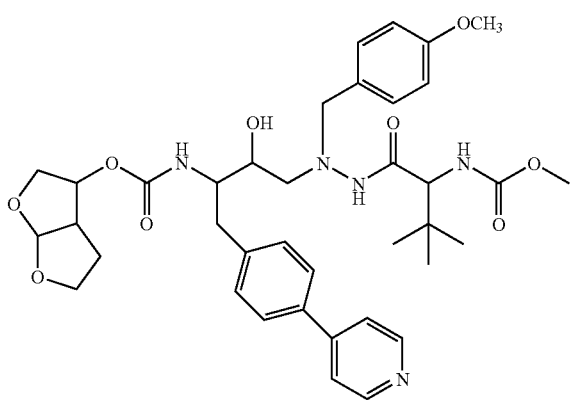
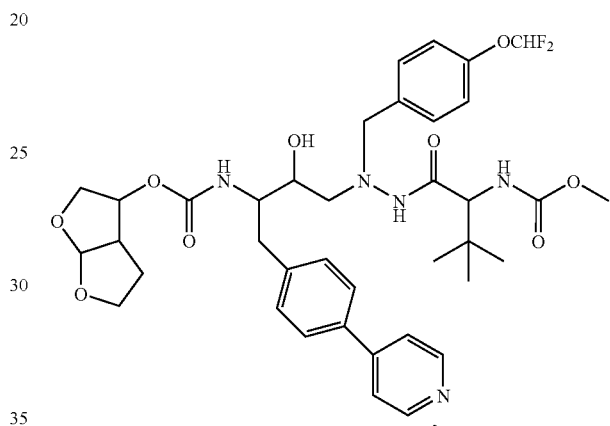
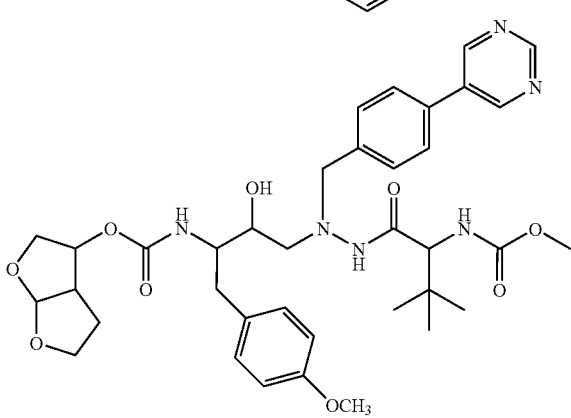
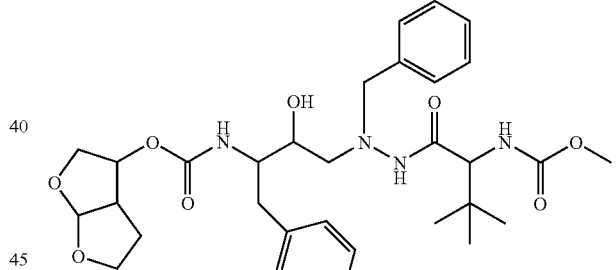
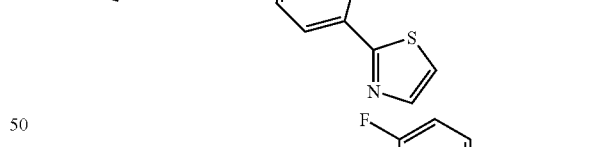
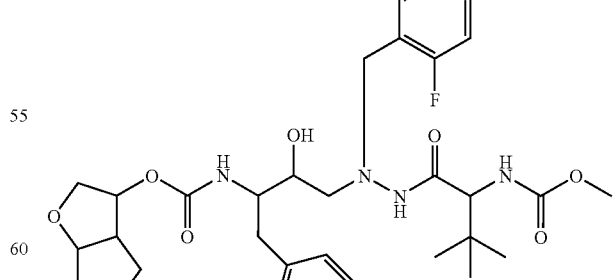

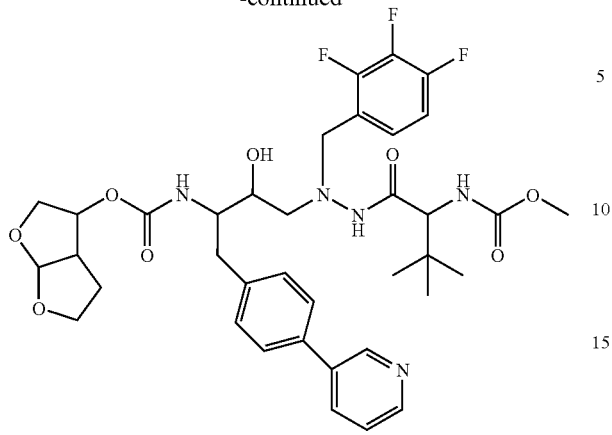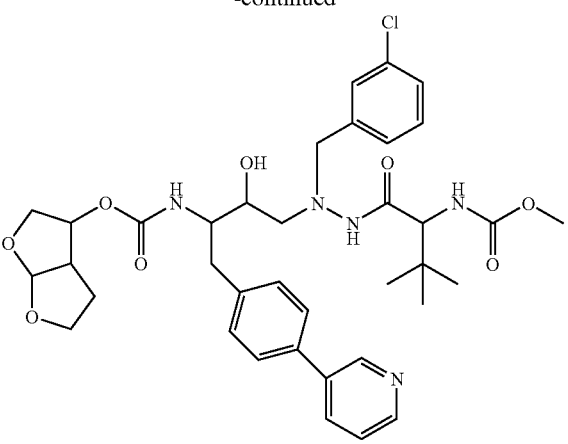
or a pharmaceutically acceptable salt, solvate, and/or ester thereof, and also including stereoisomers or mixtures of stereoisomers thereof. One skilled in the art will recognize that stereoisomers or mixtures of stereoisomers of the compounds of the present application include enantiomers, diastereomers, and other stereoisomers. For example, for:

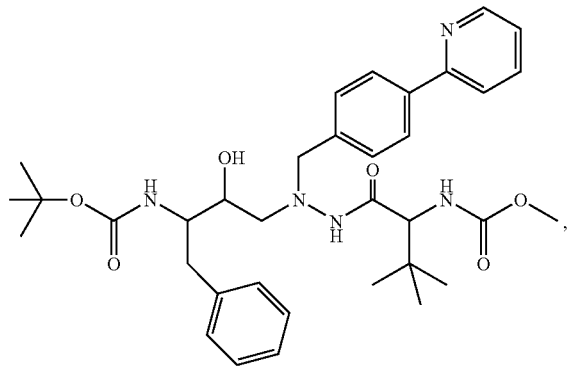 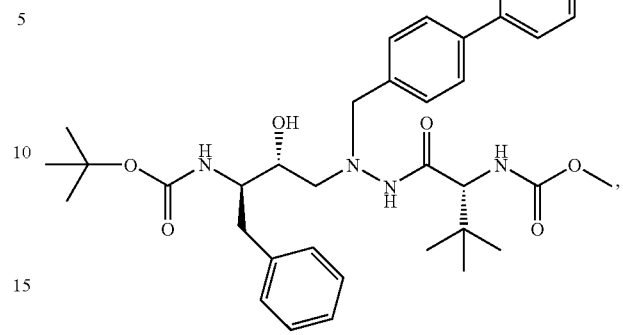
contemplated stereoisomers include at least:
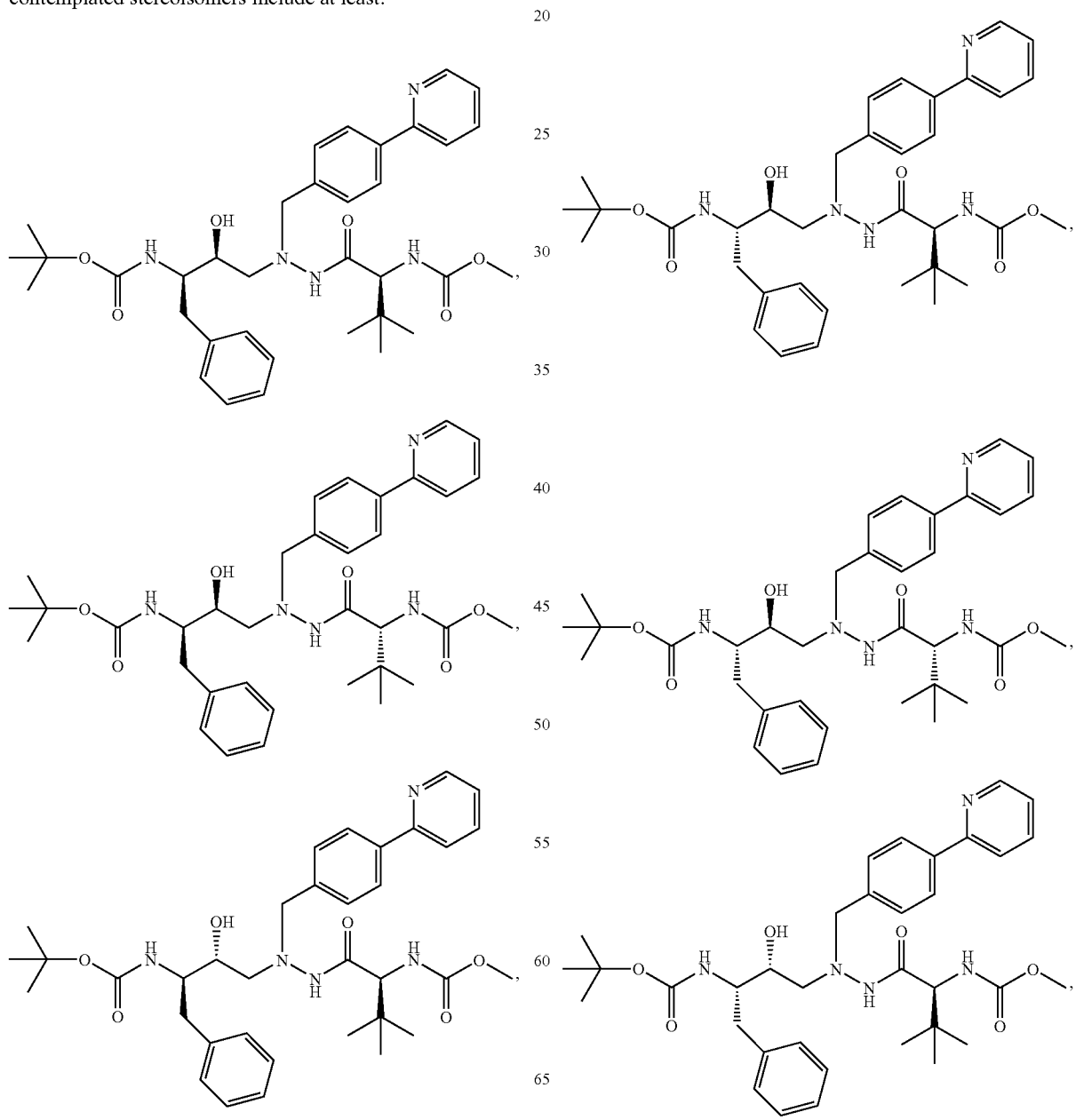

-continued

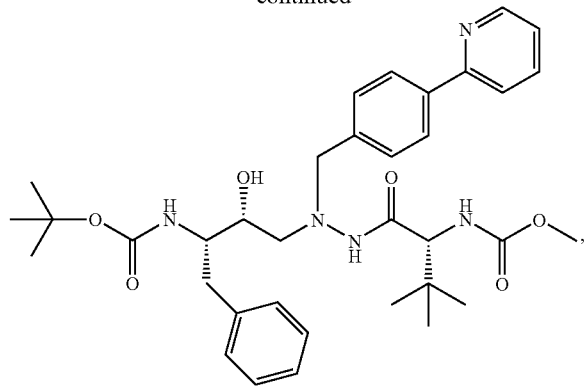

as well as mixtures of two or more of these stereoisomers.

In still another embodiment of the compounds of Formula I, n is 0, X is H, alkyl, or substituted alkyl wherein alkyl and substituted alkyl are as defined and exemplified herein.

In still another embodiment of the compounds of Formula I, n is 1, X is —C(O)—, —S(O)$_2$—, or —S(O)—, wherein alkyl, substituted alkyl are as defined and exemplified herein.

In still another embodiment of the compounds of Formula I, n is 1 X is —S— and $R^6$ is alkyl or substituted alkyl. Non-limiting examples of alkyl include methyl, ethyl, n-propyl, 2-propyl, n-butyl, 2-butyl, tert-butyl, and 2,2-dimethylpropyl.

In still another embodiment of the compounds of Formula I, n is 1; X is —C(O)— and $R^6$ is —OR$^{6a}$ wherein $R^{6a}$ is alkyl, or substituted alkyl. Non-limiting examples of alkyl or substituted alkyl include —CH$_3$, —CH(CH$_3$)$_2$, —C(CH$_3$)$_3$, —CH(alkyl), —CH(substituted alkyl), —CH(heteroalkyl), —C(alkyl)$_2$, —C(substituted alkyl)$_2$, —C(heteroalkyl)$_2$, —C(alkyl)(substituted alkyl), —C(heteroalkyl)(substituted alkyl), and —C(alkyl)(heteroalkyl), wherein alkyl, substituted alkyl, and heteroalkyl are as defined and exemplified herein.

In still another embodiment of the compounds of Formula I, n is 1; X is —C(O)— and $R^6$ is —OR$^{6a}$ wherein $R^{6a}$ is aryl, substituted aryl, arylalkyl, or substituted arylalkyl, and wherein said substituted arylalkyl is substituted on the aryl moiety and wherein aryl or arylalkyl is any aryl or arylalkyl defined or exemplified herein, and, when present, the substituents on said aryl include one or more of any substituents defined or exemplified herein. In a particular embodiment, aryl or the aryl portion of arylalkyl is phenyl.

In still another embodiment of the compounds of Formula I, n is 1; X is —C(O)—; and $R^6$ is —OR$^{6a}$ wherein $R^{6a}$ is heterocyclyl, substituted heterocyclyl, heterocyclyl alkyl, substituted heterocyclyl alkyl, wherein said substituted heterocyclyl alkyl is substituted on the heterocyclyl moiety and wherein heterocyclyl or heterocyclyl alkyl is any heterocyclyl or heterocyclyl alkyl defined or exemplified herein, and, when present, the substituents on said heterocyclyl include one or more of any substituents defined or exemplified herein. In a particular embodiment, $R^{6a}$ is heteroaryl, substituted heteroaryl, heteroarylalkyl, or substituted heteroarylalkyl.

In still another embodiment of the compounds of Formula I, n is 1, X is —C(O)—; and $R^6$ is C(R$^{6d}$R$^{6e}$)—NR$^{6f1}$—C(O)—O—R$^{14}$ wherein R$^{6d}$, R$^{6e}$R$^{6f1}$ or R$^{14}$ are independently selected from the group consisting of H, alkyl, and substituted alkyl, wherein alkyl is any alkyl defined or exemplified herein. In one particular embodiment, one of R$^{6d}$ and R$^{6e}$ is H, the other is isopropyl, and R$^{14}$ is methyl.

In still another embodiment of the compounds of Formula I, n is 1, X is —C(O)—; and R$^6$ is C(R$^{6d}$R$^{6e}$)—O-aryl wherein R$^{6d}$, R$^{6e}$ are independently selected from the group consisting of H, alkyl, and substituted alkyl, wherein alkyl and aryl is any alkyl and aryl defined or exemplified herein.

In still another embodiment of the compounds of Formula I, n is 1, X is —C(O)—, R$^6$ is C(R$^{6d}$R$^{6e}$)—NR$^{6f1}$—C(O)—O—R$^{6f2}$ wherein R$^{6d}$, R$^{6e}$ or R$^{6f1}$ are independently selected from the group consisting of H, alkyl, and substituted alkyl and R$^{6f2}$ is aryl, arylalkyl, substituted arylalkyl, wherein said substituted arylalkyl is substituted on the aryl moiety and wherein aryl or arylalkyl is any aryl or arylalkyl defined or exemplified herein, and, when present, the substituents on said aryl include one or more of any substituents defined or exemplified herein. In a particular embodiment, aryl is phenyl.

In still another embodiment of the compounds of Formula I, n is 1, X is —C(O)— and R$^6$ is C(R$^{6d}$R$^{6e}$)—NR$^{6f1}$—C(O)—O—R$^{6f2}$ wherein R$^{6d}$ and R$^{6e}$ are taken together to form a 5- or 6-membered spiro-fused non-aromatic tetrahydro heterocyclyl wherein heterocyclyl is any heterocyclyl defined or exemplified herein, and, when present, the substituents on said heterocyclyl include one or more of any substituents defined or exemplified herein.

In still another embodiment of the compounds of Formula I, n is 1, X is —C(O)— and R$^6$ is C(R$^{6d}$R$^{6e}$)—NR$^{6f1}$—C(O)—NR$^{6f1}$—R$^{6f2}$ wherein R$^{6d}$, R$^{6e}$ or R$^{6f}$ are independently selected from the group consisting of H, alkyl, and substituted alkyl and R$^{6f2}$ is alkyl or substituted alkyl, wherein heterocyclyl is any heterocyclyl defined or exemplified herein, and, when present, the substituents on said heterocyclyl include one or more of any substituents defined or exemplified herein.

In still another embodiment of the compounds of Formula I, n is 1, X is —C(O)— and R$^6$ is C(R$^{7d}$R$^{7e}$)—NR$^{7f1}$—C(O)—R$^{7f2}$ wherein R$^{7d}$ and R$^{7e}$ are independently H, alkyl, haloalkyl, hydroxyalkyl, or alkoxy; R$^{7f1}$ is H, alkyl, or substituted alkyl; R$^{7f2}$ is alkyl, haloalkyl, hydroxyalkyl, or alkoxy, wherein said alkyl, haloalkyl, hydroxyalkyl, or alkoxy are herein defined and exemplified.

In still another embodiment of the compounds of Formula I, n is 1, X is —C(O)— and R$^6$ is C(R$^{6d}$R$^{6e}$)—NR$^{6f1}$—S(O)$_2$—R$^{6f3}$, R$^{6d}$ and R$^{6e}$ are independently H, alkyl, haloalkyl, hydroxyalkyl, or alkoxy; R$^{6f1}$ is H, alkyl, or substituted alkyl; and R$^{6f3}$ is alkyl, substituted alkyl, wherein said alkyl, haloalkyl, hydroxyalkyl, or alkoxy are herein defined and exemplified.

In still another embodiment of the compounds of Formula I, n is 1, X is —C(O)— and R$^6$ is C(R$^{6d}$R$^{6e}$)—NR$^{6f1}$—S(O)$_2$—N(alkyl)$_2$, R$^{6d}$ and R$^{6e}$ are independently H, alkyl, haloalkyl, hydroxyalkyl, or alkoxy; R$^{6f1}$ is H, alkyl, or substituted alkyl, wherein said alkyl, haloalkyl, hydroxyalkyl, or alkoxy are herein defined and exemplified.

In still another embodiment of the compounds of Formula I, n is 1, X is —C(O)— and R$^6$ is heterocyclyl or substituted heterocyclyl, wherein X is attached to the heterocyclyl through a heteroatom and wherein said heterocyclyl includes any heterocyclyl defined or exemplified herein. The substituents, when present, include one or more of any substituent defined or exemplified herein.

In still another embodiment of the compounds of Formula I, n is 1, X is —C(O)— and R$^6$ heterocyclyl or substituted heterocyclyl, X is attached to the heterocyclyl through a carbon atom and wherein said heterocyclyl includes any heterocyclyl defined or exemplified herein. The substituents, when present include one or more of any substituent defined or exemplified herein.

In still another embodiment of the compounds of Formula I, $L^1$ is alkylene or substituted alkylene. Non-limiting examples of $L^1$ include —$CH_2$—, —$CH(CH_3)$—, —$CH(CH_2CH_3)$—, —$CH(CH_2CH_2CH_3)$—, —$CH(CH(CH_3)_2)$—, —$CH(CH_2CH_2CH_2CH_3)$—, —$CH(CH_2CH(CH_3)_2)$—, —$CH(CH(CH_3)CH_2CH_3)$—, —$CH(C(CH_3)_3)$—, —$C(CH_3)_2$—, —$CH(OCH_3)$—, —$CH(CH_2OH)$—, —$CH(CH_2CH_2OH)$—, etc.

In still another embodiment of the compounds of Formula I, $L^3$ is an alkylene or substituted alkylene. Non-limiting examples of alkylene and substituted alkylene include any of the alkylenes defined or disclosed herein. For example, substituted alkylenes include alkylenes substituted with one or more —OH group, alkylenes substituted with one or more ether group, e.g., a —O-Bn group, alkylenes substituted with one or more halogen, or alkylenes substituted with combinations of two or more substituents (e.g., —OH and halogen, halogen and ether, etc.).

In still another embodiment of the compounds of Formula I, $L^1$ and $L^3$ are the same, i.e., $L^1$ and $L^3$ are the same alkylene or substituted alkylene group.

In still another embodiment of the compounds of Formula I, $L^1$ and $L^3$ are different, i.e., $L^1$ is an alkylene and $L^3$ is a substituted alkylene, $L^1$ is an alkylene and $L^3$ is a different alkylene, or $L^1$ is a substituted alkylene, and $L^3$ is a different substituted alkylene.

In still another embodiment of the compounds of Formula I, $L^2$ each $L^4$ are independently selected from the group consisting of a covalent bond, —O—, —NH, —O-alkylene-, and alkylene.

In still another embodiment of the compounds of Formula I, $L^2$ and $L^4$ are different. For example, $L^2$ is a covalent bond and $L^4$ is —O—; $L^2$ is a covalent bond and $L^4$ is —NH—; $L^1$ is a —O—, $L^4$ is —NH—.

In still another embodiment of the compounds of Formula I, $L^1$ is —$CH_2$— and p is 0.

In still another embodiment of the compounds of Formula I, $L^1$ is —$CH_2$— and q is 0.

In still another embodiment of the compounds of Formula I, $L^3$ is —$CH_2$— and p is 0.

In still another embodiment of the compounds of Formula I, $L^3$ is —$CH_2$— and q is 0.

In still another embodiment of the compounds of Formula I, $Ar^1$ is substituted or unsubstituted aryl, wherein aryl is any aryl defined or exemplified herein, and, when present, the substituents on said aryl include one or more of any substituents defined or exemplified herein. Non-limiting examples of aryl include phenyl, substituted benzene, naphthalene, anthracene, biphenyl, and the like. In a particular embodiment, $Ar^1$ is phenyl.

In still another embodiment of the compounds of Formula I, $Ar^1$ is substituted or unsubstituted heteroaryl, wherein heteroaryl is any heteroaryl defined or exemplified herein, and, when present, the substituents on said heteroaryl include one or more of any substituents defined or exemplified herein.

In still another embodiment of the compounds of Formula I, $Ar^2$ is substituted or unsubstituted aryl, wherein aryl is any aryl defined or exemplified herein, and, when present, the substituents on said aryl include one or more of any substituents defined or exemplified herein. In a particular embodiment, $Ar^2$ is phenyl or substituted phenyl.

In still another embodiment of the compounds of Formula I, $Ar^2$ is substituted or unsubstituted heteroaryl, wherein heteroaryl is any heteroaryl defined or exemplified herein. Non-limiting examples of heteroaryl include thienyl, furyl, oxazolyl, isoxazolyl, thiazolyl, triazolyl, tetrazolyl, pyridyl, pyridazinyl, indazolyl, imidazopyridinyl, indolyl, benzimidazolyl, isoquinolinyl and quinolinyl.

In still another embodiment of the compounds of Formula I, $Ar^3$ is substituted or unsubstituted aryl, wherein aryl is any aryl defined or exemplified herein, and, when present, the substituents on said aryl include one or more of any substituents defined or exemplified herein. In a particular embodiment, $Ar^3$ is phenyl or substituted phenyl.

In still another embodiment of the compounds of Formula I, $Ar^3$ is substituted or unsubstituted heteroaryl, wherein heteroaryl is any heteroaryl defined or exemplified herein, and, when present, the substituents on said heteroaryl include one or more of any substituents defined or exemplified herein. Non-limiting examples of heteroaryl include thienyl, furyl, oxazolyl, isoxazolyl, thiazolyl, triazolyl, tetrazolyl, pyridyl, pyridazinyl, indazolyl, imidazopyridinyl, indolyl, benzimidazolyl, isoquinolinyl and quinolinyl.

In still another embodiment of the compounds of Formula I, $Ar^4$ is substituted or unsubstituted aryl, wherein aryl is any aryl defined or exemplified herein, and, when present, the substituents on said aryl include one or more of any substituents defined or exemplified herein. In a particular embodiment, $Ar^4$ is phenyl or substituted phenyl.

In still another embodiment of the compounds of Formula I, $Ar^4$ is substituted or unsubstituted heteroaryl, wherein heteroaryl is any heteroaryl defined or exemplified herein. Non-limiting examples of heteroaryl include thienyl, furyl, oxazolyl, isoxazolyl, thiazolyl, triazolyl, tetrazolyl, pyridyl, pyridazinyl, indazolyl, imidazopyridinyl, indolyl, benzimidazolyl, isoquinolinyl and quinolinyl.

In still another embodiment of the compounds of Formula I, $L^1$ is alkylene, $Ar^1$ is substituted or unsubstituted aryl, wherein aryl is any aryl defined or exemplified herein, and the substituents on said aryl are any substituents defined and exemplified herein. In a particular embodiment, $Ar^1$ is phenyl or substituted phenyl.

In still another embodiment of the compounds of Formula I, $L^1$ is alkylene and $Ar^1$ is substituted or unsubstituted heteroaryl, wherein heteroaryl is any heteroaryl defined or exemplified herein, and, when present, the substituents on said heteroaryl include one or more of any substituent defined or exemplified herein.

In still another embodiment of the compounds of Formula I, $L^3$ is substituted or unsubstituted alkylene, and $Ar^3$ is substituted or unsubstituted aryl, wherein alkylene and aryl are any alkylene or aryl defined or exemplified herein, and, when present, the substituents on said alkylene or aryl include one or more of any substituents defined or exemplified herein.

In still another embodiment of the compounds of Formula I, $L^3$ is substituted or unsubstituted alkylene, and $Ar^3$ is substituted or unsubstituted heteroaryl, wherein alkylene and heteroaryl are any alkylene or heteroaryl defined or exemplified herein, and, when present, the substituents on said alkylene or heteroaryl include one or more of any substituents defined or exemplified herein.

In still another embodiment of the compounds of Formula I, $Ar^1$ is substituted or unsubstituted aryl, and $Ar^3$ is substituted or unsubstituted heteroaryl, wherein aryl and heteroaryl are any aryl or heteroaryl defined or exemplified herein, and, when present, the substituents on said aryl or heteroaryl include one or more of any substituents defined or exemplified herein.

In still another embodiment of the compounds of Formula I, $Ar^3$ is substituted or unsubstituted aryl, and $Ar^1$ is substituted or unsubstituted heteroaryl, wherein aryl and heteroaryl are any aryl or heteroaryl defined or exemplified herein, and, when present, the substituents on said aryl or heteroaryl include one or more of any substituents defined or exemplified herein.

In still another embodiment of the compounds of Formula I, both $Ar^1$ and $Ar^3$ are substituted or unsubstituted aryl, wherein aryl is any aryl defined or exemplified herein, and, when present, the substituents on said aryl include one or more of any substituents defined or exemplified herein.

In still another embodiment of the compounds of Formula I, $L^2$ is a bond, $Ar^2$ is aryl, substituted aryl, wherein the aryl is any aryl defined or exemplified herein, and, when present, the substituents on the aryl include one or more of any substituents defined or exemplified herein.

In still another embodiment of the compounds of Formula I, $L^2$ is a bond, $Ar^2$ is heteroaryl, or substituted heteroaryl, wherein the heteroaryl is selected from the group consisting of thienyl, furyl, oxazolyl, isoxazolyl, thiazolyl, triazolyl, tetrazolyl, pyridyl, pyridazinyl, indazolyl, imidazopyridinyl, indolyl, benzimidazolyl, isoquinolinyl and quinolinyl.

In still another embodiment of the compounds of Formula I, $L^2$ is O-alkylene (wherein the alkylene group is attached to either $Ar^1$ or $Ar^2$), $Ar^2$ is heteroaryl, or substituted heteroaryl, wherein the heteroaryl is selected from the group consisting of thienyl, furyl, oxazolyl, isoxazolyl, thiazolyl, triazolyl, tetrazolyl, pyridyl, pyridazinyl, indazolyl, imidazopyridinyl, indolyl, benzimidazolyl, isoquinolinyl and quinolinyl.

In still another embodiment of the compounds of Formula I, p is 0, and $Ar^1$ is unsubstituted aryl.

In still another embodiment of the compounds of Formula I, p is 0, and $Ar^1$ is aryl substituted with haloalkoxy.

In still another embodiment of the compounds of Formula I, two of the $Ar^1$, $Ar^2$, $Ar^3$, or $Ar^4$ are the same and the remaining two are different, e.g. two of $Ar^1$, $Ar^2$, $Ar^3$, or $Ar^4$ are substituted or unsubstituted aryls and the other two of $Ar^1$, $Ar^2$, $Ar^3$, or $Ar^4$ are substituted or unsubstituted heteroaryls, wherein aryl and heteroaryl are any aryl or heteroaryl defined or exemplified herein, and, when present, the substituents on the aryl or heteroaryl include one or more of any substituents defined or exemplified herein.

In still another embodiment of the compounds of Formula I, q is 0, and $Ar^3$ is unsubstituted aryl.

In still another embodiment of the compounds of Formula I, q is 0, and $Ar^3$ is substituted aryl wherein the substituents are selected from the group consisting of hydroxyl, alkoxy, haloalkoxy. -$Z^1$-alkylene-$R^7$; $R^7$ is -$Z^2$-$L^5$-$R^{7b}$, or —O—PO$_3R^{7c}R^{7d}$; $L^5$ is —C(O)—, —C(O)O—, —C(O)NR$^{7e}$—, NR$^a$—S(O)$_2R^b$, —C(O)—R$^c$, —S(O)$_2$R$^b$, —S(O)$_2$NHR$^a$, —C(O)—NH—R$^a$, —S(O)$_2$—, —S(O)—, —S(O)$_2$NR$^{7e}$—, or —S(O)NR$^{7e}$—; $Z^1$ and $Z^2$ are independently O or NR$^{7a}$; R$^{7c}$, R$^{7d}$, and R$^{7e}$ are independently H, alkyl, or substituted alkyl; R$^{7b}$ is alkyl, substituted alkyl, heterocyclyl, or substituted heterocyclyl; R$^a$ is H, alkyl, or substituted alkyl; and R$^b$ is alkyl, aryl, or substituted aryl.

In still another embodiment of the compounds of Formula I, $L^4$ is a covalent bond, $Ar^4$ is aryl, substituted aryl, heteroaryl, or substituted heteroaryl, wherein the aryl or heteroaryl are any aryl or heteroaryl defined or exemplified herein, and, when present, the substituents on the aryl or heteroaryl include one or more of any substituents defined or exemplified herein.

In still another embodiment of the compounds of Formula I, q is 1, $L^4$ is a covalent bond, $Ar^4$ is aryl, substituted aryl, wherein the aryl is any aryl defined or exemplified herein, and, when present, the substituents on the aryl include one or more of any substituents defined or exemplified herein such as —NH-acyl.

In still another embodiment of the compounds of Formula I, q is 1, $L^4$ is a covalent bond, $Ar^4$ is heteroaryl, or substituted heteroaryl, wherein the heteroaryl is selected from the group consisting of thienyl, furyl, oxazolyl, isoxazolyl, thiazolyl, triazolyl, tetrazolyl, pyridyl, pyridazinyl, indazolyl, imidazopyridinyl, indolyl, benzimidazolyl, isoquinolinyl and quinolinyl.

In still another embodiment of the compounds of Formula I, q is 1, $L^4$ is O—, $Ar^4$ is aryl, or substituted aryl. In a particular embodiment, $Ar^4$ is phenyl.

In still another embodiment of the compounds of Formula I, q is 1, $L^4$ is O-alkylene (wherein the alkylene portion of the —O-alkylene group is attached to either $Ar^3$ or $Ar^4$), $Ar^4$ is heteroaryl, or substituted heteroaryl, and wherein the heteroaryl is selected from the group consisting of thienyl, furyl, oxazolyl, isoxazolyl, thiazolyl, triazolyl, tetrazolyl, pyridyl, pyridazinyl, indazolyl, imidazopyridinyl, indolyl, benzimidazolyl, isoquinolinyl and quinolinyl.

In still another embodiment of the compounds of Formula I, $R^1$ is OR$^{1c}$, wherein R$^{1c}$ is alkyl or substituted alkyl. Non-limiting examples of alkyl are methyl, ethyl, n-propyl, iso-propyl, n-butyl, iso-butyl, or tert-butyl.

In still another embodiment of the compounds of Formula I, $R^1$ is OR$^{1c}$, wherein R$^{1c}$ is arylalkyl, substituted arylalkyl, heterocyclyl alkyl, and substituted heterocyclyl alkyl, wherein alkyl, substituted alkyl, aryl, substituted aryl, heterocyclyl, substituted heterocyclyl, arylalkyl, substituted arylalkyl, heterocyclyl alkyl, and substituted heterocyclyl alkyl are any alkyl, substituted alkyl, aryl, substituted aryl, heterocyclyl, substituted heterocyclyl, arylalkyl, substituted arylalkyl, heterocyclyl alkyl, and substituted heterocyclyl alkyl defined or exemplified herein.

In still another embodiment of the compounds of Formula I, $R^1$ is OR$^{1c}$, wherein R$^{1c}$ is aryl, substituted aryl, heterocyclyl, substituted heterocyclyl, wherein the aryl, substituted aryl, heterocyclyl, and substituted heterocyclyl are any aryl, substituted aryl, heterocyclyl, substituted heterocyclyl defined or exemplified herein In still another embodiment of the compounds of Formula I, $R^1$ is OR$^{1c}$, wherein R$^{1c}$ is selected from the group consisting of

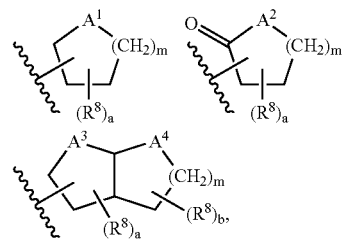

wherein $A^1$, $A^2$, $A^3$, and $A^4$ are O, and m is 1.

In still another embodiment of the compounds of Formula I, $R^1$ is aryl or substituted aryl, wherein aryl is any aryl defined or exemplified herein and, when present, the substituents on the aryl include one or more of any substituents defined or exemplified herein such as hydroxyl or methyl.

In still another embodiment of the compounds of Formula I, $R^1$ is heteroaryl or substituted heteroaryl, wherein heteroaryl is any heteroaryl defined or exemplified herein.

In still another embodiment of the compounds of Formula I, $R^1$ is —C($R^{1d}R^{1e}$)—$NR^{1f}$—C(O)—O—$R^{1g}$ wherein $R^{1d}$, $R^{1e}$, and $R^{1f}$ are independently H, alkyl, or substituted alkyl, and $R^{1g}$ is alkyl or substituted alkyl wherein alkyl and substituted alkyl include any of the alkyl or substituted alkyls defined or disclosed herein. For example, $R^{1d}$, $R^{1e}$, and $R^{1f}$ may independently be methyl, ethyl, n-propyl, iso-propyl, n-butyl, iso-butyl, or tert-butyl or substituted methyl, ethyl, n-propyl, iso-propyl, n-butyl, iso-butyl, or tert-butyl wherein the substituents may include a hydroxyl group.

In still another embodiment of the compounds of Formula I, $R^1$ is —C($R^{1d}R^{1e}$)—$NR^{1f}$—C(O)—O—$R^{1g}$ wherein $R^{1d}$ and $R^{1e}$ taken together with the carbon atom to which they are shown attached form a heterocyclyl or a substituted heterocyclyl, wherein said heterocyclyl or said substituted heterocyclyl is a 5- or 6-membered non-aromatic tetrahydro heterocyclic ring having from 1 to 3 heteroatoms selected from N, O, and S, $R^{1f}$ is H, alkyl, or substituted alkyl, and $R^{1g}$ is alkyl or substituted alkyl wherein alkyl, substituted alkyl, heterocyclyl or a substituted heterocyclyl include any of the alkyl, substituted alkyl, heterocyclyl, or substituted heterocyclyl defined or disclosed herein.

In still another embodiment of the compounds of Formula I, $R^2$, $R^4$, and $R^5$ are each independently H, alkyl, or substituted alkyl, wherein alkyl and substituted alkyl include any of the alkyl or substituted alkyls defined or disclosed herein.

In still another embodiment of the compounds of Formula I, $R^2$, $R^4$, and $R^5$ are each the same. In a particular embodiment $R^2$, $R^4$, and $R^5$ are each H. In another particular embodiment $R^1$, $R^3$, and $R^5$ are each alkyl, e.g. one of the alkyl groups defined or disclosed herein.

In still another embodiment of the compounds of Formula I, $R^2$, $R^4$, and $R^5$ are each different.

In still another embodiment of the compounds of Formula I, two of $R^2$, $R^4$, and $R^5$ are the same, and the other is different.

In still another embodiment of the compounds of Formula I, p is 0, q is 1, $R^2$, $R^4$, and $R^5$ are each independently selected from the group consisting of H, alkyl, and substituted alkyl, wherein alkyl or substituted alkyl is any alkyl or substituted alkyl, defined or disclosed herein.

In still another embodiment of the compounds of Formula I, p is 1, q is 0, $R^2$, $R^4$, and $R^5$ are each independently selected from the group consisting of H, alkyl, and substituted alkyl, wherein alkyl or substituted alkyl is any alkyl or substituted alkyl, defined or disclosed herein.

In still another embodiment of the compounds of Formula I, p and q are both 1, and $R^2$ is H.

In still another embodiment of the compounds of Formula I, p and q are both 1, and $R^4$ is H.

In still another embodiment of the compounds of Formula I, p and q are both 1, and $R^5$ is H.

In still another embodiment of the compounds of Formula I, p is 0, q is 1, and $R^2$ is H.

In still another embodiment of the compounds of Formula I, p is 0, q is 1, and $R^4$ is H.

In still another embodiment of the compounds of Formula I, p is 0, q is 1, and $R^5$ is H.

In still another embodiment of the compounds of Formula I, p is 1, q is 0, and $R^2$ is H.

In still another embodiment of the compounds of Formula I, p is 1, q is 0, and $R^4$ is H.

In still another embodiment of the compounds of Formula I, p is 1, q is 0, and $R^5$ is H.

In still another embodiment of the compounds of Formula I, p is 1, q is 0, $R^1$ is —$NR^{1a}R^{1b}$, —$OR^{1c}$, —C($R^{1d}R^{1e}$)—$NR^{1f}$-$L^6$-$R^{1g}$, aryl, substituted aryl, heteroaryl, or substituted heteroaryl, wherein aryl, substituted aryl, heteroaryl, or substituted heteroaryl is any aryl, substituted aryl, heteroaryl, or substituted heteroaryl, defined or disclosed herein.

In still another embodiment of the compounds of Formula I, p and q are both 1, and $R^1$ is —$NR^{1a}R^{1b}$, —$OR^{1c}$, —C($R^{1d}R^{1e}$)—$NR^{1f}$-$L^6$-$R^{1g}$, aryl, substituted aryl, heteroaryl, or substituted heteroaryl, wherein aryl, substituted aryl, heteroaryl, or substituted heteroaryl is any aryl, substituted aryl, heteroaryl, or substituted heteroaryl, defined or disclosed herein.

In still another embodiment of the compounds of Formula I, p is 0, q is 1, and $R^1$ is —$NR^{1a}R^{1b}$, —$OR^{1c}$, C($R^{1d}R^{1e}$)—$NR^{1f}$-$L^6$-$R^{1g}$, aryl, substituted aryl, heteroaryl, or substituted heteroaryl, wherein aryl, substituted aryl, heteroaryl, or substituted heteroaryl is any aryl, substituted aryl, heteroaryl, or substituted heteroaryl, defined or disclosed herein.

In yet another embodiment of the compounds of Formula I, q is 0, the -$L^3$-$Ar^3$-($L^4$-$Ar^4$)$_q$ moiety is an -alkylene-aryl group, wherein said alkylene and aryl moieties are any alkylene and aryl moieties defined or exemplified herein, optionally substituted on the alkylene and/or aryl with one or more of any substituents defined or exemplified herein.

In yet another embodiment of the compounds of Formula I, q is 1, the -$L^3$-$Ar^3$-($L^4$-$Ar^4$)$_q$ moiety is an -alkylene-aryl-aryl group, wherein said alkylene and aryl moieties are any alkylene and aryl moieties defined or exemplified herein, optionally substituted on the alkylene and/or aryl with one or more of any substituents defined or exemplified herein.

In yet another embodiment of the compounds of Formula I, q is 1, the -$L^3$-$Ar^3$-($L^4$-$Ar^4$)$_q$ moiety is an -alkylene-aryl-heteroaryl group, wherein said alkylene, aryl, and heteroaryl moieties are any alkylene, aryl, and heteroaryl moieties defined or exemplified herein, optionally substituted with one or more of any substituents defined or exemplified herein.

In yet another embodiment of the compounds of Formula I, q is 1, the -$L^3$-$Ar^3$-($L^4$-$Ar^4$)$_q$ moiety is an -alkylene-aryl-O-aryl group, wherein said alkylene and aryl moieties are any alkylene and aryl moieties defined or exemplified herein, optionally substituted on the alkylene and/or aryl with one or more of any substituents defined or exemplified herein.

In yet another embodiment of the compounds of Formula I, q is 1, the -$L^3$-$Ar^3$-($L^4$-$Ar^4$)$_q$ moiety is an -alkylene-aryl-$CH_2$—O-heteroaryl group, wherein said alkylene, aryl, and heteroaryl moieties are any alkylene, aryl, and heteroaryl moieties defined or exemplified herein, optionally substituted on the alkylene, heteroaryl, and/or aryl with one or more of any substituents defined or exemplified herein.

In yet another embodiment of the compounds of Formula I, q is 1, the -$L^3$-$Ar^3$-($L^4$-$Ar^4$) with q moiety is an -alkylene-aryl-O—$CH_2$-heteroaryl group, wherein said alkylene, aryl, and heteroaryl moieties are any alkylene, aryl and heteroaryl moieties defined or exemplified herein, optionally substituted with one or more of any substituents defined or exemplified herein.

In yet another embodiment of the compounds of Formula I, q is 1, the -$L^3$-$Ar^3$-($L^4$-$Ar^4$)$_q$ moiety is an -alkylene-aryl-O-alkylene-NH—C(O)—O-alkyl group, wherein said alkylene, alkyl and aryl moieties are any alkylene, alkyl, and aryl moieties defined or exemplified herein, optionally substituted with one or more of any substituents defined or exemplified herein.

In yet another embodiment of the compounds of Formula I, q is 1, the -$L^3$-$Ar^3$-($L^4$-$Ar^4$)$_q$ moiety is an -alkylene-aryl-O-alkylene-NH—S(O)$_2$-alkyl group, wherein said alkylene, alkyl, and aryl moieties are any alkylene, alkyl, and aryl moieties defined or exemplified herein, optionally substituted with one or more of any substituents defined or exemplified herein.

In yet another embodiment of the compounds of Formula I, q is 1, the -$L^3$-$Ar^3$-($L^4$-$Ar^4$)$_q$ moiety is an -alkylene-aryl-O-alkylene-NH—C(O)-heterocyclyl group, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, q is 1, the -$L^3$-$Ar^3$-($L^4$-$Ar^4$)$_q$ moiety is an -alkylene-aryl-O-alkylene-$PO_3$(alkyl)$_2$ group, wherein said alkylene and aryl moieties are any alkylene and aryl moieties defined or exemplified herein, optionally substituted on the alkylene and/or aryl with one or more of any substituents defined or exemplified herein.

In yet another embodiment of the compounds of Formula I, p is 0, the -$L^1$-$Ar^1$-($L^2$-$Ar^2$)$_p$ moiety is an -alkylene-aryl group, wherein said alkylene and aryl moieties are any alkylene and aryl moieties defined or exemplified herein, optionally substituted on the alkylene and/or aryl with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-heterocyclyl group, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-O-alkylene-heterocyclyl group, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, p is 0, the -$L^1$-$Ar^1$-($L^2$-$Ar^2$)$_p$ is an -alkylene-aryl-O-haloalkyl group, wherein said alkylene, haloalkyl, and aryl moieties are any alkylene, haloalkyl, and aryl moieties defined or exemplified herein, optionally substituted with one or more of any substituents defined or exemplified herein.

In yet another embodiment of the compounds of Formula I, p is 0, the -$L^1$-$Ar^1$-($L^2$-$Ar^2$)$_p$ moiety is an -alkylene-aryl group, q is 1, the -$L^3$-$Ar^3$-($L^4$-$Ar^4$)$_q$ moiety is an -alkylene-aryl-heteroaryl group, wherein said alkylene, aryl, and heteroaryl moieties are any alkylene, aryl, and heteroaryl moieties defined or exemplified herein, optionally substituted on the alkylene, aryl and/or heteroaryl with one or more of any substituents defined or exemplified herein.

In yet another embodiment of the compounds of Formula I, p is 0, the -$L^1$-$Ar^1$-($L^2$-$Ar^2$) moiety is an -alkylene-aryl group, q is 1, the -$L^3$-$Ar^3$-($L^4$-$Ar^4$)$_q$ moiety is an -alkylene-aryl-O—$CH_2$-heteroaryl group, wherein said alkylene, aryl, and heteroaryl moieties are any alkylene, aryl, and heteroaryl moieties defined or exemplified herein, optionally substituted on the alkylene, aryl and/or heteroaryl with one or more of any substituents defined or exemplified herein.

In yet another embodiment of the compounds of Formula I, p is 0, the -$L^1$-$Ar^1$-($L^2$-$Ar^2$)$_p$ moiety is a -alkylene-aryl group, q is 1, the -$L^3$-$Ar^3$-($L^4$-$Ar^4$)$_q$ moiety is an -alkylene-aryl-aryl group, wherein said alkylene and aryl moieties are any alkylene and aryl moieties defined or exemplified herein, optionally substituted on the alkylene and/or aryl with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-heterocyclyl group, q is 0, the -$L^3$-$Ar^3$-($L^4$-$Ar^4$)$_q$ moiety is an -alkylene-aryl group, wherein said alkylene, heterocyclyl and aryl moieties are any alkylene, heterocyclyl, and aryl moieties defined or exemplified herein, optionally substituted with one or more of any substituents defined or exemplified herein such as hydroxyl and alkoxy.

In yet another embodiment of the compounds of Formula I, p is 1, the -$L^1$-$Ar^1$-($L^2$-$Ar^2$)$_p$ moiety is an -alkylene-aryl-heterocyclyl group, q is 1, the -$L^3$-$Ar^3$-($L^4$-$Ar^4$)$_q$ moiety is an -alkylene-aryl-O—$CH_2$-aryl group, wherein said alkylene, heterocyclyl and aryl moieties are any alkylene, heterocyclyl, and aryl moieties defined or exemplified herein, optionally substituted with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-heterocyclyl group, q is 1, the -$L^3$-$Ar^3$-($L^4$-$Ar^4$)$_q$ moiety is an -alkylene-aryl-O—$CH_2$-heterocyclyl group, wherein said alkylene, heterocyclyl, and aryl moieties are any alkylene, heterocyclyl, and aryl moieties defined or exemplified herein, optionally substituted with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-heterocyclyl group, q is 1, the -$L^3$-$Ar^3$-($L^4$-$Ar^4$)$_q$ moiety is an -alkylene-aryl-O-alkylene-NH—C(O)—O-alkyl group, wherein said alkylene, alkyl, heterocyclyl, and aryl moieties are any alkylene, alkyl, heterocyclyl, and, and aryl moieties defined or exemplified herein, optionally substituted with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-heterocyclyl group, q is 1, the -$L^3$-$Ar^3$-($L^4$-$Ar^4$)$_q$ moiety is an -alkylene-aryl-O-alkylene-NH—S(O)$_2$—O-alkyl group, wherein said alkylene, alkyl, heterocyclyl, and aryl moieties are any alkylene, alkyl, heterocyclyl, and, and aryl moieties defined or exemplified herein, optionally substituted with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-heterocyclyl group, q is 1, the -$L^3$-$Ar^3$-($L^4$-$Ar^4$)$_q$ moiety is an -alkylene-aryl-O-alkylene-NH—C(O)-heteroaryl group, wherein said alkylene, alkyl, heterocyclyl, aryl, and heteroaryl moieties are any alkylene, alkyl, heterocyclyl, aryl, and heteroaryl moieties defined or exemplified herein, optionally substituted with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-heterocyclyl group, q is 1, the -$L^3$-$Ar^3$-($L^4$-$Ar^4$)$_q$ moiety is an -alkylene-aryl-O-alkylene-$PO_3$(alkyl)$_2$ group, wherein said alkylene, alkyl, heterocyclyl, and aryl moieties are any alkylene, alkyl, heterocyclyl, and aryl moieties defined or exemplified herein, optionally substituted with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-O-alkylene-heterocyclyl group, -q is 0, the -$L^3$-$Ar^3$-($L^4$-$Ar^4$)$_q$ moiety is an -alkylene-aryl group, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, p is 0, the -$L^1$-$Ar^1$-($L^2$-$Ar^2$)$_p$ moiety is an -alkylene-aryl-O-haloalkyl, q is 1, the -$L^3$-$Ar^3$-($L^4$-$Ar^4$)$_q$ moiety is an -alkylene-aryl-heteroaryl group, wherein said alkylene, haloalkyl, aryl, and heteroaryl moieties are any alkylene, haloalkyl, aryl, and heteroaryl moieties defined or exemplified herein, optionally substituted with one or more of any substituents defined or exemplified herein.

In yet another embodiment of the compounds of Formula I, p is 0, the -$L^1$-$Ar^1$-($L^2$-$Ar^2$)$_p$ moiety is an -alkylene-aryl-O-haloalkyl group, q is 0, the -$L^3$-$Ar^3$-($L^4$-$Ar^4$)$_q$ moiety is an -alkylene-aryl-O-alkyl group, wherein said alkylene, alkyl, haloalkyl, and aryl, moieties are any alkylene, alkyl, haloalkyl, and aryl heterocyclyl moieties defined or exemplified herein, optionally substituted with one or more of any substituents defined or exemplified herein.

In yet another embodiment of the compounds of Formula I, p is 0, the -$L^1$-$Ar^1$-($L^2$-$Ar^2$)$_p$ moiety is an -alkylene-aryl group, q is 1, the -$L^3$-$Ar^3$-($L^4$-$Ar^4$)$_q$ moiety is an -alkylene-aryl-heteroaryl group, $R^1$ is $OR^{1c}$, wherein $R^{1c}$ is heterocyclyl, substituted heterocyclyl, heterocyclyl alkyl, or substituted heterocyclyl alkyl, wherein said alkylene, alkyl, heterocyclyl, aryl, and heteroaryl moieties are any alkylene, alkyl, heterocyclyl, aryl, and heteroaryl moieties defined or exemplified herein, optionally substituted with one or more of any substituents defined or exemplified herein.

In yet another embodiment of the compounds of Formula I, p is 0, the -$L^1$-$Ar^1$-($L^2$-$Ar^2$)$_p$ moiety is an -alkylene-aryl group, q is 1, the -$L^3$-$Ar^3$-($L^4$-$Ar^4$)$_q$ moiety is an -alkylene-aryl-O—$CH_2$-heteroaryl group, $R^1$ is $OR^{1c}$, wherein $R^{1c}$ is heterocyclyl, substituted heterocyclyl, heterocyclyl alkyl, or substituted heterocyclyl alkyl, wherein said alkylene, alkyl, heterocyclyl, aryl, and heteroaryl moieties are any alkylene, alkyl, heterocyclyl, aryl, and heteroaryl moieties defined or exemplified herein, optionally substituted with one or more of any substituents defined or exemplified herein.

In yet another embodiment of the compounds of Formula I, p is 0, the -$L^1$-$Ar^1$-($L^2$-$Ar^2$)$_p$ moiety is an -alkylene-aryl group, q is 1, -$L^3$-$Ar^3$-($L^4$-$Ar^4$)$_q$ moiety is an -alkylene-aryl-aryl group, $R^1$ is $OR^{1c}$, wherein $R^{1c}$ is heterocyclyl, substituted heterocyclyl, heterocyclyl alkyl, or substituted heterocyclyl alkyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-heterocyclyl group, q is 0, -$L^3$-$Ar^3$-($L^4$-$Ar^4$)$_q$ moiety is an -alkylene-aryl group, $R^1$ is $OR^{1c}$, wherein $R^{1c}$ is alkyl or substituted alkyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-heterocyclyl group, q is 0, the -$L^3$-$Ar^3$-($L^4$-$Ar^4$)$_q$ moiety is an -alkylene-aryl group, $R^1$ is $OR^{1c}$, wherein $R^{1c}$ is heterocyclyl, substituted heterocyclyl, heterocyclyl alkyl, or substituted heterocyclyl alkyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-heterocyclyl group, q is 0, the -$L^3$-$Ar^3$-($L^4$-$Ar^4$)$_q$ moiety is an -alkylene-aryl group, $R^1$ is aryl or substituted aryl, wherein said alkylene, aryl, and heterocyclyl moieties are any alkylene, aryl, and heterocyclyl moieties defined or exemplified herein, optionally substituted on the alkylene, aryl and/or heterocyclyl with one or more of any substituents defined or exemplified herein. In one particular embodiment, $R^1$ is optionally substituted with one or more hydroxyl and/or methyl groups.

In yet another embodiment of the compounds of Formula I, p is 1, the -$L^1$-$Ar^1$-($L^2$-$Ar^2$)$_p$ moiety is an -alkylene-aryl-heterocyclyl group, q is 0, the -$L^3$-$Ar^3$-($L^4$-$Ar^4$)$_q$ moiety is an -alkylene-aryl group, $R^1$ is heteroaryl or substituted heteroaryl, wherein said alkylene, aryl, heteroaryl, and heterocyclyl moieties are any alkylene, aryl, heteroaryl, and heterocyclyl moieties defined or exemplified herein, optionally substituted with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-heterocyclyl group, q is 0, the -$L^3$-$Ar^3$-($L^4$-$Ar^4$)$_q$ moieties is an -alkylene-aryl group, $R^1$ is arylalkyl, substituted arylalkyl, heterocyclyl alkyl, and substituted heterocyclyl alkyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-heterocyclyl group, q is 0, the -$L^3$-$Ar^3$-($L^4$-$Ar^4$)$_q$ moiety is an -alkylene-aryl group, $R^1$ is —C($R^{1d}R^{1e}$)—$NR^{1f}$—C(O)—O—$R^{1g}$ wherein $R^{1d}$, $R^{1e}$, and $R^{1f}$ are independently H, alkyl, or substituted alkyl, and $R^{1g}$ is alkyl or substituted alkyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-heterocyclyl group, q is 0, -$L^3$-$Ar^3$-($L^4$-$Ar^4$)$_q$ moiety is an -alkylene-aryl group, $R^1$ is —C($R^{1d}R^{1e}$)—$NR^{1f}$—C(O)—O—$R^{1g}$ wherein $R^{1d}$ and $R^{1e}$ taken together with the carbon atom to which they are shown attached form a heterocyclyl or a substituted heterocyclyl, $R^{1f}$ is H, alkyl, or substituted alkyl, and $R^{1g}$ is alkyl or substituted alkyl, wherein said alkylene, alkyl, aryl, and heterocyclyl moieties are any alkylene, alkyl, aryl, and heterocyclyl moieties defined or exemplified herein, optionally substituted on the alkylene, aryl and/or heterocyclyl with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-heterocyclyl group, q is 1, the -$L^3$-$Ar^3$-($L^4$-$Ar^4$)$_q$ moiety is an -alkylene-aryl-O—$CH_2$-aryl group, $R^1$ is $OR^{1c}$, wherein $R^{1c}$ is heterocyclyl, substituted heterocyclyl, heterocyclyl alkyl, or substituted heterocyclyl alkyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-heterocyclyl group, q is 1, the -$L^3$-$Ar^3$-($L^4$-$Ar^4$)$_q$ moiety is an -alkylene-aryl-O—$CH_2$-aryl group, $R^1$ is —C($R^{1d}R^{1e}$)—$NR^{1f}$—C(O)—O—$R^{1g}$ wherein $R^{1d}$, $R^{1e}$, and $R^{1f}$ are independently H, alkyl, or substituted alkyl, and $R^{1g}$ is alkyl or substituted alkyl, wherein said alkylene, alkyl, aryl, and heterocyclyl moieties are any alkylene, alkyl, aryl, and heterocyclyl moieties defined or exemplified herein, optionally substituted on the alkylene, aryl and/or heterocyclyl with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-heterocyclyl group, q is 1, the -$L^3$-$Ar^3$-($L^4$-$Ar^4$)$_q$ moiety is an -alkylene-aryl-O—$CH_2$-heterocyclyl group, $R^1$ is $OR^c$, wherein $R^{1c}$ is heterocyclyl, substituted heterocyclyl, heterocyclyl alkyl, or substituted heterocyclyl alkyl, wherein said alkylene, alkyl, aryl, and heteroaryl moieties are any alkylene, alkyl, aryl, and heterocyclyl moieties defined or exemplified herein, optionally substituted with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-heterocyclyl group, q is 1, the -$L^3$-$Ar^3$-($L^4$-$Ar^4$)$_q$ moiety is an -alkylene-aryl-O-alkylene-NH—C(O)—O-alkyl group, $R^1$ is $OR^c$, wherein $R^{1c}$ is heterocyclyl, substituted heterocyclyl, heterocyclyl alkyl, or substituted heterocyclyl alkyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-heterocyclyl group, q is 1, the -$L^3$-$Ar^3$-($L^4$-$Ar^4$)$_q$ moiety is an -alkylene-aryl-O-alkylene-NH—S(O)$_2$—O-alkyl group, $R^1$ is $OR^{1c}$, wherein $R^{1c}$ is heterocyclyl, substituted heterocyclyl, heterocyclyl alkyl, or substituted heterocyclyl alkyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-heterocyclyl group, q is 1, the -$L^3$-$Ar^3$-($L^4$-$Ar^4$)$_q$ moiety is an -alkylene-aryl-O-alkylene-NH—C(O)-heteroaryl group, $R^1$ is $OR^{1c}$, wherein $R^{1c}$ is heterocyclyl, substituted heterocyclyl, heterocyclyl alkyl, or substituted heterocyclyl alkyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-heterocyclyl group, q is 1, the -$L^3$-$Ar^3$-($L^4$-$Ar^4$)$_q$ moiety is an -alkylene-aryl-O-alkylene-$PO_3$(alkyl)$_2$ group, $R^1$ is $OR^{1c}$, wherein $R^{1c}$ is heterocyclyl, substituted heterocyclyl, heterocyclyl alkyl, or substituted heterocyclyl alkyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-heterocyclyl group, q is 1, the -$L^3$-$Ar^3$-($L^4$-$Ar^4$)$_q$ moiety is an -alkylene-aryl-O-alkylene-$PO_3$(alkyl)$_2$ group, $R^1$ is —C($R^{1d}R^{1e}$)—$NR^{1f}$—C(O)—O—$R^{1g}$ wherein $R^{1d}$, $R^{1e}$, and $R^{1f}$ are independently H, alkyl, or substituted alkyl, and $R^{1g}$ is alkyl or substituted alkyl, wherein said alkylene, alkyl, aryl, and heteroaryl moieties are any alkyl, aryl, and heterocyclyl moieties defined or exemplified herein, optionally substituted on the alkylene, aryl and/or heterocyclyl with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-O-alkylene-heterocyclyl group, q is 0, the -$L^3$-$Ar^3$-($L^4$-$Ar^4$)$_q$ moiety is an -alkylene-aryl group, $R^1$ is $OR^{1c}$, wherein $R^{1c}$ is heterocyclyl, substituted heterocyclyl, heterocyclyl alkyl, or substituted heterocyclyl alkyl, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, p is 0, the -$L^1$-$Ar^1$-($L^2$-$Ar^2$)$_p$ moiety is an -alkylene-aryl-O-haloalkyl, -q is 1, the -$L^3$-$Ar^3$-($L^4$-$Ar^4$)$_q$ moiety is an -alkylene-aryl-heteroaryl group, $R^1$ is $OR^{1c}$, wherein $R^{1c}$ is heterocyclyl, substituted heterocyclyl, heterocyclyl alkyl, or substituted heterocyclyl alkyl, wherein said alkylene, aryl, and heterocyclyl moieties are any alkylene, aryl, and heterocyclyl moieties defined or exe that mplified herein, optionally substituted on the alkylene and/or aryl and/or heterocyclyl with one or more of any substituents defined or exemplified herein.

In yet another embodiment of the compounds of Formula I, p is 0, the -$L^1$-$Ar^1$-($L^2$-$Ar^2$)$_p$ moiety is an -alkylene-aryl-O-haloalkyl, -q is 0, the -$L^3$-$Ar^3$-($L^4$-$Ar^4$)$_q$ moiety is a -alkylene-aryl, $R^1$ is $OR^{1c}$, wherein $R^{1c}$ is heterocyclyl, substituted heterocyclyl, heterocyclyl alkyl, or substituted heterocyclyl alkyl, wherein said alkylene, alkyl, aryl, and heterocyclyl moieties are any alkylene, alkyl, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, p is 0, the -$L^1$-$Ar^1$-($L^2$-$Ar^2$)$_p$ moiety is an -alkylene-aryl group, q is 1, the -$L^3$-$Ar^3$-($L^4$-$Ar^4$)$_q$ moiety is an -alkylene-aryl-heteroaryl group, $R^1$ is $OR^{1c}$, wherein $R^{1c}$ is heterocyclyl, substituted heterocyclyl, heterocyclyl alkyl, or substituted heterocyclyl alkyl, X is —C(O)—, $R^6$ is C($R^{6d}R^{6e}$)—$NR^{6f1}$—C(O)—O—$R^{14}$ wherein $R^{6d}$, $R^{6e}R^{6f1}$ or $R^{14}$ are independently selected from the group consisting of H, alkyl, and substituted alkyl, wherein said alkylene, alkyl, aryl, and heteroaryl moieties are any alkylene, alkyl, aryl, and heteroaryl moieties defined or exemplified herein, optionally substituted with one or more of any substituents defined or exemplified herein.

In yet another embodiment of the compounds of Formula I, p is 0, the -$L^1$-$Ar^1$-($L^2$-$Ar^2$)$_p$ moiety is an -alkylene-aryl group, q is 1, the -$L^3$-$Ar^3$-($L^4$-$Ar^4$)$_q$ moiety is an -alkylene-aryl-aryl group, $R^1$ is $OR^{1c}$, wherein $R^{1c}$ is heterocyclyl, substituted heterocyclyl, heterocyclyl alkyl, or substituted heterocyclyl alkyl, X is —C(O)—, $R^6$ is C($R^{6d}R^{6e}$)—$NR^{6f1}$—C(O)—O—$R^{14}$ wherein $R^{6d}$, $R^{6e}R^{6f1}$ or $R^{14}$ are independently selected from the group consisting of H, alkyl, and substituted alkyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, p is 0, the -$L^1$-$Ar^1$-($L^2$-$Ar^2$)$_p$ moiety is an -alkylene-aryl group, q is 1, the -$L^3$-$Ar^3$-($L^4$-$Ar^4$)$_q$ moiety is an -alkylene-aryl-O—$CH_2$-heteroaryl group, $R^1$ is $OR^{1c}$, wherein $R^{1c}$ is heterocyclyl, substituted heterocyclyl, heterocyclyl alkyl, or substituted heterocyclyl alkyl, X is —C(O)—, $R^6$ is C($R^{6d}R^{6e}$)—$NR^{6f1}$—C(O)—O—$R^{14}$ wherein $R^{6d}$, $R^{6e}R^{6f1}$ or $R^{14}$ are independently selected from the group consisting of H, alkyl, and substituted alkyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-heterocyclyl group, q is 0, the -$L^3$-$Ar^3$-($L^4$-$Ar^4$)$_q$ moiety is an -alkylene-aryl group, $R^1$ is $OR^{1c}$, wherein $R^{1c}$ is alkyl or substituted alkyl, X is —C(O)—, $R^6$ is $C(R^{6d}R^{6e})$—$NR^{6f1}$—C(O)—O—$R^{14}$ wherein $R^{6d}$, $R^{6e}R^{6f1}$ or $R^{14}$ are independently selected from the group consisting of H, alkyl, and substituted alkyl, wherein said alkylene, alkyl, aryl, and heteroaryl moieties are any alkylene, alkyl, aryl, and heteroaryl moieties defined or exemplified herein, optionally substituted with one or more of any substituents defined or exemplified herein.

In yet another embodiment of the compounds of Formula I, p is 1, the $-L^1-Ar^1-(L^2-Ar^2)_p$ moiety is an -alkylene-aryl-heterocyclyl group, q is 0, the $-L^3-Ar^3-(L^4-Ar^4)_q$ moiety is an -alkylene-aryl group, $R^1$ is $OR^{1c}$, wherein $R^{1c}$ is heterocyclyl, substituted heterocyclyl, heterocyclyl alkyl, or substituted heterocyclyl alkyl, X is —C(O)—, $R^6$ is $C(R^{6d}R^{6e})$—$NR^{6f1}$—C(O)—O—R wherein $R^{6d}$, $R^{6e}R^{6f1}$ or $R^{14}$ are independently selected from the group consisting of H, alkyl, and substituted alkyl, wherein said alkylene, alkyl, aryl, and heterocyclyl moieties are any alkylene, alkyl, aryl, and heterocyclyl moieties defined or exemplified herein, optionally substituted on the alkylene, aryl and/or heterocyclyl with one or more of any substituents defined or exemplified herein.

In yet another embodiment of the compounds of Formula I, p is 1, the $-L^1-Ar^1-(L^2-Ar^2)_p$ moiety is an -alkylene-aryl-heterocyclyl group, q is 0, the $-L^3-Ar^3-(L^4-Ar^4)_q$ moiety is an -alkylene-aryl group, $R^1$ is aryl or substituted aryl, X is —C(O)—, and $R^6$ is $C(R^{6d}R^{6e})$—$NR^{6f1}$—C(O)—O—$R^{14}$ wherein $R^{6d}$, $R^{6e}R^{6f1}$ or $R^{14}$ are independently selected from the group consisting of H, alkyl, and substituted alkyl, wherein said alkylene, aryl, and heterocyclyl moieties are any alkylene, aryl, and heterocyclyl moieties defined or exemplified herein, optionally substituted on the alkylene, aryl and/or heterocyclyl with one or more of any substituents defined or exemplified herein. In one particular embodiment, $R^1$ is optionally substituted with one or more hydroxyl and/or methyl groups.

In yet another embodiment of the compounds of Formula I, p is 1, the $-L^1-Ar^1-(L^2-Ar^2)_p$ moiety is an -alkylene-aryl-heterocyclyl group, q is 0, the $-L^3-Ar^3-(L^4-Ar^4)_q$ moiety is an -alkylene-aryl group, $R^1$ is heteroaryl or substituted heteroaryl, X is —C(O)—, and $R^6$ is $C(R^{6d}R^{6e})$—$NR^{6f1}$—C(O)—O—$R^{14}$ wherein $R^{6d}$, $R^{6e}R^{6f1}$ or $R^{14}$ are independently selected from the group consisting of H, alkyl, and substituted alkyl, wherein said alkylene, aryl, and heterocyclyl moieties are any alkylene, aryl, and heterocyclyl moieties defined or exemplified herein, optionally substituted on the alkylene, aryl and/or heterocyclyl with one or more of any substituents defined or exemplified herein.

In yet another embodiment of the compounds of Formula I, p is 1, the $-L^1-Ar^1-(L^2-Ar^2)_p$ moiety is an -alkylene-aryl-heterocyclyl group, q is 0, the $-L^3-Ar^3-(L^4-Ar^4)_q$ moiety is an -alkylene-aryl group, $R^1$ is arylalkyl, substituted arylalkyl, heterocyclyl alkyl, and substituted heterocyclyl alkyl, X is —C(O)—, $R^6$ is $C(R^{6d}R^{6e})$—$NR^{6f1}$—C(O)—O—$R^{14}$ wherein $R^{6d}$, $R^{6e}R^{6f1}$ or $R^{14}$ are independently selected from the group consisting of H, alkyl, and substituted alkyl, wherein said alkylene, alkyl, aryl, and heterocyclyl moieties are any alkylene, alkyl, aryl, and heterocyclyl moieties defined or exemplified herein, optionally substituted on the alkylene, aryl and/or heterocyclyl with one or more of any substituents defined or exemplified herein.

In yet another embodiment of the compounds of Formula I, p is 1, the $-L^1-Ar^1-(L^2-Ar^2)_p$ moiety is an -alkylene-aryl-heterocyclyl group, q is 0, the $-L^3-Ar^3-(L^4-Ar^4)_q$ moiety is an -alkylene-aryl group, $R^1$ is —$C(R^{1d}R^{1e})$—$NR^{1f}$—C(O)—O—$R^{1g}$ wherein $R^{1d}$, $R^{1e}$, and $R^{1f}$ are independently H, alkyl, or substituted alkyl, and $R^{1g}$ is alkyl or substituted alkyl, X is —C(O)—, and $R^6$ is $C(R^{6d}R^{6e})$—$NR^{6f1}$—C(O)—O—$R^{14}$ wherein $R^{6d}$, $R^{6e}R^{6f1}$ or $R^{14}$ are independently selected from the group consisting of H, alkyl, and substituted alkyl, wherein said alkylene, alkyl, aryl, and heterocyclyl moieties are any alkylene, alkyl, aryl, and heterocyclyl moieties defined or exemplified herein, optionally substituted on the alkylene, aryl and/or heterocyclyl with one or more of any substituents defined or exemplified herein. $R^{1d}$, $R^{1e}$, $R^{6d}$, and $R^{6e}$ may optionally be substituted with a hydroxyl group.

In yet another embodiment of the compounds of Formula I, p is 1, the $-L^1-Ar^1-(L^2-Ar^2)_p$ moiety is an -alkylene-aryl-heterocyclyl group, q is 0, the $-L^3-Ar^3-(L^4-Ar^4)_q$ moiety is an -alkylene-aryl group, $R^1$ is —$C(R^{1d}R^{1e})$—$NR^{1f}$—C(O)—O—$R^{1g}$ wherein $R^{1d}$ and $R^{1e}$ taken together with the carbon atom to which they are shown attached form a heterocyclyl or a substituted heterocyclyl, $R^{1f}$ is H, alkyl, or substituted alkyl, and $R^{1g}$ is alkyl or substituted alkyl, X is —C(O)—, $R^6$ is $C(R^{6d}R^{6e})$—$NR^{6f1}$—C(O)—O—$R^{6f2}$ wherein $R^{6d}$ and $R^{6e}$ are taken together to form a 5- or 6-membered spiro-fused non-aromatic tetrahydro heterocyclyl, wherein said alkylene, alkyl, aryl, and heterocyclyl moieties are any alkylene, alkyl, aryl, and heterocyclyl moieties defined or exemplified herein, optionally substituted on the alkylene, aryl and/or heterocyclyl with one or more of any substituents defined or exemplified herein.

In yet another embodiment of the compounds of Formula I, p is 1, the $-L^1-Ar^1-(L^2-Ar^2)_p$ moiety is an -alkylene-aryl-heterocyclyl group, q is 1, the $-L^3-Ar^3-(L^4-Ar^4)_q$ moiety is an -alkylene-aryl-O—$CH_2$-aryl group, $R^1$ is $OR^{1c}$, wherein $R^{1c}$ is heterocyclyl, substituted heterocyclyl, heterocyclyl alkyl, or substituted heterocyclyl alkyl, X is —C(O)—, $R^6$ is $C(R^{6d}R^{6e})$—$NR^{6f1}$—C(O)—O—$R^{14}$ wherein $R^{6d}$, $R^{6e}$, $R^{6f1}$ or $R^{14}$ are independently selected from the group consisting of H, alkyl, and substituted alkyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, p is 1, the $-L^1-Ar^1-(L^2-Ar^2)_p$ moiety is an -alkylene-aryl-heterocyclyl group, q is 1, the $-L^3-Ar^3-(L^4-Ar^4)_q$ moiety is an -alkylene-aryl-O—$CH_2$-aryl group, $R^1$ is $OR^{1c}$, wherein $R^{1c}$ is heterocyclyl, substituted heterocyclyl, heterocyclyl alkyl, or substituted heterocyclyl alkyl, X is —C(O)—, and $R^6$ is $C(R^{6d}R^{6e})$—$NR^{6f1}$—C(O)—O—$R^{14}$ wherein $R^{6d}$, $R^{6e}$, $R^{6f1}$ or $R^{14}$ are independently selected from the group consisting of H, alkyl, and substituted alkyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, p is 1, the $-L^1-Ar^1-(L^2-Ar^2)_p$ moiety is an -alkylene-aryl-heterocyclyl group, q is 1, the $-L^3-Ar^3-(L^4-Ar^4)_q$ moiety is an -alkylene-aryl-O—$CH_2$-aryl group, $R^1$ is —$C(R^{1d}R^{1e})$—$NR^{1f}$—C(O)—O—$R^{1g}$ wherein $R^{1d}$, $R^{1e}$, and $R^{1f}$ are independently H, alkyl, or substituted alkyl, and $R^{1g}$ is alkyl or substituted alkyl, X is —C(O)—, $R^6$ is alkyl or substituted alkyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, p is 1, the $-L^1-Ar^1-(L^2-Ar^2)_p$ moiety is an -alkylene-aryl-heterocyclyl group, q is 1, the $-L^3-Ar^3-(L^4-Ar^4)_q$ moiety is an -alkylene-aryl-O—$CH_2$-heterocyclyl group, $R^1$ is $OR^{1c}$, wherein $R^{1c}$ is heterocyclyl, substituted heterocyclyl, heterocyclyl alkyl, or substituted heterocyclyl alkyl, X is —C(O)—, and $R^6$ is C($R^{6d}R^{6e}$)—$NR^{6f1}$—C(O)—O—$R^{14}$ wherein $R^{6d}$, $R^{6e}R^{6f1}$ or $R^{14}$ are independently selected from the group consisting of H, alkyl, and substituted alkyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-heterocyclyl group, q is 1, the -$L^3$-$Ar^3$-($L^4$-$Ar^4$)$_q$ moiety is an -alkylene-aryl-O-alkylene-NH—C(O)—O-alkyl group, $R^1$ is $OR^{1c}$, wherein $R^{1c}$ is heterocyclyl, substituted heterocyclyl, heterocyclyl alkyl, or substituted heterocyclyl alkyl, X is —C(O)—, $R^6$ is C($R^{6d}R^{6e}$)—$NR^{6f1}$—C(O)—O—$R^{14}$ wherein $R^{6d}$, $R^{6e}R^{6f1}$ or $R^{14}$ are independently selected from the group consisting of H, alkyl, and substituted alkyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-heterocyclyl group, q is 1, the -$L^3$-$Ar^3$-($L^4$-$Ar^4$)$_q$ moiety is an -alkylene-aryl-O-alkylene-NH—S(O)$_2$—O-alkyl group, $R^1$ is $OR^{1c}$, wherein $R^{1c}$ is heterocyclyl, substituted heterocyclyl, heterocyclyl alkyl, or substituted heterocyclyl alkyl, X is —C(O)—, $R^6$ is C($R^{6d}R^{6e}$)—$NR^{6f1}$—C(O)—O—$R^{14}$ wherein $R^{6d}$, $R^{6e}R^{6f1}$ or $R^{14}$ are independently selected from the group consisting of H, alkyl, and substituted alkyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-heterocyclyl group, q is 1, the -$L^3$-$Ar^3$-($L^4$-$Ar^4$)$_q$ moiety is an -alkylene-aryl-O-alkylene-NH—C(O)-heteroaryl group, $R^1$ is $OR^{1c}$, wherein $R^{1c}$ is heterocyclyl, substituted heterocyclyl, heterocyclyl alkyl, or substituted heterocyclyl alkyl, X is —C(O)—, $R^6$ is C($R^{6d}R^{6e}$)—$NR^{6f1}$—C(O)—O—$R^{14}$ wherein $R^{6d}$, $R^{6e}R^{6f1}$ or $R^{14}$ are independently selected from the group consisting of H, alkyl, and substituted alkyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-heterocyclyl group, q is 1, the -$L^3$-$Ar^3$-($L^4$-$Ar^4$)$_q$ moiety is an -alkylene-aryl-O-alkylene-PO$_3$(alkyl)$_2$ group, $R^1$ is $OR^{1c}$, wherein $R^{1c}$ is heterocyclyl, substituted heterocyclyl, heterocyclyl alkyl, or substituted heterocyclyl alkyl, X is —C(O)—, $R^6$ is C($R^{6d}R^{6e}$)—$NR^{6f1}$—C(O)—O—$R^{14}$ wherein $R^{6d}$, $R^{6e}R^{6f1}$ or $R^{14}$ are independently selected from the group consisting of H, alkyl, and substituted alkyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, p is 1, the -$L^1$-$Ar^1$-($L^2$-$Ar^2$) moiety is an -alkylene-aryl-heterocyclyl group, q is 1, the -$L^3$-$Ar^3$-($L^4$-$Ar^4$)$_q$ moiety is an -alkylene-aryl-O-alkylene-PO$_3$(alkyl)$_2$ group, $R^1$ is —C($R^{1d}R^{1e}$)—$NR^{1f}$—C(O)—O—$R^{1g}$ wherein $R^{1d}$, $R^{1e}$, and $R^{1f}$ are independently H, alkyl, or substituted alkyl, and $R^{1g}$ is alkyl or substituted alkyl, X is —C(O)—, and $R^6$ is C($R^{6d}R^{6e}$)—$NR^{6f1}$—C(O)—O—$R^{14}$ wherein $R^{6d}$, $R^{6e}R^{6f1}$ or $R^{14}$ are independently selected from the group consisting of H, alkyl, and substituted alkyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-O-alkylene-heterocyclyl group, q is 0, -$L^3$-$Ar^3$-($L^4$-$Ar^4$)$_q$ moiety is a -alkylene-aryl group, $R^1$ is $OR^{1c}$, wherein $R^{1c}$ is heterocyclyl, substitute of d heterocyclyl, heterocyclyl alkyl, or substituted heterocyclyl alkyl, X is —C(O)—, and $R^6$ is C($R^{6d}R^{6e}$)—$NR^{6f1}$—C(O)—O—$R^{14}$ wherein $R^{6d}$, $R^{6e}R^{6f1}$ or $R^{14}$ are independently selected from the group consisting of H, alkyl, and substituted alkyl, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, p is 0, the -$L^1$-$Ar^1$-($L^2$-$Ar^2$)$_p$ moiety is an -alkylene-aryl-O-haloalkyl, -q is 1, the -$L^3$-$Ar^3$-($L^4$-$Ar^4$)$_q$ moiety is an -alkylene-aryl-heteroaryl group, $R^1$ is $OR^{1c}$, wherein $R^{1c}$ is heterocyclyl, substituted heterocyclyl, heterocyclyl alkyl, or substituted heterocyclyl alkyl, X is —C(O)—, and $R^6$ is C($R^{6d}R^{6e}$)—$NR^{6f1}$—C(O)—O—$R^{14}$ wherein $R^{6d}$ $R^{6e}$, $R^{6f1}$ or $R^{14}$ are independently selected from the group consisting of H, alkyl, and substituted alkyl, wherein said alkylene, aryl, and heterocyclyl moieties are any alkylene, aryl, and heterocyclyl moieties defined or exemplified herein, optionally substituted with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-heterocyclyl group, q is 0, the -$L^3$-$Ar^3$-($L^4$-$Ar^4$)$_q$ moiety is an -alkylene-aryl group, $R^1$ is $OR^{1c}$, wherein $R^{1c}$ is heterocyclyl, substituted heterocyclyl, heterocyclyl alkyl, or substituted heterocyclyl alkyl, X is —C(O)—, $R^6$ is heterocyclyl alkyl or substituted heterocyclyl alkyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-heterocyclyl group, q is 0, the -$L^3$-$Ar^3$-($L^4$-$Ar^4$)$_q$ moiety is an -alkylene-aryl group, $R^1$ is $OR^{1c}$, wherein $R^{1c}$ is heterocyclyl, substituted heterocyclyl, heterocyclyl alkyl, or substituted heterocyclyl alkyl, X is —C(O)—, $R^6$ is C($R^{6d}R^{6e}$)—$NR^{6f1}$—S(O)$_2$—$R^{6f3}R^{6d}$ and $R^{6e}$ are independently H, alkyl, haloalkyl, hydroxyalkyl, or alkoxy; $R^{6f1}$ is H, alkyl, or substituted alkyl; and $R^{6f3}$ is alkyl, substituted alkyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-heterocyclyl group, q is 0, the -$L^3$-$Ar^3$-($L^4$-$Ar^4$)$_q$ moiety is an -alkylene-aryl group, $R^1$ is $OR^c$, wherein $R^{1c}$ is heterocyclyl, substituted heterocyclyl, heterocyclyl alkyl, or substituted heterocyclyl alkyl, X is —C(O)— and $R^6$ is C($R^{7d}R^{7e}$)—$NR^{7f1}$—C(O)—$R^{7f2}$ wherein $R^{7d}$ and $R^{7e}$ are independently H, alkyl, haloalkyl, hydroxyalkyl, or alkoxy; $R^{7f1}$ is H, alkyl, or substituted alkyl; $R^{7f2}$ is alkyl, haloalkyl, hydroxyalkyl, or alkoxy, wherein said alkylene, alkyl, aryl, and heterocyclyl moieties are any alkylene, alkyl, aryl, and heterocyclyl moieties defined or exemplified herein, optionally substituted on the alkylene, aryl and/or heteroaryl with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-heterocyclyl group, q is 0, -$L^3$-$Ar^3$-($L^4$-$Ar^4$)$_q$ moiety is an -alkylene-aryl group, $R^1$ is $OR^{1c}$, wherein $R^{1c}$ is heterocyclyl, substituted heterocyclyl, heterocyclyl alkyl, or substituted heterocyclyl alkyl, X is —C(O)— and $R^6$ is C($R^{6d}R^{6e}$)—$NR^{6f1}$—S(O)$_2$—N(alkyl)$_2$, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-heterocyclyl group, q is 0, the -$L^3$-$Ar^3$-($L^4$-$Ar^4$)$_q$ moiety is an -alkylene-aryl group, $R^1$ is $OR^{1c}$, wherein $R^{1c}$ is heterocyclyl, substituted heterocyclyl, heterocyclyl alkyl, or substituted heterocyclyl alkyl, X is —C(O)—$R^6$ is heterocyclyl or substituted heterocyclyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-heterocyclyl group, q is 0, the -$L^3$-$Ar^3$-($L^4$-$Ar^4$)$_q$ moiety is an -alkylene-aryl group, $R^1$ is $OR^{1c}$, wherein $R^{1c}$ is heterocyclyl, substituted heterocyclyl, heterocyclyl alkyl, or substituted heterocyclyl alkyl, X is —C(O)— and $R^6$ is C($R^{6d}R^{6e}$)—O-aryl wherein $R^{6d}$, $R^{6e}$ are independently selected from the group consisting of H, alkyl, and substituted alkyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-heterocyclyl group, q is 0, the -$L^3$-$Ar^3$-($L^4$-$Ar^4$)$_q$ moiety is an -alkylene-aryl group, $R^1$ is $OR^{1c}$, wherein $R^{1c}$ is heterocyclyl, substituted heterocyclyl, heterocyclyl alkyl, or substituted heterocyclyl alkyl, X is —S—, and $R^6$ is alkyl or substituted alkyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-heterocyclyl group, q is 0, the -$L^3$-$Ar^3$-($L^4$-$Ar^4$)$_q$ moiety is an -alkylene-aryl group, $R^1$ is $OR^{1c}$, wherein $R^{1c}$ is heterocyclyl, substituted heterocyclyl, heterocyclyl alkyl, or substituted heterocyclyl alkyl, X is —C(O)— and $R^6$ is —$OR^{6a}$ wherein $R^{6a}$ is heterocyclyl, substituted heterocyclyl, heterocyclyl alkyl, substituted heterocyclyl alkyl, wherein said alkylene, alkyl, aryl, and heterocyclyl moieties are any alkylene, alkyl, aryl, and heterocyclyl moieties defined or exemplified herein, optionally substituted on the alkylene, aryl and/or heteroaryl with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-heterocyclyl group, q is 0, the -$L^3$-$Ar^3$-($L^4$-$Ar^4$)$_q$ moiety is an -alkylene-aryl group, $R^1$ is $OR^{1c}$, wherein $R^{1c}$ is heterocyclyl, substituted heterocyclyl, heterocyclyl alkyl, or substituted heterocyclyl alkyl, X is —C(O)—, $R^6$ is heterocyclyl or substituted heterocyclyl, wherein X is attached to the heterocyclyl through a heteroatom, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, p is 1, the -$L^1$-$Ar^1$-($L^2$-$Ar^2$)$_p$ moiety is an -alkylene-aryl-heterocyclyl group, q is 0, the -$L^3$-$Ar^3$-($L^4$-$Ar^4$)$_q$ moiety is an -alkylene-aryl group, $R^1$ is $OR^{1c}$, wherein $R^{1c}$ is heterocyclyl, substituted heterocyclyl, heterocyclyl alkyl, or substituted heterocyclyl alkyl, X is —C(O)—, $R^6$ is heterocyclyl or substituted heterocyclyl, wherein X is attached to the heterocyclyl through a carbon atom, wherein said heterocyclyl includes any heterocyclyl defined or exemplified herein, wherein said alkylene, alkyl, aryl, and heteroaryl moieties are any alkylene, alkyl, aryl, and heterocyclyl moieties defined or exemplified herein, optionally substituted on the alkylene, aryl and/or heterocyclyl with one or more of any substituents defined or exemplified herein.

In yet another embodiment of the compounds of Formula I, X is C(O); p is 0; q is 1; $L^1$ and $L^3$ are alkylene; $L^4$ is a covalent bond; $Ar^1$, $Ar^3$, and $Ar^4$ are independently aryl, substituted aryl, heteroaryl, or substituted heteroaryl, wherein said substituted aryl or said substituted heteroaryl of $Ar^1$, $Ar^3$ and $Ar^4$ are each independently substituted by one or more substituents selected from the group consisting of alkyl, substituted alkyl, haloalkyl, halo, hydroxy, amino, alkoxy, haloalkoxy.

In yet another embodiment of the compounds of Formula I, X is C(O); p is 0; q is 1; $L^1$ and $L^3$ are alkylene; $L^4$ is a covalent bond; wherein $R^1$ is $OR^{1c}$; and $R^{1c}$ is alkyl, substituted alkyl, heterocyclyl, substituted heterocyclyl, heterocyclyl alkyl, or substituted heterocyclyl alkyl, wherein said substituted heterocyclyl alkyl is substituted on the heterocyclyl moiety, and said heterocyclyl is selected from the group consisting of: (i) a mono-cyclic 5- or 6-membered aromatic, nonaromatic dihydro, or nonaromatic tetrahydro heterocyclic ring having from 1 to 4 heteroatoms selected from N, O, and S; and (ii) a bi-cyclic 8-, 9-, or 10-membered aromatic, nonaromatic dihydro, or nonaromatic tetrahydro heterocyclic ring having from 1 to 6 heteroatoms selected from N, O, and S. Preferably, $R^1$ is $OR^{1c}$; and $R^{1c}$ is selected from the group consisting of

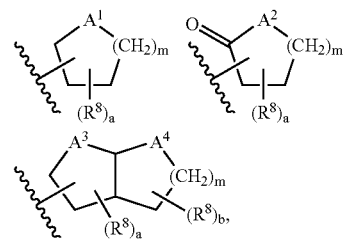

wherein $A^1$, $A^2$, $A^3$, and $A^4$ are independently $NR^9$ or O; $R^8$ is alkyl, substituted alkyl, haloalkyl, substituted haloalkyl, hydroxyalkyl, substituted hydroxyalkyl, —O-(alkyl), or —O-(substituted alkyl); $R^9$ is H, alkyl, or substituted alkyl; m is 1 or 2; and a and b are independently 0, 1, or 2.

In yet another embodiment of the compounds of Formula I, X is C(O); p is 0; q is 1; L¹ and L³ are alkylene; L⁴ is a covalent bond; R⁶ is

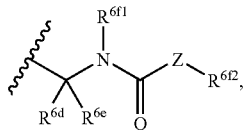

wherein $R^{6d}$ and $R^{6e}$ are independently H, alkyl, haloalkyl, hydroxyalkyl, or alkoxy; or $R^{6d}$ and $R^{6e}$ are taken together to form a 5- or 6-membered non-aromatic tetrahydro heterocyclic ring; Z is —NR¹⁴ or —O—; R¹⁴ is H, alkyl, or substituted alkyl; $R^{6f1}$ is H, alkyl, or substituted alkyl; and $R^{6f2}$ is alkyl, haloalkyl, hydroxyalkyl, or alkoxy.

In yet another embodiment of the compounds of Formula I, X is C(O); p is 0; q is 1; L¹ and L³ are alkylene; L⁴ is a covalent bond; R¹ is OR$^{1c}$; and R$^{1c}$ is selected from the group consisting of

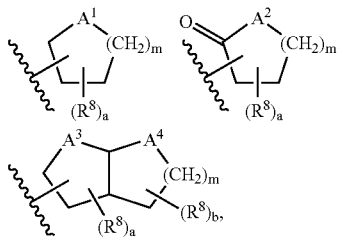

wherein A¹, A², A³, and A⁴ are independently NR⁹ or O; R⁸ is alkyl, substituted alkyl, haloalkyl, substituted haloalkyl, hydroxyalkyl, substituted hydroxyalkyl, —O-(alkyl), or —O-(substituted alkyl); R⁹ is H, alkyl, or substituted alkyl; m is 1 or 2; a and b are independently 0, 1, or 2; R⁶ is

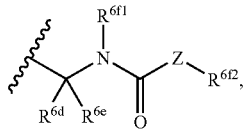

wherein $R^{6d}$ and $R^{6e}$ are independently H, alkyl, haloalkyl, hydroxyalkyl, or alkoxy; or $R^{6d}$ and $R^{6e}$ are taken together to form a 5- or 6-membered non-aromatic tetrahydro heterocyclic ring; Z is —NR¹⁴ or —O—; R¹⁴ is H, alkyl, or substituted alkyl; $R^{6f1}$ is H, alkyl, or substituted alkyl; and $R^{6f2}$ is alkyl, haloalkyl, hydroxyalkyl, or alkoxy.

In yet another embodiment of the compounds of Formula I, X is C(O); p is 1; q is 0; L¹ and L³ are alkylene; L² is a covalent bond; R¹ is OR$^{1c}$; and R$^{1c}$ is selected from the group consisting of

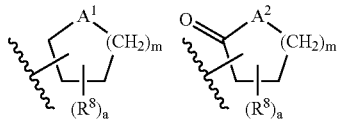

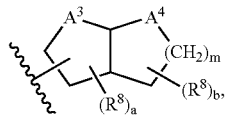

wherein A¹, A², A³, and A⁴ are independently NR⁹ or O; R⁸ is alkyl, substituted alkyl, haloalkyl, substituted haloalkyl, hydroxyalkyl, substituted hydroxyalkyl, —O-(alkyl), or —(substituted alkyl); R⁹ is H, alkyl, or substituted alkyl; m is 1 or 2; a and b are independently 0, 1, or 2; R⁶ is

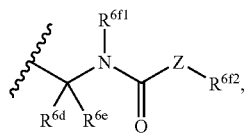

wherein $R^{6d}$ and $R^{6e}$ are independently H, alkyl, haloalkyl, hydroxyalkyl, or alkoxy; or $R^{6d}$ and $R^{6e}$ are taken together to form a 5- or 6-membered non-aromatic tetrahydro heterocyclic ring; Z is —NR¹⁴ or —O—; R¹⁴ is H, alkyl, or substituted alkyl; $R^{6f1}$ is H, alkyl, or substituted alkyl; and $R^{6f2}$ is alkyl, haloalkyl, hydroxyalkyl, or alkoxy. Preferably, Ar¹, Ar², and Ar⁴ are independently aryl, substituted aryl, heteroaryl, or substituted heteroaryl, wherein said substituted aryl or said substituted heteroaryl of Ar¹, Ar² and Ar⁴ are each independently substituted by one or more substituents selected from the group consisting of alkyl, substituted alkyl, haloalkyl, halo, hydroxy, amino, alkoxy, haloalkoxy.

In still yet another embodiment, the compounds of Formula I are named below in tabular format (Table 6) as compounds of general Formula II:

Formula II

Compounds of general formula II are depicted as a "core" structure (Z) substituted with four moieties T1, T2, X1 and X2. The core structures Z are depicted in Table 1. The points of attachment of T1, T2, X1 and X2 are indicated on each of the core structures depicted in Table 1. Tables 2-5, respectively, show the structures of the T1, T2, X1 and X2 moieties. The point of attachment of the core structure Z is indicated in each of the structures of T1, T2, X1 and X2. Each core structure Z in Table 1, and each substituent T1, T2, X1 and X2 and Tables 2-5 is represented by a "code" comprising a letter and a number. Each structure of a compound of Formula II can be designated in tabular form by combining the "code" representing each structural moiety using the following syntax: Z.T1.T2.X1.X2. Thus, for example, Z1.T1A.T2B.X1A.X2A represents the following structure:

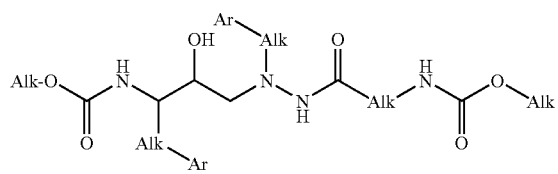

In the structures depicted in Tables 1-5, the term "Alk" means a substituted or unsubstituted alkyl or alkylene group, wherein the terms "alkyl" and "alkylene" are as defined herein. "Alk" means an alkyl group when depicted as monovalent, and an alkylene group when depicted as divalent. "Het" is a substituted or unsubstituted heterocyclyl or heterocyclylene group, wherein the term "heterocyclyl" is as defined herein, and the term "heterocyclylene" means a heterocyclyl group as defined herein, in which a hydrogen atom has been replaced by an open valence (in analogy to alkylene), thereby defining a divalent heterocyclyl. "Het" is a heterocyclyl when depicted as monovalent, and heterocyclylene when depicted as divalent. "Ar" is a substitute or unsubstituted aryl or arylene group, wherein the term "aryl" is as defined herein, and the term "arylene" means an aryl group as defined herein, in which a hydrogen atom has been replaced by an open valence (in analogy to alkylene), thereby defining a divalent aryl. "Ar" is aryl when depicted as monovalent, and arylene when depicted as divalent. When substituted, "Alk", "Het", and "Ar" can be substituted with any of the substituents defined or exemplified herein. For example, substituents of "Alk" can include ether, halogen, —OH, amide, amine, etc., substituents of "Het" can include alkyl, aryl, carbonyl, —OH, halogen, and substituents of "Ar" can include alkyl, aryl, —OH, halogen, etc., with the proviso that the resulting structure is chemically reasonable, and would provide compounds which are sufficiently stable for formulation in a pharmaceutically acceptable composition.

TABLE 1

Core Structures

| Code | Core Structure |
|---|---|
| Z1 | (structure) |
| Z2 | (structure) |
| Z3 | (structure) |

TABLE 1-continued

Core Structures

| Code | Core Structure |
|---|---|
| Z4 | (structure) |

TABLE 2

T1 Structures

| Code | T1 Structure |
|---|---|
| T1A | —O-Alk |
| T1B | —O-Het |
| T1C | —O-Alk-Het |
| T1D | -Alk-NH—C(O)—O-Alk |
| T1E | -Het-NH—C(O)—O-Alk |
| T1F | —N(Alk)(Het) |

TABLE 3

T2 Structures

| Code | T2 Structure |
|---|---|
| T2A | -Alk-NH—C(O)—O-Alk |
| T2B | -Alk-NH—C(O)—O-Alk-Ar |
| T2C | -Alk-NH—C(O)—O-Alk-Het |
| T2D | -Alk-Het |
| T2E | —O-Het |
| T2F | -Alk-NH—C(O)-Alk |

TABLE 4

X1 Structures

| Cod | X1 Structure |
|---|---|
| X1A | —Ar |
| X1B | —Ar—Ar |
| X1C | —Ar-Het |
| X1D | —Ar—O-Het |
| X1E | —Ar—O-Alk-Het |
| X1F | —Ar—NH-Het |

TABLE 5

X2 Structures

| Code | X2 Structure |
|---|---|
| X2A | —Ar |
| X2B | —Ar—Ar |
| X2C | —Ar-Het |
| X2D | —Ar—O-Het |
| X2E | —Ar—O-Alk-Het |
| X2F | —Ar—NH-Het |

TABLE 6

List of Compound Structures of Formula II

Z1.T1A.T2A.X1A.X2A, Z2.T1A.T2A.X1A.X2A,
Z3.T1A.T2A.X1A.X2A, Z4.T1A.T2A.X1A.X2A,
Z1.T1B.T2A.X1A.X2A, Z2.T1B.T2A.X1A.X2A,
Z3.T1B.T2A.X1A.X2A, Z4.T1B.T2A.X1A.X2A,
Z1.T1C.T2A.X1A.X2A, Z2.T1C.T2A.X1A.X2A,
Z3.T1C.T2A.X1A.X2A, Z4.T1C.T2A.X1A.X2A,
Z1.T1D.T2A.X1A.X2A, Z2.T1D.T2A.X1A.X2A,
Z3.T1D.T2A.X1A.X2A, Z4.T1D.T2A.X1A.X2A,
Z1.T1E.T2A.X1A.X2A, Z2.T1E.T2A.X1A.X2A,
Z3.T1E.T2A.X1A.X2A, Z4.T1E.T2A.X1A.X2A,
Z1.T1F.T2A.X1A.X2A, Z2.T1F.T2A.X1A.X2A,
Z3.T1F.T2A.X1A.X2A, Z4.T1F.T2A.X1A.X2A,
Z1.T1A.T2B.X1A.X2A, Z2.T1A.T2B.X1A.X2A,
Z3.T1A.T2B.X1A.X2A, Z4.T1A.T2B.X1A.X2A,
Z1.T1B.T2B.X1A.X2A, Z2.T1B.T2B.X1A.X2A,
Z3.T1B.T2B.X1A.X2A, Z4.T1B.T2B.X1A.X2A,
Z1.T1C.T2B.X1A.X2A, Z2.T1C.T2B.X1A.X2A,
Z3.T1C.T2B.X1A.X2A, Z4.T1C.T2B.X1A.X2A,
Z1.T1D.T2B.X1A.X2A, Z2.T1D.T2B.X1A.X2A,
Z3.T1D.T2B.X1A.X2A, Z4.T1D.T2B.X1A.X2A,
Z1.T1E.T2B.X1A.X2A, Z2.T1E.T2B.X1A.X2A,
Z3.T1E.T2B.X1A.X2A, Z4.T1E.T2B.X1A.X2A,
Z1.T1F.T2B.X1A.X2A, Z2.T1F.T2B.X1A.X2A,
Z3.T1F.T2B.X1A.X2A, Z4.T1F.T2B.X1A.X2A,
Z1.T1A.T2C.X1A.X2A, Z2.T1A.T2C.X1A.X2A,
Z3.T1A.T2C.X1A.X2A, Z4.T1A.T2C.X1A.X2A,
Z1.T1B.T2C.X1A.X2A, Z2.T1B.T2C.X1A.X2A,
Z3.T1B.T2C.X1A.X2A, Z4.T1B.T2C.X1A.X2A,
Z1.T1C.T2C.X1A.X2A, Z2.T1C.T2C.X1A.X2A,
Z3.T1C.T2C.X1A.X2A, Z4.T1C.T2C.X1A.X2A,
Z1.T1D.T2C.X1A.X2A, Z2.T1D.T2C.X1A.X2A,
Z3.T1D.T2C.X1A.X2A, Z4.T1D.T2C.X1A.X2A,
Z1.T1E.T2C.X1A.X2A, Z2.T1E.T2C.X1A.X2A,
Z3.T1E.T2C.X1A.X2A, Z4.T1E.T2C.X1A.X2A,
Z1.T1F.T2C.X1A.X2A, Z2.T1F.T2C.X1A.X2A,
Z3.T1F.T2C.X1A.X2A, Z4.T1F.T2C.X1A.X2A,
Z1.T1A.T2D.X1A.X2A, Z2.T1A.T2D.X1A.X2A,
Z3.T1A.T2D.X1A.X2A, Z4.T1A.T2D.X1A.X2A,
Z1.T1B.T2D.X1A.X2A, Z2.T1B.T2D.X1A.X2A,
Z3.T1B.T2D.X1A.X2A, Z4.T1B.T2D.X1A.X2A,
Z1.T1C.T2D.X1A.X2A, Z2.T1C.T2D.X1A.X2A,
Z3.T1C.T2D.X1A.X2A, Z4.T1C.T2D.X1A.X2A,
Z1.T1D.T2D.X1A.X2A, Z2.T1D.T2D.X1A.X2A,
Z3.T1D.T2D.X1A.X2A, Z4.T1D.T2D.X1A.X2A,
Z1.T1E.T2D.X1A.X2A, Z2.T1E.T2D.X1A.X2A,
Z3.T1E.T2D.X1A.X2A, Z4.T1E.T2D.X1A.X2A,
Z1.T1F.T2D.X1A.X2A, Z2.T1F.T2D.X1A.X2A,
Z3.T1F.T2D.X1A.X2A, Z4.T1F.T2D.X1A.X2A,
Z1.T1A.T2E.X1A.X2A, Z2.T1A.T2E.X1A.X2A,
Z3.T1A.T2E.X1A.X2A, Z4.T1A.T2E.X1A.X2A,
Z1.T1B.T2E.X1A.X2A, Z2.T1B.T2E.X1A.X2A,
Z3.T1B.T2E.X1A.X2A, Z4.T1B.T2E.X1A.X2A,
Z1.T1C.T2E.X1A.X2A, Z2.T1C.T2E.X1A.X2A,
Z3.T1C.T2E.X1A.X2A, Z4.T1C.T2E.X1A.X2A,
Z1.T1D.T2E.X1A.X2A, Z2.T1D.T2E.X1A.X2A,
Z3.T1D.T2E.X1A.X2A, Z4.T1D.T2E.X1A.X2A,
Z1.T1E.T2E.X1A.X2A, Z2.T1E.T2E.X1A.X2A,
Z3.T1E.T2E.X1A.X2A, Z4.T1E.T2E.X1A.X2A,
Z1.T1F.T2E.X1A.X2A, Z2.T1F.T2E.X1A.X2A,
Z3.T1F.T2E.X1A.X2A, Z4.T1F.T2E.X1A.X2A,
Z1.T1A.T2F.X1A.X2A, Z2.T1A.T2F.X1A.X2A,
Z3.T1A.T2F.X1A.X2A, Z4.T1A.T2F.X1A.X2A,
Z1.T1B.T2F.X1A.X2A, Z2.T1B.T2F.X1A.X2A,
Z3.T1B.T2F.X1A.X2A, Z4.T1B.T2F.X1A.X2A,
Z1.T1C.T2F.X1A.X2A, Z2.T1C.T2F.X1A.X2A,
Z3.T1C.T2F.X1A.X2A, Z4.T1C.T2F.X1A.X2A,
Z1.T1D.T2F.X1A.X2A, Z2.T1D.T2F.X1A.X2A,
Z3.T1D.T2F.X1A.X2A, Z4.T1D.T2F.X1A.X2A,
Z1.T1E.T2F.X1A.X2A, Z2.T1E.T2F.X1A.X2A,
Z3.T1E.T2F.X1A.X2A, Z4.T1E.T2F.X1A.X2A,
Z1.T1F.T2F.X1A.X2A, Z2.T1F.T2F.X1A.X2A,
Z3.T1F.T2F.X1A.X2A, Z4.T1F.T2F.X1A.X2A,
Z1.T1A.T2A.X1B.X2A, Z2.T1A.T2A.X1B.X2A,
Z3.T1A.T2A.X1B.X2A, Z4.T1A.T2A.X1B.X2A,
Z1.T1B.T2A.X1B.X2A, Z2.T1B.T2A.X1B.X2A,
Z3.T1B.T2A.X1B.X2A, Z4.T1B.T2A.X1B.X2A,
Z1.T1C.T2A.X1B.X2A, Z2.T1C.T2A.X1B.X2A,
Z3.T1C.T2A.X1B.X2A, Z4.T1C.T2A.X1B.X2A,
Z1.T1D.T2A.X1B.X2A, Z2.T1D.T2A.X1B.X2A,
Z3.T1D.T2A.X1B.X2A, Z4.T1D.T2A.X1B.X2A,
Z1.T1E.T2A.X1B.X2A, Z2.T1E.T2A.X1B.X2A,
Z3.T1E.T2A.X1B.X2A, Z4.T1E.T2A.X1B.X2A,
Z1.T1F.T2A.X1B.X2A, Z2.T1F.T2A.X1B.X2A,
Z3.T1F.T2A.X1B.X2A, Z4.T1F.T2A.X1B.X2A,
Z1.T1A.T2B.X1B.X2A, Z2.T1A.T2B.X1B.X2A,
Z3.T1A.T2B.X1B.X2A, Z4.T1A.T2B.X1B.X2A,
Z1.T1B.T2B.X1B.X2A, Z2.T1B.T2B.X1B.X2A,
Z3.T1B.T2B.X1B.X2A, Z4.T1B.T2B.X1B.X2A,
Z1.T1C.T2B.X1B.X2A, Z2.T1C.T2B.X1B.X2A,
Z3.T1C.T2B.X1B.X2A, Z4.T1C.T2B.X1B.X2A,
Z1.T1D.T2B.X1B.X2A, Z2.T1D.T2B.X1B.X2A,
Z3.T1D.T2B.X1B.X2A, Z4.T1D.T2B.X1B.X2A,
Z1.T1E.T2B.X1B.X2A, Z2.T1E.T2B.X1B.X2A,
Z3.T1E.T2B.X1B.X2A, Z4.T1E.T2B.X1B.X2A,
Z1.T1F.T2B.X1B.X2A, Z2.T1F.T2B.X1B.X2A,
Z3.T1F.T2B.X1B.X2A, Z4.T1F.T2B.X1B.X2A,
Z1.T1A.T2C.X1B.X2A, Z2.T1A.T2C.X1B.X2A,
Z3.T1A.T2C.X1B.X2A, Z4.T1A.T2C.X1B.X2A,
Z1.T1B.T2C.X1B.X2A, Z2.T1B.T2C.X1B.X2A,
Z3.T1B.T2C.X1B.X2A, Z4.T1B.T2C.X1B.X2A,
Z1.T1C.T2C.X1B.X2A, Z2.T1C.T2C.X1B.X2A,
Z3.T1C.T2C.X1B.X2A, Z4.T1C.T2C.X1B.X2A,
Z1.T1D.T2C.X1B.X2A, Z2.T1D.T2C.X1B.X2A,
Z3.T1D.T2C.X1B.X2A, Z4.T1D.T2C.X1B.X2A,
Z1.T1E.T2C.X1B.X2A, Z2.T1E.T2C.X1B.X2A,
Z3.T1E.T2C.X1B.X2A, Z4.T1E.T2C.X1B.X2A,
Z1.T1F.T2C.X1B.X2A, Z2.T1F.T2C.X1B.X2A,
Z3.T1F.T2C.X1B.X2A, Z4.T1F.T2C.X1B.X2A,
Z1.T1A.T2D.X1B.X2A, Z2.T1A.T2D.X1B.X2A,
Z3.T1A.T2D.X1B.X2A, Z4.T1A.T2D.X1B.X2A,
Z1.T1B.T2D.X1B.X2A, Z2.T1B.T2D.X1B.X2A,
Z3.T1B.T2D.X1B.X2A, Z4.T1B.T2D.X1B.X2A,
Z1.T1C.T2D.X1B.X2A, Z2.T1C.T2D.X1B.X2A,
Z3.T1C.T2D.X1B.X2A, Z4.T1C.T2D.X1B.X2A,
Z1.T1D.T2D.X1B.X2A, Z2.T1D.T2D.X1B.X2A,
Z3.T1D.T2D.X1B.X2A, Z4.T1D.T2D.X1B.X2A,
Z1.T1E.T2D.X1B.X2A, Z2.T1E.T2D.X1B.X2A,
Z3.T1E.T2D.X1B.X2A, Z4.T1E.T2D.X1B.X2A,
Z1.T1F.T2D.X1B.X2A, Z2.T1F.T2D.X1B.X2A,
Z3.T1F.T2D.X1B.X2A, Z4.T1F.T2D.X1B.X2A,
Z1.T1A.T2E.X1B.X2A, Z2.T1A.T2E.X1B.X2A,
Z3.T1A.T2E.X1B.X2A, Z4.T1A.T2E.X1B.X2A,
Z1.T1B.T2E.X1B.X2A, Z2.T1B.T2E.X1B.X2A,
Z3.T1B.T2E.X1B.X2A, Z4.T1B.T2E.X1B.X2A,
Z1.T1C.T2E.X1B.X2A, Z2.T1C.T2E.X1B.X2A,
Z3.T1C.T2E.X1B.X2A, Z4.T1C.T2E.X1B.X2A,
Z1.T1D.T2E.X1B.X2A, Z2.T1D.T2E.X1B.X2A,
Z3.T1D.T2E.X1B.X2A, Z4.T1D.T2E.X1B.X2A,
Z1.T1E.T2E.X1B.X2A, Z2.T1E.T2E.X1B.X2A,
Z3.T1E.T2E.X1B.X2A, Z4.T1E.T2E.X1B.X2A,
Z1.T1F.T2E.X1B.X2A, Z2.T1F.T2E.X1B.X2A,
Z3.T1F.T2E.X1B.X2A, Z4.T1F.T2E.X1B.X2A,
Z1.T1A.T2F.X1B.X2A, Z2.T1A.T2F.X1B.X2A,
Z3.T1A.T2F.X1B.X2A, Z4.T1A.T2F.X1B.X2A,
Z1.T1B.T2F.X1B.X2A, Z2.T1B.T2F.X1B.X2A,
Z3.T1B.T2F.X1B.X2A, Z4.T1B.T2F.X1B.X2A,
Z1.T1C.T2F.X1B.X2A, Z2.T1C.T2F.X1B.X2A,
Z3.T1C.T2F.X1B.X2A, Z4.T1C.T2F.X1B.X2A,
Z1.T1D.T2F.X1B.X2A, Z2.T1D.T2F.X1B.X2A,
Z3.T1D.T2F.X1B.X2A, Z4.T1D.T2F.X1B.X2A,
Z1.T1E.T2F.X1B.X2A, Z2.T1E.T2F.X1B.X2A,
Z3.T1E.T2F.X1B.X2A, Z4.T1E.T2F.X1B.X2A,
Z1.T1F.T2F.X1B.X2A, Z2.T1F.T2F.X1B.X2A,
Z3.T1F.T2F.X1B.X2A, Z4.T1F.T2F.X1B.X2A,
Z1.T1A.T2A.X1C.X2A, Z2.T1A.T2A.X1C.X2A,
Z3.T1A.T2A.X1C.X2A, Z4.T1A.T2A.X1C.X2A,
Z1.T1B.T2A.X1C.X2A, Z2.T1B.T2A.X1C.X2A,
Z3.T1B.T2A.X1C.X2A, Z4.T1B.T2A.X1C.X2A,
Z1.T1C.T2A.X1C.X2A, Z2.T1C.T2A.X1C.X2A,
Z3.T1C.T2A.X1C.X2A, Z4.T1C.T2A.X1C.X2A,
Z1.T1D.T2A.X1C.X2A, Z2.T1D.T2A.X1C.X2A,
Z3.T1D.T2A.X1C.X2A, Z4.T1D.T2A.X1C.X2A,
Z1.T1E.T2A.X1C.X2A, Z2.T1E.T2A.X1C.X2A,
Z3.T1E.T2A.X1C.X2A, Z4.T1E.T2A.X1C.X2A,

TABLE 6-continued

List of Compound Structures of Formula II

Z1.T1F.T2A.X1C.X2A, Z2.T1F.T2A.X1C.X2A,
Z3.T1F.T2A.X1C.X2A, Z4.T1F.T2A.X1C.X2A,
Z1.T1A.T2B.X1C.X2A, Z2.T1A.T2B.X1C.X2A,
Z3.T1A.T2B.X1C.X2A, Z4.T1A.T2B.X1C.X2A,
Z1.T1B.T2B.X1C.X2A, Z2.T1B.T2B.X1C.X2A,
Z3.T1B.T2B.X1C.X2A, Z4.T1B.T2B.X1C.X2A,
Z1.T1C.T2B.X1C.X2A, Z2.T1C.T2B.X1C.X2A,
Z3.T1C.T2B.X1C.X2A, Z4.T1C.T2B.X1C.X2A,
Z1.T1D.T2B.X1C.X2A, Z2.T1D.T2B.X1C.X2A,
Z3.T1D.T2B.X1C.X2A, Z4.T1D.T2B.X1C.X2A,
Z1.T1E.T2B.X1C.X2A, Z2.T1E.T2B.X1C.X2A,
Z3.T1E.T2B.X1C.X2A, Z4.T1E.T2B.X1C.X2A,
Z1.T1F.T2B.X1C.X2A, Z2.T1F.T2B.X1C.X2A,
Z3.T1F.T2B.X1C.X2A, Z4.T1F.T2B.X1C.X2A,
Z1.T1A.T2C.X1C.X2A, Z2.T1A.T2C.X1C.X2A,
Z3.T1A.T2C.X1C.X2A, Z4.T1A.T2C.X1C.X2A,
Z1.T1B.T2C.X1C.X2A, Z2.T1B.T2C.X1C.X2A,
Z3.T1B.T2C.X1C.X2A, Z4.T1B.T2C.X1C.X2A,
Z1.T1C.T2C.X1C.X2A, Z2.T1C.T2C.X1C.X2A,
Z3.T1C.T2C.X1C.X2A, Z4.T1C.T2C.X1C.X2A,
Z1.T1D.T2C.X1C.X2A, Z2.T1D.T2C.X1C.X2A,
Z3.T1D.T2C.X1C.X2A, Z4.T1D.T2C.X1C.X2A,
Z1.T1E.T2C.X1C.X2A, Z2.T1E.T2C.X1C.X2A,
Z3.T1E.T2C.X1C.X2A, Z4.T1E.T2C.X1C.X2A,
Z1.T1F.T2C.X1C.X2A, Z2.T1F.T2C.X1C.X2A,
Z3.T1F.T2C.X1C.X2A, Z4.T1F.T2C.X1C.X2A,
Z1.T1A.T2D.X1C.X2A, Z2.T1A.T2D.X1C.X2A,
Z3.T1A.T2D.X1C.X2A, Z4.T1A.T2D.X1C.X2A,
Z1.T1B.T2D.X1C.X2A, Z2.T1B.T2D.X1C.X2A,
Z3.T1B.T2D.X1C.X2A, Z4.T1B.T2D.X1C.X2A,
Z1.T1C.T2D.X1C.X2A, Z2.T1C.T2D.X1C.X2A,
Z3.T1C.T2D.X1C.X2A, Z4.T1C.T2D.X1C.X2A,
Z1.T1D.T2D.X1C.X2A, Z2.T1D.T2D.X1C.X2A,
Z3.T1D.T2D.X1C.X2A, Z4.T1D.T2D.X1C.X2A,
Z1.T1E.T2D.X1C.X2A, Z2.T1E.T2D.X1C.X2A,
Z3.T1E.T2D.X1C.X2A, Z4.T1E.T2D.X1C.X2A,
Z1.T1F.T2D.X1C.X2A, Z2.T1F.T2D.X1C.X2A,
Z3.T1F.T2D.X1C.X2A, Z4.T1F.T2D.X1C.X2A,
Z1.T1A.T2E.X1C.X2A, Z2.T1A.T2E.X1C.X2A,
Z3.T1A.T2E.X1C.X2A, Z4.T1A.T2E.X1C.X2A,
Z1.T1B.T2E.X1C.X2A, Z2.T1B.T2E.X1C.X2A,
Z3.T1B.T2E.X1C.X2A, Z4.T1B.T2E.X1C.X2A,
Z1.T1C.T2E.X1C.X2A, Z2.T1C.T2E.X1C.X2A,
Z3.T1C.T2E.X1C.X2A, Z4.T1C.T2E.X1C.X2A,
Z1.T1D.T2E.X1C.X2A, Z2.T1D.T2E.X1C.X2A,
Z3.T1D.T2E.X1C.X2A, Z4.T1D.T2E.X1C.X2A,
Z1.T1E.T2E.X1C.X2A, Z2.T1E.T2E.X1C.X2A,
Z3.T1E.T2E.X1C.X2A, Z4.T1E.T2E.X1C.X2A,
Z1.T1F.T2E.X1C.X2A, Z2.T1F.T2E.X1C.X2A,
Z3.T1F.T2E.X1C.X2A, Z4.T1F.T2E.X1C.X2A,
Z1.T1A.T2F.X1C.X2A, Z2.T1A.T2F.X1C.X2A,
Z3.T1A.T2F.X1C.X2A, Z4.T1A.T2F.X1C.X2A,
Z1.T1B.T2F.X1C.X2A, Z2.T1B.T2F.X1C.X2A,
Z3.T1B.T2F.X1C.X2A, Z4.T1B.T2F.X1C.X2A,
Z1.T1C.T2F.X1C.X2A, Z2.T1C.T2F.X1C.X2A,
Z3.T1C.T2F.X1C.X2A, Z4.T1C.T2F.X1C.X2A,
Z1.T1D.T2F.X1C.X2A, Z2.T1D.T2F.X1C.X2A,
Z3.T1D.T2F.X1C.X2A, Z4.T1D.T2F.X1C.X2A,
Z1.T1E.T2F.X1C.X2A, Z2.T1E.T2F.X1C.X2A,
Z3.T1E.T2F.X1C.X2A, Z4.T1E.T2F.X1C.X2A,
Z1.T1F.T2F.X1C.X2A, Z2.T1F.T2F.X1C.X2A,
Z3.T1F.T2F.X1C.X2A, Z4.T1F.T2F.X1C.X2A,
Z1.T1A.T2A.X1D.X2A, Z2.T1A.T2A.X1D.X2A,
Z3.T1A.T2A.X1D.X2A, Z4.T1A.T2A.X1D.X2A,
Z1.T1B.T2A.X1D.X2A, Z2.T1B.T2A.X1D.X2A,
Z3.T1B.T2A.X1D.X2A, Z4.T1B.T2A.X1D.X2A,
Z1.T1C.T2A.X1D.X2A, Z2.T1C.T2A.X1D.X2A,
Z3.T1C.T2A.X1D.X2A, Z4.T1C.T2A.X1D.X2A,
Z1.T1D.T2A.X1D.X2A, Z2.T1D.T2A.X1D.X2A,
Z3.T1D.T2A.X1D.X2A, Z4.T1D.T2A.X1D.X2A,
Z1.T1E.T2A.X1D.X2A, Z2.T1E.T2A.X1D.X2A,
Z3.T1E.T2A.X1D.X2A, Z4.T1E.T2A.X1D.X2A,
Z1.T1F.T2A.X1D.X2A, Z2.T1F.T2A.X1D.X2A,
Z3.T1F.T2A.X1D.X2A, Z4.T1F.T2A.X1D.X2A,
Z1.T1A.T2B.X1D.X2A, Z2.T1A.T2B.X1D.X2A,
Z3.T1A.T2B.X1D.X2A, Z4.T1A.T2B.X1D.X2A,
Z1.T1B.T2B.X1D.X2A, Z2.T1B.T2B.X1D.X2A,
Z3.T1B.T2B.X1D.X2A, Z4.T1B.T2B.X1D.X2A,
Z1.T1C.T2B.X1D.X2A, Z2.T1C.T2B.X1D.X2A,
Z3.T1C.T2B.X1D.X2A, Z4.T1C.T2B.X1D.X2A,
Z1.T1D.T2B.X1D.X2A, Z2.T1D.T2B.X1D.X2A,
Z3.T1D.T2B.X1D.X2A, Z4.T1D.T2B.X1D.X2A,
Z1.T1E.T2B.X1D.X2A, Z2.T1E.T2B.X1D.X2A,
Z3.T1E.T2B.X1D.X2A, Z4.T1E.T2B.X1D.X2A,
Z1.T1F.T2B.X1D.X2A, Z2.T1F.T2B.X1D.X2A,
Z3.T1F.T2B.X1D.X2A, Z4.T1F.T2B.X1D.X2A,
Z1.T1A.T2C.X1D.X2A, Z2.T1A.T2C.X1D.X2A,
Z3.T1A.T2C.X1D.X2A, Z4.T1A.T2C.X1D.X2A,
Z1.T1B.T2C.X1D.X2A, Z2.T1B.T2C.X1D.X2A,
Z3.T1B.T2C.X1D.X2A, Z4.T1B.T2C.X1D.X2A,
Z1.T1C.T2C.X1D.X2A, Z2.T1C.T2C.X1D.X2A,
Z3.T1C.T2C.X1D.X2A, Z4.T1C.T2C.X1D.X2A,
Z1.T1D.T2C.X1D.X2A, Z2.T1D.T2C.X1D.X2A,
Z3.T1D.T2C.X1D.X2A, Z4.T1D.T2C.X1D.X2A,
Z1.T1E.T2C.X1D.X2A, Z2.T1E.T2C.X1D.X2A,
Z3.T1E.T2C.X1D.X2A, Z4.T1E.T2C.X1D.X2A,
Z1.T1F.T2C.X1D.X2A, Z2.T1F.T2C.X1D.X2A,
Z3.T1F.T2C.X1D.X2A, Z4.T1F.T2C.X1D.X2A,
Z1.T1A.T2D.X1D.X2A, Z2.T1A.T2D.X1D.X2A,
Z3.T1A.T2D.X1D.X2A, Z4.T1A.T2D.X1D.X2A,
Z1.T1B.T2D.X1D.X2A, Z2.T1B.T2D.X1D.X2A,
Z3.T1B.T2D.X1D.X2A, Z4.T1B.T2D.X1D.X2A,
Z1.T1C.T2D.X1D.X2A, Z2.T1C.T2D.X1D.X2A,
Z3.T1C.T2D.X1D.X2A, Z4.T1C.T2D.X1D.X2A,
Z1.T1D.T2D.X1D.X2A, Z2.T1D.T2D.X1D.X2A,
Z3.T1D.T2D.X1D.X2A, Z4.T1D.T2D.X1D.X2A,
Z1.T1E.T2D.X1D.X2A, Z2.T1E.T2D.X1D.X2A,
Z3.T1E.T2D.X1D.X2A, Z4.T1E.T2D.X1D.X2A,
Z1.T1F.T2D.X1D.X2A, Z2.T1F.T2D.X1D.X2A,
Z3.T1F.T2D.X1D.X2A, Z4.T1F.T2D.X1D.X2A,
Z1.T1A.T2E.X1D.X2A, Z2.T1A.T2E.X1D.X2A,
Z3.T1A.T2E.X1D.X2A, Z4.T1A.T2E.X1D.X2A,
Z1.T1B.T2E.X1D.X2A, Z2.T1B.T2E.X1D.X2A,
Z3.T1B.T2E.X1D.X2A, Z4.T1B.T2E.X1D.X2A,
Z1.T1C.T2E.X1D.X2A, Z2.T1C.T2E.X1D.X2A,
Z3.T1C.T2E.X1D.X2A, Z4.T1C.T2E.X1D.X2A,
Z1.T1D.T2E.X1D.X2A, Z2.T1D.T2E.X1D.X2A,
Z3.T1D.T2E.X1D.X2A, Z4.T1D.T2E.X1D.X2A,
Z1.T1E.T2E.X1D.X2A, Z2.T1E.T2E.X1D.X2A,
Z3.T1E.T2E.X1D.X2A, Z4.T1E.T2E.X1D.X2A,
Z1.T1F.T2E.X1D.X2A, Z2.T1F.T2E.X1D.X2A,
Z3.T1F.T2E.X1D.X2A, Z4.T1F.T2E.X1D.X2A,
Z1.T1A.T2F.X1D.X2A, Z2.T1A.T2F.X1D.X2A,
Z3.T1A.T2F.X1D.X2A, Z4.T1A.T2F.X1D.X2A,
Z1.T1B.T2F.X1D.X2A, Z2.T1B.T2F.X1D.X2A,
Z3.T1B.T2F.X1D.X2A, Z4.T1B.T2F.X1D.X2A,
Z1.T1C.T2F.X1D.X2A, Z2.T1C.T2F.X1D.X2A,
Z3.T1C.T2F.X1D.X2A, Z4.T1C.T2F.X1D.X2A,
Z1.T1D.T2F.X1D.X2A, Z2.T1D.T2F.X1D.X2A,
Z3.T1D.T2F.X1D.X2A, Z4.T1D.T2F.X1D.X2A,
Z1.T1E.T2F.X1D.X2A, Z2.T1E.T2F.X1D.X2A,
Z3.T1E.T2F.X1D.X2A, Z4.T1E.T2F.X1D.X2A,
Z1.T1F.T2F.X1D.X2A, Z2.T1F.T2F.X1D.X2A,
Z3.T1F.T2F.X1D.X2A, Z4.T1F.T2F.X1D.X2A,
Z1.T1A.T2A.X1E.X2A, Z2.T1A.T2A.X1E.X2A,
Z3.T1A.T2A.X1E.X2A, Z4.T1A.T2A.X1E.X2A,
Z1.T1B.T2A.X1E.X2A, Z2.T1B.T2A.X1E.X2A,
Z3.T1B.T2A.X1E.X2A, Z4.T1B.T2A.X1E.X2A,
Z1.T1C.T2A.X1E.X2A, Z2.T1C.T2A.X1E.X2A,
Z3.T1C.T2A.X1E.X2A, Z4.T1C.T2A.X1E.X2A,
Z1.T1D.T2A.X1E.X2A, Z2.T1D.T2A.X1E.X2A,
Z3.T1D.T2A.X1E.X2A, Z4.T1D.T2A.X1E.X2A,
Z1.T1E.T2A.X1E.X2A, Z2.T1E.T2A.X1E.X2A,
Z3.T1E.T2A.X1E.X2A, Z4.T1E.T2A.X1E.X2A,
Z1.T1F.T2A.X1E.X2A, Z2.T1F.T2A.X1E.X2A,
Z3.T1F.T2A.X1E.X2A, Z4.T1F.T2A.X1E.X2A,
Z1.T1A.T2B.X1E.X2A, Z2.T1A.T2B.X1E.X2A,
Z3.T1A.T2B.X1E.X2A, Z4.T1A.T2B.X1E.X2A,
Z1.T1B.T2B.X1E.X2A, Z2.T1B.T2B.X1E.X2A,
Z3.T1B.T2B.X1E.X2A, Z4.T1B.T2B.X1E.X2A,
Z1.T1C.T2B.X1E.X2A, Z2.T1C.T2B.X1E.X2A,
Z3.T1C.T2B.X1E.X2A, Z4.T1C.T2B.X1E.X2A,
Z1.T1D.T2B.X1E.X2A, Z2.T1D.T2B.X1E.X2A,
Z3.T1D.T2B.X1E.X2A, Z4.T1D.T2B.X1E.X2A,

TABLE 6-continued

List of Compound Structures of Formula II

Z1.T1E.T2B.X1E.X2A, Z2.T1E.T2B.X1E.X2A,
Z3.T1E.T2B.X1E.X2A, Z4.T1E.T2B.X1E.X2A,
Z1.T1F.T2B.X1E.X2A, Z2.T1F.T2B.X1E.X2A,
Z3.T1F.T2B.X1E.X2A, Z4.T1F.T2B.X1E.X2A,
Z1.T1A.T2C.X1E.X2A, Z2.T1A.T2C.X1E.X2A,
Z3.T1A.T2C.X1E.X2A, Z4.T1A.T2C.X1E.X2A,
Z1.T1B.T2C.X1E.X2A, Z2.T1B.T2C.X1E.X2A,
Z3.T1B.T2C.X1E.X2A, Z4.T1B.T2C.X1E.X2A,
Z1.T1C.T2C.X1E.X2A, Z2.T1C.T2C.X1E.X2A,
Z3.T1C.T2C.X1E.X2A, Z4.T1C.T2C.X1E.X2A,
Z1.T1D.T2C.X1E.X2A, Z2.T1D.T2C.X1E.X2A,
Z3.T1D.T2C.X1E.X2A, Z4.T1D.T2C.X1E.X2A,
Z1.T1E.T2C.X1E.X2A, Z2.T1E.T2C.X1E.X2A,
Z3.T1E.T2C.X1E.X2A, Z4.T1E.T2C.X1E.X2A,
Z1.T1F.T2C.X1E.X2A, Z2.T1F.T2C.X1E.X2A,
Z3.T1F.T2C.X1E.X2A, Z4.T1F.T2C.X1E.X2A,
Z1.T1A.T2D.X1E.X2A, Z2.T1A.T2D.X1E.X2A,
Z3.T1A.T2D.X1E.X2A, Z4.T1A.T2D.X1E.X2A,
Z1.T1B.T2D.X1E.X2A, Z2.T1B.T2D.X1E.X2A,
Z3.T1B.T2D.X1E.X2A, Z4.T1B.T2D.X1E.X2A,
Z1.T1C.T2D.X1E.X2A, Z2.T1C.T2D.X1E.X2A,
Z3.T1C.T2D.X1E.X2A, Z4.T1C.T2D.X1E.X2A,
Z1.T1D.T2D.X1E.X2A, Z2.T1D.T2D.X1E.X2A,
Z3.T1D.T2D.X1E.X2A, Z4.T1D.T2D.X1E.X2A,
Z1.T1E.T2D.X1E.X2A, Z2.T1E.T2D.X1E.X2A,
Z3.T1E.T2D.X1E.X2A, Z4.T1E.T2D.X1E.X2A,
Z1.T1F.T2D.X1E.X2A, Z2.T1F.T2D.X1E.X2A,
Z3.T1F.T2D.X1E.X2A, Z4.T1F.T2D.X1E.X2A,
Z1.T1A.T2E.X1E.X2A, Z2.T1A.T2E.X1E.X2A,
Z3.T1A.T2E.X1E.X2A, Z4.T1A.T2E.X1E.X2A,
Z1.T1B.T2E.X1E.X2A, Z2.T1B.T2E.X1E.X2A,
Z3.T1B.T2E.X1E.X2A, Z4.T1B.T2E.X1E.X2A,
Z1.T1C.T2E.X1E.X2A, Z2.T1C.T2E.X1E.X2A,
Z3.T1C.T2E.X1E.X2A, Z4.T1C.T2E.X1E.X2A,
Z1.T1D.T2E.X1E.X2A, Z2.T1D.T2E.X1E.X2A,
Z3.T1D.T2E.X1E.X2A, Z4.T1D.T2E.X1E.X2A,
Z1.T1E.T2E.X1E.X2A, Z2.T1E.T2E.X1E.X2A,
Z3.T1E.T2E.X1E.X2A, Z4.T1E.T2E.X1E.X2A,
Z1.T1F.T2E.X1E.X2A, Z2.T1F.T2E.X1E.X2A,
Z3.T1F.T2E.X1E.X2A, Z4.T1F.T2E.X1E.X2A,
Z1.T1A.T2F.X1E.X2A, Z2.T1A.T2F.X1E.X2A,
Z3.T1A.T2F.X1E.X2A, Z4.T1A.T2F.X1E.X2A,
Z1.T1B.T2F.X1E.X2A, Z2.T1B.T2F.X1E.X2A,
Z3.T1B.T2F.X1E.X2A, Z4.T1B.T2F.X1E.X2A,
Z1.T1C.T2F.X1E.X2A, Z2.T1C.T2F.X1E.X2A,
Z3.T1C.T2F.X1E.X2A, Z4.T1C.T2F.X1E.X2A,
Z1.T1D.T2F.X1E.X2A, Z2.T1D.T2F.X1E.X2A,
Z3.T1D.T2F.X1E.X2A, Z4.T1D.T2F.X1E.X2A,
Z1.T1E.T2F.X1E.X2A, Z2.T1E.T2F.X1E.X2A,
Z3.T1E.T2F.X1E.X2A, Z4.T1E.T2F.X1E.X2A,
Z1.T1F.T2F.X1E.X2A, Z2.T1F.T2F.X1E.X2A,
Z3.T1F.T2F.X1E.X2A, Z4.T1F.T2F.X1E.X2A,
Z1.T1A.T2A.X1F.X2A, Z2.T1A.T2A.X1F.X2A,
Z3.T1A.T2A.X1F.X2A, Z4.T1A.T2A.X1F.X2A,
Z1.T1B.T2A.X1F.X2A, Z2.T1B.T2A.X1F.X2A,
Z3.T1B.T2A.X1F.X2A, Z4.T1B.T2A.X1F.X2A,
Z1.T1C.T2A.X1F.X2A, Z2.T1C.T2A.X1F.X2A,
Z3.T1C.T2A.X1F.X2A, Z4.T1C.T2A.X1F.X2A,
Z1.T1D.T2A.X1F.X2A, Z2.T1D.T2A.X1F.X2A,
Z3.T1D.T2A.X1F.X2A, Z4.T1D.T2A.X1F.X2A,
Z1.T1E.T2A.X1F.X2A, Z2.T1E.T2A.X1F.X2A,
Z3.T1E.T2A.X1F.X2A, Z4.T1E.T2A.X1F.X2A,
Z1.T1F.T2A.X1F.X2A, Z2.T1F.T2A.X1F.X2A,
Z3.T1F.T2A.X1F.X2A, Z4.T1F.T2A.X1F.X2A,
Z1.T1A.T2B.X1F.X2A, Z2.T1A.T2B.X1F.X2A,
Z3.T1A.T2B.X1F.X2A, Z4.T1A.T2B.X1F.X2A,
Z1.T1B.T2B.X1F.X2A, Z2.T1B.T2B.X1F.X2A,
Z3.T1B.T2B.X1F.X2A, Z4.T1B.T2B.X1F.X2A,
Z1.T1C.T2B.X1F.X2A, Z2.T1C.T2B.X1F.X2A,
Z3.T1C.T2B.X1F.X2A, Z4.T1C.T2B.X1F.X2A,
Z1.T1D.T2B.X1F.X2A, Z2.T1D.T2B.X1F.X2A,
Z3.T1D.T2B.X1F.X2A, Z4.T1D.T2B.X1F.X2A,
Z1.T1E.T2B.X1F.X2A, Z2.T1E.T2B.X1F.X2A,
Z3.T1E.T2B.X1F.X2A, Z4.T1E.T2B.X1F.X2A,
Z1.T1F.T2B.X1F.X2A, Z2.T1F.T2B.X1F.X2A,
Z3.T1F.T2B.X1F.X2A, Z4.T1F.T2B.X1F.X2A,
Z1.T1A.T2C.X1F.X2A, Z2.T1A.T2C.X1F.X2A,
Z3.T1A.T2C.X1F.X2A, Z4.T1A.T2C.X1F.X2A,
Z1.T1B.T2C.X1F.X2A, Z2.T1B.T2C.X1F.X2A,
Z3.T1B.T2C.X1F.X2A, Z4.T1B.T2C.X1F.X2A,
Z1.T1C.T2C.X1F.X2A, Z2.T1C.T2C.X1F.X2A,
Z3.T1C.T2C.X1F.X2A, Z4.T1C.T2C.X1F.X2A,
Z1.T1D.T2C.X1F.X2A, Z2.T1D.T2C.X1F.X2A,
Z3.T1D.T2C.X1F.X2A, Z4.T1D.T2C.X1F.X2A,
Z1.T1E.T2C.X1F.X2A, Z2.T1E.T2C.X1F.X2A,
Z3.T1E.T2C.X1F.X2A, Z4.T1E.T2C.X1F.X2A,
Z1.T1F.T2C.X1F.X2A, Z2.T1F.T2C.X1F.X2A,
Z3.T1F.T2C.X1F.X2A, Z4.T1F.T2C.X1F.X2A,
Z1.T1A.T2D.X1F.X2A, Z2.T1A.T2D.X1F.X2A,
Z3.T1A.T2D.X1F.X2A, Z4.T1A.T2D.X1F.X2A,
Z1.T1B.T2D.X1F.X2A, Z2.T1B.T2D.X1F.X2A,
Z3.T1B.T2D.X1F.X2A, Z4.T1B.T2D.X1F.X2A,
Z1.T1C.T2D.X1F.X2A, Z2.T1C.T2D.X1F.X2A,
Z3.T1C.T2D.X1F.X2A, Z4.T1C.T2D.X1F.X2A,
Z1.T1D.T2D.X1F.X2A, Z2.T1D.T2D.X1F.X2A,
Z3.T1D.T2D.X1F.X2A, Z4.T1D.T2D.X1F.X2A,
Z1.T1E.T2D.X1F.X2A, Z2.T1E.T2D.X1F.X2A,
Z3.T1E.T2D.X1F.X2A, Z4.T1E.T2D.X1F.X2A,
Z1.T1F.T2D.X1F.X2A, Z2.T1F.T2D.X1F.X2A,
Z3.T1F.T2D.X1F.X2A, Z4.T1F.T2D.X1F.X2A,
Z1.T1A.T2E.X1F.X2A, Z2.T1A.T2E.X1F.X2A,
Z3.T1A.T2E.X1F.X2A, Z4.T1A.T2E.X1F.X2A,
Z1.T1B.T2E.X1F.X2A, Z2.T1B.T2E.X1F.X2A,
Z3.T1B.T2E.X1F.X2A, Z4.T1B.T2E.X1F.X2A,
Z1.T1C.T2E.X1F.X2A, Z2.T1C.T2E.X1F.X2A,
Z3.T1C.T2E.X1F.X2A, Z4.T1C.T2E.X1F.X2A,
Z1.T1D.T2E.X1F.X2A, Z2.T1D.T2E.X1F.X2A,
Z3.T1D.T2E.X1F.X2A, Z4.T1D.T2E.X1F.X2A,
Z1.T1E.T2E.X1F.X2A, Z2.T1E.T2E.X1F.X2A,
Z3.T1E.T2E.X1F.X2A, Z4.T1E.T2F.X1F.X2A,
Z1.T1F.T2E.X1F.X2A, Z2.T1F.T2E.X1F.X2A,
Z3.T1F.T2E.X1F.X2A, Z4.T1F.T2E.X1F.X2A,
Z1.T1A.T2F.X1F.X2A, Z2.T1A.T2F.X1F.X2A,
Z3.T1A.T2F.X1F.X2A, Z4.T1A.T2F.X1F.X2A,
Z1.T1B.T2F.X1F.X2A, Z2.T1B.T2F.X1F.X2A,
Z3.T1B.T2F.X1F.X2A, Z4.T1B.T2F.X1F.X2A,
Z1.T1C.T2F.X1F.X2A, Z2.T1C.T2F.X1F.X2A,
Z3.T1C.T2F.X1F.X2A, Z4.T1C.T2F.X1F.X2A,
Z1.T1D.T2F.X1F.X2A, Z2.T1D.T2F.X1F.X2A,
Z3.T1D.T2F.X1F.X2A, Z4.T1D.T2F.X1F.X2A,
Z1.T1E.T2F.X1F.X2A, Z2.T1E.T2F.X1F.X2A,
Z3.T1E.T2F.X1F.X2A, Z4.T1E.T2F.X1F.X2A,
Z1.T1F.T2F.X1F.X2A, Z2.T1F.T2F.X1F.X2A,
Z3.T1F.T2F.X1F.X2A, Z4.T1F.T2F.X1F.X2A,
Z1.T1A.T2A.X1A.X2B, Z2.T1A.T2A.X1A.X2B,
Z3.T1A.T2A.X1A.X2B, Z4.T1A.T2A.X1A.X2B,
Z1.T1B.T2A.X1A.X2B, Z2.T1B.T2A.X1A.X2B,
Z3.T1B.T2A.X1A.X2B, Z4.T1B.T2A.X1A.X2B,
Z1.T1C.T2A.X1A.X2B, Z2.T1C.T2A.X1A.X2B,
Z3.T1C.T2A.X1A.X2B, Z4.T1C.T2A.X1A.X2B,
Z1.T1D.T2A.X1A.X2B, Z2.T1D.T2A.X1A.X2B,
Z3.T1D.T2A.X1A.X2B, Z4.T1D.T2A.X1A.X2B,
Z1.T1E.T2A.X1A.X2B, Z2.T1E.T2A.X1A.X2B,
Z3.T1E.T2A.X1A.X2B, Z4.T1E.T2A.X1A.X2B,
Z1.T1F.T2A.X1A.X2B, Z2.T1F.T2A.X1A.X2B,
Z3.T1F.T2A.X1A.X2B, Z4.T1F.T2A.X1A.X2B,
Z1.T1A.T2B.X1A.X2B, Z2.T1A.T2B.X1A.X2B,
Z3.T1A.T2B.X1A.X2B, Z4.T1A.T2B.X1A.X2B,
Z1.T1B.T2B.X1A.X2B, Z2.T1B.T2B.X1A.X2B,
Z3.T1B.T2B.X1A.X2B, Z4.T1B.T2B.X1A.X2B,
Z1.T1C.T2B.X1A.X2B, Z2.T1C.T2B.X1A.X2B,
Z3.T1C.T2B.X1A.X2B, Z4.T1C.T2B.X1A.X2B,
Z1.T1D.T2B.X1A.X2B, Z2.T1D.T2B.X1A.X2B,
Z3.T1D.T2B.X1A.X2B, Z4.T1D.T2B.X1A.X2B,
Z1.T1E.T2B.X1A.X2B, Z2.T1E.T2B.X1A.X2B,
Z3.T1E.T2B.X1A.X2B, Z4.T1E.T2B.X1A.X2B,
Z1.T1F.T2B.X1A.X2B, Z2.T1F.T2B.X1A.X2B,
Z3.T1F.T2B.X1A.X2B, Z4.T1F.T2B.X1A.X2B,
Z1.T1A.T2C.X1A.X2B, Z2.T1A.T2C.X1A.X2B,
Z3.T1A.T2C.X1A.X2B, Z4.T1A.T2C.X1A.X2B,
Z1.T1B.T2C.X1A.X2B, Z2.T1B.T2C.X1A.X2B,
Z3.T1B.T2C.X1A.X2B, Z4.T1B.T2C.X1A.X2B,
Z1.T1C.T2C.X1A.X2B, Z2.T1C.T2C.X1A.X2B,
Z3.T1C.T2C.X1A.X2B, Z4.T1C.T2C.X1A.X2B,

TABLE 6-continued

List of Compound Structures of Formula II

Z1.T1D.T2C.X1A.X2B, Z2.T1D.T2C.X1A.X2B,
Z3.T1D.T2C.X1A.X2B, Z4.T1D.T2C.X1A.X2B,
Z1.T1E.T2C.X1A.X2B, Z2.T1E.T2C.X1A.X2B,
Z3.T1E.T2C.X1A.X2B, Z4.T1E.T2C.X1A.X2B,
Z1.T1F.T2C.X1A.X2B, Z2.T1F.T2C.X1A.X2B,
Z3.T1F.T2C.X1A.X2B, Z4.T1F.T2C.X1A.X2B,
Z1.T1A.T2D.X1A.X2B, Z2.T1A.T2D.X1A.X2B,
Z3.T1A.T2D.X1A.X2B, Z4.T1A.T2D.X1A.X2B,
Z1.T1B.T2D.X1A.X2B, Z2.T1B.T2D.X1A.X2B,
Z3.T1B.T2D.X1A.X2B, Z4.T1B.T2D.X1A.X2B,
Z1.T1C.T2D.X1A.X2B, Z2.T1C.T2D.X1A.X2B,
Z3.T1C.T2D.X1A.X2B, Z4.T1C.T2D.X1A.X2B,
Z1.T1D.T2D.X1A.X2B, Z2.T1D.T2D.X1A.X2B,
Z3.T1D.T2D.X1A.X2B, Z4.T1D.T2D.X1A.X2B,
Z1.T1E.T2D.X1A.X2B, Z2.T1E.T2D.X1A.X2B,
Z3.T1E.T2D.X1A.X2B, Z4.T1E.T2D.X1A.X2B,
Z1.T1F.T2D.X1A.X2B, Z2.T1F.T2D.X1A.X2B,
Z3.T1F.T2D.X1A.X2B, Z4.T1F.T2D.X1A.X2B,
Z1.T1A.T2E.X1A.X2B, Z2.T1A.T2E.X1A.X2B,
Z3.T1A.T2E.X1A.X2B, Z4.T1A.T2E.X1A.X2B,
Z1.T1B.T2E.X1A.X2B, Z2.T1B.T2E.X1A.X2B,
Z3.T1B.T2E.X1A.X2B, Z4.T1B.T2E.X1A.X2B,
Z1.T1C.T2E.X1A.X2B, Z2.T1C.T2E.X1A.X2B,
Z3.T1C.T2E.X1A.X2B, Z4.T1C.T2E.X1A.X2B,
Z1.T1D.T2E.X1A.X2B, Z2.T1D.T2E.X1A.X2B,
Z3.T1D.T2E.X1A.X2B, Z4.T1D.T2E.X1A.X2B,
Z1.T1E.T2E.X1A.X2B, Z2.T1E.T2E.X1A.X2B,
Z3.T1E.T2E.X1A.X2B, Z4.T1E.T2E.X1A.X2B,
Z1.T1F.T2E.X1A.X2B, Z2.T1F.T2E.X1A.X2B,
Z3.T1F.T2E.X1A.X2B, Z4.T1F.T2E.X1A.X2B,
Z1.T1A.T2F.X1A.X2B, Z2.T1A.T2F.X1A.X2B,
Z3.T1A.T2F.X1A.X2B, Z4.T1A.T2F.X1A.X2B,
Z1.T1B.T2F.X1A.X2B, Z2.T1B.T2F.X1A.X2B,
Z3.T1B.T2F.X1A.X2B, Z4.T1B.T2F.X1A.X2B,
Z1.T1C.T2F.X1A.X2B, Z2.T1C.T2F.X1A.X2B,
Z3.T1C.T2F.X1A.X2B, Z4.T1C.T2F.X1A.X2B,
Z1.T1D.T2F.X1A.X2B, Z2.T1D.T2F.X1A.X2B,
Z3.T1D.T2F.X1A.X2B, Z4.T1D.T2F.X1A.X2B,
Z1.T1E.T2F.X1A.X2B, Z2.T1E.T2F.X1A.X2B,
Z3.T1E.T2F.X1A.X2B, Z4.T1E.T2F.X1A.X2B,
Z1.T1F.T2F.X1A.X2B, Z2.T1F.T2F.X1A.X2B,
Z3.T1F.T2F.X1A.X2B, Z4.T1F.T2F.X1A.X2B,
Z1.T1A.T2A.X1B.X2B, Z2.T1A.T2A.X1B.X2B,
Z3.T1A.T2A.X1B.X2B, Z4.T1A.T2A.X1B.X2B,
Z1.T1B.T2A.X1B.X2B, Z2.T1B.T2A.X1B.X2B,
Z3.T1B.T2A.X1B.X2B, Z4.T1B.T2A.X1B.X2B,
Z1.T1C.T2A.X1B.X2B, Z2.T1C.T2A.X1B.X2B,
Z3.T1C.T2A.X1B.X2B, Z4.T1C.T2A.X1B.X2B,
Z1.T1D.T2A.X1B.X2B, Z2.T1D.T2A.X1B.X2B,
Z3.T1D.T2A.X1B.X2B, Z4.T1D.T2A.X1B.X2B,
Z1.T1E.T2A.X1B.X2B, Z2.T1E.T2A.X1B.X2B,
Z3.T1E.T2A.X1B.X2B, Z4.T1E.T2A.X1B.X2B,
Z1.T1F.T2A.X1B.X2B, Z2.T1F.T2A.X1B.X2B,
Z3.T1F.T2A.X1B.X2B, Z4.T1F.T2A.X1B.X2B,
Z1.T1A.T2B.X1B.X2B, Z2.T1A.T2B.X1B.X2B,
Z3.T1A.T2B.X1B.X2B, Z4.T1A.T2B.X1B.X2B,
Z1.T1B.T2B.X1B.X2B, Z2.T1B.T2B.X1B.X2B,
Z3.T1B.T2B.X1B.X2B, Z4.T1B.T2B.X1B.X2B,
Z1.T1C.T2B.X1B.X2B, Z2.T1C.T2B.X1B.X2B,
Z3.T1C.T2B.X1B.X2B, Z4.T1C.T2B.X1B.X2B,
Z1.T1D.T2B.X1B.X2B, Z2.T1D.T2B.X1B.X2B,
Z3.T1D.T2B.X1B.X2B, Z4.T1D.T2B.X1B.X2B,
Z1.T1E.T2B.X1B.X2B, Z2.T1E.T2B.X1B.X2B,
Z3.T1E.T2B.X1B.X2B, Z4.T1E.T2B.X1B.X2B,
Z1.T1F.T2B.X1B.X2B, Z2.T1F.T2B.X1B.X2B,
Z3.T1F.T2B.X1B.X2B, Z4.T1F.T2B.X1B.X2B,
Z1.T1A.T2C.X1B.X2B, Z2.T1A.T2C.X1B.X2B,
Z3.T1A.T2C.X1B.X2B, Z4.T1A.T2C.X1B.X2B,
Z1.T1B.T2C.X1B.X2B, Z2.T1B.T2C.X1B.X2B,
Z3.T1B.T2C.X1B.X2B, Z4.T1B.T2C.X1B.X2B,
Z1.T1C.T2C.X1B.X2B, Z2.T1C.T2C.X1B.X2B,
Z3.T1C.T2C.X1B.X2B, Z4.T1C.T2C.X1B.X2B,
Z1.T1D.T2C.X1B.X2B, Z2.T1D.T2C.X1B.X2B,
Z3.T1D.T2C.X1B.X2B, Z4.T1D.T2C.X1B.X2B,
Z1.T1E.T2C.X1B.X2B, Z2.T1E.T2C.X1B.X2B,
Z3.T1E.T2C.X1B.X2B, Z4.T1E.T2C.X1B.X2B,
Z1.T1F.T2C.X1B.X2B, Z2.T1F.T2C.X1B.X2B,
Z3.T1F.T2C.X1B.X2B, Z4.T1F.T2C.X1B.X2B,
Z1.T1A.T2D.X1B.X2B, Z2.T1A.T2D.X1B.X2B,
Z3.T1A.T2D.X1B.X2B, Z4.T1A.T2D.X1B.X2B,
Z1.T1B.T2D.X1B.X2B, Z2.T1B.T2D.X1B.X2B,
Z3.T1B.T2D.X1B.X2B, Z4.T1B.T2D.X1B.X2B,
Z1.T1C.T2D.X1B.X2B, Z2.T1C.T2D.X1B.X2B,
Z3.T1C.T2D.X1B.X2B, Z4.T1C.T2D.X1B.X2B,
Z1.T1D.T2D.X1B.X2B, Z2.T1D.T2D.X1B.X2B,
Z3.T1D.T2D.X1B.X2B, Z4.T1D.T2D.X1B.X2B,
Z1.T1E.T2D.X1B.X2B, Z2.T1E.T2D.X1B.X2B,
Z3.T1E.T2D.X1B.X2B, Z4.T1E.T2D.X1B.X2B,
Z1.T1F.T2D.X1B.X2B, Z2.T1F.T2D.X1B.X2B,
Z3.T1F.T2D.X1B.X2B, Z4.T1F.T2D.X1B.X2B,
Z1.T1A.T2E.X1B.X2B, Z2.T1A.T2E.X1B.X2B,
Z3.T1A.T2E.X1B.X2B, Z4.T1A.T2E.X1B.X2B,
Z1.T1B.T2E.X1B.X2B, Z2.T1B.T2E.X1B.X2B,
Z3.T1B.T2E.X1B.X2B, Z4.T1B.T2E.X1B.X2B,
Z1.T1C.T2E.X1B.X2B, Z2.T1C.T2E.X1B.X2B,
Z3.T1C.T2E.X1B.X2B, Z4.T1C.T2E.X1B.X2B,
Z1.T1D.T2E.X1B.X2B, Z2.T1D.T2E.X1B.X2B,
Z3.T1D.T2E.X1B.X2B, Z4.T1D.T2E.X1B.X2B,
Z1.T1E.T2E.X1B.X2B, Z2.T1E.T2E.X1B.X2B,
Z3.T1E.T2E.X1B.X2B, Z4.T1E.T2E.X1B.X2B,
Z1.T1F.T2E.X1B.X2B, Z2.T1F.T2E.X1B.X2B,
Z3.T1F.T2E.X1B.X2B, Z4.T1F.T2E.X1B.X2B,
Z1.T1A.T2F.X1B.X2B, Z2.T1A.T2F.X1B.X2B,
Z3.T1A.T2F.X1B.X2B, Z4.T1A.T2F.X1B.X2B,
Z1.T1B.T2F.X1B.X2B, Z2.T1B.T2F.X1B.X2B,
Z3.T1B.T2F.X1B.X2B, Z4.T1B.T2F.X1B.X2B,
Z1.T1C.T2F.X1B.X2B, Z2.T1C.T2F.X1B.X2B,
Z3.T1C.T2F.X1B.X2B, Z4.T1C.T2F.X1B.X2B,
Z1.T1D.T2F.X1B.X2B, Z2.T1D.T2F.X1B.X2B,
Z3.T1D.T2F.X1B.X2B, Z4.T1D.T2F.X1B.X2B,
Z1.T1E.T2F.X1B.X2B, Z2.T1E.T2F.X1B.X2B,
Z3.T1E.T2F.X1B.X2B, Z4.T1E.T2F.X1B.X2B,
Z1.T1F.T2F.X1B.X2B, Z2.T1F.T2F.X1B.X2B,
Z3.T1F.T2F.X1B.X2B, Z4.T1F.T2F.X1B.X2B,
Z1.T1A.T2A.X1C.X2B, Z2.T1A.T2A.X1C.X2B,
Z3.T1A.T2A.X1C.X2B, Z4.T1A.T2A.X1C.X2B,
Z1.T1B.T2A.X1C.X2B, Z2.T1B.T2A.X1C.X2B,
Z3.T1B.T2A.X1C.X2B, Z4.T1B.T2A.X1C.X2B,
Z1.T1C.T2A.X1C.X2B, Z2.T1C.T2A.X1C.X2B,
Z3.T1C.T2A.X1C.X2B, Z4.T1C.T2A.X1C.X2B,
Z1.T1D.T2A.X1C.X2B, Z2.T1D.T2A.X1C.X2B,
Z3.T1D.T2A.X1C.X2B, Z4.T1D.T2A.X1C.X2B,
Z1.T1E.T2A.X1C.X2B, Z2.T1E.T2A.X1C.X2B,
Z3.T1E.T2A.X1C.X2B, Z4.T1E.T2A.X1C.X2B,
Z1.T1F.T2A.X1C.X2B, Z2.T1F.T2A.X1C.X2B,
Z3.T1F.T2A.X1C.X2B, Z4.T1F.T2A.X1C.X2B,
Z1.T1A.T2B.X1C.X2B, Z2.T1A.T2B.X1C.X2B,
Z3.T1A.T2B.X1C.X2B, Z4.T1A.T2B.X1C.X2B,
Z1.T1B.T2B.X1C.X2B, Z2.T1B.T2B.X1C.X2B,
Z3.T1B.T2B.X1C.X2B, Z4.T1B.T2B.X1C.X2B,
Z1.T1C.T2B.X1C.X2B, Z2.T1C.T2B.X1C.X2B,
Z3.T1C.T2B.X1C.X2B, Z4.T1C.T2B.X1C.X2B,
Z1.T1D.T2B.X1C.X2B, Z2.T1D.T2B.X1C.X2B,
Z3.T1D.T2B.X1C.X2B, Z4.T1D.T2B.X1C.X2B,
Z1.T1E.T2B.X1C.X2B, Z2.T1E.T2B.X1C.X2B,
Z3.T1E.T2B.X1C.X2B, Z4.T1E.T2B.X1C.X2B,
Z1.T1F.T2B.X1C.X2B, Z2.T1F.T2B.X1C.X2B,
Z3.T1F.T2B.X1C.X2B, Z4.T1F.T2B.X1C.X2B,
Z1.T1A.T2C.X1C.X2B, Z2.T1A.T2C.X1C.X2B,
Z3.T1A.T2C.X1C.X2B, Z4.T1A.T2C.X1C.X2B,
Z1.T1B.T2C.X1C.X2B, Z2.T1B.T2C.X1C.X2B,
Z3.T1B.T2C.X1C.X2B, Z4.T1B.T2C.X1C.X2B,
Z1.T1C.T2C.X1C.X2B, Z2.T1C.T2C.X1C.X2B,
Z3.T1C.T2C.X1C.X2B, Z4.T1C.T2C.X1C.X2B,
Z1.T1D.T2C.X1C.X2B, Z2.T1D.T2C.X1C.X2B,
Z3.T1D.T2C.X1C.X2B, Z4.T1D.T2C.X1C.X2B,
Z1.T1E.T2C.X1C.X2B, Z2.T1E.T2C.X1C.X2B,
Z3.T1E.T2C.X1C.X2B, Z4.T1E.T2C.X1C.X2B,
Z1.T1F.T2C.X1C.X2B, Z2.T1F.T2C.X1C.X2B,
Z3.T1F.T2C.X1C.X2B, Z4.T1F.T2C.X1C.X2B,
Z1.T1A.T2D.X1C.X2B, Z2.T1A.T2D.X1C.X2B,
Z3.T1A.T2D.X1C.X2B, Z4.T1A.T2D.X1C.X2B,
Z1.T1B.T2D.X1C.X2B, Z2.T1B.T2D.X1C.X2B,
Z3.T1B.T2D.X1C.X2B, Z4.T1B.T2D.X1C.X2B,

TABLE 6-continued

List of Compound Structures of Formula II

Z1.T1C.T2D.X1C.X2B, Z2.T1C.T2D.X1C.X2B,
Z3.T1C.T2D.X1C.X2B, Z4.T1C.T2D.X1C.X2B,
Z1.T1D.T2D.X1C.X2B, Z2.T1D.T2D.X1C.X2B,
Z3.T1D.T2D.X1C.X2B, Z4.T1D.T2D.X1C.X2B,
Z1.T1E.T2D.X1C.X2B, Z2.T1E.T2D.X1C.X2B,
Z3.T1E.T2D.X1C.X2B, Z4.T1E.T2D.X1C.X2B,
Z1.T1F.T2D.X1C.X2B, Z2.T1F.T2D.X1C.X2B,
Z3.T1F.T2D.X1C.X2B, Z4.T1F.T2D.X1C.X2B,
Z1.T1A.T2E.X1C.X2B, Z2.T1A.T2E.X1C.X2B,
Z3.T1A.T2E.X1C.X2B, Z4.T1A.T2E.X1C.X2B,
Z1.T1B.T2E.X1C.X2B, Z2.T1B.T2E.X1C.X2B,
Z3.T1B.T2E.X1C.X2B, Z4.T1B.T2E.X1C.X2B,
Z1.T1C.T2E.X1C.X2B, Z2.T1C.T2E.X1C.X2B,
Z3.T1C.T2E.X1C.X2B, Z4.T1C.T2E.X1C.X2B,
Z1.T1D.T2E.X1C.X2B, Z2.T1D.T2E.X1C.X2B,
Z3.T1D.T2E.X1C.X2B, Z4.T1D.T2E.X1C.X2B,
Z1.T1E.T2E.X1C.X2B, Z2.T1E.T2E.X1C.X2B,
Z3.T1E.T2E.X1C.X2B, Z4.T1E.T2E.X1C.X2B,
Z1.T1F.T2E.X1C.X2B, Z2.T1F.T2E.X1C.X2B,
Z3.T1F.T2E.X1C.X2B, Z4.T1F.T2E.X1C.X2B,
Z1.T1A.T2F.X1C.X2B, Z2.T1A.T2F.X1C.X2B,
Z3.T1A.T2F.X1C.X2B, Z4.T1A.T2F.X1C.X2B,
Z1.T1B.T2F.X1C.X2B, Z2.T1B.T2F.X1C.X2B,
Z3.T1B.T2F.X1C.X2B, Z4.T1B.T2F.X1C.X2B,
Z1.T1C.T2F.X1C.X2B, Z2.T1C.T2F.X1C.X2B,
Z3.T1C.T2F.X1C.X2B, Z4.T1C.T2F.X1C.X2B,
Z1.T1D.T2F.X1C.X2B, Z2.T1D.T2F.X1C.X2B,
Z3.T1D.T2F.X1C.X2B, Z4.T1D.T2F.X1C.X2B,
Z1.T1E.T2F.X1C.X2B, Z2.T1E.T2F.X1C.X2B,
Z3.T1E.T2F.X1C.X2B, Z4.T1E.T2F.X1C.X2B,
Z1.T1F.T2F.X1C.X2B, Z2.T1F.T2F.X1C.X2B,
Z3.T1F.T2F.X1C.X2B, Z4.T1F.T2F.X1C.X2B,
Z1.T1A.T2A.X1D.X2B, Z2.T1A.T2A.X1D.X2B,
Z3.T1A.T2A.X1D.X2B, Z4.T1A.T2A.X1D.X2B,
Z1.T1B.T2A.X1D.X2B, Z2.T1B.T2A.X1D.X2B,
Z3.T1B.T2A.X1D.X2B, Z4.T1B.T2A.X1D.X2B,
Z1.T1C.T2A.X1D.X2B, Z2.T1C.T2A.X1D.X2B,
Z3.T1C.T2A.X1D.X2B, Z4.T1C.T2A.X1D.X2B,
Z1.T1D.T2A.X1D.X2B, Z2.T1D.T2A.X1D.X2B,
Z3.T1D.T2A.X1D.X2B, Z4.T1D.T2A.X1D.X2B,
Z1.T1E.T2A.X1D.X2B, Z2.T1E.T2A.X1D.X2B,
Z3.T1E.T2A.X1D.X2B, Z4.T1E.T2A.X1D.X2B,
Z1.T1F.T2A.X1D.X2B, Z2.T1F.T2A.X1D.X2B,
Z3.T1F.T2A.X1D.X2B, Z4.T1F.T2A.X1D.X2B,
Z1.T1A.T2B.X1D.X2B, Z2.T1A.T2B.X1D.X2B,
Z3.T1A.T2B.X1D.X2B, Z4.T1A.T2B.X1D.X2B,
Z1.T1B.T2B.X1D.X2B, Z2.T1B.T2B.X1D.X2B,
Z3.T1B.T2B.X1D.X2B, Z4.T1B.T2B.X1D.X2B,
Z1.T1C.T2B.X1D.X2B, Z2.T1C.T2B.X1D.X2B,
Z3.T1C.T2B.X1D.X2B, Z4.T1C.T2B.X1D.X2B,
Z1.T1D.T2B.X1D.X2B, Z2.T1D.T2B.X1D.X2B,
Z3.T1D.T2B.X1D.X2B, Z4.T1D.T2B.X1D.X2B,
Z1.T1E.T2B.X1D.X2B, Z2.T1E.T2B.X1D.X2B,
Z3.T1E.T2B.X1D.X2B, Z4.T1E.T2B.X1D.X2B,
Z1.T1F.T2B.X1D.X2B, Z2.T1F.T2B.X1D.X2B,
Z3.T1F.T2B.X1D.X2B, Z4.T1F.T2B.X1D.X2B,
Z1.T1A.T2C.X1D.X2B, Z2.T1A.T2C.X1D.X2B,
Z3.T1A.T2C.X1D.X2B, Z4.T1A.T2C.X1D.X2B,
Z1.T1B.T2C.X1D.X2B, Z2.T1B.T2C.X1D.X2B,
Z3.T1B.T2C.X1D.X2B, Z4.T1B.T2C.X1D.X2B,
Z1.T1C.T2C.X1D.X2B, Z2.T1C.T2C.X1D.X2B,
Z3.T1C.T2C.X1D.X2B, Z4.T1C.T2C.X1D.X2B,
Z1.T1D.T2C.X1D.X2B, Z2.T1D.T2C.X1D.X2B,
Z3.T1D.T2C.X1D.X2B, Z4.T1D.T2C.X1D.X2B,
Z1.T1E.T2C.X1D.X2B, Z2.T1E.T2C.X1D.X2B,
Z3.T1E.T2C.X1D.X2B, Z4.T1E.T2C.X1D.X2B,
Z1.T1F.T2C.X1D.X2B, Z2.T1F.T2C.X1D.X2B,
Z3.T1F.T2C.X1D.X2B, Z4.T1F.T2C.X1D.X2B,
Z1.T1A.T2D.X1D.X2B, Z2.T1A.T2D.X1D.X2B,
Z3.T1A.T2D.X1D.X2B, Z4.T1A.T2D.X1D.X2B,
Z1.T1B.T2D.X1D.X2B, Z2.T1B.T2D.X1D.X2B,
Z3.T1B.T2D.X1D.X2B, Z4.T1B.T2D.X1D.X2B,
Z1.T1C.T2D.X1D.X2B, Z2.T1C.T2D.X1D.X2B,
Z3.T1C.T2D.X1D.X2B, Z4.T1C.T2D.X1D.X2B,
Z1.T1D.T2D.X1D.X2B, Z2.T1D.T2D.X1D.X2B,
Z3.T1D.T2D.X1D.X2B, Z4.T1D.T2D.X1D.X2B,
Z1.T1E.T2D.X1D.X2B, Z2.T1E.T2D.X1D.X2B,
Z3.T1E.T2D.X1D.X2B, Z4.T1E.T2D.X1D.X2B,
Z1.T1F.T2D.X1D.X2B, Z2.T1F.T2D.X1D.X2B,
Z3.T1F.T2D.X1D.X2B, Z4.T1F.T2D.X1D.X2B,
Z1.T1A.T2E.X1D.X2B, Z2.T1A.T2E.X1D.X2B,
Z3.T1A.T2E.X1D.X2B, Z4.T1A.T2E.X1D.X2B,
Z1.T1B.T2E.X1D.X2B, Z2.T1B.T2E.X1D.X2B,
Z3.T1B.T2E.X1D.X2B, Z4.T1B.T2E.X1D.X2B,
Z1.T1C.T2E.X1D.X2B, Z2.T1C.T2E.X1D.X2B,
Z3.T1C.T2E.X1D.X2B, Z4.T1C.T2E.X1D.X2B,
Z1.T1D.T2E.X1D.X2B, Z2.T1D.T2E.X1D.X2B,
Z3.T1D.T2E.X1D.X2B, Z4.T1D.T2E.X1D.X2B,
Z1.T1E.T2E.X1D.X2B, Z2.T1E.T2E.X1D.X2B,
Z3.T1E.T2E.X1D.X2B, Z4.T1E.T2E.X1D.X2B,
Z1.T1F.T2E.X1D.X2B, Z2.T1F.T2E.X1D.X2B,
Z3.T1F.T2E.X1D.X2B, Z4.T1F.T2E.X1D.X2B,
Z1.T1A.T2F.X1D.X2B, Z2.T1A.T2F.X1D.X2B,
Z3.T1A.T2F.X1D.X2B, Z4.T1A.T2F.X1D.X2B,
Z1.T1B.T2F.X1D.X2B, Z2.T1B.T2F.X1D.X2B,
Z3.T1B.T2F.X1D.X2B, Z4.T1B.T2F.X1D.X2B,
Z1.T1C.T2F.X1D.X2B, Z2.T1C.T2F.X1D.X2B,
Z3.T1C.T2F.X1D.X2B, Z4.T1C.T2F.X1D.X2B,
Z1.T1D.T2F.X1D.X2B, Z2.T1D.T2F.X1D.X2B,
Z3.T1D.T2F.X1D.X2B, Z4.T1D.T2F.X1D.X2B,
Z1.T1E.T2F.X1D.X2B, Z2.T1E.T2F.X1D.X2B,
Z3.T1F.T2F.X1D.X2B, Z4.T1E.T2F.X1D.X2B,
Z1.T1F.T2F.X1D.X2B, Z2.T1F.T2F.X1D.X2B,
Z3.T1F.T2F.X1D.X2B, Z4.T1F.T2F.X1D.X2B,
Z1.T1A.T2A.X1E.X2B, Z2.T1A.T2A.X1E.X2B,
Z3.T1A.T2A.X1E.X2B, Z4.T1A.T2A.X1E.X2B,
Z1.T1B.T2A.X1E.X2B, Z2.T1B.T2A.X1E.X2B,
Z3.T1B.T2A.X1E.X2B, Z4.T1B.T2A.X1E.X2B,
Z1.T1C.T2A.X1E.X2B, Z2.T1C.T2A.X1E.X2B,
Z3.T1C.T2A.X1E.X2B, Z4.T1C.T2A.X1E.X2B,
Z1.T1D.T2A.X1E.X2B, Z2.T1D.T2A.X1E.X2B,
Z3.T1D.T2A.X1E.X2B, Z4.T1D.T2A.X1E.X2B,
Z1.T1E.T2A.X1E.X2B, Z2.T1E.T2A.X1E.X2B,
Z3.T1E.T2A.X1E.X2B, Z4.T1E.T2A.X1E.X2B,
Z1.T1F.T2A.X1E.X2B, Z2.T1F.T2A.X1E.X2B,
Z3.T1F.T2A.X1E.X2B, Z4.T1F.T2A.X1E.X2B,
Z1.T1A.T2B.X1E.X2B, Z2.T1A.T2B.X1E.X2B,
Z3.T1A.T2B.X1E.X2B, Z4.T1A.T2B.X1E.X2B,
Z1.T1B.T2B.X1E.X2B, Z2.T1B.T2B.X1E.X2B,
Z3.T1B.T2B.X1E.X2B, Z4.T1B.T2B.X1E.X2B,
Z1.T1C.T2B.X1E.X2B, Z2.T1C.T2B.X1E.X2B,
Z3.T1C.T2B.X1E.X2B, Z4.T1C.T2B.X1E.X2B,
Z1.T1D.T2B.X1E.X2B, Z2.T1D.T2B.X1E.X2B,
Z3.T1D.T2B.X1E.X2B, Z4.T1D.T2B.X1E.X2B,
Z1.T1E.T2B.X1E.X2B, Z2.T1E.T2B.X1E.X2B,
Z3.T1E.T2B.X1E.X2B, Z4.T1E.T2B.X1E.X2B,
Z1.T1F.T2B.X1E.X2B, Z2.T1F.T2B.X1E.X2B,
Z3.T1F.T2B.X1E.X2B, Z4.T1F.T2B.X1E.X2B,
Z1.T1A.T2C.X1E.X2B, Z2.T1A.T2C.X1E.X2B,
Z3.T1A.T2C.X1E.X2B, Z4.T1A.T2C.X1E.X2B,
Z1.T1B.T2C.X1E.X2B, Z2.T1B.T2C.X1E.X2B,
Z3.T1B.T2C.X1E.X2B, Z4.T1B.T2C.X1E.X2B,
Z1.T1C.T2C.X1E.X2B, Z2.T1C.T2C.X1E.X2B,
Z3.T1C.T2C.X1E.X2B, Z4.T1C.T2C.X1E.X2B,
Z1.T1D.T2C.X1E.X2B, Z2.T1D.T2C.X1E.X2B,
Z3.T1D.T2C.X1E.X2B, Z4.T1D.T2C.X1E.X2B,
Z1.T1E.T2C.X1E.X2B, Z2.T1E.T2C.X1E.X2B,
Z3.T1E.T2C.X1E.X2B, Z4.T1E.T2C.X1E.X2B,
Z1.T1F.T2C.X1E.X2B, Z2.T1F.T2C.X1E.X2B,
Z3.T1F.T2C.X1E.X2B, Z4.T1F.T2C.X1E.X2B,
Z1.T1A.T2D.X1E.X2B, Z2.T1A.T2D.X1E.X2B,
Z3.T1A.T2D.X1E.X2B, Z4.T1A.T2D.X1E.X2B,
Z1.T1B.T2D.X1E.X2B, Z2.T1B.T2D.X1E.X2B,
Z3.T1B.T2D.X1E.X2B, Z4.T1B.T2D.X1E.X2B,
Z1.T1C.T2D.X1E.X2B, Z2.T1C.T2D.X1E.X2B,
Z3.T1C.T2D.X1E.X2B, Z4.T1C.T2D.X1E.X2B,
Z1.T1D.T2D.X1E.X2B, Z2.T1D.T2D.X1E.X2B,
Z3.T1D.T2D.X1E.X2B, Z4.T1D.T2D.X1E.X2B,
Z1.T1E.T2D.X1E.X2B, Z2.T1E.T2D.X1E.X2B,
Z3.T1E.T2D.X1E.X2B, Z4.T1E.T2D.X1E.X2B,
Z1.T1F.T2D.X1E.X2B, Z2.T1F.T2D.X1E.X2B,
Z3.T1F.T2D.X1E.X2B, Z4.T1F.T2D.X1E.X2B,
Z1.T1A.T2E.X1E.X2B, Z2.T1A.T2E.X1E.X2B,
Z3.T1A.T2E.X1E.X2B, Z4.T1A.T2E.X1E.X2B,

TABLE 6-continued

List of Compound Structures of Formula II

Z1.T1B.T2E.X1E.X2B, Z2.T1B.T2E.X1E.X2B,
Z3.T1B.T2E.X1E.X2B, Z4.T1B.T2E.X1E.X2B,
Z1.T1C.T2E.X1E.X2B, Z2.T1C.T2E.X1E.X2B,
Z3.T1C.T2E.X1E.X2B, Z4.T1C.T2E.X1E.X2B,
Z1.T1D.T2E.X1E.X2B, Z2.T1D.T2E.X1E.X2B,
Z3.T1D.T2E.X1E.X2B, Z4.T1D.T2E.X1E.X2B,
Z1.T1E.T2E.X1E.X2B, Z2.T1E.T2E.X1E.X2B,
Z3.T1E.T2E.X1E.X2B, Z4.T1E.T2E.X1E.X2B,
Z1.T1F.T2E.X1E.X2B, Z2.T1F.T2E.X1E.X2B,
Z3.T1F.T2E.X1E.X2B, Z4.T1F.T2E.X1E.X2B,
Z1.T1A.T2F.X1E.X2B, Z2.T1A.T2F.X1E.X2B,
Z3.T1A.T2F.X1E.X2B, Z4.T1A.T2F.X1E.X2B,
Z1.T1B.T2F.X1E.X2B, Z2.T1B.T2F.X1E.X2B,
Z3.T1B.T2F.X1E.X2B, Z4.T1B.T2F.X1E.X2B,
Z1.T1C.T2F.X1E.X2B, Z2.T1C.T2F.X1E.X2B,
Z3.T1C.T2F.X1E.X2B, Z4.T1C.T2F.X1E.X2B,
Z1.T1D.T2F.X1E.X2B, Z2.T1D.T2F.X1E.X2B,
Z3.T1D.T2F.X1E.X2B, Z4.T1D.T2F.X1E.X2B,
Z1.T1E.T2F.X1E.X2B, Z2.T1E.T2F.X1E.X2B,
Z3.T1E.T2F.X1E.X2B, Z4.T1E.T2F.X1E.X2B,
Z1.T1F.T2F.X1E.X2B, Z2.T1F.T2F.X1E.X2B,
Z3.T1F.T2F.X1E.X2B, Z4.T1F.T2F.X1E.X2B,
Z1.T1A.T2A.X1F.X2B, Z2.T1A.T2A.X1F.X2B,
Z3.T1A.T2A.X1F.X2B, Z4.T1A.T2A.X1F.X2B,
Z1.T1B.T2A.X1F.X2B, Z2.T1B.T2A.X1F.X2B,
Z3.T1B.T2A.X1F.X2B, Z4.T1B.T2A.X1F.X2B,
Z1.T1C.T2A.X1F.X2B, Z2.T1C.T2A.X1F.X2B,
Z3.T1C.T2A.X1F.X2B, Z4.T1C.T2A.X1F.X2B,
Z1.T1D.T2A.X1F.X2B, Z2.T1D.T2A.X1F.X2B,
Z3.T1D.T2A.X1F.X2B, Z4.T1D.T2A.X1F.X2B,
Z1.T1E.T2A.X1F.X2B, Z2.T1E.T2A.X1F.X2B,
Z3.T1E.T2A.X1F.X2B, Z4.T1E.T2A.X1F.X2B,
Z1.T1F.T2A.X1F.X2B, Z2.T1F.T2A.X1F.X2B,
Z3.T1F.T2A.X1F.X2B, Z4.T1F.T2A.X1F.X2B,
Z1.T1A.T2B.X1F.X2B, Z2.T1A.T2B.X1F.X2B,
Z3.T1A.T2B.X1F.X2B, Z4.T1A.T2B.X1F.X2B,
Z1.T1B.T2B.X1F.X2B, Z2.T1B.T2B.X1F.X2B,
Z3.T1B.T2B.X1F.X2B, Z4.T1B.T2B.X1F.X2B,
Z1.T1C.T2B.X1F.X2B, Z2.T1C.T2B.X1F.X2B,
Z3.T1C.T2B.X1F.X2B, Z4.T1C.T2B.X1F.X2B,
Z1.T1D.T2B.X1F.X2B, Z2.T1D.T2B.X1F.X2B,
Z3.T1D.T2B.X1F.X2B, Z4.T1D.T2B.X1F.X2B,
Z1.T1E.T2B.X1F.X2B, Z2.T1E.T2B.X1F.X2B,
Z3.T1E.T2B.X1F.X2B, Z4.T1E.T2B.X1F.X2B,
Z1.T1F.T2B.X1F.X2B, Z2.T1F.T2B.X1F.X2B,
Z3.T1F.T2B.X1F.X2B, Z4.T1F.T2B.X1F.X2B,
Z1.T1A.T2C.X1F.X2B, Z2.T1A.T2C.X1F.X2B,
Z3.T1A.T2C.X1F.X2B, Z4.T1A.T2C.X1F.X2B,
Z1.T1B.T2C.X1F.X2B, Z2.T1B.T2C.X1F.X2B,
Z3.T1B.T2C.X1F.X2B, Z4.T1B.T2C.X1F.X2B,
Z1.T1C.T2C.X1F.X2B, Z2.T1C.T2C.X1F.X2B,
Z3.T1C.T2C.X1F.X2B, Z4.T1C.T2C.X1F.X2B,
Z1.T1D.T2C.X1F.X2B, Z2.T1D.T2C.X1F.X2B,
Z3.T1D.T2C.X1F.X2B, Z4.T1D.T2C.X1F.X2B,
Z1.T1E.T2C.X1F.X2B, Z2.T1E.T2C.X1F.X2B,
Z3.T1E.T2C.X1F.X2B, Z4.T1E.T2C.X1F.X2B,
Z1.T1F.T2C.X1F.X2B, Z2.T1F.T2C.X1F.X2B,
Z3.T1F.T2C.X1F.X2B, Z4.T1F.T2C.X1F.X2B,
Z1.T1A.T2D.X1F.X2B, Z2.T1A.T2D.X1F.X2B,
Z3.T1A.T2D.X1F.X2B, Z4.T1A.T2D.X1F.X2B,
Z1.T1B.T2D.X1F.X2B, Z2.T1B.T2D.X1F.X2B,
Z3.T1B.T2D.X1F.X2B, Z4.T1B.T2D.X1F.X2B,
Z1.T1C.T2D.X1F.X2B, Z2.T1C.T2D.X1F.X2B,
Z3.T1C.T2D.X1F.X2B, Z4.T1C.T2D.X1F.X2B,
Z1.T1D.T2D.X1F.X2B, Z2.T1D.T2D.X1F.X2B,
Z3.T1D.T2D.X1F.X2B, Z4.T1D.T2D.X1F.X2B,
Z1.T1E.T2D.X1F.X2B, Z2.T1E.T2D.X1F.X2B,
Z3.T1E.T2D.X1F.X2B, Z4.T1E.T2D.X1F.X2B,
Z1.T1F.T2D.X1F.X2B, Z2.T1F.T2D.X1F.X2B,
Z3.T1F.T2D.X1F.X2B, Z4.T1F.T2D.X1F.X2B,
Z1.T1A.T2E.X1F.X2B, Z2.T1A.T2E.X1F.X2B,
Z3.T1A.T2E.X1F.X2B, Z4.T1A.T2E.X1F.X2B,
Z1.T1B.T2E.X1F.X2B, Z2.T1B.T2E.X1F.X2B,
Z3.T1B.T2E.X1F.X2B, Z4.T1B.T2E.X1F.X2B,
Z1.T1C.T2E.X1F.X2B, Z2.T1C.T2E.X1F.X2B,
Z3.T1C.T2E.X1F.X2B, Z4.T1C.T2E.X1F.X2B,
Z1.T1D.T2E.X1F.X2B, Z2.T1D.T2E.X1F.X2B,
Z3.T1D.T2E.X1F.X2B, Z4.T1D.T2E.X1F.X2B,
Z1.T1E.T2E.X1F.X2B, Z2.T1E.T2E.X1F.X2B,
Z3.T1E.T2E.X1F.X2B, Z4.T1E.T2E.X1F.X2B,
Z1.T1F.T2E.X1F.X2B, Z2.T1F.T2E.X1F.X2B,
Z3.T1F.T2E.X1F.X2B, Z4.T1F.T2E.X1F.X2B,
Z1.T1A.T2F.X1F.X2B, Z2.T1A.T2F.X1F.X2B,
Z3.T1A.T2F.X1F.X2B, Z4.T1A.T2F.X1F.X2B,
Z1.T1B.T2F.X1F.X2B, Z2.T1B.T2F.X1F.X2B,
Z3.T1B.T2F.X1F.X2B, Z4.T1B.T2F.X1F.X2B,
Z1.T1C.T2F.X1F.X2B, Z2.T1C.T2F.X1F.X2B,
Z3.T1C.T2F.X1F.X2B, Z4.T1C.T2F.X1F.X2B,
Z1.T1D.T2F.X1F.X2B, Z2.T1D.T2F.X1F.X2B,
Z3.T1D.T2F.X1F.X2B, Z4.T1D.T2F.X1F.X2B,
Z1.T1E.T2F.X1F.X2B, Z2.T1E.T2F.X1F.X2B,
Z3.T1E.T2F.X1F.X2B, Z4.T1E.T2F.X1F.X2B,
Z1.T1F.T2F.X1F.X2B, Z2.T1F.T2F.X1F.X2B,
Z3.T1F.T2F.X1F.X2B, Z4.T1F.T2F.X1F.X2B,
Z1.T1A.T2A.X1A.X2C, Z2.T1A.T2A.X1A.X2C,
Z3.T1A.T2A.X1A.X2C, Z4.T1A.T2A.X1A.X2C,
Z1.T1B.T2A.X1A.X2C, Z2.T1B.T2A.X1A.X2C,
Z3.T1B.T2A.X1A.X2C, Z4.T1B.T2A.X1A.X2C,
Z1.T1C.T2A.X1A.X2C, Z2.T1C.T2A.X1A.X2C,
Z3.T1C.T2A.X1A.X2C, Z4.T1C.T2A.X1A.X2C,
Z1.T1D.T2A.X1A.X2C, Z2.T1D.T2A.X1A.X2C,
Z3.T1D.T2A.X1A.X2C, Z4.T1D.T2A.X1A.X2C,
Z1.T1E.T2A.X1A.X2C, Z2.T1E.T2A.X1A.X2C,
Z3.T1E.T2A.X1A.X2C, Z4.T1E.T2A.X1A.X2C,
Z1.T1F.T2A.X1A.X2C, Z2.T1F.T2A.X1A.X2C,
Z3.T1F.T2A.X1A.X2C, Z4.T1F.T2A.X1A.X2C,
Z1.T1A.T2B.X1A.X2C, Z2.T1A.T2B.X1A.X2C,
Z3.T1A.T2B.X1A.X2C, Z4.T1A.T2B.X1A.X2C,
Z1.T1B.T2B.X1A.X2C, Z2.T1B.T2B.X1A.X2C,
Z3.T1B.T2B.X1A.X2C, Z4.T1B.T2B.X1A.X2C,
Z1.T1C.T2B.X1A.X2C, Z2.T1C.T2B.X1A.X2C,
Z3.T1C.T2B.X1A.X2C, Z4.T1C.T2B.X1A.X2C,
Z1.T1D.T2B.X1A.X2C, Z2.T1D.T2B.X1A.X2C,
Z3.T1D.T2B.X1A.X2C, Z4.T1D.T2B.X1A.X2C,
Z1.T1E.T2B.X1A.X2C, Z2.T1E.T2B.X1A.X2C,
Z3.T1E.T2B.X1A.X2C, Z4.T1E.T2B.X1A.X2C,
Z1.T1F.T2B.X1A.X2C, Z2.T1F.T2B.X1A.X2C,
Z3.T1F.T2B.X1A.X2C, Z4.T1F.T2B.X1A.X2C,
Z1.T1A.T2C.X1A.X2C, Z2.T1A.T2C.X1A.X2C,
Z3.T1A.T2C.X1A.X2C, Z4.T1A.T2C.X1A.X2C,
Z1.T1B.T2C.X1A.X2C, Z2.T1B.T2C.X1A.X2C,
Z3.T1B.T2C.X1A.X2C, Z4.T1B.T2C.X1A.X2C,
Z1.T1C.T2C.X1A.X2C, Z2.T1C.T2C.X1A.X2C,
Z3.T1C.T2C.X1A.X2C, Z4.T1C.T2C.X1A.X2C,
Z1.T1D.T2C.X1A.X2C, Z2.T1D.T2C.X1A.X2C,
Z3.T1D.T2C.X1A.X2C, Z4.T1D.T2C.X1A.X2C,
Z1.T1E.T2C.X1A.X2C, Z2.T1E.T2C.X1A.X2C,
Z3.T1E.T2C.X1A.X2C, Z4.T1E.T2C.X1A.X2C,
Z1.T1F.T2C.X1A.X2C, Z2.T1F.T2C.X1A.X2C,
Z3.T1F.T2C.X1A.X2C, Z4.T1F.T2C.X1A.X2C,
Z1.T1A.T2D.X1A.X2C, Z2.T1A.T2D.X1A.X2C,
Z3.T1A.T2D.X1A.X2C, Z4.T1A.T2D.X1A.X2C,
Z1.T1B.T2D.X1A.X2C, Z2.T1B.T2D.X1A.X2C,
Z3.T1B.T2D.X1A.X2C, Z4.T1B.T2D.X1A.X2C,
Z1.T1C.T2D.X1A.X2C, Z2.T1C.T2D.X1A.X2C,
Z3.T1C.T2D.X1A.X2C, Z4.T1C.T2D.X1A.X2C,
Z1.T1D.T2D.X1A.X2C, Z2.T1D.T2D.X1A.X2C,
Z3.T1D.T2D.X1A.X2C, Z4.T1D.T2D.X1A.X2C,
Z1.T1E.T2D.X1A.X2C, Z2.T1E.T2D.X1A.X2C,
Z3.T1E.T2D.X1A.X2C, Z4.T1E.T2D.X1A.X2C,
Z1.T1F.T2D.X1A.X2C, Z2.T1F.T2D.X1A.X2C,
Z3.T1F.T2D.X1A.X2C, Z4.T1F.T2D.X1A.X2C,
Z1.T1A.T2E.X1A.X2C, Z2.T1A.T2E.X1A.X2C,
Z3.T1A.T2E.X1A.X2C, Z4.T1A.T2E.X1A.X2C,
Z1.T1B.T2E.X1A.X2C, Z2.T1B.T2E.X1A.X2C,
Z3.T1B.T2E.X1A.X2C, Z4.T1B.T2E.X1A.X2C,
Z1.T1C.T2E.X1A.X2C, Z2.T1C.T2E.X1A.X2C,
Z3.T1C.T2E.X1A.X2C, Z4.T1C.T2E.X1A.X2C,
Z1.T1D.T2E.X1A.X2C, Z2.T1D.T2E.X1A.X2C,
Z3.T1D.T2E.X1A.X2C, Z4.T1D.T2E.X1A.X2C,
Z1.T1E.T2E.X1A.X2C, Z2.T1E.T2E.X1A.X2C,
Z3.T1E.T2E.X1A.X2C, Z4.T1E.T2E.X1A.X2C,
Z1.T1F.T2E.X1A.X2C, Z2.T1F.T2E.X1A.X2C,
Z3.T1F.T2E.X1A.X2C, Z4.T1F.T2E.X1A.X2C,

TABLE 6-continued

List of Compound Structures of Formula II

Z1.T1A.T2F.X1A.X2C, Z2.T1A.T2F.X1A.X2C,
Z3.T1A.T2F.X1A.X2C, Z4.T1A.T2F.X1A.X2C,
Z1.T1B.T2F.X1A.X2C, Z2.T1B.T2F.X1A.X2C,
Z3.T1B.T2F.X1A.X2C, Z4.T1B.T2F.X1A.X2C,
Z1.T1C.T2F.X1A.X2C, Z2.T1C.T2F.X1A.X2C,
Z3.T1C.T2F.X1A.X2C, Z4.T1C.T2F.X1A.X2C,
Z1.T1D.T2F.X1A.X2C, Z2.T1D.T2F.X1A.X2C,
Z3.T1D.T2F.X1A.X2C, Z4.T1D.T2F.X1A.X2C,
Z1.T1E.T2F.X1A.X2C, Z2.T1E.T2F.X1A.X2C,
Z3.T1E.T2F.X1A.X2C, Z4.T1E.T2F.X1A.X2C,
Z1.T1F.T2F.X1A.X2C, Z2.T1F.T2F.X1A.X2C,
Z3.T1F.T2F.X1A.X2C, Z4.T1F.T2F.X1A.X2C,
Z1.T1A.T2A.X1B.X2C, Z2.T1A.T2A.X1B.X2C,
Z3.T1A.T2A.X1B.X2C, Z4.T1A.T2A.X1B.X2C,
Z1.T1B.T2A.X1B.X2C, Z2.T1B.T2A.X1B.X2C,
Z3.T1B.T2A.X1B.X2C, Z4.T1B.T2A.X1B.X2C,
Z1.T1C.T2A.X1B.X2C, Z2.T1C.T2A.X1B.X2C,
Z3.T1C.T2A.X1B.X2C, Z4.T1C.T2A.X1B.X2C,
Z1.T1D.T2A.X1B.X2C, Z2.T1D.T2A.X1B.X2C,
Z3.T1D.T2A.X1B.X2C, Z4.T1D.T2A.X1B.X2C,
Z1.T1E.T2A.X1B.X2C, Z2.T1E.T2A.X1B.X2C,
Z3.T1E.T2A.X1B.X2C, Z4.T1E.T2A.X1B.X2C,
Z1.T1F.T2A.X1B.X2C, Z2.T1F.T2A.X1B.X2C,
Z3.T1F.T2A.X1B.X2C, Z4.T1F.T2A.X1B.X2C,
Z1.T1A.T2B.X1B.X2C, Z2.T1A.T2B.X1B.X2C,
Z3.T1A.T2B.X1B.X2C, Z4.T1A.T2B.X1B.X2C,
Z1.T1B.T2B.X1B.X2C, Z2.T1B.T2B.X1B.X2C,
Z3.T1B.T2B.X1B.X2C, Z4.T1B.T2B.X1B.X2C,
Z1.T1C.T2B.X1B.X2C, Z2.T1C.T2B.X1B.X2C,
Z3.T1C.T2B.X1B.X2C, Z4.T1C.T2B.X1B.X2C,
Z1.T1D.T2B.X1B.X2C, Z2.T1D.T2B.X1B.X2C,
Z3.T1D.T2B.X1B.X2C, Z4.T1D.T2B.X1B.X2C,
Z1.T1E.T2B.X1B.X2C, Z2.T1E.T2B.X1B.X2C,
Z3.T1E.T2B.X1B.X2C, Z4.T1E.T2B.X1B.X2C,
Z1.T1F.T2B.X1B.X2C, Z2.T1F.T2B.X1B.X2C,
Z3.T1F.T2B.X1B.X2C, Z4.T1F.T2B.X1B.X2C,
Z1.T1A.T2C.X1B.X2C, Z2.T1A.T2C.X1B.X2C,
Z3.T1A.T2C.X1B.X2C, Z4.T1A.T2C.X1B.X2C,
Z1.T1B.T2C.X1B.X2C, Z2.T1B.T2C.X1B.X2C,
Z3.T1B.T2C.X1B.X2C, Z4.T1B.T2C.X1B.X2C,
Z1.T1C.T2C.X1B.X2C, Z2.T1C.T2C.X1B.X2C,
Z3.T1C.T2C.X1B.X2C, Z4.T1C.T2C.X1B.X2C,
Z1.T1D.T2C.X1B.X2C, Z2.T1D.T2C.X1B.X2C,
Z3.T1D.T2C.X1B.X2C, Z4.T1D.T2C.X1B.X2C,
Z1.T1E.T2C.X1B.X2C, Z2.T1E.T2C.X1B.X2C,
Z3.T1E.T2C.X1B.X2C, Z4.T1E.T2C.X1B.X2C,
Z1.T1F.T2C.X1B.X2C, Z2.T1F.T2C.X1B.X2C,
Z3.T1F.T2C.X1B.X2C, Z4.T1F.T2C.X1B.X2C,
Z1.T1A.T2D.X1B.X2C, Z2.T1A.T2D.X1B.X2C,
Z3.T1A.T2D.X1B.X2C, Z4.T1A.T2D.X1B.X2C,
Z1.T1B.T2D.X1B.X2C, Z2.T1B.T2D.X1B.X2C,
Z3.T1B.T2D.X1B.X2C, Z4.T1B.T2D.X1B.X2C,
Z1.T1C.T2D.X1B.X2C, Z2.T1C.T2D.X1B.X2C,
Z3.T1C.T2D.X1B.X2C, Z4.T1C.T2D.X1B.X2C,
Z1.T1D.T2D.X1B.X2C, Z2.T1D.T2D.X1B.X2C,
Z3.T1D.T2D.X1B.X2C, Z4.T1D.T2D.X1B.X2C,
Z1.T1E.T2D.X1B.X2C, Z2.T1E.T2D.X1B.X2C,
Z3.T1E.T2D.X1B.X2C, Z4.T1E.T2D.X1B.X2C,
Z1.T1F.T2D.X1B.X2C, Z2.T1F.T2D.X1B.X2C,
Z3.T1F.T2D.X1B.X2C, Z4.T1F.T2D.X1B.X2C,
Z1.T1A.T2E.X1B.X2C, Z2.T1A.T2E.X1B.X2C,
Z3.T1A.T2E.X1B.X2C, Z4.T1A.T2E.X1B.X2C,
Z1.T1B.T2E.X1B.X2C, Z2.T1B.T2E.X1B.X2C,
Z3.T1B.T2E.X1B.X2C, Z4.T1B.T2E.X1B.X2C,
Z1.T1C.T2E.X1B.X2C, Z2.T1C.T2E.X1B.X2C,
Z3.T1C.T2E.X1B.X2C, Z4.T1C.T2E.X1B.X2C,
Z1.T1D.T2E.X1B.X2C, Z2.T1D.T2E.X1B.X2C,
Z3.T1D.T2E.X1B.X2C, Z4.T1D.T2E.X1B.X2C,
Z1.T1E.T2E.X1B.X2C, Z2.T1E.T2E.X1B.X2C,
Z3.T1E.T2E.X1B.X2C, Z4.T1E.T2E.X1B.X2C,
Z1.T1F.T2E.X1B.X2C, Z2.T1F.T2E.X1B.X2C,
Z3.T1F.T2E.X1B.X2C, Z4.T1F.T2E.X1B.X2C,
Z1.T1A.T2F.X1B.X2C, Z2.T1A.T2F.X1B.X2C,
Z3.T1A.T2F.X1B.X2C, Z4.T1A.T2F.X1B.X2C,
Z1.T1B.T2F.X1B.X2C, Z2.T1B.T2F.X1B.X2C,
Z3.T1B.T2F.X1B.X2C, Z4.T1B.T2F.X1B.X2C,
Z1.T1C.T2F.X1B.X2C, Z2.T1C.T2F.X1B.X2C,
Z3.T1C.T2F.X1B.X2C, Z4.T1C.T2F.X1B.X2C,
Z1.T1D.T2F.X1B.X2C, Z2.T1D.T2F.X1B.X2C,
Z3.T1D.T2F.X1B.X2C, Z4.T1D.T2F.X1B.X2C,
Z1.T1E.T2F.X1B.X2C, Z2.T1E.T2F.X1B.X2C,
Z3.T1E.T2F.X1B.X2C, Z4.T1E.T2F.X1B.X2C,
Z1.T1F.T2F.X1B.X2C, Z2.T1F.T2F.X1B.X2C,
Z3.T1F.T2F.X1B.X2C, Z4.T1F.T2F.X1B.X2C,
Z1.T1A.T2A.X1C.X2C, Z2.T1A.T2A.X1C.X2C,
Z3.T1A.T2A.X1C.X2C, Z4.T1A.T2A.X1C.X2C,
Z1.T1B.T2A.X1C.X2C, Z2.T1B.T2A.X1C.X2C,
Z3.T1B.T2A.X1C.X2C, Z4.T1B.T2A.X1C.X2C,
Z1.T1C.T2A.X1C.X2C, Z2.T1C.T2A.X1C.X2C,
Z3.T1C.T2A.X1C.X2C, Z4.T1C.T2A.X1C.X2C,
Z1.T1D.T2A.X1C.X2C, Z2.T1D.T2A.X1C.X2C,
Z3.T1D.T2A.X1C.X2C, Z4.T1D.T2A.X1C.X2C,
Z1.T1E.T2A.X1C.X2C, Z2.T1E.T2A.X1C.X2C,
Z3.T1E.T2A.X1C.X2C, Z4.T1E.T2A.X1C.X2C,
Z1.T1F.T2A.X1C.X2C, Z2.T1F.T2A.X1C.X2C,
Z3.T1F.T2A.X1C.X2C, Z4.T1F.T2A.X1C.X2C,
Z1.T1A.T2B.X1C.X2C, Z2.T1A.T2B.X1C.X2C,
Z3.T1A.T2B.X1C.X2C, Z4.T1A.T2B.X1C.X2C,
Z1.T1B.T2B.X1C.X2C, Z2.T1B.T2B.X1C.X2C,
Z3.T1B.T2B.X1C.X2C, Z4.T1B.T2B.X1C.X2C,
Z1.T1C.T2B.X1C.X2C, Z2.T1C.T2B.X1C.X2C,
Z3.T1C.T2B.X1C.X2C, Z4.T1C.T2B.X1C.X2C,
Z1.T1D.T2B.X1C.X2C, Z2.T1D.T2B.X1C.X2C,
Z3.T1D.T2B.X1C.X2C, Z4.T1D.T2B.X1C.X2C,
Z1.T1E.T2B.X1C.X2C, Z2.T1E.T2B.X1C.X2C,
Z3.T1E.T2B.X1C.X2C, Z4.T1E.T2B.X1C.X2C,
Z1.T1F.T2B.X1C.X2C, Z2.T1F.T2B.X1C.X2C,
Z3.T1F.T2B.X1C.X2C, Z4.T1F.T2B.X1C.X2C,
Z1.T1A.T2C.X1C.X2C, Z2.T1A.T2C.X1C.X2C,
Z3.T1A.T2C.X1C.X2C, Z4.T1A.T2C.X1C.X2C,
Z1.T1B.T2C.X1C.X2C, Z2.T1B.T2C.X1C.X2C,
Z3.T1B.T2C.X1C.X2C, Z4.T1B.T2C.X1C.X2C,
Z1.T1C.T2C.X1C.X2C, Z2.T1C.T2C.X1C.X2C,
Z3.T1C.T2C.X1C.X2C, Z4.T1C.T2C.X1C.X2C,
Z1.T1D.T2C.X1C.X2C, Z2.T1D.T2C.X1C.X2C,
Z3.T1D.T2C.X1C.X2C, Z4.T1D.T2C.X1C.X2C,
Z1.T1E.T2C.X1C.X2C, Z2.T1E.T2C.X1C.X2C,
Z3.T1E.T2C.X1C.X2C, Z4.T1E.T2C.X1C.X2C,
Z1.T1F.T2C.X1C.X2C, Z2.T1F.T2C.X1C.X2C,
Z3.T1F.T2C.X1C.X2C, Z4.T1F.T2C.X1C.X2C,
Z1.T1A.T2D.X1C.X2C, Z2.T1A.T2D.X1C.X2C,
Z3.T1A.T2D.X1C.X2C, Z4.T1A.T2D.X1C.X2C,
Z1.T1B.T2D.X1C.X2C, Z2.T1B.T2D.X1C.X2C,
Z3.T1B.T2D.X1C.X2C, Z4.T1B.T2D.X1C.X2C,
Z1.T1C.T2D.X1C.X2C, Z2.T1C.T2D.X1C.X2C,
Z3.T1C.T2D.X1C.X2C, Z4.T1C.T2D.X1C.X2C,
Z1.T1D.T2D.X1C.X2C, Z2.T1D.T2D.X1C.X2C,
Z3.T1D.T2D.X1C.X2C, Z4.T1D.T2D.X1C.X2C,
Z1.T1E.T2D.X1C.X2C, Z2.T1E.T2D.X1C.X2C,
Z3.T1E.T2D.X1C.X2C, Z4.T1E.T2D.X1C.X2C,
Z1.T1F.T2D.X1C.X2C, Z2.T1F.T2D.X1C.X2C,
Z3.T1F.T2D.X1C.X2C, Z4.T1F.T2D.X1C.X2C,
Z1.T1A.T2E.X1C.X2C, Z2.T1A.T2E.X1C.X2C,
Z3.T1A.T2E.X1C.X2C, Z4.T1A.T2E.X1C.X2C,
Z1.T1B.T2E.X1C.X2C, Z2.T1B.T2E.X1C.X2C,
Z3.T1B.T2E.X1C.X2C, Z4.T1B.T2E.X1C.X2C,
Z1.T1C.T2E.X1C.X2C, Z2.T1C.T2E.X1C.X2C,
Z3.T1C.T2E.X1C.X2C, Z4.T1C.T2E.X1C.X2C,
Z1.T1D.T2E.X1C.X2C, Z2.T1D.T2E.X1C.X2C,
Z3.T1D.T2E.X1C.X2C, Z4.T1D.T2E.X1C.X2C,
Z1.T1E.T2E.X1C.X2C, Z2.T1E.T2E.X1C.X2C,
Z3.T1E.T2E.X1C.X2C, Z4.T1E.T2E.X1C.X2C,
Z1.T1F.T2E.X1C.X2C, Z2.T1F.T2E.X1C.X2C,
Z3.T1F.T2E.X1C.X2C, Z4.T1F.T2E.X1C.X2C,
Z1.T1A.T2F.X1C.X2C, Z2.T1A.T2F.X1C.X2C,
Z3.T1A.T2F.X1C.X2C, Z4.T1A.T2F.X1C.X2C,
Z1.T1B.T2F.X1C.X2C, Z2.T1B.T2F.X1C.X2C,
Z3.T1B.T2F.X1C.X2C, Z4.T1B.T2F.X1C.X2C,
Z1.T1C.T2F.X1C.X2C, Z2.T1C.T2F.X1C.X2C,
Z3.T1C.T2F.X1C.X2C, Z4.T1C.T2F.X1C.X2C,
Z1.T1D.T2F.X1C.X2C, Z2.T1D.T2F.X1C.X2C,
Z3.T1D.T2F.X1C.X2C, Z4.T1D.T2F.X1C.X2C,
Z1.T1E.T2F.X1C.X2C, Z2.T1E.T2F.X1C.X2C,
Z3.T1E.T2F.X1C.X2C, Z4.T1E.T2F.X1C.X2C,

TABLE 6-continued

List of Compound Structures of Formula II

Z1.T1F.T2F.X1C.X2C, Z2.T1F.T2F.X1C.X2C,
Z3.T1F.T2F.X1C.X2C, Z4.T1F.T2F.X1C.X2C,
Z1.T1A.T2A.X1D.X2C, Z2.T1A.T2A.X1D.X2C,
Z3.T1A.T2A.X1D.X2C, Z4.T1A.T2A.X1D.X2C,
Z1.T1B.T2A.X1D.X2C, Z2.T1B.T2A.X1D.X2C,
Z3.T1B.T2A.X1D.X2C, Z4.T1B.T2A.X1D.X2C,
Z1.T1C.T2A.X1D.X2C, Z2.T1C.T2A.X1D.X2C,
Z3.T1C.T2A.X1D.X2C, Z4.T1C.T2A.X1D.X2C,
Z1.T1D.T2A.X1D.X2C, Z2.T1D.T2A.X1D.X2C,
Z3.T1D.T2A.X1D.X2C, Z4.T1D.T2A.X1D.X2C,
Z1.T1E.T2A.X1D.X2C, Z2.T1E.T2A.X1D.X2C,
Z3.T1E.T2A.X1D.X2C, Z4.T1E.T2A.X1D.X2C,
Z1.T1F.T2A.X1D.X2C, Z2.T1F.T2A.X1D.X2C,
Z3.T1F.T2A.X1D.X2C, Z4.T1F.T2A.X1D.X2C,
Z1.T1A.T2B.X1D.X2C, Z2.T1A.T2B.X1D.X2C,
Z3.T1A.T2B.X1D.X2C, Z4.T1A.T2B.X1D.X2C,
Z1.T1B.T2B.X1D.X2C, Z2.T1B.T2B.X1D.X2C,
Z3.T1B.T2B.X1D.X2C, Z4.T1B.T2B.X1D.X2C,
Z1.T1C.T2B.X1D.X2C, Z2.T1C.T2B.X1D.X2C,
Z3.T1C.T2B.X1D.X2C, Z4.T1C.T2B.X1D.X2C,
Z1.T1D.T2B.X1D.X2C, Z2.T1D.T2B.X1D.X2C,
Z3.T1D.T2B.X1D.X2C, Z4.T1D.T2B.X1D.X2C,
Z1.T1E.T2B.X1D.X2C, Z2.T1E.T2B.X1D.X2C,
Z3.T1E.T2B.X1D.X2C, Z4.T1E.T2B.X1D.X2C,
Z1.T1F.T2B.X1D.X2C, Z2.T1F.T2B.X1D.X2C,
Z3.T1F.T2B.X1D.X2C, Z4.T1F.T2B.X1D.X2C,
Z1.T1A.T2C.X1D.X2C, Z2.T1A.T2C.X1D.X2C,
Z3.T1A.T2C.X1D.X2C, Z4.T1A.T2C.X1D.X2C,
Z1.T1B.T2C.X1D.X2C, Z2.T1B.T2C.X1D.X2C,
Z3.T1B.T2C.X1D.X2C, Z4.T1B.T2C.X1D.X2C,
Z1.T1C.T2C.X1D.X2C, Z2.T1C.T2C.X1D.X2C,
Z3.T1C.T2C.X1D.X2C, Z4.T1C.T2C.X1D.X2C,
Z1.T1D.T2C.X1D.X2C, Z2.T1D.T2C.X1D.X2C,
Z3.T1D.T2C.X1D.X2C, Z4.T1D.T2C.X1D.X2C,
Z1.T1E.T2C.X1D.X2C, Z2.T1E.T2C.X1D.X2C,
Z3.T1E.T2C.X1D.X2C, Z4.T1E.T2C.X1D.X2C,
Z1.T1F.T2C.X1D.X2C, Z2.T1F.T2C.X1D.X2C,
Z3.T1F.T2C.X1D.X2C, Z4.T1F.T2C.X1D.X2C,
Z1.T1A.T2D.X1D.X2C, Z2.T1A.T2D.X1D.X2C,
Z3.T1A.T2D.X1D.X2C, Z4.T1A.T2D.X1D.X2C,
Z1.T1B.T2D.X1D.X2C, Z2.T1B.T2D.X1D.X2C,
Z3.T1B.T2D.X1D.X2C, Z4.T1B.T2D.X1D.X2C,
Z1.T1C.T2D.X1D.X2C, Z2.T1C.T2D.X1D.X2C,
Z3.T1C.T2D.X1D.X2C, Z4.T1C.T2D.X1D.X2C,
Z1.T1D.T2D.X1D.X2C, Z2.T1D.T2D.X1D.X2C,
Z3.T1D.T2D.X1D.X2C, Z4.T1D.T2D.X1D.X2C,
Z1.T1E.T2D.X1D.X2C, Z2.T1E.T2D.X1D.X2C,
Z3.T1E.T2D.X1D.X2C, Z4.T1E.T2D.X1D.X2C,
Z1.T1F.T2D.X1D.X2C, Z2.T1F.T2D.X1D.X2C,
Z3.T1F.T2D.X1D.X2C, Z4.T1F.T2D.X1D.X2C,
Z1.T1A.T2E.X1D.X2C, Z2.T1A.T2E.X1D.X2C,
Z3.T1A.T2E.X1D.X2C, Z4.T1A.T2E.X1D.X2C,
Z1.T1B.T2E.X1D.X2C, Z2.T1B.T2E.X1D.X2C,
Z3.T1B.T2E.X1D.X2C, Z4.T1B.T2E.X1D.X2C,
Z1.T1C.T2E.X1D.X2C, Z2.T1C.T2E.X1D.X2C,
Z3.T1C.T2E.X1D.X2C, Z4.T1C.T2E.X1D.X2C,
Z1.T1D.T2E.X1D.X2C, Z2.T1D.T2E.X1D.X2C,
Z3.T1D.T2E.X1D.X2C, Z4.T1D.T2E.X1D.X2C,
Z1.T1E.T2E.X1D.X2C, Z2.T1E.T2E.X1D.X2C,
Z3.T1E.T2E.X1D.X2C, Z4.T1E.T2E.X1D.X2C,
Z1.T1F.T2E.X1D.X2C, Z2.T1F.T2E.X1D.X2C,
Z3.T1F.T2E.X1D.X2C, Z4.T1F.T2E.X1D.X2C,
Z1.T1A.T2F.X1D.X2C, Z2.T1A.T2F.X1D.X2C,
Z3.T1A.T2F.X1D.X2C, Z4.T1A.T2F.X1D.X2C,
Z1.T1B.T2F.X1D.X2C, Z2.T1B.T2F.X1D.X2C,
Z3.T1B.T2F.X1D.X2C, Z4.T1B.T2F.X1D.X2C,
Z1.T1C.T2F.X1D.X2C, Z2.T1C.T2F.X1D.X2C,
Z3.T1C.T2F.X1D.X2C, Z4.T1C.T2F.X1D.X2C,
Z1.T1D.T2F.X1D.X2C, Z2.T1D.T2F.X1D.X2C,
Z3.T1D.T2F.X1D.X2C, Z4.T1D.T2F.X1D.X2C,
Z1.T1E.T2F.X1D.X2C, Z2.T1E.T2F.X1D.X2C,
Z3.T1E.T2F.X1D.X2C, Z4.T1E.T2F.X1D.X2C,
Z1.T1F.T2F.X1D.X2C, Z2.T1F.T2F.X1D.X2C,
Z3.T1F.T2F.X1D.X2C, Z4.T1F.T2F.X1D.X2C,
Z1.T1A.T2A.X1E.X2C, Z2.T1A.T2A.X1E.X2C,
Z3.T1A.T2A.X1E.X2C, Z4.T1A.T2A.X1E.X2C,
Z1.T1B.T2A.X1E.X2C, Z2.T1B.T2A.X1E.X2C,
Z3.T1B.T2A.X1E.X2C, Z4.T1B.T2A.X1E.X2C,
Z1.T1C.T2A.X1E.X2C, Z2.T1C.T2A.X1E.X2C,
Z3.T1C.T2A.X1E.X2C, Z4.T1C.T2A.X1E.X2C,
Z1.T1D.T2A.X1E.X2C, Z2.T1D.T2A.X1E.X2C,
Z3.T1D.T2A.X1E.X2C, Z4.T1D.T2A.X1E.X2C,
Z1.T1E.T2A.X1E.X2C, Z2.T1E.T2A.X1E.X2C,
Z3.T1E.T2A.X1E.X2C, Z4.T1E.T2A.X1E.X2C,
Z1.T1F.T2A.X1E.X2C, Z2.T1F.T2A.X1E.X2C,
Z3.T1F.T2A.X1E.X2C, Z4.T1F.T2A.X1E.X2C,
Z1.T1A.T2B.X1E.X2C, Z2.T1A.T2B.X1E.X2C,
Z3.T1A.T2B.X1E.X2C, Z4.T1A.T2B.X1E.X2C,
Z1.T1B.T2B.X1E.X2C, Z2.T1B.T2B.X1E.X2C,
Z3.T1B.T2B.X1E.X2C, Z4.T1B.T2B.X1E.X2C,
Z1.T1C.T2B.X1E.X2C, Z2.T1C.T2B.X1E.X2C,
Z3.T1C.T2B.X1E.X2C, Z4.T1C.T2B.X1E.X2C,
Z1.T1D.T2B.X1E.X2C, Z2.T1D.T2B.X1E.X2C,
Z3.T1D.T2B.X1E.X2C, Z4.T1D.T2B.X1E.X2C,
Z1.T1E.T2B.X1E.X2C, Z2.T1E.T2B.X1E.X2C,
Z3.T1E.T2B.X1E.X2C, Z4.T1E.T2B.X1E.X2C,
Z1.T1F.T2B.X1E.X2C, Z2.T1F.T2B.X1E.X2C,
Z3.T1F.T2B.X1E.X2C, Z4.T1F.T2B.X1E.X2C,
Z1.T1A.T2C.X1E.X2C, Z2.T1A.T2C.X1E.X2C,
Z3.T1A.T2C.X1E.X2C, Z4.T1A.T2C.X1E.X2C,
Z1.T1B.T2C.X1E.X2C, Z2.T1B.T2C.X1E.X2C,
Z3.T1B.T2C.X1E.X2C, Z4.T1B.T2C.X1E.X2C,
Z1.T1C.T2C.X1E.X2C, Z2.T1C.T2C.X1E.X2C,
Z3.T1C.T2C.X1E.X2C, Z4.T1C.T2C.X1E.X2C,
Z1.T1D.T2C.X1E.X2C, Z2.T1D.T2C.X1E.X2C,
Z3.T1D.T2C.X1E.X2C, Z4.T1D.T2C.X1E.X2C,
Z1.T1E.T2C.X1E.X2C, Z2.T1E.T2C.X1E.X2C,
Z3.T1E.T2C.X1E.X2C, Z4.T1E.T2C.X1E.X2C,
Z1.T1F.T2C.X1E.X2C, Z2.T1F.T2C.X1E.X2C,
Z3.T1F.T2C.X1E.X2C, Z4.T1F.T2C.X1E.X2C,
Z1.T1A.T2D.X1E.X2C, Z2.T1A.T2D.X1E.X2C,
Z3.T1A.T2D.X1E.X2C, Z4.T1A.T2D.X1E.X2C,
Z1.T1B.T2D.X1E.X2C, Z2.T1B.T2D.X1E.X2C,
Z3.T1B.T2D.X1E.X2C, Z4.T1B.T2D.X1E.X2C,
Z1.T1C.T2D.X1E.X2C, Z2.T1C.T2D.X1E.X2C,
Z3.T1C.T2D.X1E.X2C, Z4.T1C.T2D.X1E.X2C,
Z1.T1D.T2D.X1E.X2C, Z2.T1D.T2D.X1E.X2C,
Z3.T1D.T2D.X1E.X2C, Z4.T1D.T2D.X1E.X2C,
Z1.T1E.T2D.X1E.X2C, Z2.T1E.T2D.X1E.X2C,
Z3.T1E.T2D.X1E.X2C, Z4.T1E.T2D.X1E.X2C,
Z1.T1F.T2D.X1E.X2C, Z2.T1F.T2D.X1E.X2C,
Z3.T1F.T2D.X1E.X2C, Z4.T1F.T2D.X1E.X2C,
Z1.T1A.T2E.X1E.X2C, Z2.T1A.T2E.X1E.X2C,
Z3.T1A.T2E.X1E.X2C, Z4.T1A.T2E.X1E.X2C,
Z1.T1B.T2E.X1E.X2C, Z2.T1B.T2E.X1E.X2C,
Z3.T1B.T2E.X1E.X2C, Z4.T1B.T2E.X1E.X2C,
Z1.T1C.T2E.X1E.X2C, Z2.T1C.T2E.X1E.X2C,
Z3.T1C.T2E.X1E.X2C, Z4.T1C.T2E.X1E.X2C,
Z1.T1D.T2E.X1E.X2C, Z2.T1D.T2E.X1E.X2C,
Z3.T1D.T2E.X1E.X2C, Z4.T1D.T2E.X1E.X2C,
Z1.T1E.T2E.X1E.X2C, Z2.T1E.T2E.X1E.X2C,
Z3.T1E.T2E.X1E.X2C, Z4.T1E.T2E.X1E.X2C,
Z1.T1F.T2E.X1E.X2C, Z2.T1F.T2E.X1E.X2C,
Z3.T1F.T2E.X1E.X2C, Z4.T1F.T2E.X1E.X2C,
Z1.T1A.T2F.X1E.X2C, Z2.T1A.T2F.X1E.X2C,
Z3.T1A.T2F.X1E.X2C, Z4.T1A.T2F.X1E.X2C,
Z1.T1B.T2F.X1E.X2C, Z2.T1B.T2F.X1E.X2C,
Z3.T1B.T2F.X1E.X2C, Z4.T1B.T2F.X1E.X2C,
Z1.T1C.T2F.X1E.X2C, Z2.T1C.T2F.X1E.X2C,
Z3.T1C.T2F.X1E.X2C, Z4.T1C.T2F.X1E.X2C,
Z1.T1D.T2F.X1E.X2C, Z2.T1D.T2F.X1E.X2C,
Z3.T1D.T2F.X1E.X2C, Z4.T1D.T2F.X1E.X2C,
Z1.T1E.T2F.X1E.X2C, Z2.T1E.T2F.X1E.X2C,
Z3.T1E.T2F.X1E.X2C, Z4.T1E.T2F.X1E.X2C,
Z1.T1F.T2F.X1E.X2C, Z2.T1F.T2F.X1E.X2C,
Z3.T1F.T2F.X1E.X2C, Z4.T1F.T2F.X1E.X2C,
Z1.T1A.T2A.X1F.X2C, Z2.T1A.T2A.X1F.X2C,
Z3.T1A.T2A.X1F.X2C, Z4.T1A.T2A.X1F.X2C,
Z1.T1B.T2A.X1F.X2C, Z2.T1B.T2A.X1F.X2C,
Z3.T1B.T2A.X1F.X2C, Z4.T1B.T2A.X1F.X2C,
Z1.T1C.T2A.X1F.X2C, Z2.T1C.T2A.X1F.X2C,
Z3.T1C.T2A.X1F.X2C, Z4.T1C.T2A.X1F.X2C,
Z1.T1D.T2A.X1F.X2C, Z2.T1D.T2A.X1F.X2C,
Z3.T1D.T2A.X1F.X2C, Z4.T1D.T2A.X1F.X2C,

TABLE 6-continued

List of Compound Structures of Formula II

Z1.T1E.T2A.X1F.X2C, Z2.T1E.T2A.X1F.X2C,
Z3.T1E.T2A.X1F.X2C, Z4.T1E.T2A.X1F.X2C,
Z1.T1F.T2A.X1F.X2C, Z2.T1F.T2A.X1F.X2C,
Z3.T1F.T2A.X1F.X2C, Z4.T1F.T2A.X1F.X2C,
Z1.T1A.T2B.X1F.X2C, Z2.T1A.T2B.X1F.X2C,
Z3.T1A.T2B.X1F.X2C, Z4.T1A.T2B.X1F.X2C,
Z1.T1B.T2B.X1F.X2C, Z2.T1B.T2B.X1F.X2C,
Z3.T1B.T2B.X1F.X2C, Z4.T1B.T2B.X1F.X2C,
Z1.T1C.T2B.X1F.X2C, Z2.T1C.T2B.X1F.X2C,
Z3.T1C.T2B.X1F.X2C, Z4.T1C.T2B.X1F.X2C,
Z1.T1D.T2B.X1F.X2C, Z2.T1D.T2B.X1F.X2C,
Z3.T1D.T2B.X1F.X2C, Z4.T1D.T2B.X1F.X2C,
Z1.T1E.T2B.X1F.X2C, Z2.T1E.T2B.X1F.X2C,
Z3.T1E.T2B.X1F.X2C, Z4.T1E.T2B.X1F.X2C,
Z1.T1F.T2B.X1F.X2C, Z2.T1F.T2B.X1F.X2C,
Z3.T1F.T2B.X1F.X2C, Z4.T1F.T2B.X1F.X2C,
Z1.T1A.T2C.X1F.X2C, Z2.T1A.T2C.X1F.X2C,
Z3.T1A.T2C.X1F.X2C, Z4.T1A.T2C.X1F.X2C,
Z1.T1B.T2C.X1F.X2C, Z2.T1B.T2C.X1F.X2C,
Z3.T1B.T2C.X1F.X2C, Z4.T1B.T2C.X1F.X2C,
Z1.T1C.T2C.X1F.X2C, Z2.T1C.T2C.X1F.X2C,
Z3.T1C.T2C.X1F.X2C, Z4.T1C.T2C.X1F.X2C,
Z1.T1D.T2C.X1F.X2C, Z2.T1D.T2C.X1F.X2C,
Z3.T1D.T2C.X1F.X2C, Z4.T1D.T2C.X1F.X2C,
Z1.T1E.T2C.X1F.X2C, Z2.T1E.T2C.X1F.X2C,
Z3.T1E.T2C.X1F.X2C, Z4.T1E.T2C.X1F.X2C,
Z1.T1F.T2C.X1F.X2C, Z2.T1F.T2C.X1F.X2C,
Z3.T1F.T2C.X1F.X2C, Z4.T1F.T2C.X1F.X2C,
Z1.T1A.T2D.X1F.X2C, Z2.T1A.T2D.X1F.X2C,
Z3.T1A.T2D.X1F.X2C, Z4.T1A.T2D.X1F.X2C,
Z1.T1B.T2D.X1F.X2C, Z2.T1B.T2D.X1F.X2C,
Z3.T1B.T2D.X1F.X2C, Z4.T1B.T2D.X1F.X2C,
Z1.T1C.T2D.X1F.X2C, Z2.T1C.T2D.X1F.X2C,
Z3.T1C.T2D.X1F.X2C, Z4.T1C.T2D.X1F.X2C,
Z1.T1D.T2D.X1F.X2C, Z2.T1D.T2D.X1F.X2C,
Z3.T1D.T2D.X1F.X2C, Z4.T1D.T2D.X1F.X2C,
Z1.T1E.T2D.X1F.X2C, Z2.T1E.T2D.X1F.X2C,
Z3.T1E.T2D.X1F.X2C, Z4.T1E.T2D.X1F.X2C,
Z1.T1F.T2D.X1F.X2C, Z2.T1F.T2D.X1F.X2C,
Z3.T1F.T2D.X1F.X2C, Z4.T1F.T2D.X1F.X2C,
Z1.T1A.T2E.X1F.X2C, Z2.T1A.T2E.X1F.X2C,
Z3.T1A.T2E.X1F.X2C, Z4.T1A.T2E.X1F.X2C,
Z1.T1B.T2E.X1F.X2C, Z2.T1B.T2E.X1F.X2C,
Z3.T1B.T2E.X1F.X2C, Z4.T1B.T2E.X1F.X2C,
Z1.T1C.T2E.X1F.X2C, Z2.T1C.T2E.X1F.X2C,
Z3.T1C.T2E.X1F.X2C, Z4.T1C.T2E.X1F.X2C,
Z1.T1D.T2E.X1F.X2C, Z2.T1D.T2E.X1F.X2C,
Z3.T1D.T2E.X1F.X2C, Z4.T1D.T2E.X1F.X2C,
Z1.T1E.T2E.X1F.X2C, Z2.T1E.T2E.X1F.X2C,
Z3.T1E.T2E.X1F.X2C, Z4.T1E.T2E.X1F.X2C,
Z1.T1F.T2E.X1F.X2C, Z2.T1F.T2E.X1F.X2C,
Z3.T1F.T2E.X1F.X2C, Z4.T1F.T2E.X1F.X2C,
Z1.T1A.T2F.X1F.X2C, Z2.T1A.T2F.X1F.X2C,
Z3.T1A.T2F.X1F.X2C, Z4.T1A.T2F.X1F.X2C,
Z1.T1B.T2F.X1F.X2C, Z2.T1B.T2F.X1F.X2C,
Z3.T1B.T2F.X1F.X2C, Z4.T1B.T2F.X1F.X2C,
Z1.T1C.T2F.X1F.X2C, Z2.T1C.T2F.X1F.X2C,
Z3.T1C.T2F.X1F.X2C, Z4.T1C.T2F.X1F.X2C,
Z1.T1D.T2F.X1F.X2C, Z2.T1D.T2F.X1F.X2C,
Z3.T1D.T2F.X1F.X2C, Z4.T1D.T2F.X1F.X2C,
Z1.T1E.T2F.X1F.X2C, Z2.T1E.T2F.X1F.X2C,
Z3.T1E.T2F.X1F.X2C, Z4.T1E.T2F.X1F.X2C,
Z1.T1F.T2F.X1F.X2C, Z2.T1F.T2F.X1F.X2C,
Z3.T1F.T2F.X1F.X2C, Z4.T1F.T2F.X1F.X2C,
Z1.T1A.T2A.X1A.X2D, Z2.T1A.T2A.X1A.X2D,
Z3.T1A.T2A.X1A.X2D, Z4.T1A.T2A.X1A.X2D,
Z1.T1B.T2A.X1A.X2D, Z2.T1B.T2A.X1A.X2D,
Z3.T1B.T2A.X1A.X2D, Z4.T1B.T2A.X1A.X2D,
Z1.T1C.T2A.X1A.X2D, Z2.T1C.T2A.X1A.X2D,
Z3.T1C.T2A.X1A.X2D, Z4.T1C.T2A.X1A.X2D,
Z1.T1D.T2A.X1A.X2D, Z2.T1D.T2A.X1A.X2D,
Z3.T1D.T2A.X1A.X2D, Z4.T1D.T2A.X1A.X2D,
Z1.T1E.T2A.X1A.X2D, Z2.T1E.T2A.X1A.X2D,
Z3.T1E.T2A.X1A.X2D, Z4.T1E.T2A.X1A.X2D,
Z1.T1F.T2A.X1A.X2D, Z2.T1F.T2A.X1A.X2D,
Z3.T1F.T2A.X1A.X2D, Z4.T1F.T2A.X1A.X2D,
Z1.T1A.T2B.X1A.X2D, Z2.T1A.T2B.X1A.X2D,

TABLE 6-continued

List of Compound Structures of Formula II

Z3.T1A.T2B.X1A.X2D, Z4.T1A.T2B.X1A.X2D,
Z1.T1B.T2B.X1A.X2D, Z2.T1B.T2B.X1A.X2D,
Z3.T1B.T2B.X1A.X2D, Z4.T1B.T2B.X1A.X2D,
Z1.T1C.T2B.X1A.X2D, Z2.T1C.T2B.X1A.X2D,
Z3.T1C.T2B.X1A.X2D, Z4.T1C.T2B.X1A.X2D,
Z1.T1D.T2B.X1A.X2D, Z2.T1D.T2B.X1A.X2D,
Z3.T1D.T2B.X1A.X2D, Z4.T1D.T2B.X1A.X2D,
Z1.T1E.T2B.X1A.X2D, Z2.T1E.T2B.X1A.X2D,
Z3.T1E.T2B.X1A.X2D, Z4.T1E.T2B.X1A.X2D,
Z1.T1F.T2B.X1A.X2D, Z2.T1F.T2B.X1A.X2D,
Z3.T1F.T2B.X1A.X2D, Z4.T1F.T2B.X1A.X2D,
Z1.T1A.T2C.X1A.X2D, Z2.T1A.T2C.X1A.X2D,
Z3.T1A.T2C.X1A.X2D, Z4.T1A.T2C.X1A.X2D,
Z1.T1B.T2C.X1A.X2D, Z2.T1B.T2C.X1A.X2D,
Z3.T1B.T2C.X1A.X2D, Z4.T1B.T2C.X1A.X2D,
Z1.T1C.T2C.X1A.X2D, Z2.T1C.T2C.X1A.X2D,
Z3.T1C.T2C.X1A.X2D, Z4.T1C.T2C.X1A.X2D,
Z1.T1D.T2C.X1A.X2D, Z2.T1D.T2C.X1A.X2D,
Z3.T1D.T2C.X1A.X2D, Z4.T1D.T2C.X1A.X2D,
Z1.T1E.T2C.X1A.X2D, Z2.T1E.T2C.X1A.X2D,
Z3.T1E.T2C.X1A.X2D, Z4.T1E.T2C.X1A.X2D,
Z1.T1F.T2C.X1A.X2D, Z2.T1F.T2C.X1A.X2D,
Z3.T1F.T2C.X1A.X2D, Z4.T1F.T2C.X1A.X2D,
Z1.T1A.T2D.X1A.X2D, Z2.T1A.T2D.X1A.X2D,
Z3.T1A.T2D.X1A.X2D, Z4.T1A.T2D.X1A.X2D,
Z1.T1B.T2D.X1A.X2D, Z2.T1B.T2D.X1A.X2D,
Z3.T1B.T2D.X1A.X2D, Z4.T1B.T2D.X1A.X2D,
Z1.T1C.T2D.X1A.X2D, Z2.T1C.T2D.X1A.X2D,
Z3.T1C.T2D.X1A.X2D, Z4.T1C.T2D.X1A.X2D,
Z1.T1D.T2D.X1A.X2D, Z2.T1D.T2D.X1A.X2D,
Z3.T1D.T2D.X1A.X2D, Z4.T1D.T2D.X1A.X2D,
Z1.T1E.T2D.X1A.X2D, Z2.T1E.T2D.X1A.X2D,
Z3.T1E.T2D.X1A.X2D, Z4.T1E.T2D.X1A.X2D,
Z1.T1F.T2D.X1A.X2D, Z2.T1F.T2D.X1A.X2D,
Z3.T1F.T2D.X1A.X2D, Z4.T1F.T2D.X1A.X2D,
Z1.T1A.T2E.X1A.X2D, Z2.T1A.T2E.X1A.X2D,
Z3.T1A.T2E.X1A.X2D, Z4.T1A.T2E.X1A.X2D,
Z1.T1B.T2E.X1A.X2D, Z2.T1B.T2E.X1A.X2D,
Z3.T1B.T2E.X1A.X2D, Z4.T1B.T2E.X1A.X2D,
Z1.T1C.T2E.X1A.X2D, Z2.T1C.T2E.X1A.X2D,
Z3.T1C.T2E.X1A.X2D, Z4.T1C.T2E.X1A.X2D,
Z1.T1D.T2E.X1A.X2D, Z2.T1D.T2E.X1A.X2D,
Z3.T1D.T2E.X1A.X2D, Z4.T1D.T2E.X1A.X2D,
Z1.T1E.T2E.X1A.X2D, Z2.T1E.T2E.X1A.X2D,
Z3.T1E.T2E.X1A.X2D, Z4.T1E.T2E.X1A.X2D,
Z1.T1F.T2E.X1A.X2D, Z2.T1F.T2E.X1A.X2D,
Z3.T1F.T2E.X1A.X2D, Z4.T1F.T2E.X1A.X2D,
Z1.T1A.T2F.X1A.X2D, Z2.T1A.T2F.X1A.X2D,
Z3.T1A.T2F.X1A.X2D, Z4.T1A.T2F.X1A.X2D,
Z1.T1B.T2F.X1A.X2D, Z2.T1B.T2F.X1A.X2D,
Z3.T1B.T2F.X1A.X2D, Z4.T1B.T2F.X1A.X2D,
Z1.T1C.T2F.X1A.X2D, Z2.T1C.T2F.X1A.X2D,
Z3.T1C.T2F.X1A.X2D, Z4.T1C.T2F.X1A.X2D,
Z1.T1D.T2F.X1A.X2D, Z2.T1D.T2F.X1A.X2D,
Z3.T1D.T2F.X1A.X2D, Z4.T1D.T2F.X1A.X2D,
Z1.T1E.T2F.X1A.X2D, Z2.T1E.T2F.X1A.X2D,
Z3.T1E.T2F.X1A.X2D, Z4.T1E.T2F.X1A.X2D,
Z1.T1F.T2F.X1A.X2D, Z2.T1F.T2F.X1A.X2D,
Z3.T1F.T2F.X1A.X2D, Z4.T1F.T2F.X1A.X2D,
Z1.T1A.T2A.X1B.X2D, Z2.T1A.T2A.X1B.X2D,
Z3.T1A.T2A.X1B.X2D, Z4.T1A.T2A.X1B.X2D,
Z1.T1B.T2A.X1B.X2D, Z2.T1B.T2A.X1B.X2D,
Z3.T1B.T2A.X1B.X2D, Z4.T1B.T2A.X1B.X2D,
Z1.T1C.T2A.X1B.X2D, Z2.T1C.T2A.X1B.X2D,
Z3.T1C.T2A.X1B.X2D, Z4.T1C.T2A.X1B.X2D,
Z1.T1D.T2A.X1B.X2D, Z2.T1D.T2A.X1B.X2D,
Z3.T1D.T2A.X1B.X2D, Z4.T1D.T2A.X1B.X2D,
Z1.T1E.T2A.X1B.X2D, Z2.T1E.T2A.X1B.X2D,
Z3.T1E.T2A.X1B.X2D, Z4.T1E.T2A.X1B.X2D,
Z1.T1F.T2A.X1B.X2D, Z2.T1F.T2A.X1B.X2D,
Z3.T1F.T2A.X1B.X2D, Z4.T1F.T2A.X1B.X2D,
Z1.T1A.T2B.X1B.X2D, Z2.T1A.T2B.X1B.X2D,
Z3.T1A.T2B.X1B.X2D, Z4.T1A.T2B.X1B.X2D,
Z1.T1B.T2B.X1B.X2D, Z2.T1B.T2B.X1B.X2D,
Z3.T1B.T2B.X1B.X2D, Z4.T1B.T2B.X1B.X2D,
Z1.T1C.T2B.X1B.X2D, Z2.T1C.T2B.X1B.X2D,
Z3.T1C.T2B.X1B.X2D, Z4.T1C.T2B.X1B.X2D,

TABLE 6-continued

List of Compound Structures of Formula II

Z1.T1D.T2B.X1B.X2D, Z2.T1D.T2B.X1B.X2D,
Z3.T1D.T2B.X1B.X2D, Z4.T1D.T2B.X1B.X2D,
Z1.T1E.T2B.X1B.X2D, Z2.T1E.T2B.X1B.X2D,
Z3.T1E.T2B.X1B.X2D, Z4.T1E.T2B.X1B.X2D,
Z1.T1F.T2B.X1B.X2D, Z2.T1F.T2B.X1B.X2D,
Z3.T1F.T2B.X1B.X2D, Z4.T1F.T2B.X1B.X2D,
Z1.T1A.T2C.X1B.X2D, Z2.T1A.T2C.X1B.X2D,
Z3.T1A.T2C.X1B.X2D, Z4.T1A.T2C.X1B.X2D,
Z1.T1B.T2C.X1B.X2D, Z2.T1B.T2C.X1B.X2D,
Z3.T1B.T2C.X1B.X2D, Z4.T1B.T2C.X1B.X2D,
Z1.T1C.T2C.X1B.X2D, Z2.T1C.T2C.X1B.X2D,
Z3.T1C.T2C.X1B.X2D, Z4.T1C.T2C.X1B.X2D,
Z1.T1D.T2C.X1B.X2D, Z2.T1D.T2C.X1B.X2D,
Z3.T1D.T2C.X1B.X2D, Z4.T1D.T2C.X1B.X2D,
Z1.T1E.T2C.X1B.X2D, Z2.T1E.T2C.X1B.X2D,
Z3.T1E.T2C.X1B.X2D, Z4.T1E.T2C.X1B.X2D,
Z1.T1F.T2C.X1B.X2D, Z2.T1F.T2C.X1B.X2D,
Z3.T1F.T2C.X1B.X2D, Z4.T1F.T2C.X1B.X2D,
Z1.T1A.T2D.X1B.X2D, Z2.T1A.T2D.X1B.X2D,
Z3.T1A.T2D.X1B.X2D, Z4.T1A.T2D.X1B.X2D,
Z1.T1B.T2D.X1B.X2D, Z2.T1B.T2D.X1B.X2D,
Z3.T1B.T2D.X1B.X2D, Z4.T1B.T2D.X1B.X2D,
Z1.T1C.T2D.X1B.X2D, Z2.T1C.T2D.X1B.X2D,
Z3.T1C.T2D.X1B.X2D, Z4.T1C.T2D.X1B.X2D,
Z1.T1D.T2D.X1B.X2D, Z2.T1D.T2D.X1B.X2D,
Z3.T1D.T2D.X1B.X2D, Z4.T1D.T2D.X1B.X2D,
Z1.T1E.T2D.X1B.X2D, Z2.T1E.T2D.X1B.X2D,
Z3.T1E.T2D.X1B.X2D, Z4.T1E.T2D.X1B.X2D,
Z1.T1F.T2D.X1B.X2D, Z2.T1F.T2D.X1B.X2D,
Z3.T1F.T2D.X1B.X2D, Z4.T1F.T2D.X1B.X2D,
Z1.T1A.T2E.X1B.X2D, Z2.T1A.T2E.X1B.X2D,
Z3.T1A.T2E.X1B.X2D, Z4.T1A.T2E.X1B.X2D,
Z1.T1B.T2E.X1B.X2D, Z2.T1B.T2E.X1B.X2D,
Z3.T1B.T2E.X1B.X2D, Z4.T1B.T2E.X1B.X2D,
Z1.T1C.T2E.X1B.X2D, Z2.T1C.T2E.X1B.X2D,
Z3.T1C.T2E.X1B.X2D, Z4.T1C.T2E.X1B.X2D,
Z1.T1D.T2E.X1B.X2D, Z2.T1D.T2E.X1B.X2D,
Z3.T1D.T2E.X1B.X2D, Z4.T1D.T2E.X1B.X2D,
Z1.T1E.T2E.X1B.X2D, Z2.T1E.T2E.X1B.X2D,
Z3.T1E.T2E.X1B.X2D, Z4.T1E.T2E.X1B.X2D,
Z1.T1F.T2E.X1B.X2D, Z2.T1F.T2E.X1B.X2D,
Z3.T1F.T2E.X1B.X2D, Z4.T1F.T2E.X1B.X2D,
Z1.T1A.T2F.X1B.X2D, Z2.T1A.T2F.X1B.X2D,
Z3.T1A.T2F.X1B.X2D, Z4.T1A.T2F.X1B.X2D,
Z1.T1B.T2F.X1B.X2D, Z2.T1B.T2F.X1B.X2D,
Z3.T1B.T2F.X1B.X2D, Z4.T1B.T2F.X1B.X2D,
Z1.T1C.T2F.X1B.X2D, Z2.T1C.T2F.X1B.X2D,
Z3.T1C.T2F.X1B.X2D, Z4.T1C.T2F.X1B.X2D,
Z1.T1D.T2F.X1B.X2D, Z2.T1D.T2F.X1B.X2D,
Z3.T1D.T2F.X1B.X2D, Z4.T1D.T2F.X1B.X2D,
Z1.T1E.T2F.X1B.X2D, Z2.T1E.T2F.X1B.X2D,
Z3.T1E.T2F.X1B.X2D, Z4.T1E.T2F.X1B.X2D,
Z1.T1F.T2F.X1B.X2D, Z2.T1F.T2F.X1B.X2D,
Z3.T1F.T2F.X1B.X2D, Z4.T1F.T2F.X1B.X2D,
Z1.T1A.T2A.X1C.X2D, Z2.T1A.T2A.X1C.X2D,
Z3.T1A.T2A.X1C.X2D, Z4.T1A.T2A.X1C.X2D,
Z1.T1B.T2A.X1C.X2D, Z2.T1B.T2A.X1C.X2D,
Z3.T1B.T2A.X1C.X2D, Z4.T1B.T2A.X1C.X2D,
Z1.T1C.T2A.X1C.X2D, Z2.T1C.T2A.X1C.X2D,
Z3.T1C.T2A.X1C.X2D, Z4.T1C.T2A.X1C.X2D,
Z1.T1D.T2A.X1C.X2D, Z2.T1D.T2A.X1C.X2D,
Z3.T1D.T2A.X1C.X2D, Z4.T1D.T2A.X1C.X2D,
Z1.T1E.T2A.X1C.X2D, Z2.T1E.T2A.X1C.X2D,
Z3.T1E.T2A.X1C.X2D, Z4.T1E.T2A.X1C.X2D,
Z1.T1F.T2A.X1C.X2D, Z2.T1F.T2A.X1C.X2D,
Z3.T1F.T2A.X1C.X2D, Z4.T1F.T2A.X1C.X2D,
Z1.T1A.T2B.X1C.X2D, Z2.T1A.T2B.X1C.X2D,
Z3.T1A.T2B.X1C.X2D, Z4.T1A.T2B.X1C.X2D,
Z1.T1B.T2B.X1C.X2D, Z2.T1B.T2B.X1C.X2D,
Z3.T1B.T2B.X1C.X2D, Z4.T1B.T2B.X1C.X2D,
Z1.T1C.T2B.X1C.X2D, Z2.T1C.T2B.X1C.X2D,
Z3.T1C.T2B.X1C.X2D, Z4.T1C.T2B.X1C.X2D,
Z1.T1D.T2B.X1C.X2D, Z2.T1D.T2B.X1C.X2D,
Z3.T1D.T2B.X1C.X2D, Z4.T1D.T2B.X1C.X2D,
Z1.T1E.T2B.X1C.X2D, Z2.T1E.T2B.X1C.X2D,
Z3.T1E.T2B.X1C.X2D, Z4.T1E.T2B.X1C.X2D,
Z1.T1F.T2B.X1C.X2D, Z2.T1F.T2B.X1C.X2D,
Z3.T1F.T2B.X1C.X2D, Z4.T1F.T2B.X1C.X2D,
Z1.T1A.T2C.X1C.X2D, Z2.T1A.T2C.X1C.X2D,
Z3.T1A.T2C.X1C.X2D, Z4.T1A.T2C.X1C.X2D,
Z1.T1B.T2C.X1C.X2D, Z2.T1B.T2C.X1C.X2D,
Z3.T1B.T2C.X1C.X2D, Z4.T1B.T2C.X1C.X2D,
Z1.T1C.T2C.X1C.X2D, Z2.T1C.T2C.X1C.X2D,
Z3.T1C.T2C.X1C.X2D, Z4.T1C.T2C.X1C.X2D,
Z1.T1D.T2C.X1C.X2D, Z2.T1D.T2C.X1C.X2D,
Z3.T1D.T2C.X1C.X2D, Z4.T1D.T2C.X1C.X2D,
Z1.T1E.T2C.X1C.X2D, Z2.T1E.T2C.X1C.X2D,
Z3.T1E.T2C.X1C.X2D, Z4.T1E.T2C.X1C.X2D,
Z1.T1F.T2C.X1C.X2D, Z2.T1F.T2C.X1C.X2D,
Z3.T1F.T2C.X1C.X2D, Z4.T1F.T2C.X1C.X2D,
Z1.T1A.T2D.X1C.X2D, Z2.T1A.T2D.X1C.X2D,
Z3.T1A.T2D.X1C.X2D, Z4.T1A.T2D.X1C.X2D,
Z1.T1B.T2D.X1C.X2D, Z2.T1B.T2D.X1C.X2D,
Z3.T1B.T2D.X1C.X2D, Z4.T1B.T2D.X1C.X2D,
Z1.T1C.T2D.X1C.X2D, Z2.T1C.T2D.X1C.X2D,
Z3.T1C.T2D.X1C.X2D, Z4.T1C.T2D.X1C.X2D,
Z1.T1D.T2D.X1C.X2D, Z2.T1D.T2D.X1C.X2D,
Z3.T1D.T2D.X1C.X2D, Z4.T1D.T2D.X1C.X2D,
Z1.T1E.T2D.X1C.X2D, Z2.T1E.T2D.X1C.X2D,
Z3.T1E.T2D.X1C.X2D, Z4.T1E.T2D.X1C.X2D,
Z1.T1F.T2D.X1C.X2D, Z2.T1F.T2D.X1C.X2D,
Z3.T1F.T2D.X1C.X2D, Z4.T1F.T2D.X1C.X2D,
Z1.T1A.T2E.X1C.X2D, Z2.T1A.T2E.X1C.X2D,
Z3.T1A.T2E.X1C.X2D, Z4.T1A.T2E.X1C.X2D,
Z1.T1B.T2E.X1C.X2D, Z2.T1B.T2E.X1C.X2D,
Z3.T1B.T2E.X1C.X2D, Z4.T1B.T2E.X1C.X2D,
Z1.T1C.T2E.X1C.X2D, Z2.T1C.T2E.X1C.X2D,
Z3.T1C.T2E.X1C.X2D, Z4.T1C.T2E.X1C.X2D,
Z1.T1D.T2E.X1C.X2D, Z2.T1D.T2E.X1C.X2D,
Z3.T1D.T2E.X1C.X2D, Z4.T1D.T2E.X1C.X2D,
Z1.T1E.T2E.X1C.X2D, Z2.T1E.T2E.X1C.X2D,
Z3.T1E.T2E.X1C.X2D, Z4.T1E.T2E.X1C.X2D,
Z1.T1F.T2E.X1C.X2D, Z2.T1F.T2E.X1C.X2D,
Z3.T1F.T2E.X1C.X2D, Z4.T1F.T2E.X1C.X2D,
Z1.T1A.T2F.X1C.X2D, Z2.T1A.T2F.X1C.X2D,
Z3.T1A.T2F.X1C.X2D, Z4.T1A.T2F.X1C.X2D,
Z1.T1B.T2F.X1C.X2D, Z2.T1B.T2F.X1C.X2D,
Z3.T1B.T2F.X1C.X2D, Z4.T1B.T2F.X1C.X2D,
Z1.T1C.T2F.X1C.X2D, Z2.T1C.T2F.X1C.X2D,
Z3.T1C.T2F.X1C.X2D, Z4.T1C.T2F.X1C.X2D,
Z1.T1D.T2F.X1C.X2D, Z2.T1D.T2F.X1C.X2D,
Z3.T1D.T2F.X1C.X2D, Z4.T1D.T2F.X1C.X2D,
Z1.T1E.T2F.X1C.X2D, Z2.T1E.T2F.X1C.X2D,
Z3.T1E.T2F.X1C.X2D, Z4.T1E.T2F.X1C.X2D,
Z1.T1F.T2F.X1C.X2D, Z2.T1F.T2F.X1C.X2D,
Z3.T1F.T2F.X1C.X2D, Z4.T1F.T2F.X1C.X2D,
Z1.T1A.T2A.X1D.X2D, Z2.T1A.T2A.X1D.X2D,
Z3.T1A.T2A.X1D.X2D, Z4.T1A.T2A.X1D.X2D,
Z1.T1B.T2A.X1D.X2D, Z2.T1B.T2A.X1D.X2D,
Z3.T1B.T2A.X1D.X2D, Z4.T1B.T2A.X1D.X2D,
Z1.T1C.T2A.X1D.X2D, Z2.T1C.T2A.X1D.X2D,
Z3.T1C.T2A.X1D.X2D, Z4.T1C.T2A.X1D.X2D,
Z1.T1D.T2A.X1D.X2D, Z2.T1D.T2A.X1D.X2D,
Z3.T1D.T2A.X1D.X2D, Z4.T1D.T2A.X1D.X2D,
Z1.T1E.T2A.X1D.X2D, Z2.T1E.T2A.X1D.X2D,
Z3.T1E.T2A.X1D.X2D, Z4.T1E.T2A.X1D.X2D,
Z1.T1F.T2A.X1D.X2D, Z2.T1F.T2A.X1D.X2D,
Z3.T1F.T2A.X1D.X2D, Z4.T1F.T2A.X1D.X2D,
Z1.T1A.T2B.X1D.X2D, Z2.T1A.T2B.X1D.X2D,
Z3.T1A.T2B.X1D.X2D, Z4.T1A.T2B.X1D.X2D,
Z1.T1B.T2B.X1D.X2D, Z2.T1B.T2B.X1D.X2D,
Z3.T1B.T2B.X1D.X2D, Z4.T1B.T2B.X1D.X2D,
Z1.T1C.T2B.X1D.X2D, Z2.T1C.T2B.X1D.X2D,
Z3.T1C.T2B.X1D.X2D, Z4.T1C.T2B.X1D.X2D,
Z1.T1D.T2B.X1D.X2D, Z2.T1D.T2B.X1D.X2D,
Z3.T1D.T2B.X1D.X2D, Z4.T1D.T2B.X1D.X2D,
Z1.T1E.T2B.X1D.X2D, Z2.T1E.T2B.X1D.X2D,
Z3.T1E.T2B.X1D.X2D, Z4.T1E.T2B.X1D.X2D,
Z1.T1F.T2B.X1D.X2D, Z2.T1F.T2B.X1D.X2D,
Z3.T1F.T2B.X1D.X2D, Z4.T1F.T2B.X1D.X2D,
Z1.T1A.T2C.X1D.X2D, Z2.T1A.T2C.X1D.X2D,
Z3.T1A.T2C.X1D.X2D, Z4.T1A.T2C.X1D.X2D,
Z1.T1B.T2C.X1D.X2D, Z2.T1B.T2C.X1D.X2D,
Z3.T1B.T2C.X1D.X2D, Z4.T1B.T2C.X1D.X2D,

TABLE 6-continued

List of Compound Structures of Formula II

Z1.T1C.T2C.X1D.X2D, Z2.T1C.T2C.X1D.X2D,
Z3.T1C.T2C.X1D.X2D, Z4.T1C.T2C.X1D.X2D,
Z1.T1D.T2C.X1D.X2D, Z2.T1D.T2C.X1D.X2D,
Z3.T1D.T2C.X1D.X2D, Z4.T1D.T2C.X1D.X2D,
Z1.T1E.T2C.X1D.X2D, Z2.T1E.T2C.X1D.X2D,
Z3.T1E.T2C.X1D.X2D, Z4.T1E.T2C.X1D.X2D,
Z1.T1F.T2C.X1D.X2D, Z2.T1F.T2C.X1D.X2D,
Z3.T1F.T2C.X1D.X2D, Z4.T1F.T2C.X1D.X2D,
Z1.T1A.T2D.X1D.X2D, Z2.T1A.T2D.X1D.X2D,
Z3.T1A.T2D.X1D.X2D, Z4.T1A.T2D.X1D.X2D,
Z1.T1B.T2D.X1D.X2D, Z2.T1B.T2D.X1D.X2D,
Z3.T1B.T2D.X1D.X2D, Z4.T1B.T2D.X1D.X2D,
Z1.T1C.T2D.X1D.X2D, Z2.T1C.T2D.X1D.X2D,
Z3.T1C.T2D.X1D.X2D, Z4.T1C.T2D.X1D.X2D,
Z1.T1D.T2D.X1D.X2D, Z2.T1D.T2D.X1D.X2D,
Z3.T1D.T2D.X1D.X2D, Z4.T1D.T2D.X1D.X2D,
Z1.T1E.T2D.X1D.X2D, Z2.T1E.T2D.X1D.X2D,
Z3.T1E.T2D.X1D.X2D, Z4.T1E.T2D.X1D.X2D,
Z1.T1F.T2D.X1D.X2D, Z2.T1F.T2D.X1D.X2D,
Z3.T1F.T2D.X1D.X2D, Z4.T1F.T2D.X1D.X2D,
Z1.T1A.T2E.X1D.X2D, Z2.T1A.T2E.X1D.X2D,
Z3.T1A.T2E.X1D.X2D, Z4.T1A.T2E.X1D.X2D,
Z1.T1B.T2E.X1D.X2D, Z2.T1B.T2E.X1D.X2D,
Z3.T1B.T2E.X1D.X2D, Z4.T1B.T2E.X1D.X2D,
Z1.T1C.T2E.X1D.X2D, Z2.T1C.T2E.X1D.X2D,
Z3.T1C.T2E.X1D.X2D, Z4.T1C.T2E.X1D.X2D,
Z1.T1D.T2E.X1D.X2D, Z2.T1D.T2E.X1D.X2D,
Z3.T1D.T2E.X1D.X2D, Z4.T1D.T2E.X1D.X2D,
Z1.T1E.T2E.X1D.X2D, Z2.T1E.T2E.X1D.X2D,
Z3.T1E.T2E.X1D.X2D, Z4.T1E.T2E.X1D.X2D,
Z1.T1F.T2E.X1D.X2D, Z2.T1F.T2E.X1D.X2D,
Z3.T1F.T2E.X1D.X2D, Z4.T1F.T2E.X1D.X2D,
Z1.T1A.T2F.X1D.X2D, Z2.T1A.T2F.X1D.X2D,
Z3.T1A.T2F.X1D.X2D, Z4.T1A.T2F.X1D.X2D,
Z1.T1B.T2F.X1D.X2D, Z2.T1B.T2F.X1D.X2D,
Z3.T1B.T2F.X1D.X2D, Z4.T1B.T2F.X1D.X2D,
Z1.T1C.T2F.X1D.X2D, Z2.T1C.T2F.X1D.X2D,
Z3.T1C.T2F.X1D.X2D, Z4.T1C.T2F.X1D.X2D,
Z1.T1D.T2F.X1D.X2D, Z2.T1D.T2F.X1D.X2D,
Z3.T1D.T2F.X1D.X2D, Z4.T1D.T2F.X1D.X2D,
Z1.T1E.T2F.X1D.X2D, Z2.T1E.T2F.X1D.X2D,
Z3.T1E.T2F.X1D.X2D, Z4.T1E.T2F.X1D.X2D,
Z1.T1F.T2F.X1D.X2D, Z2.T1F.T2F.X1D.X2D,
Z3.T1F.T2F.X1D.X2D, Z4.T1F.T2F.X1D.X2D,
Z1.T1A.T2A.X1E.X2D, Z2.T1A.T2A.X1E.X2D,
Z3.T1A.T2A.X1E.X2D, Z4.T1A.T2A.X1E.X2D,
Z1.T1B.T2A.X1E.X2D, Z2.T1B.T2A.X1E.X2D,
Z3.T1B.T2A.X1E.X2D, Z4.T1B.T2A.X1E.X2D,
Z1.T1C.T2A.X1E.X2D, Z2.T1C.T2A.X1E.X2D,
Z3.T1C.T2A.X1E.X2D, Z4.T1C.T2A.X1E.X2D,
Z1.T1D.T2A.X1E.X2D, Z2.T1D.T2A.X1E.X2D,
Z3.T1D.T2A.X1E.X2D, Z4.T1D.T2A.X1E.X2D,
Z1.T1E.T2A.X1E.X2D, Z2.T1E.T2A.X1E.X2D,
Z3.T1E.T2A.X1E.X2D, Z4.T1E.T2A.X1E.X2D,
Z1.T1F.T2A.X1E.X2D, Z2.T1F.T2A.X1E.X2D,
Z3.T1F.T2A.X1E.X2D, Z4.T1F.T2A.X1E.X2D,
Z1.T1A.T2B.X1E.X2D, Z2.T1A.T2B.X1E.X2D,
Z3.T1A.T2B.X1E.X2D, Z4.T1A.T2B.X1E.X2D,
Z1.T1B.T2B.X1E.X2D, Z2.T1B.T2B.X1E.X2D,
Z3.T1B.T2B.X1E.X2D, Z4.T1B.T2B.X1E.X2D,
Z1.T1C.T2B.X1E.X2D, Z2.T1C.T2B.X1E.X2D,
Z3.T1C.T2B.X1E.X2D, Z4.T1C.T2B.X1E.X2D,
Z1.T1D.T2B.X1E.X2D, Z2.T1D.T2B.X1E.X2D,
Z3.T1D.T2B.X1E.X2D, Z4.T1D.T2B.X1E.X2D,
Z1.T1E.T2B.X1E.X2D, Z2.T1E.T2B.X1E.X2D,
Z3.T1E.T2B.X1E.X2D, Z4.T1E.T2B.X1E.X2D,
Z1.T1F.T2B.X1E.X2D, Z2.T1F.T2B.X1E.X2D,
Z3.T1F.T2B.X1E.X2D, Z4.T1F.T2B.X1E.X2D,
Z1.T1A.T2C.X1E.X2D, Z2.T1A.T2C.X1E.X2D,
Z3.T1A.T2C.X1E.X2D, Z4.T1A.T2C.X1E.X2D,
Z1.T1B.T2C.X1E.X2D, Z2.T1B.T2C.X1E.X2D,
Z3.T1B.T2C.X1E.X2D, Z4.T1B.T2C.X1E.X2D,
Z1.T1C.T2C.X1E.X2D, Z2.T1C.T2C.X1E.X2D,
Z3.T1C.T2C.X1E.X2D, Z4.T1C.T2C.X1E.X2D,
Z1.T1D.T2C.X1E.X2D, Z2.T1D.T2C.X1E.X2D,
Z3.T1D.T2C.X1E.X2D, Z4.T1D.T2C.X1E.X2D,
Z1.T1E.T2C.X1E.X2D, Z2.T1E.T2C.X1E.X2D,
Z3.T1E.T2C.X1E.X2D, Z4.T1E.T2C.X1E.X2D,
Z1.T1F.T2C.X1E.X2D, Z2.T1F.T2C.X1E.X2D,
Z3.T1F.T2C.X1E.X2D, Z4.T1F.T2C.X1E.X2D,
Z1.T1A.T2D.X1E.X2D, Z2.T1A.T2D.X1E.X2D,
Z3.T1A.T2D.X1E.X2D, Z4.T1A.T2D.X1E.X2D,
Z1.T1B.T2D.X1E.X2D, Z2.T1B.T2D.X1E.X2D,
Z3.T1B.T2D.X1E.X2D, Z4.T1B.T2D.X1E.X2D,
Z1.T1C.T2D.X1E.X2D, Z2.T1C.T2D.X1E.X2D,
Z3.T1C.T2D.X1E.X2D, Z4.T1C.T2D.X1E.X2D,
Z1.T1D.T2D.X1E.X2D, Z2.T1D.T2D.X1E.X2D,
Z3.T1D.T2D.X1E.X2D, Z4.T1D.T2D.X1E.X2D,
Z1.T1E.T2D.X1E.X2D, Z2.T1E.T2D.X1E.X2D,
Z3.T1E.T2D.X1E.X2D, Z4.T1E.T2D.X1E.X2D,
Z1.T1F.T2D.X1E.X2D, Z2.T1F.T2D.X1E.X2D,
Z3.T1F.T2D.X1E.X2D, Z4.T1F.T2D.X1E.X2D,
Z1.T1A.T2E.X1E.X2D, Z2.T1A.T2E.X1E.X2D,
Z3.T1A.T2E.X1E.X2D, Z4.T1A.T2E.X1E.X2D,
Z1.T1B.T2E.X1E.X2D, Z2.T1B.T2E.X1E.X2D,
Z3.T1B.T2E.X1E.X2D, Z4.T1B.T2E.X1E.X2D,
Z1.T1C.T2E.X1E.X2D, Z2.T1C.T2E.X1E.X2D,
Z3.T1C.T2E.X1E.X2D, Z4.T1C.T2E.X1E.X2D,
Z1.T1D.T2E.X1E.X2D, Z2.T1D.T2E.X1E.X2D,
Z3.T1D.T2E.X1E.X2D, Z4.T1D.T2E.X1E.X2D,
Z1.T1E.T2E.X1E.X2D, Z2.T1E.T2E.X1E.X2D,
Z3.T1E.T2E.X1E.X2D, Z4.T1E.T2E.X1E.X2D,
Z1.T1F.T2E.X1E.X2D, Z2.T1F.T2E.X1E.X2D,
Z3.T1F.T2E.X1E.X2D, Z4.T1F.T2E.X1E.X2D,
Z1.T1A.T2F.X1E.X2D, Z2.T1A.T2F.X1E.X2D,
Z3.T1A.T2F.X1E.X2D, Z4.T1A.T2F.X1E.X2D,
Z1.T1B.T2F.X1E.X2D, Z2.T1B.T2F.X1E.X2D,
Z3.T1B.T2F.X1E.X2D, Z4.T1B.T2F.X1E.X2D,
Z1.T1C.T2F.X1E.X2D, Z2.T1C.T2F.X1E.X2D,
Z3.T1C.T2F.X1E.X2D, Z4.T1C.T2F.X1E.X2D,
Z1.T1D.T2F.X1E.X2D, Z2.T1D.T2F.X1E.X2D,
Z3.T1D.T2F.X1E.X2D, Z4.T1D.T2F.X1E.X2D,
Z1.T1E.T2F.X1E.X2D, Z2.T1E.T2F.X1E.X2D,
Z3.T1E.T2F.X1E.X2D, Z4.T1E.T2F.X1E.X2D,
Z1.T1F.T2F.X1E.X2D, Z2.T1F.T2F.X1E.X2D,
Z3.T1F.T2F.X1E.X2D, Z4.T1F.T2F.X1E.X2D,
Z1.T1A.T2A.X1F.X2D, Z2.T1A.T2A.X1F.X2D,
Z3.T1A.T2A.X1F.X2D, Z4.T1A.T2A.X1F.X2D,
Z1.T1B.T2A.X1F.X2D, Z2.T1B.T2A.X1F.X2D,
Z3.T1B.T2A.X1F.X2D, Z4.T1B.T2A.X1F.X2D,
Z1.T1C.T2A.X1F.X2D, Z2.T1C.T2A.X1F.X2D,
Z3.T1C.T2A.X1F.X2D, Z4.T1C.T2A.X1F.X2D,
Z1.T1D.T2A.X1F.X2D, Z2.T1D.T2A.X1F.X2D,
Z3.T1D.T2A.X1F.X2D, Z4.T1D.T2A.X1F.X2D,
Z1.T1E.T2A.X1F.X2D, Z2.T1E.T2A.X1F.X2D,
Z3.T1E.T2A.X1F.X2D, Z4.T1E.T2A.X1F.X2D,
Z1.T1F.T2A.X1F.X2D, Z2.T1F.T2A.X1F.X2D,
Z3.T1F.T2A.X1F.X2D, Z4.T1F.T2A.X1F.X2D,
Z1.T1A.T2B.X1F.X2D, Z2.T1A.T2B.X1F.X2D,
Z3.T1A.T2B.X1F.X2D, Z4.T1A.T2B.X1F.X2D,
Z1.T1B.T2B.X1F.X2D, Z2.T1B.T2B.X1F.X2D,
Z3.T1B.T2B.X1F.X2D, Z4.T1B.T2B.X1F.X2D,
Z1.T1C.T2B.X1F.X2D, Z2.T1C.T2B.X1F.X2D,
Z3.T1C.T2B.X1F.X2D, Z4.T1C.T2B.X1F.X2D,
Z1.T1D.T2B.X1F.X2D, Z2.T1D.T2B.X1F.X2D,
Z3.T1D.T2B.X1F.X2D, Z4.T1D.T2B.X1F.X2D,
Z1.T1E.T2B.X1F.X2D, Z2.T1E.T2B.X1F.X2D,
Z3.T1E.T2B.X1F.X2D, Z4.T1E.T2B.X1F.X2D,
Z1.T1F.T2B.X1F.X2D, Z2.T1F.T2B.X1F.X2D,
Z3.T1F.T2B.X1F.X2D, Z4.T1F.T2B.X1F.X2D,
Z1.T1A.T2C.X1F.X2D, Z2.T1A.T2C.X1F.X2D,
Z3.T1A.T2C.X1F.X2D, Z4.T1A.T2C.X1F.X2D,
Z1.T1B.T2C.X1F.X2D, Z2.T1B.T2C.X1F.X2D,
Z3.T1B.T2C.X1F.X2D, Z4.T1B.T2C.X1F.X2D,
Z1.T1C.T2C.X1F.X2D, Z2.T1C.T2C.X1F.X2D,
Z3.T1C.T2C.X1F.X2D, Z4.T1C.T2C.X1F.X2D,
Z1.T1D.T2C.X1F.X2D, Z2.T1D.T2C.X1F.X2D,
Z3.T1D.T2C.X1F.X2D, Z4.T1D.T2C.X1F.X2D,
Z1.T1E.T2C.X1F.X2D, Z2.T1E.T2C.X1F.X2D,
Z3.T1E.T2C.X1F.X2D, Z4.T1E.T2C.X1F.X2D,
Z1.T1F.T2C.X1F.X2D, Z2.T1F.T2C.X1F.X2D,
Z3.T1F.T2C.X1F.X2D, Z4.T1F.T2C.X1F.X2D,
Z1.T1A.T2D.X1F.X2D, Z2.T1A.T2D.X1F.X2D,
Z3.T1A.T2D.X1F.X2D, Z4.T1A.T2D.X1F.X2D,

TABLE 6-continued

List of Compound Structures of Formula II

Z1.T1B.T2D.X1F.X2D, Z2.T1B.T2D.X1F.X2D,
Z3.T1B.T2D.X1F.X2D, Z4.T1B.T2D.X1F.X2D,
Z1.T1C.T2D.X1F.X2D, Z2.T1C.T2D.X1F.X2D,
Z3.T1C.T2D.X1F.X2D, Z4.T1C.T2D.X1F.X2D,
Z1.T1D.T2D.X1F.X2D, Z2.T1D.T2D.X1F.X2D,
Z3.T1D.T2D.X1F.X2D, Z4.T1D.T2D.X1F.X2D,
Z1.T1E.T2D.X1F.X2D, Z2.T1E.T2D.X1F.X2D,
Z3.T1E.T2D.X1F.X2D, Z4.T1E.T2D.X1F.X2D,
Z1.T1F.T2D.X1F.X2D, Z2.T1F.T2D.X1F.X2D,
Z3.T1F.T2D.X1F.X2D, Z4.T1F.T2D.X1F.X2D,
Z1.T1A.T2E.X1F.X2D, Z2.T1A.T2E.X1F.X2D,
Z3.T1A.T2E.X1F.X2D, Z4.T1A.T2E.X1F.X2D,
Z1.T1B.T2E.X1F.X2D, Z2.T1B.T2E.X1F.X2D,
Z3.T1B.T2E.X1F.X2D, Z4.T1B.T2E.X1F.X2D,
Z1.T1C.T2E.X1F.X2D, Z2.T1C.T2E.X1F.X2D,
Z3.T1C.T2E.X1F.X2D, Z4.T1C.T2E.X1F.X2D,
Z1.T1D.T2E.X1F.X2D, Z2.T1D.T2E.X1F.X2D,
Z3.T1D.T2E.X1F.X2D, Z4.T1D.T2E.X1F.X2D,
Z1.T1E.T2E.X1F.X2D, Z2.T1E.T2E.X1F.X2D,
Z3.T1E.T2E.X1F.X2D, Z4.T1E.T2E.X1F.X2D,
Z1.T1F.T2E.X1F.X2D, Z2.T1F.T2E.X1F.X2D,
Z3.T1F.T2E.X1F.X2D, Z4.T1F.T2E.X1F.X2D,
Z1.T1A.T2F.X1F.X2D, Z2.T1A.T2F.X1F.X2D,
Z3.T1A.T2F.X1F.X2D, Z4.T1A.T2F.X1F.X2D,
Z1.T1B.T2F.X1F.X2D, Z2.T1B.T2F.X1F.X2D,
Z3.T1B.T2F.X1F.X2D, Z4.T1B.T2F.X1F.X2D,
Z1.T1C.T2F.X1F.X2D, Z2.T1C.T2F.X1F.X2D,
Z3.T1C.T2F.X1F.X2D, Z4.T1C.T2F.X1F.X2D,
Z1.T1D.T2F.X1F.X2D, Z2.T1D.T2F.X1F.X2D,
Z3.T1D.T2F.X1F.X2D, Z4.T1D.T2F.X1F.X2D,
Z1.T1E.T2F.X1F.X2D, Z2.T1E.T2F.X1F.X2D,
Z3.T1E.T2F.X1F.X2D, Z4.T1E.T2F.X1F.X2D,
Z1.T1F.T2F.X1F.X2D, Z2.T1F.T2F.X1F.X2D,
Z3.T1F.T2F.X1F.X2D, Z4.T1F.T2F.X1F.X2D,
Z1.T1A.T2A.X1A.X2E, Z2.T1A.T2A.X1A.X2E,
Z3.T1A.T2A.X1A.X2E, Z4.T1A.T2A.X1A.X2E,
Z1.T1B.T2A.X1A.X2E, Z2.T1B.T2A.X1A.X2E,
Z3.T1B.T2A.X1A.X2E, Z4.T1B.T2A.X1A.X2E,
Z1.T1C.T2A.X1A.X2E, Z2.T1C.T2A.X1A.X2E,
Z3.T1C.T2A.X1A.X2E, Z4.T1C.T2A.X1A.X2E,
Z1.T1D.T2A.X1A.X2E, Z2.T1D.T2A.X1A.X2E,
Z3.T1D.T2A.X1A.X2E, Z4.T1D.T2A.X1A.X2E,
Z1.T1E.T2A.X1A.X2E, Z2.T1E.T2A.X1A.X2E,
Z3.T1E.T2A.X1A.X2E, Z4.T1E.T2A.X1A.X2E,
Z1.T1F.T2A.X1A.X2E, Z2.T1F.T2A.X1A.X2E,
Z3.T1F.T2A.X1A.X2E, Z4.T1F.T2A.X1A.X2E,
Z1.T1A.T2B.X1A.X2E, Z2.T1A.T2B.X1A.X2E,
Z3.T1A.T2B.X1A.X2E, Z4.T1A.T2B.X1A.X2E,
Z1.T1B.T2B.X1A.X2E, Z2.T1B.T2B.X1A.X2E,
Z3.T1B.T2B.X1A.X2E, Z4.T1B.T2B.X1A.X2E,
Z1.T1C.T2B.X1A.X2E, Z2.T1C.T2B.X1A.X2E,
Z3.T1C.T2B.X1A.X2E, Z4.T1C.T2B.X1A.X2E,
Z1.T1D.T2B.X1A.X2E, Z2.T1D.T2B.X1A.X2E,
Z3.T1D.T2B.X1A.X2E, Z4.T1D.T2B.X1A.X2E,
Z1.T1E.T2B.X1A.X2E, Z2.T1E.T2B.X1A.X2E,
Z3.T1E.T2B.X1A.X2E, Z4.T1E.T2B.X1A.X2E,
Z1.T1F.T2B.X1A.X2E, Z2.T1F.T2B.X1A.X2E,
Z3.T1F.T2B.X1A.X2E, Z4.T1F.T2B.X1A.X2E,
Z1.T1A.T2C.X1A.X2E, Z2.T1A.T2C.X1A.X2E,
Z3.T1A.T2C.X1A.X2E, Z4.T1A.T2C.X1A.X2E,
Z1.T1B.T2C.X1A.X2E, Z2.T1B.T2C.X1A.X2E,
Z3.T1B.T2C.X1A.X2E, Z4.T1B.T2C.X1A.X2E,
Z1.T1C.T2C.X1A.X2E, Z2.T1C.T2C.X1A.X2E,
Z3.T1C.T2C.X1A.X2E, Z4.T1C.T2C.X1A.X2E,
Z1.T1D.T2C.X1A.X2E, Z2.T1D.T2C.X1A.X2E,
Z3.T1D.T2C.X1A.X2E, Z4.T1D.T2C.X1A.X2E,
Z1.T1E.T2C.X1A.X2E, Z2.T1E.T2C.X1A.X2E,
Z3.T1E.T2C.X1A.X2E, Z4.T1E.T2C.X1A.X2E,
Z1.T1F.T2C.X1A.X2E, Z2.T1F.T2C.X1A.X2E,
Z3.T1F.T2C.X1A.X2E, Z4.T1F.T2C.X1A.X2E,
Z1.T1A.T2D.X1A.X2E, Z2.T1A.T2D.X1A.X2E,
Z3.T1A.T2D.X1A.X2E, Z4.T1A.T2D.X1A.X2E,
Z1.T1B.T2D.X1A.X2E, Z2.T1B.T2D.X1A.X2E,
Z3.T1B.T2D.X1A.X2E, Z4.T1B.T2D.X1A.X2E,
Z1.T1C.T2D.X1A.X2E, Z2.T1C.T2D.X1A.X2E,
Z3.T1C.T2D.X1A.X2E, Z4.T1C.T2D.X1A.X2E,
Z1.T1D.T2D.X1A.X2E, Z2.T1D.T2D.X1A.X2E,
Z3.T1D.T2D.X1A.X2E, Z4.T1D.T2D.X1A.X2E,
Z1.T1E.T2D.X1A.X2E, Z2.T1E.T2D.X1A.X2E,
Z3.T1E.T2D.X1A.X2E, Z4.T1E.T2D.X1A.X2E,
Z1.T1F.T2D.X1A.X2E, Z2.T1F.T2D.X1A.X2E,
Z3.T1F.T2D.X1A.X2E, Z4.T1F.T2D.X1A.X2E,
Z1.T1A.T2E.X1A.X2E, Z2.T1A.T2E.X1A.X2E,
Z3.T1A.T2E.X1A.X2E, Z4.T1A.T2E.X1A.X2E,
Z1.T1B.T2E.X1A.X2E, Z2.T1B.T2E.X1A.X2E,
Z3.T1B.T2E.X1A.X2E, Z4.T1B.T2E.X1A.X2E,
Z1.T1C.T2E.X1A.X2E, Z2.T1C.T2E.X1A.X2E,
Z3.T1C.T2E.X1A.X2E, Z4.T1C.T2E.X1A.X2E,
Z1.T1D.T2E.X1A.X2E, Z2.T1D.T2E.X1A.X2E,
Z3.T1D.T2E.X1A.X2E, Z4.T1D.T2E.X1A.X2E,
Z1.T1E.T2E.X1A.X2E, Z2.T1E.T2E.X1A.X2E,
Z3.T1E.T2E.X1A.X2E, Z4.T1E.T2E.X1A.X2E,
Z1.T1F.T2E.X1A.X2E, Z2.T1F.T2E.X1A.X2E,
Z3.T1F.T2E.X1A.X2E, Z4.T1F.T2E.X1A.X2E,
Z1.T1A.T2F.X1A.X2E, Z2.T1A.T2F.X1A.X2E,
Z3.T1A.T2F.X1A.X2E, Z4.T1A.T2F.X1A.X2E,
Z1.T1B.T2F.X1A.X2E, Z2.T1B.T2F.X1A.X2E,
Z3.T1B.T2F.X1A.X2E, Z4.T1B.T2F.X1A.X2E,
Z1.T1C.T2F.X1A.X2E, Z2.T1C.T2F.X1A.X2E,
Z3.T1C.T2F.X1A.X2E, Z4.T1C.T2F.X1A.X2E,
Z1.T1D.T2F.X1A.X2E, Z2.T1D.T2F.X1A.X2E,
Z3.T1D.T2F.X1A.X2E, Z4.T1D.T2F.X1A.X2E,
Z1.T1E.T2F.X1A.X2E, Z2.T1E.T2F.X1A.X2E,
Z3.T1E.T2F.X1A.X2E, Z4.T1E.T2F.X1A.X2E,
Z1.T1F.T2F.X1A.X2E, Z2.T1F.T2F.X1A.X2E,
Z3.T1F.T2F.X1A.X2E, Z4.T1F.T2F.X1A.X2E,
Z1.T1A.T2A.X1B.X2E, Z2.T1A.T2A.X1B.X2E,
Z3.T1A.T2A.X1B.X2E, Z4.T1A.T2A.X1B.X2E,
Z1.T1B.T2A.X1B.X2E, Z2.T1B.T2A.X1B.X2E,
Z3.T1B.T2A.X1B.X2E, Z4.T1B.T2A.X1B.X2E,
Z1.T1C.T2A.X1B.X2E, Z2.T1C.T2A.X1B.X2E,
Z3.T1C.T2A.X1B.X2E, Z4.T1C.T2A.X1B.X2E,
Z1.T1D.T2A.X1B.X2E, Z2.T1D.T2A.X1B.X2E,
Z3.T1D.T2A.X1B.X2E, Z4.T1D.T2A.X1B.X2E,
Z1.T1E.T2A.X1B.X2E, Z2.T1E.T2A.X1B.X2E,
Z3.T1E.T2A.X1B.X2E, Z4.T1E.T2A.X1B.X2E,
Z1.T1F.T2A.X1B.X2E, Z2.T1F.T2A.X1B.X2E,
Z3.T1F.T2A.X1B.X2E, Z4.T1F.T2A.X1B.X2E,
Z1.T1A.T2B.X1B.X2E, Z2.T1A.T2B.X1B.X2E,
Z3.T1A.T2B.X1B.X2E, Z4.T1A.T2B.X1B.X2E,
Z1.T1B.T2B.X1B.X2E, Z2.T1B.T2B.X1B.X2E,
Z3.T1B.T2B.X1B.X2E, Z4.T1B.T2B.X1B.X2E,
Z1.T1C.T2B.X1B.X2E, Z2.T1C.T2B.X1B.X2E,
Z3.T1C.T2B.X1B.X2E, Z4.T1C.T2B.X1B.X2E,
Z1.T1D.T2B.X1B.X2E, Z2.T1D.T2B.X1B.X2E,
Z3.T1D.T2B.X1B.X2E, Z4.T1D.T2B.X1B.X2E,
Z1.T1E.T2B.X1B.X2E, Z2.T1E.T2B.X1B.X2E,
Z3.T1E.T2B.X1B.X2E, Z4.T1E.T2B.X1B.X2E,
Z1.T1F.T2B.X1B.X2E, Z2.T1F.T2B.X1B.X2E,
Z3.T1F.T2B.X1B.X2E, Z4.T1F.T2B.X1B.X2E,
Z1.T1A.T2C.X1B.X2E, Z2.T1A.T2C.X1B.X2E,
Z3.T1A.T2C.X1B.X2E, Z4.T1A.T2C.X1B.X2E,
Z1.T1B.T2C.X1B.X2E, Z2.T1B.T2C.X1B.X2E,
Z3.T1B.T2C.X1B.X2E, Z4.T1B.T2C.X1B.X2E,
Z1.T1C.T2C.X1B.X2E, Z2.T1C.T2C.X1B.X2E,
Z3.T1C.T2C.X1B.X2E, Z4.T1C.T2C.X1B.X2E,
Z1.T1D.T2C.X1B.X2E, Z2.T1D.T2C.X1B.X2E,
Z3.T1D.T2C.X1B.X2E, Z4.T1D.T2C.X1B.X2E,
Z1.T1E.T2C.X1B.X2E, Z2.T1E.T2C.X1B.X2E,
Z3.T1E.T2C.X1B.X2E, Z4.T1E.T2C.X1B.X2E,
Z1.T1F.T2C.X1B.X2E, Z2.T1F.T2C.X1B.X2E,
Z3.T1F.T2C.X1B.X2E, Z4.T1F.T2C.X1B.X2E,
Z1.T1A.T2D.X1B.X2E, Z2.T1A.T2D.X1B.X2E,
Z3.T1A.T2D.X1B.X2E, Z4.T1A.T2D.X1B.X2E,
Z1.T1B.T2D.X1B.X2E, Z2.T1B.T2D.X1B.X2E,
Z3.T1B.T2D.X1B.X2E, Z4.T1B.T2D.X1B.X2E,
Z1.T1C.T2D.X1B.X2E, Z2.T1C.T2D.X1B.X2E,
Z3.T1C.T2D.X1B.X2E, Z4.T1C.T2D.X1B.X2E,
Z1.T1D.T2D.X1B.X2E, Z2.T1D.T2D.X1B.X2E,
Z3.T1D.T2D.X1B.X2E, Z4.T1D.T2D.X1B.X2E,
Z1.T1E.T2D.X1B.X2E, Z2.T1E.T2D.X1B.X2E,
Z3.T1E.T2D.X1B.X2E, Z4.T1E.T2D.X1B.X2E,
Z1.T1F.T2D.X1B.X2E, Z2.T1F.T2D.X1B.X2E,
Z3.T1F.T2D.X1B.X2E, Z4.T1F.T2D.X1B.X2E,

TABLE 6-continued

List of Compound Structures of Formula II

Z1.T1A.T2E.X1B.X2E, Z2.T1A.T2E.X1B.X2E,
Z3.T1A.T2E.X1B.X2E, Z4.T1A.T2E.X1B.X2E,
Z1.T1B.T2E.X1B.X2E, Z2.T1B.T2E.X1B.X2E,
Z3.T1B.T2E.X1B.X2E, Z4.T1B.T2E.X1B.X2E,
Z1.T1C.T2E.X1B.X2E, Z2.T1C.T2E.X1B.X2E,
Z3.T1C.T2E.X1B.X2E, Z4.T1C.T2E.X1B.X2E,
Z1.T1D.T2E.X1B.X2E, Z2.T1D.T2E.X1B.X2E,
Z3.T1D.T2E.X1B.X2E, Z4.T1D.T2E.X1B.X2E,
Z1.T1E.T2E.X1B.X2E, Z2.T1E.T2E.X1B.X2E,
Z3.T1E.T2E.X1B.X2E, Z4.T1E.T2E.X1B.X2E,
Z1.T1F.T2E.X1B.X2E, Z2.T1F.T2E.X1B.X2E,
Z3.T1F.T2E.X1B.X2E, Z4.T1F.T2E.X1B.X2E,
Z1.T1A.T2F.X1B.X2E, Z2.T1A.T2F.X1B.X2E,
Z3.T1A.T2F.X1B.X2E, Z4.T1A.T2F.X1B.X2E,
Z1.T1B.T2F.X1B.X2E, Z2.T1B.T2F.X1B.X2E,
Z3.T1B.T2F.X1B.X2E, Z4.T1B.T2F.X1B.X2E,
Z1.T1C.T2F.X1B.X2E, Z2.T1C.T2F.X1B.X2E,
Z3.T1C.T2F.X1B.X2E, Z4.T1C.T2F.X1B.X2E,
Z1.T1D.T2F.X1B.X2E, Z2.T1D.T2F.X1B.X2E,
Z3.T1D.T2F.X1B.X2E, Z4.T1D.T2F.X1B.X2E,
Z1.T1E.T2F.X1B.X2E, Z2.T1E.T2F.X1B.X2E,
Z3.T1E.T2F.X1B.X2E, Z4.T1E.T2F.X1B.X2E,
Z1.T1F.T2F.X1B.X2E, Z2.T1F.T2F.X1B.X2E,
Z3.T1F.T2F.X1B.X2E, Z4.T1F.T2F.X1B.X2E,
Z1.T1A.T2A.X1C.X2E, Z2.T1A.T2A.X1C.X2E,
Z3.T1A.T2A.X1C.X2E, Z4.T1A.T2A.X1C.X2E,
Z1.T1B.T2A.X1C.X2E, Z2.T1B.T2A.X1C.X2E,
Z3.T1B.T2A.X1C.X2E, Z4.T1B.T2A.X1C.X2E,
Z1.T1C.T2A.X1C.X2E, Z2.T1C.T2A.X1C.X2E,
Z3.T1C.T2A.X1C.X2E, Z4.T1C.T2A.X1C.X2E,
Z1.T1D.T2A.X1C.X2E, Z2.T1D.T2A.X1C.X2E,
Z3.T1D.T2A.X1C.X2E, Z4.T1D.T2A.X1C.X2E,
Z1.T1E.T2A.X1C.X2E, Z2.T1E.T2A.X1C.X2E,
Z3.T1E.T2A.X1C.X2E, Z4.T1E.T2A.X1C.X2E,
Z1.T1F.T2A.X1C.X2E, Z2.T1F.T2A.X1C.X2E,
Z3.T1F.T2A.X1C.X2E, Z4.T1F.T2A.X1C.X2E,
Z1.T1A.T2B.X1C.X2E, Z2.T1A.T2B.X1C.X2E,
Z3.T1A.T2B.X1C.X2E, Z4.T1A.T2B.X1C.X2E,
Z1.T1B.T2B.X1C.X2E, Z2.T1B.T2B.X1C.X2E,
Z3.T1B.T2B.X1C.X2E, Z4.T1B.T2B.X1C.X2E,
Z1.T1C.T2B.X1C.X2E, Z2.T1C.T2B.X1C.X2E,
Z3.T1C.T2B.X1C.X2E, Z4.T1C.T2B.X1C.X2E,
Z1.T1D.T2B.X1C.X2E, Z2.T1D.T2B.X1C.X2E,
Z3.T1D.T2B.X1C.X2E, Z4.T1D.T2B.X1C.X2E,
Z1.T1E.T2B.X1C.X2E, Z2.T1E.T2B.X1C.X2E,
Z3.T1E.T2B.X1C.X2E, Z4.T1E.T2B.X1C.X2E,
Z1.T1F.T2B.X1C.X2E, Z2.T1F.T2B.X1C.X2E,
Z3.T1F.T2B.X1C.X2E, Z4.T1F.T2B.X1C.X2E,
Z1.T1A.T2C.X1C.X2E, Z2.T1A.T2C.X1C.X2E,
Z3.T1A.T2C.X1C.X2E, Z4.T1A.T2C.X1C.X2E,
Z1.T1B.T2C.X1C.X2E, Z2.T1B.T2C.X1C.X2E,
Z3.T1B.T2C.X1C.X2E, Z4.T1B.T2C.X1C.X2E,
Z1.T1C.T2C.X1C.X2E, Z2.T1C.T2C.X1C.X2E,
Z3.T1C.T2C.X1C.X2E, Z4.T1C.T2C.X1C.X2E,
Z1.T1D.T2C.X1C.X2E, Z2.T1D.T2C.X1C.X2E,
Z3.T1D.T2C.X1C.X2E, Z4.T1D.T2C.X1C.X2E,
Z1.T1E.T2C.X1C.X2E, Z2.T1E.T2C.X1C.X2E,
Z3.T1E.T2C.X1C.X2E, Z4.T1E.T2C.X1C.X2E,
Z1.T1F.T2C.X1C.X2E, Z2.T1F.T2C.X1C.X2E,
Z3.T1F.T2C.X1C.X2E, Z4.T1F.T2C.X1C.X2E,
Z1.T1A.T2D.X1C.X2E, Z2.T1A.T2D.X1C.X2E,
Z3.T1A.T2D.X1C.X2E, Z4.T1A.T2D.X1C.X2E,
Z1.T1B.T2D.X1C.X2E, Z2.T1B.T2D.X1C.X2E,
Z3.T1B.T2D.X1C.X2E, Z4.T1B.T2D.X1C.X2E,
Z1.T1C.T2D.X1C.X2E, Z2.T1C.T2D.X1C.X2E,
Z3.T1C.T2D.X1C.X2E, Z4.T1C.T2D.X1C.X2E,
Z1.T1D.T2D.X1C.X2E, Z2.T1D.T2D.X1C.X2E,
Z3.T1D.T2D.X1C.X2E, Z4.T1D.T2D.X1C.X2E,
Z1.T1E.T2D.X1C.X2E, Z2.T1E.T2D.X1C.X2E,
Z3.T1E.T2D.X1C.X2E, Z4.T1E.T2D.X1C.X2E,
Z1.T1F.T2D.X1C.X2E, Z2.T1F.T2D.X1C.X2E,
Z3.T1F.T2D.X1C.X2E, Z4.T1F.T2D.X1C.X2E,
Z1.T1A.T2E.X1C.X2E, Z2.T1A.T2E.X1C.X2E,
Z3.T1A.T2E.X1C.X2E, Z4.T1A.T2E.X1C.X2E,
Z1.T1B.T2E.X1C.X2E, Z2.T1B.T2E.X1C.X2E,
Z3.T1B.T2E.X1C.X2E, Z4.T1B.T2E.X1C.X2E,
Z1.T1C.T2E.X1C.X2E, Z2.T1C.T2E.X1C.X2E,
Z3.T1C.T2E.X1C.X2E, Z4.T1C.T2E.X1C.X2E,
Z1.T1D.T2E.X1C.X2E, Z2.T1D.T2E.X1C.X2E,
Z3.T1D.T2E.X1C.X2E, Z4.T1D.T2E.X1C.X2E,
Z1.T1E.T2E.X1C.X2E, Z2.T1E.T2E.X1C.X2E,
Z3.T1E.T2E.X1C.X2E, Z4.T1E.T2E.X1C.X2E,
Z1.T1F.T2E.X1C.X2E, Z2.T1F.T2E.X1C.X2E,
Z3.T1F.T2E.X1C.X2E, Z4.T1F.T2E.X1C.X2E,
Z1.T1A.T2F.X1C.X2E, Z2.T1A.T2F.X1C.X2E,
Z3.T1A.T2F.X1C.X2E, Z4.T1A.T2F.X1C.X2E,
Z1.T1B.T2F.X1C.X2E, Z2.T1B.T2F.X1C.X2E,
Z3.T1B.T2F.X1C.X2E, Z4.T1B.T2F.X1C.X2E,
Z1.T1C.T2F.X1C.X2E, Z2.T1C.T2F.X1C.X2E,
Z3.T1C.T2F.X1C.X2E, Z4.T1C.T2F.X1C.X2E,
Z1.T1D.T2F.X1C.X2E, Z2.T1D.T2F.X1C.X2E,
Z3.T1D.T2F.X1C.X2E, Z4.T1D.T2F.X1C.X2E,
Z1.T1E.T2F.X1C.X2E, Z2.T1E.T2F.X1C.X2E,
Z3.T1E.T2F.X1C.X2E, Z4.T1E.T2F.X1C.X2E,
Z1.T1F.T2F.X1C.X2E, Z2.T1F.T2F.X1C.X2E,
Z3.T1F.T2F.X1C.X2E, Z4.T1F.T2F.X1C.X2E,
Z1.T1A.T2A.X1D.X2E, Z2.T1A.T2A.X1D.X2E,
Z3.T1A.T2A.X1D.X2E, Z4.T1A.T2A.X1D.X2E,
Z1.T1B.T2A.X1D.X2E, Z2.T1B.T2A.X1D.X2E,
Z3.T1B.T2A.X1D.X2E, Z4.T1B.T2A.X1D.X2E,
Z1.T1C.T2A.X1D.X2E, Z2.T1C.T2A.X1D.X2E,
Z3.T1C.T2A.X1D.X2E, Z4.T1C.T2A.X1D.X2E,
Z1.T1D.T2A.X1D.X2E, Z2.T1D.T2A.X1D.X2E,
Z3.T1D.T2A.X1D.X2E, Z4.T1D.T2A.X1D.X2E,
Z1.T1E.T2A.X1D.X2E, Z2.T1E.T2A.X1D.X2E,
Z3.T1E.T2A.X1D.X2E, Z4.T1E.T2A.X1D.X2E,
Z1.T1F.T2A.X1D.X2E, Z2.T1F.T2A.X1D.X2E,
Z3.T1F.T2A.X1D.X2E, Z4.T1F.T2A.X1D.X2E,
Z1.T1A.T2B.X1D.X2E, Z2.T1A.T2B.X1D.X2E,
Z3.T1A.T2B.X1D.X2E, Z4.T1A.T2B.X1D.X2E,
Z1.T1B.T2B.X1D.X2E, Z2.T1B.T2B.X1D.X2E,
Z3.T1B.T2B.X1D.X2E, Z4.T1B.T2B.X1D.X2E,
Z1.T1C.T2B.X1D.X2E, Z2.T1C.T2B.X1D.X2E,
Z3.T1C.T2B.X1D.X2E, Z4.T1C.T2B.X1D.X2E,
Z1.T1D.T2B.X1D.X2E, Z2.T1D.T2B.X1D.X2E,
Z3.T1D.T2B.X1D.X2E, Z4.T1D.T2B.X1D.X2E,
Z1.T1E.T2B.X1D.X2E, Z2.T1E.T2B.X1D.X2E,
Z3.T1E.T2B.X1D.X2E, Z4.T1E.T2B.X1D.X2E,
Z1.T1F.T2B.X1D.X2E, Z2.T1F.T2B.X1D.X2E,
Z3.T1F.T2B.X1D.X2E, Z4.T1F.T2B.X1D.X2E,
Z1.T1A.T2C.X1D.X2E, Z2.T1A.T2C.X1D.X2E,
Z3.T1A.T2C.X1D.X2E, Z4.T1A.T2C.X1D.X2E,
Z1.T1B.T2C.X1D.X2E, Z2.T1B.T2C.X1D.X2E,
Z3.T1B.T2C.X1D.X2E, Z4.T1B.T2C.X1D.X2E,
Z1.T1C.T2C.X1D.X2E, Z2.T1C.T2C.X1D.X2E,
Z3.T1C.T2C.X1D.X2E, Z4.T1C.T2C.X1D.X2E,
Z1.T1D.T2C.X1D.X2E, Z2.T1D.T2C.X1D.X2E,
Z3.T1D.T2C.X1D.X2E, Z4.T1D.T2C.X1D.X2E,
Z1.T1E.T2C.X1D.X2E, Z2.T1E.T2C.X1D.X2E,
Z3.T1E.T2C.X1D.X2E, Z4.T1E.T2C.X1D.X2E,
Z1.T1F.T2C.X1D.X2E, Z2.T1F.T2C.X1D.X2E,
Z3.T1F.T2C.X1D.X2E, Z4.T1F.T2C.X1D.X2E,
Z1.T1A.T2D.X1D.X2E, Z2.T1A.T2D.X1D.X2E,
Z3.T1A.T2D.X1D.X2E, Z4.T1A.T2D.X1D.X2E,
Z1.T1B.T2D.X1D.X2E, Z2.T1B.T2D.X1D.X2E,
Z3.T1B.T2D.X1D.X2E, Z4.T1B.T2D.X1D.X2E,
Z1.T1C.T2D.X1D.X2E, Z2.T1C.T2D.X1D.X2E,
Z3.T1C.T2D.X1D.X2E, Z4.T1C.T2D.X1D.X2E,
Z1.T1D.T2D.X1D.X2E, Z2.T1D.T2D.X1D.X2E,
Z3.T1D.T2D.X1D.X2E, Z4.T1D.T2D.X1D.X2E,
Z1.T1E.T2D.X1D.X2E, Z2.T1E.T2D.X1D.X2E,
Z3.T1E.T2D.X1D.X2E, Z4.T1E.T2D.X1D.X2E,
Z1.T1F.T2D.X1D.X2E, Z2.T1F.T2D.X1D.X2E,
Z3.T1F.T2D.X1D.X2E, Z4.T1F.T2D.X1D.X2E,
Z1.T1A.T2E.X1D.X2E, Z2.T1A.T2E.X1D.X2E,
Z3.T1A.T2E.X1D.X2E, Z4.T1A.T2E.X1D.X2E,
Z1.T1B.T2E.X1D.X2E, Z2.T1B.T2E.X1D.X2E,
Z3.T1B.T2E.X1D.X2E, Z4.T1B.T2E.X1D.X2E,
Z1.T1C.T2E.X1D.X2E, Z2.T1C.T2E.X1D.X2E,
Z3.T1C.T2E.X1D.X2E, Z4.T1C.T2E.X1D.X2E,
Z1.T1D.T2E.X1D.X2E, Z2.T1D.T2E.X1D.X2E,
Z3.T1D.T2E.X1D.X2E, Z4.T1D.T2E.X1D.X2E,
Z1.T1E.T2E.X1D.X2E, Z2.T1E.T2E.X1D.X2E,
Z3.T1E.T2E.X1D.X2E, Z4.T1E.T2E.X1D.X2E,

TABLE 6-continued

List of Compound Structures of Formula II

Z1.T1F.T2E.X1D.X2E, Z2.T1F.T2E.X1D.X2E,
Z3.T1F.T2E.X1D.X2E, Z4.T1F.T2E.X1D.X2E,
Z1.T1A.T2F.X1D.X2E, Z2.T1A.T2F.X1D.X2E,
Z3.T1A.T2F.X1D.X2E, Z4.T1A.T2F.X1D.X2E,
Z1.T1B.T2F.X1D.X2E, Z2.T1B.T2F.X1D.X2E,
Z3.T1B.T2F.X1D.X2E, Z4.T1B.T2F.X1D.X2E,
Z1.T1C.T2F.X1D.X2E, Z2.T1C.T2F.X1D.X2E,
Z3.T1C.T2F.X1D.X2E, Z4.T1C.T2F.X1D.X2E,
Z1.T1D.T2F.X1D.X2E, Z2.T1D.T2F.X1D.X2E,
Z3.T1D.T2F.X1D.X2E, Z4.T1D.T2F.X1D.X2E,
Z1.T1E.T2F.X1D.X2E, Z2.T1E.T2F.X1D.X2E,
Z3.T1E.T2F.X1D.X2E, Z4.T1E.T2F.X1D.X2E,
Z1.T1F.T2F.X1D.X2E, Z2.T1F.T2F.X1D.X2E,
Z3.T1F.T2F.X1D.X2E, Z4.T1F.T2F.X1D.X2E,
Z1.T1A.T2A.X1E.X2E, Z2.T1A.T2A.X1E.X2E,
Z3.T1A.T2A.X1E.X2E, Z4.T1A.T2A.X1E.X2E,
Z1.T1B.T2A.X1E.X2E, Z2.T1B.T2A.X1E.X2E,
Z3.T1B.T2A.X1E.X2E, Z4.T1B.T2A.X1E.X2E,
Z1.T1C.T2A.X1E.X2E, Z2.T1C.T2A.X1E.X2E,
Z3.T1C.T2A.X1E.X2E, Z4.T1C.T2A.X1E.X2E,
Z1.T1D.T2A.X1E.X2E, Z2.T1D.T2A.X1E.X2E,
Z3.T1D.T2A.X1E.X2E, Z4.T1D.T2A.X1E.X2E,
Z1.T1E.T2A.X1E.X2E, Z2.T1E.T2A.X1E.X2E,
Z3.T1E.T2A.X1E.X2E, Z4.T1E.T2A.X1E.X2E,
Z1.T1F.T2A.X1E.X2E, Z2.T1F.T2A.X1E.X2E,
Z3.T1F.T2A.X1E.X2E, Z4.T1F.T2A.X1E.X2E,
Z1.T1A.T2B.X1E.X2E, Z2.T1A.T2B.X1E.X2E,
Z3.T1A.T2B.X1E.X2E, Z4.T1A.T2B.X1E.X2E,
Z1.T1B.T2B.X1E.X2E, Z2.T1B.T2B.X1E.X2E,
Z3.T1B.T2B.X1E.X2E, Z4.T1B.T2B.X1E.X2E,
Z1.T1C.T2B.X1E.X2E, Z2.T1C.T2B.X1E.X2E,
Z3.T1C.T2B.X1E.X2E, Z4.T1C.T2B.X1E.X2E,
Z1.T1D.T2B.X1E.X2E, Z2.T1D.T2B.X1E.X2E,
Z3.T1D.T2B.X1E.X2E, Z4.T1D.T2B.X1E.X2E,
Z1.T1E.T2B.X1E.X2E, Z2.T1E.T2B.X1E.X2E,
Z3.T1E.T2B.X1E.X2E, Z4.T1E.T2B.X1E.X2E,
Z1.T1F.T2B.X1E.X2E, Z2.T1F.T2B.X1E.X2E,
Z3.T1F.T2B.X1E.X2E, Z4.T1F.T2B.X1E.X2E,
Z1.T1A.T2C.X1E.X2E, Z2.T1A.T2C.X1E.X2E,
Z3.T1A.T2C.X1E.X2E, Z4.T1A.T2C.X1E.X2E,
Z1.T1B.T2C.X1E.X2E, Z2.T1B.T2C.X1E.X2E,
Z3.T1B.T2C.X1E.X2E, Z4.T1B.T2C.X1E.X2E,
Z1.T1C.T2C.X1E.X2E, Z2.T1C.T2C.X1E.X2E,
Z3.T1C.T2C.X1E.X2E, Z4.T1C.T2C.X1E.X2E,
Z1.T1D.T2C.X1E.X2E, Z2.T1D.T2C.X1E.X2E,
Z3.T1D.T2C.X1E.X2E, Z4.T1D.T2C.X1E.X2E,
Z1.T1E.T2C.X1E.X2E, Z2.T1E.T2C.X1E.X2E,
Z3.T1E.T2C.X1E.X2E, Z4.T1E.T2C.X1E.X2E,
Z1.T1F.T2C.X1E.X2E, Z2.T1F.T2C.X1E.X2E,
Z3.T1F.T2C.X1E.X2E, Z4.T1F.T2C.X1E.X2E,
Z1.T1A.T2D.X1E.X2E, Z2.T1A.T2D.X1E.X2E,
Z3.T1A.T2D.X1E.X2E, Z4.T1A.T2D.X1E.X2E,
Z1.T1B.T2D.X1E.X2E, Z2.T1B.T2D.X1E.X2E,
Z3.T1B.T2D.X1E.X2E, Z4.T1B.T2D.X1E.X2E,
Z1.T1C.T2D.X1E.X2E, Z2.T1C.T2D.X1E.X2E,
Z3.T1C.T2D.X1E.X2E, Z4.T1C.T2D.X1E.X2E,
Z1.T1D.T2D.X1E.X2E, Z2.T1D.T2D.X1E.X2E,
Z3.T1D.T2D.X1E.X2E, Z4.T1D.T2D.X1E.X2E,
Z1.T1E.T2D.X1E.X2E, Z2.T1E.T2D.X1E.X2E,
Z3.T1E.T2D.X1E.X2E, Z4.T1E.T2D.X1E.X2E,
Z1.T1F.T2D.X1E.X2E, Z2.T1F.T2D.X1E.X2E,
Z3.T1F.T2D.X1E.X2E, Z4.T1F.T2D.X1E.X2E,
Z1.T1A.T2E.X1E.X2E, Z2.T1A.T2E.X1E.X2E,
Z3.T1A.T2E.X1E.X2E, Z4.T1A.T2E.X1E.X2E,
Z1.T1B.T2E.X1E.X2E, Z2.T1B.T2E.X1E.X2E,
Z3.T1B.T2E.X1E.X2E, Z4.T1B.T2E.X1E.X2E,
Z1.T1C.T2E.X1E.X2E, Z2.T1C.T2E.X1E.X2E,
Z3.T1C.T2E.X1E.X2E, Z4.T1C.T2E.X1E.X2E,
Z1.T1D.T2E.X1E.X2E, Z2.T1D.T2E.X1E.X2E,
Z3.T1D.T2E.X1E.X2E, Z4.T1D.T2E.X1E.X2E,
Z1.T1E.T2E.X1E.X2E, Z2.T1E.T2E.X1E.X2E,
Z3.T1E.T2E.X1E.X2E, Z4.T1E.T2E.X1E.X2E,
Z1.T1F.T2E.X1E.X2E, Z2.T1F.T2E.X1E.X2E,
Z3.T1F.T2E.X1E.X2E, Z4.T1F.T2E.X1E.X2E,
Z1.T1A.T2F.X1E.X2E, Z2.T1A.T2F.X1E.X2E,
Z3.T1A.T2F.X1E.X2E, Z4.T1A.T2F.X1E.X2E,
Z1.T1B.T2F.X1E.X2E, Z2.T1B.T2F.X1E.X2E,
Z3.T1B.T2F.X1E.X2E, Z4.T1B.T2F.X1E.X2E,
Z1.T1C.T2F.X1E.X2E, Z2.T1C.T2F.X1E.X2E,
Z3.T1C.T2F.X1E.X2E, Z4.T1C.T2F.X1E.X2E,
Z1.T1D.T2F.X1E.X2E, Z2.T1D.T2F.X1E.X2E,
Z3.T1D.T2F.X1E.X2E, Z4.T1D.T2F.X1E.X2E,
Z1.T1E.T2F.X1E.X2E, Z2.T1E.T2F.X1E.X2E,
Z3.T1E.T2F.X1E.X2E, Z4.T1E.T2F.X1E.X2E,
Z1.T1F.T2F.X1E.X2E, Z2.T1F.T2F.X1E.X2E,
Z3.T1F.T2F.X1E.X2E, Z4.T1F.T2F.X1E.X2E,
Z1.T1A.T2A.X1F.X2E, Z2.T1A.T2A.X1F.X2E,
Z3.T1A.T2A.X1F.X2E, Z4.T1A.T2A.X1F.X2E,
Z1.T1B.T2A.X1F.X2E, Z2.T1B.T2A.X1F.X2E,
Z3.T1B.T2A.X1F.X2E, Z4.T1B.T2A.X1F.X2E,
Z1.T1C.T2A.X1F.X2E, Z2.T1C.T2A.X1F.X2E,
Z3.T1C.T2A.X1F.X2E, Z4.T1C.T2A.X1F.X2E,
Z1.T1D.T2A.X1F.X2E, Z2.T1D.T2A.X1F.X2E,
Z3.T1D.T2A.X1F.X2E, Z4.T1D.T2A.X1F.X2E,
Z1.T1E.T2A.X1F.X2E, Z2.T1E.T2A.X1F.X2E,
Z3.T1E.T2A.X1F.X2E, Z4.T1E.T2A.X1F.X2E,
Z1.T1F.T2A.X1F.X2E, Z2.T1F.T2A.X1F.X2E,
Z3.T1F.T2A.X1F.X2E, Z4.T1F.T2A.X1F.X2E,
Z1.T1A.T2B.X1F.X2E, Z2.T1A.T2B.X1F.X2E,
Z3.T1A.T2B.X1F.X2E, Z4.T1A.T2B.X1F.X2E,
Z1.T1B.T2B.X1F.X2E, Z2.T1B.T2B.X1F.X2E,
Z3.T1B.T2B.X1F.X2E, Z4.T1B.T2B.X1F.X2E,
Z1.T1C.T2B.X1F.X2E, Z2.T1C.T2B.X1F.X2E,
Z3.T1C.T2B.X1F.X2E, Z4.T1C.T2B.X1F.X2E,
Z1.T1D.T2B.X1F.X2E, Z2.T1D.T2B.X1F.X2E,
Z3.T1D.T2B.X1F.X2E, Z4.T1D.T2B.X1F.X2E,
Z1.T1E.T2B.X1F.X2E, Z2.T1E.T2B.X1F.X2E,
Z3.T1E.T2B.X1F.X2E, Z4.T1E.T2B.X1F.X2E,
Z1.T1F.T2B.X1F.X2E, Z2.T1F.T2B.X1F.X2E,
Z3.T1F.T2B.X1F.X2E, Z4.T1F.T2B.X1F.X2E,
Z1.T1A.T2C.X1F.X2E, Z2.T1A.T2C.X1F.X2E,
Z3.T1A.T2C.X1F.X2E, Z4.T1A.T2C.X1F.X2E,
Z1.T1B.T2C.X1F.X2E, Z2.T1B.T2C.X1F.X2E,
Z3.T1B.T2C.X1F.X2E, Z4.T1B.T2C.X1F.X2E,
Z1.T1C.T2C.X1F.X2E, Z2.T1C.T2C.X1F.X2E,
Z3.T1C.T2C.X1F.X2E, Z4.T1C.T2C.X1F.X2E,
Z1.T1D.T2C.X1F.X2E, Z2.T1D.T2C.X1F.X2E,
Z3.T1D.T2C.X1F.X2E, Z4.T1D.T2C.X1F.X2E,
Z1.T1E.T2C.X1F.X2E, Z2.T1E.T2C.X1F.X2E,
Z3.T1E.T2C.X1F.X2E, Z4.T1E.T2C.X1F.X2E,
Z1.T1F.T2C.X1F.X2E, Z2.T1F.T2C.X1F.X2E,
Z3.T1F.T2C.X1F.X2E, Z4.T1F.T2C.X1F.X2E,
Z1.T1A.T2D.X1F.X2E, Z2.T1A.T2D.X1F.X2E,
Z3.T1A.T2D.X1F.X2E, Z4.T1A.T2D.X1F.X2E,
Z1.T1B.T2D.X1F.X2E, Z2.T1B.T2D.X1F.X2E,
Z3.T1B.T2D.X1F.X2E, Z4.T1B.T2D.X1F.X2E,
Z1.T1C.T2D.X1F.X2E, Z2.T1C.T2D.X1F.X2E,
Z3.T1C.T2D.X1F.X2E, Z4.T1C.T2D.X1F.X2E,
Z1.T1D.T2D.X1F.X2E, Z2.T1D.T2D.X1F.X2E,
Z3.T1D.T2D.X1F.X2E, Z4.T1D.T2D.X1F.X2E,
Z1.T1E.T2D.X1F.X2E, Z2.T1E.T2D.X1F.X2E,
Z3.T1E.T2D.X1F.X2E, Z4.T1E.T2D.X1F.X2E,
Z1.T1F.T2D.X1F.X2E, Z2.T1F.T2D.X1F.X2E,
Z3.T1F.T2D.X1F.X2E, Z4.T1F.T2D.X1F.X2E,
Z1.T1A.T2E.X1F.X2E, Z2.T1A.T2E.X1F.X2E,
Z3.T1A.T2E.X1F.X2E, Z4.T1A.T2E.X1F.X2E,
Z1.T1B.T2E.X1F.X2E, Z2.T1B.T2E.X1F.X2E,
Z3.T1B.T2E.X1F.X2E, Z4.T1B.T2E.X1F.X2E,
Z1.T1C.T2E.X1F.X2E, Z2.T1C.T2E.X1F.X2E,
Z3.T1C.T2E.X1F.X2E, Z4.T1C.T2E.X1F.X2E,
Z1.T1D.T2E.X1F.X2E, Z2.T1D.T2E.X1F.X2E,
Z3.T1D.T2E.X1F.X2E, Z4.T1D.T2E.X1F.X2E,
Z1.T1E.T2E.X1F.X2E, Z2.T1E.T2E.X1F.X2E,
Z3.T1E.T2E.X1F.X2E, Z4.T1E.T2E.X1F.X2E,
Z1.T1F.T2E.X1F.X2E, Z2.T1F.T2E.X1F.X2E,
Z3.T1F.T2E.X1F.X2E, Z4.T1F.T2E.X1F.X2E,
Z1.T1A.T2F.X1F.X2E, Z2.T1A.T2F.X1F.X2E,
Z3.T1A.T2F.X1F.X2E, Z4.T1A.T2F.X1F.X2E,
Z1.T1B.T2F.X1F.X2E, Z2.T1B.T2F.X1F.X2E,
Z3.T1B.T2F.X1F.X2E, Z4.T1B.T2F.X1F.X2E,
Z1.T1C.T2F.X1F.X2E, Z2.T1C.T2F.X1F.X2E,
Z3.T1C.T2F.X1F.X2E, Z4.T1C.T2F.X1F.X2E,
Z1.T1D.T2F.X1F.X2E, Z2.T1D.T2F.X1F.X2E,
Z3.T1D.T2F.X1F.X2E, Z4.T1D.T2F.X1F.X2E,

TABLE 6-continued

List of Compound Structures of Formula II

Z1.T1E.T2F.X1F.X2E, Z2.T1E.T2F.X1F.X2E,
Z3.T1E.T2E.X1F.X2E, Z4.T1E.T2F.X1F.X2E,
Z1.T1F.T2F.X1F.X2E, Z2.T1F.T2F.X1F.X2E,
Z3.T1F.T2F.X1F.X2E, Z4.T1F.T2F.X1F.X2E,
Z1.T1A.T2A.X1A.X2F, Z2.T1A.T2A.X1A.X2F,
Z3.T1A.T2A.X1A.X2F, Z4.T1A.T2A.X1A.X2F,
Z1.T1B.T2A.X1A.X2F, Z2.T1B.T2A.X1A.X2F,
Z3.T1B.T2A.X1A.X2F, Z4.T1B.T2A.X1A.X2F,
Z1.T1C.T2A.X1A.X2F, Z2.T1C.T2A.X1A.X2F,
Z3.T1C.T2A.X1A.X2F, Z4.T1C.T2A.X1A.X2F,
Z1.T1D.T2A.X1A.X2F, Z2.T1D.T2A.X1A.X2F,
Z3.T1D.T2A.X1A.X2F, Z4.T1D.T2A.X1A.X2F,
Z1.T1E.T2A.X1A.X2F, Z2.T1E.T2A.X1A.X2F,
Z3.T1E.T2A.X1A.X2F, Z4.T1E.T2A.X1A.X2F,
Z1.T1F.T2A.X1A.X2F, Z2.T1F.T2A.X1A.X2F,
Z3.T1F.T2A.X1A.X2F, Z4.T1F.T2A.X1A.X2F,
Z1.T1A.T2B.X1A.X2F, Z2.T1A.T2B.X1A.X2F,
Z3.T1A.T2B.X1A.X2F, Z4.T1A.T2B.X1A.X2F,
Z1.T1B.T2B.X1A.X2F, Z2.T1B.T2B.X1A.X2F,
Z3.T1B.T2B.X1A.X2F, Z4.T1B.T2B.X1A.X2F,
Z1.T1C.T2B.X1A.X2F, Z2.T1C.T2B.X1A.X2F,
Z3.T1C.T2B.X1A.X2F, Z4.T1C.T2B.X1A.X2F,
Z1.T1D.T2B.X1A.X2F, Z2.T1D.T2B.X1A.X2F,
Z3.T1D.T2B.X1A.X2F, Z4.T1D.T2B.X1A.X2F,
Z1.T1E.T2B.X1A.X2F, Z2.T1E.T2B.X1A.X2F,
Z3.T1E.T2B.X1A.X2F, Z4.T1E.T2B.X1A.X2F,
Z1.T1F.T2B.X1A.X2F, Z2.T1F.T2B.X1A.X2F,
Z3.T1F.T2B.X1A.X2F, Z4.T1F.T2B.X1A.X2F,
Z1.T1A.T2C.X1A.X2F, Z2.T1A.T2C.X1A.X2F,
Z3.T1A.T2C.X1A.X2F, Z4.T1A.T2C.X1A.X2F,
Z1.T1B.T2C.X1A.X2F, Z2.T1B.T2C.X1A.X2F,
Z3.T1B.T2C.X1A.X2F, Z4.T1B.T2C.X1A.X2F,
Z1.T1C.T2C.X1A.X2F, Z2.T1C.T2C.X1A.X2F,
Z3.T1C.T2C.X1A.X2F, Z4.T1C.T2C.X1A.X2F,
Z1.T1D.T2C.X1A.X2F, Z2.T1D.T2C.X1A.X2F,
Z3.T1D.T2C.X1A.X2F, Z4.T1D.T2C.X1A.X2F,
Z1.T1E.T2C.X1A.X2F, Z2.T1E.T2C.X1A.X2F,
Z3.T1E.T2C.X1A.X2F, Z4.T1E.T2C.X1A.X2F,
Z1.T1F.T2C.X1A.X2F, Z2.T1F.T2C.X1A.X2F,
Z3.T1F.T2C.X1A.X2F, Z4.T1F.T2C.X1A.X2F,
Z1.T1A.T2D.X1A.X2F, Z2.T1A.T2D.X1A.X2F,
Z3.T1A.T2D.X1A.X2F, Z4.T1A.T2D.X1A.X2F,
Z1.T1B.T2D.X1A.X2F, Z2.T1B.T2D.X1A.X2F,
Z3.T1B.T2D.X1A.X2F, Z4.T1B.T2D.X1A.X2F,
Z1.T1C.T2D.X1A.X2F, Z2.T1C.T2D.X1A.X2F,
Z3.T1C.T2D.X1A.X2F, Z4.T1C.T2D.X1A.X2F,
Z1.T1D.T2D.X1A.X2F, Z2.T1D.T2D.X1A.X2F,
Z3.T1D.T2D.X1A.X2F, Z4.T1D.T2D.X1A.X2F,
Z1.T1E.T2D.X1A.X2F, Z2.T1E.T2D.X1A.X2F,
Z3.T1E.T2D.X1A.X2F, Z4.T1E.T2D.X1A.X2F,
Z1.T1F.T2D.X1A.X2F, Z2.T1F.T2D.X1A.X2F,
Z3.T1F.T2D.X1A.X2F, Z4.T1F.T2D.X1A.X2F,
Z1.T1A.T2E.X1A.X2F, Z2.T1A.T2E.X1A.X2F,
Z3.T1A.T2E.X1A.X2F, Z4.T1A.T2E.X1A.X2F,
Z1.T1B.T2E.X1A.X2F, Z2.T1B.T2E.X1A.X2F,
Z3.T1B.T2E.X1A.X2F, Z4.T1B.T2E.X1A.X2F,
Z1.T1C.T2E.X1A.X2F, Z2.T1C.T2E.X1A.X2F,
Z3.T1C.T2E.X1A.X2F, Z4.T1C.T2E.X1A.X2F,
Z1.T1D.T2E.X1A.X2F, Z2.T1D.T2E.X1A.X2F,
Z3.T1D.T2E.X1A.X2F, Z4.T1D.T2E.X1A.X2F,
Z1.T1E.T2E.X1A.X2F, Z2.T1E.T2E.X1A.X2F,
Z3.T1E.T2E.X1A.X2F, Z4.T1E.T2E.X1A.X2F,
Z1.T1F.T2E.X1A.X2F, Z2.T1F.T2E.X1A.X2F,
Z3.T1F.T2E.X1A.X2F, Z4.T1F.T2E.X1A.X2F,
Z1.T1A.T2F.X1A.X2F, Z2.T1A.T2F.X1A.X2F,
Z3.T1A.T2F.X1A.X2F, Z4.T1A.T2F.X1A.X2F,
Z1.T1B.T2F.X1A.X2F, Z2.T1B.T2F.X1A.X2F,
Z3.T1B.T2F.X1A.X2F, Z4.T1B.T2F.X1A.X2F,
Z1.T1C.T2F.X1A.X2F, Z2.T1C.T2F.X1A.X2F,
Z3.T1C.T2F.X1A.X2F, Z4.T1C.T2F.X1A.X2F,
Z1.T1D.T2F.X1A.X2F, Z2.T1D.T2F.X1A.X2F,
Z3.T1D.T2F.X1A.X2F, Z4.T1D.T2F.X1A.X2F,
Z1.T1E.T2F.X1A.X2F, Z2.T1E.T2F.X1A.X2F,
Z3.T1E.T2F.X1A.X2F, Z4.T1E.T2F.X1A.X2F,
Z1.T1F.T2F.X1A.X2F, Z2.T1F.T2F.X1A.X2F,
Z3.T1F.T2F.X1A.X2F, Z4.T1F.T2F.X1A.X2F,
Z1.T1A.T2A.X1B.X2F, Z2.T1A.T2A.X1B.X2F,

TABLE 6-continued

List of Compound Structures of Formula II

Z3.T1A.T2A.X1B.X2F, Z4.T1A.T2A.X1B.X2F,
Z1.T1B.T2A.X1B.X2F, Z2.T1B.T2A.X1B.X2F,
Z3.T1B.T2A.X1B.X2F, Z4.T1B.T2A.X1B.X2F,
Z1.T1C.T2A.X1B.X2F, Z2.T1C.T2A.X1B.X2F,
Z3.T1C.T2A.X1B.X2F, Z4.T1C.T2A.X1B.X2F,
Z1.T1D.T2A.X1B.X2F, Z2.T1D.T2A.X1B.X2F,
Z3.T1D.T2A.X1B.X2F, Z4.T1D.T2A.X1B.X2F,
Z1.T1E.T2A.X1B.X2F, Z2.T1E.T2A.X1B.X2F,
Z3.T1E.T2A.X1B.X2F, Z4.T1E.T2A.X1B.X2F,
Z1.T1F.T2A.X1B.X2F, Z2.T1F.T2A.X1B.X2F,
Z3.T1F.T2A.X1B.X2F, Z4.T1F.T2A.X1B.X2F,
Z1.T1A.T2B.X1B.X2F, Z2.T1A.T2B.X1B.X2F,
Z3.T1A.T2B.X1B.X2F, Z4.T1A.T2B.X1B.X2F,
Z1.T1B.T2B.X1B.X2F, Z2.T1B.T2B.X1B.X2F,
Z3.T1B.T2B.X1B.X2F, Z4.T1B.T2B.X1B.X2F,
Z1.T1C.T2B.X1B.X2F, Z2.T1C.T2B.X1B.X2F,
Z3.T1C.T2B.X1B.X2F, Z4.T1C.T2B.X1B.X2F,
Z1.T1D.T2B.X1B.X2F, Z2.T1D.T2B.X1B.X2F,
Z3.T1D.T2B.X1B.X2F, Z4.T1D.T2B.X1B.X2F,
Z1.T1E.T2B.X1B.X2F, Z2.T1E.T2B.X1B.X2F,
Z3.T1E.T2B.X1B.X2F, Z4.T1E.T2B.X1B.X2F,
Z1.T1F.T2B.X1B.X2F, Z2.T1F.T2B.X1B.X2F,
Z3.T1F.T2B.X1B.X2F, Z4.T1F.T2B.X1B.X2F,
Z1.T1A.T2C.X1B.X2F, Z2.T1A.T2C.X1B.X2F,
Z3.T1A.T2C.X1B.X2F, Z4.T1A.T2C.X1B.X2F,
Z1.T1B.T2C.X1B.X2F, Z2.T1B.T2C.X1B.X2F,
Z3.T1B.T2C.X1B.X2F, Z4.T1B.T2C.X1B.X2F,
Z1.T1C.T2C.X1B.X2F, Z2.T1C.T2C.X1B.X2F,
Z3.T1C.T2C.X1B.X2F, Z4.T1C.T2C.X1B.X2F,
Z1.T1D.T2C.X1B.X2F, Z2.T1D.T2C.X1B.X2F,
Z3.T1D.T2C.X1B.X2F, Z4.T1D.T2C.X1B.X2F,
Z1.T1E.T2C.X1B.X2F, Z2.T1E.T2C.X1B.X2F,
Z3.T1E.T2C.X1B.X2F, Z4.T1E.T2C.X1B.X2F,
Z1.T1F.T2C.X1B.X2F, Z2.T1F.T2C.X1B.X2F,
Z3.T1F.T2C.X1B.X2F, Z4.T1F.T2C.X1B.X2F,
Z1.T1A.T2D.X1B.X2F, Z2.T1A.T2D.X1B.X2F,
Z3.T1A.T2D.X1B.X2F, Z4.T1A.T2D.X1B.X2F,
Z1.T1B.T2D.X1B.X2F, Z2.T1B.T2D.X1B.X2F,
Z3.T1B.T2D.X1B.X2F, Z4.T1B.T2D.X1B.X2F,
Z1.T1C.T2D.X1B.X2F, Z2.T1C.T2D.X1B.X2F,
Z3.T1C.T2D.X1B.X2F, Z4.T1C.T2D.X1B.X2F,
Z1.T1D.T2D.X1B.X2F, Z2.T1D.T2D.X1B.X2F,
Z3.T1D.T2D.X1B.X2F, Z4.T1D.T2D.X1B.X2F,
Z1.T1E.T2D.X1B.X2F, Z2.T1E.T2D.X1B.X2F,
Z3.T1E.T2D.X1B.X2F, Z4.T1E.T2D.X1B.X2F,
Z1.T1F.T2D.X1B.X2F, Z2.T1F.T2D.X1B.X2F,
Z3.T1F.T2D.X1B.X2F, Z4.T1F.T2D.X1B.X2F,
Z1.T1A.T2E.X1B.X2F, Z2.T1A.T2E.X1B.X2F,
Z3.T1A.T2E.X1B.X2F, Z4.T1A.T2E.X1B.X2F,
Z1.T1B.T2E.X1B.X2F, Z2.T1B.T2E.X1B.X2F,
Z3.T1B.T2E.X1B.X2F, Z4.T1B.T2E.X1B.X2F,
Z1.T1C.T2E.X1B.X2F, Z2.T1C.T2E.X1B.X2F,
Z3.T1C.T2E.X1B.X2F, Z4.T1C.T2E.X1B.X2F,
Z1.T1D.T2E.X1B.X2F, Z2.T1D.T2E.X1B.X2F,
Z3.T1D.T2E.X1B.X2F, Z4.T1D.T2E.X1B.X2F,
Z1.T1E.T2E.X1B.X2F, Z2.T1E.T2E.X1B.X2F,
Z3.T1E.T2E.X1B.X2F, Z4.T1E.T2E.X1B.X2F,
Z1.T1F.T2E.X1B.X2F, Z2.T1F.T2E.X1B.X2F,
Z3.T1F.T2E.X1B.X2F, Z4.T1F.T2E.X1B.X2F,
Z1.T1A.T2F.X1B.X2F, Z2.T1A.T2F.X1B.X2F,
Z3.T1A.T2F.X1B.X2F, Z4.T1A.T2F.X1B.X2F,
Z1.T1B.T2F.X1B.X2F, Z2.T1B.T2F.X1B.X2F,
Z3.T1B.T2F.X1B.X2F, Z4.T1B.T2F.X1B.X2F,
Z1.T1C.T2F.X1B.X2F, Z2.T1C.T2F.X1B.X2F,
Z3.T1C.T2F.X1B.X2F, Z4.T1C.T2F.X1B.X2F,
Z1.T1D.T2F.X1B.X2F, Z2.T1D.T2F.X1B.X2F,
Z3.T1D.T2F.X1B.X2F, Z4.T1D.T2F.X1B.X2F,
Z1.T1E.T2F.X1B.X2F, Z2.T1E.T2F.X1B.X2F,
Z3.T1E.T2F.X1B.X2F, Z4.T1E.T2F.X1B.X2F,
Z1.T1F.T2F.X1B.X2F, Z2.T1F.T2F.X1B.X2F,
Z3.T1F.T2F.X1B.X2F, Z4.T1F.T2F.X1B.X2F,
Z1.T1A.T2A.X1C.X2F, Z2.T1A.T2A.X1C.X2F,
Z3.T1A.T2A.X1C.X2F, Z4.T1A.T2A.X1C.X2F,
Z1.T1B.T2A.X1C.X2F, Z2.T1B.T2A.X1C.X2F,
Z3.T1B.T2A.X1C.X2F, Z4.T1B.T2A.X1C.X2F,
Z1.T1C.T2A.X1C.X2F, Z2.T1C.T2A.X1C.X2F,
Z3.T1C.T2A.X1C.X2F, Z4.T1C.T2A.X1C.X2F,

TABLE 6-continued

List of Compound Structures of Formula II

Z1.T1D.T2A.X1C.X2F, Z2.T1D.T2A.X1C.X2F,
Z3.T1D.T2A.X1C.X2F, Z4.T1D.T2A.X1C.X2F,
Z1.T1E.T2A.X1C.X2F, Z2.T1E.T2A.X1C.X2F,
Z3.T1E.T2A.X1C.X2F, Z4.T1E.T2A.X1C.X2F,
Z1.T1F.T2A.X1C.X2F, Z2.T1F.T2A.X1C.X2F,
Z3.T1F.T2A.X1C.X2F, Z4.T1F.T2A.X1C.X2F,
Z1.T1A.T2B.X1C.X2F, Z2.T1A.T2B.X1C.X2F,
Z3.T1A.T2B.X1C.X2F, Z4.T1A.T2B.X1C.X2F,
Z1.T1B.T2B.X1C.X2F, Z2.T1B.T2B.X1C.X2F,
Z3.T1B.T2B.X1C.X2F, Z4.T1B.T2B.X1C.X2F,
Z1.T1C.T2B.X1C.X2F, Z2.T1C.T2B.X1C.X2F,
Z3.T1C.T2B.X1C.X2F, Z4.T1C.T2B.X1C.X2F,
Z1.T1D.T2B.X1C.X2F, Z2.T1D.T2B.X1C.X2F,
Z3.T1D.T2B.X1C.X2F, Z4.T1D.T2B.X1C.X2F,
Z1.T1E.T2B.X1C.X2F, Z2.T1E.T2B.X1C.X2F,
Z3.T1E.T2B.X1C.X2F, Z4.T1E.T2B.X1C.X2F,
Z1.T1F.T2B.X1C.X2F, Z2.T1F.T2B.X1C.X2F,
Z3.T1F.T2B.X1C.X2F, Z4.T1F.T2B.X1C.X2F,
Z1.T1A.T2C.X1C.X2F, Z2.T1A.T2C.X1C.X2F,
Z3.T1A.T2C.X1C.X2F, Z4.T1A.T2C.X1C.X2F,
Z1.T1B.T2C.X1C.X2F, Z2.T1B.T2C.X1C.X2F,
Z3.T1B.T2C.X1C.X2F, Z4.T1B.T2C.X1C.X2F,
Z1.T1C.T2C.X1C.X2F, Z2.T1C.T2C.X1C.X2F,
Z3.T1C.T2C.X1C.X2F, Z4.T1C.T2C.X1C.X2F,
Z1.T1D.T2C.X1C.X2F, Z2.T1D.T2C.X1C.X2F,
Z3.T1D.T2C.X1C.X2F, Z4.T1D.T2C.X1C.X2F,
Z1.T1E.T2C.X1C.X2F, Z2.T1E.T2C.X1C.X2F,
Z3.T1E.T2C.X1C.X2F, Z4.T1E.T2C.X1C.X2F,
Z1.T1F.T2C.X1C.X2F, Z2.T1F.T2C.X1C.X2F,
Z3.T1F.T2C.X1C.X2F, Z4.T1F.T2C.X1C.X2F,
Z1.T1A.T2D.X1C.X2F, Z2.T1A.T2D.X1C.X2F,
Z3.T1A.T2D.X1C.X2F, Z4.T1A.T2D.X1C.X2F,
Z1.T1B.T2D.X1C.X2F, Z2.T1B.T2D.X1C.X2F,
Z3.T1B.T2D.X1C.X2F, Z4.T1B.T2D.X1C.X2F,
Z1.T1C.T2D.X1C.X2F, Z2.T1C.T2D.X1C.X2F,
Z3.T1C.T2D.X1C.X2F, Z4.T1C.T2D.X1C.X2F,
Z1.T1D.T2D.X1C.X2F, Z2.T1D.T2D.X1C.X2F,
Z3.T1D.T2D.X1C.X2F, Z4.T1D.T2D.X1C.X2F,
Z1.T1E.T2D.X1C.X2F, Z2.T1E.T2D.X1C.X2F,
Z3.T1E.T2D.X1C.X2F, Z4.T1E.T2D.X1C.X2F,
Z1.T1F.T2D.X1C.X2F, Z2.T1F.T2D.X1C.X2F,
Z3.T1F.T2D.X1C.X2F, Z4.T1F.T2D.X1C.X2F,
Z1.T1A.T2E.X1C.X2F, Z2.T1A.T2E.X1C.X2F,
Z3.T1A.T2E.X1C.X2F, Z4.T1A.T2E.X1C.X2F,
Z1.T1B.T2E.X1C.X2F, Z2.T1B.T2E.X1C.X2F,
Z3.T1B.T2E.X1C.X2F, Z4.T1B.T2E.X1C.X2F,
Z1.T1C.T2E.X1C.X2F, Z2.T1C.T2E.X1C.X2F,
Z3.T1C.T2E.X1C.X2F, Z4.T1C.T2E.X1C.X2F,
Z1.T1D.T2E.X1C.X2F, Z2.T1D.T2E.X1C.X2F,
Z3.T1D.T2E.X1C.X2F, Z4.T1D.T2E.X1C.X2F,
Z1.T1E.T2E.X1C.X2F, Z2.T1E.T2E.X1C.X2F,
Z3.T1E.T2E.X1C.X2F, Z4.T1E.T2E.X1C.X2F,
Z1.T1F.T2E.X1C.X2F, Z2.T1F.T2E.X1C.X2F,
Z3.T1F.T2E.X1C.X2F, Z4.T1F.T2E.X1C.X2F,
Z1.T1A.T2F.X1C.X2F, Z2.T1A.T2F.X1C.X2F,
Z3.T1A.T2F.X1C.X2F, Z4.T1A.T2F.X1C.X2F,
Z1.T1B.T2F.X1C.X2F, Z2.T1B.T2F.X1C.X2F,
Z3.T1B.T2F.X1C.X2F, Z4.T1B.T2F.X1C.X2F,
Z1.T1C.T2F.X1C.X2F, Z2.T1C.T2F.X1C.X2F,
Z3.T1C.T2F.X1C.X2F, Z4.T1C.T2F.X1C.X2F,
Z1.T1D.T2F.X1C.X2F, Z2.T1D.T2F.X1C.X2F,
Z3.T1D.T2F.X1C.X2F, Z4.T1D.T2F.X1C.X2F,
Z1.T1E.T2F.X1C.X2F, Z2.T1E.T2F.X1C.X2F,
Z3.T1E.T2F.X1C.X2F, Z4.T1E.T2F.X1C.X2F,
Z1.T1F.T2F.X1C.X2F, Z2.T1F.T2F.X1C.X2F,
Z3.T1F.T2F.X1C.X2F, Z4.T1F.T2F.X1C.X2F,
Z1.T1A.T2A.X1D.X2F, Z2.T1A.T2A.X1D.X2F,
Z3.T1A.T2A.X1D.X2F, Z4.T1A.T2A.X1D.X2F,
Z1.T1B.T2A.X1D.X2F, Z2.T1B.T2A.X1D.X2F,
Z3.T1B.T2A.X1D.X2F, Z4.T1B.T2A.X1D.X2F,
Z1.T1C.T2A.X1D.X2F, Z2.T1C.T2A.X1D.X2F,
Z3.T1C.T2A.X1D.X2F, Z4.T1C.T2A.X1D.X2F,
Z1.T1D.T2A.X1D.X2F, Z2.T1D.T2A.X1D.X2F,
Z3.T1D.T2A.X1D.X2F, Z4.T1D.T2A.X1D.X2F,
Z1.T1E.T2A.X1D.X2F, Z2.T1E.T2A.X1D.X2F,
Z3.T1E.T2A.X1D.X2F, Z4.T1E.T2A.X1D.X2F,
Z1.T1F.T2A.X1D.X2F, Z2.T1F.T2A.X1D.X2F,
Z3.T1F.T2A.X1D.X2F, Z4.T1F.T2A.X1D.X2F,
Z1.T1A.T2B.X1D.X2F, Z2.T1A.T2B.X1D.X2F,
Z3.T1A.T2B.X1D.X2F, Z4.T1A.T2B.X1D.X2F,
Z1.T1B.T2B.X1D.X2F, Z2.T1B.T2B.X1D.X2F,
Z3.T1B.T2B.X1D.X2F, Z4.T1B.T2B.X1D.X2F,
Z1.T1C.T2B.X1D.X2F, Z2.T1C.T2B.X1D.X2F,
Z3.T1C.T2B.X1D.X2F, Z4.T1C.T2B.X1D.X2F,
Z1.T1D.T2B.X1D.X2F, Z2.T1D.T2B.X1D.X2F,
Z3.T1D.T2B.X1D.X2F, Z4.T1D.T2B.X1D.X2F,
Z1.T1E.T2B.X1D.X2F, Z2.T1E.T2B.X1D.X2F,
Z3.T1E.T2B.X1D.X2F, Z4.T1E.T2B.X1D.X2F,
Z1.T1F.T2B.X1D.X2F, Z2.T1F.T2B.X1D.X2F,
Z3.T1F.T2B.X1D.X2F, Z4.T1F.T2B.X1D.X2F,
Z1.T1A.T2C.X1D.X2F, Z2.T1A.T2C.X1D.X2F,
Z3.T1A.T2C.X1D.X2F, Z4.T1A.T2C.X1D.X2F,
Z1.T1B.T2C.X1D.X2F, Z2.T1B.T2C.X1D.X2F,
Z3.T1B.T2C.X1D.X2F, Z4.T1B.T2C.X1D.X2F,
Z1.T1C.T2C.X1D.X2F, Z2.T1C.T2C.X1D.X2F,
Z3.T1C.T2C.X1D.X2F, Z4.T1C.T2C.X1D.X2F,
Z1.T1D.T2C.X1D.X2F, Z2.T1D.T2C.X1D.X2F,
Z3.T1D.T2C.X1D.X2F, Z4.T1D.T2C.X1D.X2F,
Z1.T1E.T2C.X1D.X2F, Z2.T1E.T2C.X1D.X2F,
Z3.T1E.T2C.X1D.X2F, Z4.T1E.T2C.X1D.X2F,
Z1.T1F.T2C.X1D.X2F, Z2.T1F.T2C.X1D.X2F,
Z3.T1F.T2C.X1D.X2F, Z4.T1F.T2C.X1D.X2F,
Z1.T1A.T2D.X1D.X2F, Z2.T1A.T2D.X1D.X2F,
Z3.T1A.T2D.X1D.X2F, Z4.T1A.T2D.X1D.X2F,
Z1.T1B.T2D.X1D.X2F, Z2.T1B.T2D.X1D.X2F,
Z3.T1B.T2D.X1D.X2F, Z4.T1B.T2D.X1D.X2F,
Z1.T1C.T2D.X1D.X2F, Z2.T1C.T2D.X1D.X2F,
Z3.T1C.T2D.X1D.X2F, Z4.T1C.T2D.X1D.X2F,
Z1.T1D.T2D.X1D.X2F, Z2.T1D.T2D.X1D.X2F,
Z3.T1D.T2D.X1D.X2F, Z4.T1D.T2D.X1D.X2F,
Z1.T1E.T2D.X1D.X2F, Z2.T1E.T2D.X1D.X2F,
Z3.T1E.T2D.X1D.X2F, Z4.T1E.T2D.X1D.X2F,
Z1.T1F.T2D.X1D.X2F, Z2.T1F.T2D.X1D.X2F,
Z3.T1F.T2D.X1D.X2F, Z4.T1F.T2D.X1D.X2F,
Z1.T1A.T2E.X1D.X2F, Z2.T1A.T2E.X1D.X2F,
Z3.T1A.T2E.X1D.X2F, Z4.T1A.T2E.X1D.X2F,
Z1.T1B.T2E.X1D.X2F, Z2.T1B.T2E.X1D.X2F,
Z3.T1B.T2E.X1D.X2F, Z4.T1B.T2E.X1D.X2F,
Z1.T1C.T2E.X1D.X2F, Z2.T1C.T2E.X1D.X2F,
Z3.T1C.T2E.X1D.X2F, Z4.T1C.T2E.X1D.X2F,
Z1.T1D.T2E.X1D.X2F, Z2.T1D.T2E.X1D.X2F,
Z3.T1D.T2E.X1D.X2F, Z4.T1D.T2E.X1D.X2F,
Z1.T1E.T2E.X1D.X2F, Z2.T1E.T2E.X1D.X2F,
Z3.T1E.T2E.X1D.X2F, Z4.T1E.T2E.X1D.X2F,
Z1.T1F.T2E.X1D.X2F, Z2.T1F.T2E.X1D.X2F,
Z3.T1F.T2E.X1D.X2F, Z4.T1F.T2E.X1D.X2F,
Z1.T1A.T2F.X1D.X2F, Z2.T1A.T2F.X1D.X2F,
Z3.T1A.T2F.X1D.X2F, Z4.T1A.T2F.X1D.X2F,
Z1.T1B.T2F.X1D.X2E, Z2.T1B.T2F.X1D.X2E,
Z3.T1B.T2F.X1D.X2F, Z4.T1B.T2F.X1D.X2F,
Z1.T1C.T2F.X1D.X2F, Z2.T1C.T2F.X1D.X2F,
Z3.T1C.T2F.X1D.X2F, Z4.T1C.T2F.X1D.X2F,
Z1.T1D.T2F.X1D.X2F, Z2.T1D.T2F.X1D.X2F,
Z3.T1D.T2F.X1D.X2F, Z4.T1D.T2F.X1D.X2F,
Z1.T1E.T2F.X1D.X2F, Z2.T1E.T2F.X1D.X2F,
Z3.T1E.T2F.X1D.X2F, Z4.T1E.T2F.X1D.X2F,
Z1.T1F.T2F.X1D.X2F, Z2.T1F.T2F.X1D.X2F,
Z3.T1F.T2F.X1D.X2F, Z4.T1F.T2F.X1D.X2F,
Z1.T1A.T2A.X1E.X2F, Z2.T1A.T2A.X1E.X2F,
Z3.T1A.T2A.X1E.X2F, Z4.T1A.T2A.X1E.X2F,
Z1.T1B.T2A.X1E.X2F, Z2.T1B.T2A.X1E.X2F,
Z3.T1B.T2A.X1E.X2F, Z4.T1B.T2A.X1E.X2F,
Z1.T1C.T2A.X1E.X2F, Z2.T1C.T2A.X1E.X2F,
Z3.T1C.T2A.X1E.X2F, Z4.T1C.T2A.X1E.X2F,
Z1.T1D.T2A.X1E.X2F, Z2.T1D.T2A.X1E.X2F,
Z3.T1D.T2A.X1E.X2F, Z4.T1D.T2A.X1E.X2F,
Z1.T1E.T2A.X1E.X2F, Z2.T1E.T2A.X1E.X2F,
Z3.T1E.T2A.X1E.X2F, Z4.T1E.T2A.X1E.X2F,
Z1.T1F.T2A.X1E.X2F, Z2.T1F.T2A.X1E.X2F,
Z3.T1F.T2A.X1E.X2F, Z4.T1F.T2A.X1E.X2F,
Z1.T1A.T2B.X1E.X2F, Z2.T1A.T2B.X1E.X2F,
Z3.T1A.T2B.X1E.X2F, Z4.T1A.T2B.X1E.X2F,
Z1.T1B.T2B.X1E.X2F, Z2.T1B.T2B.X1E.X2F,
Z3.T1B.T2B.X1E.X2F, Z4.T1B.T2B.X1E.X2F,

TABLE 6-continued

List of Compound Structures of Formula II

Z1.T1C.T2B.X1E.X2F, Z2.T1C.T2B.X1E.X2F,
Z3.T1C.T2B.X1E.X2F, Z4.T1C.T2B.X1E.X2F,
Z1.T1D.T2B.X1E.X2F, Z2.T1D.T2B.X1E.X2F,
Z3.T1D.T2B.X1E.X2F, Z4.T1D.T2B.X1E.X2F,
Z1.T1E.T2B.X1E.X2F, Z2.T1E.T2B.X1E.X2F,
Z3.T1E.T2B.X1E.X2F, Z4.T1E.T2B.X1E.X2F,
Z1.T1F.T2B.X1E.X2F, Z2.T1F.T2B.X1E.X2F,
Z3.T1F.T2B.X1E.X2F, Z4.T1F.T2B.X1E.X2F,
Z1.T1A.T2C.X1E.X2F, Z2.T1A.T2C.X1E.X2F,
Z3.T1A.T2C.X1E.X2F, Z4.T1A.T2C.X1E.X2F,
Z1.T1B.T2C.X1E.X2F, Z2.T1B.T2C.X1E.X2F,
Z3.T1B.T2C.X1E.X2F, Z4.T1B.T2C.X1E.X2F,
Z1.T1C.T2C.X1E.X2F, Z2.T1C.T2C.X1E.X2F,
Z3.T1C.T2C.X1E.X2F, Z4.T1C.T2C.X1E.X2F,
Z1.T1D.T2C.X1E.X2F, Z2.T1D.T2C.X1E.X2F,
Z3.T1D.T2C.X1E.X2F, Z4.T1D.T2C.X1E.X2F,
Z1.T1E.T2C.X1E.X2F, Z2.T1E.T2C.X1E.X2F,
Z3.T1E.T2C.X1E.X2F, Z4.T1E.T2C.X1E.X2F,
Z1.T1F.T2C.X1E.X2F, Z2.T1F.T2C.X1E.X2F,
Z3.T1F.T2C.X1E.X2F, Z4.T1F.T2C.X1E.X2F,
Z1.T1A.T2D.X1E.X2F, Z2.T1A.T2D.X1E.X2F,
Z3.T1A.T2D.X1E.X2F, Z4.T1A.T2D.X1E.X2F,
Z1.T1B.T2D.X1E.X2F, Z2.T1B.T2D.X1E.X2F,
Z3.T1B.T2D.X1E.X2F, Z4.T1B.T2D.X1E.X2F,
Z1.T1C.T2D.X1E.X2F, Z2.T1C.T2D.X1E.X2F,
Z3.T1C.T2D.X1E.X2F, Z4.T1C.T2D.X1E.X2F,
Z1.T1D.T2D.X1E.X2F, Z2.T1D.T2D.X1E.X2F,
Z3.T1D.T2D.X1E.X2F, Z4.T1D.T2D.X1E.X2F,
Z1.T1E.T2D.X1E.X2F, Z2.T1E.T2D.X1E.X2F,
Z3.T1E.T2D.X1E.X2F, Z4.T1E.T2D.X1E.X2F,
Z1.T1F.T2D.X1E.X2F, Z2.T1F.T2D.X1E.X2F,
Z3.T1F.T2D.X1E.X2F, Z4.T1F.T2D.X1E.X2F,
Z1.T1A.T2E.X1E.X2F, Z2.T1A.T2E.X1E.X2F,
Z3.T1A.T2E.X1E.X2F, Z4.T1A.T2E.X1E.X2F,
Z1.T1B.T2E.X1E.X2F, Z2.T1B.T2E.X1E.X2F,
Z3.T1B.T2E.X1E.X2F, Z4.T1B.T2E.X1E.X2F,
Z1.T1C.T2E.X1E.X2F, Z2.T1C.T2E.X1E.X2F,
Z3.T1C.T2E.X1E.X2F, Z4.T1C.T2E.X1E.X2F,
Z1.T1D.T2E.X1E.X2F, Z2.T1D.T2E.X1E.X2F,
Z3.T1D.T2E.X1E.X2F, Z4.T1D.T2E.X1E.X2F,
Z1.T1E.T2E.X1E.X2F, Z2.T1E.T2E.X1E.X2F,
Z3.T1E.T2E.X1E.X2F, Z4.T1E.T2E.X1E.X2F,
Z1.T1F.T2E.X1E.X2F, Z2.T1F.T2E.X1E.X2F,
Z3.T1F.T2E.X1E.X2F, Z4.T1F.T2E.X1E.X2F,
Z1.T1A.T2F.X1E.X2F, Z2.T1A.T2F.X1E.X2F,
Z3.T1A.T2F.X1E.X2F, Z4.T1A.T2F.X1E.X2F,
Z1.T1B.T2F.X1E.X2F, Z2.T1B.T2F.X1E.X2F,
Z3.T1B.T2F.X1E.X2F, Z4.T1B.T2F.X1E.X2F,
Z1.T1C.T2F.X1E.X2F, Z2.T1C.T2F.X1E.X2F,
Z3.T1C.T2F.X1E.X2F, Z4.T1C.T2F.X1E.X2F,
Z1.T1D.T2F.X1E.X2F, Z2.T1D.T2F.X1E.X2F,
Z3.T1D.T2F.X1E.X2F, Z4.T1D.T2F.X1E.X2F,
Z1.T1E.T2F.X1E.X2F, Z2.T1E.T2F.X1E.X2F,
Z3.T1E.T2F.X1E.X2F, Z4.T1E.T2F.X1E.X2F,
Z1.T1F.T2F.X1E.X2F, Z2.T1F.T2F.X1E.X2F,
Z3.T1F.T2F.X1E.X2F, Z4.T1F.T2F.X1E.X2F,
Z1.T1A.T2A.X1F.X2F, Z2.T1A.T2A.X1F.X2F,
Z3.T1A.T2A.X1F.X2F, Z4.T1A.T2A.X1F.X2F,
Z1.T1B.T2A.X1F.X2F, Z2.T1B.T2A.X1F.X2F,
Z3.T1B.T2A.X1F.X2F, Z4.T1B.T2A.X1F.X2F,
Z1.T1C.T2A.X1F.X2F, Z2.T1C.T2A.X1F.X2F,
Z3.T1C.T2A.X1F.X2F, Z4.T1C.T2A.X1F.X2F,
Z1.T1D.T2A.X1F.X2F, Z2.T1D.T2A.X1F.X2F,
Z3.T1D.T2A.X1F.X2F, Z4.T1D.T2A.X1F.X2F,
Z1.T1E.T2A.X1F.X2F, Z2.T1E.T2A.X1F.X2F,
Z3.T1E.T2A.X1F.X2F, Z4.T1E.T2A.X1F.X2F,
Z1.T1F.T2A.X1F.X2F, Z2.T1F.T2A.X1F.X2F,
Z3.T1F.T2A.X1F.X2F, Z4.T1F.T2A.X1F.X2F,
Z1.T1A.T2B.X1F.X2F, Z2.T1A.T2B.X1F.X2F,
Z3.T1A.T2B.X1F.X2F, Z4.T1A.T2B.X1F.X2F,
Z1.T1B.T2B.X1F.X2F, Z2.T1B.T2B.X1F.X2F,
Z3.T1B.T2B.X1F.X2F, Z4.T1B.T2B.X1F.X2F,
Z1.T1C.T2B.X1F.X2F, Z2.T1C.T2B.X1F.X2F,
Z3.T1C.T2B.X1F.X2F, Z4.T1C.T2B.X1F.X2F,
Z1.T1D.T2B.X1F.X2F, Z2.T1D.T2B.X1F.X2F,
Z3.T1D.T2B.X1F.X2F, Z4.T1D.T2B.X1F.X2F,
Z1.T1E.T2B.X1F.X2F, Z2.T1E.T2B.X1F.X2F,
Z3.T1E.T2B.X1F.X2F, Z4.T1E.T2B.X1F.X2F,
Z1.T1F.T2B.X1F.X2F, Z2.T1F.T2B.X1F.X2F,
Z3.T1F.T2B.X1F.X2F, Z4.T1F.T2B.X1F.X2F,
Z1.T1A.T2C.X1F.X2F, Z2.T1A.T2C.X1F.X2F,
Z3.T1A.T2C.X1F.X2F, Z4.T1A.T2C.X1F.X2F,
Z1.T1B.T2C.X1F.X2F, Z2.T1B.T2C.X1F.X2F,
Z3.T1B.T2C.X1F.X2F, Z4.T1B.T2C.X1F.X2F,
Z1.T1C.T2C.X1F.X2F, Z2.T1C.T2C.X1F.X2F,
Z3.T1C.T2C.X1F.X2F, Z4.T1C.T2C.X1F.X2F,
Z1.T1D.T2C.X1F.X2F, Z2.T1D.T2C.X1F.X2F,
Z3.T1D.T2C.X1F.X2F, Z4.T1D.T2C.X1F.X2F,
Z1.T1E.T2C.X1F.X2F, Z2.T1E.T2C.X1F.X2F,
Z3.T1E.T2C.X1F.X2F, Z4.T1E.T2C.X1F.X2F,
Z1.T1F.T2C.X1F.X2F, Z2.T1F.T2C.X1F.X2F,
Z3.T1F.T2C.X1F.X2F, Z4.T1F.T2C.X1F.X2F,
Z1.T1A.T2D.X1F.X2F, Z2.T1A.T2D.X1F.X2F,
Z3.T1A.T2D.X1F.X2F, Z4.T1A.T2D.X1F.X2F,
Z1.T1B.T2D.X1F.X2F, Z2.T1B.T2D.X1F.X2F,
Z3.T1B.T2D.X1F.X2F, Z4.T1B.T2D.X1F.X2F,
Z1.T1C.T2D.X1F.X2F, Z2.T1C.T2D.X1F.X2F,
Z3.T1C.T2D.X1F.X2F, Z4.T1C.T2D.X1F.X2F,
Z1.T1D.T2D.X1F.X2F, Z2.T1D.T2D.X1F.X2F,
Z3.T1D.T2D.X1F.X2F, Z4.T1D.T2D.X1F.X2F,
Z1.T1E.T2D.X1F.X2F, Z2.T1E.T2D.X1F.X2F,
Z3.T1E.T2D.X1F.X2F, Z4.T1E.T2D.X1F.X2F,
Z1.T1F.T2D.X1F.X2F, Z2.T1F.T2D.X1F.X2F,
Z3.T1F.T2D.X1F.X2F, Z4.T1F.T2D.X1F.X2F,
Z1.T1A.T2E.X1F.X2F, Z2.T1A.T2E.X1F.X2F,
Z3.T1A.T2E.X1F.X2F, Z4.T1A.T2E.X1F.X2F,
Z1.T1B.T2E.X1F.X2F, Z2.T1B.T2E.X1F.X2F,
Z3.T1B.T2E.X1F.X2F, Z4.T1B.T2E.X1F.X2F,
Z1.T1C.T2E.X1F.X2F, Z2.T1C.T2E.X1F.X2F,
Z3.T1C.T2E.X1F.X2F, Z4.T1C.T2E.X1F.X2F,
Z1.T1D.T2E.X1F.X2F, Z2.T1D.T2E.X1F.X2F,
Z3.T1D.T2E.X1F.X2F, Z4.T1D.T2E.X1F.X2F,
Z1.T1E.T2E.X1F.X2F, Z2.T1E.T2E.X1F.X2F,
Z3.T1E.T2E.X1F.X2F, Z4.T1E.T2E.X1F.X2F,
Z1.T1F.T2E.X1F.X2F, Z2.T1F.T2E.X1F.X2F,
Z3.T1F.T2E.X1F.X2F, Z4.T1F.T2E.X1F.X2F,
Z1.T1A.T2F.X1F.X2F, Z2.T1A.T2F.X1F.X2F,
Z3.T1A.T2F.X1F.X2F, Z4.T1A.T2F.X1F.X2F,
Z1.T1B.T2F.X1F.X2F, Z2.T1B.T2F.X1F.X2F,
Z3.T1B.T2F.X1F.X2F, Z4.T1B.T2F.X1F.X2F,
Z1.T1C.T2F.X1F.X2F, Z2.T1C.T2F.X1F.X2F,
Z3.T1C.T2F.X1F.X2F, Z4.T1C.T2F.X1F.X2F,
Z1.T1D.T2F.X1F.X2F, Z2.T1D.T2F.X1F.X2F,
Z3.T1D.T2F.X1F.X2F, Z4.T1D.T2F.X1F.X2F,
Z1.T1E.T2F.X1F.X2F, Z2.T1E.T2F.X1F.X2F,
Z3.T1E.T2F.X1F.X2F, Z4.T1E.T2F.X1F.X2F,
Z1.T1F.T2F.X1F.X2F, Z2.T1F.T2F.X1F.X2F,
Z3.T1F.T2F.X1F.X2F, Z4.T1F.T2F.X1F.X2F.

In still yet another embodiment, the compounds of Formula I are named below in tabular format (Table 30.6) as compounds of general Formula III:

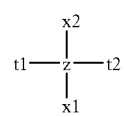

III

As discussed above, each structure of a compound of Formula III can be designated in tabular form by combining the "code" representing each structural moiety using the following syntax: z.t1.t2.x1.x2. Thus, for example, z1.t1a.t2b.x1a.x2a represents the following structure:

TABLE 30.1
Core Structures
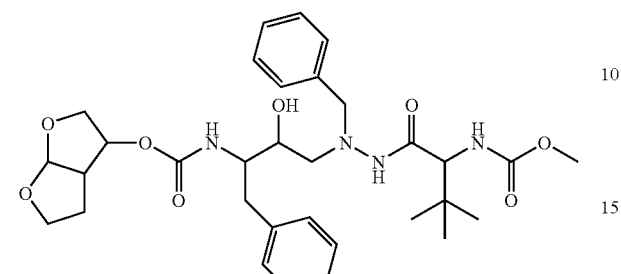
| Code | Subgenus Structure |
|---|---|
| z1 | 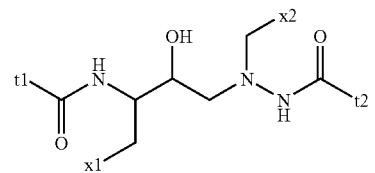 |
| z2 | 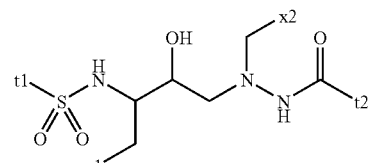 |
| z3 | 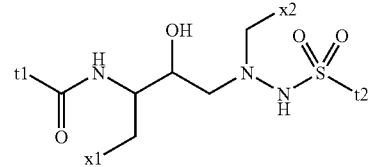 |
| z4 | 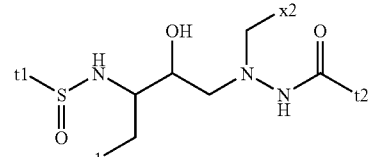 |
| z5 | 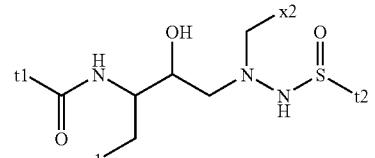 |
TABLE 30.2
t1 Structures
| Code | t1 Structure |
|---|---|
| t1a | 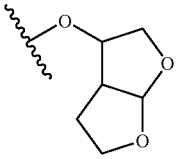 |
| t1b | 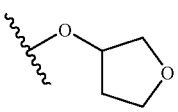 |
| t1c | 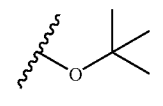 |
| t1d | 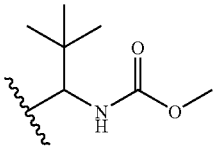 |
| t1e | 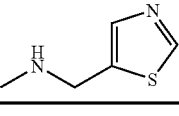 |
TABLE 30.3
t2 Structures
| Code | t2 Structure |
|---|---|
| t2a | 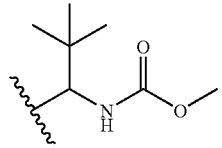 |
| t2b | 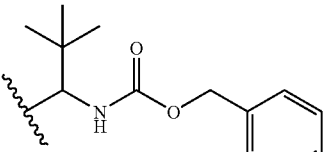 |
| t2c | 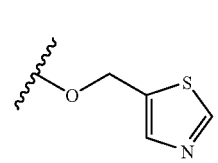 |
| t2d | 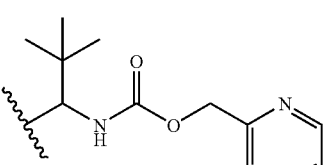 |

TABLE 30.3-continued
t2 Structures
| Code | t2 Structure |
|---|---|
| t2e | 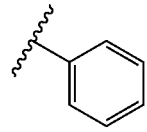 |
TABLE 30.4
x1 Structures
| Code | x1 Structure |
|---|---|
| x1a | 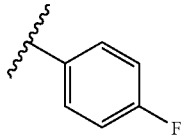 |
| x1b | 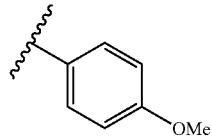 |
| x1c | 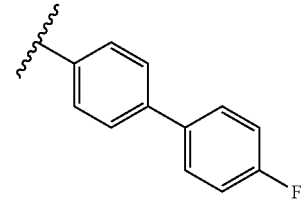 |
| x1d | 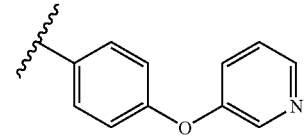 |
| x1e | 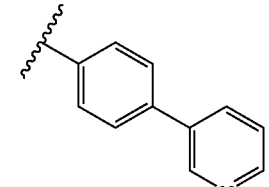 |
| x1f | 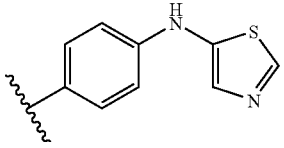 |
| x1g | 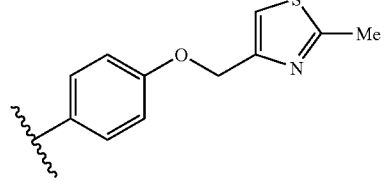 |
TABLE 30.4-continued
x1 Structures
| Code | x1 Structure |
|---|---|
| x1h | 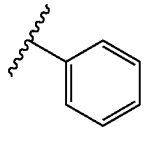 |
TABLE 30.5
x2 Structures
| Code | x2 Structure |
|---|---|
| x2a | 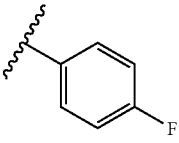 |
| x2b | 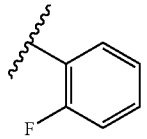 |
| x2c | 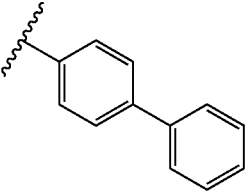 |
| x2d | 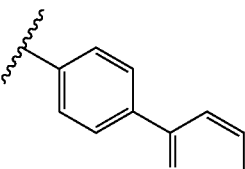 |
| x2e | 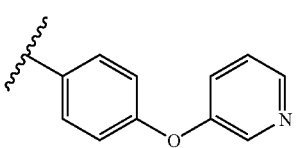 |
| x2f | 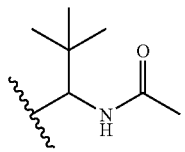 |

TABLE 30.5-continued x2 Structures

| Code | x2 Structure |
|---|---|
| x2g | 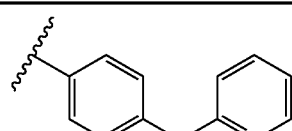 |
| x2h | 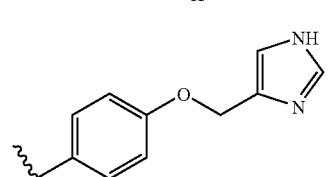 |

TABLE 30.6

List of Compound Structures of Formula III z1.t1a.t2a.x1a.x2a, z1.t1a.t2a.x1a.x2b, z1.t1a.t2a.x1a.x2c,
z1.t1a.t2a.x1a.x2d, z1.t1a.t2a.x1a.x2e, z1.t1a.t2a.x1a.x2f,
z1.t1a.t2a.x1a.x2g, z1.t1a.t2a.x1a.x2h, z1.t1a.t2a.x1b.x2a,
z1.t1a.t2a.x1b.x2b, z1.t1a.t2a.x1b.x2c, z1.t1a.t2a.x1b.x2d,
z1.t1a.t2a.x1b.x2e, z1.t1a.t2a.x1b.x2f, z1.t1a.t2a.x1b.x2g,
z1.t1a.t2a.x1b.x2h, z1.t1a.t2a.x1c.x2a, z1.t1a.t2a.x1c.x2b,
z1.t1a.t2a.x1c.x2c, z1.t1a.t2a.x1c.x2d, z1.t1a.t2a.x1c.x2e,
z1.t1a.t2a.x1c.x2f, z1.t1a.t2a.x1c.x2g, z1.t1a.t2a.x1c.x2h,
z1.t1a.t2a.x1d.x2a, z1.t1a.t2a.x1d.x2b, z1.t1a.t2a.x1d.x2c,
z1.t1a.t2a.x1d.x2d, z1.t1a.t2a.x1d.x2e, z1.t1a.t2a.x1d.x2f,
z1.t1a.t2a.x1d.x2g, z1.t1a.t2a.x1d.x2h, z1.t1a.t2a.x1e.x2a,
z1.t1a.t2a.x1e.x2b, z1.t1a.t2a.x1e.x2c, z1.t1a.t2a.x1e.x2d,
z1.t1a.t2a.x1e.x2e, z1.t1a.t2a.x1e.x2f, z1.t1a.t2a.x1e.x2g,
z1.t1a.t2a.x1e.x2h, z1.t1a.t2a.x1f.x2a, z1.t1a.t2a.x1f.x2b,
z1.t1a.t2a.x1f.x2c, z1.t1a.t2a.x1f.x2d, z1.t1a.t2a.x1f.x2e,
z1.t1a.t2a.x1f.x2f, z1.t1a.t2a.x1f.x2g, z1.t1a.t2a.x1f.x2h,
z1.t1a.t2a.x1g.x2a, z1.t1a.t2a.x1g.x2b, z1.t1a.t2a.x1g.x2c,
z1.t1a.t2a.x1g.x2d, z1.t1a.t2a.x1g.x2e, z1.t1a.t2a.x1g.x2f,
z1.t1a.t2a.x1g.x2g, z1.t1a.t2a.x1g.x2h, z1.t1a.t2a.x1h.x2a,
z1.t1a.t2a.x1h.x2b, z1.t1a.t2a.x1h.x2c, z1.t1a.t2a.x1h.x2d,
z1.t1a.t2a.x1h.x2e, z1.t1a.t2a.x1h.x2f, z1.t1a.t2a.x1h.x2g,
z1.t1a.t2a.x1h.x2h, z1.t1a.t2b.x1a.x2a, z1.t1a.t2b.x1a.x2b,
z1.t1a.t2b.x1a.x2c, z1.t1a.t2b.x1a.x2d, z1.t1a.t2b.x1a.x2e,
z1.t1a.t2b.x1a.x2f, z1.t1a.t2b.x1a.x2g, z1.t1a.t2b.x1a.x2h,
z1.t1a.t2b.x1b.x2a, z1.t1a.t2b.x1b.x2b, z1.t1a.t2b.x1b.x2c,
z1.t1a.t2b.x1b.x2d, z1.t1a.t2b.x1b.x2e, z1.t1a.t2b.x1b.x2f,
z1.t1a.t2b.x1b.x2g, z1.t1a.t2b.x1b.x2h, z1.t1a.t2b.x1c.x2a,
z1.t1a.t2b.x1c.x2b, z1.t1a.t2b.x1c.x2c, z1.t1a.t2b.x1c.x2d,
z1.t1a.t2b.x1c.x2e, z1.t1a.t2b.x1c.x2f, z1.t1a.t2b.x1c.x2g,
z1.t1a.t2b.x1c.x2h, z1.t1a.t2b.x1d.x2a, z1.t1a.t2b.x1d.x2b,
z1.t1a.t2b.x1d.x2c, z1.t1a.t2b.x1d.x2d, z1.t1a.t2b.x1d.x2e,
z1.t1a.t2b.x1d.x2f, z1.t1a.t2b.x1d.x2g, z1.t1a.t2b.x1d.x2h,
z1.t1a.t2b.x1e.x2a, z1.t1a.t2b.x1e.x2b, z1.t1a.t2b.x1e.x2c,
z1.t1a.t2b.x1e.x2d, z1.t1a.t2b.x1e.x2e, z1.t1a.t2b.x1e.x2f,
z1.t1a.t2b.x1e.x2g, z1.t1a.t2b.x1e.x2h, z1.t1a.t2b.x1f.x2a,
z1.t1a.t2b.x1f.x2b, z1.t1a.t2b.x1f.x2c, z1.t1a.t2b.x1f.x2d,
z1.t1a.t2b.x1f.x2e, z1.t1a.t2b.x1f.x2f, z1.t1a.t2b.x1f.x2g,
z1.t1a.t2b.x1f.x2h, z1.t1a.t2b.x1g.x2a, z1.t1a.t2b.x1g.x2b,
z1.t1a.t2b.x1g.x2c, z1.t1a.t2b.x1g.x2d, z1.t1a.t2b.x1g.x2e,
z1.t1a.t2b.x1g.x2f, z1.t1a.t2b.x1g.x2g, z1.t1a.t2b.x1g.x2h,
z1.t1a.t2b.x1h.x2a, z1.t1a.t2b.x1h.x2b, z1.t1a.t2b.x1h.x2c,
z1.t1a.t2b.x1h.x2d, z1.t1a.t2b.x1h.x2e, z1.t1a.t2b.x1h.x2f,
z1.t1a.t2b.x1h.x2g, z1.t1a.t2b.x1h.x2h, z1.t1a.t2c.x1a.x2a,
z1.t1a.t2c.x1a.x2b, z1.t1a.t2c.x1a.x2c, z1.t1a.t2c.x1a.x2d,
z1.t1a.t2c.x1a.x2e, z1.t1a.t2c.x1a.x2f, z1.t1a.t2c.x1a.x2g,
z1.t1a.t2c.x1a.x2h, z1.t1a.t2c.x1b.x2a, z1.t1a.t2c.x1b.x2b,
z1.t1a.t2c.x1b.x2c, z1.t1a.t2c.x1b.x2d, z1.t1a.t2c.x1b.x2e,
z1.t1a.t2c.x1b.x2f, z1.t1a.t2c.x1b.x2g, z1.t1a.t2c.x1b.x2h,
z1.t1a.t2c.x1c.x2a, z1.t1a.t2c.x1c.x2b, z1.t1a.t2c.x1c.x2c,
z1.t1a.t2c.x1c.x2d, z1.t1a.t2c.x1c.x2e, z1.t1a.t2c.x1c.x2f,
z1.t1a.t2c.x1c.x2g, z1.t1a.t2c.x1c.x2h, z1.t1a.t2c.x1d.x2a,
z1.t1a.t2c.x1d.x2b, z1.t1a.t2c.x1d.x2c, z1.t1a.t2c.x1d.x2d,
z1.t1a.t2c.x1d.x2e, z1.t1a.t2c.x1d.x2f, z1.t1a.t2c.x1d.x2g,
z1.t1a.t2c.x1d.x2h, z1.t1a.t2c.x1e.x2a, z1.t1a.t2c.x1e.x2b,
z1.t1a.t2c.x1e.x2c, z1.t1a.t2c.x1e.x2d, z1.t1a.t2c.x1e.x2e,
z1.t1a.t2c.x1e.x2f, z1.t1a.t2c.x1e.x2g, z1.t1a.t2c.x1e.x2h,
z1.t1a.t2c.x1f.x2a, z1.t1a.t2c.x1f.x2b, z1.t1a.t2c.x1f.x2c,
z1.t1a.t2c.x1f.x2d, z1.t1a.t2c.x1f.x2e, z1.t1a.t2c.x1f.x2f,
z1.t1a.t2c.x1f.x2g, z1.t1a.t2c.x1f.x2h, z1.t1a.t2c.x1g.x2a,
z1.t1a.t2c.x1g.x2b, z1.t1a.t2c.x1g.x2c, z1.t1a.t2c.x1g.x2d,
z1.t1a.t2c.x1g.x2e, z1.t1a.t2c.x1g.x2f, z1.t1a.t2c.x1g.x2g,
z1.t1a.t2c.x1g.x2h, z1.t1a.t2c.x1h.x2a, z1.t1a.t2c.x1h.x2b,
z1.t1a.t2c.x1h.x2c, z1.t1a.t2c.x1h.x2d, z1.t1a.t2c.x1h.x2e,
z1.t1a.t2c.x1h.x2f, z1.t1a.t2c.x1h.x2g, z1.t1a.t2c.x1h.x2h,
z1.t1a.t2d.x1a.x2a, z1.t1a.t2d.x1a.x2b, z1.t1a.t2d.x1a.x2c,
z1.t1a.t2d.x1a.x2d, z1.t1a.t2d.x1a.x2e, z1.t1a.t2d.x1a.x2f,
z1.t1a.t2d.x1a.x2g, z1.t1a.t2d.x1a.x2h, z1.t1a.t2d.x1b.x2a,
z1.t1a.t2d.x1b.x2b, z1.t1a.t2d.x1b.x2c, z1.t1a.t2d.x1b.x2d,
z1.t1a.t2d.x1b.x2e, z1.t1a.t2d.x1b.x2f, z1.t1a.t2d.x1b.x2g,
z1.t1a.t2d.x1b.x2h, z1.t1a.t2d.x1c.x2a, z1.t1a.t2d.x1c.x2b,
z1.t1a.t2d.x1c.x2c, z1.t1a.t2d.x1c.x2d, z1.t1a.t2d.x1c.x2e,
z1.t1a.t2d.x1c.x2f, z1.t1a.t2d.x1c.x2g, z1.t1a.t2d.x1c.x2h,
z1.t1a.t2d.x1d.x2a, z1.t1a.t2d.x1d.x2b, z1.t1a.t2d.x1d.x2c,
z1.t1a.t2d.x1d.x2d, z1.t1a.t2d.x1d.x2e, z1.t1a.t2d.x1d.x2f,
z1.t1a.t2d.x1d.x2g, z1.t1a.t2d.x1d.x2h, z1.t1a.t2d.x1e.x2a,
z1.t1a.t2d.x1e.x2b, z1.t1a.t2d.x1e.x2c, z1.t1a.t2d.x1e.x2d,
z1.t1a.t2d.x1e.x2e, z1.t1a.t2d.x1e.x2f, z1.t1a.t2d.x1e.x2g,
z1.t1a.t2d.x1e.x2h, z1.t1a.t2d.x1f.x2a, z1.t1a.t2d.x1f.x2b,
z1.t1a.t2d.x1f.x2c, z1.t1a.t2d.x1f.x2d, z1.t1a.t2d.x1f.x2e,
z1.t1a.t2d.x1f.x2f, z1.t1a.t2d.x1f.x2g, z1.t1a.t2d.x1f.x2h,
z1.t1a.t2d.x1g.x2a, z1.t1a.t2d.x1g.x2b, z1.t1a.t2d.x1g.x2c,
z1.t1a.t2d.x1g.x2d, z1.t1a.t2d.x1g.x2e, z1.t1a.t2d.x1g.x2f,
z1.t1a.t2d.x1g.x2g, z1.t1a.t2d.x1g.x2h, z1.t1a.t2d.x1h.x2a,
z1.t1a.t2d.x1h.x2b, z1.t1a.t2d.x1h.x2c, z1.t1a.t2d.x1h.x2d,
z1.t1a.t2d.x1h.x2e, z1.t1a.t2d.x1h.x2f, z1.t1a.t2d.x1h.x2g,
z1.t1a.t2d.x1h.x2h, z1.t1a.t2e.x1a.x2a, z1.t1a.t2e.x1a.x2b,
z1.t1a.t2e.x1a.x2c, z1.t1a.t2e.x1a.x2d, z1.t1a.t2e.x1a.x2e,
z1.t1a.t2e.x1a.x2f, z1.t1a.t2e.x1a.x2g, z1.t1a.t2e.x1a.x2h,
z1.t1a.t2e.x1b.x2a, z1.t1a.t2e.x1b.x2b, z1.t1a.t2e.x1b.x2c,
z1.t1a.t2e.x1b.x2d, z1.t1a.t2e.x1b.x2e, z1.t1a.t2e.x1b.x2f,
z1.t1a.t2e.x1b.x2g, z1.t1a.t2e.x1b.x2h, z1.t1a.t2e.x1c.x2a,
z1.t1a.t2e.x1c.x2b, z1.t1a.t2e.x1c.x2c, z1.t1a.t2e.x1c.x2d,
z1.t1a.t2e.x1c.x2e, z1.t1a.t2e.x1c.x2f, z1.t1a.t2e.x1c.x2g,
z1.t1a.t2e.x1c.x2h, z1.t1a.t2e.x1d.x2a, z1.t1a.t2e.x1d.x2b,
z1.t1a.t2e.x1d.x2c, z1.t1a.t2e.x1d.x2d, z1.t1a.t2e.x1d.x2e,
z1.t1a.t2e.x1d.x2f, z1.t1a.t2e.x1d.x2g, z1.t1a.t2e.x1d.x2h,
z1.t1a.t2e.x1e.x2a, z1.t1a.t2e.x1e.x2b, z1.t1a.t2e.x1e.x2c,
z1.t1a.t2e.x1e.x2d, z1.t1a.t2e.x1e.x2e, z1.t1a.t2e.x1e.x2f,
z1.t1a.t2e.x1e.x2g, z1.t1a.t2e.x1e.x2h, z1.t1a.t2e.x1f.x2a,
z1.t1a.t2e.x1f.x2b, z1.t1a.t2e.x1f.x2c, z1.t1a.t2e.x1f.x2d,
z1.t1a.t2e.x1f.x2e, z1.t1a.t2e.x1f.x2f, z1.t1a.t2e.x1f.x2g,
z1.t1a.t2e.x1f.x2h, z1.t1a.t2e.x1g.x2a, z1.t1a.t2e.x1g.x2b,
z1.t1a.t2e.x1g.x2c, z1.t1a.t2e.x1g.x2d, z1.t1a.t2e.x1g.x2e,
z1.t1a.t2e.x1g.x2f, z1.t1a.t2e.x1g.x2g, z1.t1a.t2e.x1g.x2h,
z1.t1a.t2e.x1h.x2a, z1.t1a.t2e.x1h.x2b, z1.t1a.t2e.x1h.x2c,
z1.t1a.t2e.x1h.x2d, z1.t1a.t2e.x1h.x2e, z1.t1a.t2e.x1h.x2f,
z1.t1a.t2e.x1h.x2g, z1.t1a.t2e.x1h.x2h, z1.t1b.t2a.x1a.x2a,
z1.t1b.t2a.x1a.x2b, z1.t1b.t2a.x1a.x2c, z1.t1b.t2a.x1a.x2d,
z1.t1b.t2a.x1a.x2e, z1.t1b.t2a.x1a.x2f, z1.t1b.t2a.x1a.x2g,
z1.t1b.t2a.x1a.x2h, z1.t1b.t2a.x1b.x2a, z1.t1b.t2a.x1b.x2b,
z1.t1b.t2a.x1b.x2c, z1.t1b.t2a.x1b.x2d, z1.t1b.t2a.x1b.x2e,
z1.t1b.t2a.x1b.x2f, z1.t1b.t2a.x1b.x2g, z1.t1b.t2a.x1b.x2h,
z1.t1b.t2a.x1c.x2a, z1.t1b.t2a.x1c.x2b, z1.t1b.t2a.x1c.x2c,
z1.t1b.t2a.x1c.x2d, z1.t1b.t2a.x1c.x2e, z1.t1b.t2a.x1c.x2f,
z1.t1b.t2a.x1c.x2g, z1.t1b.t2a.x1c.x2h, z1.t1b.t2a.x1d.x2a,
z1.t1b.t2a.x1d.x2b, z1.t1b.t2a.x1d.x2c, z1.t1b.t2a.x1d.x2d,
z1.t1b.t2a.x1d.x2e, z1.t1b.t2a.x1d.x2f, z1.t1b.t2a.x1d.x2g,
z1.t1b.t2a.x1d.x2h, z1.t1b.t2a.x1e.x2a, z1.t1b.t2a.x1e.x2b,
z1.t1b.t2a.x1e.x2c, z1.t1b.t2a.x1e.x2d, z1.t1b.t2a.x1e.x2e,
z1.t1b.t2a.x1e.x2f, z1.t1b.t2a.x1e.x2g, z1.t1b.t2a.x1e.x2h,
z1.t1b.t2a.x1f.x2a, z1.t1b.t2a.x1f.x2b, z1.t1b.t2a.x1f.x2c,
z1.t1b.t2a.x1f.x2d, z1.t1b.t2a.x1f.x2e, z1.t1b.t2a.x1f.x2f,
z1.t1b.t2a.x1f.x2g, z1.t1b.t2a.x1f.x2h, z1.t1b.t2a.x1g.x2a,
z1.t1b.t2a.x1g.x2b, z1.t1b.t2a.x1g.x2c, z1.t1b.t2a.x1g.x2d,
z1.t1b.t2a.x1g.x2e, z1.t1b.t2a.x1g.x2f, z1.t1b.t2a.x1g.x2g,
z1.t1b.t2a.x1g.x2h, z1.t1b.t2a.x1h.x2a, z1.t1b.t2a.x1h.x2b,
z1.t1b.t2a.x1h.x2c, z1.t1b.t2a.x1h.x2d, z1.t1b.t2a.x1h.x2e,

TABLE 30.6-continued

List of Compound Structures of Formula III z1.t1b.t2a.x1h.x2f, z1.t1b.t2a.x1h.x2g, z1.t1b.t2a.x1h.x2h,
z1.t1b.t2b.x1a.x2a, z1.t1b.t2b.x1a.x2b, z1.t1b.t2b.x1a.x2c,
z1.t1b.t2b.x1a.x2d, z1.t1b.t2b.x1a.x2e, z1.t1b.t2b.x1a.x2f,
z1.t1b.t2b.x1a.x2g, z1.t1b.t2b.x1a.x2h, z1.t1b.t2b.x1b.x2a,
z1.t1b.t2b.x1b.x2b, z1.t1b.t2b.x1b.x2c, z1.t1b.t2b.x1b.x2d,
z1.t1b.t2b.x1b.x2e, z1.t1b.t2b.x1b.x2f, z1.t1b.t2b.x1b.x2g,
z1.t1b.t2b.x1b.x2h, z1.t1b.t2b.x1c.x2a, z1.t1b.t2b.x1c.x2b,
z1.t1b.t2b.x1c.x2c, z1.t1b.t2b.x1c.x2d, z1.t1b.t2b.x1c.x2e,
z1.t1b.t2b.x1c.x2f, z1.t1b.t2b.x1c.x2g, z1.t1b.t2b.x1c.x2h,
z1.t1b.t2b.x1d.x2a, z1.t1b.t2b.x1d.x2b, z1.t1b.t2b.x1d.x2c,
z1.t1b.t2b.x1d.x2d, z1.t1b.t2b.x1d.x2e, z1.t1b.t2b.x1d.x2f,
z1.t1b.t2b.x1d.x2g, z1.t1b.t2b.x1d.x2h, z1.t1b.t2b.x1e.x2a,
z1.t1b.t2b.x1e.x2b, z1.t1b.t2b.x1e.x2c, z1.t1b.t2b.x1e.x2d,
z1.t1b.t2b.x1e.x2e, z1.t1b.t2b.x1e.x2f, z1.t1b.t2b.x1e.x2g,
z1.t1b.t2b.x1e.x2h, z1.t1b.t2b.x1f.x2a, z1.t1b.t2b.x1f.x2b,
z1.t1b.t2b.x1f.x2c, z1.t1b.t2b.x1f.x2d, z1.t1b.t2b.x1f.x2e,
z1.t1b.t2b.x1f.x2f, z1.t1b.t2b.x1f.x2g, z1.t1b.t2b.x1f.x2h,
z1.t1b.t2b.x1g.x2a, z1.t1b.t2b.x1g.x2b, z1.t1b.t2b.x1g.x2c,
z1.t1b.t2b.x1g.x2d, z1.t1b.t2b.x1g.x2e, z1.t1b.t2b.x1g.x2f,
z1.t1b.t2b.x1g.x2g, z1.t1b.t2b.x1g.x2h, z1.t1b.t2b.x1h.x2a,
z1.t1b.t2b.x1h.x2b, z1.t1b.t2b.x1h.x2c, z1.t1b.t2b.x1h.x2d,
z1.t1b.t2b.x1h.x2e, z1.t1b.t2b.x1h.x2f, z1.t1b.t2b.x1h.x2g,
z1.t1b.t2b.x1h.x2h, z1.t1b.t2c.x1a.x2a, z1.t1b.t2c.x1a.x2b,
z1.t1b.t2c.x1a.x2c, z1.t1b.t2c.x1a.x2d, z1.t1b.t2c.x1a.x2e,
z1.t1b.t2c.x1a.x2f, z1.t1b.t2c.x1a.x2g, z1.t1b.t2c.x1a.x2h,
z1.t1b.t2c.x1b.x2a, z1.t1b.t2c.x1b.x2b, z1.t1b.t2c.x1b.x2c,
z1.t1b.t2c.x1b.x2d, z1.t1b.t2c.x1b.x2e, z1.t1b.t2c.x1b.x2f,
z1.t1b.t2c.x1b.x2g, z1.t1b.t2c.x1b.x2h, z1.t1b.t2c.x1c.x2a,
z1.t1b.t2c.x1c.x2b, z1.t1b.t2c.x1c.x2c, z1.t1b.t2c.x1c.x2d,
z1.t1b.t2c.x1c.x2e, z1.t1b.t2c.x1c.x2f, z1.t1b.t2c.x1c.x2g,
z1.t1b.t2c.x1c.x2h, z1.t1b.t2c.x1d.x2a, z1.t1b.t2c.x1d.x2b,
z1.t1b.t2c.x1d.x2c, z1.t1b.t2c.x1d.x2d, z1.t1b.t2c.x1d.x2e,
z1.t1b.t2c.x1d.x2f, z1.t1b.t2c.x1d.x2g, z1.t1b.t2c.x1d.x2h,
z1.t1b.t2c.x1e.x2a, z1.t1b.t2c.x1e.x2b, z1.t1b.t2c.x1e.x2c,
z1.t1b.t2c.x1e.x2d, z1.t1b.t2c.x1e.x2e, z1.t1b.t2c.x1e.x2f,
z1.t1b.t2c.x1e.x2g, z1.t1b.t2c.x1e.x2h, z1.t1b.t2c.x1f.x2a,
z1.t1b.t2c.x1f.x2b, z1.t1b.t2c.x1f.x2c, z1.t1b.t2c.x1f.x2d,
z1.t1b.t2c.x1f.x2e, z1.t1b.t2c.x1f.x2f, z1.t1b.t2c.x1f.x2g,
z1.t1b.t2c.x1f.x2h, z1.t1b.t2c.x1g.x2a, z1.t1b.t2c.x1g.x2b,
z1.t1b.t2c.x1g.x2c, z1.t1b.t2c.x1g.x2d, z1.t1b.t2c.x1g.x2e,
z1.t1b.t2c.x1g.x2f, z1.t1b.t2c.x1g.x2g, z1.t1b.t2c.x1g.x2h,
z1.t1b.t2c.x1h.x2a, z1.t1b.t2c.x1h.x2b, z1.t1b.t2c.x1h.x2c,
z1.t1b.t2c.x1h.x2d, z1.t1b.t2c.x1h.x2e, z1.t1b.t2c.x1h.x2f,
z1.t1b.t2c.x1h.x2g, z1.t1b.t2c.x1h.x2h, z1.t1b.t2d.x1a.x2a,
z1.t1b.t2d.x1a.x2b, z1.t1b.t2d.x1a.x2c, z1.t1b.t2d.x1a.x2d,
z1.t1b.t2d.x1a.x2e, z1.t1b.t2d.x1a.x2f, z1.t1b.t2d.x1a.x2g,
z1.t1b.t2d.x1a.x2h, z1.t1b.t2d.x1b.x2a, z1.t1b.t2d.x1b.x2b,
z1.t1b.t2d.x1b.x2c, z1.t1b.t2d.x1b.x2d, z1.t1b.t2d.x1b.x2e,
z1.t1b.t2d.x1b.x2f, z1.t1b.t2d.x1b.x2g, z1.t1b.t2d.x1b.x2h,
z1.t1b.t2d.x1c.x2a, z1.t1b.t2d.x1c.x2b, z1.t1b.t2d.x1c.x2c,
z1.t1b.t2d.x1c.x2d, z1.t1b.t2d.x1c.x2e, z1.t1b.t2d.x1c.x2f,
z1.t1b.t2d.x1c.x2g, z1.t1b.t2d.x1c.x2h, z1.t1b.t2d.x1d.x2a,
z1.t1b.t2d.x1d.x2b, z1.t1b.t2d.x1d.x2c, z1.t1b.t2d.x1d.x2d,
z1.t1b.t2d.x1d.x2e, z1.t1b.t2d.x1d.x2f, z1.t1b.t2d.x1d.x2g,
z1.t1b.t2d.x1d.x2h, z1.t1b.t2d.x1e.x2a, z1.t1b.t2d.x1e.x2b,
z1.t1b.t2d.x1e.x2c, z1.t1b.t2d.x1e.x2d, z1.t1b.t2d.x1e.x2e,
z1.t1b.t2d.x1e.x2f, z1.t1b.t2d.x1e.x2g, z1.t1b.t2d.x1e.x2h,
z1.t1b.t2d.x1f.x2a, z1.t1b.t2d.x1f.x2b, z1.t1b.t2d.x1f.x2c,
z1.t1b.t2d.x1f.x2d, z1.t1b.t2d.x1f.x2e, z1.t1b.t2d.x1f.x2f,
z1.t1b.t2d.x1f.x2g, z1.t1b.t2d.x1f.x2h, z1.t1b.t2d.x1g.x2a,
z1.t1b.t2d.x1g.x2b, z1.t1b.t2d.x1g.x2c, z1.t1b.t2d.x1g.x2d,
z1.t1b.t2d.x1g.x2e, z1.t1b.t2d.x1g.x2f, z1.t1b.t2d.x1g.x2g,
z1.t1b.t2d.x1g.x2h, z1.t1b.t2d.x1h.x2a, z1.t1b.t2d.x1h.x2b,
z1.t1b.t2d.x1h.x2c, z1.t1b.t2d.x1h.x2d, z1.t1b.t2d.x1h.x2e,
z1.t1b.t2d.x1h.x2f, z1.t1b.t2d.x1h.x2g, z1.t1b.t2d.x1h.x2h,
z1.t1b.t2e.x1a.x2a, z1.t1b.t2e.x1a.x2b, z1.t1b.t2e.x1a.x2c,
z1.t1b.t2e.x1a.x2d, z1.t1b.t2e.x1a.x2e, z1.t1b.t2e.x1a.x2f,
z1.t1b.t2e.x1a.x2g, z1.t1b.t2e.x1a.x2h, z1.t1b.t2e.x1b.x2a,
z1.t1b.t2e.x1b.x2b, z1.t1b.t2e.x1b.x2c, z1.t1b.t2e.x1b.x2d,
z1.t1b.t2e.x1b.x2e, z1.t1b.t2e.x1b.x2f, z1.t1b.t2e.x1b.x2g,
z1.t1b.t2e.x1b.x2h, z1.t1b.t2e.x1c.x2a, z1.t1b.t2e.x1c.x2b,
z1.t1b.t2e.x1c.x2c, z1.t1b.t2e.x1c.x2d, z1.t1b.t2e.x1c.x2e,
z1.t1b.t2e.x1d.x2a, z1.t1b.t2e.x1d.x2b, z1.t1b.t2e.x1d.x2c,
z1.t1b.t2e.x1d.x2d, z1.t1b.t2e.x1d.x2e, z1.t1b.t2e.x1d.x2f,
z1.t1b.t2e.x1d.x2g, z1.t1b.t2e.x1d.x2h, z1.t1b.t2e.x1e.x2a,
z1.t1b.t2e.x1e.x2b, z1.t1b.t2e.x1e.x2c, z1.t1b.t2e.x1e.x2d,
z1.t1b.t2e.x1e.x2e, z1.t1b.t2e.x1e.x2f, z1.t1b.t2e.x1e.x2g,
z1.t1b.t2e.x1e.x2h, z1.t1b.t2e.x1f.x2a, z1.t1b.t2e.x1f.x2b,
z1.t1b.t2e.x1f.x2c, z1.t1b.t2e.x1f.x2d, z1.t1b.t2e.x1f.x2e,
z1.t1b.t2e.x1f.x2f, z1.t1b.t2e.x1f.x2g, z1.t1b.t2e.x1f.x2h,
z1.t1b.t2e.x1g.x2a, z1.t1b.t2e.x1g.x2b, z1.t1b.t2e.x1g.x2c,
z1.t1b.t2e.x1g.x2d, z1.t1b.t2e.x1g.x2e, z1.t1b.t2e.x1g.x2f,
z1.t1b.t2e.x1g.x2g, z1.t1b.t2e.x1g.x2h, z1.t1b.t2e.x1h.x2a,
z1.t1b.t2e.x1h.x2b, z1.t1b.t2e.x1h.x2c, z1.t1b.t2e.x1h.x2d,
z1.t1b.t2e.x1h.x2e, z1.t1b.t2e.x1h.x2f, z1.t1b.t2e.x1h.x2g,
z1.t1b.t2e.x1h.x2h, z1.t1c.t2a.x1a.x2a, z1.t1c.t2a.x1a.x2b,
z1.t1c.t2a.x1a.x2c, z1.t1c.t2a.x1a.x2d, z1.t1c.t2a.x1a.x2e,
z1.t1c.t2a.x1a.x2f, z1.t1c.t2a.x1a.x2g, z1.t1c.t2a.x1a.x2h,
z1.t1c.t2a.x1b.x2a, z1.t1c.t2a.x1b.x2b, z1.t1c.t2a.x1b.x2c,
z1.t1c.t2a.x1b.x2d, z1.t1c.t2a.x1b.x2e, z1.t1c.t2a.x1b.x2f,
z1.t1c.t2a.x1b.x2g, z1.t1c.t2a.x1b.x2h, z1.t1c.t2a.x1c.x2a,
z1.t1c.t2a.x1c.x2b, z1.t1c.t2a.x1c.x2c, z1.t1c.t2a.x1c.x2d,
z1.t1c.t2a.x1c.x2e, z1.t1c.t2a.x1c.x2f, z1.t1c.t2a.x1c.x2g,
z1.t1c.t2a.x1c.x2h, z1.t1c.t2a.x1d.x2a, z1.t1c.t2a.x1d.x2b,
z1.t1c.t2a.x1d.x2c, z1.t1c.t2a.x1d.x2d, z1.t1c.t2a.x1d.x2e,
z1.t1c.t2a.x1d.x2f, z1.t1c.t2a.x1d.x2g, z1.t1c.t2a.x1d.x2h,
z1.t1c.t2a.x1e.x2a, z1.t1c.t2a.x1e.x2b, z1.t1c.t2a.x1e.x2c,
z1.t1c.t2a.x1e.x2d, z1.t1c.t2a.x1e.x2e, z1.t1c.t2a.x1e.x2f,
z1.t1c.t2a.x1e.x2g, z1.t1c.t2a.x1e.x2h, z1.t1c.t2a.x1f.x2a,
z1.t1c.t2a.x1f.x2b, z1.t1c.t2a.x1f.x2c, z1.t1c.t2a.x1f.x2d,
z1.t1c.t2a.x1f.x2e, z1.t1c.t2a.x1f.x2f, z1.t1c.t2a.x1f.x2g,
z1.t1c.t2a.x1f.x2h, z1.t1c.t2a.x1g.x2a, z1.t1c.t2a.x1g.x2b,
z1.t1c.t2a.x1g.x2c, z1.t1c.t2a.x1g.x2d, z1.t1c.t2a.x1g.x2e,
z1.t1c.t2a.x1g.x2f, z1.t1c.t2a.x1g.x2g, z1.t1c.t2a.x1g.x2h,
z1.t1c.t2a.x1h.x2a, z1.t1c.t2a.x1h.x2b, z1.t1c.t2a.x1h.x2c,
z1.t1c.t2a.x1h.x2d, z1.t1c.t2a.x1h.x2e, z1.t1c.t2a.x1h.x2f,
z1.t1c.t2a.x1h.x2g, z1.t1c.t2a.x1h.x2h, z1.t1c.t2b.x1a.x2a,
z1.t1c.t2b.x1a.x2b, z1.t1c.t2b.x1a.x2c, z1.t1c.t2b.x1a.x2d,
z1.t1c.t2b.x1a.x2e, z1.t1c.t2b.x1a.x2f, z1.t1c.t2b.x1a.x2g,
z1.t1c.t2b.x1a.x2h, z1.t1c.t2b.x1b.x2a, z1.t1c.t2b.x1b.x2b,
z1.t1c.t2b.x1b.x2c, z1.t1c.t2b.x1b.x2d, z1.t1c.t2b.x1b.x2e,
z1.t1c.t2b.x1b.x2f, z1.t1c.t2b.x1b.x2g, z1.t1c.t2b.x1b.x2h,
z1.t1c.t2b.x1c.x2a, z1.t1c.t2b.x1c.x2b, z1.t1c.t2b.x1c.x2c,
z1.t1c.t2b.x1c.x2d, z1.t1c.t2b.x1c.x2e, z1.t1c.t2b.x1c.x2f,
z1.t1c.t2b.x1c.x2g, z1.t1c.t2b.x1c.x2h, z1.t1c.t2b.x1d.x2a,
z1.t1c.t2b.x1d.x2b, z1.t1c.t2b.x1d.x2c, z1.t1c.t2b.x1d.x2d,
z1.t1c.t2b.x1d.x2e, z1.t1c.t2b.x1d.x2f, z1.t1c.t2b.x1d.x2g,
z1.t1c.t2b.x1d.x2h, z1.t1c.t2b.x1e.x2a, z1.t1c.t2b.x1e.x2b,
z1.t1c.t2b.x1e.x2c, z1.t1c.t2b.x1e.x2d, z1.t1c.t2b.x1e.x2e,
z1.t1c.t2b.x1e.x2f, z1.t1c.t2b.x1e.x2g, z1.t1c.t2b.x1e.x2h,
z1.t1c.t2b.x1f.x2a, z1.t1c.t2b.x1f.x2b, z1.t1c.t2b.x1f.x2c,
z1.t1c.t2b.x1f.x2d, z1.t1c.t2b.x1f.x2e, z1.t1c.t2b.x1f.x2f,
z1.t1c.t2b.x1f.x2g, z1.t1c.t2b.x1f.x2h, z1.t1c.t2b.x1g.x2a,
z1.t1c.t2b.x1g.x2b, z1.t1c.t2b.x1g.x2c, z1.t1c.t2b.x1g.x2d,
z1.t1c.t2b.x1g.x2e, z1.t1c.t2b.x1g.x2f, z1.t1c.t2b.x1g.x2g,
z1.t1c.t2b.x1g.x2h, z1.t1c.t2b.x1h.x2a, z1.t1c.t2b.x1h.x2b,
z1.t1c.t2b.x1h.x2c, z1.t1c.t2b.x1h.x2d, z1.t1c.t2b.x1h.x2e,
z1.t1c.t2b.x1h.x2f, z1.t1c.t2b.x1h.x2g, z1.t1c.t2b.x1h.x2h,
z1.t1c.t2c.x1a.x2a, z1.t1c.t2c.x1a.x2b, z1.t1c.t2c.x1a.x2c,
z1.t1c.t2c.x1a.x2d, z1.t1c.t2c.x1a.x2e, z1.t1c.t2c.x1a.x2f,
z1.t1c.t2c.x1a.x2g, z1.t1c.t2c.x1a.x2h, z1.t1c.t2c.x1b.x2a,
z1.t1c.t2c.x1b.x2b, z1.t1c.t2c.x1b.x2c, z1.t1c.t2c.x1b.x2d,
z1.t1c.t2c.x1b.x2e, z1.t1c.t2c.x1b.x2f, z1.t1c.t2c.x1b.x2g,
z1.t1c.t2c.x1b.x2h, z1.t1c.t2c.x1c.x2a, z1.t1c.t2c.x1c.x2b,
z1.t1c.t2c.x1c.x2c, z1.t1c.t2c.x1c.x2d, z1.t1c.t2c.x1c.x2e,
z1.t1c.t2c.x1c.x2f, z1.t1c.t2c.x1c.x2g, z1.t1c.t2c.x1c.x2h,
z1.t1c.t2c.x1d.x2a, z1.t1c.t2c.x1d.x2b, z1.t1c.t2c.x1d.x2c,
z1.t1c.t2c.x1d.x2d, z1.t1c.t2c.x1d.x2e, z1.t1c.t2c.x1d.x2f,
z1.t1c.t2c.x1d.x2g, z1.t1c.t2c.x1d.x2h, z1.t1c.t2c.x1e.x2a,
z1.t1c.t2c.x1e.x2b, z1.t1c.t2c.x1e.x2c, z1.t1c.t2c.x1e.x2d,
z1.t1c.t2c.x1e.x2e, z1.t1c.t2c.x1e.x2f, z1.t1c.t2c.x1e.x2g,
z1.t1c.t2c.x1e.x2h, z1.t1c.t2c.x1f.x2a, z1.t1c.t2c.x1f.x2b,
z1.t1c.t2c.x1f.x2c, z1.t1c.t2c.x1f.x2d, z1.t1c.t2c.x1f.x2e,
z1.t1c.t2c.x1f.x2f, z1.t1c.t2c.x1f.x2g, z1.t1c.t2c.x1f.x2h,
z1.t1c.t2c.x1g.x2a, z1.t1c.t2c.x1g.x2b, z1.t1c.t2c.x1g.x2c,
z1.t1c.t2c.x1g.x2d, z1.t1c.t2c.x1g.x2e, z1.t1c.t2c.x1g.x2f,
z1.t1c.t2c.x1g.x2g, z1.t1c.t2c.x1g.x2h, z1.t1c.t2c.x1h.x2a,
z1.t1c.t2c.x1h.x2b, z1.t1c.t2c.x1h.x2c, z1.t1c.t2c.x1h.x2d,
z1.t1c.t2c.x1h.x2e, z1.t1c.t2c.x1h.x2f, z1.t1c.t2c.x1h.x2g,
z1.t1c.t2c.x1h.x2h, z1.t1c.t2d.x1a.x2a, z1.t1c.t2d.x1a.x2b,
z1.t1c.t2d.x1a.x2c, z1.t1c.t2d.x1a.x2d, z1.t1c.t2d.x1a.x2e,
z1.t1c.t2d.x1a.x2f, z1.t1c.t2d.x1a.x2g, z1.t1c.t2d.x1a.x2h,
z1.t1c.t2d.x1b.x2a, z1.t1c.t2d.x1b.x2b, z1.t1c.t2d.x1b.x2c, TABLE 30.6-continued List of Compound Structures of Formula III z1.t1c.t2d.x1b.x2d, z1.t1c.t2d.x1b.x2e, z1.t1c.t2d.x1b.x2f,
z1.t1c.t2d.x1b.x2g, z1.t1c.t2d.x1b.x2h, z1.t1c.t2d.x1c.x2a,
z1.t1c.t2d.x1c.x2b, z1.t1c.t2d.x1c.x2c, z1.t1c.t2d.x1c.x2d,
z1.t1c.t2d.x1c.x2e, z1.t1c.t2d.x1c.x2f, z1.t1c.t2d.x1c.x2g,
z1.t1c.t2d.x1c.x2h, z1.t1c.t2d.x1d.x2a, z1.t1c.t2d.x1d.x2b,
z1.t1c.t2d.x1d.x2c, z1.t1c.t2d.x1d.x2d, z1.t1c.t2d.x1d.x2e,
z1.t1c.t2d.x1d.x2f, z1.t1c.t2d.x1d.x2g, z1.t1c.t2d.x1d.x2h,
z1.t1c.t2d.x1e.x2a, z1.t1c.t2d.x1e.x2b, z1.t1c.t2d.x1e.x2c,
z1.t1c.t2d.x1e.x2d, z1.t1c.t2d.x1e.x2e, z1.t1c.t2d.x1e.x2f,
z1.t1c.t2d.x1e.x2g, z1.t1c.t2d.x1e.x2h, z1.t1c.t2d.x1f.x2a,
z1.t1c.t2d.x1f.x2b, z1.t1c.t2d.x1f.x2c, z1.t1c.t2d.x1f.x2d,
z1.t1c.t2d.x1f.x2e, z1.t1c.t2d.x1f.x2f, z1.t1c.t2d.x1f.x2g,
z1.t1c.t2d.x1f.x2h, z1.t1c.t2d.x1g.x2a, z1.t1c.t2d.x1g.x2b,
z1.t1c.t2d.x1g.x2c, z1.t1c.t2d.x1g.x2d, z1.t1c.t2d.x1g.x2e,
z1.t1c.t2d.x1g.x2f, z1.t1c.t2d.x1g.x2g, z1.t1c.t2d.x1g.x2h,
z1.t1c.t2d.x1h.x2a, z1.t1c.t2d.x1h.x2b, z1.t1c.t2d.x1h.x2c,
z1.t1c.t2d.x1h.x2d, z1.t1c.t2d.x1h.x2e, z1.t1c.t2d.x1h.x2f,
z1.t1c.t2d.x1h.x2g, z1.t1c.t2d.x1h.x2h, z1.t1c.t2e.x1a.x2a,
z1.t1c.t2e.x1a.x2b, z1.t1c.t2e.x1a.x2c, z1.t1c.t2e.x1a.x2d,
z1.t1c.t2e.x1a.x2e, z1.t1c.t2e.x1a.x2f, z1.t1c.t2e.x1a.x2g,
z1.t1c.t2e.x1a.x2h, z1.t1c.t2e.x1b.x2a, z1.t1c.t2e.x1b.x2b,
z1.t1c.t2e.x1b.x2c, z1.t1c.t2e.x1b.x2d, z1.t1c.t2e.x1b.x2e,
z1.t1c.t2e.x1b.x2f, z1.t1c.t2e.x1b.x2g, z1.t1c.t2e.x1b.x2h,
z1.t1c.t2e.x1c.x2a, z1.t1c.t2e.x1c.x2b, z1.t1c.t2e.x1c.x2c,
z1.t1c.t2e.x1c.x2d, z1.t1c.t2e.x1c.x2e, z1.t1c.t2e.x1c.x2f,
z1.t1c.t2e.x1c.x2g, z1.t1c.t2e.x1c.x2h, z1.t1c.t2e.x1d.x2a,
z1.t1c.t2e.x1d.x2b, z1.t1c.t2e.x1d.x2c, z1.t1c.t2e.x1d.x2d,
z1.t1c.t2e.x1d.x2e, z1.t1c.t2e.x1d.x2f, z1.t1c.t2e.x1d.x2g,
z1.t1c.t2e.x1d.x2h, z1.t1c.t2e.x1e.x2a, z1.t1c.t2e.x1e.x2b,
z1.t1c.t2e.x1e.x2c, z1.t1c.t2e.x1e.x2d, z1.t1c.t2e.x1e.x2e,
z1.t1c.t2e.x1e.x2f, z1.t1c.t2e.x1e.x2g, z1.t1c.t2e.x1e.x2h,
z1.t1c.t2e.x1f.x2a, z1.t1c.t2e.x1f.x2b, z1.t1c.t2e.x1f.x2c,
z1.t1c.t2e.x1f.x2d, z1.t1c.t2e.x1f.x2e, z1.t1c.t2e.x1f.x2f,
z1.t1c.t2e.x1f.x2g, z1.t1c.t2e.x1f.x2h, z1.t1c.t2e.x1g.x2a,
z1.t1c.t2e.x1g.x2b, z1.t1c.t2e.x1g.x2c, z1.t1c.t2e.x1g.x2d,
z1.t1c.t2e.x1g.x2e, z1.t1c.t2e.x1g.x2f, z1.t1c.t2e.x1g.x2g,
z1.t1c.t2e.x1g.x2h, z1.t1c.t2e.x1h.x2a, z1.t1c.t2e.x1h.x2b,
z1.t1c.t2e.x1h.x2c, z1.t1c.t2e.x1h.x2d, z1.t1c.t2e.x1h.x2e,
z1.t1c.t2e.x1h.x2f, z1.t1c.t2e.x1h.x2g, z1.t1c.t2e.x1h.x2h,
z1.t1d.t2a.x1a.x2a, z1.t1d.t2a.x1a.x2b, z1.t1d.t2a.x1a.x2c,
z1.t1d.t2a.x1a.x2d, z1.t1d.t2a.x1a.x2e, z1.t1d.t2a.x1a.x2f,
z1.t1d.t2a.x1a.x2g, z1.t1d.t2a.x1a.x2h, z1.t1d.t2a.x1b.x2a,
z1.t1d.t2a.x1b.x2b, z1.t1d.t2a.x1b.x2c, z1.t1d.t2a.x1b.x2d,
z1.t1d.t2a.x1b.x2e, z1.t1d.t2a.x1b.x2f, z1.t1d.t2a.x1b.x2g,
z1.t1d.t2a.x1b.x2h, z1.t1d.t2a.x1c.x2a, z1.t1d.t2a.x1c.x2b,
z1.t1d.t2a.x1c.x2c, z1.t1d.t2a.x1c.x2d, z1.t1d.t2a.x1c.x2e,
z1.t1d.t2a.x1c.x2f, z1.t1d.t2a.x1c.x2g, z1.t1d.t2a.x1c.x2h,
z1.t1d.t2a.x1d.x2a, z1.t1d.t2a.x1d.x2b, z1.t1d.t2a.x1d.x2c,
z1.t1d.t2a.x1d.x2d, z1.t1d.t2a.x1d.x2e, z1.t1d.t2a.x1d.x2f,
z1.t1d.t2a.x1d.x2g, z1.t1d.t2a.x1d.x2h, z1.t1d.t2a.x1e.x2a,
z1.t1d.t2a.x1e.x2b, z1.t1d.t2a.x1e.x2c, z1.t1d.t2a.x1e.x2d,
z1.t1d.t2a.x1e.x2e, z1.t1d.t2a.x1e.x2f, z1.t1d.t2a.x1e.x2g,
z1.t1d.t2a.x1e.x2h, z1.t1d.t2a.x1f.x2a, z1.t1d.t2a.x1f.x2b,
z1.t1d.t2a.x1f.x2c, z1.t1d.t2a.x1f.x2d, z1.t1d.t2a.x1f.x2e,
z1.t1d.t2a.x1f.x2f, z1.t1d.t2a.x1f.x2g, z1.t1d.t2a.x1f.x2h,
z1.t1d.t2a.x1g.x2a, z1.t1d.t2a.x1g.x2b, z1.t1d.t2a.x1g.x2c,
z1.t1d.t2a.x1g.x2d, z1.t1d.t2a.x1g.x2e, z1.t1d.t2a.x1g.x2f,
z1.t1d.t2a.x1g.x2g, z1.t1d.t2a.x1g.x2h, z1.t1d.t2a.x1h.x2a,
z1.t1d.t2a.x1h.x2b, z1.t1d.t2a.x1h.x2c, z1.t1d.t2a.x1h.x2d,
z1.t1d.t2a.x1h.x2e, z1.t1d.t2a.x1h.x2f, z1.t1d.t2a.x1h.x2g,
z1.t1d.t2a.x1h.x2h, z1.t1d.t2b.x1a.x2a, z1.t1d.t2b.x1a.x2b,
z1.t1d.t2b.x1a.x2c, z1.t1d.t2b.x1a.x2d, z1.t1d.t2b.x1a.x2e,
z1.t1d.t2b.x1a.x2f, z1.t1d.t2b.x1a.x2g, z1.t1d.t2b.x1a.x2h,
z1.t1d.t2b.x1b.x2a, z1.t1d.t2b.x1b.x2b, z1.t1d.t2b.x1b.x2c,
z1.t1d.t2b.x1b.x2d, z1.t1d.t2b.x1b.x2e, z1.t1d.t2b.x1b.x2f,
z1.t1d.t2b.x1b.x2g, z1.t1d.t2b.x1b.x2h, z1.t1d.t2b.x1c.x2a,
z1.t1d.t2b.x1c.x2b, z1.t1d.t2b.x1c.x2c, z1.t1d.t2b.x1c.x2d,
z1.t1d.t2b.x1c.x2e, z1.t1d.t2b.x1c.x2f, z1.t1d.t2b.x1c.x2g,
z1.t1d.t2b.x1c.x2h, z1.t1d.t2b.x1d.x2a, z1.t1d.t2b.x1d.x2b,
z1.t1d.t2b.x1d.x2c, z1.t1d.t2b.x1d.x2d, z1.t1d.t2b.x1d.x2e,
z1.t1d.t2b.x1d.x2f, z1.t1d.t2b.x1d.x2g, z1.t1d.t2b.x1d.x2h,
z1.t1d.t2b.x1e.x2a, z1.t1d.t2b.x1e.x2b, z1.t1d.t2b.x1e.x2c,
z1.t1d.t2b.x1e.x2d, z1.t1d.t2b.x1e.x2e, z1.t1d.t2b.x1e.x2f,
z1.t1d.t2b.x1e.x2g, z1.t1d.t2b.x1e.x2h, z1.t1d.t2b.x1f.x2a,
z1.t1d.t2b.x1f.x2b, z1.t1d.t2b.x1f.x2c, z1.t1d.t2b.x1f.x2d,
z1.t1d.t2b.x1f.x2e, z1.t1d.t2b.x1f.x2f, z1.t1d.t2b.x1f.x2g,
z1.t1d.t2b.x1f.x2h, z1.t1d.t2b.x1g.x2a, z1.t1d.t2b.x1g.x2b, z1.t1d.t2b.x1g.x2c, z1.t1d.t2b.x1g.x2d, z1.t1d.t2b.x1g.x2e,
z1.t1d.t2b.x1g.x2f, z1.t1d.t2b.x1g.x2g, z1.t1d.t2b.x1g.x2h,
z1.t1d.t2b.x1h.x2a, z1.t1d.t2b.x1h.x2b, z1.t1d.t2b.x1h.x2c,
z1.t1d.t2b.x1h.x2d, z1.t1d.t2b.x1h.x2e, z1.t1d.t2b.x1h.x2f,
z1.t1d.t2b.x1h.x2g, z1.t1d.t2b.x1h.x2h, z1.t1d.t2c.x1a.x2a,
z1.t1d.t2c.x1a.x2b, z1.t1d.t2c.x1a.x2c, z1.t1d.t2c.x1a.x2d,
z1.t1d.t2c.x1a.x2e, z1.t1d.t2c.x1a.x2f, z1.t1d.t2c.x1a.x2g,
z1.t1d.t2c.x1a.x2h, z1.t1d.t2c.x1b.x2a, z1.t1d.t2c.x1b.x2b,
z1.t1d.t2c.x1b.x2c, z1.t1d.t2c.x1b.x2d, z1.t1d.t2c.x1b.x2e,
z1.t1d.t2c.x1b.x2f, z1.t1d.t2c.x1b.x2g, z1.t1d.t2c.x1b.x2h,
z1.t1d.t2c.x1c.x2a, z1.t1d.t2c.x1c.x2b, z1.t1d.t2c.x1c.x2c,
z1.t1d.t2c.x1c.x2d, z1.t1d.t2c.x1c.x2e, z1.t1d.t2c.x1c.x2f,
z1.t1d.t2c.x1c.x2g, z1.t1d.t2c.x1c.x2h, z1.t1d.t2c.x1d.x2a,
z1.t1d.t2c.x1d.x2b, z1.t1d.t2c.x1d.x2c, z1.t1d.t2c.x1d.x2d,
z1.t1d.t2c.x1d.x2e, z1.t1d.t2c.x1d.x2f, z1.t1d.t2c.x1d.x2g,
z1.t1d.t2c.x1d.x2h, z1.t1d.t2c.x1e.x2a, z1.t1d.t2c.x1e.x2b,
z1.t1d.t2c.x1e.x2c, z1.t1d.t2c.x1e.x2d, z1.t1d.t2c.x1e.x2e,
z1.t1d.t2c.x1e.x2f, z1.t1d.t2c.x1e.x2g, z1.t1d.t2c.x1e.x2h,
z1.t1d.t2c.x1f.x2a, z1.t1d.t2c.x1f.x2b, z1.t1d.t2c.x1f.x2c,
z1.t1d.t2c.x1f.x2d, z1.t1d.t2c.x1f.x2e, z1.t1d.t2c.x1f.x2f,
z1.t1d.t2c.x1f.x2g, z1.t1d.t2c.x1f.x2h, z1.t1d.t2c.x1g.x2a,
z1.t1d.t2c.x1g.x2b, z1.t1d.t2c.x1g.x2c, z1.t1d.t2c.x1g.x2d,
z1.t1d.t2c.x1g.x2e, z1.t1d.t2c.x1g.x2f, z1.t1d.t2c.x1g.x2g,
z1.t1d.t2c.x1g.x2h, z1.t1d.t2c.x1h.x2a, z1.t1d.t2c.x1h.x2b,
z1.t1d.t2c.x1h.x2c, z1.t1d.t2c.x1h.x2d, z1.t1d.t2c.x1h.x2e,
z1.t1d.t2c.x1h.x2f, z1.t1d.t2c.x1h.x2g, z1.t1d.t2c.x1h.x2h,
z1.t1d.t2d.x1a.x2a, z1.t1d.t2d.x1a.x2b, z1.t1d.t2d.x1a.x2c,
z1.t1d.t2d.x1a.x2d, z1.t1d.t2d.x1a.x2e, z1.t1d.t2d.x1a.x2f,
z1.t1d.t2d.x1a.x2g, z1.t1d.t2d.x1a.x2h, z1.t1d.t2d.x1b.x2a,
z1.t1d.t2d.x1b.x2b, z1.t1d.t2d.x1b.x2c, z1.t1d.t2d.x1b.x2d,
z1.t1d.t2d.x1b.x2e, z1.t1d.t2d.x1b.x2f, z1.t1d.t2d.x1b.x2g,
z1.t1d.t2d.x1b.x2h, z1.t1d.t2d.x1c.x2a, z1.t1d.t2d.x1c.x2b,
z1.t1d.t2d.x1c.x2c, z1.t1d.t2d.x1c.x2d, z1.t1d.t2d.x1c.x2e,
z1.t1d.t2d.x1c.x2f, z1.t1d.t2d.x1c.x2g, z1.t1d.t2d.x1c.x2h,
z1.t1d.t2d.x1d.x2a, z1.t1d.t2d.x1d.x2b, z1.t1d.t2d.x1d.x2c,
z1.t1d.t2d.x1d.x2d, z1.t1d.t2d.x1d.x2e, z1.t1d.t2d.x1d.x2f,
z1.t1d.t2d.x1d.x2g, z1.t1d.t2d.x1d.x2h, z1.t1d.t2d.x1e.x2a,
z1.t1d.t2d.x1e.x2b, z1.t1d.t2d.x1e.x2c, z1.t1d.t2d.x1e.x2d,
z1.t1d.t2d.x1e.x2e, z1.t1d.t2d.x1e.x2f, z1.t1d.t2d.x1e.x2g,
z1.t1d.t2d.x1e.x2h, z1.t1d.t2d.x1f.x2a, z1.t1d.t2d.x1f.x2b,
z1.t1d.t2d.x1f.x2c, z1.t1d.t2d.x1f.x2d, z1.t1d.t2d.x1f.x2e,
z1.t1d.t2d.x1f.x2f, z1.t1d.t2d.x1f.x2g, z1.t1d.t2d.x1f.x2h,
z1.t1d.t2d.x1g.x2a, z1.t1d.t2d.x1g.x2b, z1.t1d.t2d.x1g.x2c,
z1.t1d.t2d.x1g.x2d, z1.t1d.t2d.x1g.x2e, z1.t1d.t2d.x1g.x2f,
z1.t1d.t2d.x1g.x2g, z1.t1d.t2d.x1g.x2h, z1.t1d.t2d.x1h.x2a,
z1.t1d.t2d.x1h.x2b, z1.t1d.t2d.x1h.x2c, z1.t1d.t2d.x1h.x2d,
z1.t1d.t2d.x1h.x2e, z1.t1d.t2d.x1h.x2f, z1.t1d.t2d.x1h.x2g,
z1.t1d.t2d.x1h.x2h, z1.t1d.t2e.x1a.x2a, z1.t1d.t2e.x1a.x2b,
z1.t1d.t2e.x1a.x2c, z1.t1d.t2e.x1a.x2d, z1.t1d.t2e.x1a.x2e,
z1.t1d.t2e.x1a.x2f, z1.t1d.t2e.x1a.x2g, z1.t1d.t2e.x1a.x2h,
z1.t1d.t2e.x1b.x2a, z1.t1d.t2e.x1b.x2b, z1.t1d.t2e.x1b.x2c,
z1.t1d.t2e.x1b.x2d, z1.t1d.t2e.x1b.x2e, z1.t1d.t2e.x1b.x2f,
z1.t1d.t2e.x1b.x2g, z1.t1d.t2e.x1b.x2h, z1.t1d.t2e.x1c.x2a,
z1.t1d.t2e.x1c.x2b, z1.t1d.t2e.x1c.x2c, z1.t1d.t2e.x1c.x2d,
z1.t1d.t2e.x1c.x2e, z1.t1d.t2e.x1c.x2f, z1.t1d.t2e.x1c.x2g,
z1.t1d.t2e.x1c.x2h, z1.t1d.t2e.x1d.x2a, z1.t1d.t2e.x1d.x2b,
z1.t1d.t2e.x1d.x2c, z1.t1d.t2e.x1d.x2d, z1.t1d.t2e.x1d.x2e,
z1.t1d.t2e.x1d.x2f, z1.t1d.t2e.x1d.x2g, z1.t1d.t2e.x1d.x2h,
z1.t1d.t2e.x1e.x2a, z1.t1d.t2e.x1e.x2b, z1.t1d.t2e.x1e.x2c,
z1.t1d.t2e.x1e.x2d, z1.t1d.t2e.x1e.x2e, z1.t1d.t2e.x1e.x2f,
z1.t1d.t2e.x1e.x2g, z1.t1d.t2e.x1e.x2h, z1.t1d.t2e.x1f.x2a,
z1.t1d.t2e.x1f.x2b, z1.t1d.t2e.x1f.x2c, z1.t1d.t2e.x1f.x2d,
z1.t1d.t2e.x1f.x2e, z1.t1d.t2e.x1f.x2f, z1.t1d.t2e.x1f.x2g,
z1.t1d.t2e.x1f.x2h, z1.t1d.t2e.x1g.x2a, z1.t1d.t2e.x1g.x2b,
z1.t1d.t2e.x1g.x2c, z1.t1d.t2e.x1g.x2d, z1.t1d.t2e.x1g.x2e,
z1.t1d.t2e.x1g.x2f, z1.t1d.t2e.x1g.x2g, z1.t1d.t2e.x1g.x2h,
z1.t1d.t2e.x1h.x2a, z1.t1d.t2e.x1h.x2b, z1.t1d.t2e.x1h.x2c,
z1.t1d.t2e.x1h.x2d, z1.t1d.t2e.x1h.x2e, z1.t1d.t2e.x1h.x2f,
z1.t1d.t2e.x1h.x2g, z1.t1d.t2e.x1h.x2h, z1.t1e.t2a.x1a.x2a,
z1.t1e.t2a.x1a.x2b, z1.t1e.t2a.x1a.x2c, z1.t1e.t2a.x1a.x2d,
z1.t1e.t2a.x1a.x2e, z1.t1e.t2a.x1a.x2f, z1.t1e.t2a.x1a.x2g,
z1.t1e.t2a.x1a.x2h, z1.t1e.t2a.x1b.x2a, z1.t1e.t2a.x1b.x2b,
z1.t1e.t2a.x1b.x2c, z1.t1e.t2a.x1b.x2d, z1.t1e.t2a.x1b.x2e,
z1.t1e.t2a.x1b.x2f, z1.t1e.t2a.x1b.x2g, z1.t1e.t2a.x1b.x2h,
z1.t1e.t2a.x1c.x2a, z1.t1e.t2a.x1c.x2b, z1.t1e.t2a.x1c.x2c,
z1.t1e.t2a.x1c.x2d, z1.t1e.t2a.x1c.x2e, z1.t1e.t2a.x1c.x2f,
z1.t1e.t2a.x1c.x2g, z1.t1e.t2a.x1c.x2h, z1.t1e.t2a.x1d.x2a,

TABLE 30.6-continued
List of Compound Structures of Formula III z1.t1e.t2a.x1d.x2b, z1.t1e.t2a.x1d.x2c, z1.t1e.t2a.x1d.x2d,
z1.t1e.t2a.x1d.x2e, z1.t1e.t2a.x1d.x2f, z1.t1e.t2a.x1d.x2g,
z1.t1e.t2a.x1d.x2h, z1.t1e.t2a.x1e.x2a, z1.t1e.t2a.x1e.x2b,
z1.t1e.t2a.x1e.x2c, z1.t1e.t2a.x1e.x2d, z1.t1e.t2a.x1e.x2e,
z1.t1e.t2a.x1e.x2f, z1.t1e.t2a.x1e.x2g, z1.t1e.t2a.x1e.x2h,
z1.t1e.t2a.x1f.x2a, z1.t1e.t2a.x1f.x2b, z1.t1e.t2a.x1f.x2c,
z1.t1e.t2a.x1f.x2d, z1.t1e.t2a.x1f.x2e, z1.t1e.t2a.x1f.x2f,
z1.t1e.t2a.x1f.x2g, z1.t1e.t2a.x1f.x2h, z1.t1e.t2a.x1g.x2a,
z1.t1e.t2a.x1g.x2b, z1.t1e.t2a.x1g.x2c, z1.t1e.t2a.x1g.x2d,
z1.t1e.t2a.x1g.x2e, z1.t1e.t2a.x1g.x2f, z1.t1e.t2a.x1g.x2g,
z1.t1e.t2a.x1g.x2h, z1.t1e.t2a.x1h.x2a, z1.t1e.t2a.x1h.x2b,
z1.t1e.t2a.x1h.x2c, z1.t1e.t2a.x1h.x2d, z1.t1e.t2a.x1h.x2e,
z1.t1e.t2a.x1h.x2f, z1.t1e.t2a.x1h.x2g, z1.t1e.t2a.x1h.x2h,
z1.t1e.t2b.x1a.x2a, z1.t1e.t2b.x1a.x2b, z1.t1e.t2b.x1a.x2c,
z1.t1e.t2b.x1a.x2d, z1.t1e.t2b.x1a.x2e, z1.t1e.t2b.x1a.x2f,
z1.t1e.t2b.x1a.x2g, z1.t1e.t2b.x1a.x2h, z1.t1e.t2b.x1b.x2a,
z1.t1e.t2b.x1b.x2b, z1.t1e.t2b.x1b.x2c, z1.t1e.t2b.x1b.x2d,
z1.t1e.t2b.x1b.x2e, z1.t1e.t2b.x1b.x2f, z1.t1e.t2b.x1b.x2g,
z1.t1e.t2b.x1b.x2h, z1.t1e.t2b.x1c.x2a, z1.t1e.t2b.x1c.x2b,
z1.t1e.t2b.x1c.x2c, z1.t1e.t2b.x1c.x2d, z1.t1e.t2b.x1c.x2e,
z1.t1e.t2b.x1c.x2f, z1.t1e.t2b.x1c.x2g, z1.t1e.t2b.x1c.x2h,
z1.t1e.t2b.x1d.x2a, z1.t1e.t2b.x1d.x2b, z1.t1e.t2b.x1d.x2c,
z1.t1e.t2b.x1d.x2d, z1.t1e.t2b.x1d.x2e, z1.t1e.t2b.x1d.x2f,
z1.t1e.t2b.x1d.x2g, z1.t1e.t2b.x1d.x2h, z1.t1e.t2b.x1e.x2a,
z1.t1e.t2b.x1e.x2b, z1.t1e.t2b.x1e.x2c, z1.t1e.t2b.x1e.x2d,
z1.t1e.t2b.x1e.x2e, z1.t1e.t2b.x1e.x2f, z1.t1e.t2b.x1e.x2g,
z1.t1e.t2b.x1e.x2h, z1.t1e.t2b.x1f.x2a, z1.t1e.t2b.x1f.x2b,
z1.t1e.t2b.x1f.x2c, z1.t1e.t2b.x1f.x2d, z1.t1e.t2b.x1f.x2e,
z1.t1e.t2b.x1f.x2f, z1.t1e.t2b.x1f.x2g, z1.t1e.t2b.x1f.x2h,
z1.t1e.t2b.x1g.x2a, z1.t1e.t2b.x1g.x2b, z1.t1e.t2b.x1g.x2c,
z1.t1e.t2b.x1g.x2d, z1.t1e.t2b.x1g.x2e, z1.t1e.t2b.x1g.x2f,
z1.t1e.t2b.x1g.x2g, z1.t1e.t2b.x1g.x2h, z1.t1e.t2b.x1h.x2a,
z1.t1e.t2b.x1h.x2b, z1.t1e.t2b.x1h.x2c, z1.t1e.t2b.x1h.x2d,
z1.t1e.t2b.x1h.x2e, z1.t1e.t2b.x1h.x2f, z1.t1e.t2b.x1h.x2g,
z1.t1e.t2b.x1h.x2h, z1.t1e.t2c.x1a.x2a, z1.t1e.t2c.x1a.x2b,
z1.t1e.t2c.x1a.x2c, z1.t1e.t2c.x1a.x2d, z1.t1e.t2c.x1a.x2e,
z1.t1e.t2c.x1a.x2f, z1.t1e.t2c.x1a.x2g, z1.t1e.t2c.x1a.x2h,
z1.t1e.t2c.x1b.x2a, z1.t1e.t2c.x1b.x2b, z1.t1e.t2c.x1b.x2c,
z1.t1e.t2c.x1b.x2d, z1.t1e.t2c.x1b.x2e, z1.t1e.t2c.x1b.x2f,
z1.t1e.t2c.x1b.x2g, z1.t1e.t2c.x1b.x2h, z1.t1e.t2c.x1c.x2a,
z1.t1e.t2c.x1c.x2b, z1.t1e.t2c.x1c.x2c, z1.t1e.t2c.x1c.x2d,
z1.t1e.t2c.x1c.x2e, z1.t1e.t2c.x1c.x2f, z1.t1e.t2c.x1c.x2g,
z1.t1e.t2c.x1c.x2h, z1.t1e.t2c.x1d.x2a, z1.t1e.t2c.x1d.x2b,
z1.t1e.t2c.x1d.x2c, z1.t1e.t2c.x1d.x2d, z1.t1e.t2c.x1d.x2e,
z1.t1e.t2c.x1d.x2f, z1.t1e.t2c.x1d.x2g, z1.t1e.t2c.x1d.x2h,
z1.t1e.t2c.x1e.x2a, z1.t1e.t2c.x1e.x2b, z1.t1e.t2c.x1e.x2c,
z1.t1e.t2c.x1e.x2d, z1.t1e.t2c.x1e.x2e, z1.t1e.t2c.x1e.x2f,
z1.t1e.t2c.x1e.x2g, z1.t1e.t2c.x1e.x2h, z1.t1e.t2c.x1f.x2a,
z1.t1e.t2c.x1f.x2b, z1.t1e.t2c.x1f.x2c, z1.t1e.t2c.x1f.x2d,
z1.t1e.t2c.x1f.x2e, z1.t1e.t2c.x1f.x2f, z1.t1e.t2c.x1f.x2g,
z1.t1e.t2c.x1f.x2h, z1.t1e.t2c.x1g.x2a, z1.t1e.t2c.x1g.x2b,
z1.t1e.t2c.x1g.x2c, z1.t1e.t2c.x1g.x2d, z1.t1e.t2c.x1g.x2e,
z1.t1e.t2c.x1g.x2f, z1.t1e.t2c.x1g.x2g, z1.t1e.t2c.x1g.x2h,
z1.t1e.t2c.x1h.x2a, z1.t1e.t2c.x1h.x2b, z1.t1e.t2c.x1h.x2c,
z1.t1e.t2c.x1h.x2d, z1.t1e.t2c.x1h.x2e, z1.t1e.t2c.x1h.x2f,
z1.t1e.t2c.x1h.x2g, z1.t1e.t2c.x1h.x2h, z1.t1e.t2d.x1a.x2a,
z1.t1e.t2d.x1a.x2b, z1.t1e.t2d.x1a.x2c, z1.t1e.t2d.x1a.x2d,
z1.t1e.t2d.x1a.x2e, z1.t1e.t2d.x1a.x2f, z1.t1e.t2d.x1a.x2g,
z1.t1e.t2d.x1a.x2h, z1.t1e.t2d.x1b.x2a, z1.t1e.t2d.x1b.x2b,
z1.t1e.t2d.x1b.x2c, z1.t1e.t2d.x1b.x2d, z1.t1e.t2d.x1b.x2e,
z1.t1e.t2d.x1b.x2f, z1.t1e.t2d.x1b.x2g, z1.t1e.t2d.x1b.x2h,
z1.t1e.t2d.x1c.x2a, z1.t1e.t2d.x1c.x2b, z1.t1e.t2d.x1c.x2c,
z1.t1e.t2d.x1c.x2d, z1.t1e.t2d.x1c.x2e, z1.t1e.t2d.x1c.x2f,
z1.t1e.t2d.x1c.x2g, z1.t1e.t2d.x1c.x2h, z1.t1e.t2d.x1d.x2a,
z1.t1e.t2d.x1d.x2b, z1.t1e.t2d.x1d.x2c, z1.t1e.t2d.x1d.x2d,
z1.t1e.t2d.x1d.x2e, z1.t1e.t2d.x1d.x2f, z1.t1e.t2d.x1d.x2g,
z1.t1e.t2d.x1d.x2h, z1.t1e.t2d.x1e.x2a, z1.t1e.t2d.x1e.x2b,
z1.t1e.t2d.x1e.x2c, z1.t1e.t2d.x1e.x2d, z1.t1e.t2d.x1e.x2e,
z1.t1e.t2d.x1e.x2f, z1.t1e.t2d.x1e.x2g, z1.t1e.t2d.x1e.x2h,
z1.t1e.t2d.x1f.x2a, z1.t1e.t2d.x1f.x2b, z1.t1e.t2d.x1f.x2c,
z1.t1e.t2d.x1f.x2d, z1.t1e.t2d.x1f.x2e, z1.t1e.t2d.x1f.x2f,
z1.t1e.t2d.x1f.x2g, z1.t1e.t2d.x1f.x2h, z1.t1e.t2d.x1g.x2a,
z1.t1e.t2d.x1g.x2b, z1.t1e.t2d.x1g.x2c, z1.t1e.t2d.x1g.x2d,
z1.t1e.t2d.x1g.x2e, z1.t1e.t2d.x1g.x2f, z1.t1e.t2d.x1g.x2g,
z1.t1e.t2d.x1g.x2h, z1.t1e.t2d.x1h.x2a, z1.t1e.t2d.x1h.x2b,
z1.t1e.t2d.x1h.x2c, z1.t1e.t2d.x1h.x2d, z1.t1e.t2d.x1h.x2e,
z1.t1e.t2d.x1h.x2f, z1.t1e.t2d.x1h.x2g, z1.t1e.t2d.x1h.x2h,
z1.t1e.t2e.x1a.x2a, z1.t1e.t2e.x1a.x2b, z1.t1e.t2e.x1a.x2c,
z1.t1e.t2e.x1a.x2d, z1.t1e.t2e.x1a.x2e, z1.t1e.t2e.x1a.x2f,
z1.t1e.t2e.x1a.x2g, z1.t1e.t2e.x1a.x2h, z1.t1e.t2e.x1b.x2a,
z1.t1e.t2e.x1b.x2b, z1.t1e.t2e.x1b.x2c, z1.t1e.t2e.x1b.x2d,
z1.t1e.t2e.x1b.x2e, z1.t1e.t2e.x1b.x2f, z1.t1e.t2e.x1b.x2g,
z1.t1e.t2e.x1b.x2h, z1.t1e.t2e.x1c.x2a, z1.t1e.t2e.x1c.x2b,
z1.t1e.t2e.x1c.x2c, z1.t1e.t2e.x1c.x2d, z1.t1e.t2e.x1c.x2e,
z1.t1e.t2e.x1c.x2f, z1.t1e.t2e.x1c.x2g, z1.t1e.t2e.x1c.x2h,
z1.t1e.t2e.x1d.x2a, z1.t1e.t2e.x1d.x2b, z1.t1e.t2e.x1d.x2c,
z1.t1e.t2e.x1d.x2d, z1.t1e.t2e.x1d.x2e, z1.t1e.t2e.x1d.x2f,
z1.t1e.t2e.x1d.x2g, z1.t1e.t2e.x1d.x2h, z1.t1e.t2e.x1e.x2a,
z1.t1e.t2e.x1e.x2b, z1.t1e.t2e.x1e.x2c, z1.t1e.t2e.x1e.x2d,
z1.t1e.t2e.x1e.x2e, z1.t1e.t2e.x1e.x2f, z1.t1e.t2e.x1e.x2g,
z1.t1e.t2e.x1e.x2h, z1.t1e.t2e.x1f.x2a, z1.t1e.t2e.x1f.x2b,
z1.t1e.t2e.x1f.x2c, z1.t1e.t2e.x1f.x2d, z1.t1e.t2e.x1f.x2e,
z1.t1e.t2e.x1f.x2f, z1.t1e.t2e.x1f.x2g, z1.t1e.t2e.x1f.x2h,
z1.t1e.t2e.x1g.x2a, z1.t1e.t2e.x1g.x2b, z1.t1e.t2e.x1g.x2c,
z1.t1e.t2e.x1g.x2d, z1.t1e.t2e.x1g.x2e, z1.t1e.t2e.x1g.x2f,
z1.t1e.t2e.x1g.x2g, z1.t1e.t2e.x1g.x2h, z1.t1e.t2e.x1h.x2a,
z1.t1e.t2e.x1h.x2b, z1.t1e.t2e.x1h.x2c, z1.t1e.t2e.x1h.x2d,
z1.t1e.t2e.x1h.x2e, z1.t1e.t2e.x1h.x2f, z1.t1e.t2e.x1h.x2g,
z1.t1e.t2e.x1h.x2h, z2.t1a.t2a.x1a.x2a, z2.t1a.t2a.x1a.x2b,
z2.t1a.t2a.x1a.x2c, z2.t1a.t2a.x1a.x2d, z2.t1a.t2a.x1a.x2e,
z2.t1a.t2a.x1a.x2f, z2.t1a.t2a.x1a.x2g, z2.t1a.t2a.x1a.x2h,
z2.t1a.t2a.x1b.x2a, z2.t1a.t2a.x1b.x2b, z2.t1a.t2a.x1b.x2c,
z2.t1a.t2a.x1b.x2d, z2.t1a.t2a.x1b.x2e, z2.t1a.t2a.x1b.x2f,
z2.t1a.t2a.x1b.x2g, z2.t1a.t2a.x1b.x2h, z2.t1a.t2a.x1c.x2a,
z2.t1a.t2a.x1c.x2b, z2.t1a.t2a.x1c.x2c, z2.t1a.t2a.x1c.x2d,
z2.t1a.t2a.x1c.x2e, z2.t1a.t2a.x1c.x2f, z2.t1a.t2a.x1c.x2g,
z2.t1a.t2a.x1c.x2h, z2.t1a.t2a.x1d.x2a, z2.t1a.t2a.x1d.x2b,
z2.t1a.t2a.x1d.x2c, z2.t1a.t2a.x1d.x2d, z2.t1a.t2a.x1d.x2e,
z2.t1a.t2a.x1d.x2f, z2.t1a.t2a.x1d.x2g, z2.t1a.t2a.x1d.x2h,
z2.t1a.t2a.x1e.x2a, z2.t1a.t2a.x1e.x2b, z2.t1a.t2a.x1e.x2c,
z2.t1a.t2a.x1e.x2d, z2.t1a.t2a.x1e.x2e, z2.t1a.t2a.x1e.x2f,
z2.t1a.t2a.x1e.x2g, z2.t1a.t2a.x1e.x2h, z2.t1a.t2a.x1f.x2a,
z2.t1a.t2a.x1f.x2b, z2.t1a.t2a.x1f.x2c, z2.t1a.t2a.x1f.x2d,
z2.t1a.t2a.x1f.x2e, z2.t1a.t2a.x1f.x2f, z2.t1a.t2a.x1f.x2g,
z2.t1a.t2a.x1f.x2h, z2.t1a.t2a.x1g.x2a, z2.t1a.t2a.x1g.x2b,
z2.t1a.t2a.x1g.x2c, z2.t1a.t2a.x1g.x2d, z2.t1a.t2a.x1g.x2e,
z2.t1a.t2a.x1g.x2f, z2.t1a.t2a.x1g.x2g, z2.t1a.t2a.x1g.x2h,
z2.t1a.t2a.x1h.x2a, z2.t1a.t2a.x1h.x2b, z2.t1a.t2a.x1h.x2c,
z2.t1a.t2a.x1h.x2d, z2.t1a.t2a.x1h.x2e, z2.t1a.t2a.x1h.x2f,
z2.t1a.t2a.x1h.x2g, z2.t1a.t2a.x1h.x2h, z2.t1a.t2b.x1a.x2a,
z2.t1a.t2b.x1a.x2b, z2.t1a.t2b.x1a.x2c, z2.t1a.t2b.x1a.x2d,
z2.t1a.t2b.x1a.x2e, z2.t1a.t2b.x1a.x2f, z2.t1a.t2b.x1a.x2g,
z2.t1a.t2b.x1a.x2h, z2.t1a.t2b.x1b.x2a, z2.t1a.t2b.x1b.x2b,
z2.t1a.t2b.x1b.x2c, z2.t1a.t2b.x1b.x2d, z2.t1a.t2b.x1b.x2e,
z2.t1a.t2b.x1b.x2f, z2.t1a.t2b.x1b.x2g, z2.t1a.t2b.x1b.x2h,
z2.t1a.t2b.x1c.x2a, z2.t1a.t2b.x1c.x2b, z2.t1a.t2b.x1c.x2c,
z2.t1a.t2b.x1c.x2d, z2.t1a.t2b.x1c.x2e, z2.t1a.t2b.x1c.x2f,
z2.t1a.t2b.x1c.x2g, z2.t1a.t2b.x1c.x2h, z2.t1a.t2b.x1d.x2a,
z2.t1a.t2b.x1d.x2b, z2.t1a.t2b.x1d.x2c, z2.t1a.t2b.x1d.x2d,
z2.t1a.t2b.x1d.x2e, z2.t1a.t2b.x1d.x2f, z2.t1a.t2b.x1d.x2g,
z2.t1a.t2b.x1d.x2h, z2.t1a.t2b.x1e.x2a, z2.t1a.t2b.x1e.x2b,
z2.t1a.t2b.x1e.x2c, z2.t1a.t2b.x1e.x2d, z2.t1a.t2b.x1e.x2e,
z2.t1a.t2b.x1e.x2f, z2.t1a.t2b.x1e.x2g, z2.t1a.t2b.x1e.x2h,
z2.t1a.t2b.x1f.x2a, z2.t1a.t2b.x1f.x2b, z2.t1a.t2b.x1f.x2c,
z2.t1a.t2b.x1f.x2d, z2.t1a.t2b.x1f.x2e, z2.t1a.t2b.x1f.x2f,
z2.t1a.t2b.x1f.x2g, z2.t1a.t2b.x1f.x2h, z2.t1a.t2b.x1g.x2a,
z2.t1a.t2b.x1g.x2b, z2.t1a.t2b.x1g.x2c, z2.t1a.t2b.x1g.x2d,
z2.t1a.t2b.x1g.x2e, z2.t1a.t2b.x1g.x2f, z2.t1a.t2b.x1g.x2g,
z2.t1a.t2b.x1g.x2h, z2.t1a.t2b.x1h.x2a, z2.t1a.t2b.x1h.x2b,
z2.t1a.t2b.x1h.x2c, z2.t1a.t2b.x1h.x2d, z2.t1a.t2b.x1h.x2e,
z2.t1a.t2b.x1h.x2f, z2.t1a.t2b.x1h.x2g, z2.t1a.t2b.x1h.x2h,
z2.t1a.t2c.x1a.x2a, z2.t1a.t2c.x1a.x2b, z2.t1a.t2c.x1a.x2c,
z2.t1a.t2c.x1a.x2d, z2.t1a.t2c.x1a.x2e, z2.t1a.t2c.x1a.x2f,
z2.t1a.t2c.x1a.x2g, z2.t1a.t2c.x1a.x2h, z2.t1a.t2c.x1b.x2a,
z2.t1a.t2c.x1b.x2b, z2.t1a.t2c.x1b.x2c, z2.t1a.t2c.x1b.x2d,
z2.t1a.t2c.x1b.x2e, z2.t1a.t2c.x1b.x2f, z2.t1a.t2c.x1b.x2g,
z2.t1a.t2c.x1b.x2h, z2.t1a.t2c.x1c.x2a, z2.t1a.t2c.x1c.x2b,
z2.t1a.t2c.x1c.x2c, z2.t1a.t2c.x1c.x2d, z2.t1a.t2c.x1c.x2e,
z2.t1a.t2c.x1c.x2f, z2.t1a.t2c.x1c.x2g, z2.t1a.t2c.x1c.x2h,
z2.t1a.t2c.x1d.x2a, z2.t1a.t2c.x1d.x2b, z2.t1a.t2c.x1d.x2c,
z2.t1a.t2c.x1d.x2d, z2.t1a.t2c.x1d.x2e, z2.t1a.t2c.x1d.x2f,
z2.t1a.t2c.x1d.x2g, z2.t1a.t2c.x1d.x2h, z2.t1a.t2c.x1e.x2a,
z2.t1a.t2c.x1e.x2b, z2.t1a.t2c.x1e.x2c, z2.t1a.t2c.x1e.x2d,
z2.t1a.t2c.x1e.x2e, z2.t1a.t2c.x1e.x2f, z2.t1a.t2c.x1e.x2g, TABLE 30.6-continued List of Compound Structures of Formula III z2.t1a.t2c.x1e.x2h, z2.t1a.t2c.x1f.x2a, z2.t1a.t2c.x1f.x2b,
z2.t1a.t2c.x1f.x2c, z2.t1a.t2c.x1f.x2d, z2.t1a.t2c.x1f.x2e,
z2.t1a.t2c.x1f.x2f, z2.t1a.t2c.x1f.x2g, z2.t1a.t2c.x1f.x2h,
z2.t1a.t2c.x1g.x2a, z2.t1a.t2c.x1g.x2b, z2.t1a.t2c.x1g.x2c,
z2.t1a.t2c.x1g.x2d, z2.t1a.t2c.x1g.x2e, z2.t1a.t2c.x1g.x2f,
z2.t1a.t2c.x1g.x2g, z2.t1a.t2c.x1g.x2h, z2.t1a.t2c.x1h.x2a,
z2.t1a.t2c.x1h.x2b, z2.t1a.t2c.x1h.x2c, z2.t1a.t2c.x1h.x2d,
z2.t1a.t2c.x1h.x2e, z2.t1a.t2c.x1h.x2f, z2.t1a.t2c.x1h.x2g,
z2.t1a.t2c.x1h.x2h, z2.t1a.t2d.x1a.x2a, z2.t1a.t2d.x1a.x2b,
z2.t1a.t2d.x1a.x2c, z2.t1a.t2d.x1a.x2d, z2.t1a.t2d.x1a.x2e,
z2.t1a.t2d.x1a.x2f, z2.t1a.t2d.x1a.x2g, z2.t1a.t2d.x1a.x2h,
z2.t1a.t2d.x1b.x2a, z2.t1a.t2d.x1b.x2b, z2.t1a.t2d.x1b.x2c,
z2.t1a.t2d.x1b.x2d, z2.t1a.t2d.x1b.x2e, z2.t1a.t2d.x1b.x2f,
z2.t1a.t2d.x1b.x2g, z2.t1a.t2d.x1b.x2h, z2.t1a.t2d.x1c.x2a,
z2.t1a.t2d.x1c.x2b, z2.t1a.t2d.x1c.x2c, z2.t1a.t2d.x1c.x2d,
z2.t1a.t2d.x1c.x2e, z2.t1a.t2d.x1c.x2f, z2.t1a.t2d.x1c.x2g,
z2.t1a.t2d.x1c.x2h, z2.t1a.t2d.x1d.x2a, z2.t1a.t2d.x1d.x2b,
z2.t1a.t2d.x1d.x2c, z2.t1a.t2d.x1d.x2d, z2.t1a.t2d.x1d.x2e,
z2.t1a.t2d.x1d.x2f, z2.t1a.t2d.x1d.x2g, z2.t1a.t2d.x1d.x2h,
z2.t1a.t2d.x1e.x2a, z2.t1a.t2d.x1e.x2b, z2.t1a.t2d.x1e.x2c,
z2.t1a.t2d.x1e.x2d, z2.t1a.t2d.x1e.x2e, z2.t1a.t2d.x1e.x2f,
z2.t1a.t2d.x1e.x2g, z2.t1a.t2d.x1e.x2h, z2.t1a.t2d.x1f.x2a,
z2.t1a.t2d.x1f.x2b, z2.t1a.t2d.x1f.x2c, z2.t1a.t2d.x1f.x2d,
z2.t1a.t2d.x1f.x2e, z2.t1a.t2d.x1f.x2f, z2.t1a.t2d.x1f.x2g,
z2.t1a.t2d.x1f.x2h, z2.t1a.t2d.x1g.x2a, z2.t1a.t2d.x1g.x2b,
z2.t1a.t2d.x1g.x2c, z2.t1a.t2d.x1g.x2d, z2.t1a.t2d.x1g.x2e,
z2.t1a.t2d.x1g.x2f, z2.t1a.t2d.x1g.x2g, z2.t1a.t2d.x1g.x2h,
z2.t1a.t2d.x1h.x2a, z2.t1a.t2d.x1h.x2b, z2.t1a.t2d.x1h.x2c,
z2.t1a.t2d.x1h.x2d, z2.t1a.t2d.x1h.x2e, z2.t1a.t2d.x1h.x2f,
z2.t1a.t2d.x1h.x2g, z2.t1a.t2d.x1h.x2h, z2.t1a.t2e.x1a.x2a,
z2.t1a.t2e.x1a.x2b, z2.t1a.t2e.x1a.x2c, z2.t1a.t2e.x1a.x2d,
z2.t1a.t2e.x1a.x2e, z2.t1a.t2e.x1a.x2f, z2.t1a.t2e.x1a.x2g,
z2.t1a.t2e.x1a.x2h, z2.t1a.t2e.x1b.x2a, z2.t1a.t2e.x1b.x2b,
z2.t1a.t2e.x1b.x2c, z2.t1a.t2e.x1b.x2d, z2.t1a.t2e.x1b.x2e,
z2.t1a.t2e.x1b.x2f, z2.t1a.t2e.x1b.x2g, z2.t1a.t2e.x1b.x2h,
z2.t1a.t2e.x1c.x2a, z2.t1a.t2e.x1c.x2b, z2.t1a.t2e.x1c.x2c,
z2.t1a.t2e.x1c.x2d, z2.t1a.t2e.x1c.x2e, z2.t1a.t2e.x1c.x2f,
z2.t1a.t2e.x1c.x2g, z2.t1a.t2e.x1c.x2h, z2.t1a.t2e.x1d.x2a,
z2.t1a.t2e.x1d.x2b, z2.t1a.t2e.x1d.x2c, z2.t1a.t2e.x1d.x2d,
z2.t1a.t2e.x1d.x2e, z2.t1a.t2e.x1d.x2f, z2.t1a.t2e.x1d.x2g,
z2.t1a.t2e.x1d.x2h, z2.t1a.t2e.x1e.x2a, z2.t1a.t2e.x1e.x2b,
z2.t1a.t2e.x1e.x2c, z2.t1a.t2e.x1e.x2d, z2.t1a.t2e.x1e.x2e,
z2.t1a.t2e.x1e.x2f, z2.t1a.t2e.x1e.x2g, z2.t1a.t2e.x1e.x2h,
z2.t1a.t2e.x1f.x2a, z2.t1a.t2e.x1f.x2b, z2.t1a.t2e.x1f.x2c,
z2.t1a.t2e.x1f.x2d, z2.t1a.t2e.x1f.x2e, z2.t1a.t2e.x1f.x2f,
z2.t1a.t2e.x1f.x2g, z2.t1a.t2e.x1f.x2h, z2.t1a.t2e.x1g.x2a,
z2.t1a.t2e.x1g.x2b, z2.t1a.t2e.x1g.x2c, z2.t1a.t2e.x1g.x2d,
z2.t1a.t2e.x1g.x2e, z2.t1a.t2e.x1g.x2f, z2.t1a.t2e.x1g.x2g,
z2.t1a.t2e.x1g.x2h, z2.t1a.t2e.x1h.x2a, z2.t1a.t2e.x1h.x2b,
z2.t1a.t2e.x1h.x2c, z2.t1a.t2e.x1h.x2d, z2.t1a.t2e.x1h.x2e,
z2.t1a.t2e.x1h.x2f, z2.t1a.t2e.x1h.x2g, z2.t1a.t2e.x1h.x2h,
z2.t1b.t2a.x1a.x2a, z2.t1b.t2a.x1a.x2b, z2.t1b.t2a.x1a.x2c,
z2.t1b.t2a.x1a.x2d, z2.t1b.t2a.x1a.x2e, z2.t1b.t2a.x1a.x2f,
z2.t1b.t2a.x1a.x2g, z2.t1b.t2a.x1a.x2h, z2.t1b.t2a.x1b.x2a,
z2.t1b.t2a.x1b.x2b, z2.t1b.t2a.x1b.x2c, z2.t1b.t2a.x1b.x2d,
z2.t1b.t2a.x1b.x2e, z2.t1b.t2a.x1b.x2f, z2.t1b.t2a.x1b.x2g,
z2.t1b.t2a.x1b.x2h, z2.t1b.t2a.x1c.x2a, z2.t1b.t2a.x1c.x2b,
z2.t1b.t2a.x1c.x2c, z2.t1b.t2a.x1c.x2d, z2.t1b.t2a.x1c.x2e,
z2.t1b.t2a.x1c.x2f, z2.t1b.t2a.x1c.x2g, z2.t1b.t2a.x1c.x2h,
z2.t1b.t2a.x1d.x2a, z2.t1b.t2a.x1d.x2b, z2.t1b.t2a.x1d.x2c,
z2.t1b.t2a.x1d.x2d, z2.t1b.t2a.x1d.x2e, z2.t1b.t2a.x1d.x2f,
z2.t1b.t2a.x1d.x2g, z2.t1b.t2a.x1d.x2h, z2.t1b.t2a.x1e.x2a,
z2.t1b.t2a.x1e.x2b, z2.t1b.t2a.x1e.x2c, z2.t1b.t2a.x1e.x2d,
z2.t1b.t2a.x1e.x2e, z2.t1b.t2a.x1e.x2f, z2.t1b.t2a.x1e.x2g,
z2.t1b.t2a.x1e.x2h, z2.t1b.t2a.x1f.x2a, z2.t1b.t2a.x1f.x2b,
z2.t1b.t2a.x1f.x2c, z2.t1b.t2a.x1f.x2d, z2.t1b.t2a.x1f.x2e,
z2.t1b.t2a.x1f.x2f, z2.t1b.t2a.x1f.x2g, z2.t1b.t2a.x1f.x2h,
z2.t1b.t2a.x1g.x2a, z2.t1b.t2a.x1g.x2b, z2.t1b.t2a.x1g.x2c,
z2.t1b.t2a.x1g.x2d, z2.t1b.t2a.x1g.x2e, z2.t1b.t2a.x1g.x2f,
z2.t1b.t2a.x1g.x2g, z2.t1b.t2a.x1g.x2h, z2.t1b.t2a.x1h.x2a,
z2.t1b.t2a.x1h.x2b, z2.t1b.t2a.x1h.x2c, z2.t1b.t2a.x1h.x2d,
z2.t1b.t2a.x1h.x2e, z2.t1b.t2a.x1h.x2f, z2.t1b.t2a.x1h.x2g,
z2.t1b.t2a.x1h.x2h, z2.t1b.t2b.x1a.x2a, z2.t1b.t2b.x1a.x2b,
z2.t1b.t2b.x1a.x2c, z2.t1b.t2b.x1a.x2d, z2.t1b.t2b.x1a.x2e,
z2.t1b.t2b.x1a.x2f, z2.t1b.t2b.x1a.x2g, z2.t1b.t2b.x1a.x2h,
z2.t1b.t2b.x1b.x2a, z2.t1b.t2b.x1b.x2b, z2.t1b.t2b.x1b.x2c,
z2.t1b.t2b.x1b.x2d, z2.t1b.t2b.x1b.x2e, z2.t1b.t2b.x1b.x2f, TABLE 30.6-continued List of Compound Structures of Formula III z2.t1b.t2b.x1b.x2g, z2.t1b.t2b.x1b.x2h, z2.t1b.t2b.x1c.x2a,
z2.t1b.t2b.x1c.x2b, z2.t1b.t2b.x1c.x2c, z2.t1b.t2b.x1c.x2d,
z2.t1b.t2b.x1c.x2e, z2.t1b.t2b.x1c.x2f, z2.t1b.t2b.x1c.x2g,
z2.t1b.t2b.x1c.x2h, z2.t1b.t2b.x1d.x2a, z2.t1b.t2b.x1d.x2b,
z2.t1b.t2b.x1d.x2c, z2.t1b.t2b.x1d.x2d, z2.t1b.t2b.x1d.x2e,
z2.t1b.t2b.x1d.x2f, z2.t1b.t2b.x1d.x2g, z2.t1b.t2b.x1d.x2h,
z2.t1b.t2b.x1e.x2a, z2.t1b.t2b.x1e.x2b, z2.t1b.t2b.x1e.x2c,
z2.t1b.t2b.x1e.x2d, z2.t1b.t2b.x1e.x2e, z2.t1b.t2b.x1e.x2f,
z2.t1b.t2b.x1e.x2g, z2.t1b.t2b.x1e.x2h, z2.t1b.t2b.x1f.x2a,
z2.t1b.t2b.x1f.x2b, z2.t1b.t2b.x1f.x2c, z2.t1b.t2b.x1f.x2d,
z2.t1b.t2b.x1f.x2e, z2.t1b.t2b.x1f.x2f, z2.t1b.t2b.x1f.x2g,
z2.t1b.t2b.x1f.x2h, z2.t1b.t2b.x1g.x2a, z2.t1b.t2b.x1g.x2b,
z2.t1b.t2b.x1g.x2c, z2.t1b.t2b.x1g.x2d, z2.t1b.t2b.x1g.x2e,
z2.t1b.t2b.x1g.x2f, z2.t1b.t2b.x1g.x2g, z2.t1b.t2b.x1g.x2h,
z2.t1b.t2b.x1h.x2a, z2.t1b.t2b.x1h.x2b, z2.t1b.t2b.x1h.x2c,
z2.t1b.t2b.x1h.x2d, z2.t1b.t2b.x1h.x2e, z2.t1b.t2b.x1h.x2f,
z2.t1b.t2b.x1h.x2g, z2.t1b.t2b.x1h.x2h, z2.t1b.t2c.x1a.x2a,
z2.t1b.t2c.x1a.x2b, z2.t1b.t2c.x1a.x2c, z2.t1b.t2c.x1a.x2d,
z2.t1b.t2c.x1a.x2e, z2.t1b.t2c.x1a.x2f, z2.t1b.t2c.x1a.x2g,
z2.t1b.t2c.x1a.x2h, z2.t1b.t2c.x1b.x2a, z2.t1b.t2c.x1b.x2b,
z2.t1b.t2c.x1b.x2c, z2.t1b.t2c.x1b.x2d, z2.t1b.t2c.x1b.x2e,
z2.t1b.t2c.x1b.x2f, z2.t1b.t2c.x1b.x2g, z2.t1b.t2c.x1b.x2h,
z2.t1b.t2c.x1c.x2a, z2.t1b.t2c.x1c.x2b, z2.t1b.t2c.x1c.x2c,
z2.t1b.t2c.x1c.x2d, z2.t1b.t2c.x1c.x2e, z2.t1b.t2c.x1c.x2f,
z2.t1b.t2c.x1c.x2g, z2.t1b.t2c.x1c.x2h, z2.t1b.t2c.x1d.x2a,
z2.t1b.t2c.x1d.x2b, z2.t1b.t2c.x1d.x2c, z2.t1b.t2c.x1d.x2d,
z2.t1b.t2c.x1d.x2e, z2.t1b.t2c.x1d.x2f, z2.t1b.t2c.x1d.x2g,
z2.t1b.t2c.x1d.x2h, z2.t1b.t2c.x1e.x2a, z2.t1b.t2c.x1e.x2b,
z2.t1b.t2c.x1e.x2c, z2.t1b.t2c.x1e.x2d, z2.t1b.t2c.x1e.x2e,
z2.t1b.t2c.x1e.x2f, z2.t1b.t2c.x1e.x2g, z2.t1b.t2c.x1e.x2h,
z2.t1b.t2c.x1f.x2a, z2.t1b.t2c.x1f.x2b, z2.t1b.t2c.x1f.x2c,
z2.t1b.t2c.x1f.x2d, z2.t1b.t2c.x1f.x2e, z2.t1b.t2c.x1f.x2f,
z2.t1b.t2c.x1f.x2g, z2.t1b.t2c.x1f.x2h, z2.t1b.t2c.x1g.x2a,
z2.t1b.t2c.x1g.x2b, z2.t1b.t2c.x1g.x2c, z2.t1b.t2c.x1g.x2d,
z2.t1b.t2c.x1g.x2e, z2.t1b.t2c.x1g.x2f, z2.t1b.t2c.x1g.x2g,
z2.t1b.t2c.x1g.x2h, z2.t1b.t2c.x1h.x2a, z2.t1b.t2c.x1h.x2b,
z2.t1b.t2c.x1h.x2c, z2.t1b.t2c.x1h.x2d, z2.t1b.t2c.x1h.x2e,
z2.t1b.t2c.x1h.x2f, z2.t1b.t2c.x1h.x2g, z2.t1b.t2c.x1h.x2h,
z2.t1b.t2d.x1a.x2a, z2.t1b.t2d.x1a.x2b, z2.t1b.t2d.x1a.x2c,
z2.t1b.t2d.x1a.x2d, z2.t1b.t2d.x1a.x2e, z2.t1b.t2d.x1a.x2f,
z2.t1b.t2d.x1a.x2g, z2.t1b.t2d.x1a.x2h, z2.t1b.t2d.x1b.x2a,
z2.t1b.t2d.x1b.x2b, z2.t1b.t2d.x1b.x2c, z2.t1b.t2d.x1b.x2d,
z2.t1b.t2d.x1b.x2e, z2.t1b.t2d.x1b.x2f, z2.t1b.t2d.x1b.x2g,
z2.t1b.t2d.x1b.x2h, z2.t1b.t2d.x1c.x2a, z2.t1b.t2d.x1c.x2b,
z2.t1b.t2d.x1c.x2c, z2.t1b.t2d.x1c.x2d, z2.t1b.t2d.x1c.x2e,
z2.t1b.t2d.x1c.x2f, z2.t1b.t2d.x1c.x2g, z2.t1b.t2d.x1c.x2h,
z2.t1b.t2d.x1d.x2a, z2.t1b.t2d.x1d.x2b, z2.t1b.t2d.x1d.x2c,
z2.t1b.t2d.x1d.x2d, z2.t1b.t2d.x1d.x2e, z2.t1b.t2d.x1d.x2f,
z2.t1b.t2d.x1d.x2g, z2.t1b.t2d.x1d.x2h, z2.t1b.t2d.x1e.x2a,
z2.t1b.t2d.x1e.x2b, z2.t1b.t2d.x1e.x2c, z2.t1b.t2d.x1e.x2d,
z2.t1b.t2d.x1e.x2e, z2.t1b.t2d.x1e.x2f, z2.t1b.t2d.x1e.x2g,
z2.t1b.t2d.x1e.x2h, z2.t1b.t2d.x1f.x2a, z2.t1b.t2d.x1f.x2b,
z2.t1b.t2d.x1f.x2c, z2.t1b.t2d.x1f.x2d, z2.t1b.t2d.x1f.x2e,
z2.t1b.t2d.x1f.x2f, z2.t1b.t2d.x1f.x2g, z2.t1b.t2d.x1f.x2h,
z2.t1b.t2d.x1g.x2a, z2.t1b.t2d.x1g.x2b, z2.t1b.t2d.x1g.x2c,
z2.t1b.t2d.x1g.x2d, z2.t1b.t2d.x1g.x2e, z2.t1b.t2d.x1g.x2f,
z2.t1b.t2d.x1g.x2g, z2.t1b.t2d.x1g.x2h, z2.t1b.t2d.x1h.x2a,
z2.t1b.t2d.x1h.x2b, z2.t1b.t2d.x1h.x2c, z2.t1b.t2d.x1h.x2d,
z2.t1b.t2d.x1h.x2e, z2.t1b.t2d.x1h.x2f, z2.t1b.t2d.x1h.x2g,
z2.t1b.t2d.x1h.x2h, z2.t1b.t2e.x1a.x2a, z2.t1b.t2e.x1a.x2b,
z2.t1b.t2e.x1a.x2c, z2.t1b.t2e.x1a.x2d, z2.t1b.t2e.x1a.x2e,
z2.t1b.t2e.x1a.x2f, z2.t1b.t2e.x1a.x2g, z2.t1b.t2e.x1a.x2h,
z2.t1b.t2e.x1b.x2a, z2.t1b.t2e.x1b.x2b, z2.t1b.t2e.x1b.x2c,
z2.t1b.t2e.x1b.x2d, z2.t1b.t2e.x1b.x2e, z2.t1b.t2e.x1b.x2f,
z2.t1b.t2e.x1b.x2g, z2.t1b.t2e.x1b.x2h, z2.t1b.t2e.x1c.x2a,
z2.t1b.t2e.x1c.x2b, z2.t1b.t2e.x1c.x2c, z2.t1b.t2e.x1c.x2d,
z2.t1b.t2e.x1c.x2e, z2.t1b.t2e.x1c.x2f, z2.t1b.t2e.x1c.x2g,
z2.t1b.t2e.x1c.x2h, z2.t1b.t2e.x1d.x2a, z2.t1b.t2e.x1d.x2b,
z2.t1b.t2e.x1d.x2c, z2.t1b.t2e.x1d.x2d, z2.t1b.t2e.x1d.x2e,
z2.t1b.t2e.x1d.x2f, z2.t1b.t2e.x1d.x2g, z2.t1b.t2e.x1d.x2h,
z2.t1b.t2e.x1e.x2a, z2.t1b.t2e.x1e.x2b, z2.t1b.t2e.x1e.x2c,
z2.t1b.t2e.x1e.x2d, z2.t1b.t2e.x1e.x2e, z2.t1b.t2e.x1e.x2f,
z2.t1b.t2e.x1e.x2g, z2.t1b.t2e.x1e.x2h, z2.t1b.t2e.x1f.x2a,
z2.t1b.t2e.x1f.x2b, z2.t1b.t2e.x1f.x2c, z2.t1b.t2e.x1f.x2d,
z2.t1b.t2e.x1f.x2e, z2.t1b.t2e.x1f.x2f, z2.t1b.t2e.x1f.x2g,
z2.t1b.t2e.x1f.x2h, z2.t1b.t2e.x1g.x2a, z2.t1b.t2e.x1g.x2b,
z2.t1b.t2e.x1g.x2c, z2.t1b.t2e.x1g.x2d, z2.t1b.t2e.x1g.x2e, TABLE 30.6-continued List of Compound Structures of Formula III z2.t1b.t2e.x1g.x2f, z2.t1b.t2e.x1g.x2g, z2.t1b.t2e.x1g.x2h,
z2.t1b.t2e.x1h.x2a, z2.t1b.t2e.x1h.x2b, z2.t1b.t2e.x1h.x2c,
z2.t1b.t2e.x1h.x2d, z2.t1b.t2e.x1h.x2e, z2.t1b.t2e.x1h.x2f,
z2.t1b.t2e.x1h.x2g, z2.t1b.t2e.x1h.x2h, z2.t1c.t2a.x1a.x2a,
z2.t1c.t2a.x1a.x2b, z2.t1c.t2a.x1a.x2c, z2.t1c.t2a.x1a.x2d,
z2.t1c.t2a.x1a.x2e, z2.t1c.t2a.x1a.x2f, z2.t1c.t2a.x1a.x2g,
z2.t1c.t2a.x1a.x2h, z2.t1c.t2a.x1b.x2a, z2.t1c.t2a.x1b.x2b,
z2.t1c.t2a.x1b.x2c, z2.t1c.t2a.x1b.x2d, z2.t1c.t2a.x1b.x2e,
z2.t1c.t2a.x1b.x2f, z2.t1c.t2a.x1b.x2g, z2.t1c.t2a.x1b.x2h,
z2.t1c.t2a.x1c.x2a, z2.t1c.t2a.x1c.x2b, z2.t1c.t2a.x1c.x2c,
z2.t1c.t2a.x1c.x2d, z2.t1c.t2a.x1c.x2e, z2.t1c.t2a.x1c.x2f,
z2.t1c.t2a.x1c.x2g, z2.t1c.t2a.x1c.x2h, z2.t1c.t2a.x1d.x2a,
z2.t1c.t2a.x1d.x2b, z2.t1c.t2a.x1d.x2c, z2.t1c.t2a.x1d.x2d,
z2.t1c.t2a.x1d.x2e, z2.t1c.t2a.x1d.x2f, z2.t1c.t2a.x1d.x2g,
z2.t1c.t2a.x1d.x2h, z2.t1c.t2a.x1e.x2a, z2.t1c.t2a.x1e.x2b,
z2.t1c.t2a.x1e.x2c, z2.t1c.t2a.x1e.x2d, z2.t1c.t2a.x1e.x2e,
z2.t1c.t2a.x1e.x2f, z2.t1c.t2a.x1e.x2g, z2.t1c.t2a.x1e.x2h,
z2.t1c.t2a.x1f.x2a, z2.t1c.t2a.x1f.x2b, z2.t1c.t2a.x1f.x2c,
z2.t1c.t2a.x1f.x2d, z2.t1c.t2a.x1f.x2e, z2.t1c.t2a.x1f.x2f,
z2.t1c.t2a.x1f.x2g, z2.t1c.t2a.x1f.x2h, z2.t1c.t2a.x1g.x2a,
z2.t1c.t2a.x1g.x2b, z2.t1c.t2a.x1g.x2c, z2.t1c.t2a.x1g.x2d,
z2.t1c.t2a.x1g.x2e, z2.t1c.t2a.x1g.x2f, z2.t1c.t2a.x1g.x2g,
z2.t1c.t2a.x1g.x2h, z2.t1c.t2a.x1h.x2a, z2.t1c.t2a.x1h.x2b,
z2.t1c.t2a.x1h.x2c, z2.t1c.t2a.x1h.x2d, z2.t1c.t2a.x1h.x2e,
z2.t1c.t2a.x1h.x2f, z2.t1c.t2a.x1h.x2g, z2.t1c.t2a.x1h.x2h,
z2.t1c.t2b.x1a.x2a, z2.t1c.t2b.x1a.x2b, z2.t1c.t2b.x1a.x2c,
z2.t1c.t2b.x1a.x2d, z2.t1c.t2b.x1a.x2e, z2.t1c.t2b.x1a.x2f,
z2.t1c.t2b.x1a.x2g, z2.t1c.t2b.x1a.x2h, z2.t1c.t2b.x1b.x2a,
z2.t1c.t2b.x1b.x2b, z2.t1c.t2b.x1b.x2c, z2.t1c.t2b.x1b.x2d,
z2.t1c.t2b.x1b.x2e, z2.t1c.t2b.x1b.x2f, z2.t1c.t2b.x1b.x2g,
z2.t1c.t2b.x1b.x2h, z2.t1c.t2b.x1c.x2a, z2.t1c.t2b.x1c.x2b,
z2.t1c.t2b.x1c.x2c, z2.t1c.t2b.x1c.x2d, z2.t1c.t2b.x1c.x2e,
z2.t1c.t2b.x1c.x2f, z2.t1c.t2b.x1c.x2g, z2.t1c.t2b.x1c.x2h,
z2.t1c.t2b.x1d.x2a, z2.t1c.t2b.x1d.x2b, z2.t1c.t2b.x1d.x2c,
z2.t1c.t2b.x1d.x2d, z2.t1c.t2b.x1d.x2e, z2.t1c.t2b.x1d.x2f,
z2.t1c.t2b.x1d.x2g, z2.t1c.t2b.x1d.x2h, z2.t1c.t2b.x1e.x2a,
z2.t1c.t2b.x1e.x2b, z2.t1c.t2b.x1e.x2c, z2.t1c.t2b.x1e.x2d,
z2.t1c.t2b.x1e.x2e, z2.t1c.t2b.x1e.x2f, z2.t1c.t2b.x1e.x2g,
z2.t1c.t2b.x1e.x2h, z2.t1c.t2b.x1f.x2a, z2.t1c.t2b.x1f.x2b,
z2.t1c.t2b.x1f.x2c, z2.t1c.t2b.x1f.x2d, z2.t1c.t2b.x1f.x2e,
z2.t1c.t2b.x1f.x2f, z2.t1c.t2b.x1f.x2g, z2.t1c.t2b.x1f.x2h,
z2.t1c.t2b.x1g.x2a, z2.t1c.t2b.x1g.x2b, z2.t1c.t2b.x1g.x2c,
z2.t1c.t2b.x1g.x2d, z2.t1c.t2b.x1g.x2e, z2.t1c.t2b.x1g.x2f,
z2.t1c.t2b.x1g.x2g, z2.t1c.t2b.x1g.x2h, z2.t1c.t2b.x1h.x2a,
z2.t1c.t2b.x1h.x2b, z2.t1c.t2b.x1h.x2c, z2.t1c.t2b.x1h.x2d,
z2.t1c.t2b.x1h.x2e, z2.t1c.t2b.x1h.x2f, z2.t1c.t2b.x1h.x2g,
z2.t1c.t2b.x1h.x2h, z2.t1c.t2c.x1a.x2a, z2.t1c.t2c.x1a.x2b,
z2.t1c.t2c.x1a.x2c, z2.t1c.t2c.x1a.x2d, z2.t1c.t2c.x1a.x2e,
z2.t1c.t2c.x1a.x2f, z2.t1c.t2c.x1a.x2g, z2.t1c.t2c.x1a.x2h,
z2.t1c.t2c.x1b.x2a, z2.t1c.t2c.x1b.x2b, z2.t1c.t2c.x1b.x2c,
z2.t1c.t2c.x1b.x2d, z2.t1c.t2c.x1b.x2e, z2.t1c.t2c.x1b.x2f,
z2.t1c.t2c.x1b.x2g, z2.t1c.t2c.x1b.x2h, z2.t1c.t2c.x1c.x2a,
z2.t1c.t2c.x1c.x2b, z2.t1c.t2c.x1c.x2c, z2.t1c.t2c.x1c.x2d,
z2.t1c.t2c.x1c.x2e, z2.t1c.t2c.x1c.x2f, z2.t1c.t2c.x1c.x2g,
z2.t1c.t2c.x1c.x2h, z2.t1c.t2c.x1d.x2a, z2.t1c.t2c.x1d.x2b,
z2.t1c.t2c.x1d.x2c, z2.t1c.t2c.x1d.x2d, z2.t1c.t2c.x1d.x2e,
z2.t1c.t2c.x1d.x2f, z2.t1c.t2c.x1d.x2g, z2.t1c.t2c.x1d.x2h,
z2.t1c.t2c.x1e.x2a, z2.t1c.t2c.x1e.x2b, z2.t1c.t2c.x1e.x2c,
z2.t1c.t2c.x1e.x2d, z2.t1c.t2c.x1e.x2e, z2.t1c.t2c.x1e.x2f,
z2.t1c.t2c.x1e.x2g, z2.t1c.t2c.x1e.x2h, z2.t1c.t2c.x1f.x2a,
z2.t1c.t2c.x1f.x2b, z2.t1c.t2c.x1f.x2c, z2.t1c.t2c.x1f.x2d,
z2.t1c.t2c.x1f.x2e, z2.t1c.t2c.x1f.x2f, z2.t1c.t2c.x1f.x2g,
z2.t1c.t2c.x1f.x2h, z2.t1c.t2c.x1g.x2a, z2.t1c.t2c.x1g.x2b,
z2.t1c.t2c.x1g.x2c, z2.t1c.t2c.x1g.x2d, z2.t1c.t2c.x1g.x2e,
z2.t1c.t2c.x1g.x2f, z2.t1c.t2c.x1g.x2g, z2.t1c.t2c.x1g.x2h,
z2.t1c.t2c.x1h.x2a, z2.t1c.t2c.x1h.x2b, z2.t1c.t2c.x1h.x2c,
z2.t1c.t2c.x1h.x2d, z2.t1c.t2c.x1h.x2e, z2.t1c.t2c.x1h.x2f,
z2.t1c.t2c.x1h.x2g, z2.t1c.t2c.x1h.x2h, z2.t1c.t2d.x1a.x2a,
z2.t1c.t2d.x1a.x2b, z2.t1c.t2d.x1a.x2c, z2.t1c.t2d.x1a.x2d,
z2.t1c.t2d.x1a.x2e, z2.t1c.t2d.x1a.x2f, z2.t1c.t2d.x1a.x2g,
z2.t1c.t2d.x1a.x2h, z2.t1c.t2d.x1b.x2a, z2.t1c.t2d.x1b.x2b,
z2.t1c.t2d.x1b.x2c, z2.t1c.t2d.x1b.x2d, z2.t1c.t2d.x1b.x2e,
z2.t1c.t2d.x1b.x2f, z2.t1c.t2d.x1b.x2g, z2.t1c.t2d.x1b.x2h,
z2.t1c.t2d.x1c.x2a, z2.t1c.t2d.x1c.x2b, z2.t1c.t2d.x1c.x2c,
z2.t1c.t2d.x1c.x2d, z2.t1c.t2d.x1c.x2e, z2.t1c.t2d.x1c.x2f,
z2.t1c.t2d.x1c.x2g, z2.t1c.t2d.x1c.x2h, z2.t1c.t2d.x1d.x2a,
z2.t1c.t2d.x1d.x2b, z2.t1c.t2d.x1d.x2c, z2.t1c.t2d.x1d.x2d, z2.t1c.t2d.x1d.x2e, z2.t1c.t2d.x1d.x2f, z2.t1c.t2d.x1d.x2g,
z2.t1c.t2d.x1d.x2h, z2.t1c.t2d.x1e.x2a, z2.t1c.t2d.x1e.x2b,
z2.t1c.t2d.x1e.x2c, z2.t1c.t2d.x1e.x2d, z2.t1c.t2d.x1e.x2e,
z2.t1c.t2d.x1e.x2f, z2.t1c.t2d.x1e.x2g, z2.t1c.t2d.x1e.x2h,
z2.t1c.t2d.x1f.x2a, z2.t1c.t2d.x1f.x2b, z2.t1c.t2d.x1f.x2c,
z2.t1c.t2d.x1f.x2d, z2.t1c.t2d.x1f.x2e, z2.t1c.t2d.x1f.x2f,
z2.t1c.t2d.x1f.x2g, z2.t1c.t2d.x1f.x2h, z2.t1c.t2d.x1g.x2a,
z2.t1c.t2d.x1g.x2b, z2.t1c.t2d.x1g.x2c, z2.t1c.t2d.x1g.x2d,
z2.t1c.t2d.x1g.x2e, z2.t1c.t2d.x1g.x2f, z2.t1c.t2d.x1g.x2g,
z2.t1c.t2d.x1g.x2h, z2.t1c.t2d.x1h.x2a, z2.t1c.t2d.x1h.x2b,
z2.t1c.t2d.x1h.x2c, z2.t1c.t2d.x1h.x2d, z2.t1c.t2d.x1h.x2e,
z2.t1c.t2d.x1h.x2f, z2.t1c.t2d.x1h.x2g, z2.t1c.t2d.x1h.x2h,
z2.t1c.t2e.x1a.x2a, z2.t1c.t2e.x1a.x2b, z2.t1c.t2e.x1a.x2c,
z2.t1c.t2e.x1a.x2d, z2.t1c.t2e.x1a.x2e, z2.t1c.t2e.x1a.x2f,
z2.t1c.t2e.x1a.x2g, z2.t1c.t2e.x1a.x2h, z2.t1c.t2e.x1b.x2a,
z2.t1c.t2e.x1b.x2b, z2.t1c.t2e.x1b.x2c, z2.t1c.t2e.x1b.x2d,
z2.t1c.t2e.x1b.x2e, z2.t1c.t2e.x1b.x2f, z2.t1c.t2e.x1b.x2g,
z2.t1c.t2e.x1b.x2h, z2.t1c.t2e.x1c.x2a, z2.t1c.t2e.x1c.x2b,
z2.t1c.t2e.x1c.x2c, z2.t1c.t2e.x1c.x2d, z2.t1c.t2e.x1c.x2e,
z2.t1c.t2e.x1c.x2f, z2.t1c.t2e.x1c.x2g, z2.t1c.t2e.x1c.x2h,
z2.t1c.t2e.x1d.x2a, z2.t1c.t2e.x1d.x2b, z2.t1c.t2e.x1d.x2c,
z2.t1c.t2e.x1d.x2d, z2.t1c.t2e.x1d.x2e, z2.t1c.t2e.x1d.x2f,
z2.t1c.t2e.x1d.x2g, z2.t1c.t2e.x1d.x2h, z2.t1c.t2e.x1e.x2a,
z2.t1c.t2e.x1e.x2b, z2.t1c.t2e.x1e.x2c, z2.t1c.t2e.x1e.x2d,
z2.t1c.t2e.x1e.x2e, z2.t1c.t2e.x1e.x2f, z2.t1c.t2e.x1e.x2g,
z2.t1c.t2e.x1e.x2h, z2.t1c.t2e.x1f.x2a, z2.t1c.t2e.x1f.x2b,
z2.t1c.t2e.x1f.x2c, z2.t1c.t2e.x1f.x2d, z2.t1c.t2e.x1f.x2e,
z2.t1c.t2e.x1f.x2f, z2.t1c.t2e.x1f.x2g, z2.t1c.t2e.x1f.x2h,
z2.t1c.t2e.x1g.x2a, z2.t1c.t2e.x1g.x2b, z2.t1c.t2e.x1g.x2c,
z2.t1c.t2e.x1g.x2d, z2.t1c.t2e.x1g.x2e, z2.t1c.t2e.x1g.x2f,
z2.t1c.t2e.x1g.x2g, z2.t1c.t2e.x1g.x2h, z2.t1c.t2e.x1h.x2a,
z2.t1c.t2e.x1h.x2b, z2.t1c.t2e.x1h.x2c, z2.t1c.t2e.x1h.x2d,
z2.t1c.t2e.x1h.x2e, z2.t1c.t2e.x1h.x2f, z2.t1c.t2e.x1h.x2g,
z2.t1c.t2e.x1h.x2h, z2.t1d.t2a.x1a.x2a, z2.t1d.t2a.x1a.x2b,
z2.t1d.t2a.x1a.x2c, z2.t1d.t2a.x1a.x2d, z2.t1d.t2a.x1a.x2e,
z2.t1d.t2a.x1a.x2f, z2.t1d.t2a.x1a.x2g, z2.t1d.t2a.x1a.x2h,
z2.t1d.t2a.x1b.x2a, z2.t1d.t2a.x1b.x2b, z2.t1d.t2a.x1b.x2c,
z2.t1d.t2a.x1b.x2d, z2.t1d.t2a.x1b.x2e, z2.t1d.t2a.x1b.x2f,
z2.t1d.t2a.x1b.x2g, z2.t1d.t2a.x1b.x2h, z2.t1d.t2a.x1c.x2a,
z2.t1d.t2a.x1c.x2b, z2.t1d.t2a.x1c.x2c, z2.t1d.t2a.x1c.x2d,
z2.t1d.t2a.x1c.x2e, z2.t1d.t2a.x1c.x2f, z2.t1d.t2a.x1c.x2g,
z2.t1d.t2a.x1c.x2h, z2.t1d.t2a.x1d.x2a, z2.t1d.t2a.x1d.x2b,
z2.t1d.t2a.x1d.x2c, z2.t1d.t2a.x1d.x2d, z2.t1d.t2a.x1d.x2e,
z2.t1d.t2a.x1d.x2f, z2.t1d.t2a.x1d.x2g, z2.t1d.t2a.x1d.x2h,
z2.t1d.t2a.x1e.x2a, z2.t1d.t2a.x1e.x2b, z2.t1d.t2a.x1e.x2c,
z2.t1d.t2a.x1e.x2d, z2.t1d.t2a.x1e.x2e, z2.t1d.t2a.x1e.x2f,
z2.t1d.t2a.x1e.x2g, z2.t1d.t2a.x1e.x2h, z2.t1d.t2a.x1f.x2a,
z2.t1d.t2a.x1f.x2b, z2.t1d.t2a.x1f.x2c, z2.t1d.t2a.x1f.x2d,
z2.t1d.t2a.x1f.x2e, z2.t1d.t2a.x1f.x2f, z2.t1d.t2a.x1f.x2g,
z2.t1d.t2a.x1f.x2h, z2.t1d.t2a.x1g.x2a, z2.t1d.t2a.x1g.x2b,
z2.t1d.t2a.x1g.x2c, z2.t1d.t2a.x1g.x2d, z2.t1d.t2a.x1g.x2e,
z2.t1d.t2a.x1g.x2f, z2.t1d.t2a.x1g.x2g, z2.t1d.t2a.x1g.x2h,
z2.t1d.t2a.x1h.x2a, z2.t1d.t2a.x1h.x2b, z2.t1d.t2a.x1h.x2c,
z2.t1d.t2a.x1h.x2d, z2.t1d.t2a.x1h.x2e, z2.t1d.t2a.x1h.x2f,
z2.t1d.t2a.x1h.x2g, z2.t1d.t2a.x1h.x2h, z2.t1d.t2b.x1a.x2a,
z2.t1d.t2b.x1a.x2b, z2.t1d.t2b.x1a.x2c, z2.t1d.t2b.x1a.x2d,
z2.t1d.t2b.x1a.x2e, z2.t1d.t2b.x1a.x2f, z2.t1d.t2b.x1a.x2g,
z2.t1d.t2b.x1a.x2h, z2.t1d.t2b.x1b.x2a, z2.t1d.t2b.x1b.x2b,
z2.t1d.t2b.x1b.x2c, z2.t1d.t2b.x1b.x2d, z2.t1d.t2b.x1b.x2e,
z2.t1d.t2b.x1b.x2f, z2.t1d.t2b.x1b.x2g, z2.t1d.t2b.x1b.x2h,
z2.t1d.t2b.x1c.x2a, z2.t1d.t2b.x1c.x2b, z2.t1d.t2b.x1c.x2c,
z2.t1d.t2b.x1c.x2d, z2.t1d.t2b.x1c.x2e, z2.t1d.t2b.x1c.x2f,
z2.t1d.t2b.x1c.x2g, z2.t1d.t2b.x1c.x2h, z2.t1d.t2b.x1d.x2a,
z2.t1d.t2b.x1d.x2b, z2.t1d.t2b.x1d.x2c, z2.t1d.t2b.x1d.x2d,
z2.t1d.t2b.x1d.x2e, z2.t1d.t2b.x1d.x2f, z2.t1d.t2b.x1d.x2g,
z2.t1d.t2b.x1d.x2h, z2.t1d.t2b.x1e.x2a, z2.t1d.t2b.x1e.x2b,
z2.t1d.t2b.x1e.x2c, z2.t1d.t2b.x1e.x2d, z2.t1d.t2b.x1e.x2e,
z2.t1d.t2b.x1e.x2f, z2.t1d.t2b.x1e.x2g, z2.t1d.t2b.x1e.x2h,
z2.t1d.t2b.x1f.x2a, z2.t1d.t2b.x1f.x2b, z2.t1d.t2b.x1f.x2c,
z2.t1d.t2b.x1f.x2d, z2.t1d.t2b.x1f.x2e, z2.t1d.t2b.x1f.x2f,
z2.t1d.t2b.x1f.x2g, z2.t1d.t2b.x1f.x2h, z2.t1d.t2b.x1g.x2a,
z2.t1d.t2b.x1g.x2b, z2.t1d.t2b.x1g.x2c, z2.t1d.t2b.x1g.x2d,
z2.t1d.t2b.x1g.x2e, z2.t1d.t2b.x1g.x2f, z2.t1d.t2b.x1g.x2g,
z2.t1d.t2b.x1g.x2h, z2.t1d.t2b.x1h.x2a, z2.t1d.t2b.x1h.x2b,
z2.t1d.t2b.x1h.x2c, z2.t1d.t2b.x1h.x2d, z2.t1d.t2b.x1h.x2e,
z2.t1d.t2b.x1h.x2f, z2.t1d.t2b.x1h.x2g, z2.t1d.t2b.x1h.x2h,
z2.t1d.t2c.x1a.x2a, z2.t1d.t2c.x1a.x2b, z2.t1d.t2c.x1a.x2c, TABLE 30.6-continued List of Compound Structures of Formula III z2.t1d.t2c.x1a.x2d, z2.t1d.t2c.x1a.x2e, z2.t1d.t2c.x1a.x2f,
z2.t1d.t2c.x1a.x2g, z2.t1d.t2c.x1a.x2h, z2.t1d.t2c.x1b.x2a,
z2.t1d.t2c.x1b.x2b, z2.t1d.t2c.x1b.x2c, z2.t1d.t2c.x1b.x2d,
z2.t1d.t2c.x1b.x2e, z2.t1d.t2c.x1b.x2f, z2.t1d.t2c.x1b.x2g,
z2.t1d.t2c.x1b.x2h, z2.t1d.t2c.x1c.x2a, z2.t1d.t2c.x1c.x2b,
z2.t1d.t2c.x1c.x2c, z2.t1d.t2c.x1c.x2d, z2.t1d.t2c.x1c.x2e,
z2.t1d.t2c.x1c.x2f, z2.t1d.t2c.x1c.x2g, z2.t1d.t2c.x1c.x2h,
z2.t1d.t2c.x1d.x2a, z2.t1d.t2c.x1d.x2b, z2.t1d.t2c.x1d.x2c,
z2.t1d.t2c.x1d.x2d, z2.t1d.t2c.x1d.x2e, z2.t1d.t2c.x1d.x2f,
z2.t1d.t2c.x1d.x2g, z2.t1d.t2c.x1d.x2h, z2.t1d.t2c.x1e.x2a,
z2.t1d.t2c.x1e.x2b, z2.t1d.t2c.x1e.x2c, z2.t1d.t2c.x1e.x2d,
z2.t1d.t2c.x1e.x2e, z2.t1d.t2c.x1e.x2f, z2.t1d.t2c.x1e.x2g,
z2.t1d.t2c.x1e.x2h, z2.t1d.t2c.x1f.x2a, z2.t1d.t2c.x1f.x2b,
z2.t1d.t2c.x1f.x2c, z2.t1d.t2c.x1f.x2d, z2.t1d.t2c.x1f.x2e,
z2.t1d.t2c.x1f.x2f, z2.t1d.t2c.x1f.x2g, z2.t1d.t2c.x1f.x2h,
z2.t1d.t2c.x1g.x2a, z2.t1d.t2c.x1g.x2b, z2.t1d.t2c.x1g.x2c,
z2.t1d.t2c.x1g.x2d, z2.t1d.t2c.x1g.x2e, z2.t1d.t2c.x1g.x2f,
z2.t1d.t2c.x1g.x2g, z2.t1d.t2c.x1g.x2h, z2.t1d.t2c.x1h.x2a,
z2.t1d.t2c.x1h.x2b, z2.t1d.t2c.x1h.x2c, z2.t1d.t2c.x1h.x2d,
z2.t1d.t2c.x1h.x2e, z2.t1d.t2c.x1h.x2f, z2.t1d.t2c.x1h.x2g,
z2.t1d.t2c.x1h.x2h, z2.t1d.t2d.x1a.x2a, z2.t1d.t2d.x1a.x2b,
z2.t1d.t2d.x1a.x2c, z2.t1d.t2d.x1a.x2d, z2.t1d.t2d.x1a.x2e,
z2.t1d.t2d.x1a.x2f, z2.t1d.t2d.x1a.x2g, z2.t1d.t2d.x1a.x2h,
z2.t1d.t2d.x1b.x2a, z2.t1d.t2d.x1b.x2b, z2.t1d.t2d.x1b.x2c,
z2.t1d.t2d.x1b.x2d, z2.t1d.t2d.x1b.x2e, z2.t1d.t2d.x1b.x2f,
z2.t1d.t2d.x1b.x2g, z2.t1d.t2d.x1b.x2h, z2.t1d.t2d.x1c.x2a,
z2.t1d.t2d.x1c.x2b, z2.t1d.t2d.x1c.x2c, z2.t1d.t2d.x1c.x2d,
z2.t1d.t2d.x1c.x2e, z2.t1d.t2d.x1c.x2f, z2.t1d.t2d.x1c.x2g,
z2.t1d.t2d.x1c.x2h, z2.t1d.t2d.x1d.x2a, z2.t1d.t2d.x1d.x2b,
z2.t1d.t2d.x1d.x2c, z2.t1d.t2d.x1d.x2d, z2.t1d.t2d.x1d.x2e,
z2.t1d.t2d.x1d.x2f, z2.t1d.t2d.x1d.x2g, z2.t1d.t2d.x1d.x2h,
z2.t1d.t2d.x1e.x2a, z2.t1d.t2d.x1e.x2b, z2.t1d.t2d.x1e.x2c,
z2.t1d.t2d.x1e.x2d, z2.t1d.t2d.x1e.x2e, z2.t1d.t2d.x1e.x2f,
z2.t1d.t2d.x1e.x2g, z2.t1d.t2d.x1e.x2h, z2.t1d.t2d.x1f.x2a,
z2.t1d.t2d.x1f.x2b, z2.t1d.t2d.x1f.x2c, z2.t1d.t2d.x1f.x2d,
z2.t1d.t2d.x1f.x2e, z2.t1d.t2d.x1f.x2f, z2.t1d.t2d.x1f.x2g,
z2.t1d.t2d.x1f.x2h, z2.t1d.t2d.x1g.x2a, z2.t1d.t2d.x1g.x2b,
z2.t1d.t2d.x1g.x2c, z2.t1d.t2d.x1g.x2d, z2.t1d.t2d.x1g.x2e,
z2.t1d.t2d.x1g.x2f, z2.t1d.t2d.x1g.x2g, z2.t1d.t2d.x1g.x2h,
z2.t1d.t2d.x1h.x2a, z2.t1d.t2d.x1h.x2b, z2.t1d.t2d.x1h.x2c,
z2.t1d.t2d.x1h.x2d, z2.t1d.t2d.x1h.x2e, z2.t1d.t2d.x1h.x2f,
z2.t1d.t2d.x1h.x2g, z2.t1d.t2d.x1h.x2h, z2.t1d.t2e.x1a.x2a,
z2.t1d.t2e.x1a.x2b, z2.t1d.t2e.x1a.x2c, z2.t1d.t2e.x1a.x2d,
z2.t1d.t2e.x1a.x2e, z2.t1d.t2e.x1a.x2f, z2.t1d.t2e.x1a.x2g,
z2.t1d.t2e.x1a.x2h, z2.t1d.t2e.x1b.x2a, z2.t1d.t2e.x1b.x2b,
z2.t1d.t2e.x1b.x2c, z2.t1d.t2e.x1b.x2d, z2.t1d.t2e.x1b.x2e,
z2.t1d.t2e.x1b.x2f, z2.t1d.t2e.x1b.x2g, z2.t1d.t2e.x1b.x2h,
z2.t1d.t2e.x1c.x2a, z2.t1d.t2e.x1c.x2b, z2.t1d.t2e.x1c.x2c,
z2.t1d.t2e.x1c.x2d, z2.t1d.t2e.x1c.x2e, z2.t1d.t2e.x1c.x2f,
z2.t1d.t2e.x1c.x2g, z2.t1d.t2e.x1c.x2h, z2.t1d.t2e.x1d.x2a,
z2.t1d.t2e.x1d.x2b, z2.t1d.t2e.x1d.x2c, z2.t1d.t2e.x1d.x2d,
z2.t1d.t2e.x1d.x2e, z2.t1d.t2e.x1d.x2f, z2.t1d.t2e.x1d.x2g,
z2.t1d.t2e.x1d.x2h, z2.t1d.t2e.x1e.x2a, z2.t1d.t2e.x1e.x2b,
z2.t1d.t2e.x1e.x2c, z2.t1d.t2e.x1e.x2d, z2.t1d.t2e.x1e.x2e,
z2.t1d.t2e.x1e.x2f, z2.t1d.t2e.x1e.x2g, z2.t1d.t2e.x1e.x2h,
z2.t1d.t2e.x1f.x2a, z2.t1d.t2e.x1f.x2b, z2.t1d.t2e.x1f.x2c,
z2.t1d.t2e.x1f.x2d, z2.t1d.t2e.x1f.x2e, z2.t1d.t2e.x1f.x2f,
z2.t1d.t2e.x1f.x2g, z2.t1d.t2e.x1f.x2h, z2.t1d.t2e.x1g.x2a,
z2.t1d.t2e.x1g.x2b, z2.t1d.t2e.x1g.x2c, z2.t1d.t2e.x1g.x2d,
z2.t1d.t2e.x1g.x2e, z2.t1d.t2e.x1g.x2f, z2.t1d.t2e.x1g.x2g,
z2.t1d.t2e.x1g.x2h, z2.t1d.t2e.x1h.x2a, z2.t1d.t2e.x1h.x2b,
z2.t1d.t2e.x1h.x2c, z2.t1d.t2e.x1h.x2d, z2.t1d.t2e.x1h.x2e,
z2.t1d.t2e.x1h.x2f, z2.t1d.t2e.x1h.x2g, z2.t1d.t2e.x1h.x2h,
z2.t1e.t2a.x1a.x2a, z2.t1e.t2a.x1a.x2b, z2.t1e.t2a.x1a.x2c,
z2.t1e.t2a.x1a.x2d, z2.t1e.t2a.x1a.x2e, z2.t1e.t2a.x1a.x2f,
z2.t1e.t2a.x1a.x2g, z2.t1e.t2a.x1a.x2h, z2.t1e.t2a.x1b.x2a,
z2.t1e.t2a.x1b.x2b, z2.t1e.t2a.x1b.x2c, z2.t1e.t2a.x1b.x2d,
z2.t1e.t2a.x1b.x2e, z2.t1e.t2a.x1b.x2f, z2.t1e.t2a.x1b.x2g,
z2.t1e.t2a.x1b.x2h, z2.t1e.t2a.x1c.x2a, z2.t1e.t2a.x1c.x2b,
z2.t1e.t2a.x1c.x2c, z2.t1e.t2a.x1c.x2d, z2.t1e.t2a.x1c.x2e,
z2.t1e.t2a.x1c.x2f, z2.t1e.t2a.x1c.x2g, z2.t1e.t2a.x1c.x2h,
z2.t1e.t2a.x1d.x2a, z2.t1e.t2a.x1d.x2b, z2.t1e.t2a.x1d.x2c,
z2.t1e.t2a.x1d.x2d, z2.t1e.t2a.x1d.x2e, z2.t1e.t2a.x1d.x2f,
z2.t1e.t2a.x1d.x2g, z2.t1e.t2a.x1d.x2h, z2.t1e.t2a.x1e.x2a,
z2.t1e.t2a.x1e.x2b, z2.t1e.t2a.x1e.x2c, z2.t1e.t2a.x1e.x2d,
z2.t1e.t2a.x1e.x2e, z2.t1e.t2a.x1e.x2f, z2.t1e.t2a.x1e.x2g,
z2.t1e.t2a.x1e.x2h, z2.t1e.t2a.x1f.x2a, z2.t1e.t2a.x1f.x2b,
z2.t1e.t2a.x1f.x2c, z2.t1e.t2a.x1f.x2d, z2.t1e.t2a.x1f.x2e,
z2.t1e.t2a.x1f.x2f, z2.t1e.t2a.x1f.x2g, z2.t1e.t2a.x1f.x2h,
z2.t1e.t2a.x1g.x2a, z2.t1e.t2a.x1g.x2b, z2.t1e.t2a.x1g.x2c,
z2.t1e.t2a.x1g.x2d, z2.t1e.t2a.x1g.x2e, z2.t1e.t2a.x1g.x2f,
z2.t1e.t2a.x1g.x2g, z2.t1e.t2a.x1g.x2h, z2.t1e.t2a.x1h.x2a,
z2.t1e.t2a.x1h.x2b, z2.t1e.t2a.x1h.x2c, z2.t1e.t2a.x1h.x2d,
z2.t1e.t2a.x1h.x2e, z2.t1e.t2a.x1h.x2f, z2.t1e.t2a.x1h.x2g,
z2.t1e.t2a.x1h.x2h, z2.t1e.t2b.x1a.x2a, z2.t1e.t2b.x1a.x2b,
z2.t1e.t2b.x1a.x2c, z2.t1e.t2b.x1a.x2d, z2.t1e.t2b.x1a.x2e,
z2.t1e.t2b.x1a.x2f, z2.t1e.t2b.x1a.x2g, z2.t1e.t2b.x1a.x2h,
z2.t1e.t2b.x1b.x2a, z2.t1e.t2b.x1b.x2b, z2.t1e.t2b.x1b.x2c,
z2.t1e.t2b.x1b.x2d, z2.t1e.t2b.x1b.x2e, z2.t1e.t2b.x1b.x2f,
z2.t1e.t2b.x1b.x2g, z2.t1e.t2b.x1b.x2h, z2.t1e.t2b.x1c.x2a,
z2.t1e.t2b.x1c.x2b, z2.t1e.t2b.x1c.x2c, z2.t1e.t2b.x1c.x2d,
z2.t1e.t2b.x1c.x2e, z2.t1e.t2b.x1c.x2f, z2.t1e.t2b.x1c.x2g,
z2.t1e.t2b.x1c.x2h, z2.t1e.t2b.x1d.x2a, z2.t1e.t2b.x1d.x2b,
z2.t1e.t2b.x1d.x2c, z2.t1e.t2b.x1d.x2d, z2.t1e.t2b.x1d.x2e,
z2.t1e.t2b.x1d.x2f, z2.t1e.t2b.x1d.x2g, z2.t1e.t2b.x1d.x2h,
z2.t1e.t2b.x1e.x2a, z2.t1e.t2b.x1e.x2b, z2.t1e.t2b.x1e.x2c,
z2.t1e.t2b.x1e.x2d, z2.t1e.t2b.x1e.x2e, z2.t1e.t2b.x1e.x2f,
z2.t1e.t2b.x1e.x2g, z2.t1e.t2b.x1e.x2h, z2.t1e.t2b.x1f.x2a,
z2.t1e.t2b.x1f.x2b, z2.t1e.t2b.x1f.x2c, z2.t1e.t2b.x1f.x2d,
z2.t1e.t2b.x1f.x2e, z2.t1e.t2b.x1f.x2f, z2.t1e.t2b.x1f.x2g,
z2.t1e.t2b.x1f.x2h, z2.t1e.t2b.x1g.x2a, z2.t1e.t2b.x1g.x2b,
z2.t1e.t2b.x1g.x2c, z2.t1e.t2b.x1g.x2d, z2.t1e.t2b.x1g.x2e,
z2.t1e.t2b.x1g.x2f, z2.t1e.t2b.x1g.x2g, z2.t1e.t2b.x1g.x2h,
z2.t1e.t2b.x1h.x2a, z2.t1e.t2b.x1h.x2b, z2.t1e.t2b.x1h.x2c,
z2.t1e.t2b.x1h.x2d, z2.t1e.t2b.x1h.x2e, z2.t1e.t2b.x1h.x2f,
z2.t1e.t2b.x1h.x2g, z2.t1e.t2b.x1h.x2h, z2.t1e.t2c.x1a.x2a,
z2.t1e.t2c.x1a.x2b, z2.t1e.t2c.x1a.x2c, z2.t1e.t2c.x1a.x2d,
z2.t1e.t2c.x1a.x2e, z2.t1e.t2c.x1a.x2f, z2.t1e.t2c.x1a.x2g,
z2.t1e.t2c.x1a.x2h, z2.t1e.t2c.x1b.x2a, z2.t1e.t2c.x1b.x2b,
z2.t1e.t2c.x1b.x2c, z2.t1e.t2c.x1b.x2d, z2.t1e.t2c.x1b.x2e,
z2.t1e.t2c.x1b.x2f, z2.t1e.t2c.x1b.x2g, z2.t1e.t2c.x1b.x2h,
z2.t1e.t2c.x1c.x2a, z2.t1e.t2c.x1c.x2b, z2.t1e.t2c.x1c.x2c,
z2.t1e.t2c.x1c.x2d, z2.t1e.t2c.x1c.x2e, z2.t1e.t2c.x1c.x2f,
z2.t1e.t2c.x1c.x2g, z2.t1e.t2c.x1c.x2h, z2.t1e.t2c.x1d.x2a,
z2.t1e.t2c.x1d.x2b, z2.t1e.t2c.x1d.x2c, z2.t1e.t2c.x1d.x2d,
z2.t1e.t2c.x1d.x2e, z2.t1e.t2c.x1d.x2f, z2.t1e.t2c.x1d.x2g,
z2.t1e.t2c.x1d.x2h, z2.t1e.t2c.x1e.x2a, z2.t1e.t2c.x1e.x2b,
z2.t1e.t2c.x1e.x2c, z2.t1e.t2c.x1e.x2d, z2.t1e.t2c.x1e.x2e,
z2.t1e.t2c.x1e.x2f, z2.t1e.t2c.x1e.x2g, z2.t1e.t2c.x1e.x2h,
z2.t1e.t2c.x1f.x2a, z2.t1e.t2c.x1f.x2b, z2.t1e.t2c.x1f.x2c,
z2.t1e.t2c.x1f.x2d, z2.t1e.t2c.x1f.x2e, z2.t1e.t2c.x1f.x2f,
z2.t1e.t2c.x1f.x2g, z2.t1e.t2c.x1f.x2h, z2.t1e.t2c.x1g.x2a,
z2.t1e.t2c.x1g.x2b, z2.t1e.t2c.x1g.x2c, z2.t1e.t2c.x1g.x2d,
z2.t1e.t2c.x1g.x2e, z2.t1e.t2c.x1g.x2f, z2.t1e.t2c.x1g.x2g,
z2.t1e.t2c.x1g.x2h, z2.t1e.t2c.x1h.x2a, z2.t1e.t2c.x1h.x2b,
z2.t1e.t2c.x1h.x2c, z2.t1e.t2c.x1h.x2d, z2.t1e.t2c.x1h.x2e,
z2.t1e.t2c.x1h.x2f, z2.t1e.t2c.x1h.x2g, z2.t1e.t2c.x1h.x2h,
z2.t1e.t2d.x1a.x2a, z2.t1e.t2d.x1a.x2b, z2.t1e.t2d.x1a.x2c,
z2.t1e.t2d.x1a.x2d, z2.t1e.t2d.x1a.x2e, z2.t1e.t2d.x1a.x2f,
z2.t1e.t2d.x1a.x2g, z2.t1e.t2d.x1a.x2h, z2.t1e.t2d.x1b.x2a,
z2.t1e.t2d.x1b.x2b, z2.t1e.t2d.x1b.x2c, z2.t1e.t2d.x1b.x2d,
z2.t1e.t2d.x1b.x2e, z2.t1e.t2d.x1b.x2f, z2.t1e.t2d.x1b.x2g,
z2.t1e.t2d.x1b.x2h, z2.t1e.t2d.x1c.x2a, z2.t1e.t2d.x1c.x2b,
z2.t1e.t2d.x1c.x2c, z2.t1e.t2d.x1c.x2d, z2.t1e.t2d.x1c.x2e,
z2.t1e.t2d.x1c.x2f, z2.t1e.t2d.x1c.x2g, z2.t1e.t2d.x1c.x2h,
z2.t1e.t2d.x1d.x2a, z2.t1e.t2d.x1d.x2b, z2.t1e.t2d.x1d.x2c,
z2.t1e.t2d.x1d.x2d, z2.t1e.t2d.x1d.x2e, z2.t1e.t2d.x1d.x2f,
z2.t1e.t2d.x1d.x2g, z2.t1e.t2d.x1d.x2h, z2.t1e.t2d.x1e.x2a,
z2.t1e.t2d.x1e.x2b, z2.t1e.t2d.x1e.x2c, z2.t1e.t2d.x1e.x2d,
z2.t1e.t2d.x1e.x2e, z2.t1e.t2d.x1e.x2f, z2.t1e.t2d.x1e.x2g,
z2.t1e.t2d.x1e.x2h, z2.t1e.t2d.x1f.x2a, z2.t1e.t2d.x1f.x2b,
z2.t1e.t2d.x1f.x2c, z2.t1e.t2d.x1f.x2d, z2.t1e.t2d.x1f.x2e,
z2.t1e.t2d.x1f.x2f, z2.t1e.t2d.x1f.x2g, z2.t1e.t2d.x1f.x2h,
z2.t1e.t2d.x1g.x2a, z2.t1e.t2d.x1g.x2b, z2.t1e.t2d.x1g.x2c,
z2.t1e.t2d.x1g.x2d, z2.t1e.t2d.x1g.x2e, z2.t1e.t2d.x1g.x2f,
z2.t1e.t2d.x1g.x2g, z2.t1e.t2d.x1g.x2h, z2.t1e.t2d.x1h.x2a,
z2.t1e.t2d.x1h.x2b, z2.t1e.t2d.x1h.x2c, z2.t1e.t2d.x1h.x2d,
z2.t1e.t2d.x1h.x2e, z2.t1e.t2d.x1h.x2f, z2.t1e.t2d.x1h.x2g,
z2.t1e.t2d.x1h.x2h, z2.t1e.t2e.x1a.x2a, z2.t1e.t2e.x1a.x2b,
z2.t1e.t2e.x1a.x2c, z2.t1e.t2e.x1a.x2d, z2.t1e.t2e.x1a.x2e,
z2.t1e.t2e.x1a.x2f, z2.t1e.t2e.x1a.x2g, z2.t1e.t2e.x1a.x2h,
z2.t1e.t2e.x1b.x2a, z2.t1e.t2e.x1b.x2b, z2.t1e.t2e.x1b.x2c,
z2.t1e.t2e.x1b.x2d, z2.t1e.t2e.x1b.x2e, z2.t1e.t2e.x1b.x2f,
z2.t1e.t2e.x1b.x2g, z2.t1e.t2e.x1b.x2h, z2.t1e.t2e.x1c.x2a,

TABLE 30.6-continued

List of Compound Structures of Formula III z2.t1e.t2e.x1c.x2b, z2.t1e.t2e.x1c.x2c, z2.t1e.t2e.x1c.x2d,
z2.t1e.t2e.x1c.x2e, z2.t1e.t2e.x1c.x2f, z2.t1e.t2e.x1c.x2g,
z2.t1e.t2e.x1c.x2h, z2.t1e.t2e.x1d.x2a, z2.t1e.t2e.x1d.x2b,
z2.t1e.t2e.x1d.x2c, z2.t1e.t2e.x1d.x2d, z2.t1e.t2e.x1d.x2e,
z2.t1e.t2e.x1d.x2f, z2.t1e.t2e.x1d.x2g, z2.t1e.t2e.x1d.x2h,
z2.t1e.t2e.x1e.x2a, z2.t1e.t2e.x1e.x2b, z2.t1e.t2e.x1e.x2c,
z2.t1e.t2e.x1e.x2d, z2.t1e.t2e.x1e.x2e, z2.t1e.t2e.x1e.x2f,
z2.t1e.t2e.x1e.x2g, z2.t1e.t2e.x1e.x2h, z2.t1e.t2e.x1f.x2a,
z2.t1e.t2e.x1f.x2b, z2.t1e.t2e.x1f.x2c, z2.t1e.t2e.x1f.x2d,
z2.t1e.t2e.x1f.x2e, z2.t1e.t2e.x1f.x2f, z2.t1e.t2e.x1f.x2g,
z2.t1e.t2e.x1f.x2h, z2.t1e.t2e.x1g.x2a, z2.t1e.t2e.x1g.x2b,
z2.t1e.t2e.x1g.x2c, z2.t1e.t2e.x1g.x2d, z2.t1e.t2e.x1g.x2e,
z2.t1e.t2e.x1g.x2f, z2.t1e.t2e.x1g.x2g, z2.t1e.t2e.x1g.x2h,
z2.t1e.t2e.x1h.x2a, z2.t1e.t2e.x1h.x2b, z2.t1e.t2e.x1h.x2c,
z2.t1e.t2e.x1h.x2d, z2.t1e.t2e.x1h.x2e, z2.t1e.t2e.x1h.x2f,
z2.t1e.t2e.x1h.x2g, z2.t1e.t2e.x1h.x2h, z3.t1a.t2a.x1a.x2a,
z3.t1a.t2a.x1a.x2b, z3.t1a.t2a.x1a.x2c, z3.t1a.t2a.x1a.x2d,
z3.t1a.t2a.x1a.x2e, z3.t1a.t2a.x1a.x2f, z3.t1a.t2a.x1a.x2g,
z3.t1a.t2a.x1a.x2h, z3.t1a.t2a.x1b.x2a, z3.t1a.t2a.x1b.x2b,
z3.t1a.t2a.x1b.x2c, z3.t1a.t2a.x1b.x2d, z3.t1a.t2a.x1b.x2e,
z3.t1a.t2a.x1b.x2f, z3.t1a.t2a.x1b.x2g, z3.t1a.t2a.x1b.x2h,
z3.t1a.t2a.x1c.x2a, z3.t1a.t2a.x1c.x2b, z3.t1a.t2a.x1c.x2c,
z3.t1a.t2a.x1c.x2d, z3.t1a.t2a.x1c.x2e, z3.t1a.t2a.x1c.x2f,
z3.t1a.t2a.x1c.x2g, z3.t1a.t2a.x1c.x2h, z3.t1a.t2a.x1d.x2a,
z3.t1a.t2a.x1d.x2b, z3.t1a.t2a.x1d.x2c, z3.t1a.t2a.x1d.x2d,
z3.t1a.t2a.x1d.x2e, z3.t1a.t2a.x1d.x2f, z3.t1a.t2a.x1d.x2g,
z3.t1a.t2a.x1d.x2h, z3.t1a.t2a.x1e.x2a, z3.t1a.t2a.x1e.x2b,
z3.t1a.t2a.x1e.x2c, z3.t1a.t2a.x1e.x2d, z3.t1a.t2a.x1e.x2e,
z3.t1a.t2a.x1e.x2f, z3.t1a.t2a.x1e.x2g, z3.t1a.t2a.x1e.x2h,
z3.t1a.t2a.x1f.x2a, z3.t1a.t2a.x1f.x2b, z3.t1a.t2a.x1f.x2c,
z3.t1a.t2a.x1f.x2d, z3.t1a.t2a.x1f.x2e, z3.t1a.t2a.x1f.x2f,
z3.t1a.t2a.x1f.x2g, z3.t1a.t2a.x1f.x2h, z3.t1a.t2a.x1g.x2a,
z3.t1a.t2a.x1g.x2b, z3.t1a.t2a.x1g.x2c, z3.t1a.t2a.x1g.x2d,
z3.t1a.t2a.x1g.x2e, z3.t1a.t2a.x1g.x2f, z3.t1a.t2a.x1g.x2g,
z3.t1a.t2a.x1g.x2h, z3.t1a.t2a.x1h.x2a, z3.t1a.t2a.x1h.x2b,
z3.t1a.t2a.x1h.x2c, z3.t1a.t2a.x1h.x2d, z3.t1a.t2a.x1h.x2e,
z3.t1a.t2a.x1h.x2f, z3.t1a.t2a.x1h.x2g, z3.t1a.t2a.x1h.x2h,
z3.t1a.t2b.x1a.x2a, z3.t1a.t2b.x1a.x2b, z3.t1a.t2b.x1a.x2c,
z3.t1a.t2b.x1a.x2d, z3.t1a.t2b.x1a.x2e, z3.t1a.t2b.x1a.x2f,
z3.t1a.t2b.x1a.x2g, z3.t1a.t2b.x1a.x2h, z3.t1a.t2b.x1b.x2a,
z3.t1a.t2b.x1b.x2b, z3.t1a.t2b.x1b.x2c, z3.t1a.t2b.x1b.x2d,
z3.t1a.t2b.x1b.x2e, z3.t1a.t2b.x1b.x2f, z3.t1a.t2b.x1b.x2g,
z3.t1a.t2b.x1b.x2h, z3.t1a.t2b.x1c.x2a, z3.t1a.t2b.x1c.x2b,
z3.t1a.t2b.x1c.x2c, z3.t1a.t2b.x1c.x2d, z3.t1a.t2b.x1c.x2e,
z3.t1a.t2b.x1c.x2f, z3.t1a.t2b.x1c.x2g, z3.t1a.t2b.x1c.x2h,
z3.t1a.t2b.x1d.x2a, z3.t1a.t2b.x1d.x2b, z3.t1a.t2b.x1d.x2c,
z3.t1a.t2b.x1d.x2d, z3.t1a.t2b.x1d.x2e, z3.t1a.t2b.x1d.x2f,
z3.t1a.t2b.x1d.x2g, z3.t1a.t2b.x1d.x2h, z3.t1a.t2b.x1e.x2a,
z3.t1a.t2b.x1e.x2b, z3.t1a.t2b.x1e.x2c, z3.t1a.t2b.x1e.x2d,
z3.t1a.t2b.x1e.x2e, z3.t1a.t2b.x1e.x2f, z3.t1a.t2b.x1e.x2g,
z3.t1a.t2b.x1e.x2h, z3.t1a.t2b.x1f.x2a, z3.t1a.t2b.x1f.x2b,
z3.t1a.t2b.x1f.x2c, z3.t1a.t2b.x1f.x2d, z3.t1a.t2b.x1f.x2e,
z3.t1a.t2b.x1f.x2f, z3.t1a.t2b.x1f.x2g, z3.t1a.t2b.x1f.x2h,
z3.t1a.t2b.x1g.x2a, z3.t1a.t2b.x1g.x2b, z3.t1a.t2b.x1g.x2c,
z3.t1a.t2b.x1g.x2d, z3.t1a.t2b.x1g.x2e, z3.t1a.t2b.x1g.x2f,
z3.t1a.t2b.x1g.x2g, z3.t1a.t2b.x1g.x2h, z3.t1a.t2b.x1h.x2a,
z3.t1a.t2b.x1h.x2b, z3.t1a.t2b.x1h.x2c, z3.t1a.t2b.x1h.x2d,
z3.t1a.t2b.x1h.x2e, z3.t1a.t2b.x1h.x2f, z3.t1a.t2b.x1h.x2g,
z3.t1a.t2b.x1h.x2h, z3.t1a.t2c.x1a.x2a, z3.t1a.t2c.x1a.x2b,
z3.t1a.t2c.x1a.x2c, z3.t1a.t2c.x1a.x2d, z3.t1a.t2c.x1a.x2e,
z3.t1a.t2c.x1a.x2f, z3.t1a.t2c.x1a.x2g, z3.t1a.t2c.x1a.x2h,
z3.t1a.t2c.x1b.x2a, z3.t1a.t2c.x1b.x2b, z3.t1a.t2c.x1b.x2c,
z3.t1a.t2c.x1b.x2d, z3.t1a.t2c.x1b.x2e, z3.t1a.t2c.x1b.x2f,
z3.t1a.t2c.x1b.x2g, z3.t1a.t2c.x1b.x2h, z3.t1a.t2c.x1c.x2a,
z3.t1a.t2c.x1c.x2b, z3.t1a.t2c.x1c.x2c, z3.t1a.t2c.x1c.x2d,
z3.t1a.t2c.x1c.x2e, z3.t1a.t2c.x1c.x2f, z3.t1a.t2c.x1c.x2g,
z3.t1a.t2c.x1c.x2h, z3.t1a.t2c.x1d.x2a, z3.t1a.t2c.x1d.x2b,
z3.t1a.t2c.x1d.x2c, z3.t1a.t2c.x1d.x2d, z3.t1a.t2c.x1d.x2e,
z3.t1a.t2c.x1d.x2f, z3.t1a.t2c.x1d.x2g, z3.t1a.t2c.x1d.x2h,
z3.t1a.t2c.x1e.x2a, z3.t1a.t2c.x1e.x2b, z3.t1a.t2c.x1e.x2c,
z3.t1a.t2c.x1e.x2d, z3.t1a.t2c.x1e.x2e, z3.t1a.t2c.x1e.x2f,
z3.t1a.t2c.x1e.x2g, z3.t1a.t2c.x1e.x2h, z3.t1a.t2c.x1f.x2a,
z3.t1a.t2c.x1f.x2b, z3.t1a.t2c.x1f.x2c, z3.t1a.t2c.x1f.x2d,
z3.t1a.t2c.x1f.x2e, z3.t1a.t2c.x1f.x2f, z3.t1a.t2c.x1f.x2g,
z3.t1a.t2c.x1f.x2h, z3.t1a.t2c.x1g.x2a, z3.t1a.t2c.x1g.x2b,
z3.t1a.t2c.x1g.x2c, z3.t1a.t2c.x1g.x2d, z3.t1a.t2c.x1g.x2e,
z3.t1a.t2c.x1g.x2f, z3.t1a.t2c.x1g.x2g, z3.t1a.t2c.x1g.x2h,
z3.t1a.t2c.x1h.x2a, z3.t1a.t2c.x1h.x2b, z3.t1a.t2c.x1h.x2c,
z3.t1a.t2c.x1h.x2d, z3.t1a.t2c.x1h.x2e, z3.t1a.t2c.x1h.x2f,
z3.t1a.t2c.x1h.x2g, z3.t1a.t2c.x1h.x2h, z3.t1a.t2d.x1a.x2a,
z3.t1a.t2d.x1a.x2b, z3.t1a.t2d.x1a.x2c, z3.t1a.t2d.x1a.x2d,
z3.t1a.t2d.x1a.x2e, z3.t1a.t2d.x1a.x2f, z3.t1a.t2d.x1a.x2g,
z3.t1a.t2d.x1a.x2h, z3.t1a.t2d.x1b.x2a, z3.t1a.t2d.x1b.x2b,
z3.t1a.t2d.x1b.x2c, z3.t1a.t2d.x1b.x2d, z3.t1a.t2d.x1b.x2e,
z3.t1a.t2d.x1b.x2f, z3.t1a.t2d.x1b.x2g, z3.t1a.t2d.x1b.x2h,
z3.t1a.t2d.x1c.x2a, z3.t1a.t2d.x1c.x2b, z3.t1a.t2d.x1c.x2c,
z3.t1a.t2d.x1c.x2d, z3.t1a.t2d.x1c.x2e, z3.t1a.t2d.x1c.x2f,
z3.t1a.t2d.x1c.x2g, z3.t1a.t2d.x1c.x2h, z3.t1a.t2d.x1d.x2a,
z3.t1a.t2d.x1d.x2b, z3.t1a.t2d.x1d.x2c, z3.t1a.t2d.x1d.x2d,
z3.t1a.t2d.x1d.x2e, z3.t1a.t2d.x1d.x2f, z3.t1a.t2d.x1d.x2g,
z3.t1a.t2d.x1d.x2h, z3.t1a.t2d.x1e.x2a, z3.t1a.t2d.x1e.x2b,
z3.t1a.t2d.x1e.x2c, z3.t1a.t2d.x1e.x2d, z3.t1a.t2d.x1e.x2e,
z3.t1a.t2d.x1e.x2f, z3.t1a.t2d.x1e.x2g, z3.t1a.t2d.x1e.x2h,
z3.t1a.t2d.x1f.x2a, z3.t1a.t2d.x1f.x2b, z3.t1a.t2d.x1f.x2c,
z3.t1a.t2d.x1f.x2d, z3.t1a.t2d.x1f.x2e, z3.t1a.t2d.x1f.x2f,
z3.t1a.t2d.x1f.x2g, z3.t1a.t2d.x1f.x2h, z3.t1a.t2d.x1g.x2a,
z3.t1a.t2d.x1g.x2b, z3.t1a.t2d.x1g.x2c, z3.t1a.t2d.x1g.x2d,
z3.t1a.t2d.x1g.x2e, z3.t1a.t2d.x1g.x2f, z3.t1a.t2d.x1g.x2g,
z3.t1a.t2d.x1g.x2h, z3.t1a.t2d.x1h.x2a, z3.t1a.t2d.x1h.x2b,
z3.t1a.t2d.x1h.x2c, z3.t1a.t2d.x1h.x2d, z3.t1a.t2d.x1h.x2e,
z3.t1a.t2d.x1h.x2f, z3.t1a.t2d.x1h.x2g, z3.t1a.t2d.x1h.x2h,
z3.t1a.t2e.x1a.x2a, z3.t1a.t2e.x1a.x2b, z3.t1a.t2e.x1a.x2c,
z3.t1a.t2e.x1a.x2d, z3.t1a.t2e.x1a.x2e, z3.t1a.t2e.x1a.x2f,
z3.t1a.t2e.x1a.x2g, z3.t1a.t2e.x1a.x2h, z3.t1a.t2e.x1b.x2a,
z3.t1a.t2e.x1b.x2b, z3.t1a.t2e.x1b.x2c, z3.t1a.t2e.x1b.x2d,
z3.t1a.t2e.x1b.x2e, z3.t1a.t2e.x1b.x2f, z3.t1a.t2e.x1b.x2g,
z3.t1a.t2e.x1b.x2h, z3.t1a.t2e.x1c.x2a, z3.t1a.t2e.x1c.x2b,
z3.t1a.t2e.x1c.x2c, z3.t1a.t2e.x1c.x2d, z3.t1a.t2e.x1c.x2e,
z3.t1a.t2e.x1c.x2f, z3.t1a.t2e.x1c.x2g, z3.t1a.t2e.x1c.x2h,
z3.t1a.t2e.x1d.x2a, z3.t1a.t2e.x1d.x2b, z3.t1a.t2e.x1d.x2c,
z3.t1a.t2e.x1d.x2d, z3.t1a.t2e.x1d.x2e, z3.t1a.t2e.x1d.x2f,
z3.t1a.t2e.x1d.x2g, z3.t1a.t2e.x1d.x2h, z3.t1a.t2e.x1e.x2a,
z3.t1a.t2e.x1e.x2b, z3.t1a.t2e.x1e.x2c, z3.t1a.t2e.x1e.x2d,
z3.t1a.t2e.x1e.x2e, z3.t1a.t2e.x1e.x2f, z3.t1a.t2e.x1e.x2g,
z3.t1a.t2e.x1e.x2h, z3.t1a.t2e.x1f.x2a, z3.t1a.t2e.x1f.x2b,
z3.t1a.t2e.x1f.x2c, z3.t1a.t2e.x1f.x2d, z3.t1a.t2e.x1f.x2e,
z3.t1a.t2e.x1f.x2f, z3.t1a.t2e.x1f.x2g, z3.t1a.t2e.x1f.x2h,
z3.t1a.t2e.x1g.x2a, z3.t1a.t2e.x1g.x2b, z3.t1a.t2e.x1g.x2c,
z3.t1a.t2e.x1g.x2d, z3.t1a.t2e.x1g.x2e, z3.t1a.t2e.x1g.x2f,
z3.t1a.t2e.x1g.x2g, z3.t1a.t2e.x1g.x2h, z3.t1a.t2e.x1h.x2a,
z3.t1a.t2e.x1h.x2b, z3.t1a.t2e.x1h.x2c, z3.t1a.t2e.x1h.x2d,
z3.t1a.t2e.x1h.x2e, z3.t1a.t2e.x1h.x2f, z3.t1a.t2e.x1h.x2g,
z3.t1a.t2e.x1h.x2h, z3.t1b.t2a.x1a.x2a, z3.t1b.t2a.x1a.x2b,
z3.t1b.t2a.x1a.x2c, z3.t1b.t2a.x1a.x2d, z3.t1b.t2a.x1a.x2e,
z3.t1b.t2a.x1a.x2f, z3.t1b.t2a.x1a.x2g, z3.t1b.t2a.x1a.x2h,
z3.t1b.t2a.x1b.x2a, z3.t1b.t2a.x1b.x2b, z3.t1b.t2a.x1b.x2c,
z3.t1b.t2a.x1b.x2d, z3.t1b.t2a.x1b.x2e, z3.t1b.t2a.x1b.x2f,
z3.t1b.t2a.x1b.x2g, z3.t1b.t2a.x1b.x2h, z3.t1b.t2a.x1c.x2a,
z3.t1b.t2a.x1c.x2b, z3.t1b.t2a.x1c.x2c, z3.t1b.t2a.x1c.x2d,
z3.t1b.t2a.x1c.x2e, z3.t1b.t2a.x1c.x2f, z3.t1b.t2a.x1c.x2g,
z3.t1b.t2a.x1c.x2h, z3.t1b.t2a.x1d.x2a, z3.t1b.t2a.x1d.x2b,
z3.t1b.t2a.x1d.x2c, z3.t1b.t2a.x1d.x2d, z3.t1b.t2a.x1d.x2e,
z3.t1b.t2a.x1d.x2f, z3.t1b.t2a.x1d.x2g, z3.t1b.t2a.x1d.x2h,
z3.t1b.t2a.x1e.x2a, z3.t1b.t2a.x1e.x2b, z3.t1b.t2a.x1e.x2c,
z3.t1b.t2a.x1e.x2d, z3.t1b.t2a.x1e.x2e, z3.t1b.t2a.x1e.x2f,
z3.t1b.t2a.x1e.x2g, z3.t1b.t2a.x1e.x2h, z3.t1b.t2a.x1f.x2a,
z3.t1b.t2a.x1f.x2b, z3.t1b.t2a.x1f.x2c, z3.t1b.t2a.x1f.x2d,
z3.t1b.t2a.x1f.x2e, z3.t1b.t2a.x1f.x2f, z3.t1b.t2a.x1f.x2g,
z3.t1b.t2a.x1f.x2h, z3.t1b.t2a.x1g.x2a, z3.t1b.t2a.x1g.x2b,
z3.t1b.t2a.x1g.x2c, z3.t1b.t2a.x1g.x2d, z3.t1b.t2a.x1g.x2e,
z3.t1b.t2a.x1g.x2f, z3.t1b.t2a.x1g.x2g, z3.t1b.t2a.x1g.x2h,
z3.t1b.t2a.x1h.x2a, z3.t1b.t2a.x1h.x2b, z3.t1b.t2a.x1h.x2c,
z3.t1b.t2a.x1h.x2d, z3.t1b.t2a.x1h.x2e, z3.t1b.t2a.x1h.x2f,
z3.t1b.t2a.x1h.x2g, z3.t1b.t2a.x1h.x2h, z3.t1b.t2b.x1a.x2a,
z3.t1b.t2b.x1a.x2b, z3.t1b.t2b.x1a.x2c, z3.t1b.t2b.x1a.x2d,
z3.t1b.t2b.x1a.x2e, z3.t1b.t2b.x1a.x2f, z3.t1b.t2b.x1a.x2g,
z3.t1b.t2b.x1a.x2h, z3.t1b.t2b.x1b.x2a, z3.t1b.t2b.x1b.x2b,
z3.t1b.t2b.x1b.x2c, z3.t1b.t2b.x1b.x2d, z3.t1b.t2b.x1b.x2e,
z3.t1b.t2b.x1b.x2f, z3.t1b.t2b.x1b.x2g, z3.t1b.t2b.x1b.x2h,
z3.t1b.t2b.x1c.x2a, z3.t1b.t2b.x1c.x2b, z3.t1b.t2b.x1c.x2c,
z3.t1b.t2b.x1c.x2d, z3.t1b.t2b.x1c.x2e, z3.t1b.t2b.x1c.x2f,
z3.t1b.t2b.x1c.x2g, z3.t1b.t2b.x1c.x2h, z3.t1b.t2b.x1d.x2a,
z3.t1b.t2b.x1d.x2b, z3.t1b.t2b.x1d.x2c, z3.t1b.t2b.x1d.x2d,
z3.t1b.t2b.x1d.x2e, z3.t1b.t2b.x1d.x2f, z3.t1b.t2b.x1d.x2g,

TABLE 30.6-continued

List of Compound Structures of Formula III z3.t1b.t2b.x1d.x2h, z3.t1b.t2b.x1e.x2a, z3.t1b.t2b.x1e.x2b,
z3.t1b.t2b.x1e.x2c, z3.t1b.t2b.x1e.x2d, z3.t1b.t2b.x1e.x2e,
z3.t1b.t2b.x1e.x2f, z3.t1b.t2b.x1e.x2g, z3.t1b.t2b.x1e.x2h,
z3.t1b.t2b.x1f.x2a, z3.t1b.t2b.x1f.x2b, z3.t1b.t2b.x1f.x2c,
z3.t1b.t2b.x1f.x2d, z3.t1b.t2b.x1f.x2e, z3.t1b.t2b.x1f.x2f,
z3.t1b.t2b.x1f.x2g, z3.t1b.t2b.x1f.x2h, z3.t1b.t2b.x1g.x2a,
z3.t1b.t2b.x1g.x2b, z3.t1b.t2b.x1g.x2c, z3.t1b.t2b.x1g.x2d,
z3.t1b.t2b.x1g.x2e, z3.t1b.t2b.x1g.x2f, z3.t1b.t2b.x1g.x2g,
z3.t1b.t2b.x1g.x2h, z3.t1b.t2b.x1h.x2a, z3.t1b.t2b.x1h.x2b,
z3.t1b.t2b.x1h.x2c, z3.t1b.t2b.x1h.x2d, z3.t1b.t2b.x1h.x2e,
z3.t1b.t2b.x1h.x2f, z3.t1b.t2b.x1h.x2g, z3.t1b.t2b.x1h.x2h,
z3.t1b.t2c.x1a.x2a, z3.t1b.t2c.x1a.x2b, z3.t1b.t2c.x1a.x2c,
z3.t1b.t2c.x1a.x2d, z3.t1b.t2c.x1a.x2e, z3.t1b.t2c.x1a.x2f,
z3.t1b.t2c.x1a.x2g, z3.t1b.t2c.x1a.x2h, z3.t1b.t2c.x1b.x2a,
z3.t1b.t2c.x1b.x2b, z3.t1b.t2c.x1b.x2c, z3.t1b.t2c.x1b.x2d,
z3.t1b.t2c.x1b.x2e, z3.t1b.t2c.x1b.x2f, z3.t1b.t2c.x1b.x2g,
z3.t1b.t2c.x1b.x2h, z3.t1b.t2c.x1c.x2a, z3.t1b.t2c.x1c.x2b,
z3.t1b.t2c.x1c.x2c, z3.t1b.t2c.x1c.x2d, z3.t1b.t2c.x1c.x2e,
z3.t1b.t2c.x1c.x2f, z3.t1b.t2c.x1c.x2g, z3.t1b.t2c.x1c.x2h,
z3.t1b.t2c.x1d.x2a, z3.t1b.t2c.x1d.x2b, z3.t1b.t2c.x1d.x2c,
z3.t1b.t2c.x1d.x2d, z3.t1b.t2c.x1d.x2e, z3.t1b.t2c.x1d.x2f,
z3.t1b.t2c.x1d.x2g, z3.t1b.t2c.x1d.x2h, z3.t1b.t2c.x1e.x2a,
z3.t1b.t2c.x1e.x2b, z3.t1b.t2c.x1e.x2c, z3.t1b.t2c.x1e.x2d,
z3.t1b.t2c.x1e.x2e, z3.t1b.t2c.x1e.x2f, z3.t1b.t2c.x1e.x2g,
z3.t1b.t2c.x1e.x2h, z3.t1b.t2c.x1f.x2a, z3.t1b.t2c.x1f.x2b,
z3.t1b.t2c.x1f.x2c, z3.t1b.t2c.x1f.x2d, z3.t1b.t2c.x1f.x2e,
z3.t1b.t2c.x1f.x2f, z3.t1b.t2c.x1f.x2g, z3.t1b.t2c.x1f.x2h,
z3.t1b.t2c.x1g.x2a, z3.t1b.t2c.x1g.x2b, z3.t1b.t2c.x1g.x2c,
z3.t1b.t2c.x1g.x2d, z3.t1b.t2c.x1g.x2e, z3.t1b.t2c.x1g.x2f,
z3.t1b.t2c.x1g.x2g, z3.t1b.t2c.x1g.x2h, z3.t1b.t2c.x1h.x2a,
z3.t1b.t2c.x1h.x2b, z3.t1b.t2c.x1h.x2c, z3.t1b.t2c.x1h.x2d,
z3.t1b.t2c.x1h.x2e, z3.t1b.t2c.x1h.x2f, z3.t1b.t2c.x1h.x2g,
z3.t1b.t2c.x1h.x2h, z3.t1b.t2d.x1a.x2a, z3.t1b.t2d.x1a.x2b,
z3.t1b.t2d.x1a.x2c, z3.t1b.t2d.x1a.x2d, z3.t1b.t2d.x1a.x2e,
z3.t1b.t2d.x1a.x2f, z3.t1b.t2d.x1a.x2g, z3.t1b.t2d.x1a.x2h,
z3.t1b.t2d.x1b.x2a, z3.t1b.t2d.x1b.x2b, z3.t1b.t2d.x1b.x2c,
z3.t1b.t2d.x1b.x2d, z3.t1b.t2d.x1b.x2e, z3.t1b.t2d.x1b.x2f,
z3.t1b.t2d.x1b.x2g, z3.t1b.t2d.x1b.x2h, z3.t1b.t2d.x1c.x2a,
z3.t1b.t2d.x1c.x2b, z3.t1b.t2d.x1c.x2c, z3.t1b.t2d.x1c.x2d,
z3.t1b.t2d.x1c.x2e, z3.t1b.t2d.x1c.x2f, z3.t1b.t2d.x1c.x2g,
z3.t1b.t2d.x1c.x2h, z3.t1b.t2d.x1d.x2a, z3.t1b.t2d.x1d.x2b,
z3.t1b.t2d.x1d.x2c, z3.t1b.t2d.x1d.x2d, z3.t1b.t2d.x1d.x2e,
z3.t1b.t2d.x1d.x2f, z3.t1b.t2d.x1d.x2g, z3.t1b.t2d.x1d.x2h,
z3.t1b.t2d.x1e.x2a, z3.t1b.t2d.x1e.x2b, z3.t1b.t2d.x1e.x2c,
z3.t1b.t2d.x1e.x2d, z3.t1b.t2d.x1e.x2e, z3.t1b.t2d.x1e.x2f,
z3.t1b.t2d.x1e.x2g, z3.t1b.t2d.x1e.x2h, z3.t1b.t2d.x1f.x2a,
z3.t1b.t2d.x1f.x2b, z3.t1b.t2d.x1f.x2c, z3.t1b.t2d.x1f.x2d,
z3.t1b.t2d.x1f.x2e, z3.t1b.t2d.x1f.x2f, z3.t1b.t2d.x1f.x2g,
z3.t1b.t2d.x1f.x2h, z3.t1b.t2d.x1g.x2a, z3.t1b.t2d.x1g.x2b,
z3.t1b.t2d.x1g.x2c, z3.t1b.t2d.x1g.x2d, z3.t1b.t2d.x1g.x2e,
z3.t1b.t2d.x1g.x2f, z3.t1b.t2d.x1g.x2g, z3.t1b.t2d.x1g.x2h,
z3.t1b.t2d.x1h.x2a, z3.t1b.t2d.x1h.x2b, z3.t1b.t2d.x1h.x2c,
z3.t1b.t2d.x1h.x2d, z3.t1b.t2d.x1h.x2e, z3.t1b.t2d.x1h.x2f,
z3.t1b.t2d.x1h.x2g, z3.t1b.t2d.x1h.x2h, z3.t1b.t2e.x1a.x2a,
z3.t1b.t2e.x1a.x2b, z3.t1b.t2e.x1a.x2c, z3.t1b.t2e.x1a.x2d,
z3.t1b.t2e.x1a.x2e, z3.t1b.t2e.x1a.x2f, z3.t1b.t2e.x1a.x2g,
z3.t1b.t2e.x1a.x2h, z3.t1b.t2e.x1b.x2a, z3.t1b.t2e.x1b.x2b,
z3.t1b.t2e.x1b.x2c, z3.t1b.t2e.x1b.x2d, z3.t1b.t2e.x1b.x2e,
z3.t1b.t2e.x1b.x2f, z3.t1b.t2e.x1b.x2g, z3.t1b.t2e.x1b.x2h,
z3.t1b.t2e.x1c.x2a, z3.t1b.t2e.x1c.x2b, z3.t1b.t2e.x1c.x2c,
z3.t1b.t2e.x1c.x2d, z3.t1b.t2e.x1c.x2e, z3.t1b.t2e.x1c.x2f,
z3.t1b.t2e.x1c.x2g, z3.t1b.t2e.x1c.x2h, z3.t1b.t2e.x1d.x2a,
z3.t1b.t2e.x1d.x2b, z3.t1b.t2e.x1d.x2c, z3.t1b.t2e.x1d.x2d,
z3.t1b.t2e.x1d.x2e, z3.t1b.t2e.x1d.x2f, z3.t1b.t2e.x1d.x2g,
z3.t1b.t2e.x1d.x2h, z3.t1b.t2e.x1e.x2a, z3.t1b.t2e.x1e.x2b,
z3.t1b.t2e.x1e.x2c, z3.t1b.t2e.x1e.x2d, z3.t1b.t2e.x1e.x2e,
z3.t1b.t2e.x1e.x2f, z3.t1b.t2e.x1e.x2g, z3.t1b.t2e.x1e.x2h,
z3.t1b.t2e.x1f.x2a, z3.t1b.t2e.x1f.x2b, z3.t1b.t2e.x1f.x2c,
z3.t1b.t2e.x1f.x2d, z3.t1b.t2e.x1f.x2e, z3.t1b.t2e.x1f.x2f,
z3.t1b.t2e.x1f.x2g, z3.t1b.t2e.x1f.x2h, z3.t1b.t2e.x1g.x2a,
z3.t1b.t2e.x1g.x2b, z3.t1b.t2e.x1g.x2c, z3.t1b.t2e.x1g.x2d,
z3.t1b.t2e.x1g.x2e, z3.t1b.t2e.x1g.x2f, z3.t1b.t2e.x1g.x2g,
z3.t1b.t2e.x1g.x2h, z3.t1b.t2e.x1h.x2a, z3.t1b.t2e.x1h.x2b,
z3.t1b.t2e.x1h.x2c, z3.t1b.t2e.x1h.x2d, z3.t1b.t2e.x1h.x2e,
z3.t1b.t2e.x1h.x2f, z3.t1b.t2e.x1h.x2g, z3.t1b.t2e.x1h.x2h,
z3.t1c.t2a.x1a.x2a, z3.t1c.t2a.x1a.x2b, z3.t1c.t2a.x1a.x2c,
z3.t1c.t2a.x1a.x2d, z3.t1c.t2a.x1a.x2e, z3.t1c.t2a.x1a.x2f,
z3.t1c.t2a.x1a.x2g, z3.t1c.t2a.x1a.x2h, z3.t1c.t2a.x1b.x2a,
z3.t1c.t2a.x1b.x2b, z3.t1c.t2a.x1b.x2c, z3.t1c.t2a.x1b.x2d,
z3.t1c.t2a.x1b.x2e, z3.t1c.t2a.x1b.x2f, z3.t1c.t2a.x1b.x2g,
z3.t1c.t2a.x1b.x2h, z3.t1c.t2a.x1c.x2a, z3.t1c.t2a.x1c.x2b,
z3.t1c.t2a.x1c.x2c, z3.t1c.t2a.x1c.x2d, z3.t1c.t2a.x1c.x2e,
z3.t1c.t2a.x1c.x2f, z3.t1c.t2a.x1c.x2g, z3.t1c.t2a.x1c.x2h,
z3.t1c.t2a.x1d.x2a, z3.t1c.t2a.x1d.x2b, z3.t1c.t2a.x1d.x2c,
z3.t1c.t2a.x1d.x2d, z3.t1c.t2a.x1d.x2e, z3.t1c.t2a.x1d.x2f,
z3.t1c.t2a.x1d.x2g, z3.t1c.t2a.x1d.x2h, z3.t1c.t2a.x1e.x2a,
z3.t1c.t2a.x1e.x2b, z3.t1c.t2a.x1e.x2c, z3.t1c.t2a.x1e.x2d,
z3.t1c.t2a.x1e.x2e, z3.t1c.t2a.x1e.x2f, z3.t1c.t2a.x1e.x2g,
z3.t1c.t2a.x1e.x2h, z3.t1c.t2a.x1f.x2a, z3.t1c.t2a.x1f.x2b,
z3.t1c.t2a.x1f.x2c, z3.t1c.t2a.x1f.x2d, z3.t1c.t2a.x1f.x2e,
z3.t1c.t2a.x1f.x2f, z3.t1c.t2a.x1f.x2g, z3.t1c.t2a.x1f.x2h,
z3.t1c.t2a.x1g.x2a, z3.t1c.t2a.x1g.x2b, z3.t1c.t2a.x1g.x2c,
z3.t1c.t2a.x1g.x2d, z3.t1c.t2a.x1g.x2e, z3.t1c.t2a.x1g.x2f,
z3.t1c.t2a.x1g.x2g, z3.t1c.t2a.x1g.x2h, z3.t1c.t2a.x1h.x2a,
z3.t1c.t2a.x1h.x2b, z3.t1c.t2a.x1h.x2c, z3.t1c.t2a.x1h.x2d,
z3.t1c.t2a.x1h.x2e, z3.t1c.t2a.x1h.x2f, z3.t1c.t2a.x1h.x2g,
z3.t1c.t2a.x1h.x2h, z3.t1c.t2b.x1a.x2a, z3.t1c.t2b.x1a.x2b,
z3.t1c.t2b.x1a.x2c, z3.t1c.t2b.x1a.x2d, z3.t1c.t2b.x1a.x2e,
z3.t1c.t2b.x1a.x2f, z3.t1c.t2b.x1a.x2g, z3.t1c.t2b.x1a.x2h,
z3.t1c.t2b.x1b.x2a, z3.t1c.t2b.x1b.x2b, z3.t1c.t2b.x1b.x2c,
z3.t1c.t2b.x1b.x2d, z3.t1c.t2b.x1b.x2e, z3.t1c.t2b.x1b.x2f,
z3.t1c.t2b.x1b.x2g, z3.t1c.t2b.x1b.x2h, z3.t1c.t2b.x1c.x2a,
z3.t1c.t2b.x1c.x2b, z3.t1c.t2b.x1c.x2c, z3.t1c.t2b.x1c.x2d,
z3.t1c.t2b.x1c.x2e, z3.t1c.t2b.x1c.x2f, z3.t1c.t2b.x1c.x2g,
z3.t1c.t2b.x1c.x2h, z3.t1c.t2b.x1d.x2a, z3.t1c.t2b.x1d.x2b,
z3.t1c.t2b.x1d.x2c, z3.t1c.t2b.x1d.x2d, z3.t1c.t2b.x1d.x2e,
z3.t1c.t2b.x1d.x2f, z3.t1c.t2b.x1d.x2g, z3.t1c.t2b.x1d.x2h,
z3.t1c.t2b.x1e.x2a, z3.t1c.t2b.x1e.x2b, z3.t1c.t2b.x1e.x2c,
z3.t1c.t2b.x1e.x2d, z3.t1c.t2b.x1e.x2e, z3.t1c.t2b.x1e.x2f,
z3.t1c.t2b.x1e.x2g, z3.t1c.t2b.x1e.x2h, z3.t1c.t2b.x1f.x2a,
z3.t1c.t2b.x1f.x2b, z3.t1c.t2b.x1f.x2c, z3.t1c.t2b.x1f.x2d,
z3.t1c.t2b.x1f.x2e, z3.t1c.t2b.x1f.x2f, z3.t1c.t2b.x1f.x2g,
z3.t1c.t2b.x1f.x2h, z3.t1c.t2b.x1g.x2a, z3.t1c.t2b.x1g.x2b,
z3.t1c.t2b.x1g.x2c, z3.t1c.t2b.x1g.x2d, z3.t1c.t2b.x1g.x2e,
z3.t1c.t2b.x1g.x2f, z3.t1c.t2b.x1g.x2g, z3.t1c.t2b.x1g.x2h,
z3.t1c.t2b.x1h.x2a, z3.t1c.t2b.x1h.x2b, z3.t1c.t2b.x1h.x2c,
z3.t1c.t2b.x1h.x2d, z3.t1c.t2b.x1h.x2e, z3.t1c.t2b.x1h.x2f,
z3.t1c.t2b.x1h.x2g, z3.t1c.t2b.x1h.x2h, z3.t1c.t2c.x1a.x2a,
z3.t1c.t2c.x1a.x2b, z3.t1c.t2c.x1a.x2c, z3.t1c.t2c.x1a.x2d,
z3.t1c.t2c.x1a.x2e, z3.t1c.t2c.x1a.x2f, z3.t1c.t2c.x1a.x2g,
z3.t1c.t2c.x1a.x2h, z3.t1c.t2c.x1b.x2a, z3.t1c.t2c.x1b.x2b,
z3.t1c.t2c.x1b.x2c, z3.t1c.t2c.x1b.x2d, z3.t1c.t2c.x1b.x2e,
z3.t1c.t2c.x1b.x2f, z3.t1c.t2c.x1b.x2g, z3.t1c.t2c.x1b.x2h,
z3.t1c.t2c.x1c.x2a, z3.t1c.t2c.x1c.x2b, z3.t1c.t2c.x1c.x2c,
z3.t1c.t2c.x1c.x2d, z3.t1c.t2c.x1c.x2e, z3.t1c.t2c.x1c.x2f,
z3.t1c.t2c.x1c.x2g, z3.t1c.t2c.x1c.x2h, z3.t1c.t2c.x1d.x2a,
z3.t1c.t2c.x1d.x2b, z3.t1c.t2c.x1d.x2c, z3.t1c.t2c.x1d.x2d,
z3.t1c.t2c.x1d.x2e, z3.t1c.t2c.x1d.x2f, z3.t1c.t2c.x1d.x2g,
z3.t1c.t2c.x1d.x2h, z3.t1c.t2c.x1e.x2a, z3.t1c.t2c.x1e.x2b,
z3.t1c.t2c.x1e.x2c, z3.t1c.t2c.x1e.x2d, z3.t1c.t2c.x1e.x2e,
z3.t1c.t2c.x1e.x2f, z3.t1c.t2c.x1e.x2g, z3.t1c.t2c.x1e.x2h,
z3.t1c.t2c.x1f.x2a, z3.t1c.t2c.x1f.x2b, z3.t1c.t2c.x1f.x2c,
z3.t1c.t2c.x1f.x2d, z3.t1c.t2c.x1f.x2e, z3.t1c.t2c.x1f.x2f,
z3.t1c.t2c.x1f.x2g, z3.t1c.t2c.x1f.x2h, z3.t1c.t2c.x1g.x2a,
z3.t1c.t2c.x1g.x2b, z3.t1c.t2c.x1g.x2c, z3.t1c.t2c.x1g.x2d,
z3.t1c.t2c.x1g.x2e, z3.t1c.t2c.x1g.x2f, z3.t1c.t2c.x1g.x2g,
z3.t1c.t2c.x1g.x2h, z3.t1c.t2c.x1h.x2a, z3.t1c.t2c.x1h.x2b,
z3.t1c.t2c.x1h.x2c, z3.t1c.t2c.x1h.x2d, z3.t1c.t2c.x1h.x2e,
z3.t1c.t2c.x1h.x2f, z3.t1c.t2c.x1h.x2g, z3.t1c.t2c.x1h.x2h,
z3.t1c.t2d.x1a.x2a, z3.t1c.t2d.x1a.x2b, z3.t1c.t2d.x1a.x2c,
z3.t1c.t2d.x1a.x2d, z3.t1c.t2d.x1a.x2e, z3.t1c.t2d.x1a.x2f,
z3.t1c.t2d.x1a.x2g, z3.t1c.t2d.x1a.x2h, z3.t1c.t2d.x1b.x2a,
z3.t1c.t2d.x1b.x2b, z3.t1c.t2d.x1b.x2c, z3.t1c.t2d.x1b.x2d,
z3.t1c.t2d.x1b.x2e, z3.t1c.t2d.x1b.x2f, z3.t1c.t2d.x1b.x2g,
z3.t1c.t2d.x1b.x2h, z3.t1c.t2d.x1c.x2a, z3.t1c.t2d.x1c.x2b,
z3.t1c.t2d.x1c.x2c, z3.t1c.t2d.x1c.x2d, z3.t1c.t2d.x1c.x2e,
z3.t1c.t2d.x1c.x2f, z3.t1c.t2d.x1c.x2g, z3.t1c.t2d.x1c.x2h,
z3.t1c.t2d.x1d.x2a, z3.t1c.t2d.x1d.x2b, z3.t1c.t2d.x1d.x2c,
z3.t1c.t2d.x1d.x2d, z3.t1c.t2d.x1d.x2e, z3.t1c.t2d.x1d.x2f,
z3.t1c.t2d.x1d.x2g, z3.t1c.t2d.x1d.x2h, z3.t1c.t2d.x1e.x2a,
z3.t1c.t2d.x1e.x2b, z3.t1c.t2d.x1e.x2c, z3.t1c.t2d.x1e.x2d,
z3.t1c.t2d.x1e.x2e, z3.t1c.t2d.x1e.x2f, z3.t1c.t2d.x1e.x2g,
z3.t1c.t2d.x1e.x2h, z3.t1c.t2d.x1f.x2a, z3.t1c.t2d.x1f.x2b,
z3.t1c.t2d.x1f.x2c, z3.t1c.t2d.x1f.x2d, z3.t1c.t2d.x1f.x2e,

TABLE 30.6-continued

List of Compound Structures of Formula III z3.t1c.t2d.x1f.x2f, z3.t1c.t2d.x1f.x2g, z3.t1c.t2d.x1f.x2h,
z3.t1c.t2d.x1g.x2a, z3.t1c.t2d.x1g.x2b, z3.t1c.t2d.x1g.x2c,
z3.t1c.t2d.x1g.x2d, z3.t1c.t2d.x1g.x2e, z3.t1c.t2d.x1g.x2f,
z3.t1c.t2d.x1g.x2g, z3.t1c.t2d.x1g.x2h, z3.t1c.t2d.x1h.x2a,
z3.t1c.t2d.x1h.x2b, z3.t1c.t2d.x1h.x2c, z3.t1c.t2d.x1h.x2d,
z3.t1c.t2d.x1h.x2e, z3.t1c.t2d.x1h.x2f, z3.t1c.t2d.x1h.x2g,
z3.t1c.t2d.x1h.x2h, z3.t1c.t2e.x1a.x2a, z3.t1c.t2e.x1a.x2b,
z3.t1c.t2e.x1a.x2c, z3.t1c.t2e.x1a.x2d, z3.t1c.t2e.x1a.x2e,
z3.t1c.t2e.x1a.x2f, z3.t1c.t2e.x1a.x2g, z3.t1c.t2e.x1a.x2h,
z3.t1c.t2e.x1b.x2a, z3.t1c.t2e.x1b.x2b, z3.t1c.t2e.x1b.x2c,
z3.t1c.t2e.x1b.x2d, z3.t1c.t2e.x1b.x2e, z3.t1c.t2e.x1b.x2f,
z3.t1c.t2e.x1b.x2g, z3.t1c.t2e.x1b.x2h, z3.t1c.t2e.x1c.x2a,
z3.t1c.t2e.x1c.x2b, z3.t1c.t2e.x1c.x2c, z3.t1c.t2e.x1c.x2d,
z3.t1c.t2e.x1c.x2e, z3.t1c.t2e.x1c.x2f, z3.t1c.t2e.x1c.x2g,
z3.t1c.t2e.x1c.x2h, z3.t1c.t2e.x1d.x2a, z3.t1c.t2e.x1d.x2b,
z3.t1c.t2e.x1d.x2c, z3.t1c.t2e.x1d.x2d, z3.t1c.t2e.x1d.x2e,
z3.t1c.t2e.x1d.x2f, z3.t1c.t2e.x1d.x2g, z3.t1c.t2e.x1d.x2h,
z3.t1c.t2e.x1e.x2a, z3.t1c.t2e.x1e.x2b, z3.t1c.t2e.x1e.x2c,
z3.t1c.t2e.x1e.x2d, z3.t1c.t2e.x1e.x2e, z3.t1c.t2e.x1e.x2f,
z3.t1c.t2e.x1e.x2g, z3.t1c.t2e.x1e.x2h, z3.t1c.t2e.x1f.x2a,
z3.t1c.t2e.x1f.x2b, z3.t1c.t2e.x1f.x2c, z3.t1c.t2e.x1f.x2d,
z3.t1c.t2e.x1f.x2e, z3.t1c.t2e.x1f.x2f, z3.t1c.t2e.x1f.x2g,
z3.t1c.t2e.x1f.x2h, z3.t1c.t2e.x1g.x2a, z3.t1c.t2e.x1g.x2b,
z3.t1c.t2e.x1g.x2c, z3.t1c.t2e.x1g.x2d, z3.t1c.t2e.x1g.x2e,
z3.t1c.t2e.x1g.x2f, z3.t1c.t2e.x1g.x2g, z3.t1c.t2e.x1g.x2h,
z3.t1c.t2e.x1h.x2a, z3.t1c.t2e.x1h.x2b, z3.t1c.t2e.x1h.x2c,
z3.t1c.t2e.x1h.x2d, z3.t1c.t2e.x1h.x2e, z3.t1c.t2e.x1h.x2f,
z3.t1c.t2e.x1h.x2g, z3.t1c.t2e.x1h.x2h, z3.t1d.t2a.x1a.x2a,
z3.t1d.t2a.x1a.x2b, z3.t1d.t2a.x1a.x2c, z3.t1d.t2a.x1a.x2d,
z3.t1d.t2a.x1a.x2e, z3.t1d.t2a.x1a.x2f, z3.t1d.t2a.x1a.x2g,
z3.t1d.t2a.x1a.x2h, z3.t1d.t2a.x1b.x2a, z3.t1d.t2a.x1b.x2b,
z3.t1d.t2a.x1b.x2c, z3.t1d.t2a.x1b.x2d, z3.t1d.t2a.x1b.x2e,
z3.t1d.t2a.x1b.x2f, z3.t1d.t2a.x1b.x2g, z3.t1d.t2a.x1b.x2h,
z3.t1d.t2a.x1c.x2a, z3.t1d.t2a.x1c.x2b, z3.t1d.t2a.x1c.x2c,
z3.t1d.t2a.x1c.x2d, z3.t1d.t2a.x1c.x2e, z3.t1d.t2a.x1c.x2f,
z3.t1d.t2a.x1c.x2g, z3.t1d.t2a.x1c.x2h, z3.t1d.t2a.x1d.x2a,
z3.t1d.t2a.x1d.x2b, z3.t1d.t2a.x1d.x2c, z3.t1d.t2a.x1d.x2d,
z3.t1d.t2a.x1d.x2e, z3.t1d.t2a.x1d.x2f, z3.t1d.t2a.x1d.x2g,
z3.t1d.t2a.x1d.x2h, z3.t1d.t2a.x1e.x2a, z3.t1d.t2a.x1e.x2b,
z3.t1d.t2a.x1e.x2c, z3.t1d.t2a.x1e.x2d, z3.t1d.t2a.x1e.x2e,
z3.t1d.t2a.x1e.x2f, z3.t1d.t2a.x1e.x2g, z3.t1d.t2a.x1e.x2h,
z3.t1d.t2a.x1f.x2a, z3.t1d.t2a.x1f.x2b, z3.t1d.t2a.x1f.x2c,
z3.t1d.t2a.x1f.x2d, z3.t1d.t2a.x1f.x2e, z3.t1d.t2a.x1f.x2f,
z3.t1d.t2a.x1f.x2g, z3.t1d.t2a.x1f.x2h, z3.t1d.t2a.x1g.x2a,
z3.t1d.t2a.x1g.x2b, z3.t1d.t2a.x1g.x2c, z3.t1d.t2a.x1g.x2d,
z3.t1d.t2a.x1g.x2e, z3.t1d.t2a.x1g.x2f, z3.t1d.t2a.x1g.x2g,
z3.t1d.t2a.x1g.x2h, z3.t1d.t2a.x1h.x2a, z3.t1d.t2a.x1h.x2b,
z3.t1d.t2a.x1h.x2c, z3.t1d.t2a.x1h.x2d, z3.t1d.t2a.x1h.x2e,
z3.t1d.t2a.x1h.x2f, z3.t1d.t2a.x1h.x2g, z3.t1d.t2a.x1h.x2h,
z3.t1d.t2b.x1a.x2a, z3.t1d.t2b.x1a.x2b, z3.t1d.t2b.x1a.x2c,
z3.t1d.t2b.x1a.x2d, z3.t1d.t2b.x1a.x2e, z3.t1d.t2b.x1a.x2f,
z3.t1d.t2b.x1a.x2g, z3.t1d.t2b.x1a.x2h, z3.t1d.t2b.x1b.x2a,
z3.t1d.t2b.x1b.x2b, z3.t1d.t2b.x1b.x2c, z3.t1d.t2b.x1b.x2d,
z3.t1d.t2b.x1b.x2e, z3.t1d.t2b.x1b.x2f, z3.t1d.t2b.x1b.x2g,
z3.t1d.t2b.x1b.x2h, z3.t1d.t2b.x1c.x2a, z3.t1d.t2b.x1c.x2b,
z3.t1d.t2b.x1c.x2c, z3.t1d.t2b.x1c.x2d, z3.t1d.t2b.x1c.x2e,
z3.t1d.t2b.x1c.x2f, z3.t1d.t2b.x1c.x2g, z3.t1d.t2b.x1c.x2h,
z3.t1d.t2b.x1d.x2a, z3.t1d.t2b.x1d.x2b, z3.t1d.t2b.x1d.x2c,
z3.t1d.t2b.x1d.x2d, z3.t1d.t2b.x1d.x2e, z3.t1d.t2b.x1d.x2f,
z3.t1d.t2b.x1d.x2g, z3.t1d.t2b.x1d.x2h, z3.t1d.t2b.x1e.x2a,
z3.t1d.t2b.x1e.x2b, z3.t1d.t2b.x1e.x2c, z3.t1d.t2b.x1e.x2d,
z3.t1d.t2b.x1e.x2e, z3.t1d.t2b.x1e.x2f, z3.t1d.t2b.x1e.x2g,
z3.t1d.t2b.x1e.x2h, z3.t1d.t2b.x1f.x2a, z3.t1d.t2b.x1f.x2b,
z3.t1d.t2b.x1f.x2c, z3.t1d.t2b.x1f.x2d, z3.t1d.t2b.x1f.x2e,
z3.t1d.t2b.x1f.x2f, z3.t1d.t2b.x1f.x2g, z3.t1d.t2b.x1f.x2h,
z3.t1d.t2b.x1g.x2a, z3.t1d.t2b.x1g.x2b, z3.t1d.t2b.x1g.x2c,
z3.t1d.t2b.x1g.x2d, z3.t1d.t2b.x1g.x2e, z3.t1d.t2b.x1g.x2f,
z3.t1d.t2b.x1g.x2g, z3.t1d.t2b.x1g.x2h, z3.t1d.t2b.x1h.x2a,
z3.t1d.t2b.x1h.x2b, z3.t1d.t2b.x1h.x2c, z3.t1d.t2b.x1h.x2d,
z3.t1d.t2b.x1h.x2e, z3.t1d.t2b.x1h.x2f, z3.t1d.t2b.x1h.x2g,
z3.t1d.t2b.x1h.x2h, z3.t1d.t2c.x1a.x2a, z3.t1d.t2c.x1a.x2b,
z3.t1d.t2c.x1a.x2c, z3.t1d.t2c.x1a.x2d, z3.t1d.t2c.x1a.x2e,
z3.t1d.t2c.x1a.x2f, z3.t1d.t2c.x1a.x2g, z3.t1d.t2c.x1a.x2h,
z3.t1d.t2c.x1b.x2a, z3.t1d.t2c.x1b.x2b, z3.t1d.t2c.x1b.x2c,
z3.t1d.t2c.x1b.x2d, z3.t1d.t2c.x1b.x2e, z3.t1d.t2c.x1b.x2f,
z3.t1d.t2c.x1b.x2g, z3.t1d.t2c.x1b.x2h, z3.t1d.t2c.x1c.x2a,
z3.t1d.t2c.x1c.x2b, z3.t1d.t2c.x1c.x2c, z3.t1d.t2c.x1c.x2d,
z3.t1d.t2c.x1c.x2e, z3.t1d.t2c.x1c.x2f, z3.t1d.t2c.x1c.x2g,
z3.t1d.t2c.x1c.x2h, z3.t1d.t2c.x1d.x2a, z3.t1d.t2c.x1d.x2b,
z3.t1d.t2c.x1d.x2c, z3.t1d.t2c.x1d.x2d, z3.t1d.t2c.x1d.x2e,
z3.t1d.t2c.x1d.x2f, z3.t1d.t2c.x1d.x2g, z3.t1d.t2c.x1d.x2h,
z3.t1d.t2c.x1e.x2a, z3.t1d.t2c.x1e.x2b, z3.t1d.t2c.x1e.x2c,
z3.t1d.t2c.x1e.x2d, z3.t1d.t2c.x1e.x2e, z3.t1d.t2c.x1e.x2f,
z3.t1d.t2c.x1e.x2g, z3.t1d.t2c.x1e.x2h, z3.t1d.t2c.x1f.x2a,
z3.t1d.t2c.x1f.x2b, z3.t1d.t2c.x1f.x2c, z3.t1d.t2c.x1f.x2d,
z3.t1d.t2c.x1f.x2e, z3.t1d.t2c.x1f.x2f, z3.t1d.t2c.x1f.x2g,
z3.t1d.t2c.x1f.x2h, z3.t1d.t2c.x1g.x2a, z3.t1d.t2c.x1g.x2b,
z3.t1d.t2c.x1g.x2c, z3.t1d.t2c.x1g.x2d, z3.t1d.t2c.x1g.x2e,
z3.t1d.t2c.x1g.x2f, z3.t1d.t2c.x1g.x2g, z3.t1d.t2c.x1g.x2h,
z3.t1d.t2c.x1h.x2a, z3.t1d.t2c.x1h.x2b, z3.t1d.t2c.x1h.x2c,
z3.t1d.t2c.x1h.x2d, z3.t1d.t2c.x1h.x2e, z3.t1d.t2c.x1h.x2f,
z3.t1d.t2c.x1h.x2g, z3.t1d.t2c.x1h.x2h, z3.t1d.t2d.x1a.x2a,
z3.t1d.t2d.x1a.x2b, z3.t1d.t2d.x1a.x2c, z3.t1d.t2d.x1a.x2d,
z3.t1d.t2d.x1a.x2e, z3.t1d.t2d.x1a.x2f, z3.t1d.t2d.x1a.x2g,
z3.t1d.t2d.x1a.x2h, z3.t1d.t2d.x1b.x2a, z3.t1d.t2d.x1b.x2b,
z3.t1d.t2d.x1b.x2c, z3.t1d.t2d.x1b.x2d, z3.t1d.t2d.x1b.x2e,
z3.t1d.t2d.x1b.x2f, z3.t1d.t2d.x1b.x2g, z3.t1d.t2d.x1b.x2h,
z3.t1d.t2d.x1c.x2a, z3.t1d.t2d.x1c.x2b, z3.t1d.t2d.x1c.x2c,
z3.t1d.t2d.x1c.x2d, z3.t1d.t2d.x1c.x2e, z3.t1d.t2d.x1c.x2f,
z3.t1d.t2d.x1c.x2g, z3.t1d.t2d.x1c.x2h, z3.t1d.t2d.x1d.x2a,
z3.t1d.t2d.x1d.x2b, z3.t1d.t2d.x1d.x2c, z3.t1d.t2d.x1d.x2d,
z3.t1d.t2d.x1d.x2e, z3.t1d.t2d.x1d.x2f, z3.t1d.t2d.x1d.x2g,
z3.t1d.t2d.x1d.x2h, z3.t1d.t2d.x1e.x2a, z3.t1d.t2d.x1e.x2b,
z3.t1d.t2d.x1e.x2c, z3.t1d.t2d.x1e.x2d, z3.t1d.t2d.x1e.x2e,
z3.t1d.t2d.x1e.x2f, z3.t1d.t2d.x1e.x2g, z3.t1d.t2d.x1e.x2h,
z3.t1d.t2d.x1f.x2a, z3.t1d.t2d.x1f.x2b, z3.t1d.t2d.x1f.x2c,
z3.t1d.t2d.x1f.x2d, z3.t1d.t2d.x1f.x2e, z3.t1d.t2d.x1f.x2f,
z3.t1d.t2d.x1f.x2g, z3.t1d.t2d.x1f.x2h, z3.t1d.t2d.x1g.x2a,
z3.t1d.t2d.x1g.x2b, z3.t1d.t2d.x1g.x2c, z3.t1d.t2d.x1g.x2d,
z3.t1d.t2d.x1g.x2e, z3.t1d.t2d.x1g.x2f, z3.t1d.t2d.x1g.x2g,
z3.t1d.t2d.x1g.x2h, z3.t1d.t2d.x1h.x2a, z3.t1d.t2d.x1h.x2b,
z3.t1d.t2d.x1h.x2c, z3.t1d.t2d.x1h.x2d, z3.t1d.t2d.x1h.x2e,
z3.t1d.t2d.x1h.x2f, z3.t1d.t2d.x1h.x2g, z3.t1d.t2d.x1h.x2h,
z3.t1d.t2e.x1a.x2a, z3.t1d.t2e.x1a.x2b, z3.t1d.t2e.x1a.x2c,
z3.t1d.t2e.x1a.x2d, z3.t1d.t2e.x1a.x2e, z3.t1d.t2e.x1a.x2f,
z3.t1d.t2e.x1a.x2g, z3.t1d.t2e.x1a.x2h, z3.t1d.t2e.x1b.x2a,
z3.t1d.t2e.x1b.x2b, z3.t1d.t2e.x1b.x2c, z3.t1d.t2e.x1b.x2d,
z3.t1d.t2e.x1b.x2e, z3.t1d.t2e.x1b.x2f, z3.t1d.t2e.x1b.x2g,
z3.t1d.t2e.x1b.x2h, z3.t1d.t2e.x1c.x2a, z3.t1d.t2e.x1c.x2b,
z3.t1d.t2e.x1c.x2c, z3.t1d.t2e.x1c.x2d, z3.t1d.t2e.x1c.x2e,
z3.t1d.t2e.x1c.x2f, z3.t1d.t2e.x1c.x2g, z3.t1d.t2e.x1c.x2h,
z3.t1d.t2e.x1d.x2a, z3.t1d.t2e.x1d.x2b, z3.t1d.t2e.x1d.x2c,
z3.t1d.t2e.x1d.x2d, z3.t1d.t2e.x1d.x2e, z3.t1d.t2e.x1d.x2f,
z3.t1d.t2e.x1d.x2g, z3.t1d.t2e.x1d.x2h, z3.t1d.t2e.x1e.x2a,
z3.t1d.t2e.x1e.x2b, z3.t1d.t2e.x1e.x2c, z3.t1d.t2e.x1e.x2d,
z3.t1d.t2e.x1e.x2e, z3.t1d.t2e.x1e.x2f, z3.t1d.t2e.x1e.x2g,
z3.t1d.t2e.x1e.x2h, z3.t1d.t2e.x1f.x2a, z3.t1d.t2e.x1f.x2b,
z3.t1d.t2e.x1f.x2c, z3.t1d.t2e.x1f.x2d, z3.t1d.t2e.x1f.x2e,
z3.t1d.t2e.x1f.x2f, z3.t1d.t2e.x1f.x2g, z3.t1d.t2e.x1f.x2h,
z3.t1d.t2e.x1g.x2a, z3.t1d.t2e.x1g.x2b, z3.t1d.t2e.x1g.x2c,
z3.t1d.t2e.x1g.x2d, z3.t1d.t2e.x1g.x2e, z3.t1d.t2e.x1g.x2f,
z3.t1d.t2e.x1g.x2g, z3.t1d.t2e.x1g.x2h, z3.t1d.t2e.x1h.x2a,
z3.t1d.t2e.x1h.x2b, z3.t1d.t2e.x1h.x2c, z3.t1d.t2e.x1h.x2d,
z3.t1d.t2e.x1h.x2e, z3.t1d.t2e.x1h.x2f, z3.t1d.t2e.x1h.x2g,
z3.t1d.t2e.x1h.x2h, z3.t1e.t2a.x1a.x2a, z3.t1e.t2a.x1a.x2b,
z3.t1e.t2a.x1a.x2c, z3.t1e.t2a.x1a.x2d, z3.t1e.t2a.x1a.x2e,
z3.t1e.t2a.x1a.x2f, z3.t1e.t2a.x1a.x2g, z3.t1e.t2a.x1a.x2h,
z3.t1e.t2a.x1b.x2a, z3.t1e.t2a.x1b.x2b, z3.t1e.t2a.x1b.x2c,
z3.t1e.t2a.x1b.x2d, z3.t1e.t2a.x1b.x2e, z3.t1e.t2a.x1b.x2f,
z3.t1e.t2a.x1b.x2g, z3.t1e.t2a.x1b.x2h, z3.t1e.t2a.x1c.x2a,
z3.t1e.t2a.x1c.x2b, z3.t1e.t2a.x1c.x2c, z3.t1e.t2a.x1c.x2d,
z3.t1e.t2a.x1c.x2e, z3.t1e.t2a.x1c.x2f, z3.t1e.t2a.x1c.x2g,
z3.t1e.t2a.x1c.x2h, z3.t1e.t2a.x1d.x2a, z3.t1e.t2a.x1d.x2b,
z3.t1e.t2a.x1d.x2c, z3.t1e.t2a.x1d.x2d, z3.t1e.t2a.x1d.x2e,
z3.t1e.t2a.x1d.x2f, z3.t1e.t2a.x1d.x2g, z3.t1e.t2a.x1d.x2h,
z3.t1e.t2a.x1e.x2a, z3.t1e.t2a.x1e.x2b, z3.t1e.t2a.x1e.x2c,
z3.t1e.t2a.x1e.x2d, z3.t1e.t2a.x1e.x2e, z3.t1e.t2a.x1e.x2f,
z3.t1e.t2a.x1e.x2g, z3.t1e.t2a.x1e.x2h, z3.t1e.t2a.x1f.x2a,
z3.t1e.t2a.x1f.x2b, z3.t1e.t2a.x1f.x2c, z3.t1e.t2a.x1f.x2d,
z3.t1e.t2a.x1f.x2e, z3.t1e.t2a.x1f.x2f, z3.t1e.t2a.x1f.x2g,
z3.t1e.t2a.x1f.x2h, z3.t1e.t2a.x1g.x2a, z3.t1e.t2a.x1g.x2b,
z3.t1e.t2a.x1g.x2c, z3.t1e.t2a.x1g.x2d, z3.t1e.t2a.x1g.x2e,
z3.t1e.t2a.x1g.x2f, z3.t1e.t2a.x1g.x2g, z3.t1e.t2a.x1g.x2h,
z3.t1e.t2a.x1h.x2a, z3.t1e.t2a.x1h.x2b, z3.t1e.t2a.x1h.x2c,

TABLE 30.6-continued

List of Compound Structures of Formula III z3.t1e.t2a.x1h.x2d, z3.t1e.t2a.x1h.x2e, z3.t1e.t2a.x1h.x2f,
z3.t1e.t2a.x1h.x2g, z3.t1e.t2a.x1h.x2h, z3.t1e.t2b.x1a.x2a,
z3.t1e.t2b.x1a.x2b, z3.t1e.t2b.x1a.x2c, z3.t1e.t2b.x1a.x2d,
z3.t1e.t2b.x1a.x2e, z3.t1e.t2b.x1a.x2f, z3.t1e.t2b.x1a.x2g,
z3.t1e.t2b.x1a.x2h, z3.t1e.t2b.x1b.x2a, z3.t1e.t2b.x1b.x2b,
z3.t1e.t2b.x1b.x2c, z3.t1e.t2b.x1b.x2d, z3.t1e.t2b.x1b.x2e,
z3.t1e.t2b.x1b.x2f, z3.t1e.t2b.x1b.x2g, z3.t1e.t2b.x1b.x2h,
z3.t1e.t2b.x1c.x2a, z3.t1e.t2b.x1c.x2b, z3.t1e.t2b.x1c.x2c,
z3.t1e.t2b.x1c.x2d, z3.t1e.t2b.x1c.x2e, z3.t1e.t2b.x1c.x2f,
z3.t1e.t2b.x1c.x2g, z3.t1e.t2b.x1c.x2h, z3.t1e.t2b.x1d.x2a,
z3.t1e.t2b.x1d.x2b, z3.t1e.t2b.x1d.x2c, z3.t1e.t2b.x1d.x2d,
z3.t1e.t2b.x1d.x2e, z3.t1e.t2b.x1d.x2f, z3.t1e.t2b.x1d.x2g,
z3.t1e.t2b.x1d.x2h, z3.t1e.t2b.x1e.x2a, z3.t1e.t2b.x1e.x2b,
z3.t1e.t2b.x1e.x2c, z3.t1e.t2b.x1e.x2d, z3.t1e.t2b.x1e.x2e,
z3.t1e.t2b.x1e.x2f, z3.t1e.t2b.x1e.x2g, z3.t1e.t2b.x1e.x2h,
z3.t1e.t2b.x1f.x2a, z3.t1e.t2b.x1f.x2b, z3.t1e.t2b.x1f.x2c,
z3.t1e.t2b.x1f.x2d, z3.t1e.t2b.x1f.x2e, z3.t1e.t2b.x1f.x2f,
z3.t1e.t2b.x1f.x2g, z3.t1e.t2b.x1f.x2h, z3.t1e.t2b.x1g.x2a,
z3.t1e.t2b.x1g.x2b, z3.t1e.t2b.x1g.x2c, z3.t1e.t2b.x1g.x2d,
z3.t1e.t2b.x1g.x2e, z3.t1e.t2b.x1g.x2f, z3.t1e.t2b.x1g.x2g,
z3.t1e.t2b.x1g.x2h, z3.t1e.t2b.x1h.x2a, z3.t1e.t2b.x1h.x2b,
z3.t1e.t2b.x1h.x2c, z3.t1e.t2b.x1h.x2d, z3.t1e.t2b.x1h.x2e,
z3.t1e.t2b.x1h.x2f, z3.t1e.t2b.x1h.x2g, z3.t1e.t2b.x1h.x2h,
z3.t1e.t2c.x1a.x2a, z3.t1e.t2c.x1a.x2b, z3.t1e.t2c.x1a.x2c,
z3.t1e.t2c.x1a.x2d, z3.t1e.t2c.x1a.x2e, z3.t1e.t2c.x1a.x2f,
z3.t1e.t2c.x1a.x2g, z3.t1e.t2c.x1a.x2h, z3.t1e.t2c.x1b.x2a,
z3.t1e.t2c.x1b.x2b, z3.t1e.t2c.x1b.x2c, z3.t1e.t2c.x1b.x2d,
z3.t1e.t2c.x1b.x2e, z3.t1e.t2c.x1b.x2f, z3.t1e.t2c.x1b.x2g,
z3.t1e.t2c.x1b.x2h, z3.t1e.t2c.x1c.x2a, z3.t1e.t2c.x1c.x2b,
z3.t1e.t2c.x1c.x2c, z3.t1e.t2c.x1c.x2d, z3.t1e.t2c.x1c.x2e,
z3.t1e.t2c.x1c.x2f, z3.t1e.t2c.x1c.x2g, z3.t1e.t2c.x1c.x2h,
z3.t1e.t2c.x1d.x2a, z3.t1e.t2c.x1d.x2b, z3.t1e.t2c.x1d.x2c,
z3.t1e.t2c.x1d.x2d, z3.t1e.t2c.x1d.x2e, z3.t1e.t2c.x1d.x2f,
z3.t1e.t2c.x1d.x2g, z3.t1e.t2c.x1d.x2h, z3.t1e.t2c.x1e.x2a,
z3.t1e.t2c.x1e.x2b, z3.t1e.t2c.x1e.x2c, z3.t1e.t2c.x1e.x2d,
z3.t1e.t2c.x1e.x2e, z3.t1e.t2c.x1e.x2f, z3.t1e.t2c.x1e.x2g,
z3.t1e.t2c.x1e.x2h, z3.t1e.t2c.x1f.x2a, z3.t1e.t2c.x1f.x2b,
z3.t1e.t2c.x1f.x2c, z3.t1e.t2c.x1f.x2d, z3.t1e.t2c.x1f.x2e,
z3.t1e.t2c.x1f.x2f, z3.t1e.t2c.x1f.x2g, z3.t1e.t2c.x1f.x2h,
z3.t1e.t2c.x1g.x2a, z3.t1e.t2c.x1g.x2b, z3.t1e.t2c.x1g.x2c,
z3.t1e.t2c.x1g.x2d, z3.t1e.t2c.x1g.x2e, z3.t1e.t2c.x1g.x2f,
z3.t1e.t2c.x1g.x2g, z3.t1e.t2c.x1g.x2h, z3.t1e.t2c.x1h.x2a,
z3.t1e.t2c.x1h.x2b, z3.t1e.t2c.x1h.x2c, z3.t1e.t2c.x1h.x2d,
z3.t1e.t2c.x1h.x2e, z3.t1e.t2c.x1h.x2f, z3.t1e.t2c.x1h.x2g,
z3.t1e.t2c.x1h.x2h, z3.t1e.t2d.x1a.x2a, z3.t1e.t2d.x1a.x2b,
z3.t1e.t2d.x1a.x2c, z3.t1e.t2d.x1a.x2d, z3.t1e.t2d.x1a.x2e,
z3.t1e.t2d.x1a.x2f, z3.t1e.t2d.x1a.x2g, z3.t1e.t2d.x1a.x2h,
z3.t1e.t2d.x1b.x2a, z3.t1e.t2d.x1b.x2b, z3.t1e.t2d.x1b.x2c,
z3.t1e.t2d.x1b.x2d, z3.t1e.t2d.x1b.x2e, z3.t1e.t2d.x1b.x2f,
z3.t1e.t2d.x1b.x2g, z3.t1e.t2d.x1b.x2h, z3.t1e.t2d.x1c.x2a,
z3.t1e.t2d.x1c.x2b, z3.t1e.t2d.x1c.x2c, z3.t1e.t2d.x1c.x2d,
z3.t1e.t2d.x1c.x2e, z3.t1e.t2d.x1c.x2f, z3.t1e.t2d.x1c.x2g,
z3.t1e.t2d.x1c.x2h, z3.t1e.t2d.x1d.x2a, z3.t1e.t2d.x1d.x2b,
z3.t1e.t2d.x1d.x2c, z3.t1e.t2d.x1d.x2d, z3.t1e.t2d.x1d.x2e,
z3.t1e.t2d.x1d.x2f, z3.t1e.t2d.x1d.x2g, z3.t1e.t2d.x1d.x2h,
z3.t1e.t2d.x1e.x2a, z3.t1e.t2d.x1e.x2b, z3.t1e.t2d.x1e.x2c,
z3.t1e.t2d.x1e.x2d, z3.t1e.t2d.x1e.x2e, z3.t1e.t2d.x1e.x2f,
z3.t1e.t2d.x1e.x2g, z3.t1e.t2d.x1e.x2h, z3.t1e.t2d.x1f.x2a,
z3.t1e.t2d.x1f.x2b, z3.t1e.t2d.x1f.x2c, z3.t1e.t2d.x1f.x2d,
z3.t1e.t2d.x1f.x2e, z3.t1e.t2d.x1f.x2f, z3.t1e.t2d.x1f.x2g,
z3.t1e.t2d.x1f.x2h, z3.t1e.t2d.x1g.x2a, z3.t1e.t2d.x1g.x2b,
z3.t1e.t2d.x1g.x2c, z3.t1e.t2d.x1g.x2d, z3.t1e.t2d.x1g.x2e,
z3.t1e.t2d.x1g.x2f, z3.t1e.t2d.x1g.x2g, z3.t1e.t2d.x1g.x2h,
z3.t1e.t2d.x1h.x2a, z3.t1e.t2d.x1h.x2b, z3.t1e.t2d.x1h.x2c,
z3.t1e.t2d.x1h.x2d, z3.t1e.t2d.x1h.x2e, z3.t1e.t2d.x1h.x2f,
z3.t1e.t2d.x1h.x2g, z3.t1e.t2d.x1h.x2h, z3.t1e.t2e.x1a.x2a,
z3.t1e.t2e.x1a.x2b, z3.t1e.t2e.x1a.x2c, z3.t1e.t2e.x1a.x2d,
z3.t1e.t2e.x1a.x2e, z3.t1e.t2e.x1a.x2f, z3.t1e.t2e.x1a.x2g,
z3.t1e.t2e.x1a.x2h, z3.t1e.t2e.x1b.x2a, z3.t1e.t2e.x1b.x2b,
z3.t1e.t2e.x1b.x2c, z3.t1e.t2e.x1b.x2d, z3.t1e.t2e.x1b.x2e,
z3.t1e.t2e.x1b.x2f, z3.t1e.t2e.x1b.x2g, z3.t1e.t2e.x1b.x2h,
z3.t1e.t2e.x1c.x2a, z3.t1e.t2e.x1c.x2b, z3.t1e.t2e.x1c.x2c,
z3.t1e.t2e.x1c.x2d, z3.t1e.t2e.x1c.x2e, z3.t1e.t2e.x1c.x2f,
z3.t1e.t2e.x1c.x2g, z3.t1e.t2e.x1c.x2h, z3.t1e.t2e.x1d.x2a,
z3.t1e.t2e.x1d.x2b, z3.t1e.t2e.x1d.x2c, z3.t1e.t2e.x1d.x2d,
z3.t1e.t2e.x1d.x2e, z3.t1e.t2e.x1d.x2f, z3.t1e.t2e.x1d.x2g,
z3.t1e.t2e.x1d.x2h, z3.t1e.t2e.x1e.x2a, z3.t1e.t2e.x1e.x2b,
z3.t1e.t2e.x1e.x2c, z3.t1e.t2e.x1e.x2d, z3.t1e.t2e.x1e.x2e,
z3.t1e.t2e.x1e.x2f, z3.t1e.t2e.x1e.x2g, z3.t1e.t2e.x1e.x2h,
z3.t1e.t2e.x1f.x2a, z3.t1e.t2e.x1f.x2b, z3.t1e.t2e.x1f.x2c,
z3.t1e.t2e.x1f.x2d, z3.t1e.t2e.x1f.x2e, z3.t1e.t2e.x1f.x2f,
z3.t1e.t2e.x1f.x2g, z3.t1e.t2e.x1f.x2h, z3.t1e.t2e.x1g.x2a,
z3.t1e.t2e.x1g.x2b, z3.t1e.t2e.x1g.x2c, z3.t1e.t2e.x1g.x2d,
z3.t1e.t2e.x1g.x2e, z3.t1e.t2e.x1g.x2f, z3.t1e.t2e.x1g.x2g,
z3.t1e.t2e.x1g.x2h, z3.t1e.t2e.x1h.x2a, z3.t1e.t2e.x1h.x2b,
z3.t1e.t2e.x1h.x2c, z3.t1e.t2e.x1h.x2d, z3.t1e.t2e.x1h.x2e,
z3.t1e.t2e.x1h.x2f, z3.t1e.t2e.x1h.x2g, z3.t1e.t2e.x1h.x2h,
z4.t1a.t2a.x1a.x2a, z4.t1a.t2a.x1a.x2b, z4.t1a.t2a.x1a.x2c,
z4.t1a.t2a.x1a.x2d, z4.t1a.t2a.x1a.x2e, z4.t1a.t2a.x1a.x2f,
z4.t1a.t2a.x1a.x2g, z4.t1a.t2a.x1a.x2h, z4.t1a.t2a.x1b.x2a,
z4.t1a.t2a.x1b.x2b, z4.t1a.t2a.x1b.x2c, z4.t1a.t2a.x1b.x2d,
z4.t1a.t2a.x1b.x2e, z4.t1a.t2a.x1b.x2f, z4.t1a.t2a.x1b.x2g,
z4.t1a.t2a.x1b.x2h, z4.t1a.t2a.x1c.x2a, z4.t1a.t2a.x1c.x2b,
z4.t1a.t2a.x1c.x2c, z4.t1a.t2a.x1c.x2d, z4.t1a.t2a.x1c.x2e,
z4.t1a.t2a.x1c.x2f, z4.t1a.t2a.x1c.x2g, z4.t1a.t2a.x1c.x2h,
z4.t1a.t2a.x1d.x2a, z4.t1a.t2a.x1d.x2b, z4.t1a.t2a.x1d.x2c,
z4.t1a.t2a.x1d.x2d, z4.t1a.t2a.x1d.x2e, z4.t1a.t2a.x1d.x2f,
z4.t1a.t2a.x1d.x2g, z4.t1a.t2a.x1d.x2h, z4.t1a.t2a.x1e.x2a,
z4.t1a.t2a.x1e.x2b, z4.t1a.t2a.x1e.x2c, z4.t1a.t2a.x1e.x2d,
z4.t1a.t2a.x1e.x2e, z4.t1a.t2a.x1e.x2f, z4.t1a.t2a.x1e.x2g,
z4.t1a.t2a.x1e.x2h, z4.t1a.t2a.x1f.x2a, z4.t1a.t2a.x1f.x2b,
z4.t1a.t2a.x1f.x2c, z4.t1a.t2a.x1f.x2d, z4.t1a.t2a.x1f.x2e,
z4.t1a.t2a.x1f.x2f, z4.t1a.t2a.x1f.x2g, z4.t1a.t2a.x1f.x2h,
z4.t1a.t2a.x1g.x2a, z4.t1a.t2a.x1g.x2b, z4.t1a.t2a.x1g.x2c,
z4.t1a.t2a.x1g.x2d, z4.t1a.t2a.x1g.x2e, z4.t1a.t2a.x1g.x2f,
z4.t1a.t2a.x1g.x2g, z4.t1a.t2a.x1g.x2h, z4.t1a.t2a.x1h.x2a,
z4.t1a.t2a.x1h.x2b, z4.t1a.t2a.x1h.x2c, z4.t1a.t2a.x1h.x2d,
z4.t1a.t2a.x1h.x2e, z4.t1a.t2a.x1h.x2f, z4.t1a.t2a.x1h.x2g,
z4.t1a.t2a.x1h.x2h, z4.t1a.t2b.x1a.x2a, z4.t1a.t2b.x1a.x2b,
z4.t1a.t2b.x1a.x2c, z4.t1a.t2b.x1a.x2d, z4.t1a.t2b.x1a.x2e,
z4.t1a.t2b.x1a.x2f, z4.t1a.t2b.x1a.x2g, z4.t1a.t2b.x1a.x2h,
z4.t1a.t2b.x1b.x2a, z4.t1a.t2b.x1b.x2b, z4.t1a.t2b.x1b.x2c,
z4.t1a.t2b.x1b.x2d, z4.t1a.t2b.x1b.x2e, z4.t1a.t2b.x1b.x2f,
z4.t1a.t2b.x1b.x2g, z4.t1a.t2b.x1b.x2h, z4.t1a.t2b.x1c.x2a,
z4.t1a.t2b.x1c.x2b, z4.t1a.t2b.x1c.x2c, z4.t1a.t2b.x1c.x2d,
z4.t1a.t2b.x1c.x2e, z4.t1a.t2b.x1c.x2f, z4.t1a.t2b.x1c.x2g,
z4.t1a.t2b.x1c.x2h, z4.t1a.t2b.x1d.x2a, z4.t1a.t2b.x1d.x2b,
z4.t1a.t2b.x1d.x2c, z4.t1a.t2b.x1d.x2d, z4.t1a.t2b.x1d.x2e,
z4.t1a.t2b.x1d.x2f, z4.t1a.t2b.x1d.x2g, z4.t1a.t2b.x1d.x2h,
z4.t1a.t2b.x1e.x2a, z4.t1a.t2b.x1e.x2b, z4.t1a.t2b.x1e.x2c,
z4.t1a.t2b.x1e.x2d, z4.t1a.t2b.x1e.x2e, z4.t1a.t2b.x1e.x2f,
z4.t1a.t2b.x1e.x2g, z4.t1a.t2b.x1e.x2h, z4.t1a.t2b.x1f.x2a,
z4.t1a.t2b.x1f.x2b, z4.t1a.t2b.x1f.x2c, z4.t1a.t2b.x1f.x2d,
z4.t1a.t2b.x1f.x2e, z4.t1a.t2b.x1f.x2f, z4.t1a.t2b.x1f.x2g,
z4.t1a.t2b.x1f.x2h, z4.t1a.t2b.x1g.x2a, z4.t1a.t2b.x1g.x2b,
z4.t1a.t2b.x1g.x2c, z4.t1a.t2b.x1g.x2d, z4.t1a.t2b.x1g.x2e,
z4.t1a.t2b.x1g.x2f, z4.t1a.t2b.x1g.x2g, z4.t1a.t2b.x1g.x2h,
z4.t1a.t2b.x1h.x2a, z4.t1a.t2b.x1h.x2b, z4.t1a.t2b.x1h.x2c,
z4.t1a.t2b.x1h.x2d, z4.t1a.t2b.x1h.x2e, z4.t1a.t2b.x1h.x2f,
z4.t1a.t2b.x1h.x2g, z4.t1a.t2b.x1h.x2h, z4.t1a.t2c.x1a.x2a,
z4.t1a.t2c.x1a.x2b, z4.t1a.t2c.x1a.x2c, z4.t1a.t2c.x1a.x2d,
z4.t1a.t2c.x1a.x2e, z4.t1a.t2c.x1a.x2f, z4.t1a.t2c.x1a.x2g,
z4.t1a.t2c.x1a.x2h, z4.t1a.t2c.x1b.x2a, z4.t1a.t2c.x1b.x2b,
z4.t1a.t2c.x1b.x2c, z4.t1a.t2c.x1b.x2d, z4.t1a.t2c.x1b.x2e,
z4.t1a.t2c.x1b.x2f, z4.t1a.t2c.x1b.x2g, z4.t1a.t2c.x1b.x2h,
z4.t1a.t2c.x1c.x2a, z4.t1a.t2c.x1c.x2b, z4.t1a.t2c.x1c.x2c,
z4.t1a.t2c.x1c.x2d, z4.t1a.t2c.x1c.x2e, z4.t1a.t2c.x1c.x2f,
z4.t1a.t2c.x1c.x2g, z4.t1a.t2c.x1c.x2h, z4.t1a.t2c.x1d.x2a,
z4.t1a.t2c.x1d.x2b, z4.t1a.t2c.x1d.x2c, z4.t1a.t2c.x1d.x2d,
z4.t1a.t2c.x1d.x2e, z4.t1a.t2c.x1d.x2f, z4.t1a.t2c.x1d.x2g,
z4.t1a.t2c.x1d.x2h, z4.t1a.t2c.x1e.x2a, z4.t1a.t2c.x1e.x2b,
z4.t1a.t2c.x1e.x2c, z4.t1a.t2c.x1e.x2d, z4.t1a.t2c.x1e.x2e,
z4.t1a.t2c.x1e.x2f, z4.t1a.t2c.x1e.x2g, z4.t1a.t2c.x1e.x2h,
z4.t1a.t2c.x1f.x2a, z4.t1a.t2c.x1f.x2b, z4.t1a.t2c.x1f.x2c,
z4.t1a.t2c.x1f.x2d, z4.t1a.t2c.x1f.x2e, z4.t1a.t2c.x1f.x2f,
z4.t1a.t2c.x1f.x2g, z4.t1a.t2c.x1f.x2h, z4.t1a.t2c.x1g.x2a,
z4.t1a.t2c.x1g.x2b, z4.t1a.t2c.x1g.x2c, z4.t1a.t2c.x1g.x2d,
z4.t1a.t2c.x1g.x2e, z4.t1a.t2c.x1g.x2f, z4.t1a.t2c.x1g.x2g,
z4.t1a.t2c.x1g.x2h, z4.t1a.t2c.x1h.x2a, z4.t1a.t2c.x1h.x2b,
z4.t1a.t2c.x1h.x2c, z4.t1a.t2c.x1h.x2d, z4.t1a.t2c.x1h.x2e,
z4.t1a.t2c.x1h.x2f, z4.t1a.t2c.x1h.x2g, z4.t1a.t2c.x1h.x2h,
z4.t1a.t2d.x1a.x2a, z4.t1a.t2d.x1a.x2b, z4.t1a.t2d.x1a.x2c,
z4.t1a.t2d.x1a.x2d, z4.t1a.t2d.x1a.x2e, z4.t1a.t2d.x1a.x2f,
z4.t1a.t2d.x1a.x2g, z4.t1a.t2d.x1a.x2h, z4.t1a.t2d.x1b.x2a,

TABLE 30.6-continued

List of Compound Structures of Formula III z4.t1a.t2d.x1b.x2b, z4.t1a.t2d.x1b.x2c, z4.t1a.t2d.x1b.x2d,
z4.t1a.t2d.x1b.x2e, z4.t1a.t2d.x1b.x2f, z4.t1a.t2d.x1b.x2g,
z4.t1a.t2d.x1b.x2h, z4.t1a.t2d.x1c.x2a, z4.t1a.t2d.x1c.x2b,
z4.t1a.t2d.x1c.x2c, z4.t1a.t2d.x1c.x2d, z4.t1a.t2d.x1c.x2e,
z4.t1a.t2d.x1c.x2f, z4.t1a.t2d.x1c.x2g, z4.t1a.t2d.x1c.x2h,
z4.t1a.t2d.x1d.x2a, z4.t1a.t2d.x1d.x2b, z4.t1a.t2d.x1d.x2c,
z4.t1a.t2d.x1d.x2d, z4.t1a.t2d.x1d.x2e, z4.t1a.t2d.x1d.x2f,
z4.t1a.t2d.x1d.x2g, z4.t1a.t2d.x1d.x2h, z4.t1a.t2d.x1e.x2a,
z4.t1a.t2d.x1e.x2b, z4.t1a.t2d.x1e.x2c, z4.t1a.t2d.x1e.x2d,
z4.t1a.t2d.x1e.x2e, z4.t1a.t2d.x1e.x2f, z4.t1a.t2d.x1e.x2g,
z4.t1a.t2d.x1e.x2h, z4.t1a.t2d.x1f.x2a, z4.t1a.t2d.x1f.x2b,
z4.t1a.t2d.x1f.x2c, z4.t1a.t2d.x1f.x2d, z4.t1a.t2d.x1f.x2e,
z4.t1a.t2d.x1f.x2f, z4.t1a.t2d.x1f.x2g, z4.t1a.t2d.x1f.x2h,
z4.t1a.t2d.x1g.x2a, z4.t1a.t2d.x1g.x2b, z4.t1a.t2d.x1g.x2c,
z4.t1a.t2d.x1g.x2d, z4.t1a.t2d.x1g.x2e, z4.t1a.t2d.x1g.x2f,
z4.t1a.t2d.x1g.x2g, z4.t1a.t2d.x1g.x2h, z4.t1a.t2d.x1h.x2a,
z4.t1a.t2d.x1h.x2b, z4.t1a.t2d.x1h.x2c, z4.t1a.t2d.x1h.x2d,
z4.t1a.t2d.x1h.x2e, z4.t1a.t2d.x1h.x2f, z4.t1a.t2d.x1h.x2g,
z4.t1a.t2d.x1h.x2h, z4.t1a.t2e.x1a.x2a, z4.t1a.t2e.x1a.x2b,
z4.t1a.t2e.x1a.x2c, z4.t1a.t2e.x1a.x2d, z4.t1a.t2e.x1a.x2e,
z4.t1a.t2e.x1a.x2f, z4.t1a.t2e.x1a.x2g, z4.t1a.t2e.x1a.x2h,
z4.t1a.t2e.x1b.x2a, z4.t1a.t2e.x1b.x2b, z4.t1a.t2e.x1b.x2c,
z4.t1a.t2e.x1b.x2d, z4.t1a.t2e.x1b.x2e, z4.t1a.t2e.x1b.x2f,
z4.t1a.t2e.x1b.x2g, z4.t1a.t2e.x1b.x2h, z4.t1a.t2e.x1c.x2a,
z4.t1a.t2e.x1c.x2b, z4.t1a.t2e.x1c.x2c, z4.t1a.t2e.x1c.x2d,
z4.t1a.t2e.x1c.x2e, z4.t1a.t2e.x1c.x2f, z4.t1a.t2e.x1c.x2g,
z4.t1a.t2e.x1c.x2h, z4.t1a.t2e.x1d.x2a, z4.t1a.t2e.x1d.x2b,
z4.t1a.t2e.x1d.x2c, z4.t1a.t2e.x1d.x2d, z4.t1a.t2e.x1d.x2e,
z4.t1a.t2e.x1d.x2f, z4.t1a.t2e.x1d.x2g, z4.t1a.t2e.x1d.x2h,
z4.t1a.t2e.x1e.x2a, z4.t1a.t2e.x1e.x2b, z4.t1a.t2e.x1e.x2c,
z4.t1a.t2e.x1e.x2d, z4.t1a.t2e.x1e.x2e, z4.t1a.t2e.x1e.x2f,
z4.t1a.t2e.x1e.x2g, z4.t1a.t2e.x1e.x2h, z4.t1a.t2e.x1f.x2a,
z4.t1a.t2e.x1f.x2b, z4.t1a.t2e.x1f.x2c, z4.t1a.t2e.x1f.x2d,
z4.t1a.t2e.x1f.x2e, z4.t1a.t2e.x1f.x2f, z4.t1a.t2e.x1f.x2g,
z4.t1a.t2e.x1f.x2h, z4.t1a.t2e.x1g.x2a, z4.t1a.t2e.x1g.x2b,
z4.t1a.t2e.x1g.x2c, z4.t1a.t2e.x1g.x2d, z4.t1a.t2e.x1g.x2e,
z4.t1a.t2e.x1g.x2f, z4.t1a.t2e.x1g.x2g, z4.t1a.t2e.x1g.x2h,
z4.t1a.t2e.x1h.x2a, z4.t1a.t2e.x1h.x2b, z4.t1a.t2e.x1h.x2c,
z4.t1a.t2e.x1h.x2d, z4.t1a.t2e.x1h.x2e, z4.t1a.t2e.x1h.x2f,
z4.t1a.t2e.x1h.x2g, z4.t1a.t2e.x1h.x2h, z4.t1b.t2a.x1a.x2a,
z4.t1b.t2a.x1a.x2b, z4.t1b.t2a.x1a.x2c, z4.t1b.t2a.x1a.x2d,
z4.t1b.t2a.x1a.x2e, z4.t1b.t2a.x1a.x2f, z4.t1b.t2a.x1a.x2g,
z4.t1b.t2a.x1a.x2h, z4.t1b.t2a.x1b.x2a, z4.t1b.t2a.x1b.x2b,
z4.t1b.t2a.x1b.x2c, z4.t1b.t2a.x1b.x2d, z4.t1b.t2a.x1b.x2e,
z4.t1b.t2a.x1b.x2f, z4.t1b.t2a.x1b.x2g, z4.t1b.t2a.x1b.x2h,
z4.t1b.t2a.x1c.x2a, z4.t1b.t2a.x1c.x2b, z4.t1b.t2a.x1c.x2c,
z4.t1b.t2a.x1c.x2d, z4.t1b.t2a.x1c.x2e, z4.t1b.t2a.x1c.x2f,
z4.t1b.t2a.x1c.x2g, z4.t1b.t2a.x1c.x2h, z4.t1b.t2a.x1d.x2a,
z4.t1b.t2a.x1d.x2b, z4.t1b.t2a.x1d.x2c, z4.t1b.t2a.x1d.x2d,
z4.t1b.t2a.x1d.x2e, z4.t1b.t2a.x1d.x2f, z4.t1b.t2a.x1d.x2g,
z4.t1b.t2a.x1d.x2h, z4.t1b.t2a.x1e.x2a, z4.t1b.t2a.x1e.x2b,
z4.t1b.t2a.x1e.x2c, z4.t1b.t2a.x1e.x2d, z4.t1b.t2a.x1e.x2e,
z4.t1b.t2a.x1e.x2f, z4.t1b.t2a.x1e.x2g, z4.t1b.t2a.x1e.x2h,
z4.t1b.t2a.x1f.x2a, z4.t1b.t2a.x1f.x2b, z4.t1b.t2a.x1f.x2c,
z4.t1b.t2a.x1f.x2d, z4.t1b.t2a.x1f.x2e, z4.t1b.t2a.x1f.x2f,
z4.t1b.t2a.x1f.x2g, z4.t1b.t2a.x1f.x2h, z4.t1b.t2a.x1g.x2a,
z4.t1b.t2a.x1g.x2b, z4.t1b.t2a.x1g.x2c, z4.t1b.t2a.x1g.x2d,
z4.t1b.t2a.x1g.x2e, z4.t1b.t2a.x1g.x2f, z4.t1b.t2a.x1g.x2g,
z4.t1b.t2a.x1g.x2h, z4.t1b.t2a.x1h.x2a, z4.t1b.t2a.x1h.x2b,
z4.t1b.t2a.x1h.x2c, z4.t1b.t2a.x1h.x2d, z4.t1b.t2a.x1h.x2e,
z4.t1b.t2a.x1h.x2f, z4.t1b.t2a.x1h.x2g, z4.t1b.t2a.x1h.x2h,
z4.t1b.t2b.x1a.x2a, z4.t1b.t2b.x1a.x2b, z4.t1b.t2b.x1a.x2c,
z4.t1b.t2b.x1a.x2d, z4.t1b.t2b.x1a.x2e, z4.t1b.t2b.x1a.x2f,
z4.t1b.t2b.x1a.x2g, z4.t1b.t2b.x1a.x2h, z4.t1b.t2b.x1b.x2a,
z4.t1b.t2b.x1b.x2b, z4.t1b.t2b.x1b.x2c, z4.t1b.t2b.x1b.x2d,
z4.t1b.t2b.x1b.x2e, z4.t1b.t2b.x1b.x2f, z4.t1b.t2b.x1b.x2g,
z4.t1b.t2b.x1b.x2h, z4.t1b.t2b.x1c.x2a, z4.t1b.t2b.x1c.x2b,
z4.t1b.t2b.x1c.x2c, z4.t1b.t2b.x1c.x2d, z4.t1b.t2b.x1c.x2e,
z4.t1b.t2b.x1c.x2f, z4.t1b.t2b.x1c.x2g, z4.t1b.t2b.x1c.x2h,
z4.t1b.t2b.x1d.x2a, z4.t1b.t2b.x1d.x2b, z4.t1b.t2b.x1d.x2c,
z4.t1b.t2b.x1d.x2d, z4.t1b.t2b.x1d.x2e, z4.t1b.t2b.x1d.x2f,
z4.t1b.t2b.x1d.x2g, z4.t1b.t2b.x1d.x2h, z4.t1b.t2b.x1e.x2a,
z4.t1b.t2b.x1e.x2b, z4.t1b.t2b.x1e.x2c, z4.t1b.t2b.x1e.x2d,
z4.t1b.t2b.x1e.x2e, z4.t1b.t2b.x1e.x2f, z4.t1b.t2b.x1e.x2g,
z4.t1b.t2b.x1e.x2h, z4.t1b.t2b.x1f.x2a, z4.t1b.t2b.x1f.x2b,
z4.t1b.t2b.x1f.x2c, z4.t1b.t2b.x1f.x2d, z4.t1b.t2b.x1f.x2e,
z4.t1b.t2b.x1f.x2f, z4.t1b.t2b.x1f.x2g, z4.t1b.t2b.x1f.x2h,
z4.t1b.t2b.x1g.x2a, z4.t1b.t2b.x1g.x2b, z4.t1b.t2b.x1g.x2c,
z4.t1b.t2b.x1g.x2d, z4.t1b.t2b.x1g.x2e, z4.t1b.t2b.x1g.x2f,
z4.t1b.t2b.x1g.x2g, z4.t1b.t2b.x1g.x2h, z4.t1b.t2b.x1h.x2a,
z4.t1b.t2b.x1h.x2b, z4.t1b.t2b.x1h.x2c, z4.t1b.t2b.x1h.x2d,
z4.t1b.t2b.x1h.x2e, z4.t1b.t2b.x1h.x2f, z4.t1b.t2b.x1h.x2g,
z4.t1b.t2b.x1h.x2h, z4.t1b.t2c.x1a.x2a, z4.t1b.t2c.x1a.x2b,
z4.t1b.t2c.x1a.x2c, z4.t1b.t2c.x1a.x2d, z4.t1b.t2c.x1a.x2e,
z4.t1b.t2c.x1a.x2f, z4.t1b.t2c.x1a.x2g, z4.t1b.t2c.x1a.x2h,
z4.t1b.t2c.x1b.x2a, z4.t1b.t2c.x1b.x2b, z4.t1b.t2c.x1b.x2c,
z4.t1b.t2c.x1b.x2d, z4.t1b.t2c.x1b.x2e, z4.t1b.t2c.x1b.x2f,
z4.t1b.t2c.x1b.x2g, z4.t1b.t2c.x1b.x2h, z4.t1b.t2c.x1c.x2a,
z4.t1b.t2c.x1c.x2b, z4.t1b.t2c.x1c.x2c, z4.t1b.t2c.x1c.x2d,
z4.t1b.t2c.x1c.x2e, z4.t1b.t2c.x1c.x2f, z4.t1b.t2c.x1c.x2g,
z4.t1b.t2c.x1c.x2h, z4.t1b.t2c.x1d.x2a, z4.t1b.t2c.x1d.x2b,
z4.t1b.t2c.x1d.x2c, z4.t1b.t2c.x1d.x2d, z4.t1b.t2c.x1d.x2e,
z4.t1b.t2c.x1d.x2f, z4.t1b.t2c.x1d.x2g, z4.t1b.t2c.x1d.x2h,
z4.t1b.t2c.x1e.x2a, z4.t1b.t2c.x1e.x2b, z4.t1b.t2c.x1e.x2c,
z4.t1b.t2c.x1e.x2d, z4.t1b.t2c.x1e.x2e, z4.t1b.t2c.x1e.x2f,
z4.t1b.t2c.x1e.x2g, z4.t1b.t2c.x1e.x2h, z4.t1b.t2c.x1f.x2a,
z4.t1b.t2c.x1f.x2b, z4.t1b.t2c.x1f.x2c, z4.t1b.t2c.x1f.x2d,
z4.t1b.t2c.x1f.x2e, z4.t1b.t2c.x1f.x2f, z4.t1b.t2c.x1f.x2g,
z4.t1b.t2c.x1f.x2h, z4.t1b.t2c.x1g.x2a, z4.t1b.t2c.x1g.x2b,
z4.t1b.t2c.x1g.x2c, z4.t1b.t2c.x1g.x2d, z4.t1b.t2c.x1g.x2e,
z4.t1b.t2c.x1g.x2f, z4.t1b.t2c.x1g.x2g, z4.t1b.t2c.x1g.x2h,
z4.t1b.t2c.x1h.x2a, z4.t1b.t2c.x1h.x2b, z4.t1b.t2c.x1h.x2c,
z4.t1b.t2c.x1h.x2d, z4.t1b.t2c.x1h.x2e, z4.t1b.t2c.x1h.x2f,
z4.t1b.t2c.x1h.x2g, z4.t1b.t2c.x1h.x2h, z4.t1b.t2d.x1a.x2a,
z4.t1b.t2d.x1a.x2b, z4.t1b.t2d.x1a.x2c, z4.t1b.t2d.x1a.x2d,
z4.t1b.t2d.x1a.x2e, z4.t1b.t2d.x1a.x2f, z4.t1b.t2d.x1a.x2g,
z4.t1b.t2d.x1a.x2h, z4.t1b.t2d.x1b.x2a, z4.t1b.t2d.x1b.x2b,
z4.t1b.t2d.x1b.x2c, z4.t1b.t2d.x1b.x2d, z4.t1b.t2d.x1b.x2e,
z4.t1b.t2d.x1b.x2f, z4.t1b.t2d.x1b.x2g, z4.t1b.t2d.x1b.x2h,
z4.t1b.t2d.x1c.x2a, z4.t1b.t2d.x1c.x2b, z4.t1b.t2d.x1c.x2c,
z4.t1b.t2d.x1c.x2d, z4.t1b.t2d.x1c.x2e, z4.t1b.t2d.x1c.x2f,
z4.t1b.t2d.x1c.x2g, z4.t1b.t2d.x1c.x2h, z4.t1b.t2d.x1d.x2a,
z4.t1b.t2d.x1d.x2b, z4.t1b.t2d.x1d.x2c, z4.t1b.t2d.x1d.x2d,
z4.t1b.t2d.x1d.x2e, z4.t1b.t2d.x1d.x2f, z4.t1b.t2d.x1d.x2g,
z4.t1b.t2d.x1d.x2h, z4.t1b.t2d.x1e.x2a, z4.t1b.t2d.x1e.x2b,
z4.t1b.t2d.x1e.x2c, z4.t1b.t2d.x1e.x2d, z4.t1b.t2d.x1e.x2e,
z4.t1b.t2d.x1e.x2f, z4.t1b.t2d.x1e.x2g, z4.t1b.t2d.x1e.x2h,
z4.t1b.t2d.x1f.x2a, z4.t1b.t2d.x1f.x2b, z4.t1b.t2d.x1f.x2c,
z4.t1b.t2d.x1f.x2d, z4.t1b.t2d.x1f.x2e, z4.t1b.t2d.x1f.x2f,
z4.t1b.t2d.x1f.x2g, z4.t1b.t2d.x1f.x2h, z4.t1b.t2d.x1g.x2a,
z4.t1b.t2d.x1g.x2b, z4.t1b.t2d.x1g.x2c, z4.t1b.t2d.x1g.x2d,
z4.t1b.t2d.x1g.x2e, z4.t1b.t2d.x1g.x2f, z4.t1b.t2d.x1g.x2g,
z4.t1b.t2d.x1g.x2h, z4.t1b.t2d.x1h.x2a, z4.t1b.t2d.x1h.x2b,
z4.t1b.t2d.x1h.x2c, z4.t1b.t2d.x1h.x2d, z4.t1b.t2d.x1h.x2e,
z4.t1b.t2d.x1h.x2f, z4.t1b.t2d.x1h.x2g, z4.t1b.t2d.x1h.x2h,
z4.t1b.t2e.x1a.x2a, z4.t1b.t2e.x1a.x2b, z4.t1b.t2e.x1a.x2c,
z4.t1b.t2e.x1a.x2d, z4.t1b.t2e.x1a.x2e, z4.t1b.t2e.x1a.x2f,
z4.t1b.t2e.x1a.x2g, z4.t1b.t2e.x1a.x2h, z4.t1b.t2e.x1b.x2a,
z4.t1b.t2e.x1b.x2b, z4.t1b.t2e.x1b.x2c, z4.t1b.t2e.x1b.x2d,
z4.t1b.t2e.x1b.x2e, z4.t1b.t2e.x1b.x2f, z4.t1b.t2e.x1b.x2g,
z4.t1b.t2e.x1b.x2h, z4.t1b.t2e.x1c.x2a, z4.t1b.t2e.x1c.x2b,
z4.t1b.t2e.x1c.x2c, z4.t1b.t2e.x1c.x2d, z4.t1b.t2e.x1c.x2e,
z4.t1b.t2e.x1c.x2f, z4.t1b.t2e.x1c.x2g, z4.t1b.t2e.x1c.x2h,
z4.t1b.t2e.x1d.x2a, z4.t1b.t2e.x1d.x2b, z4.t1b.t2e.x1d.x2c,
z4.t1b.t2e.x1d.x2d, z4.t1b.t2e.x1d.x2e, z4.t1b.t2e.x1d.x2f,
z4.t1b.t2e.x1d.x2g, z4.t1b.t2e.x1d.x2h, z4.t1b.t2e.x1e.x2a,
z4.t1b.t2e.x1e.x2b, z4.t1b.t2e.x1e.x2c, z4.t1b.t2e.x1e.x2d,
z4.t1b.t2e.x1e.x2e, z4.t1b.t2e.x1e.x2f, z4.t1b.t2e.x1e.x2g,
z4.t1b.t2e.x1e.x2h, z4.t1b.t2e.x1f.x2a, z4.t1b.t2e.x1f.x2b,
z4.t1b.t2e.x1f.x2c, z4.t1b.t2e.x1f.x2d, z4.t1b.t2e.x1f.x2e,
z4.t1b.t2e.x1f.x2f, z4.t1b.t2e.x1f.x2g, z4.t1b.t2e.x1f.x2h,
z4.t1b.t2e.x1g.x2a, z4.t1b.t2e.x1g.x2b, z4.t1b.t2e.x1g.x2c,
z4.t1b.t2e.x1g.x2d, z4.t1b.t2e.x1g.x2e, z4.t1b.t2e.x1g.x2f,
z4.t1b.t2e.x1g.x2g, z4.t1b.t2e.x1g.x2h, z4.t1b.t2e.x1h.x2a,
z4.t1b.t2e.x1h.x2b, z4.t1b.t2e.x1h.x2c, z4.t1b.t2e.x1h.x2d,
z4.t1b.t2e.x1h.x2e, z4.t1b.t2e.x1h.x2f, z4.t1b.t2e.x1h.x2g,
z4.t1b.t2e.x1h.x2h, z4.t1c.t2a.x1a.x2a, z4.t1c.t2a.x1a.x2b,
z4.t1c.t2a.x1a.x2c, z4.t1c.t2a.x1a.x2d, z4.t1c.t2a.x1a.x2e,
z4.t1c.t2a.x1a.x2f, z4.t1c.t2a.x1a.x2g, z4.t1c.t2a.x1a.x2h,
z4.t1c.t2a.x1b.x2a, z4.t1c.t2a.x1b.x2b, z4.t1c.t2a.x1b.x2c,
z4.t1c.t2a.x1b.x2d, z4.t1c.t2a.x1b.x2e, z4.t1c.t2a.x1b.x2f,
z4.t1c.t2a.x1b.x2g, z4.t1c.t2a.x1b.x2h, z4.t1c.t2a.x1c.x2a,
z4.t1c.t2a.x1c.x2b, z4.t1c.t2a.x1c.x2c, z4.t1c.t2a.x1c.x2d,
z4.t1c.t2a.x1c.x2e, z4.t1c.t2a.x1c.x2f, z4.t1c.t2a.x1c.x2g,

TABLE 30.6-continued

List of Compound Structures of Formula III z4.t1c.t2a.x1c.x2h, z4.t1c.t2a.x1d.x2a, z4.t1c.t2a.x1d.x2b,
z4.t1c.t2a.x1d.x2c, z4.t1c.t2a.x1d.x2d, z4.t1c.t2a.x1d.x2e,
z4.t1c.t2a.x1d.x2f, z4.t1c.t2a.x1d.x2g, z4.t1c.t2a.x1d.x2h,
z4.t1c.t2a.x1e.x2a, z4.t1c.t2a.x1e.x2b, z4.t1c.t2a.x1e.x2c,
z4.t1c.t2a.x1e.x2d, z4.t1c.t2a.x1e.x2e, z4.t1c.t2a.x1e.x2f,
z4.t1c.t2a.x1e.x2g, z4.t1c.t2a.x1e.x2h, z4.t1c.t2a.x1f.x2a,
z4.t1c.t2a.x1f.x2b, z4.t1c.t2a.x1f.x2c, z4.t1c.t2a.x1f.x2d,
z4.t1c.t2a.x1f.x2e, z4.t1c.t2a.x1f.x2f, z4.t1c.t2a.x1f.x2g,
z4.t1c.t2a.x1f.x2h, z4.t1c.t2a.x1g.x2a, z4.t1c.t2a.x1g.x2b,
z4.t1c.t2a.x1g.x2c, z4.t1c.t2a.x1g.x2d, z4.t1c.t2a.x1g.x2e,
z4.t1c.t2a.x1g.x2f, z4.t1c.t2a.x1g.x2g, z4.t1c.t2a.x1g.x2h,
z4.t1c.t2a.x1h.x2a, z4.t1c.t2a.x1h.x2b, z4.t1c.t2a.x1h.x2c,
z4.t1c.t2a.x1h.x2d, z4.t1c.t2a.x1h.x2e, z4.t1c.t2a.x1h.x2f,
z4.t1c.t2a.x1h.x2g, z4.t1c.t2a.x1h.x2h, z4.t1c.t2b.x1a.x2a,
z4.t1c.t2b.x1a.x2b, z4.t1c.t2b.x1a.x2c, z4.t1c.t2b.x1a.x2d,
z4.t1c.t2b.x1a.x2e, z4.t1c.t2b.x1a.x2f, z4.t1c.t2b.x1a.x2g,
z4.t1c.t2b.x1a.x2h, z4.t1c.t2b.x1b.x2a, z4.t1c.t2b.x1b.x2b,
z4.t1c.t2b.x1b.x2c, z4.t1c.t2b.x1b.x2d, z4.t1c.t2b.x1b.x2e,
z4.t1c.t2b.x1b.x2f, z4.t1c.t2b.x1b.x2g, z4.t1c.t2b.x1b.x2h,
z4.t1c.t2b.x1c.x2a, z4.t1c.t2b.x1c.x2b, z4.t1c.t2b.x1c.x2c,
z4.t1c.t2b.x1c.x2d, z4.t1c.t2b.x1c.x2e, z4.t1c.t2b.x1c.x2f,
z4.t1c.t2b.x1c.x2g, z4.t1c.t2b.x1c.x2h, z4.t1c.t2b.x1d.x2a,
z4.t1c.t2b.x1d.x2b, z4.t1c.t2b.x1d.x2c, z4.t1c.t2b.x1d.x2d,
z4.t1c.t2b.x1d.x2e, z4.t1c.t2b.x1d.x2f, z4.t1c.t2b.x1d.x2g,
z4.t1c.t2b.x1d.x2h, z4.t1c.t2b.x1e.x2a, z4.t1c.t2b.x1e.x2b,
z4.t1c.t2b.x1e.x2c, z4.t1c.t2b.x1e.x2d, z4.t1c.t2b.x1e.x2e,
z4.t1c.t2b.x1e.x2f, z4.t1c.t2b.x1e.x2g, z4.t1c.t2b.x1e.x2h,
z4.t1c.t2b.x1f.x2a, z4.t1c.t2b.x1f.x2b, z4.t1c.t2b.x1f.x2c,
z4.t1c.t2b.x1f.x2d, z4.t1c.t2b.x1f.x2e, z4.t1c.t2b.x1f.x2f,
z4.t1c.t2b.x1f.x2g, z4.t1c.t2b.x1f.x2h, z4.t1c.t2b.x1g.x2a,
z4.t1c.t2b.x1g.x2b, z4.t1c.t2b.x1g.x2c, z4.t1c.t2b.x1g.x2d,
z4.t1c.t2b.x1g.x2e, z4.t1c.t2b.x1g.x2f, z4.t1c.t2b.x1g.x2g,
z4.t1c.t2b.x1g.x2h, z4.t1c.t2b.x1h.x2a, z4.t1c.t2b.x1h.x2b,
z4.t1c.t2b.x1h.x2c, z4.t1c.t2b.x1h.x2d, z4.t1c.t2b.x1h.x2e,
z4.t1c.t2b.x1h.x2f, z4.t1c.t2b.x1h.x2g, z4.t1c.t2b.x1h.x2h,
z4.t1c.t2c.x1a.x2a, z4.t1c.t2c.x1a.x2b, z4.t1c.t2c.x1a.x2c,
z4.t1c.t2c.x1a.x2d, z4.t1c.t2c.x1a.x2e, z4.t1c.t2c.x1a.x2f,
z4.t1c.t2c.x1a.x2g, z4.t1c.t2c.x1a.x2h, z4.t1c.t2c.x1b.x2a,
z4.t1c.t2c.x1b.x2b, z4.t1c.t2c.x1b.x2c, z4.t1c.t2c.x1b.x2d,
z4.t1c.t2c.x1b.x2e, z4.t1c.t2c.x1b.x2f, z4.t1c.t2c.x1b.x2g,
z4.t1c.t2c.x1b.x2h, z4.t1c.t2c.x1c.x2a, z4.t1c.t2c.x1c.x2b,
z4.t1c.t2c.x1c.x2c, z4.t1c.t2c.x1c.x2d, z4.t1c.t2c.x1c.x2e,
z4.t1c.t2c.x1c.x2f, z4.t1c.t2c.x1c.x2g, z4.t1c.t2c.x1c.x2h,
z4.t1c.t2c.x1d.x2a, z4.t1c.t2c.x1d.x2b, z4.t1c.t2c.x1d.x2c,
z4.t1c.t2c.x1d.x2d, z4.t1c.t2c.x1d.x2e, z4.t1c.t2c.x1d.x2f,
z4.t1c.t2c.x1d.x2g, z4.t1c.t2c.x1d.x2h, z4.t1c.t2c.x1e.x2a,
z4.t1c.t2c.x1e.x2b, z4.t1c.t2c.x1e.x2c, z4.t1c.t2c.x1e.x2d,
z4.t1c.t2c.x1e.x2e, z4.t1c.t2c.x1e.x2f, z4.t1c.t2c.x1e.x2g,
z4.t1c.t2c.x1e.x2h, z4.t1c.t2c.x1f.x2a, z4.t1c.t2c.x1f.x2b,
z4.t1c.t2c.x1f.x2c, z4.t1c.t2c.x1f.x2d, z4.t1c.t2c.x1f.x2e,
z4.t1c.t2c.x1f.x2f, z4.t1c.t2c.x1f.x2g, z4.t1c.t2c.x1f.x2h,
z4.t1c.t2c.x1g.x2a, z4.t1c.t2c.x1g.x2b, z4.t1c.t2c.x1g.x2c,
z4.t1c.t2c.x1g.x2d, z4.t1c.t2c.x1g.x2e, z4.t1c.t2c.x1g.x2f,
z4.t1c.t2c.x1g.x2g, z4.t1c.t2c.x1g.x2h, z4.t1c.t2c.x1h.x2a,
z4.t1c.t2c.x1h.x2b, z4.t1c.t2c.x1h.x2c, z4.t1c.t2c.x1h.x2d,
z4.t1c.t2c.x1h.x2e, z4.t1c.t2c.x1h.x2f, z4.t1c.t2c.x1h.x2g,
z4.t1c.t2c.x1h.x2h, z4.t1c.t2d.x1a.x2a, z4.t1c.t2d.x1a.x2b,
z4.t1c.t2d.x1a.x2c, z4.t1c.t2d.x1a.x2d, z4.t1c.t2d.x1a.x2e,
z4.t1c.t2d.x1a.x2f, z4.t1c.t2d.x1a.x2g, z4.t1c.t2d.x1a.x2h,
z4.t1c.t2d.x1b.x2a, z4.t1c.t2d.x1b.x2b, z4.t1c.t2d.x1b.x2c,
z4.t1c.t2d.x1b.x2d, z4.t1c.t2d.x1b.x2e, z4.t1c.t2d.x1b.x2f,
z4.t1c.t2d.x1b.x2g, z4.t1c.t2d.x1b.x2h, z4.t1c.t2d.x1c.x2a,
z4.t1c.t2d.x1c.x2b, z4.t1c.t2d.x1c.x2c, z4.t1c.t2d.x1c.x2d,
z4.t1c.t2d.x1c.x2e, z4.t1c.t2d.x1c.x2f, z4.t1c.t2d.x1c.x2g,
z4.t1c.t2d.x1c.x2h, z4.t1c.t2d.x1d.x2a, z4.t1c.t2d.x1d.x2b,
z4.t1c.t2d.x1d.x2c, z4.t1c.t2d.x1d.x2d, z4.t1c.t2d.x1d.x2e,
z4.t1c.t2d.x1d.x2f, z4.t1c.t2d.x1d.x2g, z4.t1c.t2d.x1d.x2h,
z4.t1c.t2d.x1e.x2a, z4.t1c.t2d.x1e.x2b, z4.t1c.t2d.x1e.x2c,
z4.t1c.t2d.x1e.x2d, z4.t1c.t2d.x1e.x2e, z4.t1c.t2d.x1e.x2f,
z4.t1c.t2d.x1e.x2g, z4.t1c.t2d.x1e.x2h, z4.t1c.t2d.x1f.x2a,
z4.t1c.t2d.x1f.x2b, z4.t1c.t2d.x1f.x2c, z4.t1c.t2d.x1f.x2d,
z4.t1c.t2d.x1f.x2e, z4.t1c.t2d.x1f.x2f, z4.t1c.t2d.x1f.x2g,
z4.t1c.t2d.x1f.x2h, z4.t1c.t2d.x1g.x2a, z4.t1c.t2d.x1g.x2b,
z4.t1c.t2d.x1g.x2c, z4.t1c.t2d.x1g.x2d, z4.t1c.t2d.x1g.x2e,
z4.t1c.t2d.x1g.x2f, z4.t1c.t2d.x1g.x2g, z4.t1c.t2d.x1g.x2h,
z4.t1c.t2d.x1h.x2a, z4.t1c.t2d.x1h.x2b, z4.t1c.t2d.x1h.x2c,
z4.t1c.t2d.x1h.x2d, z4.t1c.t2d.x1h.x2e, z4.t1c.t2d.x1h.x2f,
z4.t1c.t2d.x1h.x2g, z4.t1c.t2d.x1h.x2h, z4.t1c.t2e.x1a.x2a,
z4.t1c.t2e.x1a.x2b, z4.t1c.t2e.x1a.x2c, z4.t1c.t2e.x1a.x2d,
z4.t1c.t2e.x1a.x2e, z4.t1c.t2e.x1a.x2f, z4.t1c.t2e.x1a.x2g,
z4.t1c.t2e.x1a.x2h, z4.t1c.t2e.x1b.x2a, z4.t1c.t2e.x1b.x2b,
z4.t1c.t2e.x1b.x2c, z4.t1c.t2e.x1b.x2d, z4.t1c.t2e.x1b.x2e,
z4.t1c.t2e.x1b.x2f, z4.t1c.t2e.x1b.x2g, z4.t1c.t2e.x1b.x2h,
z4.t1c.t2e.x1c.x2a, z4.t1c.t2e.x1c.x2b, z4.t1c.t2e.x1c.x2c,
z4.t1c.t2e.x1c.x2d, z4.t1c.t2e.x1c.x2e, z4.t1c.t2e.x1c.x2f,
z4.t1c.t2e.x1c.x2g, z4.t1c.t2e.x1c.x2h, z4.t1c.t2e.x1d.x2a,
z4.t1c.t2e.x1d.x2b, z4.t1c.t2e.x1d.x2c, z4.t1c.t2e.x1d.x2d,
z4.t1c.t2e.x1d.x2e, z4.t1c.t2e.x1d.x2f, z4.t1c.t2e.x1d.x2g,
z4.t1c.t2e.x1d.x2h, z4.t1c.t2e.x1e.x2a, z4.t1c.t2e.x1e.x2b,
z4.t1c.t2e.x1e.x2c, z4.t1c.t2e.x1e.x2d, z4.t1c.t2e.x1e.x2e,
z4.t1c.t2e.x1e.x2f, z4.t1c.t2e.x1e.x2g, z4.t1c.t2e.x1e.x2h,
z4.t1c.t2e.x1f.x2a, z4.t1c.t2e.x1f.x2b, z4.t1c.t2e.x1f.x2c,
z4.t1c.t2e.x1f.x2d, z4.t1c.t2e.x1f.x2e, z4.t1c.t2e.x1f.x2f,
z4.t1c.t2e.x1f.x2g, z4.t1c.t2e.x1f.x2h, z4.t1c.t2e.x1g.x2a,
z4.t1c.t2e.x1g.x2b, z4.t1c.t2e.x1g.x2c, z4.t1c.t2e.x1g.x2d,
z4.t1c.t2e.x1g.x2e, z4.t1c.t2e.x1g.x2f, z4.t1c.t2e.x1g.x2g,
z4.t1c.t2e.x1g.x2h, z4.t1c.t2e.x1h.x2a, z4.t1c.t2e.x1h.x2b,
z4.t1c.t2e.x1h.x2c, z4.t1c.t2e.x1h.x2d, z4.t1c.t2e.x1h.x2e,
z4.t1c.t2e.x1h.x2f, z4.t1c.t2e.x1h.x2g, z4.t1c.t2e.x1h.x2h,
z4.t1d.t2a.x1a.x2a, z4.t1d.t2a.x1a.x2b, z4.t1d.t2a.x1a.x2c,
z4.t1d.t2a.x1a.x2d, z4.t1d.t2a.x1a.x2e, z4.t1d.t2a.x1a.x2f,
z4.t1d.t2a.x1a.x2g, z4.t1d.t2a.x1a.x2h, z4.t1d.t2a.x1b.x2a,
z4.t1d.t2a.x1b.x2b, z4.t1d.t2a.x1b.x2c, z4.t1d.t2a.x1b.x2d,
z4.t1d.t2a.x1b.x2e, z4.t1d.t2a.x1b.x2f, z4.t1d.t2a.x1b.x2g,
z4.t1d.t2a.x1b.x2h, z4.t1d.t2a.x1c.x2a, z4.t1d.t2a.x1c.x2b,
z4.t1d.t2a.x1c.x2c, z4.t1d.t2a.x1c.x2d, z4.t1d.t2a.x1c.x2e,
z4.t1d.t2a.x1c.x2f, z4.t1d.t2a.x1c.x2g, z4.t1d.t2a.x1c.x2h,
z4.t1d.t2a.x1d.x2a, z4.t1d.t2a.x1d.x2b, z4.t1d.t2a.x1d.x2c,
z4.t1d.t2a.x1d.x2d, z4.t1d.t2a.x1d.x2e, z4.t1d.t2a.x1d.x2f,
z4.t1d.t2a.x1d.x2g, z4.t1d.t2a.x1d.x2h, z4.t1d.t2a.x1e.x2a,
z4.t1d.t2a.x1e.x2b, z4.t1d.t2a.x1e.x2c, z4.t1d.t2a.x1e.x2d,
z4.t1d.t2a.x1e.x2e, z4.t1d.t2a.x1e.x2f, z4.t1d.t2a.x1e.x2g,
z4.t1d.t2a.x1e.x2h, z4.t1d.t2a.x1f.x2a, z4.t1d.t2a.x1f.x2b,
z4.t1d.t2a.x1f.x2c, z4.t1d.t2a.x1f.x2d, z4.t1d.t2a.x1f.x2e,
z4.t1d.t2a.x1f.x2f, z4.t1d.t2a.x1f.x2g, z4.t1d.t2a.x1f.x2h,
z4.t1d.t2a.x1g.x2a, z4.t1d.t2a.x1g.x2b, z4.t1d.t2a.x1g.x2c,
z4.t1d.t2a.x1g.x2d, z4.t1d.t2a.x1g.x2e, z4.t1d.t2a.x1g.x2f,
z4.t1d.t2a.x1g.x2g, z4.t1d.t2a.x1g.x2h, z4.t1d.t2a.x1h.x2a,
z4.t1d.t2a.x1h.x2b, z4.t1d.t2a.x1h.x2c, z4.t1d.t2a.x1h.x2d,
z4.t1d.t2a.x1h.x2e, z4.t1d.t2a.x1h.x2f, z4.t1d.t2a.x1h.x2g,
z4.t1d.t2a.x1h.x2h, z4.t1d.t2b.x1a.x2a, z4.t1d.t2b.x1a.x2b,
z4.t1d.t2b.x1a.x2c, z4.t1d.t2b.x1a.x2d, z4.t1d.t2b.x1a.x2e,
z4.t1d.t2b.x1a.x2f, z4.t1d.t2b.x1a.x2g, z4.t1d.t2b.x1a.x2h,
z4.t1d.t2b.x1b.x2a, z4.t1d.t2b.x1b.x2b, z4.t1d.t2b.x1b.x2c,
z4.t1d.t2b.x1b.x2d, z4.t1d.t2b.x1b.x2e, z4.t1d.t2b.x1b.x2f,
z4.t1d.t2b.x1b.x2g, z4.t1d.t2b.x1b.x2h, z4.t1d.t2b.x1c.x2a,
z4.t1d.t2b.x1c.x2b, z4.t1d.t2b.x1c.x2c, z4.t1d.t2b.x1c.x2d,
z4.t1d.t2b.x1c.x2e, z4.t1d.t2b.x1c.x2f, z4.t1d.t2b.x1c.x2g,
z4.t1d.t2b.x1c.x2h, z4.t1d.t2b.x1d.x2a, z4.t1d.t2b.x1d.x2b,
z4.t1d.t2b.x1d.x2c, z4.t1d.t2b.x1d.x2d, z4.t1d.t2b.x1d.x2e,
z4.t1d.t2b.x1d.x2f, z4.t1d.t2b.x1d.x2g, z4.t1d.t2b.x1d.x2h,
z4.t1d.t2b.x1e.x2a, z4.t1d.t2b.x1e.x2b, z4.t1d.t2b.x1e.x2c,
z4.t1d.t2b.x1e.x2d, z4.t1d.t2b.x1e.x2e, z4.t1d.t2b.x1e.x2f,
z4.t1d.t2b.x1e.x2g, z4.t1d.t2b.x1e.x2h, z4.t1d.t2b.x1f.x2a,
z4.t1d.t2b.x1f.x2b, z4.t1d.t2b.x1f.x2c, z4.t1d.t2b.x1f.x2d,
z4.t1d.t2b.x1f.x2e, z4.t1d.t2b.x1f.x2f, z4.t1d.t2b.x1f.x2g,
z4.t1d.t2b.x1f.x2h, z4.t1d.t2b.x1g.x2a, z4.t1d.t2b.x1g.x2b,
z4.t1d.t2b.x1g.x2c, z4.t1d.t2b.x1g.x2d, z4.t1d.t2b.x1g.x2e,
z4.t1d.t2b.x1g.x2f, z4.t1d.t2b.x1g.x2g, z4.t1d.t2b.x1g.x2h,
z4.t1d.t2b.x1h.x2a, z4.t1d.t2b.x1h.x2b, z4.t1d.t2b.x1h.x2c,
z4.t1d.t2b.x1h.x2d, z4.t1d.t2b.x1h.x2e, z4.t1d.t2b.x1h.x2f,
z4.t1d.t2b.x1h.x2g, z4.t1d.t2b.x1h.x2h, z4.t1d.t2c.x1a.x2a,
z4.t1d.t2c.x1a.x2b, z4.t1d.t2c.x1a.x2c, z4.t1d.t2c.x1a.x2d,
z4.t1d.t2c.x1a.x2e, z4.t1d.t2c.x1a.x2f, z4.t1d.t2c.x1a.x2g,
z4.t1d.t2c.x1a.x2h, z4.t1d.t2c.x1b.x2a, z4.t1d.t2c.x1b.x2b,
z4.t1d.t2c.x1b.x2c, z4.t1d.t2c.x1b.x2d, z4.t1d.t2c.x1b.x2e,
z4.t1d.t2c.x1b.x2f, z4.t1d.t2c.x1b.x2g, z4.t1d.t2c.x1b.x2h,
z4.t1d.t2c.x1c.x2a, z4.t1d.t2c.x1c.x2b, z4.t1d.t2c.x1c.x2c,
z4.t1d.t2c.x1c.x2d, z4.t1d.t2c.x1c.x2e, z4.t1d.t2c.x1c.x2f,
z4.t1d.t2c.x1c.x2g, z4.t1d.t2c.x1c.x2h, z4.t1d.t2c.x1d.x2a,
z4.t1d.t2c.x1d.x2b, z4.t1d.t2c.x1d.x2c, z4.t1d.t2c.x1d.x2d,
z4.t1d.t2c.x1d.x2e, z4.t1d.t2c.x1d.x2f, z4.t1d.t2c.x1d.x2g,
z4.t1d.t2c.x1d.x2h, z4.t1d.t2c.x1e.x2a, z4.t1d.t2c.x1e.x2b,
z4.t1d.t2c.x1e.x2c, z4.t1d.t2c.x1e.x2d, z4.t1d.t2c.x1e.x2e, TABLE 30.6-continued List of Compound Structures of Formula III z4.t1d.t2c.x1e.x2f, z4.t1d.t2c.x1e.x2g, z4.t1d.t2c.x1e.x2h,
z4.t1d.t2c.x1f.x2a, z4.t1d.t2c.x1f.x2b, z4.t1d.t2c.x1f.x2c,
z4.t1d.t2c.x1f.x2d, z4.t1d.t2c.x1f.x2e, z4.t1d.t2c.x1f.x2f,
z4.t1d.t2c.x1f.x2g, z4.t1d.t2c.x1f.x2h, z4.t1d.t2c.x1g.x2a,
z4.t1d.t2c.x1g.x2b, z4.t1d.t2c.x1g.x2c, z4.t1d.t2c.x1g.x2d,
z4.t1d.t2c.x1g.x2e, z4.t1d.t2c.x1g.x2f, z4.t1d.t2c.x1g.x2g,
z4.t1d.t2c.x1g.x2h, z4.t1d.t2c.x1h.x2a, z4.t1d.t2c.x1h.x2b,
z4.t1d.t2c.x1h.x2c, z4.t1d.t2c.x1h.x2d, z4.t1d.t2c.x1h.x2e,
z4.t1d.t2c.x1h.x2f, z4.t1d.t2c.x1h.x2g, z4.t1d.t2c.x1h.x2h,
z4.t1d.t2d.x1a.x2a, z4.t1d.t2d.x1a.x2b, z4.t1d.t2d.x1a.x2c,
z4.t1d.t2d.x1a.x2d, z4.t1d.t2d.x1a.x2e, z4.t1d.t2d.x1a.x2f,
z4.t1d.t2d.x1a.x2g, z4.t1d.t2d.x1a.x2h, z4.t1d.t2d.x1b.x2a,
z4.t1d.t2d.x1b.x2b, z4.t1d.t2d.x1b.x2c, z4.t1d.t2d.x1b.x2d,
z4.t1d.t2d.x1b.x2e, z4.t1d.t2d.x1b.x2f, z4.t1d.t2d.x1b.x2g,
z4.t1d.t2d.x1b.x2h, z4.t1d.t2d.x1c.x2a, z4.t1d.t2d.x1c.x2b,
z4.t1d.t2d.x1c.x2c, z4.t1d.t2d.x1c.x2d, z4.t1d.t2d.x1c.x2e,
z4.t1d.t2d.x1c.x2f, z4.t1d.t2d.x1c.x2g, z4.t1d.t2d.x1c.x2h,
z4.t1d.t2d.x1d.x2a, z4.t1d.t2d.x1d.x2b, z4.t1d.t2d.x1d.x2c,
z4.t1d.t2d.x1d.x2d, z4.t1d.t2d.x1d.x2e, z4.t1d.t2d.x1d.x2f,
z4.t1d.t2d.x1d.x2g, z4.t1d.t2d.x1d.x2h, z4.t1d.t2d.x1e.x2a,
z4.t1d.t2d.x1e.x2b, z4.t1d.t2d.x1e.x2c, z4.t1d.t2d.x1e.x2d,
z4.t1d.t2d.x1e.x2e, z4.t1d.t2d.x1e.x2f, z4.t1d.t2d.x1e.x2g,
z4.t1d.t2d.x1e.x2h, z4.t1d.t2d.x1f.x2a, z4.t1d.t2d.x1f.x2b,
z4.t1d.t2d.x1f.x2c, z4.t1d.t2d.x1f.x2d, z4.t1d.t2d.x1f.x2e,
z4.t1d.t2d.x1f.x2f, z4.t1d.t2d.x1f.x2g, z4.t1d.t2d.x1f.x2h,
z4.t1d.t2d.x1g.x2a, z4.t1d.t2d.x1g.x2b, z4.t1d.t2d.x1g.x2c,
z4.t1d.t2d.x1g.x2d, z4.t1d.t2d.x1g.x2e, z4.t1d.t2d.x1g.x2f,
z4.t1d.t2d.x1g.x2g, z4.t1d.t2d.x1g.x2h, z4.t1d.t2d.x1h.x2a,
z4.t1d.t2d.x1h.x2b, z4.t1d.t2d.x1h.x2c, z4.t1d.t2d.x1h.x2d,
z4.t1d.t2d.x1h.x2e, z4.t1d.t2d.x1h.x2f, z4.t1d.t2d.x1h.x2g,
z4.t1d.t2d.x1h.x2h, z4.t1d.t2e.x1a.x2a, z4.t1d.t2e.x1a.x2b,
z4.t1d.t2e.x1a.x2c, z4.t1d.t2e.x1a.x2d, z4.t1d.t2e.x1a.x2e,
z4.t1d.t2e.x1a.x2f, z4.t1d.t2e.x1a.x2g, z4.t1d.t2e.x1a.x2h,
z4.t1d.t2e.x1b.x2a, z4.t1d.t2e.x1b.x2b, z4.t1d.t2e.x1b.x2c,
z4.t1d.t2e.x1b.x2d, z4.t1d.t2e.x1b.x2e, z4.t1d.t2e.x1b.x2f,
z4.t1d.t2e.x1b.x2g, z4.t1d.t2e.x1b.x2h, z4.t1d.t2e.x1c.x2a,
z4.t1d.t2e.x1c.x2b, z4.t1d.t2e.x1c.x2c, z4.t1d.t2e.x1c.x2d,
z4.t1d.t2e.x1c.x2e, z4.t1d.t2e.x1c.x2f, z4.t1d.t2e.x1c.x2g,
z4.t1d.t2e.x1c.x2h, z4.t1d.t2e.x1d.x2a, z4.t1d.t2e.x1d.x2b,
z4.t1d.t2e.x1d.x2c, z4.t1d.t2e.x1d.x2d, z4.t1d.t2e.x1d.x2e,
z4.t1d.t2e.x1d.x2f, z4.t1d.t2e.x1d.x2g, z4.t1d.t2e.x1d.x2h,
z4.t1d.t2e.x1e.x2a, z4.t1d.t2e.x1e.x2b, z4.t1d.t2e.x1e.x2c,
z4.t1d.t2e.x1e.x2d, z4.t1d.t2e.x1e.x2e, z4.t1d.t2e.x1e.x2f,
z4.t1d.t2e.x1e.x2g, z4.t1d.t2e.x1e.x2h, z4.t1d.t2e.x1f.x2a,
z4.t1d.t2e.x1f.x2b, z4.t1d.t2e.x1f.x2c, z4.t1d.t2e.x1f.x2d,
z4.t1d.t2e.x1f.x2e, z4.t1d.t2e.x1f.x2f, z4.t1d.t2e.x1f.x2g,
z4.t1d.t2e.x1f.x2h, z4.t1d.t2e.x1g.x2a, z4.t1d.t2e.x1g.x2b,
z4.t1d.t2e.x1g.x2c, z4.t1d.t2e.x1g.x2d, z4.t1d.t2e.x1g.x2e,
z4.t1d.t2e.x1g.x2f, z4.t1d.t2e.x1g.x2g, z4.t1d.t2e.x1g.x2h,
z4.t1d.t2e.x1h.x2a, z4.t1d.t2e.x1h.x2b, z4.t1d.t2e.x1h.x2c,
z4.t1d.t2e.x1h.x2d, z4.t1d.t2e.x1h.x2e, z4.t1d.t2e.x1h.x2f,
z4.t1d.t2e.x1h.x2g, z4.t1d.t2e.x1h.x2h, z4.t1e.t2a.x1a.x2a,
z4.t1e.t2a.x1a.x2b, z4.t1e.t2a.x1a.x2c, z4.t1e.t2a.x1a.x2d,
z4.t1e.t2a.x1a.x2e, z4.t1e.t2a.x1a.x2f, z4.t1e.t2a.x1a.x2g,
z4.t1e.t2a.x1a.x2h, z4.t1e.t2a.x1b.x2a, z4.t1e.t2a.x1b.x2b,
z4.t1e.t2a.x1b.x2c, z4.t1e.t2a.x1b.x2d, z4.t1e.t2a.x1b.x2e,
z4.t1e.t2a.x1b.x2f, z4.t1e.t2a.x1b.x2g, z4.t1e.t2a.x1b.x2h,
z4.t1e.t2a.x1c.x2a, z4.t1e.t2a.x1c.x2b, z4.t1e.t2a.x1c.x2c,
z4.t1e.t2a.x1c.x2d, z4.t1e.t2a.x1c.x2e, z4.t1e.t2a.x1c.x2f,
z4.t1e.t2a.x1c.x2g, z4.t1e.t2a.x1c.x2h, z4.t1e.t2a.x1d.x2a,
z4.t1e.t2a.x1d.x2b, z4.t1e.t2a.x1d.x2c, z4.t1e.t2a.x1d.x2d,
z4.t1e.t2a.x1d.x2e, z4.t1e.t2a.x1d.x2f, z4.t1e.t2a.x1d.x2g,
z4.t1e.t2a.x1d.x2h, z4.t1e.t2a.x1e.x2a, z4.t1e.t2a.x1e.x2b,
z4.t1e.t2a.x1e.x2c, z4.t1e.t2a.x1e.x2d, z4.t1e.t2a.x1e.x2e,
z4.t1e.t2a.x1e.x2f, z4.t1e.t2a.x1e.x2g, z4.t1e.t2a.x1e.x2h,
z4.t1e.t2a.x1f.x2a, z4.t1e.t2a.x1f.x2b, z4.t1e.t2a.x1f.x2c,
z4.t1e.t2a.x1f.x2d, z4.t1e.t2a.x1f.x2e, z4.t1e.t2a.x1f.x2f,
z4.t1e.t2a.x1f.x2g, z4.t1e.t2a.x1f.x2h, z4.t1e.t2a.x1g.x2a,
z4.t1e.t2a.x1g.x2b, z4.t1e.t2a.x1g.x2c, z4.t1e.t2a.x1g.x2d,
z4.t1e.t2a.x1g.x2e, z4.t1e.t2a.x1g.x2f, z4.t1e.t2a.x1g.x2g,
z4.t1e.t2a.x1g.x2h, z4.t1e.t2a.x1h.x2a, z4.t1e.t2a.x1h.x2b,
z4.t1e.t2a.x1h.x2c, z4.t1e.t2a.x1h.x2d, z4.t1e.t2a.x1h.x2e,
z4.t1e.t2a.x1h.x2f, z4.t1e.t2a.x1h.x2g, z4.t1e.t2a.x1h.x2h,
z4.t1e.t2b.x1a.x2a, z4.t1e.t2b.x1a.x2b, z4.t1e.t2b.x1a.x2c,
z4.t1e.t2b.x1a.x2d, z4.t1e.t2b.x1a.x2e, z4.t1e.t2b.x1a.x2f,
z4.t1e.t2b.x1a.x2g, z4.t1e.t2b.x1a.x2h, z4.t1e.t2b.x1b.x2a,
z4.t1e.t2b.x1b.x2b, z4.t1e.t2b.x1b.x2c, z4.t1e.t2b.x1b.x2d, TABLE 30.6-continued List of Compound Structures of Formula III z4.t1e.t2b.x1b.x2e, z4.t1e.t2b.x1b.x2f, z4.t1e.t2b.x1b.x2g,
z4.t1e.t2b.x1b.x2h, z4.t1e.t2b.x1c.x2a, z4.t1e.t2b.x1c.x2b,
z4.t1e.t2b.x1c.x2c, z4.t1e.t2b.x1c.x2d, z4.t1e.t2b.x1c.x2e,
z4.t1e.t2b.x1c.x2f, z4.t1e.t2b.x1c.x2g, z4.t1e.t2b.x1c.x2h,
z4.t1e.t2b.x1d.x2a, z4.t1e.t2b.x1d.x2b, z4.t1e.t2b.x1d.x2c,
z4.t1e.t2b.x1d.x2d, z4.t1e.t2b.x1d.x2e, z4.t1e.t2b.x1d.x2f,
z4.t1e.t2b.x1d.x2g, z4.t1e.t2b.x1d.x2h, z4.t1e.t2b.x1e.x2a,
z4.t1e.t2b.x1e.x2b, z4.t1e.t2b.x1e.x2c, z4.t1e.t2b.x1e.x2d,
z4.t1e.t2b.x1e.x2e, z4.t1e.t2b.x1e.x2f, z4.t1e.t2b.x1e.x2g,
z4.t1e.t2b.x1e.x2h, z4.t1e.t2b.x1f.x2a, z4.t1e.t2b.x1f.x2b,
z4.t1e.t2b.x1f.x2c, z4.t1e.t2b.x1f.x2d, z4.t1e.t2b.x1f.x2e,
z4.t1e.t2b.x1f.x2f, z4.t1e.t2b.x1f.x2g, z4.t1e.t2b.x1f.x2h,
z4.t1e.t2b.x1g.x2a, z4.t1e.t2b.x1g.x2b, z4.t1e.t2b.x1g.x2c,
z4.t1e.t2b.x1g.x2d, z4.t1e.t2b.x1g.x2e, z4.t1e.t2b.x1g.x2f,
z4.t1e.t2b.x1g.x2g, z4.t1e.t2b.x1g.x2h, z4.t1e.t2b.x1h.x2a,
z4.t1e.t2b.x1h.x2b, z4.t1e.t2b.x1h.x2c, z4.t1e.t2b.x1h.x2d,
z4.t1e.t2b.x1h.x2e, z4.t1e.t2b.x1h.x2f, z4.t1e.t2b.x1h.x2g,
z4.t1e.t2b.x1h.x2h, z4.t1e.t2c.x1a.x2a, z4.t1e.t2c.x1a.x2b,
z4.t1e.t2c.x1a.x2c, z4.t1e.t2c.x1a.x2d, z4.t1e.t2c.x1a.x2e,
z4.t1e.t2c.x1a.x2f, z4.t1e.t2c.x1a.x2g, z4.t1e.t2c.x1a.x2h,
z4.t1e.t2c.x1b.x2a, z4.t1e.t2c.x1b.x2b, z4.t1e.t2c.x1b.x2c,
z4.t1e.t2c.x1b.x2d, z4.t1e.t2c.x1b.x2e, z4.t1e.t2c.x1b.x2f,
z4.t1e.t2c.x1b.x2g, z4.t1e.t2c.x1b.x2h, z4.t1e.t2c.x1c.x2a,
z4.t1e.t2c.x1c.x2b, z4.t1e.t2c.x1c.x2c, z4.t1e.t2c.x1c.x2d,
z4.t1e.t2c.x1c.x2e, z4.t1e.t2c.x1c.x2f, z4.t1e.t2c.x1c.x2g,
z4.t1e.t2c.x1c.x2h, z4.t1e.t2c.x1d.x2a, z4.t1e.t2c.x1d.x2b,
z4.t1e.t2c.x1d.x2c, z4.t1e.t2c.x1d.x2d, z4.t1e.t2c.x1d.x2e,
z4.t1e.t2c.x1d.x2f, z4.t1e.t2c.x1d.x2g, z4.t1e.t2c.x1d.x2h,
z4.t1e.t2c.x1e.x2a, z4.t1e.t2c.x1e.x2b, z4.t1e.t2c.x1e.x2c,
z4.t1e.t2c.x1e.x2d, z4.t1e.t2c.x1e.x2e, z4.t1e.t2c.x1e.x2f,
z4.t1e.t2c.x1e.x2g, z4.t1e.t2c.x1e.x2h, z4.t1e.t2c.x1f.x2a,
z4.t1e.t2c.x1f.x2b, z4.t1e.t2c.x1f.x2c, z4.t1e.t2c.x1f.x2d,
z4.t1e.t2c.x1f.x2e, z4.t1e.t2c.x1f.x2f, z4.t1e.t2c.x1f.x2g,
z4.t1e.t2c.x1f.x2h, z4.t1e.t2c.x1g.x2a, z4.t1e.t2c.x1g.x2b,
z4.t1e.t2c.x1g.x2c, z4.t1e.t2c.x1g.x2d, z4.t1e.t2c.x1g.x2e,
z4.t1e.t2c.x1g.x2f, z4.t1e.t2c.x1g.x2g, z4.t1e.t2c.x1g.x2h,
z4.t1e.t2c.x1h.x2a, z4.t1e.t2c.x1h.x2b, z4.t1e.t2c.x1h.x2c,
z4.t1e.t2c.x1h.x2d, z4.t1e.t2c.x1h.x2e, z4.t1e.t2c.x1h.x2f,
z4.t1e.t2c.x1h.x2g, z4.t1e.t2c.x1h.x2h, z4.t1e.t2d.x1a.x2a,
z4.t1e.t2d.x1a.x2b, z4.t1e.t2d.x1a.x2c, z4.t1e.t2d.x1a.x2d,
z4.t1e.t2d.x1a.x2e, z4.t1e.t2d.x1a.x2f, z4.t1e.t2d.x1a.x2g,
z4.t1e.t2d.x1a.x2h, z4.t1e.t2d.x1b.x2a, z4.t1e.t2d.x1b.x2b,
z4.t1e.t2d.x1b.x2c, z4.t1e.t2d.x1b.x2d, z4.t1e.t2d.x1b.x2e,
z4.t1e.t2d.x1b.x2f, z4.t1e.t2d.x1b.x2g, z4.t1e.t2d.x1b.x2h,
z4.t1e.t2d.x1c.x2a, z4.t1e.t2d.x1c.x2b, z4.t1e.t2d.x1c.x2c,
z4.t1e.t2d.x1c.x2d, z4.t1e.t2d.x1c.x2e, z4.t1e.t2d.x1c.x2f,
z4.t1e.t2d.x1c.x2g, z4.t1e.t2d.x1c.x2h, z4.t1e.t2d.x1d.x2a,
z4.t1e.t2d.x1d.x2b, z4.t1e.t2d.x1d.x2c, z4.t1e.t2d.x1d.x2d,
z4.t1e.t2d.x1d.x2e, z4.t1e.t2d.x1d.x2f, z4.t1e.t2d.x1d.x2g,
z4.t1e.t2d.x1d.x2h, z4.t1e.t2d.x1e.x2a, z4.t1e.t2d.x1e.x2b,
z4.t1e.t2d.x1e.x2c, z4.t1e.t2d.x1e.x2d, z4.t1e.t2d.x1e.x2e,
z4.t1e.t2d.x1e.x2f, z4.t1e.t2d.x1e.x2g, z4.t1e.t2d.x1e.x2h,
z4.t1e.t2d.x1f.x2a, z4.t1e.t2d.x1f.x2b, z4.t1e.t2d.x1f.x2c,
z4.t1e.t2d.x1f.x2d, z4.t1e.t2d.x1f.x2e, z4.t1e.t2d.x1f.x2f,
z4.t1e.t2d.x1f.x2g, z4.t1e.t2d.x1f.x2h, z4.t1e.t2d.x1g.x2a,
z4.t1e.t2d.x1g.x2b, z4.t1e.t2d.x1g.x2c, z4.t1e.t2d.x1g.x2d,
z4.t1e.t2d.x1g.x2e, z4.t1e.t2d.x1g.x2f, z4.t1e.t2d.x1g.x2g,
z4.t1e.t2d.x1g.x2h, z4.t1e.t2d.x1h.x2a, z4.t1e.t2d.x1h.x2b,
z4.t1e.t2d.x1h.x2c, z4.t1e.t2d.x1h.x2d, z4.t1e.t2d.x1h.x2e,
z4.t1e.t2d.x1h.x2f, z4.t1e.t2d.x1h.x2g, z4.t1e.t2d.x1h.x2h,
z4.t1e.t2e.x1a.x2a, z4.t1e.t2e.x1a.x2b, z4.t1e.t2e.x1a.x2c,
z4.t1e.t2e.x1a.x2d, z4.t1e.t2e.x1a.x2e, z4.t1e.t2e.x1a.x2f,
z4.t1e.t2e.x1a.x2g, z4.t1e.t2e.x1a.x2h, z4.t1e.t2e.x1b.x2a,
z4.t1e.t2e.x1b.x2b, z4.t1e.t2e.x1b.x2c, z4.t1e.t2e.x1b.x2d,
z4.t1e.t2e.x1b.x2e, z4.t1e.t2e.x1b.x2f, z4.t1e.t2e.x1b.x2g,
z4.t1e.t2e.x1b.x2h, z4.t1e.t2e.x1c.x2a, z4.t1e.t2e.x1c.x2b,
z4.t1e.t2e.x1c.x2c, z4.t1e.t2e.x1c.x2d, z4.t1e.t2e.x1c.x2e,
z4.t1e.t2e.x1c.x2f, z4.t1e.t2e.x1c.x2g, z4.t1e.t2e.x1c.x2h,
z4.t1e.t2e.x1d.x2a, z4.t1e.t2e.x1d.x2b, z4.t1e.t2e.x1d.x2c,
z4.t1e.t2e.x1d.x2d, z4.t1e.t2e.x1d.x2e, z4.t1e.t2e.x1d.x2f,
z4.t1e.t2e.x1d.x2g, z4.t1e.t2e.x1d.x2h, z4.t1e.t2e.x1e.x2a,
z4.t1e.t2e.x1e.x2b, z4.t1e.t2e.x1e.x2c, z4.t1e.t2e.x1e.x2d,
z4.t1e.t2e.x1e.x2e, z4.t1e.t2e.x1e.x2f, z4.t1e.t2e.x1e.x2g,
z4.t1e.t2e.x1e.x2h, z4.t1e.t2e.x1f.x2a, z4.t1e.t2e.x1f.x2b,
z4.t1e.t2e.x1f.x2c, z4.t1e.t2e.x1f.x2d, z4.t1e.t2e.x1f.x2e,
z4.t1e.t2e.x1f.x2f, z4.t1e.t2e.x1f.x2g, z4.t1e.t2e.x1f.x2h,
z4.t1e.t2e.x1g.x2a, z4.t1e.t2e.x1g.x2b, z4.t1e.t2e.x1g.x2c,

TABLE 30.6-continued

List of Compound Structures of Formula III z4.t1e.t2e.x1g.x2d, z4.t1e.t2e.x1g.x2e, z4.t1e.t2e.x1g.x2f,
z4.t1e.t2e.x1g.x2g, z4.t1e.t2e.x1g.x2h, z4.t1e.t2e.x1h.x2a,
z4.t1e.t2e.x1h.x2b, z4.t1e.t2e.x1h.x2c, z4.t1e.t2e.x1h.x2d,
z4.t1e.t2e.x1h.x2e, z4.t1e.t2e.x1h.x2f, z4.t1e.t2e.x1h.x2g,
z4.t1e.t2e.x1h.x2h, z5.t1a.t2a.x1a.x2a, z5.t1a.t2a.x1a.x2b,
z5.t1a.t2a.x1a.x2c, z5.t1a.t2a.x1a.x2d, z5.t1a.t2a.x1a.x2e,
z5.t1a.t2a.x1a.x2f, z5.t1a.t2a.x1a.x2g, z5.t1a.t2a.x1a.x2h,
z5.t1a.t2a.x1b.x2a, z5.t1a.t2a.x1b.x2b, z5.t1a.t2a.x1b.x2c,
z5.t1a.t2a.x1b.x2d, z5.t1a.t2a.x1b.x2e, z5.t1a.t2a.x1b.x2f,
z5.t1a.t2a.x1b.x2g, z5.t1a.t2a.x1b.x2h, z5.t1a.t2a.x1c.x2a,
z5.t1a.t2a.x1c.x2b, z5.t1a.t2a.x1c.x2c, z5.t1a.t2a.x1c.x2d,
z5.t1a.t2a.x1c.x2e, z5.t1a.t2a.x1c.x2f, z5.t1a.t2a.x1c.x2g,
z5.t1a.t2a.x1c.x2h, z5.t1a.t2a.x1d.x2a, z5.t1a.t2a.x1d.x2b,
z5.t1a.t2a.x1d.x2c, z5.t1a.t2a.x1d.x2d, z5.t1a.t2a.x1d.x2e,
z5.t1a.t2a.x1d.x2f, z5.t1a.t2a.x1d.x2g, z5.t1a.t2a.x1d.x2h,
z5.t1a.t2a.x1e.x2a, z5.t1a.t2a.x1e.x2b, z5.t1a.t2a.x1e.x2c,
z5.t1a.t2a.x1e.x2d, z5.t1a.t2a.x1e.x2e, z5.t1a.t2a.x1e.x2f,
z5.t1a.t2a.x1e.x2g, z5.t1a.t2a.x1e.x2h, z5.t1a.t2a.x1f.x2a,
z5.t1a.t2a.x1f.x2b, z5.t1a.t2a.x1f.x2c, z5.t1a.t2a.x1f.x2d,
z5.t1a.t2a.x1f.x2e, z5.t1a.t2a.x1f.x2f, z5.t1a.t2a.x1f.x2g,
z5.t1a.t2a.x1f.x2h, z5.t1a.t2a.x1g.x2a, z5.t1a.t2a.x1g.x2b,
z5.t1a.t2a.x1g.x2c, z5.t1a.t2a.x1g.x2d, z5.t1a.t2a.x1g.x2e,
z5.t1a.t2a.x1g.x2f, z5.t1a.t2a.x1g.x2g, z5.t1a.t2a.x1g.x2h,
z5.t1a.t2a.x1h.x2a, z5.t1a.t2a.x1h.x2b, z5.t1a.t2a.x1h.x2c,
z5.t1a.t2a.x1h.x2d, z5.t1a.t2a.x1h.x2e, z5.t1a.t2a.x1h.x2f,
z5.t1a.t2a.x1h.x2g, z5.t1a.t2a.x1h.x2h, z5.t1a.t2b.x1a.x2a,
z5.t1a.t2b.x1a.x2b, z5.t1a.t2b.x1a.x2c, z5.t1a.t2b.x1a.x2d,
z5.t1a.t2b.x1a.x2e, z5.t1a.t2b.x1a.x2f, z5.t1a.t2b.x1a.x2g,
z5.t1a.t2b.x1a.x2h, z5.t1a.t2b.x1b.x2a, z5.t1a.t2b.x1b.x2b,
z5.t1a.t2b.x1b.x2c, z5.t1a.t2b.x1b.x2d, z5.t1a.t2b.x1b.x2e,
z5.t1a.t2b.x1b.x2f, z5.t1a.t2b.x1b.x2g, z5.t1a.t2b.x1b.x2h,
z5.t1a.t2b.x1c.x2a, z5.t1a.t2b.x1c.x2b, z5.t1a.t2b.x1c.x2c,
z5.t1a.t2b.x1c.x2d, z5.t1a.t2b.x1c.x2e, z5.t1a.t2b.x1c.x2f,
z5.t1a.t2b.x1c.x2g, z5.t1a.t2b.x1c.x2h, z5.t1a.t2b.x1d.x2a,
z5.t1a.t2b.x1d.x2b, z5.t1a.t2b.x1d.x2c, z5.t1a.t2b.x1d.x2d,
z5.t1a.t2b.x1d.x2e, z5.t1a.t2b.x1d.x2f, z5.t1a.t2b.x1d.x2g,
z5.t1a.t2b.x1d.x2h, z5.t1a.t2b.x1e.x2a, z5.t1a.t2b.x1e.x2b,
z5.t1a.t2b.x1e.x2c, z5.t1a.t2b.x1e.x2d, z5.t1a.t2b.x1e.x2e,
z5.t1a.t2b.x1e.x2f, z5.t1a.t2b.x1e.x2g, z5.t1a.t2b.x1e.x2h,
z5.t1a.t2b.x1f.x2a, z5.t1a.t2b.x1f.x2b, z5.t1a.t2b.x1f.x2c,
z5.t1a.t2b.x1f.x2d, z5.t1a.t2b.x1f.x2e, z5.t1a.t2b.x1f.x2f,
z5.t1a.t2b.x1f.x2g, z5.t1a.t2f.x1f.x2h, z5.t1a.t2b.x1g.x2a,
z5.t1a.t2b.x1g.x2b, z5.t1a.t2b.x1g.x2c, z5.t1a.t2b.x1g.x2d,
z5.t1a.t2b.x1g.x2e, z5.t1a.t2b.x1g.x2f, z5.t1a.t2b.x1g.x2g,
z5.t1a.t2b.x1g.x2h, z5.t1a.t2b.x1h.x2a, z5.t1a.t2b.x1h.x2b,
z5.t1a.t2b.x1h.x2c, z5.t1a.t2b.x1h.x2d, z5.t1a.t2b.x1h.x2e,
z5.t1a.t2b.x1h.x2f, z5.t1a.t2b.x1h.x2g, z5.t1a.t2b.x1h.x2h,
z5.t1a.t2c.x1a.x2a, z5.t1a.t2c.x1a.x2b, z5.t1a.t2c.x1a.x2c,
z5.t1a.t2c.x1a.x2d, z5.t1a.t2c.x1a.x2e, z5.t1a.t2c.x1a.x2f,
z5.t1a.t2c.x1a.x2g, z5.t1a.t2c.x1a.x2h, z5.t1a.t2c.x1b.x2a,
z5.t1a.t2c.x1b.x2b, z5.t1a.t2c.x1b.x2c, z5.t1a.t2c.x1b.x2d,
z5.t1a.t2c.x1b.x2e, z5.t1a.t2c.x1b.x2f, z5.t1a.t2c.x1b.x2g,
z5.t1a.t2c.x1b.x2h, z5.t1a.t2c.x1c.x2a, z5.t1a.t2c.x1c.x2b,
z5.t1a.t2c.x1c.x2c, z5.t1a.t2c.x1c.x2d, z5.t1a.t2c.x1c.x2e,
z5.t1a.t2c.x1c.x2f, z5.t1a.t2c.x1c.x2g, z5.t1a.t2c.x1c.x2h,
z5.t1a.t2c.x1d.x2a, z5.t1a.t2c.x1d.x2b, z5.t1a.t2c.x1d.x2c,
z5.t1a.t2c.x1d.x2d, z5.t1a.t2c.x1d.x2e, z5.t1a.t2c.x1d.x2f,
z5.t1a.t2c.x1d.x2g, z5.t1a.t2c.x1d.x2h, z5.t1a.t2c.x1e.x2a,
z5.t1a.t2c.x1e.x2b, z5.t1a.t2c.x1e.x2c, z5.t1a.t2c.x1e.x2d,
z5.t1a.t2c.x1e.x2e, z5.t1a.t2c.x1e.x2f, z5.t1a.t2c.x1e.x2g,
z5.t1a.t2c.x1e.x2h, z5.t1a.t2c.x1f.x2a, z5.t1a.t2c.x1f.x2b,
z5.t1a.t2c.x1f.x2c, z5.t1a.t2c.x1f.x2d, z5.t1a.t2c.x1f.x2e,
z5.t1a.t2c.x1f.x2f, z5.t1a.t2c.x1f.x2g, z5.t1a.t2c.x1f.x2h,
z5.t1a.t2c.x1g.x2a, z5.t1a.t2c.x1g.x2b, z5.t1a.t2c.x1g.x2c,
z5.t1a.t2c.x1g.x2d, z5.t1a.t2c.x1g.x2e, z5.t1a.t2c.x1g.x2f,
z5.t1a.t2c.x1g.x2g, z5.t1a.t2c.x1g.x2h, z5.t1a.t2c.x1h.x2a,
z5.t1a.t2c.x1h.x2b, z5.t1a.t2c.x1h.x2c, z5.t1a.t2c.x1h.x2d,
z5.t1a.t2c.x1h.x2e, z5.t1a.t2c.x1h.x2f, z5.t1a.t2c.x1h.x2g,
z5.t1a.t2c.x1h.x2h, z5.t1a.t2d.x1a.x2a, z5.t1a.t2d.x1a.x2b,
z5.t1a.t2d.x1a.x2c, z5.t1a.t2d.x1a.x2d, z5.t1a.t2d.x1a.x2e,
z5.t1a.t2d.x1a.x2f, z5.t1a.t2d.x1a.x2g, z5.t1a.t2d.x1a.x2h,
z5.t1a.t2d.x1b.x2a, z5.t1a.t2d.x1b.x2b, z5.t1a.t2d.x1b.x2c,
z5.t1a.t2d.x1b.x2d, z5.t1a.t2d.x1b.x2e, z5.t1a.t2d.x1b.x2f,
z5.t1a.t2d.x1b.x2g, z5.t1a.t2d.x1b.x2h, z5.t1a.t2d.x1c.x2a,
z5.t1a.t2d.x1c.x2b, z5.t1a.t2d.x1c.x2c, z5.t1a.t2d.x1c.x2d,
z5.t1a.t2d.x1c.x2e, z5.t1a.t2d.x1c.x2f, z5.t1a.t2d.x1c.x2g,
z5.t1a.t2d.x1c.x2h, z5.t1a.t2d.x1d.x2a, z5.t1a.t2d.x1d.x2b,
z5.t1a.t2d.x1d.x2c, z5.t1a.t2d.x1d.x2d, z5.t1a.t2d.x1d.x2e,
z5.t1a.t2d.x1d.x2f, z5.t1a.t2d.x1d.x2g, z5.t1a.t2d.x1d.x2h,
z5.t1a.t2d.x1e.x2a, z5.t1a.t2d.x1e.x2b, z5.t1a.t2d.x1e.x2c,
z5.t1a.t2d.x1e.x2d, z5.t1a.t2d.x1e.x2e, z5.t1a.t2d.x1e.x2f,
z5.t1a.t2d.x1e.x2g, z5.t1a.t2d.x1e.x2h, z5.t1a.t2d.x1f.x2a,
z5.t1a.t2d.x1f.x2b, z5.t1a.t2d.x1f.x2c, z5.t1a.t2d.x1f.x2d,
z5.t1a.t2d.x1f.x2e, z5.t1a.t2d.x1f.x2f, z5.t1a.t2d.x1f.x2g,
z5.t1a.t2d.x1f.x2h, z5.t1a.t2d.x1g.x2a, z5.t1a.t2d.x1g.x2b,
z5.t1a.t2d.x1g.x2c, z5.t1a.t2d.x1g.x2d, z5.t1a.t2d.x1g.x2e,
z5.t1a.t2d.x1g.x2f, z5.t1a.t2d.x1g.x2g, z5.t1a.t2d.x1g.x2h,
z5.t1a.t2d.x1h.x2a, z5.t1a.t2d.x1h.x2b, z5.t1a.t2d.x1h.x2c,
z5.t1a.t2d.x1h.x2d, z5.t1a.t2d.x1h.x2e, z5.t1a.t2d.x1h.x2f,
z5.t1a.t2d.x1h.x2g, z5.t1a.t2d.x1h.x2h, z5.t1a.t2e.x1a.x2a,
z5.t1a.t2e.x1a.x2b, z5.t1a.t2e.x1a.x2c, z5.t1a.t2e.x1a.x2d,
z5.t1a.t2e.x1a.x2e, z5.t1a.t2e.x1a.x2f, z5.t1a.t2e.x1a.x2g,
z5.t1a.t2e.x1a.x2h, z5.t1a.t2e.x1b.x2a, z5.t1a.t2e.x1b.x2b,
z5.t1a.t2e.x1b.x2c, z5.t1a.t2e.x1b.x2d, z5.t1a.t2e.x1b.x2e,
z5.t1a.t2e.x1b.x2f, z5.t1a.t2e.x1b.x2g, z5.t1a.t2e.x1b.x2h,
z5.t1a.t2e.x1c.x2a, z5.t1a.t2e.x1c.x2b, z5.t1a.t2e.x1c.x2c,
z5.t1a.t2e.x1c.x2d, z5.t1a.t2e.x1c.x2e, z5.t1a.t2e.x1c.x2f,
z5.t1a.t2e.x1c.x2g, z5.t1a.t2e.x1c.x2h, z5.t1a.t2e.x1d.x2a,
z5.t1a.t2e.x1d.x2b, z5.t1a.t2e.x1d.x2c, z5.t1a.t2e.x1d.x2d,
z5.t1a.t2e.x1d.x2e, z5.t1a.t2e.x1d.x2f, z5.t1a.t2e.x1d.x2g,
z5.t1a.t2e.x1d.x2h, z5.t1a.t2e.x1e.x2a, z5.t1a.t2e.x1e.x2b,
z5.t1a.t2e.x1e.x2c, z5.t1a.t2e.x1e.x2d, z5.t1a.t2e.x1e.x2e,
z5.t1a.t2e.x1e.x2f, z5.t1a.t2e.x1e.x2g, z5.t1a.t2e.x1e.x2h,
z5.t1a.t2e.x1f.x2a, z5.t1a.t2e.x1f.x2b, z5.t1a.t2e.x1f.x2c,
z5.t1a.t2e.x1f.x2d, z5.t1a.t2e.x1f.x2e, z5.t1a.t2e.x1f.x2f,
z5.t1a.t2e.x1f.x2g, z5.t1a.t2e.x1f.x2h, z5.t1a.t2e.x1g.x2a,
z5.t1a.t2e.x1g.x2b, z5.t1a.t2e.x1g.x2c, z5.t1a.t2e.x1g.x2d,
z5.t1a.t2e.x1g.x2e, z5.t1a.t2e.x1g.x2f, z5.t1a.t2e.x1g.x2g,
z5.t1a.t2e.x1g.x2h, z5.t1a.t2e.x1h.x2a, z5.t1a.t2e.x1h.x2b,
z5.t1a.t2e.x1h.x2c, z5.t1a.t2e.x1h.x2d, z5.t1a.t2e.x1h.x2e,
z5.t1a.t2e.x1h.x2f, z5.t1a.t2e.x1h.x2g, z5.t1a.t2e.x1h.x2h,
z5.t1b.t2a.x1a.x2a, z5.t1b.t2a.x1a.x2b, z5.t1b.t2a.x1a.x2c,
z5.t1b.t2a.x1a.x2d, z5.t1b.t2a.x1a.x2e, z5.t1b.t2a.x1a.x2f,
z5.t1b.t2a.x1a.x2g, z5.t1b.t2a.x1a.x2h, z5.t1b.t2a.x1b.x2a,
z5.t1b.t2a.x1b.x2b, z5.t1b.t2a.x1b.x2c, z5.t1b.t2a.x1b.x2d,
z5.t1b.t2a.x1b.x2e, z5.t1b.t2a.x1b.x2f, z5.t1b.t2a.x1b.x2g,
z5.t1b.t2a.x1b.x2h, z5.t1b.t2a.x1c.x2a, z5.t1b.t2a.x1c.x2b,
z5.t1b.t2a.x1c.x2c, z5.t1b.t2a.x1c.x2d, z5.t1b.t2a.x1c.x2e,
z5.t1b.t2a.x1c.x2f, z5.t1b.t2a.x1c.x2g, z5.t1b.t2a.x1c.x2h,
z5.t1b.t2a.x1d.x2a, z5.t1b.t2a.x1d.x2b, z5.t1b.t2a.x1d.x2c,
z5.t1b.t2a.x1d.x2d, z5.t1b.t2a.x1d.x2e, z5.t1b.t2a.x1d.x2f,
z5.t1b.t2a.x1d.x2g, z5.t1b.t2a.x1d.x2h, z5.t1b.t2a.x1e.x2a,
z5.t1b.t2a.x1e.x2b, z5.t1b.t2a.x1e.x2c, z5.t1b.t2a.x1e.x2d,
z5.t1b.t2a.x1e.x2e, z5.t1b.t2a.x1e.x2f, z5.t1b.t2a.x1e.x2g,
z5.t1b.t2a.x1e.x2h, z5.t1b.t2a.x1f.x2a, z5.t1b.t2a.x1f.x2b,
z5.t1b.t2a.x1f.x2c, z5.t1b.t2a.x1f.x2d, z5.t1b.t2a.x1f.x2e,
z5.t1b.t2a.x1f.x2f, z5.t1b.t2a.x1f.x2g, z5.t1b.t2a.x1f.x2h,
z5.t1b.t2a.x1g.x2a, z5.t1b.t2a.x1g.x2b, z5.t1b.t2a.x1g.x2c,
z5.t1b.t2a.x1g.x2d, z5.t1b.t2a.x1g.x2e, z5.t1b.t2a.x1g.x2f,
z5.t1b.t2a.x1g.x2g, z5.t1b.t2a.x1g.x2h, z5.t1b.t2a.x1h.x2a,
z5.t1b.t2a.x1h.x2b, z5.t1b.t2a.x1h.x2c, z5.t1b.t2a.x1h.x2d,
z5.t1b.t2a.x1h.x2e, z5.t1b.t2a.x1h.x2f, z5.t1b.t2a.x1h.x2g,
z5.t1b.t2a.x1h.x2h, z5.t1b.t2b.x1a.x2a, z5.t1b.t2b.x1a.x2b,
z5.t1b.t2b.x1a.x2c, z5.t1b.t2b.x1a.x2d, z5.t1b.t2b.x1a.x2e,
z5.t1b.t2b.x1a.x2f, z5.t1b.t2b.x1a.x2g, z5.t1b.t2b.x1a.x2h,
z5.t1b.t2b.x1b.x2a, z5.t1b.t2b.x1b.x2b, z5.t1b.t2b.x1b.x2c,
z5.t1b.t2b.x1b.x2d, z5.t1b.t2b.x1b.x2e, z5.t1b.t2b.x1b.x2f,
z5.t1b.t2b.x1b.x2g, z5.t1b.t2b.x1b.x2h, z5.t1b.t2b.x1c.x2a,
z5.t1b.t2b.x1c.x2b, z5.t1b.t2b.x1c.x2c, z5.t1b.t2b.x1c.x2d,
z5.t1b.t2b.x1c.x2e, z5.t1b.t2b.x1c.x2f, z5.t1b.t2b.x1c.x2g,
z5.t1b.t2b.x1c.x2h, z5.t1b.t2b.x1d.x2a, z5.t1b.t2b.x1d.x2b,
z5.t1b.t2b.x1d.x2c, z5.t1b.t2b.x1d.x2d, z5.t1b.t2b.x1d.x2e,
z5.t1b.t2b.x1d.x2f, z5.t1b.t2b.x1d.x2g, z5.t1b.t2b.x1d.x2h,
z5.t1b.t2b.x1e.x2a, z5.t1b.t2b.x1e.x2b, z5.t1b.t2b.x1e.x2c,
z5.t1b.t2b.x1e.x2d, z5.t1b.t2b.x1e.x2e, z5.t1b.t2b.x1e.x2f,
z5.t1b.t2b.x1e.x2g, z5.t1b.t2b.x1e.x2h, z5.t1b.t2b.x1f.x2a,
z5.t1b.t2b.x1f.x2b, z5.t1b.t2b.x1f.x2c, z5.t1b.t2b.x1f.x2d,
z5.t1b.t2b.x1f.x2e, z5.t1b.t2b.x1f.x2f, z5.t1b.t2b.x1f.x2g,
z5.t1b.t2b.x1f.x2h, z5.t1b.t2b.x1g.x2a, z5.t1b.t2b.x1g.x2b,
z5.t1b.t2b.x1g.x2c, z5.t1b.t2b.x1g.x2d, z5.t1b.t2b.x1g.x2e,
z5.t1b.t2b.x1g.x2f, z5.t1b.t2b.x1g.x2g, z5.t1b.t2b.x1g.x2h,
z5.t1b.t2b.x1h.x2a, z5.t1b.t2b.x1h.x2b, z5.t1b.t2b.x1h.x2c,
z5.t1b.t2b.x1h.x2d, z5.t1b.t2b.x1h.x2e, z5.t1b.t2b.x1h.x2f,
z5.t1b.t2b.x1h.x2g, z5.t1b.t2b.x1h.x2h, z5.t1b.t2c.x1a.x2a, TABLE 30.6-continued List of Compound Structures of Formula III z5.t1b.t2c.x1a.x2b, z5.t1b.t2c.x1a.x2c, z5.t1b.t2c.x1a.x2d,
z5.t1b.t2c.x1a.x2e, z5.t1b.t2c.x1a.x2f, z5.t1b.t2c.x1a.x2g,
z5.t1b.t2c.x1a.x2h, z5.t1b.t2c.x1b.x2a, z5.t1b.t2c.x1b.x2b,
z5.t1b.t2c.x1b.x2c, z5.t1b.t2c.x1b.x2d, z5.t1b.t2c.x1b.x2e,
z5.t1b.t2c.x1b.x2f, z5.t1b.t2c.x1b.x2g, z5.t1b.t2c.x1b.x2h,
z5.t1b.t2c.x1c.x2a, z5.t1b.t2c.x1c.x2b, z5.t1b.t2c.x1c.x2c,
z5.t1b.t2c.x1c.x2d, z5.t1b.t2c.x1c.x2e, z5.t1b.t2c.x1c.x2f,
z5.t1b.t2c.x1c.x2g, z5.t1b.t2c.x1c.x2h, z5.t1b.t2c.x1d.x2a,
z5.t1b.t2c.x1d.x2b, z5.t1b.t2c.x1d.x2c, z5.t1b.t2c.x1d.x2d,
z5.t1b.t2c.x1d.x2e, z5.t1b.t2c.x1d.x2f, z5.t1b.t2c.x1d.x2g,
z5.t1b.t2c.x1d.x2h, z5.t1b.t2c.x1e.x2a, z5.t1b.t2c.x1e.x2b,
z5.t1b.t2c.x1e.x2c, z5.t1b.t2c.x1e.x2d, z5.t1b.t2c.x1e.x2e,
z5.t1b.t2c.x1e.x2f, z5.t1b.t2c.x1e.x2g, z5.t1b.t2c.x1e.x2h,
z5.t1b.t2c.x1f.x2a, z5.t1b.t2c.x1f.x2b, z5.t1b.t2c.x1f.x2c,
z5.t1b.t2c.x1f.x2d, z5.t1b.t2c.x1f.x2e, z5.t1b.t2c.x1f.x2f,
z5.t1b.t2c.x1f.x2g, z5.t1b.t2c.x1f.x2h, z5.t1b.t2c.x1g.x2a,
z5.t1b.t2c.x1g.x2b, z5.t1b.t2c.x1g.x2c, z5.t1b.t2c.x1g.x2d,
z5.t1b.t2c.x1g.x2e, z5.t1b.t2c.x1g.x2f, z5.t1b.t2c.x1g.x2g,
z5.t1b.t2c.x1g.x2h, z5.t1b.t2c.x1h.x2a, z5.t1b.t2c.x1h.x2b,
z5.t1b.t2c.x1h.x2c, z5.t1b.t2c.x1h.x2d, z5.t1b.t2c.x1h.x2e,
z5.t1b.t2c.x1h.x2f, z5.t1b.t2c.x1h.x2g, z5.t1b.t2c.x1h.x2h,
z5.t1b.t2d.x1a.x2a, z5.t1b.t2d.x1a.x2b, z5.t1b.t2d.x1a.x2c,
z5.t1b.t2d.x1a.x2d, z5.t1b.t2d.x1a.x2e, z5.t1b.t2d.x1a.x2f,
z5.t1b.t2d.x1a.x2g, z5.t1b.t2d.x1a.x2h, z5.t1b.t2d.x1b.x2a,
z5.t1b.t2d.x1b.x2b, z5.t1b.t2d.x1b.x2c, z5.t1b.t2d.x1b.x2d,
z5.t1b.t2d.x1b.x2e, z5.t1b.t2d.x1b.x2f, z5.t1b.t2d.x1b.x2g,
z5.t1b.t2d.x1b.x2h, z5.t1b.t2d.x1c.x2a, z5.t1b.t2d.x1c.x2b,
z5.t1b.t2d.x1c.x2c, z5.t1b.t2d.x1c.x2d, z5.t1b.t2d.x1c.x2e,
z5.t1b.t2d.x1c.x2f, z5.t1b.t2d.x1c.x2g, z5.t1b.t2d.x1c.x2h,
z5.t1b.t2d.x1d.x2a, z5.t1b.t2d.x1d.x2b, z5.t1b.t2d.x1d.x2c,
z5.t1b.t2d.x1d.x2d, z5.t1b.t2d.x1d.x2e, z5.t1b.t2d.x1d.x2f,
z5.t1b.t2d.x1d.x2g, z5.t1b.t2d.x1d.x2h, z5.t1b.t2d.x1e.x2a,
z5.t1b.t2d.x1e.x2b, z5.t1b.t2d.x1e.x2c, z5.t1b.t2d.x1e.x2d,
z5.t1b.t2d.x1e.x2e, z5.t1b.t2d.x1e.x2f, z5.t1b.t2d.x1e.x2g,
z5.t1b.t2d.x1e.x2h, z5.t1b.t2d.x1f.x2a, z5.t1b.t2d.x1f.x2b,
z5.t1b.t2d.x1f.x2c, z5.t1b.t2d.x1f.x2d, z5.t1b.t2d.x1f.x2e,
z5.t1b.t2d.x1f.x2f, z5.t1b.t2d.x1f.x2g, z5.t1b.t2d.x1f.x2h,
z5.t1b.t2d.x1g.x2a, z5.t1b.t2d.x1g.x2b, z5.t1b.t2d.x1g.x2c,
z5.t1b.t2d.x1g.x2d, z5.t1b.t2d.x1g.x2e, z5.t1b.t2d.x1g.x2f,
z5.t1b.t2d.x1g.x2g, z5.t1b.t2d.x1g.x2h, z5.t1b.t2d.x1h.x2a,
z5.t1b.t2d.x1h.x2b, z5.t1b.t2d.x1h.x2c, z5.t1b.t2d.x1h.x2d,
z5.t1b.t2d.x1h.x2e, z5.t1b.t2d.x1h.x2f, z5.t1b.t2d.x1h.x2g,
z5.t1b.t2d.x1h.x2h, z5.t1b.t2e.x1a.x2a, z5.t1b.t2e.x1a.x2b,
z5.t1b.t2e.x1a.x2c, z5.t1b.t2e.x1a.x2d, z5.t1b.t2e.x1a.x2e,
z5.t1b.t2e.x1a.x2f, z5.t1b.t2e.x1a.x2g, z5.t1b.t2e.x1a.x2h,
z5.t1b.t2e.x1b.x2a, z5.t1b.t2e.x1b.x2b, z5.t1b.t2e.x1b.x2c,
z5.t1b.t2e.x1b.x2d, z5.t1b.t2e.x1b.x2e, z5.t1b.t2e.x1b.x2f,
z5.t1b.t2e.x1b.x2g, z5.t1b.t2e.x1b.x2h, z5.t1b.t2e.x1c.x2a,
z5.t1b.t2e.x1c.x2b, z5.t1b.t2e.x1c.x2c, z5.t1b.t2e.x1c.x2d,
z5.t1b.t2e.x1c.x2e, z5.t1b.t2e.x1c.x2f, z5.t1b.t2e.x1c.x2g,
z5.t1b.t2e.x1c.x2h, z5.t1b.t2e.x1d.x2a, z5.t1b.t2e.x1d.x2b,
z5.t1b.t2e.x1d.x2c, z5.t1b.t2e.x1d.x2d, z5.t1b.t2e.x1d.x2e,
z5.t1b.t2e.x1d.x2f, z5.t1b.t2e.x1d.x2g, z5.t1b.t2e.x1d.x2h,
z5.t1b.t2e.x1e.x2a, z5.t1b.t2e.x1e.x2b, z5.t1b.t2e.x1e.x2c,
z5.t1b.t2e.x1e.x2d, z5.t1b.t2e.x1e.x2e, z5.t1b.t2e.x1e.x2f,
z5.t1b.t2e.x1e.x2g, z5.t1b.t2e.x1e.x2h, z5.t1b.t2e.x1f.x2a,
z5.t1b.t2e.x1f.x2b, z5.t1b.t2e.x1f.x2c, z5.t1b.t2e.x1f.x2d,
z5.t1b.t2e.x1f.x2e, z5.t1b.t2e.x1f.x2f, z5.t1b.t2e.x1f.x2g,
z5.t1b.t2e.x1f.x2h, z5.t1b.t2e.x1g.x2a, z5.t1b.t2e.x1g.x2b,
z5.t1b.t2e.x1g.x2c, z5.t1b.t2e.x1g.x2d, z5.t1b.t2e.x1g.x2e,
z5.t1b.t2e.x1g.x2f, z5.t1b.t2e.x1g.x2g, z5.t1b.t2e.x1g.x2h,
z5.t1b.t2e.x1h.x2a, z5.t1b.t2e.x1h.x2b, z5.t1b.t2e.x1h.x2c,
z5.t1b.t2e.x1h.x2d, z5.t1b.t2e.x1h.x2e, z5.t1b.t2e.x1h.x2f,
z5.t1b.t2e.x1h.x2g, z5.t1b.t2e.x1h.x2h, z5.t1c.t2a.x1a.x2a,
z5.t1c.t2a.x1a.x2b, z5.t1c.t2a.x1a.x2c, z5.t1c.t2a.x1a.x2d,
z5.t1c.t2a.x1a.x2e, z5.t1c.t2a.x1a.x2f, z5.t1c.t2a.x1a.x2g,
z5.t1c.t2a.x1a.x2h, z5.t1c.t2a.x1b.x2a, z5.t1c.t2a.x1b.x2b,
z5.t1c.t2a.x1b.x2c, z5.t1c.t2a.x1b.x2d, z5.t1c.t2a.x1b.x2e,
z5.t1c.t2a.x1b.x2f, z5.t1c.t2a.x1b.x2g, z5.t1c.t2a.x1b.x2h,
z5.t1c.t2a.x1c.x2a, z5.t1c.t2a.x1c.x2b, z5.t1c.t2a.x1c.x2c,
z5.t1c.t2a.x1c.x2d, z5.t1c.t2a.x1c.x2e, z5.t1c.t2a.x1c.x2f,
z5.t1c.t2a.x1c.x2g, z5.t1c.t2a.x1c.x2h, z5.t1c.t2a.x1d.x2a,
z5.t1c.t2a.x1d.x2b, z5.t1c.t2a.x1d.x2c, z5.t1c.t2a.x1d.x2d,
z5.t1c.t2a.x1d.x2e, z5.t1c.t2a.x1d.x2f, z5.t1c.t2a.x1d.x2g,
z5.t1c.t2a.x1d.x2h, z5.t1c.t2a.x1e.x2a, z5.t1c.t2a.x1e.x2b,
z5.t1c.t2a.x1e.x2c, z5.t1c.t2a.x1e.x2d, z5.t1c.t2a.x1e.x2e,
z5.t1c.t2a.x1e.x2f, z5.t1c.t2a.x1e.x2g, z5.t1c.t2a.x1e.x2h,
z5.t1c.t2a.x1f.x2a, z5.t1c.t2a.x1f.x2b, z5.t1c.t2a.x1f.x2c,
z5.t1c.t2a.x1f.x2d, z5.t1c.t2a.x1f.x2e, z5.t1c.t2a.x1f.x2f,
z5.t1c.t2a.x1f.x2g, z5.t1c.t2a.x1f.x2h, z5.t1c.t2a.x1g.x2a,
z5.t1c.t2a.x1g.x2b, z5.t1c.t2a.x1g.x2c, z5.t1c.t2a.x1g.x2d,
z5.t1c.t2a.x1g.x2e, z5.t1c.t2a.x1g.x2f, z5.t1c.t2a.x1g.x2g,
z5.t1c.t2a.x1g.x2h, z5.t1c.t2a.x1h.x2a, z5.t1c.t2a.x1h.x2b,
z5.t1c.t2a.x1h.x2c, z5.t1c.t2a.x1h.x2d, z5.t1c.t2a.x1h.x2e,
z5.t1c.t2a.x1h.x2f, z5.t1c.t2a.x1h.x2g, z5.t1c.t2a.x1h.x2h,
z5.t1c.t2b.x1a.x2a, z5.t1c.t2b.x1a.x2b, z5.t1c.t2b.x1a.x2c,
z5.t1c.t2b.x1a.x2d, z5.t1c.t2b.x1a.x2e, z5.t1c.t2b.x1a.x2f,
z5.t1c.t2b.x1a.x2g, z5.t1c.t2b.x1a.x2h, z5.t1c.t2b.x1b.x2a,
z5.t1c.t2b.x1b.x2b, z5.t1c.t2b.x1b.x2c, z5.t1c.t2b.x1b.x2d,
z5.t1c.t2b.x1b.x2e, z5.t1c.t2b.x1b.x2f, z5.t1c.t2b.x1b.x2g,
z5.t1c.t2b.x1b.x2h, z5.t1c.t2b.x1c.x2a, z5.t1c.t2b.x1c.x2b,
z5.t1c.t2b.x1c.x2c, z5.t1c.t2b.x1c.x2d, z5.t1c.t2b.x1c.x2e,
z5.t1c.t2b.x1c.x2f, z5.t1c.t2b.x1c.x2g, z5.t1c.t2b.x1c.x2h,
z5.t1c.t2b.x1d.x2a, z5.t1c.t2b.x1d.x2b, z5.t1c.t2b.x1d.x2c,
z5.t1c.t2b.x1d.x2d, z5.t1c.t2b.x1d.x2e, z5.t1c.t2b.x1d.x2f,
z5.t1c.t2b.x1d.x2g, z5.t1c.t2b.x1d.x2h, z5.t1c.t2b.x1e.x2a,
z5.t1c.t2b.x1e.x2b, z5.t1c.t2b.x1e.x2c, z5.t1c.t2b.x1e.x2d,
z5.t1c.t2b.x1e.x2e, z5.t1c.t2b.x1e.x2f, z5.t1c.t2b.x1e.x2g,
z5.t1c.t2b.x1e.x2h, z5.t1c.t2b.x1f.x2a, z5.t1c.t2b.x1f.x2b,
z5.t1c.t2b.x1f.x2c, z5.t1c.t2b.x1f.x2d, z5.t1c.t2b.x1f.x2e,
z5.t1c.t2b.x1f.x2f, z5.t1c.t2b.x1f.x2g, z5.t1c.t2b.x1f.x2h,
z5.t1c.t2b.x1g.x2a, z5.t1c.t2b.x1g.x2b, z5.t1c.t2b.x1g.x2c,
z5.t1c.t2b.x1g.x2d, z5.t1c.t2b.x1g.x2e, z5.t1c.t2b.x1g.x2f,
z5.t1c.t2b.x1g.x2g, z5.t1c.t2b.x1g.x2h, z5.t1c.t2b.x1h.x2a,
z5.t1c.t2b.x1h.x2b, z5.t1c.t2b.x1h.x2c, z5.t1c.t2b.x1h.x2d,
z5.t1c.t2b.x1h.x2e, z5.t1c.t2b.x1h.x2f, z5.t1c.t2b.x1h.x2g,
z5.t1c.t2b.x1h.x2h, z5.t1c.t2c.x1a.x2a, z5.t1c.t2c.x1a.x2b,
z5.t1c.t2c.x1a.x2c, z5.t1c.t2c.x1a.x2d, z5.t1c.t2c.x1a.x2e,
z5.t1c.t2c.x1a.x2f, z5.t1c.t2c.x1a.x2g, z5.t1c.t2c.x1a.x2h,
z5.t1c.t2c.x1b.x2a, z5.t1c.t2c.x1b.x2b, z5.t1c.t2c.x1b.x2c,
z5.t1c.t2c.x1b.x2d, z5.t1c.t2c.x1b.x2e, z5.t1c.t2c.x1b.x2f,
z5.t1c.t2c.x1b.x2g, z5.t1c.t2c.x1b.x2h, z5.t1c.t2c.x1c.x2a,
z5.t1c.t2c.x1c.x2b, z5.t1c.t2c.x1c.x2c, z5.t1c.t2c.x1c.x2d,
z5.t1c.t2c.x1c.x2e, z5.t1c.t2c.x1c.x2f, z5.t1c.t2c.x1c.x2g,
z5.t1c.t2c.x1c.x2h, z5.t1c.t2c.x1d.x2a, z5.t1c.t2c.x1d.x2b,
z5.t1c.t2c.x1d.x2c, z5.t1c.t2c.x1d.x2d, z5.t1c.t2c.x1d.x2e,
z5.t1c.t2c.x1d.x2f, z5.t1c.t2c.x1d.x2g, z5.t1c.t2c.x1d.x2h,
z5.t1c.t2c.x1e.x2a, z5.t1c.t2c.x1e.x2b, z5.t1c.t2c.x1e.x2c,
z5.t1c.t2c.x1e.x2d, z5.t1c.t2c.x1e.x2e, z5.t1c.t2c.x1e.x2f,
z5.t1c.t2c.x1e.x2g, z5.t1c.t2c.x1e.x2h, z5.t1c.t2c.x1f.x2a,
z5.t1c.t2c.x1f.x2b, z5.t1c.t2c.x1f.x2c, z5.t1c.t2c.x1f.x2d,
z5.t1c.t2c.x1f.x2e, z5.t1c.t2c.x1f.x2f, z5.t1c.t2c.x1f.x2g,
z5.t1c.t2c.x1f.x2h, z5.t1c.t2c.x1g.x2a, z5.t1c.t2c.x1g.x2b,
z5.t1c.t2c.x1g.x2c, z5.t1c.t2c.x1g.x2d, z5.t1c.t2c.x1g.x2e,
z5.t1c.t2c.x1g.x2f, z5.t1c.t2c.x1g.x2g, z5.t1c.t2c.x1g.x2h,
z5.t1c.t2c.x1h.x2a, z5.t1c.t2c.x1h.x2b, z5.t1c.t2c.x1h.x2c,
z5.t1c.t2c.x1h.x2d, z5.t1c.t2c.x1h.x2e, z5.t1c.t2c.x1h.x2f,
z5.t1c.t2c.x1h.x2g, z5.t1c.t2c.x1h.x2h, z5.t1c.t2d.x1a.x2a,
z5.t1c.t2d.x1a.x2b, z5.t1c.t2d.x1a.x2c, z5.t1c.t2d.x1a.x2d,
z5.t1c.t2d.x1a.x2e, z5.t1c.t2d.x1a.x2f, z5.t1c.t2d.x1a.x2g,
z5.t1c.t2d.x1a.x2h, z5.t1c.t2d.x1b.x2a, z5.t1c.t2d.x1b.x2b,
z5.t1c.t2d.x1b.x2c, z5.t1c.t2d.x1b.x2d, z5.t1c.t2d.x1b.x2e,
z5.t1c.t2d.x1b.x2f, z5.t1c.t2d.x1b.x2g, z5.t1c.t2d.x1b.x2h,
z5.t1c.t2d.x1c.x2a, z5.t1c.t2d.x1c.x2b, z5.t1c.t2d.x1c.x2c,
z5.t1c.t2d.x1c.x2d, z5.t1c.t2d.x1c.x2e, z5.t1c.t2d.x1c.x2f,
z5.t1c.t2d.x1c.x2g, z5.t1c.t2d.x1c.x2h, z5.t1c.t2d.x1d.x2a,
z5.t1c.t2d.x1d.x2b, z5.t1c.t2d.x1d.x2c, z5.t1c.t2d.x1d.x2d,
z5.t1c.t2d.x1d.x2e, z5.t1c.t2d.x1d.x2f, z5.t1c.t2d.x1d.x2g,
z5.t1c.t2d.x1d.x2h, z5.t1c.t2d.x1e.x2a, z5.t1c.t2d.x1e.x2b,
z5.t1c.t2d.x1e.x2c, z5.t1c.t2d.x1e.x2d, z5.t1c.t2d.x1e.x2e,
z5.t1c.t2d.x1e.x2f, z5.t1c.t2d.x1e.x2g, z5.t1c.t2d.x1e.x2h,
z5.t1c.t2d.x1f.x2a, z5.t1c.t2d.x1f.x2b, z5.t1c.t2d.x1f.x2c,
z5.t1c.t2d.x1f.x2d, z5.t1c.t2d.x1f.x2e, z5.t1c.t2d.x1f.x2f,
z5.t1c.t2d.x1f.x2g, z5.t1c.t2d.x1f.x2h, z5.t1c.t2d.x1g.x2a,
z5.t1c.t2d.x1g.x2b, z5.t1c.t2d.x1g.x2c, z5.t1c.t2d.x1g.x2d,
z5.t1c.t2d.x1g.x2e, z5.t1c.t2d.x1g.x2f, z5.t1c.t2d.x1g.x2g,
z5.t1c.t2d.x1g.x2h, z5.t1c.t2d.x1h.x2a, z5.t1c.t2d.x1h.x2b,
z5.t1c.t2d.x1h.x2c, z5.t1c.t2d.x1h.x2d, z5.t1c.t2d.x1h.x2e,
z5.t1c.t2d.x1h.x2f, z5.t1c.t2d.x1h.x2g, z5.t1c.t2d.x1h.x2h,
z5.t1c.t2e.x1a.x2a, z5.t1c.t2e.x1a.x2b, z5.t1c.t2e.x1a.x2c,
z5.t1c.t2e.x1a.x2d, z5.t1c.t2e.x1a.x2e, z5.t1c.t2e.x1a.x2f,
z5.t1c.t2e.x1a.x2g, z5.t1c.t2e.x1a.x2h, z5.t1c.t2e.x1b.x2a,
z5.t1c.t2e.x1b.x2b, z5.t1c.t2e.x1b.x2c, z5.t1c.t2e.x1b.x2d,
z5.t1c.t2e.x1b.x2e, z5.t1c.t2e.x1b.x2f, z5.t1c.t2e.x1b.x2g,

TABLE 30.6-continued

List of Compound Structures of Formula III z5.t1c.t2e.x1b.x2h, z5.t1c.t2e.x1c.x2a, z5.t1c.t2e.x1c.x2b,
z5.t1c.t2e.x1c.x2c, z5.t1c.t2e.x1c.x2d, z5.t1c.t2e.x1c.x2e,
z5.t1c.t2e.x1c.x2f, z5.t1c.t2e.x1c.x2g, z5.t1c.t2e.x1c.x2h,
z5.t1c.t2e.x1d.x2a, z5.t1c.t2e.x1d.x2b, z5.t1c.t2e.x1d.x2c,
z5.t1c.t2e.x1d.x2d, z5.t1c.t2e.x1d.x2e, z5.t1c.t2e.x1d.x2f,
z5.t1c.t2e.x1d.x2g, z5.t1c.t2e.x1d.x2h, z5.t1c.t2e.x1e.x2a,
z5.t1c.t2e.x1e.x2b, z5.t1c.t2e.x1e.x2c, z5.t1c.t2e.x1e.x2d,
z5.t1c.t2e.x1e.x2e, z5.t1c.t2e.x1e.x2f, z5.t1c.t2e.x1e.x2g,
z5.t1c.t2e.x1e.x2h, z5.t1c.t2e.x1f.x2a, z5.t1c.t2e.x1f.x2b,
z5.t1c.t2e.x1f.x2c, z5.t1c.t2e.x1f.x2d, z5.t1c.t2e.x1f.x2e,
z5.t1c.t2e.x1f.x2f, z5.t1c.t2e.x1f.x2g, z5.t1c.t2e.x1f.x2h,
z5.t1c.t2e.x1g.x2a, z5.t1c.t2e.x1g.x2b, z5.t1c.t2e.x1g.x2c,
z5.t1c.t2e.x1g.x2d, z5.t1c.t2e.x1g.x2e, z5.t1c.t2e.x1g.x2f,
z5.t1c.t2e.x1g.x2g, z5.t1c.t2e.x1g.x2h, z5.t1c.t2e.x1h.x2a,
z5.t1c.t2e.x1h.x2b, z5.t1c.t2e.x1h.x2c, z5.t1c.t2e.x1h.x2d,
z5.t1c.t2e.x1h.x2e, z5.t1c.t2e.x1h.x2f, z5.t1c.t2e.x1h.x2g,
z5.t1c.t2e.x1h.x2h, z5.t1d.t2a.x1a.x2a, z5.t1d.t2a.x1a.x2b,
z5.t1d.t2a.x1a.x2c, z5.t1d.t2a.x1a.x2d, z5.t1d.t2a.x1a.x2e,
z5.t1d.t2a.x1a.x2f, z5.t1d.t2a.x1a.x2g, z5.t1d.t2a.x1a.x2h,
z5.t1d.t2a.x1b.x2a, z5.t1d.t2a.x1b.x2b, z5.t1d.t2a.x1b.x2c,
z5.t1d.t2a.x1b.x2d, z5.t1d.t2a.x1b.x2e, z5.t1d.t2a.x1b.x2f,
z5.t1d.t2a.x1b.x2g, z5.t1d.t2a.x1b.x2h, z5.t1d.t2a.x1c.x2a,
z5.t1d.t2a.x1c.x2b, z5.t1d.t2a.x1c.x2c, z5.t1d.t2a.x1c.x2d,
z5.t1d.t2a.x1c.x2e, z5.t1d.t2a.x1c.x2f, z5.t1d.t2a.x1c.x2g,
z5.t1d.t2a.x1c.x2h, z5.t1d.t2a.x1d.x2a, z5.t1d.t2a.x1d.x2b,
z5.t1d.t2a.x1d.x2c, z5.t1d.t2a.x1d.x2d, z5.t1d.t2a.x1d.x2e,
z5.t1d.t2a.x1d.x2f, z5.t1d.t2a.x1d.x2g, z5.t1d.t2a.x1d.x2h,
z5.t1d.t2a.x1e.x2a, z5.t1d.t2a.x1e.x2b, z5.t1d.t2a.x1e.x2c,
z5.t1d.t2a.x1e.x2d, z5.t1d.t2a.x1e.x2e, z5.t1d.t2a.x1e.x2f,
z5.t1d.t2a.x1e.x2g, z5.t1d.t2a.x1e.x2h, z5.t1d.t2a.x1f.x2a,
z5.t1d.t2a.x1f.x2b, z5.t1d.t2a.x1f.x2c, z5.t1d.t2a.x1f.x2d,
z5.t1d.t2a.x1f.x2e, z5.t1d.t2a.x1f.x2f, z5.t1d.t2a.x1f.x2g,
z5.t1d.t2a.x1f.x2h, z5.t1d.t2a.x1g.x2a, z5.t1d.t2a.x1g.x2b,
z5.t1d.t2a.x1g.x2c, z5.t1d.t2a.x1g.x2d, z5.t1d.t2a.x1g.x2e,
z5.t1d.t2a.x1g.x2f, z5.t1d.t2a.x1g.x2g, z5.t1d.t2a.x1g.x2h,
z5.t1d.t2a.x1h.x2a, z5.t1d.t2a.x1h.x2b, z5.t1d.t2a.x1h.x2c,
z5.t1d.t2a.x1h.x2d, z5.t1d.t2a.x1h.x2e, z5.t1d.t2a.x1h.x2f,
z5.t1d.t2a.x1h.x2g, z5.t1d.t2a.x1h.x2h, z5.t1d.t2b.x1a.x2a,
z5.t1d.t2b.x1a.x2b, z5.t1d.t2b.x1a.x2c, z5.t1d.t2b.x1a.x2d,
z5.t1d.t2b.x1a.x2e, z5.t1d.t2b.x1a.x2f, z5.t1d.t2b.x1a.x2g,
z5.t1d.t2b.x1a.x2h, z5.t1d.t2b.x1b.x2a, z5.t1d.t2b.x1b.x2b,
z5.t1d.t2b.x1b.x2c, z5.t1d.t2b.x1b.x2d, z5.t1d.t2b.x1b.x2e,
z5.t1d.t2b.x1b.x2f, z5.t1d.t2b.x1b.x2g, z5.t1d.t2b.x1b.x2h,
z5.t1d.t2b.x1c.x2a, z5.t1d.t2b.x1c.x2b, z5.t1d.t2b.x1c.x2c,
z5.t1d.t2b.x1c.x2d, z5.t1d.t2b.x1c.x2e, z5.t1d.t2b.x1c.x2f,
z5.t1d.t2b.x1c.x2g, z5.t1d.t2b.x1c.x2h, z5.t1d.t2b.x1d.x2a,
z5.t1d.t2b.x1d.x2b, z5.t1d.t2b.x1d.x2c, z5.t1d.t2b.x1d.x2d,
z5.t1d.t2b.x1d.x2e, z5.t1d.t2b.x1d.x2f, z5.t1d.t2b.x1d.x2g,
z5.t1d.t2b.x1d.x2h, z5.t1d.t2b.x1e.x2a, z5.t1d.t2b.x1e.x2b,
z5.t1d.t2b.x1e.x2c, z5.t1d.t2b.x1e.x2d, z5.t1d.t2b.x1e.x2e,
z5.t1d.t2b.x1e.x2f, z5.t1d.t2b.x1e.x2g, z5.t1d.t2b.x1e.x2h,
z5.t1d.t2b.x1f.x2a, z5.t1d.t2b.x1f.x2b, z5.t1d.t2b.x1f.x2c,
z5.t1d.t2b.x1f.x2d, z5.t1d.t2b.x1f.x2e, z5.t1d.t2b.x1f.x2f,
z5.t1d.t2b.x1f.x2g, z5.t1d.t2b.x1f.x2h, z5.t1d.t2b.x1g.x2a,
z5.t1d.t2b.x1g.x2b, z5.t1d.t2b.x1g.x2c, z5.t1d.t2b.x1g.x2d,
z5.t1d.t2b.x1g.x2e, z5.t1d.t2b.x1g.x2f, z5.t1d.t2b.x1g.x2g,
z5.t1d.t2b.x1g.x2h, z5.t1d.t2b.x1h.x2a, z5.t1d.t2b.x1h.x2b,
z5.t1d.t2b.x1h.x2c, z5.t1d.t2b.x1h.x2d, z5.t1d.t2b.x1h.x2e,
z5.t1d.t2b.x1h.x2f, z5.t1d.t2b.x1h.x2g, z5.t1d.t2b.x1h.x2h,
z5.t1d.t2c.x1a.x2a, z5.t1d.t2c.x1a.x2b, z5.t1d.t2c.x1a.x2c,
z5.t1d.t2c.x1a.x2d, z5.t1d.t2c.x1a.x2e, z5.t1d.t2c.x1a.x2f,
z5.t1d.t2c.x1a.x2g, z5.t1d.t2c.x1a.x2h, z5.t1d.t2c.x1b.x2a,
z5.t1d.t2c.x1b.x2b, z5.t1d.t2c.x1b.x2c, z5.t1d.t2c.x1b.x2d,
z5.t1d.t2c.x1b.x2e, z5.t1d.t2c.x1b.x2f, z5.t1d.t2c.x1b.x2g,
z5.t1d.t2c.x1b.x2h, z5.t1d.t2c.x1c.x2a, z5.t1d.t2c.x1c.x2b,
z5.t1d.t2c.x1c.x2c, z5.t1d.t2c.x1c.x2d, z5.t1d.t2c.x1c.x2e,
z5.t1d.t2c.x1c.x2f, z5.t1d.t2c.x1c.x2g, z5.t1d.t2c.x1c.x2h,
z5.t1d.t2c.x1d.x2a, z5.t1d.t2c.x1d.x2b, z5.t1d.t2c.x1d.x2c,
z5.t1d.t2c.x1d.x2d, z5.t1d.t2c.x1d.x2e, z5.t1d.t2c.x1d.x2f,
z5.t1d.t2c.x1d.x2g, z5.t1d.t2c.x1d.x2h, z5.t1d.t2c.x1e.x2a,
z5.t1d.t2c.x1e.x2b, z5.t1d.t2c.x1e.x2c, z5.t1d.t2c.x1e.x2d,
z5.t1d.t2c.x1e.x2e, z5.t1d.t2c.x1e.x2f, z5.t1d.t2c.x1e.x2g,
z5.t1d.t2c.x1e.x2h, z5.t1d.t2c.x1f.x2a, z5.t1d.t2c.x1f.x2b,
z5.t1d.t2c.x1f.x2c, z5.t1d.t2c.x1f.x2d, z5.t1d.t2c.x1f.x2e,
z5.t1d.t2c.x1f.x2f, z5.t1d.t2c.x1g.x2a, z5.t1d.t2c.x1g.x2b, z5.t1d.t2c.x1g.x2c,
z5.t1d.t2c.x1g.x2d, z5.t1d.t2c.x1g.x2e, z5.t1d.t2c.x1g.x2f,
z5.t1d.t2c.x1g.x2g, z5.t1d.t2c.x1g.x2h, z5.t1d.t2c.x1h.x2a,
z5.t1d.t2c.x1h.x2b, z5.t1d.t2c.x1h.x2c, z5.t1d.t2c.x1h.x2d,
z5.t1d.t2c.x1h.x2e, z5.t1d.t2c.x1h.x2f, z5.t1d.t2c.x1h.x2g,
z5.t1d.t2c.x1h.x2h, z5.t1d.t2d.x1a.x2a, z5.t1d.t2d.x1a.x2b,
z5.t1d.t2d.x1a.x2c, z5.t1d.t2d.x1a.x2d, z5.t1d.t2d.x1a.x2e,
z5.t1d.t2d.x1a.x2f, z5.t1d.t2d.x1a.x2g, z5.t1d.t2d.x1a.x2h,
z5.t1d.t2d.x1b.x2a, z5.t1d.t2d.x1b.x2b, z5.t1d.t2d.x1b.x2c,
z5.t1d.t2d.x1b.x2d, z5.t1d.t2d.x1b.x2e, z5.t1d.t2d.x1b.x2f,
z5.t1d.t2d.x1b.x2g, z5.t1d.t2d.x1b.x2h, z5.t1d.t2d.x1c.x2a,
z5.t1d.t2d.x1c.x2b, z5.t1d.t2d.x1c.x2c, z5.t1d.t2d.x1c.x2d,
z5.t1d.t2d.x1c.x2e, z5.t1d.t2d.x1c.x2f, z5.t1d.t2d.x1c.x2g,
z5.t1d.t2d.x1c.x2h, z5.t1d.t2d.x1d.x2a, z5.t1d.t2d.x1d.x2b,
z5.t1d.t2d.x1d.x2c, z5.t1d.t2d.x1d.x2d, z5.t1d.t2d.x1d.x2e,
z5.t1d.t2d.x1d.x2f, z5.t1d.t2d.x1d.x2g, z5.t1d.t2d.x1d.x2h,
z5.t1d.t2d.x1e.x2a, z5.t1d.t2d.x1e.x2b, z5.t1d.t2d.x1e.x2c,
z5.t1d.t2d.x1e.x2d, z5.t1d.t2d.x1e.x2e, z5.t1d.t2d.x1e.x2f,
z5.t1d.t2d.x1e.x2g, z5.t1d.t2d.x1e.x2h, z5.t1d.t2d.x1f.x2a,
z5.t1d.t2d.x1f.x2b, z5.t1d.t2d.x1f.x2c, z5.t1d.t2d.x1f.x2d,
z5.t1d.t2d.x1f.x2e, z5.t1d.t2d.x1f.x2f, z5.t1d.t2d.x1f.x2g,
z5.t1d.t2d.x1f.x2h, z5.t1d.t2d.x1g.x2a, z5.t1d.t2d.x1g.x2b,
z5.t1d.t2d.x1g.x2c, z5.t1d.t2d.x1g.x2d, z5.t1d.t2d.x1g.x2e,
z5.t1d.t2d.x1g.x2f, z5.t1d.t2d.x1g.x2g, z5.t1d.t2d.x1g.x2h,
z5.t1d.t2d.x1h.x2a, z5.t1d.t2d.x1h.x2b, z5.t1d.t2d.x1h.x2c,
z5.t1d.t2d.x1h.x2d, z5.t1d.t2d.x1h.x2e, z5.t1d.t2d.x1h.x2f,
z5.t1d.t2d.x1h.x2g, z5.t1d.t2d.x1h.x2h, z5.t1d.t2e.x1a.x2a,
z5.t1d.t2e.x1a.x2b, z5.t1d.t2e.x1a.x2c, z5.t1d.t2e.x1a.x2d,
z5.t1d.t2e.x1a.x2e, z5.t1d.t2e.x1a.x2f, z5.t1d.t2e.x1a.x2g,
z5.t1d.t2e.x1a.x2h, z5.t1d.t2e.x1b.x2a, z5.t1d.t2e.x1b.x2b,
z5.t1d.t2e.x1b.x2c, z5.t1d.t2e.x1b.x2d, z5.t1d.t2e.x1b.x2e,
z5.t1d.t2e.x1b.x2f, z5.t1d.t2e.x1b.x2g, z5.t1d.t2e.x1b.x2h,
z5.t1d.t2e.x1c.x2a, z5.t1d.t2e.x1c.x2b, z5.t1d.t2e.x1c.x2c,
z5.t1d.t2e.x1c.x2d, z5.t1d.t2e.x1c.x2e, z5.t1d.t2e.x1c.x2f,
z5.t1d.t2e.x1c.x2g, z5.t1d.t2e.x1c.x2h, z5.t1d.t2e.x1d.x2a,
z5.t1d.t2e.x1d.x2b, z5.t1d.t2e.x1d.x2c, z5.t1d.t2e.x1d.x2d,
z5.t1d.t2e.x1d.x2e, z5.t1d.t2e.x1d.x2f, z5.t1d.t2e.x1d.x2g,
z5.t1d.t2e.x1d.x2h, z5.t1d.t2e.x1e.x2a, z5.t1d.t2e.x1e.x2b,
z5.t1d.t2e.x1e.x2c, z5.t1d.t2e.x1e.x2d, z5.t1d.t2e.x1e.x2e,
z5.t1d.t2e.x1e.x2f, z5.t1d.t2e.x1e.x2g, z5.t1d.t2e.x1e.x2h,
z5.t1d.t2e.x1f.x2a, z5.t1d.t2e.x1f.x2b, z5.t1d.t2e.x1f.x2c,
z5.t1d.t2e.x1f.x2d, z5.t1d.t2e.x1f.x2e, z5.t1d.t2e.x1f.x2f,
z5.t1d.t2e.x1f.x2g, z5.t1d.t2e.x1f.x2h, z5.t1d.t2e.x1g.x2a,
z5.t1d.t2e.x1g.x2b, z5.t1d.t2e.x1g.x2c, z5.t1d.t2e.x1g.x2d,
z5.t1d.t2e.x1g.x2e, z5.t1d.t2e.x1g.x2f, z5.t1d.t2e.x1g.x2g,
z5.t1d.t2e.x1g.x2h, z5.t1d.t2e.x1h.x2a, z5.t1d.t2e.x1h.x2b,
z5.t1d.t2e.x1h.x2c, z5.t1d.t2e.x1h.x2d, z5.t1d.t2e.x1h.x2e,
z5.t1d.t2e.x1h.x2f, z5.t1d.t2e.x1h.x2g, z5.t1d.t2e.x1h.x2h,
z5.t1e.t2a.x1a.x2a, z5.t1e.t2a.x1a.x2b, z5.t1e.t2a.x1a.x2c,
z5.t1e.t2a.x1a.x2d, z5.t1e.t2a.x1a.x2e, z5.t1e.t2a.x1a.x2f,
z5.t1e.t2a.x1a.x2g, z5.t1e.t2a.x1a.x2h, z5.t1e.t2a.x1b.x2a,
z5.t1e.t2a.x1b.x2b, z5.t1e.t2a.x1b.x2c, z5.t1e.t2a.x1b.x2d,
z5.t1e.t2a.x1b.x2e, z5.t1e.t2a.x1b.x2f, z5.t1e.t2a.x1b.x2g,
z5.t1e.t2a.x1b.x2h, z5.t1e.t2a.x1c.x2a, z5.t1e.t2a.x1c.x2b,
z5.t1e.t2a.x1c.x2c, z5.t1e.t2a.x1c.x2d, z5.t1e.t2a.x1c.x2e,
z5.t1e.t2a.x1c.x2f, z5.t1e.t2a.x1c.x2g, z5.t1e.t2a.x1c.x2h,
z5.t1e.t2a.x1d.x2a, z5.t1e.t2a.x1d.x2b, z5.t1e.t2a.x1d.x2c,
z5.t1e.t2a.x1d.x2d, z5.t1e.t2a.x1d.x2e, z5.t1e.t2a.x1d.x2f,
z5.t1e.t2a.x1d.x2g, z5.t1e.t2a.x1d.x2h, z5.t1e.t2a.x1e.x2a,
z5.t1e.t2a.x1e.x2b, z5.t1e.t2a.x1e.x2c, z5.t1e.t2a.x1e.x2d,
z5.t1e.t2a.x1e.x2e, z5.t1e.t2a.x1e.x2f, z5.t1e.t2a.x1e.x2g,
z5.t1e.t2a.x1e.x2h, z5.t1e.t2a.x1f.x2a, z5.t1e.t2a.x1f.x2b,
z5.t1e.t2a.x1f.x2c, z5.t1e.t2a.x1f.x2d, z5.t1e.t2a.x1f.x2e,
z5.t1e.t2a.x1f.x2f, z5.t1e.t2a.x1f.x2g, z5.t1e.t2a.x1f.x2h,
z5.t1e.t2a.x1g.x2a, z5.t1e.t2a.x1g.x2b, z5.t1e.t2a.x1g.x2c,
z5.t1e.t2a.x1g.x2d, z5.t1e.t2a.x1g.x2e, z5.t1e.t2a.x1g.x2f,
z5.t1e.t2a.x1g.x2g, z5.t1e.t2a.x1g.x2h, z5.t1e.t2a.x1h.x2a,
z5.t1e.t2a.x1h.x2b, z5.t1e.t2a.x1h.x2c, z5.t1e.t2a.x1h.x2d,
z5.t1e.t2a.x1h.x2e, z5.t1e.t2a.x1h.x2f, z5.t1e.t2a.x1h.x2g,
z5.t1e.t2a.x1h.x2h, z5.t1e.t2b.x1a.x2a, z5.t1e.t2b.x1a.x2b,
z5.t1e.t2b.x1a.x2c, z5.t1e.t2b.x1a.x2d, z5.t1e.t2b.x1a.x2e,
z5.t1e.t2b.x1a.x2f, z5.t1e.t2b.x1a.x2g, z5.t1e.t2b.x1a.x2h,
z5.t1e.t2b.x1b.x2a, z5.t1e.t2b.x1b.x2b, z5.t1e.t2b.x1b.x2c,
z5.t1e.t2b.x1b.x2d, z5.t1e.t2b.x1b.x2e, z5.t1e.t2b.x1b.x2f,
z5.t1e.t2b.x1b.x2g, z5.t1e.t2b.x1b.x2h, z5.t1e.t2b.x1c.x2a,
z5.t1e.t2b.x1c.x2b, z5.t1e.t2b.x1c.x2c, z5.t1e.t2b.x1c.x2d,
z5.t1e.t2b.x1c.x2e, z5.t1e.t2b.x1c.x2f, z5.t1e.t2b.x1c.x2g,
z5.t1e.t2b.x1c.x2h, z5.t1e.t2b.x1d.x2a, z5.t1e.t2b.x1d.x2b,
z5.t1e.t2b.x1d.x2c, z5.t1e.t2b.x1d.x2d, z5.t1e.t2b.x1d.x2e,

TABLE 30.6-continued

List of Compound Structures of Formula III z5.t1e.t2b.x1d.x2f, z5.t1e.t2b.x1d.x2g, z5.t1e.t2b.x1d.x2h,
z5.t1e.t2b.x1e.x2a, z5.t1e.t2b.x1e.x2b, z5.t1e.t2b.x1e.x2c,
z5.t1e.t2b.x1e.x2d, z5.t1e.t2b.x1e.x2e, z5.t1e.t2b.x1e.x2f,
z5.t1e.t2b.x1e.x2g, z5.t1e.t2b.x1e.x2h, z5.t1e.t2b.x1f.x2a,
z5.t1e.t2b.x1f.x2b, z5.t1e.t2b.x1f.x2c, z5.t1e.t2b.x1f.x2d,
z5.t1e.t2b.x1f.x2e, z5.t1e.t2b.x1f.x2f, z5.t1e.t2b.x1f.x2g,
z5.t1e.t2b.x1f.x2h, z5.t1e.t2b.x1g.x2a, z5.t1e.t2b.x1g.x2b,
z5.t1e.t2b.x1g.x2c, z5.t1e.t2b.x1g.x2d, z5.t1e.t2b.x1g.x2e,
z5.t1e.t2b.x1g.x2f, z5.t1e.t2b.x1g.x2g, z5.t1e.t2b.x1g.x2h,
z5.t1e.t2b.x1h.x2a, z5.t1e.t2b.x1h.x2b, z5.t1e.t2b.x1h.x2c,
z5.t1e.t2b.x1h.x2d, z5.t1e.t2b.x1h.x2e, z5.t1e.t2b.x1h.x2f,
z5.t1e.t2b.x1h.x2g, z5.t1e.t2b.x1h.x2h, z5.t1e.t2c.x1a.x2a,
z5.t1e.t2c.x1a.x2b, z5.t1e.t2c.x1a.x2c, z5.t1e.t2c.x1a.x2d,
z5.t1e.t2c.x1a.x2e, z5.t1e.t2c.x1a.x2f, z5.t1e.t2c.x1a.x2g,
z5.t1e.t2c.x1a.x2h, z5.t1e.t2c.x1b.x2a, z5.t1e.t2c.x1b.x2b,
z5.t1e.t2c.x1b.x2c, z5.t1e.t2c.x1b.x2d, z5.t1e.t2c.x1b.x2e,
z5.t1e.t2c.x1b.x2f, z5.t1e.t2c.x1b.x2g, z5.t1e.t2c.x1b.x2h,
z5.t1e.t2c.x1c.x2a, z5.t1e.t2c.x1c.x2b, z5.t1e.t2c.x1c.x2c,
z5.t1e.t2c.x1c.x2d, z5.t1e.t2c.x1c.x2e, z5.t1e.t2c.x1c.x2f,
z5.t1e.t2c.x1c.x2g, z5.t1e.t2c.x1c.x2h, z5.t1e.t2c.x1d.x2a,
z5.t1e.t2c.x1d.x2b, z5.t1e.t2c.x1d.x2c, z5.t1e.t2c.x1d.x2d,
z5.t1e.t2c.x1d.x2e, z5.t1e.t2c.x1d.x2f, z5.t1e.t2c.x1d.x2g,
z5.t1e.t2c.x1d.x2h, z5.t1e.t2c.x1e.x2a, z5.t1e.t2c.x1e.x2b,
z5.t1e.t2c.x1e.x2c, z5.t1e.t2c.x1e.x2d, z5.t1e.t2c.x1e.x2e,
z5.t1e.t2c.x1e.x2f, z5.t1e.t2c.x1e.x2g, z5.t1e.t2c.x1e.x2h,
z5.t1e.t2c.x1f.x2a, z5.t1e.t2c.x1f.x2b, z5.t1e.t2c.x1f.x2c,
z5.t1e.t2c.x1f.x2d, z5.t1e.t2c.x1f.x2e, z5.t1e.t2c.x1f.x2f,
z5.t1e.t2c.x1f.x2g, z5.t1e.t2c.x1f.x2h, z5.t1e.t2c.x1g.x2a,
z5.t1e.t2c.x1g.x2b, z5.t1e.t2c.x1g.x2c, z5.t1e.t2c.x1g.x2d,
z5.t1e.t2c.x1g.x2e, z5.t1e.t2c.x1g.x2f, z5.t1e.t2c.x1g.x2g,
z5.t1e.t2c.x1g.x2h, z5.t1e.t2c.x1h.x2a, z5.t1e.t2c.x1h.x2b,
z5.t1e.t2c.x1h.x2c, z5.t1e.t2c.x1h.x2d, z5.t1e.t2c.x1h.x2e,
z5.t1e.t2c.x1h.x2f, z5.t1e.t2c.x1h.x2g, z5.t1e.t2c.x1h.x2h,
z5.t1e.t2d.x1a.x2a, z5.t1e.t2d.x1a.x2b, z5.t1e.t2d.x1a.x2c,
z5.t1e.t2d.x1a.x2d, z5.t1e.t2d.x1a.x2e, z5.t1e.t2d.x1a.x2f,
z5.t1e.t2d.x1a.x2g, z5.t1e.t2d.x1a.x2h, z5.t1e.t2d.x1b.x2a,
z5.t1e.t2d.x1b.x2b, z5.t1e.t2d.x1b.x2c, z5.t1e.t2d.x1b.x2d,
z5.t1e.t2d.x1b.x2e, z5.t1e.t2d.x1b.x2f, z5.t1e.t2d.x1b.x2g,
z5.t1e.t2d.x1b.x2h, z5.t1e.t2d.x1c.x2a, z5.t1e.t2d.x1c.x2b,
z5.t1e.t2d.x1c.x2c, z5.t1e.t2d.x1c.x2d, z5.t1e.t2d.x1c.x2e,
z5.t1e.t2d.x1c.x2f, z5.t1e.t2d.x1c.x2g, z5.t1e.t2d.x1c.x2h,
z5.t1e.t2d.x1d.x2a, z5.t1e.t2d.x1d.x2b, z5.t1e.t2d.x1d.x2c,
z5.t1e.t2d.x1d.x2d, z5.t1e.t2d.x1d.x2e, z5.t1e.t2d.x1d.x2f,
z5.t1e.t2d.x1d.x2g, z5.t1e.t2d.x1d.x2h, z5.t1e.t2d.x1e.x2a,
z5.t1e.t2d.x1e.x2b, z5.t1e.t2d.x1e.x2c, z5.t1e.t2d.x1e.x2d,
z5.t1e.t2d.x1e.x2e, z5.t1e.t2d.x1e.x2f, z5.t1e.t2d.x1e.x2g,
z5.t1e.t2d.x1e.x2h, z5.t1e.t2d.x1f.x2a, z5.t1e.t2d.x1f.x2b,
z5.t1e.t2d.x1f.x2c, z5.t1e.t2d.x1f.x2d, z5.t1e.t2d.x1f.x2e,
z5.t1e.t2d.x1f.x2f, z5.t1e.t2d.x1f.x2g, z5.t1e.t2d.x1f.x2h,
z5.t1e.t2d.x1g.x2a, z5.t1e.t2d.x1g.x2b, z5.t1e.t2d.x1g.x2c,
z5.t1e.t2d.x1g.x2d, z5.t1e.t2d.x1g.x2e, z5.t1e.t2d.x1g.x2f,
z5.t1e.t2d.x1g.x2g, z5.t1e.t2d.x1g.x2h, z5.t1e.t2d.x1h.x2a,
z5.t1e.t2d.x1h.x2b, z5.t1e.t2d.x1h.x2c, z5.t1e.t2d.x1h.x2d,
z5.t1e.t2d.x1h.x2e, z5.t1e.t2d.x1h.x2f, z5.t1e.t2d.x1h.x2g,
z5.t1e.t2d.x1h.x2h, z5.t1e.t2e.x1a.x2a, z5.t1e.t2e.x1a.x2b,
z5.t1e.t2e.x1a.x2c, z5.t1e.t2e.x1a.x2d, z5.t1e.t2e.x1a.x2e,
z5.t1e.t2e.x1a.x2f, z5.t1e.t2e.x1a.x2g, z5.t1e.t2e.x1a.x2h,
z5.t1e.t2e.x1b.x2a, z5.t1e.t2e.x1b.x2b, z5.t1e.t2e.x1b.x2c,
z5.t1e.t2e.x1b.x2d, z5.t1e.t2e.x1b.x2e, z5.t1e.t2e.x1b.x2f,
z5.t1e.t2e.x1b.x2g, z5.t1e.t2e.x1b.x2h, z5.t1e.t2e.x1c.x2a,
z5.t1e.t2e.x1c.x2b, z5.t1e.t2e.x1c.x2c, z5.t1e.t2e.x1c.x2d,
z5.t1e.t2e.x1c.x2e, z5.t1e.t2e.x1c.x2f, z5.t1e.t2e.x1c.x2g,
z5.t1e.t2e.x1c.x2h, z5.t1e.t2e.x1d.x2a, z5.t1e.t2e.x1d.x2b,
z5.t1e.t2e.x1d.x2c, z5.t1e.t2e.x1d.x2d, z5.t1e.t2e.x1d.x2e,
z5.t1e.t2e.x1d.x2f, z5.t1e.t2e.x1d.x2g, z5.t1e.t2e.x1d.x2h,
z5.t1e.t2e.x1e.x2a, z5.t1e.t2e.x1e.x2b, z5.t1e.t2e.x1e.x2c,
z5.t1e.t2e.x1e.x2d, z5.t1e.t2e.x1e.x2e, z5.t1e.t2e.x1e.x2f,
z5.t1e.t2e.x1e.x2g, z5.t1e.t2e.x1e.x2h, z5.t1e.t2e.x1f.x2a,
z5.t1e.t2e.x1f.x2b, z5.t1e.t2e.x1f.x2c, z5.t1e.t2e.x1f.x2d,
z5.t1e.t2e.x1f.x2e, z5.t1e.t2e.x1f.x2f, z5.t1e.t2e.x1f.x2g,
z5.t1e.t2e.x1f.x2h, z5.t1e.t2e.x1g.x2a, z5.t1e.t2e.x1g.x2b,
z5.t1e.t2e.x1g.x2c, z5.t1e.t2e.x1g.x2d, z5.t1e.t2e.x1g.x2e,
z5.t1e.t2e.x1g.x2f, z5.t1e.t2e.x1g.x2g, z5.t1e.t2e.x1g.x2h,
z5.t1e.t2e.x1h.x2a, z5.t1e.t2e.x1h.x2b, z5.t1e.t2e.x1h.x2c,
z5.t1e.t2e.x1h.x2d, z5.t1e.t2e.x1h.x2e, z5.t1e.t2e.x1h.x2f,
z5.t1e.t2e.x1h.x2g, z5.t1e.t2e.x1h.x2h Phosphonate Prodrug Compounds The compounds of this invention can be phosphonate prodrug compounds (or conjugates) derived from the compounds of Formula I. For example, the compounds of Formula I can be associated, e.g., structurally linked directly or indirectly with one or more phosphonate groups, especially phosphonate groups capable of modifying bioavailability, efficacy, or targeting site(s) of the compounds. Usually the compounds of Formula I can be directly linked to one or more phosphonate groups through a covalent bond or through a linking group, e.g., a linker. The nature of the linker is not critical provided it does not interfere with the ability of the phosphonate containing compound to function as a therapeutic agent. In general, the phosphonate or the linker can be linked to the compound at any synthetically feasible position on the compound, e.g., any solvent accessible surface by removing a hydrogen or any portion of the compound to provide an open valence for attachment of the phosphonate or the linker.

The variables and definitions of these variables used in the present Phosphonate Prodrug Compound section of this application (e.g., $A^1$, $R^1$, etc.) pertain only to this section of the application, unless otherwise indicated.

In one embodiment, the linking group or linker (which can be designated "L") can include all or a portion of the group $A^0$, $A^1$, $A^2$, $A^3$, or $W^3$ described herein, such as for example, repeating units of alkyloxy (e.g., polyethylenoxy, PEG, polymethyleneoxy) and alkylamino (e.g., polyethyleneamino, Jeffamine™); and diacid ester and amides including succinate, succinamide, diglycolate, malonate, and caproamide.

In another embodiment, the linking group or linker has a molecular weight of from about 20 daltons to about 400 daltons. In yet another embodiment, the linking group or linker has a length of about 5 angstroms to about 300 angstroms. In yet another embodiment, the linking group or linker separates the compound of this invention and the phosphorous of the phosphonate group by about 5 angstroms to about 200 angstroms, inclusive, in length.

In yet another embodiment, the linking group or linker is a divalent, branched or unbranched, saturated or unsaturated, hydrocarbon chain, having from 2 to 25 carbon atoms, wherein one or more (e.g. 1, 2, 3, or 4) of the carbon atoms is optionally replaced by (—O—), and wherein the chain is optionally substituted on carbon with one or more (e.g. 1, 2, 3, or 4) substituents selected from ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo (=O), carboxy, aryl, aryloxy, heteroaryl, and heteroaryloxy.

In yet another embodiment, the linking group or linker is of the formula W-A wherein A is ($C_1$-$C_{24}$)alkyl, ($C_2$-$C_{24}$)alkenyl, ($C_2$-$C_{24}$)alkynyl, ($C_3$-$C_8$)cycloalkyl, ($C_6$-$C_{10}$)aryl or a combination thereof, wherein W is —N(R)C(=O)—, —C(=O)N(R)—, —OC(=O)—, —C(=O)O—, —O—, —S—, —S(O)—, —S(O)$_2$—, —N(R)—, —C(=O)—, or a direct bond; wherein each R is independently H or ($C_1$-$C_6$) alkyl.

In yet another embodiment, the linking group or linker is a divalent radical formed from a peptide or amino acid. In yet another embodiment, the linking group or linker is a divalent radical formed from poly-L-glutamic acid, poly-L-aspartic acid, poly-L-histidine, poly-L-ornithine, poly-L-serine, poly-L-threonine, poly-L-tyrosine, poly-L-leucine, poly-L-lysine-L-phenylalanine, poly-L-lysine or poly-L-lysine-L-tyrosine.

In yet another embodiment, the linking group or linker is of the formula W—(CH$_2$)$_n$ wherein, n is between about 1 and about 10; and W is —N(R)C(=O)—, —C(=O)N(R)—, —OC(=O)—, —C(=O)O—, —O—, —S—, —S(O)—, —S(O)$_2$—, —C(=O)—, —N(R)—, or a direct bond; wherein each R is independently H or (C$_1$-C$_6$)alkyl. In yet another embodiment, the linking group or linker is methylene, ethylene, or propylene. In still another embodiment, the linking group or linker is attached to the phosphonate group through a carbon atom of the linker.

In one aspect, the compounds of this invention can be linked to one or more phosphonate groups capable of providing tissue or cell selection to the compounds, e.g., capable of directing the compounds to desired target tissue(s) or cell(s), especially tissues or cells associated with infections or inflammations including without any limitation white blood cells.

In another aspect, the compounds of this invention can be linked to one or more phosphonate groups capable of inducing or triggering an enzymatic activation, e.g., one or more in vivo enzymatic cleavages or modifications which could result in an intracellular accumulation of the cleaved or modified compounds. For example, the phosphonate group of the compounds of this invention may cleave in vivo in stages after they have reached the desired site of action, e.g., inside a cell. One mechanism of action inside a cell may entail a first cleavage, e.g., by esterase, to provide a negatively-charged "locked-in" intermediate. Cleavage of a terminal ester grouping in a compound of the invention thus affords an unstable intermediate which releases a negatively charged "locked in" intermediate. After passage inside a cell, intracellular enzymatic cleavage or modification of the phosphonate or prodrug compound may result in an intracellular accumulation of the cleaved or modified compound by a "trapping" mechanism. The cleaved or modified compound may then be "locked-in" the cell by a significant change in charge, polarity, or other physical property change which decreases the rate at which the cleaved or modified compound can exit the cell, relative to the rate at which it entered as the phosphonate prodrug. Other mechanisms by which a therapeutic effect is achieved may be operative as well. In general, enzymes capable of an enzymatic activation mechanism with the phosphonate prodrug compounds of the invention include, but are not limited to, amidases, esterases, microbial enzymes, phospholipases, cholinesterases, and phosphatases.

In one particular aspect, the compounds of this invention can be linked with one or more groups A$^0$; or a pharmaceutically acceptable salt thereof, wherein:

A$^0$ is A$^1$, A$^2$ or W$^3$;
A$^1$ is:

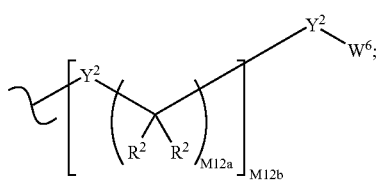

A$^2$ is:

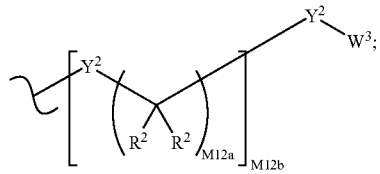

A$^3$ is:

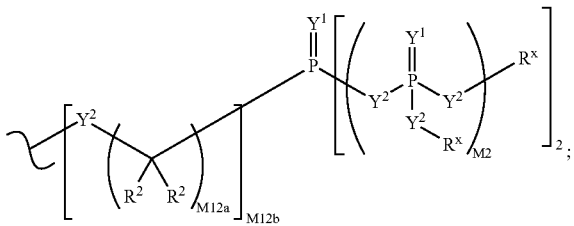

Y$^1$ is independently O, S, N(R$^x$), N(O)(R$^x$), N(OR$^x$), N(O)(OR$^x$), or N(N(R$^x$)(R$^x$));

Y$^2$ is independently a bond, O, N(R$^x$), N(O)(R$^x$), N(OR$^x$), N(O)(OR$^x$), N(N(R$^x$)(R$^x$)), —S(O)$_{M2}$—, or —S(O)$_{M2}$—S(O)$_{M2}$—;

R$^x$ is independently H, R$^1$, W$^3$, a protecting group, or the formula:

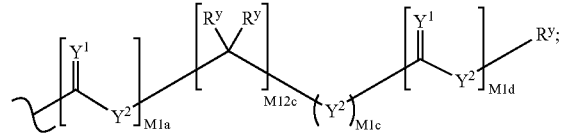

wherein:
R$^y$ is independently H, W$^3$, R$^2$ or a protecting group;
R$^1$ is independently H or alkyl of 1 to 18 carbon atoms;
R$^2$ is independently H, R$^1$, R$^3$ or R$^4$ wherein each R$^4$ is independently substituted with 0 to 3 R$^3$ groups or taken together at a carbon atom, two R$^2$ groups form a ring of 3 to 8 carbons and the ring may be substituted with 0 to 3 R$^3$ groups;
R$^3$ is R$^{3a}$, R$^{3b}$, R$^{3c}$ or R$^{3d}$, provided that when R$^3$ is bound to a heteroatom, then R$^3$ is R$^{3c}$ or R$^{3d}$;
R$^{3a}$ is F, Cl, Br, I, —CN, N$_3$ or —NO$_2$;
R$^{3b}$ is Y$^1$;
R$^{3c}$ is —R$^x$, —N(R$^x$)(R$^x$), —SR$^x$, —S(O)R$^x$, —S(O)$_2$R$^x$, —S(O)(OR$^x$), —S(O)$_2$(OR$^x$), —OC(Y$^1$)R$^x$, —OC(Y$^1$)OR$^x$, —OC(Y$^1$)(N(R$^x$)(R$^x$)), —SC(Y$^1$)R$^x$, —SC(Y$^1$)OR$^x$, —SC(Y$^1$)(N(R$^x$)(R$^x$)), —N(R$^x$)C(Y$^1$)R$^x$, —N(R$^x$)C(Y$^1$)OR$^x$, or —N(R$^x$)C(Y$^1$)(N(R$^x$)(R$^x$));
R$^{3d}$ is —C(Y$^1$)R$^x$, —C(Y$^1$)OR$^x$ or —C(Y$^1$)(N(R$^x$)(R$^x$));
R$^4$ is an alkyl of 1 to 18 carbon atoms, alkenyl of 2 to 18 carbon atoms, or alkynyl of 2 to 18 carbon atoms;
R$^5$ is R$^4$ wherein each R$^4$ is substituted with 0 to 3 R$^3$ groups;
R$^{5a}$ is independently alkylene of 1 to 18 carbon atoms, alkenylene of 2 to 18 carbon atoms, or alkynylene of 2-18 carbon atoms any one of which alkylene, alkenylene or alkynylene is substituted with 0-3 R$^3$ groups;
W$^3$ is W$^4$ or W$^5$;
W$^4$ is R$^5$, —C(Y$^1$)R$^5$, —C(Y$^1$)W$^5$, —SO$_2$R$^5$, or —SO$_2$W$^5$;

$W^5$ is carbocycle or heterocycle wherein $W^5$ is independently substituted with 0 to 3 $R^2$ groups;

$W^6$ is $W^3$ independently substituted with 1, 2, or 3 $A^3$ groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1; and

M12c is 0, 1, 2, 3, 4, 5, 6, 7, 8, 9, 10, 11 or 12.

In one specific embodiment, $A^1$ is of the formula:

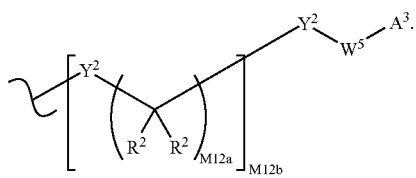

In another specific embodiment $A^1$ is of the formula:

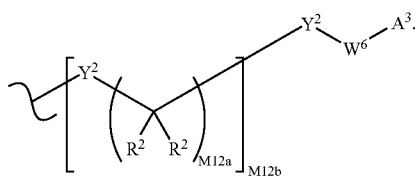

In another specific embodiment $A^1$ is of the formula:

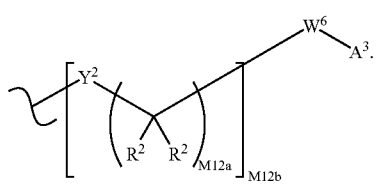

In another specific embodiment $A^1$ is of the formula:

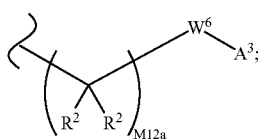

In another specific embodiment $A^1$ is of the formula:

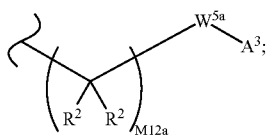

and $W^{5a}$ is a carbocycle or a heterocycle where $W^{5a}$ is independently substituted with 0 or 1 $R^2$ groups. A specific value for M12a is 1.

In another specific embodiment $A^1$ is of the formula:

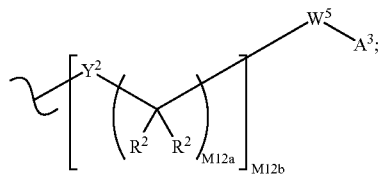

In another specific embodiment $A^1$ is of the formula:

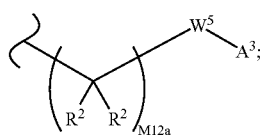

In another specific embodiment $A^1$ is of the formula:

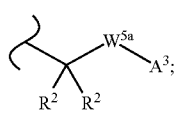

wherein $W^{5a}$ is a carbocycle independently substituted with 0 or 1 $R^2$ groups;

In another specific embodiment $A^1$ is of the formula:

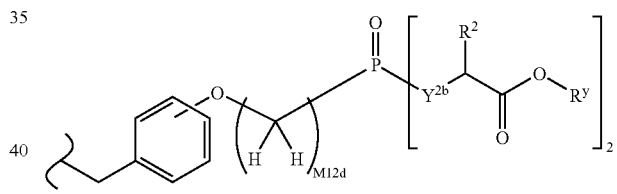

wherein $Y^{2b}$ is O or $N(R^2)$; and M12d is 1, 2, 3, 4, 5, 6, 7 or 8.

In another specific embodiment $A^1$ is of the formula:

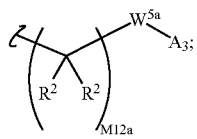

wherein $W^{5a}$ is a carbocycle independently substituted with 0 or 1 $R^2$ groups;

In another specific embodiment $A^1$ is of the formula:

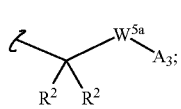

wherein $W^{5a}$ is a carbocycle or heterocycle where $W^{5a}$ is independently substituted with 0 or 1 $R^2$ groups.

In another specific embodiment $A^1$ is of the formula:

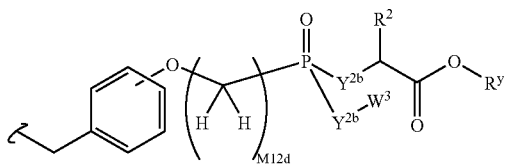

wherein $Y^{2b}$ is O or $N(R^2)$; and M12d is 1, 2, 3, 4, 5, 6, 7 or 8.

In yet another specific embodiment $A^2$ is of the formula:

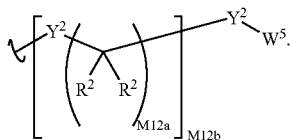

In another specific embodiment $A^2$ is of the formula:

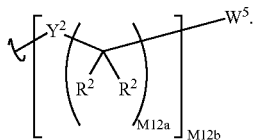

In another specific embodiment M12b is 1.

In another specific embodiment M12b is 0, $Y^2$ is a bond and $W^5$ is a carbocycle or heterocycle where $W^5$ is optionally and independently substituted with 1, 2, or 3 $R^2$ groups.

In another specific embodiment $A^2$ is of the formula:

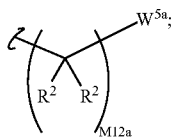

wherein $W^{5a}$ is a carbocycle or heterocycle where $W^{5a}$ is optionally and independently substituted with 1, 2, or 3 $R^2$ groups.

In another specific embodiment M12a is 1.

In another specific embodiment $A^2$ is selected from phenyl, substituted phenyl, benzyl, substituted benzyl, pyridyl and substituted pyridyl.

In another specific embodiment $A^2$ is of the formula:

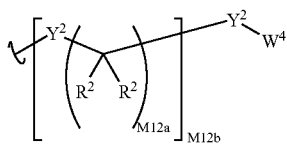

In another specific embodiment $A^2$ is of the formula:

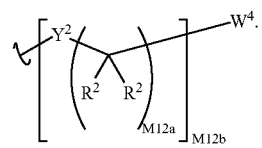

In another specific embodiment M12b is 1.

In yet another specific embodiment $A^3$ is of the formula:

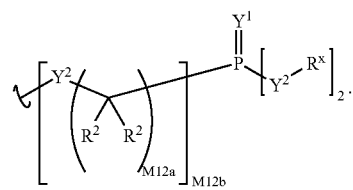

In another specific embodiment $A^3$ is of the formula:

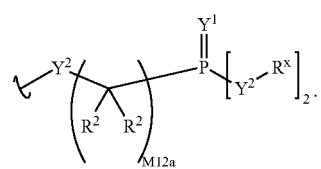

In another specific embodiment $A^3$ is of the formula:

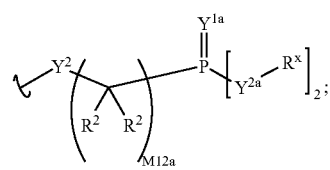

wherein $Y^{1a}$ is O or S; and $Y^{2a}$ is O, $N(R^x)$ or S.

In another specific embodiment $A^3$ is of the formula:

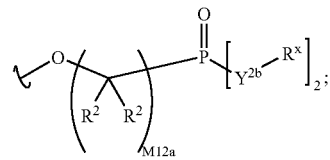

wherein $Y^{2b}$ is O or $N(R^x)$.

In another specific embodiment $A^3$ is of the formula:

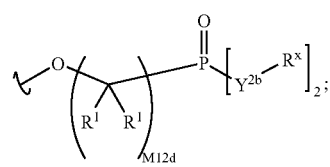

wherein $Y^{2b}$ is O or $N(R^x)$; and M12d is 1, 2, 3, 4, 5, 6, 7 or 8.

In another specific embodiment $A^3$ is of the formula:

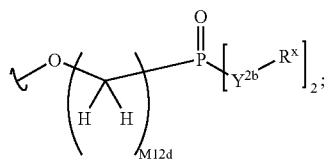

wherein $Y^{2b}$ is O or $N(R^x)$; and M12d is 1, 2, 3, 4, 5, 6, 7 or 8.
In another specific embodiment M12d is 1.
In another specific embodiment $A^3$ is of the formula:

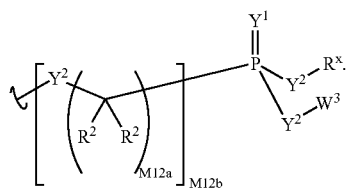

In another specific embodiment $A^3$ is of the formula:

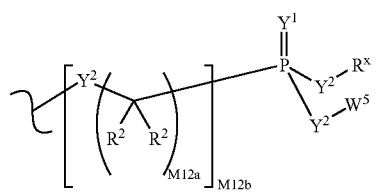

In another specific embodiment $W^5$ is a carbocycle.

In another specific embodiment $A^3$ is of the formula:

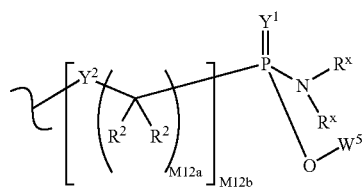

In another specific embodiment $W^5$ is phenyl.
In another specific embodiment $A^3$ is of the formula:

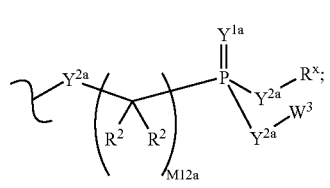

wherein $Y^{1a}$ is O or S; and $Y^{2a}$ is O, $N(R^x)$ or S.

In another specific embodiment $A^3$ is of the formula:

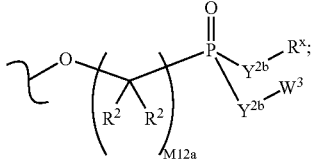

wherein $Y^{2b}$ is O or $N(R^x)$.
In another specific embodiment $A^3$ is of the formula:

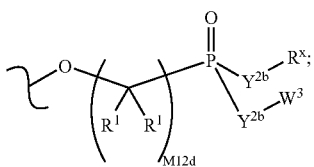

wherein $Y^{2b}$ is O or $N(R^x)$; and M12d is 1, 2, 3, 4, 5, 6, 7 or 8.
In another specific embodiment $R^1$ is H.
In another specific embodiment $A^3$ is of the formula:

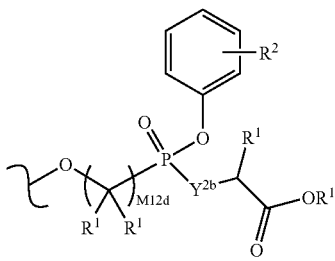

wherein the phenyl carbocycle is substituted with 0, 1, 2, or 3 $R^2$ groups.
In another specific embodiment $A^3$ is of the formula:

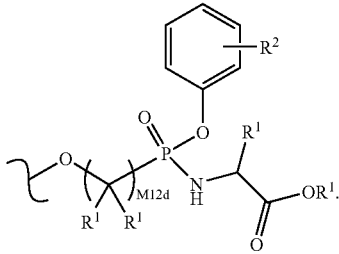

In another specific embodiment $A^3$ is of the formula:

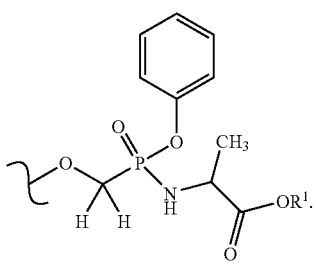

In another specific embodiment $A^3$ is of the formula:

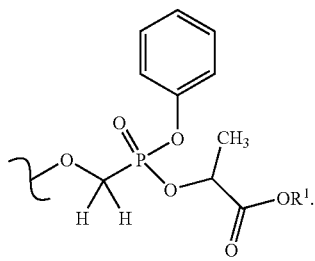

In another specific embodiment $A^3$ is of the formula:

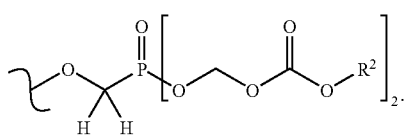

In another specific embodiment $A^3$ is of the formula:

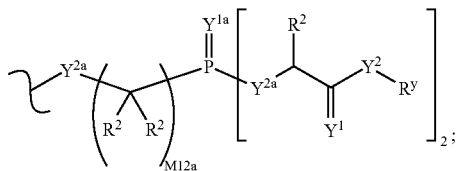

wherein $Y^{1a}$ is O or S; and $Y^{2a}$ is O, $N(R^2)$ or S.

In another specific embodiment $A^3$ is of the formula:

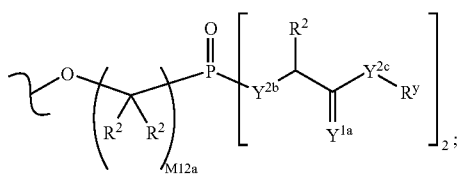

wherein $Y^{1a}$ is O or S; $Y^{2b}$ is O or $N(R^2)$; and $Y^{2c}$ is O, $N(R^y)$ or S.

In another specific embodiment $A^3$ is of the formula:

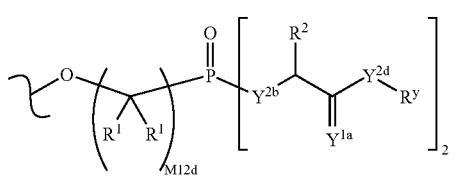

wherein $Y^{1a}$ is O or S; $Y^{2b}$ is O or $N(R^2)$; $Y^{2d}$ is O or $N(R^y)$; and M12d is 1, 2, 3, 4, 5, 6, 7 or 8.

In another specific embodiment $A^3$ is of the formula:

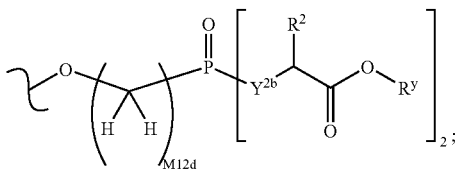

wherein $Y^{2b}$ is O or $N(R^2)$; and M12d is 1, 2, 3, 4, 5, 6, 7 or 8.

In another specific embodiment $A^3$ is of the formula:

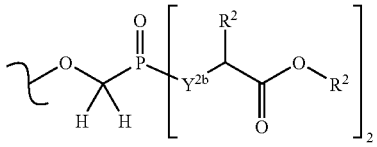

wherein $Y^{2b}$ is O or $N(R^2)$.

In another specific embodiment $A^3$ is of the formula:

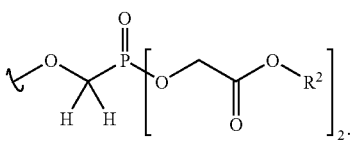

In another specific embodiment $A^3$ is of the formula:

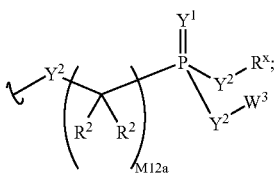

In another specific embodiment $A^3$ is of the formula:

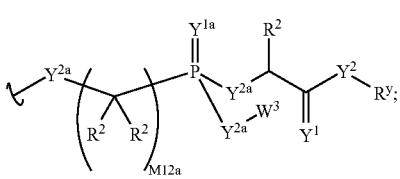

wherein $Y^{1a}$ is O or S; and $Y^{2a}$ is O, $N(R^2)$ or S.

In another specific embodiment $A^3$ is of the formula:

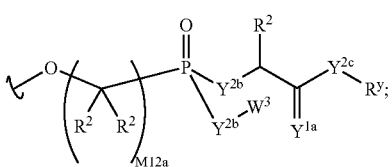

wherein $Y^{1a}$ is O or S; $Y^{2b}$ is O or N($R^2$); and $Y^{2c}$ is O, N($R^y$) or S.

In another specific embodiment $A^3$ is of the formula:

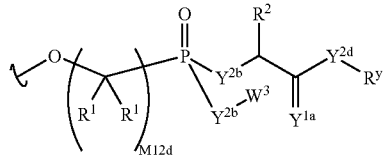

wherein $Y^{1a}$ is O or S; $Y^{2b}$ is O or N($R^2$); $Y^{2d}$ is O or N($R^y$); and M12d is 1, 2, 3, 4, 5, 6, 7 or 8.

In another specific embodiment $A^3$ is of the formula:

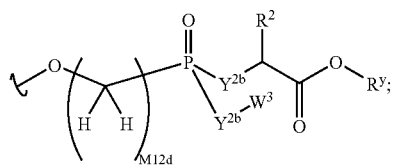

wherein $Y^{2b}$ is O or N($R^2$); and M12d is 1, 2, 3, 4, 5, 6, 7 or 8.

In another specific embodiment $A^3$ is of the formula:

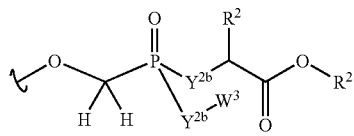

wherein $Y^{2b}$ is O or N($R^2$).

In another specific embodiment $A^3$ is of the formula:

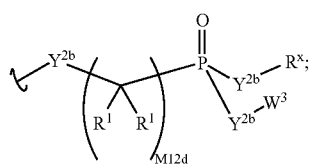

wherein: $Y^{2b}$ is O or N($R^x$); and M12d is 1, 2, 3, 4, 5, 6, 7 or 8.

In another specific embodiment $A^3$ is of the formula:

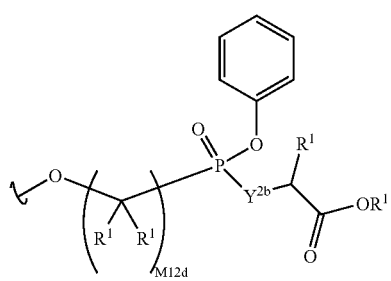

wherein the phenyl carbocycle is substituted with 0, 1, 2, or 3 $R^2$ groups.

In another specific embodiment $A^3$ is of the formula:

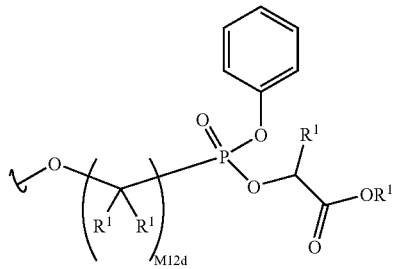

wherein the phenyl carbocycle is substituted with 0, 1, 2, or 3 $R^2$ groups.

In another specific embodiment $A^3$ is of the formula:

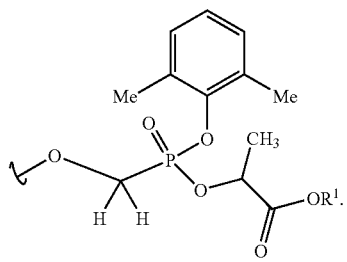

In yet another specific embodiment $A^0$ is of the formula:

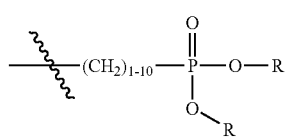

wherein each R is independently $(C_1-C_6)$alkyl.

In yet another specific embodiment $R^x$ is independently H, $R^1$, $W^3$, a protecting group, or the formula:

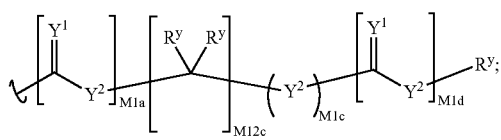

wherein:
$R^y$ is independently H, $W^3$, $R^2$ or a protecting group;
$R^1$ is independently H or alkyl of 1 to 18 carbon atoms;
$R^2$ is independently H, $R^1$, $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups;

In yet another specific embodiment $R^x$ is of the formula:

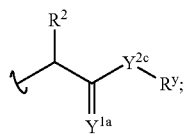

wherein $Y^{1a}$ is O or S; and $Y^{2c}$ is O, N($R^y$) or S.

In yet another specific embodiment $R^x$ is of the formula:

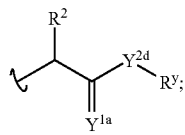

wherein $Y^{1a}$ is O or S; and $Y^{2d}$ is O or N($R^y$).

In yet another specific embodiment $R^x$ is of the formula:

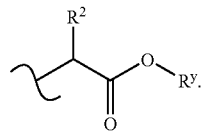

In yet another specific embodiment $R^y$ is hydrogen or alkyl of 1 to 10 carbons.

In yet another specific embodiment $R^x$ is of the formula:

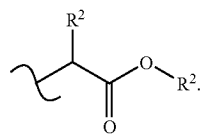

In yet another specific embodiment $R^x$ is of the formula:

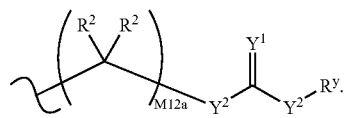

In yet another specific embodiment $R^x$ is of the formula:

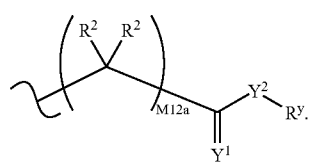

In yet another specific embodiment $Y^1$ is O or S

In yet another specific embodiment $Y^2$ is O, N($R^y$) or S.

In yet another specific embodiment $R^x$ is a group of the formula:

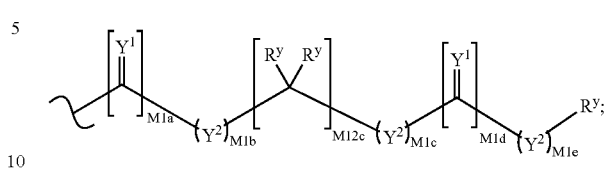

wherein:

m1a, m1b, m1c, m1d and m1e are independently 0 or 1;

m12c is 0, 1, 2, 3, 4, 5, 6, 7, 8, 9, 10, 11 or 12;

$R^y$ is H, $W^3$, $R^2$ or a protecting group;

provided that:

if m1a, m12c, and m1d are 0, then m1b, m1c and m1e are 0;

if m1a and m12c are 0 and m1d is not 0, then m1b and m1c are 0;

if m1a and m1d are 0 and m12c is not 0, then m1b and at least one of m1c and m1e are 0;

if m1a is 0 and m12c and m1d are not 0, then m1b is 0;

if m12c and m1d are 0 and m1a is not 0, then at least two of m1b, m1c and m1e are 0;

if m12c is 0 and m1a and m1d are not 0, then at least one of m1b and m1c are 0; and if m1d is 0 and m1a and m12c are not 0, then at least one of m1c and m1e are 0.

In yet another specific embodiment, the phosphonate prodrug compound of this invention has the formula:

[DRUG]-($A^0$)$_{nn}$ or a pharmaceutically acceptable salt thereof wherein,

DRUG is a compound of this invention nn is 1, 2, or 3;

$A^0$ is $A^1$, $A^2$ or $W^3$ with the proviso that the compound includes at least one $A^1$;

$A^1$ is:

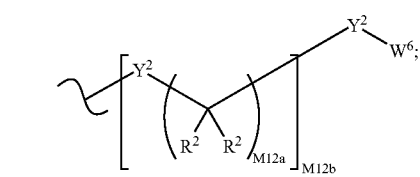

$A^2$ is:

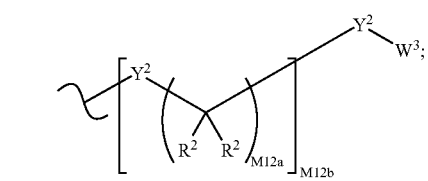

$A^3$ is:

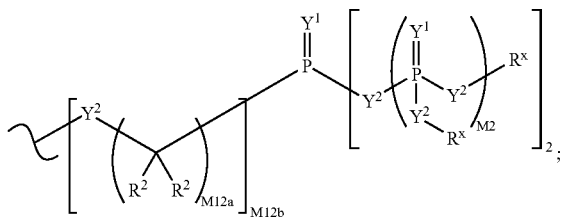

$Y^1$ is independently O, S, $N(R^x)$, $N(O)(R^x)$, $N(OR^x)$, $N(O)(OR^x)$, or $N(N(R^x)(R^x))$;

$Y^2$ is independently a bond, O, $N(R^x)$, $N(O)(R^x)$, $N(OR^x)$, $N(O)(OR^x)$, $N(N(R^x)(R^x))$, $-S(O)_{M2}-$, or $-S(O)_{M2}-S(O)_{M2}-$;

$R^x$ is independently H, $R^1$, $W^3$, a protecting group, or the formula:

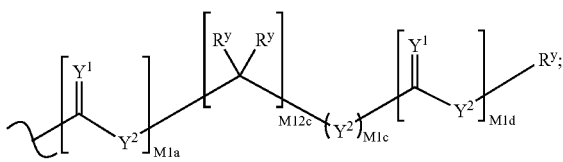

wherein:

$R^y$ is independently H, $W^3$, $R^2$ or a protecting group;

$R^1$ is independently H or alkyl of 1 to 18 carbon atoms;

$R^2$ is independently H, $R^1$, $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, $-CN$, $N_3$ or $-NO_2$;

$R^{3b}$ is $Y^1$;

$R^{3c}$ is $-R^x$, $-N(R^x)(R^x)$, $-SR^x$, $-S(O)R^x$, $-S(O)_2R^x$, $-S(O)(OR^x)$, $-S(O)_2(OR^x)$, $-OC(Y^1)R^x$, $-OC(Y^1)OR^x$, $-OC(Y^1)(N(R^x)(R^x))$, $-SC(Y^1)R^x$, $-SC(Y^1)OR^x$, $-SC(Y^1)(N(R^x)(R^x))$, $-N(R^x)C(Y^1)R^x$, $-N(R^x)C(Y^1)OR^x$, or $-N(R^x)C(Y^1)(N(R^x)(R^x))$;

$R^{3d}$ is $-C(Y^1)R^x$, $-C(Y^1)OR^x$ or $-C(Y^1)(N(R^x)(R^x))$;

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$R^{5a}$ is independently alkylene of 1 to 18 carbon atoms, alkenylene of 2 to 18 carbon atoms, or alkynylene of 2-18 carbon atoms any one of which alkylene, alkenylene or alkynylene is substituted with 0-3 $R^3$ groups;

$W^3$ is $W^4$ or $W^5$;

$W^4$ is $R^5$, $-C(Y^1)R^5$, $-C(Y^1)W^5$, $-SO_2R^5$, or $-SO_2W^5$;

$W^5$ is carbocycle or heterocycle wherein $W^5$ is independently substituted with 0 to 3 $R^2$ groups;

$W^6$ is $W^3$ independently substituted with 1, 2, or 3 $A^3$ groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1;

M12c is 0, 1, 2, 3, 4, 5, 6, 7, 8, 9, 10, 11 or 12;

$X^{66}$ is hydrogen or fluorine; and $X^{67}$ is hydrogen, hydroxy, or acyloxy.

In yet another specific embodiment, the phosphonate prodrug compound of this invention has the formula:

[DRUG]-[L-P(=$Y^1$)—$Y^2$—$R^x$]$_{nn}$ or a pharmaceutically acceptable salt thereof wherein, DRUG is a compound of this invention;

$Y^1$ is independently O, S, $N(R^x)$, $N(O)(R^x)$, $N(OR^x)$, $N(O)(OR^x)$, or $N(N(R^x)(R^x))$;

$Y^2$ is independently a bond, O, $N(R^x)$, $N(O)(R^x)$, $N(OR^x)$, $N(O)(OR^x)$, $N(N(R^x)(R^x))$, $-S(O)_{M2}-$, or $-S(O)_{M2}-S(O)_{M2}-$;

$R^x$ is independently H, $W^3$, a protecting group, or the formula:

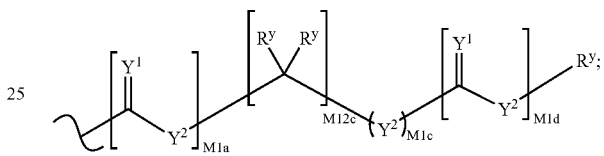

$R^y$ is independently H, $W^3$, $R^2$ or a protecting group;

$R^2$ is independently H, $R^3$ or $R^4$ wherein each $R^4$ is independently substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, $-CN$, $N_3$ or $-NO_2$;

$R^{3b}$ is $Y^1$;

$R^{3c}$ is $-R^x$, $-N(R^x)(R^x)$, $-SR^x$, $-S(O)R^x$, $-S(O)_2R^x$, $-S(O)(OR^x)$, $-S(O)_2(OR^x)$, $-OC(Y^1)R^x$, $-OC(Y^1)OR^x$, $-OC(Y^1)(N(R^x)(R^x))$, $-SC(Y^1)R^x$, $-SC(Y^1)OR^x$, $-SC(Y^1)(N(R^x)(R^x))$, $-N(R^x)C(Y^1)R^x$, $-N(R^x)C(Y^1)OR^x$, or $-N(R^x)C(Y^1)(N(R^x)(R^x))$;

$R^{3d}$ is $-C(Y^1)R^x$, $-C(Y^1)OR^x$ or $-C(Y^1)(N(R^x)(R^x))$;

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$W^3$ is $W^4$ or $W^5$;

$W^4$ is $R^5$, $-C(Y^1)R^5$, $-C(Y^1)W^5$, $-SO_2R^5$, or $-SO_2W^5$;

$W^5$ is carbocycle or heterocycle wherein $W^5$ is independently substituted with 0 to 3 $R^2$ groups;

M2 is 1, 2, or 3;

M1a, M1c, and M1d are independently 0 or 1;

M12c is 0, 1, 2, 3, 4, 5, 6, 7, 8, 9, 10, 11 or 12;

$X^{66}$ is hydrogen or fluorine; and $X^{67}$ is hydrogen, hydroxy, or acyloxy;

nn is 1, 2, or 3; and

L is a linking group.

In another specific embodiment, the phosphonate prodrug compound of this invention has the formula:

[DRUG]-($A^0$)$_{nn}$ or a pharmaceutically acceptable salt thereof wherein,

DRUG is a compound of this invention;

nn is 1, 2, or 3;

$A^0$ is $A^1$, $A^2$, or $W^3$ with the proviso that the compound includes at least one $A^1$;

$A^1$ is:

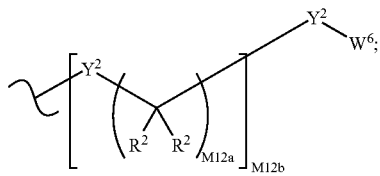

$A^2$ is:

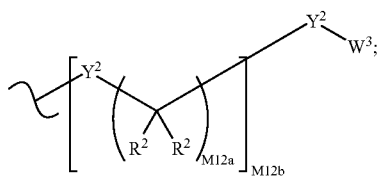

$A^3$ is:

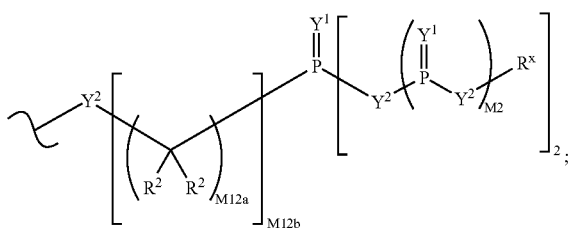

$Y^1$ is independently O, S, N($R^x$), N(O)($R^x$), N(O$R^x$), N(O)(O$R^x$), or N(N($R^x$)($R^x$));

$Y^2$ is independently a bond, O, N($R^x$), N(O)($R^x$), N(O$R^x$), N(O)(O$R^x$), N(N($R^x$)($R^x$)), —S(O)$_{M2}$—, or —S(O)$_{M2}$—S(O)$_{M2}$—;

$R^x$ is independently H, $W^3$, a protecting group, or the formula:

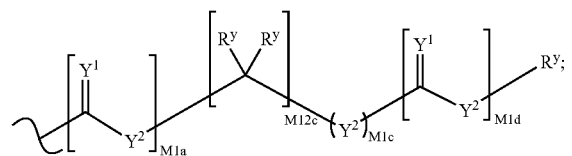

$R^y$ is independently H, $W^3$, $R^2$ or a protecting group;

$R^2$ is independently H, $R^3$ or $R^4$ wherein each $R^4$ is independently substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, —CN, $N_3$ or —$NO_2$;

$R^{3b}$ is $Y^1$;

$R^{3c}$ is —$R^x$, —N($R^x$)($R^x$), —S$R^x$, —S(O)$R^x$, —S(O)$_2R^x$, —S(O)(O$R^x$), —S(O)$_2$(O$R^x$), —OC($Y^1$)$R^x$, —OC($Y^1$)O$R^x$, —OC($Y^1$)(N($R^x$)($R^x$)), —SC($Y^1$)$R^x$, —SC($Y^1$)O$R^x$, —SC($Y^1$)(N($R^x$)($R^x$)), —N($R^x$)C($Y^1$)$R^x$, —N($R^x$)C($Y^1$)O$R^x$, or —N($R^x$)C($Y^1$)(N($R^x$)($R^x$));

$R^{3d}$ is —C($Y^1$)$R^x$, —C($Y^1$)O$R^x$ or —C($Y^1$)(N($R^x$)($R^x$));

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$W^3$ is $W^4$ or $W^5$;

$W^4$ is $R^5$, —C($Y^1$)$R^5$, —C($Y^1$)$W^5$, —SO$_2R^5$, or —SO$_2W^5$;

$W^5$ is carbocycle or heterocycle wherein $W^5$ is independently substituted with 0 to 3 $R^2$ groups;

$W^6$ is $W^3$ independently substituted with 1, 2, or 3 $A^3$ groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1;

M12c is 0, 1, 2, 3, 4, 5, 6, 7, 8, 9, 10, 11 or 12;

$X^{66}$ is hydrogen or fluorine; and $X^{67}$ is hydrogen, hydroxy, or acyloxy.

In one specific embodiment $X^{61}$ is methoxy, ethoxy, n-propoxy, difluoromethoxy, trifluoromethoxy, ethyl, methyl, propyl, or n-butyl)

In phosphonate prodrug compounds of this invention, $W^5$ carbocycles and $W^5$ heterocycles may be independently substituted with 0 to 3 $R^2$ groups. $W^5$ may be a saturated, unsaturated or aromatic ring comprising a mono- or bicyclic carbocycle or heterocycle. $W^5$ may have 3 to 10 ring atoms, e.g., 3 to 7 ring atoms. The $W^5$ rings are saturated when containing 3 ring atoms, saturated or mono-unsaturated when containing 4 ring atoms, saturated, or mono- or di-unsaturated when containing 5 ring atoms, and saturated, mono- or di-unsaturated, or aromatic when containing 6 ring atoms.

A $W^5$ heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S). $W^5$ heterocyclic monocycles may have 3 to 6 ring atoms (2 to 5 carbon atoms and 1 to 2 heteroatoms selected from N, O, and S); or 5 or 6 ring atoms (3 to 5 carbon atoms and 1 to 2 heteroatoms selected from N and S). $W^5$ heterocyclic bicycles have 7 to 10 ring atoms (6 to 9 carbon atoms and 1 to 2 heteroatoms selected from N, O, and S) arranged as a bicyclo [4,5], [5,5], [5,6], or [6,6] system; or 9 to 10 ring atoms (8 to 9 carbon atoms and 1 to 2 hetero atoms selected from N and S) arranged as a bicyclo [5,6] or [6,6] system. The $W^5$ heterocycle may be bonded to $Y^2$ through a carbon, nitrogen, sulfur or other atom by a stable covalent bond.

$W^5$ heterocycles include for example, pyridyl, dihydropyridyl isomers, piperidine, pyridazinyl, pyrimidinyl, pyrazinyl, s-triazinyl, oxazolyl, imidazolyl, thiazolyl, isoxazolyl, pyrazolyl, isothiazolyl, furanyl, thiofuranyl, thienyl, and pyrrolyl. $W^5$ also includes, but is not limited to, examples such as:

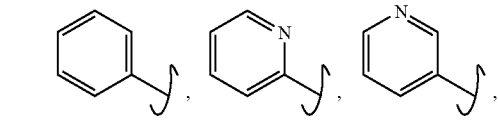

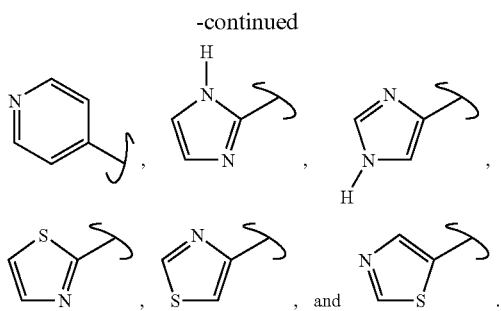

W⁵ carbocycles and heterocycles may be independently substituted with 0 to 3 $R^2$ groups, as defined above. For example, substituted W⁵ carbocycles include:

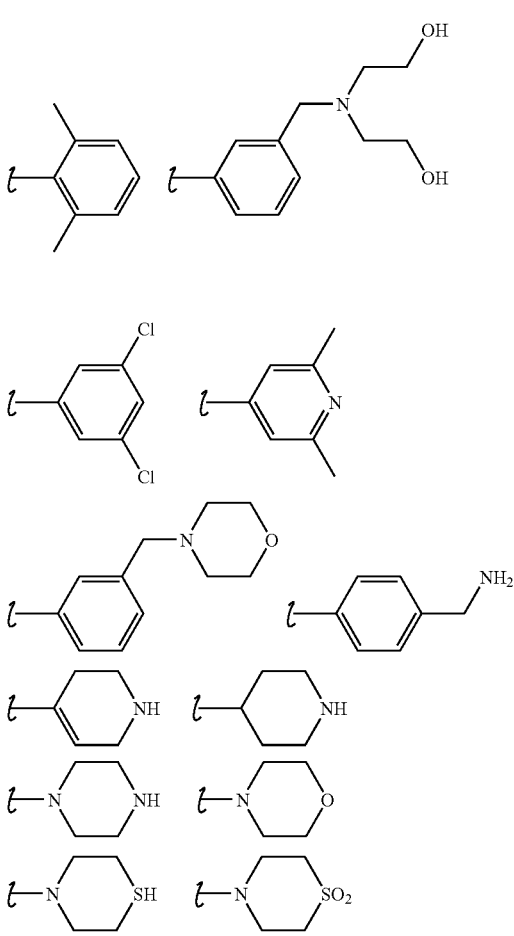

Examples of substituted phenyl carbocycles include:

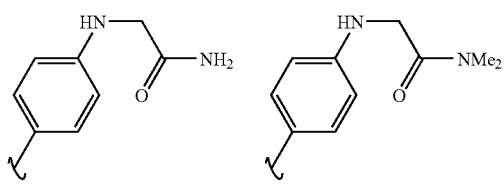

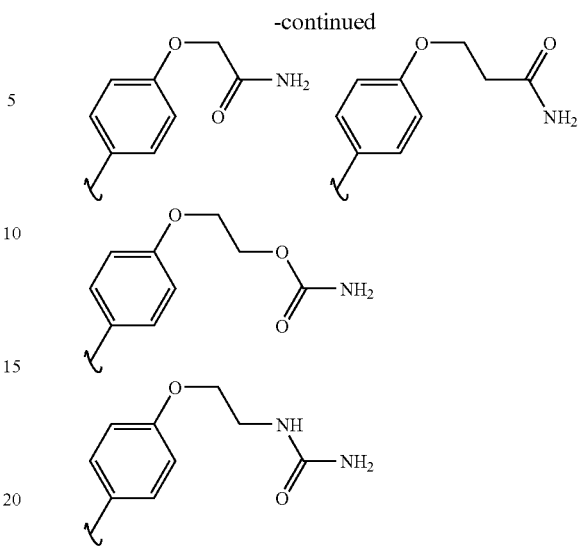

Additional phosphonate groups are disclosed in U.S. patent application U.S. Publication No. 2004100960, the entirety of which is incorporated herein by reference. One skilled in the art will recognize that substituents and other moieties of the compounds under the present Phosphonate Prodrug Compound section of this application should be selected in order to provide a compound which is sufficiently stable, bioavailable, and suitable for providing a pharmaceutically useful compound which has a minimum level of biological activity and can be formulated into an acceptably stable and suitable pharmaceutical composition.

By way of example and not limitation, phosphonate prodrug embodiments of the invention are named below in tabular format (Table 7). These embodiments are of the general formula "MBF":

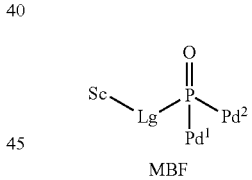

MBF

Each embodiment of MBF is depicted as a substituted nucleus (Sc). Sc is described in formulae 1-14 of Table 1.1 herein, wherein Sc is a generic formula for a compound of Formula I, $A^0$ is the point of covalent attachment of Sc to Lg, nn designates the number of $-Lg-P(O)Pd^1Pd^2$ groups attached to Sc, and T1A, T2A, X1A, X2A, etc. and the terms "Alk", "Ar", and "Het" are as defined above (e.g., in Tables 1-5, and the text preceeding Tables 1-5).

For those embodiments described in Table 7, Sc is a nucleus designated by a number, and each substituent is designated in order by letter or number. Table 1.1 is a schedule of nuclei used in forming the embodiments of Table 7. Each nucleus (Sc) is given a number designation from Table 1.1, and this designation appears first in each embodiment name. Similarly, Tables 10.1 to 10.19 and 20.1 to 20.37 list the selected linking groups (Lg) and prodrug ($Pd^1$ and $Pd^2$) substituents, again by letter or number designation, respectively. Accordingly, a compound of the formula MBF includes compounds having Sc groups based on formula 1-14 herein as well as compounds according to Table 7 below. In all cases, compounds of the formula MBF have groups Lg, $Pd^1$ and $Pd^2$ set forth in the Tables below.

Accordingly, each named embodiment of Table 7 is depicted by a number designating the nucleus from Table 1.1, followed by a letter designating the linking group (Lg) from Table 10.1-10.19, and two numbers designating the two pro-drug groups ($Pd^1$ and $Pd^2$) from Table 20.1-20.36. In graphical tabular form, each embodiment of Table 100 appears as a name having the syntax:

$Sc.Lg.Pd^1.Pd^2$ $Q^1$ and $Q^2$ of the linking groups (Lg), it should be understood, do not represent groups or atoms but are simply connectivity designations. $Q^1$ is the site of the covalent bond to the nucleus (Sc) and $Q^2$ is the site of the covalent bond to the phosphorous atom of formula MBF. Each prodrug group ($Pd^1$ and $Pd^2$) are covalently bonded to the phosphorous atom of MBF at the $A^0$ symbol. Some embodiments of Tables 10.1-10.19 and 20.1-20.36 may be designated as a combination of letters and numbers (Table 10.1-10.19) or number and letter (Table 20.1-20.36). For example there are Table 10 entries for BJ1 and BJ2. In any event, entries of Table 10.1-10.19 always begin with a letter and those of Table 20.1-20.36 always begin with a number. When a nucleus (Sc) is shown enclosed within square brackets ("[ ]") and a covalent bond extends outside the brackets, the point of covalent attachment of Sc to Lg may be at any substitutable site on Sc. Selection of the point of attachment is described herein. By way of example and not limitation, the point of attachment is selected from those depicted in the schemes and examples.

TABLE 1.1

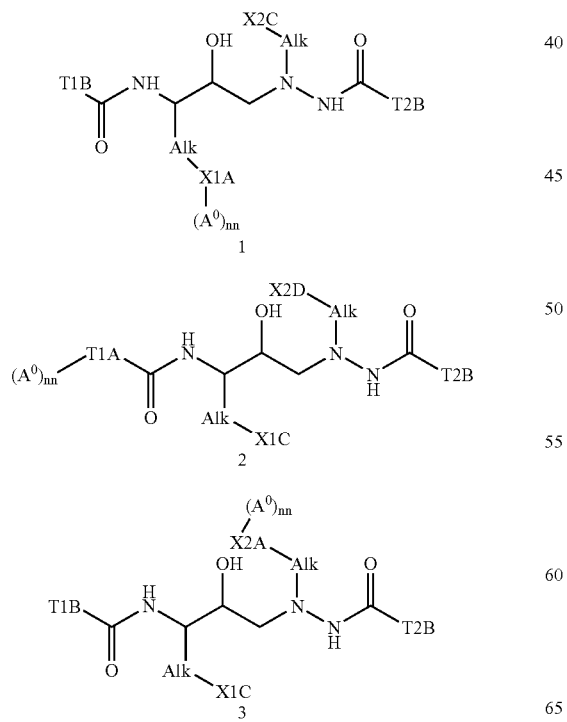

TABLE 1.1-continued

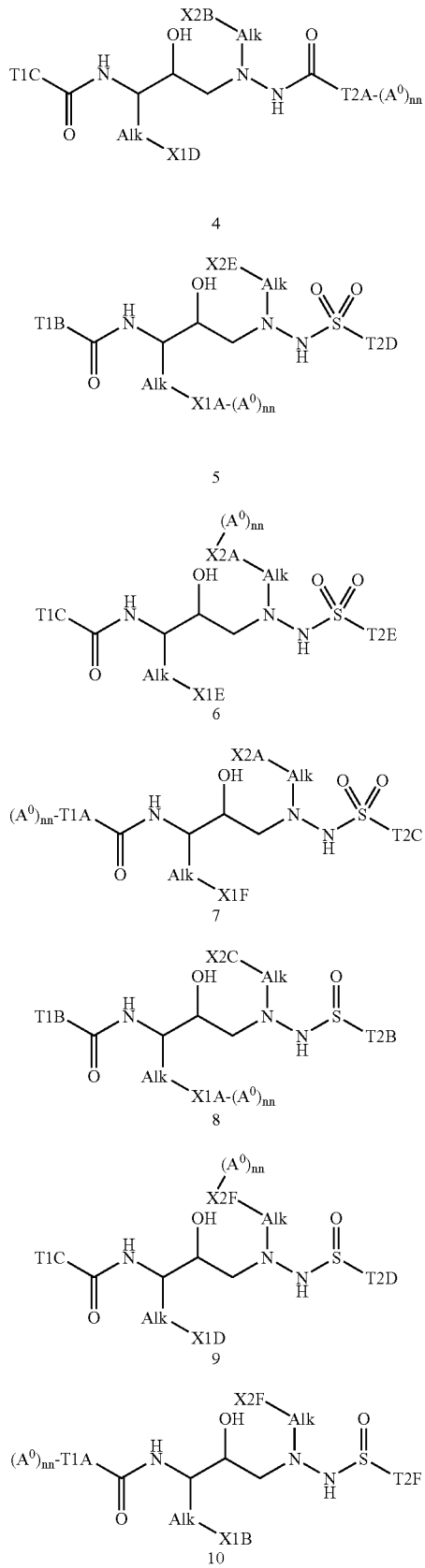

TABLE 1.1-continued
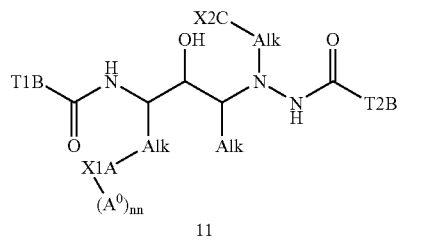
11
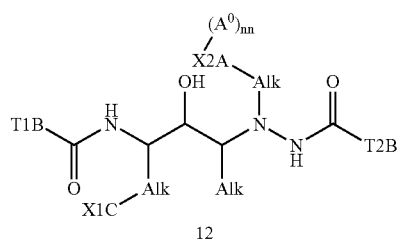
12
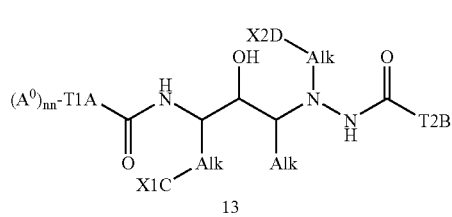
13
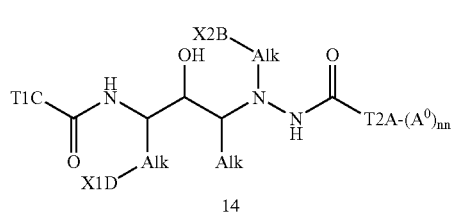
14
TABLE 10.1
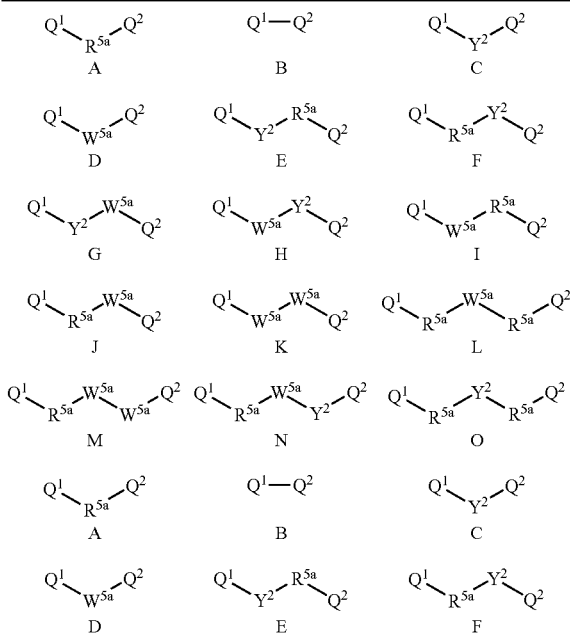
TABLE 10.1-continued
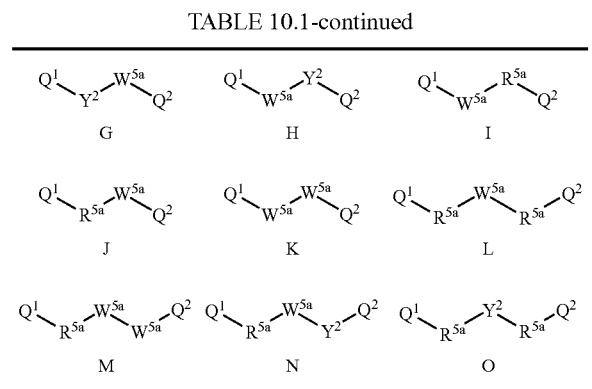
TABLE 10.2
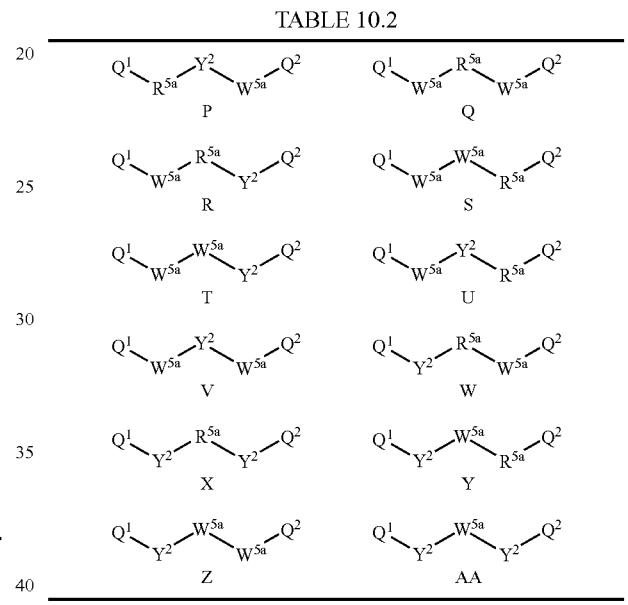
TABLE 10.3
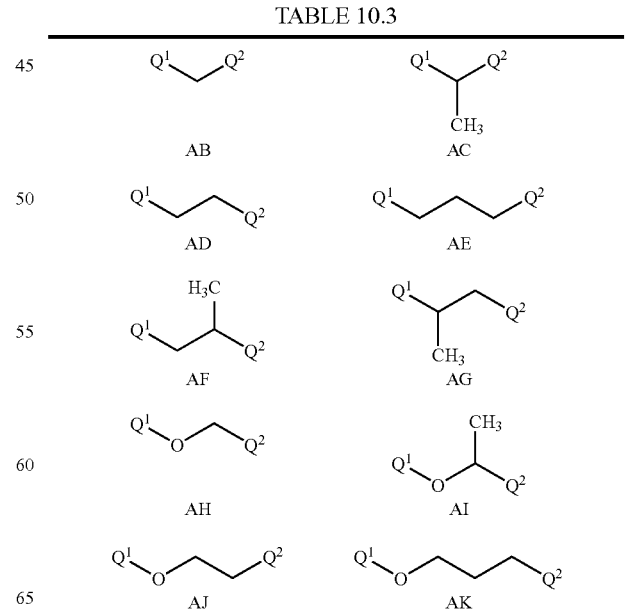

TABLE 10.3-continued
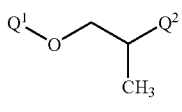
AL
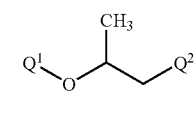
AM
TABLE 10.4
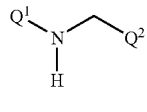
AN
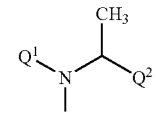
AO
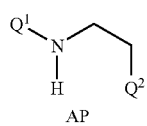
AP
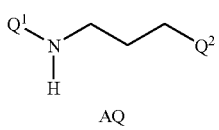
AQ
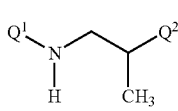
AR
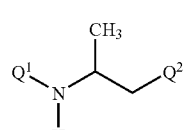
AS
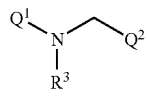
AT
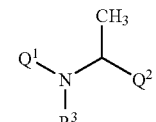
AU
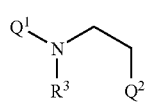
AV
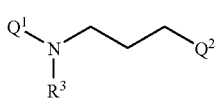
AW
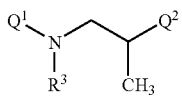
AX
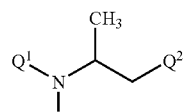
AY
TABLE 10.5
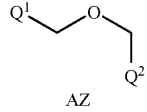
AZ
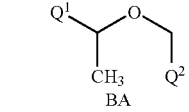
BA
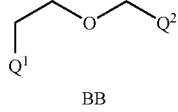
BB
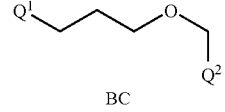
BC
TABLE 10.5-continued
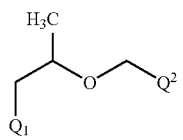
BD
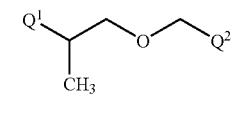
BE
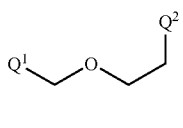
BF
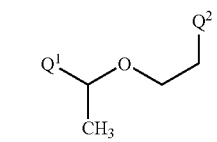
BG
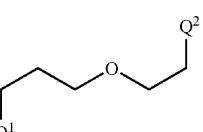
BH
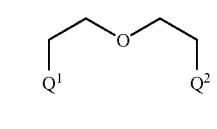
BI
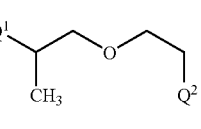
BJ1
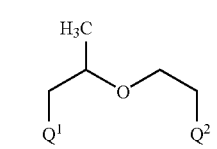
BJ2
TABLE 10.6
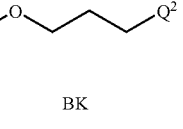
BK
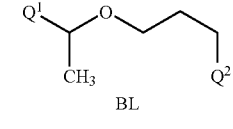
BL
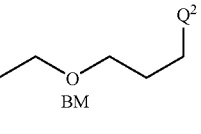
BM
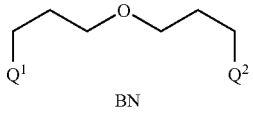
BN
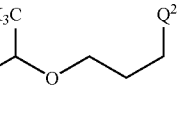
BO
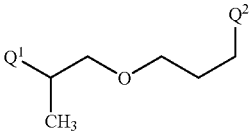
BP
TABLE 10.7
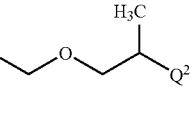
BQ
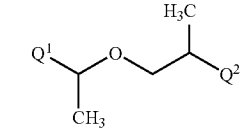
BR
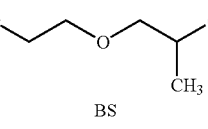
BS
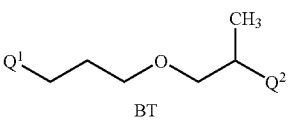
BT TABLE 10.7-continued
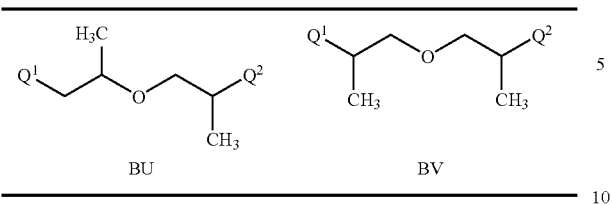
TABLE 10.8
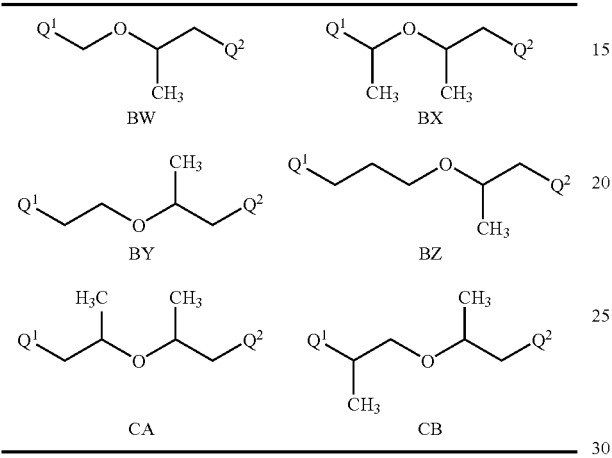
TABLE 10.9
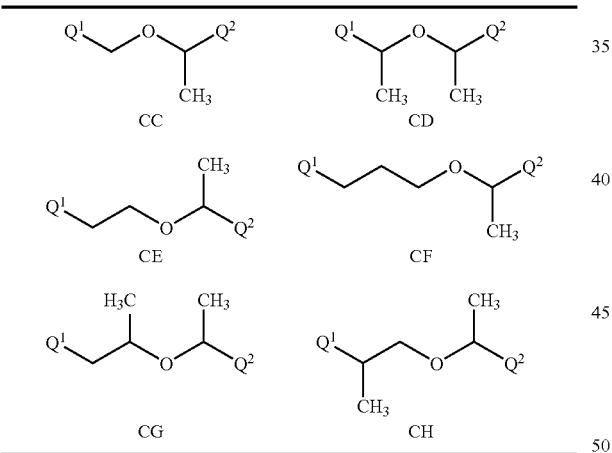
TABLE 10.10
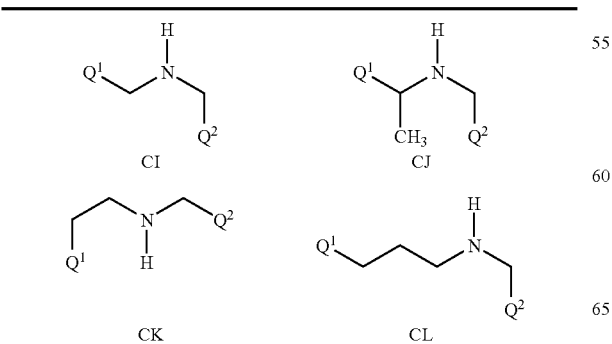
TABLE 10.10-continued
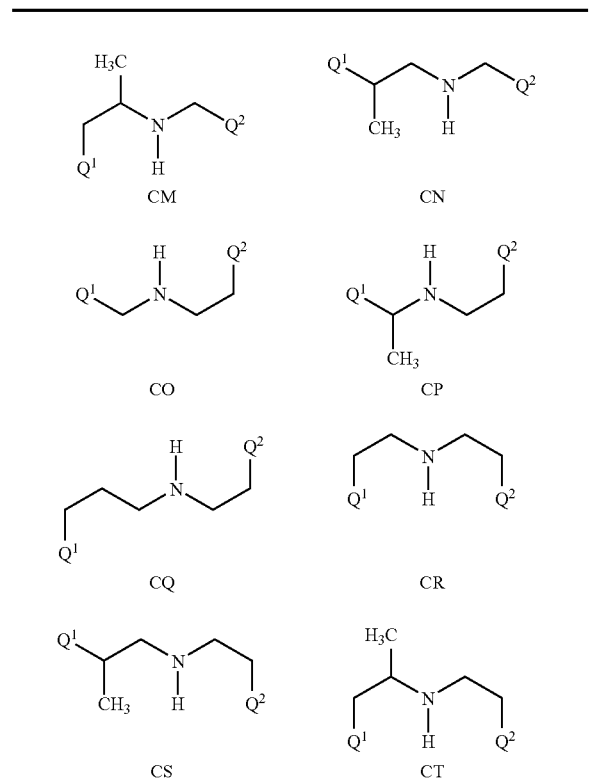
TABLE 10.11
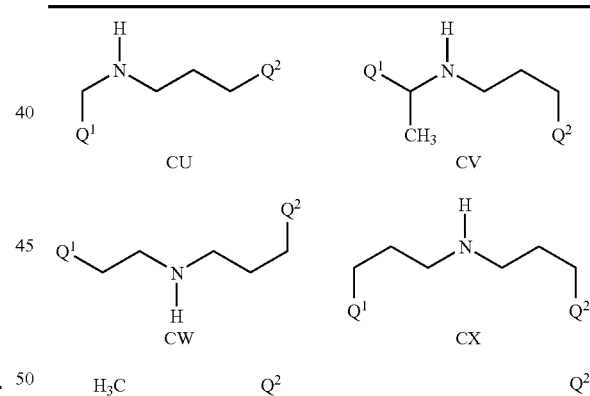
TABLE 10.12
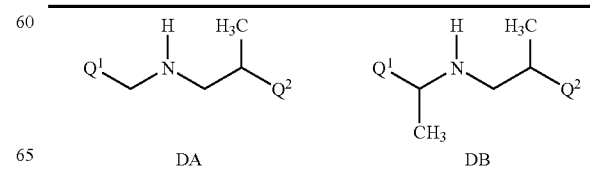

TABLE 10.12-continued
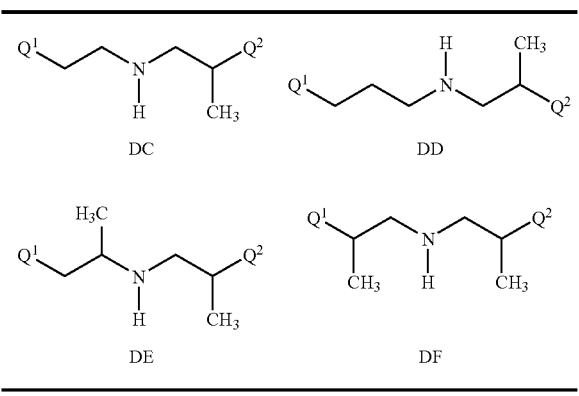
TABLE 10.13
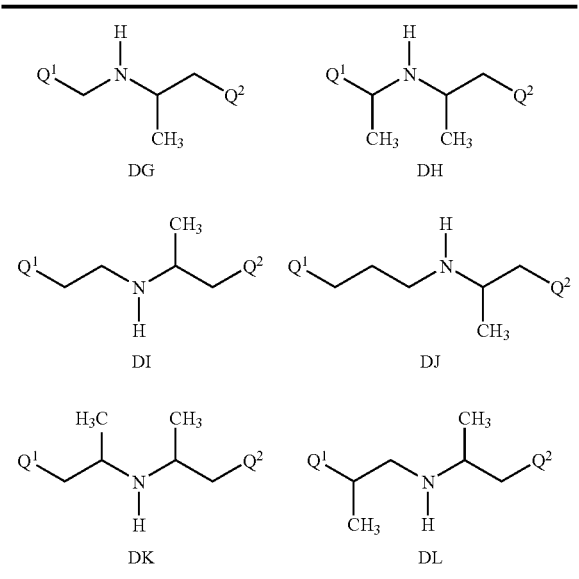
TABLE 10.14
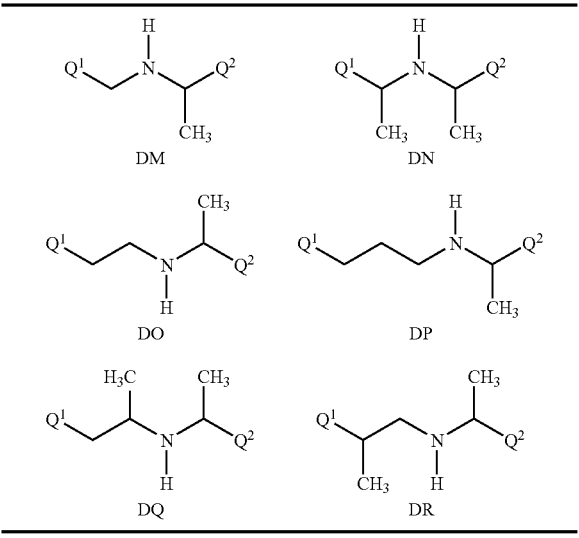
TABLE 10.15
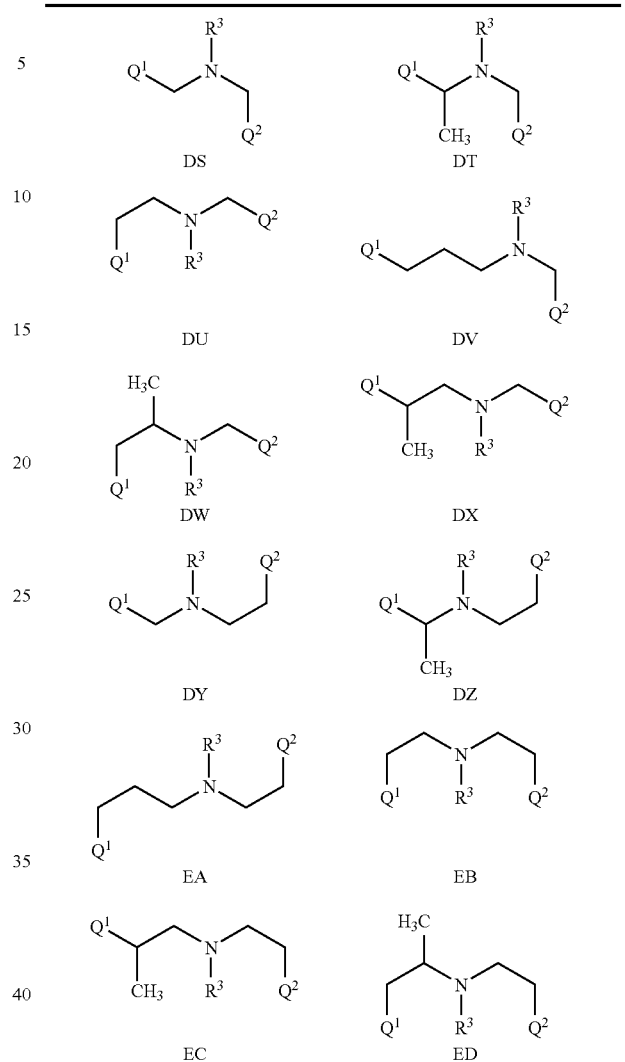
TABLE 10.16
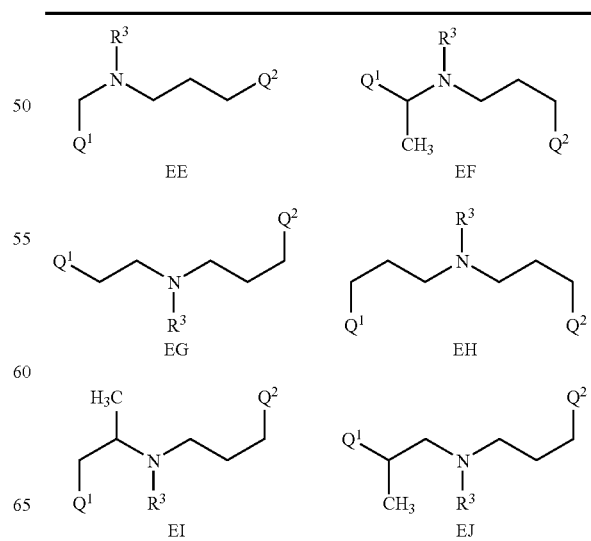

TABLE 10.16-continued
TABLE 10.17
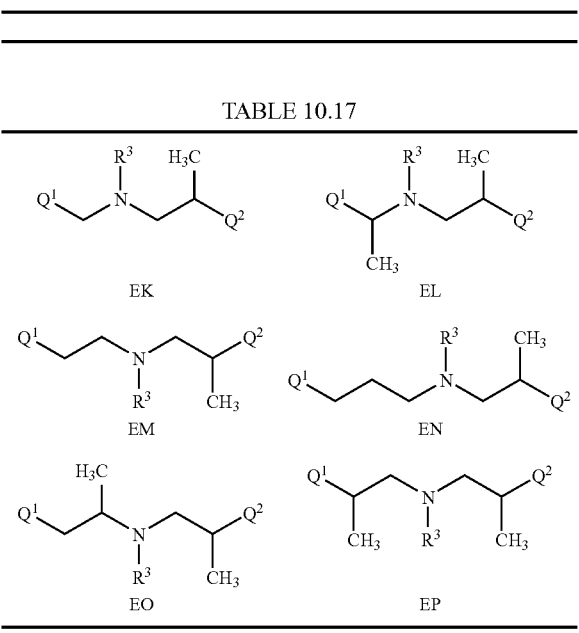
TABLE 10.18
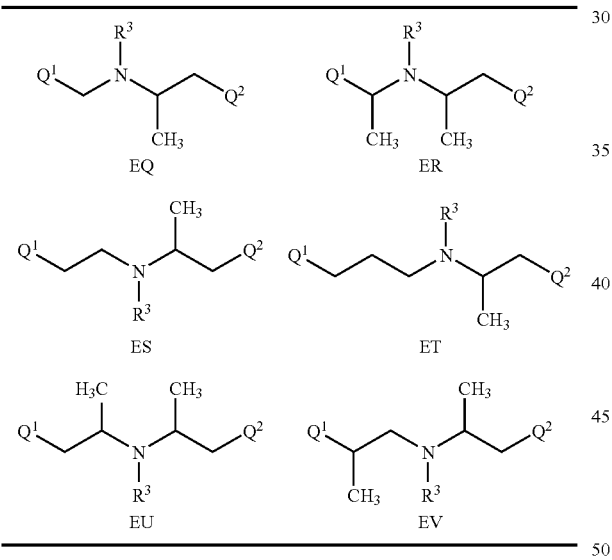
TABLE 10.19
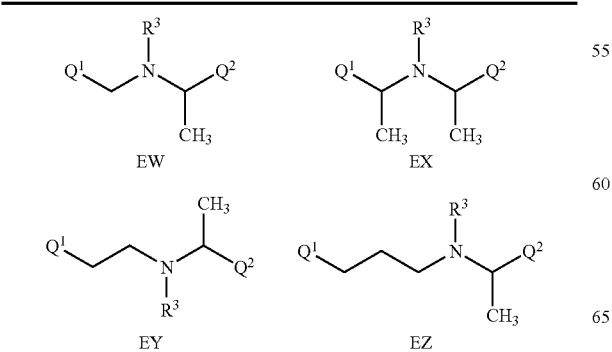
TABLE 10.19-continued
TABLE 20.1
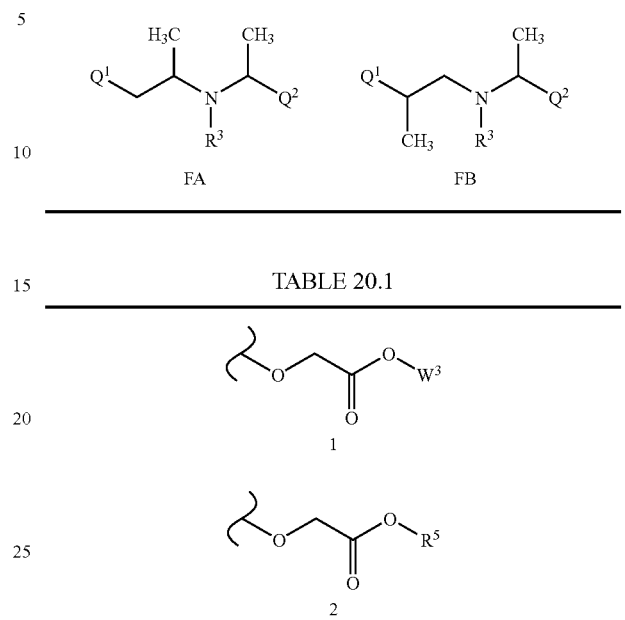

TABLE 20.2
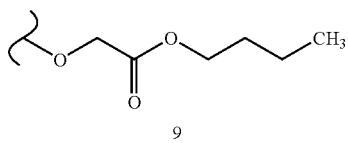
9
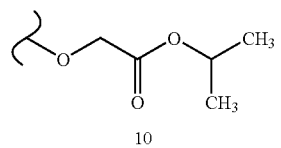
10
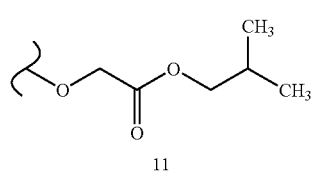
11
TABLE 20.3
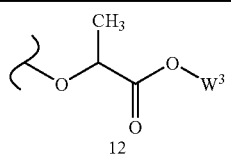
12
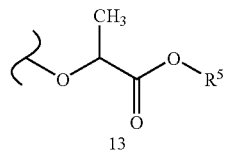
13
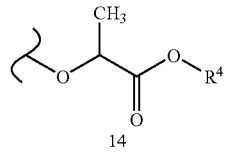
14
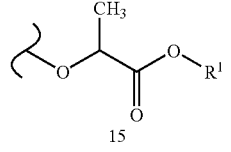
15
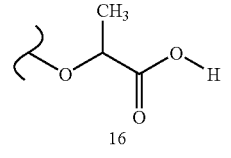
16
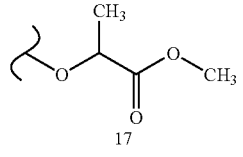
17
TABLE 20.3-continued
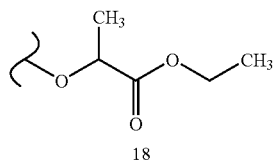
18
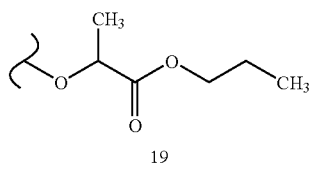
19
TABLE 20.4
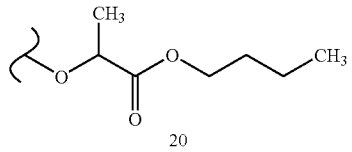
20
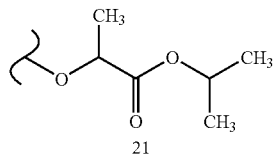
21
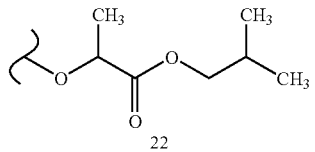
22
TABLE 20.5
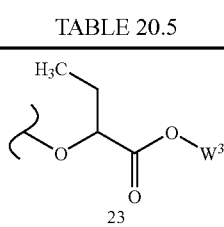
23
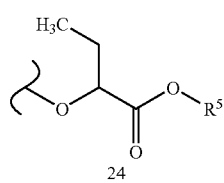
24
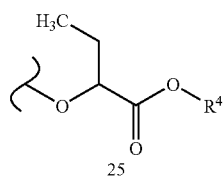
25

TABLE 20.5-continued
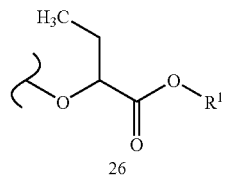
26
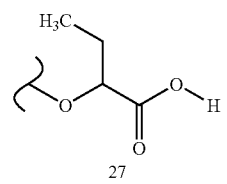
27
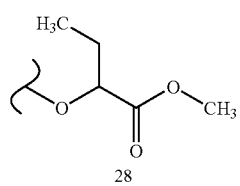
28
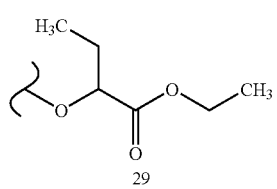
29
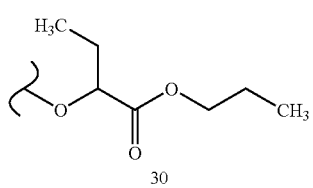
30
TABLE 20.6
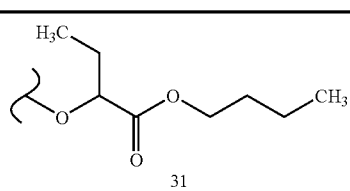
31
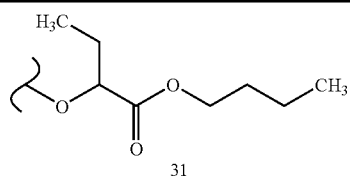
32
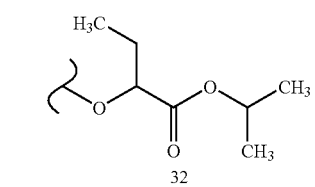
33
TABLE 20.7
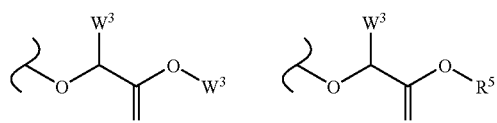
34
35
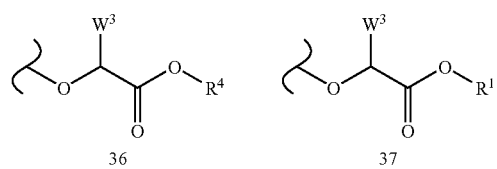
36
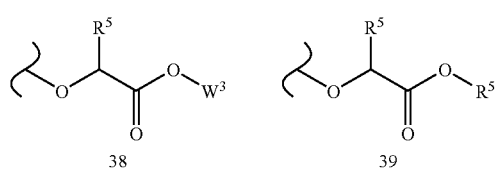
37
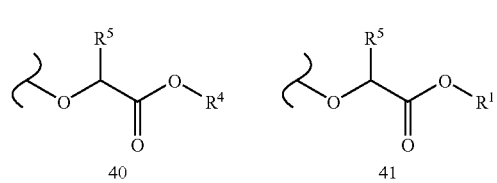
38
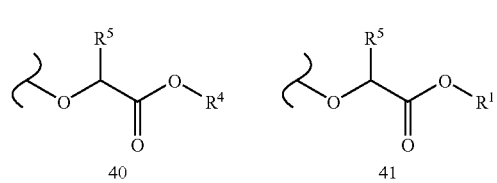
39
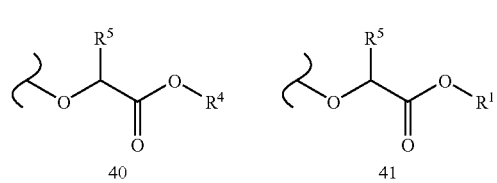
40
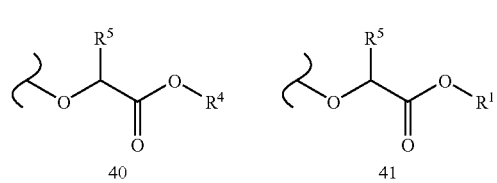
41
TABLE 20.8
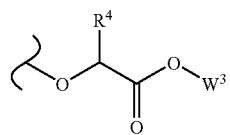
42
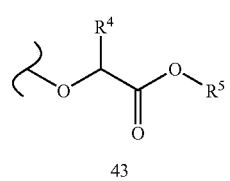
43
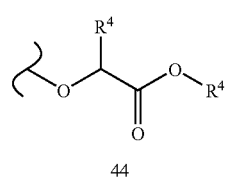
44
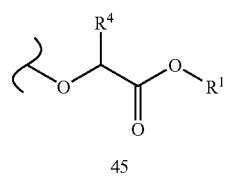
45

TABLE 20.8-continued
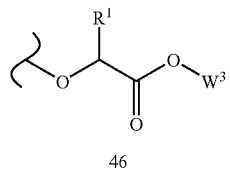
46
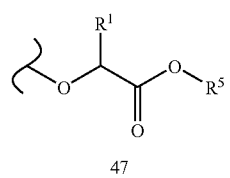
47
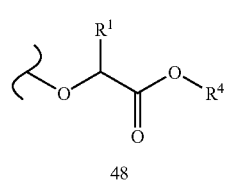
48
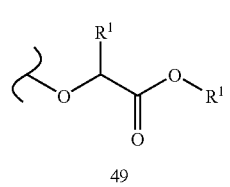
49
TABLE 20.9
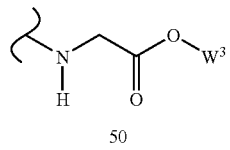
50
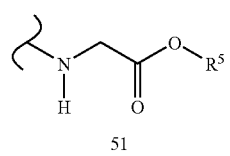
51
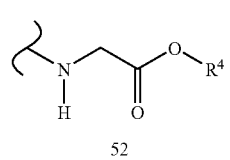
52
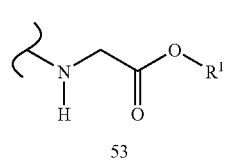
53
TABLE 20.9-continued
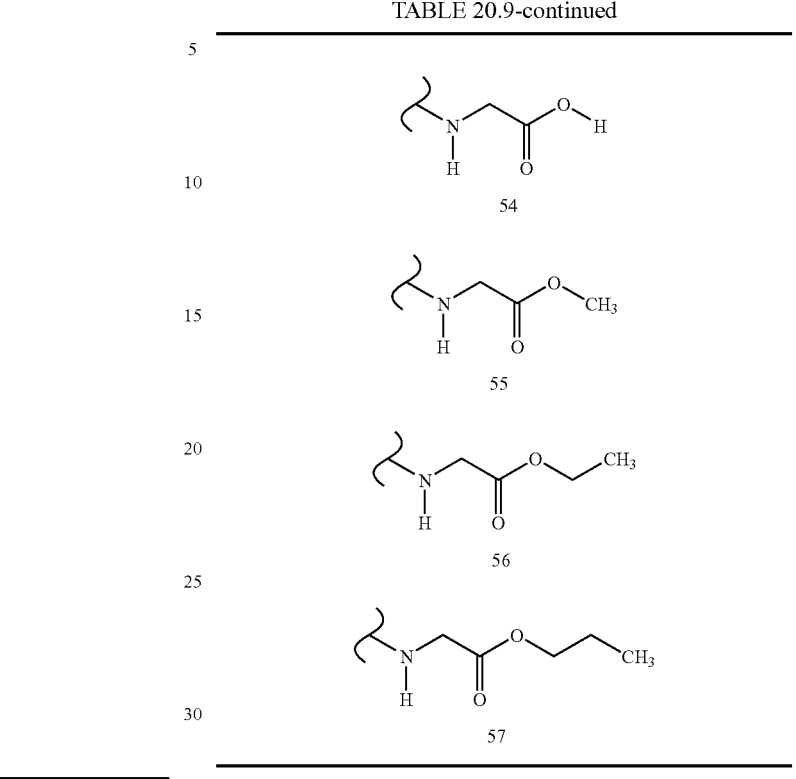
54
55
56
57
TABLE 20.10
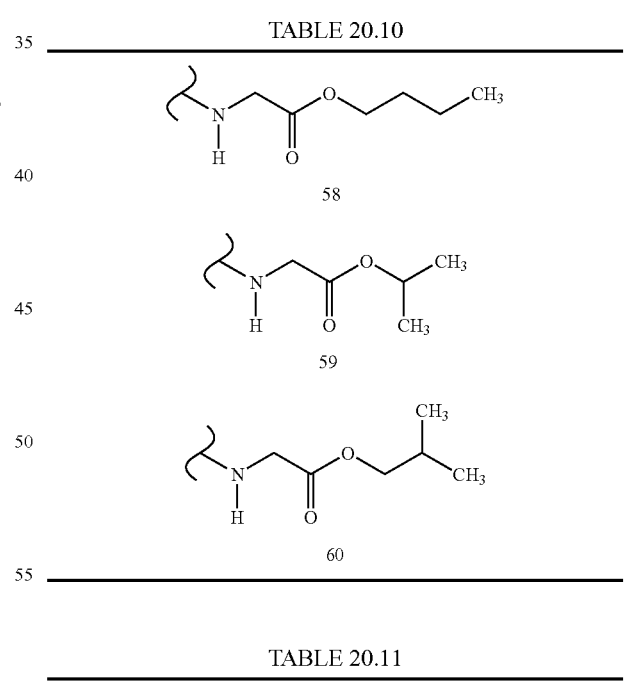
58
59
60
TABLE 20.11
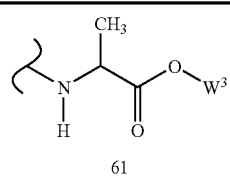
61

TABLE 20.11-continued
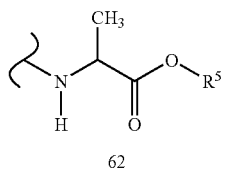
62
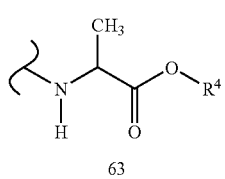
63
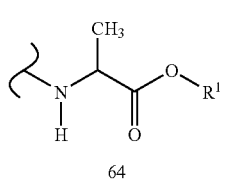
64
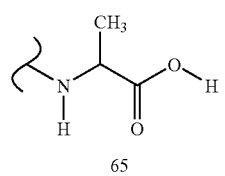
65
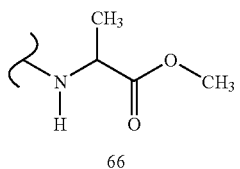
66
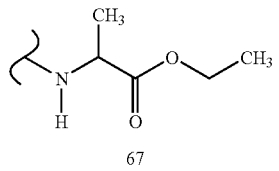
67
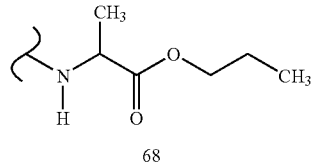
68
TABLE 20.12
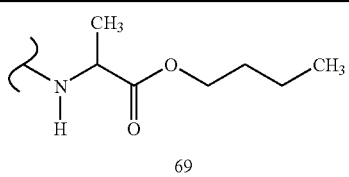
69
TABLE 20.12-continued
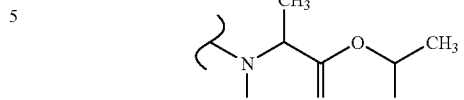
70
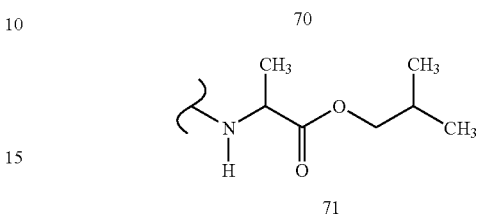
71
TABLE 20.13
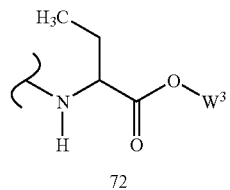
72
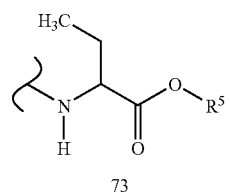
73
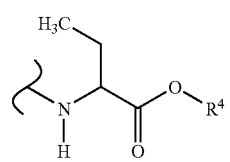
74
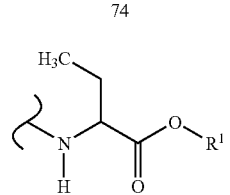
75
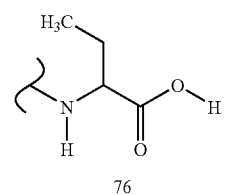
76

TABLE 20.13-continued
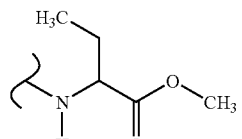
77
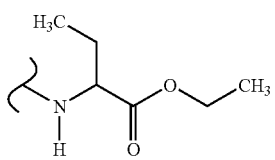
78
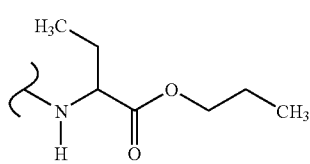
79
TABLE 20.14
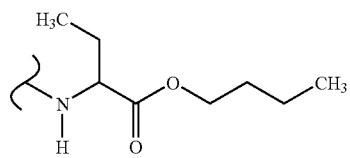
80
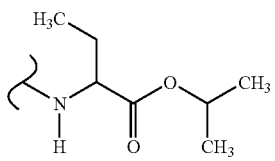
81
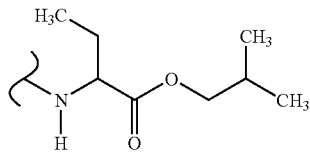
82
TABLE 20.15
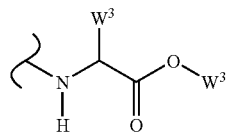
83
TABLE 20.15-continued
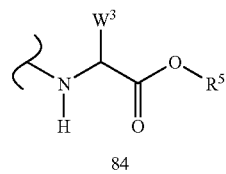
84
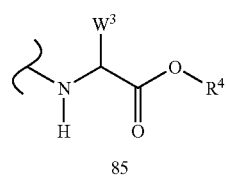
85
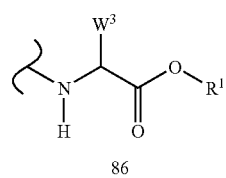
86
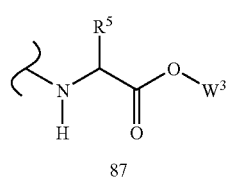
87
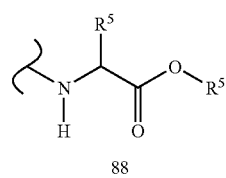
88
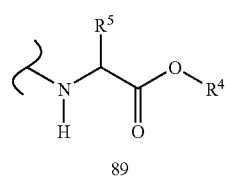
89
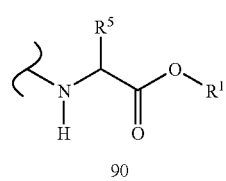
90
TABLE 20.16
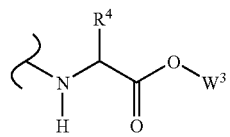
91

TABLE 20.16-continued
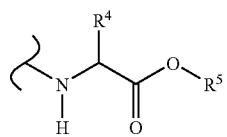
92
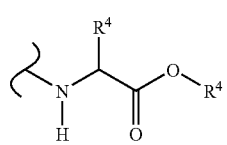
93
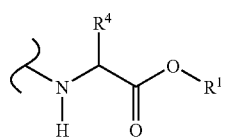
94
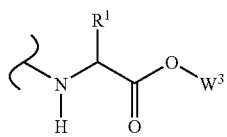
95
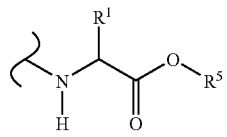
96
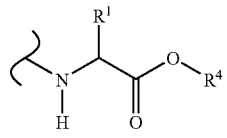
97
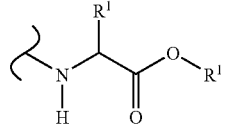
98
TABLE 20.17
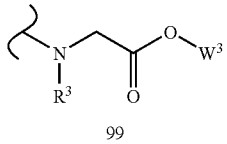
99
TABLE 20.17-continued
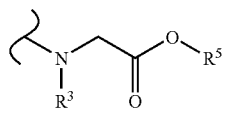
100
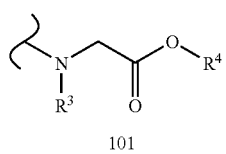
101
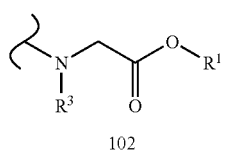
102
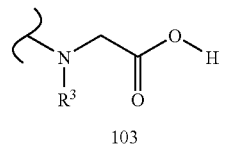
103
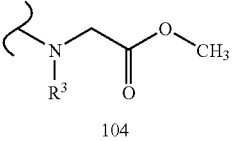
104
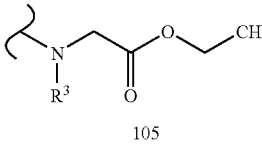
105
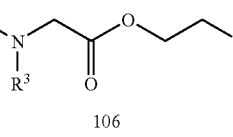
106
TABLE 20.18
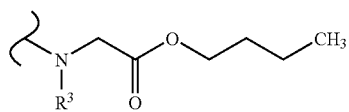
107
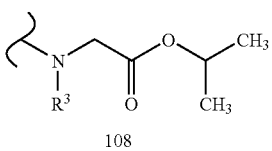
108

TABLE 20.18-continued
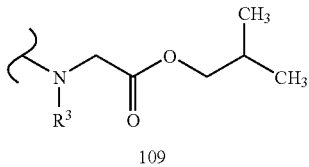
109
TABLE 20.19
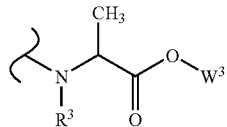
110
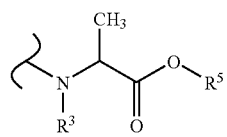
111
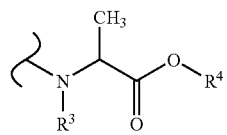
112
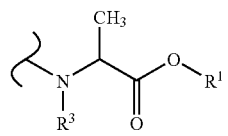
113
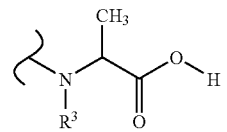
114
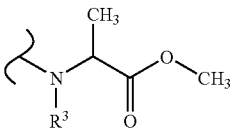
115
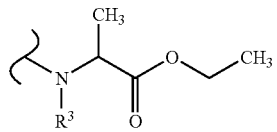
116
TABLE 20.19-continued
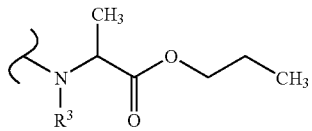
117
TABLE 20.20
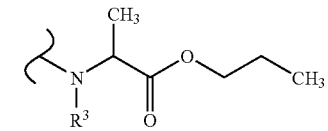
118
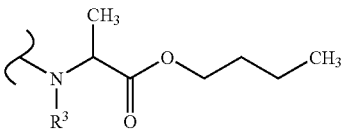
119
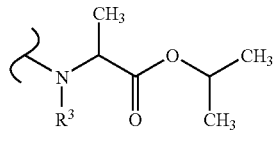
120
TABLE 20.21
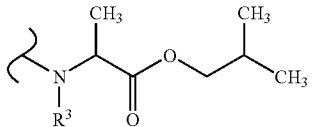
121
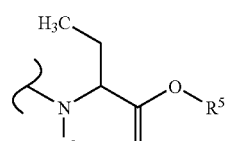
122
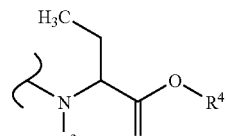
123

TABLE 20.21-continued
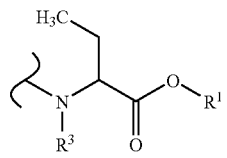
124
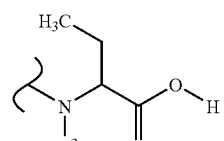
125
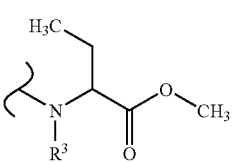
126
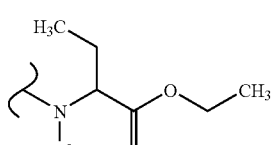
127
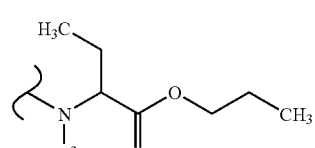
128
TABLE 20.22
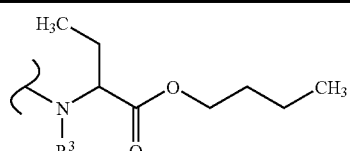
129
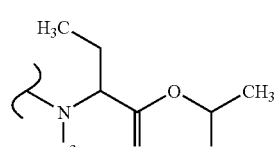
130
TABLE 20.22-continued
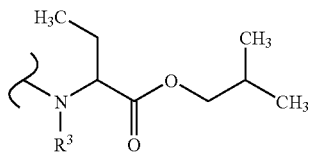
131
TABLE 20.23
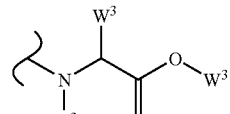　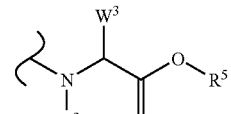
132　　　　133
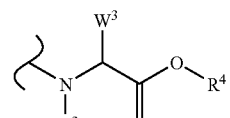　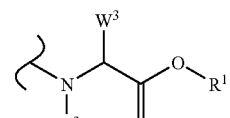
134　　　　135
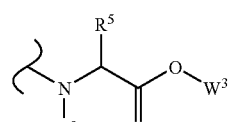　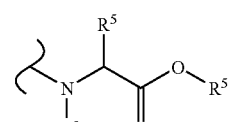
136　　　　137
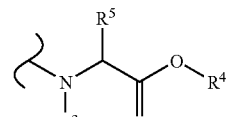　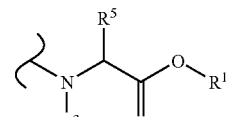
138　　　　139
TABLE 20.24
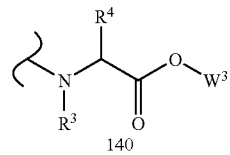　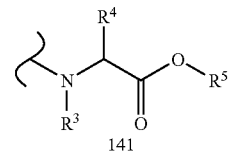
140　　　　141
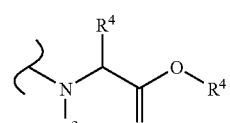　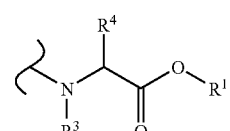
142　　　　143
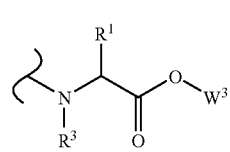　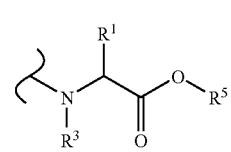
144　　　　145

TABLE 20.24-continued
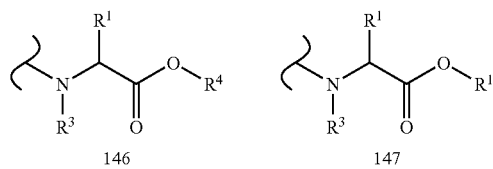
TABLE 20.25
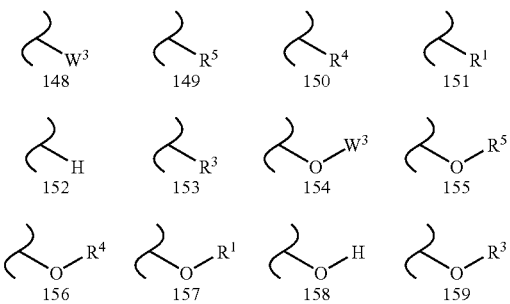
TABLE 20.26
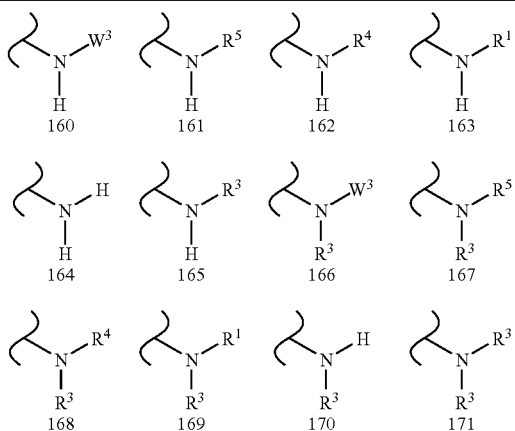
TABLE 20.27
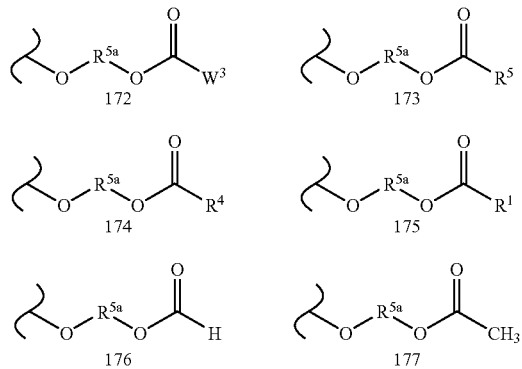
TABLE 20.27-continued
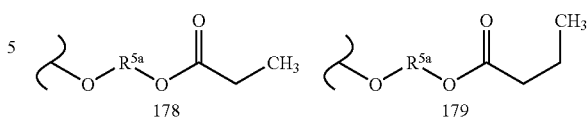
TABLE 20.28
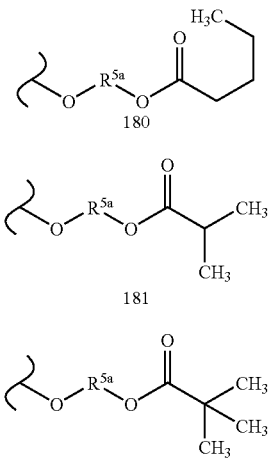
TABLE 20.29
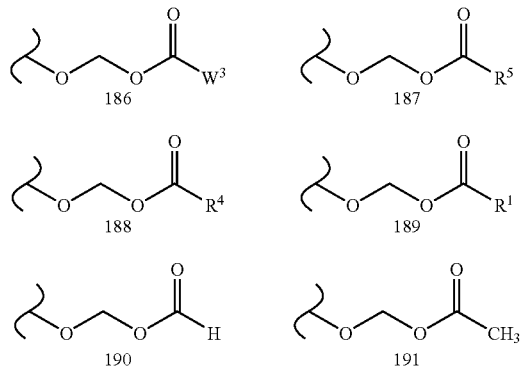

TABLE 20.29-continued
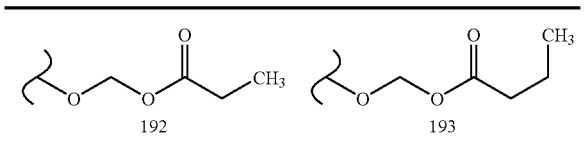
TABLE 20.30
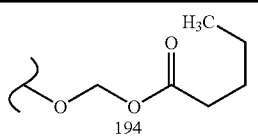
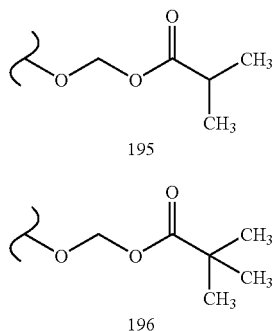
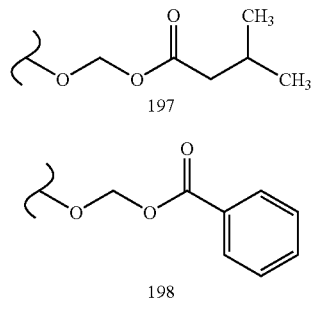
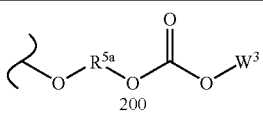
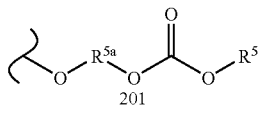
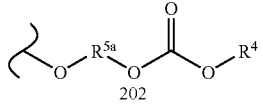
TABLE 20.31
TABLE 20.31-continued
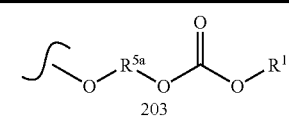
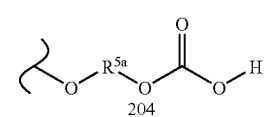
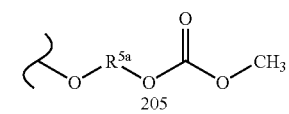
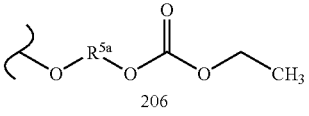
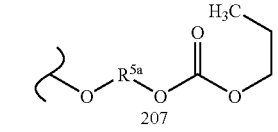
TABLE 20.32
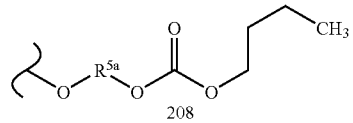
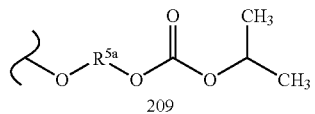
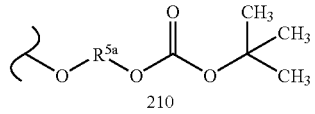
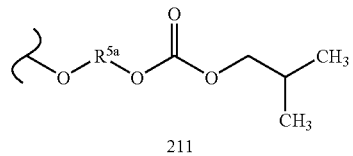
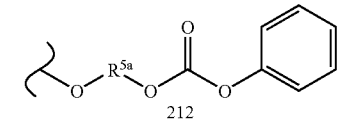
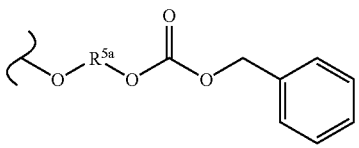

TABLE 20.33
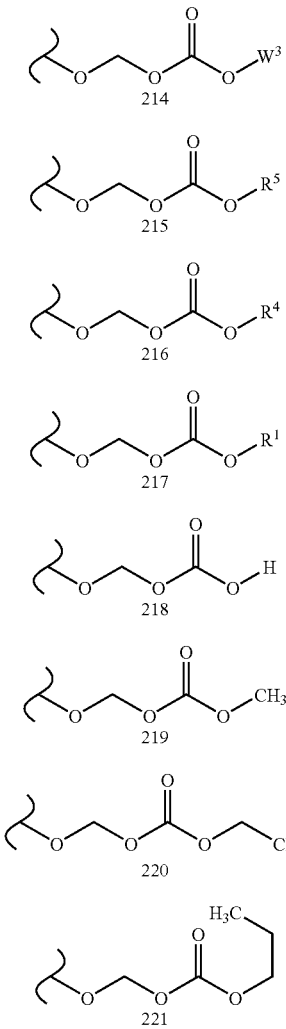
TABLE 20.34
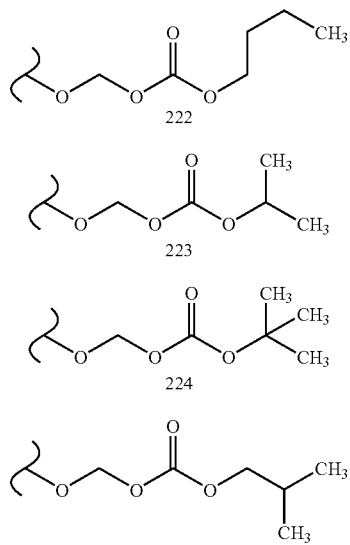
TABLE 20.34-continued
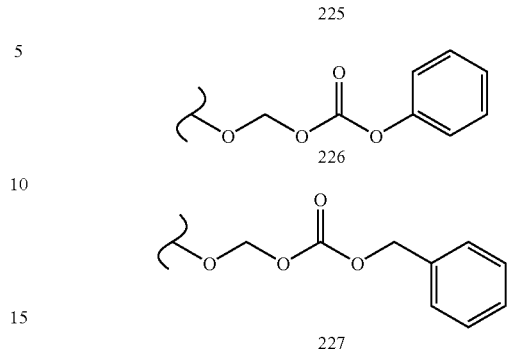
TABLE 20.35
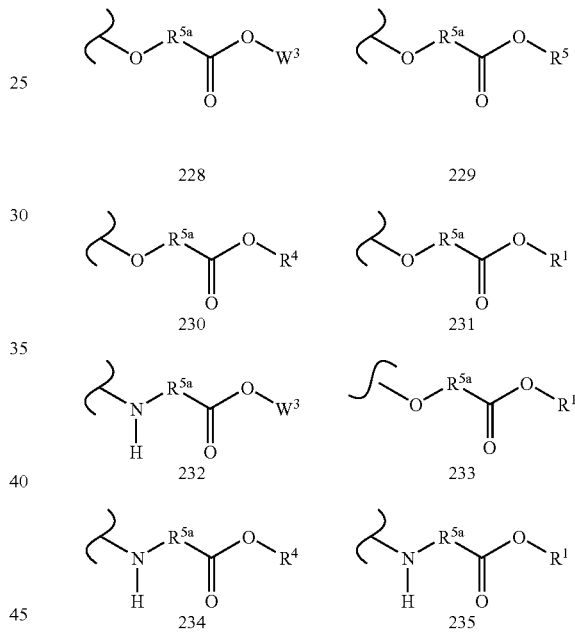
TABLE 20.36
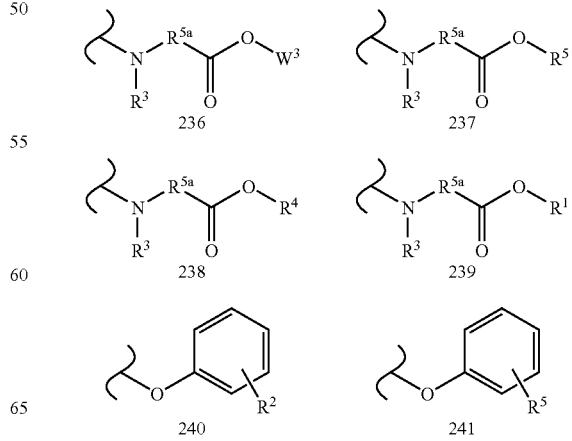

TABLE 20.36-continued 242 (phenyl with R³, CH₂-O linker)
243 (phenyl, CH₂-O linker)

TABLE 20.37

244 (benzyl-O with R²)
245 (benzyl-O with R⁵)
246 (benzyl-O with R³)
247 (benzyl-O)

TABLE 7

Prodrugs of 1.B

1.B.228.228; 1.B.228.229; 1.B.228.230; 1.B.228.231; 1.B.228.236; 1.B.228.237; 1.B.228.238; 1.B.228.239; 1.B.228.154; 1.B.228.157; 1.B.228.166; 1.B.228.169; 1.B.228.172; 1.B.228.175; 1.B.228.240; 1.B.228.244; 1.B.229.228; 1.B.229.229; 1.B.229.230; 1.B.229.231; 1.B.229.236; 1.B.229.237; 1.B.229.238; 1.B.229.239; 1.B.229.154; 1.B.229.157; 1.B.229.166; 1.B.229.169; 1.B.229.172; 1.B.229.175; 1.B.229.240; 1.B.229.244; 1.B.230.228; 1.B.230.229; 1.B.230.230; 1.B.230.231; 1.B.230.236; 1.B.230.237; 1.B.230.238; 1.B.230.239; 1.B.230.154; 1.B.230.157; 1.B.230.166; 1.B.230.169; 1.B.230.172; 1.B.230.175; 1.B.230.240; 1.B.230.244; 1.B.231.228; 1.B.231.229; 1.B.231.230; 1.B.231.231; 1.B.231.236; 1.B.231.237; 1.B.231.238; 1.B.231.239; 1.B.231.154; 1.B.231.157; 1.B.231.166; 1.B.231.169; 1.B.231.172; 1.B.231.175; 1.B.231.240; 1.B.231.244; 1.B.236.228; 1.B.236.229; 1.B.236.230; 1.B.236.231; 1.B.236.236; 1.B.236.237; 1.B.236.238; 1.B.236.239; 1.B.236.154; 1.B.236.157; 1.B.236.166; 1.B.236.169; 1.B.236.172; 1.B.236.175; 1.B.236.240; 1.B.236.244; 1.B.237.228; 1.B.237.229; 1.B.237.230; 1.B.237.231; 1.B.237.236; 1.B.237.237; 1.B.237.238; 1.B.237.239; 1.B.237.154; 1.B.237.157; 1.B.237.166; 1.B.237.169; 1.B.237.172; 1.B.237.175; 1.B.237.240; 1.B.237.244; 1.B.238.228; 1.B.238.229; 1.B.238.230; 1.B.238.231; 1.B.238.236; 1.B.238.237; 1.B.238.238; 1.B.238.239; 1.B.238.154; 1.B.238.157; 1.B.238.166; 1.B.238.169; 1.B.238.172; 1.B.238.175; 1.B.238.240; 1.B.238.244; 1.B.239.228; 1.B.239.229; 1.B.239.230; 1.B.239.231; 1.B.239.236; 1.B.239.237; 1.B.239.238; 1.B.239.239; 1.B.239.154; 1.B.239.157; 1.B.239.166; 1.B.239.169; 1.B.239.172; 1.B.239.175; 1.B.239.240; 1.B.239.244; 1.B.154.228; 1.B.154.229; 1.B.154.230; 1.B.154.231; 1.B.154.236; 1.B.154.237; 1.B.154.238; 1.B.154.239; 1.B.154.154; 1.B.154.157; 1.B.154.166; 1.B.154.169; 1.B.154.172; 1.B.154.175; 1.B.154.240; 1.B.154.244; 1.B.157.228; 1.B.157.229; 1.B.157.230; 1.B.157.231; 1.B.157.236; 1.B.157.237; 1.B.157.238; 1.B.157.239; 1.B.157.154; 1.B.157.157; 1.B.157.166; 1.B.157.169; 1.B.157.172; 1.B.157.175; 1.B.157.240; 1.B.157.244; 1.B.166.228; 1.B.166.229; 1.B.166.230; 1.B.166.231; 1.B.166.236; 1.B.166.237; 1.B.166.238; 1.B.166.239; 1.B.166.154; 1.B.166.157; 1.B.166.166; 1.B.166.169; 1.B.166.172; 1.B.166.175; 1.B.166.240; 1.B.166.244; 1.B.169.228; 1.B.169.229; 1.B.169.230; 1.B.169.231; 1.B.169.236; 1.B.169.237; 1.B.169.238; 1.B.169.239; 1.B.169.154; 1.B.169.157; 1.B.169.166; 1.B.169.169; 1.B.169.172; 1.B.169.175; 1.B.169.240; 1.B.169.244; 1.B.172.228; 1.B.172.229; 1.B.172.230; 1.B.172.231; 1.B.172.236; 1.B.172.237; 1.B.172.238; 1.B.172.239; 1.B.172.154; 1.B.172.157; 1.B.172.166; 1.B.172.169; 1.B.172.172; 1.B.172.175; 1.B.172.240; 1.B.172.244; 1.B.175.228; 1.B.175.229; 1.B.175.230; 1.B.175.231; 1.B.175.236; 1.B.175.237; 1.B.175.238; 1.B.175.239; 1.B.175.154; 1.B.175.157; 1.B.175.166; 1.B.175.169; 1.B.175.172; 1.B.175.175; 1.B.175.240; 1.B.175.244; 1.B.240.228; 1.B.240.229; 1.B.240.230; 1.B.240.231; 1.B.240.236; 1.B.240.237; 1.B.240.238; 1.B.240.239; 1.B.240.154; 1.B.240.157; 1.B.240.166; 1.B.240.169; 1.B.240.172; 1.B.240.175; 1.B.240.240; 1.B.240.244; 1.B.244.228; 1.B.244.229; 1.B.244.230; 1.B.244.231; 1.B.244.236; 1.B.244.237; 1.B.244.238; 1.B.244.239; 1.B.244.154; 1.B.244.157; 1.B.244.166; 1.B.244.169; 1.B.244.172; 1.B.244.175; 1.B.244.240; 1.B.244.244;

Prodrugs of 1.D

1.D.228.228; 1.D.228.229; 1.D.228.230; 1.D.228.231; 1.D.228.236; 1.D.228.237; 1.D.228.238; 1.D.228.239; 1.D.228.154; 1.D.228.157; 1.D.228.166; 1.D.228.169; 1.D.228.172; 1.D.228.175; 1.D.228.240; 1.D.228.244; 1.D.229.228; 1.D.229.229; 1.D.229.230; 1.D.229.231; 1.D.229.236; 1.D.229.237; 1.D.229.238; 1.D.229.239; 1.D.229.154; 1.D.229.157; 1.D.229.166; 1.D.229.169; 1.D.229.172; 1.D.229.175; 1.D.229.240; 1.D.229.244; 1.D.230.228; 1.D.230.229; 1.D.230.230; 1.D.230.231; 1.D.230.236; 1.D.230.237; 1.D.230.238; 1.D.230.239; 1.D.230.154; 1.D.230.157; 1.D.230.166; 1.D.230.169; 1.D.230.172; 1.D.230.175; 1.D.230.240; 1.D.230.244; 1.D.231.228; 1.D.231.229; 1.D.231.230; 1.D.231.231; 1.D.231.236; 1.D.231.237; 1.D.231.238; 1.D.231.239; 1.D.231.154; 1.D.231.157; 1.D.231.166; 1.D.231.169; 1.D.231.172; 1.D.231.175; 1.D.231.240; 1.D.231.244; 1.D.236.228; 1.D.236.229; 1.D.236.230; 1.D.236.231; 1.D.236.236; 1.D.236.237; 1.D.236.238; 1.D.236.239; 1.D.236.154; 1.D.236.157; 1.D.236.166; 1.D.236.169; 1.D.236.172; 1.D.236.175; 1.D.236.240; 1.D.236.244; 1.D.237.228; 1.D.237.229; 1.D.237.230; 1.D.237.231; 1.D.237.236; 1.D.237.237; 1.D.237.238; 1.D.237.239; 1.D.237.154; 1.D.237.157; 1.D.237.166; 1.D.237.169; 1.D.237.172; 1.D.237.175; 1.D.237.240; 1.D.237.244; 1.D.238.228; 1.D.238.229; 1.D.238.230; 1.D.238.231; 1.D.238.236; 1.D.238.237; 1.D.238.238; 1.D.238.239; 1.D.238.154; 1.D.238.157; 1.D.238.166; 1.D.238.169; 1.D.238.172; 1.D.238.175; 1.D.238.240; 1.D.238.244; 1.D.239.228; 1.D.239.229; 1.D.239.230; 1.D.239.231; 1.D.239.236; 1.D.239.237; 1.D.239.238; 1.D.239.239; 1.D.239.154; 1.D.239.157; 1.D.239.166; 1.D.239.169; 1.D.239.172; 1.D.239.175; 1.D.239.240; 1.D.239.244; 1.D.154.228; 1.D.154.229; 1.D.154.230; 1.D.154.231; 1.D.154.236; 1.D.154.237; 1.D.154.238; 1.D.154.239; 1.D.154.154; 1.D.154.157; 1.D.154.166; 1.D.154.169; 1.D.154.172; 1.D.154.175; 1.D.154.240; 1.D.154.244; 1.D.157.228; 1.D.157.229; 1.D.157.230; 1.D.157.231; 1.D.157.236; 1.D.157.237; 1.D.157.238; 1.D.157.239; 1.D.157.154; 1.D.157.157; 1.D.157.166; 1.D.157.169; 1.D.157.172; 1.D.157.175; 1.D.157.240; 1.D.157.244; 1.D.166.228; 1.D.166.229; 1.D.166.230; 1.D.166.231; 1.D.166.236; 1.D.166.237; 1.D.166.238; 1.D.166.239; 1.D.166.154; 1.D.166.157; 1.D.166.166; 1.D.166.169; 1.D.166.172; 1.D.166.175; 1.D.166.240; 1.D.166.244; 1.D.169.228; 1.D.169.229; 1.D.169.230; 1.D.169.231; 1.D.169.236; 1.D.169.237; 1.D.169.238; 1.D.169.239; 1.D.169.154; 1.D.169.157; 1.D.169.166; 1.D.169.169; 1.D.169.172; 1.D.169.175; 1.D.169.240; 1.D.169.244; 1.D.172.228; 1.D.172.229; 1.D.172.230; 1.D.172.231; 1.D.172.236; 1.D.172.237; 1.D.172.238; 1.D.172.239; 1.D.172.154; 1.D.172.157; 1.D.172.166; 1.D.172.169; 1.D.172.172; 1.D.172.175; 1.D.172.240; 1.D.172.244; 1.D.175.228; 1.D.175.229; 1.D.175.230; 1.D.175.231; 1.D.175.236; 1.D.175.237; 1.D.175.238; 1.D.175.239; 1.D.175.154; 1.D.175.157; 1.D.175.166; 1.D.175.169; 1.D.175.172; 1.D.175.175; 1.D.175.240; 1.D.175.244; 1.D.240.228; 1.D.240.229; 1.D.240.230; 1.D.240.231; 1.D.240.236; 1.D.240.237; 1.D.240.238; 1.D.240.239; 1.D.240.154; 1.D.240.157; 1.D.240.166; 1.D.240.169; 1.D.240.172; 1.D.240.175; 1.D.240.240; 1.D.240.244; 1.D.244.228; 1.D.244.229; 1.D.244.230; 1.D.244.231; 1.D.244.236; 1.D.244.237; 1.D.244.238; 1.D.244.239; 1.D.244.154; 1.D.244.157; 1.D.244.166; 1.D.244.169; 1.D.244.172; 1.D.244.175; 1.D.244.240; 1.D.244.244;

Prodrugs of 1.E

1.E.228.228; 1.E.228.229; 1.E.228.230; 1.E.228.231; 1.E.228.236; 1.E.228.237; 1.E.228.238; 1.E.228.239; 1.E.228.154; 1.E.228.157; 1.E.228.166; 1.E.228.169; 1.E.228.172; 1.E.228.175; 1.E.228.240; 1.E.228.244; 1.E.229.228; 1.E.229.229; 1.E.229.230; 1.E.229.231; 1.E.229.236; 1.E.229.237; 1.E.229.238; 1.E.229.239; 1.E.229.154; 1.E.229.157; 1.E.229.166; 1.E.229.169; 1.E.229.172; 1.E.229.175; 1.E.229.240; 1.E.229.244; 1.E.230.228; 1.E.230.229; 1.E.230.230; 1.E.230.231; 1.E.230.236; 1.E.230.237; 1.E.230.238; 1.E.230.239; 1.E.230.154; 1.E.230.157; 1.E.230.166; 1.E.230.169; 1.E.230.172; 1.E.230.175; 1.E.230.240; 1.E.230.244; 1.E.231.228; 1.E.231.229; 1.E.231.230; 1.E.231.231; 1.E.231.236; 1.E.231.237; 1.E.231.238; 1.E.231.239; 1.E.231.154; 1.E.231.157; 1.E.231.166; 1.E.231.169; 1.E.231.172; 1.E.231.175; 1.E.231.240; 1.E.231.244; 1.E.236.228; 1.E.236.229; 1.E.236.230; 1.E.236.231; 1.E.236.236; 1.E.236.237; 1.E.236.238; 1.E.236.239; 1.E.236.154; 1.E.236.157; 1.E.236.166; 1.E.236.169; 1.E.236.172; 1.E.236.175; 1.E.236.240; 1.E.236.244;

TABLE 7-continued

1.E.237.228; 1.E.237.229; 1.E.237.230; 1.E.237.231; 1.E.237.236; 1.E.237.237; 1.E.237.238; 1.E.237.239; 1.E.237.154; 1.E.237.157; 1.E.237.166; 1.E.237.169; 1.E.237.172; 1.E.237.175; 1.E.237.240; 1.E.237.244; 1.E.238.228; 1.E.238.229; 1.E.238.230; 1.E.238.231; 1.E.238.236; 1.E.238.237; 1.E.238.238; 1.E.238.239; 1.E.238.154; 1.E.238.157; 1.E.238.166; 1.E.238.169; 1.E.238.172; 1.E.238.175; 1.E.238.240; 1.E.238.244; 1.E.239.228; 1.E.239.229; 1.E.239.230; 1.E.239.231; 1.E.239.236; 1.E.239.237; 1.E.239.238; 1.E.239.239; 1.E.239.154; 1.E.239.157; 1.E.239.166; 1.E.239.169; 1.E.239.172; 1.E.239.175; 1.E.239.240; 1.E.239.244; 1.E.154.228; 1.E.154.229; 1.E.154.230; 1.E.154.231; 1.E.154.236; 1.E.154.237; 1.E.154.238; 1.E.154.239; 1.E.154.154; 1.E.154.157; 1.E.154.166; 1.E.154.169; 1.E.154.172; 1.E.154.175; 1.E.154.240; 1.E.154.244; 1.E.157.228; 1.E.157.229; 1.E.157.230; 1.E.157.231; 1.E.157.236; 1.E.157.237; 1.E.157.238; 1.E.157.239; 1.E.157.154; 1.E.157.157; 1.E.157.166; 1.E.157.169; 1.E.157.172; 1.E.157.175; 1.E.157.240; 1.E.157.244; 1.E.166.228; 1.E.166.229; 1.E.166.230; 1.E.166.231; 1.E.166.236; 1.E.166.237; 1.E.166.238; 1.E.166.239; 1.E.166.154; 1.E.166.157; 1.E.166.166; 1.E.166.169; 1.E.166.172; 1.E.166.175; 1.E.166.240; 1.E.166.244; 1.E.169.228; 1.E.169.229; 1.E.169.230; 1.E.169.231; 1.E.169.236; 1.E.169.237; 1.E.169.238; 1.E.169.239; 1.E.169.154; 1.E.169.157; 1.E.169.166; 1.E.169.169; 1.E.169.172; 1.E.169.175; 1.E.169.240; 1.E.169.244; 1.E.172.228; 1.E.172.229; 1.E.172.230; 1.E.172.231; 1.E.172.236; 1.E.172.237; 1.E.172.238; 1.E.172.239; 1.E.172.154; 1.E.172.157; 1.E.172.166; 1.E.172.169; 1.E.172.172; 1.E.172.175; 1.E.172.240; 1.E.172.244; 1.E.175.228; 1.E.175.229; 1.E.175.230; 1.E.175.231; 1.E.175.236; 1.E.175.237; 1.E.175.238; 1.E.175.239; 1.E.175.154; 1.E.175.157; 1.E.175.166; 1.E.175.169; 1.E.175.172; 1.E.175.175; 1.E.175.240; 1.E.175.244; 1.E.240.228; 1.E.240.229; 1.E.240.230; 1.E.240.231; 1.E.240.236; 1.E.240.237; 1.E.240.238; 1.E.240.239; 1.E.240.154; 1.E.240.157; 1.E.240.166; 1.E.240.169; 1.E.240.172; 1.E.240.175; 1.E.240.240; 1.E.240.244; 1.E.244.228; 1.E.244.229; 1.E.244.230; 1.E.244.231; 1.E.244.236; 1.E.244.237; 1.E.244.238; 1.E.244.239; 1.E.244.154; 1.E.244.157; 1.E.244.166; 1.E.244.169; 1.E.244.172; 1.E.244.175; 1.E.244.240; 1.E.244.244;

Prodrugs of 1.G

1.G.228.228; 1.G.228.229; 1.G.228.230; 1.G.228.231; 1.G.228.236; 1.G.228.237; 1.G.228.238; 1.G.228.239; 1.G.228.154; 1.G.228.157; 1.G.228.166; 1.G.228.169; 1.G.228.172; 1.G.228.175; 1.G.228.240; 1.G.228.244; 1.G.229.228; 1.G.229.229; 1.G.229.230; 1.G.229.231; 1.G.229.236; 1.G.229.237; 1.G.229.238; 1.G.229.239; 1.G.229.154; 1.G.229.157; 1.G.229.166; 1.G.229.169; 1.G.229.172; 1.G.229.175; 1.G.229.240; 1.G.229.244; 1.G.230.228; 1.G.230.229; 1.G.230.230; 1.G.230.231; 1.G.230.236; 1.G.230.237; 1.G.230.238; 1.G.230.239; 1.G.230.154; 1.G.230.157; 1.G.230.166; 1.G.230.169; 1.G.230.172; 1.G.230.175; 1.G.230.240; 1.G.230.244; 1.G.231.228; 1.G.231.229; 1.G.231.230; 1.G.231.231; 1.G.231.236; 1.G.231.237; 1.G.231.238; 1.G.231.239; 1.G.231.154; 1.G.231.157; 1.G.231.166; 1.G.231.169; 1.G.231.172; 1.G.231.175; 1.G.231.240; 1.G.231.244; 1.G.236.228; 1.G.236.229; 1.G.236.230; 1.G.236.231; 1.G.236.236; 1.G.236.237; 1.G.236.238; 1.G.236.239; 1.G.236.154; 1.G.236.157; 1.G.236.166; 1.G.236.169; 1.G.236.172; 1.G.236.175; 1.G.236.240; 1.G.236.244; 1.G.237.228; 1.G.237.229; 1.G.237.230; 1.G.237.231; 1.G.237.236; 1.G.237.237; 1.G.237.238; 1.G.237.239; 1.G.237.154; 1.G.237.157; 1.G.237.166; 1.G.237.169; 1.G.237.172; 1.G.237.175; 1.G.237.240; 1.G.237.244; 1.G.238.228; 1.G.238.229; 1.G.238.230; 1.G.238.231; 1.G.238.236; 1.G.238.237; 1.G.238.238; 1.G.238.239; 1.G.238.154; 1.G.238.157; 1.G.238.166; 1.G.238.169; 1.G.238.172; 1.G.238.175; 1.G.238.240; 1.G.238.244; 1.G.239.228; 1.G.239.229; 1.G.239.230; 1.G.239.231; 1.G.239.236; 1.G.239.237; 1.G.239.238; 1.G.239.239; 1.G.239.154; 1.G.239.157; 1.G.239.166; 1.G.239.169; 1.G.239.172; 1.G.239.175; 1.G.239.240; 1.G.239.244; 1.G.154.228; 1.G.154.229; 1.G.154.230; 1.G.154.231; 1.G.154.236; 1.G.154.237; 1.G.154.238; 1.G.154.239; 1.G.154.154; 1.G.154.157; 1.G.154.166; 1.G.154.169; 1.G.154.172; 1.G.154.175; 1.G.154.240; 1.G.154.244; 1.G.157.228; 1.G.157.229; 1.G.157.230; 1.G.157.231; 1.G.157.236; 1.G.157.237; 1.G.157.238; 1.G.157.239; 1.G.157.154; 1.G.157.157; 1.G.157.166; 1.G.157.169; 1.G.157.172; 1.G.157.175; 1.G.157.240; 1.G.157.244; 1.G.166.228; 1.G.166.229; 1.G.166.230; 1.G.166.231; 1.G.166.236; 1.G.166.237; 1.G.166.238; 1.G.166.239; 1.G.166.154; 1.G.166.157; 1.G.166.166; 1.G.166.169; 1.G.166.172; 1.G.166.175; 1.G.166.240; 1.G.166.244; 1.G.169.228; 1.G.169.229; 1.G.169.230; 1.G.169.231; 1.G.169.236; 1.G.169.237; 1.G.169.238; 1.G.169.239; 1.G.169.154; 1.G.169.157; 1.G.169.166; 1.G.169.169; 1.G.169.172; 1.G.169.175; 1.G.169.240; 1.G.169.244; 1.G.172.228; 1.G.172.229; 1.G.172.230; 1.G.172.231; 1.G.172.236; 1.G.172.237; 1.G.172.238; 1.G.172.239; 1.G.172.154; 1.G.172.157; 1.G.172.166; 1.G.172.169; 1.G.172.172; 1.G.172.175; 1.G.172.240; 1.G.172.244; 1.G.175.228; 1.G.175.229; 1.G.175.230; 1.G.175.231; 1.G.175.236; 1.G.175.237; 1.G.175.238; 1.G.175.239; 1.G.175.154; 1.G.175.157; 1.G.175.166; 1.G.175.169; 1.G.175.172; 1.G.175.175; 1.G.175.240; 1.G.175.244; 1.G.240.228; 1.G.240.229; 1.G.240.230; 1.G.240.231; 1.G.240.236; 1.G.240.237; 1.G.240.238; 1.G.240.239; 1.G.240.154; 1.G.240.157; 1.G.240.166; 1.G.240.169; 1.G.240.172; 1.G.240.175; 1.G.240.240; 1.G.240.244; 1.G.244.228; 1.G.244.229; 1.G.244.230; 1.G.244.231; 1.G.244.236; 1.G.244.237; 1.G.244.238; 1.G.244.239; 1.G.244.154; 1.G.244.157; 1.G.244.166; 1.G.244.169; 1.G.244.172; 1.G.244.175; 1.G.244.240; 1.G.244.244;

Prodrugs of 1.I

1.I.228.228; 1.I.228.229; 1.I.228.230; 1.I.228.231; 1.I.228.236; 1.I.228.237; 1.I.228.238; 1.I.228.239; 1.I.228.154; 1.I.228.157; 1.I.228.166; 1.I.228.169; 1.I.228.172; 1.I.228.175; 1.I.228.240; 1.I.228.244; 1.I.229.228; 1.I.229.229; 1.I.229.230; 1.I.229.231; 1.I.229.236; 1.I.229.237; 1.I.229.238; 1.I.229.239; 1.I.229.154; 1.I.229.157; 1.I.229.166; 1.I.229.169; 1.I.229.172; 1.I.229.175; 1.I.229.240; 1.I.229.244; 1.I.230.228; 1.I.230.229; 1.I.230.230; 1.I.230.231; 1.I.230.236; 1.I.230.237; 1.I.230.238; 1.I.230.239; 1.I.230.154; 1.I.230.157; 1.I.230.166; 1.I.230.169; 1.I.230.172; 1.I.230.175; 1.I.230.240; 1.I.230.244; 1.I.231.228; 1.I.231.229; 1.I.231.230; 1.I.231.231; 1.I.231.236; 1.I.231.237; 1.I.231.238; 1.I.231.239; 1.I.231.154; 1.I.231.157; 1.I.231.166; 1.I.231.169; 1.I.231.172; 1.I.231.175; 1.I.231.240; 1.I.231.244; 1.I.236.228; 1.I.236.229; 1.I.236.230; 1.I.236.231; 1.I.236.236; 1.I.236.237; 1.I.236.238; 1.I.236.239; 1.I.236.154; 1.I.236.157; 1.I.236.166; 1.I.236.169; 1.I.236.172; 1.I.236.175; 1.I.236.240; 1.I.236.244; 1.I.237.228; 1.I.237.229; 1.I.237.230; 1.I.237.231; 1.I.237.236; 1.I.237.237; 1.I.237.238; 1.I.237.239; 1.I.237.154; 1.I.237.157; 1.I.237.166; 1.I.237.169; 1.I.237.172; 1.I.237.175; 1.I.237.240; 1.I.237.244; 1.I.238.228; 1.I.238.229; 1.I.238.230; 1.I.238.231; 1.I.238.236; 1.I.238.237; 1.I.238.238; 1.I.238.239; 1.I.238.154; 1.I.238.157; 1.I.238.166; 1.I.238.169; 1.I.238.172; 1.I.238.175; 1.I.238.240; 1.I.238.244; 1.I.239.228; 1.I.239.229; 1.I.239.230; 1.I.239.231; 1.I.239.236; 1.I.239.237; 1.I.239.238; 1.I.239.239; 1.I.239.154; 1.I.239.157; 1.I.239.166; 1.I.239.169; 1.I.239.172; 1.I.239.175; 1.I.239.240; 1.I.239.244; 1.I.154.228; 1.I.154.229; 1.I.154.230; 1.I.154.231; 1.I.154.236; 1.I.154.237; 1.I.154.238; 1.I.154.239; 1.I.154.154; 1.I.154.157; 1.I.154.166; 1.I.154.169; 1.I.154.172; 1.I.154.175; 1.I.154.240; 1.I.154.244; 1.I.157.228; 1.I.157.229; 1.I.157.230; 1.I.157.231; 1.I.157.236; 1.I.157.237; 1.I.157.238; 1.I.157.239; 1.I.157.154; 1.I.157.157; 1.I.157.166; 1.I.157.169; 1.I.157.172; 1.I.157.175; 1.I.157.240; 1.I.157.244; 1.I.166.228; 1.I.166.229; 1.I.166.230; 1.I.166.231; 1.I.166.236; 1.I.166.237; 1.I.166.238; 1.I.166.239; 1.I.166.154; 1.I.166.157; 1.I.166.166; 1.I.166.169; 1.I.166.172; 1.I.166.175; 1.I.166.240; 1.I.166.244; 1.I.169.228; 1.I.169.229; 1.I.169.230; 1.I.169.231; 1.I.169.236; 1.I.169.237; 1.I.169.238; 1.I.169.239; 1.I.169.154; 1.I.169.157; 1.I.169.166; 1.I.169.169; 1.I.169.172; 1.I.169.175; 1.I.169.240; 1.I.169.244; 1.I.172.228; 1.I.172.229; 1.I.172.230; 1.I.172.231; 1.I.172.236; 1.I.172.237; 1.I.172.238; 1.I.172.239; 1.I.172.154; 1.I.172.157; 1.I.172.166; 1.I.172.169; 1.I.172.172; 1.I.172.175; 1.I.172.240; 1.I.172.244; 1.I.175.228; 1.I.175.229; 1.I.175.230; 1.I.175.231; 1.I.175.236; 1.I.175.237; 1.I.175.238; 1.I.175.239; 1.I.175.154; 1.I.175.157; 1.I.175.166; 1.I.175.169; 1.I.175.172; 1.I.175.175; 1.I.175.240; 1.I.175.244; 1.I.240.228; 1.I.240.229; 1.I.240.230; 1.I.240.231; 1.I.240.236; 1.I.240.237; 1.I.240.238; 1.I.240.239; 1.I.240.154; 1.I.240.157; 1.I.240.166; 1.I.240.169; 1.I.240.172; 1.I.240.175; 1.I.240.240; 1.I.240.244; 1.I.244.228; 1.I.244.229; 1.I.244.230; 1.I.244.231; 1.I.244.236; 1.I.244.237; 1.I.244.238; 1.I.244.239; 1.I.244.154; 1.I.244.157; 1.I.244.166; 1.I.244.169; 1.I.244.172; 1.I.244.175; 1.I.244.240; 1.I.244.244;

Prodrugs of 1.J

1.J.228.228; 1.J.228.229; 1.J.228.230; 1.J.228.231; 1.J.228.236; 1.J.228.237; 1.J.228.238; 1.J.228.239; 1.J.228.154; 1.J.228.157; 1.J.228.166; 1.J.228.169; 1.J.228.172; 1.J.228.175; 1.J.228.240; 1.J.228.244; 1.J.229.228; 1.J.229.229; 1.J.229.230; 1.J.229.231; 1.J.229.236; 1.J.229.237; 1.J.229.238; 1.J.229.239; 1.J.229.154; 1.J.229.157; 1.J.229.166; 1.J.229.169; 1.J.229.172; 1.J.229.175; 1.J.229.240; 1.J.229.244; 1.J.230.228; 1.J.230.229; 1.J.230.230; 1.J.230.231; 1.J.230.236; 1.J.230.237; 1.J.230.238; 1.J.230.239; 1.J.230.154; 1.J.230.157; 1.J.230.166; 1.J.230.169; 1.J.230.172; 1.J.230.175; 1.J.230.240; 1.J.230.244; 1.J.231.228; 1.J.231.229; 1.J.231.230; 1.J.231.231; 1.J.231.236; 1.J.231.237; 1.J.231.238; 1.J.231.239; 1.J.231.154; 1.J.231.157; 1.J.231.166; 1.J.231.169;

TABLE 7-continued

1.J.231.172; 1.J.231.175; 1.J.231.240; 1.J.231.244; 1.J.236.228;
1.J.236.229; 1.J.236.230; 1.J.236.231; 1.J.236.236; 1.J.236.237;
1.J.236.238; 1.J.236.239; 1.J.236.154; 1.J.236.157; 1.J.236.166;
1.J.236.169; 1.J.236.172; 1.J.236.175; 1.J.236.240; 1.J.236.244;
1.J.237.228; 1.J.237.229; 1.J.237.230; 1.J.237.231; 1.J.237.236;
1.J.237.237; 1.J.237.238; 1.J.237.239; 1.J.237.154; 1.J.237.157;
1.J.237.166; 1.J.237.169; 1.J.237.172; 1.J.237.175; 1.J.237.240;
1.J.237.244; 1.J.238.228; 1.J.238.229; 1.J.238.230; 1.J.238.231;
1.J.238.236; 1.J.238.237; 1.J.238.238; 1.J.238.239; 1.J.238.154;
1.J.238.157; 1.J.238.166; 1.J.238.169; 1.J.238.172; 1.J.238.175;
1.J.238.240; 1.J.238.244; 1.J.239.228; 1.J.239.229; 1.J.239.230;
1.J.239.231; 1.J.239.236; 1.J.239.237; 1.J.239.238; 1.J.239.239;
1.J.239.154; 1.J.239.157; 1.J.239.166; 1.J.239.169; 1.J.239.172;
1.J.239.175; 1.J.239.240; 1.J.239.244; 1.J.154.228; 1.J.154.229;
1.J.154.230; 1.J.154.231; 1.J.154.236; 1.J.154.237; 1.J.154.238;
1.J.154.239; 1.J.154.154; 1.J.154.157; 1.J.154.166; 1.J.154.169;
1.J.154.172; 1.J.154.175; 1.J.154.240; 1.J.154.244; 1.J.157.228;
1.J.157.229; 1.J.157.230; 1.J.157.231; 1.J.157.236; 1.J.157.237;
1.J.157.238; 1.J.157.239; 1.J.157.154; 1.J.157.157; 1.J.157.166;
1.J.157.169; 1.J.157.172; 1.J.157.175; 1.J.157.240; 1.J.157.244;
1.J.166.228; 1.J.166.229; 1.J.166.230; 1.J.166.231; 1.J.166.236;
1.J.166.237; 1.J.166.238; 1.J.166.239; 1.J.166.154; 1.J.166.157;
1.J.166.166; 1.J.166.169; 1.J.166.172; 1.J.166.175; 1.J.166.240;
1.J.166.244; 1.J.169.228; 1.J.169.229; 1.J.169.230; 1.J.169.231;
1.J.169.236; 1.J.169.237; 1.J.169.238; 1.J.169.239; 1.J.169.154;
1.J.169.157; 1.J.169.166; 1.J.169.169; 1.J.169.172; 1.J.169.175;
1.J.169.240; 1.J.169.244; 1.J.172.228; 1.J.172.229; 1.J.172.230;
1.J.172.231; 1.J.172.236; 1.J.172.237; 1.J.172.238; 1.J.172.239;
1.J.172.154; 1.J.172.157; 1.J.172.166; 1.J.172.169; 1.J.172.172;
1.J.172.175; 1.J.172.240; 1.J.172.244; 1.J.175.228; 1.J.175.229;
1.J.175.230; 1.J.175.231; 1.J.175.236; 1.J.175.237; 1.J.175.238;
1.J.175.239; 1.J.175.154; 1.J.175.157; 1.J.175.166; 1.J.175.169;
1.J.175.172; 1.J.175.175; 1.J.175.240; 1.J.175.244; 1.J.240.228;
1.J.240.229; 1.J.240.230; 1.J.240.231; 1.J.240.236; 1.J.240.237;
1.J.240.238; 1.J.240.239; 1.J.240.154; 1.J.240.157; 1.J.240.166;
1.J.240.169; 1.J.240.172; 1.J.240.175; 1.J.240.240; 1.J.240.244;
1.J.244.228; 1.J.244.229; 1.J.244.230; 1.J.244.231; 1.J.244.236;
1.J.244.237; 1.J.244.238; 1.J.244.239; 1.J.244.154; 1.J.244.157;
1.J.244.166; 1.J.244.169; 1.J.244.172; 1.J.244.175; 1.J.244.240;
1.J.244.244;
Prodrugs of 1.L 1.L.228.228; 1.L.228.229; 1.L.228.230; 1.L.228.231; 1.L.228.236;
1.L.228.237; 1.L.228.238; 1.L.228.239; 1.L.228.154; 1.L.228.157;
1.L.228.166; 1.L.228.169; 1.L.228.172; 1.L.228.175; 1.L.228.240;
1.L.228.244; 1.L.229.228; 1.L.229.229; 1.L.229.230; 1.L.229.231;
1.L.229.236; 1.L.229.237; 1.L.229.238; 1.L.229.239; 1.L.229.154;
1.L.229.157; 1.L.229.166; 1.L.229.169; 1.L.229.172; 1.L.229.175;
1.L.229.240; 1.L.229.244; 1.L.230.228; 1.L.230.229; 1.L.230.230;
1.L.230.231; 1.L.230.236; 1.L.230.237; 1.L.230.238; 1.L.230.239;
1.L.230.154; 1.L.230.157; 1.L.230.166; 1.L.230.169; 1.L.230.172;
1.L.230.175; 1.L.230.240; 1.L.230.244; 1.L.231.228; 1.L.231.229;
1.L.231.230; 1.L.231.231; 1.L.231.236; 1.L.231.237; 1.L.231.238;
1.L.231.239; 1.L.231.154; 1.L.231.157; 1.L.231.166; 1.L.231.169;
1.L.231.172; 1.L.231.175; 1.L.231.240; 1.L.231.244; 1.L.236.228;
1.L.236.229; 1.L.236.230; 1.L.236.231; 1.L.236.236; 1.L.236.237;
1.L.236.238; 1.L.236.239; 1.L.236.154; 1.L.236.157; 1.L.236.166;
1.L.236.169; 1.L.236.172; 1.L.236.175; 1.L.236.240; 1.L.236.244;
1.L.237.228; 1.L.237.229; 1.L.237.230; 1.L.237.231; 1.L.237.236;
1.L.237.237; 1.L.237.238; 1.L.237.239; 1.L.237.154; 1.L.237.157;
1.L.237.166; 1.L.237.169; 1.L.237.172; 1.L.237.175; 1.L.237.240;
1.L.237.244; 1.L.238.228; 1.L.238.229; 1.L.238.230; 1.L.238.231;
1.L.238.236; 1.L.238.237; 1.L.238.238; 1.L.238.239; 1.L.238.154;
1.L.238.157; 1.L.238.166; 1.L.238.169; 1.L.238.172; 1.L.238.175;
1.L.238.240; 1.L.238.244; 1.L.239.228; 1.L.239.229; 1.L.239.230;
1.L.239.231; 1.L.239.236; 1.L.239.237; 1.L.239.238; 1.L.239.239;
1.L.239.154; 1.L.239.157; 1.L.239.166; 1.L.239.169; 1.L.239.172;
1.L.239.175; 1.L.239.240; 1.L.239.244; 1.L.154.228; 1.L.154.229;
1.L.154.230; 1.L.154.231; 1.L.154.236; 1.L.154.237; 1.L.154.238;
1.L.154.239; 1.L.154.154; 1.L.154.157; 1.L.154.166; 1.L.154.169;
1.L.154.172; 1.L.154.175; 1.L.154.240; 1.L.154.244; 1.L.157.228;
1.L.157.229; 1.L.157.230; 1.L.157.231; 1.L.157.236; 1.L.157.237;
1.L.157.238; 1.L.157.239; 1.L.157.154; 1.L.157.157; 1.L.157.166;
1.L.157.169; 1.L.157.172; 1.L.157.175; 1.L.157.240; 1.L.157.244;
1.L.166.228; 1.L.166.229; 1.L.166.230; 1.L.166.231; 1.L.166.236;
1.L.166.237; 1.L.166.238; 1.L.166.239; 1.L.166.154; 1.L.166.157;
1.L.166.166; 1.L.166.169; 1.L.166.172; 1.L.166.175; 1.L.166.240;
1.L.166.244; 1.L.169.228; 1.L.169.229; 1.L.169.230; 1.L.169.231;
1.L.169.236; 1.L.169.237; 1.L.169.238; 1.L.169.239; 1.L.169.154;
1.L.169.157; 1.L.169.166; 1.L.169.169; 1.L.169.172; 1.L.169.175;
1.L.169.240; 1.L.169.244; 1.L.172.228; 1.L.172.229; 1.L.172.230;
1.L.172.231; 1.L.172.236; 1.L.172.237; 1.L.172.238; 1.L.172.239;
1.L.172.154; 1.L.172.157; 1.L.172.166; 1.L.172.169; 1.L.172.172;
1.L.172.175; 1.L.172.240; 1.L.172.244; 1.L.175.228; 1.L.175.229;
1.L.175.230; 1.L.175.231; 1.L.175.236; 1.L.175.237; 1.L.175.238;
1.L.175.239; 1.L.175.154; 1.L.175.157; 1.L.175.166; 1.L.175.169;
1.L.175.172; 1.L.175.175; 1.L.175.240; 1.L.175.244; 1.L.240.228;
1.L.240.229; 1.L.240.230; 1.L.240.231; 1.L.240.236; 1.L.240.237;
1.L.240.238; 1.L.240.239; 1.L.240.154; 1.L.240.157; 1.L.240.166;
1.L.240.169; 1.L.240.172; 1.L.240.175; 1.L.240.240; 1.L.240.244;
1.L.244.228; 1.L.244.229; 1.L.244.230; 1.L.244.231; 1.L.244.236;
1.L.244.237; 1.L.244.238; 1.L.244.239; 1.L.244.154; 1.L.244.157;
1.L.244.166; 1.L.244.169; 1.L.244.172; 1.L.244.175; 1.L.244.240;
1.L.244.244;
Prodrugs of 1.O 1.O.228.228; 1.O.228.229; 1.O.228.230; 1.O.228.231; 1.O.228.236;
1.O.228.237; 1.O.228.238; 1.O.228.239; 1.O.228.154; 1.O.228.157;
1.O.228.166; 1.O.228.169; 1.O.228.172; 1.O.228.175; 1.O.228.240;
1.O.228.244; 1.O.229.228; 1.O.229.229; 1.O.229.230; 1.O.229.231;
1.O.229.236; 1.O.229.237; 1.O.229.238; 1.O.229.239; 1.O.229.154;
1.O.229.157; 1.O.229.166; 1.O.229.169; 1.O.229.172; 1.O.229.175;
1.O.229.240; 1.O.229.244; 1.O.230.228; 1.O.230.229; 1.O.230.230;
1.O.230.231; 1.O.230.236; 1.O.230.237; 1.O.230.238; 1.O.230.239;
1.O.230.154; 1.O.230.157; 1.O.230.166; 1.O.230.169; 1.O.230.172;
1.O.230.175; 1.O.230.240; 1.O.230.244; 1.O.231.228; 1.O.231.229;
1.O.231.230; 1.O.231.231; 1.O.231.236; 1.O.231.237; 1.O.231.238;
1.O.231.239; 1.O.231.154; 1.O.231.157; 1.O.231.166; 1.O.231.169;
1.O.231.172; 1.O.231.175; 1.O.231.240; 1.O.231.244; 1.O.236.228;
1.O.236.229; 1.O.236.230; 1.O.236.231; 1.O.236.236; 1.O.236.237;
1.O.236.238; 1.O.236.239; 1.O.236.154; 1.O.236.157; 1.O.236.166;
1.O.236.169; 1.O.236.172; 1.O.236.175; 1.O.236.240; 1.O.236.244;
1.O.237.228; 1.O.237.229; 1.O.237.230; 1.O.237.231; 1.O.237.236;
1.O.237.237; 1.O.237.238; 1.O.237.239; 1.O.237.154; 1.O.237.157;
1.O.237.166; 1.O.237.169; 1.O.237.172; 1.O.237.175; 1.O.237.240;
1.O.237.244; 1.O.238.228; 1.O.238.229; 1.O.238.230; 1.O.238.231;
1.O.238.236; 1.O.238.237; 1.O.238.238; 1.O.238.239; 1.O.238.154;
1.O.238.157; 1.O.238.166; 1.O.238.169; 1.O.238.172; 1.O.238.175;
1.O.238.240; 1.O.238.244; 1.O.239.228; 1.O.239.229; 1.O.239.230;
1.O.239.231; 1.O.239.236; 1.O.239.237; 1.O.239.238; 1.O.239.239;
1.O.239.154; 1.O.239.157; 1.O.239.166; 1.O.239.169; 1.O.239.172;
1.O.239.175; 1.O.239.240; 1.O.239.244; 1.O.154.228; 1.O.154.229;
1.O.154.230; 1.O.154.231; 1.O.154.236; 1.O.154.237; 1.O.154.238;
1.O.154.239; 1.O.154.154; 1.O.154.157; 1.O.154.166; 1.O.154.169;
1.O.154.172; 1.O.154.175; 1.O.154.240; 1.O.154.244; 1.O.157.228;
1.O.157.229; 1.O.157.230; 1.O.157.231; 1.O.157.236; 1.O.157.237;
1.O.157.238; 1.O.157.239; 1.O.157.154; 1.O.157.157; 1.O.157.166;
1.O.157.169; 1.O.157.172; 1.O.157.175; 1.O.157.240; 1.O.157.244;
1.O.166.228; 1.O.166.229; 1.O.166.230; 1.O.166.231; 1.O.166.236;
1.O.166.237; 1.O.166.238; 1.O.166.239; 1.O.166.154; 1.O.166.157;
1.O.166.166; 1.O.166.169; 1.O.166.172; 1.O.166.175; 1.O.166.240;
1.O.166.244; 1.O.169.228; 1.O.169.229; 1.O.169.230; 1.O.169.231;
1.O.169.236; 1.O.169.237; 1.O.169.238; 1.O.169.239; 1.O.169.154;
1.O.169.157; 1.O.169.166; 1.O.169.169; 1.O.169.172; 1.O.169.175;
1.O.169.240; 1.O.169.244; 1.O.172.228; 1.O.172.229; 1.O.172.230;
1.O.172.231; 1.O.172.236; 1.O.172.237; 1.O.172.238; 1.O.172.239;
1.O.172.154; 1.O.172.157; 1.O.172.166; 1.O.172.169; 1.O.172.172;
1.O.172.175; 1.O.172.240; 1.O.172.244; 1.O.175.228; 1.O.175.229;
1.O.175.230; 1.O.175.231; 1.O.175.236; 1.O.175.237; 1.O.175.238;
1.O.175.239; 1.O.175.154; 1.O.175.157; 1.O.175.166; 1.O.175.169;
1.O.175.172; 1.O.175.175; 1.O.175.240; 1.O.175.244; 1.O.240.228;
1.O.240.229; 1.O.240.230; 1.O.240.231; 1.O.240.236; 1.O.240.237;
1.O.240.238; 1.O.240.239; 1.O.240.154; 1.O.240.157; 1.O.240.166;
1.O.240.169; 1.O.240.172; 1.O.240.175; 1.O.240.240; 1.O.240.244;
1.O.244.228; 1.O.244.229; 1.O.244.230; 1.O.244.231; 1.O.244.236;
1.O.244.237; 1.O.244.238; 1.O.244.239; 1.O.244.154; 1.O.244.157;
1.O.244.166; 1.O.244.169; 1.O.244.172; 1.O.244.175; 1.O.244.240;
1.O.244.244;
Prodrugs of 1.P 1.P.228.228; 1.P.228.229; 1.P.228.230; 1.P.228.231; 1.P.228.236;
1.P.228.237; 1.P.228.238; 1.P.228.239; 1.P.228.154; 1.P.228.157;
1.P.228.166; 1.P.228.169; 1.P.228.172; 1.P.228.175; 1.P.228.240;
1.P.228.244; 1.P.229.228; 1.P.229.229; 1.P.229.230; 1.P.229.231;
1.P.229.236; 1.P.229.237; 1.P.229.238; 1.P.229.239; 1.P.229.154;
1.P.229.157; 1.P.229.166; 1.P.229.169; 1.P.229.172; 1.P.229.175;
1.P.229.240; 1.P.229.244; 1.P.230.228; 1.P.230.229; 1.P.230.230;
1.P.230.231; 1.P.230.236; 1.P.230.237; 1.P.230.238; 1.P.230.239;

TABLE 7-continued

1.P.230.154; 1.P.230.157; 1.P.230.166; 1.P.230.169; 1.P.230.172; 1.P.230.175; 1.P.230.240; 1.P.230.244; 1.P.231.228; 1.P.231.229; 1.P.231.230; 1.P.231.231; 1.P.231.236; 1.P.231.237; 1.P.231.238; 1.P.231.239; 1.P.231.154; 1.P.231.157; 1.P.231.166; 1.P.231.169; 1.P.231.172; 1.P.231.175; 1.P.231.240; 1.P.231.244; 1.P.236.228; 1.P.236.229; 1.P.236.230; 1.P.236.231; 1.P.236.236; 1.P.236.237; 1.P.236.238; 1.P.236.239; 1.P.236.154; 1.P.236.157; 1.P.236.166; 1.P.236.169; 1.P.236.172; 1.P.236.175; 1.P.236.240; 1.P.236.244; 1.P.237.228; 1.P.237.229; 1.P.237.230; 1.P.237.231; 1.P.237.236; 1.P.237.237; 1.P.237.238; 1.P.237.239; 1.P.237.154; 1.P.237.157; 1.P.237.166; 1.P.237.169; 1.P.237.172; 1.P.237.175; 1.P.237.240; 1.P.237.244; 1.P.238.228; 1.P.238.229; 1.P.238.230; 1.P.238.231; 1.P.238.236; 1.P.238.237; 1.P.238.238; 1.P.238.239; 1.P.238.154; 1.P.238.157; 1.P.238.166; 1.P.238.169; 1.P.238.172; 1.P.238.175; 1.P.238.240; 1.P.238.244; 1.P.239.228; 1.P.239.229; 1.P.239.230; 1.P.239.231; 1.P.239.236; 1.P.239.237; 1.P.239.238; 1.P.239.239; 1.P.239.154; 1.P.239.157; 1.P.239.166; 1.P.239.169; 1.P.239.172; 1.P.239.175; 1.P.239.240; 1.P.239.244; 1.P.154.228; 1.P.154.229; 1.P.154.230; 1.P.154.231; 1.P.154.236; 1.P.154.237; 1.P.154.238; 1.P.154.239; 1.P.154.154; 1.P.154.157; 1.P.154.166; 1.P.154.169; 1.P.154.172; 1.P.154.175; 1.P.154.240; 1.P.154.244; 1.P.157.228; 1.P.157.229; 1.P.157.230; 1.P.157.231; 1.P.157.236; 1.P.157.237; 1.P.157.238; 1.P.157.239; 1.P.157.154; 1.P.157.157; 1.P.157.166; 1.P.157.169; 1.P.157.172; 1.P.157.175; 1.P.157.240; 1.P.157.244; 1.P.166.228; 1.P.166.229; 1.P.166.230; 1.P.166.231; 1.P.166.236; 1.P.166.237; 1.P.166.238; 1.P.166.239; 1.P.166.154; 1.P.166.157; 1.P.166.166; 1.P.166.169; 1.P.166.172; 1.P.166.175; 1.P.166.240; 1.P.166.244; 1.P.169.228; 1.P.169.229; 1.P.169.230; 1.P.169.231; 1.P.169.236; 1.P.169.237; 1.P.169.238; 1.P.169.239; 1.P.169.154; 1.P.169.157; 1.P.169.166; 1.P.169.169; 1.P.169.172; 1.P.169.175; 1.P.169.240; 1.P.169.244; 1.P.172.228; 1.P.172.229; 1.P.172.230; 1.P.172.231; 1.P.172.236; 1.P.172.237; 1.P.172.238; 1.P.172.239; 1.P.172.154; 1.P.172.157; 1.P.172.166; 1.P.172.169; 1.P.172.172; 1.P.172.175; 1.P.172.240; 1.P.172.244; 1.P.175.228; 1.P.175.229; 1.P.175.230; 1.P.175.231; 1.P.175.236; 1.P.175.237; 1.P.175.238; 1.P.175.239; 1.P.175.154; 1.P.175.157; 1.P.175.166; 1.P.175.169; 1.P.175.172; 1.P.175.175; 1.P.175.240; 1.P.175.244; 1.P.240.228; 1.P.240.229; 1.P.240.230; 1.P.240.231; 1.P.240.236; 1.P.240.237; 1.P.240.238; 1.P.240.239; 1.P.240.154; 1.P.240.157; 1.P.240.166; 1.P.240.169; 1.P.240.172; 1.P.240.175; 1.P.240.240; 1.P.240.244; 1.P.244.228; 1.P.244.229; 1.P.244.230; 1.P.244.231; 1.P.244.236; 1.P.244.237; 1.P.244.238; 1.P.244.239; 1.P.244.154; 1.P.244.157; 1.P.244.166; 1.P.244.169; 1.P.244.172; 1.P.244.175; 1.P.244.240; 1.P.244.244;

Prodrugs of 1.U

1.U.228.228; 1.U.228.229; 1.U.228.230; 1.U.228.231; 1.U.228.236; 1.U.228.237; 1.U.228.238; 1.U.228.239; 1.U.228.154; 1.U.228.157; 1.U.228.166; 1.U.228.169; 1.U.228.172; 1.U.228.175; 1.U.228.240; 1.U.228.244; 1.U.229.228; 1.U.229.229; 1.U.229.230; 1.U.229.231; 1.U.229.236; 1.U.229.237; 1.U.229.238; 1.U.229.239; 1.U.229.154; 1.U.229.157; 1.U.229.166; 1.U.229.169; 1.U.229.172; 1.U.229.175; 1.U.229.240; 1.U.229.244; 1.U.230.228; 1.U.230.229; 1.U.230.230; 1.U.230.231; 1.U.230.236; 1.U.230.237; 1.U.230.238; 1.U.230.239; 1.U.230.154; 1.U.230.157; 1.U.230.166; 1.U.230.169; 1.U.230.172; 1.U.230.175; 1.U.230.240; 1.U.230.244; 1.U.231.228; 1.U.231.229; 1.U.231.230; 1.U.231.231; 1.U.231.236; 1.U.231.237; 1.U.231.238; 1.U.231.239; 1.U.231.154; 1.U.231.157; 1.U.231.166; 1.U.231.169; 1.U.231.172; 1.U.231.175; 1.U.231.240; 1.U.231.244; 1.U.236.228; 1.U.236.229; 1.U.236.230; 1.U.236.231; 1.U.236.236; 1.U.236.237; 1.U.236.238; 1.U.236.239; 1.U.236.154; 1.U.236.157; 1.U.236.166; 1.U.236.169; 1.U.236.172; 1.U.236.175; 1.U.236.240; 1.U.236.244; 1.U.237.228; 1.U.237.229; 1.U.237.230; 1.U.237.231; 1.U.237.236; 1.U.237.237; 1.U.237.238; 1.U.237.239; 1.U.237.154; 1.U.237.157; 1.U.237.166; 1.U.237.169; 1.U.237.172; 1.U.237.175; 1.U.237.240; 1.U.237.244; 1.U.238.228; 1.U.238.229; 1.U.238.230; 1.U.238.231; 1.U.238.236; 1.U.238.237; 1.U.238.238; 1.U.238.239; 1.U.238.154; 1.U.238.157; 1.U.238.166; 1.U.238.169; 1.U.238.172; 1.U.238.175; 1.U.238.240; 1.U.238.244; 1.U.239.228; 1.U.239.229; 1.U.239.230; 1.U.239.231; 1.U.239.236; 1.U.239.237; 1.U.239.238; 1.U.239.239; 1.U.239.154; 1.U.239.157; 1.U.239.166; 1.U.239.169; 1.U.239.172; 1.U.239.175; 1.U.239.240; 1.U.239.244; 1.U.154.228; 1.U.154.229; 1.U.154.230; 1.U.154.231; 1.U.154.236; 1.U.154.237; 1.U.154.238; 1.U.154.239; 1.U.154.154; 1.U.154.157; 1.U.154.166; 1.U.154.169; 1.U.154.172; 1.U.154.175; 1.U.154.240; 1.U.154.244; 1.U.157.228; 1.U.157.229; 1.U.157.230; 1.U.157.231; 1.U.157.236; 1.U.157.237; 1.U.157.238; 1.U.157.239; 1.U.157.154; 1.U.157.157; 1.U.157.166; 1.U.157.169; 1.U.157.172; 1.U.157.175; 1.U.157.240; 1.U.157.244; 1.U.166.228; 1.U.166.229; 1.U.166.230; 1.U.166.231; 1.U.166.236; 1.U.166.237; 1.U.166.238; 1.U.166.239; 1.U.166.154; 1.U.166.157; 1.U.166.166; 1.U.166.169; 1.U.166.172; 1.U.166.175; 1.U.166.240; 1.U.166.244; 1.U.169.228; 1.U.169.229; 1.U.169.230; 1.U.169.231; 1.U.169.236; 1.U.169.237; 1.U.169.238; 1.U.169.239; 1.U.169.154; 1.U.169.157; 1.U.169.166; 1.U.169.169; 1.U.169.172; 1.U.169.175; 1.U.169.240; 1.U.169.244; 1.U.172.228; 1.U.172.229; 1.U.172.230; 1.U.172.231; 1.U.172.236; 1.U.172.237; 1.U.172.238; 1.U.172.239; 1.U.172.154; 1.U.172.157; 1.U.172.166; 1.U.172.169; 1.U.172.172; 1.U.172.175; 1.U.172.240; 1.U.172.244; 1.U.175.228; 1.U.175.229; 1.U.175.230; 1.U.175.231; 1.U.175.236; 1.U.175.237; 1.U.175.238; 1.U.175.239; 1.U.175.154; 1.U.175.157; 1.U.175.166; 1.U.175.169; 1.U.175.172; 1.U.175.175; 1.U.175.240; 1.U.175.244; 1.U.240.228; 1.U.240.229; 1.U.240.230; 1.U.240.231; 1.U.240.236; 1.U.240.237; 1.U.240.238; 1.U.240.239; 1.U.240.154; 1.U.240.157; 1.U.240.166; 1.U.240.169; 1.U.240.172; 1.U.240.175; 1.U.240.240; 1.U.240.244; 1.U.244.228; 1.U.244.229; 1.U.244.230; 1.U.244.231; 1.U.244.236; 1.U.244.237; 1.U.244.238; 1.U.244.239; 1.U.244.154; 1.U.244.157; 1.U.244.166; 1.U.244.169; 1.U.244.172; 1.U.244.175; 1.U.244.240; 1.U.244.244;

Prodrugs of 1.W

1.W.228.228; 1.W.228.229; 1.W.228.230; 1.W.228.231; 1.W.228.236; 1.W.228.237; 1.W.228.238; 1.W.228.239; 1.W.228.154; 1.W.228.157; 1.W.228.166; 1.W.228.169; 1.W.228.172; 1.W.228.175; 1.W.228.240; 1.W.228.244; 1.W.229.228; 1.W.229.229; 1.W.229.230; 1.W.229.231; 1.W.229.236; 1.W.229.237; 1.W.229.238; 1.W.229.239; 1.W.229.154; 1.W.229.157; 1.W.229.166; 1.W.229.169; 1.W.229.172; 1.W.229.175; 1.W.229.240; 1.W.229.244; 1.W.230.228; 1.W.230.229; 1.W.230.230; 1.W.230.231; 1.W.230.236; 1.W.230.237; 1.W.230.238; 1.W.230.239; 1.W.230.154; 1.W.230.157; 1.W.230.166; 1.W.230.169; 1.W.230.172; 1.W.230.175; 1.W.230.240; 1.W.230.244; 1.W.231.228; 1.W.231.229; 1.W.231.230; 1.W.231.231; 1.W.231.236; 1.W.231.237; 1.W.231.238; 1.W.231.239; 1.W.231.154; 1.W.231.157; 1.W.231.166; 1.W.231.169; 1.W.231.172; 1.W.231.175; 1.W.231.240; 1.W.231.244; 1.W.236.228; 1.W.236.229; 1.W.236.230; 1.W.236.231; 1.W.236.236; 1.W.236.237; 1.W.236.238; 1.W.236.239; 1.W.236.154; 1.W.236.157; 1.W.236.166; 1.W.236.169; 1.W.236.172; 1.W.236.175; 1.W.236.240; 1.W.236.244; 1.W.237.228; 1.W.237.229; 1.W.237.230; 1.W.237.231; 1.W.237.236; 1.W.237.237; 1.W.237.238; 1.W.237.239; 1.W.237.154; 1.W.237.157; 1.W.237.166; 1.W.237.169; 1.W.237.172; 1.W.237.175; 1.W.237.240; 1.W.237.244; 1.W.238.228; 1.W.238.229; 1.W.238.230; 1.W.238.231; 1.W.238.236; 1.W.238.237; 1.W.238.238; 1.W.238.239; 1.W.238.154; 1.W.238.157; 1.W.238.166; 1.W.238.169; 1.W.238.172; 1.W.238.175; 1.W.238.240; 1.W.238.244; 1.W.239.228; 1.W.239.229; 1.W.239.230; 1.W.239.231; 1.W.239.236; 1.W.239.237; 1.W.239.238; 1.W.239.239; 1.W.239.154; 1.W.239.157; 1.W.239.166; 1.W.239.169; 1.W.239.172; 1.W.239.175; 1.W.239.240; 1.W.239.244; 1.W.154.228; 1.W.154.229; 1.W.154.230; 1.W.154.231; 1.W.154.236; 1.W.154.237; 1.W.154.238; 1.W.154.239; 1.W.154.154; 1.W.154.157; 1.W.154.166; 1.W.154.169; 1.W.154.172; 1.W.154.175; 1.W.154.240; 1.W.154.244; 1.W.157.228; 1.W.157.229; 1.W.157.230; 1.W.157.231; 1.W.157.236; 1.W.157.237; 1.W.157.238; 1.W.157.239; 1.W.157.154; 1.W.157.157; 1.W.157.166; 1.W.157.169; 1.W.157.172; 1.W.157.175; 1.W.157.240; 1.W.157.244; 1.W.166.228; 1.W.166.229; 1.W.166.230; 1.W.166.231; 1.W.166.236; 1.W.166.237; 1.W.166.238; 1.W.166.239; 1.W.166.154; 1.W.166.157; 1.W.166.166; 1.W.166.169; 1.W.166.172; 1.W.166.175; 1.W.166.240; 1.W.166.244; 1.W.169.228; 1.W.169.229; 1.W.169.230; 1.W.169.231; 1.W.169.236; 1.W.169.237; 1.W.169.238; 1.W.169.239; 1.W.169.154; 1.W.169.157; 1.W.169.166; 1.W.169.169; 1.W.169.172; 1.W.169.175; 1.W.169.240; 1.W.169.244; 1.W.172.228; 1.W.172.229; 1.W.172.230; 1.W.172.231; 1.W.172.236; 1.W.172.237; 1.W.172.238; 1.W.172.239; 1.W.172.154; 1.W.172.157; 1.W.172.166; 1.W.172.169; 1.W.172.172; 1.W.172.175; 1.W.172.240; 1.W.172.244; 1.W.175.228; 1.W.175.229; 1.W.175.230; 1.W.175.231; 1.W.175.236; 1.W.175.237; 1.W.175.238; 1.W.175.239; 1.W.175.154; 1.W.175.157; 1.W.175.166; 1.W.175.169; 1.W.175.172; 1.W.175.175; 1.W.175.240; 1.W.175.244; 1.W.240.228; 1.W.240.229; 1.W.240.230; 1.W.240.231; 1.W.240.236; 1.W.240.237; 1.W.240.238; 1.W.240.239; 1.W.240.154; 1.W.240.157; 1.W.240.166; 1.W.240.169; 1.W.240.172; 1.W.240.175; 1.W.240.240; 1.W.240.244; 1.W.244.228; 1.W.244.229; 1.W.244.230; 1.W.244.231; 1.W.244.236; 1.W.244.237; 1.W.244.238; 1.W.244.239; 1.W.244.154; 1.W.244.157; 1.W.244.166; 1.W.244.169; 1.W.244.172; 1.W.244.175; 1.W.244.240; 1.W.244.244;

Prodrugs of 1.Y

1.Y.228.228; 1.Y.228.229; 1.Y.228.230; 1.Y.228.231; 1.Y.228.236; 1.Y.228.237; 1.Y.228.238; 1.Y.228.239; 1.Y.228.154; 1.Y.228.157; 1.Y.228.166; 1.Y.228.169; 1.Y.228.172; 1.Y.228.175; 1.Y.228.240; 1.Y.228.244; 1.Y.229.228; 1.Y.229.229; 1.Y.229.230; 1.Y.229.231;

TABLE 7-continued

1.Y.229.236; 1.Y.229.237; 1.Y.229.238; 1.Y.229.239; 1.Y.229.154;
1.Y.229.157; 1.Y.229.166; 1.Y.229.169; 1.Y.229.172; 1.Y.229.175;
1.Y.229.240; 1.Y.229.244; 1.Y.230.228; 1.Y.230.229; 1.Y.230.230;
1.Y.230.231; 1.Y.230.236; 1.Y.230.237; 1.Y.230.238; 1.Y.230.239;
1.Y.230.154; 1.Y.230.157; 1.Y.230.166; 1.Y.230.169; 1.Y.230.172;
1.Y.230.175; 1.Y.230.240; 1.Y.230.244; 1.Y.231.228; 1.Y.231.229;
1.Y.231.230; 1.Y.231.231; 1.Y.231.236; 1.Y.231.237; 1.Y.231.238;
1.Y.231.239; 1.Y.231.154; 1.Y.231.157; 1.Y.231.166; 1.Y.231.169;
1.Y.231.172; 1.Y.231.175; 1.Y.231.240; 1.Y.231.244; 1.Y.236.228;
1.Y.236.229; 1.Y.236.230; 1.Y.236.231; 1.Y.236.236; 1.Y.236.237;
1.Y.236.238; 1.Y.236.239; 1.Y.236.154; 1.Y.236.157; 1.Y.236.166;
1.Y.236.169; 1.Y.236.172; 1.Y.236.154; 1.Y.236.240; 1.Y.236.244;
1.Y.237.228; 1.Y.237.229; 1.Y.237.230; 1.Y.237.231; 1.Y.237.236;
1.Y.237.237; 1.Y.237.238; 1.Y.237.239; 1.Y.237.154; 1.Y.237.157;
1.Y.237.166; 1.Y.237.169; 1.Y.237.172; 1.Y.237.175; 1.Y.237.240;
1.Y.237.244; 1.Y.238.228; 1.Y.238.229; 1.Y.238.230; 1.Y.238.231;
1.Y.238.236; 1.Y.238.237; 1.Y.238.238; 1.Y.238.239; 1.Y.238.154;
1.Y.238.157; 1.Y.238.166; 1.Y.238.169; 1.Y.238.172; 1.Y.238.175;
1.Y.238.240; 1.Y.238.244; 1.Y.239.228; 1.Y.239.229; 1.Y.239.230;
1.Y.239.231; 1.Y.239.236; 1.Y.239.237; 1.Y.239.238; 1.Y.239.239;
1.Y.239.154; 1.Y.239.157; 1.Y.239.166; 1.Y.239.169; 1.Y.239.172;
1.Y.239.175; 1.Y.239.240; 1.Y.239.244; 1.Y.154.228; 1.Y.154.229;
1.Y.154.230; 1.Y.154.231; 1.Y.154.236; 1.Y.154.237; 1.Y.154.238;
1.Y.154.239; 1.Y.154.154; 1.Y.154.157; 1.Y.154.166; 1.Y.154.169;
1.Y.154.172; 1.Y.154.175; 1.Y.154.240; 1.Y.154.244; 1.Y.157.228;
1.Y.157.229; 1.Y.157.230; 1.Y.157.231; 1.Y.157.236; 1.Y.157.237;
1.Y.157.238; 1.Y.157.239; 1.Y.157.154; 1.Y.157.157; 1.Y.157.166;
1.Y.157.169; 1.Y.157.172; 1.Y.157.175; 1.Y.157.240; 1.Y.157.244;
1.Y.166.228; 1.Y.166.229; 1.Y.166.230; 1.Y.166.231; 1.Y.166.236;
1.Y.166.237; 1.Y.166.238; 1.Y.166.239; 1.Y.166.154; 1.Y.166.157;
1.Y.166.166; 1.Y.166.169; 1.Y.166.172; 1.Y.166.175; 1.Y.166.240;
1.Y.166.244; 1.Y.169.228; 1.Y.169.229; 1.Y.169.230; 1.Y.169.231;
1.Y.169.236; 1.Y.169.237; 1.Y.169.238; 1.Y.169.239; 1.Y.169.154;
1.Y.169.157; 1.Y.169.166; 1.Y.169.169; 1.Y.169.172; 1.Y.169.175;
1.Y.169.240; 1.Y.169.244; 1.Y.172.228; 1.Y.172.229; 1.Y.172.230;
1.Y.172.231; 1.Y.172.236; 1.Y.172.237; 1.Y.172.238; 1.Y.172.239;
1.Y.172.254; 1.Y.172.157; 1.Y.172.166; 1.Y.172.169; 1.Y.172.172;
1.Y.172.175; 1.Y.172.240; 1.Y.172.244; 1.Y.175.228; 1.Y.175.229;
1.Y.175.230; 1.Y.175.231; 1.Y.175.236; 1.Y.175.237; 1.Y.175.238;
1.Y.175.239; 1.Y.175.154; 1.Y.175.157; 1.Y.175.166; 1.Y.175.169;
1.Y.175.172; 1.Y.175.175; 1.Y.175.240; 1.Y.175.244; 1.Y.240.228;
1.Y.240.229; 1.Y.240.230; 1.Y.240.231; 1.Y.240.236; 1.Y.240.237;
1.Y.240.238; 1.Y.240.239; 1.Y.240.154; 1.Y.240.157; 1.Y.240.166;
1.Y.240.169; 1.Y.240.172; 1.Y.240.175; 1.Y.240.240; 1.Y.240.244;
1.Y.244.228; 1.Y.244.229; 1.Y.244.230; 1.Y.244.231; 1.Y.244.236;
1.Y.244.237; 1.Y.244.238; 1.Y.244.239; 1.Y.244.154; 1.Y.244.157;
1.Y.244.166; 1.Y.244.169; 1.Y.244.172; 1.Y.244.175; 1.Y.244.240;
1.Y.244.244;
Prodrugs of 2.B 2.B.228.228; 2.B.228.229; 2.B.228.230; 2.B.228.231; 2.B.228.236;
2.B.228.237; 2.B.228.238; 2.B.228.239; 2.B.228.154; 2.B.228.157;
2.B.228.166; 2.B.228.169; 2.B.228.172; 2.B.228.175; 2.B.228.240;
2.B.228.244; 2.B.229.228; 2.B.229.229; 2.B.229.230; 2.B.229.231;
2.B.229.236; 2.B.229.237; 2.B.229.238; 2.B.229.239; 2.B.229.154;
2.B.229.157; 2.B.229.166; 2.B.229.169; 2.B.229.172; 2.B.229.175;
2.B.229.240; 2.B.229.244; 2.B.230.228; 2.B.230.229; 2.B.230.230;
2.B.230.231; 2.B.230.236; 2.B.230.237; 2.B.230.238; 2.B.230.239;
2.B.230.154; 2.B.230.157; 2.B.230.166; 2.B.230.169; 2.B.230.172;
2.B.230.175; 2.B.230.240; 2.B.230.244; 2.B.231.228; 2.B.231.229;
2.B.231.230; 2.B.231.231; 2.B.231.236; 2.B.231.237; 2.B.231.238;
2.B.231.239; 2.B.231.154; 2.B.231.157; 2.B.231.166; 2.B.231.169;
2.B.231.172; 2.B.231.175; 2.B.231.240; 2.B.231.244; 2.B.236.228;
2.B.236.229; 2.B.236.230; 2.B.236.231; 2.B.236.236; 2.B.236.237;
2.B.236.238; 2.B.236.239; 2.B.236.154; 2.B.236.157; 2.B.236.166;
2.B.236.169; 2.B.236.172; 2.B.236.175; 2.B.236.240; 2.B.236.244;
2.B.237.228; 2.B.237.229; 2.B.237.230; 2.B.237.231; 2.B.237.236;
2.B.237.237; 2.B.237.238; 2.B.237.239; 2.B.237.154; 2.B.237.157;
2.B.237.166; 2.B.237.169; 2.B.237.172; 2.B.237.175; 2.B.237.240;
2.B.237.244; 2.B.238.228; 2.B.238.229; 2.B.238.230; 2.B.238.231;
2.B.238.236; 2.B.238.237; 2.B.238.238; 2.B.238.239; 2.B.238.154;
2.B.238.157; 2.B.238.166; 2.B.238.169; 2.B.238.172; 2.B.238.175;
2.B.238.240; 2.B.238.244; 2.B.239.228; 2.B.239.229; 2.B.239.230;
2.B.239.231; 2.B.239.236; 2.B.239.237; 2.B.239.238; 2.B.239.239;
2.B.239.154; 2.B.239.157; 2.B.239.166; 2.B.239.169; 2.B.239.172;
2.B.239.175; 2.B.239.240; 2.B.239.244; 2.B.154.228; 2.B.154.229;
2.B.154.230; 2.B.154.231; 2.B.154.236; 2.B.154.237; 2.B.154.238;
2.B.154.239; 2.B.154.154; 2.B.154.157; 2.B.154.166; 2.B.154.169;
2.B.154.172; 2.B.154.175; 2.B.154.240; 2.B.154.244; 2.B.157.228;
2.B.157.229; 2.B.157.230; 2.B.157.231; 2.B.157.236; 2.B.157.237;
2.B.157.238; 2.B.157.239; 2.B.157.154; 2.B.157.157; 2.B.157.166;
2.B.157.169; 2.B.157.172; 2.B.157.175; 2.B.157.240; 2.B.157.244;
2.B.166.228; 2.B.166.229; 2.B.166.230; 2.B.166.231; 2.B.166.236;
2.B.166.237; 2.B.166.238; 2.B.166.239; 2.B.166.154; 2.B.166.157;
2.B.166.166; 2.B.166.169; 2.B.166.172; 2.B.166.175; 2.B.166.240;
2.B.166.244; 2.B.169.228; 2.B.169.229; 2.B.169.230; 2.B.169.231;
2.B.169.236; 2.B.169.237; 2.B.169.238; 2.B.169.239; 2.B.169.154;
2.B.169.157; 2.B.169.166; 2.B.169.169; 2.B.169.172; 2.B.169.175;
2.B.169.240; 2.B.169.244; 2.B.172.228; 2.B.172.229; 2.B.172.230;
2.B.172.231; 2.B.172.236; 2.B.172.237; 2.B.172.238; 2.B.172.239;
2.B.172.154; 2.B.172.157; 2.B.172.166; 2.B.172.169; 2.B.172.172;
2.B.172.175; 2.B.172.240; 2.B.172.244; 2.B.175.228; 2.B.175.229;
2.B.175.230; 2.B.175.231; 2.B.175.236; 2.B.175.237; 2.B.175.238;
2.B.175.239; 2.B.175.154; 2.B.175.157; 2.B.175.166; 2.B.175.169;
2.B.175.172; 2.B.175.175; 2.B.175.240; 2.B.175.244; 2.B.240.228;
2.B.240.229; 2.B.240.230; 2.B.240.231; 2.B.240.236; 2.B.240.237;
2.B.240.238; 2.B.240.239; 2.B.240.154; 2.B.240.157; 2.B.240.166;
2.B.240.169; 2.B.240.172; 2.B.240.175; 2.B.240.240; 2.B.240.244;
2.B.244.228; 2.B.244.229; 2.B.244.230; 2.B.244.231; 2.B.244.236;
2.B.244.237; 2.B.244.238; 2.B.244.239; 2.B.244.154; 2.B.244.157;
2.B.244.166; 2.B.244.169; 2.B.244.172; 2.B.244.175; 2.B.244.240;
2.B.244.244;
Prodrugs of 2.D 2.D.228.228; 2.D.228.229; 2.D.228.230; 2.D.228.231; 2.D.228.236;
2.D.228.237; 2.D.228.238; 2.D.228.239; 2.D.228.154; 2.D.228.157;
2.D.228.166; 2.D.228.169; 2.D.228.172; 2.D.228.175; 2.D.228.240;
2.D.228.244; 2.D.229.228; 2.D.229.229; 2.D.229.230; 2.D.229.231;
2.D.229.236; 2.D.229.237; 2.D.229.238; 2.D.229.239; 2.D.229.154;
2.D.229.157; 2.D.229.166; 2.D.229.169; 2.D.229.172; 2.D.229.175;
2.D.229.240; 2.D.229.244; 2.D.230.228; 2.D.230.229; 2.D.230.230;
2.D.230.231; 2.D.230.236; 2.D.230.237; 2.D.230.238; 2.D.230.239;
2.D.230.154; 2.D.230.157; 2.D.230.166; 2.D.230.169; 2.D.230.172;
2.D.230.175; 2.D.230.240; 2.D.230.244; 2.D.231.228; 2.D.231.229;
2.D.231.230; 2.D.231.231; 2.D.231.236; 2.D.231.237; 2.D.231.238;
2.D.231.239; 2.D.231.154; 2.D.231.157; 2.D.231.166; 2.D.231.169;
2.D.231.172; 2.D.231.175; 2.D.231.240; 2.D.231.244; 2.D.236.228;
2.D.236.229; 2.D.236.230; 2.D.236.231; 2.D.236.236; 2.D.236.237;
2.D.236.238; 2.D.236.239; 2.D.236.154; 2.D.236.157; 2.D.236.166;
2.D.236.169; 2.D.236.172; 2.D.236.175; 2.D.236.240; 2.D.236.244;
2.D.237.228; 2.D.237.229; 2.D.237.230; 2.D.237.231; 2.D.237.236;
2.D.237.237; 2.D.237.238; 2.D.237.239; 2.D.237.154; 2.D.237.157;
2.D.237.166; 2.D.237.169; 2.D.237.172; 2.D.237.175; 2.D.237.240;
2.D.237.244; 2.D.238.228; 2.D.238.229; 2.D.238.230; 2.D.238.231;
2.D.238.236; 2.D.238.237; 2.D.238.238; 2.D.238.239; 2.D.238.154;
2.D.238.157; 2.D.238.166; 2.D.238.169; 2.D.238.172; 2.D.238.175;
2.D.238.240; 2.D.238.244; 2.D.239.228; 2.D.239.229; 2.D.239.230;
2.D.239.231; 2.D.239.236; 2.D.239.237; 2.D.239.238; 2.D.239.239;
2.D.239.154; 2.D.239.157; 2.D.239.166; 2.D.239.169; 2.D.239.172;
2.D.239.175; 2.D.239.240; 2.D.239.244; 2.D.154.228; 2.D.154.229;
2.D.154.230; 2.D.154.231; 2.D.154.236; 2.D.154.237; 2.D.154.238;
2.D.154.239; 2.D.154.154; 2.D.154.157; 2.D.154.166; 2.D.154.169;
2.D.154.172; 2.D.154.175; 2.D.154.240; 2.D.154.244; 2.D.157.228;
2.D.157.229; 2.D.157.230; 2.D.157.231; 2.D.157.236; 2.D.157.237;
2.D.157.238; 2.D.157.239; 2.D.157.154; 2.D.157.157; 2.D.157.166;
2.D.157.169; 2.D.157.172; 2.D.157.175; 2.D.157.240; 2.D.157.244;
2.D.166.228; 2.D.166.229; 2.D.166.230; 2.D.166.231; 2.D.166.236;
2.D.166.237; 2.D.166.238; 2.D.166.239; 2.D.166.154; 2.D.166.157;
2.D.166.166; 2.D.166.169; 2.D.166.172; 2.D.166.175; 2.D.166.240;
2.D.166.244; 2.D.169.228; 2.D.169.229; 2.D.169.230; 2.D.169.231;
2.D.169.236; 2.D.169.237; 2.D.169.238; 2.D.169.239; 2.D.169.154;
2.D.169.157; 2.D.169.166; 2.D.169.169; 2.D.169.172; 2.D.169.175;
2.D.169.240; 2.D.169.244; 2.D.172.228; 2.D.172.229; 2.D.172.230;
2.D.172.231; 2.D.172.236; 2.D.172.237; 2.D.172.238; 2.D.172.239;
2.D.172.154; 2.D.172.157; 2.D.172.166; 2.D.172.169; 2.D.172.172;
2.D.172.175; 2.D.172.240; 2.D.172.244; 2.D.175.228; 2.D.175.229;
2.D.175.230; 2.D.175.231; 2.D.175.236; 2.D.175.237; 2.D.175.238;
2.D.175.239; 2.D.175.154; 2.D.175.157; 2.D.175.166; 2.D.175.169;
2.D.175.172; 2.D.175.175; 2.D.175.240; 2.D.175.244; 2.D.240.228;
2.D.240.229; 2.D.240.230; 2.D.240.231; 2.D.240.236; 2.D.240.237;
2.D.240.238; 2.D.240.239; 2.D.240.154; 2.D.240.157; 2.D.240.166;
2.D.240.169; 2.D.240.172; 2.D.240.175; 2.D.240.240; 2.D.240.244;
2.D.244.228; 2.D.244.229; 2.D.244.230; 2.D.244.231; 2.D.244.236;
2.D.244.237; 2.D.244.238; 2.D.244.239; 2.D.244.154; 2.D.244.157;
2.D.244.166; 2.D.244.169; 2.D.244.172; 2.D.244.175; 2.D.244.240;
2.D.244.244;

TABLE 7-continued

Prodrugs of 2.E

2.E.228.228; 2.E.228.229; 2.E.228.230; 2.E.228.231; 2.E.228.236; 2.E.228.237; 2.E.228.238; 2.E.228.239; 2.E.228.154; 2.E.228.157; 2.E.228.166; 2.E.228.169; 2.E.228.172; 2.E.228.175; 2.E.228.240; 2.E.228.244; 2.E.229.228; 2.E.229.229; 2.E.229.230; 2.E.229.231; 2.E.229.236; 2.E.229.237; 2.E.229.238; 2.E.229.239; 2.E.229.154; 2.E.229.157; 2.E.229.166; 2.E.229.169; 2.E.229.172; 2.E.229.175; 2.E.229.240; 2.E.229.244; 2.E.230.228; 2.E.230.229; 2.E.230.230; 2.E.230.231; 2.E.230.236; 2.E.230.237; 2.E.230.238; 2.E.230.239; 2.E.230.154; 2.E.230.157; 2.E.230.166; 2.E.230.169; 2.E.230.172; 2.E.230.175; 2.E.230.240; 2.E.230.244; 2.E.231.228; 2.E.231.229; 2.E.231.230; 2.E.231.231; 2.E.231.236; 2.E.231.237; 2.E.231.238; 2.E.231.239; 2.E.231.154; 2.E.231.157; 2.E.231.166; 2.E.231.169; 2.E.231.172; 2.E.231.175; 2.E.231.240; 2.E.231.244; 2.E.236.228; 2.E.236.229; 2.E.236.230; 2.E.236.231; 2.E.236.236; 2.E.236.237; 2.E.236.238; 2.E.236.239; 2.E.236.154; 2.E.236.157; 2.E.236.166; 2.E.236.169; 2.E.236.172; 2.E.236.175; 2.E.236.240; 2.E.236.244; 2.E.237.228; 2.E.237.229; 2.E.237.230; 2.E.237.231; 2.E.237.236; 2.E.237.237; 2.E.237.238; 2.E.237.239; 2.E.237.154; 2.E.237.157; 2.E.237.166; 2.E.237.169; 2.E.237.172; 2.E.237.175; 2.E.237.240; 2.E.237.244; 2.E.238.228; 2.E.238.229; 2.E.238.230; 2.E.238.231; 2.E.238.236; 2.E.238.237; 2.E.238.238; 2.E.238.239; 2.E.238.154; 2.E.238.157; 2.E.238.166; 2.E.238.169; 2.E.238.172; 2.E.238.175; 2.E.238.240; 2.E.238.244; 2.E.239.228; 2.E.239.229; 2.E.239.230; 2.E.239.231; 2.E.239.236; 2.E.239.237; 2.E.239.238; 2.E.239.239; 2.E.239.154; 2.E.239.157; 2.E.239.166; 2.E.239.169; 2.E.239.172; 2.E.239.175; 2.E.239.240; 2.E.239.244; 2.E.154.228; 2.E.154.229; 2.E.154.230; 2.E.154.231; 2.E.154.236; 2.E.154.237; 2.E.154.238; 2.E.154.239; 2.E.154.154; 2.E.154.157; 2.E.154.166; 2.E.154.169; 2.E.154.172; 2.E.154.175; 2.E.154.240; 2.E.154.244; 2.E.157.228; 2.E.157.229; 2.E.157.230; 2.E.157.231; 2.E.157.236; 2.E.157.237; 2.E.157.238; 2.E.157.239; 2.E.157.154; 2.E.157.157; 2.E.157.166; 2.E.157.169; 2.E.157.172; 2.E.157.175; 2.E.157.240; 2.E.157.244; 2.E.166.228; 2.E.166.229; 2.E.166.230; 2.E.166.231; 2.E.166.236; 2.E.166.237; 2.E.166.238; 2.E.166.239; 2.E.166.154; 2.E.166.157; 2.E.166.166; 2.E.166.169; 2.E.166.172; 2.E.166.175; 2.E.166.240; 2.E.166.244; 2.E.169.228; 2.E.169.229; 2.E.169.230; 2.E.169.231; 2.E.169.236; 2.E.169.237; 2.E.169.238; 2.E.169.239; 2.E.169.154; 2.E.169.157; 2.E.169.166; 2.E.169.169; 2.E.169.172; 2.E.169.175; 2.E.169.240; 2.E.169.244; 2.E.172.228; 2.E.172.229; 2.E.172.230; 2.E.172.231; 2.E.172.236; 2.E.172.237; 2.E.172.238; 2.E.172.239; 2.E.172.154; 2.E.172.157; 2.E.172.166; 2.E.172.169; 2.E.172.172; 2.E.172.175; 2.E.172.240; 2.E.172.244; 2.E.175.228; 2.E.175.229; 2.E.175.230; 2.E.175.231; 2.E.175.236; 2.E.175.237; 2.E.175.238; 2.E.175.239; 2.E.175.154; 2.E.175.157; 2.E.175.166; 2.E.175.169; 2.E.175.172; 2.E.175.175; 2.E.175.240; 2.E.175.244; 2.E.240.228; 2.E.240.229; 2.E.240.230; 2.E.240.231; 2.E.240.236; 2.E.240.237; 2.E.240.238; 2.E.240.239; 2.E.240.154; 2.E.240.157; 2.E.240.166; 2.E.240.169; 2.E.240.172; 2.E.240.175; 2.E.240.240; 2.E.240.244; 2.E.244.228; 2.E.244.229; 2.E.244.230; 2.E.244.231; 2.E.244.236; 2.E.244.237; 2.E.244.238; 2.E.244.239; 2.E.244.154; 2.E.244.157; 2.E.244.166; 2.E.244.169; 2.E.244.172; 2.E.244.175; 2.E.244.240; 2.E.244.244;

Prodrugs of 2.G

2.G.228.228; 2.G.228.229; 2.G.228.230; 2.G.228.231; 2.G.228.236; 2.G.228.237; 2.G.228.238; 2.G.228.239; 2.G.228.154; 2.G.228.157; 2.G.228.166; 2.G.228.169; 2.G.228.172; 2.G.228.175; 2.G.228.240; 2.G.228.244; 2.G.229.228; 2.G.229.229; 2.G.229.230; 2.G.229.231; 2.G.229.236; 2.G.229.237; 2.G.229.238; 2.G.229.239; 2.G.229.154; 2.G.229.157; 2.G.229.166; 2.G.229.169; 2.G.229.172; 2.G.229.175; 2.G.229.240; 2.G.229.244; 2.G.230.228; 2.G.230.229; 2.G.230.230; 2.G.230.231; 2.G.230.236; 2.G.230.237; 2.G.230.238; 2.G.230.239; 2.G.230.154; 2.G.230.157; 2.G.230.166; 2.G.230.169; 2.G.230.172; 2.G.230.175; 2.G.230.240; 2.G.230.244; 2.G.231.228; 2.G.231.229; 2.G.231.230; 2.G.231.231; 2.G.231.236; 2.G.231.237; 2.G.231.238; 2.G.231.239; 2.G.231.154; 2.G.231.157; 2.G.231.166; 2.G.231.169; 2.G.231.172; 2.G.231.175; 2.G.231.240; 2.G.231.244; 2.G.236.228; 2.G.236.229; 2.G.236.230; 2.G.236.231; 2.G.236.236; 2.G.236.237; 2.G.236.238; 2.G.236.239; 2.G.236.154; 2.G.236.157; 2.G.236.166; 2.G.236.169; 2.G.236.172; 2.G.236.175; 2.G.236.240; 2.G.236.244; 2.G.237.228; 2.G.237.229; 2.G.237.230; 2.G.237.231; 2.G.237.236; 2.G.237.237; 2.G.237.238; 2.G.237.239; 2.G.237.154; 2.G.237.157; 2.G.237.166; 2.G.237.169; 2.G.237.172; 2.G.237.175; 2.G.237.240; 2.G.237.244; 2.G.238.228; 2.G.238.229; 2.G.238.230; 2.G.238.231; 2.G.238.236; 2.G.238.237; 2.G.238.238; 2.G.238.239; 2.G.238.154; 2.G.238.157; 2.G.238.166; 2.G.238.169; 2.G.238.172; 2.G.238.175; 2.G.238.240; 2.G.238.244; 2.G.239.228; 2.G.239.229; 2.G.239.230; 2.G.239.231; 2.G.239.236; 2.G.239.237; 2.G.239.238; 2.G.239.239; 2.G.239.154; 2.G.239.157; 2.G.239.166; 2.G.239.169; 2.G.239.172; 2.G.239.175; 2.G.239.240; 2.G.239.244; 2.G.154.228; 2.G.154.229; 2.G.154.230; 2.G.154.231; 2.G.154.236; 2.G.154.237; 2.G.154.238; 2.G.154.239; 2.G.154.154; 2.G.154.157; 2.G.154.166; 2.G.154.169; 2.G.154.172; 2.G.154.175; 2.G.154.240; 2.G.154.244; 2.G.157.228; 2.G.157.229; 2.G.157.230; 2.G.157.231; 2.G.157.236; 2.G.157.237; 2.G.157.238; 2.G.157.239; 2.G.157.154; 2.G.157.157; 2.G.157.166; 2.G.157.169; 2.G.157.172; 2.G.157.175; 2.G.157.240; 2.G.157.244; 2.G.166.228; 2.G.166.229; 2.G.166.230; 2.G.166.231; 2.G.166.236; 2.G.166.237; 2.G.166.238; 2.G.166.239; 2.G.166.154; 2.G.166.157; 2.G.166.166; 2.G.166.169; 2.G.166.172; 2.G.166.175; 2.G.166.240; 2.G.166.244; 2.G.169.228; 2.G.169.229; 2.G.169.230; 2.G.169.231; 2.G.169.236; 2.G.169.237; 2.G.169.238; 2.G.169.239; 2.G.169.154; 2.G.169.157; 2.G.169.166; 2.G.169.169; 2.G.169.172; 2.G.169.175; 2.G.169.240; 2.G.169.244; 2.G.172.228; 2.G.172.229; 2.G.172.230; 2.G.172.231; 2.G.172.236; 2.G.172.237; 2.G.172.238; 2.G.172.239; 2.G.172.154; 2.G.172.157; 2.G.172.166; 2.G.172.169; 2.G.172.172; 2.G.172.175; 2.G.172.240; 2.G.172.244; 2.G.175.228; 2.G.175.229; 2.G.175.230; 2.G.175.231; 2.G.175.236; 2.G.175.237; 2.G.175.238; 2.G.175.239; 2.G.175.154; 2.G.175.157; 2.G.175.166; 2.G.175.169; 2.G.175.172; 2.G.175.175; 2.G.175.240; 2.G.175.244; 2.G.240.228; 2.G.240.229; 2.G.240.230; 2.G.240.231; 2.G.240.236; 2.G.240.237; 2.G.240.238; 2.G.240.239; 2.G.240.154; 2.G.240.157; 2.G.240.166; 2.G.240.169; 2.G.240.172; 2.G.240.175; 2.G.240.240; 2.G.240.244; 2.G.244.228; 2.G.244.229; 2.G.244.230; 2.G.244.231; 2.G.244.236; 2.G.244.237; 2.G.244.238; 2.G.244.239; 2.G.244.154; 2.G.244.157; 2.G.244.166; 2.G.244.169; 2.G.244.172; 2.G.244.175; 2.G.244.240; 2.G.244.244;

Prodrugs of 2.I

2.I.228.228; 2.I.228.229; 2.I.228.230; 2.I.228.231; 2.I.228.236; 2.I.228.237; 2.I.228.238; 2.I.228.239; 2.I.228.154; 2.I.228.157; 2.I.228.166; 2.I.228.169; 2.I.228.172; 2.I.228.175; 2.I.228.240; 2.I.228.244; 2.I.229.228; 2.I.229.229; 2.I.229.230; 2.I.229.231; 2.I.229.236; 2.I.229.237; 2.I.229.238; 2.I.229.239; 2.I.229.154; 2.I.229.157; 2.I.229.166; 2.I.229.169; 2.I.229.172; 2.I.229.175; 2.I.229.240; 2.I.229.244; 2.I.230.228; 2.I.230.229; 2.I.230.230; 2.I.230.231; 2.I.230.236; 2.I.230.237; 2.I.230.238; 2.I.230.239; 2.I.230.154; 2.I.230.157; 2.I.230.166; 2.I.230.169; 2.I.230.172; 2.I.230.175; 2.I.230.240; 2.I.230.244; 2.I.231.228; 2.I.231.229; 2.I.231.230; 2.I.231.231; 2.I.231.236; 2.I.231.237; 2.I.231.238; 2.I.231.239; 2.I.231.154; 2.I.231.157; 2.I.231.166; 2.I.231.169; 2.I.231.172; 2.I.231.175; 2.I.231.240; 2.I.231.244; 2.I.236.228; 2.I.236.229; 2.I.236.230; 2.I.236.231; 2.I.236.236; 2.I.236.237; 2.I.236.238; 2.I.236.239; 2.I.236.154; 2.I.236.157; 2.I.236.166; 2.I.236.169; 2.I.236.172; 2.I.236.175; 2.I.236.240; 2.I.236.244; 2.I.237.228; 2.I.237.229; 2.I.237.230; 2.I.237.231; 2.I.237.236; 2.I.237.237; 2.I.237.238; 2.I.237.239; 2.I.237.154; 2.I.237.157; 2.I.237.166; 2.I.237.169; 2.I.237.172; 2.I.237.175; 2.I.237.240; 2.I.237.244; 2.I.238.228; 2.I.238.229; 2.I.238.230; 2.I.238.231; 2.I.238.236; 2.I.238.237; 2.I.238.238; 2.I.238.239; 2.I.238.154; 2.I.238.157; 2.I.238.166; 2.I.238.169; 2.I.238.172; 2.I.238.175; 2.I.238.240; 2.I.238.244; 2.I.239.228; 2.I.239.229; 2.I.239.230; 2.I.239.231; 2.I.239.236; 2.I.239.237; 2.I.239.238; 2.I.239.239; 2.I.239.154; 2.I.239.157; 2.I.239.166; 2.I.239.169; 2.I.239.172; 2.I.239.175; 2.I.239.240; 2.I.239.244; 2.I.154.228; 2.I.154.229; 2.I.154.230; 2.I.154.231; 2.I.154.236; 2.I.154.237; 2.I.154.238; 2.I.154.239; 2.I.154.154; 2.I.154.157; 2.I.154.166; 2.I.154.169; 2.I.154.172; 2.I.154.175; 2.I.154.240; 2.I.154.244; 2.I.157.228; 2.I.157.229; 2.I.157.230; 2.I.157.231; 2.I.157.236; 2.I.157.237; 2.I.157.238; 2.I.157.239; 2.I.157.154; 2.I.157.157; 2.I.157.166; 2.I.157.169; 2.I.157.172; 2.I.157.175; 2.I.157.240; 2.I.157.244; 2.I.166.228; 2.I.166.229; 2.I.166.230; 2.I.166.231; 2.I.166.236; 2.I.166.237; 2.I.166.238; 2.I.166.239; 2.I.166.154; 2.I.166.157; 2.I.166.166; 2.I.166.169; 2.I.166.172; 2.I.166.175; 2.I.166.240; 2.I.166.244; 2.I.169.228; 2.I.169.229; 2.I.169.230; 2.I.169.231; 2.I.169.236; 2.I.169.237; 2.I.169.238; 2.I.169.239; 2.I.169.154; 2.I.169.157; 2.I.169.166; 2.I.169.169; 2.I.169.172; 2.I.169.175; 2.I.169.240; 2.I.169.244; 2.I.172.228; 2.I.172.229; 2.I.172.230; 2.I.172.231; 2.I.172.236; 2.I.172.237; 2.I.172.238; 2.I.172.239; 2.I.172.154; 2.I.172.157; 2.I.172.166; 2.I.172.169; 2.I.172.172; 2.I.172.175; 2.I.172.240; 2.I.172.244; 2.I.175.228; 2.I.175.229; 2.I.175.230; 2.I.175.231; 2.I.175.236; 2.I.175.237; 2.I.175.238; 2.I.175.239; 2.I.175.154; 2.I.175.157; 2.I.175.166; 2.I.175.169; 2.I.175.172; 2.I.175.175; 2.I.175.240; 2.I.175.244; 2.I.240.228; 2.I.240.229; 2.I.240.230; 2.I.240.231; 2.I.240.236; 2.I.240.237; 2.I.240.238; 2.I.240.239; 2.I.240.154; 2.I.240.157; 2.I.240.166; 2.I.240.169; 2.I.240.172; 2.I.240.175; 2.I.240.240; 2.I.240.244;

TABLE 7-continued

2.I.244.228; 2.I.244.229; 2.I.244.230; 2.I.244.231; 2.I.244.236; 2.I.244.237; 2.I.244.238; 2.I.244.239; 2.I.244.154; 2.I.244.157; 2.I.244.166; 2.I.244.169; 2.I.244.172; 2.I.244.175; 2.I.244.240; 2.I.244.244;

Prodrugs of 2.J

2.J.228.228; 2.J.228.229; 2.J.228.230; 2.J.228.231; 2.J.228.236; 2.J.228.237; 2.J.228.238; 2.J.228.239; 2.J.228.154; 2.J.228.157; 2.J.228.166; 2.J.228.169; 2.J.228.172; 2.J.228.175; 2.J.228.240; 2.J.228.244; 2.J.229.228; 2.J.229.229; 2.J.229.230; 2.j.229.231; 2.J.229.236; 2.J.229.237; 2.J.229.238; 2.J.229.239; 2.J.229.154; 2.J.229.157; 2.J.229.166; 2.J.229.169; 2.J.229.172; 2.J.229.175; 2.J.229.240; 2.J.229.244; 2.J.230.228; 2.J.230.229; 2.J.230.230; 2.J.230.231; 2.J.230.236; 2.J.230.237; 2.J.230.238; 2.J.230.239; 2.J.230.154; 2.J.230.157; 2.J.230.166; 2.J.230.169; 2.J.230.172; 2.J.230.175; 2.J.230.240; 2.J.230.244; 2.J.231.228; 2.J.231.229; 2.J.231.230; 2.J.231.231; 2.J.231.236; 2.J.231.237; 2.J.231.238; 2.J.231.239; 2.J.231.154; 2.J.231.157; 2.J.231.166; 2.J.231.169; 2.J.231.172; 2.J.231.175; 2.J.231.240; 2.J.231.244; 2.J.236.228; 2.J.236.229; 2.J.236.230; 2.J.236.231; 2.J.236.236; 2.J.236.237; 2.J.236.238; 2.J.236.239; 2.J.236.154; 2.J.236.157; 2.J.236.166; 2.J.236.169; 2.J.236.172; 2.J.236.175; 2.J.236.240; 2.J.236.244; 2.J.237.228; 2.J.237.229; 2.J.237.230; 2.J.237.231; 2.J.237.236; 2.J.237.237; 2.J.237.238; 2.J.237.239; 2.J.237.154; 2.J.237.157; 2.J.237.166; 2.J.237.169; 2.J.237.172; 2.J.237.175; 2.J.237.240; 2.J.237.244; 2.J.238.228; 2.J.238.229; 2.J.238.230; 2.J.238.231; 2.J.238.236; 2.J.238.237; 2.J.238.238; 2.J.238.239; 2.J.238.154; 2.J.238.157; 2.J.238.166; 2.J.238.169; 2.J.238.172; 2.J.238.175; 2.J.238.240; 2.J.238.244; 2.J.239.228; 2.J.239.229; 2.J.239.230; 2.J.239.231; 2.J.239.236; 2.J.239.237; 2.J.239.238; 2.J.239.239; 2.J.239.154; 2.J.239.157; 2.J.239.166; 2.J.239.169; 2.J.239.172; 2.J.239.175; 2.J.239.240; 2.J.239.244; 2.J.154.228; 2.J.154.229; 2.J.154.230; 2.J.154.231; 2.J.154.236; 2.J.154.237; 2.J.154.238; 2.J.154.239; 2.J.154.154; 2.J.154.157; 2.J.154.166; 2.J.154.169; 2.J.154.172; 2.J.154.175; 2.J.154.240; 2.J.154.244; 2.J.157.228; 2.J.157.229; 2.J.157.230; 2.J.157.231; 2.J.157.236; 2.J.157.237; 2.J.157.238; 2.J.157.239; 2.J.157.154; 2.J.157.157; 2.J.157.166; 2.J.157.169; 2.J.157.172; 2.J.157.175; 2.J.157.240; 2.J.157.244; 2.J.166.228; 2.J.166.229; 2.J.166.230; 2.J.166.231; 2.J.166.236; 2.J.166.237; 2.J.166.238; 2.J.166.239; 2.J.166.154; 2.J.166.157; 2.J.166.166; 2.J.166.169; 2.J.166.172; 2.J.166.175; 2.J.166.240; 2.J.166.244; 2.J.169.228; 2.J.169.229; 2.J.169.230; 2.J.169.231; 2.J.169.236; 2.J.169.237; 2.J.169.238; 2.J.169.239; 2.J.169.154; 2.J.169.157; 2.J.169.166; 2.J.169.169; 2.J.169.172; 2.J.169.175; 2.J.169.240; 2.J.169.244; 2.J.172.228; 2.J.172.229; 2.J.172.230; 2.J.172.231; 2.J.172.236; 2.J.172.237; 2.J.172.238; 2.J.172.239; 2.J.172.154; 2.J.172.157; 2.J.172.166; 2.J.172.169; 2.J.172.172; 2.J.172.175; 2.J.172.240; 2.J.172.244; 2.J.175.228; 2.J.175.229; 2.J.175.230; 2.J.175.231; 2.J.175.236; 2.J.175.237; 2.J.175.238; 2.J.175.239; 2.J.175.154; 2.J.175.157; 2.J.175.166; 2.J.175.169; 2.J.175.172; 2.J.175.175; 2.J.175.240; 2.J.175.244; 2.J.240.228; 2.J.240.229; 2.J.240.230; 2.J.240.231; 2.J.240.236; 2.J.240.237; 2.J.240.238; 2.J.240.239; 2.J.240.154; 2.J.240.157; 2.J.240.166; 2.J.240.169; 2.J.240.172; 2.J.240.175; 2.J.240.240; 2.J.240.244; 2.J.244.228; 2.J.244.229; 2.J.244.230; 2.J.244.231; 2.J.244.236; 2.J.244.237; 2.J.244.238; 2.J.244.239; 2.J.244.154; 2.J.244.157; 2.J.244.166; 2.J.244.169; 2.J.244.172; 2.J.244.175; 2.J.244.240; 2.J.244.244;

Prodrugs of 2.L

2.L.228.228; 2.L.228.229; 2.L.228.230; 2.L.228.231; 2.L.228.236; 2.L.228.237; 2.L.228.238; 2.L.228.239; 2.L.228.154; 2.L.228.157; 2.L.228.166; 2.L.228.169; 2.L.228.172; 2.L.228.175; 2.L.228.240; 2.L.228.244; 2.L.229.228; 2.L.229.229; 2.L.229.230; 2.L.229.231; 2.L.229.236; 2.L.229.237; 2.L.229.238; 2.L.229.239; 2.L.229.154; 2.L.229.157; 2.L.229.166; 2.L.229.169; 2.L.229.172; 2.L.229.175; 2.L.229.240; 2.L.229.244; 2.L.230.228; 2.L.230.229; 2.L.230.230; 2.L.230.231; 2.L.230.236; 2.L.230.237; 2.L.230.238; 2.L.230.239; 2.L.230.154; 2.L.230.157; 2.L.230.166; 2.L.230.169; 2.L.230.172; 2.L.230.175; 2.L.230.240; 2.L.230.244; 2.L.231.228; 2.L.231.229; 2.L.231.230; 2.L.231.231; 2.L.231.236; 2.L.231.237; 2.L.231.238; 2.L.231.239; 2.L.231.154; 2.L.231.157; 2.L.231.166; 2.L.231.169; 2.L.231.172; 2.L.231.175; 2.L.231.240; 2.L.231.244; 2.L.236.228; 2.L.236.229; 2.L.236.230; 2.L.236.231; 2.L.236.236; 2.L.236.237; 2.L.236.238; 2.L.236.239; 2.L.236.154; 2.L.236.157; 2.L.236.166; 2.L.236.169; 2.L.236.172; 2.L.236.175; 2.L.236.240; 2.L.236.244; 2.L.237.228; 2.L.237.229; 2.L.237.230; 2.L.237.231; 2.L.237.236; 2.L.237.237; 2.L.237.238; 2.L.237.239; 2.L.237.154; 2.L.237.157; 2.L.237.166; 2.L.237.169; 2.L.237.172; 2.L.237.175; 2.L.237.240; 2.L.237.244; 2.L.238.228; 2.L.238.229; 2.L.238.230; 2.L.238.231; 2.L.238.236; 2.L.238.237; 2.L.238.238; 2.L.238.239; 2.L.238.154; 2.L.238.157; 2.L.238.166; 2.L.238.169; 2.L.238.172; 2.L.238.175; 2.L.238.240; 2.L.238.244; 2.L.239.228; 2.L.239.229; 2.L.239.230; 2.L.239.231; 2.L.239.236; 2.L.239.237; 2.L.239.238; 2.L.239.239; 2.L.239.154; 2.L.239.157; 2.L.239.166; 2.L.239.169; 2.L.239.172; 2.L.239.175; 2.L.239.240; 2.L.239.244; 2.L.154.228; 2.L.154.229; 2.L.154.230; 2.L.154.231; 2.L.154.236; 2.L.154.237; 2.L.154.238; 2.L.154.239; 2.L.154.154; 2.L.154.157; 2.L.154.166; 2.L.154.169; 2.L.154.172; 2.L.154.175; 2.L.154.240; 2.L.154.244; 2.L.157.228; 2.L.157.229; 2.L.157.230; 2.L.157.231; 2.L.157.236; 2.L.157.237; 2.L.157.238; 2.L.157.239; 2.L.157.154; 2.L.157.157; 2.L.157.166; 2.L.157.169; 2.L.157.172; 2.L.157.175; 2.L.157.240; 2.L.157.244; 2.L.166.228; 2.L.166.229; 2.L.166.230; 2.L.166.231; 2.L.166.236; 2.L.166.237; 2.L.166.238; 2.L.166.239; 2.L.166.154; 2.L.166.157; 2.L.166.166; 2.L.166.169; 2.L.166.172; 2.L.166.175; 2.L.166.240; 2.L.166.244; 2.L.169.228; 2.L.169.229; 2.L.169.230; 2.L.169.231; 2.L.169.236; 2.L.169.237; 2.L.169.238; 2.L.169.239; 2.L.169.154; 2.L.169.157; 2.L.169.166; 2.L.169.169; 2.L.169.172; 2.L.169.175; 2.L.169.240; 2.L.169.244; 2.L.172.228; 2.L.172.229; 2.L.172.230; 2.L.172.231; 2.L.172.236; 2.L.172.237; 2.L.172.238; 2.L.172.239; 2.L.172.154; 2.L.172.157; 2.L.172.166; 2.L.172.169; 2.L.172.172; 2.L.172.175; 2.L.172.240; 2.L.172.244; 2.L.175.228; 2.L.175.229; 2.L.175.230; 2.L.175.231; 2.L.175.236; 2.L.175.237; 2.L.175.238; 2.L.175.239; 2.L.175.154; 2.L.175.157; 2.L.175.166; 2.L.175.169; 2.L.175.172; 2.L.175.175; 2.L.175.240; 2.L.175.244; 2.L.240.228; 2.L.240.229; 2.L.240.230; 2.L.240.231; 2.L.240.236; 2.L.240.237; 2.L.240.238; 2.L.240.239; 2.L.240.154; 2.L.240.157; 2.L.240.166; 2.L.240.169; 2.L.240.172; 2.L.240.175; 2.L.240.240; 2.L.240.244; 2.L.244.228; 2.L.244.229; 2.L.244.230; 2.L.244.231; 2.L.244.236; 2.L.244.237; 2.L.244.238; 2.L.244.239; 2.L.244.154; 2.L.244.157; 2.L.244.166; 2.L.244.169; 2.L.244.172; 2.L.244.175; 2.L.244.240; 2.L.244.244;

Prodrugs of 2.O

2.O.228.228; 2.O.228.229; 2.O.228.230; 2.O.228.231; 2.O.228.236; 2.O.228.237; 2.O.228.238; 2.O.228.239; 2.O.228.154; 2.O.228.157; 2.O.228.166; 2.O.228.169; 2.O.228.172; 2.O.228.175; 2.O.228.240; 2.O.228.244; 2.O.229.228; 2.O.229.229; 2.O.229.230; 2.O.229.231; 2.O.229.236; 2.O.229.237; 2.O.229.238; 2.O.229.239; 2.O.229.154; 2.O.229.157; 2.O.229.166; 2.O.229.169; 2.O.229.172; 2.O.229.175; 2.O.229.240; 2.O.229.244; 2.O.230.228; 2.O.230.229; 2.O.230.230; 2.O.230.231; 2.O.230.236; 2.O.230.237; 2.O.230.238; 2.O.230.239; 2.O.230.154; 2.O.230.157; 2.O.230.166; 2.O.230.169; 2.O.230.172; 2.O.230.175; 2.O.230.240; 2.O.230.244; 2.O.231.228; 2.O.231.229; 2.O.231.230; 2.O.231.231; 2.O.231.236; 2.O.231.237; 2.O.231.238; 2.O.231.239; 2.O.231.154; 2.O.231.157; 2.O.231.166; 2.O.231.169; 2.O.231.172; 2.O.231.175; 2.O.231.240; 2.O.231.244; 2.O.236.228; 2.O.236.229; 2.O.236.230; 2.O.236.231; 2.O.236.236; 2.O.236.237; 2.O.236.238; 2.O.236.239; 2.O.236.154; 2.O.236.157; 2.O.236.166; 2.O.236.169; 2.O.236.172; 2.O.236.175; 2.O.236.240; 2.O.236.244; 2.O.237.228; 2.O.237.229; 2.O.237.230; 2.O.237.231; 2.O.237.236; 2.O.237.237; 2.O.237.238; 2.O.237.239; 2.O.237.154; 2.O.237.157; 2.O.237.166; 2.O.237.169; 2.O.237.172; 2.O.237.175; 2.O.237.240; 2.O.237.244; 2.O.238.228; 2.O.238.229; 2.O.238.230; 2.O.238.231; 2.O.238.236; 2.O.238.237; 2.O.238.238; 2.O.238.239; 2.O.238.154; 2.O.238.157; 2.O.238.166; 2.O.238.169; 2.O.238.172; 2.O.238.175; 2.O.238.240; 2.O.238.244; 2.O.239.228; 2.O.239.229; 2.O.239.230; 2.O.239.231; 2.O.239.236; 2.O.239.237; 2.O.239.238; 2.O.239.239; 2.O.239.154; 2.O.239.157; 2.O.239.166; 2.O.239.169; 2.O.239.172; 2.O.239.175; 2.O.239.240; 2.O.239.244; 2.O.154.228; 2.O.154.229; 2.O.154.230; 2.O.154.231; 2.O.154.236; 2.O.154.237; 2.O.154.238; 2.O.154.239; 2.O.154.154; 2.O.154.157; 2.O.154.166; 2.O.154.169; 2.O.154.172; 2.O.154.175; 2.O.154.240; 2.O.154.244; 2.O.157.228; 2.O.157.229; 2.O.157.230; 2.O.157.231; 2.O.157.236; 2.O.157.237; 2.O.157.238; 2.O.157.239; 2.O.157.154; 2.O.157.157; 2.O.157.166; 2.O.157.169; 2.O.157.172; 2.O.157.175; 2.O.157.240; 2.O.157.244; 2.O.166.228; 2.O.166.229; 2.O.166.230; 2.O.166.231; 2.O.166.236; 2.O.166.237; 2.O.166.238; 2.O.166.239; 2.O.166.154; 2.O.166.157; 2.O.166.166; 2.O.166.169; 2.O.166.172; 2.O.166.175; 2.O.166.240; 2.O.166.244; 2.O.169.228; 2.O.169.229; 2.O.169.230; 2.O.169.231; 2.O.169.236; 2.O.169.237; 2.O.169.238; 2.O.169.239; 2.O.169.154; 2.O.169.157; 2.O.169.166; 2.O.169.169; 2.O.169.172; 2.O.169.175; 2.O.169.240; 2.O.169.244; 2.O.172.228; 2.O.172.229; 2.O.172.230; 2.O.172.231; 2.O.172.236; 2.O.172.237; 2.O.172.238; 2.O.172.239; 2.O.172.154; 2.O.172.157; 2.O.172.166; 2.O.172.169; 2.O.172.172; 2.O.172.175; 2.O.172.240; 2.O.172.244; 2.O.175.228; 2.O.175.229; 2.O.175.230; 2.O.175.231; 2.O.175.236; 2.O.175.237; 2.O.175.238; 2.O.175.239; 2.O.175.154; 2.O.175.157; 2.O.175.166; 2.O.175.169;

TABLE 7-continued

2.O.175.172; 2.O.175.175; 2.O.175.240; 2.O.175.244; 2.O.240.228;
2.O.240.229; 2.O.240.230; 2.O.240.231; 2.O.240.236; 2.O.240.237;
2.O.240.238; 2.O.240.239; 2.O.240.154; 2.O.240.157; 2.O.240.166;
2.O.240.169; 2.O.240.172; 2.O.240.175; 2.O.240.240; 2.O.240.244;
2.O.244.228; 2.O.244.229; 2.O.244.230; 2.O.244.231; 2.O.244.236;
2.O.244.237; 2.O.244.238; 2.O.244.239; 2.O.244.154; 2.O.244.157;
2.O.244.166; 2.O.244.169; 2.O.244.172; 2.O.244.175; 2.O.244.240;
2.O.244.244;
Prodrugs of 2.P 2.P.228.228; 2.P.228.229; 2.P.228.230; 2.P.228.231; 2.P.228.236;
2.P.228.237; 2.P.228.238; 2.P.228.239; 2.P.228.154; 2.P.228.157;
2.P.228.166; 2.P.228.169; 2.P.228.172; 2.P.228.175; 2.P.228.240;
2.P.228.244; 2.P.229.228; 2.P.229.229; 2.P.229.230; 2.P.229.231;
2.P.229.236; 2.P.229.237; 2.P.229.238; 2.P.229.239; 2.P.229.154;
2.P.229.157; 2.P.229.166; 2.P.229.169; 2.P.229.172; 2.P.229.175;
2.P.229.240; 2.P.229.244; 2.P.230.228; 2.P.230.229; 2.P.230.230;
2.P.230.231; 2.P.230.236; 2.P.230.237; 2.P.230.238; 2.P.230.239;
2.P.230.154; 2.P.230.157; 2.P.230.166; 2.P.230.169; 2.P.230.172;
2.P.230.175; 2.P.230.240; 2.P.230.244; 2.P.231.228; 2.P.231.229;
2.P.231.230; 2.P.231.231; 2.P.231.236; 2.P.231.237; 2.P.231.238;
2.P.231.239; 2.P.231.154; 2.P.231.157; 2.P.231.166; 2.P.231.169;
2.P.231.172; 2.P.231.175; 2.P.231.240; 2.P.231.244; 2.P.236.228;
2.P.236.229; 2.P.236.230; 2.P.236.231; 2.P.236.236; 2.P.236.237;
2.P.236.238; 2.P.236.239; 2.P.236.154; 2.P.236.157; 2.P.236.166;
2.P.236.169; 2.P.236.172; 2.P.236.175; 2.P.236.240; 2.P.236.244;
2.P.237.228; 2.P.237.229; 2.P.237.230; 2.P.237.231; 2.P.237.236;
2.P.237.237; 2.P.237.238; 2.P.237.239; 2.P.237.154; 2.P.237.157;
2.P.237.166; 2.P.237.169; 2.P.237.172; 2.P.237.175; 2.P.237.240;
2.P.237.244; 2.P.238.228; 2.P.238.229; 2.P.238.230; 2.P.238.231;
2.P.238.236; 2.P.238.237; 2.P.238.238; 2.P.238.239; 2.P.238.154;
2.P.238.157; 2.P.238.166; 2.P.238.169; 2.P.238.172; 2.P.238.175;
2.P.238.240; 2.P.238.244; 2.P.239.228; 2.P.239.229; 2.P.239.230;
2.P.239.231; 2.P.239.236; 2.P.239.237; 2.P.239.238; 2.P.239.239;
2.P.239.154; 2.P.239.157; 2.P.239.166; 2.P.239.169; 2.P.239.172;
2.P.239.175; 2.P.239.240; 2.P.239.244; 2.P.154.228; 2.P.154.229;
2.P.154.230; 2.P.154.231; 2.P.154.236; 2.P.154.237; 2.P.154.238;
2.P.154.239; 2.P.154.154; 2.P.154.157; 2.P.154.166; 2.P.154.169;
2.P.154.172; 2.P.154.175; 2.P.154.240; 2.P.154.244; 2.P.157.228;
2.P.157.229; 2.P.157.230; 2.P.157.231; 2.P.157.236; 2.P.157.237;
2.P.157.238; 2.P.157.239; 2.P.157.154; 2.P.157.157; 2.P.157.166;
2.P.157.169; 2.P.157.172; 2.P.157.175; 2.P.157.240; 2.P.157.244;
2.P.166.228; 2.P.166.229; 2.P.166.230; 2.P.166.231; 2.P.166.236;
2.P.166.237; 2.P.166.238; 2.P.166.239; 2.P.166.154; 2.P.166.157;
2.P.166.166; 2.P.166.169; 2.P.166.172; 2.P.166.175; 2.P.166.240;
2.P.166.244; 2.P.169.228; 2.P.169.229; 2.P.169.230; 2.P.169.231;
2.P.169.236; 2.P.169.237; 2.P.169.238; 2.P.169.239; 2.P.169.154;
2.P.169.157; 2.P.169.166; 2.P.169.169; 2.P.169.172; 2.P.169.175;
2.P.169.240; 2.P.169.244; 2.P.172.228; 2.P.172.229; 2.P.172.230;
2.P.172.231; 2.P.172.236; 2.P.172.237; 2.P.172.238; 2.P.172.239;
2.P.172.154; 2.P.172.157; 2.P.172.166; 2.P.172.169; 2.P.172.172;
2.P.172.175; 2.P.172.240; 2.P.172.244; 2.P.175.228; 2.P.175.229;
2.P.175.230; 2.P.175.231; 2.P.175.236; 2.P.175.237; 2.P.175.238;
2.P.175.239; 2.P.175.154; 2.P.175.157; 2.P.175.166; 2.P.175.169;
2.P.175.172; 2.P.175.175; 2.P.175.240; 2.P.175.244; 2.P.240.228;
2.P.240.229; 2.P.240.230; 2.P.240.231; 2.P.240.236; 2.P.240.237;
2.P.240.238; 2.P.240.239; 2.P.240.154; 2.P.240.157; 2.P.240.166;
2.P.240.169; 2.P.240.172; 2.P.240.175; 2.P.240.240; 2.P.240.244;
2.P.244.228; 2.P.244.229; 2.P.244.230; 2.P.244.231; 2.P.244.236;
2.P.244.237; 2.P.244.238; 2.P.244.239; 2.P.244.154; 2.P.244.157;
2.P.244.166; 2.P.244.169; 2.P.244.172; 2.P.244.175; 2.P.244.240;
2.P.244.244;
Prodrugs of 2.U 2.U.228.228; 2.U.228.229; 2.U.228.230; 2.U.228.231; 2.U.228.236;
2.U.228.237; 2.U.228.238; 2.U.228.239; 2.U.228.154; 2.U.228.157;
2.U.228.166; 2.U.228.169; 2.U.228.172; 2.U.228.175; 2.U.228.240;
2.U.228.244; 2.U.229.228; 2.U.229.229; 2.U.229.230; 2.U.229.231;
2.U.229.236; 2.U.229.237; 2.U.229.238; 2.U.229.239; 2.U.229.154;
2.U.229.157; 2.U.229.166; 2.U.229.169; 2.U.229.172; 2.U.229.175;
2.U.229.240; 2.U.229.244; 2.U.230.228; 2.U.230.229; 2.U.230.230;
2.U.230.231; 2.U.230.236; 2.U.230.237; 2.U.230.238; 2.U.230.239;
2.U.230.154; 2.U.230.157; 2.U.230.166; 2.U.230.169; 2.U.230.172;
2.U.230.175; 2.U.230.240; 2.U.230.244; 2.U.231.228; 2.U.231.229;
2.U.231.230; 2.U.231.231; 2.U.231.236; 2.U.231.237; 2.U.231.238;
2.U.231.239; 2.U.231.154; 2.U.231.157; 2.U.231.166; 2.U.231.169;
2.U.231.172; 2.U.231.175; 2.U.231.240; 2.U.231.244; 2.U.236.228;
2.U.236.229; 2.U.236.230; 2.U.236.231; 2.U.236.236; 2.U.236.237;
2.U.236.238; 2.U.236.239; 2.U.236.154; 2.U.236.157; 2.U.236.166;
2.U.236.169; 2.U.236.172; 2.U.236.175; 2.U.236.240; 2.U.236.244;
2.U.237.228; 2.U.237.229; 2.U.237.230; 2.U.237.231; 2.U.237.236;
2.U.237.237; 2.U.237.238; 2.U.237.239; 2.U.237.154; 2.U.237.157;
2.U.237.166; 2.U.237.169; 2.U.237.172; 2.U.237.175; 2.U.237.240;
2.U.237.244; 2.U.238.228; 2.U.238.229; 2.U.238.230; 2.U.238.231;
2.U.238.236; 2.U.238.237; 2.U.238.238; 2.U.238.239; 2.U.238.154;
2.U.238.157; 2.U.238.166; 2.U.238.169; 2.U.238.172; 2.U.238.175;
2.U.238.240; 2.U.238.244; 2.U.239.228; 2.U.239.229; 2.U.239.230;
2.U.239.231; 2.U.239.236; 2.U.239.237; 2.U.239.238; 2.U.239.239;
2.U.239.154; 2.U.239.157; 2.U.239.166; 2.U.239.169; 2.U.239.172;
2.U.239.175; 2.U.239.240; 2.U.239.244; 2.U.154.228; 2.U.154.229;
2.U.154.230; 2.U.154.231; 2.U.154.236; 2.U.154.237; 2.U.154.238;
2.U.154.239; 2.U.154.154; 2.U.154.157; 2.U.154.166; 2.U.154.169;
2.U.154.172; 2.U.154.175; 2.U.154.240; 2.U.154.244; 2.U.157.228;
2.U.157.229; 2.U.157.230; 2.U.157.231; 2.U.157.236; 2.U.157.237;
2.U.157.238; 2.U.157.239; 2.U.157.154; 2.U.157.157; 2.U.157.166;
2.U.157.169; 2.U.157.172; 2.U.157.175; 2.U.157.240; 2.U.157.244;
2.U.166.228; 2.U.166.229; 2.U.166.230; 2.U.166.231; 2.U.166.236;
2.U.166.237; 2.U.166.238; 2.U.166.239; 2.U.166.154; 2.U.166.157;
2.U.166.166; 2.U.166.169; 2.U.166.172; 2.U.166.175; 2.U.166.240;
2.U.166.244; 2.U.169.228; 2.U.169.229; 2.U.169.230; 2.U.169.231;
2.U.169.236; 2.U.169.237; 2.U.169.238; 2.U.169.239; 2.U.169.154;
2.U.169.157; 2.U.169.166; 2.U.169.169; 2.U.169.172; 2.U.169.175;
2.U.169.240; 2.U.169.244; 2.U.172.228; 2.U.172.229; 2.U.172.230;
2.U.172.231; 2.U.172.236; 2.U.172.237; 2.U.172.238; 2.U.172.239;
2.U.172.154; 2.U.172.157; 2.U.172.166; 2.U.172.169; 2.U.172.172;
2.U.172.175; 2.U.172.240; 2.U.172.244; 2.U.175.228; 2.U.175.229;
2.U.175.230; 2.U.175.231; 2.U.175.236; 2.U.175.237; 2.U.175.238;
2.U.175.239; 2.U.175.154; 2.U.175.157; 2.U.175.166; 2.U.175.169;
2.U.175.172; 2.U.175.175; 2.U.175.240; 2.U.175.244; 2.U.240.228;
2.U.240.229; 2.U.240.230; 2.U.240.231; 2.U.240.236; 2.U.240.237;
2.U.240.238; 2.U.240.239; 2.U.240.154; 2.U.240.157; 2.U.240.166;
2.U.240.169; 2.U.240.172; 2.U.240.175; 2.U.240.240; 2.U.240.244;
2.U.244.228; 2.U.244.229; 2.U.244.230; 2.U.244.231; 2.U.244.236;
2.U.244.237; 2.U.244.238; 2.U.244.239; 2.U.244.154; 2.U.244.157;
2.U.244.166; 2.U.244.169; 2.U.244.172; 2.U.244.175; 2.U.244.240;
2.U.244.244;
Prodrugs of 2.W 2.W.228.228; 2.W.228.229; 2.W.228.230; 2.W.228.231; 2.W.228.236;
2.W.228.237; 2.W.228.238; 2.W.228.239; 2.W.228.154; 2.W.228.157;
2.W.228.166; 2.W.228.169; 2.W.228.172; 2.W.228.175; 2.W.228.240;
2.W.228.244; 2.W.229.228; 2.W.229.229; 2.W.229.230; 2.W.229.231;
2.W.229.236; 2.W.229.237; 2.W.229.238; 2.W.229.239; 2.W.229.154;
2.W.229.157; 2.W.229.166; 2.W.229.169; 2.W.229.172; 2.W.229.175;
2.W.229.240; 2.W.229.244; 2.W.230.228; 2.W.230.229; 2.W.230.230;
2.W.230.231; 2.W.230.236; 2.W.230.237; 2.W.230.238; 2.W.230.239;
2.W.230.154; 2.W.230.157; 2.W.230.166; 2.W.230.169; 2.W.230.172;
2.W.230.175; 2.W.230.240; 2.W.230.244; 2.W.231.228; 2.W.231.229;
2.W.231.230; 2.W.231.231; 2.W.231.236; 2.W.231.237; 2.W.231.238;
2.W.231.239; 2.W.231.154; 2.W.231.157; 2.W.231.166; 2.W.231.169;
2.W.231.172; 2.W.231.175; 2.W.231.240; 2.W.231.244; 2.W.236.228;
2.W.236.229; 2.W.236.230; 2.W.236.231; 2.W.236.236; 2.W.236.237;
2.W.236.238; 2.W.236.239; 2.W.236.154; 2.W.236.157; 2.W.236.166;
2.W.236.169; 2.W.236.172; 2.W.236.175; 2.W.236.240; 2.W.236.244;
2.W.237.228; 2.W.237.229; 2.W.237.230; 2.W.237.231; 2.W.237.236;
2.W.237.237; 2.W.237.238; 2.W.237.239; 2.W.237.154; 2.W.237.157;
2.W.237.166; 2.W.237.169; 2.W.237.172; 2.W.237.175; 2.W.237.240;
2.W.237.244; 2.W.238.228; 2.W.238.229; 2.W.238.230; 2.W.238.231;
2.W.238.236; 2.W.238.237; 2.W.238.238; 2.W.238.239; 2.W.238.154;
2.W.238.157; 2.W.238.166; 2.W.238.169; 2.W.238.172; 2.W.238.175;
2.W.238.240; 2.W.238.244; 2.W.239.228; 2.W.239.229; 2.W.239.230;
2.W.239.231; 2.W.239.236; 2.W.239.237; 2.W.239.238; 2.W.239.239;
2.W.239.154; 2.W.239.157; 2.W.239.166; 2.W.239.169; 2.W.239.172;
2.W.239.175; 2.W.239.240; 2.W.239.244; 2.W.154.228; 2.W.154.229;
2.W.154.230; 2.W.154.231; 2.W.154.236; 2.W.154.237; 2.W.154.238;
2.W.154.239; 2.W.154.154; 2.W.154.157; 2.W.154.166; 2.W.154.169;
2.W.154.172; 2.W.154.175; 2.W.154.240; 2.W.154.244; 2.W.157.228;
2.W.157.229; 2.W.157.230; 2.W.157.231; 2.W.157.236; 2.W.157.237;
2.W.157.238; 2.W.157.239; 2.W.157.154; 2.W.157.157; 2.W.157.166;
2.W.157.169; 2.W.157.172; 2.W.157.175; 2.W.157.240; 2.W.157.244;
2.W.166.228; 2.W.166.229; 2.W.166.230; 2.W.166.231; 2.W.166.236;
2.W.166.237; 2.W.166.238; 2.W.166.239; 2.W.166.154; 2.W.166.157;
2.W.166.166; 2.W.166.169; 2.W.166.172; 2.W.166.175; 2.W.166.240;
2.W.166.244; 2.W.169.228; 2.W.169.229; 2.W.169.230; 2.W.169.231;
2.W.169.236; 2.W.169.237; 2.W.169.238; 2.W.169.239; 2.W.169.154;
2.W.169.157; 2.W.169.166; 2.W.169.169; 2.W.169.172; 2.W.169.175;
2.W.169.240; 2.W.169.244; 2.W.172.228; 2.W.172.229; 2.W.172.230;
2.W.172.231; 2.W.172.236; 2.W.172.237; 2.W.172.238; 2.W.172.239;

TABLE 7-continued

2.W.172.154; 2.W.172.157; 2.W.172.166; 2.W.172.169; 2.W.172.172; 2.W.172.175; 2.W.172.240; 2.W.172.244; 2.W.175.228; 2.W.175.229; 2.W.175.230; 2.W.175.231; 2.W.175.236; 2.W.175.237; 2.W.175.238; 2.W.175.239; 2.W.175.154; 2.W.175.157; 2.W.175.166; 2.W.175.169; 2.W.175.172; 2.W.175.175; 2.W.175.240; 2.W.175.244; 2.W.240.228; 2.W.240.229; 2.W.240.230; 2.W.240.231; 2.W.240.236; 2.W.240.237; 2.W.240.238; 2.W.240.239; 2.W.240.154; 2.W.240.157; 2.W.240.166; 2.W.240.169; 2.W.240.172; 2.W.240.175; 2.W.240.240; 2.W.240.244; 2.W.244.228; 2.W.244.229; 2.W.244.230; 2.W.244.231; 2.W.244.236; 2.W.244.237; 2.W.244.238; 2.W.244.239; 2.W.244.154; 2.W.244.157; 2.W.244.166; 2.W.244.169; 2.W.244.172; 2.W.244.175; 2.W.244.240; 2.W.244.244;
Prodrugs of 2.Y 2.Y.228.228; 2.Y.228.229; 2.Y.228.230; 2.Y.228.231; 2.Y.228.236; 2.Y.228.237; 2.Y.228.238; 2.Y.228.239; 2.Y.228.154; 2.Y.228.157; 2.Y.228.166; 2.Y.228.169; 2.Y.228.172; 2.Y.228.175; 2.Y.228.240; 2.Y.228.244; 2.Y.229.228; 2.Y.229.229; 2.Y.229.230; 2.Y.229.231; 2.Y.229.236; 2.Y.229.237; 2.Y.229.238; 2.Y.229.239; 2.Y.229.154; 2.Y.229.157; 2.Y.229.166; 2.Y.229.169; 2.Y.229.172; 2.Y.229.175; 2.Y.229.240; 2.Y.229.244; 2.Y.230.228; 2.Y.230.229; 2.Y.230.230; 2.Y.230.231; 2.Y.230.236; 2.Y.230.237; 2.Y.230.238; 2.Y.230.239; 2.Y.230.154; 2.Y.230.157; 2.Y.230.166; 2.Y.230.169; 2.Y.230.172; 2.Y.230.175; 2.Y.230.240; 2.Y.230.244; 2.Y.231.228; 2.Y.231.229; 2.Y.231.230; 2.Y.231.231; 2.Y.231.236; 2.Y.231.237; 2.Y.231.238; 2.Y.231.239; 2.Y.231.154; 2.Y.231.157; 2.Y.231.166; 2.Y.231.169; 2.Y.231.172; 2.Y.231.175; 2.Y.231.240; 2.Y.231.244; 2.Y.236.228; 2.Y.236.229; 2.Y.236.230; 2.Y.236.231; 2.Y.236.236; 2.Y.236.237; 2.Y.236.238; 2.Y.236.239; 2.Y.236.154; 2.Y.236.157; 2.Y.236.166; 2.Y.236.169; 2.Y.236.172; 2.Y.236.175; 2.Y.236.240; 2.Y.236.244; 2.Y.237.228; 2.Y.237.229; 2.Y.237.230; 2.Y.237.231; 2.Y.237.236; 2.Y.237.237; 2.Y.237.238; 2.Y.237.239; 2.Y.237.154; 2.Y.237.157; 2.Y.237.166; 2.Y.237.169; 2.Y.237.172; 2.Y.237.175; 2.Y.237.240; 2.Y.237.244; 2.Y.238.228; 2.Y.238.229; 2.Y.238.230; 2.Y.238.231; 2.Y.238.236; 2.Y.238.237; 2.Y.238.238; 2.Y.238.239; 2.Y.238.154; 2.Y.238.157; 2.Y.238.166; 2.Y.238.169; 2.Y.238.172; 2.Y.238.175; 2.Y.238.240; 2.Y.238.244; 2.Y.239.228; 2.Y.239.229; 2.Y.239.230; 2.Y.239.231; 2.Y.239.236; 2.Y.239.237; 2.Y.239.238; 2.Y.239.239; 2.Y.239.154; 2.Y.239.157; 2.Y.239.166; 2.Y.239.169; 2.Y.239.172; 2.Y.239.175; 2.Y.239.240; 2.Y.239.244; 2.Y.154.228; 2.Y.154.229; 2.Y.154.230; 2.Y.154.231; 2.Y.154.236; 2.Y.154.237; 2.Y.154.238; 2.Y.154.239; 2.Y.154.154; 2.Y.154.157; 2.Y.154.166; 2.Y.154.169; 2.Y.154.172; 2.Y.154.175; 2.Y.154.240; 2.Y.154.244; 2.Y.157.228; 2.Y.157.229; 2.Y.157.230; 2.Y.157.231; 2.Y.157.236; 2.Y.157.237; 2.Y.157.238; 2.Y.157.239; 2.Y.157.154; 2.Y.157.157; 2.Y.157.166; 2.Y.157.169; 2.Y.157.172; 2.Y.157.175; 2.Y.157.240; 2.Y.157.244; 2.Y.166.228; 2.Y.166.229; 2.Y.166.230; 2.Y.166.231; 2.Y.166.236; 2.Y.166.237; 2.Y.166.238; 2.Y.166.239; 2.Y.166.154; 2.Y.166.157; 2.Y.166.166; 2.Y.166.169; 2.Y.166.172; 2.Y.166.175; 2.Y.166.240; 2.Y.166.244; 2.Y.169.228; 2.Y.169.229; 2.Y.169.230; 2.Y.169.231; 2.Y.169.236; 2.Y.169.237; 2.Y.169.238; 2.Y.169.239; 2.Y.169.154; 2.Y.169.157; 2.Y.169.166; 2.Y.169.169; 2.Y.169.172; 2.Y.169.175; 2.Y.169.240; 2.Y.169.244; 2.Y.172.228; 2.Y.172.229; 2.Y.172.230; 2.Y.172.231; 2.Y.172.236; 2.Y.172.237; 2.Y.172.238; 2.Y.172.239; 2.Y.172.154; 2.Y.172.157; 2.Y.172.166; 2.Y.172.169; 2.Y.172.172; 2.Y.172.175; 2.Y.172.240; 2.Y.172.244; 2.Y.175.228; 2.Y.175.229; 2.Y.175.230; 2.Y.175.231; 2.Y.175.236; 2.Y.175.237; 2.Y.175.238; 2.Y.175.239; 2.Y.175.154; 2.Y.175.157; 2.Y.175.166; 2.Y.175.169; 2.Y.175.172; 2.Y.175.175; 2.Y.175.240; 2.Y.175.244; 2.Y.240.228; 2.Y.240.229; 2.Y.240.230; 2.Y.240.231; 2.Y.240.236; 2.Y.240.237; 2.Y.240.238; 2.Y.240.239; 2.Y.240.154; 2.Y.240.157; 2.Y.240.166; 2.Y.240.169; 2.Y.240.172; 2.Y.240.175; 2.Y.240.240; 2.Y.240.244; 2.Y.244.228; 2.Y.244.229; 2.Y.244.230; 2.Y.244.231; 2.Y.244.236; 2.Y.244.237; 2.Y.244.238; 2.Y.244.239; 2.Y.244.154; 2.Y.244.157; 2.Y.244.166; 2.Y.244.169; 2.Y.244.172; 2.Y.244.175; 2.Y.244.240; 2.Y.244.244;
Prodrugs of 3.B 3.B.228.228; 3.B.228.229; 3.B.228.230; 3.B.228.231; 3.B.228.236; 3.B.228.237; 3.B.228.238; 3.B.228.239; 3.B.228.154; 3.B.228.157; 3.B.228.166; 3.B.228.169; 3.B.228.172; 3.B.228.175; 3.B.228.240; 3.B.228.244; 3.B.229.228; 3.B.229.229; 3.B.229.230; 3.B.229.231; 3.B.229.236; 3.B.229.237; 3.B.229.238; 3.B.229.239; 3.B.229.154; 3.B.229.157; 3.B.229.166; 3.B.229.169; 3.B.229.172; 3.B.229.175; 3.B.229.240; 3.B.229.244; 3.B.230.228; 3.B.230.229; 3.B.230.230; 3.B.230.231; 3.B.230.236; 3.B.230.237; 3.B.230.238; 3.B.230.239; 3.B.230.154; 3.B.230.157; 3.B.230.166; 3.B.230.169; 3.B.230.172; 3.B.230.175; 3.B.230.240; 3.B.230.244; 3.B.231.228; 3.B.231.229; 3.B.231.230; 3.B.231.231; 3.B.231.236; 3.B.231.237; 3.B.231.238; 3.B.231.239; 3.B.231.154; 3.B.231.157; 3.B.231.166; 3.B.231.169; 3.B.231.172; 3.B.231.175; 3.B.231.240; 3.B.231.244; 3.B.236.228; 3.B.236.229; 3.B.236.230; 3.B.236.231; 3.B.236.236; 3.B.236.237; 3.B.236.238; 3.B.236.239; 3.B.236.154; 3.B.236.157; 3.B.236.166; 3.B.236.169; 3.B.236.172; 3.B.236.175; 3.B.236.240; 3.B.236.244; 3.B.237.228; 3.B.237.229; 3.B.237.230; 3.B.237.231; 3.B.237.236; 3.B.237.237; 3.B.237.238; 3.B.237.239; 3.B.237.154; 3.B.237.157; 3.B.237.166; 3.B.237.169; 3.B.237.172; 3.B.237.175; 3.B.237.240; 3.B.237.244; 3.B.238.228; 3.B.238.229; 3.B.238.230; 3.B.238.231; 3.B.238.236; 3.B.238.237; 3.B.238.238; 3.B.238.239; 3.B.238.154; 3.B.238.157; 3.B.238.166; 3.B.238.169; 3.B.238.172; 3.B.238.175; 3.B.238.240; 3.B.238.244; 3.B.239.228; 3.B.239.229; 3.B.239.230; 3.B.239.231; 3.B.239.236; 3.B.239.237; 3.B.239.238; 3.B.239.239; 3.B.239.154; 3.B.239.157; 3.B.239.166; 3.B.239.169; 3.B.239.172; 3.B.239.175; 3.B.239.240; 3.B.239.244; 3.B.154.228; 3.B.154.229; 3.B.154.230; 3.B.154.231; 3.B.154.236; 3.B.154.237; 3.B.154.238; 3.B.154.239; 3.B.154.154; 3.B.154.157; 3.B.154.166; 3.B.154.169; 3.B.154.172; 3.B.154.175; 3.B.154.240; 3.B.154.244; 3.B.157.228; 3.B.157.229; 3.B.157.230; 3.B.157.231; 3.B.157.236; 3.B.157.237; 3.B.157.238; 3.B.157.239; 3.B.157.154; 3.B.157.157; 3.B.157.166; 3.B.157.169; 3.B.157.172; 3.B.157.175; 3.B.157.240; 3.B.157.244; 3.B.166.228; 3.B.166.229; 3.B.166.230; 3.B.166.231; 3.B.166.236; 3.B.166.237; 3.B.166.238; 3.B.166.239; 3.B.166.154; 3.B.166.157; 3.B.166.166; 3.B.166.169; 3.B.166.172; 3.B.166.175; 3.B.166.240; 3.B.166.244; 3.B.169.228; 3.B.169.229; 3.B.169.230; 3.B.169.231; 3.B.169.236; 3.B.169.237; 3.B.169.238; 3.B.169.239; 3.B.169.154; 3.B.169.157; 3.B.169.166; 3.B.169.169; 3.B.169.172; 3.B.169.175; 3.B.169.240; 3.B.169.244; 3.B.172.228; 3.B.172.229; 3.B.172.230; 3.B.172.231; 3.B.172.236; 3.B.172.237; 3.B.172.238; 3.B.172.239; 3.B.172.154; 3.B.172.157; 3.B.172.166; 3.B.172.169; 3.B.172.172; 3.B.172.175; 3.B.172.240; 3.B.172.244; 3.B.175.228; 3.B.175.229; 3.B.175.230; 3.B.175.231; 3.B.175.236; 3.B.175.237; 3.B.175.238; 3.B.175.239; 3.B.175.154; 3.B.175.157; 3.B.175.166; 3.B.175.169; 3.B.175.172; 3.B.175.175; 3.B.175.240; 3.B.175.244; 3.B.240.228; 3.B.240.229; 3.B.240.230; 3.B.240.231; 3.B.240.236; 3.B.240.237; 3.B.240.238; 3.B.240.239; 3.B.240.154; 3.B.240.157; 3.B.240.166; 3.B.240.169; 3.B.240.172; 3.B.240.175; 3.B.240.240; 3.B.240.244; 3.B.244.228; 3.B.244.229; 3.B.244.230; 3.B.244.231; 3.B.244.236; 3.B.244.237; 3.B.244.238; 3.B.244.239; 3.B.244.154; 3.B.244.157; 3.B.244.166; 3.B.244.169; 3.B.244.172; 3.B.244.175; 3.B.244.240; 3.B.244.244;
Prodrugs of 3.D 3.D.228.228; 3.D.228.229; 3.D.228.230; 3.D.228.231; 3.D.228.236; 3.D.228.237; 3.D.228.238; 3.D.228.239; 3.D.228.154; 3.D.228.157; 3.D.228.166; 3.D.228.169; 3.D.228.172; 3.D.228.175; 3.D.228.240; 3.D.228.244; 3.D.229.228; 3.D.229.229; 3.D.229.230; 3.D.229.231; 3.D.229.236; 3.D.229.237; 3.D.229.238; 3.D.229.239; 3.D.229.154; 3.D.229.157; 3.D.229.166; 3.D.229.169; 3.D.229.172; 3.D.229.175; 3.D.229.240; 3.D.229.244; 3.D.230.228; 3.D.230.229; 3.D.230.230; 3.D.230.231; 3.D.230.236; 3.D.230.237; 3.D.230.238; 3.D.230.239; 3.D.230.154; 3.D.230.157; 3.D.230.166; 3.D.230.169; 3.D.230.172; 3.D.230.175; 3.D.230.240; 3.D.230.244; 3.D.231.228; 3.D.231.229; 3.D.231.230; 3.D.231.231; 3.D.231.236; 3.D.231.237; 3.D.231.238; 3.D.231.239; 3.D.231.154; 3.D.231.157; 3.D.231.166; 3.D.231.169; 3.D.231.172; 3.D.231.175; 3.D.231.240; 3.D.231.244; 3.D.236.228; 3.D.236.229; 3.D.236.230; 3.D.236.231; 3.D.236.236; 3.D.236.237; 3.D.236.238; 3.D.236.239; 3.D.236.154; 3.D.236.157; 3.D.236.166; 3.D.236.169; 3.D.236.172; 3.D.236.175; 3.D.236.240; 3.D.236.244; 3.D.237.228; 3.D.237.229; 3.D.237.230; 3.D.237.231; 3.D.237.236; 3.D.237.237; 3.D.237.238; 3.D.237.239; 3.D.237.154; 3.D.237.157; 3.D.237.166; 3.D.237.169; 3.D.237.172; 3.D.237.175; 3.D.237.240; 3.D.237.244; 3.D.238.228; 3.D.238.229; 3.D.238.230; 3.D.238.231; 3.D.238.236; 3.D.238.237; 3.D.238.238; 3.D.238.239; 3.D.238.154; 3.D.238.157; 3.D.238.166; 3.D.238.169; 3.D.238.172; 3.D.238.175; 3.D.238.240; 3.D.238.244; 3.D.239.228; 3.D.239.229; 3.D.239.230; 3.D.239.231; 3.D.239.236; 3.D.239.237; 3.D.239.238; 3.D.239.239; 3.D.239.154; 3.D.239.157; 3.D.239.166; 3.D.239.169; 3.D.239.172; 3.D.239.175; 3.D.239.240; 3.D.239.244; 3.D.154.228; 3.D.154.229; 3.D.154.230; 3.D.154.231; 3.D.154.236; 3.D.154.237; 3.D.154.238; 3.D.154.239; 3.D.154.154; 3.D.154.157; 3.D.154.166; 3.D.154.169; 3.D.154.172; 3.D.154.175; 3.D.154.240; 3.D.154.244; 3.D.157.228; 3.D.157.229; 3.D.157.230; 3.D.157.231; 3.D.157.236; 3.D.157.237; 3.D.157.238; 3.D.157.239; 3.D.157.154; 3.D.157.157; 3.D.157.166; 3.D.157.169; 3.D.157.172; 3.D.157.175; 3.D.157.240; 3.D.157.244; 3.D.166.228; 3.D.166.229; 3.D.166.230; 3.D.166.231; 3.D.166.236; 3.D.166.237; 3.D.166.238; 3.D.166.239; 3.D.166.154; 3.D.166.157; 3.D.166.166; 3.D.166.169; 3.D.166.172; 3.D.166.175; 3.D.166.240; 3.D.166.244; 3.D.169.228; 3.D.169.229; 3.D.169.230; 3.D.169.231;

TABLE 7-continued

3.D.169.236; 3.D.169.237; 3.D.169.238; 3.D.169.239; 3.D.169.154;
3.D.169.157; 3.D.169.166; 3.D.169.169; 3.D.169.172; 3.D.169.175;
3.D.169.240; 3.D.169.244; 3.D.172.228; 3.D.172.229; 3.D.172.230;
3.D.172.231; 3.D.172.236; 3.D.172.237; 3.D.172.238; 3.D.172.239;
3.D.172.154; 3.D.172.157; 3.D.172.166; 3.D.172.169; 3.D.172.172;
3.D.172.175; 3.D.172.240; 3.D.172.244; 3.D.175.228; 3.D.175.229;
3.D.175.230; 3.D.175.231; 3.D.175.236; 3.D.175.237; 3.D.175.238;
3.D.175.239; 3.D.175.154; 3.D.175.157; 3.D.175.166; 3.D.175.169;
3.D.175.172; 3.D.175.175; 3.D.175.240; 3.D.175.244; 3.D.240.228;
3.D.240.229; 3.D.240.230; 3.D.240.231; 3.D.240.236; 3.D.240.237;
3.D.240.238; 3.D.240.239; 3.D.240.154; 3.D.240.157; 3.D.240.166;
3.D.240.169; 3.D.240.172; 3.D.240.175; 3.D.240.240; 3.D.240.244;
3.D.244.228; 3.D.244.229; 3.D.244.230; 3.D.244.231; 3.D.244.236;
3.D.244.237; 3.D.244.238; 3.D.244.239; 3.D.244.154; 3.D.244.157;
3.D.244.166; 3.D.244.169; 3.D.244.172; 3.D.244.175; 3.D.244.240;
3.D.244.244;

Prodrugs of 3.E

3.E.228.228; 3.E.228.229; 3.E.228.230; 3.E.228.231; 3.E.228.236;
3.E.228.237; 3.E.228.238; 3.E.228.239; 3.E.228.154; 3.E.228.157;
3.E.228.166; 3.E.228.169; 3.E.228.172; 3.E.228.175; 3.E.228.240;
3.E.228.244; 3.E.229.228; 3.E.229.229; 3.E.229.230; 3.E.229.231;
3.E.229.236; 3.E.229.237; 3.E.229.238; 3.E.229.239; 3.E.229.154;
3.E.229.157; 3.E.229.166; 3.E.229.169; 3.E.229.172; 3.E.229.175;
3.E.229.240; 3.E.229.244; 3.E.230.228; 3.E.230.229; 3.E.230.230;
3.E.230.231; 3.E.230.236; 3.E.230.237; 3.E.230.238; 3.E.230.239;
3.E.230.154; 3.E.230.157; 3.E.230.166; 3.E.230.169; 3.E.230.172;
3.E.230.175; 3.E.230.240; 3.E.230.244; 3.E.231.228; 3.E.231.229;
3.E.231.230; 3.E.231.231; 3.E.231.236; 3.E.231.237; 3.E.231.238;
3.E.231.239; 3.E.231.154; 3.E.231.157; 3.E.231.166; 3.E.231.169;
3.E.231.172; 3.E.231.175; 3.E.231.240; 3.E.231.244; 3.E.236.228;
3.E.236.229; 3.E.236.230; 3.E.236.231; 3.E.236.236; 3.E.236.237;
3.E.236.238; 3.E.236.239; 3.E.236.154; 3.E.236.157; 3.E.236.166;
3.E.236.169; 3.E.236.172; 3.E.236.175; 3.E.236.240; 3.E.236.244;
3.E.237.228; 3.E.237.229; 3.E.237.230; 3.E.237.231; 3.E.237.236;
3.E.237.237; 3.E.237.238; 3.E.237.239; 3.E.237.154; 3.E.237.157;
3.E.237.166; 3.E.237.169; 3.E.237.172; 3.E.237.175; 3.E.237.240;
3.E.237.244; 3.E.238.228; 3.E.238.229; 3.E.238.230; 3.E.238.231;
3.E.238.236; 3.E.238.237; 3.E.238.238; 3.E.238.239; 3.E.238.154;
3.E.238.157; 3.E.238.166; 3.E.238.169; 3.E.238.172; 3.E.238.175;
3.E.238.240; 3.E.238.244; 3.E.239.228; 3.E.239.229; 3.E.239.230;
3.E.239.231; 3.E.239.236; 3.E.239.237; 3.E.239.238; 3.E.239.239;
3.E.239.154; 3.E.239.157; 3.E.239.166; 3.E.239.169; 3.E.239.172;
3.E.239.175; 3.E.239.240; 3.E.239.244; 3.E.154.228; 3.E.154.229;
3.E.154.230; 3.E.154.231; 3.E.154.236; 3.E.154.237; 3.E.154.238;
3.E.154.239; 3.E.154.154; 3.E.154.157; 3.E.154.166; 3.E.154.169;
3.E.154.172; 3.E.154.175; 3.E.154.240; 3.E.154.244; 3.E.157.228;
3.E.157.229; 3.E.157.230; 3.E.157.231; 3.E.157.236; 3.E.157.237;
3.E.157.238; 3.E.157.239; 3.E.157.154; 3.E.157.157; 3.E.157.166;
3.E.157.169; 3.E.157.172; 3.E.157.175; 3.E.157.240; 3.E.157.244;
3.E.166.228; 3.E.166.229; 3.E.166.230; 3.E.166.231; 3.E.166.236;
3.E.166.237; 3.E.166.238; 3.E.166.239; 3.E.166.154; 3.E.166.157;
3.E.166.166; 3.E.166.169; 3.E.166.172; 3.E.166.175; 3.E.166.240;
3.E.166.244; 3.E.169.228; 3.E.169.229; 3.E.169.230; 3.E.169.231;
3.E.169.236; 3.E.169.237; 3.E.169.238; 3.E.169.239; 3.E.169.154;
3.E.169.157; 3.E.169.166; 3.E.169.169; 3.E.169.172; 3.E.169.175;
3.E.169.240; 3.E.169.244; 3.E.172.228; 3.E.172.229; 3.E.172.230;
3.E.172.231; 3.E.172.236; 3.E.172.237; 3.E.172.238; 3.E.172.239;
3.E.172.154; 3.E.172.157; 3.E.172.166; 3.E.172.169; 3.E.172.172;
3.E.172.175; 3.E.172.240; 3.E.172.244; 3.E.175.228; 3.E.175.229;
3.E.175.230; 3.E.175.231; 3.E.175.236; 3.E.175.237; 3.E.175.238;
3.E.175.239; 3.E.175.154; 3.E.175.157; 3.E.175.166; 3.E.175.169;
3.E.175.172; 3.E.175.175; 3.E.175.240; 3.E.175.244; 3.E.240.228;
3.E.240.229; 3.E.240.230; 3.E.240.231; 3.E.240.236; 3.E.240.237;
3.E.240.238; 3.E.240.239; 3.E.240.154; 3.E.240.157; 3.E.240.166;
3.E.240.169; 3.E.240.172; 3.E.240.175; 3.E.240.240; 3.E.240.244;
3.E.244.228; 3.E.244.229; 3.E.244.230; 3.E.244.231; 3.E.244.236;
3.E.244.237; 3.E.244.238; 3.E.244.239; 3.E.244.154; 3.E.244.157;
3.E.244.166; 3.E.244.169; 3.E.244.172; 3.E.244.175; 3.E.244.240;
3.E.244.244;

Prodrugs of 3.G

3.G.228.228; 3.G.228.229; 3.G.228.230; 3.G.228.231; 3.G.228.236;
3.G.228.237; 3.G.228.238; 3.G.228.239; 3.G.228.154; 3.G.228.157;
3.G.228.166; 3.G.228.169; 3.G.228.172; 3.G.228.175; 3.G.228.240;
3.G.228.244; 3.G.229.228; 3.G.229.229; 3.G.229.230; 3.G.229.231;
3.G.229.236; 3.G.229.237; 3.G.229.238; 3.G.229.239; 3.G.229.154;
3.G.229.157; 3.G.229.166; 3.G.229.169; 3.G.229.172; 3.G.229.175;
3.G.229.240; 3.G.229.244; 3.G.230.228; 3.G.230.229; 3.G.230.230;
3.G.230.231; 3.G.230.236; 3.G.230.237; 3.G.230.238; 3.G.230.239;
3.G.230.154; 3.G.230.157; 3.G.230.166; 3.G.230.169; 3.G.230.172;
3.G.230.175; 3.G.230.240; 3.G.230.244; 3.G.231.228; 3.G.231.229;
3.G.231.230; 3.G.231.231; 3.G.231.236; 3.G.231.237; 3.G.231.238;
3.G.231.239; 3.G.231.154; 3.G.231.157; 3.G.231.166; 3.G.231.169;
3.G.231.172; 3.G.231.175; 3.G.231.240; 3.G.231.244; 3.G.236.228;
3.G.236.229; 3.G.236.230; 3.G.236.231; 3.G.236.236; 3.G.236.237;
3.G.236.238; 3.G.236.239; 3.G.236.154; 3.G.236.157; 3.G.236.166;
3.G.236.169; 3.G.236.172; 3.G.236.175; 3.G.236.240; 3.G.236.244;
3.G.237.228; 3.G.237.229; 3.G.237.230; 3.G.237.231; 3.G.237.236;
3.G.237.237; 3.G.237.238; 3.G.237.239; 3.G.237.154; 3.G.237.157;
3.G.237.166; 3.G.237.169; 3.G.237.172; 3.G.237.175; 3.G.237.240;
3.G.237.244; 3.G.238.228; 3.G.238.229; 3.G.238.230; 3.G.238.231;
3.G.238.236; 3.G.238.237; 3.G.238.238; 3.G.238.239; 3.G.238.154;
3.G.238.157; 3.G.238.166; 3.G.238.169; 3.G.238.172; 3.G.238.175;
3.G.238.240; 3.G.238.244; 3.G.239.228; 3.G.239.229; 3.G.239.230;
3.G.239.231; 3.G.239.236; 3.G.239.237; 3.G.239.238; 3.G.239.239;
3.G.239.154; 3.G.239.157; 3.G.239.166; 3.G.239.169; 3.G.239.172;
3.G.239.175; 3.G.239.240; 3.G.239.244; 3.G.154.228; 3.G.154.229;
3.G.154.230; 3.G.154.231; 3.G.154.236; 3.G.154.237; 3.G.154.238;
3.G.154.239; 3.G.154.154; 3.G.154.157; 3.G.154.166; 3.G.154.169;
3.G.154.172; 3.G.154.175; 3.G.154.240; 3.G.154.244; 3.G.157.228;
3.G.157.229; 3.G.157.230; 3.G.157.231; 3.G.157.236; 3.G.157.237;
3.G.157.238; 3.G.157.239; 3.G.157.154; 3.G.157.157; 3.G.157.166;
3.G.157.169; 3.G.157.172; 3.G.157.175; 3.G.157.240; 3.G.157.244;
3.G.166.228; 3.G.166.229; 3.G.166.230; 3.G.166.231; 3.G.166.236;
3.G.166.237; 3.G.166.238; 3.G.166.239; 3.G.166.154; 3.G.166.157;
3.G.166.166; 3.G.166.169; 3.G.166.172; 3.G.166.175; 3.G.166.240;
3.G.166.244; 3.G.169.228; 3.G.169.229; 3.G.169.230; 3.G.169.231;
3.G.169.236; 3.G.169.237; 3.G.169.238; 3.G.169.239; 3.G.169.154;
3.G.169.157; 3.G.169.166; 3.G.169.169; 3.G.169.172; 3.G.169.175;
3.G.169.240; 3.G.169.244; 3.G.172.228; 3.G.172.229; 3.G.172.230;
3.G.172.231; 3.G.172.236; 3.G.172.237; 3.G.172.238; 3.G.172.239;
3.G.172.154; 3.G.172.157; 3.G.172.166; 3.G.172.169; 3.G.172.172;
3.G.172.175; 3.G.172.240; 3.G.172.244; 3.G.175.228; 3.G.175.229;
3.G.175.230; 3.G.175.231; 3.G.175.236; 3.G.175.237; 3.G.175.238;
3.G.175.239; 3.G.175.154; 3.G.175.157; 3.G.175.166; 3.G.175.169;
3.G.175.172; 3.G.175.175; 3.G.175.240; 3.G.175.244; 3.G.240.228;
3.G.240.229; 3.G.240.230; 3.G.240.231; 3.G.240.236; 3.G.240.237;
3.G.240.238; 3.G.240.239; 3.G.240.154; 3.G.240.157; 3.G.240.166;
3.G.240.169; 3.G.240.172; 3.G.240.175; 3.G.240.240; 3.G.240.244;
3.G.244.228; 3.G.244.229; 3.G.244.230; 3.G.244.231; 3.G.244.236;
3.G.244.237; 3.G.244.238; 3.G.244.239; 3.G.244.154; 3.G.244.157;
3.G.244.166; 3.G.244.169; 3.G.244.172; 3.G.244.175; 3.G.244.240;
3.G.244.244;

Prodrugs of 3.I

3.I.228.228; 3.I.228.229; 3.I.228.230; 3.I.228.231; 3.I.228.236;
3.I.228.237; 3.I.228.238; 3.I.228.239; 3.I.228.154; 3.I.228.157;
3.I.228.166; 3.I.228.169; 3.I.228.172; 3.I.228.175; 3.I.228.240;
3.I.228.244; 3.I.229.228; 3.I.229.229; 3.I.229.230; 3.I.229.231;
3.I.229.236; 3.I.229.237; 3.I.229.238; 3.I.229.239; 3.I.229.154;
3.I.229.157; 3.I.229.166; 3.I.229.169; 3.I.229.172; 3.I.229.175;
3.I.229.240; 3.I.229.244; 3.I.230.228; 3.I.230.229; 3.I.230.230;
3.I.230.231; 3.I.230.236; 3.I.230.237; 3.I.230.238; 3.I.230.239;
3.I.230.154; 3.I.230.157; 3.I.230.166; 3.I.230.169; 3.I.230.172;
3.I.230.175; 3.I.230.240; 3.I.230.244; 3.I.231.228; 3.I.231.229;
3.I.231.230; 3.I.231.231; 3.I.231.236; 3.I.231.237; 3.I.231.238;
3.I.231.239; 3.I.231.154; 3.I.231.157; 3.I.231.166; 3.I.231.169;
3.I.231.172; 3.I.231.175; 3.I.231.240; 3.I.231.244; 3.I.236.228;
3.I.236.229; 3.I.236.230; 3.I.236.231; 3.I.236.236; 3.I.236.237;
3.I.236.238; 3.I.236.239; 3.I.236.154; 3.I.236.157; 3.I.236.166;
3.I.236.169; 3.I.236.172; 3.I.236.175; 3.I.236.240; 3.I.236.244;
3.I.237.228; 3.I.237.229; 3.I.237.230; 3.I.237.231; 3.I.237.236;
3.I.237.237; 3.I.237.238; 3.I.237.239; 3.I.237.154; 3.I.237.157;
3.I.237.166; 3.I.237.169; 3.I.237.172; 3.I.237.175; 3.I.237.240;
3.I.237.244; 3.I.238.228; 3.I.238.229; 3.I.238.230; 3.I.238.231;
3.I.238.236; 3.I.238.237; 3.I.238.238; 3.I.238.239; 3.I.238.154;
3.I.238.157; 3.I.238.166; 3.I.238.169; 3.I.238.172; 3.I.238.175;
3.I.238.240; 3.I.238.244; 3.I.239.228; 3.I.239.229; 3.I.239.230;
3.I.239.231; 3.I.239.236; 3.I.239.237; 3.I.239.238; 3.I.239.239;
3.I.239.154; 3.I.239.157; 3.I.239.166; 3.I.239.169; 3.I.239.172;
3.I.239.175; 3.I.239.240; 3.I.239.244; 3.I.154.228; 3.I.154.229;
3.I.154.230; 3.I.154.231; 3.I.154.236; 3.I.154.237; 3.I.154.238;
3.I.154.239; 3.I.154.154; 3.I.154.157; 3.I.154.166; 3.I.154.169;
3.I.154.172; 3.I.154.175; 3.I.154.240; 3.I.154.244; 3.I.157.228;
3.I.157.229; 3.I.157.230; 3.I.157.231; 3.I.157.236; 3.I.157.237;
3.I.157.238; 3.I.157.239; 3.I.157.154; 3.I.157.157; 3.I.157.166;
3.I.157.169; 3.I.157.172; 3.I.157.175; 3.I.157.240; 3.I.157.244;

TABLE 7-continued

3.I.166.228; 3.I.166.229; 3.I.166.230; 3.I.166.231; 3.I.166.236; 3.I.166.237; 3.I.166.238; 3.I.166.239; 3.I.166.154; 3.I.166.157; 3.I.166.166; 3.I.166.169; 3.I.166.172; 3.I.166.175; 3.I.166.240; 3.I.166.244; 3.I.169.228; 3.I.169.229; 3.I.169.230; 3.I.169.231; 3.I.169.236; 3.I.169.237; 3.I.169.238; 3.I.169.239; 3.I.169.154; 3.I.169.157; 3.I.169.166; 3.I.169.169; 3.I.169.172; 3.I.169.175; 3.I.169.240; 3.I.169.244; 3.I.172.228; 3.I.172.229; 3.I.172.230; 3.I.172.231; 3.I.172.236; 3.I.172.237; 3.I.172.238; 3.I.172.239; 3.I.172.154; 3.I.172.157; 3.I.172.166; 3.I.172.169; 3.I.172.172; 3.I.172.175; 3.I.172.240; 3.I.172.244; 3.I.175.228; 3.I.175.229; 3.I.175.230; 3.I.175.231; 3.I.175.236; 3.I.175.237; 3.I.175.238; 3.I.175.239; 3.I.175.154; 3.I.175.157; 3.I.175.166; 3.I.175.169; 3.I.175.172; 3.I.175.175; 3.I.175.240; 3.I.175.244; 3.I.240.228; 3.I.240.229; 3.I.240.230; 3.I.240.231; 3.I.240.236; 3.I.240.237; 3.I.240.238; 3.I.240.239; 3.I.240.154; 3.I.240.157; 3.I.240.166; 3.I.240.169; 3.I.240.172; 3.I.240.175; 3.I.240.240; 3.I.240.244; 3.I.244.228; 3.I.244.229; 3.I.244.230; 3.I.244.231; 3.I.244.236; 3.I.244.237; 3.I.244.238; 3.I.244.239; 3.I.244.154; 3.I.244.157; 3.I.244.166; 3.I.244.169; 3.I.244.172; 3.I.244.175; 3.I.244.240; 3.I.244.244;
Prodrugs of 3.J 3.J.228.228; 3.J.228.229; 3.J.228.230; 3.J.228.231; 3.J.228.236; 3.J.228.237; 3.J.228.238; 3.J.228.239; 3.J.228.154; 3.J.228.157; 3.J.228.166; 3.J.228.169; 3.J.228.172; 3.J.228.175; 3.J.228.240; 3.J.228.244; 3.J.229.228; 3.J.229.229; 3.J.229.230; 3.J.229.231; 3.J.229.236; 3.J.229.237; 3.J.229.238; 3.J.229.239; 3.J.229.154; 3.J.229.157; 3.J.229.166; 3.J.229.169; 3.J.229.172; 3.J.229.175; 3.J.229.240; 3.J.229.244; 3.J.230.228; 3.J.230.229; 3.J.230.230; 3.J.230.231; 3.J.230.236; 3.J.230.237; 3.J.230.238; 3.J.230.239; 3.J.230.154; 3.J.230.157; 3.J.230.166; 3.J.230.169; 3.J.230.172; 3.J.230.175; 3.J.230.240; 3.J.230.244; 3.J.231.228; 3.J.231.229; 3.J.231.230; 3.J.231.231; 3.J.231.236; 3.J.231.237; 3.J.231.238; 3.J.231.239; 3.J.231.154; 3.J.231.157; 3.J.231.166; 3.J.231.169; 3.J.231.172; 3.J.231.175; 3.J.231.240; 3.J.231.244; 3.J.236.228; 3.J.236.229; 3.J.236.230; 3.J.236.231; 3.J.236.236; 3.J.236.237; 3.J.236.238; 3.J.236.239; 3.J.236.154; 3.J.236.157; 3.J.236.166; 3.J.236.169; 3.J.236.172; 3.J.236.175; 3.J.236.240; 3.J.236.244; 3.J.237.228; 3.J.237.229; 3.J.237.230; 3.J.237.231; 3.J.237.236; 3.J.237.237; 3.J.237.238; 3.J.237.239; 3.J.237.154; 3.J.237.157; 3.J.237.166; 3.J.237.169; 3.J.237.172; 3.J.237.175; 3.J.237.240; 3.J.237.244; 3.J.238.228; 3.J.238.229; 3.J.238.230; 3.J.238.231; 3.J.238.236; 3.J.238.237; 3.J.238.238; 3.J.238.239; 3.J.238.154; 3.J.238.157; 3.J.238.166; 3.J.238.169; 3.J.238.172; 3.J.238.175; 3.J.238.240; 3.J.238.244; 3.J.239.228; 3.J.239.229; 3.J.239.230; 3.J.239.231; 3.J.239.236; 3.J.239.237; 3.J.239.238; 3.J.239.239; 3.J.239.154; 3.J.239.157; 3.J.239.166; 3.J.239.169; 3.J.239.172; 3.J.239.175; 3.J.239.240; 3.J.239.244; 3.J.154.228; 3.J.154.229; 3.J.154.230; 3.J.154.231; 3.J.154.236; 3.J.154.237; 3.J.154.238; 3.J.154.239; 3.J.154.154; 3.J.154.157; 3.J.154.166; 3.J.154.169; 3.J.154.172; 3.J.154.175; 3.J.154.240; 3.J.154.244; 3.J.157.228; 3.J.157.229; 3.J.157.230; 3.J.157.231; 3.J.157.236; 3.J.157.237; 3.J.157.238; 3.J.157.239; 3.J.157.154; 3.J.157.157; 3.J.157.166; 3.J.157.169; 3.J.157.172; 3.J.157.175; 3.J.157.240; 3.J.157.244; 3.J.166.228; 3.J.166.229; 3.J.166.230; 3.J.166.231; 3.J.166.236; 3.J.166.237; 3.J.166.238; 3.J.166.239; 3.J.166.154; 3.J.166.157; 3.J.166.166; 3.J.166.169; 3.J.166.172; 3.J.166.175; 3.J.166.240; 3.J.166.244; 3.J.169.228; 3.J.169.229; 3.J.169.230; 3.J.169.231; 3.J.169.236; 3.J.169.237; 3.J.169.238; 3.J.169.239; 3.J.169.154; 3.J.169.157; 3.J.169.166; 3.J.169.169; 3.J.169.172; 3.J.169.175; 3.J.169.240; 3.J.169.244; 3.J.172.228; 3.J.172.229; 3.J.172.230; 3.J.172.231; 3.J.172.236; 3.J.172.237; 3.J.172.238; 3.J.172.239; 3.J.172.154; 3.J.172.157; 3.J.172.166; 3.J.172.169; 3.J.172.172; 3.J.172.175; 3.J.172.240; 3.J.172.244; 3.J.175.228; 3.J.175.229; 3.J.175.230; 3.J.175.231; 3.J.175.236; 3.J.175.237; 3.J.175.238; 3.J.175.239; 3.J.175.154; 3.J.175.157; 3.J.175.166; 3.J.175.169; 3.J.175.172; 3.J.175.175; 3.J.175.240; 3.J.175.244; 3.J.240.228; 3.J.240.229; 3.J.240.230; 3.J.240.231; 3.J.240.236; 3.J.240.237; 3.J.240.238; 3.J.240.239; 3.J.240.154; 3.J.240.157; 3.J.240.166; 3.J.240.169; 3.J.240.172; 3.J.240.175; 3.J.240.240; 3.J.240.244; 3.J.244.228; 3.J.244.229; 3.J.244.230; 3.J.244.231; 3.J.244.236; 3.J.244.237; 3.J.244.238; 3.J.244.239; 3.J.244.154; 3.J.244.157; 3.J.244.166; 3.J.244.169; 3.J.244.172; 3.J.244.175; 3.J.244.240; 3.J.244.244;
Prodrugs of 3.L 3.L.228.228; 3.L.228.229; 3.L.228.230; 3.L.228.231; 3.L.228.236; 3.L.228.237; 3.L.228.238; 3.L.228.239; 3.L.228.154; 3.L.228.157; 3.L.228.166; 3.L.228.169; 3.L.228.172; 3.L.228.175; 3.L.228.240; 3.L.228.244; 3.L.229.228; 3.L.229.229; 3.L.229.230; 3.L.229.231; 3.L.229.236; 3.L.229.237; 3.L.229.238; 3.L.229.239; 3.L.229.154; 3.L.229.157; 3.L.229.166; 3.L.229.169; 3.L.229.172; 3.L.229.175; 3.L.229.240; 3.L.229.244; 3.L.230.228; 3.L.230.229; 3.L.230.230; 3.L.230.231; 3.L.230.236; 3.L.230.237; 3.L.230.238; 3.L.230.239; 3.L.230.154; 3.L.230.157; 3.L.230.166; 3.L.230.169; 3.L.230.172; 3.L.230.175; 3.L.230.240; 3.L.230.244; 3.L.231.228; 3.L.231.229; 3.L.231.230; 3.L.231.231; 3.L.231.236; 3.L.231.237; 3.L.231.238; 3.L.231.239; 3.L.231.154; 3.L.231.157; 3.L.231.166; 3.L.231.169; 3.L.231.172; 3.L.231.175; 3.L.231.240; 3.L.231.244; 3.L.236.228; 3.L.236.229; 3.L.236.230; 3.L.236.231; 3.L.236.236; 3.L.236.237; 3.L.236.238; 3.L.236.239; 3.L.236.154; 3.L.236.157; 3.L.236.166; 3.L.236.169; 3.L.236.172; 3.L.236.175; 3.L.236.240; 3.L.236.244; 3.L.237.228; 3.L.237.229; 3.L.237.230; 3.L.237.231; 3.L.237.236; 3.L.237.237; 3.L.237.238; 3.L.237.239; 3.L.237.154; 3.L.237.157; 3.L.237.166; 3.L.237.169; 3.L.237.172; 3.L.237.175; 3.L.237.240; 3.L.237.244; 3.L.238.228; 3.L.238.229; 3.L.238.230; 3.L.238.231; 3.L.238.236; 3.L.238.237; 3.L.238.238; 3.L.238.239; 3.L.238.154; 3.L.238.157; 3.L.238.166; 3.L.238.169; 3.L.238.172; 3.L.238.175; 3.L.238.240; 3.L.238.244; 3.L.239.228; 3.L.239.229; 3.L.239.230; 3.L.239.231; 3.L.239.236; 3.L.239.237; 3.L.239.238; 3.L.239.239; 3.L.239.154; 3.L.239.157; 3.L.239.166; 3.L.239.169; 3.L.239.172; 3.L.239.175; 3.L.239.240; 3.L.239.244; 3.L.154.228; 3.L.154.229; 3.L.154.230; 3.L.154.231; 3.L.154.236; 3.L.154.237; 3.L.154.238; 3.L.154.239; 3.L.154.154; 3.L.154.157; 3.L.154.166; 3.L.154.169; 3.L.154.172; 3.L.154.175; 3.L.154.240; 3.L.154.244; 3.L.157.228; 3.L.157.229; 3.L.157.230; 3.L.157.231; 3.L.157.236; 3.L.157.237; 3.L.157.238; 3.L.157.239; 3.L.157.154; 3.L.157.157; 3.L.157.166; 3.L.157.169; 3.L.157.172; 3.L.157.175; 3.L.157.240; 3.L.157.244; 3.L.166.228; 3.L.166.229; 3.L.166.230; 3.L.166.231; 3.L.166.236; 3.L.166.237; 3.L.166.238; 3.L.166.239; 3.L.166.154; 3.L.166.157; 3.L.166.166; 3.L.166.169; 3.L.166.172; 3.L.166.175; 3.L.166.240; 3.L.166.244; 3.L.169.228; 3.L.169.229; 3.L.169.230; 3.L.169.231; 3.L.169.236; 3.L.169.237; 3.L.169.238; 3.L.169.239; 3.L.169.154; 3.L.169.157; 3.L.169.166; 3.L.169.169; 3.L.169.172; 3.L.169.175; 3.L.169.240; 3.L.169.244; 3.L.172.228; 3.L.172.229; 3.L.172.230; 3.L.172.231; 3.L.172.236; 3.L.172.237; 3.L.172.238; 3.L.172.239; 3.L.172.154; 3.L.172.157; 3.L.172.166; 3.L.172.169; 3.L.172.172; 3.L.172.175; 3.L.172.240; 3.L.172.244; 3.L.175.228; 3.L.175.229; 3.L.175.230; 3.L.175.231; 3.L.175.236; 3.L.175.237; 3.L.175.238; 3.L.175.239; 3.L.175.154; 3.L.175.157; 3.L.175.166; 3.L.175.169; 3.L.175.172; 3.L.175.175; 3.L.175.240; 3.L.175.244; 3.L.240.228; 3.L.240.229; 3.L.240.230; 3.L.240.231; 3.L.240.236; 3.L.240.237; 3.L.240.238; 3.L.240.239; 3.L.240.154; 3.L.240.157; 3.L.240.166; 3.L.240.169; 3.L.240.172; 3.L.240.175; 3.L.240.240; 3.L.240.244; 3.L.244.228; 3.L.244.229; 3.L.244.230; 3.L.244.231; 3.L.244.236; 3.L.244.237; 3.L.244.238; 3.L.244.239; 3.L.244.154; 3.L.244.157; 3.L.244.166; 3.L.244.169; 3.L.244.172; 3.L.244.175; 3.L.244.240; 3.L.244.244;
Prodrugs of 3.O 3.O.228.228; 3.O.228.229; 3.O.228.230; 3.O.228.231; 3.O.228.236; 3.O.228.237; 3.O.228.238; 3.O.228.239; 3.O.228.154; 3.O.228.157; 3.O.228.166; 3.O.228.169; 3.O.228.172; 3.O.228.175; 3.O.228.240; 3.O.228.244; 3.O.229.228; 3.O.229.229; 3.O.229.230; 3.O.229.231; 3.O.229.236; 3.O.229.237; 3.O.229.238; 3.O.229.239; 3.O.229.154; 3.O.229.157; 3.O.229.166; 3.O.229.169; 3.O.229.172; 3.O.229.175; 3.O.229.240; 3.O.229.244; 3.O.230.228; 3.O.230.229; 3.O.230.230; 3.O.230.231; 3.O.230.236; 3.O.230.237; 3.O.230.238; 3.O.230.239; 3.O.230.154; 3.O.230.157; 3.O.230.166; 3.O.230.169; 3.O.230.172; 3.O.230.175; 3.O.230.240; 3.O.230.244; 3.O.231.228; 3.O.231.229; 3.O.231.230; 3.O.231.231; 3.O.231.236; 3.O.231.237; 3.O.231.238; 3.O.231.239; 3.O.231.154; 3.O.231.157; 3.O.231.166; 3.O.231.169; 3.O.231.172; 3.O.231.175; 3.O.231.240; 3.O.231.244; 3.O.236.228; 3.O.236.229; 3.O.236.230; 3.O.236.231; 3.O.236.236; 3.O.236.237; 3.O.236.238; 3.O.236.239; 3.O.236.154; 3.O.236.157; 3.O.236.166; 3.O.236.169; 3.O.236.172; 3.O.236.175; 3.O.236.240; 3.O.236.244; 3.O.237.228; 3.O.237.229; 3.O.237.230; 3.O.237.231; 3.O.237.236; 3.O.237.237; 3.O.237.238; 3.O.237.239; 3.O.237.154; 3.O.237.157; 3.O.237.166; 3.O.237.169; 3.O.237.172; 3.O.237.175; 3.O.237.240; 3.O.237.244; 3.O.238.228; 3.O.238.229; 3.O.238.230; 3.O.238.231; 3.O.238.236; 3.O.238.237; 3.O.238.238; 3.O.238.239; 3.O.238.154; 3.O.238.157; 3.O.238.166; 3.O.238.169; 3.O.238.172; 3.O.238.175; 3.O.238.240; 3.O.238.244; 3.O.239.228; 3.O.239.229; 3.O.239.230; 3.O.239.231; 3.O.239.236; 3.O.239.237; 3.O.239.238; 3.O.239.239; 3.O.239.154; 3.O.239.157; 3.O.239.166; 3.O.239.169; 3.O.239.172; 3.O.239.175; 3.O.239.240; 3.O.239.244; 3.O.154.228; 3.O.154.229; 3.O.154.230; 3.O.154.231; 3.O.154.236; 3.O.154.237; 3.O.154.238; 3.O.154.239; 3.O.154.154; 3.O.154.157; 3.O.154.166; 3.O.154.169;

TABLE 7-continued

3.O.154.172; 3.O.154.175; 3.O.154.240; 3.O.154.244; 3.O.157.228;
3.O.157.229; 3.O.157.230; 3.O.157.231; 3.O.157.236; 3.O.157.237;
3.O.157.238; 3.O.157.239; 3.O.157.154; 3.O.157.157; 3.O.157.166;
3.O.157.169; 3.O.157.172; 3.O.157.175; 3.O.157.240; 3.O.157.244;
3.O.166.228; 3.O.166.229; 3.O.166.230; 3.O.166.231; 3.O.166.236;
3.O.166.237; 3.O.166.238; 3.O.166.239; 3.O.166.154; 3.O.166.157;
3.O.166.166; 3.O.166.169; 3.O.166.172; 3.O.166.175; 3.O.166.240;
3.O.166.244; 3.O.169.228; 3.O.169.229; 3.O.169.230; 3.O.169.231;
3.O.169.236; 3.O.169.237; 3.O.169.238; 3.O.169.239; 3.O.169.154;
3.O.169.157; 3.O.169.166; 3.O.169.169; 3.O.169.172; 3.O.169.175;
3.O.169.240; 3.O.169.244; 3.O.172.228; 3.O.172.229; 3.O.172.230;
3.O.172.231; 3.O.172.236; 3.O.172.237; 3.O.172.238; 3.O.172.239;
3.O.172.154; 3.O.172.157; 3.O.172.166; 3.O.172.169; 3.O.172.172;
3.O.172.175; 3.O.172.240; 3.O.172.244; 3.O.175.228; 3.O.175.229;
3.O.175.230; 3.O.175.231; 3.O.175.236; 3.O.175.237; 3.O.175.238;
3.O.175.239; 3.O.175.154; 3.O.175.157; 3.O.175.166; 3.O.175.169;
3.O.175.172; 3.O.175.175; 3.O.175.240; 3.O.175.244; 3.O.240.228;
3.O.240.229; 3.O.240.230; 3.O.240.231; 3.O.240.236; 3.O.240.237;
3.O.240.238; 3.O.240.239; 3.O.240.154; 3.O.240.157; 3.O.240.166;
3.O.240.169; 3.O.240.172; 3.O.240.175; 3.O.240.240; 3.O.240.244;
3.O.244.228; 3.O.244.229; 3.O.244.230; 3.O.244.231; 3.O.244.236;
3.O.244.237; 3.O.244.238; 3.O.244.239; 3.O.244.154; 3.O.244.157;
3.O.244.166; 3.O.244.169; 3.O.244.172; 3.O.244.175; 3.O.244.240;
3.O.244.244;
Prodrugs of 3.P 3.P.228.228; 3.P.228.229; 3.P.228.230; 3.P.228.231; 3.P.228.236;
3.P.228.237; 3.P.228.238; 3.P.228.239; 3.P.228.154; 3.P.228.157;
3.P.228.166; 3.P.228.169; 3.P.228.172; 3.P.228.175; 3.P.228.240;
3.P.228.244; 3.P.229.228; 3.P.229.229; 3.P.229.230; 3.P.229.231;
3.P.229.236; 3.P.229.237; 3.P.229.238; 3.P.229.239; 3.P.229.154;
3.P.229.157; 3.P.229.166; 3.P.229.169; 3.P.229.172; 3.P.229.175;
3.P.229.240; 3.P.229.244; 3.P.230.228; 3.P.230.229; 3.P.230.230;
3.P.230.231; 3.P.230.236; 3.P.230.237; 3.P.230.238; 3.P.230.239;
3.P.230.154; 3.P.230.157; 3.P.230.166; 3.P.230.169; 3.P.230.172;
3.P.230.175; 3.P.230.240; 3.P.230.244; 3.P.231.228; 3.P.231.229;
3.P.231.230; 3.P.231.231; 3.P.231.236; 3.P.231.237; 3.P.231.238;
3.P.231.239; 3.P.231.154; 3.P.231.157; 3.P.231.166; 3.P.231.169;
3.P.231.172; 3.P.231.175; 3.P.231.240; 3.P.231.244; 3.P.236.228;
3.P.236.229; 3.P.236.230; 3.P.236.231; 3.P.236.236; 3.P.236.237;
3.P.236.238; 3.P.236.239; 3.P.236.154; 3.P.236.157; 3.P.236.166;
3.P.236.169; 3.P.236.172; 3.P.236.175; 3.P.236.240; 3.P.236.244;
3.P.237.228; 3.P.237.229; 3.P.237.230; 3.P.237.231; 3.P.237.236;
3.P.237.237; 3.P.237.238; 3.P.237.239; 3.P.237.154; 3.P.237.157;
3.P.237.166; 3.P.237.169; 3.P.237.172; 3.P.237.175; 3.P.237.240;
3.P.237.244; 3.P.238.228; 3.P.238.229; 3.P.238.230; 3.P.238.231;
3.P.238.236; 3.P.238.237; 3.P.238.238; 3.P.238.239; 3.P.238.154;
3.P.238.157; 3.P.238.166; 3.P.238.169; 3.P.238.172; 3.P.238.175;
3.P.238.240; 3.P.238.244; 3.P.239.228; 3.P.239.229; 3.P.239.230;
3.P.239.231; 3.P.239.236; 3.P.239.237; 3.P.239.238; 3.P.239.239;
3.P.239.154; 3.P.239.157; 3.P.239.166; 3.P.239.169; 3.P.239.172;
3.P.239.175; 3.P.239.240; 3.P.239.244; 3.P.154.228; 3.P.154.229;
3.P.154.230; 3.P.154.231; 3.P.154.236; 3.P.154.237; 3.P.154.238;
3.P.154.239; 3.P.154.154; 3.P.154.157; 3.P.154.166; 3.P.154.169;
3.P.154.172; 3.P.154.175; 3.P.154.240; 3.P.154.244; 3.P.157.228;
3.P.157.229; 3.P.157.230; 3.P.157.231; 3.P.157.236; 3.P.157.237;
3.P.157.238; 3.P.157.239; 3.P.157.154; 3.P.157.157; 3.P.157.166;
3.P.157.169; 3.P.157.172; 3.P.157.175; 3.P.157.240; 3.P.157.244;
3.P.166.228; 3.P.166.229; 3.P.166.230; 3.P.166.231; 3.P.166.236;
3.P.166.237; 3.P.166.238; 3.P.166.239; 3.P.166.154; 3.P.166.157;
3.P.166.166; 3.P.166.169; 3.P.166.172; 3.P.166.175; 3.P.166.240;
3.P.166.244; 3.P.169.228; 3.P.169.229; 3.P.169.230; 3.P.169.231;
3.P.169.236; 3.P.169.237; 3.P.169.238; 3.P.169.239; 3.P.169.154;
3.P.169.157; 3.P.169.166; 3.P.169.169; 3.P.169.172; 3.P.169.175;
3.P.169.240; 3.P.169.244; 3.P.172.228; 3.P.172.229; 3.P.172.230;
3.P.172.231; 3.P.172.236; 3.P.172.237; 3.P.172.238; 3.P.172.239;
3.P.172.154; 3.P.172.157; 3.P.172.166; 3.P.172.169; 3.P.172.172;
3.P.172.175; 3.P.172.240; 3.P.172.244; 3.P.175.228; 3.P.175.229;
3.P.175.230; 3.P.175.231; 3.P.175.236; 3.P.175.237; 3.P.175.238;
3.P.175.239; 3.P.175.154; 3.P.175.157; 3.P.175.166; 3.P.175.169;
3.P.175.172; 3.P.175.175; 3.P.175.240; 3.P.175.244; 3.P.240.228;
3.P.240.229; 3.P.240.230; 3.P.240.231; 3.P.240.236; 3.P.240.237;
3.P.240.238; 3.P.240.239; 3.P.240.154; 3.P.240.157; 3.P.240.166;
3.P.240.169; 3.P.240.172; 3.P.240.175; 3.P.240.240; 3.P.240.244;
3.P.244.228; 3.P.244.229; 3.P.244.230; 3.P.244.231; 3.P.244.236;
3.P.244.237; 3.P.244.238; 3.P.244.239; 3.P.244.154; 3.P.244.157;
3.P.244.166; 3.P.244.169; 3.P.244.172; 3.P.244.175; 3.P.244.240;
3.P.244.244;

Prodrugs of 3.U

3.U.228.228; 3.U.228.229; 3.U.228.230; 3.U.228.231; 3.U.228.236;
3.U.228.237; 3.U.228.238; 3.U.228.239; 3.U.228.154; 3.U.228.157;
3.U.228.166; 3.U.228.169; 3.U.228.172; 3.U.228.175; 3.U.228.240;
3.U.228.244; 3.U.229.228; 3.U.229.229; 3.U.229.230; 3.U.229.231;
3.U.229.236; 3.U.229.237; 3.U.229.238; 3.U.229.239; 3.U.229.154;
3.U.229.157; 3.U.229.166; 3.U.229.169; 3.U.229.172; 3.U.229.175;
3.U.229.240; 3.U.229.244; 3.U.230.228; 3.U.230.229; 3.U.230.230;
3.U.230.231; 3.U.230.236; 3.U.230.237; 3.U.230.238; 3.U.230.239;
3.U.230.154; 3.U.230.157; 3.U.230.166; 3.U.230.169; 3.U.230.172;
3.U.230.175; 3.U.230.240; 3.U.230.244; 3.U.231.228; 3.U.231.229;
3.U.231.230; 3.U.231.231; 3.U.231.236; 3.U.231.237; 3.U.231.238;
3.U.231.239; 3.U.231.154; 3.U.231.157; 3.U.231.166; 3.U.231.169;
3.U.231.172; 3.U.231.175; 3.U.231.240; 3.U.231.244; 3.U.236.228;
3.U.236.229; 3.U.236.230; 3.U.236.231; 3.U.236.236; 3.U.236.237;
3.U.236.238; 3.U.236.239; 3.U.236.154; 3.U.236.157; 3.U.236.166;
3.U.236.169; 3.U.236.172; 3.U.236.175; 3.U.236.240; 3.U.236.244;
3.U.237.228; 3.U.237.229; 3.U.237.230; 3.U.237.231; 3.U.237.236;
3.U.237.237; 3.U.237.238; 3.U.237.239; 3.U.237.154; 3.U.237.157;
3.U.237.166; 3.U.237.169; 3.U.237.172; 3.U.237.175; 3.U.237.240;
3.U.237.244; 3.U.238.228; 3.U.238.229; 3.U.238.230; 3.U.238.231;
3.U.238.236; 3.U.238.237; 3.U.238.238; 3.U.238.239; 3.U.238.154;
3.U.238.157; 3.U.238.166; 3.U.238.169; 3.U.238.172; 3.U.238.175;
3.U.238.240; 3.U.238.244; 3.U.239.228; 3.U.239.229; 3.U.239.230;
3.U.239.231; 3.U.239.236; 3.U.239.237; 3.U.239.238; 3.U.239.239;
3.U.239.154; 3.U.239.157; 3.U.239.166; 3.U.239.169; 3.U.239.172;
3.U.239.175; 3.U.239.240; 3.U.239.244; 3.U.154.228; 3.U.154.229;
3.U.154.230; 3.U.154.231; 3.U.154.236; 3.U.154.237; 3.U.154.238;
3.U.154.239; 3.U.154.154; 3.U.154.157; 3.U.154.166; 3.U.154.169;
3.U.154.172; 3.U.154.175; 3.U.154.240; 3.U.154.244; 3.U.157.228;
3.U.157.229; 3.U.157.230; 3.U.157.231; 3.U.157.236; 3.U.157.237;
3.U.157.238; 3.U.157.239; 3.U.157.154; 3.U.157.157; 3.U.157.166;
3.U.157.169; 3.U.157.172; 3.U.157.175; 3.U.157.240; 3.U.157.244;
3.U.166.228; 3.U.166.229; 3.U.166.230; 3.U.166.231; 3.U.166.236;
3.U.166.237; 3.U.166.238; 3.U.166.239; 3.U.166.154; 3.U.166.157;
3.U.166.166; 3.U.166.169; 3.U.166.172; 3.U.166.175; 3.U.166.240;
3.U.166.244; 3.U.169.228; 3.U.169.229; 3.U.169.230; 3.U.169.231;
3.U.169.236; 3.U.169.237; 3.U.169.238; 3.U.169.239; 3.U.169.154;
3.U.169.157; 3.U.169.166; 3.U.169.169; 3.U.169.172; 3.U.169.175;
3.U.169.240; 3.U.169.244; 3.U.172.228; 3.U.172.229; 3.U.172.230;
3.U.172.231; 3.U.172.236; 3.U.172.237; 3.U.172.238; 3.U.172.239;
3.U.172.154; 3.U.172.157; 3.U.172.166; 3.U.172.169; 3.U.172.172;
3.U.172.175; 3.U.172.240; 3.U.172.244; 3.U.175.228; 3.U.175.229;
3.U.175.230; 3.U.175.231; 3.U.175.236; 3.U.175.237; 3.U.175.238;
3.U.175.239; 3.U.175.154; 3.U.175.157; 3.U.175.166; 3.U.175.169;
3.U.175.172; 3.U.175.175; 3.U.175.240; 3.U.175.244; 3.U.240.228;
3.U.240.229; 3.U.240.230; 3.U.240.231; 3.U.240.236; 3.U.240.237;
3.U.240.238; 3.U.240.239; 3.U.240.154; 3.U.240.157; 3.U.240.166;
3.U.240.169; 3.U.240.172; 3.U.240.175; 3.U.240.240; 3.U.240.244;
3.U.244.228; 3.U.244.229; 3.U.244.230; 3.U.244.231; 3.U.244.236;
3.U.244.237; 3.U.244.238; 3.U.244.239; 3.U.244.154; 3.U.244.157;
3.U.244.166; 3.U.244.169; 3.U.244.172; 3.U.244.175; 3.U.244.240;
3.U.244.244;
Prodrugs of 3.W 3.W.228.228; 3.W.228.229; 3.W.228.230; 3.W.228.231; 3.W.228.236;
3.W.228.237; 3.W.228.238; 3.W.228.239; 3.W.228.154; 3.W.228.157;
3.W.228.166; 3.W.228.169; 3.W.228.172; 3.W.228.175; 3.W.228.240;
3.W.228.244; 3.W.229.228; 3.W.229.229; 3.W.229.230; 3.W.229.231;
3.W.229.236; 3.W.229.237; 3.W.229.238; 3.W.229.239; 3.W.229.154;
3.W.229.157; 3.W.229.166; 3.W.229.169; 3.W.229.172; 3.W.229.175;
3.W.229.240; 3.W.229.244; 3.W.230.228; 3.W.230.229; 3.W.230.230;
3.W.230.231; 3.W.230.236; 3.W.230.237; 3.W.230.238; 3.W.230.239;
3.W.230.154; 3.W.230.157; 3.W.230.166; 3.W.230.169; 3.W.230.172;
3.W.230.175; 3.W.230.240; 3.W.230.244; 3.W.231.228; 3.W.231.229;
3.W.231.230; 3.W.231.231; 3.W.231.236; 3.W.231.237; 3.W.231.238;
3.W.231.239; 3.W.231.154; 3.W.231.157; 3.W.231.166; 3.W.231.169;
3.W.231.172; 3.W.231.175; 3.W.231.240; 3.W.231.244; 3.W.236.228;
3.W.236.229; 3.W.236.230; 3.W.236.231; 3.W.236.236; 3.W.236.237;
3.W.236.238; 3.W.236.239; 3.W.236.154; 3.W.236.157; 3.W.236.166;
3.W.236.169; 3.W.236.172; 3.W.236.175; 3.W.236.240; 3.W.236.244;
3.W.237.228; 3.W.237.229; 3.W.237.230; 3.W.237.231; 3.W.237.236;
3.W.237.237; 3.W.237.238; 3.W.237.239; 3.W.237.154; 3.W.237.157;
3.W.237.166; 3.W.237.169; 3.W.237.172; 3.W.237.175; 3.W.237.240;
3.W.237.244; 3.W.238.228; 3.W.238.229; 3.W.238.230; 3.W.238.231;
3.W.238.236; 3.W.238.237; 3.W.238.238; 3.W.238.239; 3.W.238.154;
3.W.238.157; 3.W.238.166; 3.W.238.169; 3.W.238.172; 3.W.238.175;
3.W.238.240; 3.W.238.244; 3.W.239.228; 3.W.239.229; 3.W.239.230;

TABLE 7-continued

3.W.239.231; 3.W.239.236; 3.W.239.237; 3.W.239.238; 3.W.239.239; 3.W.239.154; 3.W.239.157; 3.W.239.166; 3.W.239.169; 3.W.239.172; 3.W.239.175; 3.W.239.240; 3.W.239.244; 3.W.154.228; 3.W.154.229; 3.W.154.230; 3.W.154.231; 3.W.154.236; 3.W.154.237; 3.W.154.238; 3.W.154.239; 3.W.154.154; 3.W.154.157; 3.W.154.166; 3.W.154.169; 3.W.154.172; 3.W.154.175; 3.W.154.240; 3.W.154.244; 3.W.157.228; 3.W.157.229; 3.W.157.230; 3.W.157.231; 3.W.157.236; 3.W.157.237; 3.W.157.238; 3.W.157.239; 3.W.157.154; 3.W.157.157; 3.W.157.166; 3.W.157.169; 3.W.157.172; 3.W.157.175; 3.W.157.240; 3.W.157.244; 3.W.166.228; 3.W.166.229; 3.W.166.230; 3.W.166.231; 3.W.166.236; 3.W.166.237; 3.W.166.238; 3.W.166.239; 3.W.166.154; 3.W.166.157; 3.W.166.166; 3.W.166.169; 3.W.166.172; 3.W.166.175; 3.W.166.240; 3.W.166.244; 3.W.169.228; 3.W.169.229; 3.W.169.230; 3.W.169.231; 3.W.169.236; 3.W.169.237; 3.W.169.238; 3.W.169.239; 3.W.169.154; 3.W.169.157; 3.W.169.166; 3.W.169.169; 3.W.169.172; 3.W.169.175; 3.W.169.240; 3.W.169.244; 3.W.172.228; 3.W.172.229; 3.W.172.231; 3.W.172.236; 3.W.172.237; 3.W.172.238; 3.W.172.239; 3.W.172.154; 3.W.172.157; 3.W.172.166; 3.W.172.169; 3.W.172.172; 3.W.172.175; 3.W.172.240; 3.W.172.244; 3.W.175.228; 3.W.175.229; 3.W.175.230; 3.W.175.231; 3.W.175.236; 3.W.175.237; 3.W.175.238; 3.W.175.239; 3.W.175.154; 3.W.175.157; 3.W.175.166; 3.W.175.169; 3.W.175.172; 3.W.175.175; 3.W.175.240; 3.W.175.244; 3.W.240.228; 3.W.240.229; 3.W.240.230; 3.W.240.231; 3.W.240.236; 3.W.240.237; 3.W.240.238; 3.W.240.239; 3.W.240.154; 3.W.240.157; 3.W.240.166; 3.W.240.169; 3.W.240.172; 3.W.240.175; 3.W.240.240; 3.W.240.244; 3.W.244.228; 3.W.244.229; 3.W.244.230; 3.W.244.231; 3.W.244.236; 3.W.244.237; 3.W.244.238; 3.W.244.239; 3.W.244.154; 3.W.244.157; 3.W.244.166; 3.W.244.169; 3.W.244.172; 3.W.244.175; 3.W.244.240; 3.W.244.244;

Prodrugs of 3.Y

3.Y.228.228; 3.Y.228.229; 3.Y.228.230; 3.Y.228.231; 3.Y.228.236; 3.Y.228.237; 3.Y.228.238; 3.Y.228.239; 3.Y.228.154; 3.Y.228.157; 3.Y.228.166; 3.Y.228.169; 3.Y.228.172; 3.Y.228.175; 3.Y.228.240; 3.Y.228.244; 3.Y.229.228; 3.Y.229.229; 3.Y.229.230; 3.Y.229.231; 3.Y.229.236; 3.Y.229.237; 3.Y.229.238; 3.Y.229.239; 3.Y.229.154; 3.Y.229.157; 3.Y.229.166; 3.Y.229.169; 3.Y.229.172; 3.Y.229.175; 3.Y.229.240; 3.Y.229.244; 3.Y.230.228; 3.Y.230.229; 3.Y.230.230; 3.Y.230.231; 3.Y.230.236; 3.Y.230.237; 3.Y.230.238; 3.Y.230.239; 3.Y.230.154; 3.Y.230.157; 3.Y.230.166; 3.Y.230.169; 3.Y.230.172; 3.Y.230.175; 3.Y.230.240; 3.Y.230.244; 3.Y.231.228; 3.Y.231.229; 3.Y.231.230; 3.Y.231.231; 3.Y.231.236; 3.Y.231.237; 3.Y.231.238; 3.Y.231.239; 3.Y.231.154; 3.Y.231.157; 3.Y.231.166; 3.Y.231.169; 3.Y.231.172; 3.Y.231.175; 3.Y.231.240; 3.Y.231.244; 3.Y.236.228; 3.Y.236.229; 3.Y.236.230; 3.Y.236.231; 3.Y.236.236; 3.Y.236.237; 3.Y.236.238; 3.Y.236.239; 3.Y.236.154; 3.Y.236.157; 3.Y.236.166; 3.Y.236.169; 3.Y.236.172; 3.Y.236.175; 3.Y.236.240; 3.Y.236.244; 3.Y.237.228; 3.Y.237.229; 3.Y.237.230; 3.Y.237.231; 3.Y.237.236; 3.Y.237.237; 3.Y.237.238; 3.Y.237.239; 3.Y.237.154; 3.Y.237.157; 3.Y.237.166; 3.Y.237.169; 3.Y.237.172; 3.Y.237.175; 3.Y.237.240; 3.Y.237.244; 3.Y.238.228; 3.Y.238.229; 3.Y.238.230; 3.Y.238.231; 3.Y.238.236; 3.Y.238.237; 3.Y.238.238; 3.Y.238.239; 3.Y.238.154; 3.Y.238.157; 3.Y.238.166; 3.Y.238.169; 3.Y.238.172; 3.Y.238.175; 3.Y.238.240; 3.Y.238.244; 3.Y.239.228; 3.Y.239.229; 3.Y.239.230; 3.Y.239.231; 3.Y.239.236; 3.Y.239.237; 3.Y.239.238; 3.Y.239.239; 3.Y.239.154; 3.Y.239.157; 3.Y.239.166; 3.Y.239.169; 3.Y.239.172; 3.Y.239.175; 3.Y.239.240; 3.Y.239.244; 3.Y.154.228; 3.Y.154.229; 3.Y.154.230; 3.Y.154.231; 3.Y.154.236; 3.Y.154.237; 3.Y.154.238; 3.Y.154.239; 3.Y.154.154; 3.Y.154.157; 3.Y.154.166; 3.Y.154.169; 3.Y.154.172; 3.Y.154.175; 3.Y.154.240; 3.Y.154.244; 3.Y.157.228; 3.Y.157.229; 3.Y.157.230; 3.Y.157.231; 3.Y.157.236; 3.Y.157.237; 3.Y.157.238; 3.Y.157.239; 3.Y.157.154; 3.Y.157.157; 3.Y.157.166; 3.Y.157.169; 3.Y.157.172; 3.Y.157.175; 3.Y.157.240; 3.Y.157.244; 3.Y.166.228; 3.Y.166.229; 3.Y.166.230; 3.Y.166.231; 3.Y.166.236; 3.Y.166.237; 3.Y.166.238; 3.Y.166.239; 3.Y.166.154; 3.Y.166.157; 3.Y.166.166; 3.Y.166.169; 3.Y.166.172; 3.Y.166.175; 3.Y.166.240; 3.Y.166.244; 3.Y.169.228; 3.Y.169.229; 3.Y.169.230; 3.Y.169.231; 3.Y.169.236; 3.Y.169.237; 3.Y.169.238; 3.Y.169.239; 3.Y.169.154; 3.Y.169.157; 3.Y.169.166; 3.Y.169.169; 3.Y.169.172; 3.Y.169.175; 3.Y.169.240; 3.Y.169.244; 3.Y.172.228; 3.Y.172.229; 3.Y.172.230; 3.Y.172.231; 3.Y.172.236; 3.Y.172.237; 3.Y.172.238; 3.Y.172.239; 3.Y.172.154; 3.Y.172.157; 3.Y.172.166; 3.Y.172.169; 3.Y.172.172; 3.Y.172.175; 3.Y.172.240; 3.Y.172.244; 3.Y.175.228; 3.Y.175.229; 3.Y.175.230; 3.Y.175.231; 3.Y.175.236; 3.Y.175.237; 3.Y.175.238; 3.Y.175.239; 3.Y.175.154; 3.Y.175.157; 3.Y.175.166; 3.Y.175.169; 3.Y.175.172; 3.Y.175.175; 3.Y.175.240; 3.Y.175.244; 3.Y.240.228; 3.Y.240.229; 3.Y.240.230; 3.Y.240.231; 3.Y.240.236; 3.Y.240.237; 3.Y.240.238; 3.Y.240.239; 3.Y.240.154; 3.Y.240.157; 3.Y.240.166; 3.Y.240.169; 3.Y.240.172; 3.Y.240.175; 3.Y.240.240; 3.Y.240.244; 3.Y.244.228; 3.Y.244.229; 3.Y.244.230; 3.Y.244.231; 3.Y.244.236; 3.Y.244.237; 3.Y.244.238; 3.Y.244.239; 3.Y.244.154; 3.Y.244.157; 3.Y.244.166; 3.Y.244.169; 3.Y.244.172; 3.Y.244.175; 3.Y.244.240; 3.Y.244.244;

Prodrugs of 4.B

4.B.228.228; 4.B.228.229; 4.B.228.230; 4.B.228.231; 4.B.228.236; 4.B.228.237; 4.B.228.238; 4.B.228.239; 4.B.228.154; 4.B.228.157; 4.B.228.166; 4.B.228.169; 4.B.228.172; 4.B.228.175; 4.B.228.240; 4.B.228.244; 4.B.229.228; 4.B.229.229; 4.B.229.230; 4.B.229.231; 4.B.229.236; 4.B.229.237; 4.B.229.238; 4.B.229.239; 4.B.229.154; 4.B.229.157; 4.B.229.166; 4.B.229.169; 4.B.229.172; 4.B.229.175; 4.B.229.240; 4.B.229.244; 4.B.230.228; 4.B.230.229; 4.B.230.230; 4.B.230.231; 4.B.230.236; 4.B.230.237; 4.B.230.238; 4.B.230.239; 4.B.230.154; 4.B.230.157; 4.B.230.166; 4.B.230.169; 4.B.230.172; 4.B.230.175; 4.B.230.240; 4.B.230.244; 4.B.231.228; 4.B.231.229; 4.B.231.230; 4.B.231.231; 4.B.231.236; 4.B.231.237; 4.B.231.238; 4.B.231.239; 4.B.231.154; 4.B.231.157; 4.B.231.166; 4.B.231.169; 4.B.231.172; 4.B.231.175; 4.B.231.240; 4.B.231.244; 4.B.236.228; 4.B.236.229; 4.B.236.230; 4.B.236.231; 4.B.236.236; 4.B.236.237; 4.B.236.238; 4.B.236.239; 4.B.236.154; 4.B.236.157; 4.B.236.166; 4.B.236.169; 4.B.236.172; 4.B.236.175; 4.B.236.240; 4.B.236.244; 4.B.237.228; 4.B.237.229; 4.B.237.230; 4.B.237.231; 4.B.237.236; 4.B.237.237; 4.B.237.238; 4.B.237.239; 4.B.237.154; 4.B.237.157; 4.B.237.166; 4.B.237.169; 4.B.237.172; 4.B.237.175; 4.B.237.240; 4.B.237.244; 4.B.238.228; 4.B.238.229; 4.B.238.230; 4.B.238.231; 4.B.238.236; 4.B.238.237; 4.B.238.238; 4.B.238.239; 4.B.238.154; 4.B.238.157; 4.B.238.166; 4.B.238.169; 4.B.238.172; 4.B.238.175; 4.B.238.240; 4.B.238.244; 4.B.239.228; 4.B.239.229; 4.B.239.230; 4.B.239.231; 4.B.239.236; 4.B.239.237; 4.B.239.238; 4.B.239.239; 4.B.239.154; 4.B.239.157; 4.B.239.166; 4.B.239.169; 4.B.239.172; 4.B.239.175; 4.B.239.240; 4.B.239.244; 4.B.154.228; 4.B.154.229; 4.B.154.230; 4.B.154.231; 4.B.154.236; 4.B.154.237; 4.B.154.238; 4.B.154.239; 4.B.154.154; 4.B.154.157; 4.B.154.166; 4.B.154.169; 4.B.154.172; 4.B.154.175; 4.B.154.240; 4.B.154.244; 4.B.157.228; 4.B.157.229; 4.B.157.230; 4.B.157.231; 4.B.157.236; 4.B.157.237; 4.B.157.238; 4.B.157.239; 4.B.157.154; 4.B.157.157; 4.B.157.166; 4.B.157.169; 4.B.157.172; 4.B.157.175; 4.B.157.240; 4.B.157.244; 4.B.166.228; 4.B.166.229; 4.B.166.230; 4.B.166.231; 4.B.166.236; 4.B.166.237; 4.B.166.238; 4.B.166.239; 4.B.166.154; 4.B.166.157; 4.B.166.166; 4.B.166.169; 4.B.166.172; 4.B.166.175; 4.B.166.240; 4.B.166.244; 4.B.169.228; 4.B.169.229; 4.B.169.230; 4.B.169.231; 4.B.169.236; 4.B.169.237; 4.B.169.238; 4.B.169.239; 4.B.169.154; 4.B.169.157; 4.B.169.166; 4.B.169.169; 4.B.169.172; 4.B.169.175; 4.B.169.240; 4.B.169.244; 4.B.172.228; 4.B.172.229; 4.B.172.230; 4.B.172.231; 4.B.172.236; 4.B.172.237; 4.B.172.238; 4.B.172.239; 4.B.172.154; 4.B.172.157; 4.B.172.166; 4.B.172.169; 4.B.172.172; 4.B.172.175; 4.B.172.240; 4.B.172.244; 4.B.175.228; 4.B.175.229; 4.B.175.230; 4.B.175.231; 4.B.175.236; 4.B.175.237; 4.B.175.238; 4.B.175.239; 4.B.175.154; 4.B.175.157; 4.B.175.166; 4.B.175.169; 4.B.175.172; 4.B.175.175; 4.B.175.240; 4.B.175.244; 4.B.240.228; 4.B.240.229; 4.B.240.230; 4.B.240.231; 4.B.240.236; 4.B.240.237; 4.B.240.238; 4.B.240.239; 4.B.240.154; 4.B.240.157; 4.B.240.166; 4.B.240.169; 4.B.240.172; 4.B.240.175; 4.B.240.240; 4.B.240.244; 4.B.244.228; 4.B.244.229; 4.B.244.230; 4.B.244.231; 4.B.244.236; 4.B.244.237; 4.B.244.238; 4.B.244.239; 4.B.244.154; 4.B.244.157; 4.B.244.166; 4.B.244.169; 4.B.244.172; 4.B.244.175; 4.B.244.240; 4.B.244.244;

Prodrugs of 4.D

4.D.228.228; 4.D.228.229; 4.D.228.230; 4.D.228.231; 4.D.228.236; 4.D.228.237; 4.D.228.238; 4.D.228.239; 4.D.228.154; 4.D.228.157; 4.D.228.166; 4.D.228.169; 4.D.228.172; 4.D.228.175; 4.D.228.240; 4.D.228.244; 4.D.229.228; 4.D.229.229; 4.D.229.230; 4.D.229.231; 4.D.229.236; 4.D.229.237; 4.D.229.238; 4.D.229.239; 4.D.229.154; 4.D.229.157; 4.D.229.166; 4.D.229.169; 4.D.229.172; 4.D.229.175; 4.D.229.240; 4.D.229.244; 4.D.230.228; 4.D.230.229; 4.D.230.230; 4.D.230.231; 4.D.230.236; 4.D.230.237; 4.D.230.238; 4.D.230.239; 4.D.230.154; 4.D.230.157; 4.D.230.166; 4.D.230.169; 4.D.230.172; 4.D.230.175; 4.D.230.240; 4.D.230.244; 4.D.231.228; 4.D.231.229; 4.D.231.230; 4.D.231.231; 4.D.231.236; 4.D.231.237; 4.D.231.238; 4.D.231.239; 4.D.231.154; 4.D.231.157; 4.D.231.166; 4.D.231.169; 4.D.231.172; 4.D.231.175; 4.D.231.240; 4.D.231.244; 4.D.236.228; 4.D.236.229; 4.D.236.230; 4.D.236.231; 4.D.236.236; 4.D.236.237; 4.D.236.238; 4.D.236.239; 4.D.236.154; 4.D.236.157; 4.D.236.166; 4.D.236.169; 4.D.236.172; 4.D.236.175; 4.D.236.240; 4.D.236.244; 4.D.237.228; 4.D.237.229; 4.D.237.230; 4.D.237.231; 4.D.237.236; 4.D.237.237; 4.D.237.238; 4.D.237.239; 4.D.237.154; 4.D.237.157; 4.D.237.166; 4.D.237.169; 4.D.237.172; 4.D.237.175; 4.D.237.240;

TABLE 7-continued

4.D.237.244; 4.D.238.228; 4.D.238.229; 4.D.238.230; 4.D.238.231;
4.D.238.236; 4.D.238.237; 4.D.238.238; 4.D.238.239; 4.D.238.154;
4.D.238.157; 4.D.238.166; 4.D.238.169; 4.D.238.172; 4.D.238.175;
4.D.238.240; 4.D.238.244; 4.D.239.228; 4.D.239.229; 4.D.239.230;
4.D.239.231; 4.D.239.236; 4.D.239.237; 4.D.239.238; 4.D.239.239;
4.D.239.154; 4.D.239.157; 4.D.239.166; 4.D.239.169; 4.D.239.172;
4.D.239.175; 4.D.239.240; 4.D.239.244; 4.D.154.228; 4.D.154.229;
4.D.154.230; 4.D.154.231; 4.D.154.236; 4.D.154.237; 4.D.154.238;
4.D.154.239; 4.D.154.154; 4.D.154.157; 4.D.154.166; 4.D.154.169;
4.D.154.172; 4.D.154.175; 4.D.154.240; 4.D.154.244; 4.D.157.228;
4.D.157.229; 4.D.157.230; 4.D.157.231; 4.D.157.236; 4.D.157.237;
4.D.157.238; 4.D.157.239; 4.D.157.154; 4.D.157.157; 4.D.157.166;
4.D.157.169; 4.D.157.172; 4.D.157.175; 4.D.157.240; 4.D.157.244;
4.D.166.228; 4.D.166.229; 4.D.166.230; 4.D.166.231; 4.D.166.236;
4.D.166.237; 4.D.166.238; 4.D.166.239; 4.D.166.154; 4.D.166.157;
4.D.166.166; 4.D.166.169; 4.D.166.172; 4.D.166.175; 4.D.166.240;
4.D.166.244; 4.D.169.228; 4.D.169.229; 4.D.169.230; 4.D.169.231;
4.D.169.236; 4.D.169.237; 4.D.169.238; 4.D.169.239; 4.D.169.154;
4.D.169.157; 4.D.169.166; 4.D.169.169; 4.D.169.172; 4.D.169.175;
4.D.169.240; 4.D.169.244; 4.D.172.228; 4.D.172.229; 4.D.172.230;
4.D.172.231; 4.D.172.236; 4.D.172.237; 4.D.172.238; 4.D.172.239;
4.D.172.154; 4.D.172.157; 4.D.172.166; 4.D.172.169; 4.D.172.172;
4.D.172.175; 4.D.172.240; 4.D.172.244; 4.D.175.228; 4.D.175.229;
4.D.175.230; 4.D.175.231; 4.D.175.236; 4.D.175.237; 4.D.175.238;
4.D.175.239; 4.D.175.154; 4.D.175.157; 4.D.175.166; 4.D.175.169;
4.D.175.172; 4.D.175.175; 4.D.175.240; 4.D.175.244; 4.D.240.228;
4.D.240.229; 4.D.240.230; 4.D.240.231; 4.D.240.236; 4.D.240.237;
4.D.240.238; 4.D.240.239; 4.D.240.154; 4.D.240.157; 4.D.240.166;
4.D.240.169; 4.D.240.172; 4.D.240.175; 4.D.240.240; 4.D.240.244;
4.D.244.228; 4.D.244.229; 4.D.244.230; 4.D.244.231; 4.D.244.236;
4.D.244.237; 4.D.244.238; 4.D.244.239; 4.D.244.154; 4.D.244.157;
4.D.244.166; 4.D.244.169; 4.D.244.172; 4.D.244.175; 4.D.244.240;
4.D.244.244;

Prodrugs of 4.E

4.E.228.228; 4.E.228.229; 4.E.228.230; 4.E.228.231; 4.E.228.236;
4.E.228.237; 4.E.228.238; 4.E.228.239; 4.E.228.154; 4.E.228.157;
4.E.228.166; 4.E.228.169; 4.E.228.172; 4.E.228.175; 4.E.228.240;
4.E.228.244; 4.E.229.228; 4.E.229.229; 4.E.229.230; 4.E.229.231;
4.E.229.236; 4.E.229.237; 4.E.229.238; 4.E.229.239; 4.E.229.154;
4.E.229.157; 4.E.229.166; 4.E.229.169; 4.E.229.172; 4.E.229.175;
4.E.229.240; 4.E.229.244; 4.E.230.228; 4.E.230.229; 4.E.230.230;
4.E.230.231; 4.E.230.236; 4.E.230.237; 4.E.230.238; 4.E.230.239;
4.E.230.154; 4.E.230.157; 4.E.230.166; 4.E.230.169; 4.E.230.172;
4.E.230.175; 4.E.230.240; 4.E.230.244; 4.E.231.228; 4.E.231.229;
4.E.231.230; 4.E.231.231; 4.E.231.236; 4.E.231.237; 4.E.231.238;
4.E.231.239; 4.E.231.154; 4.E.231.157; 4.E.231.166; 4.E.231.169;
4.E.231.172; 4.E.231.175; 4.E.231.240; 4.E.231.244; 4.E.236.228;
4.E.236.229; 4.E.236.230; 4.E.236.231; 4.E.236.236; 4.E.236.237;
4.E.236.238; 4.E.236.239; 4.E.236.154; 4.E.236.157; 4.E.236.166;
4.E.236.169; 4.E.236.172; 4.E.236.175; 4.E.236.240; 4.E.236.244;
4.E.237.228; 4.E.237.229; 4.E.237.230; 4.E.237.231; 4.E.237.236;
4.E.237.237; 4.E.237.238; 4.E.237.239; 4.E.237.154; 4.E.237.157;
4.E.237.166; 4.E.237.169; 4.E.237.172; 4.E.237.175; 4.E.237.240;
4.E.237.244; 4.E.238.228; 4.E.238.229; 4.E.238.230; 4.E.238.231;
4.E.238.236; 4.E.238.237; 4.E.238.238; 4.E.238.239; 4.E.238.154;
4.E.238.157; 4.E.238.166; 4.E.238.169; 4.E.238.172; 4.E.238.175;
4.E.238.240; 4.E.238.244; 4.E.239.228; 4.E.239.229; 4.E.239.230;
4.E.239.231; 4.E.239.236; 4.E.239.237; 4.E.239.238; 4.E.239.239;
4.E.239.154; 4.E.239.157; 4.E.239.166; 4.E.239.169; 4.E.239.172;
4.E.239.175; 4.E.239.240; 4.E.239.244; 4.E.154.228; 4.E.154.229;
4.E.154.230; 4.E.154.231; 4.E.154.236; 4.E.154.237; 4.E.154.238;
4.E.154.239; 4.E.154.154; 4.E.154.157; 4.E.154.166; 4.E.154.169;
4.E.154.172; 4.E.154.175; 4.E.154.240; 4.E.154.244; 4.E.157.228;
4.E.157.229; 4.E.157.230; 4.E.157.231; 4.E.157.236; 4.E.157.237;
4.E.157.238; 4.E.157.239; 4.E.157.154; 4.E.157.157; 4.E.157.166;
4.E.157.169; 4.E.157.172; 4.E.157.175; 4.E.157.240; 4.E.157.244;
4.E.166.228; 4.E.166.229; 4.E.166.230; 4.E.166.231; 4.E.166.236;
4.E.166.237; 4.E.166.238; 4.E.166.239; 4.E.166.154; 4.E.166.157;
4.E.166.166; 4.E.166.169; 4.E.166.172; 4.E.166.175; 4.E.166.240;
4.E.166.244; 4.E.169.228; 4.E.169.229; 4.E.169.230; 4.E.169.231;
4.E.169.236; 4.E.169.237; 4.E.169.238; 4.E.169.239; 4.E.169.154;
4.E.169.157; 4.E.169.166; 4.E.169.169; 4.E.169.172; 4.E.169.175;
4.E.169.240; 4.E.169.244; 4.E.172.228; 4.E.172.229; 4.E.172.230;
4.E.172.231; 4.E.172.236; 4.E.172.237; 4.E.172.238; 4.E.172.239;
4.E.172.154; 4.E.172.157; 4.E.172.166; 4.E.172.169; 4.E.172.172;
4.E.172.175; 4.E.172.240; 4.E.172.244; 4.E.175.228; 4.E.175.229;
4.E.175.230; 4.E.175.231; 4.E.175.236; 4.E.175.237; 4.E.175.238;
4.E.175.239; 4.E.175.154; 4.E.175.157; 4.E.175.166; 4.E.175.169;
4.E.175.172; 4.E.175.175; 4.E.175.240; 4.E.175.244; 4.E.240.228;
4.E.240.229; 4.E.240.230; 4.E.240.231; 4.E.240.236; 4.E.240.237;
4.E.240.238; 4.E.240.239; 4.E.240.154; 4.E.240.157; 4.E.240.166;
4.E.240.169; 4.E.240.172; 4.E.240.175; 4.E.240.240; 4.E.240.244;
4.E.244.228; 4.E.244.229; 4.E.244.230; 4.E.244.231; 4.E.244.236;
4.E.244.237; 4.E.244.238; 4.E.244.239; 4.E.244.154; 4.E.244.157;
4.E.244.166; 4.E.244.169; 4.E.244.172; 4.E.244.175; 4.E.244.240;
4.E.244.244;

Prodrugs of 4.G

4.G.228.228; 4.G.228.229; 4.G.228.230; 4.G.228.231; 4.G.228.236;
4.G.228.237; 4.G.228.238; 4.G.228.239; 4.G.228.154; 4.G.228.157;
4.G.228.166; 4.G.228.169; 4.G.228.172; 4.G.228.175; 4.G.228.240;
4.G.228.244; 4.G.229.228; 4.G.229.229; 4.G.229.230; 4.G.229.231;
4.G.229.236; 4.G.229.237; 4.G.229.238; 4.G.229.239; 4.G.229.154;
4.G.229.157; 4.G.229.166; 4.G.229.169; 4.G.229.172; 4.G.229.175;
4.G.229.240; 4.G.229.244; 4.G.230.228; 4.G.230.229; 4.G.230.230;
4.G.230.231; 4.G.230.236; 4.G.230.237; 4.G.230.238; 4.G.230.239;
4.G.230.154; 4.G.230.157; 4.G.230.166; 4.G.230.169; 4.G.230.172;
4.G.230.175; 4.G.230.240; 4.G.230.244; 4.G.231.228; 4.G.231.229;
4.G.231.230; 4.G.231.231; 4.G.231.236; 4.G.231.237; 4.G.231.238;
4.G.231.239; 4.G.231.154; 4.G.231.157; 4.G.231.166; 4.G.231.169;
4.G.231.172; 4.G.231.175; 4.G.231.240; 4.G.231.244; 4.G.236.228;
4.G.236.229; 4.G.236.230; 4.G.236.231; 4.G.236.236; 4.G.236.237;
4.G.236.238; 4.G.236.239; 4.G.236.154; 4.G.236.157; 4.G.236.166;
4.G.236.169; 4.G.236.172; 4.G.236.175; 4.G.236.240; 4.G.236.244;
4.G.237.228; 4.G.237.229; 4.G.237.230; 4.G.237.231; 4.G.237.236;
4.G.237.237; 4.G.237.238; 4.G.237.239; 4.G.237.154; 4.G.237.157;
4.G.237.166; 4.G.237.169; 4.G.237.172; 4.G.237.175; 4.G.237.240;
4.G.237.244; 4.G.238.228; 4.G.238.229; 4.G.238.230; 4.G.238.231;
4.G.238.236; 4.G.238.237; 4.G.238.238; 4.G.238.239; 4.G.238.154;
4.G.238.157; 4.G.238.166; 4.G.238.169; 4.G.238.172; 4.G.238.175;
4.G.238.240; 4.G.238.244; 4.G.239.228; 4.G.239.229; 4.G.239.230;
4.G.239.231; 4.G.239.236; 4.G.239.237; 4.G.239.238; 4.G.239.239;
4.G.239.154; 4.G.239.157; 4.G.239.166; 4.G.239.169; 4.G.239.172;
4.G.239.175; 4.G.239.240; 4.G.239.244; 4.G.154.228; 4.G.154.229;
4.G.154.230; 4.G.154.231; 4.G.154.236; 4.G.154.237; 4.G.154.238;
4.G.154.239; 4.G.154.154; 4.G.154.157; 4.G.154.166; 4.G.154.169;
4.G.154.172; 4.G.154.175; 4.G.154.240; 4.G.154.244; 4.G.157.228;
4.G.157.229; 4.G.157.230; 4.G.157.231; 4.G.157.236; 4.G.157.237;
4.G.157.238; 4.G.157.239; 4.G.157.154; 4.G.157.157; 4.G.157.166;
4.G.157.169; 4.G.157.172; 4.G.157.175; 4.G.157.240; 4.G.157.244;
4.G.166.228; 4.G.166.229; 4.G.166.230; 4.G.166.231; 4.G.166.236;
4.G.166.237; 4.G.166.238; 4.G.166.239; 4.G.166.154; 4.G.166.157;
4.G.166.166; 4.G.166.169; 4.G.166.172; 4.G.166.175; 4.G.166.240;
4.G.166.244; 4.G.169.228; 4.G.169.229; 4.G.169.230; 4.G.169.231;
4.G.169.236; 4.G.169.237; 4.G.169.238; 4.G.169.239; 4.G.169.154;
4.G.169.157; 4.G.169.166; 4.G.169.169; 4.G.169.172; 4.G.169.175;
4.G.169.240; 4.G.169.244; 4.G.172.228; 4.G.172.229; 4.G.172.230;
4.G.172.231; 4.G.172.236; 4.G.172.237; 4.G.172.238; 4.G.172.239;
4.G.172.154; 4.G.172.157; 4.G.172.166; 4.G.172.169; 4.G.172.172;
4.G.172.175; 4.G.172.240; 4.G.172.244; 4.G.175.228; 4.G.175.229;
4.G.175.230; 4.G.175.231; 4.G.175.236; 4.G.175.237; 4.G.175.238;
4.G.175.239; 4.G.175.154; 4.G.175.157; 4.G.175.166; 4.G.175.169;
4.G.175.172; 4.G.175.175; 4.G.175.240; 4.G.175.244; 4.G.240.228;
4.G.240.229; 4.G.240.230; 4.G.240.231; 4.G.240.236; 4.G.240.237;
4.G.240.238; 4.G.240.239; 4.G.240.154; 4.G.240.157; 4.G.240.166;
4.G.240.169; 4.G.240.172; 4.G.240.175; 4.G.240.240; 4.G.240.244;
4.G.244.228; 4.G.244.229; 4.G.244.230; 4.G.244.231; 4.G.244.236;
4.G.244.237; 4.G.244.238; 4.G.244.239; 4.G.244.154; 4.G.244.157;
4.G.244.166; 4.G.244.169; 4.G.244.172; 4.G.244.175; 4.G.244.240;
4.G.244.244;

Prodrugs of 4.I

4.I.228.228; 4.I.228.229; 4.I.228.230; 4.I.228.231; 4.I.228.236;
4.I.228.237; 4.I.228.238; 4.I.228.239; 4.I.228.154; 4.I.228.157;
4.I.228.166; 4.I.228.169; 4.I.228.172; 4.I.228.175; 4.I.228.240;
4.I.228.244; 4.I.229.228; 4.I.229.229; 4.I.229.230; 4.I.229.231;
4.I.229.236; 4.I.229.237; 4.I.229.238; 4.I.229.239; 4.I.229.154;
4.I.229.157; 4.I.229.166; 4.I.229.169; 4.I.229.172; 4.I.229.175;
4.I.229.240; 4.I.229.244; 4.I.230.228; 4.I.230.229; 4.I.230.230;
4.I.230.231; 4.I.230.236; 4.I.230.237; 4.I.230.238; 4.I.230.239;
4.I.230.154; 4.I.230.157; 4.I.230.166; 4.I.230.169; 4.I.230.172;
4.I.230.175; 4.I.230.240; 4.I.230.244; 4.I.231.228; 4.I.231.229;
4.I.231.230; 4.I.231.231; 4.I.231.236; 4.I.231.237; 4.I.231.238;
4.I.231.239; 4.I.231.154; 4.I.231.157; 4.I.231.166; 4.I.231.169;
4.I.231.172; 4.I.231.175; 4.I.231.240; 4.I.231.244; 4.I.236.228;
4.I.236.229; 4.I.236.230; 4.I.236.231; 4.I.236.236; 4.I.236.237;
4.I.236.238; 4.I.236.239; 4.I.236.154; 4.I.236.157; 4.I.236.166;

TABLE 7-continued

4.I.236.169; 4.I.236.172; 4.I.236.175; 4.I.236.240; 4.I.236.244;
4.I.237.228; 4.I.237.229; 4.I.237.230; 4.I.237.231; 4.I.237.236;
4.I.237.237; 4.I.237.238; 4.I.237.239; 4.I.237.154; 4.I.237.157;
4.I.237.166; 4.I.237.169; 4.I.237.172; 4.I.237.175; 4.I.237.240;
4.I.237.244; 4.I.238.228; 4.I.238.229; 4.I.238.230; 4.I.238.231;
4.I.238.236; 4.I.238.237; 4.I.238.238; 4.I.238.239; 4.I.238.154;
4.I.238.157; 4.I.238.166; 4.I.238.169; 4.I.238.172; 4.I.238.175;
4.I.238.240; 4.I.238.244; 4.I.239.228; 4.I.239.229; 4.I.239.230;
4.I.239.231; 4.I.239.236; 4.I.239.237; 4.I.239.238; 4.I.239.239;
4.I.239.154; 4.I.239.157; 4.I.239.166; 4.I.239.169; 4.I.239.172;
4.I.239.175; 4.I.239.240; 4.I.239.244; 4.I.154.228; 4.I.154.229;
4.I.154.230; 4.I.154.231; 4.I.154.236; 4.I.154.237; 4.I.154.238;
4.I.154.239; 4.I.154.154; 4.I.154.157; 4.I.154.166; 4.I.154.169;
4.I.154.172; 4.I.154.175; 4.I.154.240; 4.I.154.244; 4.I.157.228;
4.I.157.229; 4.I.157.230; 4.I.157.231; 4.I.157.236; 4.I.157.237;
4.I.157.238; 4.I.157.239; 4.I.157.154; 4.I.157.157; 4.I.157.166;
4.I.157.169; 4.I.157.172; 4.I.157.175; 4.I.157.240; 4.I.157.244;
4.I.166.228; 4.I.166.229; 4.I.166.230; 4.I.166.231; 4.I.166.236;
4.I.166.237; 4.I.166.238; 4.I.166.239; 4.I.166.154; 4.I.166.157;
4.I.166.166; 4.I.166.169; 4.I.166.172; 4.I.166.175; 4.I.166.240;
4.I.166.244; 4.I.169.228; 4.I.169.229; 4.I.169.230; 4.I.169.231;
4.I.169.236; 4.I.169.237; 4.I.169.238; 4.I.169.239; 4.I.169.154;
4.I.169.157; 4.I.169.166; 4.I.169.169; 4.I.169.172; 4.I.169.175;
4.I.169.240; 4.I.169.244; 4.I.172.228; 4.I.172.229; 4.I.172.230;
4.I.172.231; 4.I.172.236; 4.I.172.237; 4.I.172.238; 4.I.172.239;
4.I.172.154; 4.I.172.157; 4.I.172.166; 4.I.172.169; 4.I.172.172;
4.I.172.175; 4.I.172.240; 4.I.172.244; 4.I.175.228; 4.I.175.229;
4.I.175.230; 4.I.175.231; 4.I.175.236; 4.I.175.237; 4.I.175.238;
4.I.175.239; 4.I.175.154; 4.I.175.157; 4.I.175.166; 4.I.175.169;
4.I.175.172; 4.I.175.175; 4.I.175.240; 4.I.175.244; 4.I.240.228;
4.I.240.229; 4.I.240.230; 4.I.240.231; 4.I.240.236; 4.I.240.237;
4.I.240.238; 4.I.240.239; 4.I.240.154; 4.I.240.157; 4.I.240.166;
4.I.240.169; 4.I.240.172; 4.I.240.175; 4.I.240.240; 4.I.240.244;
4.I.244.228; 4.I.244.229; 4.I.244.230; 4.I.244.231; 4.I.244.236;
4.I.244.237; 4.I.244.238; 4.I.244.239; 4.I.244.154; 4.I.244.157;
4.I.244.166; 4.I.244.169; 4.I.244.172; 4.I.244.175; 4.I.244.240;
4.I.244.244;

Prodrugs of 4.J

4.J.228.228; 4.J.228.229; 4.J.228.230; 4.J.228.231; 4.J.228.236;
4.J.228.237; 4.J.228.238; 4.J.228.239; 4.J.228.154; 4.J.228.157;
4.J.228.166; 4.J.228.169; 4.J.228.172; 4.J.228.175; 4.J.228.240;
4.J.228.244; 4.J.229.228; 4.J.229.229; 4.J.229.230; 4.J.229.231;
4.J.229.236; 4.J.229.237; 4.J.229.238; 4.J.229.239; 4.J.229.154;
4.J.229.157; 4.J.229.238; 4.J.229.166; 4.J.229.169; 4.J.229.172; 4.J.229.175;
4.J.229.240; 4.J.229.244; 4.J.230.228; 4.J.230.229; 4.J.230.230;
4.J.230.231; 4.J.230.236; 4.J.230.237; 4.J.230.238; 4.J.230.239;
4.J.230.154; 4.J.230.157; 4.J.230.166; 4.J.230.169; 4.J.230.172;
4.J.230.175; 4.J.230.240; 4.J.230.244; 4.J.231.228; 4.J.231.229;
4.J.231.230; 4.J.231.231; 4.J.231.236; 4.J.231.237; 4.J.231.238;
4.J.231.239; 4.J.231.154; 4.J.231.157; 4.J.231.166; 4.J.231.169;
4.J.231.172; 4.J.231.175; 4.J.231.240; 4.J.231.244; 4.J.236.228;
4.J.236.229; 4.J.236.230; 4.J.236.231; 4.J.236.236; 4.J.236.237;
4.J.236.238; 4.J.236.239; 4.J.236.154; 4.J.236.157; 4.J.236.166;
4.J.236.169; 4.J.236.172; 4.J.236.175; 4.J.236.240; 4.J.236.244;
4.J.237.228; 4.J.237.229; 4.J.237.230; 4.J.237.231; 4.J.237.236;
4.J.237.237; 4.J.237.238; 4.J.237.239; 4.J.237.154; 4.J.237.157;
4.J.237.166; 4.J.237.169; 4.J.237.172; 4.J.237.175; 4.J.237.240;
4.J.237.244; 4.J.238.228; 4.J.238.229; 4.J.238.230; 4.J.238.231;
4.J.238.236; 4.J.238.237; 4.J.238.238; 4.J.238.239; 4.J.238.154;
4.J.238.157; 4.J.238.166; 4.J.238.169; 4.J.238.172; 4.J.238.175;
4.J.238.240; 4.J.238.244; 4.J.239.228; 4.J.239.229; 4.J.239.230;
4.J.239.231; 4.J.239.236; 4.J.239.237; 4.J.239.238; 4.J.239.239;
4.J.239.154; 4.J.239.157; 4.J.239.166; 4.J.239.169; 4.J.239.172;
4.J.239.175; 4.J.239.240; 4.J.239.244; 4.J.154.228; 4.J.154.229;
4.J.154.230; 4.J.154.231; 4.J.154.236; 4.J.154.237; 4.J.154.238;
4.J.154.239; 4.J.154.154; 4.J.154.157; 4.J.154.166; 4.J.154.169;
4.J.154.172; 4.J.154.175; 4.J.154.240; 4.J.154.244; 4.J.157.228;
4.J.157.229; 4.J.157.230; 4.J.157.231; 4.J.157.236; 4.J.157.237;
4.J.157.238; 4.J.157.239; 4.J.157.154; 4.J.157.157; 4.J.157.166;
4.J.157.169; 4.J.157.172; 4.J.157.175; 4.J.157.240; 4.J.157.244;
4.J.166.228; 4.J.166.229; 4.J.166.230; 4.J.166.231; 4.J.166.236;
4.J.166.237; 4.J.166.238; 4.J.166.239; 4.J.166.154; 4.J.166.157;
4.J.166.166; 4.J.166.169; 4.J.166.172; 4.J.166.175; 4.J.166.240;
4.J.166.244; 4.J.169.228; 4.J.169.229; 4.J.169.230; 4.J.169.231;
4.J.169.236; 4.J.169.237; 4.J.169.238; 4.J.169.239; 4.J.169.154;
4.J.169.157; 4.J.169.166; 4.J.169.169; 4.J.169.172; 4.J.169.175;
4.J.169.240; 4.J.169.244; 4.J.172.228; 4.J.172.229; 4.J.172.230;
4.J.172.231; 4.J.172.236; 4.J.172.237; 4.J.172.238; 4.J.172.239;
4.J.172.154; 4.J.172.157; 4.J.172.166; 4.J.172.169; 4.J.172.172;
4.J.172.175; 4.J.172.240; 4.J.172.244; 4.J.175.228; 4.J.175.229;
4.J.175.230; 4.J.175.231; 4.J.175.236; 4.J.175.237; 4.J.175.238;
4.J.175.239; 4.J.175.154; 4.J.175.157; 4.J.175.166; 4.J.175.169;
4.J.175.172; 4.J.175.175; 4.J.175.240; 4.J.175.244; 4.J.240.228;
4.J.240.229; 4.J.240.230; 4.J.240.231; 4.J.240.236; 4.J.240.237;
4.J.240.238; 4.J.240.239; 4.J.240.154; 4.J.240.157; 4.J.240.166;
4.J.240.169; 4.J.240.172; 4.J.240.175; 4.J.240.240; 4.J.240.244;
4.J.244.228; 4.J.244.229; 4.J.244.230; 4.J.244.231; 4.J.244.236;
4.J.244.237; 4.J.244.238; 4.J.244.239; 4.J.244.154; 4.J.244.157;
4.J.244.166; 4.J.244.169; 4.J.244.172; 4.J.244.175; 4.J.244.240;
4.J.244.244;

Prodrugs of 4.L

4.L.228.228; 4.L.228.229; 4.L.228.230; 4.L.228.231; 4.L.228.236;
4.L.228.237; 4.L.228.238; 4.L.228.239; 4.L.228.154; 4.L.228.157;
4.L.228.166; 4.L.228.169; 4.L.228.172; 4.L.228.175; 4.L.228.240;
4.L.228.244; 4.L.229.228; 4.L.229.229; 4.L.229.230; 4.L.229.231;
4.L.229.236; 4.L.229.237; 4.L.229.238; 4.L.229.239; 4.L.229.154;
4.L.229.240; 4.L.229.244; 4.L.229.166; 4.L.229.169; 4.L.229.172; 4.L.229.175;
4.L.230.228; 4.L.230.229; 4.L.230.230;
4.L.230.231; 4.L.230.236; 4.L.230.237; 4.L.230.238; 4.L.230.239;
4.L.230.154; 4.L.230.157; 4.L.230.166; 4.L.230.169; 4.L.230.172;
4.L.230.175; 4.L.230.240; 4.L.230.244; 4.L.231.228; 4.L.231.229;
4.L.231.230; 4.L.231.231; 4.L.231.236; 4.L.231.237; 4.L.231.238;
4.L.231.239; 4.L.231.154; 4.L.231.157; 4.L.231.166; 4.L.231.169;
4.L.231.172; 4.L.231.175; 4.L.231.240; 4.L.231.244; 4.L.236.228;
4.L.236.229; 4.L.236.230; 4.L.236.231; 4.L.236.236; 4.L.236.237;
4.L.236.238; 4.L.236.239; 4.L.236.154; 4.L.236.157; 4.L.236.166;
4.L.236.169; 4.L.236.172; 4.L.236.175; 4.L.236.240; 4.L.236.244;
4.L.237.228; 4.L.237.229; 4.L.237.230; 4.L.237.231; 4.L.237.236;
4.L.237.237; 4.L.237.238; 4.L.237.239; 4.L.237.154; 4.L.237.157;
4.L.237.166; 4.L.237.169; 4.L.237.172; 4.L.237.175; 4.L.237.240;
4.L.237.244; 4.L.238.228; 4.L.238.229; 4.L.238.230; 4.L.238.231;
4.L.238.236; 4.L.238.237; 4.L.238.238; 4.L.238.239; 4.L.238.154;
4.L.238.157; 4.L.238.166; 4.L.238.169; 4.L.238.172; 4.L.238.175;
4.L.238.240; 4.L.238.244; 4.L.239.228; 4.L.239.229; 4.L.239.230;
4.L.239.231; 4.L.239.236; 4.L.239.237; 4.L.239.238; 4.L.239.239;
4.L.239.154; 4.L.239.157; 4.L.239.166; 4.L.239.169; 4.L.239.172;
4.L.239.175; 4.L.239.240; 4.L.239.244; 4.L.154.228; 4.L.154.229;
4.L.154.230; 4.L.154.231; 4.L.154.236; 4.L.154.237; 4.L.154.238;
4.L.154.239; 4.L.154.154; 4.L.154.157; 4.L.154.166; 4.L.154.169;
4.L.154.172; 4.L.154.175; 4.L.154.240; 4.L.154.244; 4.L.157.228;
4.L.157.229; 4.L.157.230; 4.L.157.231; 4.L.157.236; 4.L.157.237;
4.L.157.238; 4.L.157.239; 4.L.157.154; 4.L.157.157; 4.L.157.166;
4.L.157.169; 4.L.157.172; 4.L.157.175; 4.L.157.240; 4.L.157.244;
4.L.166.228; 4.L.166.229; 4.L.166.230; 4.L.166.231; 4.L.166.236;
4.L.166.237; 4.L.166.238; 4.L.166.239; 4.L.166.154; 4.L.166.157;
4.L.166.166; 4.L.166.169; 4.L.166.172; 4.L.166.175; 4.L.166.240;
4.L.166.244; 4.L.169.228; 4.L.169.229; 4.L.169.230; 4.L.169.231;
4.L.169.236; 4.L.169.237; 4.L.169.238; 4.L.169.239; 4.L.169.154;
4.L.169.157; 4.L.169.166; 4.L.169.169; 4.L.169.172; 4.L.169.175;
4.L.169.240; 4.L.169.244; 4.L.172.228; 4.L.172.229; 4.L.172.230;
4.L.172.231; 4.L.172.236; 4.L.172.237; 4.L.172.238; 4.L.172.239;
4.L.172.154; 4.L.172.157; 4.L.172.166; 4.L.172.169; 4.L.172.172;
4.L.172.175; 4.L.172.240; 4.L.172.244; 4.L.175.228; 4.L.175.229;
4.L.175.230; 4.L.175.231; 4.L.175.236; 4.L.175.237; 4.L.175.238;
4.L.175.239; 4.L.175.154; 4.L.175.157; 4.L.175.166; 4.L.175.169;
4.L.175.172; 4.L.175.175; 4.L.175.240; 4.L.175.244; 4.L.240.228;
4.L.240.229; 4.L.240.230; 4.L.240.231; 4.L.240.236; 4.L.240.237;
4.L.240.238; 4.L.240.239; 4.L.240.154; 4.L.240.157; 4.L.240.166;
4.L.240.169; 4.L.240.172; 4.L.240.175; 4.L.240.240; 4.L.240.244;
4.L.244.228; 4.L.244.229; 4.L.244.230; 4.L.244.231; 4.L.244.236;
4.L.244.237; 4.L.244.238; 4.L.244.239; 4.L.244.154; 4.L.244.157;
4.L.244.166; 4.L.244.169; 4.L.244.172; 4.L.244.175; 4.L.244.240;
4.L.244.244;

Prodrugs of 4.O

4.O.228.228; 4.O.228.229; 4.O.228.230; 4.O.228.231; 4.O.228.236;
4.O.228.237; 4.O.228.238; 4.O.228.239; 4.O.228.154; 4.O.228.157;
4.O.228.166; 4.O.228.169; 4.O.228.172; 4.O.228.175; 4.O.228.240;
4.O.228.244; 4.O.229.228; 4.O.229.229; 4.O.229.230; 4.O.229.231;
4.O.229.236; 4.O.229.237; 4.O.229.238; 4.O.229.239; 4.O.229.154;
4.O.229.157; 4.O.229.166; 4.O.229.169; 4.O.229.172; 4.O.229.175;
4.O.229.240; 4.O.229.244; 4.O.230.228; 4.O.230.229; 4.O.230.230;
4.O.230.231; 4.O.230.236; 4.O.230.237; 4.O.230.238; 4.O.230.239;
4.O.230.154; 4.O.230.157; 4.O.230.166; 4.O.230.169; 4.O.230.172;
4.O.230.175; 4.O.230.240; 4.O.230.244; 4.O.231.228; 4.O.231.229;
4.O.231.230; 4.O.231.231; 4.O.231.236; 4.O.231.237; 4.O.231.238;

TABLE 7-continued

4.O.231.239; 4.O.231.154; 4.O.231.157; 4.O.231.166; 4.O.231.169;
4.O.231.172; 4.O.231.175; 4.O.231.240; 4.O.231.244; 4.O.236.228;
4.O.236.229; 4.O.236.230; 4.O.236.231; 4.O.236.236; 4.O.236.237;
4.O.236.238; 4.O.236.239; 4.O.236.154; 4.O.236.157; 4.O.236.166;
4.O.236.169; 4.O.236.172; 4.O.236.175; 4.O.236.240; 4.O.236.244;
4.O.237.228; 4.O.237.229; 4.O.237.230; 4.O.237.231; 4.O.237.236;
4.O.237.237; 4.O.237.238; 4.O.237.239; 4.O.237.154; 4.O.237.157;
4.O.237.166; 4.O.237.169; 4.O.237.172; 4.O.237.175; 4.O.237.240;
4.O.237.244; 4.O.238.228; 4.O.238.229; 4.O.238.230; 4.O.238.231;
4.O.238.236; 4.O.238.237; 4.O.238.238; 4.O.238.239; 4.O.238.154;
4.O.238.157; 4.O.238.166; 4.O.238.169; 4.O.238.172; 4.O.238.175;
4.O.238.240; 4.O.238.244; 4.O.239.228; 4.O.239.229; 4.O.239.230;
4.O.239.231; 4.O.239.236; 4.O.239.237; 4.O.239.238; 4.O.239.239;
4.O.239.154; 4.O.239.157; 4.O.239.166; 4.O.239.169; 4.O.239.172;
4.O.239.175; 4.O.239.240; 4.O.239.244; 4.O.154.228; 4.O.154.229;
4.O.154.230; 4.O.154.231; 4.O.154.236; 4.O.154.237; 4.O.154.238;
4.O.154.239; 4.O.154.154; 4.O.154.157; 4.O.154.166; 4.O.154.169;
4.O.154.172; 4.O.154.175; 4.O.154.240; 4.O.154.244; 4.O.157.228;
4.O.157.229; 4.O.157.230; 4.O.157.231; 4.O.157.236; 4.O.157.237;
4.O.157.238; 4.O.157.239; 4.O.157.154; 4.O.157.157; 4.O.157.166;
4.O.157.169; 4.O.157.172; 4.O.157.175; 4.O.157.240; 4.O.157.244;
4.O.166.228; 4.O.166.229; 4.O.166.230; 4.O.166.231; 4.O.166.236;
4.O.166.237; 4.O.166.238; 4.O.166.239; 4.O.166.154; 4.O.166.157;
4.O.166.166; 4.O.166.169; 4.O.166.172; 4.O.166.175; 4.O.166.240;
4.O.166.244; 4.O.169.228; 4.O.169.229; 4.O.169.230; 4.O.169.231;
4.O.169.236; 4.O.169.237; 4.O.169.238; 4.O.169.239; 4.O.169.154;
4.O.169.157; 4.O.169.166; 4.O.169.169; 4.O.169.172; 4.O.169.175;
4.O.169.240; 4.O.169.244; 4.O.172.228; 4.O.172.229; 4.O.172.230;
4.O.172.231; 4.O.172.236; 4.O.172.237; 4.O.172.238; 4.O.172.239;
4.O.172.154; 4.O.172.157; 4.O.172.166; 4.O.172.169; 4.O.172.172;
4.O.172.175; 4.O.172.240; 4.O.172.244; 4.O.175.228; 4.O.175.229;
4.O.175.230; 4.O.175.231; 4.O.175.236; 4.O.175.237; 4.O.175.238;
4.O.175.239; 4.O.175.154; 4.O.175.157; 4.O.175.166; 4.O.175.169;
4.O.175.172; 4.O.175.175; 4.O.175.240; 4.O.175.244; 4.O.240.228;
4.O.240.229; 4.O.240.230; 4.O.240.231; 4.O.240.236; 4.O.240.237;
4.O.240.238; 4.O.240.239; 4.O.240.154; 4.O.240.157; 4.O.240.166;
4.O.240.169; 4.O.240.172; 4.O.240.175; 4.O.240.240; 4.O.240.244;
4.O.244.228; 4.O.244.229; 4.O.244.230; 4.O.244.231; 4.O.244.236;
4.O.244.237; 4.O.244.238; 4.O.244.239; 4.O.244.154; 4.O.244.157;
4.O.244.166; 4.O.244.169; 4.O.244.172; 4.O.244.175; 4.O.244.240;
4.O.244.244;

Prodrugs of 4.P

4.P.228.228; 4.P.228.229; 4.P.228.230; 4.P.228.231; 4.P.228.236;
4.P.228.237; 4.P.228.238; 4.P.228.239; 4.P.228.154; 4.P.228.157;
4.P.228.166; 4.P.228.169; 4.P.228.172; 4.P.228.175; 4.P.228.240;
4.P.228.244; 4.P.229.228; 4.P.229.229; 4.P.229.230; 4.P.229.231;
4.P.229.236; 4.P.229.237; 4.P.229.238; 4.P.229.239; 4.P.229.154;
4.P.229.157; 4.P.229.166; 4.P.229.169; 4.P.229.172; 4.P.229.175;
4.P.229.240; 4.P.229.244; 4.P.230.228; 4.P.230.229; 4.P.230.230;
4.P.230.231; 4.P.230.236; 4.P.230.237; 4.P.230.238; 4.P.230.239;
4.P.230.154; 4.P.230.157; 4.P.230.166; 4.P.230.169; 4.P.230.172;
4.P.230.175; 4.P.230.240; 4.P.230.244; 4.P.231.228; 4.P.231.229;
4.P.231.230; 4.P.231.231; 4.P.231.236; 4.P.231.237; 4.P.231.238;
4.P.231.239; 4.P.231.154; 4.P.231.157; 4.P.231.166; 4.P.231.169;
4.P.231.172; 4.P.231.175; 4.P.231.240; 4.P.231.244; 4.P.236.228;
4.P.236.229; 4.P.236.230; 4.P.236.231; 4.P.236.236; 4.P.236.237;
4.P.236.238; 4.P.236.239; 4.P.236.154; 4.P.236.157; 4.P.236.166;
4.P.236.169; 4.P.236.172; 4.P.236.175; 4.P.236.240; 4.P.236.244;
4.P.237.228; 4.P.237.229; 4.P.237.230; 4.P.237.231; 4.P.237.236;
4.P.237.237; 4.P.237.238; 4.P.237.239; 4.P.237.154; 4.P.237.157;
4.P.237.166; 4.P.237.169; 4.P.237.172; 4.P.237.175; 4.P.237.240;
4.P.237.244; 4.P.238.228; 4.P.238.229; 4.P.238.230; 4.P.238.231;
4.P.238.236; 4.P.238.237; 4.P.238.238; 4.P.238.239; 4.P.238.154;
4.P.238.157; 4.P.238.166; 4.P.238.169; 4.P.238.172; 4.P.238.175;
4.P.238.240; 4.P.238.244; 4.P.239.228; 4.P.239.229; 4.P.239.230;
4.P.239.231; 4.P.239.236; 4.P.239.237; 4.P.239.238; 4.P.239.239;
4.P.239.154; 4.P.239.157; 4.P.239.166; 4.P.239.169; 4.P.239.172;
4.P.239.175; 4.P.239.240; 4.P.239.244; 4.P.154.228; 4.P.154.229;
4.P.154.230; 4.P.154.231; 4.P.154.236; 4.P.154.237; 4.P.154.238;
4.P.154.239; 4.P.154.154; 4.P.154.157; 4.P.154.166; 4.P.154.169;
4.P.154.172; 4.P.154.175; 4.P.154.240; 4.P.154.244; 4.P.157.228;
4.P.157.229; 4.P.157.230; 4.P.157.231; 4.P.157.236; 4.P.157.237;
4.P.157.238; 4.P.157.239; 4.P.157.154; 4.P.157.157; 4.P.157.166;
4.P.157.169; 4.P.157.172; 4.P.157.175; 4.P.157.240; 4.P.157.244;
4.P.166.228; 4.P.166.229; 4.P.166.230; 4.P.166.231; 4.P.166.236;
4.P.166.237; 4.P.166.238; 4.P.166.239; 4.P.166.154; 4.P.166.157;
4.P.166.166; 4.P.166.169; 4.P.166.172; 4.P.166.175; 4.P.166.240;
4.P.166.244; 4.P.169.228; 4.P.169.229; 4.P.169.230; 4.P.169.231;
4.P.169.236; 4.P.169.237; 4.P.169.238; 4.P.169.239; 4.P.169.154;
4.P.169.157; 4.P.169.166; 4.P.169.169; 4.P.169.172; 4.P.169.175;
4.P.169.240; 4.P.169.244; 4.P.172.228; 4.P.172.229; 4.P.172.230;
4.P.172.231; 4.P.172.236; 4.P.172.237; 4.P.172.238; 4.P.172.239;
4.P.172.154; 4.P.172.157; 4.P.172.166; 4.P.172.169; 4.P.172.172;
4.P.172.175; 4.P.172.240; 4.P.172.244; 4.P.175.228; 4.P.175.229;
4.P.175.230; 4.P.175.231; 4.P.175.236; 4.P.175.237; 4.P.175.238;
4.P.175.239; 4.P.175.154; 4.P.175.157; 4.P.175.166; 4.P.175.169;
4.P.175.172; 4.P.175.175; 4.P.175.240; 4.P.175.244; 4.P.240.228;
4.P.240.229; 4.P.240.230; 4.P.240.231; 4.P.240.236; 4.P.240.237;
4.P.240.238; 4.P.240.239; 4.P.240.154; 4.P.240.157; 4.P.240.166;
4.P.240.169; 4.P.240.172; 4.P.240.175; 4.P.240.240; 4.P.240.244;
4.P.244.228; 4.P.244.229; 4.P.244.230; 4.P.244.231; 4.P.244.236;
4.P.244.237; 4.P.244.238; 4.P.244.239; 4.P.244.154; 4.P.244.157;
4.P.244.166; 4.P.244.169; 4.P.244.172; 4.P.244.175; 4.P.244.240;
4.P.244.244;

Prodrugs of 4.U

4.U.228.228; 4.U.228.229; 4.U.228.230; 4.U.228.231; 4.U.228.236;
4.U.228.237; 4.U.228.238; 4.U.228.239; 4.U.228.154; 4.U.228.157;
4.U.228.166; 4.U.228.169; 4.U.228.172; 4.U.228.175; 4.U.228.240;
4.U.228.244; 4.U.229.228; 4.U.229.229; 4.U.229.230; 4.U.229.231;
4.U.229.236; 4.U.229.237; 4.U.229.238; 4.U.229.239; 4.U.229.154;
4.U.229.157; 4.U.229.166; 4.U.229.169; 4.U.229.172; 4.U.229.175;
4.U.229.240; 4.U.229.244; 4.U.230.228; 4.U.230.229; 4.U.230.230;
4.U.230.231; 4.U.230.236; 4.U.230.237; 4.U.230.238; 4.U.230.239;
4.U.230.154; 4.U.230.157; 4.U.230.166; 4.U.230.169; 4.U.230.172;
4.U.230.175; 4.U.230.240; 4.U.230.244; 4.U.231.228; 4.U.231.229;
4.U.231.230; 4.U.231.231; 4.U.231.236; 4.U.231.237; 4.U.231.238;
4.U.231.239; 4.U.231.154; 4.U.231.157; 4.U.231.166; 4.U.231.169;
4.U.231.172; 4.U.231.175; 4.U.231.240; 4.U.231.244; 4.U.236.228;
4.U.236.229; 4.U.236.230; 4.U.236.231; 4.U.236.236; 4.U.236.237;
4.U.236.238; 4.U.236.239; 4.U.236.154; 4.U.236.157; 4.U.236.166;
4.U.236.169; 4.U.236.172; 4.U.236.175; 4.U.236.240; 4.U.236.244;
4.U.237.228; 4.U.237.229; 4.U.237.230; 4.U.237.231; 4.U.237.236;
4.U.237.237; 4.U.237.238; 4.U.237.239; 4.U.237.154; 4.U.237.157;
4.U.237.166; 4.U.237.169; 4.U.237.172; 4.U.237.175; 4.U.237.240;
4.U.237.244; 4.U.238.228; 4.U.238.229; 4.U.238.230; 4.U.238.231;
4.U.238.236; 4.U.238.237; 4.U.238.238; 4.U.238.239; 4.U.238.154;
4.U.238.157; 4.U.238.166; 4.U.238.169; 4.U.238.172; 4.U.238.175;
4.U.238.240; 4.U.238.244; 4.U.239.228; 4.U.239.229; 4.U.239.230;
4.U.239.231; 4.U.239.236; 4.U.239.237; 4.U.239.238; 4.U.239.239;
4.U.239.154; 4.U.239.157; 4.U.239.166; 4.U.239.169; 4.U.239.172;
4.U.239.175; 4.U.239.240; 4.U.239.244; 4.U.154.228; 4.U.154.229;
4.U.154.230; 4.U.154.231; 4.U.154.236; 4.U.154.237; 4.U.154.238;
4.U.154.239; 4.U.154.154; 4.U.154.157; 4.U.154.166; 4.U.154.169;
4.U.154.172; 4.U.154.175; 4.U.154.240; 4.U.154.244; 4.U.157.228;
4.U.157.229; 4.U.157.230; 4.U.157.231; 4.U.157.236; 4.U.157.237;
4.U.157.238; 4.U.157.239; 4.U.157.154; 4.U.157.157; 4.U.157.166;
4.U.157.169; 4.U.157.172; 4.U.157.175; 4.U.157.240; 4.U.157.244;
4.U.166.228; 4.U.166.229; 4.U.166.230; 4.U.166.231; 4.U.166.236;
4.U.166.237; 4.U.166.238; 4.U.166.239; 4.U.166.154; 4.U.166.157;
4.U.166.166; 4.U.166.169; 4.U.166.172; 4.U.166.175; 4.U.166.240;
4.U.166.244; 4.U.169.228; 4.U.169.229; 4.U.169.230; 4.U.169.231;
4.U.169.236; 4.U.169.237; 4.U.169.238; 4.U.169.239; 4.U.169.154;
4.U.169.157; 4.U.169.166; 4.U.169.169; 4.U.169.172; 4.U.169.175;
4.U.169.240; 4.U.169.244; 4.U.172.228; 4.U.172.229; 4.U.172.230;
4.U.172.231; 4.U.172.236; 4.U.172.237; 4.U.172.238; 4.U.172.239;
4.U.172.154; 4.U.172.157; 4.U.172.166; 4.U.172.169; 4.U.172.172;
4.U.172.175; 4.U.172.240; 4.U.172.244; 4.U.175.228; 4.U.175.229;
4.U.175.230; 4.U.175.231; 4.U.175.236; 4.U.175.237; 4.U.175.238;
4.U.175.239; 4.U.175.154; 4.U.175.157; 4.U.175.166; 4.U.175.169;
4.U.175.172; 4.U.175.175; 4.U.175.240; 4.U.175.244; 4.U.240.228;
4.U.240.229; 4.U.240.230; 4.U.240.231; 4.U.240.236; 4.U.240.237;
4.U.240.238; 4.U.240.239; 4.U.240.154; 4.U.240.157; 4.U.240.166;
4.U.240.169; 4.U.240.172; 4.U.240.175; 4.U.240.240; 4.U.240.244;
4.U.244.228; 4.U.244.229; 4.U.244.230; 4.U.244.231; 4.U.244.236;
4.U.244.237; 4.U.244.238; 4.U.244.239; 4.U.244.154; 4.U.244.157;
4.U.244.166; 4.U.244.169; 4.U.244.172; 4.U.244.175; 4.U.244.240;
4.U.244.244;

Prodrugs of 4.W

4.W.228.228; 4.W.228.229; 4.W.228.230; 4.W.228.231; 4.W.228.236;
4.W.228.237; 4.W.228.238; 4.W.228.239; 4.W.228.154; 4.W.228.157;
4.W.228.166; 4.W.228.169; 4.W.228.172; 4.W.228.175; 4.W.228.240;
4.W.228.244; 4.W.229.228; 4.W.229.229; 4.W.229.230; 4.W.229.231;
4.W.229.236; 4.W.229.237; 4.W.229.238; 4.W.229.239; 4.W.229.154;
4.W.229.157; 4.W.229.166; 4.W.229.169; 4.W.229.172; 4.W.229.175;
4.W.229.240; 4.W.229.244; 4.W.230.228; 4.W.230.229; 4.W.230.230;

TABLE 7-continued

4.W.230.231; 4.W.230.236; 4.W.230.237; 4.W.230.238; 4.W.230.239;
4.W.230.154; 4.W.230.157; 4.W.230.166; 4.W.230.169; 4.W.230.172;
4.W.230.175; 4.W.230.240; 4.W.230.244; 4.W.231.228; 4.W.231.229;
4.W.231.230; 4.W.231.231; 4.W.231.236; 4.W.231.237; 4.W.231.238;
4.W.231.239; 4.W.231.154; 4.W.231.157; 4.W.231.166; 4.W.231.169;
4.W.231.172; 4.W.231.175; 4.W.231.240; 4.W.231.244; 4.W.236.228;
4.W.236.229; 4.W.236.230; 4.W.236.231; 4.W.236.236; 4.W.236.237;
4.W.236.238; 4.W.236.239; 4.W.236.154; 4.W.236.157; 4.W.236.166;
4.W.236.169; 4.W.236.172; 4.W.236.175; 4.W.236.240; 4.W.236.244;
4.W.237.228; 4.W.237.229; 4.W.237.230; 4.W.237.231; 4.W.237.236;
4.W.237.237; 4.W.237.238; 4.W.237.239; 4.W.237.154; 4.W.237.157;
4.W.237.166; 4.W.237.169; 4.W.237.172; 4.W.237.175; 4.W.237.240;
4.W.237.244; 4.W.238.228; 4.W.238.229; 4.W.238.230; 4.W.238.231;
4.W.238.236; 4.W.238.237; 4.W.238.238; 4.W.238.239; 4.W.238.154;
4.W.238.157; 4.W.238.166; 4.W.238.169; 4.W.238.172; 4.W.238.175;
4.W.238.240; 4.W.238.244; 4.W.239.228; 4.W.239.229; 4.W.239.230;
4.W.239.231; 4.W.239.236; 4.W.239.237; 4.W.239.238; 4.W.239.239;
4.W.239.154; 4.W.239.157; 4.W.239.166; 4.W.239.169; 4.W.239.172;
4.W.239.175; 4.W.239.240; 4.W.239.244; 4.W.154.228; 4.W.154.229;
4.W.154.230; 4.W.154.231; 4.W.154.236; 4.W.154.237; 4.W.154.238;
4.W.154.239; 4.W.154.154; 4.W.154.157; 4.W.154.166; 4.W.154.169;
4.W.154.172; 4.W.154.175; 4.W.154.240; 4.W.154.244; 4.W.157.228;
4.W.157.229; 4.W.157.230; 4.W.157.231; 4.W.157.236; 4.W.157.237;
4.W.157.238; 4.W.157.239; 4.W.157.154; 4.W.157.157; 4.W.157.166;
4.W.157.169; 4.W.157.172; 4.W.157.175; 4.W.157.240; 4.W.157.244;
4.W.166.228; 4.W.166.229; 4.W.166.230; 4.W.166.231; 4.W.166.236;
4.W.166.237; 4.W.166.238; 4.W.166.239; 4.W.166.154; 4.W.166.157;
4.W.166.166; 4.W.166.169; 4.W.166.172; 4.W.166.175; 4.W.166.240;
4.W.166.244; 4.W.169.228; 4.W.169.229; 4.W.169.230; 4.W.169.231;
4.W.169.236; 4.W.169.237; 4.W.169.238; 4.W.169.239; 4.W.169.154;
4.W.169.157; 4.W.169.166; 4.W.169.169; 4.W.169.172; 4.W.169.175;
4.W.169.240; 4.W.169.244; 4.W.172.228; 4.W.172.229; 4.W.172.230;
4.W.172.231; 4.W.172.236; 4.W.172.237; 4.W.172.238; 4.W.172.239;
4.W.172.154; 4.W.172.157; 4.W.172.166; 4.W.172.169; 4.W.172.172;
4.W.172.175; 4.W.172.240; 4.W.172.244; 4.W.175.228; 4.W.175.229;
4.W.175.230; 4.W.175.231; 4.W.175.236; 4.W.175.237; 4.W.175.238;
4.W.175.239; 4.W.175.154; 4.W.175.157; 4.W.175.166; 4.W.175.169;
4.W.175.172; 4.W.175.175; 4.W.175.240; 4.W.175.244; 4.W.240.228;
4.W.240.229; 4.W.240.230; 4.W.240.231; 4.W.240.236; 4.W.240.237;
4.W.240.238; 4.W.240.239; 4.W.240.154; 4.W.240.157; 4.W.240.166;
4.W.240.169; 4.W.240.172; 4.W.240.175; 4.W.240.240; 4.W.240.244;
4.W.244.228; 4.W.244.229; 4.W.244.230; 4.W.244.231; 4.W.244.236;
4.W.244.237; 4.W.244.238; 4.W.244.239; 4.W.244.154; 4.W.244.157;
4.W.244.166; 4.W.244.169; 4.W.244.172; 4.W.244.175; 4.W.244.240;
4.W.244.244;

Prodrugs of 4.Y

4.Y.228.228; 4.Y.228.229; 4.Y.228.230; 4.Y.228.231; 4.Y.228.236;
4.Y.228.237; 4.Y.228.238; 4.Y.228.239; 4.Y.228.154; 4.Y.228.157;
4.Y.228.166; 4.Y.228.169; 4.Y.228.172; 4.Y.228.175; 4.Y.228.240;
4.Y.228.244; 4.Y.229.228; 4.Y.229.229; 4.Y.229.230; 4.Y.229.231;
4.Y.229.236; 4.Y.229.237; 4.Y.229.238; 4.Y.229.239; 4.Y.229.154;
4.Y.229.157; 4.Y.229.166; 4.Y.229.169; 4.Y.229.172; 4.Y.229.175;
4.Y.229.240; 4.Y.229.244; 4.Y.230.228; 4.Y.230.229; 4.Y.230.230;
4.Y.230.231; 4.Y.230.236; 4.Y.230.237; 4.Y.230.238; 4.Y.230.239;
4.Y.230.154; 4.Y.230.157; 4.Y.230.166; 4.Y.230.169; 4.Y.230.172;
4.Y.230.175; 4.Y.230.240; 4.Y.230.244; 4.Y.231.228; 4.Y.231.229;
4.Y.231.230; 4.Y.231.231; 4.Y.231.236; 4.Y.231.237; 4.Y.231.238;
4.Y.231.239; 4.Y.231.154; 4.Y.231.157; 4.Y.231.166; 4.Y.231.169;
4.Y.231.172; 4.Y.231.175; 4.Y.231.240; 4.Y.231.244; 4.Y.236.228;
4.Y.236.229; 4.Y.236.230; 4.Y.236.231; 4.Y.236.236; 4.Y.236.237;
4.Y.236.238; 4.Y.236.239; 4.Y.236.154; 4.Y.236.157; 4.Y.236.166;
4.Y.236.169; 4.Y.236.172; 4.Y.236.175; 4.Y.236.240; 4.Y.236.244;
4.Y.237.228; 4.Y.237.229; 4.Y.237.230; 4.Y.237.231; 4.Y.237.236;
4.Y.237.237; 4.Y.237.238; 4.Y.237.239; 4.Y.237.154; 4.Y.237.157;
4.Y.237.166; 4.Y.237.169; 4.Y.237.172; 4.Y.237.175; 4.Y.237.240;
4.Y.237.244; 4.Y.238.228; 4.Y.238.229; 4.Y.238.230; 4.Y.238.231;
4.Y.238.236; 4.Y.238.237; 4.Y.238.238; 4.Y.238.239; 4.Y.238.154;
4.Y.238.157; 4.Y.238.166; 4.Y.238.169; 4.Y.238.172; 4.Y.238.175;
4.Y.238.240; 4.Y.238.244; 4.Y.239.228; 4.Y.239.229; 4.Y.239.230;
4.Y.239.231; 4.Y.239.236; 4.Y.239.237; 4.Y.239.238; 4.Y.239.239;
4.Y.239.154; 4.Y.239.157; 4.Y.239.166; 4.Y.239.169; 4.Y.239.172;
4.Y.239.175; 4.Y.239.240; 4.Y.239.244; 4.Y.154.228; 4.Y.154.229;
4.Y.154.230; 4.Y.154.231; 4.Y.154.236; 4.Y.154.237; 4.Y.154.238;
4.Y.154.239; 4.Y.154.154; 4.Y.154.157; 4.Y.154.166; 4.Y.154.169;
4.Y.154.172; 4.Y.154.175; 4.Y.154.240; 4.Y.154.244; 4.Y.157.228;
4.Y.157.229; 4.Y.157.230; 4.Y.157.231; 4.Y.157.236; 4.Y.157.237;
4.Y.157.238; 4.Y.157.239; 4.Y.157.154; 4.Y.157.157; 4.Y.157.166;
4.Y.157.169; 4.Y.157.172; 4.Y.157.175; 4.Y.157.240; 4.Y.157.244;
4.Y.166.228; 4.Y.166.229; 4.Y.166.230; 4.Y.166.231; 4.Y.166.236;
4.Y.166.237; 4.Y.166.238; 4.Y.166.239; 4.Y.166.154; 4.Y.166.157;
4.Y.166.166; 4.Y.166.169; 4.Y.166.172; 4.Y.166.175; 4.Y.166.240;
4.Y.166.244; 4.Y.169.228; 4.Y.169.229; 4.Y.169.230; 4.Y.169.231;
4.Y.169.236; 4.Y.169.237; 4.Y.169.238; 4.Y.169.239; 4.Y.169.154;
4.Y.169.157; 4.Y.169.166; 4.Y.169.169; 4.Y.169.172; 4.Y.169.175;
4.Y.169.240; 4.Y.169.244; 4.Y.172.228; 4.Y.172.229; 4.Y.172.230;
4.Y.172.231; 4.Y.172.236; 4.Y.172.237; 4.Y.172.238; 4.Y.172.239;
4.Y.172.154; 4.Y.172.157; 4.Y.172.166; 4.Y.172.169; 4.Y.172.172;
4.Y.172.175; 4.Y.172.240; 4.Y.172.244; 4.Y.175.228; 4.Y.175.229;
4.Y.175.230; 4.Y.175.231; 4.Y.175.236; 4.Y.175.237; 4.Y.175.238;
4.Y.175.239; 4.Y.175.154; 4.Y.175.157; 4.Y.175.166; 4.Y.175.169;
4.Y.175.172; 4.Y.175.175; 4.Y.175.240; 4.Y.175.244; 4.Y.240.228;
4.Y.240.229; 4.Y.240.230; 4.Y.240.231; 4.Y.240.236; 4.Y.240.237;
4.Y.240.238; 4.Y.240.239; 4.Y.240.154; 4.Y.240.157; 4.Y.240.166;
4.Y.240.169; 4.Y.240.172; 4.Y.240.175; 4.Y.240.240; 4.Y.240.244;
4.Y.244.228; 4.Y.244.229; 4.Y.244.230; 4.Y.244.231; 4.Y.244.236;
4.Y.244.237; 4.Y.244.238; 4.Y.244.239; 4.Y.244.154; 4.Y.244.157;
4.Y.244.166; 4.Y.244.169; 4.Y.244.172; 4.Y.244.175; 4.Y.244.240;
4.Y.244.244;

Prodrugs of 5.B

5.B.228.228; 5.B.228.229; 5.B.228.230; 5.B.228.231; 5.B.228.236;
5.B.228.237; 5.B.228.238; 5.B.228.239; 5.B.228.154; 5.B.228.157;
5.B.228.166; 5.B.228.169; 5.B.228.172; 5.B.228.175; 5.B.228.240;
5.B.228.244; 5.B.229.228; 5.B.229.229; 5.B.229.230; 5.B.229.231;
5.B.229.236; 5.B.229.237; 5.B.229.238; 5.B.229.239; 5.B.229.154;
5.B.229.157; 5.B.229.166; 5.B.229.169; 5.B.229.172; 5.B.229.175;
5.B.229.240; 5.B.229.244; 5.B.230.228; 5.B.230.229; 5.B.230.230;
5.B.230.231; 5.B.230.236; 5.B.230.237; 5.B.230.238; 5.B.230.239;
5.B.230.154; 5.B.230.157; 5.B.230.166; 5.B.230.169; 5.B.230.172;
5.B.230.175; 5.B.230.240; 5.B.230.244; 5.B.231.228; 5.B.231.229;
5.B.231.230; 5.B.231.231; 5.B.231.236; 5.B.231.237; 5.B.231.238;
5.B.231.239; 5.B.231.154; 5.B.231.157; 5.B.231.166; 5.B.231.169;
5.B.231.172; 5.B.231.175; 5.B.231.240; 5.B.231.244; 5.B.236.228;
5.B.236.229; 5.B.236.230; 5.B.236.231; 5.B.236.236; 5.B.236.237;
5.B.236.238; 5.B.236.239; 5.B.236.154; 5.B.236.157; 5.B.236.166;
5.B.236.169; 5.B.236.172; 5.B.236.175; 5.B.236.240; 5.B.236.244;
5.B.237.228; 5.B.237.229; 5.B.237.230; 5.B.237.231; 5.B.237.236;
5.B.237.237; 5.B.237.238; 5.B.237.239; 5.B.237.154; 5.B.237.157;
5.B.237.166; 5.B.237.169; 5.B.237.172; 5.B.237.175; 5.B.237.240;
5.B.237.244; 5.B.238.228; 5.B.238.229; 5.B.238.230; 5.B.238.231;
5.B.238.236; 5.B.238.237; 5.B.238.238; 5.B.238.239; 5.B.238.154;
5.B.238.157; 5.B.238.166; 5.B.238.169; 5.B.238.172; 5.B.238.175;
5.B.238.240; 5.B.238.244; 5.B.239.228; 5.B.239.229; 5.B.239.230;
5.B.239.231; 5.B.239.236; 5.B.239.237; 5.B.239.238; 5.B.239.239;
5.B.239.154; 5.B.239.157; 5.B.239.166; 5.B.239.169; 5.B.239.172;
5.B.239.175; 5.B.239.240; 5.B.239.244; 5.B.154.228; 5.B.154.229;
5.B.154.230; 5.B.154.231; 5.B.154.236; 5.B.154.237; 5.B.154.238;
5.B.154.239; 5.B.154.154; 5.B.154.157; 5.B.154.166; 5.B.154.169;
5.B.154.172; 5.B.154.175; 5.B.154.240; 5.B.154.244; 5.B.157.228;
5.B.157.229; 5.B.157.230; 5.B.157.231; 5.B.157.236; 5.B.157.237;
5.B.157.238; 5.B.157.239; 5.B.157.154; 5.B.157.157; 5.B.157.166;
5.B.157.169; 5.B.157.172; 5.B.157.175; 5.B.157.240; 5.B.157.244;
5.B.166.228; 5.B.166.229; 5.B.166.230; 5.B.166.231; 5.B.166.236;
5.B.166.237; 5.B.166.238; 5.B.166.239; 5.B.166.154; 5.B.166.157;
5.B.166.166; 5.B.166.169; 5.B.166.172; 5.B.166.175; 5.B.166.240;
5.B.166.244; 5.B.169.228; 5.B.169.229; 5.B.169.230; 5.B.169.231;
5.B.169.236; 5.B.169.237; 5.B.169.238; 5.B.169.239; 5.B.169.154;
5.B.169.157; 5.B.169.166; 5.B.169.169; 5.B.169.172; 5.B.169.175;
5.B.169.240; 5.B.169.244; 5.B.172.228; 5.B.172.229; 5.B.172.230;
5.B.172.231; 5.B.172.236; 5.B.172.237; 5.B.172.238; 5.B.172.239;
5.B.172.154; 5.B.172.157; 5.B.172.166; 5.B.172.169; 5.B.172.172;
5.B.172.175; 5.B.172.240; 5.B.172.244; 5.B.175.228; 5.B.175.229;
5.B.175.230; 5.B.175.231; 5.B.175.236; 5.B.175.237; 5.B.175.238;
5.B.175.239; 5.B.175.154; 5.B.175.157; 5.B.175.166; 5.B.175.169;
5.B.175.172; 5.B.175.175; 5.B.175.240; 5.B.175.244; 5.B.240.228;
5.B.240.229; 5.B.240.230; 5.B.240.231; 5.B.240.236; 5.B.240.237;
5.B.240.238; 5.B.240.239; 5.B.240.154; 5.B.240.157; 5.B.240.166;
5.B.240.169; 5.B.240.172; 5.B.240.175; 5.B.240.240; 5.B.240.244;
5.B.244.228; 5.B.244.229; 5.B.244.230; 5.B.244.231; 5.B.244.236;
5.B.244.237; 5.B.244.238; 5.B.244.239; 5.B.244.154; 5.B.244.157;
5.B.244.166; 5.B.244.169; 5.B.244.172; 5.B.244.175; 5.B.244.240;
5.B.244.244;

Prodrugs of 5.D

5.D.228.228; 5.D.228.229; 5.D.228.230; 5.D.228.231; 5.D.228.236;
5.D.228.237; 5.D.228.238; 5.D.228.239; 5.D.228.154; 5.D.228.157;
5.D.228.166; 5.D.228.169; 5.D.228.172; 5.D.228.175; 5.D.228.240;

TABLE 7-continued

5.D.228.244; 5.D.229.228; 5.D.229.229; 5.D.229.230; 5.D.229.231;
5.D.229.236; 5.D.229.237; 5.D.229.238; 5.D.229.239; 5.D.229.154;
5.D.229.157; 5.D.229.166; 5.D.229.169; 5.D.229.172; 5.D.229.175;
5.D.229.240; 5.D.229.244; 5.D.230.228; 5.D.230.229; 5.D.230.230;
5.D.230.231; 5.D.230.236; 5.D.230.237; 5.D.230.238; 5.D.230.239;
5.D.230.154; 5.D.230.157; 5.D.230.166; 5.D.230.169; 5.D.230.172;
5.D.230.175; 5.D.230.240; 5.D.230.244; 5.D.231.228; 5.D.231.229;
5.D.231.230; 5.D.231.231; 5.D.231.236; 5.D.231.237; 5.D.231.238;
5.D.231.239; 5.D.231.154; 5.D.231.157; 5.D.231.166; 5.D.231.169;
5.D.231.172; 5.D.231.175; 5.D.231.240; 5.D.231.244; 5.D.236.228;
5.D.236.229; 5.D.236.230; 5.D.236.231; 5.D.236.236; 5.D.236.237;
5.D.236.238; 5.D.236.239; 5.D.236.154; 5.D.236.157; 5.D.236.166;
5.D.236.169; 5.D.236.172; 5.D.236.175; 5.D.236.240; 5.D.236.244;
5.D.237.228; 5.D.237.229; 5.D.237.230; 5.D.237.231; 5.D.237.236;
5.D.237.237; 5.D.237.238; 5.D.237.239; 5.D.237.154; 5.D.237.157;
5.D.237.166; 5.D.237.169; 5.D.237.172; 5.D.237.175; 5.D.237.240;
5.D.237.244; 5.D.238.228; 5.D.238.229; 5.D.238.230; 5.D.238.231;
5.D.238.236; 5.D.238.237; 5.D.238.238; 5.D.238.239; 5.D.238.154;
5.D.238.157; 5.D.238.166; 5.D.238.169; 5.D.238.172; 5.D.238.175;
5.D.238.240; 5.D.238.244; 5.D.239.228; 5.D.239.229; 5.D.239.230;
5.D.239.231; 5.D.239.236; 5.D.239.237; 5.D.239.238; 5.D.239.239;
5.D.239.154; 5.D.239.157; 5.D.239.166; 5.D.239.169; 5.D.239.172;
5.D.239.175; 5.D.239.240; 5.D.239.244; 5.D.154.228; 5.D.154.229;
5.D.154.230; 5.D.154.231; 5.D.154.236; 5.D.154.237; 5.D.154.238;
5.D.154.239; 5.D.154.154; 5.D.154.157; 5.D.154.166; 5.D.154.169;
5.D.154.172; 5.D.154.175; 5.D.154.240; 5.D.154.244; 5.D.157.228;
5.D.157.229; 5.D.157.230; 5.D.157.231; 5.D.157.236; 5.D.157.237;
5.D.157.238; 5.D.157.239; 5.D.157.154; 5.D.157.157; 5.D.157.166;
5.D.157.169; 5.D.157.172; 5.D.157.175; 5.D.157.240; 5.D.157.244;
5.D.166.228; 5.D.166.229; 5.D.166.230; 5.D.166.231; 5.D.166.236;
5.D.166.237; 5.D.166.238; 5.D.166.239; 5.D.166.154; 5.D.166.157;
5.D.166.166; 5.D.166.169; 5.D.166.172; 5.D.166.175; 5.D.166.240;
5.D.166.244; 5.D.169.228; 5.D.169.229; 5.D.169.230; 5.D.169.231;
5.D.169.236; 5.D.169.237; 5.D.169.238; 5.D.169.239; 5.D.169.154;
5.D.169.157; 5.D.169.166; 5.D.169.169; 5.D.169.172; 5.D.169.175;
5.D.169.240; 5.D.169.244; 5.D.172.228; 5.D.172.229; 5.D.172.230;
5.D.172.231; 5.D.172.236; 5.D.172.237; 5.D.172.238; 5.D.172.239;
5.D.172.154; 5.D.172.157; 5.D.172.166; 5.D.172.169; 5.D.172.172;
5.D.172.175; 5.D.172.240; 5.D.172.244; 5.D.175.228; 5.D.175.229;
5.D.175.230; 5.D.175.231; 5.D.175.236; 5.D.175.237; 5.D.175.238;
5.D.175.239; 5.D.175.154; 5.D.175.157; 5.D.175.166; 5.D.175.169;
5.D.175.172; 5.D.175.175; 5.D.175.240; 5.D.175.244; 5.D.240.228;
5.D.240.229; 5.D.240.230; 5.D.240.231; 5.D.240.236; 5.D.240.237;
5.D.240.238; 5.D.240.239; 5.D.240.154; 5.D.240.157; 5.D.240.166;
5.D.240.169; 5.D.240.172; 5.D.240.175; 5.D.240.240; 5.D.240.244;
5.D.244.228; 5.D.244.229; 5.D.244.230; 5.D.244.231; 5.D.244.236;
5.D.244.237; 5.D.244.238; 5.D.244.239; 5.D.244.154; 5.D.244.157;
5.D.244.166; 5.D.244.169; 5.D.244.172; 5.D.244.175; 5.D.244.240;
5.D.244.244;
Prodrugs of 5.E 5.E.228.228; 5.E.228.229; 5.E.228.230; 5.E.228.231; 5.E.228.236;
5.E.228.237; 5.E.228.238; 5.E.228.239; 5.E.228.154; 5.E.228.157;
5.E.228.166; 5.E.228.169; 5.E.228.172; 5.E.228.175; 5.E.228.240;
5.E.228.244; 5.E.229.228; 5.E.229.229; 5.E.229.230; 5.E.229.231;
5.E.229.236; 5.E.229.237; 5.E.229.238; 5.E.229.239; 5.E.229.154;
5.E.229.157; 5.E.229.166; 5.E.229.169; 5.E.229.172; 5.E.229.175;
5.E.229.240; 5.E.229.244; 5.E.230.228; 5.E.230.229; 5.E.230.230;
5.E.230.231; 5.E.230.236; 5.E.230.237; 5.E.230.238; 5.E.230.239;
5.E.230.154; 5.E.230.157; 5.E.230.166; 5.E.230.169; 5.E.230.172;
5.E.230.175; 5.E.230.240; 5.E.230.244; 5.E.231.228; 5.E.231.229;
5.E.231.230; 5.E.231.231; 5.E.231.236; 5.E.231.237; 5.E.231.238;
5.E.231.239; 5.E.231.154; 5.E.231.157; 5.E.231.166; 5.E.231.169;
5.E.231.172; 5.E.231.175; 5.E.231.240; 5.E.231.244; 5.E.236.228;
5.E.236.229; 5.E.236.230; 5.E.236.231; 5.E.236.236; 5.E.236.237;
5.E.236.238; 5.E.236.239; 5.E.236.154; 5.E.236.157; 5.E.236.166;
5.E.236.169; 5.E.236.172; 5.E.236.175; 5.E.236.240; 5.E.236.244;
5.E.237.228; 5.E.237.229; 5.E.237.230; 5.E.237.231; 5.E.237.236;
5.E.237.237; 5.E.237.238; 5.E.237.239; 5.E.237.154; 5.E.237.157;
5.E.237.166; 5.E.237.169; 5.E.237.172; 5.E.237.175; 5.E.237.240;
5.E.237.244; 5.E.238.228; 5.E.238.229; 5.E.238.230; 5.E.238.231;
5.E.238.236; 5.E.238.237; 5.E.238.238; 5.E.238.239; 5.E.238.154;
5.E.238.157; 5.E.238.166; 5.E.238.169; 5.E.238.172; 5.E.238.175;
5.E.238.240; 5.E.238.244; 5.E.239.228; 5.E.239.229; 5.E.239.230;
5.E.239.231; 5.E.239.236; 5.E.239.237; 5.E.239.238; 5.E.239.239;
5.E.239.175; 5.E.239.240; 5.E.239.244; 5.E.154.228; 5.E.154.229;
5.E.154.230; 5.E.154.231; 5.E.154.236; 5.E.154.237; 5.E.154.238;
5.E.154.239; 5.E.154.154; 5.E.154.157; 5.E.154.166; 5.E.154.169;

TABLE 7-continued

5.E.154.172; 5.E.154.175; 5.E.154.240; 5.E.154.244; 5.E.157.228;
5.E.157.229; 5.E.157.230; 5.E.157.231; 5.E.157.236; 5.E.157.237;
5.E.157.238; 5.E.157.239; 5.E.157.154; 5.E.157.157; 5.E.157.166;
5.E.157.169; 5.E.157.172; 5.E.157.175; 5.E.157.240; 5.E.157.244;
5.E.166.228; 5.E.166.229; 5.E.166.230; 5.E.166.231; 5.E.166.236;
5.E.166.237; 5.E.166.238; 5.E.166.239; 5.E.166.154; 5.E.166.157;
5.E.166.166; 5.E.166.169; 5.E.166.172; 5.E.166.175; 5.E.166.240;
5.E.166.244; 5.E.169.228; 5.E.169.229; 5.E.169.230; 5.E.169.231;
5.E.169.236; 5.E.169.237; 5.E.169.238; 5.E.169.239; 5.E.169.154;
5.E.169.157; 5.E.169.166; 5.E.169.169; 5.E.169.172; 5.E.169.175;
5.E.169.240; 5.E.169.244; 5.E.172.228; 5.E.172.229; 5.E.172.230;
5.E.172.231; 5.E.172.236; 5.E.172.237; 5.E.172.238; 5.E.172.239;
5.E.172.154; 5.E.172.157; 5.E.172.166; 5.E.172.169; 5.E.172.172;
5.E.172.175; 5.E.172.240; 5.E.172.244; 5.E.175.228; 5.E.175.229;
5.E.175.230; 5.E.175.231; 5.E.175.236; 5.E.175.237; 5.E.175.238;
5.E.175.239; 5.E.175.154; 5.E.175.157; 5.E.175.166; 5.E.175.169;
5.E.175.172; 5.E.175.175; 5.E.175.240; 5.E.175.244; 5.E.240.228;
5.E.240.229; 5.E.240.230; 5.E.240.231; 5.E.240.236; 5.E.240.237;
5.E.240.238; 5.E.240.239; 5.E.240.154; 5.E.240.157; 5.E.240.166;
5.E.240.169; 5.E.240.172; 5.E.240.175; 5.E.240.240; 5.E.240.244;
5.E.244.228; 5.E.244.229; 5.E.244.230; 5.E.244.231; 5.E.244.236;
5.E.244.237; 5.E.244.238; 5.E.244.239; 5.E.244.154; 5.E.244.157;
5.E.244.166; 5.E.244.169; 5.E.244.172; 5.E.244.175; 5.E.244.240;
5.E.244.244;
Prodrugs of 5.G 5.G.228.228; 5.G.228.229; 5.G.228.230; 5.G.228.231; 5.G.228.236;
5.G.228.237; 5.G.228.238; 5.G.228.239; 5.G.228.154; 5.G.228.157;
5.G.228.166; 5.G.228.169; 5.G.228.172; 5.G.228.175; 5.G.228.240;
5.G.228.244; 5.G.229.228; 5.G.229.229; 5.G.229.230; 5.G.229.231;
5.G.229.236; 5.G.229.237; 5.G.229.238; 5.G.229.239; 5.G.229.154;
5.G.229.157; 5.G.229.166; 5.G.229.169; 5.G.229.172; 5.G.229.175;
5.G.229.240; 5.G.229.244; 5.G.230.228; 5.G.230.229; 5.G.230.230;
5.G.230.231; 5.G.230.236; 5.G.230.237; 5.G.230.238; 5.G.230.239;
5.G.230.154; 5.G.230.157; 5.G.230.166; 5.G.230.169; 5.G.230.172;
5.G.230.175; 5.G.230.240; 5.G.230.244; 5.G.231.228; 5.G.231.229;
5.G.231.230; 5.G.231.231; 5.G.231.236; 5.G.231.237; 5.G.231.238;
5.G.231.239; 5.G.231.154; 5.G.231.157; 5.G.231.166; 5.G.231.169;
5.G.231.172; 5.G.231.175; 5.G.231.240; 5.G.231.244; 5.G.236.228;
5.G.236.229; 5.G.236.230; 5.G.236.231; 5.G.236.236; 5.G.236.237;
5.G.236.238; 5.G.236.239; 5.G.236.154; 5.G.236.157; 5.G.236.166;
5.G.236.169; 5.G.236.172; 5.G.236.175; 5.G.236.240; 5.G.236.244;
5.G.237.228; 5.G.237.229; 5.G.237.230; 5.G.237.231; 5.G.237.236;
5.G.237.237; 5.G.237.238; 5.G.237.239; 5.G.237.154; 5.G.237.157;
5.G.237.166; 5.G.237.169; 5.G.237.172; 5.G.237.175; 5.G.237.240;
5.G.237.244; 5.G.238.228; 5.G.238.229; 5.G.238.230; 5.G.238.231;
5.G.238.236; 5.G.238.237; 5.G.238.238; 5.G.238.239; 5.G.238.154;
5.G.238.157; 5.G.238.166; 5.G.238.169; 5.G.238.172; 5.G.238.175;
5.G.238.240; 5.G.238.244; 5.G.239.228; 5.G.239.229; 5.G.239.230;
5.G.239.231; 5.G.239.236; 5.G.239.237; 5.G.239.238; 5.G.239.239;
5.G.239.154; 5.G.239.157; 5.G.239.166; 5.G.239.169; 5.G.239.172;
5.G.239.175; 5.G.239.240; 5.G.239.244; 5.G.154.228; 5.G.154.229;
5.G.154.230; 5.G.154.231; 5.G.154.236; 5.G.154.237; 5.G.154.238;
5.G.154.239; 5.G.154.154; 5.G.154.157; 5.G.154.166; 5.G.154.169;
5.G.154.172; 5.G.154.175; 5.G.154.240; 5.G.154.244; 5.G.157.228;
5.G.157.229; 5.G.157.230; 5.G.157.231; 5.G.157.236; 5.G.157.237;
5.G.157.238; 5.G.157.239; 5.G.157.154; 5.G.157.157; 5.G.157.166;
5.G.157.169; 5.G.157.172; 5.G.157.175; 5.G.157.240; 5.G.157.244;
5.G.166.228; 5.G.166.229; 5.G.166.230; 5.G.166.231; 5.G.166.236;
5.G.166.237; 5.G.166.238; 5.G.166.239; 5.G.166.154; 5.G.166.157;
5.G.166.166; 5.G.166.169; 5.G.166.172; 5.G.166.175; 5.G.166.240;
5.G.166.244; 5.G.169.228; 5.G.169.229; 5.G.169.230; 5.G.169.231;
5.G.169.236; 5.G.169.237; 5.G.169.238; 5.G.169.239; 5.G.169.154;
5.G.169.157; 5.G.169.166; 5.G.169.169; 5.G.169.172; 5.G.169.175;
5.G.169.240; 5.G.169.244; 5.G.172.228; 5.G.172.229; 5.G.172.230;
5.G.172.231; 5.G.172.236; 5.G.172.237; 5.G.172.238; 5.G.172.239;
5.G.172.154; 5.G.172.157; 5.G.172.166; 5.G.172.169; 5.G.172.172;
5.G.172.175; 5.G.172.240; 5.G.172.244; 5.G.175.228; 5.G.175.229;
5.G.175.230; 5.G.175.231; 5.G.175.236; 5.G.175.237; 5.G.175.238;
5.G.175.239; 5.G.175.154; 5.G.175.157; 5.G.175.166; 5.G.175.169;
5.G.175.172; 5.G.175.175; 5.G.175.240; 5.G.175.244; 5.G.240.228;
5.G.240.229; 5.G.240.230; 5.G.240.231; 5.G.240.236; 5.G.240.237;
5.G.240.238; 5.G.240.239; 5.G.240.154; 5.G.240.157; 5.G.240.166;
5.G.240.169; 5.G.240.172; 5.G.240.175; 5.G.240.240; 5.G.240.244;
5.G.244.228; 5.G.244.229; 5.G.244.230; 5.G.244.231; 5.G.244.236;
5.G.244.237; 5.G.244.238; 5.G.244.239; 5.G.244.154; 5.G.244.157;
5.G.244.166; 5.G.244.169; 5.G.244.172; 5.G.244.175; 5.G.244.240;
5.G.244.244;

TABLE 7-continued

Prodrugs of 5.I

5.I.228.228; 5.I.228.229; 5.I.228.230; 5.I.228.231; 5.I.228.236;
5.I.228.237; 5.I.228.238; 5.I.228.239; 5.I.228.154; 5.I.228.157;
5.I.228.166; 5.I.228.169; 5.I.228.172; 5.I.228.175; 5.I.228.240;
5.I.228.244; 5.I.229.228; 5.I.229.229; 5.I.229.230; 5.I.229.231;
5.I.229.236; 5.I.229.237; 5.I.229.238; 5.I.229.239; 5.I.229.154;
5.I.229.157; 5.I.229.166; 5.I.229.169; 5.I.229.172; 5.I.229.175;
5.I.229.240; 5.I.229.244; 5.I.230.228; 5.I.230.229; 5.I.230.230;
5.I.230.231; 5.I.230.236; 5.I.230.237; 5.I.230.238; 5.I.230.239;
5.I.230.154; 5.I.230.157; 5.I.230.166; 5.I.230.169; 5.I.230.172;
5.I.230.175; 5.I.230.240; 5.I.230.244; 5.I.231.228; 5.I.231.229;
5.I.231.230; 5.I.231.231; 5.I.231.236; 5.I.231.237; 5.I.231.238;
5.I.231.239; 5.I.231.154; 5.I.231.157; 5.I.231.166; 5.I.231.169;
5.I.231.172; 5.I.231.175; 5.I.231.240; 5.I.231.244; 5.I.236.228;
5.I.236.229; 5.I.236.230; 5.I.236.231; 5.I.236.236; 5.I.236.237;
5.I.236.238; 5.I.236.239; 5.I.236.154; 5.I.236.157; 5.I.236.166;
5.I.236.169; 5.I.236.172; 5.I.236.175; 5.I.236.240; 5.I.236.244;
5.I.237.228; 5.I.237.229; 5.I.237.230; 5.I.237.231; 5.I.237.236;
5.I.237.237; 5.I.237.238; 5.I.237.239; 5.I.237.154; 5.I.237.157;
5.I.237.166; 5.I.237.169; 5.I.237.172; 5.I.237.175; 5.I.237.240;
5.I.237.244; 5.I.238.228; 5.I.238.229; 5.I.238.230; 5.I.238.231;
5.I.238.236; 5.I.238.237; 5.I.238.238; 5.I.238.239; 5.I.238.154;
5.I.238.157; 5.I.238.166; 5.I.238.169; 5.I.238.172; 5.I.238.175;
5.I.238.240; 5.I.238.244; 5.I.239.228; 5.I.239.229; 5.I.239.230;
5.I.239.231; 5.I.239.236; 5.I.239.237; 5.I.239.238; 5.I.239.239;
5.I.239.154; 5.I.239.157; 5.I.239.166; 5.I.239.169; 5.I.239.172;
5.I.239.175; 5.I.239.240; 5.I.239.244; 5.I.154.228; 5.I.154.229;
5.I.154.230; 5.I.154.231; 5.I.154.236; 5.I.154.237; 5.I.154.238;
5.I.154.239; 5.I.154.154; 5.I.154.157; 5.I.154.166; 5.I.154.169;
5.I.154.172; 5.I.154.175; 5.I.154.240; 5.I.154.244; 5.I.157.228;
5.I.157.229; 5.I.157.230; 5.I.157.231; 5.I.157.236; 5.I.157.237;
5.I.157.238; 5.I.157.239; 5.I.157.154; 5.I.157.157; 5.I.157.166;
5.I.157.169; 5.I.157.172; 5.I.157.175; 5.I.157.240; 5.I.157.244;
5.I.166.228; 5.I.166.229; 5.I.166.230; 5.I.166.231; 5.I.166.236;
5.I.166.237; 5.I.166.238; 5.I.166.239; 5.I.166.154; 5.I.166.157;
5.I.166.166; 5.I.166.169; 5.I.166.172; 5.I.166.175; 5.I.166.240;
5.I.166.244; 5.I.169.228; 5.I.169.229; 5.I.169.230; 5.I.169.231;
5.I.169.236; 5.I.169.237; 5.I.169.238; 5.I.169.239; 5.I.169.154;
5.I.169.157; 5.I.169.166; 5.I.169.169; 5.I.169.172; 5.I.169.175;
5.I.169.240; 5.I.169.244; 5.I.172.228; 5.I.172.229; 5.I.172.230;
5.I.172.231; 5.I.172.236; 5.I.172.237; 5.I.172.238; 5.I.172.239;
5.I.172.154; 5.I.172.157; 5.I.172.166; 5.I.172.169; 5.I.172.172;
5.I.172.175; 5.I.172.240; 5.I.172.244; 5.I.175.228; 5.I.175.229;
5.I.175.230; 5.I.175.231; 5.I.175.236; 5.I.175.237; 5.I.175.238;
5.I.175.239; 5.I.175.154; 5.I.175.157; 5.I.175.166; 5.I.175.169;
5.I.175.172; 5.I.175.175; 5.I.175.240; 5.I.175.244; 5.I.240.228;
5.I.240.229; 5.I.240.230; 5.I.240.231; 5.I.240.236; 5.I.240.237;
5.I.240.238; 5.I.240.239; 5.I.240.154; 5.I.240.157; 5.I.240.166;
5.I.240.169; 5.I.240.172; 5.I.240.175; 5.I.240.240; 5.I.240.244;
5.I.244.228; 5.I.244.229; 5.I.244.230; 5.I.244.231; 5.I.244.236;
5.I.244.237; 5.I.244.238; 5.I.244.239; 5.I.244.154; 5.I.244.157;
5.I.244.166; 5.I.244.169; 5.I.244.172; 5.I.244.175; 5.I.244.240;
5.I.244.244;

Prodrugs of 5.J

5.J.228.228; 5.J.228.229; 5.J.228.230; 5.J.228.231; 5.J.228.236;
5.J.228.237; 5.J.228.238; 5.J.228.239; 5.J.228.154; 5.J.228.157;
5.J.228.166; 5.J.228.169; 5.J.228.172; 5.J.228.175; 5.J.228.240;
5.J.228.244; 5.J.229.228; 5.J.229.229; 5.J.229.230; 5.J.229.231;
5.J.229.236; 5.J.229.237; 5.J.229.238; 5.J.229.239; 5.J.229.154;
5.J.229.157; 5.J.229.166; 5.J.229.169; 5.J.229.172; 5.J.229.175;
5.J.229.240; 5.J.229.244; 5.J.230.228; 5.J.230.229; 5.J.230.230;
5.J.230.231; 5.J.230.236; 5.J.230.237; 5.J.230.238; 5.J.230.239;
5.J.230.154; 5.J.230.157; 5.J.230.166; 5.J.230.169; 5.J.230.172;
5.J.230.175; 5.J.230.240; 5.J.230.244; 5.J.231.228; 5.J.231.229;
5.J.231.230; 5.J.231.231; 5.J.231.236; 5.J.231.237; 5.J.231.238;
5.J.231.239; 5.J.231.154; 5.J.231.157; 5.J.231.166; 5.J.231.169;
5.J.231.172; 5.J.231.175; 5.J.231.240; 5.J.231.244; 5.J.236.228;
5.J.236.229; 5.J.236.230; 5.J.236.231; 5.J.236.236; 5.J.236.237;
5.J.236.238; 5.J.236.239; 5.J.236.154; 5.J.236.157; 5.J.236.166;
5.J.236.169; 5.J.236.172; 5.J.236.175; 5.J.236.240; 5.J.236.244;
5.J.237.228; 5.J.237.229; 5.J.237.230; 5.J.237.231; 5.J.237.236;
5.J.237.237; 5.J.237.238; 5.J.237.239; 5.J.237.154; 5.J.237.157;
5.J.237.166; 5.J.237.169; 5.J.237.172; 5.J.237.175; 5.J.237.240;
5.J.237.244; 5.J.238.228; 5.J.238.229; 5.J.238.230; 5.J.238.231;
5.J.238.236; 5.J.238.237; 5.J.238.238; 5.J.238.239; 5.J.238.154;
5.J.238.157; 5.J.238.166; 5.J.238.169; 5.J.238.172; 5.J.238.175;
5.J.238.240; 5.J.238.244; 5.J.239.228; 5.J.239.229; 5.J.239.230;
5.J.239.231; 5.J.239.236; 5.J.239.237; 5.J.239.238; 5.J.239.239;
5.J.239.154; 5.J.239.157; 5.J.239.166; 5.J.239.169; 5.J.239.172;
5.J.239.175; 5.J.239.240; 5.J.239.244; 5.J.154.228; 5.J.154.229;
5.J.154.230; 5.J.154.231; 5.J.154.236; 5.J.154.237; 5.J.154.238;
5.J.154.239; 5.J.154.154; 5.J.154.157; 5.J.154.166; 5.J.154.169;
5.J.154.172; 5.J.154.175; 5.J.154.240; 5.J.154.244; 5.J.157.228;
5.J.157.229; 5.J.157.230; 5.J.157.231; 5.J.157.236; 5.J.157.237;
5.J.157.238; 5.J.157.239; 5.J.157.154; 5.J.157.157; 5.J.157.166;
5.J.157.169; 5.J.157.172; 5.J.157.175; 5.J.157.240; 5.J.157.244;
5.J.166.228; 5.J.166.229; 5.J.166.230; 5.J.166.231; 5.J.166.236;
5.J.166.237; 5.J.166.238; 5.J.166.239; 5.J.166.154; 5.J.166.157;
5.J.166.166; 5.J.166.169; 5.J.166.172; 5.J.166.175; 5.J.166.240;
5.J.166.244; 5.J.169.228; 5.J.169.229; 5.J.169.230; 5.J.169.231;
5.J.169.236; 5.J.169.237; 5.J.169.238; 5.J.169.239; 5.J.169.154;
5.J.169.157; 5.J.169.166; 5.J.169.169; 5.J.169.172; 5.J.169.175;
5.J.169.240; 5.J.169.244; 5.J.172.228; 5.J.172.229; 5.J.172.230;
5.J.172.231; 5.J.172.236; 5.J.172.237; 5.J.172.238; 5.J.172.239;
5.J.172.154; 5.J.172.157; 5.J.172.166; 5.J.172.169; 5.J.172.172;
5.J.172.175; 5.J.172.240; 5.J.172.244; 5.J.175.228; 5.J.175.229;
5.J.175.230; 5.J.175.231; 5.J.175.236; 5.J.175.237; 5.J.175.238;
5.J.175.239; 5.J.175.154; 5.J.175.157; 5.J.175.166; 5.J.175.169;
5.J.175.172; 5.J.175.175; 5.J.175.240; 5.J.175.244; 5.J.240.228;
5.J.240.229; 5.J.240.230; 5.J.240.231; 5.J.240.236; 5.J.240.237;
5.J.240.238; 5.J.240.239; 5.J.240.154; 5.J.240.157; 5.J.240.166;
5.J.240.169; 5.J.240.172; 5.J.240.175; 5.J.240.240; 5.J.240.244;
5.J.244.228; 5.J.244.229; 5.J.244.230; 5.J.244.231; 5.J.244.236;
5.J.244.237; 5.J.244.238; 5.J.244.239; 5.J.244.154; 5.J.244.157;
5.J.244.166; 5.J.244.169; 5.J.244.172; 5.J.244.175; 5.J.244.240;
5.J.244.244;

Prodrugs of 5.L

5.L.228.228; 5.L.228.229; 5.L.228.230; 5.L.228.231; 5.L.228.236;
5.L.228.237; 5.L.228.238; 5.L.228.239; 5.L.228.154; 5.L.228.157;
5.L.228.166; 5.L.228.169; 5.L.228.172; 5.L.228.175; 5.L.228.240;
5.L.228.244; 5.L.229.228; 5.L.229.229; 5.L.229.230; 5.L.229.231;
5.L.229.236; 5.L.229.237; 5.L.229.238; 5.L.229.239; 5.L.229.154;
5.L.229.157; 5.L.229.166; 5.L.229.169; 5.L.229.172; 5.L.229.175;
5.L.229.240; 5.L.229.244; 5.L.230.228; 5.L.230.229; 5.L.230.230;
5.L.230.231; 5.L.230.236; 5.L.230.237; 5.L.230.238; 5.L.230.239;
5.L.230.154; 5.L.230.157; 5.L.230.166; 5.L.230.169; 5.L.230.172;
5.L.230.175; 5.L.230.240; 5.L.230.244; 5.L.231.228; 5.L.231.229;
5.L.231.230; 5.L.231.231; 5.L.231.236; 5.L.231.237; 5.L.231.238;
5.L.231.239; 5.L.231.154; 5.L.231.157; 5.L.231.166; 5.L.231.169;
5.L.231.172; 5.L.231.175; 5.L.231.240; 5.L.231.244; 5.L.236.228;
5.L.236.229; 5.L.236.230; 5.L.236.231; 5.L.236.236; 5.L.236.237;
5.L.236.238; 5.L.236.239; 5.L.236.154; 5.L.236.157; 5.L.236.166;
5.L.236.169; 5.L.236.172; 5.L.236.175; 5.L.236.240; 5.L.236.244;
5.L.237.228; 5.L.237.229; 5.L.237.230; 5.L.237.231; 5.L.237.236;
5.L.237.237; 5.L.237.238; 5.L.237.239; 5.L.237.154; 5.L.237.157;
5.L.237.166; 5.L.237.169; 5.L.237.172; 5.L.237.175; 5.L.237.240;
5.L.237.244; 5.L.238.228; 5.L.238.229; 5.L.238.230; 5.L.238.231;
5.L.238.236; 5.L.238.237; 5.L.238.238; 5.L.238.239; 5.L.238.154;
5.L.238.157; 5.L.238.166; 5.L.238.169; 5.L.238.172; 5.L.238.175;
5.L.238.240; 5.L.238.244; 5.L.239.228; 5.L.239.229; 5.L.239.230;
5.L.239.231; 5.L.239.236; 5.L.239.237; 5.L.239.238; 5.L.239.239;
5.L.239.154; 5.L.239.157; 5.L.239.166; 5.L.239.169; 5.L.239.172;
5.L.239.175; 5.L.239.240; 5.L.239.244; 5.L.154.228; 5.L.154.229;
5.L.154.230; 5.L.154.231; 5.L.154.236; 5.L.154.237; 5.L.154.238;
5.L.154.239; 5.L.154.154; 5.L.154.157; 5.L.154.166; 5.L.154.169;
5.L.154.172; 5.L.154.175; 5.L.154.240; 5.L.154.244; 5.L.157.228;
5.L.157.229; 5.L.157.230; 5.L.157.231; 5.L.157.236; 5.L.157.237;
5.L.157.238; 5.L.157.239; 5.L.157.154; 5.L.157.157; 5.L.157.166;
5.L.157.169; 5.L.157.172; 5.L.157.175; 5.L.157.240; 5.L.157.244;
5.L.166.228; 5.L.166.229; 5.L.166.230; 5.L.166.231; 5.L.166.236;
5.L.166.237; 5.L.166.238; 5.L.166.239; 5.L.166.154; 5.L.166.157;
5.L.166.166; 5.L.166.169; 5.L.166.172; 5.L.166.175; 5.L.166.240;
5.L.166.244; 5.L.169.228; 5.L.169.229; 5.L.169.230; 5.L.169.231;
5.L.169.236; 5.L.169.237; 5.L.169.238; 5.L.169.239; 5.L.169.154;
5.L.169.157; 5.L.169.166; 5.L.169.169; 5.L.169.172; 5.L.169.175;
5.L.169.240; 5.L.169.244; 5.L.172.228; 5.L.172.229; 5.L.172.230;
5.L.172.231; 5.L.172.236; 5.L.172.237; 5.L.172.238; 5.L.172.239;
5.L.172.154; 5.L.172.157; 5.L.172.166; 5.L.172.169; 5.L.172.172;
5.L.172.175; 5.L.172.240; 5.L.172.244; 5.L.175.228; 5.L.175.229;
5.L.175.230; 5.L.175.231; 5.L.175.236; 5.L.175.237; 5.L.175.238;
5.L.175.239; 5.L.175.154; 5.L.175.157; 5.L.175.166; 5.L.175.169;
5.L.175.172; 5.L.175.175; 5.L.175.240; 5.L.175.244; 5.L.240.228;
5.L.240.229; 5.L.240.230; 5.L.240.231; 5.L.240.236; 5.L.240.237;
5.L.240.238; 5.L.240.239; 5.L.240.154; 5.L.240.157; 5.L.240.166;
5.L.240.169; 5.L.240.172; 5.L.240.175; 5.L.240.240; 5.L.240.244;

TABLE 7-continued

5.L.244.228; 5.L.244.229; 5.L.244.230; 5.L.244.231; 5.L.244.236;
5.L.244.237; 5.L.244.238; 5.L.244.239; 5.L.244.154; 5.L.244.157;
5.L.244.166; 5.L.244.169; 5.L.244.172; 5.L.244.175; 5.L.244.240;
5.L.244.244;
Prodrugs of 5.O 5.O.228.228; 5.O.228.229; 5.O.228.230; 5.O.228.231; 5.O.228.236;
5.O.228.237; 5.O.228.238; 5.O.228.239; 5.O.228.154; 5.O.228.157;
5.O.228.166; 5.O.228.169; 5.O.228.172; 5.O.228.175; 5.O.228.240;
5.O.228.244; 5.O.229.228; 5.O.229.229; 5.O.229.230; 5.O.229.231;
5.O.229.236; 5.O.229.237; 5.O.229.238; 5.O.229.239; 5.O.229.154;
5.O.229.157; 5.O.229.166; 5.O.229.169; 5.O.229.172; 5.O.229.175;
5.O.229.240; 5.O.229.244; 5.O.230.228; 5.O.230.229; 5.O.230.230;
5.O.230.231; 5.O.230.236; 5.O.230.237; 5.O.230.238; 5.O.230.239;
5.O.230.154; 5.O.230.157; 5.O.230.166; 5.O.230.169; 5.O.230.172;
5.O.230.175; 5.O.230.240; 5.O.230.244; 5.O.231.228; 5.O.231.229;
5.O.231.230; 5.O.231.231; 5.O.231.236; 5.O.231.237; 5.O.231.238;
5.O.231.239; 5.O.231.154; 5.O.231.157; 5.O.231.166; 5.O.231.169;
5.O.231.172; 5.O.231.175; 5.O.231.240; 5.O.231.244; 5.O.236.228;
5.O.236.229; 5.O.236.230; 5.O.236.231; 5.O.236.236; 5.O.236.237;
5.O.236.238; 5.O.236.239; 5.O.236.154; 5.O.236.157; 5.O.236.166;
5.O.236.169; 5.O.236.172; 5.O.236.175; 5.O.236.240; 5.O.236.244;
5.O.237.228; 5.O.237.229; 5.O.237.230; 5.O.237.231; 5.O.237.236;
5.O.237.237; 5.O.237.238; 5.O.237.239; 5.O.237.154; 5.O.237.157;
5.O.237.166; 5.O.237.169; 5.O.237.172; 5.O.237.175; 5.O.237.240;
5.O.237.244; 5.O.238.228; 5.O.238.229; 5.O.238.230; 5.O.238.231;
5.O.238.236; 5.O.238.237; 5.O.238.238; 5.O.238.239; 5.O.238.154;
5.O.238.157; 5.O.238.166; 5.O.238.169; 5.O.238.172; 5.O.238.175;
5.O.238.240; 5.O.238.244; 5.O.239.228; 5.O.239.229; 5.O.239.230;
5.O.239.231; 5.O.239.236; 5.O.239.237; 5.O.239.238; 5.O.239.239;
5.O.239.154; 5.O.239.157; 5.O.239.166; 5.O.239.169; 5.O.239.172;
5.O.239.175; 5.O.239.240; 5.O.239.244; 5.O.154.228; 5.O.154.229;
5.O.154.230; 5.O.154.231; 5.O.154.236; 5.O.154.237; 5.O.154.238;
5.O.154.239; 5.O.154.154; 5.O.154.157; 5.O.154.166; 5.O.154.169;
5.O.154.172; 5.O.154.175; 5.O.154.240; 5.O.154.244; 5.O.157.228;
5.O.157.229; 5.O.157.230; 5.O.157.231; 5.O.157.236; 5.O.157.237;
5.O.157.238; 5.O.157.239; 5.O.157.154; 5.O.157.157; 5.O.157.166;
5.O.157.169; 5.O.157.172; 5.O.157.175; 5.O.157.240; 5.O.157.244;
5.O.166.228; 5.O.166.229; 5.O.166.230; 5.O.166.231; 5.O.166.236;
5.O.166.237; 5.O.166.238; 5.O.166.239; 5.O.166.154; 5.O.166.157;
5.O.166.166; 5.O.166.169; 5.O.166.172; 5.O.166.175; 5.O.166.240;
5.O.166.244; 5.O.169.228; 5.O.169.229; 5.O.169.230; 5.O.169.231;
5.O.169.236; 5.O.169.237; 5.O.169.238; 5.O.169.239; 5.O.169.154;
5.O.169.157; 5.O.169.166; 5.O.169.169; 5.O.169.172; 5.O.169.175;
5.O.169.240; 5.O.169.244; 5.O.172.228; 5.O.172.229; 5.O.172.230;
5.O.172.231; 5.O.172.236; 5.O.172.237; 5.O.172.238; 5.O.172.239;
5.O.172.154; 5.O.172.157; 5.O.172.166; 5.O.172.169; 5.O.172.172;
5.O.172.175; 5.O.172.240; 5.O.172.244; 5.O.175.228; 5.O.175.229;
5.O.175.230; 5.O.175.231; 5.O.175.236; 5.O.175.237; 5.O.175.238;
5.O.175.239; 5.O.175.154; 5.O.175.157; 5.O.175.166; 5.O.175.169;
5.O.175.172; 5.O.175.175; 5.O.175.240; 5.O.175.244; 5.O.240.228;
5.O.240.229; 5.O.240.230; 5.O.240.231; 5.O.240.236; 5.O.240.237;
5.O.240.238; 5.O.240.239; 5.O.240.154; 5.O.240.157; 5.O.240.166;
5.O.240.169; 5.O.240.172; 5.O.240.175; 5.O.240.240; 5.O.240.244;
5.O.244.228; 5.O.244.229; 5.O.244.230; 5.O.244.231; 5.O.244.236;
5.O.244.237; 5.O.244.238; 5.O.244.239; 5.O.244.154; 5.O.244.157;
5.O.244.166; 5.O.244.169; 5.O.244.172; 5.O.244.175; 5.O.244.240;
5.O.244.244;
Prodrugs of 5.P 5.P.228.228; 5.P.228.229; 5.P.228.230; 5.P.228.231; 5.P.228.236;
5.P.228.237; 5.P.228.238; 5.P.228.239; 5.P.228.154; 5.P.228.157;
5.P.228.166; 5.P.228.169; 5.P.228.172; 5.P.228.175; 5.P.228.240;
5.P.228.244; 5.P.229.228; 5.P.229.229; 5.P.229.230; 5.P.229.231;
5.P.229.236; 5.P.229.237; 5.P.229.238; 5.P.229.239; 5.P.229.154;
5.P.229.157; 5.P.229.166; 5.P.229.169; 5.P.229.172; 5.P.229.175;
5.P.229.240; 5.P.229.244; 5.P.230.228; 5.P.230.229; 5.P.230.230;
5.P.230.231; 5.P.230.236; 5.P.230.237; 5.P.230.238; 5.P.230.239;
5.P.230.154; 5.P.230.157; 5.P.230.166; 5.P.230.169; 5.P.230.172;
5.P.230.175; 5.P.230.240; 5.P.230.244; 5.P.231.228; 5.P.231.229;
5.P.231.230; 5.P.231.231; 5.P.231.236; 5.P.231.237; 5.P.231.238;
5.P.231.239; 5.P.231.154; 5.P.231.157; 5.P.231.166; 5.P.231.169;
5.P.231.172; 5.P.231.175; 5.P.231.240; 5.P.231.244; 5.P.236.228;
5.P.236.229; 5.P.236.230; 5.P.236.231; 5.P.236.236; 5.P.236.237;
5.P.236.238; 5.P.236.239; 5.P.236.154; 5.P.236.157; 5.P.236.166;
5.P.236.169; 5.P.236.172; 5.P.236.175; 5.P.236.240; 5.P.236.244;
5.P.237.228; 5.P.237.229; 5.P.237.230; 5.P.237.231; 5.P.237.236;
5.P.237.237; 5.P.237.238; 5.P.237.239; 5.P.237.154; 5.P.237.157;
5.P.237.166; 5.P.237.169; 5.P.237.172; 5.P.237.175; 5.P.237.240;
5.P.237.244; 5.P.238.228; 5.P.238.229; 5.P.238.230; 5.P.238.231;
5.P.238.236; 5.P.238.237; 5.P.238.238; 5.P.238.239; 5.P.238.154;
5.P.238.157; 5.P.238.166; 5.P.238.169; 5.P.238.172; 5.P.238.175;
5.P.238.240; 5.P.238.244; 5.P.239.228; 5.P.239.229; 5.P.239.230;
5.P.239.231; 5.P.239.236; 5.P.239.237; 5.P.239.238; 5.P.239.239;
5.P.239.154; 5.P.239.157; 5.P.239.166; 5.P.239.169; 5.P.239.172;
5.P.239.175; 5.P.239.240; 5.P.239.244; 5.P.154.228; 5.P.154.229;
5.P.154.230; 5.P.154.231; 5.P.154.236; 5.P.154.237; 5.P.154.238;
5.P.154.239; 5.P.154.154; 5.P.154.157; 5.P.154.166; 5.P.154.169;
5.P.154.172; 5.P.154.175; 5.P.154.240; 5.P.154.244; 5.P.157.228;
5.P.157.229; 5.P.157.230; 5.P.157.231; 5.P.157.236; 5.P.157.237;
5.P.157.238; 5.P.157.239; 5.P.157.154; 5.P.157.157; 5.P.157.166;
5.P.157.169; 5.P.157.172; 5.P.157.175; 5.P.157.240; 5.P.157.244;
5.P.166.228; 5.P.166.229; 5.P.166.230; 5.P.166.231; 5.P.166.236;
5.P.166.237; 5.P.166.238; 5.P.166.239; 5.P.166.154; 5.P.166.157;
5.P.166.166; 5.P.166.169; 5.P.166.172; 5.P.166.175; 5.P.166.240;
5.P.166.244; 5.P.169.228; 5.P.169.229; 5.P.169.230; 5.P.169.231;
5.P.169.236; 5.P.169.237; 5.P.169.238; 5.P.169.239; 5.P.169.154;
5.P.169.157; 5.P.169.166; 5.P.169.169; 5.P.169.172; 5.P.169.175;
5.P.169.240; 5.P.169.244; 5.P.172.228; 5.P.172.229; 5.P.172.230;
5.P.172.231; 5.P.172.236; 5.P.172.237; 5.P.172.238; 5.P.172.239;
5.P.172.154; 5.P.172.157; 5.P.172.166; 5.P.172.169; 5.P.172.172;
5.P.172.175; 5.P.172.240; 5.P.172.244; 5.P.175.228; 5.P.175.229;
5.P.175.230; 5.P.175.231; 5.P.175.236; 5.P.175.237; 5.P.175.238;
5.P.175.239; 5.P.175.154; 5.P.175.157; 5.P.175.166; 5.P.175.169;
5.P.175.172; 5.P.175.175; 5.P.175.240; 5.P.175.244; 5.P.240.228;
5.P.240.229; 5.P.240.230; 5.P.240.231; 5.P.240.236; 5.P.240.237;
5.P.240.238; 5.P.240.239; 5.P.240.154; 5.P.240.157; 5.P.240.166;
5.P.240.169; 5.P.240.172; 5.P.240.175; 5.P.240.240; 5.P.240.244;
5.P.244.228; 5.P.244.229; 5.P.244.230; 5.P.244.231; 5.P.244.236;
5.P.244.237; 5.P.244.238; 5.P.244.239; 5.P.244.154; 5.P.244.157;
5.P.244.166; 5.P.244.169; 5.P.244.172; 5.P.244.175; 5.P.244.240;
5.P.244.244;
Prodrugs of 5.U 5.U.228.228; 5.U.228.229; 5.U.228.230; 5.U.228.231; 5.U.228.236;
5.U.228.237; 5.U.228.238; 5.U.228.239; 5.U.228.154; 5.U.228.157;
5.U.228.166; 5.U.228.169; 5.U.228.172; 5.U.228.175; 5.U.228.240;
5.U.228.244; 5.U.229.228; 5.U.229.229; 5.U.229.230; 5.U.229.231;
5.U.229.236; 5.U.229.237; 5.U.229.238; 5.U.229.239; 5.U.229.154;
5.U.229.157; 5.U.229.166; 5.U.229.169; 5.U.229.172; 5.U.229.175;
5.U.229.240; 5.U.229.244; 5.U.230.228; 5.U.230.229; 5.U.230.230;
5.U.230.231; 5.U.230.236; 5.U.230.237; 5.U.230.238; 5.U.230.239;
5.U.230.154; 5.U.230.157; 5.U.230.166; 5.U.230.169; 5.U.230.172;
5.U.230.175; 5.U.230.240; 5.U.230.244; 5.U.231.228; 5.U.231.229;
5.U.231.230; 5.U.231.231; 5.U.231.236; 5.U.231.237; 5.U.231.238;
5.U.231.239; 5.U.231.154; 5.U.231.157; 5.U.231.166; 5.U.231.169;
5.U.231.172; 5.U.231.175; 5.U.231.240; 5.U.231.244; 5.U.236.228;
5.U.236.229; 5.U.236.230; 5.U.236.231; 5.U.236.236; 5.U.236.237;
5.U.236.238; 5.U.236.239; 5.U.236.154; 5.U.236.157; 5.U.236.166;
5.U.236.169; 5.U.236.172; 5.U.236.175; 5.U.236.240; 5.U.236.244;
5.U.237.228; 5.U.237.229; 5.U.237.230; 5.U.237.231; 5.U.237.236;
5.U.237.237; 5.U.237.238; 5.U.237.239; 5.U.237.154; 5.U.237.157;
5.U.237.166; 5.U.237.169; 5.U.237.172; 5.U.237.175; 5.U.237.240;
5.U.237.244; 5.U.238.228; 5.U.238.229; 5.U.238.230; 5.U.238.231;
5.U.238.236; 5.U.238.237; 5.U.238.238; 5.U.238.239; 5.U.238.154;
5.U.238.157; 5.U.238.166; 5.U.238.169; 5.U.238.172; 5.U.238.175;
5.U.238.240; 5.U.238.244; 5.U.239.228; 5.U.239.229; 5.U.239.230;
5.U.239.231; 5.U.239.236; 5.U.239.237; 5.U.239.238; 5.U.239.239;
5.U.239.154; 5.U.239.157; 5.U.239.166; 5.U.239.169; 5.U.239.172;
5.U.239.175; 5.U.239.240; 5.U.239.244; 5.U.154.228; 5.U.154.229;
5.U.154.230; 5.U.154.231; 5.U.154.236; 5.U.154.237; 5.U.154.238;
5.U.154.239; 5.U.154.154; 5.U.154.157; 5.U.154.166; 5.U.154.169;
5.U.154.172; 5.U.154.175; 5.U.154.240; 5.U.154.244; 5.U.157.228;
5.U.157.229; 5.U.157.230; 5.U.157.231; 5.U.157.236; 5.U.157.237;
5.U.157.238; 5.U.157.239; 5.U.157.154; 5.U.157.157; 5.U.157.166;
5.U.157.169; 5.U.157.172; 5.U.157.175; 5.U.157.240; 5.U.157.244;
5.U.166.228; 5.U.166.229; 5.U.166.230; 5.U.166.231; 5.U.166.236;
5.U.166.237; 5.U.166.238; 5.U.166.239; 5.U.166.154; 5.U.166.157;
5.U.166.166; 5.U.166.169; 5.U.166.172; 5.U.166.175; 5.U.166.240;
5.U.166.244; 5.U.169.228; 5.U.169.229; 5.U.169.230; 5.U.169.231;
5.U.169.236; 5.U.169.237; 5.U.169.238; 5.U.169.239; 5.U.169.154;
5.U.169.157; 5.U.169.166; 5.U.169.169; 5.U.169.172; 5.U.169.175;
5.U.169.240; 5.U.169.244; 5.U.172.228; 5.U.172.229; 5.U.172.230;
5.U.172.231; 5.U.172.236; 5.U.172.237; 5.U.172.238; 5.U.172.239;
5.U.172.154; 5.U.172.157; 5.U.172.166; 5.U.172.169; 5.U.172.172;
5.U.172.175; 5.U.172.240; 5.U.172.244; 5.U.175.228; 5.U.175.229;
5.U.175.230; 5.U.175.231; 5.U.175.236; 5.U.175.237; 5.U.175.238;
5.U.175.239; 5.U.175.154; 5.U.175.157; 5.U.175.166; 5.U.175.169;

TABLE 7-continued

5.U.175.172; 5.U.175.175; 5.U.175.240; 5.U.175.244; 5.U.240.228; 5.U.240.229; 5.U.240.230; 5.U.240.231; 5.U.240.236; 5.U.240.237; 5.U.240.238; 5.U.240.239; 5.U.240.154; 5.U.240.157; 5.U.240.166; 5.U.240.169; 5.U.240.172; 5.U.240.240; 5.U.240.244; 5.U.244.228; 5.U.244.229; 5.U.244.230; 5.U.244.231; 5.U.244.236; 5.U.244.237; 5.U.244.238; 5.U.244.239; 5.U.244.154; 5.U.244.157; 5.U.244.166; 5.U.244.169; 5.U.244.172; 5.U.244.175; 5.U.244.240; 5.U.244.244;

Prodrugs of 5.W

5.W.228.228; 5.W.228.229; 5.W.228.230; 5.W.228.231; 5.W.228.236; 5.W.228.237; 5.W.228.238; 5.W.228.239; 5.W.228.154; 5.W.228.157; 5.W.228.166; 5.W.228.169; 5.W.228.172; 5.W.228.175; 5.W.228.240; 5.W.228.244; 5.W.229.228; 5.W.229.229; 5.W.229.230; 5.W.229.231; 5.W.229.236; 5.W.229.237; 5.W.229.238; 5.W.229.239; 5.W.229.154; 5.W.229.157; 5.W.229.166; 5.W.229.169; 5.W.229.172; 5.W.229.175; 5.W.229.240; 5.W.229.244; 5.W.230.228; 5.W.230.229; 5.W.230.230; 5.W.230.231; 5.W.230.236; 5.W.230.237; 5.W.230.238; 5.W.230.239; 5.W.230.154; 5.W.230.157; 5.W.230.166; 5.W.230.169; 5.W.230.172; 5.W.230.175; 5.W.230.240; 5.W.230.244; 5.W.231.228; 5.W.231.229; 5.W.231.230; 5.W.231.231; 5.W.231.236; 5.W.231.237; 5.W.231.238; 5.W.231.239; 5.W.231.154; 5.W.231.157; 5.W.231.166; 5.W.231.169; 5.W.231.172; 5.W.231.175; 5.W.231.240; 5.W.231.244; 5.W.236.228; 5.W.236.229; 5.W.236.230; 5.W.236.231; 5.W.236.236; 5.W.236.237; 5.W.236.238; 5.W.236.239; 5.W.236.154; 5.W.236.157; 5.W.236.166; 5.W.236.169; 5.W.236.172; 5.W.236.175; 5.W.236.240; 5.W.236.244; 5.W.237.228; 5.W.237.229; 5.W.237.230; 5.W.237.231; 5.W.237.236; 5.W.237.237; 5.W.237.238; 5.W.237.239; 5.W.237.154; 5.W.237.157; 5.W.237.166; 5.W.237.169; 5.W.237.172; 5.W.237.175; 5.W.237.240; 5.W.237.244; 5.W.238.228; 5.W.238.229; 5.W.238.230; 5.W.238.231; 5.W.238.236; 5.W.238.237; 5.W.238.238; 5.W.238.239; 5.W.238.154; 5.W.238.157; 5.W.238.166; 5.W.238.169; 5.W.238.172; 5.W.238.175; 5.W.238.240; 5.W.238.244; 5.W.239.228; 5.W.239.229; 5.W.239.230; 5.W.239.231; 5.W.239.236; 5.W.239.237; 5.W.239.238; 5.W.239.239; 5.W.239.154; 5.W.239.157; 5.W.239.166; 5.W.239.169; 5.W.239.172; 5.W.239.175; 5.W.239.240; 5.W.239.244; 5.W.154.228; 5.W.154.229; 5.W.154.230; 5.W.154.231; 5.W.154.236; 5.W.154.237; 5.W.154.238; 5.W.154.239; 5.W.154.154; 5.W.154.157; 5.W.154.166; 5.W.154.169; 5.W.154.172; 5.W.154.175; 5.W.154.240; 5.W.154.244; 5.W.157.228; 5.W.157.229; 5.W.157.230; 5.W.157.231; 5.W.157.236; 5.W.157.237; 5.W.157.238; 5.W.157.239; 5.W.157.154; 5.W.157.157; 5.W.157.166; 5.W.157.169; 5.W.157.172; 5.W.157.175; 5.W.157.240; 5.W.157.244; 5.W.166.228; 5.W.166.229; 5.W.166.230; 5.W.166.231; 5.W.166.236; 5.W.166.237; 5.W.166.238; 5.W.166.239; 5.W.166.154; 5.W.166.157; 5.W.166.166; 5.W.166.169; 5.W.166.172; 5.W.166.175; 5.W.166.240; 5.W.166.244; 5.W.169.228; 5.W.169.229; 5.W.169.230; 5.W.169.231; 5.W.169.236; 5.W.169.237; 5.W.169.238; 5.W.169.239; 5.W.169.154; 5.W.169.157; 5.W.169.166; 5.W.169.169; 5.W.169.172; 5.W.169.175; 5.W.169.240; 5.W.169.244; 5.W.172.228; 5.W.172.229; 5.W.172.230; 5.W.172.231; 5.W.172.236; 5.W.172.237; 5.W.172.238; 5.W.172.239; 5.W.172.154; 5.W.172.157; 5.W.172.166; 5.W.172.169; 5.W.172.172; 5.W.172.175; 5.W.172.240; 5.W.172.244; 5.W.175.228; 5.W.175.229; 5.W.175.230; 5.W.175.231; 5.W.175.236; 5.W.175.237; 5.W.175.238; 5.W.175.239; 5.W.175.154; 5.W.175.157; 5.W.175.166; 5.W.175.169; 5.W.175.172; 5.W.175.175; 5.W.175.240; 5.W.175.244; 5.W.240.228; 5.W.240.229; 5.W.240.230; 5.W.240.231; 5.W.240.236; 5.W.240.237; 5.W.240.238; 5.W.240.239; 5.W.240.154; 5.W.240.157; 5.W.240.166; 5.W.240.169; 5.W.240.172; 5.W.240.175; 5.W.240.240; 5.W.240.244; 5.W.244.228; 5.W.244.229; 5.W.244.230; 5.W.244.231; 5.W.244.236; 5.W.244.237; 5.W.244.238; 5.W.244.239; 5.W.244.154; 5.W.244.157; 5.W.244.166; 5.W.244.169; 5.W.244.172; 5.W.244.175; 5.W.244.240; 5.W.244.244;

Prodrugs of 5.Y

5.Y.228.228; 5.Y.228.229; 5.Y.228.230; 5.Y.228.231; 5.Y.228.236; 5.Y.228.237; 5.Y.228.238; 5.Y.228.239; 5.Y.228.154; 5.Y.228.157; 5.Y.228.166; 5.Y.228.169; 5.Y.228.172; 5.Y.228.175; 5.Y.228.240; 5.Y.228.244; 5.Y.229.228; 5.Y.229.229; 5.Y.229.230; 5.Y.229.231; 5.Y.229.236; 5.Y.229.237; 5.Y.229.238; 5.Y.229.239; 5.Y.229.154; 5.Y.229.157; 5.Y.229.166; 5.Y.229.169; 5.Y.229.172; 5.Y.229.175; 5.Y.229.240; 5.Y.229.244; 5.Y.230.228; 5.Y.230.229; 5.Y.230.230; 5.Y.230.231; 5.Y.230.236; 5.Y.230.237; 5.Y.230.238; 5.Y.230.239; 5.Y.230.154; 5.Y.230.157; 5.Y.230.166; 5.Y.230.169; 5.Y.230.172; 5.Y.230.175; 5.Y.230.240; 5.Y.230.244; 5.Y.231.228; 5.Y.231.229; 5.Y.231.230; 5.Y.231.231; 5.Y.231.236; 5.Y.231.237; 5.Y.231.238; 5.Y.231.239; 5.Y.231.154; 5.Y.231.157; 5.Y.231.166; 5.Y.231.169; 5.Y.231.172; 5.Y.231.175; 5.Y.231.240; 5.Y.231.244; 5.Y.236.228; 5.Y.236.229; 5.Y.236.230; 5.Y.236.231; 5.Y.236.236; 5.Y.236.237; 5.Y.236.238; 5.Y.236.239; 5.Y.236.154; 5.Y.236.157; 5.Y.236.166; 5.Y.236.169; 5.Y.236.172; 5.Y.236.175; 5.Y.236.240; 5.Y.236.244; 5.Y.237.228; 5.Y.237.229; 5.Y.237.230; 5.Y.237.231; 5.Y.237.236; 5.Y.237.237; 5.Y.237.238; 5.Y.237.239; 5.Y.237.154; 5.Y.237.157; 5.Y.237.166; 5.Y.237.169; 5.Y.237.172; 5.Y.237.175; 5.Y.237.240; 5.Y.237.244; 5.Y.238.228; 5.Y.238.229; 5.Y.238.230; 5.Y.238.231; 5.Y.238.236; 5.Y.238.237; 5.Y.238.238; 5.Y.238.239; 5.Y.238.154; 5.Y.238.157; 5.Y.238.166; 5.Y.238.169; 5.Y.238.172; 5.Y.238.175; 5.Y.238.240; 5.Y.238.244; 5.Y.239.228; 5.Y.239.229; 5.Y.239.230; 5.Y.239.231; 5.Y.239.236; 5.Y.239.237; 5.Y.239.238; 5.Y.239.239; 5.Y.239.154; 5.Y.239.157; 5.Y.239.166; 5.Y.239.169; 5.Y.239.172; 5.Y.239.175; 5.Y.239.240; 5.Y.239.244; 5.Y.154.228; 5.Y.154.229; 5.Y.154.230; 5.Y.154.231; 5.Y.154.236; 5.Y.154.237; 5.Y.154.238; 5.Y.154.239; 5.Y.154.154; 5.Y.154.157; 5.Y.154.166; 5.Y.154.169; 5.Y.154.172; 5.Y.154.175; 5.Y.154.240; 5.Y.154.244; 5.Y.157.228; 5.Y.157.229; 5.Y.157.230; 5.Y.157.231; 5.Y.157.236; 5.Y.157.237; 5.Y.157.238; 5.Y.157.239; 5.Y.157.154; 5.Y.157.157; 5.Y.157.166; 5.Y.157.169; 5.Y.157.172; 5.Y.157.175; 5.Y.157.240; 5.Y.157.244; 5.Y.166.228; 5.Y.166.229; 5.Y.166.230; 5.Y.166.231; 5.Y.166.236; 5.Y.166.237; 5.Y.166.238; 5.Y.166.239; 5.Y.166.154; 5.Y.166.157; 5.Y.166.166; 5.Y.166.169; 5.Y.166.172; 5.Y.166.175; 5.Y.166.240; 5.Y.166.244; 5.Y.169.228; 5.Y.169.229; 5.Y.169.230; 5.Y.169.231; 5.Y.169.236; 5.Y.169.237; 5.Y.169.238; 5.Y.169.239; 5.Y.169.154; 5.Y.169.157; 5.Y.169.166; 5.Y.169.169; 5.Y.169.172; 5.Y.169.175; 5.Y.169.240; 5.Y.169.244; 5.Y.172.228; 5.Y.172.229; 5.Y.172.230; 5.Y.172.231; 5.Y.172.236; 5.Y.172.237; 5.Y.172.238; 5.Y.172.239; 5.Y.172.154; 5.Y.172.157; 5.Y.172.166; 5.Y.172.169; 5.Y.172.172; 5.Y.172.175; 5.Y.172.240; 5.Y.172.244; 5.Y.175.228; 5.Y.175.229; 5.Y.175.230; 5.Y.175.231; 5.Y.175.236; 5.Y.175.237; 5.Y.175.238; 5.Y.175.239; 5.Y.175.154; 5.Y.175.157; 5.Y.175.166; 5.Y.175.169; 5.Y.175.172; 5.Y.175.175; 5.Y.175.240; 5.Y.175.244; 5.Y.240.228; 5.Y.240.229; 5.Y.240.230; 5.Y.240.231; 5.Y.240.236; 5.Y.240.237; 5.Y.240.238; 5.Y.240.239; 5.Y.240.154; 5.Y.240.157; 5.Y.240.166; 5.Y.240.169; 5.Y.240.172; 5.Y.240.175; 5.Y.240.240; 5.Y.240.244; 5.Y.244.228; 5.Y.244.229; 5.Y.244.230; 5.Y.244.231; 5.Y.244.236; 5.Y.244.237; 5.Y.244.238; 5.Y.244.239; 5.Y.244.154; 5.Y.244.157; 5.Y.244.166; 5.Y.244.169; 5.Y.244.172; 5.Y.244.175; 5.Y.244.240; 5.Y.244.244;

Prodrugs of 6.B

6.B.228.228; 6.B.228.229; 6.B.228.230; 6.B.228.231; 6.B.228.236; 6.B.228.237; 6.B.228.238; 6.B.228.239; 6.B.228.154; 6.B.228.157; 6.B.228.166; 6.B.228.169; 6.B.228.172; 6.B.228.175; 6.B.228.240; 6.B.228.244; 6.B.229.228; 6.B.229.229; 6.B.229.230; 6.B.229.231; 6.B.229.236; 6.B.229.237; 6.B.229.238; 6.B.229.239; 6.B.229.154; 6.B.229.157; 6.B.229.166; 6.B.229.169; 6.B.229.172; 6.B.229.175; 6.B.229.240; 6.B.229.244; 6.B.230.228; 6.B.230.229; 6.B.230.230; 6.B.230.231; 6.B.230.236; 6.B.230.237; 6.B.230.238; 6.B.230.239; 6.B.230.154; 6.B.230.157; 6.B.230.166; 6.B.230.169; 6.B.230.172; 6.B.230.175; 6.B.230.240; 6.B.230.244; 6.B.231.228; 6.B.231.229; 6.B.231.230; 6.B.231.231; 6.B.231.236; 6.B.231.237; 6.B.231.238; 6.B.231.239; 6.B.231.154; 6.B.231.157; 6.B.231.166; 6.B.231.169; 6.B.231.172; 6.B.231.175; 6.B.231.240; 6.B.231.244; 6.B.236.228; 6.B.236.229; 6.B.236.230; 6.B.236.231; 6.B.236.236; 6.B.236.237; 6.B.236.238; 6.B.236.239; 6.B.236.154; 6.B.236.157; 6.B.236.166; 6.B.236.169; 6.B.236.172; 6.B.236.175; 6.B.236.240; 6.B.236.244; 6.B.237.228; 6.B.237.229; 6.B.237.230; 6.B.237.231; 6.B.237.236; 6.B.237.237; 6.B.237.238; 6.B.237.239; 6.B.237.154; 6.B.237.157; 6.B.237.166; 6.B.237.169; 6.B.237.172; 6.B.237.175; 6.B.237.240; 6.B.237.244; 6.B.238.228; 6.B.238.229; 6.B.238.230; 6.B.238.231; 6.B.238.236; 6.B.238.237; 6.B.238.238; 6.B.238.239; 6.B.238.154; 6.B.238.157; 6.B.238.166; 6.B.238.169; 6.B.238.172; 6.B.238.175; 6.B.238.240; 6.B.238.244; 6.B.239.228; 6.B.239.229; 6.B.239.230; 6.B.239.231; 6.B.239.236; 6.B.239.237; 6.B.239.238; 6.B.239.239; 6.B.239.154; 6.B.239.157; 6.B.239.166; 6.B.239.169; 6.B.239.172; 6.B.239.175; 6.B.239.240; 6.B.239.244; 6.B.154.228; 6.B.154.229; 6.B.154.230; 6.B.154.231; 6.B.154.236; 6.B.154.237; 6.B.154.238; 6.B.154.239; 6.B.154.154; 6.B.154.157; 6.B.154.166; 6.B.154.169; 6.B.154.172; 6.B.154.175; 6.B.154.240; 6.B.154.244; 6.B.157.228; 6.B.157.229; 6.B.157.230; 6.B.157.231; 6.B.157.236; 6.B.157.237; 6.B.157.238; 6.B.157.239; 6.B.157.154; 6.B.157.157; 6.B.157.166; 6.B.157.169; 6.B.157.172; 6.B.157.175; 6.B.157.240; 6.B.157.244; 6.B.166.228; 6.B.166.229; 6.B.166.230; 6.B.166.231; 6.B.166.236; 6.B.166.237; 6.B.166.238; 6.B.166.239; 6.B.166.154; 6.B.166.157; 6.B.166.166; 6.B.166.169; 6.B.166.172; 6.B.166.175; 6.B.166.240; 6.B.166.244; 6.B.169.228; 6.B.169.229; 6.B.169.230; 6.B.169.231; 6.B.169.236; 6.B.169.237; 6.B.169.238; 6.B.169.239; 6.B.169.154; 6.B.169.157; 6.B.169.166; 6.B.169.169; 6.B.169.172; 6.B.169.175; 6.B.169.240; 6.B.169.244; 6.B.172.228; 6.B.172.229; 6.B.172.230; 6.B.172.231; 6.B.172.236; 6.B.172.237; 6.B.172.238; 6.B.172.239;

TABLE 7-continued

6.B.172.154; 6.B.172.157; 6.B.172.166; 6.B.172.169; 6.B.172.172; 6.B.172.175; 6.B.172.240; 6.B.172.244; 6.B.175.228; 6.B.175.229; 6.B.175.230; 6.B.175.231; 6.B.175.236; 6.B.175.237; 6.B.175.238; 6.B.175.239; 6.B.175.154; 6.B.175.157; 6.B.175.166; 6.B.175.169; 6.B.175.172; 6.B.175.175; 6.B.175.240; 6.B.175.244; 6.B.240.228; 6.B.240.229; 6.B.240.230; 6.B.240.231; 6.B.240.236; 6.B.240.237; 6.B.240.238; 6.B.240.239; 6.B.240.154; 6.B.240.157; 6.B.240.166; 6.B.240.169; 6.B.240.172; 6.B.240.175; 6.B.240.240; 6.B.240.244; 6.B.244.228; 6.B.244.229; 6.B.244.230; 6.B.244.231; 6.B.244.236; 6.B.244.237; 6.B.244.238; 6.B.244.239; 6.B.244.154; 6.B.244.157; 6.B.244.166; 6.B.244.169; 6.B.244.172; 6.B.244.175; 6.B.244.240; 6.B.244.244;
Prodrugs of 6.D 6.D.228.228; 6.D.228.229; 6.D.228.230; 6.D.228.231; 6.D.228.236; 6.D.228.237; 6.D.228.238; 6.D.228.239; 6.D.228.154; 6.D.228.157; 6.D.228.166; 6.D.228.169; 6.D.228.172; 6.D.228.175; 6.D.228.240; 6.D.228.244; 6.D.229.228; 6.D.229.229; 6.D.229.230; 6.D.229.231; 6.D.229.236; 6.D.229.237; 6.D.229.238; 6.D.229.239; 6.D.229.154; 6.D.229.157; 6.D.229.166; 6.D.229.169; 6.D.229.172; 6.D.229.175; 6.D.229.240; 6.D.229.244; 6.D.230.228; 6.D.230.229; 6.D.230.230; 6.D.230.231; 6.D.230.236; 6.D.230.237; 6.D.230.238; 6.D.230.239; 6.D.230.154; 6.D.230.157; 6.D.230.166; 6.D.230.169; 6.D.230.172; 6.D.230.175; 6.D.230.240; 6.D.230.244; 6.D.231.228; 6.D.231.229; 6.D.231.230; 6.D.231.231; 6.D.231.236; 6.D.231.237; 6.D.231.238; 6.D.231.239; 6.D.231.154; 6.D.231.157; 6.D.231.166; 6.D.231.169; 6.D.231.172; 6.D.231.175; 6.D.231.240; 6.D.231.244; 6.D.236.228; 6.D.236.229; 6.D.236.230; 6.D.236.231; 6.D.236.236; 6.D.236.237; 6.D.236.238; 6.D.236.239; 6.D.236.154; 6.D.236.157; 6.D.236.166; 6.D.236.169; 6.D.236.172; 6.D.236.175; 6.D.236.240; 6.D.236.244; 6.D.237.228; 6.D.237.229; 6.D.237.230; 6.D.237.231; 6.D.237.236; 6.D.237.237; 6.D.237.238; 6.D.237.239; 6.D.237.154; 6.D.237.157; 6.D.237.166; 6.D.237.169; 6.D.237.172; 6.D.237.175; 6.D.237.240; 6.D.237.244; 6.D.238.228; 6.D.238.229; 6.D.238.230; 6.D.238.231; 6.D.238.236; 6.D.238.237; 6.D.238.238; 6.D.238.239; 6.D.238.154; 6.D.238.157; 6.D.238.166; 6.D.238.169; 6.D.238.172; 6.D.238.175; 6.D.238.240; 6.D.238.244; 6.D.239.228; 6.D.239.229; 6.D.239.230; 6.D.239.231; 6.D.239.236; 6.D.239.237; 6.D.239.238; 6.D.239.239; 6.D.239.154; 6.D.239.157; 6.D.239.166; 6.D.239.169; 6.D.239.172; 6.D.239.175; 6.D.239.240; 6.D.239.244; 6.D.154.228; 6.D.154.229; 6.D.154.230; 6.D.154.231; 6.D.154.236; 6.D.154.237; 6.D.154.238; 6.D.154.239; 6.D.154.154; 6.D.154.157; 6.D.154.166; 6.D.154.169; 6.D.154.172; 6.D.154.175; 6.D.154.240; 6.D.154.244; 6.D.157.228; 6.D.157.229; 6.D.157.230; 6.D.157.231; 6.D.157.236; 6.D.157.237; 6.D.157.238; 6.D.157.239; 6.D.157.154; 6.D.157.157; 6.D.157.166; 6.D.157.169; 6.D.157.172; 6.D.157.175; 6.D.157.240; 6.D.157.244; 6.D.166.228; 6.D.166.229; 6.D.166.230; 6.D.166.231; 6.D.166.236; 6.D.166.237; 6.D.166.238; 6.D.166.239; 6.D.166.154; 6.D.166.157; 6.D.166.166; 6.D.166.169; 6.D.166.172; 6.D.166.175; 6.D.166.240; 6.D.166.244; 6.D.169.228; 6.D.169.229; 6.D.169.230; 6.D.169.231; 6.D.169.236; 6.D.169.237; 6.D.169.238; 6.D.169.239; 6.D.169.154; 6.D.169.157; 6.D.169.166; 6.D.169.169; 6.D.169.172; 6.D.169.175; 6.D.169.240; 6.D.169.244; 6.D.172.228; 6.D.172.229; 6.D.172.230; 6.D.172.231; 6.D.172.236; 6.D.172.237; 6.D.172.238; 6.D.172.239; 6.D.172.154; 6.D.172.157; 6.D.172.166; 6.D.172.169; 6.D.172.172; 6.D.172.175; 6.D.172.240; 6.D.172.244; 6.D.175.228; 6.D.175.229; 6.D.175.230; 6.D.175.231; 6.D.175.236; 6.D.175.237; 6.D.175.238; 6.D.175.239; 6.D.175.154; 6.D.175.157; 6.D.175.166; 6.D.175.169; 6.D.175.172; 6.D.175.175; 6.D.175.240; 6.D.175.244; 6.D.240.228; 6.D.240.229; 6.D.240.230; 6.D.240.231; 6.D.240.236; 6.D.240.237; 6.D.240.238; 6.D.240.239; 6.D.240.154; 6.D.240.157; 6.D.240.166; 6.D.240.169; 6.D.240.172; 6.D.240.175; 6.D.240.240; 6.D.240.244; 6.D.244.228; 6.D.244.229; 6.D.244.230; 6.D.244.231; 6.D.244.236; 6.D.244.237; 6.D.244.238; 6.D.244.239; 6.D.244.154; 6.D.244.157; 6.D.244.166; 6.D.244.169; 6.D.244.172; 6.D.244.175; 6.D.244.240; 6.D.244.244;
Prodrugs of 6.E 6.E.228.228; 6.E.228.229; 6.E.228.230; 6.E.228.231; 6.E.228.236; 6.E.228.237; 6.E.228.238; 6.E.228.239; 6.E.228.154; 6.E.228.157; 6.E.228.166; 6.E.228.169; 6.E.228.172; 6.E.228.175; 6.E.228.240; 6.E.228.244; 6.E.229.228; 6.E.229.229; 6.E.229.230; 6.E.229.231; 6.E.229.236; 6.E.229.237; 6.E.229.238; 6.E.229.239; 6.E.229.154; 6.E.229.157; 6.E.229.166; 6.E.229.169; 6.E.229.172; 6.E.229.175; 6.E.229.240; 6.E.229.244; 6.E.230.228; 6.E.230.229; 6.E.230.230; 6.E.230.231; 6.E.230.236; 6.E.230.237; 6.E.230.238; 6.E.230.239; 6.E.230.154; 6.E.230.157; 6.E.230.166; 6.E.230.169; 6.E.230.172; 6.E.230.175; 6.E.230.240; 6.E.230.244; 6.E.231.228; 6.E.231.229; 6.E.231.230; 6.E.231.231; 6.E.231.236; 6.E.231.237; 6.E.231.238; 6.E.231.239; 6.E.231.154; 6.E.231.157; 6.E.231.166; 6.E.231.169; 6.E.231.172; 6.E.231.175; 6.E.231.240; 6.E.231.244; 6.E.236.228; 6.E.236.229; 6.E.236.230; 6.E.236.231; 6.E.236.236; 6.E.236.237; 6.E.236.238; 6.E.236.239; 6.E.236.154; 6.E.236.157; 6.E.236.166; 6.E.236.169; 6.E.236.172; 6.E.236.175; 6.E.236.240; 6.E.236.244; 6.E.237.228; 6.E.237.229; 6.E.237.230; 6.E.237.231; 6.E.237.236; 6.E.237.237; 6.E.237.238; 6.E.237.239; 6.E.237.154; 6.E.237.157; 6.E.237.166; 6.E.237.169; 6.E.237.172; 6.E.237.175; 6.E.237.240; 6.E.237.244; 6.E.238.228; 6.E.238.229; 6.E.238.230; 6.E.238.231; 6.E.238.236; 6.E.238.237; 6.E.238.238; 6.E.238.239; 6.E.238.154; 6.E.238.157; 6.E.238.166; 6.E.238.169; 6.E.238.172; 6.E.238.175; 6.E.238.240; 6.E.238.244; 6.E.239.228; 6.E.239.229; 6.E.239.230; 6.E.239.231; 6.E.239.236; 6.E.239.237; 6.E.239.238; 6.E.239.239; 6.E.239.154; 6.E.239.157; 6.E.239.166; 6.E.239.169; 6.E.239.172; 6.E.239.175; 6.E.239.240; 6.E.239.244; 6.E.154.228; 6.E.154.229; 6.E.154.230; 6.E.154.231; 6.E.154.236; 6.E.154.237; 6.E.154.238; 6.E.154.239; 6.E.154.154; 6.E.154.157; 6.E.154.166; 6.E.154.169; 6.E.154.172; 6.E.154.175; 6.E.154.240; 6.E.154.244; 6.E.157.228; 6.E.157.229; 6.E.157.230; 6.E.157.231; 6.E.157.236; 6.E.157.237; 6.E.157.238; 6.E.157.239; 6.E.157.154; 6.E.157.157; 6.E.157.166; 6.E.157.169; 6.E.157.172; 6.E.157.175; 6.E.157.240; 6.E.157.244; 6.E.166.228; 6.E.166.229; 6.E.166.230; 6.E.166.231; 6.E.166.236; 6.E.166.237; 6.E.166.238; 6.E.166.239; 6.E.166.154; 6.E.166.157; 6.E.166.166; 6.E.166.169; 6.E.166.172; 6.E.166.175; 6.E.166.240; 6.E.166.244; 6.E.169.228; 6.E.169.229; 6.E.169.230; 6.E.169.231; 6.E.169.236; 6.E.169.237; 6.E.169.238; 6.E.169.239; 6.E.169.154; 6.E.169.157; 6.E.169.166; 6.E.169.169; 6.E.169.172; 6.E.169.175; 6.E.169.240; 6.E.169.244; 6.E.172.228; 6.E.172.229; 6.E.172.230; 6.E.172.231; 6.E.172.236; 6.E.172.237; 6.E.172.238; 6.E.172.239; 6.E.172.154; 6.E.172.157; 6.E.172.166; 6.E.172.169; 6.E.172.172; 6.E.172.175; 6.E.172.240; 6.E.172.244; 6.E.175.228; 6.E.175.229; 6.E.175.230; 6.E.175.231; 6.E.175.236; 6.E.175.237; 6.E.175.238; 6.E.175.239; 6.E.175.154; 6.E.175.157; 6.E.175.166; 6.E.175.169; 6.E.175.172; 6.E.175.175; 6.E.175.240; 6.E.175.244; 6.E.240.228; 6.E.240.229; 6.E.240.230; 6.E.240.231; 6.E.240.236; 6.E.240.237; 6.E.240.238; 6.E.240.239; 6.E.240.154; 6.E.240.157; 6.E.240.166; 6.E.240.169; 6.E.240.172; 6.E.240.175; 6.E.240.240; 6.E.240.244; 6.E.244.228; 6.E.244.229; 6.E.244.230; 6.E.244.231; 6.E.244.236; 6.E.244.237; 6.E.244.238; 6.E.244.239; 6.E.244.154; 6.E.244.157; 6.E.244.166; 6.E.244.169; 6.E.244.172; 6.E.244.175; 6.E.244.240; 6.E.244.244;
Prodrugs of 6.G 6.G.228.228; 6.G.228.229; 6.G.228.230; 6.G.228.231; 6.G.228.236; 6.G.228.237; 6.G.228.238; 6.G.228.239; 6.G.228.154; 6.G.228.157; 6.G.228.166; 6.G.228.169; 6.G.228.172; 6.G.228.175; 6.G.228.240; 6.G.228.244; 6.G.229.228; 6.G.229.229; 6.G.229.230; 6.G.229.231; 6.G.229.236; 6.G.229.237; 6.G.229.238; 6.G.229.239; 6.G.229.154; 6.G.229.157; 6.G.229.166; 6.G.229.169; 6.G.229.172; 6.G.229.175; 6.G.229.240; 6.G.229.244; 6.G.230.228; 6.G.230.229; 6.G.230.230; 6.G.230.231; 6.G.230.236; 6.G.230.237; 6.G.230.238; 6.G.230.239; 6.G.230.154; 6.G.230.157; 6.G.230.166; 6.G.230.169; 6.G.230.172; 6.G.230.175; 6.G.230.240; 6.G.230.244; 6.G.231.228; 6.G.231.229; 6.G.231.230; 6.G.231.231; 6.G.231.236; 6.G.231.237; 6.G.231.238; 6.G.231.239; 6.G.231.154; 6.G.231.157; 6.G.231.166; 6.G.231.169; 6.G.231.172; 6.G.231.175; 6.G.231.240; 6.G.231.244; 6.G.236.228; 6.G.236.229; 6.G.236.230; 6.G.236.231; 6.G.236.236; 6.G.236.237; 6.G.236.238; 6.G.236.239; 6.G.236.154; 6.G.236.157; 6.G.236.166; 6.G.236.169; 6.G.236.172; 6.G.236.175; 6.G.236.240; 6.G.236.244; 6.G.237.228; 6.G.237.229; 6.G.237.230; 6.G.237.231; 6.G.237.236; 6.G.237.237; 6.G.237.238; 6.G.237.239; 6.G.237.154; 6.G.237.157; 6.G.237.166; 6.G.237.169; 6.G.237.172; 6.G.237.175; 6.G.237.240; 6.G.237.244; 6.G.238.228; 6.G.238.229; 6.G.238.230; 6.G.238.231; 6.G.238.236; 6.G.238.237; 6.G.238.238; 6.G.238.239; 6.G.238.154; 6.G.238.157; 6.G.238.166; 6.G.238.169; 6.G.238.172; 6.G.238.175; 6.G.238.240; 6.G.238.244; 6.G.239.228; 6.G.239.229; 6.G.239.230; 6.G.239.231; 6.G.239.236; 6.G.239.237; 6.G.239.238; 6.G.239.239; 6.G.239.154; 6.G.239.157; 6.G.239.166; 6.G.239.169; 6.G.239.172; 6.G.239.175; 6.G.239.240; 6.G.239.244; 6.G.154.228; 6.G.154.229; 6.G.154.230; 6.G.154.231; 6.G.154.236; 6.G.154.237; 6.G.154.238; 6.G.154.239; 6.G.154.154; 6.G.154.157; 6.G.154.166; 6.G.154.169; 6.G.154.172; 6.G.154.175; 6.G.154.240; 6.G.154.244; 6.G.157.228; 6.G.157.229; 6.G.157.230; 6.G.157.231; 6.G.157.236; 6.G.157.237; 6.G.157.238; 6.G.157.239; 6.G.157.154; 6.G.157.157; 6.G.157.166; 6.G.157.169; 6.G.157.172; 6.G.157.175; 6.G.157.240; 6.G.157.244; 6.G.166.228; 6.G.166.229; 6.G.166.230; 6.G.166.231; 6.G.166.236; 6.G.166.237; 6.G.166.238; 6.G.166.239; 6.G.166.154; 6.G.166.157; 6.G.166.166; 6.G.166.169; 6.G.166.172; 6.G.166.175; 6.G.166.240; 6.G.166.244; 6.G.169.228; 6.G.169.229; 6.G.169.230; 6.G.169.231;

TABLE 7-continued

6.G.169.236; 6.G.169.237; 6.G.169.238; 6.G.169.239; 6.G.169.154;
6.G.169.157; 6.G.169.166; 6.G.169.169; 6.G.169.172; 6.G.169.175;
6.G.169.240; 6.G.169.244; 6.G.172.228; 6.G.172.229; 6.G.172.230;
6.G.172.231; 6.G.172.236; 6.G.172.237; 6.G.172.238; 6.G.172.239;
6.G.172.154; 6.G.172.157; 6.G.172.166; 6.G.172.169; 6.G.172.172;
6.G.172.175; 6.G.172.240; 6.G.172.244; 6.G.175.228; 6.G.175.229;
6.G.175.230; 6.G.175.231; 6.G.175.236; 6.G.175.237; 6.G.175.238;
6.G.175.239; 6.G.175.154; 6.G.175.157; 6.G.175.166; 6.G.175.169;
6.G.175.172; 6.G.175.175; 6.G.175.240; 6.G.175.244; 6.G.240.228;
6.G.240.229; 6.G.240.230; 6.G.240.231; 6.G.240.236; 6.G.240.237;
6.G.240.238; 6.G.240.239; 6.G.240.154; 6.G.240.157; 6.G.240.166;
6.G.240.169; 6.G.240.172; 6.G.240.175; 6.G.240.240; 6.G.240.244;
6.G.244.228; 6.G.244.229; 6.G.244.230; 6.G.244.231; 6.G.244.236;
6.G.244.237; 6.G.244.238; 6.G.244.239; 6.G.244.154; 6.G.244.157;
6.G.244.166; 6.G.244.169; 6.G.244.172; 6.G.244.175; 6.G.244.240;
6.G.244.244;
Prodrugs of 6.I 6.I.228.228; 6.I.228.229; 6.I.228.230; 6.I.228.231; 6.I.228.236;
6.I.228.237; 6.I.228.238; 6.I.228.239; 6.I.228.154; 6.I.228.157;
6.I.228.166; 6.I.228.169; 6.I.228.172; 6.I.228.175; 6.I.228.240;
6.I.228.244; 6.I.229.228; 6.I.229.229; 6.I.229.230; 6.I.229.231;
6.I.229.236; 6.I.229.237; 6.I.229.238; 6.I.229.239; 6.I.229.154;
6.I.229.157; 6.I.229.166; 6.I.229.169; 6.I.229.172; 6.I.229.175;
6.I.229.240; 6.I.229.244; 6.I.230.228; 6.I.230.229; 6.I.230.230;
6.I.230.231; 6.I.230.236; 6.I.230.237; 6.I.230.238; 6.I.230.239;
6.I.230.154; 6.I.230.157; 6.I.230.166; 6.I.230.169; 6.I.230.172;
6.I.230.175; 6.I.230.240; 6.I.230.244; 6.I.231.228; 6.I.231.229;
6.I.231.230; 6.I.231.231; 6.I.231.236; 6.I.231.237; 6.I.231.238;
6.I.231.239; 6.I.231.154; 6.I.231.157; 6.I.231.166; 6.I.231.169;
6.I.231.172; 6.I.231.175; 6.I.231.240; 6.I.231.244; 6.I.236.228;
6.I.236.229; 6.I.236.230; 6.I.236.231; 6.I.236.236; 6.I.236.237;
6.I.236.238; 6.I.236.239; 6.I.236.154; 6.I.236.157; 6.I.236.166;
6.I.236.169; 6.I.236.172; 6.I.236.175; 6.I.236.240; 6.I.236.244;
6.I.237.228; 6.I.237.229; 6.I.237.230; 6.I.237.231; 6.I.237.236;
6.I.237.237; 6.I.237.238; 6.I.237.239; 6.I.237.154; 6.I.237.157;
6.I.237.166; 6.I.237.169; 6.I.237.172; 6.I.237.175; 6.I.237.240;
6.I.237.244; 6.I.238.228; 6.I.238.229; 6.I.238.230; 6.I.238.231;
6.I.238.236; 6.I.238.237; 6.I.238.238; 6.I.238.239; 6.I.238.154;
6.I.238.157; 6.I.238.166; 6.I.238.169; 6.I.238.172; 6.I.238.175;
6.I.238.240; 6.I.238.244; 6.I.239.228; 6.I.239.229; 6.I.239.230;
6.I.239.231; 6.I.239.236; 6.I.239.237; 6.I.239.238; 6.I.239.239;
6.I.239.154; 6.I.239.157; 6.I.239.166; 6.I.239.169; 6.I.239.172;
6.I.239.175; 6.I.239.240; 6.I.239.244; 6.I.154.228; 6.I.154.229;
6.I.154.230; 6.I.154.231; 6.I.154.236; 6.I.154.237; 6.I.154.238;
6.I.154.239; 6.I.154.154; 6.I.154.157; 6.I.154.166; 6.I.154.169;
6.I.154.172; 6.I.154.175; 6.I.154.240; 6.I.154.244; 6.I.157.228;
6.I.157.229; 6.I.157.230; 6.I.157.231; 6.I.157.236; 6.I.157.237;
6.I.157.238; 6.I.157.239; 6.I.157.154; 6.I.157.157; 6.I.157.166;
6.I.157.169; 6.I.157.172; 6.I.157.175; 6.I.157.240; 6.I.157.244;
6.I.166.228; 6.I.166.229; 6.I.166.230; 6.I.166.231; 6.I.166.236;
6.I.166.237; 6.I.166.238; 6.I.166.239; 6.I.166.154; 6.I.166.157;
6.I.166.166; 6.I.166.169; 6.I.166.172; 6.I.166.175; 6.I.166.240;
6.I.166.244; 6.I.169.228; 6.I.169.229; 6.I.169.230; 6.I.169.231;
6.I.169.236; 6.I.169.237; 6.I.169.238; 6.I.169.239; 6.I.169.154;
6.I.169.157; 6.I.169.166; 6.I.169.169; 6.I.169.172; 6.I.169.175;
6.I.169.240; 6.I.169.244; 6.I.172.228; 6.I.172.229; 6.I.172.230;
6.I.172.231; 6.I.172.236; 6.I.172.237; 6.I.172.238; 6.I.172.239;
6.I.172.154; 6.I.172.157; 6.I.172.166; 6.I.172.169; 6.I.172.172;
6.I.172.175; 6.I.172.240; 6.I.172.244; 6.I.175.228; 6.I.175.229;
6.I.175.230; 6.I.175.231; 6.I.175.236; 6.I.175.237; 6.I.175.238;
6.I.175.239; 6.I.175.154; 6.I.175.157; 6.I.175.166; 6.I.175.169;
6.I.175.172; 6.I.175.175; 6.I.175.240; 6.I.175.244; 6.I.240.228;
6.I.240.229; 6.I.240.230; 6.I.240.231; 6.I.240.236; 6.I.240.237;
6.I.240.238; 6.I.240.239; 6.I.240.154; 6.I.240.157; 6.I.240.166;
6.I.240.169; 6.I.240.172; 6.I.240.175; 6.I.240.240; 6.I.240.244;
6.I.244.228; 6.I.244.229; 6.I.244.230; 6.I.244.231; 6.I.244.236;
6.I.244.237; 6.I.244.238; 6.I.244.239; 6.I.244.154; 6.I.244.157;
6.I.244.166; 6.I.244.169; 6.I.244.172; 6.I.244.175; 6.I.244.240;
6.I.244.244;
Prodrugs of 6.J 6.J.228.228; 6.J.228.229; 6.J.228.230; 6.J.228.231; 6.J.228.236;
6.J.228.237; 6.J.228.238; 6.J.228.239; 6.J.228.154; 6.J.228.157;
6.J.228.166; 6.J.228.169; 6.J.228.172; 6.J.228.175; 6.J.228.240;
6.J.228.244; 6.J.229.228; 6.J.229.229; 6.J.229.230; 6.J.229.231;
6.J.229.236; 6.J.229.237; 6.J.229.238; 6.J.229.239; 6.J.229.154;
6.J.229.157; 6.J.229.166; 6.J.229.169; 6.J.229.172; 6.J.229.175;
6.J.229.240; 6.J.229.244; 6.J.230.228; 6.J.230.229; 6.J.230.230;
6.J.230.231; 6.J.230.236; 6.J.230.237; 6.J.230.238; 6.J.230.239;
6.J.230.154; 6.J.230.157; 6.J.230.166; 6.J.230.169; 6.J.230.172;
6.J.230.175; 6.J.230.240; 6.J.230.244; 6.J.231.228; 6.J.231.229;
6.J.231.230; 6.J.231.231; 6.J.231.236; 6.J.231.237; 6.J.231.238;
6.J.231.239; 6.J.231.154; 6.J.231.157; 6.J.231.166; 6.J.231.169;
6.J.231.172; 6.J.231.175; 6.J.231.240; 6.J.231.244; 6.J.236.228;
6.J.236.229; 6.J.236.230; 6.J.236.231; 6.J.236.236; 6.J.236.237;
6.J.236.238; 6.J.236.239; 6.J.236.154; 6.J.236.157; 6.J.236.166;
6.J.236.169; 6.J.236.172; 6.J.236.175; 6.J.236.240; 6.J.236.244;
6.J.237.228; 6.J.237.229; 6.J.237.230; 6.J.237.231; 6.J.237.236;
6.J.237.237; 6.J.237.238; 6.J.237.239; 6.J.237.154; 6.J.237.157;
6.J.237.166; 6.J.237.169; 6.J.237.172; 6.J.237.175; 6.J.237.240;
6.J.237.244; 6.J.238.228; 6.J.238.229; 6.J.238.230; 6.J.238.231;
6.J.238.236; 6.J.238.237; 6.J.238.238; 6.J.238.239; 6.J.238.154;
6.J.238.157; 6.J.238.166; 6.J.238.169; 6.J.238.172; 6.J.238.175;
6.J.238.240; 6.J.238.244; 6.J.239.228; 6.J.239.229; 6.J.239.230;
6.J.239.231; 6.J.239.236; 6.J.239.237; 6.J.239.238; 6.J.239.239;
6.J.239.154; 6.J.239.157; 6.J.239.166; 6.J.239.169; 6.J.239.172;
6.J.239.175; 6.J.239.240; 6.J.239.244; 6.J.154.228; 6.J.154.229;
6.J.154.230; 6.J.154.231; 6.J.154.236; 6.J.154.237; 6.J.154.238;
6.J.154.239; 6.J.154.154; 6.J.154.157; 6.J.154.166; 6.J.154.169;
6.J.154.172; 6.J.154.175; 6.J.154.240; 6.J.154.244; 6.J.157.228;
6.J.157.229; 6.J.157.230; 6.J.157.231; 6.J.157.236; 6.J.157.237;
6.J.157.238; 6.J.157.239; 6.J.157.154; 6.J.157.157; 6.J.157.166;
6.J.157.169; 6.J.157.172; 6.J.157.175; 6.J.157.240; 6.J.157.244;
6.J.166.228; 6.J.166.229; 6.J.166.230; 6.J.166.231; 6.J.166.236;
6.J.166.237; 6.J.166.238; 6.J.166.239; 6.J.166.154; 6.J.166.157;
6.J.166.166; 6.J.166.169; 6.J.166.172; 6.J.166.175; 6.J.166.240;
6.J.166.244; 6.J.169.228; 6.J.169.229; 6.J.169.230; 6.J.169.231;
6.J.169.236; 6.J.169.237; 6.J.169.238; 6.J.169.239; 6.J.169.154;
6.J.169.157; 6.J.169.166; 6.J.169.169; 6.J.169.172; 6.J.169.175;
6.J.169.240; 6.J.169.244; 6.J.172.228; 6.J.172.229; 6.J.172.230;
6.J.172.231; 6.J.172.236; 6.J.172.237; 6.J.172.238; 6.J.172.239;
6.J.172.154; 6.J.172.157; 6.J.172.166; 6.J.172.169; 6.J.172.172;
6.J.172.175; 6.J.172.240; 6.J.172.244; 6.J.175.228; 6.J.175.229;
6.J.175.230; 6.J.175.231; 6.J.175.236; 6.J.175.237; 6.J.175.238;
6.J.175.239; 6.J.175.154; 6.J.175.157; 6.J.175.166; 6.J.175.169;
6.J.175.172; 6.J.175.175; 6.J.175.240; 6.J.175.244; 6.J.240.228;
6.J.240.229; 6.J.240.230; 6.J.240.231; 6.J.240.236; 6.J.240.237;
6.J.240.238; 6.J.240.239; 6.J.240.154; 6.J.240.157; 6.J.240.166;
6.J.240.169; 6.J.240.172; 6.J.240.175; 6.J.240.240; 6.J.240.244;
6.J.244.228; 6.J.244.229; 6.J.244.230; 6.J.244.231; 6.J.244.236;
6.J.244.237; 6.J.244.238; 6.J.244.239; 6.J.244.154; 6.J.244.157;
6.J.244.166; 6.J.244.169; 6.J.244.172; 6.J.244.175; 6.J.244.240;
6.J.244.244;
Prodrugs of 6.L 6.L.228.228; 6.L.228.229; 6.L.228.230; 6.L.228.231; 6.L.228.236;
6.L.228.237; 6.L.228.238; 6.L.228.239; 6.L.228.154; 6.L.228.157;
6.L.228.166; 6.L.228.169; 6.L.228.172; 6.L.228.175; 6.L.228.240;
6.L.228.244; 6.L.229.228; 6.L.229.229; 6.L.229.230; 6.L.229.231;
6.L.229.236; 6.L.229.237; 6.L.229.238; 6.L.229.239; 6.L.229.154;
6.L.229.157; 6.L.229.166; 6.L.229.169; 6.L.229.172; 6.L.229.175;
6.L.229.240; 6.L.229.244; 6.L.230.228; 6.L.230.229; 6.L.230.230;
6.L.230.231; 6.L.230.236; 6.L.230.237; 6.L.230.238; 6.L.230.239;
6.L.230.154; 6.L.230.157; 6.L.230.166; 6.L.230.169; 6.L.230.172;
6.L.230.175; 6.L.230.240; 6.L.230.244; 6.L.231.228; 6.L.231.229;
6.L.231.230; 6.L.231.231; 6.L.231.236; 6.L.231.237; 6.L.231.238;
6.L.231.239; 6.L.231.154; 6.L.231.157; 6.L.231.166; 6.L.231.169;
6.L.231.172; 6.L.231.175; 6.L.231.240; 6.L.231.244; 6.L.236.228;
6.L.236.229; 6.L.236.230; 6.L.236.231; 6.L.236.236; 6.L.236.237;
6.L.236.238; 6.L.236.239; 6.L.236.154; 6.L.236.157; 6.L.236.166;
6.L.236.169; 6.L.236.172; 6.L.236.175; 6.L.236.240; 6.L.236.244;
6.L.237.228; 6.L.237.229; 6.L.237.230; 6.L.237.231; 6.L.237.236;
6.L.237.237; 6.L.237.238; 6.L.237.239; 6.L.237.154; 6.L.237.157;
6.L.237.166; 6.L.237.169; 6.L.237.172; 6.L.237.175; 6.L.237.240;
6.L.237.244; 6.L.238.228; 6.L.238.229; 6.L.238.230; 6.L.238.231;
6.L.238.236; 6.L.238.237; 6.L.238.238; 6.L.238.239; 6.L.238.154;
6.L.238.157; 6.L.238.166; 6.L.238.169; 6.L.238.172; 6.L.238.175;
6.L.238.240; 6.L.238.244; 6.L.239.228; 6.L.239.229; 6.L.239.230;
6.L.239.231; 6.L.239.236; 6.L.239.237; 6.L.239.238; 6.L.239.239;
6.L.239.154; 6.L.239.157; 6.L.239.166; 6.L.239.169; 6.L.239.172;
6.L.239.175; 6.L.239.240; 6.L.239.244; 6.L.154.228; 6.L.154.229;
6.L.154.230; 6.L.154.231; 6.L.154.236; 6.L.154.237; 6.L.154.238;
6.L.154.239; 6.L.154.154; 6.L.154.157; 6.L.154.166; 6.L.154.169;
6.L.154.172; 6.L.154.175; 6.L.154.240; 6.L.154.244; 6.L.157.228;
6.L.157.229; 6.L.157.230; 6.L.157.231; 6.L.157.236; 6.L.157.237;
6.L.157.238; 6.L.157.239; 6.L.157.154; 6.L.157.157; 6.L.157.166;
6.L.157.169; 6.L.157.172; 6.L.157.175; 6.L.157.240; 6.L.157.244;

TABLE 7-continued

6.L.166.228; 6.L.166.229; 6.L.166.230; 6.L.166.231; 6.L.166.236; 6.L.166.237; 6.L.166.238; 6.L.166.239; 6.L.166.154; 6.L.166.157; 6.L.166.166; 6.L.166.169; 6.L.166.172; 6.L.166.175; 6.L.166.240; 6.L.166.244; 6.L.169.228; 6.L.169.229; 6.L.169.230; 6.L.169.231; 6.L.169.236; 6.L.169.237; 6.L.169.238; 6.L.169.239; 6.L.169.154; 6.L.169.157; 6.L.169.166; 6.L.169.169; 6.L.169.172; 6.L.169.175; 6.L.169.240; 6.L.169.244; 6.L.172.228; 6.L.172.229; 6.L.172.230; 6.L.172.231; 6.L.172.236; 6.L.172.237; 6.L.172.238; 6.L.172.239; 6.L.172.154; 6.L.172.157; 6.L.172.166; 6.L.172.169; 6.L.172.172; 6.L.172.175; 6.L.172.240; 6.L.172.244; 6.L.175.228; 6.L.175.229; 6.L.175.230; 6.L.175.231; 6.L.175.236; 6.L.175.237; 6.L.175.238; 6.L.175.239; 6.L.175.154; 6.L.175.157; 6.L.175.166; 6.L.175.169; 6.L.175.172; 6.L.175.175; 6.L.175.240; 6.L.175.244; 6.L.240.228; 6.L.240.229; 6.L.240.230; 6.L.240.231; 6.L.240.236; 6.L.240.237; 6.L.240.238; 6.L.240.239; 6.L.240.154; 6.L.240.157; 6.L.240.166; 6.L.240.169; 6.L.240.172; 6.L.240.175; 6.L.240.240; 6.L.240.244; 6.L.244.228; 6.L.244.229; 6.L.244.230; 6.L.244.231; 6.L.244.236; 6.L.244.237; 6.L.244.238; 6.L.244.239; 6.L.244.154; 6.L.244.157; 6.L.244.166; 6.L.244.169; 6.L.244.172; 6.L.244.175; 6.L.244.240; 6.L.244.244;
Prodrugs of 6.O 6.O.228.228; 6.O.228.229; 6.O.228.230; 6.O.228.231; 6.O.228.236; 6.O.228.237; 6.O.228.238; 6.O.228.239; 6.O.228.154; 6.O.228.157; 6.O.228.166; 6.O.228.169; 6.O.228.172; 6.O.228.175; 6.O.228.240; 6.O.228.244; 6.O.229.228; 6.O.229.229; 6.O.229.230; 6.O.229.231; 6.O.229.236; 6.O.229.237; 6.O.229.238; 6.O.229.239; 6.O.229.154; 6.O.229.157; 6.O.229.166; 6.O.229.169; 6.O.229.172; 6.O.229.175; 6.O.229.240; 6.O.229.244; 6.O.230.228; 6.O.230.229; 6.O.230.230; 6.O.230.231; 6.O.230.236; 6.O.230.237; 6.O.230.238; 6.O.230.239; 6.O.230.154; 6.O.230.157; 6.O.230.166; 6.O.230.169; 6.O.230.172; 6.O.230.175; 6.O.230.240; 6.O.230.244; 6.O.231.228; 6.O.231.229; 6.O.231.230; 6.O.231.231; 6.O.231.236; 6.O.231.237; 6.O.231.238; 6.O.231.239; 6.O.231.154; 6.O.231.157; 6.O.231.166; 6.O.231.169; 6.O.231.172; 6.O.231.175; 6.O.231.240; 6.O.231.244; 6.O.236.228; 6.O.236.229; 6.O.236.230; 6.O.236.231; 6.O.236.236; 6.O.236.237; 6.O.236.238; 6.O.236.239; 6.O.236.154; 6.O.236.157; 6.O.236.166; 6.O.236.169; 6.O.236.172; 6.O.236.175; 6.O.236.240; 6.O.236.244; 6.O.237.228; 6.O.237.229; 6.O.237.230; 6.O.237.231; 6.O.237.236; 6.O.237.237; 6.O.237.238; 6.O.237.239; 6.O.237.154; 6.O.237.157; 6.O.237.166; 6.O.237.169; 6.O.237.172; 6.O.237.175; 6.O.237.240; 6.O.237.244; 6.O.238.228; 6.O.238.229; 6.O.238.230; 6.O.238.231; 6.O.238.236; 6.O.238.237; 6.O.238.238; 6.O.238.239; 6.O.238.154; 6.O.238.157; 6.O.238.166; 6.O.238.169; 6.O.238.172; 6.O.238.175; 6.O.238.240; 6.O.238.244; 6.O.239.228; 6.O.239.229; 6.O.239.230; 6.O.239.231; 6.O.239.236; 6.O.239.237; 6.O.239.238; 6.O.239.239; 6.O.239.154; 6.O.239.157; 6.O.239.166; 6.O.239.169; 6.O.239.172; 6.O.239.175; 6.O.239.240; 6.O.239.244; 6.O.154.228; 6.O.154.229; 6.O.154.230; 6.O.154.231; 6.O.154.236; 6.O.154.237; 6.O.154.238; 6.O.154.239; 6.O.154.154; 6.O.154.157; 6.O.154.166; 6.O.154.169; 6.O.154.172; 6.O.154.175; 6.O.154.240; 6.O.154.244; 6.O.157.228; 6.O.157.229; 6.O.157.230; 6.O.157.231; 6.O.157.236; 6.O.157.237; 6.O.157.238; 6.O.157.239; 6.O.157.154; 6.O.157.157; 6.O.157.166; 6.O.157.169; 6.O.157.172; 6.O.157.175; 6.O.157.240; 6.O.157.244; 6.O.166.228; 6.O.166.229; 6.O.166.230; 6.O.166.231; 6.O.166.236; 6.O.166.237; 6.O.166.238; 6.O.166.239; 6.O.166.154; 6.O.166.157; 6.O.166.166; 6.O.166.169; 6.O.166.172; 6.O.166.175; 6.O.166.240; 6.O.166.244; 6.O.169.228; 6.O.169.229; 6.O.169.230; 6.O.169.231; 6.O.169.236; 6.O.169.237; 6.O.169.238; 6.O.169.239; 6.O.169.154; 6.O.169.157; 6.O.169.166; 6.O.169.169; 6.O.169.172; 6.O.169.175; 6.O.169.240; 6.O.169.244; 6.O.172.228; 6.O.172.229; 6.O.172.230; 6.O.172.231; 6.O.172.236; 6.O.172.237; 6.O.172.238; 6.O.172.239; 6.O.172.154; 6.O.172.157; 6.O.172.166; 6.O.172.169; 6.O.172.172; 6.O.172.175; 6.O.172.240; 6.O.172.244; 6.O.175.228; 6.O.175.229; 6.O.175.230; 6.O.175.231; 6.O.175.236; 6.O.175.237; 6.O.175.238; 6.O.175.239; 6.O.175.154; 6.O.175.157; 6.O.175.166; 6.O.175.169; 6.O.175.172; 6.O.175.175; 6.O.175.240; 6.O.175.244; 6.O.240.228; 6.O.240.229; 6.O.240.230; 6.O.240.231; 6.O.240.236; 6.O.240.237; 6.O.240.238; 6.O.240.239; 6.O.240.154; 6.O.240.157; 6.O.240.166; 6.O.240.169; 6.O.240.172; 6.O.240.175; 6.O.240.240; 6.O.240.244; 6.O.244.228; 6.O.244.229; 6.O.244.230; 6.O.244.231; 6.O.244.236; 6.O.244.237; 6.O.244.238; 6.O.244.239; 6.O.244.154; 6.O.244.157; 6.O.244.166; 6.O.244.169; 6.O.244.172; 6.O.244.175; 6.O.244.240; 6.O.244.244;
Prodrugs of 6.P 6.P.228.228; 6.P.228.229; 6.P.228.230; 6.P.228.231; 6.P.228.236; 6.P.228.237; 6.P.228.238; 6.P.228.239; 6.P.228.154; 6.P.228.157; 6.P.228.166; 6.P.228.169; 6.P.228.172; 6.P.228.175; 6.P.228.240; 6.P.228.244; 6.P.229.228; 6.P.229.229; 6.P.229.230; 6.P.229.231; 6.P.229.236; 6.P.229.237; 6.P.229.238; 6.P.229.239; 6.P.229.154; 6.P.229.157; 6.P.229.166; 6.P.229.169; 6.P.229.172; 6.P.229.175; 6.P.229.240; 6.P.229.244; 6.P.230.228; 6.P.230.229; 6.P.230.230; 6.P.230.231; 6.P.230.236; 6.P.230.237; 6.P.230.238; 6.P.230.239; 6.P.230.154; 6.P.230.157; 6.P.230.166; 6.P.230.169; 6.P.230.172; 6.P.230.175; 6.P.230.240; 6.P.230.244; 6.P.231.228; 6.P.231.229; 6.P.231.230; 6.P.231.231; 6.P.231.236; 6.P.231.237; 6.P.231.238; 6.P.231.239; 6.P.231.154; 6.P.231.157; 6.P.231.166; 6.P.231.169; 6.P.231.172; 6.P.231.175; 6.P.231.240; 6.P.231.244; 6.P.236.228; 6.P.236.229; 6.P.236.230; 6.P.236.231; 6.P.236.236; 6.P.236.237; 6.P.236.238; 6.P.236.239; 6.P.236.154; 6.P.236.157; 6.P.236.166; 6.P.236.169; 6.P.236.172; 6.P.236.175; 6.P.236.240; 6.P.236.244; 6.P.237.228; 6.P.237.229; 6.P.237.230; 6.P.237.231; 6.P.237.236; 6.P.237.237; 6.P.237.238; 6.P.237.239; 6.P.237.154; 6.P.237.157; 6.P.237.166; 6.P.237.169; 6.P.237.172; 6.P.237.175; 6.P.237.240; 6.P.237.244; 6.P.238.228; 6.P.238.229; 6.P.238.230; 6.P.238.231; 6.P.238.236; 6.P.238.237; 6.P.238.238; 6.P.238.239; 6.P.238.154; 6.P.238.157; 6.P.238.166; 6.P.238.169; 6.P.238.172; 6.P.238.175; 6.P.238.240; 6.P.238.244; 6.P.239.228; 6.P.239.229; 6.P.239.230; 6.P.239.231; 6.P.239.236; 6.P.239.237; 6.P.239.238; 6.P.239.239; 6.P.239.154; 6.P.239.157; 6.P.239.166; 6.P.239.169; 6.P.239.172; 6.P.239.175; 6.P.239.240; 6.P.239.244; 6.P.154.228; 6.P.154.229; 6.P.154.230; 6.P.154.231; 6.P.154.236; 6.P.154.237; 6.P.154.238; 6.P.154.239; 6.P.154.154; 6.P.154.157; 6.P.154.166; 6.P.154.169; 6.P.154.172; 6.P.154.175; 6.P.154.240; 6.P.154.244; 6.P.157.228; 6.P.157.229; 6.P.157.230; 6.P.157.231; 6.P.157.236; 6.P.157.237; 6.P.157.238; 6.P.157.239; 6.P.157.154; 6.P.157.157; 6.P.157.166; 6.P.157.169; 6.P.157.172; 6.P.157.175; 6.P.157.240; 6.P.157.244; 6.P.166.228; 6.P.166.229; 6.P.166.230; 6.P.166.231; 6.P.166.236; 6.P.166.237; 6.P.166.238; 6.P.166.239; 6.P.166.154; 6.P.166.157; 6.P.166.166; 6.P.166.169; 6.P.166.172; 6.P.166.175; 6.P.166.240; 6.P.166.244; 6.P.169.228; 6.P.169.229; 6.P.169.230; 6.P.169.231; 6.P.169.236; 6.P.169.237; 6.P.169.238; 6.P.169.239; 6.P.169.154; 6.P.169.157; 6.P.169.166; 6.P.169.169; 6.P.169.172; 6.P.169.175; 6.P.169.240; 6.P.169.244; 6.P.172.228; 6.P.172.229; 6.P.172.230; 6.P.172.231; 6.P.172.236; 6.P.172.237; 6.P.172.238; 6.P.172.239; 6.P.172.154; 6.P.172.157; 6.P.172.166; 6.P.172.169; 6.P.172.172; 6.P.172.175; 6.P.172.240; 6.P.172.244; 6.P.175.228; 6.P.175.229; 6.P.175.230; 6.P.175.231; 6.P.175.236; 6.P.175.237; 6.P.175.238; 6.P.175.239; 6.P.175.154; 6.P.175.157; 6.P.175.166; 6.P.175.169; 6.P.175.172; 6.P.175.175; 6.P.175.240; 6.P.175.244; 6.P.240.228; 6.P.240.229; 6.P.240.230; 6.P.240.231; 6.P.240.236; 6.P.240.237; 6.P.240.238; 6.P.240.239; 6.P.240.154; 6.P.240.157; 6.P.240.166; 6.P.240.169; 6.P.240.172; 6.P.240.175; 6.P.240.240; 6.P.240.244; 6.P.244.228; 6.P.244.229; 6.P.244.230; 6.P.244.231; 6.P.244.236; 6.P.244.237; 6.P.244.238; 6.P.244.239; 6.P.244.154; 6.P.244.157; 6.P.244.166; 6.P.244.169; 6.P.244.172; 6.P.244.175; 6.P.244.240; 6.P.244.244;
Prodrugs of 6.U 6.U.228.228; 6.U.228.229; 6.U.228.230; 6.U.228.231; 6.U.228.236; 6.U.228.237; 6.U.228.238; 6.U.228.239; 6.U.228.154; 6.U.228.157; 6.U.228.166; 6.U.228.169; 6.U.228.172; 6.U.228.175; 6.U.228.240; 6.U.228.244; 6.U.229.228; 6.U.229.229; 6.U.229.230; 6.U.229.231; 6.U.229.236; 6.U.229.237; 6.U.229.238; 6.U.229.239; 6.U.229.154; 6.U.229.157; 6.U.229.166; 6.U.229.169; 6.U.229.172; 6.U.229.175; 6.U.229.240; 6.U.229.244; 6.U.230.228; 6.U.230.229; 6.U.230.230; 6.U.230.231; 6.U.230.236; 6.U.230.237; 6.U.230.238; 6.U.230.239; 6.U.230.154; 6.U.230.157; 6.U.230.166; 6.U.230.169; 6.U.230.172; 6.U.230.175; 6.U.230.240; 6.U.230.244; 6.U.231.228; 6.U.231.229; 6.U.231.230; 6.U.231.231; 6.U.231.236; 6.U.231.237; 6.U.231.238; 6.U.231.239; 6.U.231.154; 6.U.231.157; 6.U.231.166; 6.U.231.169; 6.U.231.172; 6.U.231.175; 6.U.231.240; 6.U.231.244; 6.U.236.228; 6.U.236.229; 6.U.236.230; 6.U.236.231; 6.U.236.236; 6.U.236.237; 6.U.236.238; 6.U.236.239; 6.U.236.154; 6.U.236.157; 6.U.236.166; 6.U.236.169; 6.U.236.172; 6.U.236.175; 6.U.236.240; 6.U.236.244; 6.U.237.228; 6.U.237.229; 6.U.237.230; 6.U.237.231; 6.U.237.236; 6.U.237.237; 6.U.237.238; 6.U.237.239; 6.U.237.154; 6.U.237.157; 6.U.237.166; 6.U.237.169; 6.U.237.172; 6.U.237.175; 6.U.237.240; 6.U.237.244; 6.U.238.228; 6.U.238.229; 6.U.238.230; 6.U.238.231; 6.U.238.236; 6.U.238.237; 6.U.238.238; 6.U.238.239; 6.U.238.154; 6.U.238.157; 6.U.238.166; 6.U.238.169; 6.U.238.172; 6.U.238.175; 6.U.238.240; 6.U.238.244; 6.U.239.228; 6.U.239.229; 6.U.239.230; 6.U.239.231; 6.U.239.236; 6.U.239.237; 6.U.239.238; 6.U.239.239; 6.U.239.154; 6.U.239.157; 6.U.239.166; 6.U.239.169; 6.U.239.172; 6.U.239.175; 6.U.239.240; 6.U.239.244; 6.U.154.228; 6.U.154.229; 6.U.154.230; 6.U.154.231; 6.U.154.236; 6.U.154.237; 6.U.154.238; 6.U.154.239; 6.U.154.154; 6.U.154.157; 6.U.154.166; 6.U.154.169;

TABLE 7-continued

6.U.154.172; 6.U.154.175; 6.U.154.240; 6.U.154.244; 6.U.157.228; 6.U.157.229; 6.U.157.230; 6.U.157.231; 6.U.157.236; 6.U.157.237; 6.U.157.238; 6.U.157.239; 6.U.157.154; 6.U.157.157; 6.U.157.166; 6.U.157.169; 6.U.157.172; 6.U.157.175; 6.U.157.240; 6.U.157.244; 6.U.166.228; 6.U.166.229; 6.U.166.230; 6.U.166.231; 6.U.166.236; 6.U.166.237; 6.U.166.238; 6.U.166.239; 6.U.166.154; 6.U.166.157; 6.U.166.166; 6.U.166.169; 6.U.166.172; 6.U.166.175; 6.U.166.240; 6.U.166.244; 6.U.169.228; 6.U.169.229; 6.U.169.230; 6.U.169.231; 6.U.169.236; 6.U.169.237; 6.U.169.238; 6.U.169.239; 6.U.169.154; 6.U.169.157; 6.U.169.166; 6.U.169.169; 6.U.169.172; 6.U.169.175; 6.U.169.240; 6.U.169.244; 6.U.172.228; 6.U.172.229; 6.U.172.230; 6.U.172.231; 6.U.172.236; 6.U.172.237; 6.U.172.238; 6.U.172.239; 6.U.172.154; 6.U.172.157; 6.U.172.166; 6.U.172.169; 6.U.172.172; 6.U.172.175; 6.U.172.240; 6.U.172.244; 6.U.175.228; 6.U.175.229; 6.U.175.230; 6.U.175.231; 6.U.175.236; 6.U.175.237; 6.U.175.238; 6.U.175.239; 6.U.175.154; 6.U.175.157; 6.U.175.166; 6.U.175.169; 6.U.175.172; 6.U.175.175; 6.U.175.240; 6.U.175.244; 6.U.240.228; 6.U.240.229; 6.U.240.230; 6.U.240.231; 6.U.240.236; 6.U.240.237; 6.U.240.238; 6.U.240.239; 6.U.240.154; 6.U.240.157; 6.U.240.166; 6.U.240.169; 6.U.240.172; 6.U.240.175; 6.U.240.240; 6.U.240.244; 6.U.244.228; 6.U.244.229; 6.U.244.230; 6.U.244.231; 6.U.244.236; 6.U.244.237; 6.U.244.238; 6.U.244.239; 6.U.244.154; 6.U.244.157; 6.U.244.166; 6.U.244.169; 6.U.244.172; 6.U.244.175; 6.U.244.240; 6.U.244.244;

Prodrugs of 6.W

6.W.228.228; 6.W.228.229; 6.W.228.230; 6.W.228.231; 6.W.228.236; 6.W.228.237; 6.W.228.238; 6.W.228.239; 6.W.228.154; 6.W.228.157; 6.W.228.166; 6.W.228.169; 6.W.228.172; 6.W.228.175; 6.W.228.240; 6.W.228.244; 6.W.229.228; 6.W.229.229; 6.W.229.230; 6.W.229.231; 6.W.229.236; 6.W.229.237; 6.W.229.238; 6.W.229.239; 6.W.229.154; 6.W.229.157; 6.W.229.166; 6.W.229.169; 6.W.229.172; 6.W.229.175; 6.W.229.240; 6.W.229.244; 6.W.230.228; 6.W.230.229; 6.W.230.230; 6.W.230.231; 6.W.230.236; 6.W.230.237; 6.W.230.238; 6.W.230.239; 6.W.230.154; 6.W.230.157; 6.W.230.166; 6.W.230.169; 6.W.230.172; 6.W.230.175; 6.W.230.240; 6.W.230.244; 6.W.231.228; 6.W.231.229; 6.W.231.230; 6.W.231.231; 6.W.231.236; 6.W.231.237; 6.W.231.238; 6.W.231.239; 6.W.231.154; 6.W.231.157; 6.W.231.166; 6.W.231.169; 6.W.231.172; 6.W.231.175; 6.W.231.240; 6.W.231.244; 6.W.236.228; 6.W.236.229; 6.W.236.230; 6.W.236.231; 6.W.236.236; 6.W.236.237; 6.W.236.238; 6.W.236.239; 6.W.236.154; 6.W.236.157; 6.W.236.166; 6.W.236.169; 6.W.236.172; 6.W.236.175; 6.W.236.240; 6.W.236.244; 6.W.237.228; 6.W.237.229; 6.W.237.230; 6.W.237.231; 6.W.237.236; 6.W.237.237; 6.W.237.238; 6.W.237.239; 6.W.237.154; 6.W.237.157; 6.W.237.166; 6.W.237.169; 6.W.237.172; 6.W.237.175; 6.W.237.240; 6.W.237.244; 6.W.238.228; 6.W.238.229; 6.W.238.230; 6.W.238.231; 6.W.238.236; 6.W.238.237; 6.W.238.238; 6.W.238.239; 6.W.238.154; 6.W.238.157; 6.W.238.166; 6.W.238.169; 6.W.238.172; 6.W.238.175; 6.W.238.240; 6.W.238.244; 6.W.239.228; 6.W.239.229; 6.W.239.230; 6.W.239.231; 6.W.239.236; 6.W.239.237; 6.W.239.238; 6.W.239.239; 6.W.239.154; 6.W.239.157; 6.W.239.166; 6.W.239.169; 6.W.239.172; 6.W.239.175; 6.W.239.240; 6.W.239.244; 6.W.154.228; 6.W.154.229; 6.W.154.230; 6.W.154.231; 6.W.154.236; 6.W.154.237; 6.W.154.238; 6.W.154.239; 6.W.154.154; 6.W.154.157; 6.W.154.166; 6.W.154.169; 6.W.154.172; 6.W.154.175; 6.W.154.240; 6.W.154.244; 6.W.157.228; 6.W.157.229; 6.W.157.230; 6.W.157.231; 6.W.157.236; 6.W.157.237; 6.W.157.238; 6.W.157.239; 6.W.157.154; 6.W.157.157; 6.W.157.166; 6.W.157.169; 6.W.157.172; 6.W.157.175; 6.W.157.240; 6.W.157.244; 6.W.166.228; 6.W.166.229; 6.W.166.230; 6.W.166.231; 6.W.166.236; 6.W.166.237; 6.W.166.238; 6.W.166.239; 6.W.166.154; 6.W.166.157; 6.W.166.166; 6.W.166.169; 6.W.166.172; 6.W.166.175; 6.W.166.240; 6.W.166.244; 6.W.169.228; 6.W.169.229; 6.W.169.230; 6.W.169.231; 6.W.169.236; 6.W.169.237; 6.W.169.238; 6.W.169.239; 6.W.169.154; 6.W.169.157; 6.W.169.166; 6.W.169.169; 6.W.169.172; 6.W.169.175; 6.W.169.240; 6.W.169.244; 6.W.172.228; 6.W.172.229; 6.W.172.230; 6.W.172.231; 6.W.172.236; 6.W.172.237; 6.W.172.238; 6.W.172.239; 6.W.172.154; 6.W.172.157; 6.W.172.166; 6.W.172.169; 6.W.172.172; 6.W.172.175; 6.W.172.240; 6.W.172.244; 6.W.175.228; 6.W.175.229; 6.W.175.230; 6.W.175.231; 6.W.175.236; 6.W.175.237; 6.W.175.238; 6.W.175.239; 6.W.175.154; 6.W.175.157; 6.W.175.166; 6.W.175.169; 6.W.175.172; 6.W.175.175; 6.W.175.240; 6.W.175.244; 6.W.240.228; 6.W.240.229; 6.W.240.230; 6.W.240.231; 6.W.240.236; 6.W.240.237; 6.W.240.238; 6.W.240.239; 6.W.240.154; 6.W.240.157; 6.W.240.166; 6.W.240.169; 6.W.240.172; 6.W.240.175; 6.W.240.240; 6.W.240.244; 6.W.244.228; 6.W.244.229; 6.W.244.230; 6.W.244.231; 6.W.244.236; 6.W.244.237; 6.W.244.238; 6.W.244.239; 6.W.244.154; 6.W.244.157; 6.W.244.166; 6.W.244.169; 6.W.244.172; 6.W.244.175; 6.W.244.240; 6.W.244.244;

Prodrugs of 6.Y

6.Y.228.228; 6.Y.228.229; 6.Y.228.230; 6.Y.228.231; 6.Y.228.236; 6.Y.228.237; 6.Y.228.238; 6.Y.228.239; 6.Y.228.154; 6.Y.228.157; 6.Y.228.166; 6.Y.228.169; 6.Y.228.172; 6.Y.228.175; 6.Y.228.240; 6.Y.228.244; 6.Y.229.228; 6.Y.229.229; 6.Y.229.230; 6.Y.229.231; 6.Y.229.236; 6.Y.229.237; 6.Y.229.238; 6.Y.229.239; 6.Y.229.154; 6.Y.229.157; 6.Y.229.166; 6.Y.229.169; 6.Y.229.172; 6.Y.229.175; 6.Y.229.240; 6.Y.229.244; 6.Y.230.228; 6.Y.230.229; 6.Y.230.230; 6.Y.230.231; 6.Y.230.236; 6.Y.230.237; 6.Y.230.238; 6.Y.230.239; 6.Y.230.154; 6.Y.230.157; 6.Y.230.166; 6.Y.230.169; 6.Y.230.172; 6.Y.230.175; 6.Y.230.240; 6.Y.230.244; 6.Y.231.228; 6.Y.231.229; 6.Y.231.230; 6.Y.231.231; 6.Y.231.236; 6.Y.231.237; 6.Y.231.238; 6.Y.231.239; 6.Y.231.154; 6.Y.231.157; 6.Y.231.166; 6.Y.231.169; 6.Y.231.172; 6.Y.231.175; 6.Y.231.240; 6.Y.231.244; 6.Y.236.228; 6.Y.236.229; 6.Y.236.230; 6.Y.236.231; 6.Y.236.236; 6.Y.236.237; 6.Y.236.238; 6.Y.236.239; 6.Y.236.154; 6.Y.236.157; 6.Y.236.166; 6.Y.236.169; 6.Y.236.172; 6.Y.236.175; 6.Y.236.240; 6.Y.236.244; 6.Y.237.228; 6.Y.237.229; 6.Y.237.230; 6.Y.237.231; 6.Y.237.236; 6.Y.237.237; 6.Y.237.238; 6.Y.237.239; 6.Y.237.154; 6.Y.237.157; 6.Y.237.166; 6.Y.237.169; 6.Y.237.172; 6.Y.237.175; 6.Y.237.240; 6.Y.237.244; 6.Y.238.228; 6.Y.238.229; 6.Y.238.230; 6.Y.238.231; 6.Y.238.236; 6.Y.238.237; 6.Y.238.238; 6.Y.238.239; 6.Y.238.154; 6.Y.238.157; 6.Y.238.166; 6.Y.238.169; 6.Y.238.172; 6.Y.238.175; 6.Y.238.240; 6.Y.238.244; 6.Y.239.228; 6.Y.239.229; 6.Y.239.230; 6.Y.239.231; 6.Y.239.236; 6.Y.239.237; 6.Y.239.238; 6.Y.239.239; 6.Y.239.154; 6.Y.239.157; 6.Y.239.166; 6.Y.239.169; 6.Y.239.172; 6.Y.239.175; 6.Y.239.240; 6.Y.239.244; 6.Y.154.228; 6.Y.154.229; 6.Y.154.230; 6.Y.154.231; 6.Y.154.236; 6.Y.154.237; 6.Y.154.238; 6.Y.154.239; 6.Y.154.154; 6.Y.154.157; 6.Y.154.166; 6.Y.154.169; 6.Y.154.172; 6.Y.154.175; 6.Y.154.240; 6.Y.154.244; 6.Y.157.228; 6.Y.157.229; 6.Y.157.230; 6.Y.157.231; 6.Y.157.236; 6.Y.157.237; 6.Y.157.238; 6.Y.157.239; 6.Y.157.154; 6.Y.157.157; 6.Y.157.166; 6.Y.157.169; 6.Y.157.172; 6.Y.157.175; 6.Y.157.240; 6.Y.157.244; 6.Y.166.228; 6.Y.166.229; 6.Y.166.230; 6.Y.166.231; 6.Y.166.236; 6.Y.166.237; 6.Y.166.238; 6.Y.166.239; 6.Y.166.154; 6.Y.166.157; 6.Y.166.166; 6.Y.166.169; 6.Y.166.172; 6.Y.166.175; 6.Y.166.240; 6.Y.166.244; 6.Y.169.228; 6.Y.169.229; 6.Y.169.230; 6.Y.169.231; 6.Y.169.236; 6.Y.169.237; 6.Y.169.238; 6.Y.169.239; 6.Y.169.154; 6.Y.169.157; 6.Y.169.166; 6.Y.169.169; 6.Y.169.172; 6.Y.169.175; 6.Y.169.240; 6.Y.169.244; 6.Y.172.228; 6.Y.172.229; 6.Y.172.230; 6.Y.172.231; 6.Y.172.236; 6.Y.172.237; 6.Y.172.238; 6.Y.172.239; 6.Y.172.154; 6.Y.172.157; 6.Y.172.166; 6.Y.172.169; 6.Y.172.172; 6.Y.172.175; 6.Y.172.240; 6.Y.172.244; 6.Y.175.228; 6.Y.175.229; 6.Y.175.230; 6.Y.175.231; 6.Y.175.236; 6.Y.175.237; 6.Y.175.238; 6.Y.175.239; 6.Y.175.154; 6.Y.175.157; 6.Y.175.166; 6.Y.175.169; 6.Y.175.172; 6.Y.175.175; 6.Y.175.240; 6.Y.175.244; 6.Y.240.228; 6.Y.240.229; 6.Y.240.230; 6.Y.240.231; 6.Y.240.236; 6.Y.240.237; 6.Y.240.238; 6.Y.240.239; 6.Y.240.154; 6.Y.240.157; 6.Y.240.166; 6.Y.240.169; 6.Y.240.172; 6.Y.240.175; 6.Y.240.240; 6.Y.240.244; 6.Y.244.228; 6.Y.244.229; 6.Y.244.230; 6.Y.244.231; 6.Y.244.236; 6.Y.244.237; 6.Y.244.238; 6.Y.244.239; 6.Y.244.154; 6.Y.244.157; 6.Y.244.166; 6.Y.244.169; 6.Y.244.172; 6.Y.244.175; 6.Y.244.240; 6.Y.244.244;

Prodrugs of 7.AH

7.AH.4.157; 7.AH.4.158; 7.AH.4.196; 7.AH.4.223; 7.AH.4.240; 7.AH.4.244; 7.AH.4.243; 7.AH.4.247; 7.AH.5.157; 7.AH.5.158; 7.AH.5.196; 7.AH.5.223; 7.AH.5.240; 7.AH.5.244; 7.AH.5.243; 7.AH.5.247; 7.AH.7.157; 7.AH.7.158; 7.AH.7.196; 7.AH.7.223; 7.AH.7.240; 7.AH.7.244; 7.AH.7.243; 7.AH.7.247; 7.AH.15.157; 7.AH.15.158; 7.AH.15.196; 7.AH.15.223; 7.AH.15.240; 7.AH.15.244; 7.AH.15.243; 7.AH.15.247; 7.AH.16.157; 7.AH.16.158; 7.AH.16.196; 7.AH.16.223; 7.AH.16.240; 7.AH.16.244; 7.AH.16.243; 7.AH.16.247; 7.AH.18.157; 7.AH.18.158; 7.AH.18.196; 7.AH.18.223; 7.AH.18.240; 7.AH.18.244; 7.AH.18.243; 7.AH.18.247; 7.AH.26.157; 7.AH.26.158; 7.AH.26.196; 7.AH.26.223; 7.AH.26.240; 7.AH.26.244; 7.AH.26.243; 7.AH.26.247; 7.AH.27.157; 7.AH.27.158; 7.AH.27.196; 7.AH.27.223; 7.AH.27.240; 7.AH.27.244; 7.AH.27.243; 7.AH.27.247; 7.AH.29.157; 7.AH.29.158; 7.AH.29.196; 7.AH.29.223; 7.AH.29.240; 7.AH.29.244; 7.AH.29.243; 7.AH.29.247; 7.AH.54.157; 7.AH.54.158; 7.AH.54.196; 7.AH.54.223; 7.AH.54.240; 7.AH.54.244; 7.AH.54.243; 7.AH.54.247; 7.AH.55.157; 7.AH.55.158; 7.AH.55.196; 7.AH.55.223; 7.AH.55.240; 7.AH.55.244; 7.AH.55.243; 7.AH.55.247; 7.AH.56.157; 7.AH.56.158; 7.AH.56.196; 7.AH.56.223; 7.AH.56.240; 7.AH.56.244; 7.AH.56.243; 7.AH.56.247; 7.AH.157.157; 7.AH.157.158; 7.AH.157.196; 7.AH.157.223; 7.AH.157.240; 7.AH.157.244; 7.AH.157.243; 7.AH.157.247; 7.AH.196.157; 7.AH.196.158; 7.AH.196.196; 7.AH.196.223; 7.AH.196.240; 7.AH.196.244; 7.AH.196.243;

TABLE 7-continued

7.AH.196.247; 7.AH.223.157; 7.AH.223.158; 7.AH.223.196; 7.AH.223.223; 7.AH.223.240; 7.AH.223.244; 7.AH.223.243; 7.AH.223.247; 7.AH.240.157; 7.AH.240.158; 7.AH.240.196; 7.AH.240.223; 7.AH.240.240; 7.AH.240.244; 7.AH.240.243; 7.AH.240.247; 7.AH.244.157; 7.AH.244.158; 7.AH.244.196; 7.AH.244.223; 7.AH.244.240; 7.AH.244.244; 7.AH.244.243; 7.AH.244.247; 7.AH.247.157; 7.AH.247.158; 7.AH.247.196; 7.AH.247.223; 7.AH.247.240; 7.AH.247.244; 7.AH.247.243; 7.AH.247.247;
Prodrugs of 7.AJ 7.AJ.4.157; 7.AJ.4.158; 7.AJ.4.196; 7.AJ.4.223; 7.AJ.4.240; 7.AJ.4.244; 7.AJ.4.243; 7.AJ.4.247; 7.AJ.5.157; 7.AJ.5.158; 7.AJ.5.196; 7.AJ.5.223; 7.AJ.5.240; 7.AJ.5.244; 7.AJ.5.243; 7.AJ.5.247; 7.AJ.7.157; 7.AJ.7.158; 7.AJ.7.196; 7.AJ.7.223; 7.AJ.7.240; 7.AJ.7.244; 7.AJ.7.243; 7.AJ.7.247; 7.AJ.15.157; 7.AJ.15.158; 7.AJ.15.196; 7.AJ.15.223; 7.AJ.15.240; 7.AJ.15.244; 7.AJ.15.243; 7.AJ.15.247; 7.AJ.16.157; 7.AJ.16.158; 7.AJ.16.196; 7.AJ.16.223; 7.AJ.16.240; 7.AJ.16.244; 7.AJ.16.243; 7.AJ.16.247; 7.AJ.18.157; 7.AJ.18.158; 7.AJ.18.196; 7.AJ.18.223; 7.AJ.18.240; 7.AJ.18.244; 7.AJ.18.243; 7.AJ.18.247; 7.AJ.26.157; 7.AJ.26.158; 7.AJ.26.196; 7.AJ.26.223; 7.AJ.26.240; 7.AJ.26.244; 7.AJ.26.243; 7.AJ.26.247; 7.AJ.27.157; 7.AJ.27.158; 7.AJ.27.196; 7.AJ.27.223; 7.AJ.27.240; 7.AJ.27.244; 7.AJ.27.243; 7.AJ.27.247; 7.AJ.29.157; 7.AJ.29.158; 7.AJ.29.196; 7.AJ.29.223; 7.AJ.29.240; 7.AJ.29.244; 7.AJ.29.243; 7.AJ.29.247; 7.AJ.54.157; 7.AJ.54.158; 7.AJ.54.196; 7.AJ.54.223; 7.AJ.54.240; 7.AJ.54.244; 7.AJ.54.243; 7.AJ.54.247; 7.AJ.55.157; 7.AJ.55.158; 7.AJ.55.196; 7.AJ.55.223; 7.AJ.55.240; 7.AJ.55.244; 7.AJ.55.243; 7.AJ.55.247; 7.AJ.56.157; 7.AJ.56.158; 7.AJ.56.196; 7.AJ.56.223; 7.AJ.56.240; 7.AJ.56.244; 7.AJ.56.243; 7.AJ.56.247; 7.AJ.157.157; 7.AJ.157.158; 7.AJ.157.196; 7.AJ.157.223; 7.AJ.157.240; 7.AJ.157.244; 7.AJ.157.243; 7.AJ.157.247; 7.AJ.196.157; 7.AJ.196.158; 7.AJ.196.196; 7.AJ.196.223; 7.AJ.196.240; 7.AJ.196.244; 7.AJ.196.243; 7.AJ.196.247; 7.AJ.223.157; 7.AJ.223.158; 7.AJ.223.196; 7.AJ.223.223; 7.AJ.223.240; 7.AJ.223.244; 7.AJ.223.243; 7.AJ.223.247; 7.AJ.240.157; 7.AJ.240.158; 7.AJ.240.196; 7.AJ.240.223; 7.AJ.240.240; 7.AJ.240.244; 7.AJ.240.243; 7.AJ.240.247; 7.AJ.244.157; 7.AJ.244.158; 7.AJ.244.196; 7.AJ.244.223; 7.AJ.244.240; 7.AJ.244.244; 7.AJ.244.243; 7.AJ.244.247; 7.AJ.247.157; 7.AJ.247.158; 7.AJ.247.196; 7.AJ.247.223; 7.AJ.247.240; 7.AJ.247.244; 7.AJ.247.243; 7.AJ.247.247;
Prodrugs of 7.AN 7.AN.4.157; 7.AN.4.158; 7.AN.4.196; 7.AN.4.223; 7.AN.4.240; 7.AN.4.244; 7.AN.4.243; 7.AN.4.247; 7.AN.5.157; 7.AN.5.158; 7.AN.5.196; 7.AN.5.223; 7.AN.5.240; 7.AN.5.244; 7.AN.5.243; 7.AN.5.247; 7.AN.7.157; 7.AN.7.158; 7.AN.7.196; 7.AN.7.223; 7.AN.7.240; 7.AN.7.244; 7.AN.7.243; 7.AN.7.247; 7.AN.15.157; 7.AN.15.158; 7.AN.15.196; 7.AN.15.223; 7.AN.15.240; 7.AN.15.244; 7.AN.15.243; 7.AN.15.247; 7.AN.16.157; 7.AN.16.158; 7.AN.16.196; 7.AN.16.223; 7.AN.16.240; 7.AN.16.244; 7.AN.16.243; 7.AN.16.247; 7.AN.18.157; 7.AN.18.158; 7.AN.18.196; 7.AN.18.223; 7.AN.18.240; 7.AN.18.244; 7.AN.18.243; 7.AN.18.247; 7.AN.26.157; 7.AN.26.158; 7.AN.26.196; 7.AN.26.223; 7.AN.26.240; 7.AN.26.244; 7.AN.26.243; 7.AN.26.247; 7.AN.27.157; 7.AN.27.158; 7.AN.27.196; 7.AN.27.223; 7.AN.27.240; 7.AN.27.244; 7.AN.27.243; 7.AN.27.247; 7.AN.29.157; 7.AN.29.158; 7.AN.29.196; 7.AN.29.223; 7.AN.29.240; 7.AN.29.244; 7.AN.29.243; 7.AN.29.247; 7.AN.54.157; 7.AN.54.158; 7.AN.54.196; 7.AN.54.223; 7.AN.54.240; 7.AN.54.244; 7.AN.54.243; 7.AN.54.247; 7.AN.55.157; 7.AN.55.158; 7.AN.55.196; 7.AN.55.223; 7.AN.55.240; 7.AN.55.244; 7.AN.55.243; 7.AN.55.247; 7.AN.56.157; 7.AN.56.158; 7.AN.56.196; 7.AN.56.223; 7.AN.56.240; 7.AN.56.244; 7.AN.56.243; 7.AN.56.247; 7.AN.157.157; 7.AN.157.158; 7.AN.157.196; 7.AN.157.223; 7.AN.157.240; 7.AN.157.244; 7.AN.157.243; 7.AN.157.247; 7.AN.196.157; 7.AN.196.158; 7.AN.196.196; 7.AN.196.223; 7.AN.196.240; 7.AN.196.244; 7.AN.196.243; 7.AN.196.247; 7.AN.223.157; 7.AN.223.158; 7.AN.223.196; 7.AN.223.223; 7.AN.223.240; 7.AN.223.244; 7.AN.223.243; 7.AN.223.247; 7.AN.240.157; 7.AN.240.158; 7.AN.240.196; 7.AN.240.223; 7.AN.240.240; 7.AN.240.244; 7.AN.240.243; 7.AN.240.247; 7.AN.244.157; 7.AN.244.158; 7.AN.244.196; 7.AN.244.223; 7.AN.244.240; 7.AN.244.244; 7.AN.244.243; 7.AN.244.247; 7.AN.247.157; 7.AN.247.158; 7.AN.247.196; 7.AN.247.223; 7.AN.247.240; 7.AN.247.244; 7.AN.247.243; 7.AN.247.247;
Prodrugs of 7.AP 7.AP.4.157; 7.AP.4.158; 7.AP.4.196; 7.AP.4.223; 7.AP.4.240; 7.AP.4.244; 7.AP.4.243; 7.AP.4.247; 7.AP.5.157; 7.AP.5.158; 7.AP.5.196; 7.AP.5.223; 7.AP.5.240; 7.AP.5.244; 7.AP.5.243; 7.AP.5.247; 7.AP.7.157; 7.AP.7.158; 7.AP.7.196; 7.AP.7.223; 7.AP.7.240; 7.AP.7.244; 7.AP.7.243; 7.AP.7.247; 7.AP.15.157; 7.AP.15.158; 7.AP.15.196; 7.AP.15.223; 7.AP.15.240; 7.AP.15.244; 7.AP.15.243; 7.AP.15.247; 7.AP.16.157; 7.AP.16.158; 7.AP.16.196; 7.AP.16.223; 7.AP.16.240; 7.AP.16.244; 7.AP.16.243; 7.AP.16.247; 7.AP.18.157; 7.AP.18.158; 7.AP.18.196; 7.AP.18.223; 7.AP.18.240; 7.AP.18.244; 7.AP.18.243; 7.AP.18.247; 7.AP.26.157; 7.AP.26.158; 7.AP.26.196; 7.AP.26.223; 7.AP.26.240; 7.AP.26.244; 7.AP.26.243; 7.AP.26.247; 7.AP.27.157; 7.AP.27.158; 7.AP.27.196; 7.AP.27.223; 7.AP.27.240; 7.AP.27.244; 7.AP.27.243; 7.AP.27.247; 7.AP.29.157; 7.AP.29.158; 7.AP.29.196; 7.AP.29.223; 7.AP.29.240; 7.AP.29.244; 7.AP.29.243; 7.AP.29.247; 7.AP.54.157; 7.AP.54.158; 7.AP.54.196; 7.AP.54.223; 7.AP.54.240; 7.AP.54.244; 7.AP.54.243; 7.AP.54.247; 7.AP.55.157; 7.AP.55.158; 7.AP.55.196; 7.AP.55.223; 7.AP.55.240; 7.AP.55.244; 7.AP.55.243; 7.AP.55.247; 7.AP.56.157; 7.AP.56.158; 7.AP.56.196; 7.AP.56.223; 7.AP.56.240; 7.AP.56.244; 7.AP.56.243; 7.AP.56.247; 7.AP.157.157; 7.AP.157.158; 7.AP.157.196; 7.AP.157.223; 7.AP.157.240; 7.AP.157.244; 7.AP.157.243; 7.AP.157.247; 7.AP.196.157; 7.AP.196.158; 7.AP.196.196; 7.AP.196.223; 7.AP.196.240; 7.AP.196.244; 7.AP.196.243; 7.AP.196.247; 7.AP.223.157; 7.AP.223.158; 7.AP.223.196; 7.AP.223.223; 7.AP.223.240; 7.AP.223.244; 7.AP.223.243; 7.AP.223.247; 7.AP.240.157; 7.AP.240.158; 7.AP.240.196; 7.AP.240.223; 7.AP.240.240; 7.AP.240.244; 7.AP.240.243; 7.AP.240.247; 7.AP.244.157; 7.AP.244.158; 7.AP.244.223; 7.AP.244.240; 7.AP.244.244; 7.AP.244.243; 7.AP.244.247; 7.AP.247.157; 7.AP.247.158; 7.AP.247.196; 7.AP.247.223; 7.AP.247.240; 7.AP.247.244; 7.AP.247.243; 7.AP.247.247;
Prodrugs of 7.AZ 7.AZ.4.157; 7.AZ.4.158; 7.AZ.4.196; 7.AZ.4.223; 7.AZ.4.240; 7.AZ.4.244; 7.AZ.4.243; 7.AZ.4.247; 7.AZ.5.157; 7.AZ.5.158; 7.AZ.5.196; 7.AZ.5.223; 7.AZ.5.240; 7.AZ.5.244; 7.AZ.5.243; 7.AZ.5.247; 7.AZ.7.157; 7.AZ.7.158; 7.AZ.7.196; 7.AZ.7.223; 7.AZ.7.240; 7.AZ.7.244; 7.AZ.7.243; 7.AZ.7.247; 7.AZ.15.157; 7.AZ.15.158; 7.AZ.15.196; 7.AZ.15.223; 7.AZ.15.240; 7.AZ.15.244; 7.AZ.15.243; 7.AZ.15.247; 7.AZ.16.157; 7.AZ.16.158; 7.AZ.16.196; 7.AZ.16.223; 7.AZ.16.240; 7.AZ.16.244; 7.AZ.16.243; 7.AZ.16.247; 7.AZ.18.157; 7.AZ.18.158; 7.AZ.18.196; 7.AZ.18.223; 7.AZ.18.240; 7.AZ.18.244; 7.AZ.18.243; 7.AZ.18.247; 7.AZ.26.157; 7.AZ.26.158; 7.AZ.26.196; 7.AZ.26.223; 7.AZ.26.240; 7.AZ.26.244; 7.AZ.26.243; 7.AZ.26.247; 7.AZ.27.157; 7.AZ.27.158; 7.AZ.27.196; 7.AZ.27.223; 7.AZ.27.240; 7.AZ.27.244; 7.AZ.27.243; 7.AZ.27.247; 7.AZ.29.157; 7.AZ.29.158; 7.AZ.29.196; 7.AZ.29.223; 7.AZ.29.240; 7.AZ.29.244; 7.AZ.29.243; 7.AZ.29.247; 7.AZ.54.157; 7.AZ.54.158; 7.AZ.54.196; 7.AZ.54.223; 7.AZ.54.240; 7.AZ.54.244; 7.AZ.54.243; 7.AZ.54.247; 7.AZ.55.157; 7.AZ.55.158; 7.AZ.55.196; 7.AZ.55.223; 7.AZ.55.240; 7.AZ.55.244; 7.AZ.55.243; 7.AZ.55.247; 7.AZ.56.157; 7.AZ.56.158; 7.AZ.56.196; 7.AZ.56.223; 7.AZ.56.240; 7.AZ.56.244; 7.AZ.56.243; 7.AZ.56.247; 7.AZ.157.157; 7.AZ.157.158; 7.AZ.157.196; 7.AZ.157.223; 7.AZ.157.240; 7.AZ.157.244; 7.AZ.157.243; 7.AZ.157.247; 7.AZ.196.157; 7.AZ.196.158; 7.AZ.196.196; 7.AZ.196.223; 7.AZ.196.240; 7.AZ.196.244; 7.AZ.196.243; 7.AZ.196.247; 7.AZ.223.157; 7.AZ.223.158; 7.AZ.223.196; 7.AZ.223.223; 7.AZ.223.240; 7.AZ.223.244; 7.AZ.223.243; 7.AZ.223.247; 7.AZ.240.157; 7.AZ.240.158; 7.AZ.240.196; 7.AZ.240.223; 7.AZ.240.240; 7.AZ.240.244; 7.AZ.240.243; 7.AZ.240.247; 7.AZ.244.157; 7.AZ.244.158; 7.AZ.244.196; 7.AZ.244.223; 7.AZ.244.240; 7.AZ.244.244; 7.AZ.244.243; 7.AZ.244.247; 7.AZ.247.157; 7.AZ.247.158; 7.AZ.247.196; 7.AZ.247.223; 7.AZ.247.240; 7.AZ.247.244; 7.AZ.247.243; 7.AZ.247.247;
Prodrugs of 7.BF 7.BF.4.157; 7.BF.4.158; 7.BF.4.196; 7.BF.4.223; 7.BF.4.240; 7.BF.4.244; 7.BF.4.243; 7.BF.4.247; 7.BF.5.157; 7.BF.5.158; 7.BF.5.196; 7.BF.5.223; 7.BF.5.240; 7.BF.5.244; 7.BF.5.243; 7.BF.5.247; 7.BF.7.157; 7.BF.7.158; 7.BF.7.196; 7.BF.7.223; 7.BF.7.240; 7.BF.7.244; 7.BF.7.243; 7.BF.7.247; 7.BF.15.157; 7.BF.15.158; 7.BF.15.196; 7.BF.15.223; 7.BF.15.240; 7.BF.15.244; 7.BF.15.243; 7.BF.15.247; 7.BF.16.157; 7.BF.16.158; 7.BF.16.196; 7.BF.16.223; 7.BF.16.240; 7.BF.16.244; 7.BF.16.243; 7.BF.16.247; 7.BF.18.157; 7.BF.18.158; 7.BF.18.196; 7.BF.18.223; 7.BF.18.240; 7.BF.18.244; 7.BF.18.243; 7.BF.18.247; 7.BF.26.157; 7.BF.26.158; 7.BF.26.196; 7.BF.26.223; 7.BF.26.240; 7.BF.26.244; 7.BF.26.243; 7.BF.26.247; 7.BF.27.157; 7.BF.27.158; 7.BF.27.196; 7.BF.27.223; 7.BF.27.240; 7.BF.27.244; 7.BF.27.243; 7.BF.27.247; 7.BF.29.157; 7.BF.29.158; 7.BF.29.196; 7.BF.29.223; 7.BF.29.240; 7.BF.29.244; 7.BF.29.243; 7.BF.29.247; 7.BF.54.157; 7.BF.54.158; 7.BF.54.196; 7.BF.54.223; 7.BF.54.240; 7.BF.54.244; 7.BF.54.243; 7.BF.54.247;

TABLE 7-continued

7.BF.55.157; 7.BF.55.158; 7.BF.55.196; 7.BF.55.223; 7.BF.55.240;
7.BF.55.244; 7.BF.55.243; 7.BF.55.247; 7.BF.56.157; 7.BF.56.158;
7.BF.56.196; 7.BF.56.223; 7.BF.56.240; 7.BF.56.244; 7.BF.56.243;
7.BF.56.247; 7.BF.157.157; 7.BF.157.158; 7.BF.157.196; 7.BF.157.223;
7.BF.157.240; 7.BF.157.244; 7.BF.157.243; 7.BF.157.247; 7.BF.196.157;
7.BF.196.158; 7.BF.196.196; 7.BF.196.223; 7.BF.196.240; 7.BF.196.244;
7.BF.196.243; 7.BF.196.247; 7.BF.223.157; 7.BF.223.158; 7.BF.223.196;
7.BF.223.223; 7.BF.223.240; 7.BF.223.244; 7.BF.223.243; 7.BF.223.247;
7.BF.240.157; 7.BF.240.158; 7.BF.240.196; 7.BF.240.223; 7.BF.240.240;
7.BF.240.244; 7.BF.240.243; 7.BF.240.247; 7.BF.244.157; 7.BF.244.158;
7.BF.244.196; 7.BF.244.223; 7.BF.244.240; 7.BF.244.244; 7.BF.244.243;
7.BF.244.247; 7.BF.247.157; 7.BF.247.158; 7.BF.247.196; 7.BF.247.223;
7.BF.247.240; 7.BF.247.244; 7.BF.247.243; 7.BF.247.247;
Prodrugs of 7.CI 7.CI.4.157; 7.CI.4.158; 7.CI.4.196; 7.CI.4.223; 7.CI.4.240;
7.CI.4.244; 7.CI.4.243; 7.CI.4.247; 7.CI.5.157; 7.CI.5.158;
7.CI.5.196; 7.CI.5.223; 7.CI.5.240; 7.CI.5.244; 7.CI.5.243;
7.CI.5.247; 7.CI.7.157; 7.CI.7.158; 7.CI.7.196; 7.CI.7.223;
7.CI.7.240; 7.CI.7.244; 7.CI.7.243; 7.CI.7.247; 7.CI.15.157;
7.CI.15.158; 7.CI.15.196; 7.CI.15.223; 7.CI.15.240; 7.CI.15.244;
7.CI.15.243; 7.CI.15.247; 7.CI.16.157; 7.CI.16.158; 7.CI.16.196;
7.CI.16.223; 7.CI.16.240; 7.CI.16.244; 7.CI.16.243; 7.CI.16.247;
7.CI.18.157; 7.CI.18.158; 7.CI.18.196; 7.CI.18.223; 7.CI.18.240;
7.CI.18.244; 7.CI.18.243; 7.CI.18.247; 7.CI.26.157; 7.CI.26.158;
7.CI.26.196; 7.CI.26.223; 7.CI.26.240; 7.CI.26.244; 7.CI.26.243;
7.CI.26.247; 7.CI.27.157; 7.CI.27.158; 7.CI.27.196; 7.CI.27.223;
7.CI.27.240; 7.CI.27.244; 7.CI.27.243; 7.CI.27.247; 7.CI.29.157;
7.CI.29.158; 7.CI.29.196; 7.CI.29.223; 7.CI.29.240; 7.CI.29.244;
7.CI.29.243; 7.CI.29.247; 7.CI.54.157; 7.CI.54.158; 7.CI.54.196;
7.CI.54.223; 7.CI.54.240; 7.CI.54.244; 7.CI.54.243; 7.CI.54.247;
7.CI.55.157; 7.CI.55.158; 7.CI.55.196; 7.CI.55.223; 7.CI.55.240;
7.CI.55.244; 7.CI.55.243; 7.CI.55.247; 7.CI.56.157; 7.CI.56.158;
7.CI.56.196; 7.CI.56.223; 7.CI.56.240; 7.CI.56.244; 7.CI.56.243;
7.CI.56.247; 7.CI.157.157; 7.CI.157.158; 7.CI.157.196; 7.CI.157.223;
7.CI.157.240; 7.CI.157.244; 7.CI.157.243; 7.CI.157.247; 7.CI.196.157;
7.CI.196.158; 7.CI.196.196; 7.CI.196.223; 7.CI.196.240; 7.CI.196.244;
7.CI.196.243; 7.CI.196.247; 7.CI.223.157; 7.CI.223.158; 7.CI.223.196;
7.CI.223.223; 7.CI.223.240; 7.CI.223.244; 7.CI.223.243; 7.CI.223.247;
7.CI.240.157; 7.CI.240.158; 7.CI.240.196; 7.CI.240.223; 7.CI.240.240;
7.CI.240.244; 7.CI.240.243; 7.CI.240.247; 7.CI.244.157; 7.CI.244.158;
7.CI.244.196; 7.CI.244.223; 7.CI.244.240; 7.CI.244.244; 7.CI.244.243;
7.CI.244.247; 7.CI.247.157; 7.CI.247.158; 7.CI.247.196; 7.CI.247.223;
7.CI.247.240; 7.CI.247.244; 7.CI.247.243; 7.CI.247.247;
Prodrugs of 7.CO 7.CO.4.157; 7.CO.4.158; 7.CO.4.196; 7.CO.4.223; 7.CO.4.240;
7.CO.4.244; 7.CO.4.243; 7.CO.4.247; 7.CO.5.157; 7.CO.5.158;
7.CO.5.196; 7.CO.5.223; 7.CO.5.240; 7.CO.5.244; 7.CO.5.243;
7.CO.5.247; 7.CO.7.157; 7.CO.7.158; 7.CO.7.196; 7.CO.7.223;
7.CO.7.240; 7.CO.7.244; 7.CO.7.243; 7.CO.7.247; 7.CO.15.157;
7.CO.15.158; 7.CO.15.196; 7.CO.15.223; 7.CO.15.240; 7.CO.15.244;
7.CO.15.243; 7.CO.15.247; 7.CO.16.157; 7.CO.16.158; 7.CO.16.196;
7.CO.16.223; 7.CO.16.240; 7.CO.16.244; 7.CO.16.243; 7.CO.16.247;
7.CO.18.157; 7.CO.18.158; 7.CO.18.196; 7.CO.18.223; 7.CO.18.240;
7.CO.18.244; 7.CO.18.243; 7.CO.18.247; 7.CO.26.157; 7.CO.26.158;
7.CO.26.196; 7.CO.26.223; 7.CO.26.240; 7.CO.26.244; 7.CO.26.243;
7.CO.26.247; 7.CO.27.157; 7.CO.27.158; 7.CO.27.196; 7.CO.27.223;
7.CO.27.240; 7.CO.27.244; 7.CO.27.243; 7.CO.27.247; 7.CO.29.157;
7.CO.29.158; 7.CO.29.196; 7.CO.29.223; 7.CO.29.240; 7.CO.29.244;
7.CO.29.243; 7.CO.29.247; 7.CO.54.157; 7.CO.54.158; 7.CO.54.196;
7.CO.54.223; 7.CO.54.240; 7.CO.54.244; 7.CO.54.243; 7.CO.54.247;
7.CO.55.157; 7.CO.55.158; 7.CO.55.196; 7.CO.55.223; 7.CO.55.240;
7.CO.55.244; 7.CO.55.243; 7.CO.55.247; 7.CO.56.157; 7.CO.56.158;
7.CO.56.196; 7.CO.56.223; 7.CO.56.240; 7.CO.56.244; 7.CO.56.243;
7.CO.56.247; 7.CO.157.157; 7.CO.157.158; 7.CO.157.196;
7.CO.157.223; 7.CO.157.240; 7.CO.157.244; 7.CO.157.243;
7.CO.157.247; 7.CO.196.157; 7.CO.196.158; 7.CO.196.196;
7.CO.196.223; 7.CO.196.240; 7.CO.196.244; 7.CO.196.243;
7.CO.196.247; 7.CO.223.157; 7.CO.223.158; 7.CO.223.196;
7.CO.223.223; 7.CO.223.240; 7.CO.223.244; 7.CO.223.243;
7.CO.223.247; 7.CO.240.157; 7.CO.240.158; 7.CO.240.196;
7.CO.240.223; 7.CO.240.240; 7.CO.240.244; 7.CO.240.243;
7.CO.240.247; 7.CO.244.157; 7.CO.244.158; 7.CO.244.196;
7.CO.244.223; 7.CO.244.240; 7.CO.244.244; 7.CO.244.243;
7.CO.244.247; 7.CO.4.157; 7.CO.4.158; 7.CO.4.196; 7.CO.4.223;
7.CO.4.240; 7.CO.4.244; 7.CO.4.243; 7.CO.4.247;

Prodrugs of 8.AH

8.AH.4.157; 8.AH.4.158; 8.AH.4.196; 8.AH.4.223; 8.AH.4.240;
8.AH.4.244; 8.AH.4.243; 8.AH.4.247; 8.AH.5.157; 8.AH.5.158;
8.AH.5.196; 8.AH.5.223; 8.AH.5.240; 8.AH.5.244; 8.AH.5.243;
8.AH.5.247; 8.AH.7.157; 8.AH.7.158; 8.AH.7.196; 8.AH.7.223;
8.AH.7.240; 8.AH.7.244; 8.AH.7.243; 8.AH.7.247; 8.AH.15.157;
8.AH.15.158; 8.AH.15.196; 8.AH.15.223; 8.AH.15.240; 8.AH.15.244;
8.AH.15.243; 8.AH.15.247; 8.AH.16.157; 8.AH.16.158; 8.AH.16.196;
8.AH.16.223; 8.AH.16.240; 8.AH.16.244; 8.AH.16.243; 8.AH.16.247;
8.AH.18.157; 8.AH.18.158; 8.AH.18.196; 8.AH.18.223; 8.AH.18.240;
8.AH.18.244; 8.AH.18.243; 8.AH.18.247; 8.AH.26.157; 8.AH.26.158;
8.AH.26.196; 8.AH.26.223; 8.AH.26.240; 8.AH.26.244; 8.AH.26.243;
8.AH.26.247; 8.AH.27.157; 8.AH.27.158; 8.AH.27.196; 8.AH.27.223;
8.AH.27.240; 8.AH.27.244; 8.AH.27.243; 8.AH.27.247; 8.AH.29.157;
8.AH.29.158; 8.AH.29.196; 8.AH.29.223; 8.AH.29.240; 8.AH.29.244;
8.AH.29.243; 8.AH.29.247; 8.AH.54.157; 8.AH.54.158; 8.AH.54.196;
8.AH.54.223; 8.AH.54.240; 8.AH.54.244; 8.AH.54.243; 8.AH.54.247;
8.AH.55.157; 8.AH.55.158; 8.AH.55.196; 8.AH.55.223; 8.AH.55.240;
8.AH.55.244; 8.AH.55.243; 8.AH.55.247; 8.AH.56.157; 8.AH.56.158;
8.AH.56.196; 8.AH.56.223; 8.AH.56.240; 8.AH.56.244; 8.AH.56.243;
8.AH.56.247; 8.AH.157.157; 8.AH.157.158; 8.AH.157.196;
8.AH.157.223; 8.AH.157.240; 8.AH.157.244; 8.AH.157.243;
8.AH.157.247; 8.AH.196.157; 8.AH.196.158; 8.AH.196.196;
8.AH.196.223; 8.AH.196.240; 8.AH.196.244; 8.AH.196.243;
8.AH.196.247; 8.AH.223.157; 8.AH.223.158; 8.AH.223.196;
8.AH.223.223; 8.AH.223.240; 8.AH.223.244; 8.AH.223.243;
8.AH.223.247; 8.AH.240.157; 8.AH.240.158; 8.AH.240.196;
8.AH.240.223; 8.AH.240.240; 8.AH.240.244; 8.AH.240.243;
8.AH.240.247; 8.AH.244.157; 8.AH.244.158; 8.AH.244.196;
8.AH.244.223; 8.AH.244.240; 8.AH.244.244; 8.AH.244.243;
8.AH.244.247; 8.AH.247.157; 8.AH.247.158; 8.AH.247.196;
8.AH.247.223; 8.AH.247.240; 8.AH.247.244; 8.AH.247.243;
8.AH.247.247;
Prodrugs of 8.AJ 8.AJ.4.157; 8.AJ.4.158; 8.AJ.4.196; 8.AJ.4.223; 8.AJ.4.240;
8.AJ.4.244; 8.AJ.4.243; 8.AJ.4.247; 8.AJ.5.157; 8.AJ.5.158;
8.AJ.5.196; 8.AJ.5.223; 8.AJ.5.240; 8.AJ.5.244; 8.AJ.5.243;
8.AJ.5.247; 8.AJ.7.157; 8.AJ.7.158; 8.AJ.7.196; 8.AJ.7.223;
8.AJ.7.240; 8.AJ.7.244; 8.AJ.7.243; 8.AJ.7.247; 8.AJ.15.157;
8.AJ.15.158; 8.AJ.15.196; 8.AJ.15.223; 8.AJ.15.240; 8.AJ.15.244;
8.AJ.15.243; 8.AJ.15.247; 8.AJ.16.157; 8.AJ.16.158; 8.AJ.16.196;
8.AJ.16.223; 8.AJ.16.240; 8.AJ.16.244; 8.AJ.16.243; 8.AJ.16.247;
8.AJ.18.157; 8.AJ.18.158; 8.AJ.18.196; 8.AJ.18.223; 8.AJ.18.240;
8.AJ.18.244; 8.AJ.18.243; 8.AJ.18.247; 8.AJ.26.157; 8.AJ.26.158;
8.AJ.26.196; 8.AJ.26.223; 8.AJ.26.240; 8.AJ.26.244; 8.AJ.26.243;
8.AJ.26.247; 8.AJ.27.157; 8.AJ.27.158; 8.AJ.27.196; 8.AJ.27.223;
8.AJ.27.240; 8.AJ.27.244; 8.AJ.27.243; 8.AJ.27.247; 8.AJ.29.157;
8.AJ.29.158; 8.AJ.29.196; 8.AJ.29.223; 8.AJ.29.240; 8.AJ.29.244;
8.AJ.29.243; 8.AJ.29.247; 8.AJ.54.157; 8.AJ.54.158; 8.AJ.54.196;
8.AJ.54.223; 8.AJ.54.240; 8.AJ.54.244; 8.AJ.54.243; 8.AJ.54.247;
8.AJ.55.157; 8.AJ.55.158; 8.AJ.55.196; 8.AJ.55.223; 8.AJ.55.240;
8.AJ.55.244; 8.AJ.55.243; 8.AJ.55.247; 8.AJ.56.157; 8.AJ.56.158;
8.AJ.56.196; 8.AJ.56.223; 8.AJ.56.240; 8.AJ.56.244; 8.AJ.56.243;
8.AJ.56.247; 8.AJ.157.157; 8.AJ.157.158; 8.AJ.157.196; 8.AJ.157.223;
8.AJ.157.240; 8.AJ.157.244; 8.AJ.157.243; 8.AJ.157.247; 8.AJ.196.157;
8.AJ.196.158; 8.AJ.196.196; 8.AJ.196.223; 8.AJ.196.240; 8.AJ.196.244;
8.AJ.196.243; 8.AJ.196.247; 8.AJ.223.157; 8.AJ.223.158; 8.AJ.223.196;
8.AJ.223.223; 8.AJ.223.240; 8.AJ.223.244; 8.AJ.223.243; 8.AJ.223.247;
8.AJ.240.157; 8.AJ.240.158; 8.AJ.240.196; 8.AJ.240.223; 8.AJ.240.240;
8.AJ.240.244; 8.AJ.240.243; 8.AJ.240.247; 8.AJ.244.157; 8.AJ.244.158;
8.AJ.244.196; 8.AJ.244.223; 8.AJ.244.240; 8.AJ.244.244; 8.AJ.244.243;
8.AJ.244.247; 8.AJ.247.157; 8.AJ.247.158; 8.AJ.247.196; 8.AJ.247.223;
8.AJ.247.240; 8.AJ.247.244; 8.AJ.247.243; 8.AJ.247.247;
Prodrugs of 8.AN 8.AN.4.157; 8.AN.4.158; 8.AN.4.196; 8.AN.4.223; 8.AN.4.240;
8.AN.4.244; 8.AN.4.243; 8.AN.4.247; 8.AN.5.157; 8.AN.5.158;
8.AN.5.196; 8.AN.5.223; 8.AN.5.240; 8.AN.5.244; 8.AN.5.243;
8.AN.5.247; 8.AN.7.157; 8.AN.7.158; 8.AN.7.196; 8.AN.7.223;
8.AN.7.240; 8.AN.7.244; 8.AN.7.243; 8.AN.7.247; 8.AN.15.157;
8.AN.15.158; 8.AN.15.196; 8.AN.15.223; 8.AN.15.240; 8.AN.15.244;
8.AN.15.243; 8.AN.15.247; 8.AN.16.157; 8.AN.16.158; 8.AN.16.196;
8.AN.16.223; 8.AN.16.240; 8.AN.16.244; 8.AN.16.243; 8.AN.16.247;
8.AN.18.157; 8.AN.18.158; 8.AN.18.196; 8.AN.18.223; 8.AN.18.240;
8.AN.18.244; 8.AN.18.243; 8.AN.18.247; 8.AN.26.157; 8.AN.26.158;
8.AN.26.196; 8.AN.26.223; 8.AN.26.240; 8.AN.26.244; 8.AN.26.243;
8.AN.26.247; 8.AN.27.157; 8.AN.27.158; 8.AN.27.196; 8.AN.27.223;

TABLE 7-continued

8.AN.27.240; 8.AN.27.244; 8.AN.27.243; 8.AN.27.247; 8.AN.29.157;
8.AN.29.158; 8.AN.29.196; 8.AN.29.223; 8.AN.29.240; 8.AN.29.244;
8.AN.29.243; 8.AN.29.247; 8.AN.54.157; 8.AN.54.158; 8.AN.54.196;
8.AN.54.223; 8.AN.54.157; 8.AN.54.240; 8.AN.54.244; 8.AN.54.243; 8.AN.54.247;
8.AN.55.157; 8.AN.55.158; 8.AN.55.196; 8.AN.55.223; 8.AN.55.240;
8.AN.55.244; 8.AN.55.243; 8.AN.55.247; 8.AN.56.157; 8.AN.56.158;
8.AN.56.196; 8.AN.56.223; 8.AN.56.240; 8.AN.56.244; 8.AN.56.243;
8.AN.56.247; 8.AN.157.157; 8.AN.157.158; 8.AN.157.196;
8.AN.157.223; 8.AN.157.240; 8.AN.157.244; 8.AN.157.243;
8.AN.157.247; 8.AN.196.157; 8.AN.196.158; 8.AN.196.196;
8.AN.196.223; 8.AN.196.240; 8.AN.196.244; 8.AN.196.243;
8.AN.196.247; 8.AN.223.157; 8.AN.223.158; 8.AN.223.196;
8.AN.223.223; 8.AN.223.240; 8.AN.223.244; 8.AN.223.243;
8.AN.223.247; 8.AN.240.157; 8.AN.240.158; 8.AN.240.196;
8.AN.240.223; 8.AN.240.240; 8.AN.240.244; 8.AN.240.243;
8.AN.240.247; 8.AN.244.157; 8.AN.244.158; 8.AN.244.196;
8.AN.244.223; 8.AN.244.240; 8.AN.244.244; 8.AN.244.243;
8.AN.244.247; 8.AN.247.157; 8.AN.247.158; 8.AN.247.196;
8.AN.247.223; 8.AN.247.240; 8.AN.247.244; 8.AN.247.243;
8.AN.247.247;

Prodrugs of 8.AP

8.AP.4.157; 8.AP.4.158; 8.AP.4.196; 8.AP.4.223; 8.AP.4.240;
8.AP.4.244; 8.AP.4.243; 8.AP.4.247; 8.AP.5.157; 8.AP.5.158;
8.AP.5.196; 8.AP.5.223; 8.AP.5.240; 8.AP.5.244; 8.AP.5.243;
8.AP.5.247; 8.AP.7.157; 8.AP.7.158; 8.AP.7.196; 8.AP.7.223;
8.AP.7.240; 8.AP.7.244; 8.AP.7.243; 8.AP.7.247; 8.AP.15.157;
8.AP.15.158; 8.AP.15.196; 8.AP.15.223; 8.AP.15.240; 8.AP.15.244;
8.AP.15.243; 8.AP.15.247; 8.AP.16.157; 8.AP.16.158; 8.AP.16.196;
8.AP.16.223; 8.AP.16.240; 8.AP.16.244; 8.AP.16.243; 8.AP.16.247;
8.AP.18.157; 8.AP.18.158; 8.AP.18.196; 8.AP.18.223; 8.AP.18.240;
8.AP.18.244; 8.AP.18.243; 8.AP.18.247; 8.AP.26.157; 8.AP.26.158;
8.AP.26.196; 8.AP.26.223; 8.AP.26.240; 8.AP.26.244; 8.AP.26.243;
8.AP.26.247; 8.AP.27.157; 8.AP.27.158; 8.AP.27.196; 8.AP.27.223;
8.AP.27.240; 8.AP.27.244; 8.AP.27.243; 8.AP.27.247; 8.AP.29.157;
8.AP.29.158; 8.AP.29.196; 8.AP.29.223; 8.AP.29.240; 8.AP.29.244;
8.AP.29.243; 8.AP.29.247; 8.AP.54.157; 8.AP.54.158; 8.AP.54.196;
8.AP.54.223; 8.AP.54.240; 8.AP.54.244; 8.AP.54.243; 8.AP.54.247;
8.AP.55.157; 8.AP.55.158; 8.AP.55.196; 8.AP.55.223; 8.AP.55.240;
8.AP.55.244; 8.AP.55.243; 8.AP.55.247; 8.AP.56.157; 8.AP.56.158;
8.AP.56.196; 8.AP.56.223; 8.AP.56.240; 8.AP.56.244; 8.AP.56.243;
8.AP.56.247; 8.AP.157.157; 8.AP.157.158; 8.AP.157.196; 8.AP.157.223;
8.AP.157.240; 8.AP.157.244; 8.AP.157.243; 8.AP.157.247;
8.AP.196.157; 8.AP.196.158; 8.AP.196.196; 8.AP.196.223;
8.AP.196.240; 8.AP.196.244; 8.AP.196.243; 8.AP.196.247;
8.AP.223.157; 8.AP.223.158; 8.AP.223.196; 8.AP.223.223;
8.AP.223.240; 8.AP.223.244; 8.AP.223.243; 8.AP.223.247;
8.AP.240.157; 8.AP.240.158; 8.AP.240.196; 8.AP.240.223;
8.AP.240.240; 8.AP.240.244; 8.AP.240.243; 8.AP.240.247;
8.AP.244.157; 8.AP.244.158; 8.AP.244.196; 8.AP.244.223;
8.AP.244.240; 8.AP.244.244; 8.AP.244.243; 8.AP.244.247;
8.AP.247.157; 8.AP.247.158; 8.AP.247.196; 8.AP.247.223;
8.AP.247.240; 8.AP.247.244; 8.AP.247.243; 8.AP.247.247;

Prodrugs of 8.AZ

8.AZ.4.157; 8.AZ.4.158; 8.AZ.4.196; 8.AZ.4.223; 8.AZ.4.240;
8.AZ.4.244; 8.AZ.4.243; 8.AZ.4.247; 8.AZ.5.157; 8.AZ.5.158;
8.AZ.5.196; 8.AZ.5.223; 8.AZ.5.240; 8.AZ.5.244; 8.AZ.5.243;
8.AZ.5.247; 8.AZ.7.157; 8.AZ.7.158; 8.AZ.7.196; 8.AZ.7.223;
8.AZ.7.240; 8.AZ.7.244; 8.AZ.7.243; 8.AZ.7.247; 8.AZ.15.157;
8.AZ.15.158; 8.AZ.15.196; 8.AZ.15.223; 8.AZ.15.240; 8.AZ.15.244;
8.AZ.15.243; 8.AZ.15.247; 8.AZ.16.157; 8.AZ.16.158; 8.AZ.16.196;
8.AZ.16.223; 8.AZ.16.240; 8.AZ.16.244; 8.AZ.16.243; 8.AZ.16.247;
8.AZ.18.157; 8.AZ.18.158; 8.AZ.18.196; 8.AZ.18.223; 8.AZ.18.240;
8.AZ.18.244; 8.AZ.18.243; 8.AZ.18.247; 8.AZ.26.157; 8.AZ.26.158;
8.AZ.26.196; 8.AZ.26.223; 8.AZ.26.240; 8.AZ.26.244; 8.AZ.26.243;
8.AZ.26.247; 8.AZ.27.157; 8.AZ.27.158; 8.AZ.27.196; 8.AZ.27.223;
8.AZ.27.240; 8.AZ.27.244; 8.AZ.27.243; 8.AZ.27.247; 8.AZ.29.157;
8.AZ.29.158; 8.AZ.29.196; 8.AZ.29.223; 8.AZ.29.240; 8.AZ.29.244;
8.AZ.29.243; 8.AZ.29.247; 8.AZ.54.157; 8.AZ.54.158; 8.AZ.54.196;
8.AZ.54.223; 8.AZ.54.240; 8.AZ.54.244; 8.AZ.54.243; 8.AZ.54.247;
8.AZ.55.157; 8.AZ.55.158; 8.AZ.55.196; 8.AZ.55.223; 8.AZ.55.240;
8.AZ.55.244; 8.AZ.55.243; 8.AZ.55.247; 8.AZ.56.157; 8.AZ.56.158;
8.AZ.56.196; 8.AZ.56.223; 8.AZ.56.240; 8.AZ.56.244; 8.AZ.56.243;
8.AZ.56.247; 8.AZ.157.157; 8.AZ.157.158; 8.AZ.157.196; 8.AZ.157.223;
8.AZ.157.240; 8.AZ.157.244; 8.AZ.157.243; 8.AZ.157.247;
8.AZ.196.157; 8.AZ.196.158; 8.AZ.196.196; 8.AZ.196.223;
8.AZ.196.240; 8.AZ.196.244; 8.AZ.196.243; 8.AZ.196.247;
8.AZ.223.157; 8.AZ.223.158; 8.AZ.223.196; 8.AZ.223.223;
8.AZ.223.240; 8.AZ.223.244; 8.AZ.223.243; 8.AZ.223.247;
8.AZ.240.157; 8.AZ.240.158; 8.AZ.240.196; 8.AZ.240.223;
8.AZ.240.240; 8.AZ.240.244; 8.AZ.240.243; 8.AZ.240.247;
8.AZ.244.157; 8.AZ.244.158; 8.AZ.244.196; 8.AZ.244.223;
8.AZ.244.240; 8.AZ.244.244; 8.AZ.244.243; 8.AZ.244.247;
8.AZ.247.157; 8.AZ.247.158; 8.AZ.247.196; 8.AZ.247.223;
8.AZ.247.240; 8.AZ.247.244; 8.AZ.247.243; 8.AZ.247.247;

Prodrugs of 8.BF

8.BF.4.157; 8.BF.4.158; 8.BF.4.196; 8.BF.4.223; 8.BF.4.240;
8.BF.4.244; 8.BF.4.243; 8.BF.4.247; 8.BF.5.157; 8.BF.5.158;
8.BF.5.196; 8.BF.5.223; 8.BF.5.240; 8.BF.5.244; 8.BF.5.243;
8.BF.5.247; 8.BF.7.157; 8.BF.7.158; 8.BF.7.196; 8.BF.7.223;
8.BF.7.240; 8.BF.7.244; 8.BF.7.243; 8.BF.7.247; 8.BF.15.157;
8.BF.15.158; 8.BF.15.196; 8.BF.15.223; 8.BF.15.240; 8.BF.15.244;
8.BF.15.243; 8.BF.15.247; 8.BF.16.157; 8.BF.16.158; 8.BF.16.196;
8.BF.16.223; 8.BF.16.240; 8.BF.16.244; 8.BF.16.243; 8.BF.16.247;
8.BF.18.157; 8.BF.18.158; 8.BF.18.196; 8.BF.18.223; 8.BF.18.240;
8.BF.18.244; 8.BF.18.243; 8.BF.18.247; 8.BF.26.157; 8.BF.26.158;
8.BF.26.196; 8.BF.26.223; 8.BF.26.240; 8.BF.26.244; 8.BF.26.243;
8.BF.26.247; 8.BF.27.157; 8.BF.27.158; 8.BF.27.196; 8.BF.27.223;
8.BF.27.240; 8.BF.27.244; 8.BF.27.243; 8.BF.27.247; 8.BF.29.157;
8.BF.29.158; 8.BF.29.196; 8.BF.29.223; 8.BF.29.240; 8.BF.29.244;
8.BF.29.243; 8.BF.29.247; 8.BF.54.157; 8.BF.54.158; 8.BF.54.196;
8.BF.54.223; 8.BF.54.240; 8.BF.54.244; 8.BF.54.243; 8.BF.54.247;
8.BF.55.157; 8.BF.55.158; 8.BF.55.196; 8.BF.55.223; 8.BF.55.240;
8.BF.55.244; 8.BF.55.243; 8.BF.55.247; 8.BF.56.157; 8.BF.56.158;
8.BF.56.196; 8.BF.56.223; 8.BF.56.240; 8.BF.56.244; 8.BF.56.243;
8.BF.56.247; 8.BF.157.157; 8.BF.157.158; 8.BF.157.196; 8.BF.157.223;
8.BF.157.240; 8.BF.157.244; 8.BF.157.243; 8.BF.157.247; 8.BF.196.157;
8.BF.196.158; 8.BF.196.196; 8.BF.196.223; 8.BF.196.240; 8.BF.196.244;
8.BF.196.243; 8.BF.196.247; 8.BF.223.157; 8.BF.223.158; 8.BF.223.196;
8.BF.223.223; 8.BF.223.240; 8.BF.223.244; 8.BF.223.243; 8.BF.223.247;
8.BF.240.157; 8.BF.240.158; 8.BF.240.196; 8.BF.240.223; 8.BF.240.240;
8.BF.240.244; 8.BF.240.243; 8.BF.240.247; 8.BF.244.157; 8.BF.244.158;
8.BF.244.196; 8.BF.244.223; 8.BF.244.240; 8.BF.244.244; 8.BF.244.243;
8.BF.244.247; 8.BF.247.157; 8.BF.247.158; 8.BF.247.196; 8.BF.247.223;
8.BF.247.240; 8.BF.247.244; 8.BF.247.243; 8.BF.247.247;

Prodrugs of 8.CI

8.CI.4.157; 8.CI.4.158; 8.CI.4.196; 8.CI.4.223; 8.CI.4.240;
8.CI.4.244; 8.CI.4.243; 8.CI.4.247; 8.CI.5.157; 8.CI.5.158;
8.CI.5.196; 8.CI.5.223; 8.CI.5.240; 8.CI.5.244; 8.CI.5.243;
8.CI.5.247; 8.CI.7.157; 8.CI.7.158; 8.CI.7.196; 8.CI.7.223;
8.CI.7.240; 8.CI.7.244; 8.CI.7.243; 8.CI.7.247; 8.CI.15.157;
8.CI.15.158; 8.CI.15.196; 8.CI.15.223; 8.CI.15.240; 8.CI.15.244;
8.CI.15.243; 8.CI.15.247; 8.CI.16.157; 8.CI.16.158; 8.CI.16.196;
8.CI.16.223; 8.CI.16.240; 8.CI.16.244; 8.CI.16.243; 8.CI.16.247;
8.CI.18.157; 8.CI.18.158; 8.CI.18.196; 8.CI.18.223; 8.CI.18.240;
8.CI.18.244; 8.CI.18.243; 8.CI.18.247; 8.CI.26.157; 8.CI.26.158;
8.CI.26.196; 8.CI.26.223; 8.CI.26.240; 8.CI.26.244; 8.CI.26.243;
8.CI.26.247; 8.CI.27.157; 8.CI.27.158; 8.CI.27.196; 8.CI.27.223;
8.CI.27.240; 8.CI.27.244; 8.CI.27.243; 8.CI.27.247; 8.CI.29.157;
8.CI.29.158; 8.CI.29.196; 8.CI.29.223; 8.CI.29.240; 8.CI.29.244;
8.CI.29.243; 8.CI.29.247; 8.CI.54.157; 8.CI.54.158; 8.CI.54.196;
8.CI.54.223; 8.CI.54.240; 8.CI.54.244; 8.CI.54.243; 8.CI.54.247;
8.CI.55.157; 8.CI.55.158; 8.CI.55.196; 8.CI.55.223; 8.CI.55.240;
8.CI.55.244; 8.CI.55.243; 8.CI.55.247; 8.CI.56.157; 8.CI.56.158;
8.CI.56.196; 8.CI.56.223; 8.CI.56.240; 8.CI.56.244; 8.CI.56.243;
8.CI.56.247; 8.CI.157.157; 8.CI.157.158; 8.CI.157.196; 8.CI.157.223;
8.CI.157.240; 8.CI.157.244; 8.CI.157.243; 8.CI.157.247; 8.CI.196.157;
8.CI.196.158; 8.CI.196.196; 8.CI.196.223; 8.CI.196.240; 8.CI.196.244;
8.CI.196.243; 8.CI.196.247; 8.CI.223.157; 8.CI.223.158; 8.CI.223.196;
8.CI.223.223; 8.CI.223.240; 8.CI.223.244; 8.CI.223.243; 8.CI.223.247;
8.CI.240.157; 8.CI.240.158; 8.CI.240.196; 8.CI.240.223; 8.CI.240.240;
8.CI.240.244; 8.CI.240.243; 8.CI.240.247; 8.CI.244.157; 8.CI.244.158;
8.CI.244.196; 8.CI.244.223; 8.CI.244.240; 8.CI.244.244; 8.CI.244.243;
8.CI.244.247; 8.CI.247.157; 8.CI.247.158; 8.CI.247.196; 8.CI.247.223;
8.CI.247.240; 8.CI.247.244; 8.CI.247.243; 8.CI.247.247;

Prodrugs of 8.CO

8.CO.4.157; 8.CO.4.158; 8.CO.4.196; 8.CO.4.223; 8.CO.4.240;
8.CO.4.244; 8.CO.4.243; 8.CO.4.247; 8.CO.5.157; 8.CO.5.158;
8.CO.5.196; 8.CO.5.223; 8.CO.5.240; 8.CO.5.244; 8.CO.5.243;
8.CO.5.247; 8.CO.7.157; 8.CO.7.158; 8.CO.7.196; 8.CO.7.223;
8.CO.7.240; 8.CO.7.244; 8.CO.7.243; 8.CO.7.247; 8.CO.15.157;
8.CO.15.158; 8.CO.15.196; 8.CO.15.223; 8.CO.15.240; 8.CO.15.244;
8.CO.15.243; 8.CO.15.247; 8.CO.16.157; 8.CO.16.158; 8.CO.16.196;
8.CO.16.223; 8.CO.16.240; 8.CO.16.244; 8.CO.16.243; 8.CO.16.247;

TABLE 7-continued

8.CO.18.157; 8.CO.18.158; 8.CO.18.196; 8.CO.18.223; 8.CO.18.240;
8.CO.18.244; 8.CO.18.243; 8.CO.18.247; 8.CO.26.157; 8.CO.26.158;
8.CO.26.196; 8.CO.26.223; 8.CO.26.240; 8.CO.26.244; 8.CO.26.243;
8.CO.26.247; 8.CO.27.157; 8.CO.27.158; 8.CO.27.196; 8.CO.27.223;
8.CO.27.240; 8.CO.27.244; 8.CO.27.243; 8.CO.27.247; 8.CO.29.157;
8.CO.29.158; 8.CO.29.196; 8.CO.29.223; 8.CO.29.240; 8.CO.29.244;
8.CO.29.243; 8.CO.29.247; 8.CO.54.157; 8.CO.54.158; 8.CO.54.196;
8.CO.54.223; 8.CO.54.240; 8.CO.54.244; 8.CO.54.243; 8.CO.54.247;
8.CO.55.157; 8.CO.55.158; 8.CO.55.196; 8.CO.55.223; 8.CO.55.240;
8.CO.55.244; 8.CO.55.243; 8.CO.55.247; 8.CO.56.157; 8.CO.56.158;
8.CO.56.196; 8.CO.56.223; 8.CO.56.240; 8.CO.56.244; 8.CO.56.243;
8.CO.56.247; 8.CO.157.157; 8.CO.157.158; 8.CO.157.196;
8.CO.157.223; 8.CO.157.240; 8.CO.157.244; 8.CO.157.243;
8.CO.157.247; 8.CO.196.157; 8.CO.196.158; 8.CO.196.196;
8.CO.196.223; 8.CO.196.240; 8.CO.196.244; 8.CO.196.243;
8.CO.196.247; 8.CO.223.157; 8.CO.223.158; 8.CO.223.196;
8.CO.223.223; 8.CO.223.240; 8.CO.223.244; 8.CO.223.243;
8.CO.223.247; 8.CO.240.157; 8.CO.240.158; 8.CO.240.196;
8.CO.240.223; 8.CO.240.240; 8.CO.240.244; 8.CO.240.243;
8.CO.240.247; 8.CO.244.157; 8.CO.244.158; 8.CO.244.196;
8.CO.244.223; 8.CO.244.240; 8.CO.244.244; 8.CO.244.243;
8.CO.244.247; 8.CO.247.157; 8.CO.247.158; 8.CO.247.196;
8.CO.247.223; 8.CO.247.240; 8.CO.247.244; 8.CO.247.243;
8.CO.247.247;
Prodrugs of 9.AH 9.AH.4.157; 9.AH.4.158; 9.AH.4.196; 9.AH.4.223; 9.AH.4.240;
9.AH.4.244; 9.AH.4.243; 9.AH.4.247; 9.AH.5.157; 9.AH.5.158;
9.AH.5.196; 9.AH.5.223; 9.AH.5.240; 9.AH.5.244; 9.AH.5.243;
9.AH.5.247; 9.AH.7.157; 9.AH.7.158; 9.AH.7.196; 9.AH.7.223;
9.AH.7.240; 9.AH.7.244; 9.AH.7.243; 9.AH.7.247; 9.AH.15.157;
9.AH.15.158; 9.AH.15.196; 9.AH.15.223; 9.AH.15.240; 9.AH.15.244;
9.AH.15.243; 9.AH.15.247; 9.AH.16.157; 9.AH.16.158; 9.AH.16.196;
9.AH.16.223; 9.AH.16.240; 9.AH.16.244; 9.AH.16.243; 9.AH.16.247;
9.AH.18.157; 9.AH.18.158; 9.AH.18.196; 9.AH.18.223; 9.AH.18.240;
9.AH.18.244; 9.AH.18.243; 9.AH.18.247; 9.AH.26.157; 9.AH.26.158;
9.AH.26.196; 9.AH.26.223; 9.AH.26.240; 9.AH.26.244; 9.AH.26.243;
9.AH.26.247; 9.AH.27.157; 9.AH.27.158; 9.AH.27.196; 9.AH.27.223;
9.AH.27.240; 9.AH.27.244; 9.AH.27.243; 9.AH.27.247; 9.AH.29.157;
9.AH.29.158; 9.AH.29.196; 9.AH.29.223; 9.AH.29.240; 9.AH.29.244;
9.AH.29.243; 9.AH.29.247; 9.AH.54.157; 9.AH.54.158; 9.AH.54.196;
9.AH.54.223; 9.AH.54.240; 9.AH.54.244; 9.AH.54.243; 9.AH.54.247;
9.AH.55.157; 9.AH.55.158; 9.AH.55.196; 9.AH.55.223; 9.AH.55.240;
9.AH.55.244; 9.AH.55.243; 9.AH.55.247; 9.AH.56.157; 9.AH.56.158;
9.AH.56.196; 9.AH.56.223; 9.AH.56.240; 9.AH.56.244; 9.AH.56.243;
9.AH.56.247; 9.AH.157.157; 9.AH.157.158; 9.AH.157.196;
9.AH.157.223; 9.AH.157.240; 9.AH.157.244; 9.AH.157.243;
9.AH.157.247; 9.AH.196.157; 9.AH.196.158; 9.AH.196.196;
9.AH.196.223; 9.AH.196.240; 9.AH.196.244; 9.AH.196.243;
9.AH.196.247; 9.AH.223.157; 9.AH.223.158; 9.AH.223.196;
9.AH.223.223; 9.AH.223.240; 9.AH.223.244; 9.AH.223.243;
9.AH.223.247; 9.AH.240.157; 9.AH.240.158; 9.AH.240.196;
9.AH.240.223; 9.AH.240.240; 9.AH.240.244; 9.AH.240.243;
9.AH.240.247; 9.AH.244.157; 9.AH.244.158; 9.AH.244.196;
9.AH.244.223; 9.AH.244.240; 9.AH.244.244; 9.AH.244.243;
9.AH.244.247; 9.AH.247.157; 9.AH.247.158; 9.AH.247.196;
9.AH.247.223; 9.AH.247.240; 9.AH.247.244; 9.AH.247.243;
9.AH.247.247;
Prodrugs of 9.AJ 9.AJ.4.157; 9.AJ.4.158; 9.AJ.4.196; 9.AJ.4.223; 9.AJ.4.240;
9.AJ.4.244; 9.AJ.4.243; 9.AJ.4.247; 9.AJ.5.157; 9.AJ.5.158;
9.AJ.5.196; 9.AJ.5.223; 9.AJ.5.240; 9.AJ.5.244; 9.AJ.5.243;
9.AJ.5.247; 9.AJ.7.157; 9.AJ.7.158; 9.AJ.7.196; 9.AJ.7.223;
9.AJ.7.240; 9.AJ.7.244; 9.AJ.7.243; 9.AJ.7.247; 9.AJ.15.157;
9.AJ.15.158; 9.AJ.15.196; 9.AJ.15.223; 9.AJ.15.240; 9.AJ.15.244;
9.AJ.15.243; 9.AJ.15.247; 9.AJ.16.157; 9.AJ.16.158; 9.AJ.16.196;
9.AJ.16.223; 9.AJ.16.240; 9.AJ.16.244; 9.AJ.16.243; 9.AJ.16.247;
9.AJ.18.157; 9.AJ.18.158; 9.AJ.18.196; 9.AJ.18.223; 9.AJ.18.240;
9.AJ.18.244; 9.AJ.18.243; 9.AJ.18.247; 9.AJ.26.157; 9.AJ.26.158;
9.AJ.26.196; 9.AJ.26.223; 9.AJ.26.240; 9.AJ.26.244; 9.AJ.26.243;
9.AJ.26.247; 9.AJ.27.157; 9.AJ.27.158; 9.AJ.27.196; 9.AJ.27.223;
9.AJ.27.240; 9.AJ.27.244; 9.AJ.27.243; 9.AJ.27.247; 9.AJ.29.157;
9.AJ.29.158; 9.AJ.29.196; 9.AJ.29.223; 9.AJ.29.240; 9.AJ.29.244;
9.AJ.29.243; 9.AJ.29.247; 9.AJ.54.157; 9.AJ.54.158; 9.AJ.54.196;
9.AJ.54.223; 9.AJ.54.240; 9.AJ.54.244; 9.AJ.54.243; 9.AJ.54.247;
9.AJ.55.157; 9.AJ.55.158; 9.AJ.55.196; 9.AJ.55.223; 9.AJ.55.240;

9.AJ.55.244; 9.AJ.55.243; 9.AJ.55.247; 9.AJ.56.157; 9.AJ.56.158;
9.AJ.56.196; 9.AJ.56.223; 9.AJ.56.240; 9.AJ.56.244; 9.AJ.56.243;
9.AJ.56.247; 9.AJ.157.157; 9.AJ.157.158; 9.AJ.157.196; 9.AJ.157.223;
9.AJ.157.240; 9.AJ.157.244; 9.AJ.157.243; 9.AJ.157.247; 9.AJ.196.157;
9.AJ.196.158; 9.AJ.196.196; 9.AJ.196.223; 9.AJ.196.240; 9.AJ.196.244;
9.AJ.196.243; 9.AJ.196.247; 9.AJ.223.157; 9.AJ.223.158; 9.AJ.223.196;
9.AJ.223.223; 9.AJ.223.240; 9.AJ.223.244; 9.AJ.223.243; 9.AJ.223.247;
9.AJ.240.157; 9.AJ.240.158; 9.AJ.240.196; 9.AJ.240.223; 9.AJ.240.240;
9.AJ.240.244; 9.AJ.240.243; 9.AJ.240.247; 9.AJ.244.157; 9.AJ.244.158;
9.AJ.244.196; 9.AJ.244.223; 9.AJ.244.240; 9.AJ.244.244; 9.AJ.244.243;
9.AJ.244.247; 9.AJ.247.157; 9.AJ.247.158; 9.AJ.247.196; 9.AJ.247.223;
9.AJ.247.240; 9.AJ.247.244; 9.AJ.247.243; 9.AJ.247.247;
Prodrugs of 9.AN 9.AN.4.157; 9.AN.4.158; 9.AN.4.196; 9.AN.4.223; 9.AN.4.240;
9.AN.4.244; 9.AN.4.243; 9.AN.4.247; 9.AN.5.157; 9.AN.5.158;
9.AN.5.196; 9.AN.5.223; 9.AN.5.240; 9.AN.5.244; 9.AN.5.243;
9.AN.5.247; 9.AN.7.157; 9.AN.7.158; 9.AN.7.196; 9.AN.7.223;
9.AN.7.240; 9.AN.7.244; 9.AN.7.243; 9.AN.7.247; 9.AN.15.157;
9.AN.15.158; 9.AN.15.196; 9.AN.15.223; 9.AN.15.240; 9.AN.15.244;
9.AN.15.243; 9.AN.15.247; 9.AN.16.157; 9.AN.16.158; 9.AN.16.196;
9.AN.16.223; 9.AN.16.240; 9.AN.16.244; 9.AN.16.243; 9.AN.16.247;
9.AN.18.157; 9.AN.18.158; 9.AN.18.196; 9.AN.18.223; 9.AN.18.240;
9.AN.18.244; 9.AN.18.243; 9.AN.18.247; 9.AN.26.157; 9.AN.26.158;
9.AN.26.196; 9.AN.26.223; 9.AN.26.240; 9.AN.26.244; 9.AN.26.243;
9.AN.26.247; 9.AN.27.157; 9.AN.27.158; 9.AN.27.196; 9.AN.27.223;
9.AN.27.240; 9.AN.27.244; 9.AN.27.243; 9.AN.27.247; 9.AN.29.157;
9.AN.29.158; 9.AN.29.196; 9.AN.29.223; 9.AN.29.240; 9.AN.29.244;
9.AN.29.243; 9.AN.29.247; 9.AN.54.157; 9.AN.54.158; 9.AN.54.196;
9.AN.54.223; 9.AN.54.240; 9.AN.54.244; 9.AN.54.243; 9.AN.54.247;
9.AN.55.157; 9.AN.55.158; 9.AN.55.196; 9.AN.55.223; 9.AN.55.240;
9.AN.55.244; 9.AN.55.243; 9.AN.55.247; 9.AN.56.157; 9.AN.56.158;
9.AN.56.196; 9.AN.56.223; 9.AN.56.240; 9.AN.56.244; 9.AN.56.243;
9.AN.56.247; 9.AN.157.157; 9.AN.157.158; 9.AN.157.196;
9.AN.157.223; 9.AN.157.240; 9.AN.157.244; 9.AN.157.243;
9.AN.157.247; 9.AN.196.157; 9.AN.196.158; 9.AN.196.196;
9.AN.196.223; 9.AN.196.240; 9.AN.196.244; 9.AN.196.243;
9.AN.196.247; 9.AN.223.157; 9.AN.223.158; 9.AN.223.196;
9.AN.223.223; 9.AN.223.240; 9.AN.223.244; 9.AN.223.243;
9.AN.223.247; 9.AN.240.157; 9.AN.240.158; 9.AN.240.196;
9.AN.240.223; 9.AN.240.240; 9.AN.240.244; 9.AN.240.243;
9.AN.240.247; 9.AN.244.157; 9.AN.244.158; 9.AN.244.196;
9.AN.244.223; 9.AN.244.240; 9.AN.244.244; 9.AN.244.243;
9.AN.244.247; 9.AN.247.157; 9.AN.247.158; 9.AN.247.196;
9.AN.247.223; 9.AN.247.240; 9.AN.247.244; 9.AN.247.243;
9.AN.247.247;
Prodrugs of 9.AP 9.AP.4.157; 9.AP.4.158; 9.AP.4.196; 9.AP.4.223; 9.AP.4.240;
9.AP.4.244; 9.AP.4.243; 9.AP.4.247; 9.AP.5.157; 9.AP.5.158;
9.AP.5.196; 9.AP.5.223; 9.AP.5.240; 9.AP.5.244; 9.AP.5.243;
9.AP.5.247; 9.AP.7.157; 9.AP.7.158; 9.AP.7.196; 9.AP.7.223;
9.AP.7.240; 9.AP.7.244; 9.AP.7.243; 9.AP.7.247; 9.AP.15.157;
9.AP.15.158; 9.AP.15.196; 9.AP.15.223; 9.AP.15.240; 9.AP.15.244;
9.AP.15.243; 9.AP.15.247; 9.AP.16.157; 9.AP.16.158; 9.AP.16.196;
9.AP.16.223; 9.AP.16.240; 9.AP.16.244; 9.AP.16.243; 9.AP.16.247;
9.AP.18.157; 9.AP.18.158; 9.AP.18.196; 9.AP.18.223; 9.AP.18.240;
9.AP.18.244; 9.AP.18.243; 9.AP.18.247; 9.AP.26.157; 9.AP.26.158;
9.AP.26.196; 9.AP.26.223; 9.AP.26.240; 9.AP.26.244; 9.AP.26.243;
9.AP.26.247; 9.AP.27.157; 9.AP.27.158; 9.AP.27.196; 9.AP.27.223;
9.AP.27.240; 9.AP.27.244; 9.AP.27.243; 9.AP.27.247; 9.AP.29.157;
9.AP.29.158; 9.AP.29.196; 9.AP.29.223; 9.AP.29.240; 9.AP.29.244;
9.AP.29.243; 9.AP.29.247; 9.AP.54.157; 9.AP.54.158; 9.AP.54.196;
9.AP.54.223; 9.AP.54.240; 9.AP.54.244; 9.AP.54.243; 9.AP.54.247;
9.AP.55.157; 9.AP.55.158; 9.AP.55.196; 9.AP.55.223; 9.AP.55.240;
9.AP.55.244; 9.AP.55.243; 9.AP.55.247; 9.AP.56.157; 9.AP.56.158;
9.AP.56.196; 9.AP.56.223; 9.AP.56.240; 9.AP.56.244; 9.AP.56.243;
9.AP.56.247; 9.AP.157.157; 9.AP.157.158; 9.AP.157.196; 9.AP.157.223;
9.AP.157.240; 9.AP.157.244; 9.AP.157.243; 9.AP.157.247;
9.AP.196.157; 9.AP.196.158; 9.AP.196.196; 9.AP.196.223;
9.AP.196.240; 9.AP.196.244; 9.AP.196.243; 9.AP.196.247;
9.AP.223.157; 9.AP.223.158; 9.AP.223.196; 9.AP.223.223;
9.AP.223.240; 9.AP.223.244; 9.AP.223.243; 9.AP.223.247;
9.AP.240.157; 9.AP.240.158; 9.AP.240.196; 9.AP.240.223;
9.AP.240.240; 9.AP.240.244; 9.AP.240.243; 9.AP.240.247;
9.AP.244.157; 9.AP.244.158; 9.AP.244.196; 9.AP.244.223;
9.AP.244.240; 9.AP.244.244; 9.AP.244.243; 9.AP.244.247;
9.AP.247.157; 9.AP.247.158; 9.AP.247.196; 9.AP.247.223;
9.AP.247.240; 9.AP.247.244; 9.AP.247.243; 9.AP.247.247;

TABLE 7-continued

Prodrugs of 9.AZ

9.AZ.4.157; 9.AZ.4.158; 9.AZ.4.196; 9.AZ.4.223; 9.AZ.4.240;
9.AZ.4.244; 9.AZ.4.243; 9.AZ.4.247; 9.AZ.5.157; 9.AZ.5.158;
9.AZ.5.196; 9.AZ.5.223; 9.AZ.5.240; 9.AZ.5.244; 9.AZ.5.243;
9.AZ.5.247; 9.AZ.7.157; 9.AZ.7.158; 9.AZ.7.196; 9.AZ.7.223;
9.AZ.7.240; 9.AZ.7.244; 9.AZ.7.243; 9.AZ.7.247; 9.AZ.15.157;
9.AZ.15.158; 9.AZ.15.196; 9.AZ.15.223; 9.AZ.15.240; 9.AZ.15.244;
9.AZ.15.243; 9.AZ.15.247; 9.AZ.16.157; 9.AZ.16.158; 9.AZ.16.196;
9.AZ.16.223; 9.AZ.16.240; 9.AZ.16.244; 9.AZ.16.243; 9.AZ.16.247;
9.AZ.18.157; 9.AZ.18.158; 9.AZ.18.196; 9.AZ.18.223; 9.AZ.18.240;
9.AZ.18.244; 9.AZ.18.243; 9.AZ.18.247; 9.AZ.26.157; 9.AZ.26.158;
9.AZ.26.196; 9.AZ.26.223; 9.AZ.26.240; 9.AZ.26.244; 9.AZ.26.243;
9.AZ.26.247; 9.AZ.27.157; 9.AZ.27.158; 9.AZ.27.196; 9.AZ.27.223;
9.AZ.27.240; 9.AZ.27.244; 9.AZ.27.243; 9.AZ.27.247; 9.AZ.29.157;
9.AZ.29.158; 9.AZ.29.196; 9.AZ.29.223; 9.AZ.29.240; 9.AZ.29.244;
9.AZ.29.243; 9.AZ.29.247; 9.AZ.54.157; 9.AZ.54.158; 9.AZ.54.196;
9.AZ.54.223; 9.AZ.54.240; 9.AZ.54.244; 9.AZ.54.243; 9.AZ.54.247;
9.AZ.55.157; 9.AZ.55.158; 9.AZ.55.196; 9.AZ.55.223; 9.AZ.55.240;
9.AZ.55.244; 9.AZ.55.243; 9.AZ.55.247; 9.AZ.56.157; 9.AZ.56.158;
9.AZ.56.196; 9.AZ.56.223; 9.AZ.56.240; 9.AZ.56.244; 9.AZ.56.243;
9.AZ.56.247; 9.AZ.157.157; 9.AZ.157.158; 9.AZ.157.196; 9.AZ.157.223;
9.AZ.157.240; 9.AZ.157.244; 9.AZ.157.243; 9.AZ.157.247;
9.AZ.196.157; 9.AZ.196.158; 9.AZ.196.196; 9.AZ.196.223;
9.AZ.196.240; 9.AZ.196.244; 9.AZ.196.243; 9.AZ.196.247;
9.AZ.223.157; 9.AZ.223.158; 9.AZ.223.196; 9.AZ.223.223;
9.AZ.223.240; 9.AZ.223.244; 9.AZ.223.243; 9.AZ.223.247;
9.AZ.240.157; 9.AZ.240.158; 9.AZ.240.196; 9.AZ.240.223;
9.AZ.240.240; 9.AZ.240.244; 9.AZ.240.243; 9.AZ.240.247;
9.AZ.244.157; 9.AZ.244.158; 9.AZ.244.196; 9.AZ.244.223;
9.AZ.244.240; 9.AZ.244.244; 9.AZ.244.243; 9.AZ.244.247;
9.AZ.247.157; 9.AZ.247.158; 9.AZ.247.196; 9.AZ.247.223;
9.AZ.247.240; 9.AZ.247.244; 9.AZ.247.243; 9.AZ.247.247;

Prodrugs of 9.BF

9.BF.4.157; 9.BF.4.158; 9.BF.4.196; 9.BF.4.223; 9.BF.4.240;
9.BF.4.244; 9.BF.4.243; 9.BF.4.247; 9.BF.5.157; 9.BF.5.158;
9.BF.5.196; 9.BF.5.223; 9.BF.5.240; 9.BF.5.244; 9.BF.5.243;
9.BF.5.247; 9.BF.7.157; 9.BF.7.158; 9.BF.7.196; 9.BF.7.223;
9.BF.7.240; 9.BF.7.244; 9.BF.7.243; 9.BF.7.247; 9.BF.15.157;
9.BF.15.158; 9.BF.15.196; 9.BF.15.223; 9.BF.15.240; 9.BF.15.244;
9.BF.15.243; 9.BF.15.247; 9.BF.16.157; 9.BF.16.158; 9.BF.16.196;
9.BF.16.223; 9.BF.16.240; 9.BF.16.244; 9.BF.16.243; 9.BF.16.247;
9.BF.18.157; 9.BF.18.158; 9.BF.18.196; 9.BF.18.223; 9.BF.18.240;
9.BF.18.244; 9.BF.18.243; 9.BF.18.247; 9.BF.26.157; 9.BF.26.158;
9.BF.26.196; 9.BF.26.223; 9.BF.26.240; 9.BF.26.244; 9.BF.26.243;
9.BF.26.247; 9.BF.27.157; 9.BF.27.158; 9.BF.27.196; 9.BF.27.223;
9.BF.27.240; 9.BF.27.244; 9.BF.27.243; 9.BF.27.247; 9.BF.29.157;
9.BF.29.158; 9.BF.29.196; 9.BF.29.223; 9.BF.29.240; 9.BF.29.244;
9.BF.29.243; 9.BF.29.247; 9.BF.54.157; 9.BF.54.158; 9.BF.54.196;
9.BF.54.223; 9.BF.54.240; 9.BF.54.244; 9.BF.54.243; 9.BF.54.247;
9.BF.55.157; 9.BF.55.158; 9.BF.55.196; 9.BF.55.223; 9.BF.55.240;
9.BF.55.244; 9.BF.55.243; 9.BF.55.247; 9.BF.56.157; 9.BF.56.158;
9.BF.56.196; 9.BF.56.223; 9.BF.56.240; 9.BF.56.244; 9.BF.56.243;
9.BF.56.247; 9.BF.157.157; 9.BF.157.158; 9.BF.157.196; 9.BF.157.223;
9.BF.157.240; 9.BF.157.244; 9.BF.157.243; 9.BF.157.247; 9.BF.196.157;
9.BF.196.158; 9.BF.196.196; 9.BF.196.223; 9.BF.196.240; 9.BF.196.244;
9.BF.196.243; 9.BF.196.247; 9.BF.223.157; 9.BF.223.158; 9.BF.223.196;
9.BF.223.223; 9.BF.223.240; 9.BF.223.244; 9.BF.223.243; 9.BF.223.247;
9.BF.240.157; 9.BF.240.158; 9.BF.240.196; 9.BF.240.223; 9.BF.240.240;
9.BF.240.244; 9.BF.240.243; 9.BF.240.247; 9.BF.244.157; 9.BF.244.158;
9.BF.244.196; 9.BF.244.223; 9.BF.244.240; 9.BF.244.244; 9.BF.244.243;
9.BF.244.247; 9.BF.247.157; 9.BF.247.158; 9.BF.247.196; 9.BF.247.223;
9.BF.247.240; 9.BF.247.244; 9.BF.247.243; 9.BF.247.247;

Prodrugs of 9.CI

9.CI.4.157; 9.CI.4.158; 9.CI.4.196; 9.CI.4.223; 9.CI.4.240;
9.CI.4.244; 9.CI.4.243; 9.CI.4.247; 9.CI.5.157; 9.CI.5.158;
9.CI.5.196; 9.CI.5.223; 9.CI.5.240; 9.CI.5.244; 9.CI.5.243;
9.CI.5.247; 9.CI.7.157; 9.CI.7.158; 9.CI.7.196; 9.CI.7.223;
9.CI.7.240; 9.CI.7.244; 9.CI.7.243; 9.CI.7.247; 9.CI.15.157;
9.CI.15.158; 9.CI.15.196; 9.CI.15.223; 9.CI.15.240; 9.CI.15.244;
9.CI.15.243; 9.CI.15.247; 9.CI.16.157; 9.CI.16.158; 9.CI.16.196;
9.CI.16.223; 9.CI.16.240; 9.CI.16.244; 9.CI.16.243; 9.CI.16.247;
9.CI.18.157; 9.CI.18.158; 9.CI.18.196; 9.CI.18.223; 9.CI.18.240;
9.CI.18.244; 9.CI.18.243; 9.CI.18.247; 9.CI.26.157; 9.CI.26.158;
9.CI.26.196; 9.CI.26.223; 9.CI.26.240; 9.CI.26.244; 9.CI.26.243;
9.CI.26.247; 9.CI.27.157; 9.CI.27.158; 9.CI.27.196; 9.CI.27.223;
9.CI.27.240; 9.CI.27.244; 9.CI.27.243; 9.CI.27.247; 9.CI.29.157;
9.CI.29.158; 9.CI.29.196; 9.CI.29.223; 9.CI.29.240; 9.CI.29.244;
9.CI.29.243; 9.CI.29.247; 9.CI.54.157; 9.CI.54.158; 9.CI.54.196;
9.CI.54.223; 9.CI.54.240; 9.CI.54.244; 9.CI.54.243; 9.CI.54.247;
9.CI.55.157; 9.CI.55.158; 9.CI.55.196; 9.CI.55.223; 9.CI.55.240;
9.CI.55.244; 9.CI.55.243; 9.CI.55.247; 9.CI.56.157; 9.CI.56.158;
9.CI.56.196; 9.CI.56.223; 9.CI.56.240; 9.CI.56.244; 9.CI.56.243;
9.CI.56.247; 9.CI.157.157; 9.CI.157.158; 9.CI.157.196; 9.CI.157.223;
9.CI.157.240; 9.CI.157.244; 9.CI.157.243; 9.CI.157.247; 9.CI.196.157;
9.CI.196.158; 9.CI.196.196; 9.CI.196.223; 9.CI.196.240; 9.CI.196.244;
9.CI.196.243; 9.CI.196.247; 9.CI.223.157; 9.CI.223.158; 9.CI.223.196;
9.CI.223.223; 9.CI.223.240; 9.CI.223.244; 9.CI.223.243; 9.CI.223.247;
9.CI.240.157; 9.CI.240.158; 9.CI.240.196; 9.CI.240.223; 9.CI.240.240;
9.CI.240.244; 9.CI.240.243; 9.CI.240.247; 9.CI.244.157; 9.CI.244.158;
9.CI.244.196; 9.CI.244.223; 9.CI.244.240; 9.CI.244.244; 9.CI.244.243;
9.CI.244.247; 9.CI.247.157; 9.CI.247.158; 9.CI.247.196; 9.CI.247.223;
9.CI.247.240; 9.CI.247.244; 9.CI.247.243; 9.CI.247.247;

Prodrugs of 9.CO

9.CO.4.157; 9.CO.4.158; 9.CO.4.196; 9.CO.4.223; 9.CO.4.240;
9.CO.4.244; 9.CO.4.243; 9.CO.4.247; 9.CO.5.157; 9.CO.5.158;
9.CO.5.196; 9.CO.5.223; 9.CO.5.240; 9.CO.5.244; 9.CO.5.243;
9.CO.5.247; 9.CO.7.157; 9.CO.7.158; 9.CO.7.196; 9.CO.7.223;
9.CO.7.240; 9.CO.7.244; 9.CO.7.243; 9.CO.7.247; 9.CO.15.157;
9.CO.15.158; 9.CO.15.196; 9.CO.15.223; 9.CO.15.240; 9.CO.15.244;
9.CO.15.243; 9.CO.15.247; 9.CO.16.157; 9.CO.16.158; 9.CO.16.196;
9.CO.16.223; 9.CO.16.240; 9.CO.16.244; 9.CO.16.243; 9.CO.16.247;
9.CO.18.157; 9.CO.18.158; 9.CO.18.196; 9.CO.18.223; 9.CO.18.240;
9.CO.18.244; 9.CO.18.243; 9.CO.18.247; 9.CO.26.157; 9.CO.26.158;
9.CO.26.196; 9.CO.26.223; 9.CO.26.240; 9.CO.26.244; 9.CO.26.243;
9.CO.26.247; 9.CO.27.157; 9.CO.27.158; 9.CO.27.196; 9.CO.27.223;
9.CO.27.240; 9.CO.27.244; 9.CO.27.243; 9.CO.27.247; 9.CO.29.157;
9.CO.29.158; 9.CO.29.196; 9.CO.29.223; 9.CO.29.240; 9.CO.29.244;
9.CO.29.243; 9.CO.29.247; 9.CO.54.157; 9.CO.54.158; 9.CO.54.196;
9.CO.54.223; 9.CO.54.240; 9.CO.54.244; 9.CO.54.243; 9.CO.54.247;
9.CO.55.157; 9.CO.55.158; 9.CO.55.196; 9.CO.55.223; 9.CO.55.240;
9.CO.55.244; 9.CO.55.243; 9.CO.55.247; 9.CO.56.157; 9.CO.56.158;
9.CO.56.196; 9.CO.56.223; 9.CO.56.240; 9.CO.56.244; 9.CO.56.243;
9.CO.56.247; 9.CO.157.157; 9.CO.157.158; 9.CO.157.196;
9.CO.157.223; 9.CO.157.240; 9.CO.157.244; 9.CO.157.243;
9.CO.157.247; 9.CO.196.157; 9.CO.196.158; 9.CO.196.196;
9.CO.196.223; 9.CO.196.240; 9.CO.196.244; 9.CO.196.243;
9.CO.196.247; 9.CO.223.157; 9.CO.223.158; 9.CO.223.196;
9.CO.223.223; 9.CO.223.240; 9.CO.223.244; 9.CO.223.243;
9.CO.223.247; 9.CO.240.157; 9.CO.240.158; 9.CO.240.196;
9.CO.240.223; 9.CO.240.240; 9.CO.240.244; 9.CO.240.243;
9.CO.240.247; 9.CO.244.157; 9.CO.244.158; 9.CO.244.196;
9.CO.244.223; 9.CO.244.240; 9.CO.244.244; 9.CO.244.243;
9.CO.244.247; 9.CO.247.157; 9.CO.247.158; 9.CO.247.196;
9.CO.247.223; 9.CO.247.240; 9.CO.247.244; 9.CO.247.243;
9.CO.247.247;

Prodrugs of 10.AH

10.AH.4.157; 10.AH.4.158; 10.AH.4.196; 10.AH.4.223; 10.AH.4.240;
10.AH.4.244; 10.AH.4.243; 10.AH.4.247; 10.AH.5.157; 10.AH.5.158;
10.AH.5.196; 10.AH.5.223; 10.AH.5.240; 10.AH.5.244; 10.AH.5.243;
10.AH.5.247; 10.AH.7.157; 10.AH.7.158; 10.AH.7.196; 10.AH.7.223;
10.AH.7.240; 10.AH.7.244; 10.AH.7.243; 10.AH.7.247; 10.AH.15.157;
10.AH.15.158; 10.AH.15.196; 10.AH.15.223; 10.AH.15.240;
10.AH.15.244; 10.AH.15.243; 10.AH.15.247; 10.AH.16.157;
10.AH.16.158; 10.AH.16.196; 10.AH.16.223; 10.AH.16.240;
10.AH.16.244; 10.AH.16.243; 10.AH.16.247; 10.AH.18.157;
10.AH.18.158; 10.AH.18.196; 10.AH.18.223; 10.AH.18.240;
10.AH.18.244; 10.AH.18.243; 10.AH.18.247; 10.AH.26.157;
10.AH.26.158; 10.AH.26.196; 10.AH.26.223; 10.AH.26.240;
10.AH.26.244; 10.AH.26.243; 10.AH.26.247; 10.AH.27.157;
10.AH.27.158; 10.AH.27.196; 10.AH.27.223; 10.AH.27.240;
10.AH.27.244; 10.AH.27.243; 10.AH.27.247; 10.AH.29.157;
10.AH.29.158; 10.AH.29.196; 10.AH.29.223; 10.AH.29.240;
10.AH.29.244; 10.AH.29.243; 10.AH.29.247; 10.AH.54.157;
10.AH.54.158; 10.AH.54.196; 10.AH.54.223; 10.AH.54.240;
10.AH.54.244; 10.AH.54.243; 10.AH.54.247; 10.AH.55.157;
10.AH.55.158; 10.AH.55.196; 10.AH.55.223; 10.AH.55.240;
10.AH.55.244; 10.AH.55.243; 10.AH.55.247; 10.AH.56.157;
10.AH.56.158; 10.AH.56.196; 10.AH.56.223; 10.AH.56.240;
10.AH.56.244; 10.AH.56.243; 10.AH.56.247; 10.AH.157.157;
10.AH.157.158; 10.AH.157.196; 10.AH.157.223; 10.AH.157.240;
10.AH.157.244; 10.AH.157.243; 10.AH.157.247; 10.AH.196.157;
10.AH.196.158; 10.AH.196.196; 10.AH.196.223; 10.AH.196.240;
10.AH.196.244; 10.AH.196.243; 10.AH.196.247; 10.AH.223.157;

TABLE 7-continued

10.AH.223.158; 10.AH.223.196; 10.AH.223.223; 10.AH.223.240; 10.AH.223.244; 10.AH.223.243; 10.AH.223.247; 10.AH.240.157; 10.AH.240.158; 10.AH.240.196; 10.AH.240.223; 10.AH.240.240; 10.AH.240.244; 10.AH.240.243; 10.AH.240.247; 10.AH.244.157; 10.AH.244.158; 10.AH.244.196; 10.AH.244.223; 10.AH.244.240; 10.AH.244.244; 10.AH.244.243; 10.AH.244.247; 10.AH.247.157; 10.AH.247.158; 10.AH.247.196; 10.AH.247.223; 10.AH.247.240; 10.AH.247.244; 10.AH.247.243; 10.AH.247.247;

Prodrugs of 10.AJ

10.AJ.4.157; 10.AJ.4.158; 10.AJ.4.196; 10.AJ.4.223; 10.AJ.4.240; 10.AJ.4.244; 10.AJ.4.243; 10.AJ.4.247; 10.AJ.5.157; 10.AJ.5.158; 10.AJ.5.196; 10.AJ.5.223; 10.AJ.5.240; 10.AJ.5.244; 10.AJ.5.243; 10.AJ.5.247; 10.AJ.7.157; 10.AJ.7.158; 10.AJ.7.196; 10.AJ.7.223; 10.AJ.7.240; 10.AJ.7.244; 10.AJ.7.243; 10.AJ.7.247; 10.AJ.15.157; 10.AJ.15.158; 10.AJ.15.196; 10.AJ.15.223; 10.AJ.15.240; 10.AJ.15.244; 10.AJ.15.243; 10.AJ.15.247; 10.AJ.16.157; 10.AJ.16.158; 10.AJ.16.196; 10.AJ.16.223; 10.AJ.16.240; 10.AJ.16.244; 10.AJ.16.243; 10.AJ.16.247; 10.AJ.18.157; 10.AJ.18.158; 10.AJ.18.196; 10.AJ.18.223; 10.AJ.18.240; 10.AJ.18.244; 10.AJ.18.243; 10.AJ.18.247; 10.AJ.26.157; 10.AJ.26.158; 10.AJ.26.196; 10.AJ.26.223; 10.AJ.26.240; 10.AJ.26.244; 10.AJ.26.243; 10.AJ.26.247; 10.AJ.27.157; 10.AJ.27.158; 10.AJ.27.196; 10.AJ.27.223; 10.AJ.27.240; 10.AJ.27.244; 10.AJ.27.243; 10.AJ.27.247; 10.AJ.29.157; 10.AJ.29.158; 10.AJ.29.196; 10.AJ.29.223; 10.AJ.29.240; 10.AJ.29.244; 10.AJ.29.243; 10.AJ.29.247; 10.AJ.54.157; 10.AJ.54.158; 10.AJ.54.196; 10.AJ.54.223; 10.AJ.54.240; 10.AJ.54.244; 10.AJ.54.243; 10.AJ.54.247; 10.AJ.55.157; 10.AJ.55.158; 10.AJ.55.196; 10.AJ.55.223; 10.AJ.55.240; 10.AJ.55.244; 10.AJ.55.243; 10.AJ.55.247; 10.AJ.56.157; 10.AJ.56.158; 10.AJ.56.196; 10.AJ.56.223; 10.AJ.56.240; 10.AJ.56.244; 10.AJ.56.243; 10.AJ.56.247; 10.AJ.157.157; 10.AJ.157.158; 10.AJ.157.196; 10.AJ.157.223; 10.AJ.157.240; 10.AJ.157.244; 10.AJ.157.243; 10.AJ.157.247; 10.AJ.196.157; 10.AJ.196.158; 10.AJ.196.196; 10.AJ.196.223; 10.AJ.196.240; 10.AJ.196.244; 10.AJ.196.243; 10.AJ.196.247; 10.AJ.223.157; 10.AJ.223.158; 10.AJ.223.196; 10.AJ.223.223; 10.AJ.223.240; 10.AJ.223.244; 10.AJ.223.243; 10.AJ.223.247; 10.AJ.240.157; 10.AJ.240.158; 10.AJ.240.196; 10.AJ.240.223; 10.AJ.240.240; 10.AJ.240.244; 10.AJ.240.243; 10.AJ.240.247; 10.AJ.244.157; 10.AJ.244.158; 10.AJ.244.196; 10.AJ.244.223; 10.AJ.244.240; 10.AJ.244.244; 10.AJ.244.243; 10.AJ.244.247; 10.AJ.247.157; 10.AJ.247.158; 10.AJ.247.196; 10.AJ.247.223; 10.AJ.247.240; 10.AJ.247.244; 10.AJ.247.243; 10.AJ.247.247;

Prodrugs of 10.AN

10.AN.4.157; 10.AN.4.158; 10.AN.4.196; 10.AN.4.223; 10.AN.4.240; 10.AN.4.244; 10.AN.4.243; 10.AN.4.247; 10.AN.5.157; 10.AN.5.158; 10.AN.5.196; 10.AN.5.223; 10.AN.5.240; 10.AN.5.244; 10.AN.5.243; 10.AN.5.247; 10.AN.7.157; 10.AN.7.158; 10.AN.7.196; 10.AN.7.223; 10.AN.7.240; 10.AN.7.244; 10.AN.7.243; 10.AN.7.247; 10.AN.15.157; 10.AN.15.158; 10.AN.15.196; 10.AN.15.223; 10.AN.15.240; 10.AN.15.244; 10.AN.15.243; 10.AN.15.247; 10.AN.16.157; 10.AN.16.158; 10.AN.16.196; 10.AN.16.223; 10.AN.16.240; 10.AN.16.244; 10.AN.16.243; 10.AN.16.247; 10.AN.18.157; 10.AN.18.158; 10.AN.18.196; 10.AN.18.223; 10.AN.18.240; 10.AN.18.244; 10.AN.18.243; 10.AN.18.247; 10.AN.26.157; 10.AN.26.158; 10.AN.26.196; 10.AN.26.223; 10.AN.26.240; 10.AN.26.244; 10.AN.26.243; 10.AN.26.247; 10.AN.27.157; 10.AN.27.158; 10.AN.27.196; 10.AN.27.223; 10.AN.27.240; 10.AN.27.244; 10.AN.27.243; 10.AN.27.247; 10.AN.29.157; 10.AN.29.158; 10.AN.29.196; 10.AN.29.223; 10.AN.29.240; 10.AN.29.244; 10.AN.29.243; 10.AN.29.247; 10.AN.54.157; 10.AN.54.158; 10.AN.54.196; 10.AN.54.223; 10.AN.54.240; 10.AN.54.244; 10.AN.54.243; 10.AN.54.247; 10.AN.55.157; 10.AN.55.158; 10.AN.55.196; 10.AN.55.223; 10.AN.55.240; 10.AN.55.244; 10.AN.55.243; 10.AN.55.247; 10.AN.56.157; 10.AN.56.158; 10.AN.56.196; 10.AN.56.223; 10.AN.56.240; 10.AN.56.244; 10.AN.56.243; 10.AN.56.247; 10.AN.157.157; 10.AN.157.158; 10.AN.157.196; 10.AN.157.223; 10.AN.157.240; 10.AN.157.244; 10.AN.157.243; 10.AN.157.247; 10.AN.196.157; 10.AN.196.158; 10.AN.196.196; 10.AN.196.223; 10.AN.196.240; 10.AN.196.244; 10.AN.196.243; 10.AN.196.247; 10.AN.223.157; 10.AN.223.158; 10.AN.223.196; 10.AN.223.223; 10.AN.223.240; 10.AN.223.244; 10.AN.223.243; 10.AN.223.247; 10.AN.240.157; 10.AN.240.158; 10.AN.240.196; 10.AN.240.223; 10.AN.240.240; 10.AN.240.244; 10.AN.240.243; 10.AN.240.247; 10.AN.244.157; 10.AN.244.158; 10.AN.244.196; 10.AN.244.223; 10.AN.244.240; 10.AN.244.244; 10.AN.244.243; 10.AN.244.247; 10.AN.247.157; 10.AN.247.158; 10.AN.247.196; 10.AN.247.223; 10.AN.247.240; 10.AN.247.244; 10.AN.247.243; 10.AN.247.247;

Prodrugs of 10.AP

10.AP.4.157; 10.AP.4.158; 10.AP.4.196; 10.AP.4.223; 10.AP.4.240; 10.AP.4.244; 10.AP.4.243; 10.AP.4.247; 10.AP.5.157; 10.AP.5.158; 10.AP.5.196; 10.AP.5.223; 10.AP.5.240; 10.AP.5.244; 10.AP.5.243; 10.AP.5.247; 10.AP.7.157; 10.AP.7.158; 10.AP.7.196; 10.AP.7.223; 10.AP.7.240; 10.AP.7.244; 10.AP.7.243; 10.AP.7.247; 10.AP.15.157; 10.AP.15.158; 10.AP.15.196; 10.AP.15.223; 10.AP.15.240; 10.AP.15.244; 10.AP.15.243; 10.AP.15.247; 10.AP.16.157; 10.AP.16.158; 10.AP.16.196; 10.AP.16.223; 10.AP.16.240; 10.AP.16.244; 10.AP.16.243; 10.AP.16.247; 10.AP.18.157; 10.AP.18.158; 10.AP.18.196; 10.AP.18.223; 10.AP.18.240; 10.AP.18.244; 10.AP.18.243; 10.AP.18.247; 10.AP.26.157; 10.AP.26.158; 10.AP.26.196; 10.AP.26.223; 10.AP.26.240; 10.AP.26.244; 10.AP.26.243; 10.AP.26.247; 10.AP.27.157; 10.AP.27.158; 10.AP.27.196; 10.AP.27.223; 10.AP.27.240; 10.AP.27.244; 10.AP.27.243; 10.AP.27.247; 10.AP.29.157; 10.AP.29.158; 10.AP.29.196; 10.AP.29.223; 10.AP.29.240; 10.AP.29.244; 10.AP.29.243; 10.AP.29.247; 10.AP.54.157; 10.AP.54.158; 10.AP.54.196; 10.AP.54.223; 10.AP.54.240; 10.AP.54.244; 10.AP.54.243; 10.AP.54.247; 10.AP.55.157; 10.AP.55.158; 10.AP.55.196; 10.AP.55.223; 10.AP.55.240; 10.AP.55.244; 10.AP.55.243; 10.AP.55.247; 10.AP.56.157; 10.AP.56.158; 10.AP.56.196; 10.AP.56.223; 10.AP.56.240; 10.AP.56.244; 10.AP.56.243; 10.AP.56.247; 10.AP.157.157; 10.AP.157.158; 10.AP.157.196; 10.AP.157.223; 10.AP.157.240; 10.AP.157.244; 10.AP.157.243; 10.AP.157.247; 10.AP.196.157; 10.AP.196.158; 10.AP.196.196; 10.AP.196.223; 10.AP.196.240; 10.AP.196.244; 10.AP.196.243; 10.AP.196.247; 10.AP.223.157; 10.AP.223.158; 10.AP.223.196; 10.AP.223.223; 10.AP.223.240; 10.AP.223.244; 10.AP.223.243; 10.AP.223.247; 10.AP.240.157; 10.AP.240.158; 10.AP.240.196; 10.AP.240.223; 10.AP.240.240; 10.AP.240.244; 10.AP.240.243; 10.AP.240.247; 10.AP.244.157; 10.AP.244.158; 10.AP.244.196; 10.AP.244.223; 10.AP.244.240; 10.AP.244.244; 10.AP.244.243; 10.AP.244.247; 10.AP.247.157; 10.AP.247.158; 10.AP.247.196; 10.AP.247.223; 10.AP.247.240; 10.AP.247.244; 10.AP.247.243; 10.AP.247.247;

Prodrugs of 10.AZ

10.AZ.4.157; 10.AZ.4.158; 10.AZ.4.196; 10.AZ.4.223; 10.AZ.4.240; 10.AZ.4.244; 10.AZ.4.243; 10.AZ.4.247; 10.AZ.5.157; 10.AZ.5.158; 10.AZ.5.196; 10.AZ.5.223; 10.AZ.5.240; 10.AZ.5.244; 10.AZ.5.243; 10.AZ.5.247; 10.AZ.7.157; 10.AZ.7.158; 10.AZ.7.196; 10.AZ.7.223; 10.AZ.7.240; 10.AZ.7.244; 10.AZ.7.243; 10.AZ.7.247; 10.AZ.15.157; 10.AZ.15.158; 10.AZ.15.196; 10.AZ.15.223; 10.AZ.15.240; 10.AZ.15.244; 10.AZ.15.243; 10.AZ.15.247; 10.AZ.16.157; 10.AZ.16.158; 10.AZ.16.196; 10.AZ.16.223; 10.AZ.16.240; 10.AZ.16.244; 10.AZ.16.243; 10.AZ.16.247; 10.AZ.18.157; 10.AZ.18.158; 10.AZ.18.196; 10.AZ.18.223; 10.AZ.18.240; 10.AZ.18.244; 10.AZ.18.243; 10.AZ.18.247; 10.AZ.26.157; 10.AZ.26.158; 10.AZ.26.196; 10.AZ.26.223; 10.AZ.26.240; 10.AZ.26.244; 10.AZ.26.243; 10.AZ.26.247; 10.AZ.27.157; 10.AZ.27.158; 10.AZ.27.196; 10.AZ.27.223; 10.AZ.27.240; 10.AZ.27.244; 10.AZ.27.243; 10.AZ.27.247; 10.AZ.29.157; 10.AZ.29.158; 10.AZ.29.196; 10.AZ.29.223; 10.AZ.29.240; 10.AZ.29.244; 10.AZ.29.243; 10.AZ.29.247; 10.AZ.54.157; 10.AZ.54.158; 10.AZ.54.196; 10.AZ.54.223; 10.AZ.54.240; 10.AZ.54.244; 10.AZ.54.243; 10.AZ.54.247; 10.AZ.55.157; 10.AZ.55.158; 10.AZ.55.196; 10.AZ.55.223; 10.AZ.55.240; 10.AZ.55.244; 10.AZ.55.243; 10.AZ.55.247; 10.AZ.56.157; 10.AZ.56.158; 10.AZ.56.196; 10.AZ.56.223; 10.AZ.56.240; 10.AZ.56.244; 10.AZ.56.243; 10.AZ.56.247; 10.AZ.157.157; 10.AZ.157.158; 10.AZ.157.196; 10.AZ.157.223; 10.AZ.157.240; 10.AZ.157.244; 10.AZ.157.243; 10.AZ.157.247; 10.AZ.196.157; 10.AZ.196.158; 10.AZ.196.196; 10.AZ.196.223; 10.AZ.196.240; 10.AZ.196.244; 10.AZ.196.243; 10.AZ.196.247; 10.AZ.223.157; 10.AZ.223.158; 10.AZ.223.196; 10.AZ.223.223; 10.AZ.223.240; 10.AZ.223.244; 10.AZ.223.243; 10.AZ.223.247; 10.AZ.240.157; 10.AZ.240.158; 10.AZ.240.196; 10.AZ.240.223; 10.AZ.240.240; 10.AZ.240.244; 10.AZ.240.243; 10.AZ.240.247; 10.AZ.244.157; 10.AZ.244.158; 10.AZ.244.196; 10.AZ.244.223; 10.AZ.244.240; 10.AZ.244.244; 10.AZ.244.243; 10.AZ.244.247; 10.AZ.247.157; 10.AZ.247.158; 10.AZ.247.196; 10.AZ.247.223; 10.AZ.247.240; 10.AZ.247.244; 10.AZ.247.243; 10.AZ.247.247;

Prodrugs of 10.BF

10.BF.4.157; 10.BF.4.158; 10.BF.4.196; 10.BF.4.223; 10.BF.4.240; 10.BF.4.244; 10.BF.4.243; 10.BF.4.247; 10.BF.5.157; 10.BF.5.158; 10.BF.5.196; 10.BF.5.223; 10.BF.5.240; 10.BF.5.244; 10.BF.5.243;

TABLE 7-continued

10.BF.5.247; 10.BF.7.157; 10.BF.7.158; 10.BF.7.196; 10.BF.7.223;
10.BF.7.240; 10.BF.7.244; 10.BF.7.243; 10.BF.7.247; 10.BF.15.157;
10.BF.15.158; 10.BF.15.196; 10.BF.15.223; 10.BF.15.240; 10.BF.15.244;
10.BF.15.243; 10.BF.15.247; 10.BF.16.157; 10.BF.16.158; 10.BF.16.196;
10.BF.16.223; 10.BF.16.240; 10.BF.16.244; 10.BF.16.243; 10.BF.16.247;
10.BF.18.157; 10.BF.18.158; 10.BF.18.196; 10.BF.18.223; 10.BF.18.240;
10.BF.18.244; 10.BF.18.243; 10.BF.18.247; 10.BF.26.157; 10.BF.26.158;
10.BF.26.196; 10.BF.26.223; 10.BF.26.240; 10.BF.26.244; 10.BF.26.243;
10.BF.26.247; 10.BF.27.157; 10.BF.27.158; 10.BF.27.196; 10.BF.27.223;
10.BF.27.240; 10.BF.27.244; 10.BF.27.243; 10.BF.27.247; 10.BF.29.157;
10.BF.29.158; 10.BF.29.196; 10.BF.29.223; 10.BF.29.240; 10.BF.29.244;
10.BF.29.243; 10.BF.29.247; 10.BF.54.157; 10.BF.54.158; 10.BF.54.196;
10.BF.54.223; 10.BF.54.240; 10.BF.54.244; 10.BF.54.243; 10.BF.54.247;
10.BF.55.157; 10.BF.55.158; 10.BF.55.196; 10.BF.55.223; 10.BF.55.240;
10.BF.55.244; 10.BF.55.243; 10.BF.55.247; 10.BF.56.157; 10.BF.56.158;
10.BF.56.196; 10.BF.56.223; 10.BF.56.240; 10.BF.56.244; 10.BF.56.243;
10.BF.56.247; 10.BF.157.157; 10.BF.157.158; 10.BF.157.196;
10.BF.157.223; 10.BF.157.240; 10.BF.157.244; 10.BF.157.243;
10.BF.157.247; 10.BF.196.157; 10.BF.196.158; 10.BF.196.196;
10.BF.196.223; 10.BF.196.240; 10.BF.196.244; 10.BF.196.243;
10.BF.196.247; 10.BF.223.157; 10.BF.223.158; 10.BF.223.196;
10.BF.223.223; 10.BF.223.240; 10.BF.223.244; 10.BF.223.243;
10.BF.223.247; 10.BF.240.157; 10.BF.240.158; 10.BF.240.196;
10.BF.240.223; 10.BF.240.240; 10.BF.240.244; 10.BF.240.243;
10.BF.240.247; 10.BF.244.157; 10.BF.244.158; 10.BF.244.196;
10.BF.244.223; 10.BF.244.240; 10.BF.244.244; 10.BF.244.243;
10.BF.244.247; 10.BF.247.157; 10.BF.247.158; 10.BF.247.196;
10.BF.247.223; 10.BF.247.240; 10.BF.247.244; 10.BF.247.243;
10.BF.247.247;
Prodrugs of 10.CI 10.CI.4.157; 10.CI.4.158; 10.CI.4.196; 10.CI.4.223; 10.CI.4.240;
10.CI.4.244; 10.CI.4.243; 10.CI.4.247; 10.CI.5.157; 10.CI.5.158;
10.CI.5.196; 10.CI.5.223; 10.CI.5.240; 10.CI.5.244; 10.CI.5.243;
10.CI.5.247; 10.CI.7.157; 10.CI.7.158; 10.CI.7.196; 10.CI.7.223;
10.CI.7.240; 10.CI.7.244; 10.CI.7.243; 10.CI.7.247; 10.CI.15.157;
10.CI.15.158; 10.CI.15.196; 10.CI.15.223; 10.CI.15.240; 10.CI.15.244;
10.CI.15.243; 10.CI.15.247; 10.CI.16.157; 10.CI.16.158; 10.CI.16.196;
10.CI.16.223; 10.CI.16.240; 10.CI.16.244; 10.CI.16.243; 10.CI.16.247;
10.CI.18.157; 10.CI.18.158; 10.CI.18.196; 10.CI.18.223; 10.CI.18.240;
10.CI.18.244; 10.CI.18.243; 10.CI.18.247; 10.CI.26.157; 10.CI.26.158;
10.CI.26.196; 10.CI.26.223; 10.CI.26.240; 10.CI.26.244; 10.CI.26.243;
10.CI.26.247; 10.CI.27.157; 10.CI.27.158; 10.CI.27.196; 10.CI.27.223;
10.CI.27.240; 10.CI.27.244; 10.CI.27.243; 10.CI.27.247; 10.CI.29.157;
10.CI.29.158; 10.CI.29.196; 10.CI.29.223; 10.CI.29.240; 10.CI.29.244;
10.CI.29.243; 10.CI.29.247; 10.CI.54.157; 10.CI.54.158; 10.CI.54.196;
10.CI.54.223; 10.CI.54.240; 10.CI.54.244; 10.CI.54.243; 10.CI.54.247;
10.CI.55.157; 10.CI.55.158; 10.CI.55.196; 10.CI.55.223; 10.CI.55.240;
10.CI.55.244; 10.CI.55.243; 10.CI.55.247; 10.CI.56.157; 10.CI.56.158;
10.CI.56.196; 10.CI.56.223; 10.CI.56.240; 10.CI.56.244; 10.CI.56.243;
10.CI.56.247; 10.CI.157.157; 10.CI.157.158; 10.CI.157.196;
10.CI.157.223; 10.CI.157.240; 10.CI.157.244; 10.CI.157.243;
10.CI.157.247; 10.CI.196.157; 10.CI.196.158; 10.CI.196.196;
10.CI.196.223; 10.CI.196.240; 10.CI.196.244; 10.CI.196.243;
10.CI.196.247; 10.CI.223.157; 10.CI.223.158; 10.CI.223.196;
10.CI.223.223; 10.CI.223.240; 10.CI.223.244; 10.CI.223.243;
10.CI.223.247; 10.CI.240.157; 10.CI.240.158; 10.CI.240.196;
10.CI.240.223; 10.CI.240.240; 10.CI.240.244; 10.CI.240.243;
10.CI.240.247; 10.CI.244.157; 10.CI.244.158; 10.CI.244.196;
10.CI.244.223; 10.CI.244.240; 10.CI.244.244; 10.CI.244.243;
10.CI.244.247; 10.CI.247.157; 10.CI.247.158; 10.CI.247.196;
10.CI.247.223; 10.CI.247.240; 10.CI.247.244; 10.CI.247.243;
10.CI.247.247;
Prodrugs of 10.CO 10.CO.4.157; 10.CO.4.158; 10.CO.4.196; 10.CO.4.223; 10.CO.4.240;
10.CO.4.244; 10.CO.4.243; 10.CO.4.247; 10.CO.5.157; 10.CO.5.158;
10.CO.5.196; 10.CO.5.223; 10.CO.5.240; 10.CO.5.244; 10.CO.5.243;
10.CO.5.247; 10.CO.7.157; 10.CO.7.158; 10.CO.7.196; 10.CO.7.223;
10.CO.7.240; 10.CO.7.244; 10.CO.7.243; 10.CO.7.247; 10.CO.15.157;
10.CO.15.158; 10.CO.15.196; 10.CO.15.223; 10.CO.15.240;
10.CO.15.244; 10.CO.15.243; 10.CO.15.247; 10.CO.16.157;
10.CO.16.158; 10.CO.16.196; 10.CO.16.223; 10.CO.16.240;
10.CO.16.244; 10.CO.16.243; 10.CO.16.247; 10.CO.18.157;
10.CO.18.158; 10.CO.18.196; 10.CO.18.223; 10.CO.18.240;
10.CO.18.244; 10.CO.18.243; 10.CO.18.247; 10.CO.26.157;
10.CO.26.158; 10.CO.26.196; 10.CO.26.223; 10.CO.26.240;
10.CO.26.244; 10.CO.26.243; 10.CO.26.247; 10.CO.27.157;
10.CO.27.158; 10.CO.27.196; 10.CO.27.223; 10.CO.27.240;
10.CO.27.244; 10.CO.27.243; 10.CO.27.247; 10.CO.29.157;
10.CO.29.158; 10.CO.29.196; 10.CO.29.223; 10.CO.29.240;
10.CO.29.244; 10.CO.29.243; 10.CO.29.247; 10.CO.54.157;
10.CO.54.158; 10.CO.54.196; 10.CO.54.223; 10.CO.54.240;
10.CO.54.244; 10.CO.54.243; 10.CO.54.247; 10.CO.55.157;
10.CO.55.158; 10.CO.55.196; 10.CO.55.223; 10.CO.55.240;
10.CO.55.244; 10.CO.55.243; 10.CO.55.247; 10.CO.56.157;
10.CO.56.158; 10.CO.56.196; 10.CO.56.223; 10.CO.56.240;
10.CO.56.244; 10.CO.56.243; 10.CO.56.247; 10.CO.157.157;
10.CO.157.158; 10.CO.157.196; 10.CO.157.223; 10.CO.157.240;
10.CO.157.244; 10.CO.157.243; 10.CO.157.247; 10.CO.196.157;
10.CO.196.158; 10.CO.196.196; 10.CO.196.223; 10.CO.196.240;
10.CO.196.244; 10.CO.196.243; 10.CO.196.247; 10.CO.223.157;
10.CO.223.158; 10.CO.223.196; 10.CO.223.223; 10.CO.223.240;
10.CO.223.244; 10.CO.223.243; 10.CO.223.247; 10.CO.240.157;
10.CO.240.158; 10.CO.240.196; 10.CO.240.223; 10.CO.240.240;
10.CO.240.244; 10.CO.240.243; 10.CO.240.247; 10.CO.244.157;
10.CO.244.158; 10.CO.244.196; 10.CO.244.223; 10.CO.244.240;
10.CO.244.244; 10.CO.244.243; 10.CO.244.247; 10.CO.247.157;
10.CO.247.158; 10.CO.247.196; 10.CO.247.223; 10.CO.247.240;
10.CO.247.244; 10.CO.247.243; 10.CO.247.247;
Prodrugs of 11.AH 11.AH.4.157; 11.AH.4.158; 11.AH.4.196; 11.AH.4.223; 11.AH.4.240;
11.AH.4.244; 11.AH.4.243; 11.AH.4.247; 11.AH.5.157; 11.AH.5.158;
11.AH.5.196; 11.AH.5.223; 11.AH.5.240; 11.AH.5.244; 11.AH.5.243;
11.AH.5.247; 11.AH.7.157; 11.AH.7.158; 11.AH.7.196; 11.AH.7.223;
11.AH.7.240; 11.AH.7.244; 11.AH.7.243; 11.AH.7.247; 11.AH.15.157;
11.AH.15.158; 11.AH.15.196; 11.AH.15.223; 11.AH.15.240;
11.AH.15.244; 11.AH.15.243; 11.AH.15.247; 11.AH.16.157;
11.AH.16.158; 11.AH.16.196; 11.AH.16.223; 11.AH.16.240;
11.AH.16.244; 11.AH.16.243; 11.AH.16.247; 11.AH.18.157;
11.AH.18.158; 11.AH.18.196; 11.AH.18.223; 11.AH.18.240;
11.AH.18.244; 11.AH.18.243; 11.AH.18.247; 11.AH.26.157;
11.AH.26.158; 11.AH.26.196; 11.AH.26.223; 11.AH.26.240;
11.AH.26.244; 11.AH.26.243; 11.AH.26.247; 11.AH.27.157;
11.AH.27.158; 11.AH.27.196; 11.AH.27.223; 11.AH.27.240;
11.AH.27.244; 11.AH.27.243; 11.AH.27.247; 11.AH.29.157;
11.AH.29.158; 11.AH.29.196; 11.AH.29.223; 11.AH.29.240;
11.AH.29.244; 11.AH.29.243; 11.AH.29.247; 11.AH.54.157;
11.AH.54.158; 11.AH.54.196; 11.AH.54.223; 11.AH.54.240;
11.AH.54.244; 11.AH.54.243; 11.AH.54.247; 11.AH.55.157;
11.AH.55.158; 11.AH.55.196; 11.AH.55.223; 11.AH.55.240;
11.AH.55.244; 11.AH.55.243; 11.AH.55.247; 11.AH.56.157;
11.AH.56.158; 11.AH.56.196; 11.AH.56.223; 11.AH.56.240;
11.AH.56.244; 11.AH.56.243; 11.AH.56.247; 11.AH.157.157;
11.AH.157.158; 11.AH.157.196; 11.AH.157.223; 11.AH.157.240;
11.AH.157.244; 11.AH.157.243; 11.AH.157.247; 11.AH.196.157;
11.AH.196.158; 11.AH.196.196; 11.AH.196.223; 11.AH.196.240;
11.AH.196.244; 11.AH.196.243; 11.AH.196.247; 11.AH.223.157;
11.AH.223.158; 11.AH.223.196; 11.AH.223.223; 11.AH.223.240;
11.AH.223.244; 11.AH.223.243; 11.AH.223.247; 11.AH.240.157;
11.AH.240.158; 11.AH.240.196; 11.AH.240.223; 11.AH.240.240;
11.AH.240.244; 11.AH.240.243; 11.AH.240.247; 11.AH.244.157;
11.AH.244.158; 11.AH.244.196; 11.AH.244.223; 11.AH.244.240;
11.AH.244.244; 11.AH.244.243; 11.AH.244.247; 11.AH.247.157;
11.AH.247.158; 11.AH.247.196; 11.AH.247.223; 11.AH.247.240;
11.AH.247.244; 11.AH.247.243; 11.AH.247.247;
Prodrugs of 11.AJ 11.AJ.4.157; 11.AJ.4.158; 11.AJ.4.196; 11.AJ.4.223; 11.AJ.4.240;
11.AJ.4.244; 11.AJ.4.243; 11.AJ.4.247; 11.AJ.5.157; 11.AJ.5.158;
11.AJ.5.196; 11.AJ.5.223; 11.AJ.5.240; 11.AJ.5.244; 11.AJ.5.243;
11.AJ.5.247; 11.AJ.7.157; 11.AJ.7.158; 11.AJ.7.196; 11.AJ.7.223;
11.AJ.7.240; 11.AJ.7.244; 11.AJ.7.243; 11.AJ.7.247; 11.AJ.15.157;
11.AJ.15.158; 11.AJ.15.196; 11.AJ.15.223; 11.AJ.15.240; 11.AJ.15.244;
11.AJ.15.243; 11.AJ.15.247; 11.AJ.16.157; 11.AJ.16.158; 11.AJ.16.196;
11.AJ.16.223; 11.AJ.16.240; 11.AJ.16.244; 11.AJ.16.243; 11.AJ.16.247;
11.AJ.18.157; 11.AJ.18.158; 11.AJ.18.196; 11.AJ.18.223; 11.AJ.18.240;
11.AJ.18.244; 11.AJ.18.243; 11.AJ.18.247; 11.AJ.26.157; 11.AJ.26.158;
11.AJ.26.196; 11.AJ.26.223; 11.AJ.26.240; 11.AJ.26.244; 11.AJ.26.243;
11.AJ.26.247; 11.AJ.27.157; 11.AJ.27.158; 11.AJ.27.196; 11.AJ.27.223;
11.AJ.27.240; 11.AJ.27.244; 11.AJ.27.243; 11.AJ.27.247; 11.AJ.29.157;
11.AJ.29.158; 11.AJ.29.196; 11.AJ.29.223; 11.AJ.29.240; 11.AJ.29.244;
11.AJ.29.243; 11.AJ.29.247; 11.AJ.54.157; 11.AJ.54.158; 11.AJ.54.196;
11.AJ.54.223; 11.AJ.54.240; 11.AJ.54.244; 11.AJ.54.243; 11.AJ.54.247;
11.AJ.55.157; 11.AJ.55.158; 11.AJ.55.196; 11.AJ.55.223; 11.AJ.55.240;
11.AJ.55.244; 11.AJ.55.243; 11.AJ.55.247; 11.AJ.56.157; 11.AJ.56.158;
11.AJ.56.196; 11.AJ.56.223; 11.AJ.56.240; 11.AJ.56.244; 11.AJ.56.243;

TABLE 7-continued

11.AJ.56.247; 11.AJ.157.157; 11.AJ.157.158; 11.AJ.157.196;
11.AJ.157.223; 11.AJ.157.240; 11.AJ.157.244; 11.AJ.157.243;
11.AJ.157.247; 11.AJ.196.157; 11.AJ.196.158; 11.AJ.196.196;
11.AJ.196.223; 11.AJ.196.240; 11.AJ.196.244; 11.AJ.196.243;
11.AJ.196.247; 11.AJ.223.157; 11.AJ.223.158; 11.AJ.223.196;
11.AJ.223.223; 11.AJ.223.240; 11.AJ.223.244; 11.AJ.223.243;
11.AJ.223.247; 11.AJ.240.157; 11.AJ.240.158; 11.AJ.240.196;
11.AJ.240.223; 11.AJ.240.244; 11.AJ.240.244; 11.AJ.240.243;
11.AJ.240.247; 11.AJ.244.157; 11.AJ.244.158; 11.AJ.244.196;
11.AJ.244.223; 11.AJ.244.240; 11.AJ.244.244; 11.AJ.244.243;
11.AJ.244.247; 11.AJ.247.157; 11.AJ.247.158; 11.AJ.247.196;
11.AJ.247.223; 11.AJ.247.240; 11.AJ.247.244; 11.AJ.247.243;
11.AJ.247.247;

Prodrugs of 11.AN

11.AN.4.157; 11.AN.4.158; 11.AN.4.196; 11.AN.4.223; 11.AN.4.240;
11.AN.4.244; 11.AN.4.243; 11.AN.4.247; 11.AN.5.157; 11.AN.5.158;
11.AN.5.196; 11.AN.5.223; 11.AN.5.240; 11.AN.5.244; 11.AN.5.243;
11.AN.5.247; 11.AN.7.157; 11.AN.7.158; 11.AN.7.196; 11.AN.7.223;
11.AN.7.240; 11.AN.7.244; 11.AN.7.243; 11.AN.7.247; 11.AN.15.157;
11.AN.15.158; 11.AN.15.196; 11.AN.15.223; 11.AN.15.240;
11.AN.15.244; 11.AN.15.243; 11.AN.15.247; 11.AN.16.157;
11.AN.16.158; 11.AN.16.196; 11.AN.16.223; 11.AN.16.240;
11.AN.16.244; 11.AN.16.243; 11.AN.16.247; 11.AN.18.157;
11.AN.18.158; 11.AN.18.196; 11.AN.18.223; 11.AN.18.240;
11.AN.18.244; 11.AN.18.243; 11.AN.18.247; 11.AN.26.157;
11.AN.26.158; 11.AN.26.196; 11.AN.26.223; 11.AN.26.240;
11.AN.26.244; 11.AN.26.243; 11.AN.26.247; 11.AN.27.157;
11.AN.27.158; 11.AN.27.196; 11.AN.27.223; 11.AN.27.240;
11.AN.27.244; 11.AN.27.243; 11.AN.27.247; 11.AN.29.157;
11.AN.29.158; 11.AN.29.196; 11.AN.29.223; 11.AN.29.240;
11.AN.29.244; 11.AN.29.243; 11.AN.29.247; 11.AN.54.157;
11.AN.54.158; 11.AN.54.196; 11.AN.54.223; 11.AN.54.240;
11.AN.54.244; 11.AN.54.243; 11.AN.54.247; 11.AN.55.157;
11.AN.55.158; 11.AN.55.196; 11.AN.55.223; 11.AN.55.240;
11.AN.55.244; 11.AN.55.243; 11.AN.55.247; 11.AN.56.157;
11.AN.56.158; 11.AN.56.196; 11.AN.56.223; 11.AN.56.240;
11.AN.56.244; 11.AN.56.243; 11.AN.56.247; 11.AN.157.157;
11.AN.157.158; 11.AN.157.196; 11.AN.157.223; 11.AN.157.240;
11.AN.157.244; 11.AN.157.243; 11.AN.157.247; 11.AN.196.157;
11.AN.196.158; 11.AN.196.196; 11.AN.196.223; 11.AN.196.240;
11.AN.196.244; 11.AN.196.243; 11.AN.196.247; 11.AN.223.157;
11.AN.223.158; 11.AN.223.196; 11.AN.223.223; 11.AN.223.240;
11.AN.223.244; 11.AN.223.243; 11.AN.223.247; 11.AN.240.157;
11.AN.240.158; 11.AN.240.196; 11.AN.240.223; 11.AN.240.240;
11.AN.240.244; 11.AN.240.243; 11.AN.240.247; 11.AN.244.157;
11.AN.244.158; 11.AN.244.196; 11.AN.244.223; 11.AN.244.240;
11.AN.244.244; 11.AN.244.243; 11.AN.244.247; 11.AN.247.157;
11.AN.247.158; 11.AN.247.196; 11.AN.247.223; 11.AN.247.240;
11.AN.247.244; 11.AN.247.243; 11.AN.247.247;

Prodrugs of 11.AP

11.AP.4.157; 11.AP.4.158; 11.AP.4.196; 11.AP.4.223; 11.AP.4.240;
11.AP.4.244; 11.AP.4.243; 11.AP.4.247; 11.AP.5.157; 11.AP.5.158;
11.AP.5.196; 11.AP.5.223; 11.AP.5.240; 11.AP.5.244; 11.AP.5.243;
11.AP.5.247; 11.AP.7.157; 11.AP.7.158; 11.AP.7.196; 11.AP.7.223;
11.AP.7.240; 11.AP.7.244; 11.AP.7.243; 11.AP.7.247; 11.AP.15.157;
11.AP.15.158; 11.AP.15.196; 11.AP.15.223; 11.AP.15.240;
11.AP.15.244; 11.AP.15.243; 11.AP.15.247; 11.AP.16.157;
11.AP.16.158; 11.AP.16.196; 11.AP.16.223; 11.AP.16.240;
11.AP.16.244; 11.AP.16.243; 11.AP.16.247; 11.AP.18.157;
11.AP.18.158; 11.AP.18.196; 11.AP.18.223; 11.AP.18.240;
11.AP.18.244; 11.AP.18.243; 11.AP.18.247; 11.AP.26.157;
11.AP.26.158; 11.AP.26.196; 11.AP.26.223; 11.AP.26.240;
11.AP.26.244; 11.AP.26.243; 11.AP.26.247; 11.AP.27.157;
11.AP.27.158; 11.AP.27.196; 11.AP.27.223; 11.AP.27.240;
11.AP.27.244; 11.AP.27.243; 11.AP.27.247; 11.AP.29.157;
11.AP.29.158; 11.AP.29.196; 11.AP.29.223; 11.AP.29.240;
11.AP.29.244; 11.AP.29.243; 11.AP.29.247; 11.AP.54.157;
11.AP.54.158; 11.AP.54.196; 11.AP.54.223; 11.AP.54.240;
11.AP.54.244; 11.AP.54.243; 11.AP.54.247; 11.AP.55.157;
11.AP.55.158; 11.AP.55.196; 11.AP.55.223; 11.AP.55.240;
11.AP.55.244; 11.AP.55.243; 11.AP.55.247; 11.AP.56.157;
11.AP.56.158; 11.AP.56.196; 11.AP.56.223; 11.AP.56.240;
11.AP.56.244; 11.AP.56.243; 11.AP.56.247; 11.AP.157.157;
11.AP.157.158; 11.AP.157.196; 11.AP.157.223; 11.AP.157.240;
11.AP.157.244; 11.AP.157.243; 11.AP.157.247; 11.AP.196.157;
11.AP.196.158; 11.AP.196.196; 11.AP.196.223; 11.AP.196.240;
11.AP.196.244; 11.AP.196.243; 11.AP.196.247; 11.AP.223.157;
11.AP.223.158; 11.AP.223.196; 11.AP.223.223; 11.AP.223.240;
11.AP.223.244; 11.AP.223.243; 11.AP.223.247; 11.AP.240.157;
11.AP.240.158; 11.AP.240.196; 11.AP.240.223; 11.AP.240.240;
11.AP.240.244; 11.AP.240.243; 11.AP.240.244; 11.AP.244.157;
11.AP.244.158; 11.AP.244.196; 11.AP.244.223; 11.AP.244.240;
11.AP.244.244; 11.AP.244.243; 11.AP.244.247; 11.AP.247.157;
11.AP.247.158; 11.AP.247.196; 11.AP.247.223; 11.AP.247.240;
11.AP.247.244; 11.AP.247.243; 11.AP.247.247;

Prodrugs of 11.AZ

11.AZ.4.157; 11.AZ.4.158; 11.AZ.4.196; 11.AZ.4.223; 11.AZ.4.240;
11.AZ.4.244; 11.AZ.4.243; 11.AZ.4.247; 11.AZ.5.157; 11.AZ.5.158;
11.AZ.5.196; 11.AZ.5.223; 11.AZ.5.240; 11.AZ.5.244; 11.AZ.5.243;
11.AZ.5.247; 11.AZ.7.157; 11.AZ.7.158; 11.AZ.7.196; 11.AZ.7.223;
11.AZ.7.240; 11.AZ.7.244; 11.AZ.7.243; 11.AZ.7.247; 11.AZ.15.157;
11.AZ.15.158; 11.AZ.15.196; 11.AZ.15.223; 11.AZ.15.240;
11.AZ.15.244; 11.AZ.15.243; 11.AZ.15.247; 11.AZ.16.157;
11.AZ.16.158; 11.AZ.16.196; 11.AZ.16.223; 11.AZ.16.240;
11.AZ.16.244; 11.AZ.16.243; 11.AZ.16.247; 11.AZ.18.157;
11.AZ.18.158; 11.AZ.18.196; 11.AZ.18.223; 11.AZ.18.240;
11.AZ.18.244; 11.AZ.18.243; 11.AZ.18.247; 11.AZ.26.157;
11.AZ.26.158; 11.AZ.26.196; 11.AZ.26.223; 11.AZ.26.240;
11.AZ.26.244; 11.AZ.26.243; 11.AZ.26.247; 11.AZ.27.157;
11.AZ.27.158; 11.AZ.27.196; 11.AZ.27.223; 11.AZ.27.240;
11.AZ.27.244; 11.AZ.27.243; 11.AZ.27.247; 11.AZ.29.157;
11.AZ.29.158; 11.AZ.29.196; 11.AZ.29.223; 11.AZ.29.240;
11.AZ.29.244; 11.AZ.29.243; 11.AZ.29.247; 11.AZ.54.157;
11.AZ.54.158; 11.AZ.54.196; 11.AZ.54.223; 11.AZ.54.240;
11.AZ.54.244; 11.AZ.54.243; 11.AZ.54.247; 11.AZ.55.157;
11.AZ.55.158; 11.AZ.55.196; 11.AZ.55.223; 11.AZ.55.240;
11.AZ.55.244; 11.AZ.55.243; 11.AZ.55.247; 11.AZ.56.157;
11.AZ.56.158; 11.AZ.56.196; 11.AZ.56.223; 11.AZ.56.240;
11.AZ.56.244; 11.AZ.56.243; 11.AZ.56.247; 11.AZ.157.157;
11.AZ.157.158; 11.AZ.157.196; 11.AZ.157.223; 11.AZ.157.240;
11.AZ.157.244; 11.AZ.157.243; 11.AZ.157.247; 11.AZ.196.157;
11.AZ.196.158; 11.AZ.196.196; 11.AZ.196.223; 11.AZ.196.240;
11.AZ.196.244; 11.AZ.196.243; 11.AZ.196.247; 11.AZ.223.157;
11.AZ.223.158; 11.AZ.223.196; 11.AZ.223.223; 11.AZ.223.240;
11.AZ.223.244; 11.AZ.223.243; 11.AZ.223.247; 11.AZ.240.157;
11.AZ.240.158; 11.AZ.240.196; 11.AZ.240.223; 11.AZ.240.240;
11.AZ.240.244; 11.AZ.240.243; 11.AZ.240.247; 11.AZ.244.157;
11.AZ.244.158; 11.AZ.244.196; 11.AZ.244.223; 11.AZ.244.240;
11.AZ.244.244; 11.AZ.244.243; 11.AZ.244.247; 11.AZ.247.157;
11.AZ.247.158; 11.AZ.247.196; 11.AZ.247.223; 11.AZ.247.240;
11.AZ.247.244; 11.AZ.247.243; 11.AZ.247.247;

Prodrugs of 11.BF

11.BF.4.157; 11.BF.4.158; 11.BF.4.196; 11.BF.4.223; 11.BF.4.240;
11.BF.4.244; 11.BF.4.243; 11.BF.4.247; 11.BF.5.157; 11.BF.5.158;
11.BF.5.196; 11.BF.5.223; 11.BF.5.240; 11.BF.5.244; 11.BF.5.243;
11.BF.5.247; 11.BF.7.157; 11.BF.7.158; 11.BF.7.196; 11.BF.7.223;
11.BF.7.240; 11.BF.7.244; 11.BF.7.243; 11.BF.7.247; 11.BF.15.157;
11.BF.15.158; 11.BF.15.196; 11.BF.15.223; 11.BF.15.240; 11.BF.15.244;
11.BF.15.243; 11.BF.15.247; 11.BF.16.157; 11.BF.16.158; 11.BF.16.196;
11.BF.16.223; 11.BF.16.240; 11.BF.16.244; 11.BF.16.243; 11.BF.16.247;
11.BF.18.157; 11.BF.18.158; 11.BF.18.196; 11.BF.18.223; 11.BF.18.240;
11.BF.18.244; 11.BF.18.243; 11.BF.18.247; 11.BF.26.157; 11.BF.26.158;
11.BF.26.196; 11.BF.26.223; 11.BF.26.240; 11.BF.26.244; 11.BF.26.243;
11.BF.26.247; 11.BF.27.157; 11.BF.27.158; 11.BF.27.196; 11.BF.27.223;
11.BF.27.240; 11.BF.27.244; 11.BF.27.243; 11.BF.27.247; 11.BF.29.157;
11.BF.29.158; 11.BF.29.196; 11.BF.29.223; 11.BF.29.240; 11.BF.29.244;
11.BF.29.243; 11.BF.29.247; 11.BF.54.157; 11.BF.54.158; 11.BF.54.196;
11.BF.54.223; 11.BF.54.240; 11.BF.54.244; 11.BF.54.243; 11.BF.54.247;
11.BF.55.157; 11.BF.55.158; 11.BF.55.196; 11.BF.55.223; 11.BF.55.240;
11.BF.55.244; 11.BF.55.243; 11.BF.55.247; 11.BF.56.157; 11.BF.56.158;
11.BF.56.196; 11.BF.56.223; 11.BF.56.240; 11.BF.56.244; 11.BF.56.243;
11.BF.56.247; 11.BF.157.157; 11.BF.157.158; 11.BF.157.196;
11.BF.157.223; 11.BF.157.240; 11.BF.157.244; 11.BF.157.243;
11.BF.157.247; 11.BF.196.157; 11.BF.196.158; 11.BF.196.196;
11.BF.196.223; 11.BF.196.240; 11.BF.196.244; 11.BF.196.243;
11.BF.196.247; 11.BF.223.157; 11.BF.223.158; 11.BF.223.196;
11.BF.223.223; 11.BF.223.240; 11.BF.223.244; 11.BF.223.243;
11.BF.223.247; 11.BF.240.157; 11.BF.240.158; 11.BF.240.196;
11.BF.240.223; 11.BF.240.240; 11.BF.240.244; 11.BF.240.243;
11.BF.240.247; 11.BF.244.157; 11.BF.244.158; 11.BF.244.196;
11.BF.244.223; 11.BF.244.240; 11.BF.244.244; 11.BF.244.243;
11.BF.244.247; 11.BF.247.157; 11.BF.247.158; 11.BF.247.196;
11.BF.247.223; 11.BF.247.240; 11.BF.247.244; 11.BF.247.243;
11.BF.247.247;

TABLE 7-continued

Prodrugs of 11.CI

11.CI.4.157; 11.CI.4.158; 11.CI.4.196; 11.CI.4.223; 11.CI.4.240;
11.CI.4.244; 11.CI.4.243; 11.CI.4.247; 11.CI.5.157; 11.CI.5.158;
11.CI.5.196; 11.CI.5.223; 11.CI.5.240; 11.CI.5.244; 11.CI.5.243;
11.CI.5.247; 11.CI.7.157; 11.CI.7.158; 11.CI.7.196; 11.CI.7.223;
11.CI.7.240; 11.CI.7.244; 11.CI.7.243; 11.CI.7.247; 11.CI.15.157;
11.CI.15.158; 11.CI.15.196; 11.CI.15.223; 11.CI.15.240; 11.CI.15.244;
11.CI.15.243; 11.CI.15.247; 11.CI.16.157; 11.CI.16.158; 11.CI.16.196;
11.CI.16.223; 11.CI.16.240; 11.CI.16.244; 11.CI.16.243; 11.CI.16.247;
11.CI.18.157; 11.CI.18.158; 11.CI.18.196; 11.CI.18.223; 11.CI.18.240;
11.CI.18.244; 11.CI.18.243; 11.CI.18.247; 11.CI.26.157; 11.CI.26.158;
11.CI.26.196; 11.CI.26.223; 11.CI.26.240; 11.CI.26.244; 11.CI.26.243;
11.CI.26.247; 11.CI.27.157; 11.CI.27.158; 11.CI.27.196; 11.CI.27.223;
11.CI.27.240; 11.CI.27.244; 11.CI.27.243; 11.CI.27.247; 11.CI.29.157;
11.CI.29.158; 11.CI.29.196; 11.CI.29.223; 11.CI.29.240; 11.CI.29.244;
11.CI.29.243; 11.CI.29.247; 11.CI.54.157; 11.CI.54.158; 11.CI.54.196;
11.CI.54.223; 11.CI.54.240; 11.CI.54.244; 11.CI.54.243; 11.CI.54.247;
11.CI.55.157; 11.CI.55.158; 11.CI.55.196; 11.CI.55.223; 11.CI.55.240;
11.CI.55.244; 11.CI.55.243; 11.CI.55.247; 11.CI.56.157; 11.CI.56.158;
11.CI.56.196; 11.CI.56.223; 11.CI.56.240; 11.CI.56.244; 11.CI.56.243;
11.CI.56.247; 11.CI.157.157; 11.CI.157.158; 11.CI.157.196;
11.CI.157.223; 11.CI.157.240; 11.CI.157.244; 11.CI.157.243;
11.CI.157.247; 11.CI.196.157; 11.CI.196.158; 11.CI.196.196;
11.CI.196.223; 11.CI.196.240; 11.CI.196.244; 11.CI.196.243;
11.CI.196.247; 11.CI.223.157; 11.CI.223.158; 11.CI.223.196;
11.CI.223.223; 11.CI.223.240; 11.CI.223.244; 11.CI.223.243;
11.CI.223.247; 11.CI.240.157; 11.CI.240.158; 11.CI.240.196;
11.CI.240.223; 11.CI.240.240; 11.CI.240.244; 11.CI.240.243;
11.CI.240.247; 11.CI.244.157; 11.CI.244.158; 11.CI.244.196;
11.CI.244.223; 11.CI.244.240; 11.CI.244.244; 11.CI.244.243;
11.CI.244.247; 11.CI.247.157; 11.CI.247.158; 11.CI.247.196;
11.CI.247.223; 11.CI.247.240; 11.CI.247.244; 11.CI.247.243;
11.CI.247.247;

Prodrugs of 11.CO

11.CO.4.157; 11.CO.4.158; 11.CO.4.196; 11.CO.4.223; 11.CO.4.240;
11.CO.4.244; 11.CO.4.243; 11.CO.4.247; 11.CO.5.157; 11.CO.5.158;
11.CO.5.196; 11.CO.5.223; 11.CO.5.240; 11.CO.5.244; 11.CO.5.243;
11.CO.5.247; 11.CO.7.157; 11.CO.7.158; 11.CO.7.196; 11.CO.7.223;
11.CO.7.240; 11.CO.7.244; 11.CO.7.243; 11.CO.7.247; 11.CO.15.157;
11.CO.15.158; 11.CO.15.196; 11.CO.15.223; 11.CO.15.240;
11.CO.15.244; 11.CO.15.243; 11.CO.15.247; 11.CO.16.157;
11.CO.16.158; 11.CO.16.196; 11.CO.16.223; 11.CO.16.240;
11.CO.16.244; 11.CO.16.243; 11.CO.16.247; 11.CO.18.157;
11.CO.18.158; 11.CO.18.196; 11.CO.18.223; 11.CO.18.240;
11.CO.18.244; 11.CO.18.243; 11.CO.18.247; 11.CO.26.157;
11.CO.26.158; 11.CO.26.196; 11.CO.26.223; 11.CO.26.240;
11.CO.26.244; 11.CO.26.243; 11.CO.26.247; 11.CO.27.157;
11.CO.27.158; 11.CO.27.196; 11.CO.27.223; 11.CO.27.240;
11.CO.27.244; 11.CO.27.243; 11.CO.27.247; 11.CO.29.157;
11.CO.29.158; 11.CO.29.196; 11.CO.29.223; 11.CO.29.240;
11.CO.29.244; 11.CO.29.243; 11.CO.29.247; 11.CO.54.157;
11.CO.54.158; 11.CO.54.196; 11.CO.54.223; 11.CO.54.240;
11.CO.54.244; 11.CO.54.243; 11.CO.54.247; 11.CO.55.157;
11.CO.55.158; 11.CO.55.196; 11.CO.55.223; 11.CO.55.240;
11.CO.55.244; 11.CO.55.243; 11.CO.55.247; 11.CO.56.157;
11.CO.56.158; 11.CO.56.196; 11.CO.56.223; 11.CO.56.240;
11.CO.56.244; 11.CO.56.243; 11.CO.56.247; 11.CO.157.157;
11.CO.157.158; 11.CO.157.196; 11.CO.157.223; 11.CO.157.240;
11.CO.157.244; 11.CO.157.243; 11.CO.157.247; 11.CO.196.157;
11.CO.196.158; 11.CO.196.196; 11.CO.196.223; 11.CO.196.240;
11.CO.196.244; 11.CO.196.243; 11.CO.196.247; 11.CO.223.157;
11.CO.223.158; 11.CO.223.196; 11.CO.223.223; 11.CO.223.240;
11.CO.223.244; 11.CO.223.243; 11.CO.223.247; 11.CO.240.157;
11.CO.240.158; 11.CO.240.196; 11.CO.240.223; 11.CO.240.240;
11.CO.240.244; 11.CO.240.243; 11.CO.240.247; 11.CO.244.157;
11.CO.244.158; 11.CO.244.196; 11.CO.244.223; 11.CO.244.240;
11.CO.244.244; 11.CO.244.243; 11.CO.244.247; 11.CO.247.157;
11.CO.247.158; 11.CO.247.196; 11.CO.247.223; 11.CO.247.240;
11.CO.247.244; 11.CO.247.243; 11.CO.247.247;

Prodrugs of 12.AH

12.AH.4.157; 12.AH.4.158; 12.AH.4.196; 12.AH.4.223; 12.AH.4.240;
12.AH.4.244; 12.AH.4.243; 12.AH.4.247; 12.AH.5.157; 12.AH.5.158;
12.AH.5.196; 12.AH.5.223; 12.AH.5.240; 12.AH.5.244; 12.AH.5.243;
12.AH.5.247; 12.AH.7.157; 12.AH.7.158; 12.AH.7.196; 12.AH.7.223;
12.AH.7.240; 12.AH.7.244; 12.AH.7.243; 12.AH.7.247; 12.AH.15.157;
12.AH.15.158; 12.AH.15.196; 12.AH.15.223; 12.AH.15.240;
12.AH.15.244; 12.AH.15.243; 12.AH.15.247; 12.AH.16.157;
12.AH.16.158; 12.AH.16.196; 12.AH.16.223; 12.AH.16.240;
12.AH.16.244; 12.AH.16.243; 12.AH.16.247; 12.AH.18.157;
12.AH.18.158; 12.AH.18.196; 12.AH.18.223; 12.AH.18.240;
12.AH.18.244; 12.AH.18.243; 12.AH.18.247; 12.AH.26.157;
12.AH.26.158; 12.AH.26.196; 12.AH.26.223; 12.AH.26.240;
12.AH.26.244; 12.AH.26.243; 12.AH.26.247; 12.AH.27.157;
12.AH.27.158; 12.AH.27.196; 12.AH.27.223; 12.AH.27.240;
12.AH.27.244; 12.AH.27.243; 12.AH.27.247; 12.AH.29.157;
12.AH.29.158; 12.AH.29.196; 12.AH.29.223; 12.AH.29.240;
12.AH.29.244; 12.AH.29.243; 12.AH.29.247; 12.AH.54.157;
12.AH.54.158; 12.AH.54.196; 12.AH.54.223; 12.AH.54.240;
12.AH.54.244; 12.AH.54.243; 12.AH.54.247; 12.AH.55.157;
12.AH.55.158; 12.AH.55.196; 12.AH.55.223; 12.AH.55.240;
12.AH.55.244; 12.AH.55.243; 12.AH.55.247; 12.AH.56.157;
12.AH.56.158; 12.AH.56.196; 12.AH.56.223; 12.AH.56.240;
12.AH.56.244; 12.AH.56.243; 12.AH.56.247; 12.AH.157.157;
12.AH.157.158; 12.AH.157.196; 12.AH.157.223; 12.AH.157.240;
12.AH.157.244; 12.AH.157.243; 12.AH.157.247; 12.AH.196.157;
12.AH.196.158; 12.AH.196.196; 12.AH.196.223; 12.AH.196.240;
12.AH.196.244; 12.AH.196.243; 12.AH.196.247; 12.AH.223.157;
12.AH.223.158; 12.AH.223.196; 12.AH.223.223; 12.AH.223.240;
12.AH.223.244; 12.AH.223.243; 12.AH.223.247; 12.AH.240.157;
12.AH.240.158; 12.AH.240.196; 12.AH.240.223; 12.AH.240.240;
12.AH.240.244; 12.AH.240.243; 12.AH.240.247; 12.AH.244.157;
12.AH.244.158; 12.AH.244.196; 12.AH.244.223; 12.AH.244.240;
12.AH.244.244; 12.AH.244.243; 12.AH.244.247; 12.AH.247.157;
12.AH.247.158; 12.AH.247.196; 12.AH.247.223; 12.AH.247.240;
12.AH.247.244; 12.AH.247.243; 12.AH.247.247;

Prodrugs of 12.AJ

12.AJ.4.157; 12.AJ.4.158; 12.AJ.4.196; 12.AJ.4.223; 12.AJ.4.240;
12.AJ.4.244; 12.AJ.4.243; 12.AJ.4.247; 12.AJ.5.157; 12.AJ.5.158;
12.AJ.5.196; 12.AJ.5.223; 12.AJ.5.240; 12.AJ.5.244; 12.AJ.5.243;
12.AJ.5.247; 12.AJ.7.157; 12.AJ.7.158; 12.AJ.7.196; 12.AJ.7.223;
12.AJ.7.240; 12.AJ.7.244; 12.AJ.7.243; 12.AJ.7.247; 12.AJ.15.157;
12.AJ.15.158; 12.AJ.15.196; 12.AJ.15.223; 12.AJ.15.240; 12.AJ.15.244;
12.AJ.15.243; 12.AJ.15.247; 12.AJ.16.157; 12.AJ.16.158; 12.AJ.16.196;
12.AJ.16.223; 12.AJ.16.240; 12.AJ.16.244; 12.AJ.16.243; 12.AJ.16.247;
12.AJ.18.157; 12.AJ.18.158; 12.AJ.18.196; 12.AJ.18.223; 12.AJ.18.240;
12.AJ.18.244; 12.AJ.18.243; 12.AJ.18.247; 12.AJ.26.157; 12.AJ.26.158;
12.AJ.26.196; 12.AJ.26.223; 12.AJ.26.240; 12.AJ.26.244; 12.AJ.26.243;
12.AJ.26.247; 12.AJ.27.157; 12.AJ.27.158; 12.AJ.27.196; 12.AJ.27.223;
12.AJ.27.240; 12.AJ.27.244; 12.AJ.27.243; 12.AJ.27.247; 12.AJ.29.157;
12.AJ.29.158; 12.AJ.29.196; 12.AJ.29.223; 12.AJ.29.240; 12.AJ.29.244;
12.AJ.29.243; 12.AJ.29.247; 12.AJ.54.157; 12.AJ.54.158; 12.AJ.54.196;
12.AJ.54.223; 12.AJ.54.240; 12.AJ.54.244; 12.AJ.54.243; 12.AJ.54.247;
12.AJ.55.157; 12.AJ.55.158; 12.AJ.55.196; 12.AJ.55.223; 12.AJ.55.240;
12.AJ.55.244; 12.AJ.55.243; 12.AJ.55.247; 12.AJ.56.157; 12.AJ.56.158;
12.AJ.56.196; 12.AJ.56.223; 12.AJ.56.240; 12.AJ.56.244; 12.AJ.56.243;
12.AJ.56.247; 12.AJ.157.157; 12.AJ.157.158; 12.AJ.157.196;
12.AJ.157.223; 12.AJ.157.240; 12.AJ.157.244; 12.AJ.157.243;
12.AJ.157.247; 12.AJ.196.157; 12.AJ.196.158; 12.AJ.196.196;
12.AJ.196.223; 12.AJ.196.240; 12.AJ.196.244; 12.AJ.196.243;
12.AJ.196.247; 12.AJ.223.157; 12.AJ.223.158; 12.AJ.223.196;
12.AJ.223.223; 12.AJ.223.240; 12.AJ.223.244; 12.AJ.223.243;
12.AJ.223.247; 12.AJ.240.157; 12.AJ.240.158; 12.AJ.240.196;
12.AJ.240.223; 12.AJ.240.240; 12.AJ.240.244; 12.AJ.240.243;
12.AJ.240.247; 12.AJ.244.157; 12.AJ.244.158; 12.AJ.244.196;
12.AJ.244.223; 12.AJ.244.240; 12.AJ.244.244; 12.AJ.244.243;
12.AJ.244.247; 12.AJ.247.157; 12.AJ.247.158; 12.AJ.247.196;
12.AJ.247.223; 12.AJ.247.240; 12.AJ.247.244; 12.AJ.247.243;
12.AJ.247.247;

Prodrugs of 12.AN

12.AN.4.157; 12.AN.4.158; 12.AN.4.196; 12.AN.4.223; 12.AN.4.240;
12.AN.4.244; 12.AN.4.243; 12.AN.4.247; 12.AN.5.157; 12.AN.5.158;
12.AN.5.196; 12.AN.5.223; 12.AN.5.240; 12.AN.5.244; 12.AN.5.243;
12.AN.5.247; 12.AN.7.157; 12.AN.7.158; 12.AN.7.196; 12.AN.7.223;
12.AN.7.240; 12.AN.7.244; 12.AN.7.243; 12.AN.7.247; 12.AN.15.157;
12.AN.15.158; 12.AN.15.196; 12.AN.15.223; 12.AN.15.240;
12.AN.15.244; 12.AN.15.243; 12.AN.15.247; 12.AN.16.157;
12.AN.16.158; 12.AN.16.196; 12.AN.16.223; 12.AN.16.240;
12.AN.16.244; 12.AN.16.243; 12.AN.16.247; 12.AN.18.157;
12.AN.18.158; 12.AN.18.196; 12.AN.18.223; 12.AN.18.240;
12.AN.18.244; 12.AN.18.243; 12.AN.18.247; 12.AN.26.157;
12.AN.26.158; 12.AN.26.196; 12.AN.26.223; 12.AN.26.240;
12.AN.26.244; 12.AN.26.243; 12.AN.26.247; 12.AN.27.157;
12.AN.27.158; 12.AN.27.196; 12.AN.27.223; 12.AN.27.240;

TABLE 7-continued

12.AN.27.244; 12.AN.27.243; 12.AN.27.247; 12.AN.29.157;
12.AN.29.158; 12.AN.29.196; 12.AN.29.223; 12.AN.29.240;
12.AN.29.244; 12.AN.29.243; 12.AN.29.247; 12.AN.54.157;
12.AN.54.158; 12.AN.54.196; 12.AN.54.223; 12.AN.54.240;
12.AN.54.244; 12.AN.54.243; 12.AN.54.247; 12.AN.55.157;
12.AN.55.158; 12.AN.55.196; 12.AN.55.223; 12.AN.55.240;
12.AN.55.244; 12.AN.55.243; 12.AN.55.247; 12.AN.56.157;
12.AN.56.158; 12.AN.56.196; 12.AN.56.223; 12.AN.56.240;
12.AN.56.244; 12.AN.56.243; 12.AN.56.247; 12.AN.157.157;
12.AN.157.158; 12.AN.157.196; 12.AN.157.223; 12.AN.157.240;
12.AN.157.244; 12.AN.157.243; 12.AN.157.247; 12.AN.196.157;
12.AN.196.158; 12.AN.196.196; 12.AN.196.223; 12.AN.196.240;
12.AN.196.244; 12.AN.196.243; 12.AN.196.247; 12.AN.223.157;
12.AN.223.158; 12.AN.223.196; 12.AN.223.223; 12.AN.223.240;
12.AN.223.244; 12.AN.223.243; 12.AN.223.247; 12.AN.240.157;
12.AN.240.158; 12.AN.240.196; 12.AN.240.223; 12.AN.240.240;
12.AN.240.244; 12.AN.240.243; 12.AN.240.247; 12.AN.244.157;
12.AN.244.158; 12.AN.244.196; 12.AN.244.223; 12.AN.244.240;
12.AN.244.244; 12.AN.244.243; 12.AN.244.247; 12.AN.247.157;
12.AN.247.158; 12.AN.247.196; 12.AN.247.223; 12.AN.247.240;
12.AN.247.244; 12.AN.247.243; 12.AN.247.247;
Prodrugs of 12.AP 12.AP.4.157; 12.AP.4.158; 12.AP.4.196; 12.AP.4.223; 12.AP.4.240;
12.AP.4.244; 12.AP.4.243; 12.AP.4.247; 12.AP.5.157; 12.AP.5.158;
12.AP.5.196; 12.AP.5.223; 12.AP.5.240; 12.AP.5.244; 12.AP.5.243;
12.AP.5.247; 12.AP.7.157; 12.AP.7.158; 12.AP.7.196; 12.AP.7.223;
12.AP.7.240; 12.AP.7.244; 12.AP.7.243; 12.AP.7.247; 12.AP.15.157;
12.AP.15.158; 12.AP.15.196; 12.AP.15.223; 12.AP.15.240;
12.AP.15.244; 12.AP.15.243; 12.AP.15.247; 12.AP.16.157;
12.AP.16.158; 12.AP.16.196; 12.AP.16.223; 12.AP.16.240;
12.AP.16.244; 12.AP.16.243; 12.AP.16.247; 12.AP.18.157;
12.AP.18.158; 12.AP.18.196; 12.AP.18.223; 12.AP.18.240;
12.AP.18.244; 12.AP.18.243; 12.AP.18.247; 12.AP.26.157;
12.AP.26.158; 12.AP.26.196; 12.AP.26.223; 12.AP.26.240;
12.AP.26.244; 12.AP.26.243; 12.AP.26.247; 12.AP.27.157;
12.AP.27.158; 12.AP.27.196; 12.AP.27.223; 12.AP.27.240;
12.AP.27.244; 12.AP.27.243; 12.AP.27.247; 12.AP.29.157;
12.AP.29.158; 12.AP.29.196; 12.AP.29.223; 12.AP.29.240;
12.AP.29.244; 12.AP.29.243; 12.AP.29.247; 12.AP.54.157;
12.AP.54.158; 12.AP.54.196; 12.AP.54.223; 12.AP.54.240;
12.AP.54.244; 12.AP.54.243; 12.AP.54.247; 12.AP.55.157;
12.AP.55.158; 12.AP.55.196; 12.AP.55.223; 12.AP.55.240;
12.AP.55.244; 12.AP.55.243; 12.AP.55.247; 12.AP.56.157;
12.AP.56.158; 12.AP.56.196; 12.AP.56.223; 12.AP.56.240;
12.AP.56.244; 12.AP.56.243; 12.AP.56.247; 12.AP.157.157;
12.AP.157.158; 12.AP.157.196; 12.AP.157.223; 12.AP.157.240;
12.AP.157.244; 12.AP.157.243; 12.AP.157.247; 12.AP.196.157;
12.AP.196.158; 12.AP.196.196; 12.AP.196.223; 12.AP.196.240;
12.AP.196.244; 12.AP.196.243; 12.AP.196.247; 12.AP.223.157;
12.AP.223.158; 12.AP.223.196; 12.AP.223.223; 12.AP.223.240;
12.AP.223.244; 12.AP.223.243; 12.AP.223.247; 12.AP.240.157;
12.AP.240.158; 12.AP.240.196; 12.AP.240.223; 12.AP.240.240;
12.AP.240.244; 12.AP.240.243; 12.AP.240.247; 12.AP.244.157;
12.AP.244.158; 12.AP.244.196; 12.AP.244.223; 12.AP.244.240;
12.AP.244.244; 12.AP.244.243; 12.AP.244.247; 12.AP.247.157;
12.AP.247.158; 12.AP.247.196; 12.AP.247.223; 12.AP.247.240;
12.AP.247.244; 12.AP.247.243; 12.AP.247.247;
Prodrugs of 12.AZ 12.AZ.4.157; 12.AZ.4.158; 12.AZ.4.196; 12.AZ.4.223; 12.AZ.4.240;
12.AZ.4.244; 12.AZ.4.243; 12.AZ.4.247; 12.AZ.5.157; 12.AZ.5.158;
12.AZ.5.196; 12.AZ.5.223; 12.AZ.5.240; 12.AZ.5.244; 12.AZ.5.243;
12.AZ.5.247; 12.AZ.7.157; 12.AZ.7.158; 12.AZ.7.196; 12.AZ.7.223;
12.AZ.7.240; 12.AZ.7.244; 12.AZ.7.243; 12.AZ.7.247; 12.AZ.15.157;
12.AZ.15.158; 12.AZ.15.196; 12.AZ.15.223; 12.AZ.15.240;
12.AZ.15.244; 12.AZ.15.243; 12.AZ.15.247; 12.AZ.16.157;
12.AZ.16.158; 12.AZ.16.196; 12.AZ.16.223; 12.AZ.16.240;
12.AZ.16.244; 12.AZ.16.243; 12.AZ.16.247; 12.AZ.18.157;
12.AZ.18.158; 12.AZ.18.196; 12.AZ.18.223; 12.AZ.18.240;
12.AZ.18.244; 12.AZ.18.243; 12.AZ.18.247; 12.AZ.26.157;
12.AZ.26.158; 12.AZ.26.196; 12.AZ.26.223; 12.AZ.26.240;
12.AZ.26.244; 12.AZ.26.243; 12.AZ.26.247; 12.AZ.27.157;
12.AZ.27.158; 12.AZ.27.196; 12.AZ.27.223; 12.AZ.27.240;
12.AZ.27.244; 12.AZ.27.243; 12.AZ.27.247; 12.AZ.29.157;
12.AZ.29.158; 12.AZ.29.196; 12.AZ.29.223; 12.AZ.29.240;
12.AZ.29.244; 12.AZ.29.243; 12.AZ.29.247; 12.AZ.54.157;
12.AZ.54.158; 12.AZ.54.196; 12.AZ.54.223; 12.AZ.54.240;
12.AZ.54.244; 12.AZ.54.243; 12.AZ.54.247; 12.AZ.55.157;

TABLE 7-continued

12.AZ.55.158; 12.AZ.55.196; 12.AZ.55.223; 12.AZ.55.240;
12.AZ.55.244; 12.AZ.55.243; 12.AZ.55.247; 12.AZ.56.157;
12.AZ.56.158; 12.AZ.56.196; 12.AZ.56.223; 12.AZ.56.240;
12.AZ.56.244; 12.AZ.56.243; 12.AZ.56.247; 12.AZ.157.157;
12.AZ.157.158; 12.AZ.157.196; 12.AZ.157.223; 12.AZ.157.240;
12.AZ.157.244; 12.AZ.157.243; 12.AZ.157.247; 12.AZ.196.157;
12.AZ.196.158; 12.AZ.196.196; 12.AZ.196.223; 12.AZ.196.240;
12.AZ.196.244; 12.AZ.196.243; 12.AZ.196.247; 12.AZ.223.157;
12.AZ.223.158; 12.AZ.223.196; 12.AZ.223.223; 12.AZ.223.240;
12.AZ.223.244; 12.AZ.223.243; 12.AZ.223.247; 12.AZ.240.157;
12.AZ.240.158; 12.AZ.240.196; 12.AZ.240.223; 12.AZ.240.240;
12.AZ.240.244; 12.AZ.240.243; 12.AZ.240.247; 12.AZ.244.157;
12.AZ.244.158; 12.AZ.244.196; 12.AZ.244.223; 12.AZ.244.240;
12.AZ.244.244; 12.AZ.244.243; 12.AZ.244.247; 12.AZ.247.157;
12.AZ.247.158; 12.AZ.247.196; 12.AZ.247.223; 12.AZ.247.240;
12.AZ.247.244; 12.AZ.247.243; 12.AZ.247.247;
Prodrugs of 12.BF 12.BF.4.157; 12.BF.4.158; 12.BF.4.196; 12.BF.4.223; 12.BF.4.240;
12.BF.4.244; 12.BF.4.243; 12.BF.4.247; 12.BF.5.157; 12.BF.5.158;
12.BF.5.196; 12.BF.5.223; 12.BF.5.240; 12.BF.5.244; 12.BF.5.243;
12.BF.5.247; 12.BF.7.157; 12.BF.7.158; 12.BF.7.196; 12.BF.7.223;
12.BF.7.240; 12.BF.7.244; 12.BF.7.243; 12.BF.7.247; 12.BF.15.157;
12.BF.15.158; 12.BF.15.196; 12.BF.15.223; 12.BF.15.240; 12.BF.15.244;
12.BF.15.243; 12.BF.15.247; 12.BF.16.157; 12.BF.16.158; 12.BF.16.196;
12.BF.16.223; 12.BF.16.240; 12.BF.16.244; 12.BF.16.243; 12.BF.16.247;
12.BF.18.157; 12.BF.18.158; 12.BF.18.196; 12.BF.18.223; 12.BF.18.240;
12.BF.18.244; 12.BF.18.243; 12.BF.18.247; 12.BF.26.157; 12.BF.26.158;
12.BF.26.196; 12.BF.26.223; 12.BF.26.240; 12.BF.26.244; 12.BF.26.243;
12.BF.26.247; 12.BF.27.157; 12.BF.27.158; 12.BF.27.196; 12.BF.27.223;
12.BF.27.240; 12.BF.27.244; 12.BF.27.243; 12.BF.27.247; 12.BF.29.157;
12.BF.29.158; 12.BF.29.196; 12.BF.29.223; 12.BF.29.240; 12.BF.29.244;
12.BF.29.243; 12.BF.29.247; 12.BF.54.157; 12.BF.54.158; 12.BF.54.196;
12.BF.54.223; 12.BF.54.240; 12.BF.54.244; 12.BF.54.243; 12.BF.54.247;
12.BF.55.157; 12.BF.55.158; 12.BF.55.196; 12.BF.55.223; 12.BF.55.240;
12.BF.55.244; 12.BF.55.243; 12.BF.55.247; 12.BF.56.157; 12.BF.56.158;
12.BF.56.196; 12.BF.56.223; 12.BF.56.240; 12.BF.56.244; 12.BF.56.243;
12.BF.56.247; 12.BF.157.157; 12.BF.157.158; 12.BF.157.196;
12.BF.157.223; 12.BF.157.240; 12.BF.157.244; 12.BF.157.243;
12.BF.157.247; 12.BF.196.157; 12.BF.196.196; 12.BF.196.223;
12.BF.196.240; 12.BF.196.244; 12.BF.196.196; 12.BF.196.247;
12.BF.223.157; 12.BF.223.158; 12.BF.223.196; 12.BF.223.223;
12.BF.223.240; 12.BF.223.244; 12.BF.223.243; 12.BF.223.247;
12.BF.240.157; 12.BF.240.158; 12.BF.240.196; 12.BF.240.223;
12.BF.240.240; 12.BF.240.244; 12.BF.240.243; 12.BF.240.247;
12.BF.244.157; 12.BF.244.158; 12.BF.244.196; 12.BF.244.223;
12.BF.244.240; 12.BF.244.244; 12.BF.244.243; 12.BF.244.247;
12.BF.247.157; 12.BF.247.158; 12.BF.247.196; 12.BF.247.223;
12.BF.247.240; 12.BF.247.244; 12.BF.247.243; 12.BF.247.247;
Prodrugs of 12.CI 12.CI.4.157; 12.CI.4.158; 12.CI.4.196; 12.CI.4.223; 12.CI.4.240;
12.CI.4.244; 12.CI.4.243; 12.CI.4.247; 12.CI.5.157; 12.CI.5.158;
12.CI.5.196; 12.CI.5.223; 12.CI.5.240; 12.CI.5.244; 12.CI.5.243;
12.CI.5.247; 12.CI.7.157; 12.CI.7.158; 12.CI.7.196; 12.CI.7.223;
12.CI.7.240; 12.CI.7.244; 12.CI.7.243; 12.CI.7.247; 12.CI.15.157;
12.CI.15.158; 12.CI.15.196; 12.CI.15.223; 12.CI.15.240; 12.CI.15.244;
12.CI.15.243; 12.CI.15.247; 12.CI.16.157; 12.CI.16.158; 12.CI.16.196;
12.CI.16.223; 12.CI.16.240; 12.CI.16.244; 12.CI.16.243; 12.CI.16.247;
12.CI.18.157; 12.CI.18.158; 12.CI.18.196; 12.CI.18.223; 12.CI.18.240;
12.CI.18.244; 12.CI.18.243; 12.CI.18.247; 12.CI.26.157; 12.CI.26.158;
12.CI.26.196; 12.CI.26.223; 12.CI.26.240; 12.CI.26.244; 12.CI.26.243;
12.CI.26.247; 12.CI.27.157; 12.CI.27.158; 12.CI.27.196; 12.CI.27.223;
12.CI.27.240; 12.CI.27.244; 12.CI.27.243; 12.CI.27.247; 12.CI.29.157;
12.CI.29.158; 12.CI.29.196; 12.CI.29.223; 12.CI.29.240; 12.CI.29.244;
12.CI.29.243; 12.CI.29.247; 12.CI.54.157; 12.CI.54.158; 12.CI.54.196;
12.CI.54.223; 12.CI.54.240; 12.CI.54.244; 12.CI.54.243; 12.CI.54.247;
12.CI.55.157; 12.CI.55.158; 12.CI.55.196; 12.CI.55.223; 12.CI.55.240;
12.CI.55.244; 12.CI.55.243; 12.CI.55.247; 12.CI.56.157; 12.CI.56.158;
12.CI.56.196; 12.CI.56.223; 12.CI.56.240; 12.CI.56.244; 12.CI.56.243;
12.CI.56.247; 12.CI.157.157; 12.CI.157.158; 12.CI.157.196;
12.CI.157.223; 12.CI.157.240; 12.CI.157.244; 12.CI.157.243;
12.CI.157.247; 12.CI.196.157; 12.CI.196.158; 12.CI.196.196;
12.CI.196.223; 12.CI.196.240; 12.CI.196.244; 12.CI.196.243;
12.CI.196.247; 12.CI.223.157; 12.CI.223.158; 12.CI.223.196;
12.CI.223.223; 12.CI.223.240; 12.CI.223.244; 12.CI.223.243;
12.CI.223.247; 12.CI.240.157; 12.CI.240.158; 12.CI.240.196;
12.CI.240.223; 12.CI.240.240; 12.CI.240.244; 12.CI.240.243;
12.CI.240.247; 12.CI.244.157; 12.CI.244.158; 12.CI.244.196;

TABLE 7-continued

12.CI.244.223; 12.CI.244.240; 12.CI.244.244; 12.CI.244.243; 12.CI.244.247; 12.CI.247.157; 12.CI.247.158; 12.CI.247.196; 12.CI.247.223; 12.CI.247.240; 12.CI.247.244; 12.CI.247.243; 12.CI.247.247;
Prodrugs of 12.CO 12.CO.4.157; 12.CO.4.158; 12.CO.4.196; 12.CO.4.223; 12.CO.4.240; 12.CO.4.244; 12.CO.4.243; 12.CO.4.247; 12.CO.5.157; 12.CO.5.158; 12.CO.5.196; 12.CO.5.223; 12.CO.5.240; 12.CO.5.244; 12.CO.5.243; 12.CO.5.247; 12.CO.7.157; 12.CO.7.158; 12.CO.7.196; 12.CO.7.223; 12.CO.7.240; 12.CO.7.244; 12.CO.7.243; 12.CO.7.247; 12.CO.15.157; 12.CO.15.158; 12.CO.15.196; 12.CO.15.223; 12.CO.15.240; 12.CO.15.244; 12.CO.15.243; 12.CO.15.247; 12.CO.16.157; 12.CO.16.158; 12.CO.16.196; 12.CO.16.223; 12.CO.16.240; 12.CO.16.244; 12.CO.16.243; 12.CO.16.247; 12.CO.18.157; 12.CO.18.158; 12.CO.18.196; 12.CO.18.223; 12.CO.18.240; 12.CO.18.244; 12.CO.18.243; 12.CO.18.247; 12.CO.26.157; 12.CO.26.158; 12.CO.26.196; 12.CO.26.223; 12.CO.26.240; 12.CO.26.244; 12.CO.26.243; 12.CO.26.247; 12.CO.27.157; 12.CO.27.158; 12.CO.27.196; 12.CO.27.223; 12.CO.27.240; 12.CO.27.244; 12.CO.27.243; 12.CO.27.247; 12.CO.29.157; 12.CO.29.158; 12.CO.29.196; 12.CO.29.223; 12.CO.29.240; 12.CO.29.244; 12.CO.29.243; 12.CO.29.247; 12.CO.54.157; 12.CO.54.158; 12.CO.54.196; 12.CO.54.223; 12.CO.54.240; 12.CO.54.244; 12.CO.54.243; 12.CO.54.247; 12.CO.55.157; 12.CO.55.158; 12.CO.55.196; 12.CO.55.223; 12.CO.55.240; 12.CO.55.244; 12.CO.55.243; 12.CO.55.247; 12.CO.56.157; 12.CO.56.158; 12.CO.56.196; 12.CO.56.223; 12.CO.56.240; 12.CO.56.244; 12.CO.56.243; 12.CO.56.247; 12.CO.157.157; 12.CO.157.158; 12.CO.157.196; 12.CO.157.223; 12.CO.157.240; 12.CO.157.244; 12.CO.157.243; 12.CO.157.247; 12.CO.196.157; 12.CO.196.158; 12.CO.196.196; 12.CO.196.223; 12.CO.196.240; 12.CO.196.244; 12.CO.196.243; 12.CO.196.247; 12.CO.223.157; 12.CO.223.158; 12.CO.223.196; 12.CO.223.223; 12.CO.223.240; 12.CO.223.244; 12.CO.223.243; 12.CO.223.247; 12.CO.240.157; 12.CO.240.158; 12.CO.240.196; 12.CO.240.223; 12.CO.240.240; 12.CO.240.244; 12.CO.240.243; 12.CO.240.247; 12.CO.244.157; 12.CO.244.158; 12.CO.244.196; 12.CO.244.223; 12.CO.244.240; 12.CO.244.244; 12.CO.244.243; 12.CO.244.247; 12.CO.247.157; 12.CO.247.158; 12.CO.247.196; 12.CO.247.223; 12.CO.247.240; 12.CO.247.244; 12.CO.247.243; 12.CO.247.247.
Prodrugs of 13.B 13.B.228.228; 13.B.228.229; 13.B.228.230; 13.B.228.231; 13.B.228.236; 13.B.228.237; 13.B.228.238; 13.B.228.239; 13.B.228.154; 13.B.228.157; 13.B.228.166; 13.B.228.169; 13.B.228.172; 13.B.228.175; 13.B.228.240; 13.B.228.244; 13.B.229.228; 13.B.229.229; 13.B.229.230; 13.B.229.231; 13.B.229.236; 13.B.229.237; 13.B.229.238; 13.B.229.239; 13.B.229.154; 13.B.229.157; 13.B.229.166; 13.B.229.169; 13.B.229.172; 13.B.229.175; 13.B.229.240; 13.B.229.244; 13.B.230.228; 13.B.230.229; 13.B.230.230; 13.B.230.231; 13.B.230.236; 13.B.230.237; 13.B.230.238; 13.B.230.239; 13.B.230.154; 13.B.230.157; 13.B.230.166; 13.B.230.169; 13.B.230.172; 13.B.230.175; 13.B.230.240; 13.B.230.244; 13.B.231.228; 13.B.231.229; 13.B.231.230; 13.B.231.231; 13.B.231.236; 13.B.231.237; 13.B.231.238; 13.B.231.239; 13.B.231.154; 13.B.231.157; 13.B.231.166; 13.B.231.169; 13.B.231.172; 13.B.231.175; 13.B.231.240; 13.B.231.244; 13.B.236.228; 13.B.236.229; 13.B.236.230; 13.B.236.231; 13.B.236.236; 13.B.236.237; 13.B.236.238; 13.B.236.239; 13.B.236.154; 13.B.236.157; 13.B.236.166; 13.B.236.169; 13.B.236.172; 13.B.236.175; 13.B.236.240; 13.B.236.244; 13.B.237.228; 13.B.237.229; 13.B.237.230; 13.B.237.231; 13.B.237.236; 13.B.237.237; 13.B.237.238; 13.B.237.239; 13.B.237.154; 13.B.237.157; 13.B.237.166; 13.B.237.169; 13.B.237.172; 13.B.237.175; 13.B.237.240; 13.B.237.244; 13.B.238.228; 13.B.238.229; 13.B.238.230; 13.B.238.231; 13.B.238.236; 13.B.238.237; 13.B.238.238; 13.B.238.239; 13.B.238.154; 13.B.238.157; 13.B.238.166; 13.B.238.169; 13.B.238.172; 13.B.238.175; 13.B.238.240; 13.B.238.244; 13.B.239.228; 13.B.239.229; 13.B.239.230; 13.B.239.231; 13.B.239.236; 13.B.239.237; 13.B.239.238; 13.B.239.239; 13.B.239.154; 13.B.239.157; 13.B.239.166; 13.B.239.169; 13.B.239.172; 13.B.239.175; 13.B.239.240; 13.B.239.244; 13.B.154.228; 13.B.154.229; 13.B.154.230; 13.B.154.231; 13.B.154.236; 13.B.154.237; 13.B.154.238; 13.B.154.239; 13.B.154.154; 13.B.154.157; 13.B.154.166; 13.B.154.169; 13.B.154.172; 13.B.154.175; 13.B.154.240; 13.B.154.244; 13.B.157.228; 13.B.157.229; 13.B.157.230; 13.B.157.231; 13.B.157.236; 13.B.157.237; 13.B.157.238; 13.B.157.239; 13.B.157.154; 13.B.157.157; 13.B.157.166; 13.B.157.169; 13.B.157.172; 13.B.157.175; 13.B.157.240; 13.B.157.244; 13.B.166.228; 13.B.166.229; 13.B.166.230; 13.B.166.231; 13.B.166.236; 13.B.166.237; 13.B.166.238; 13.B.166.239; 13.B.166.154; 13.B.166.157; 13.B.166.166; 13.B.166.169; 13.B.166.172; 13.B.166.175; 13.B.166.240; 13.B.166.244; 13.B.169.228; 13.B.169.229; 13.B.169.230; 13.B.169.231; 13.B.169.236; 13.B.169.237; 13.B.169.238; 13.B.169.239; 13.B.169.154; 13.B.169.157; 13.B.169.166; 13.B.169.169; 13.B.169.172; 13.B.169.175; 13.B.169.240; 13.B.169.244; 13.B.172.228; 13.B.172.229; 13.B.172.230; 13.B.172.231; 13.B.172.236; 13.B.172.237; 13.B.172.238; 13.B.172.239; 13.B.172.154; 13.B.172.157; 13.B.172.166; 13.B.172.169; 13.B.172.172; 13.B.172.175; 13.B.172.240; 13.B.172.244; 13.B.175.228; 13.B.175.229; 13.B.175.230; 13.B.175.231; 13.B.175.236; 13.B.175.237; 13.B.175.238; 13.B.175.239; 13.B.175.154; 13.B.175.157; 13.B.175.166; 13.B.175.169; 13.B.175.172; 13.B.175.175; 13.B.175.240; 13.B.175.244; 13.B.240.228; 13.B.240.229; 13.B.240.230; 13.B.240.231; 13.B.240.236; 13.B.240.237; 13.B.240.238; 13.B.240.239; 13.B.240.154; 13.B.240.157; 13.B.240.166; 13.B.240.169; 13.B.240.172; 13.B.240.175; 13.B.240.240; 13.B.240.244; 13.B.244.228; 13.B.244.229; 13.B.244.230; 13.B.244.231; 13.B.244.236; 13.B.244.237; 13.B.244.238; 13.B.244.239; 13.B.244.154; 13.B.244.157; 13.B.244.166; 13.B.244.169; 13.B.244.172; 13.B.244.175; 13.B.244.240; 13.B.244.244;
Prodrugs of 13.D 13.D.228.228; 13.D.228.229; 13.D.228.230; 13.D.228.231; 13.D.228.236; 13.D.228.237; 13.D.228.238; 13.D.228.239; 13.D.228.154; 13.D.228.157; 13.D.228.166; 13.D.228.169; 13.D.228.172; 13.D.228.175; 13.D.228.240; 13.D.228.244; 13.D.229.228; 13.D.229.229; 13.D.229.230; 13.D.229.231; 13.D.229.236; 13.D.229.237; 13.D.229.238; 13.D.229.239; 13.D.229.154; 13.D.229.157; 13.D.229.166; 13.D.229.169; 13.D.229.172; 13.D.229.175; 13.D.229.240; 13.D.229.244; 13.D.230.228; 13.D.230.229; 13.D.230.230; 13.D.230.231; 13.D.230.236; 13.D.230.237; 13.D.230.238; 13.D.230.239; 13.D.230.154; 13.D.230.157; 13.D.230.166; 13.D.230.169; 13.D.230.172; 13.D.230.175; 13.D.230.240; 13.D.230.244; 13.D.231.228; 13.D.231.229; 13.D.231.230; 13.D.231.231; 13.D.231.236; 13.D.231.237; 13.D.231.238; 13.D.231.239; 13.D.231.154; 13.D.231.157; 13.D.231.166; 13.D.231.169; 13.D.231.172; 13.D.231.175; 13.D.231.240; 13.D.231.244; 13.D.236.228; 13.D.236.229; 13.D.236.230; 13.D.236.231; 13.D.236.236; 13.D.236.237; 13.D.236.238; 13.D.236.239; 13.D.236.154; 13.D.236.157; 13.D.236.166; 13.D.236.169; 13.D.236.172; 13.D.236.175; 13.D.236.240; 13.D.236.244; 13.D.237.228; 13.D.237.229; 13.D.237.230; 13.D.237.231; 13.D.237.236; 13.D.237.237; 13.D.237.238; 13.D.237.239; 13.D.237.154; 13.D.237.157; 13.D.237.166; 13.D.237.169; 13.D.237.172; 13.D.237.175; 13.D.237.240; 13.D.237.244; 13.D.238.228; 13.D.238.229; 13.D.238.230; 13.D.238.231; 13.D.238.236; 13.D.238.237; 13.D.238.238; 13.D.238.239; 13.D.238.154; 13.D.238.157; 13.D.238.166; 13.D.238.169; 13.D.238.172; 13.D.238.175; 13.D.238.240; 13.D.238.244; 13.D.239.228; 13.D.239.229; 13.D.239.230; 13.D.239.231; 13.D.239.236; 13.D.239.237; 13.D.239.238; 13.D.239.239; 13.D.239.154; 13.D.239.157; 13.D.239.166; 13.D.239.169; 13.D.239.172; 13.D.239.175; 13.D.239.240; 13.D.239.244; 13.D.154.228; 13.D.154.229; 13.D.154.230; 13.D.154.231; 13.D.154.236; 13.D.154.237; 13.D.154.238; 13.D.154.239; 13.D.154.154; 13.D.154.157; 13.D.154.166; 13.D.154.169; 13.D.154.172; 13.D.154.175; 13.D.154.240; 13.D.154.244; 13.D.157.228; 13.D.157.229; 13.D.157.230; 13.D.157.231; 13.D.157.236; 13.D.157.237; 13.D.157.238; 13.D.157.239; 13.D.157.154; 13.D.157.157; 13.D.157.166; 13.D.157.169; 13.D.157.172; 13.D.157.175; 13.D.157.240; 13.D.157.244; 13.D.166.228; 13.D.166.229; 13.D.166.230; 13.D.166.231; 13.D.166.236; 13.D.166.237; 13.D.166.238; 13.D.166.239; 13.D.166.154; 13.D.166.157; 13.D.166.166; 13.D.166.169; 13.D.166.172; 13.D.166.175; 13.D.166.240; 13.D.166.244; 13.D.169.228; 13.D.169.229; 13.D.169.230; 13.D.169.231; 13.D.169.236; 13.D.169.237; 13.D.169.238; 13.D.169.239; 13.D.169.154; 13.D.169.157; 13.D.169.166; 13.D.169.169; 13.D.169.172; 13.D.169.175; 13.D.169.240; 13.D.169.244; 13.D.172.228; 13.D.172.229; 13.D.172.230; 13.D.172.231; 13.D.172.236; 13.D.172.237; 13.D.172.238; 13.D.172.239; 13.D.172.154; 13.D.172.157; 13.D.172.166; 13.D.172.169; 13.D.172.172; 13.D.172.175; 13.D.172.240; 13.D.172.244; 13.D.175.228; 13.D.175.229; 13.D.175.230; 13.D.175.231; 13.D.175.236; 13.D.175.237; 13.D.175.238; 13.D.175.239; 13.D.175.154; 13.D.175.157; 13.D.175.166; 13.D.175.169; 13.D.175.172; 13.D.175.175; 13.D.175.240; 13.D.175.244; 13.D.240.228; 13.D.240.229; 13.D.240.230; 13.D.240.231; 13.D.240.236; 13.D.240.237; 13.D.240.238; 13.D.240.239; 13.D.240.154; 13.D.240.157; 13.D.240.166; 13.D.240.169; 13.D.240.172; 13.D.240.175; 13.D.240.240; 13.D.240.244; 13.D.244.228; 13.D.244.229; 13.D.244.230; 13.D.244.231; 13.D.244.236; 13.D.244.237; 13.D.244.238; 13.D.244.239; 13.D.244.154; 13.D.244.157; 13.D.244.166; 13.D.244.169; 13.D.244.172; 13.D.244.175; 13.D.244.240; 13.D.244.244;
Prodrugs of 13.E 13.E.228.228; 13.E.228.229; 13.E.228.230; 13.E.228.231; 13.E.228.236; 13.E.228.237; 13.E.228.238; 13.E.228.239; 13.E.228.154; 13.E.228.157; 13.E.228.166; 13.E.228.169; 13.E.228.172; 13.E.228.175; 13.E.228.240; 13.E.228.244; 13.E.229.228; 13.E.229.229; 13.E.229.230; 13.E.229.231; 13.E.229.236; 13.E.229.237; 13.E.229.238; 13.E.229.239; 13.E.229.154; 13.E.229.157; 13.E.229.166; 13.E.229.169; 13.E.229.172; 13.E.229.175; 13.E.229.240; 13.E.229.244; 13.E.230.228; 13.E.230.229; 13.E.230.230;

TABLE 7-continued

13.E.230.231; 13.E.230.236; 13.E.230.237; 13.E.230.238; 13.E.230.239;
13.E.230.154; 13.E.230.157; 13.E.230.166; 13.E.230.169; 13.E.230.172;
13.E.230.175; 13.E.230.240; 13.E.230.244; 13.E.231.228; 13.E.231.229;
13.E.231.230; 13.E.231.231; 13.E.231.236; 13.E.231.237; 13.E.231.238;
13.E.231.239; 13.E.231.154; 13.E.231.157; 13.E.231.166; 13.E.231.169;
13.E.231.172; 13.E.231.175; 13.E.231.240; 13.E.231.244; 13.E.236.228;
13.E.236.229; 13.E.236.230; 13.E.236.231; 13.E.236.236; 13.E.236.237;
13.E.236.238; 13.E.236.239; 13.E.236.154; 13.E.236.157; 13.E.236.166;
13.E.236.169; 13.E.236.172; 13.E.236.175; 13.E.236.240; 13.E.236.244;
13.E.237.228; 13.E.237.229; 13.E.237.230; 13.E.237.231; 13.E.237.236;
13.E.237.237; 13.E.237.238; 13.E.237.239; 13.E.237.154; 13.E.237.157;
13.E.237.166; 13.E.237.169; 13.E.237.172; 13.E.237.175; 13.E.237.240;
13.E.237.244; 13.E.238.228; 13.E.238.229; 13.E.238.230; 13.E.238.231;
13.E.238.236; 13.E.238.237; 13.E.238.238; 13.E.238.239; 13.E.238.154;
13.E.238.157; 13.E.238.166; 13.E.238.169; 13.E.238.172; 13.E.238.175;
13.E.238.240; 13.E.238.244; 13.E.239.228; 13.E.239.229; 13.E.239.230;
13.E.239.231; 13.E.239.236; 13.E.239.237; 13.E.239.238; 13.E.239.239;
13.E.239.154; 13.E.239.157; 13.E.239.166; 13.E.239.169; 13.E.239.172;
13.E.239.175; 13.E.239.240; 13.E.239.244; 13.E.154.228; 13.E.154.229;
13.E.154.230; 13.E.154.231; 13.E.154.236; 13.E.154.237; 13.E.154.238;
13.E.154.239; 13.E.154.154; 13.E.154.157; 13.E.154.166; 13.E.154.169;
13.E.154.172; 13.E.154.175; 13.E.154.240; 13.E.154.244; 13.E.157.228;
13.E.157.229; 13.E.157.230; 13.E.157.231; 13.E.157.236; 13.E.157.237;
13.E.157.238; 13.E.157.239; 13.E.157.154; 13.E.157.157; 13.E.157.166;
13.E.157.169; 13.E.157.172; 13.E.157.175; 13.E.157.240; 13.E.157.244;
13.E.166.228; 13.E.166.229; 13.E.166.230; 13.E.166.231; 13.E.166.236;
13.E.166.237; 13.E.166.238; 13.E.166.239; 13.E.166.154; 13.E.166.157;
13.E.166.166; 13.E.166.169; 13.E.166.172; 13.E.166.175; 13.E.166.240;
13.E.166.244; 13.E.169.228; 13.E.169.229; 13.E.169.230; 13.E.169.231;
13.E.169.236; 13.E.169.237; 13.E.169.238; 13.E.169.239; 13.E.169.154;
13.E.169.157; 13.E.169.166; 13.E.169.169; 13.E.169.172; 13.E.169.175;
13.E.169.240; 13.E.169.244; 13.E.172.228; 13.E.172.229; 13.E.172.230;
13.E.172.231; 13.E.172.236; 13.E.172.237; 13.E.172.238; 13.E.172.239;
13.E.172.154; 13.E.172.157; 13.E.172.166; 13.E.172.169; 13.E.172.172;
13.E.172.175; 13.E.172.240; 13.E.172.244; 13.E.175.228; 13.E.175.229;
13.E.175.230; 13.E.175.231; 13.E.175.236; 13.E.175.237; 13.E.175.238;
13.E.175.239; 13.E.175.154; 13.E.175.157; 13.E.175.166; 13.E.175.169;
13.E.175.172; 13.E.175.175; 13.E.175.240; 13.E.175.244; 13.E.240.228;
13.E.240.229; 13.E.240.230; 13.E.240.231; 13.E.240.236; 13.E.240.237;
13.E.240.238; 13.E.240.239; 13.E.240.154; 13.E.240.157; 13.E.240.166;
13.E.240.169; 13.E.240.172; 13.E.240.175; 13.E.240.240; 13.E.240.244;
13.E.244.228; 13.E.244.229; 13.E.244.230; 13.E.244.231; 13.E.244.236;
13.E.244.237; 13.E.244.238; 13.E.244.239; 13.E.244.154; 13.E.244.157;
13.E.244.166; 13.E.244.169; 13.E.244.172; 13.E.244.175; 13.E.244.240;
13.E.244.244;

Prodrugs of 13.G

13.G.228.228; 13.G.228.229; 13.G.228.230; 13.G.228.231; 13.G.228.236;
13.G.228.237; 13.G.228.238; 13.G.228.239; 13.G.228.154; 13.G.228.157;
13.G.228.166; 13.G.228.169; 13.G.228.172; 13.G.228.175; 13.G.228.240;
13.G.228.244; 13.G.229.228; 13.G.229.229; 13.G.229.230; 13.G.229.231;
13.G.229.236; 13.G.229.237; 13.G.229.238; 13.G.229.239; 13.G.229.154;
13.G.229.157; 13.G.229.166; 13.G.229.169; 13.G.229.172; 13.G.229.175;
13.G.229.240; 13.G.229.244; 13.G.230.228; 13.G.230.229; 13.G.230.244;
13.G.230.231; 13.G.230.236; 13.G.230.237; 13.G.230.238; 13.G.230.239;
13.G.230.154; 13.G.230.157; 13.G.230.166; 13.G.230.169; 13.G.230.172;
13.G.230.175; 13.G.230.240; 13.G.230.244; 13.G.231.228; 13.G.231.229;
13.G.231.230; 13.G.231.231; 13.G.231.236; 13.G.231.237; 13.G.231.238;
13.G.231.239; 13.G.231.154; 13.G.231.157; 13.G.231.166; 13.G.231.169;
13.G.231.172; 13.G.231.175; 13.G.231.240; 13.G.231.244; 13.G.236.228;
13.G.236.229; 13.G.236.230; 13.G.236.231; 13.G.236.236; 13.G.236.237;
13.G.236.238; 13.G.236.239; 13.G.236.154; 13.G.236.157; 13.G.236.166;
13.G.236.169; 13.G.236.172; 13.G.236.175; 13.G.236.240; 13.G.236.244;
13.G.237.228; 13.G.237.229; 13.G.237.230; 13.G.237.231; 13.G.237.236;
13.G.237.237; 13.G.237.238; 13.G.237.239; 13.G.237.154; 13.G.237.157;
13.G.237.166; 13.G.237.169; 13.G.237.172; 13.G.237.175; 13.G.237.240;
13.G.237.244; 13.G.238.228; 13.G.238.229; 13.G.238.230; 13.G.238.231;
13.G.238.236; 13.G.238.237; 13.G.238.238; 13.G.238.239; 13.G.238.154;
13.G.238.157; 13.G.238.166; 13.G.238.169; 13.G.238.172; 13.G.238.175;
13.G.238.240; 13.G.238.244; 13.G.239.228; 13.G.239.229; 13.G.239.230;
13.G.239.231; 13.G.239.236; 13.G.239.237; 13.G.239.238; 13.G.239.239;
13.G.239.154; 13.G.239.157; 13.G.239.166; 13.G.239.169; 13.G.239.172;
13.G.239.175; 13.G.239.240; 13.G.239.244; 13.G.154.228; 13.G.154.229;
13.G.154.230; 13.G.154.231; 13.G.154.236; 13.G.154.237; 13.G.154.238;
13.G.154.239; 13.G.154.154; 13.G.154.157; 13.G.154.166; 13.G.154.169;
13.G.154.172; 13.G.154.175; 13.G.154.240; 13.G.154.244; 13.G.157.228;
13.G.157.229; 13.G.157.230; 13.G.157.231; 13.G.157.236; 13.G.157.237;
13.G.157.238; 13.G.157.239; 13.G.157.154; 13.G.157.157; 13.G.157.166;
13.G.157.169; 13.G.157.172; 13.G.157.175; 13.G.157.240; 13.G.157.244;
13.G.166.228; 13.G.166.229; 13.G.166.230; 13.G.166.231; 13.G.166.236;
13.G.166.237; 13.G.166.238; 13.G.166.239; 13.G.166.154; 13.G.166.157;
13.G.166.166; 13.G.166.169; 13.G.166.172; 13.G.166.175; 13.G.166.240;
13.G.166.244; 13.G.169.228; 13.G.169.229; 13.G.169.230; 13.G.169.231;
13.G.169.236; 13.G.169.237; 13.G.169.238; 13.G.169.239; 13.G.169.154;
13.G.169.157; 13.G.169.166; 13.G.169.169; 13.G.169.172; 13.G.169.175;
13.G.169.240; 13.G.169.244; 13.G.172.228; 13.G.172.229; 13.G.172.230;
13.G.172.231; 13.G.172.236; 13.G.172.237; 13.G.172.238; 13.G.172.239;
13.G.172.154; 13.G.172.157; 13.G.172.166; 13.G.172.169; 13.G.172.172;
13.G.172.175; 13.G.172.240; 13.G.172.244; 13.G.175.228; 13.G.175.229;
13.G.175.230; 13.G.175.231; 13.G.175.236; 13.G.175.237; 13.G.175.238;
13.G.175.239; 13.G.175.154; 13.G.175.157; 13.G.175.166; 13.G.175.169;
13.G.175.172; 13.G.175.175; 13.G.175.240; 13.G.175.244; 13.G.240.228;
13.G.240.229; 13.G.240.230; 13.G.240.231; 13.G.240.236; 13.G.240.237;
13.G.240.238; 13.G.240.239; 13.G.240.154; 13.G.240.157; 13.G.240.166;
13.G.240.169; 13.G.240.172; 13.G.240.175; 13.G.240.240; 13.G.240.244;
13.G.244.228; 13.G.244.229; 13.G.244.230; 13.G.244.231; 13.G.244.236;
13.G.244.237; 13.G.244.238; 13.G.244.239; 13.G.244.154; 13.G.244.157;
13.G.244.166; 13.G.244.169; 13.G.244.172; 13.G.244.175; 13.G.244.240;
13.G.244.244;

Prodrugs of 13.I

13.I.228.228; 13.I.228.229; 13.I.228.230; 13.I.228.231; 13.I.228.236;
13.I.228.237; 13.I.228.238; 13.I.228.239; 13.I.228.154; 13.I.228.157;
13.I.228.166; 13.I.228.169; 13.I.228.172; 13.I.228.175; 13.I.228.240;
13.I.228.244; 13.I.229.228; 13.I.229.229; 13.I.229.230; 13.I.229.231;
13.I.229.236; 13.I.229.237; 13.I.229.238; 13.I.229.239; 13.I.229.154;
13.I.229.157; 13.I.229.166; 13.I.229.169; 13.I.229.172; 13.I.229.175;
13.I.229.240; 13.I.229.244; 13.I.230.228; 13.I.230.229; 13.I.230.230;
13.I.230.231; 13.I.230.236; 13.I.230.237; 13.I.230.238; 13.I.230.239;
13.I.230.154; 13.I.230.157; 13.I.230.166; 13.I.230.169; 13.I.230.172;
13.I.230.175; 13.I.230.240; 13.I.230.244; 13.I.231.228; 13.I.231.229;
13.I.231.230; 13.I.231.231; 13.I.231.236; 13.I.231.237; 13.I.231.238;
13.I.231.239; 13.I.231.154; 13.I.231.157; 13.I.231.166; 13.I.231.169;
13.I.231.172; 13.I.231.175; 13.I.231.240; 13.I.231.244; 13.I.236.228;
13.I.236.229; 13.I.236.230; 13.I.236.231; 13.I.236.236; 13.I.236.237;
13.I.236.238; 13.I.236.239; 13.I.236.154; 13.I.236.157; 13.I.236.166;
13.I.236.169; 13.I.236.172; 13.I.236.175; 13.I.236.240; 13.I.236.244;
13.I.237.228; 13.I.237.229; 13.I.237.230; 13.I.237.231; 13.I.237.236;
13.I.237.237; 13.I.237.238; 13.I.237.239; 13.I.237.154; 13.I.237.157;
13.I.237.166; 13.I.237.169; 13.I.237.172; 13.I.237.175; 13.I.237.240;
13.I.237.244; 13.I.238.228; 13.I.238.229; 13.I.238.230; 13.I.238.231;
13.I.238.236; 13.I.238.237; 13.I.238.238; 13.I.238.239; 13.I.238.154;
13.I.238.157; 13.I.238.166; 13.I.238.169; 13.I.238.172; 13.I.238.175;
13.I.238.240; 13.I.238.244; 13.I.239.228; 13.I.239.229; 13.I.239.230;
13.I.239.231; 13.I.239.236; 13.I.239.237; 13.I.239.238; 13.I.239.239;
13.I.239.154; 13.I.239.157; 13.I.239.166; 13.I.239.169; 13.I.239.172;
13.I.239.175; 13.I.239.240; 13.I.239.244; 13.I.154.228; 13.I.154.229;
13.I.154.230; 13.I.154.231; 13.I.154.236; 13.I.154.237; 13.I.154.238;
13.I.154.239; 13.I.154.154; 13.I.154.157; 13.I.154.166; 13.I.154.169;
13.I.154.172; 13.I.154.175; 13.I.154.240; 13.I.154.244; 13.I.157.228;
13.I.157.229; 13.I.157.230; 13.I.157.231; 13.I.157.236; 13.I.157.237;
13.I.157.238; 13.I.157.239; 13.I.157.154; 13.I.157.157; 13.I.157.166;
13.I.157.169; 13.I.157.172; 13.I.157.175; 13.I.157.240; 13.I.157.244;
13.I.166.228; 13.I.166.229; 13.I.166.230; 13.I.166.231; 13.I.166.236;
13.I.166.237; 13.I.166.238; 13.I.166.239; 13.I.166.154; 13.I.166.157;
13.I.166.166; 13.I.166.169; 13.I.166.172; 13.I.166.175; 13.I.166.240;
13.I.166.244; 13.I.169.228; 13.I.169.229; 13.I.169.230; 13.I.169.231;
13.I.169.236; 13.I.169.237; 13.I.169.238; 13.I.169.239; 13.I.169.154;
13.I.169.157; 13.I.169.166; 13.I.169.169; 13.I.169.172; 13.I.169.175;
13.I.169.240; 13.I.169.244; 13.I.172.228; 13.I.172.229; 13.I.172.230;
13.I.172.231; 13.I.172.236; 13.I.172.237; 13.I.172.238; 13.I.172.239;
13.I.172.154; 13.I.172.157; 13.I.172.166; 13.I.172.169; 13.I.172.172;
13.I.172.175; 13.I.172.240; 13.I.172.244; 13.I.175.228; 13.I.175.229;
13.I.175.230; 13.I.175.231; 13.I.175.236; 13.I.175.237; 13.I.175.238;
13.I.175.239; 13.I.175.154; 13.I.175.157; 13.I.175.166; 13.I.175.169;
13.I.175.172; 13.I.175.175; 13.I.175.240; 13.I.175.244; 13.I.240.228;
13.I.240.229; 13.I.240.230; 13.I.240.231; 13.I.240.236; 13.I.240.237;
13.I.240.238; 13.I.240.239; 13.I.240.154; 13.I.240.157; 13.I.240.166;
13.I.240.169; 13.I.240.172; 13.I.240.175; 13.I.240.240; 13.I.240.244;
13.I.244.228; 13.I.244.229; 13.I.244.230; 13.I.244.231; 13.I.244.236;
13.I.244.237; 13.I.244.238; 13.I.244.239; 13.I.244.154; 13.I.244.157;
13.I.244.166; 13.I.244.169; 13.I.244.172; 13.I.244.175; 13.I.244.240;
13.I.244.244;

Prodrugs of 13.J

13.J.228.228; 13.J.228.229; 13.J.228.230; 13.J.228.231; 13.J.228.236;
13.J.228.237; 13.J.228.238; 13.J.228.239; 13.J.228.154; 13.J.228.157;
13.J.228.166; 13.J.228.169; 13.J.228.172; 13.J.228.175; 13.J.228.240;

TABLE 7-continued

13.J.228.244; 13.J.229.228; 13.J.229.229; 13.J.229.230; 13.J.229.231;
13.J.229.236; 13.J.229.237; 13.J.229.238; 13.J.229.239; 13.J.229.154;
13.J.229.157; 13.J.229.166; 13.J.229.169; 13.J.229.172; 13.J.229.175;
13.J.229.240; 13.J.229.244; 13.J.230.228; 13.J.230.229; 13.J.230.230;
13.J.230.231; 13.J.230.236; 13.J.230.237; 13.J.230.238; 13.J.230.239;
13.J.230.154; 13.J.230.157; 13.J.230.166; 13.J.230.169; 13.J.230.172;
13.J.230.175; 13.J.230.240; 13.J.230.244; 13.J.231.228; 13.J.231.229;
13.J.231.230; 13.J.231.231; 13.J.231.236; 13.J.231.237; 13.J.231.238;
13.J.231.239; 13.J.231.154; 13.J.231.157; 13.J.231.166; 13.J.231.169;
13.J.231.172; 13.J.231.175; 13.J.231.240; 13.J.231.244; 13.J.236.228;
13.J.236.229; 13.J.236.230; 13.J.236.231; 13.J.236.236; 13.J.236.237;
13.J.236.238; 13.J.236.239; 13.J.236.154; 13.J.236.157; 13.J.236.166;
13.J.236.169; 13.J.236.172; 13.J.236.175; 13.J.236.240; 13.J.236.244;
13.J.237.228; 13.J.237.229; 13.J.237.230; 13.J.237.231; 13.J.237.236;
13.J.237.237; 13.J.237.238; 13.J.237.239; 13.J.237.154; 13.J.237.157;
13.J.237.166; 13.J.237.169; 13.J.237.172; 13.J.237.175; 13.J.237.240;
13.J.237.244; 13.J.238.228; 13.J.238.229; 13.J.238.230; 13.J.238.231;
13.J.238.236; 13.J.238.237; 13.J.238.238; 13.J.238.239; 13.J.238.154;
13.J.238.157; 13.J.238.166; 13.J.238.169; 13.J.238.172; 13.J.238.175;
13.J.238.240; 13.J.238.244; 13.J.239.228; 13.J.239.229; 13.J.239.230;
13.J.239.231; 13.J.239.236; 13.J.239.237; 13.J.239.238; 13.J.239.239;
13.J.239.154; 13.J.239.157; 13.J.239.166; 13.J.239.169; 13.J.239.172;
13.J.239.175; 13.J.239.240; 13.J.239.244; 13.J.154.228; 13.J.154.229;
13.J.154.230; 13.J.154.231; 13.J.154.236; 13.J.154.237; 13.J.154.238;
13.J.154.239; 13.J.154.154; 13.J.154.157; 13.J.154.166; 13.J.154.169;
13.J.154.172; 13.J.154.175; 13.J.154.240; 13.J.154.244; 13.J.157.228;
13.J.157.229; 13.J.157.230; 13.J.157.231; 13.J.157.236; 13.J.157.237;
13.J.157.238; 13.J.157.239; 13.J.157.154; 13.J.157.157; 13.J.157.166;
13.J.157.169; 13.J.157.172; 13.J.157.175; 13.J.157.240; 13.J.157.244;
13.J.166.228; 13.J.166.229; 13.J.166.230; 13.J.166.231; 13.J.166.236;
13.J.166.237; 13.J.166.238; 13.J.166.239; 13.J.166.154; 13.J.166.157;
13.J.166.166; 13.J.166.169; 13.J.166.172; 13.J.166.175; 13.J.166.240;
13.J.166.244; 13.J.169.228; 13.J.169.229; 13.J.169.230; 13.J.169.231;
13.J.169.236; 13.J.169.237; 13.J.169.238; 13.J.169.239; 13.J.169.154;
13.J.169.157; 13.J.169.166; 13.J.169.169; 13.J.169.172; 13.J.169.175;
13.J.169.240; 13.J.169.244; 13.J.172.228; 13.J.172.229; 13.J.172.230;
13.J.172.231; 13.J.172.236; 13.J.172.237; 13.J.172.238; 13.J.172.239;
13.J.172.154; 13.J.172.157; 13.J.172.166; 13.J.172.169; 13.J.172.172;
13.J.172.175; 13.J.172.240; 13.J.172.244; 13.J.175.228; 13.J.175.229;
13.J.175.230; 13.J.175.231; 13.J.175.236; 13.J.175.237; 13.J.175.238;
13.J.175.239; 13.J.175.154; 13.J.175.157; 13.J.175.166; 13.J.175.169;
13.J.175.172; 13.J.175.175; 13.J.175.240; 13.J.175.244; 13.J.240.228;
13.J.240.229; 13.J.240.230; 13.J.240.231; 13.J.240.236; 13.J.240.237;
13.J.240.238; 13.J.240.239; 13.J.240.154; 13.J.240.157; 13.J.240.166;
13.J.240.169; 13.J.240.172; 13.J.240.175; 13.J.240.240; 13.J.240.244;
13.J.244.228; 13.J.244.229; 13.J.244.230; 13.J.244.231; 13.J.244.236;
13.J.244.237; 13.J.244.238; 13.J.244.239; 13.J.244.154; 13.J.244.157;
13.J.244.166; 13.J.244.169; 13.J.244.172; 13.J.244.175; 13.J.244.240;
13.J.244.244;

Prodrugs of 13.L

13.L.228.228; 13.L.228.229; 13.L.228.230; 13.L.228.231; 13.L.228.236;
13.L.228.237; 13.L.228.238; 13.L.228.239; 13.L.228.154; 13.L.228.157;
13.L.228.166; 13.L.228.169; 13.L.228.172; 13.L.228.175; 13.L.228.240;
13.L.228.244; 13.L.229.228; 13.L.229.229; 13.L.229.230; 13.L.229.231;
13.L.229.236; 13.L.229.237; 13.L.229.238; 13.L.229.239; 13.L.229.154;
13.L.229.157; 13.L.229.166; 13.L.229.169; 13.L.229.172; 13.L.229.175;
13.L.229.240; 13.L.229.244; 13.L.230.228; 13.L.230.229; 13.L.230.230;
13.L.230.231; 13.L.230.236; 13.L.230.237; 13.L.230.238; 13.L.230.239;
13.L.230.154; 13.L.230.157; 13.L.230.166; 13.L.230.169; 13.L.230.172;
13.L.230.175; 13.L.230.240; 13.L.230.244; 13.L.231.228; 13.L.231.229;
13.L.231.230; 13.L.231.231; 13.L.231.236; 13.L.231.237; 13.L.231.238;
13.L.231.239; 13.L.231.154; 13.L.231.157; 13.L.231.166; 13.L.231.169;
13.L.231.172; 13.L.231.175; 13.L.231.240; 13.L.231.244; 13.L.236.228;
13.L.236.229; 13.L.236.230; 13.L.236.231; 13.L.236.236; 13.L.236.237;
13.L.236.238; 13.L.236.239; 13.L.236.154; 13.L.236.157; 13.L.236.166;
13.L.236.169; 13.L.236.172; 13.L.236.175; 13.L.236.240; 13.L.236.244;
13.L.237.228; 13.L.237.229; 13.L.237.230; 13.L.237.231; 13.L.237.236;
13.L.237.237; 13.L.237.238; 13.L.237.239; 13.L.237.154; 13.L.237.157;
13.L.237.166; 13.L.237.169; 13.L.237.172; 13.L.237.175; 13.L.237.240;
13.L.237.244; 13.L.238.228; 13.L.238.229; 13.L.238.230; 13.L.238.231;
13.L.238.236; 13.L.238.237; 13.L.238.238; 13.L.238.239; 13.L.238.154;
13.L.238.157; 13.L.238.166; 13.L.238.169; 13.L.238.172; 13.L.238.175;
13.L.238.240; 13.L.238.244; 13.L.239.228; 13.L.239.229; 13.L.239.230;
13.L.239.231; 13.L.239.236; 13.L.239.237; 13.L.239.238; 13.L.239.239;
13.L.239.154; 13.L.239.157; 13.L.239.166; 13.L.239.169; 13.L.239.172;
13.L.239.175; 13.L.239.240; 13.L.239.244; 13.L.154.228; 13.L.154.229;
13.L.154.230; 13.L.154.231; 13.L.154.236; 13.L.154.237; 13.L.154.238;
13.L.154.239; 13.L.154.154; 13.L.154.157; 13.L.154.166; 13.L.154.169;
13.L.154.172; 13.L.154.175; 13.L.154.240; 13.L.154.244; 13.L.157.228;
13.L.157.229; 13.L.157.230; 13.L.157.231; 13.L.157.236; 13.L.157.237;
13.L.157.238; 13.L.157.239; 13.L.157.154; 13.L.157.157; 13.L.157.166;
13.L.157.169; 13.L.157.172; 13.L.157.175; 13.L.157.240; 13.L.157.244;
13.L.166.228; 13.L.166.229; 13.L.166.230; 13.L.166.231; 13.L.166.236;
13.L.166.237; 13.L.166.238; 13.L.166.239; 13.L.166.154; 13.L.166.157;
13.L.166.166; 13.L.166.169; 13.L.166.172; 13.L.166.175; 13.L.166.240;
13.L.166.244; 13.L.169.228; 13.L.169.229; 13.L.169.230; 13.L.169.231;
13.L.169.236; 13.L.169.237; 13.L.169.238; 13.L.169.239; 13.L.169.154;
13.L.169.157; 13.L.169.166; 13.L.169.169; 13.L.169.172; 13.L.169.175;
13.L.169.240; 13.L.169.244; 13.L.172.228; 13.L.172.229; 13.L.172.230;
13.L.172.231; 13.L.172.236; 13.L.172.237; 13.L.172.238; 13.L.172.239;
13.L.172.154; 13.L.172.157; 13.L.172.166; 13.L.172.169; 13.L.172.172;
13.L.172.175; 13.L.172.240; 13.L.172.244; 13.L.175.228; 13.L.175.229;
13.L.175.230; 13.L.175.231; 13.L.175.236; 13.L.175.237; 13.L.175.238;
13.L.175.239; 13.L.175.154; 13.L.175.157; 13.L.175.166; 13.L.175.169;
13.L.175.172; 13.L.175.175; 13.L.175.240; 13.L.175.244; 13.L.240.228;
13.L.240.229; 13.L.240.230; 13.L.240.231; 13.L.240.236; 13.L.240.237;
13.L.240.238; 13.L.240.239; 13.L.240.154; 13.L.240.157; 13.L.240.166;
13.L.240.169; 13.L.240.172; 13.L.240.175; 13.L.240.240; 13.L.240.244;
13.L.244.228; 13.L.244.229; 13.L.244.230; 13.L.244.231; 13.L.244.236;
13.L.244.237; 13.L.244.238; 13.L.244.239; 13.L.244.154; 13.L.244.157;
13.L.244.166; 13.L.244.169; 13.L.244.172; 13.L.244.175; 13.L.244.240;
13.L.244.244;

Prodrugs of 13.O

13.O.228.228; 13.O.228.229; 13.O.228.230; 13.O.228.231; 13.O.228.236;
13.O.228.237; 13.O.228.238; 13.O.228.239; 13.O.228.154; 13.O.228.157;
13.O.228.166; 13.O.228.169; 13.O.228.172; 13.O.228.175; 13.O.228.240;
13.O.228.244; 13.O.229.228; 13.O.229.229; 13.O.229.230; 13.O.229.231;
13.O.229.236; 13.O.229.237; 13.O.229.238; 13.O.229.239; 13.O.229.154;
13.O.229.157; 13.O.229.166; 13.O.229.169; 13.O.229.172; 13.O.229.175;
13.O.229.240; 13.O.229.244; 13.O.230.228; 13.O.230.229; 13.O.230.230;
13.O.230.231; 13.O.230.236; 13.O.230.237; 13.O.230.238; 13.O.230.239;
13.O.230.154; 13.O.230.157; 13.O.230.166; 13.O.230.169; 13.O.230.172;
13.O.230.175; 13.O.230.240; 13.O.230.244; 13.O.231.228; 13.O.231.229;
13.O.231.230; 13.O.231.231; 13.O.231.236; 13.O.231.237; 13.O.231.238;
13.O.231.239; 13.O.231.154; 13.O.231.157; 13.O.231.166; 13.O.231.169;
13.O.231.172; 13.O.231.175; 13.O.231.240; 13.O.231.244; 13.O.236.228;
13.O.236.229; 13.O.236.230; 13.O.236.231; 13.O.236.236; 13.O.236.237;
13.O.236.238; 13.O.236.239; 13.O.236.154; 13.O.236.157; 13.O.236.166;
13.O.236.169; 13.O.236.172; 13.O.236.175; 13.O.236.240; 13.O.236.244;
13.O.237.228; 13.O.237.229; 13.O.237.230; 13.O.237.231; 13.O.237.236;
13.O.237.237; 13.O.237.238; 13.O.237.239; 13.O.237.154; 13.O.237.157;
13.O.237.166; 13.O.237.169; 13.O.237.172; 13.O.237.175; 13.O.237.240;
13.O.237.244; 13.O.238.228; 13.O.238.229; 13.O.238.230; 13.O.238.231;
13.O.238.236; 13.O.238.237; 13.O.238.238; 13.O.238.239; 13.O.238.154;
13.O.238.157; 13.O.238.166; 13.O.238.169; 13.O.238.172; 13.O.238.175;
13.O.238.240; 13.O.238.244; 13.O.239.228; 13.O.239.229; 13.O.239.230;
13.O.239.231; 13.O.239.236; 13.O.239.237; 13.O.239.238; 13.O.239.239;
13.O.239.154; 13.O.239.157; 13.O.239.166; 13.O.239.169; 13.O.239.172;
13.O.239.175; 13.O.239.240; 13.O.239.244; 13.O.154.228; 13.O.154.229;
13.O.154.230; 13.O.154.231; 13.O.154.236; 13.O.154.237; 13.O.154.238;
13.O.154.239; 13.O.154.154; 13.O.154.157; 13.O.154.166; 13.O.154.169;
13.O.154.172; 13.O.154.175; 13.O.154.240; 13.O.154.244; 13.O.157.228;
13.O.157.229; 13.O.157.230; 13.O.157.231; 13.O.157.236; 13.O.157.237;
13.O.157.238; 13.O.157.239; 13.O.157.154; 13.O.157.157; 13.O.157.166;
13.O.157.169; 13.O.157.172; 13.O.157.175; 13.O.157.240; 13.O.157.244;
13.O.166.228; 13.O.166.229; 13.O.166.230; 13.O.166.231; 13.O.166.236;
13.O.166.237; 13.O.166.238; 13.O.166.239; 13.O.166.154; 13.O.166.157;
13.O.166.166; 13.O.166.169; 13.O.166.172; 13.O.166.175; 13.O.166.240;
13.O.166.244; 13.O.169.228; 13.O.169.229; 13.O.169.230; 13.O.169.231;
13.O.169.236; 13.O.169.237; 13.O.169.238; 13.O.169.239; 13.O.169.154;
13.O.169.157; 13.O.169.166; 13.O.169.169; 13.O.169.172; 13.O.169.175;
13.O.169.240; 13.O.169.244; 13.O.172.228; 13.O.172.229; 13.O.172.230;
13.O.172.231; 13.O.172.236; 13.O.172.237; 13.O.172.238; 13.O.172.239;
13.O.172.154; 13.O.172.157; 13.O.172.166; 13.O.172.169; 13.O.172.172;
13.O.172.175; 13.O.172.240; 13.O.172.244; 13.O.175.228; 13.O.175.229;
13.O.175.230; 13.O.175.231; 13.O.175.236; 13.O.175.237; 13.O.175.238;
13.O.175.239; 13.O.175.154; 13.O.175.157; 13.O.175.166; 13.O.175.169;
13.O.175.172; 13.O.175.175; 13.O.175.240; 13.O.175.244; 13.O.240.228;
13.O.240.229; 13.O.240.230; 13.O.240.231; 13.O.240.236; 13.O.240.237;
13.O.240.238; 13.O.240.239; 13.O.240.154; 13.O.240.157; 13.O.240.166;
13.O.240.169; 13.O.240.172; 13.O.240.175; 13.O.240.240; 13.O.240.244;
13.O.244.228; 13.O.244.229; 13.O.244.230; 13.O.244.231; 13.O.244.236;
13.O.244.237; 13.O.244.238; 13.O.244.239; 13.O.244.154; 13.O.244.157;
13.O.244.166; 13.O.244.169; 13.O.244.172; 13.O.244.175; 13.O.244.240;
13.O.244.244;

TABLE 7-continued

Prodrugs of 13.P

13.P.228.228; 13.P.228.229; 13.P.228.230; 13.P.228.231; 13.P.228.236;
13.P.228.237; 13.P.228.238; 13.P.228.239; 13.P.228.154; 13.P.228.157;
13.P.228.166; 13.P.228.169; 13.P.228.172; 13.P.228.175; 13.P.228.240;
13.P.228.244; 13.P.229.228; 13.P.229.229; 13.P.229.230; 13.P.229.231;
13.P.229.236; 13.P.229.237; 13.P.229.238; 13.P.229.239; 13.P.229.154;
13.P.229.157; 13.P.229.166; 13.P.229.169; 13.P.229.172; 13.P.229.175;
13.P.229.240; 13.P.229.244; 13.P.230.228; 13.P.230.229; 13.P.230.230;
13.P.230.231; 13.P.230.236; 13.P.230.237; 13.P.230.238; 13.P.230.239;
13.P.230.154; 13.P.230.157; 13.P.230.166; 13.P.230.169; 13.P.230.172;
13.P.230.175; 13.P.230.240; 13.P.230.244; 13.P.231.228; 13.P.231.229;
13.P.231.230; 13.P.231.231; 13.P.231.236; 13.P.231.237; 13.P.231.238;
13.P.231.239; 13.P.231.154; 13.P.231.157; 13.P.231.166; 13.P.231.169;
13.P.231.172; 13.P.231.175; 13.P.231.240; 13.P.231.244; 13.P.236.228;
13.P.236.229; 13.P.236.230; 13.P.236.231; 13.P.236.236; 13.P.236.237;
13.P.236.238; 13.P.236.239; 13.P.236.154; 13.P.236.157; 13.P.236.166;
13.P.236.169; 13.P.236.172; 13.P.236.175; 13.P.236.240; 13.P.236.244;
13.P.237.228; 13.P.237.229; 13.P.237.230; 13.P.237.231; 13.P.237.236;
13.P.237.237; 13.P.237.238; 13.P.237.239; 13.P.237.154; 13.P.237.157;
13.P.237.166; 13.P.237.169; 13.P.237.172; 13.P.237.175; 13.P.237.240;
13.P.237.244; 13.P.238.228; 13.P.238.229; 13.P.238.230; 13.P.238.231;
13.P.238.236; 13.P.238.237; 13.P.238.238; 13.P.238.239; 13.P.238.154;
13.P.238.157; 13.P.238.166; 13.P.238.169; 13.P.238.172; 13.P.238.175;
13.P.238.240; 13.P.238.244; 13.P.239.228; 13.P.239.229; 13.P.239.230;
13.P.239.231; 13.P.239.236; 13.P.239.237; 13.P.239.238; 13.P.239.239;
13.P.239.154; 13.P.239.157; 13.P.239.166; 13.P.239.169; 13.P.239.172;
13.P.239.175; 13.P.239.240; 13.P.239.244; 13.P.154.228; 13.P.154.229;
13.P.154.230; 13.P.154.231; 13.P.154.236; 13.P.154.237; 13.P.154.238;
13.P.154.239; 13.P.154.154; 13.P.154.157; 13.P.154.166; 13.P.154.169;
13.P.154.172; 13.P.154.175; 13.P.154.240; 13.P.154.244; 13.P.157.228;
13.P.157.229; 13.P.157.230; 13.P.157.231; 13.P.157.236; 13.P.157.237;
13.P.157.238; 13.P.157.239; 13.P.157.154; 13.P.157.157; 13.P.157.166;
13.P.157.169; 13.P.157.172; 13.P.157.175; 13.P.157.240; 13.P.157.244;
13.P.166.228; 13.P.166.229; 13.P.166.230; 13.P.166.231; 13.P.166.236;
13.P.166.237; 13.P.166.238; 13.P.166.239; 13.P.166.154; 13.P.166.157;
13.P.166.166; 13.P.166.169; 13.P.166.172; 13.P.166.175; 13.P.166.240;
13.P.166.244; 13.P.169.228; 13.P.169.229; 13.P.169.230; 13.P.169.231;
13.P.169.236; 13.P.169.237; 13.P.169.238; 13.P.169.239; 13.P.169.154;
13.P.169.157; 13.P.169.166; 13.P.169.169; 13.P.169.172; 13.P.169.175;
13.P.169.240; 13.P.169.244; 13.P.172.228; 13.P.172.229; 13.P.172.230;
13.P.172.231; 13.P.172.236; 13.P.172.237; 13.P.172.238; 13.P.172.239;
13.P.172.154; 13.P.172.157; 13.P.172.166; 13.P.172.169; 13.P.172.172;
13.P.172.175; 13.P.172.240; 13.P.172.244; 13.P.175.228; 13.P.175.229;
13.P.175.230; 13.P.175.231; 13.P.175.236; 13.P.175.237; 13.P.175.238;
13.P.175.239; 13.P.175.154; 13.P.175.157; 13.P.175.166; 13.P.175.169;
13.P.175.172; 13.P.175.175; 13.P.175.240; 13.P.175.244; 13.P.240.228;
13.P.240.229; 13.P.240.230; 13.P.240.231; 13.P.240.236; 13.P.240.237;
13.P.240.238; 13.P.240.239; 13.P.240.154; 13.P.240.157; 13.P.240.166;
13.P.240.169; 13.P.240.172; 13.P.240.175; 13.P.240.240; 13.P.240.244;
13.P.244.228; 13.P.244.229; 13.P.244.230; 13.P.244.231; 13.P.244.236;
13.P.244.237; 13.P.244.238; 13.P.244.239; 13.P.244.154; 13.P.244.157;
13.P.244.166; 13.P.244.169; 13.P.244.172; 13.P.244.175; 13.P.244.240;
13.P.244.244;

Prodrugs of 13.U

13.U.228.228; 13.U.228.229; 13.U.228.230; 13.U.228.231; 13.U.228.236;
13.U.228.237; 13.U.228.238; 13.U.228.239; 13.U.228.154; 13.U.228.157;
13.U.228.166; 13.U.228.169; 13.U.228.172; 13.U.228.175; 13.U.228.240;
13.U.228.244; 13.U.229.228; 13.U.229.229; 13.U.229.230; 13.U.229.231;
13.U.229.236; 13.U.229.237; 13.U.229.238; 13.U.229.239; 13.U.229.154;
13.U.229.157; 13.U.229.166; 13.U.229.169; 13.U.229.172; 13.U.229.175;
13.U.229.240; 13.U.229.244; 13.U.230.228; 13.U.230.229; 13.U.230.230;
13.U.230.231; 13.U.230.236; 13.U.230.237; 13.U.230.238; 13.U.230.239;
13.U.230.154; 13.U.230.157; 13.U.230.166; 13.U.230.169; 13.U.230.172;
13.U.230.175; 13.U.230.240; 13.U.230.244; 13.U.231.228; 13.U.231.229;
13.U.231.230; 13.U.231.231; 13.U.231.236; 13.U.231.237; 13.U.231.238;
13.U.231.239; 13.U.231.154; 13.U.231.157; 13.U.231.166; 13.U.231.169;
13.U.231.172; 13.U.231.175; 13.U.231.240; 13.U.231.244; 13.U.236.228;
13.U.236.229; 13.U.236.230; 13.U.236.231; 13.U.236.236; 13.U.236.237;
13.U.236.238; 13.U.236.239; 13.U.236.154; 13.U.236.157; 13.U.236.166;
13.U.236.169; 13.U.236.172; 13.U.236.175; 13.U.236.240; 13.U.236.244;
13.U.237.228; 13.U.237.229; 13.U.237.230; 13.U.237.231; 13.U.237.236;
13.U.237.237; 13.U.237.238; 13.U.237.239; 13.U.237.154; 13.U.237.157;
13.U.237.166; 13.U.237.169; 13.U.237.172; 13.U.237.175; 13.U.237.240;
13.U.237.244; 13.U.238.228; 13.U.238.229; 13.U.238.230; 13.U.238.231;
13.U.238.236; 13.U.238.237; 13.U.238.238; 13.U.238.239; 13.U.238.154;
13.U.238.157; 13.U.238.166; 13.U.238.169; 13.U.238.172; 13.U.238.175;
13.U.238.240; 13.U.238.244; 13.U.239.228; 13.U.239.229; 13.U.239.230;
13.U.239.231; 13.U.239.236; 13.U.239.237; 13.U.239.238; 13.U.239.239;
13.U.239.154; 13.U.239.157; 13.U.239.166; 13.U.239.169; 13.U.239.172;
13.U.239.175; 13.U.239.240; 13.U.239.244; 13.U.154.228; 13.U.154.229;
13.U.154.230; 13.U.154.231; 13.U.154.236; 13.U.154.237; 13.U.154.238;
13.U.154.239; 13.U.154.154; 13.U.154.157; 13.U.154.166; 13.U.154.169;
13.U.154.172; 13.U.154.175; 13.U.154.240; 13.U.154.244; 13.U.157.228;
13.U.157.229; 13.U.157.230; 13.U.157.231; 13.U.157.236; 13.U.157.237;
13.U.157.238; 13.U.157.239; 13.U.157.154; 13.U.157.157; 13.U.157.166;
13.U.157.169; 13.U.157.172; 13.U.157.175; 13.U.157.240; 13.U.157.244;
13.U.166.228; 13.U.166.229; 13.U.166.230; 13.U.166.231; 13.U.166.236;
13.U.166.237; 13.U.166.238; 13.U.166.239; 13.U.166.154; 13.U.166.157;
13.U.166.166; 13.U.166.169; 13.U.166.172; 13.U.166.175; 13.U.166.240;
13.U.166.244; 13.U.169.228; 13.U.169.229; 13.U.169.230; 13.U.169.231;
13.U.169.236; 13.U.169.237; 13.U.169.238; 13.U.169.239; 13.U.169.154;
13.U.169.157; 13.U.169.166; 13.U.169.169; 13.U.169.172; 13.U.169.175;
13.U.169.240; 13.U.169.244; 13.U.172.228; 13.U.172.229; 13.U.172.230;
13.U.172.231; 13.U.172.236; 13.U.172.237; 13.U.172.238; 13.U.172.239;
13.U.172.154; 13.U.172.157; 13.U.172.166; 13.U.172.169; 13.U.172.172;
13.U.172.175; 13.U.172.240; 13.U.172.244; 13.U.175.228; 13.U.175.229;
13.U.175.230; 13.U.175.231; 13.U.175.236; 13.U.175.237; 13.U.175.238;
13.U.175.239; 13.U.175.154; 13.U.175.157; 13.U.175.166; 13.U.175.169;
13.U.175.172; 13.U.175.175; 13.U.175.240; 13.U.175.244; 13.U.240.228;
13.U.240.229; 13.U.240.230; 13.U.240.231; 13.U.240.236; 13.U.240.237;
13.U.240.238; 13.U.240.239; 13.U.240.154; 13.U.240.157; 13.U.240.166;
13.U.240.169; 13.U.240.172; 13.U.240.175; 13.U.240.240; 13.U.240.244;
13.U.244.228; 13.U.244.229; 13.U.244.230; 13.U.244.231; 13.U.244.236;
13.U.244.237; 13.U.244.238; 13.U.244.239; 13.U.244.154; 13.U.244.157;
13.U.244.166; 13.U.244.169; 13.U.244.172; 13.U.244.175; 13.U.244.240;
13.U.244.244;

Prodrugs of 13.W

13.W.228.228; 13.W.228.229; 13.W.228.230; 13.W.228.231;
13.W.228.236; 13.W.228.237; 13.W.228.238; 13.W.228.239;
13.W.228.154; 13.W.228.157; 13.W.228.166; 13.W.228.169;
13.W.228.172; 13.W.228.175; 13.W.228.240; 13.W.228.244;
13.W.229.228; 13.W.229.229; 13.W.229.230; 13.W.229.231;
13.W.229.236; 13.W.229.237; 13.W.229.238; 13.W.229.239;
13.W.229.154; 13.W.229.157; 13.W.229.166; 13.W.229.169;
13.W.229.172; 13.W.229.175; 13.W.229.240; 13.W.229.244;
13.W.230.228; 13.W.230.229; 13.W.230.230; 13.W.230.231;
13.W.230.236; 13.W.230.237; 13.W.230.238; 13.W.230.239;
13.W.230.154; 13.W.230.157; 13.W.230.166; 13.W.230.169;
13.W.230.172; 13.W.230.175; 13.W.230.240; 13.W.230.244;
13.W.231.228; 13.W.231.229; 13.W.231.230; 13.W.231.231;
13.W.231.236; 13.W.231.237; 13.W.231.238; 13.W.231.239;
13.W.231.154; 13.W.231.157; 13.W.231.166; 13.W.231.169;
13.W.231.172; 13.W.231.175; 13.W.231.240; 13.W.231.244;
13.W.236.228; 13.W.236.229; 13.W.236.230; 13.W.236.231;
13.W.236.236; 13.W.236.237; 13.W.236.238; 13.W.236.239;
13.W.236.154; 13.W.236.157; 13.W.236.166; 13.W.236.169;
13.W.236.172; 13.W.236.175; 13.W.236.240; 13.W.236.244;
13.W.237.228; 13.W.237.229; 13.W.237.230; 13.W.237.231;
13.W.237.236; 13.W.237.237; 13.W.237.238; 13.W.237.239;
13.W.237.154; 13.W.237.157; 13.W.237.166; 13.W.237.169;
13.W.237.172; 13.W.237.175; 13.W.237.240; 13.W.237.244;
13.W.238.228; 13.W.238.229; 13.W.238.230; 13.W.238.231;
13.W.238.236; 13.W.238.237; 13.W.238.238; 13.W.238.239;
13.W.238.154; 13.W.238.157; 13.W.238.166; 13.W.238.169;
13.W.238.172; 13.W.238.175; 13.W.238.240; 13.W.238.244;
13.W.239.228; 13.W.239.229; 13.W.239.230; 13.W.239.231;
13.W.239.236; 13.W.239.237; 13.W.239.238; 13.W.239.239;
13.W.239.154; 13.W.239.157; 13.W.239.166; 13.W.239.169;
13.W.239.172; 13.W.239.175; 13.W.239.240; 13.W.239.244;
13.W.154.228; 13.W.154.229; 13.W.154.230; 13.W.154.231;
13.W.154.236; 13.W.154.237; 13.W.154.238; 13.W.154.239;
13.W.154.154; 13.W.154.157; 13.W.154.166; 13.W.154.169;
13.W.154.172; 13.W.154.175; 13.W.154.240; 13.W.154.244;
13.W.157.228; 13.W.157.229; 13.W.157.230; 13.W.157.231;
13.W.157.236; 13.W.157.237; 13.W.157.238; 13.W.157.239;
13.W.157.154; 13.W.157.157; 13.W.157.166; 13.W.157.169;
13.W.157.172; 13.W.157.175; 13.W.157.240; 13.W.157.244;
13.W.166.228; 13.W.166.229; 13.W.166.230; 13.W.166.231;
13.W.166.236; 13.W.166.237; 13.W.166.238; 13.W.166.239;
13.W.166.154; 13.W.166.157; 13.W.166.166; 13.W.166.169;
13.W.166.172; 13.W.166.175; 13.W.166.240; 13.W.166.244;
13.W.169.228; 13.W.169.229; 13.W.169.230; 13.W.169.231;
13.W.169.236; 13.W.169.237; 13.W.169.238; 13.W.169.239;
13.W.169.154; 13.W.169.157; 13.W.169.166; 13.W.169.169;
13.W.169.172; 13.W.169.175; 13.W.169.240; 13.W.169.244;

TABLE 7-continued

13.W.172.228; 13.W.172.229; 13.W.172.230; 13.W.172.231;
13.W.172.236; 13.W.172.237; 13.W.172.238; 13.W.172.239;
13.W.172.154; 13.W.172.157; 13.W.172.166; 13.W.172.169;
13.W.172.172; 13.W.172.175; 13.W.172.240; 13.W.172.244;
13.W.175.228; 13.W.175.229; 13.W.175.230; 13.W.175.231;
13.W.175.236; 13.W.175.237; 13.W.175.238; 13.W.175.239;
13.W.175.154; 13.W.175.157; 13.W.175.166; 13.W.175.169;
13.W.175.172; 13.W.175.175; 13.W.175.240; 13.W.175.244;
13.W.240.228; 13.W.240.229; 13.W.240.230; 13.W.240.231;
13.W.240.236; 13.W.240.237; 13.W.240.238; 13.W.240.239;
13.W.240.154; 13.W.240.157; 13.W.240.166; 13.W.240.169;
13.W.240.172; 13.W.240.175; 13.W.240.240; 13.W.240.244;
13.W.244.228; 13.W.244.229; 13.W.244.230; 13.W.244.231;
13.W.244.236; 13.W.244.237; 13.W.244.238; 13.W.244.239;
13.W.244.154; 13.W.244.157; 13.W.244.166; 13.W.244.169;
13.W.244.172; 13.W.244.175; 13.W.244.240; 13.W.244.244;
Prodrugs of 13.Y 13.Y.228.228; 13.Y.228.229; 13.Y.228.230; 13.Y.228.231; 13.Y.228.236;
13.Y.228.237; 13.Y.228.238; 13.Y.228.239; 13.Y.228.154; 13.Y.228.157;
13.Y.228.166; 13.Y.228.169; 13.Y.228.172; 13.Y.228.175; 13.Y.228.240;
13.Y.228.244; 13.Y.229.228; 13.Y.229.229; 13.Y.229.230; 13.Y.229.231;
13.Y.229.236; 13.Y.229.237; 13.Y.229.238; 13.Y.229.239; 13.Y.229.154;
13.Y.229.157; 13.Y.229.166; 13.Y.229.169; 13.Y.229.172; 13.Y.229.175;
13.Y.229.240; 13.Y.229.244; 13.Y.230.228; 13.Y.230.229; 13.Y.230.230;
13.Y.230.231; 13.Y.230.236; 13.Y.230.237; 13.Y.230.238; 13.Y.230.239;
13.Y.230.154; 13.Y.230.157; 13.Y.230.166; 13.Y.230.169; 13.Y.230.172;
13.Y.230.175; 13.Y.230.240; 13.Y.230.244; 13.Y.231.228; 13.Y.231.229;
13.Y.231.230; 13.Y.231.231; 13.Y.231.236; 13.Y.231.237; 13.Y.231.238;
13.Y.231.239; 13.Y.231.154; 13.Y.231.157; 13.Y.231.166; 13.Y.231.169;
13.Y.231.172; 13.Y.231.175; 13.Y.231.240; 13.Y.231.244; 13.Y.236.228;
13.Y.236.229; 13.Y.236.230; 13.Y.236.231; 13.Y.236.236; 13.Y.236.237;
13.Y.236.238; 13.Y.236.239; 13.Y.236.154; 13.Y.236.157; 13.Y.236.166;
13.Y.236.169; 13.Y.236.172; 13.Y.236.175; 13.Y.236.240; 13.Y.236.244;
13.Y.237.228; 13.Y.237.229; 13.Y.237.230; 13.Y.237.231; 13.Y.237.236;
13.Y.237.237; 13.Y.237.238; 13.Y.237.239; 13.Y.237.154; 13.Y.237.157;
13.Y.237.166; 13.Y.237.169; 13.Y.237.172; 13.Y.237.175; 13.Y.237.240;
13.Y.237.244; 13.Y.238.228; 13.Y.238.229; 13.Y.238.230; 13.Y.238.231;
13.Y.238.236; 13.Y.238.237; 13.Y.238.238; 13.Y.238.239; 13.Y.238.154;
13.Y.238.157; 13.Y.238.166; 13.Y.238.169; 13.Y.238.172; 13.Y.238.175;
13.Y.238.240; 13.Y.238.244; 13.Y.239.228; 13.Y.239.229; 13.Y.239.230;
13.Y.239.231; 13.Y.239.236; 13.Y.239.237; 13.Y.239.238; 13.Y.239.239;
13.Y.239.154; 13.Y.239.157; 13.Y.239.166; 13.Y.239.169; 13.Y.239.172;
13.Y.239.175; 13.Y.239.240; 13.Y.239.244; 13.Y.154.228; 13.Y.154.229;
13.Y.154.230; 13.Y.154.231; 13.Y.154.236; 13.Y.154.237; 13.Y.154.238;
13.Y.154.239; 13.Y.154.154; 13.Y.154.157; 13.Y.154.166; 13.Y.154.169;
13.Y.154.172; 13.Y.154.175; 13.Y.154.240; 13.Y.154.244; 13.Y.157.228;
13.Y.157.229; 13.Y.157.230; 13.Y.157.231; 13.Y.157.236; 13.Y.157.237;
13.Y.157.238; 13.Y.157.239; 13.Y.157.154; 13.Y.157.157; 13.Y.157.166;
13.Y.157.169; 13.Y.157.172; 13.Y.157.175; 13.Y.157.240; 13.Y.157.244;
13.Y.166.228; 13.Y.166.229; 13.Y.166.230; 13.Y.166.231; 13.Y.166.236;
13.Y.166.237; 13.Y.166.238; 13.Y.166.239; 13.Y.166.154; 13.Y.166.157;
13.Y.166.166; 13.Y.166.169; 13.Y.166.172; 13.Y.166.175; 13.Y.166.240;
13.Y.166.244; 13.Y.169.228; 13.Y.169.229; 13.Y.169.230; 13.Y.169.231;
13.Y.169.236; 13.Y.169.237; 13.Y.169.238; 13.Y.169.239; 13.Y.169.154;
13.Y.169.157; 13.Y.169.166; 13.Y.169.169; 13.Y.169.172; 13.Y.169.175;
13.Y.169.240; 13.Y.169.244; 13.Y.172.228; 13.Y.172.229; 13.Y.172.230;
13.Y.172.231; 13.Y.172.236; 13.Y.172.237; 13.Y.172.238; 13.Y.172.239;
13.Y.172.154; 13.Y.172.157; 13.Y.172.166; 13.Y.172.169; 13.Y.172.172;
13.Y.172.175; 13.Y.172.240; 13.Y.172.244; 13.Y.175.228; 13.Y.175.229;
13.Y.175.230; 13.Y.175.231; 13.Y.175.236; 13.Y.175.237; 13.Y.175.238;
13.Y.175.239; 13.Y.175.154; 13.Y.175.157; 13.Y.175.166; 13.Y.175.169;
13.Y.175.172; 13.Y.175.175; 13.Y.175.240; 13.Y.175.244; 13.Y.240.228;
13.Y.240.229; 13.Y.240.230; 13.Y.240.231; 13.Y.240.236; 13.Y.240.237;
13.Y.240.238; 13.Y.240.239; 13.Y.240.154; 13.Y.240.157; 13.Y.240.166;
13.Y.240.169; 13.Y.240.172; 13.Y.240.175; 13.Y.240.240; 13.Y.240.244;
13.Y.244.228; 13.Y.244.229; 13.Y.244.230; 13.Y.244.231; 13.Y.244.236;
13.Y.244.237; 13.Y.244.238; 13.Y.244.239; 13.Y.244.154; 13.Y.244.157;
13.Y.244.166; 13.Y.244.169; 13.Y.244.172; 13.Y.244.175; 13.Y.244.240;
13.Y.244.244;
Prodrugs of 14.AH 14.AH.4.157; 14.AH.4.158; 14.AH.4.196; 14.AH.4.223; 14.AH.4.240;
14.AH.4.244; 14.AH.4.243; 14.AH.4.247; 14.AH.5.157; 14.AH.5.158;
14.AH.5.196; 14.AH.5.223; 14.AH.5.240; 14.AH.5.244; 14.AH.5.243;
14.AH.5.247; 14.AH.7.157; 14.AH.7.158; 14.AH.7.196; 14.AH.7.223;
14.AH.7.240; 14.AH.7.244; 14.AH.7.243; 14.AH.7.247; 14.AH.15.157;
14.AH.15.158; 14.AH.15.196; 14.AH.15.223; 14.AH.15.240;
14.AH.15.244; 14.AH.15.243; 14.AH.15.247; 14.AH.16.157;
14.AH.16.158; 14.AH.16.196; 14.AH.16.223; 14.AH.16.240;
14.AH.16.244; 14.AH.16.243; 14.AH.16.247; 14.AH.18.157;
14.AH.18.158; 14.AH.18.196; 14.AH.18.223; 14.AH.18.240;
14.AH.18.244; 14.AH.18.243; 14.AH.18.247; 14.AH.26.157;
14.AH.26.158; 14.AH.26.196; 14.AH.26.223; 14.AH.26.240;
14.AH.26.244; 14.AH.26.243; 14.AH.26.247; 14.AH.27.157;
14.AH.27.158; 14.AH.27.196; 14.AH.27.223; 14.AH.27.240;
14.AH.27.244; 14.AH.27.243; 14.AH.27.247; 14.AH.29.157;
14.AH.29.158; 14.AH.29.196; 14.AH.29.223; 14.AH.29.240;
14.AH.29.244; 14.AH.29.243; 14.AH.29.247; 14.AH.54.157;
14.AH.54.158; 14.AH.54.196; 14.AH.54.223; 14.AH.54.240;
14.AH.54.244; 14.AH.54.243; 14.AH.54.247; 14.AH.55.157;
14.AH.55.158; 14.AH.55.196; 14.AH.55.223; 14.AH.55.240;
14.AH.55.244; 14.AH.55.243; 14.AH.55.247; 14.AH.56.157;
14.AH.56.158; 14.AH.56.196; 14.AH.56.223; 14.AH.56.240;
14.AH.56.244; 14.AH.56.243; 14.AH.56.247; 14.AH.157.157;
14.AH.157.158; 14.AH.157.196; 14.AH.157.223; 14.AH.157.240;
14.AH.157.244; 14.AH.157.243; 14.AH.157.247; 14.AH.196.157;
14.AH.196.158; 14.AH.196.196; 14.AH.196.223; 14.AH.196.240;
14.AH.196.244; 14.AH.196.243; 14.AH.196.247; 14.AH.223.157;
14.AH.223.158; 14.AH.223.196; 14.AH.223.223; 14.AH.223.240;
14.AH.223.244; 14.AH.223.243; 14.AH.223.247; 14.AH.240.157;
14.AH.240.158; 14.AH.240.196; 14.AH.240.223; 14.AH.240.240;
14.AH.240.244; 14.AH.240.243; 14.AH.240.247; 14.AH.244.157;
14.AH.244.158; 14.AH.244.196; 14.AH.244.223; 14.AH.244.240;
14.AH.244.244; 14.AH.244.243; 14.AH.244.247; 14.AH.247.157;
14.AH.247.158; 14.AH.247.196; 14.AH.247.223; 14.AH.247.240;
14.AH.247.244; 14.AH.247.243; 14.AH.247.247;
Prodrugs of 14.AJ 14.AJ.4.157; 14.AJ.4.158; 14.AJ.4.196; 14.AJ.4.223; 14.AJ.4.240;
14.AJ.4.244; 14.AJ.4.243; 14.AJ.4.247; 14.AJ.5.157; 14.AJ.5.158;
14.AJ.5.196; 14.AJ.5.223; 14.AJ.5.240; 14.AJ.5.244; 14.AJ.5.243;
14.AJ.5.247; 14.AJ.7.157; 14.AJ.7.158; 14.AJ.7.196; 14.AJ.7.223;
14.AJ.7.240; 14.AJ.7.244; 14.AJ.7.243; 14.AJ.7.247; 14.AJ.15.157;
14.AJ.15.158; 14.AJ.15.196; 14.AJ.15.223; 14.AJ.15.240; 14.AJ.15.244;
14.AJ.15.243; 14.AJ.15.247; 14.AJ.16.157; 14.AJ.16.158; 14.AJ.16.196;
14.AJ.16.223; 14.AJ.16.240; 14.AJ.16.244; 14.AJ.16.243; 14.AJ.16.247;
14.AJ.18.157; 14.AJ.18.158; 14.AJ.18.196; 14.AJ.18.223; 14.AJ.18.240;
14.AJ.18.244; 14.AJ.18.243; 14.AJ.18.247; 14.AJ.26.157; 14.AJ.26.158;
14.AJ.26.196; 14.AJ.26.223; 14.AJ.26.240; 14.AJ.26.244; 14.AJ.26.243;
14.AJ.26.247; 14.AJ.27.157; 14.AJ.27.158; 14.AJ.27.196; 14.AJ.27.223;
14.AJ.27.240; 14.AJ.27.244; 14.AJ.27.243; 14.AJ.27.247; 14.AJ.29.157;
14.AJ.29.158; 14.AJ.29.196; 14.AJ.29.223; 14.AJ.29.240; 14.AJ.29.244;
14.AJ.29.243; 14.AJ.29.247; 14.AJ.54.157; 14.AJ.54.158; 14.AJ.54.196;
14.AJ.54.223; 14.AJ.54.240; 14.AJ.54.244; 14.AJ.54.243; 14.AJ.54.247;
14.AJ.55.157; 14.AJ.55.158; 14.AJ.55.196; 14.AJ.55.223; 14.AJ.55.240;
14.AJ.55.244; 14.AJ.55.243; 14.AJ.55.247; 14.AJ.56.157; 14.AJ.56.158;
14.AJ.56.196; 14.AJ.56.223; 14.AJ.56.240; 14.AJ.56.244; 14.AJ.56.243;
14.AJ.56.247; 14.AJ.157.157; 14.AJ.157.158; 14.AJ.157.196;
14.AJ.157.223; 14.AJ.157.240; 14.AJ.157.244; 14.AJ.157.243;
14.AJ.157.247; 14.AJ.196.157; 14.AJ.196.158; 14.AJ.196.196;
14.AJ.196.223; 14.AJ.196.240; 14.AJ.196.244; 14.AJ.196.243;
14.AJ.196.247; 14.AJ.223.157; 14.AJ.223.158; 14.AJ.223.196;
14.AJ.223.223; 14.AJ.223.240; 14.AJ.223.244; 14.AJ.223.243;
14.AJ.223.247; 14.AJ.240.157; 14.AJ.240.158; 14.AJ.240.196;
14.AJ.240.223; 14.AJ.240.240; 14.AJ.240.244; 14.AJ.240.243;
14.AJ.240.247; 14.AJ.244.157; 14.AJ.244.158; 14.AJ.244.196;
14.AJ.244.223; 14.AJ.244.240; 14.AJ.244.244; 14.AJ.244.243;
14.AJ.244.247; 14.AJ.247.157; 14.AJ.247.158; 14.AJ.247.196;
14.AJ.247.223; 14.AJ.247.240; 14.AJ.247.244; 14.AJ.247.243;
14.AJ.247.247;
Prodrugs of 14.AN 14.AN.4.157; 14.AN.4.158; 14.AN.4.196; 14.AN.4.223; 14.AN.4.240;
14.AN.4.244; 14.AN.4.243; 14.AN.4.247; 14.AN.5.157; 14.AN.5.158;
14.AN.5.196; 14.AN.5.223; 14.AN.5.240; 14.AN.5.244; 14.AN.5.243;
14.AN.5.247; 14.AN.7.157; 14.AN.7.158; 14.AN.7.196; 14.AN.7.223;
14.AN.7.240; 14.AN.7.244; 14.AN.7.243; 14.AN.7.247; 14.AN.15.157;
14.AN.15.158; 14.AN.15.196; 14.AN.15.223; 14.AN.15.240;
14.AN.15.244; 14.AN.15.243; 14.AN.15.247; 14.AN.16.157;
14.AN.16.158; 14.AN.16.196; 14.AN.16.223; 14.AN.16.240;
14.AN.16.244; 14.AN.16.243; 14.AN.16.247; 14.AN.18.157;
14.AN.18.158; 14.AN.18.196; 14.AN.18.223; 14.AN.18.240;
14.AN.18.244; 14.AN.18.243; 14.AN.18.247; 14.AN.26.157;
14.AN.26.158; 14.AN.26.196; 14.AN.26.223; 14.AN.26.240;
14.AN.26.244; 14.AN.26.243; 14.AN.26.247; 14.AN.27.157;
14.AN.27.158; 14.AN.27.196; 14.AN.27.223; 14.AN.27.240;
14.AN.27.244; 14.AN.27.243; 14.AN.27.247; 14.AN.29.157;

TABLE 7-continued

14.AN.29.158; 14.AN.29.196; 14.AN.29.223; 14.AN.29.240;
14.AN.29.244; 14.AN.29.243; 14.AN.29.247; 14.AN.54.157;
14.AN.54.158; 14.AN.54.196; 14.AN.54.223; 14.AN.54.240;
14.AN.54.244; 14.AN.54.243; 14.AN.54.247; 14.AN.55.157;
14.AN.55.158; 14.AN.55.196; 14.AN.55.223; 14.AN.55.240;
14.AN.55.244; 14.AN.55.243; 14.AN.55.247; 14.AN.56.157;
14.AN.56.158; 14.AN.56.196; 14.AN.56.223; 14.AN.56.240;
14.AN.56.244; 14.AN.56.243; 14.AN.56.247; 14.AN.157.157;
14.AN.157.158; 14.AN.157.196; 14.AN.157.223; 14.AN.157.240;
14.AN.157.244; 14.AN.157.243; 14.AN.157.247; 14.AN.196.157;
14.AN.196.158; 14.AN.196.196; 14.AN.196.223; 14.AN.196.240;
14.AN.196.244; 14.AN.196.243; 14.AN.196.247; 14.AN.223.157;
14.AN.223.158; 14.AN.223.196; 14.AN.223.223; 14.AN.223.240;
14.AN.223.244; 14.AN.223.243; 14.AN.223.247; 14.AN.240.157;
14.AN.240.158; 14.AN.240.196; 14.AN.240.223; 14.AN.240.240;
14.AN.240.244; 14.AN.240.243; 14.AN.240.247; 14.AN.244.157;
14.AN.244.158; 14.AN.244.196; 14.AN.244.223; 14.AN.244.240;
14.AN.244.244; 14.AN.244.243; 14.AN.244.247; 14.AN.247.157;
14.AN.247.158; 14.AN.247.196; 14.AN.247.223; 14.AN.247.240;
14.AN.247.244; 14.AN.247.243; 14.AN.247.247;
Prodrugs of 14.AP 14.AP.4.157; 14.AP.4.158; 14.AP.4.196; 14.AP.4.223; 14.AP.4.240;
14.AP.4.244; 14.AP.4.243; 14.AP.4.247; 14.AP.5.157; 14.AP.5.158;
14.AP.5.196; 14.AP.5.223; 14.AP.5.240; 14.AP.5.244; 14.AP.5.243;
14.AP.5.247; 14.AP.7.157; 14.AP.7.158; 14.AP.7.196; 14.AP.7.223;
14.AP.7.240; 14.AP.7.244; 14.AP.7.243; 14.AP.7.247; 14.AP.15.157;
14.AP.15.158; 14.AP.15.196; 14.AP.15.223; 14.AP.15.240;
14.AP.15.244; 14.AP.15.243; 14.AP.15.247; 14.AP.16.157;
14.AP.16.158; 14.AP.16.196; 14.AP.16.223; 14.AP.16.240;
14.AP.16.244; 14.AP.16.243; 14.AP.16.247; 14.AP.18.157;
14.AP.18.158; 14.AP.18.196; 14.AP.18.223; 14.AP.18.240;
14.AP.18.244; 14.AP.18.243; 14.AP.18.247; 14.AP.26.157;
14.AP.26.158; 14.AP.26.196; 14.AP.26.223; 14.AP.26.240;
14.AP.26.244; 14.AP.26.243; 14.AP.26.247; 14.AP.27.157;
14.AP.27.158; 14.AP.27.196; 14.AP.27.223; 14.AP.27.240;
14.AP.27.244; 14.AP.27.243; 14.AP.27.247; 14.AP.29.157;
14.AP.29.158; 14.AP.29.196; 14.AP.29.223; 14.AP.29.240;
14.AP.29.244; 14.AP.29.243; 14.AP.29.247; 14.AP.54.157;
14.AP.54.158; 14.AP.54.196; 14.AP.54.223; 14.AP.54.240;
14.AP.54.244; 14.AP.54.243; 14.AP.54.247; 14.AP.55.157;
14.AP.55.158; 14.AP.55.196; 14.AP.55.223; 14.AP.55.240;
14.AP.55.244; 14.AP.55.243; 14.AP.55.247; 14.AP.56.157;
14.AP.56.158; 14.AP.56.196; 14.AP.56.223; 14.AP.56.240;
14.AP.56.244; 14.AP.56.243; 14.AP.56.247; 14.AP.157.157;
14.AP.157.158; 14.AP.157.196; 14.AP.157.223; 14.AP.157.240;
14.AP.157.244; 14.AP.157.243; 14.AP.157.247; 14.AP.196.157;
14.AP.196.158; 14.AP.196.196; 14.AP.196.223; 14.AP.196.240;
14.AP.196.244; 14.AP.196.243; 14.AP.196.247; 14.AP.223.157;
14.AP.223.158; 14.AP.223.196; 14.AP.223.223; 14.AP.223.240;
14.AP.223.244; 14.AP.223.243; 14.AP.223.247; 14.AP.240.157;
14.AP.240.158; 14.AP.240.196; 14.AP.240.223; 14.AP.240.240;
14.AP.240.244; 14.AP.240.243; 14.AP.240.247; 14.AP.244.157;
14.AP.244.158; 14.AP.244.196; 14.AP.244.223; 14.AP.244.240;
14.AP.244.244; 14.AP.244.243; 14.AP.244.247; 14.AP.247.157;
14.AP.247.158; 14.AP.247.196; 14.AP.247.223; 14.AP.247.240;
14.AP.247.244; 14.AP.247.243; 14.AP.247.247;
Prodrugs of 14.AZ 14.AZ.4.157; 14.AZ.4.158; 14.AZ.4.196; 14.AZ.4.223; 14.AZ.4.240;
14.AZ.4.244; 14.AZ.4.243; 14.AZ.4.247; 14.AZ.5.157; 14.AZ.5.158;
14.AZ.5.196; 14.AZ.5.223; 14.AZ.5.240; 14.AZ.5.244; 14.AZ.5.243;
14.AZ.5.247; 14.AZ.7.157; 14.AZ.7.158; 14.AZ.7.196; 14.AZ.7.223;
14.AZ.7.240; 14.AZ.7.244; 14.AZ.7.243; 14.AZ.7.247; 14.AZ.15.157;
14.AZ.15.158; 14.AZ.15.196; 14.AZ.15.223; 14.AZ.15.240;
14.AZ.15.244; 14.AZ.15.243; 14.AZ.15.247; 14.AZ.16.157;
14.AZ.16.158; 14.AZ.16.196; 14.AZ.16.223; 14.AZ.16.240;
14.AZ.16.244; 14.AZ.16.243; 14.AZ.16.247; 14.AZ.18.157;
14.AZ.18.158; 14.AZ.18.196; 14.AZ.18.223; 14.AZ.18.240;
14.AZ.18.244; 14.AZ.18.243; 14.AZ.18.247; 14.AZ.26.157;
14.AZ.26.158; 14.AZ.26.196; 14.AZ.26.223; 14.AZ.26.240;
14.AZ.26.244; 14.AZ.26.243; 14.AZ.26.247; 14.AZ.27.157;
14.AZ.27.158; 14.AZ.27.196; 14.AZ.27.223; 14.AZ.27.240;
14.AZ.27.244; 14.AZ.27.243; 14.AZ.27.247; 14.AZ.29.157;
14.AZ.29.158; 14.AZ.29.196; 14.AZ.29.223; 14.AZ.29.240;
14.AZ.29.244; 14.AZ.29.243; 14.AZ.29.247; 14.AZ.54.157;
14.AZ.54.158; 14.AZ.54.196; 14.AZ.54.223; 14.AZ.54.240;
14.AZ.54.244; 14.AZ.54.243; 14.AZ.54.247; 14.AZ.55.157;
14.AZ.55.158; 14.AZ.55.196; 14.AZ.55.223; 14.AZ.55.240;
14.AZ.55.244; 14.AZ.55.243; 14.AZ.55.247; 14.AZ.56.157;
14.AZ.56.158; 14.AZ.56.196; 14.AZ.56.223; 14.AZ.56.240;
14.AZ.56.244; 14.AZ.56.243; 14.AZ.56.247; 14.AZ.157.157;
14.AZ.157.158; 14.AZ.157.196; 14.AZ.157.223; 14.AZ.157.240;
14.AZ.157.244; 14.AZ.157.243; 14.AZ.157.247; 14.AZ.196.157;
14.AZ.196.158; 14.AZ.196.196; 14.AZ.196.223; 14.AZ.196.240;
14.AZ.196.244; 14.AZ.196.243; 14.AZ.196.247; 14.AZ.223.157;
14.AZ.223.158; 14.AZ.223.196; 14.AZ.223.223; 14.AZ.223.240;
14.AZ.223.244; 14.AZ.223.243; 14.AZ.223.247; 14.AZ.240.157;
14.AZ.240.158; 14.AZ.240.196; 14.AZ.240.223; 14.AZ.240.240;
14.AZ.240.244; 14.AZ.240.243; 14.AZ.240.247; 14.AZ.244.157;
14.AZ.244.158; 14.AZ.244.196; 14.AZ.244.223; 14.AZ.244.240;
14.AZ.244.244; 14.AZ.244.243; 14.AZ.244.247; 14.AZ.247.157;
14.AZ.247.158; 14.AZ.247.196; 14.AZ.247.223; 14.AZ.247.240;
14.AZ.247.244; 14.AZ.247.243; 14.AZ.247.247;
Prodrugs of 14.BF 14.BF.4.157; 14.BF.4.158; 14.BF.4.196; 14.BF.4.223; 14.BF.4.240;
14.BF.4.244; 14.BF.4.243; 14.BF.4.247; 14.BF.5.157; 14.BF.5.158;
14.BF.5.196; 14.BF.5.223; 14.BF.5.240; 14.BF.5.244; 14.BF.5.243;
14.BF.5.247; 14.BF.7.157; 14.BF.7.158; 14.BF.7.196; 14.BF.7.223;
14.BF.7.240; 14.BF.7.244; 14.BF.7.243; 14.BF.7.247; 14.BF.15.157;
14.BF.15.158; 14.BF.15.196; 14.BF.15.223; 14.BF.15.240; 14.BF.15.244;
14.BF.15.243; 14.BF.15.247; 14.BF.16.157; 14.BF.16.158; 14.BF.16.196;
14.BF.16.223; 14.BF.16.240; 14.BF.16.244; 14.BF.16.243; 14.BF.16.247;
14.BF.18.157; 14.BF.18.158; 14.BF.18.196; 14.BF.18.223; 14.BF.18.240;
14.BF.18.244; 14.BF.18.243; 14.BF.18.247; 14.BF.26.157; 14.BF.26.158;
14.BF.26.196; 14.BF.26.223; 14.BF.26.240; 14.BF.26.244; 14.BF.26.243;
14.BF.26.247; 14.BF.27.157; 14.BF.27.158; 14.BF.27.196; 14.BF.27.223;
14.BF.27.240; 14.BF.27.244; 14.BF.27.243; 14.BF.27.247; 14.BF.29.157;
14.BF.29.158; 14.BF.29.196; 14.BF.29.223; 14.BF.29.240; 14.BF.29.244;
14.BF.29.243; 14.BF.29.247; 14.BF.54.157; 14.BF.54.158; 14.BF.54.196;
14.BF.54.223; 14.BF.54.240; 14.BF.54.244; 14.BF.54.243; 14.BF.54.247;
14.BF.55.157; 14.BF.55.158; 14.BF.55.196; 14.BF.55.223; 14.BF.55.240;
14.BF.55.244; 14.BF.55.243; 14.BF.55.247; 14.BF.56.157; 14.BF.56.158;
14.BF.56.196; 14.BF.56.223; 14.BF.56.240; 14.BF.56.244; 14.BF.56.243;
14.BF.56.247; 14.BF.157.157; 14.BF.157.158; 14.BF.157.196;
14.BF.157.223; 14.BF.157.240; 14.BF.157.244; 14.BF.157.243;
14.BF.157.247; 14.BF.196.157; 14.BF.196.158; 14.BF.196.196;
14.BF.196.223; 14.BF.196.240; 14.BF.196.244; 14.BF.196.243;
14.BF.196.247; 14.BF.223.157; 14.BF.223.158; 14.BF.223.196;
14.BF.223.223; 14.BF.223.240; 14.BF.223.244; 14.BF.223.243;
14.BF.223.247; 14.BF.240.157; 14.BF.240.158; 14.BF.240.196;
14.BF.240.223; 14.BF.240.240; 14.BF.240.244; 14.BF.240.243;
14.BF.240.247; 14.BF.244.157; 14.BF.244.158; 14.BF.244.196;
14.BF.244.223; 14.BF.244.240; 14.BF.244.244; 14.BF.244.243;
14.BF.244.247; 14.BF.247.157; 14.BF.247.158; 14.BF.247.196;
14.BF.247.223; 14.BF.247.240; 14.BF.247.244; 14.BF.247.243;
14.BF.247.247;
Prodrugs of 14.CI 14.CI.4.157; 14.CI.4.158; 14.CI.4.196; 14.CI.4.223; 14.CI.4.240;
14.CI.4.244; 14.CI.4.243; 14.CI.4.247; 14.CI.5.157; 14.CI.5.158;
14.CI.5.196; 14.CI.5.223; 14.CI.5.240; 14.CI.5.244; 14.CI.5.243;
14.CI.5.247; 14.CI.7.157; 14.CI.7.158; 14.CI.7.196; 14.CI.7.223;
14.CI.7.240; 14.CI.7.244; 14.CI.7.243; 14.CI.7.247; 14.CI.15.157;
14.CI.15.158; 14.CI.15.196; 14.CI.15.223; 14.CI.15.240; 14.CI.15.244;
14.CI.15.243; 14.CI.15.247; 14.CI.16.157; 14.CI.16.158; 14.CI.16.196;
14.CI.16.223; 14.CI.16.240; 14.CI.16.244; 14.CI.16.243; 14.CI.16.247;
14.CI.18.157; 14.CI.18.158; 14.CI.18.196; 14.CI.18.223; 14.CI.18.240;
14.CI.18.244; 14.CI.18.243; 14.CI.18.247; 14.CI.26.157; 14.CI.26.158;
14.CI.26.196; 14.CI.26.223; 14.CI.26.240; 14.CI.26.244; 14.CI.26.243;
14.CI.26.247; 14.CI.27.157; 14.CI.27.158; 14.CI.27.196; 14.CI.27.223;
14.CI.27.240; 14.CI.27.244; 14.CI.27.243; 14.CI.27.247; 14.CI.29.157;
14.CI.29.158; 14.CI.29.196; 14.CI.29.223; 14.CI.29.240; 14.CI.29.244;
14.CI.29.243; 14.CI.29.247; 14.CI.54.157; 14.CI.54.158; 14.CI.54.196;
14.CI.54.223; 14.CI.54.240; 14.CI.54.244; 14.CI.54.243; 14.CI.54.247;
14.CI.55.157; 14.CI.55.158; 14.CI.55.196; 14.CI.55.223; 14.CI.55.240;
14.CI.55.244; 14.CI.55.243; 14.CI.55.247; 14.CI.56.157; 14.CI.56.158;
14.CI.56.196; 14.CI.56.223; 14.CI.56.240; 14.CI.56.244; 14.CI.56.243;
14.CI.56.247; 14.CI.157.157; 14.CI.157.158; 14.CI.157.196;
14.CI.157.223; 14.CI.157.240; 14.CI.157.244; 14.CI.157.243;
14.CI.157.247; 14.CI.196.157; 14.CI.196.158; 14.CI.196.196;
14.CI.196.223; 14.CI.196.240; 14.CI.196.244; 14.CI.196.243;
14.CI.196.247; 14.CI.223.157; 14.CI.223.158; 14.CI.223.196;
14.CI.223.223; 14.CI.223.240; 14.CI.223.244; 14.CI.223.243;
14.CI.223.247; 14.CI.240.157; 14.CI.240.158; 14.CI.240.196;
14.CI.240.223; 14.CI.240.240; 14.CI.240.244; 14.CI.240.243;
14.CI.240.247; 14.CI.244.157; 14.CI.244.158; 14.CI.244.196;

TABLE 7-continued

14.CI.244.223; 14.CI.244.240; 14.CI.244.244; 14.CI.244.243;
14.CI.244.247; 14.CI.247.157; 14.CI.247.158; 14.CI.247.196;
14.CI.247.223; 14.CI.247.240; 14.CI.247.244; 14.CI.247.243;
14.CI.247.247;
Prodrugs of 14.CO 14.CO.4.157; 14.CO.4.158; 14.CO.4.196; 14.CO.4.223; 14.CO.4.240;
14.CO.4.244; 14.CO.4.243; 14.CO.4.247; 14.CO.5.157; 14.CO.5.158;
14.CO.5.196; 14.CO.5.223; 14.CO.5.240; 14.CO.5.244; 14.CO.5.243;
14.CO.5.247; 14.CO.7.157; 14.CO.7.158; 14.CO.7.196; 14.CO.7.223;
14.CO.7.240; 14.CO.7.244; 14.CO.7.243; 14.CO.7.247; 14.CO.15.157;
14.CO.15.158; 14.CO.15.196; 14.CO.15.223; 14.CO.15.240;
14.CO.15.244; 14.CO.15.243; 14.CO.15.247; 14.CO.16.157;
14.CO.16.158; 14.CO.16.196; 14.CO.16.223; 14.CO.16.240;
14.CO.16.244; 14.CO.16.243; 14.CO.16.247; 14.CO.18.157;
14.CO.18.158; 14.CO.18.196; 14.CO.18.223; 14.CO.18.240;
14.CO.18.244; 14.CO.18.243; 14.CO.18.247; 14.CO.26.157;
14.CO.26.158; 14.CO.26.196; 14.CO.26.223; 14.CO.26.240;
14.CO.26.244; 14.CO.26.243; 14.CO.26.247; 14.CO.27.157;
14.CO.27.158; 14.CO.27.196; 14.CO.27.223; 14.CO.27.240;
14.CO.27.244; 14.CO.27.243; 14.CO.27.247; 14.CO.29.157;
14.CO.29.158; 14.CO.29.196; 14.CO.29.223; 14.CO.29.240;
14.CO.29.244; 14.CO.29.243; 14.CO.29.247; 14.CO.54.157;
14.CO.54.158; 14.CO.54.196; 14.CO.54.223; 14.CO.54.240;
14.CO.54.244; 14.CO.54.243; 14.CO.54.247; 14.CO.55.157;
14.CO.55.158; 14.CO.55.196; 14.CO.55.223; 14.CO.55.240;
14.CO.55.244; 14.CO.55.243; 14.CO.55.247; 14.CO.56.157;
14.CO.56.158; 14.CO.56.196; 14.CO.56.223; 14.CO.56.240;
14.CO.56.244; 14.CO.56.243; 14.CO.56.247; 14.CO.157.157;
14.CO.157.158; 14.CO.157.196; 14.CO.157.223; 14.CO.157.240;
14.CO.157.244; 14.CO.157.243; 14.CO.157.247; 14.CO.196.157;
14.CO.196.158; 14.CO.196.196; 14.CO.196.223; 14.CO.196.240;
14.CO.196.244; 14.CO.196.243; 14.CO.196.247; 14.CO.223.157;
14.CO.223.158; 14.CO.223.196; 14.CO.223.223; 14.CO.223.240;
14.CO.223.244; 14.CO.223.243; 14.CO.223.247; 14.CO.240.157;
14.CO.240.158; 14.CO.240.196; 14.CO.240.223; 14.CO.240.240;
14.CO.240.244; 14.CO.240.243; 14.CO.240.247; 14.CO.244.157;
14.CO.244.158; 14.CO.244.196; 14.CO.244.223; 14.CO.244.240;
14.CO.244.244; 14.CO.244.243; 14.CO.244.247; 14.CO.4.157;
14.CO.4.158; 14.CO.4.196; 14.CO.4.223; 14.CO.4.240; 14.CO.4.244;
14.CO.4.243; 14.CO.4.247;

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the Handbook of Pharmaceutical Excipients (1986), herein incorporated by reference in its entirety. Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations of the invention, both for veterinary and for human use, comprise at least one active ingredient, as defined above, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.), herein incorporated by reference in its entirety. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth herein, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned herein. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 µm (including particle sizes in a range between 0.1 and 500 µm in increments such as 0.5 µm, 1 µm, 30 µm, 35 µm, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of infections as described herein.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can also be formulated to provide controlled release of the active ingredient to allow less frequent dosing or to improve the pharmacokinetic or toxicity profile of the active ingredient. Accordingly, the invention also provided compositions comprising one or more compounds of the invention formulated for sustained or controlled release.

The effective dose of an active ingredient depends at least on the nature of the condition being treated, toxicity, whether the compound is being used prophylactically (lower doses) or against an active disease or condition, the method of delivery, and the pharmaceutical formulation, and will be determined by the clinician using conventional dose escalation studies. The effective dose can be expected to be from about 0.0001 to about 100 mg/kg body weight per day. Typically, from about 0.01 to about 10 mg/kg body weight per day. More typically, from about 0.01 to about 5 mg/kg body weight per day. More typically, from about 0.05 to about 0.5 mg/kg body weight per day. For example, the daily candidate dose for an adult human of approximately 70 kg body weight will range from 1 mg to 1000 mg, or between 5 mg and 500 mg, and may take the form of single or multiple doses.

In another embodiment, the present application provides a pharmaceutical composition comprising a therapeutically effective amount of a compound of the present invention, or a pharmaceutically acceptable salt, solvate, and/or ester thereof, and a pharmaceutically acceptable carrier.

In another embodiment, the present application provides a pharmaceutical composition comprising a therapeutically effective amount of a compound of the present invention, or a pharmaceutically acceptable salt, solvate, and/or ester thereof, in combination with at least one additional active therapeutic agent and a pharmaceutically acceptable carrier.

In another embodiment, the present application provides a pharmaceutical composition comprising a therapeutically effective amount of a compound of the present invention, or a pharmaceutically acceptable salt, solvate, and/or ester thereof, in combination with at least one additional active therapeutic agent and a pharmaceutically acceptable carrier; wherein said at least one additional active therapeutic agent is selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, entry inhibitors, gp120 inhibitors, G6PD and NADH-oxidase inhibitors, CCR5 inhibitors, other drugs for treating HIV, and mixtures thereof.

In another embodiment, the present application provides a pharmaceutical composition comprising a therapeutically effective amount of a compound of the present invention, or a pharmaceutically acceptable salt, solvate, and/or ester thereof, in combination with at least one additional active therapeutic agent and a pharmaceutically acceptable carrier; wherein said at least one additional active therapeutic agent is selected from the group consisting of (1) HIV protease inhibitors are selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, RO0334649, KNI-272, DPC-681, DPC-684, GW640385X, DG17, PPL-100, DG35, and AG 1859; (2) HIV non-nucleoside inhibitors of reverse transcriptase are selected from the group consisting of capravirine, emivirine, delaviridine, efavirenz, nevirapine, (+) calanolide A, etravirine, GW5634, DPC-083, DPC-961, DPC-963, MIV-150, TMC-120, TMC-278 (rilpivirene), efavirenz, BILR355 BS, VRX 840773, UK-453061, and RDEA806; (3) HIV nucleoside inhibitors of reverse transcriptase are selected from the group consisting of zidovudine, emtricitabine, didanosine, stavudine, zalcitabine, lamivudine, abacavir, amdoxovir, elvucitabine, alovudine, MIV-210, racivir (±-FTC), D-d4FC, emtricitabine, phosphazide, fozivudine tidoxil, apricitibine (AVX754), GS-7340, amdoxovir, KP-1461, and fosalvudine tidoxil (formerly HDP 99.0003); (4) HIV nucleotide inhibitors of reverse transcriptase are selected from the group consisting of tenofovir and adefovir; (5) HIV integrase inhibitors are selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), elvitegravir, L-870812, and L-870810, MK-0518 (raltegravir), BMS-538158, GSK364735C, BMS-707035, MK-2048, and BA 011; (6) gp41 inhibitor are selected from the group consisting of enfuvirtide, sifuvirtide, FB006M, and TRI-1144; (7) CXCR4 inhibitor is AMD-070; (8) entry inhibitor is SP01A; (9) gp120 inhibitor is BMS-488043 or BlockAide/CR; (10) G6PD and NADH-oxidase inhibitor is immunitin; (11) CCR5 inhibitors are selected from the group consisting of aplaviroc, vicriviroc, maraviroc, PRO-140, INCB15050, PF-232798 (Pfizer), and CCR5 mAb004; and (12) other drugs for treating HIV are selected from the group consisting of BAS-100, SPI-452, REP 9, SP-01A, TNX-355, DES6, ODN-93, ODN-112, VGV-1, PA-457 (bevirimat), Ampligen, HRG214, Cytolin, VGX-410, KD-247, AMZ 0026, CYT 99007A-221 HIV, DEBIO-025, BAY 50-4798, MDX010 (ipilimumab), PBS 119, ALG 889, and PA-1050040 (PA-040).

In another embodiment, the present application provides a combination pharmaceutical product or kit comprising: a first pharmaceutical composition comprising a compound of the present invention, or a pharmaceutically acceptable salt, solvate, or ester thereof; and a second pharmaceutical composition comprising at least one additional active agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, entry inhibitors, gp120 inhibitors, G6PD and NADH-oxidase inhibitors, CCR5 inhibitors, other drugs for treating HIV, and mixtures thereof.

In another embodiment, suitable combinations include combinations of one or more compounds of the present invention with one or more HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, entry inhibitors, gp120 inhibitors, G6PD and NADH-oxidase inhibitors, CCR5 inhibitors, other drugs for treating HIV, and mixtures thereof.

In another embodiment, one or more compounds of the present invention may be combined with one or more compounds selected from the group consisting of (1) HIV protease inhibitors are selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, RO0334649, KNI-272, DPC-681, DPC-684, GW640385X, DG17, PPL-100, DG35, and AG 1859; (2) HIV non-nucleoside inhibitors of reverse transcriptase are selected from the group consisting of capravirine, emivirine, delaviridine, efavirenz, nevirapine, (+)calanolide A, etravirine, GW5634, DPC-083, DPC-961, DPC-963, MIV-150, TMC-120, TMC-278 (rilpivirene), efavirenz, BILR355 BS, VRX 840773, UK-453061, and RDEA806; (3) HIV nucleoside inhibitors of reverse transcriptase are selected from the group consisting of zidovudine, emtricitabine, didanosine, stavudine, zalcitabine, lamivudine, abacavir, amdoxovir, elvucitabine, alovudine, MIV-210, racivir (±-FTC), D-d4FC, emtricitabine, phosphazide, fozivudine tidoxil, apricitibine (AVX754), GS-7340, amdoxovir, KP-1461, and fosalvudine tidoxil (formerly HDP 99.0003); (4) HIV nucleotide inhibitors of reverse transcriptase are selected from the group consisting of tenofovir and adefovir; (5) HIV integrase inhibitors are selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), elvitegravir, L-870812, and L-870810, MK-0518 (raltegravir), BMS-538158, GSK364735C, BMS-707035, MK-2048, and BA 011; (6) gp41 inhibitor are selected from the group consisting of enfuvirtide, sifuvirtide, FB006M, and TRI-1144; (7) CXCR4 inhibitor is AMD-070; (8) entry inhibitor is SP01A; (9) gp120 inhibitor is BMS-488043 or BlockAide/CR; (10) G6PD and NADH-oxidase inhibitor is immunitin; (11) CCR5 inhibitors are selected from the group consisting of aplaviroc, vicriviroc, maraviroc, PRO-140, INCB15050, PF-232798 (Pfizer), and CCR5 mAb004; and (12) other drugs for treating HIV are selected from the group consisting of BAS-100, SPI-452, REP 9, SP-01A, TNX-355, DES6, ODN-93, ODN-112, VGV-1, PA-457 (bevirimat), Ampligen, HRG214, Cytolin, VGX-410, KD-247, AMZ 0026, CYT 99007A-221 HIV, DEBIO-025, BAY 50-4798, MDX010 (ipilimumab), PBS 119, ALG 889, and PA-1050040 (PA-040).

In yet another embodiment, the present application provides for use of one or more compounds of the present invention, or pharmaceutically acceptable salts, solvates, and/or esters thereof, in the preparation of a medicament for the treatment of HIV and/or HCV.

In yet another embodiment, the present application provides for use of one or more compounds of the present invention, or pharmaceutically acceptable salts, solvates, and/or esters thereof, in combination with one or more HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, entry inhibitors, gp120 inhibitors, G6PD and NADH-oxidase inhibitors, CCR5 inhibitors, other drugs for treating HIV, and mixtures thereof.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy

In one embodiment, the compounds of the present invention can be administered alone, e.g., without other active therapeutic in ingredients or agents. In another embodiment, the compounds of the present invention are used in combination with other active therapeutic ingredients or agents. Preferably, the other active therapeutic ingredients or agents are HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, entry inhibitors, gp120 inhibitors, G6PD and NADH-oxidase inhibitors, CCR5 inhibitors, other drugs for treating HIV, and mixtures thereof.

Combinations of the compounds of the present invention are typically selected based on the condition to be treated, cross-reactivities of ingredients and pharmaco-properties of the combination. For example, when treating and infection (e.g., HIV or HCV), the compositions of the invention are combined with active agents (such as those described herein).

Non-limiting examples of suitable active agents suitable for combining with the compounds of the present invention include HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, entry inhibitors, gp120 inhibitors, G6PD and NADH-oxidase inhibitors, CCR5 inhibitors, other drugs for treating HIV, and mixtures thereof.

More specifically, one or more compounds of the present invention may be combined with one or more compounds selected from the group consisting of
(1) HIV protease inhibitors are selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, RO0334649, KNI-272, DPC-681, DPC-684, GW640385X, DG17, PPL-100, DG35, and AG 1859; (2) HIV non-nucleoside inhibitors of reverse transcriptase are selected from the group consisting of capravirine, emivirine, delaviridine, efavirenz, nevirapine, (+) calanolide A, etravirine, GW5634, DPC-083, DPC-961, DPC-963, MIV-150, TMC-120, TMC-278 (rilpivirene), efavirenz, BILR355 BS, VRX 840773, UK-453061, and RDEA806; (3) HIV nucleoside inhibitors of reverse transcriptase are selected from the group consisting of zidovudine, emtricitabine, didanosine, stavudine, zalcitabine, lamivudine, abacavir, amdoxovir, elvucitabine, alovudine, MIV-210, racivir (±-FTC), D-d4FC, emtricitabine, phosphazide, fozivudine tidoxil, apricitibine (AVX754), GS-7340, amdoxovir, KP-1461, and fosalvudine tidoxil (formerly HDP 99.0003); (4) HIV nucleotide inhibitors of reverse transcriptase are selected from the group consisting of tenofovir and adefovir; (5) HIV integrase inhibitors are selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), elvitegravir, L-870812, and L-870810, MK-0518 (raltegravir), BMS-538158, GSK364735C, BMS-707035, MK-2048, and BA 011; (6) gp41 inhibitor are selected from the group consisting of enfuvirtide, sifuvirtide, FB006M, and TRI-1144; (7) CXCR4 inhibitor is AMD-070; (8) entry inhibitor is SP01A; (9) gp120 inhibitor is BMS-488043 or BlockAide/CR; (10) G6PD and NADH-oxidase inhibitor is immunitin; (11) CCR5 inhibitors are selected from the group consisting of aplaviroc, vicriviroc, maraviroc, PRO-140, INCB15050, PF-232798 (Pfizer), and CCR5 mAb004; and (12) other drugs for treating HIV are selected from the group consisting of BAS-100, SPI-452, REP 9, SP-01A, TNX-355, DES6, ODN-93, ODN-112, VGV-1, PA-457 (bevirimat), Ampligen, HRG214, Cytolin, VGX-410, KD-247, AMZ 0026, CYT 99007A-221 HIV, DEBIO-025, BAY 50-4798, MDX010 (ipilimumab), PBS 119, ALG 889, and PA-1050040 (PA-040).

It is also possible to combine any compound of the invention with one or more other active therapeutic agents in a unitary dosage form for simultaneous or sequential administration to a patient. The combination therapy may be administered as a simultaneous or sequential regimen. When administered sequentially, the combination may be administered in two or more administrations.

Co-administration of a compound of the invention with one or more other active therapeutic agents generally refers to simultaneous or sequential administration of a compound of the invention and one or more other active therapeutic agents, such that therapeutically effective amounts of the compound of the invention and one or more other active therapeutic agents are both present in the body of the patient.

Co-administration includes administration of unit dosages of the compounds of the invention before or after administration of unit dosages of one or more other active therapeutic agents, for example, administration of the compounds of the invention within seconds, minutes, or hours of the administration of one or more other active therapeutic agents. For example, a unit dose of a compound of the invention can be administered first, followed within seconds or minutes by administration of a unit dose of one or more other active therapeutic agents. Alternatively, a unit dose of one or more other therapeutic agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound of the invention.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

In another embodiment, the present invention provides a method for inhibiting HIV protease comprising administering a therapeutically effective amount of a compound of the present invention, or a pharmaceutically acceptable salt, solvate, or ester thereof, to a patient in need of such treatment.

In another embodiment, the present invention provides a method for inhibiting HIV protease, further comprising co-administering a therapeutic amount of at least one additional active agent selected from the group consisting of one or more HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, entry inhibitors, gp120 inhibitors, G6PD and NADH-oxidase inhibitors, CCR5 inhibitors, other drugs for treating HIV, and mixtures thereof.

In another embodiment, the present invention provides a method for treating AIDS or AIDS Related Complex comprising administering a therapeutically effective amount of a compound of the present invention, or a pharmaceutically acceptable salt, solvate, and/or ester thereof, to a patient in need of such treatment.

In another embodiment, the present invention provides a method for treating AIDS or AIDS Related Complex comprising co-administering a therapeutically effective amount of a compound of the present invention, or a pharmaceutically acceptable salt, solvate, and/or ester thereof and a therapeutic amount of at least one additional active agent selected from the group consisting of one or more HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, entry inhibitors, gp120 inhibitors, G6PD and NADH-oxidase inhibitors, CCR5 inhibitors, other drugs for treating HIV, and mixtures thereof.

In another embodiment, the present invention provides a method of inhibiting the replication of a retrovirus comprising contacting said retrovirus with a compound of the present invention, or a pharmaceutically acceptable salt, solvate, and/or ester thereof.

In another embodiment, the present invention provides a method of inhibiting the replication of a retrovirus comprising contacting said retrovirus with a compound of the present invention, or a pharmaceutically acceptable salt, solvate, and/or ester thereof and at least one additional active agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, entry inhibitors, gp120 inhibitors, G6PD and NADH-oxidase inhibitors, CCR5 inhibitors, other drugs for treating HIV, and mixtures thereof.

EXAMPLES

Preparation of Examples A, B, C, D, E, and F

Scheme 1

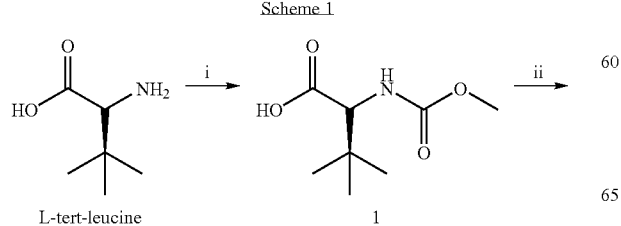

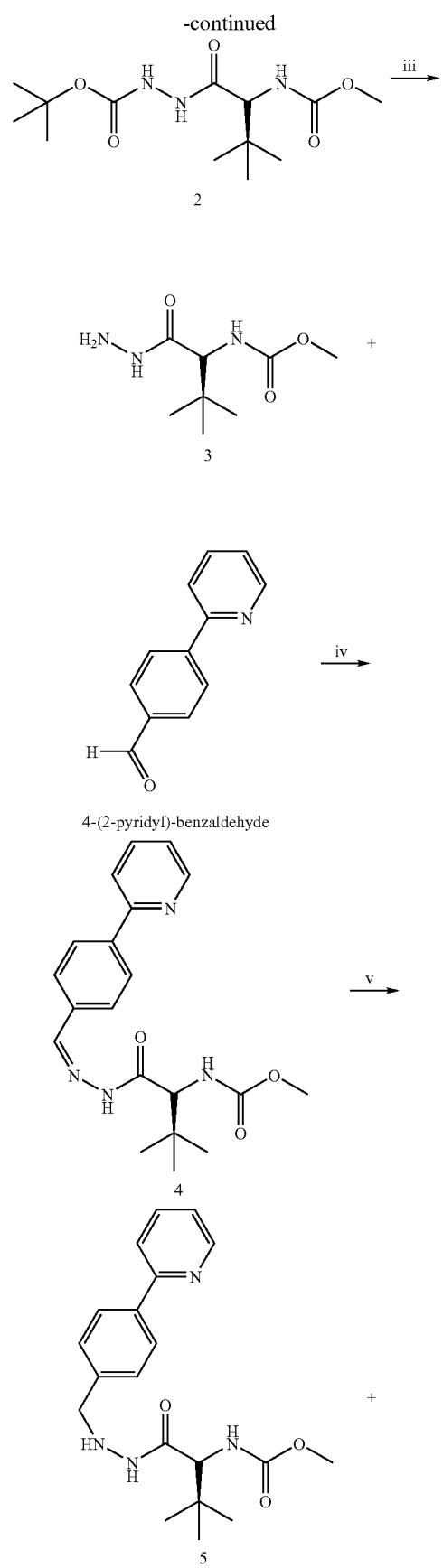

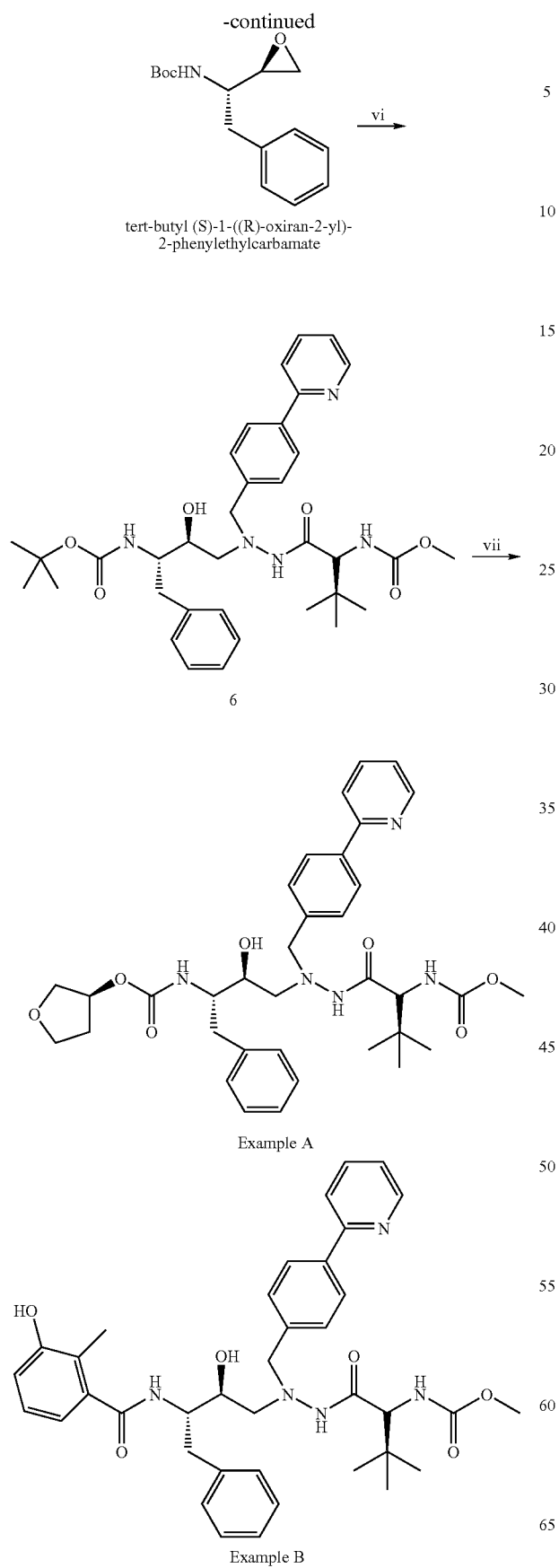
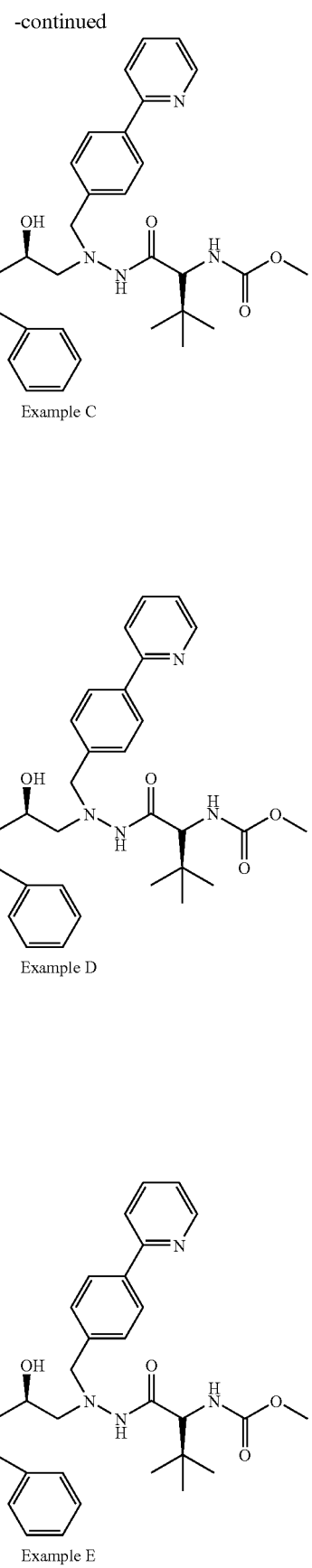

-continued

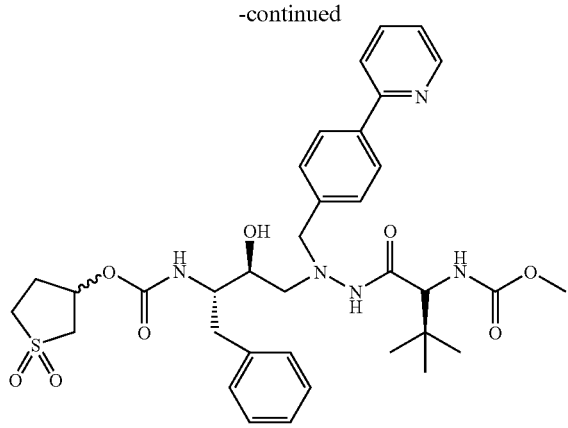

Example F

Reagents and Conditions: i. NaOH, diaxane, methyl chloroformate, 60° C.; ii. EDC, HOBT, NMM, EtoAc, t-butyl carbazate; iii. HCl/dioxane; iv. i-PrOH, 80° C.; v. a. NaCNBH$_3$, THF, p-TsOH; b. H$_2$O, THF, Na$_2$B$_4$O$_7$; vi. i-PrOH, 80° C.; vii. a. TFA, DCM; b. DMAP, DIPEA, (R)-4-nitrophenyl tetrahydrofuran-3-yl carbonate, CH$_3$CN.

Compound 1

L-tert-leucine (12.251 g, 93.4 mmol) was dissolved in a mixture of NaOH (2N, 154 mL) and dioxane (50.5 mL). Methyl chloroformate (14.30 mL, 185.84 mmol) was added slowly (e.g., dropwise) to the solution at room temperature ("r.t."). The resulting reaction mixture was heated to 60° C. and stirred for 20 hours ("h"). The reaction mixture was cooled to r.t. and washed with dichloromethane ("DCM.") The aqueous layer was acidified to pH 2 using concentrated HCl. The aqueous layer was then extracted with ethyl acetate, and the combined organic layers were dried over Na$_2$SO$_4$, and concentrated. The resulting oil was crystallized from hexane to give Compound 1 as a white solid (13.354 g, 70.6 mmol, 76%). TLC R$_f$ (silica gel 60 plate, methanol/DCM, 1:19)= 0.78.

Compound 2

EDC (1-(3-dimethylaminopropyl)-3-ethylcarbodiimide hydrochloride) (13.530 g, 77.6 mmol), HOBT (N-hydroxybenzotriazole) (10.805 g, 77.6 mmol), and 4-methylmorpholine (9.3 mL 84.7 mmol) were added to a solution of Compound 1 (13.354 g, 70.6 mmol) in ethyl acetate (177 mL) and the resulting reaction mixture was stirred at r.t. for 45 min. Then, DMF ("dimethyl formamide") (6 mL) was added followed by tert-butyl carbazate (9.328 g, 77.6 mmol). The reaction mixture was stirred for 18 h and then was diluted with ethyl acetate. The diluted solution was washed with saturated aqueous NaHCO$_3$ solution, water, and brine, sequentially. The combined aqueous layers were extracted with ethyl acetate and the combined organic layers were dried over Na$_2$SO$_4$ and concentrated to give Compound 2 as a white solid (21.417 g, 70.6 mmol, 100%). TLC R$_f$ silica gel 60 plate, ethyl acetate/hexane, 1:1, ninhydrin stain)=0.50.

Compound 3

Compound 2 (21.417 g, 70.6 mmol) in a solution of 4M HCl in dioxane (180 mL) was stirred at r.t. for 2 h. The reaction solution was diluted with saturated aqueous NaHCO$_3$ solution and brought to pH 9 using concentrated NaOH solution. The reaction mixture was extracted four times with DCM and twice with THF ("tetrahydrofuran").

The combined organic layers were dried over Na$_2$SO$_4$ and concentrated to give Compound 3 as an off white solid (14.349 g, 70.6 mmol, 100%). TLC R$_f$ (silica gel 60 plate, ethyl acetate/hexane, 1:1, ninhydrin stain)=0.96.

Compound 4

Compound 3 (14.349 g, 70.6 mmol) and 4-(2-pyridyl)-benzaldehyde (9.960 g, 0.77) were dissolved in isopropanol (214 mL) and the solution was heated to 80° C. and stirred for 24 h. The product was precipitated out of the solution by addition of ice, then was filtered and dried under vacuum at 50° C. to give Compound 4 as an off-white solid (20.043 g, 70.6 mmol, 100%). Mass spectrum: (M+H)$^+$=369.2.

Compound 5

Sodium cyanoborohydride (4.147 g, 66.0 mmol) and Compound 4 (20.043 g, 54.4 mmol) were dissolved in THF (100 mL) and cooled to 0° C. A solution of p-toluenesulfonic acid (12.205 g, 64.2 mmol) in THF (100 mL) was added dropwise. The reaction mixture was warmed to r.t. and stirred for 22 h before it was diluted with H$_2$O and extracted three times with ethyl acetate. The organic layer was washed with saturated aqueous NaHCO$_3$ solution and brine, and then concentrated. The remaining residue was dissolved in a mixture of THF (180 mL) and H$_2$O (180 mL). Na$_2$B$_4$O$_7$ (51.952 g) was added and the resulting reaction mixture was stirred at r.t. for 16 h. The reaction was diluted with ethyl acetate and washed with saturated aqueous NaHCO$_3$ solution. The aqueous layer was extracted three times with ethyl acetate and the combined organic layers were dried over Na$_2$SO$_4$ and concentrated. Purification on silica gel (30-100% ethyl acetate/hexane) yielded Compound 5 (12.173 g, 32.9 mmol, 60%). Mass spectrum: (M+H)$^+$=371.1.

Compound 6

Tert-butyl (S)-1-((R)-oxiran-2-yl)-2-phenylethylcarbamate (177.0 mg, 0.7 mmol), purchased from Kaneka Corporation and Compound 5 (248.2 mg, 0.7 mmol) were dissolved in isopropanol. The solution was heated to 80° C. and stirred for 18 h. Then the reaction mixture was cooled to r.t., concentrated, and purified using silica gel chromatography (ethyl acetate/hexane, 30-50%) to give Compound 6 (75.4 mg, 0.12 mmol, 18%). TLC R$_f$ (silica gel 60 plate, ethyl acetate/hexane, 1:1)=0.83. Mass spectrum: (M+Na)$^+$=656.2.

Example A

TFA ("trifluoroacetic acid") (1.82 mL) was added to Compound 6 (69.1 mg, 0.11 mmol) in DCM (5.5 mL) and the mixture was stirred at r.t. for 1.5 h. The solution was concentrated and co-evaporated three times with DCM and three times with acetonitrile. The resulting residue was dissolved in anhydrous acetonitrile (1.8 mL) and cooled to 0° C. DMAP ("dimethylaminopyridine") (1.3 mg, 0.011 mmol) was added followed by diisopropylethylamine ("DIPEA") (160 µL, 0.92 mmol) until the solution reached pH 9. (R)-4-nitrophenyl tetrahydrofuran-3-yl carbonate (27.6 mg, 0.11 mmol) was added. The reaction mixture was stirred for 2 h at 0° C. and for 16 h at r.t. The reaction mixture was concentrated and purified by reverse phase HPLC (Phenomenex Synergi® column, 25-100% acetonitrile/H$_2$O+0.1% TFA) to give Example A (6.8 mg, 0.009 mmol, 8%). $^1$H NMR (300 MHz, CD$_3$OD): δ 8.73 (d, j=6.0 Hz, 1H), 8.48 (m, 1H), 8.24 (d, j=7.5 Hz, 1H), 7.84 (m, 3H), 7.67 (d, j=8.1 Hz, 2H), 7.10-7.21 (m, 5H), 4.95

(m, 1H), 3.40-4.15 (m, 10H), 3.54 (s, 3H), 2.70-2.90 (m, 5H), 0.68 (s, 9H). Mass spectrum: (M+Na)$^+$=670.3.

Example B

TFA (1.0 mL) was added to a solution of Compound 6 (120.0 mg, 0.19 mmol) in DCM (3.0 mL) and the mixture was stirred at r.t. for 1.5 h. The solution was concentrated and co-evaporated three times with DCM and three times with acetonitrile. In a separate flask, a solution of 3-hydroxy-2-methyl benzoic acid (15 mg, 0.1 mmol) and EDC (39.9 mg, 0.21 mmol), HOBT (31.9 mg, 0.21 mmol), and 4-methylmorpholine (145 μL, 1.32 mmol) in DMF (2.6 mL) was stirred for 45 minutes ("min"). The residue from the first flask was dissolved in DMF (2.4 mL) and added to the second flask after the allotted stirring time. The resulting mixture was stirred at r.t. for 24 h. The reaction solution was diluted with ethyl acetate, washed with saturated aqueous NaHCO$_3$ solution and brine. The combined aqueous layers were extracted with ethyl acetate and the combined organic layers were dried over Na$_2$SO$_4$ and concentrated. The resulting residue was purified by reverse phase HPLC (Phenomenex Synergi® column, 25-100% acetonitrile/H$_2$O+0.1% TFA) to give Example B as a white solid (30.9 mg; 0.040 mmol, 21%). $^1$H NMR (300 MHz, CD$_3$OD): δ 8.73 (d, j=5.1 Hz, 1H), 8.48 (m, 1H), 8.22 (d, j=8.1 Hz), 7.88 (m, 1H), 7.81 (d, j=8.4 Hz, 2H), 7.68 (d, J=8.1 Hz, 2H), 7.10-7.20 (m, 5H), 6.83 (m, 1H) 6.66 (d, J=8.1 Hz, 1H), 6.42 (d, J=7.2 Hz), 4.40 (m, 1H), 4.06 (s, 2H), 3.84 (m, 1H), 3.68 (m, 1H), 3.55 (s, 3H), 2.80-3.00 (m, 4H), 1.80 (s, 3H), 0.75 (s, 9H). Mass spectrum: (M+H)$^+$=668.2.

Scheme 2

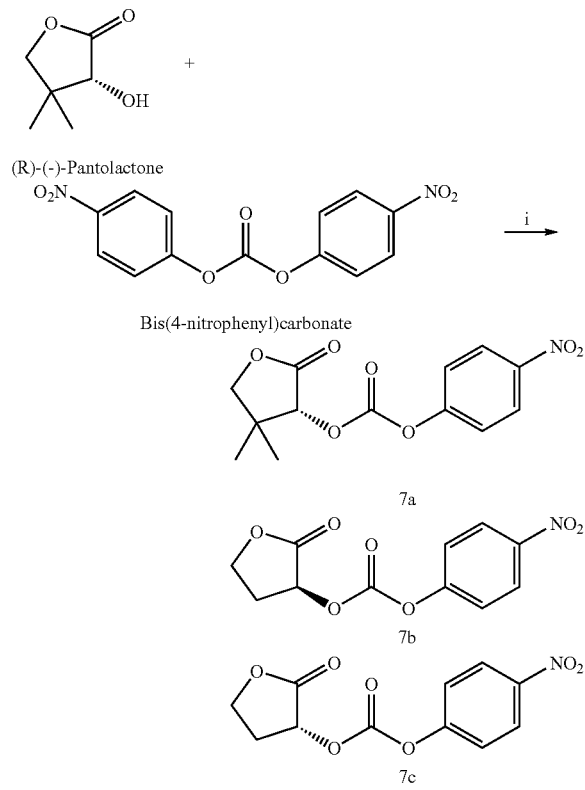

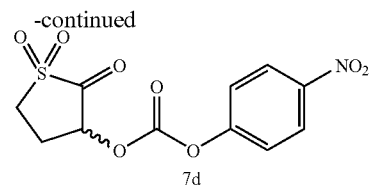

Reagents and Conditions: i. TEA, DCM

Compound 7a

TEA ("triethylamine") (4.3 mL, 30.6 mmol) was added to a solution of (R)-(−)-Pantolactone (1.991 g, 15.3 mmol), purchased from Aldrich, and bis(4-nitrophenyl)carbonate in DCM (77 mL) and the reaction was stirred at r.t. for 2 h. The reaction mixture was concentrated and then diluted with ethyl acetate, washed four times with an aqueous NaOH solution (1N), once with a solution of saturated NaHCO$_3$, and once with brine before it was dried over Na$_2$SO$_4$ and concentrated. The crude residue was purified using silica gel chromatography (10-30% ethyl acetate in hexane) to give Compound 7a (3.83 g, 12.4 mmol, 81%). Mass spectrum: (M+H)$^+$=310.9.

Compound 7b

Compound 7b (1.080 g, 4.04 mmol, 41%) was prepared from (S)-(−)-alpha-hydroxy-gamma-butyrolactone, purchased from Aldrich, using procedures similar to those used to prepare Compound 7a.

Compound 7c

Compound 7c (715 mg, 2.68 mmol, 26%) was prepared from (R)-(+)-alpha-hydroxy-gamma-butyrolactone, purchased from Aldrich, using procedures similar to those used to prepare Compound 7a.

Compound 7d

Compound 7d was prepared from 3-hydroxysulfolane (available from Maybridge) using procedures similar to those used to prepare Compound 7a.

Example C

Example C was prepared from Compound 6 using procedures similar to those used to prepare Example A, except that Compound 7a was used instead of (R)-4-nitrophenyl tetrahydrofuran-3-yl carbonate. The product formed a precipitate which was filtered off and dried under vacuum to give Example C as a white solid (46.5 mg, 0.067 mmol, 50%). $^1$H NMR (300 MHz, CD$_3$OD): δ 8.54 (d, J=4.5 Hz, 1H), 7.75-7.90 (m, 4H), 7.50 (d, J=5.4 Hz, 2H), 7.30 (m, 1H), 7.05-7.25 (m, 5H), 5.12 (s, 1H), 3.85-4.15 (m, 3H), 3.78 (m, 1H), 3.64 (s, 1H), 3.55 (s, 3H), 2.75-3.05 (m, 4H), 0.92 (d, J=4.5 Hz, 6H), 0.65 (s, 9H). Mass spectrum: (M+H)$^+$=690.2

Example D

Example D (27.7 mg, 0.036 mmol, 29%) was prepared from Compound 6 using procedures similar to those used to prepare Example A, except that Compound 7b was used instead of (R)-4-nitrophenyl tetrahydrofuran-3-yl carbonate. $^1$H NMR (300 MHz, CD$_3$OD): δ 8.72 (d, J=5.7 Hz, 1H), 8.42 (m, 1H), 8.21 (d, J=8.1 Hz), 7.87 (m, 3H), 7.71 (d, J=8.4 Hz, 2H), 7.10-7.30 (m, 5H), 4.79 (m, 1H), 4.39 (m, 1H), 4.05-4.25 (m, 3H), 3.66 (s, 1H), 3.58 (s, 3H), 2.85-3.55 (m, 8H), 0.71 (s, 9H). Mass spectrum: (M+H)$^+$=662.2, (M+Na)$^+$=684.3.

Example E

Example E (36.4 mg, 0.047 mmol, 38%) was prepared from Compound 6 using procedures similar to those used to prepare Example A, except that Compound 7c was used instead of (R)-4-nitrophenyl tetrahydrofuran-3-yl carbonate. $^1$H NMR (300 MHz, CD$_3$OD): δ 7.76 (d, J=6.0 Hz, 1H), 8.57 (m, 1H), 8.29 (d, J=8.1 Hz, 1H), 7.93 (m, 1H), 7.86 (d, J=8.4 Hz, 2H), 7.74 (d, J=8.4 Hz, 2H), 7.10-7.30 (m, 5H), 4.69 (m, 1H), 4.36 (m, 1H), 4.05-4.25 (m, 3H), 3.65 (s, 1H), 3.59 (s, 3H), 2.85-3.30 (m, 8H), 0.71 (s, 9H). Mass spectrum: (M+H)$^+$= 662.2, (M+Na)$^+$=684.2

Example F

Example F (177.5 mg, 0.22 mmol, 65%) was prepared from Compound 6 using procedures similar to those used to prepare Example A, except that Compound 7d was used instead of (R)-4-nitrophenyl tetrahydrofuran-3-yl carbonate. $^1$H NMR (300 MHz, CD$_3$OD): δ 8.71 (m, 1H), 8.41 (m, 1H), 8.19 (m, 1H), 7.67-7.86 (m, 3H), 7.60-7.65 (m, 2H), 7.05-7.24 (m, 5H), 5.17 (m, 1H), 3.65-4.15 (m, 4H), 3.63 (m, 1H), 3.55 (m, 3H), 2.70-3.35 (m, 8H), 2.20-2.30 (m, 2H), 0.70 (m, 9H). Mass spectrum: (M+H)$^+$=696.2, (M+Na)$^+$=718.2.

Preparation of Examples G and H

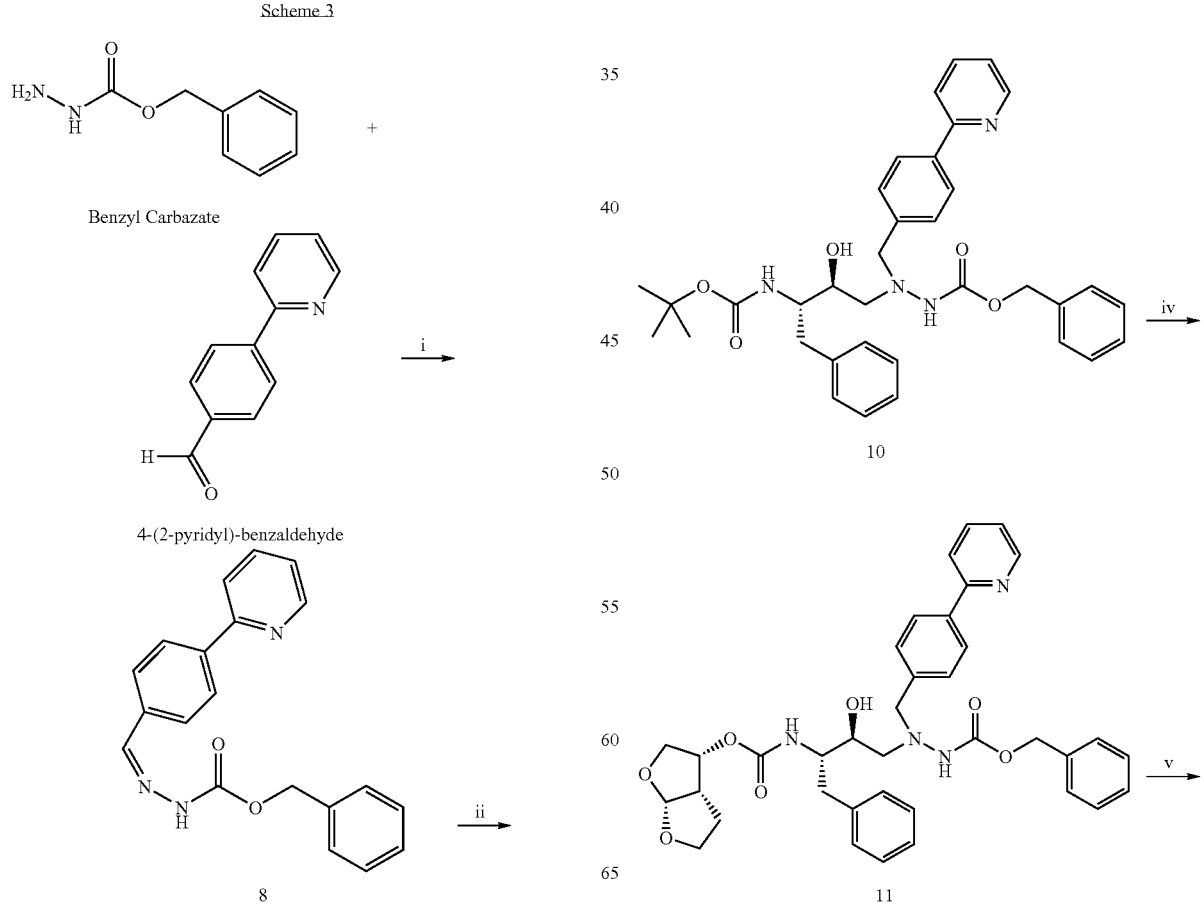

301

-continued

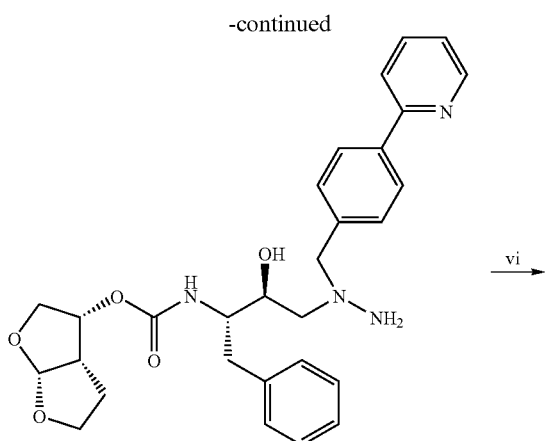

Example G

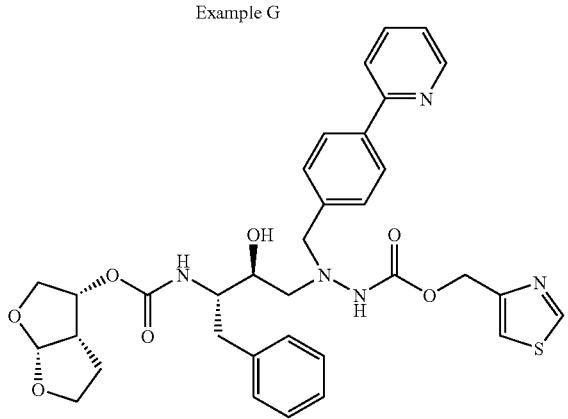

Example H

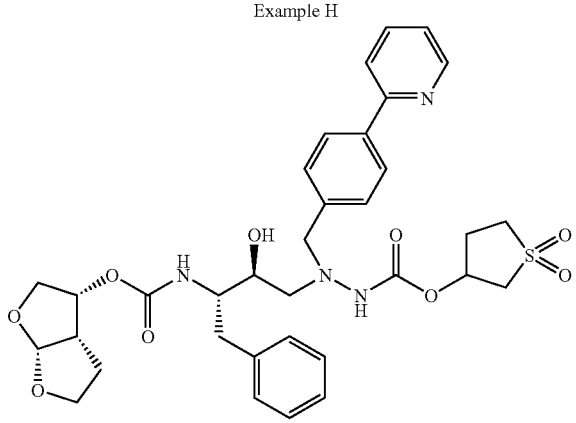

Example I

Reagents and conditions: i. i-PrOH, 80° C.; ii. a. NaCNBH$_3$, THF, p-TsOH; b. H$_2$O, THF, Na$_2$B$_4$O$_7$; iii. i-PrOH, 80° C.; iv. a. TFA, DCM; b. DMAP, DIPEA, 4-nitrophenyl (3R,3aS,6aR)-tetrahydro-2H-furo[2,3-b]furan-3-yl carbonate, CH$_3$CN; v. Pd/C, H$_2$, MeOH, i-PrOH; vi. DMAP, DIPEA, 4-nitrophenyl thiazol-4-ylmethyl carbonate, CH$_3$CN.

Compound 8

Benzyl carbazate (17.3195 g, 104.2 mmol) and 4-(2-pyridyl)benzaldehyde (20.047 g, 109.4 mmol) were dissolved in isopropanol (315 mL) and stirred at 80° C. for 16 h. The product, i.e., Compound 8, was precipitated out of solution by addition of ice, filtered and dried under vacuum at 40° C. to give a solid (34.529 g, 104.2 mmol, 100%). Mass spectrum: (M+H)$^+$=332.1.

302

Compound 9

Sodium cyanoborohydride (3.894 g, 62.0 mmol) and Compound 8 (19.555 g, 59.0 mmol) were dissolved in THF (100 mL) and cooled to 0° C. A solution of p-toluenesulfonic acid (11.449 g, 60.2 mmol) in THF (100 mL) was added dropwise. The resulting reaction mixture was warmed to r.t. and stirred for 22 h before it was diluted with H$_2$O and extracted three times with ethyl acetate. The combined organic layers were washed with saturated NaHCO$_3$ and brine, and then concentrated. The remaining residue was dissolved in THF (200 mL) and H$_2$O (200 mL) followed by the addition of Na$_2$B$_4$O$_7$ (43.840 g) and the reaction mixture was stirred at r.t. for 16 h. The reaction mixture was diluted with ethyl acetate and washed with saturated NaHCO$_3$. The aqueous layer was extracted three times with ethyl acetate and the combined organic layers were washed with saturated NaHCO$_3$, dried over Na$_2$SO$_4$ and concentrated. Purification using silica gel chromatography (30-60% ethyl acetate/hexane) yielded Compound 9 as a solid (16.975 g, 50.9 mmol, 86%). Mass spectrum: (M+H)$^+$=334.1.

Compound 10

Compound 9 (248.2 mg, 0.7 mmol) and tert-butyl (S)-1-((R)-oxiran-2-yl)-2-phenylethylcarbamate purchased from Kaneka Corporation (177.0 mg, 0.7 mmol) were dissolved in isopropanol and heated to 80° C. The reaction mixture was stirred for 27 h before it was cooled to r.t. and concentrated. The resulting solid was crystallized in hexane and purified using silica gel chromatography (20-50% ethyl acetate/hexane) to give Compound 10 as a yellow solid (18.815 g, 31.5 mmol, 68%). Mass spectrum: (M+H)$^+$=597.1.

Compound 11

TFA (27.0 mL) was added to a solution of Compound 10 (20.063 g, 27.6 mmol) in DCM (125 mL) and the resulting mixture was stirred at r.t. for 3 h. The solution was then concentrated and co-evaporated three times with DCM and three times with acetonitrile. The resulting residue was dissolved in anhydrous acetonitrile (125 mL) and cooled to 0° C. DMAP (342 mg, 2.8 mmol) was added followed by DIPEA (37.0 mL, 212 mmol) until pH 9 was reached. Then, 4-nitrophenyl (3R,3aS,6aR)-tetrahydro-2H-furo[2,3-b]furan-3-yl carbonate, prepared according to Miller et al Bioorg. Med. Chem. Lett. 2005, 15, 3496-3500, (6.90 g, 27.6 mmol) was added. The reaction was stirred for 2 h at 0° C. and for 16 h at r.t. The reaction was concentrated and dissolved in ethyl acetate. The organic layer was washed three times with H$_2$O, three times with NaOH (1N), and once with brine before it was dried over Na$_2$SO$_4$ and concentrated. Crystallization in ethyl acetate gave Compound 11 as a solid (9.631 g, 54%). Mass spectrum: (M+H)$^+$=653.1.

Example G

Methanol (59 mL) at 60° C. was used to dissolve Compound 11 (526.3 mg, 0.8 mmol). Isopropanol (50 mL) was added and the reaction mixture was cooled to r.t. The reaction flask was purged with hydrogen gas three times after the addition of 10% palladium on carbon (200 mg) and the flask was stirred under hydrogen at room temperature for 2 h. The catalyst was filtered off and the filtrate was concentrated. The resulting residue was purified by reverse phase HPLC (Phenomenex Synergi® column, 25-100% acetonitrile/H$_2$O) and yielded Example G as a solid (14.2 mg, 0.09 mmol, 11%). $^1$H NMR (300 MHz, CD$_3$OD): δ b 8.56 (d, J=4.8 Hz, 1H), 7.80-7.89 (m, 4H), 7.45 (d, J=8.1 Hz, 2H), 7.32 (m, 1H), 7.05-7.205 (m, 5H), 5.53 (d, J=5.4 Hz, 1H), 4.91 (m, 1H), 3.55-3.95 (m, 8H), 2.50-2.90 (m, 5H), 1.46 (m, 2H). Mass spectrum: (M+H)$^+$=519.1, (M+Na)$^+$=541.2.

Example H

Anhydrous acetonitrile (1.5 mL) was used to dissolve Example G (49.1 mg, 0.07 mmol) and then the solution was cooled to 0° C. DMAP (0.9 mg, 0.007 mmol) was added followed by DIPEA (42 μL, 0.24 mmol). Then, 4-nitrophenyl thiazol-4-ylmethyl carbonate, prepared according to Kempf et al in EP486948A2, (28.4 mg, 0.10 mmol) was added. The reaction mixture was stirred at 0° C. for 2 h, and then at r.t. for 18 h. The reaction mixture was diluted with ethyl acetate and washed three times with H$_2$O, three times with NaOH (1N), and once with brine before it was dried over Na$_2$SO$_4$ and concentrated. Purification by reverse phase HPLC (Phenomenex Synergi® column, 25-100% acetonitrile/H$_2$O+0.1% TFA) yielded Example H a solid (12.2 mg, 0.02 mmol, 26%). $^1$H NMR (300 MHz, CD$_3$OD): δ 8.90 (s, 1H), 8.76 (d, J=6.0 Hz, 1H), 8.54 (m, 1H), 8.31 (m, 1H), 7.84-7.93 (m, 3H), 7.67 (d, J=8.1 Hz, 2H), 7.10-7.35 (m, 6H), 5.53 (d, J=5.1 Hz, 1H), 5.06 (s, 2H), 4.00 (m, 2H), 3.55-3.90 (m, 5H), 2.70-2.95 (m, 5H), 1.40-1.60 (m, 2H). Mass spectrum: (M+H)$^+$=660.1, (M+Na)$^+$=682.3.

Example I

Example I (15.2 mg, 0.02 mmol, 22%) was prepared from Example G using a procedure similar to that used to prepare Example H, except that Compound 7d was used instead of 4-nitrophenyl thiazol-4-ylmethyl carbonate. $^1$H NMR (300 MHz, CD$_3$OD): δ 8.72 (d, J=5.7 Hz, 1H), 8.43 (m, 1H), 8.24 (m, 1H), 7.81-7.92 (m, 3H), 7.58-7.66 (m, 2H), 7.12-7.24 (m, 5H), 5.54 (m, 1H), 5.20 (m, 1H), 4.92 (m, 1H), 3.63-4.08 (m, 8H), 2.77-3.61 (m, 9H), 2.15-2.35 (m, 2H), 1.54 (m, 2H). Mass spectrum: (M+H)$^+$=681.1, (M+Na)$^+$=703.2.

Preparation of Examples J, K, L, and M

Scheme 4

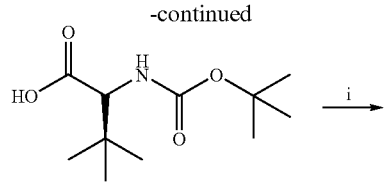

Boc-L-tert-leucine

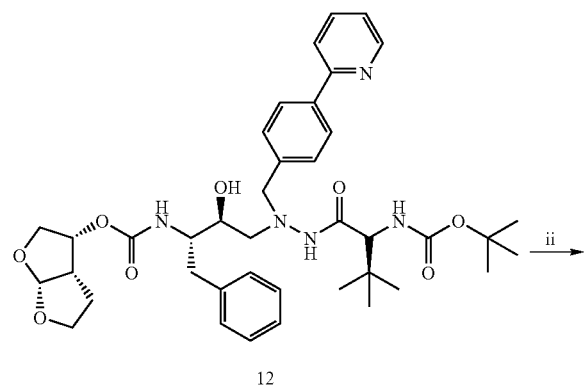

12

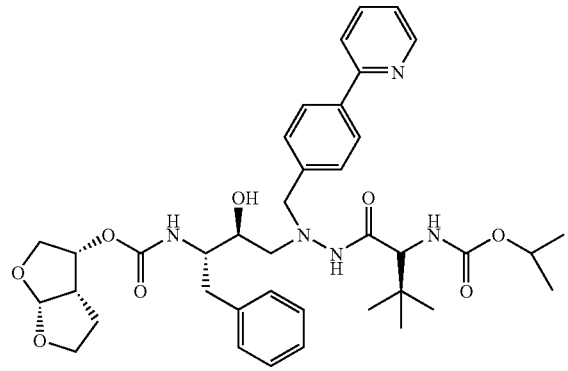

Example J

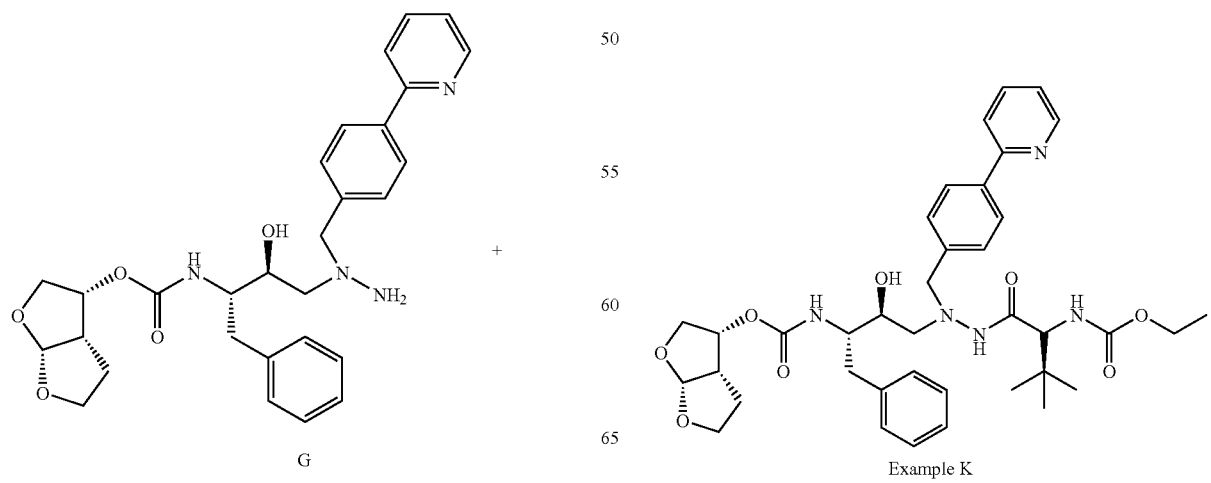

G

Example K

-continued

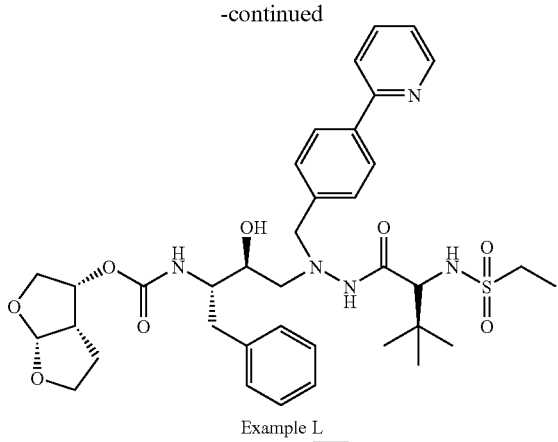

Example L

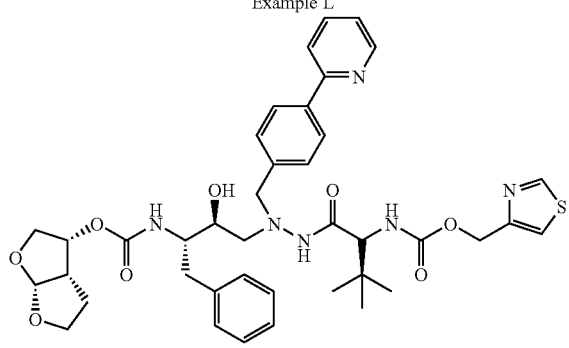

Example M

Reagents and Conditions: i. DMF, TPTU, NMM; ii. a. TFA, DCM; b. H₂O, isopropylchloroformate/toluene, NaHCO₃.

Compound 12

To a solution of Boc-L-tert-leucine, purchased from Acros (360.6 mg, 1.56 mmol) in DMF (3 mL) at r.t. was added TPTU (O-(1,2-dihydro-2-oxo-1-pyridyl)-N,N,N',N'-tetramethyluroniumtetrafluoroborate) (463.1 mg, 1.56 mmol), and the reaction mixture was stirred for 20 min. A solution of Example G (404.3 mg, 0.78 mmol) in DMF (4 mL) was added to the reaction mixture followed by 4-methylmorpholine (0.26 mL, 2.34 mmol). The reaction was stirred at r.t. for 1 h and then diluted with H₂O and extracted three times with DCM. The combined organic layers were dried over Na₂SO₄, and concentrated. Purification by reverse phase HPLC (Phenomenex Synergi® column, 25-100% acetonitrile/H₂O) yielded Compound 12 as a solid (95.0 mg, 0.13 mmol, 17%). Mass spectrum: (M+H)⁺=732.2, (M+Na)⁺=754.3.

Example J

TFA (0.1 mL) was added to a solution of Compound 12 (20 mg, 0.028 mmol) in DCM (1.0 mL) and the reaction was stirred at r.t. for 1.5 h. The reaction mixture was concentrated followed by the addition of H₂O (0.5 mL) and isopropyl chloroformate (35.7 µL, 0.0357 mmol) in toluene. The reaction solution was stirred vigorously while saturated aqueous NaHCO₃ solution was added dropwise until pH 8 was reached. The reaction was stirred at r.t. for 2 h before it was diluted with ethyl acetate and washed with brine and H₂O. The organic layer was dried over Na₂SO₄ and concentrated. The crude residue was purified by reverse phase HPLC (Phenomenex Synergi® column, 25-100% acetonitrile/H₂O+ 0.1% TFA) to yield Example J as a solid (17.6 mg, 0.02 mmol, 77%). $^1$H NMR (300 MHz, CD₃OD): δ 8.73 (d, J=5.7 Hz, 1H), 8.47 (m, 1H), 8.25 (d, J=7.8 Hz, 1H), 7.87 (m, 3H), 7.69 (d, J=8.4 Hz, 2H), 7.11-7.21 (m, 5H), 5.53 (d, J=5.4 Hz, 1H), 4.86 (m, 1H), 3.61-4.09 (m, 10H), 2.78-2.85 (m, 5H), 1.47 (m, 2H), 1.11-1.17 (m, 6H), 0.69 (s, 9H). Mass spectrum: (M+H)⁺=718.3, (M+Na)⁺=740.3.

Example K

Example K (11.5 mg, 0.014 mmol, 68%) was prepared from Compound 12 using procedure similar to those used to prepare Example J, except that ethyl chloroformate was used instead of isopropyl chloroformate. $^1$H NMR (300 MHz, CD₃OD): δ 8.74 (d, J=4.8 Hz, 1H), 8.49 (m, 1H), 8.26 (d, J=8.1 Hz, 1H), 7.84-7.91 (m, 3H), 7.69 (d, J=8.4 Hz, 2H), 7.11-7.21 (m, 5H), 5.53 (d, J=5.1 Hz, 1H), 4.88 (m, 1H), 3.58-4.08 (m, 11H), 2.78-2.89 (m, 5H), 1.49 (m, 2H), 1.14 (t, J=7.1 Hz, 3H), 0.70 (s, 9H). Mass spectrum: (M+H)⁺=704.3, (M+Na)⁺=726.3.

Example L

TFA (0.1 mL) was added to a solution of Compound 12 (15.4 mg, 0.021 mmol) in DCM (1.0 mL) and the reaction mixture was stirred at r.t. for 1.5 h. The reaction mixture was concentrated and the residue was dissolved in DCM (1.0 mL). DIPEA (38 µL, 0.22 mmol) was added followed by ethanesulfonyl chloride (3.0 µL, 0.032 mmol) and the reaction mixture was stirred at r.t. for 2 h. The reaction mixture was concentrated and the crude residue was purified by reverse phase HPLC (Phenomenex Synergi® column, 25-100% acetonitrile/H₂O+0.1% TFA) and yielded Example L as a solid (1.7 mg, 0.002 mmol, 10%). $^1$H NMR (300 MHz, CD₃OD): δ 8.70 (d, J=5.4 Hz, 1H), 8.36 (m, 1H), 8.16 (d, J=7.8 Hz, 1H), 7.87 (d, J=8.4 Hz, 2H), 7.67-7.77 (m, 3H), 7.12-7.21 (m, 5H), 5.53 (d, J=5.4 Hz, 1H), 4.87 (m, 1H), 3.57-4.07 (m, 9H), 3.36 (s, 1H), 2.74-2.91 (m, 5H), 1.49 (m, 2H), 1.16 (t, J=7.2 Hz, 3H), 0.76 (s, 9H). Mass spectrum: (M+H)⁺=724.2.

Example M

TFA (0.1 mL) was added to a solution of Compound 12 (30.8 mg, 0.042 mmol) in DCM (1.0 mL) and the reaction mixture was stirred at r.t. for 1 h. The reaction mixture was concentrated and co-evaporated three times with DCM and three times with acetonitrile. The resulting residue was dissolved in anhydrous acetonitrile and the reaction flask was cooled to 0° C. DMAP (0.5 mg, 0.005 mmol) was added followed by DIPEA (66 µL, 0.38 mmol). Addition of 4-nitrophenyl thiazol-4-ylmethyl carbonate (6.90 g, 27.6 mmol) followed. The reaction mixture was stirred for 2 h at 0° C. and for 21 h at r.t. The reaction mixture was diluted with ethyl acetate. The organic layer was washed three times with H₂O, three times with NaOH (1N), and once with brine before it was dried over Na₂SO₄ and concentrated. The residue was purified by reverse phase HPLC (25-100% acetonitrile/H₂O+ 0.1% TFA) and yielded Example M as a solid (19.2 mg, 0.02 mmol, 52%). $^1$H NMR (300 MHz, CD₃OD): δ 8.90 (s, 1H), 8.72 (d, J=5.7 Hz, 1H), 8.46 (m, 1H), 8.23 (d, J=8.1 Hz, 1H), 7.85 (m, 3H), 7.68 (d, J=8.4 Hz, 2H), 7.12-7.20 (m, 5H), 5.53

(d, J=5.4 Hz, 1H), 5.12 (s, 2H), 4.89 (m, 1H), 3.63-4.84 (m, 9H), 2.74-2.85 (m, 5H), 1.48 (m, 2H), 0.70 (s, 9H). Mass spectrum: (M+H)$^+$=773.2.

Preparation of Example N

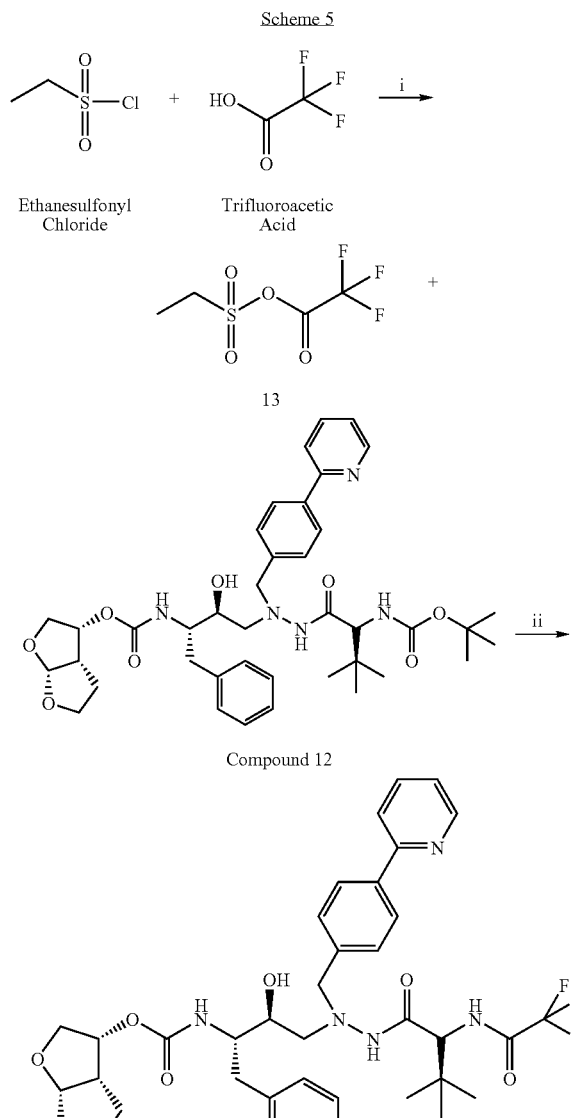

Example N

Reagents and Conditions: i. a. TFA, DCM; ii. DIPEA, DCM, ethanesulfonyl chloride;

Example N

The in-situ generated Compound 13 reacted with Compound 12, and the reaction yielded Example N as a solid (11.4 mg, 0.013 mmol, 64%) after purification by reversed phase HPLC-(Phenomenex Synergi® column, 25-100% acetonitrile/water with 0.1% TFA. $^1$H NMR (300 MHz, CD$_3$OD): δ 8.74 (d, J=5.7 Hz, 1H), 8.47 (m, 1H), 8.24 (d, J=7.8 Hz, 1H), 7.87 (m, 3H), 7.68 (d, J=8.4 Hz, 2H), 7.13-7.21 (m, 5H), 5.54 (d, J=8.4 Hz, 1H), 4.89 (m, 1H), 3.59-4.84 (m, 9H), 2.77-2.89 (m, 5H), 1.50 (m, 2H), 0.74 (s, 9H). Mass spectrum: (M+H)$^+$= 728.2, (M+Na)$^+$=750.3.

Preparation of Example O

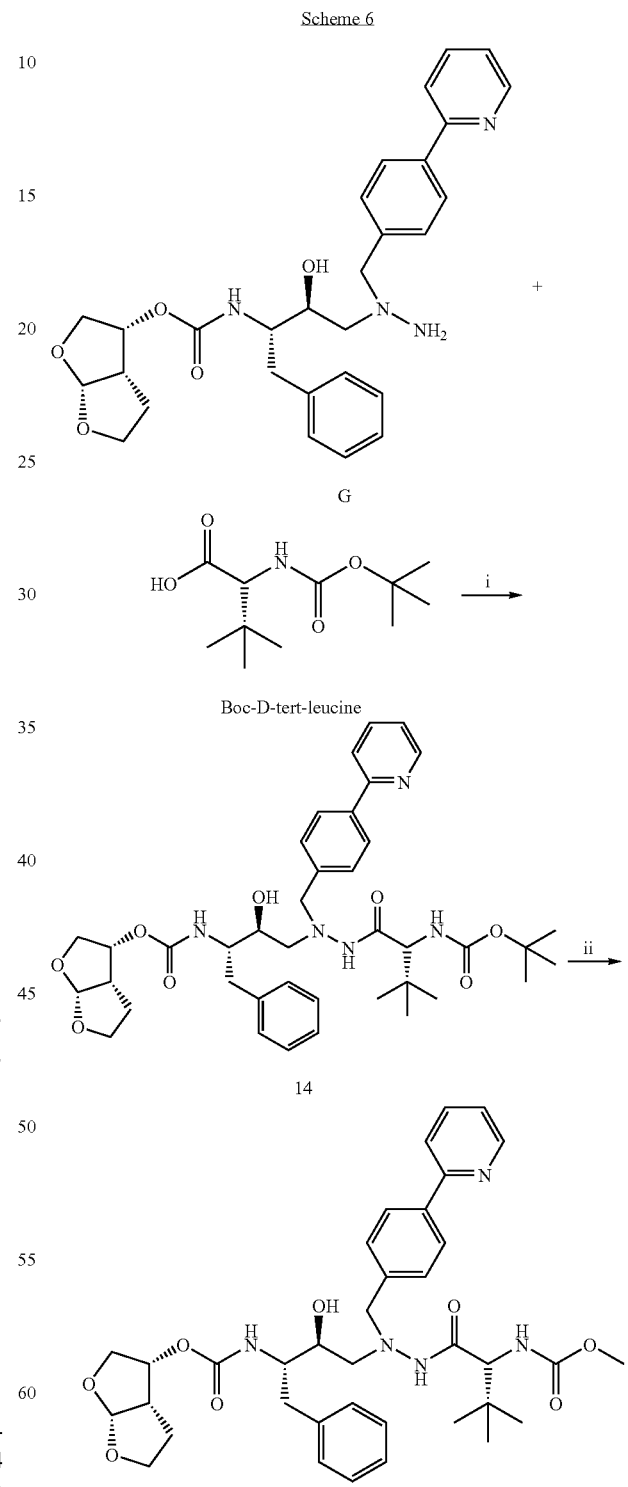

Example O

Reagents and Conditions: i. EDC, HOBT, NMM, DMF; ii. a. TFA, DCM; b. H$_2$O, methyl chloroformate/toluene, NaHCO$_3$.

Compound 14

To a solution of Boc-D-tert-leucine (121.7 mg, 0.526 mmol), purchased from Bachem, in DMF (2 mL) at r.t. were added EDC (463.1 mg, 1.56 mmol) and HOBT (71.1 mg, 0.526 mmol) and the reaction mixture was stirred for 30 min. Then a solution of Example G (210 mg, 0.40 mmol) in DMF (2 mL) was added to the reaction mixture after the addition of 4-methylmorpholine ("NMM") (0.26 mL, 2.34 mmol). The reaction was stirred at r.t. for 18 h and then the reaction was diluted with ethyl acetate and washed with saturated $NaHCO_3$ and brine before it was dried over $Na_2SO_4$, and concentrated. The crude residue was purified using silica gel chromatography (0-10% methanol/DCM), and again using silica gel chromatography (25-75% ethyl acetate/hexane) and yielded Compound 14 as a solid (189.9 mg, 0.260 mmol, 64%). Mass spectrum: $(M+H)^+=732.2$.

Example O

TFA (0.1 mL) was added to a solution of Compound 14 (30.9 mg, 0.0295 mmol) in DCM (1.0 mL) and the reaction mixture was stirred at r.t. for 2 h. The reaction mixture was concentrated followed by the addition of $H_2O$ (0.5 mL) and methyl chloroformate (2.9 µL, 0.038 mmol) in toluene. The reaction mixture was stirred vigorously while saturated aqueous $NaHCO_3$ was added drop-wise until pH 8 was reached. The reaction mixture was stirred at r.t. for 2 h before it was diluted with ethyl acetate and washed with brine and $H_2O$. The organic layer was dried over $Na_2SO_4$ and concentrated before it was purified by reverse phase HPLC (Phenomenex Synergi® column, 25-100% acetonitrile/$H_2O$+0.1% TFA) and yielded Example O as a solid (8.4 mg, 0.01 mmol, 35%). $^1H$ NMR (300 MHz, $CD_3OD$): δ 8.74 (d, J=5.1 Hz, 1H), 8.49 (m, 1H), 8.25 (d, J=8.4 Hz, 1H), 7.81-7.88 (m, 3H), 7.65 (d, J=8.4 Hz, 2H), 7.12-7.21 (m, 5H), 5.55 (d, J=8.4 Hz, 1H), 4.92 (m, 1H), 3.59-4.02 (m, 9H), 3.44 (s, 3H), 2.75-2.92 (m, 5H), 1.57 (m, 2H), 0.72 (s, 9H). Mass spectrum: $(M+H)^+=690.2$.

Preparation of Example P

Scheme 7

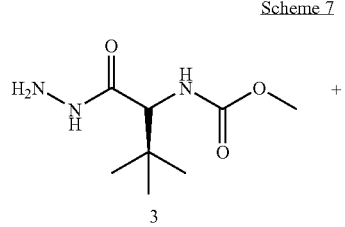

3

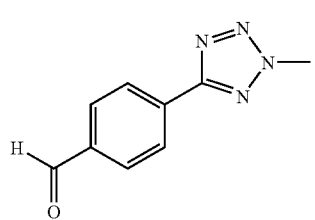

15

-continued

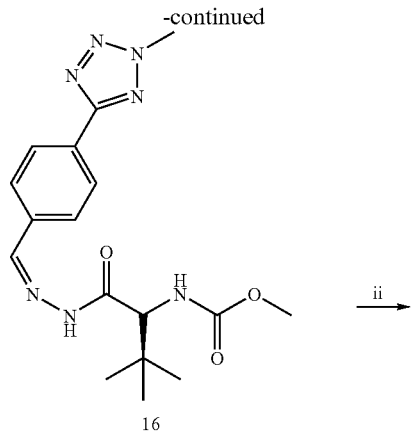

16

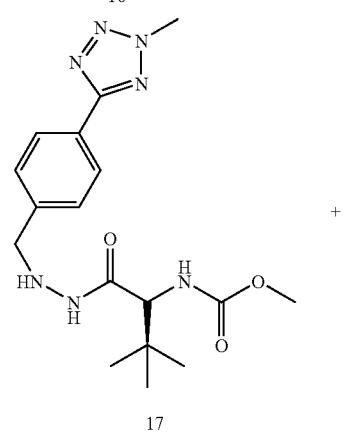

17

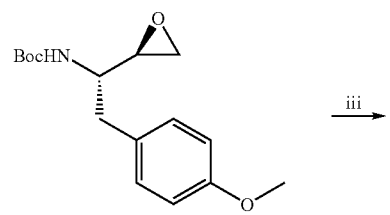

tert-butyl (S)-2-(4-methoxyphenyl)-1-((R)-oxiran-2-yl)ethylcarbamate

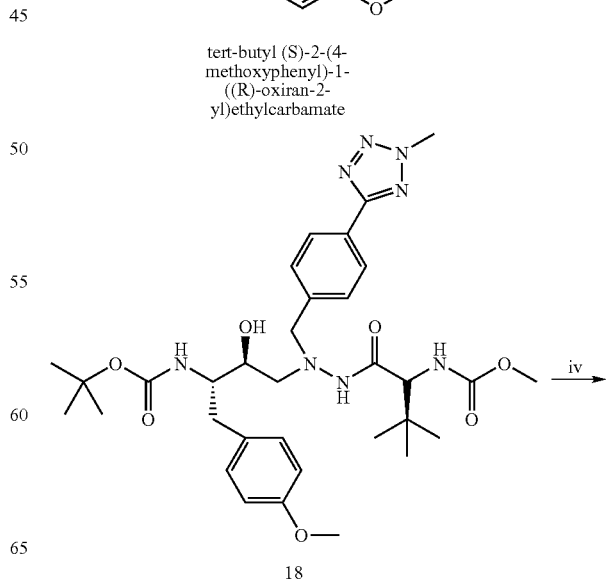

18

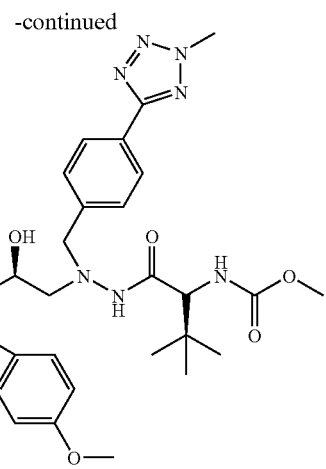

Example P
Reagents and Conditions: i. i-PrOH, 80° C.; ii. a. NaCNBH₃, THF, p-TsOH; b. H₂O, THF, Na₂B₄O₇; iii. i-PrOH, CH₃COOH, 80° C.; iv. a. TFA, DCM; b. DMAP, DIPEA, 4-nitrophenyl (3R,3aS,6aR) tetrahydro-2H-furo[2,3-b]furan-3-yl carbonate, CH₃CN.

Compound 15

Compound 15 was prepared using the method described in Bold, G., et al. New Aza-Dipeptide Analogues as Potent and Orally Absorbed HIV-1 Protease Inhibitors: Candidates for Clinical Development. *J. Med. Chem.* 1998, 41, 3387-3401, which is herein incorporated by reference.

Compound 16

A suspension of Compound 15 (1.320 g, 5.70 mmol) and Compound 3 (1.141 g, 5.60 mmol) in isopropanol was heated to 80° C. for 18 h. The product was precipitated by the addition of ice, then filtered and dried under vacuum at 50° C. Compound 16 was obtained as a solid (1.815 g, 33.3 mmol, 87%). Mass spectrum: $(M+H)^+=374.2$.

Compound 17

Reduction of Compound 16 using procedures similar to that is used to prepare Compound 5 yielded Compound 17 as a solid (1.105 g, 2.94 mmol, 61%). Mass spectrum: $(M+H)^+= 376.0$.

Compound 18

Acetic acid (11 μL, 0.19 mmol) was added to a mixture of Compound 17 (98.6 mg, 0.26 mmol) and tert-butyl (S)-2-(4-methoxyphenyl)-1-((R)-oxiran-2-yl)ethylcarbamate (70.1 mg, 0.24 mmol) in isopropanol (1.5 mL) and the reaction mixture was heated to 80° C. for 24 h. The reaction mixture was concentrated and purified using silica gel chromatography (50-100% ethyl acetate/hexane) and yielded Compound 18 as a solid (85.9 mg, 0.13 mmol, 49%). Mass spectrum: $(M+H)^+=669.0$.

Example P

TFA (0.15 mL) was added to a solution of Compound 18 (85.9 mg, 0.128 mmol) in DCM (1.0 mL) and the mixture was stirred at r.t. for 2.5 h. The solution was concentrated and co-evaporated twice with DCM and four times with acetonitrile. The resulting residue was dissolved in anhydrous acetonitrile (1.0 mL) and cooled to 0° C. DMAP (1.6 mg, 0.013 mmol) was added followed by DIPEA (70 μL, 0.401 mmol) until pH 9 was reached. Compound 70 (32.1 mg, 0.128 mmol) was added. The reaction mixture was stirred for 2 h at 0° C. and for 13 h at r.t. The reaction mixture was concentrated and dissolved in ethyl acetate. The organic layer was washed four times with H₂O, four times with NaOH (1N), and once with brine before it was dried over Na₂SO₄ and concentrated. The crude product was purified by reverse phase HPLC (Phenomenex Synergi® column, 25-100% acetonitrile/H₂O) and yielded Example P as a solid (29.0 mg, 0.04 mmol, 31%). ¹H NMR (300 MHz, CD₃OD): δ 7.96 (d, J=8.4, 2H), 7.52 (d, J=8.1, 2H), 7.11 (d, J=8.4, 2H), 6.75 (d, J=8.4, 2H), 5.53 (d, J=5.4, 1H), 4.89 (m, 1H), 4.36 (s, 3H), 3.56-4.00 (m, 15H), 2.71-2.86 (m, 5H), 1.40-1.60 (m, 2H), 0.67 (s, 9H). Mass spectrum: $(M+H)^+=725.1$, $(M+Na)^+=747.2$.

Preparation of Example Q

Scheme 8

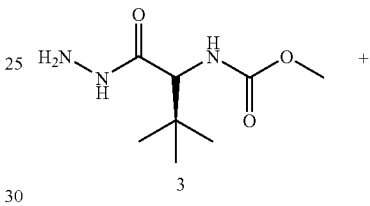

3

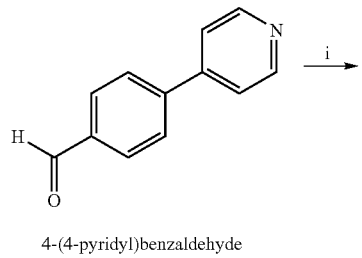

4-(4-pyridyl)benzaldehyde

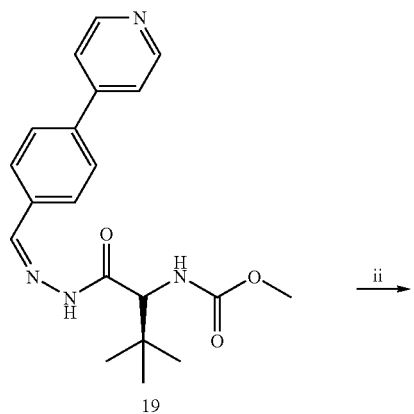

19

-continued

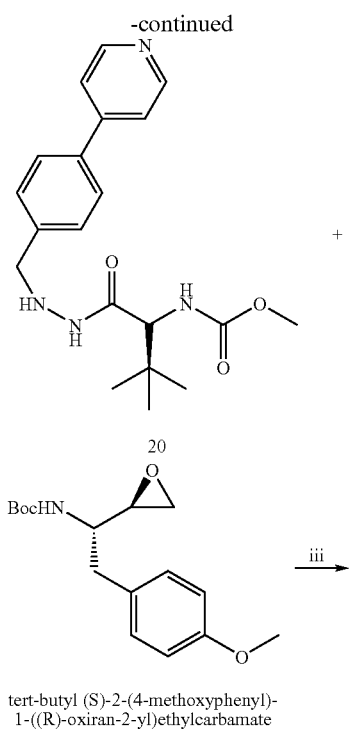

20 tert-butyl (S)-2-(4-methoxyphenyl)-
1-((R)-oxiran-2-yl)ethylcarbamate

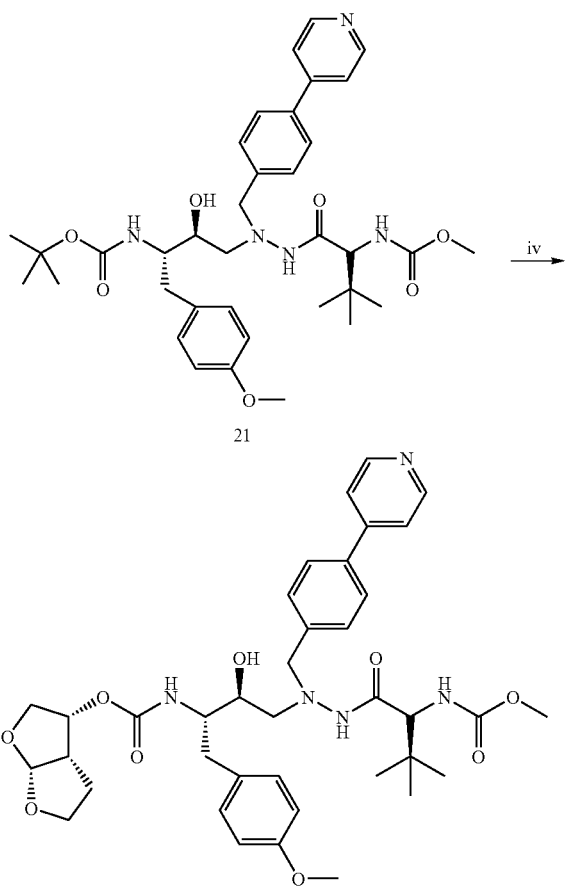

Example Q

Reagents and Conditions: i. i-PrOH, 80° C.; ii. Pd(OH)₂, H₂, EtOH, CH₃COOH
iii. i-PrOH, CH₃COOH, 80° C.; iv. a. TFA, DCM; b. DMAP, DIPEA, 4-nitrophenyl
(3R,3aS,6aR)-tetrahydro-2H-furo[2,3-b]furan-3-yl carbonate, CH₃CN.

Compound 19

Compound 19 (734.3 mg, 2.0 mmol, 91%) was prepared from commercially available 4-(4-pyridyl)benzaldehyde using a procedure similar to that described for preparing Compound 16. Mass spectrum: $(M+H)^+=369.2$.

Compound 20

Pd(OH)₂ (146.8 mg) was added to a solution of Compound 19 (734.3 mg, 2.0 mmol) in ethanol (20 mL) and acetic acid (0.23 mL, 4.0 mmol). The reaction flask was purged with hydrogen and the reaction was stirred for 2 h at r.t. under hydrogen. Removal of the catalyst by filtration and purification on silica gel (25-100% ethyl acetate/hexane) provided Compound 20 (472.7 mg, 1.1 mmol, 64%). Mass spectrum: $(M+H)^+=371.2$.

Compound 21

Compound 21 (102.1 mg, 0.15 mmol, 14%) was prepared from Compound 20 using procedures similar to those used prepare Compound 18. Mass spectrum: $(M+H)^+=664.2$.

Example Q

Example Q was prepared from Compound 21 using procedures similar to those used to prepare Example P. Additional purification of the crude residue by reverse phase HPLC (Phenomenex Synergi® column, 25-100% acetonitrile/H₂O+0.1% TFA) yielded Example Q as a solid (68.5 mg, 0.08 mmol, 55%). ¹H NMR (300 MHz, CD₃OD): δ 8.76 (d, J=6.9, 2H), 8.27 (d, J=6.9, 2H), 7.87 (d, J=8.4, 2H), 7.65 (d, J=8.1, 2H), 7.11 (d, J=8.4, 2H), 6.75 (d, J=8.4, 2H), 5.55 (d, J=5.4, 1H), 4.90 (m, 1H), 3.55-4.06 (m, 15H), 2.70-2.84 (m, 5H), 1.53 (m, 2H), 0.68 (s, 9H). Mass spectrum: $(M+H)^+=720.3$.

Preparation of Example R

Scheme 9

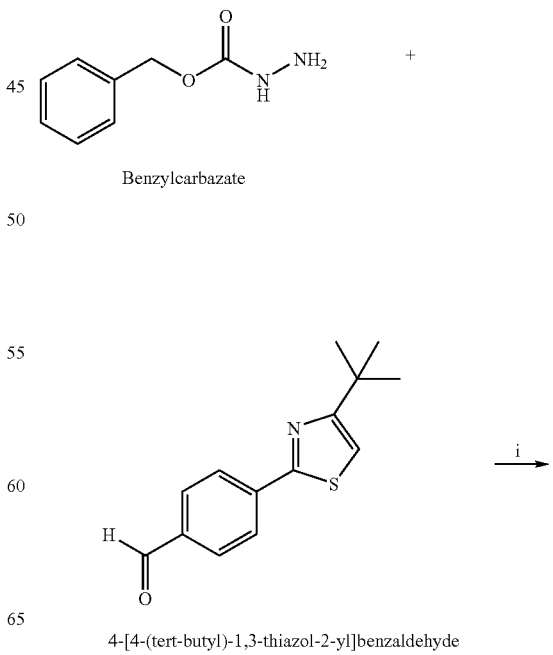

Benzylcarbazate

4-[4-(tert-butyl)-1,3-thiazol-2-yl]benzaldehyde

315
-continued
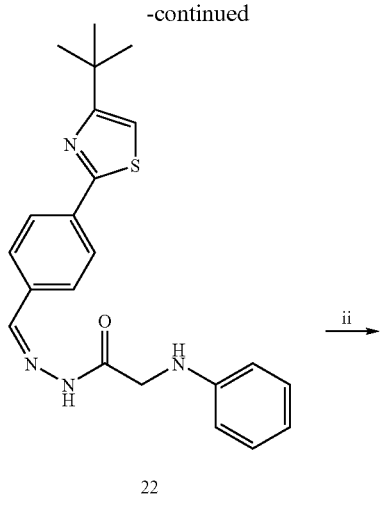
22
316
-continued
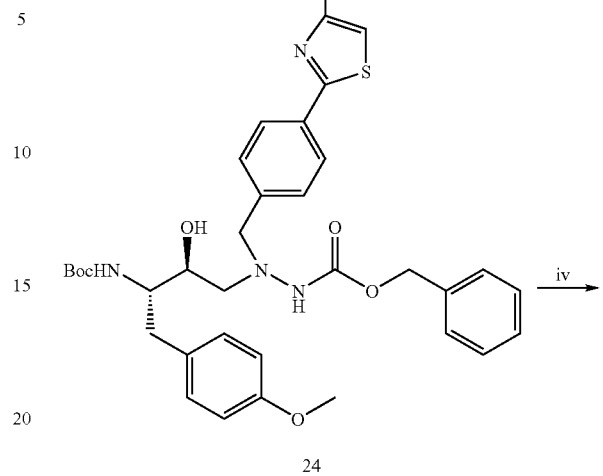
24
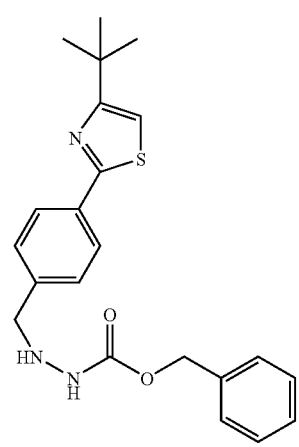
23
+
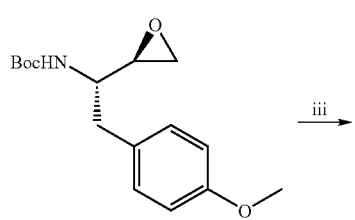
tert-butyl (S)-2-(4-methoxyphenyl)-
1-((R)-oxiran-2-yl)ethylcarbamate
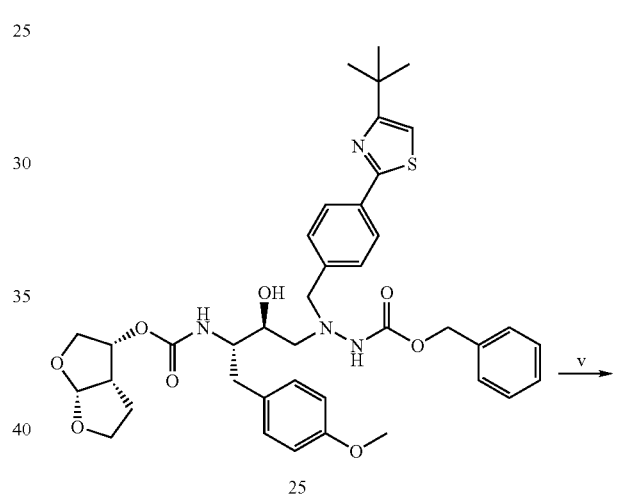
25
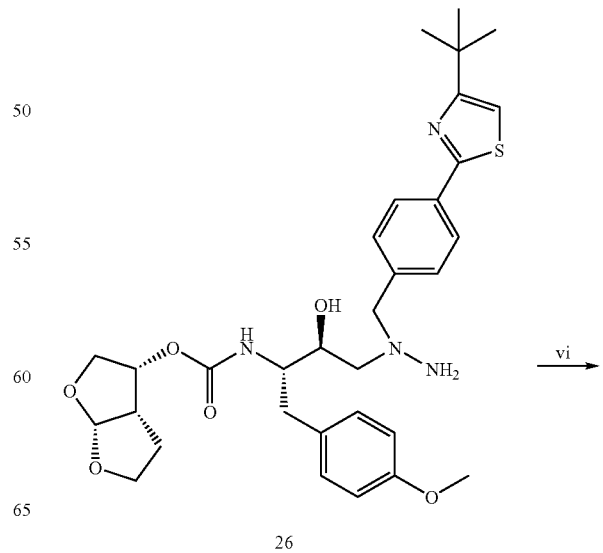
26

317

-continued

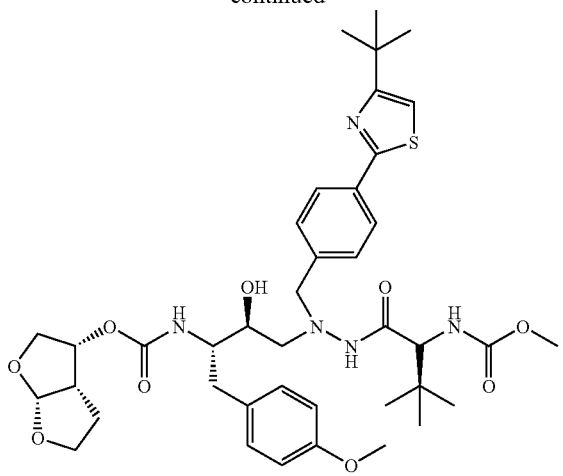

Example R

Reagents and conditions: i. i-PrOH, 80° C.; ii. a. NaCNBH₃, THF, p-TsOH; b. H₂O, THF, NaB₄O₇; iii. i-PrOH, CH₃COOH, 80° C.; iv. a. TFA, DCM; b. DMAP, DIPEA, 4-nitrophenyl (3R,3aS,6aR)-tetrahydro-2H-furo[2,3-b]furan-3-yl carbonate, CH₃CN; v. Me₂/TFA, DCM; vi. Compound 1, EDC, HOBT, NMM, DMF.

Compound 22

Benzyl carbazate (1.475 g, 8.88 mmol) and 4-[4-(tert-butyl)-1,3-thiazol-2-yl]benzaldehyde (2.175 g, 8.88 mmol) were suspended in isopropanol (27.0 mL) and heated to 80° C. for 18 h. The reaction was cooled to r.t. and the precipitate that formed was filtered off and dried under vacuum at 40° C. to give Compound 22 as a white solid (3.467 g, 8.81 mmol, 99%). Mass spectrum: (M+H)$^+$=394.2.

Compound 23

Reduction of Compound 22 using a procedure similar to that used to prepare Compound 5 yielded Compound 23 as a solid (2.608 g, 6.59 mmol, 75%). Mass spectrum: (M+H)$^+$=396.1.

Compound 24

Compound 24 (189.6 mg, 0.28 mmol, 80%) was prepared from Compound 23 using a procedure similar to that used to prepare Compound 18. Mass spectrum: (M+Na)$^+$=711.1.

Compound 25

Compound 25 was prepared from Compound 24 using a procedure similar to that used to prepare Example P. The crude product was purified using silica gel chromatography (20-70% ethyl acetate/hexane) affording Compound 25 as a solid (86.5 mg, 0.12 mmol, 56%) was obtained. Mass spectrum: (M+H)$^+$=745.1.

Compound 26

DCM (1.6 mL) was used to dissolve Compound 25 and a solution of methyl sulfide in TFA (1:4) was added. The reaction was stirred at r.t. for 12 h then the reaction was concentrated. The reaction was partitioned between ethyl acetate and saturated NaHCO₃. The aqueous layer was extracted twice with ethyl acetate and the combined organic layers were dried over Na₂SO₄ and concentrated to give Compound 26 (67.2 mg, 0.11 mmol, 100%) without further purification. Mass spectrum: (M+H)$^+$=611.2.

318

Example R

A solution of EDC (27.4 mg, 0.14 mmol), HOBT (19.3 mg, 0.14 mmol), and Compound 1 (27.1 mg, 0.14 mmol) in DMF (2.0 mL) was stirred for 45 minutes before 4-methylmorpholine (41 µL, 0.37 mmol) and Compound 26 (67.2 mg, 0.11 mmol) were added. The reaction mixture was stirred at r.t. for 1 h before the reaction was concentrated. The residue was purified by reverse phase HPLC (Phenomenex Synergi® column, 25-100% acetonitrile/H₂O) and yielded Example R as a white solid (22.4 mg, 0.02 mmol, 26%). $^1$H NMR (300 MHz, CD₃OD): δ 7.81 (d, J=8.4, 2H), 7.45 (d, J=8.1, 2H), 7.09 (m, 3H), 6.75 (d, J=8.4, 2H), 5.53 (d, J=5.4, 1H), 4.87 (m, 1H), 3.55-3.94 (m, 15H), 2.70-2.85 (m, 5H), 1.05-1.60 (m, 11H), 0.70 (s, 9H). Mass spectrum: (M+H)$^+$=782.2, (M+Na)$^+$=804.3.

Preparation of Example S

Scheme 10

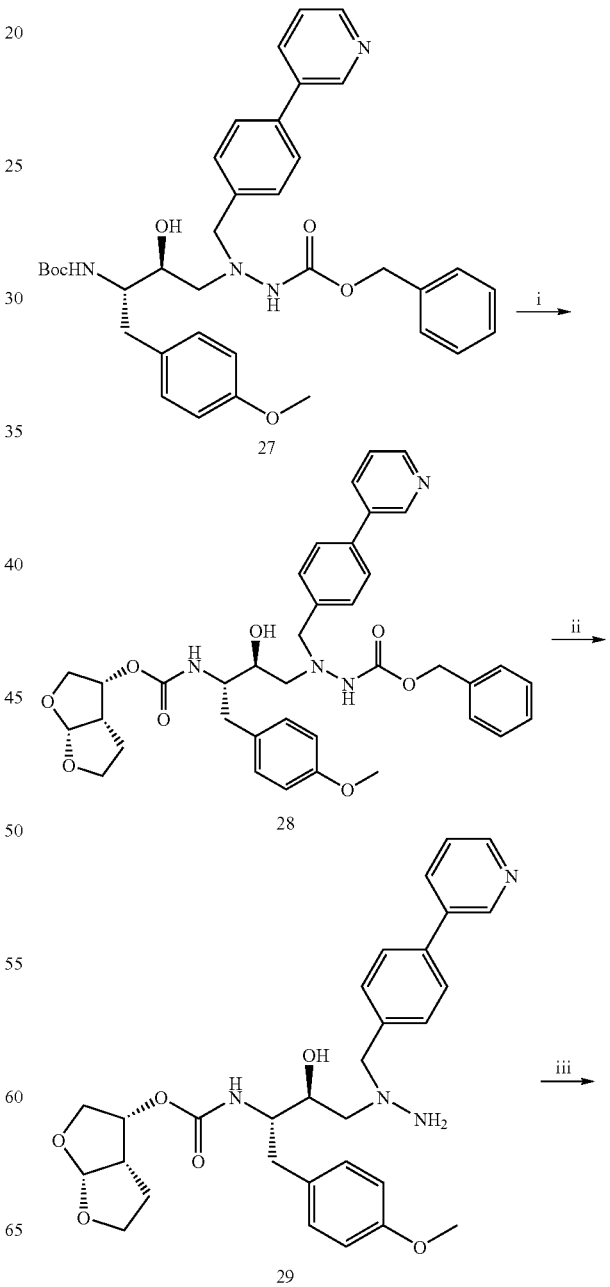

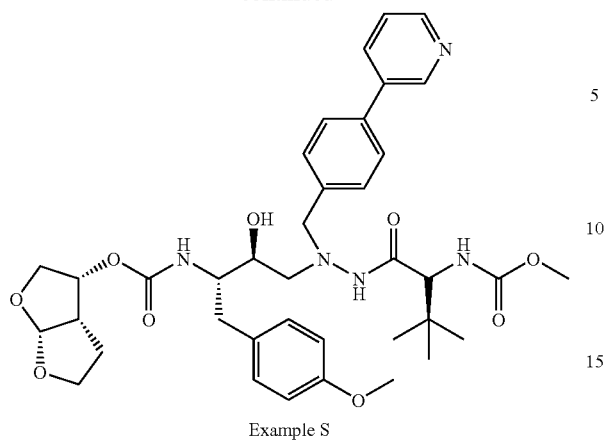

Example S

Reagents and conditions: i.a. TFA, DCM; b. DMAP, DIPEA, 4-nitrophenyl (3R,3aS,6aR)-tetrahydro-2H-furo[2, 3-b]furan-3yl carbonate, CH₃CN; ii. Me₂/TFA, DCM; iii. Compound 1, EDC, HOBT, NMM, DMF.

Compound 27

Compound 27 was prepared from commercially available 4-(3-pyridyl)benzaldehyde using a method similar to that used to prepare Compound 24.

Compound 28

Compound 28 was prepared from Compound 27 using a method similar to that used to prepare Compound 25, and yielded Compound 28 as a solid (61.2 mg, 0.09 mmol, 77%). Mass spectrum: $(M+H)^+=683.1$.

Compound 29

Compound 29 was prepared from Compound 28 using a method similar to that used to prepare Compound 26, and yielded Compound 29 (48.9 mg, 0.09 mmol, 100%). Mass spectrum: $(M+H)^+=549.2$.

Example S

Example S (white solid, 12.0 mg, 0.017 mmol, 19%) was prepared from Compound 29 using a method similar to that used to prepare Example R. $^1$H NMR (300 MHz, CD₃OD): δ 8.74 (m 1H), 8.47 (d, J=4.8, 1H), 8.04 (m, 1H), 7.45-7.60 (m, 5H), 714 (d, J=8.4, 2H), 6.75 (d, J=9.0, 2H), 5.55 (d, J=5.4, 1H), 4.90 (m, 1H), 3.55-4.01 (m, 15H), 2.69-2.90 (m, 5H), 1.50 (m, 2H), 0.67 (s, 9H). Mass spectrum: $(M+H)^+=720.1$.

Preparation of Examples T, U, V

Scheme 11

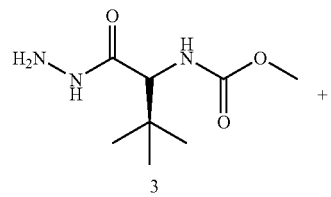

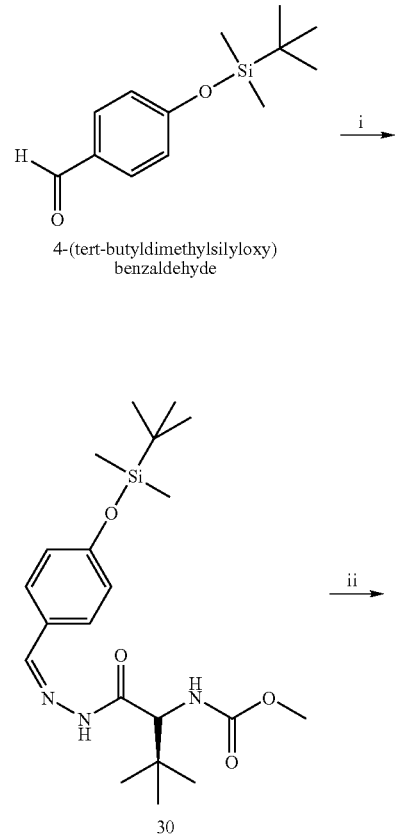

4-(tert-butyldimethylsilyloxy) benzaldehyde

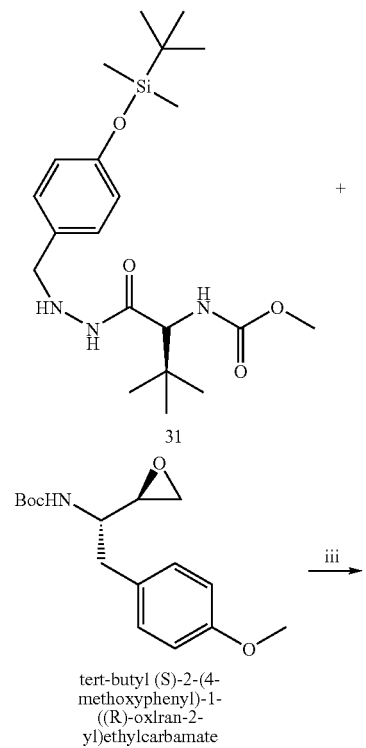

tert-butyl (S)-2-(4-methoxyphenyl)-1-((R)-oxlran-2-yl)ethylcarbamate

-continued

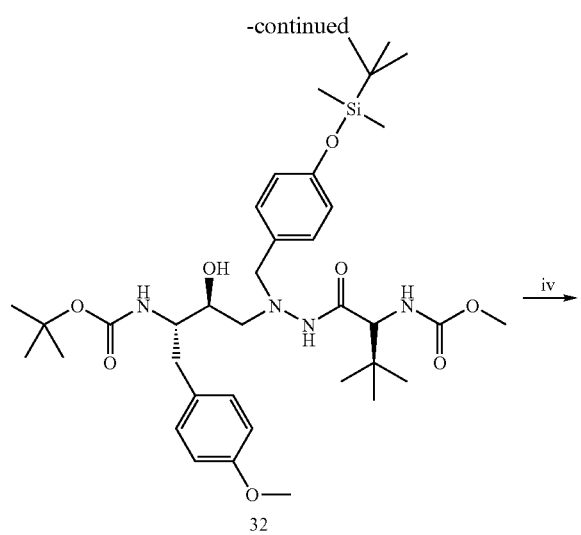

32

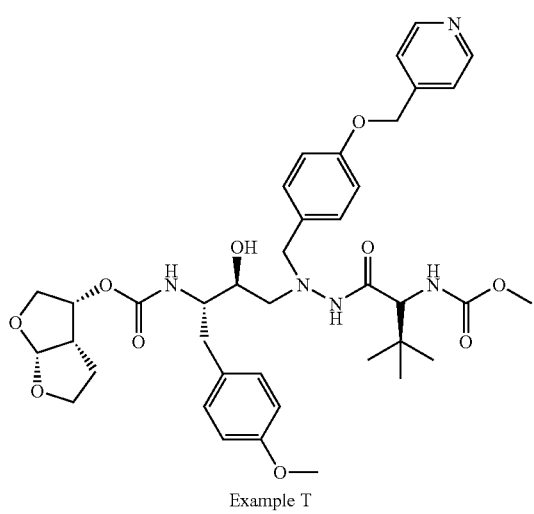

33

Example T

-continued

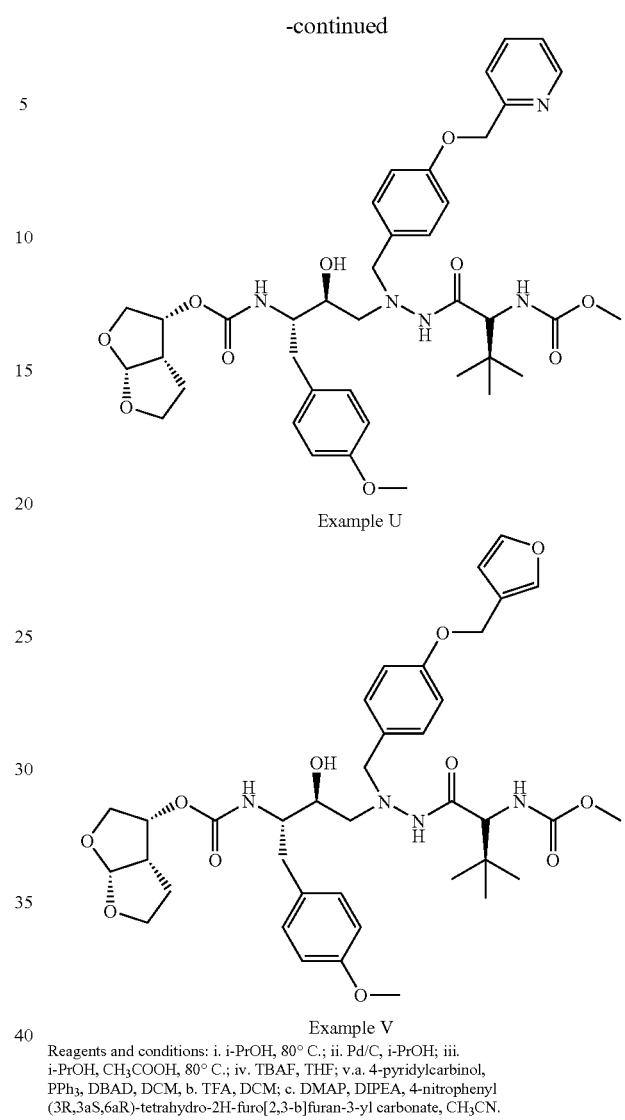

Example U

Example V

Reagents and conditions: i. i-PrOH, 80° C.; ii. Pd/C, i-PrOH; iii. i-PrOH, CH₃COOH, 80° C.; iv. TBAF, THF; v.a. 4-pyridylcarbinol, PPh₃, DBAD, DCM, b. TFA, DCM; c. DMAP, DIPEA, 4-nitrophenyl (3R,3aS,6aR)-tetrahydro-2H-furo[2,3-b]furan-3-yl carbonate, CH₃CN.

Compound 30

A mixture of compound 3 (3.008 g, 14.8 mmol) and 4-(tert-butyldimethylsilyloxy)benzaldehyde (3.50 g, 14.8 mmol) was dissolved in isopropanol (45 mL) and the reaction flask was heated to 80° C. and allowed to stir for 24 h. The reaction mixture was cooled to room temperature, diluted with H$_2$O (50 mL) and extracted with ethyl acetate (4×100 mL). The organic extract was washed with brine, dried over sodium sulfate, concentrated to give a crude residue, which was purified using silica gel chromatography (30-100% ethyl acetate/hexane) to give Compound 30 (2.996 g. 7.1 mmol, 48%). Mass spectrum: (M+H)$^+$=422.1.

Compound 31

Compound 30 (2.818 g, 6.68 mmol) was dissolved in isopropanol (55 mL) and Pd/C (845 mg) was added. The reaction flask was purged with hydrogen gas three times and then the flask was filled with hydrogen and allowed to stir at room temperature for one and one half hours. The reaction mixture was filtered through a pad of CELITE and the filtrate was concentrated, providing Compound 31 as a colorless oil (2.8298 g, 6.68 mmol, 100%). Mass spectrum: (M+H)$^+$=423.9.

Compound 32

A suspension of Compound 31 (2.8298 g, 6.68 mmol) and tert-butyl (S)-2-(4-methoxyphenyl)-1-((R)-oxiran-2-yl)ethylcarbamate (1.507 g, 5.14 mmol) in isopropanol (16 mL) and glacial acetic acid (0.24 mL, 4.11 mmol) was heated to 80° C. for 19 h. The reaction mixture was cooled to room temperature and concentrated. The crude residue was purified using silica gel chromatography (0-35%, then 35-50% ethyl acetate/hexane) and yielded Compound 32 as a white foamy solid (2.563 g, 3.57 mmol, 54%). Mass spectrum: $(M+H)^+=$ 717.2, $(M+Na)^+=739.4$.

Compound 33

Compound 32 (2.555 mg, 3.56 mmol) was dissolved in anhydrous tetrahydrofuran (11 mL) and the reaction flask was cooled to 0° C. Tetrabutylammonium fluoride in tetrahydrofuran (5.35 mL, 5.35 mmol) was added drop-wise and the reaction was allowed to stir for 15 minutes. The reaction mixture was warmed to room temperature and diluted with $H_2O$ (10 mL) and extracted with methylene chloride (2×100 mL). The organic layer was washed with brine, dried over $Na_2SO_4$ and concentrated to provide Compound 33 as an off white foamy solid (2.148 g, 3.56 mmol, 100%). Mass spectrum: $(M+H)^+=603.2$, $(M+Na)^+=625.3$.

Example T

Compound 33 (80.0 mg, 0.13 mmol) and 4-pyridylcarbinol (29.0 mg, 0.26 mmol) were dissolved in anhydrous methylene chloride (2.6 mL). Triphenylphosphine (69.6 mg, 0.26 mmol) was added followed by di-tert-butylazodicarboxilate (61.6 mg, 0.26 mmol) and the reaction mixture was allowed to stir at room temperature for 2 h. The reaction mixture was concentrated and partially purified using silica gel chromatography (25-75% ethyl acetate/hexane) to yield a yellow oil. The oil was dissolved in methylene chloride (1.2 mL) and trifluoroacetic acid was added (0.25 mL) and the reaction mixture was allowed to stir at room temperature for 2 h. The reaction mixture was concentrated and co-evaporated with methylene chloride (3×) and acetonitrile (4×). The resulting residue was dissolved in anhydrous acetonitrile and cooled to 0° C. Dimethylaminopyridine (1.2 mg, 0.01 mmol) was added followed by diisopropylethylamine (0.09 mL, 0.5 mmol) until pH=8 was reached. After addition of 4-nitrophenyl (3R,3aS,6aR)-tetrahydro-2H-furo[2,3-b]furan-3-yl carbonate (28.5 mg, 0.096 mmol), prepared according to Miller et al Bioorg. Med. Chem. Lett. 2005, 15, 3946-3500, the reaction mixture was allowed to stir at 0° C. for 2 h and then at room temperature for 18 h. The reaction mixture was diluted with ethyl acetate and washed with $H_2O$ (3×), NaOH solution (1N, 3×), and brine (1×). The organic layer was dried over $Na_2SO_4$ and concentrated. The crude residue was purified by silica gel chromatography (75-100% ethyl acetate/hexane) and then by reverse phase HPLC (Phenomenex Synergi® column, 25-100% acetonitrile/$H_2O$) to give Example T as a white solid (13.4 mg, 0.018 mmol, 19%). $^1H$ NMR (300 MHz, $CD_3OD$): δ 8.47 (d, J=6.0, 2H), 7.46 (d, J=3.0, 2H), 7.28 (d, J=8.7, 2H), 7.09 (d, J=8.7, 2H), 6.88 (d, J=8.7, 2H), 6.75 (d, J=8.4, 2H), 5.55 (d, J=5.4, 1H), 5.12 (s, 2H), 4.90 (m, 1H), 3.58-3.89 (m, 15H), 2.67-2.81 (m, 5H), 1.46-1.58 (m, 2H), 0.67 (s, 9H). Mass spectrum: $(M+H)^+=750.3$, $(M+Na)^+= 772.4$.

Example U

Example U was prepared from Compound 33 using procedures similar to that used to prepare Example T, except that 2-pyridalcarbinol was used instead of 4-pyridylcarbinol. Compound U (16.7 mg, 0.022 mmol, 17%). $^1H$ NMR (300 MHz, $CD_3OD$): δ 8.49 (d, J=4.8, 1H), 7.81 (m, 1H), 7.54 (d, J=8.1, 1H), 7.26-7.34 (m, 3H), 7.27 (d, J=8.4, 2H), 6.88 (d, J=8.7, 2H), 6.75 (d, J=8.4, 2H), 5.55 (d, J=5.4, 1H), 5.11 (s, 2H), 4.90 (m, 1H), 3.58-3.89 (m, 15H), 2.67-2.81 (m, 5H), 1.46-1.58 (m, 2H), 0.67 (s, 9H). Mass spectrum: $(M+H)^+=750.3$, $(M+Na)^+=772.4$.

Example V

Example U was prepared from Compound 33 using procedures similar to that used to prepare Example T, except that 3-furanamethanol was used instead of 4-pyridylcarbinol. Example V (13.9 mg, 0.019 mmol, 11%). $^1H$ NMR (300 MHz, $CDCl_3$): δ 7.45 (s, 1H), 7.38 (s, 1H), 7.20 (d, J=9.3, 2H), 7.07 (d, J=8.4, 2H), 6.84 (d, J=8.7, 2H), 6.74 (d, J=8.4, 2H), 6.43 (s, 1H), 5.62 (d, J=5.1, 1H), 4.98 (m, 1H), 4.87 (s, 2H), 3.54-3.96 (m, 15H), 2.79-2.90 (m, 4H), 2.60 (m, 1H), 1.57-1.63 (m, 2H), 0.70 (s, 9H). Mass spectrum: $(M+H)^+=739.2$, $(M+Na)^+=761.4$.

Preparation of Examples W, X, Y

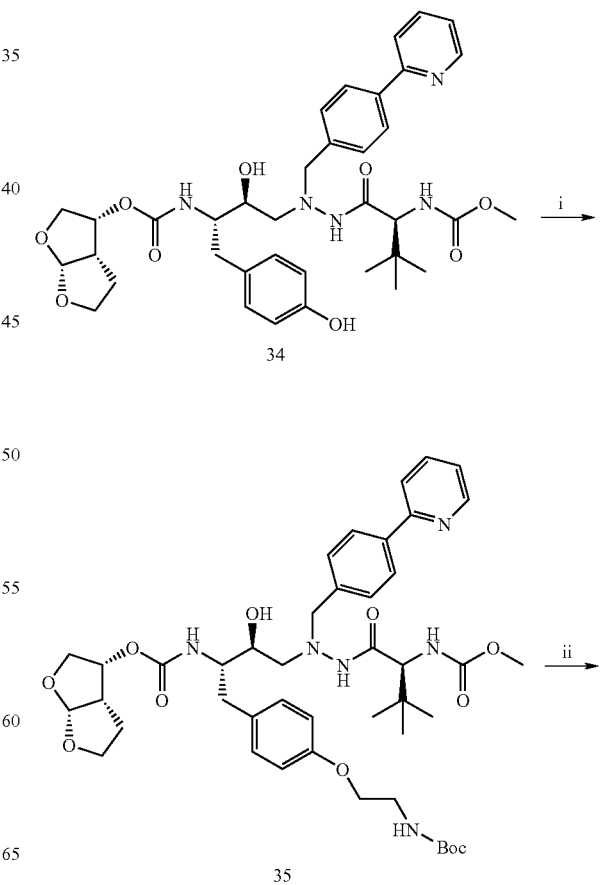

Scheme 12

325

-continued

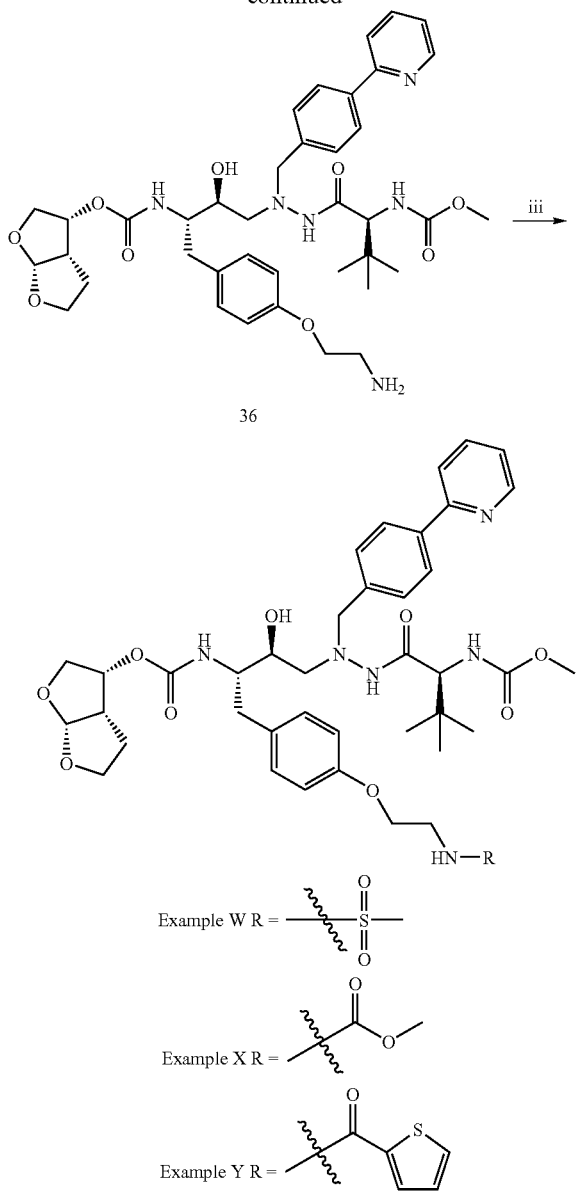

Reagents and conditions: i. PPh₃, di-tert-butyl azodicarboxylate, DCM, (2-Hydroxy-ethyl)-carbamic acid tert-butyl ester; ii. TFA, DCM; iii. DCM, DIEA, 0° C., acid chloride.

Compound 35

In a 25 mL round bottom flask, di-tert-butyl azodicarboxylate (44 mg, 2.0 eq) was added to Compound 34 (67.8 mg, 0.096 mmol, 1.0 eq), (2-hydroxy-ethyl)-carbamic acid tert-butyl ester (30 μL, 2.0 eq.) and triphenylphosphane (50 mg, 2.0 eq.) in 1.2 mL dichloromethane at room temperature. The reaction mixture was stirred at room temperature for 3 hours. The completion of the reaction was monitored by TLC (silica gel, 5% MeOH/DCM). The reaction mixture was concentrated, and the resulting residue was purified by silica gel chromatography, 40-100% EtOAc/hexane, to 2-10% MeOH/DCM) to give Compound 35 as a white foam (59 mg, 0.069 mmol, 72%). LC-MS of the compound shows 871.4 (M+Na)⁺.

326

Compound 36

20% TFA/DCM solution (4 mL) was added to Compound 35 in a 25 mL round bottom flask at 0° C. The reaction was complete after stirring at 0° C. for 40 minutes. The reaction mixture was concentrated and extracted using EtOAc (3×)/saturated NaHCO₃. The organic layers were combined, dried over Na₂SO₄, concentrated to give Compound 36 as a colorless oil (46 mg, 88%).

Example W

DIEA (9 μL, 0.05 mmol, 1.5 eq.) was added to Compound 36 (25 mg, 0.0334 mmol, 1.0 eq.) in 0.5 mL DCM. Methanesulfonyl chloride (3.1 μL, 1.2 eq.) was added at 0° C. The reaction was complete after stirring at 0° C. for 30 minutes. The reaction mixture was concentrated and purified by reverse phase HPLC (Phenomenex Synergi® column, 0.05% TFA in MeCN/0.05% TFA in water) to give Example W as a white solid (14.3 mg, 52%). LC-MS shows 827.3 (M+H)⁺. ¹H NMR (300 MHz, CDCl₃): δ 8.92 (s, 1H), 7.96 (d, 2H), 7.68 (m, 2H), 7.44 (d, 2H), 7.10 (d, 2H), 6.88 (d, 2H), 6.70 (s, 1H), 5.68 (d, 1H), 5.42 (m, 2H), 5.08 (m, 1H), 3.44-4.16 (m, 14H), 2.84 (m, 7H), 2.52 (m, 1H), 1.80 (m, 2H), 0.65 (s, 9H).

Example X

Example X was prepared using a procedure similar to that used to prepare Example W, except that methyl chloroformate was used instead of methanesulfonyl chloride, to give Example X as a white powder (2.8 mg, 23%). LC-MS shows 829.4 (M+Na)⁺. ¹H NMR (300 MHz, CD₃OD): δ 8.22 (d, 1H), 8.30 (m, 1H), 8.12 (d, 1H), 7.90 (d, 2H), 7.65 (m, 3H), 7.15 (d, 2H), 6.80 (d, 2H), 5.58 (d, 1H), 4.96 (m, 1H), 3.32-4.40 (m, 19H), 2.80 (m, 5H), 1.50 (m, 2H), 0.65 (s, 9H).

Example Y

Example Y was prepared using a procedure similar to that used to prepare Example W, except that thiophene-2-carbonyl chloride was used instead of methanesulfonyl chloride. The crude product was purified by silica gel chromatography (2-10% MeOH/DCM) to give Example Y as a white powder (13 mg, 45%). LC-MS shows 859.3 (M+H)⁺. ¹H NMR (300 MHz, CDCl₃): δ 8.82 (s, 1H), 7.76 (m, 2H), 7.58 (m, 1H), 7.42 (m, 3H), 7.25 (m, 1H), 7.12 (d, 2H), 7.03 (m, 1H), 6.80 (d, 2H), 6.60 (s, 1H), 5.62 (d, 1H), 5.38 (m, 2H), 5.03 (m, 1H), 3.44-4.16 (m, 14H), 2.84 (m, 4H), 2.52 (m, 1H), 1.70 (m, 2H), 0.65 (s, 9H).

Preparation of Examples Z and AA

Scheme 13

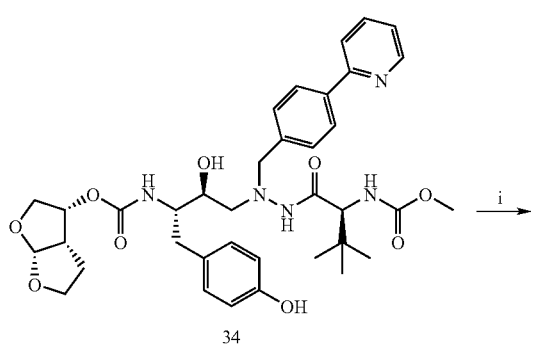

-continued

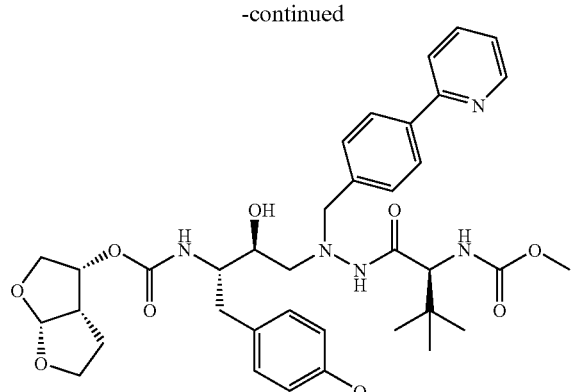

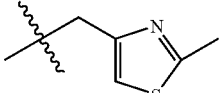

Example Z R =

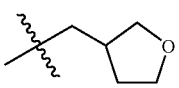

Example AA R =

Reagents and conditions: i. PPh₃, di-tert-butyl azodicarboxylate, DCM, alcohol.

Example Z

In a 25 mL round bottom flask, di-tert-butyl azodicarboxylate (28 mg, 4.0 eq) was added to Compound 34 (21.4 mg, 0.03 mmol, 1.0 eq), (2-methyl-thiazol-4-yl)-methanol (7.8 mg, 2.0 eq.) and triphenylphosphane (31.5 mg, 4.0 eq.), in dichloromethane (1.5 mL) at room temperature. The reaction mixture was stirred at room temperature overnight. The reaction mixture was concentrated, and the resulting residue was purified by silica gel chromatography (40-100% EtOAc/hexane, to 2-10% MeOH/DCM) to give Example Z as a white solid (5.4 mg, 0.069 mmol, 22%). LC-MS of the compound shows 839.3 (M+Na)⁺. ¹H NMR (300 MHz, CDCl₃): δ 8.78 (d, 1H), 8.0 (d, 2H), 7.88 (m, 1H), 7.80 (m, 1H), 7.50 (d, 2H), 7.38 (m, 1H), 7.12 (m, 2H), 6.86 (d, 2H), 6.60 (s, 1H), 5.62 (d, 1H), 5.38 (m, 2H), 5.10 (s, 2H), 5.03 (m, 1H), 3.58-4.16 (m, 11H), 2.84 (m, 3H), 2.70 (m, 4H), 1.70 (m, 2H), 0.72 (s, 9H).

Example AA

Example AA was prepared using a procedure similar to that used to prepare Example Z, using Compound 34 (10.6 mg, 0.015 mmol, 1.0 eq) and (tetrahydro-furan-3-yl)-methanol (3.1 mg, 2.0 eq.) to give Example AA as a white solid (5.8 mg, 0.007 mmol, 49%). LC-MS of the compound shows 790.2 (M+H)⁺. ¹H NMR (300 MHz, CDCl₃): δ 8.78 (d, 1H); 8.0 (d, 2H), 7.88 (m, 1H), 7.78 (m, 1H), 7.48 (d, 2H), 7.35 (m, 1H), 7.12 (m, 2H), 6.80 (d, 2H), 6.56 (s, 1H), 5.62 (d, 1H), 5.30 (m, 2H), 5.05 (s, 2H), 5.03 (m, 1H), 3.58-4.16 (m, 15H), 2.84 (m, 4H), 2.70 (m, 2H), 2.40 (m, 1H), 2.07 (m, 2H) 1.68 (m, 2H), 0.72 (s, 9H).

Preparation of Example AB

Scheme 14

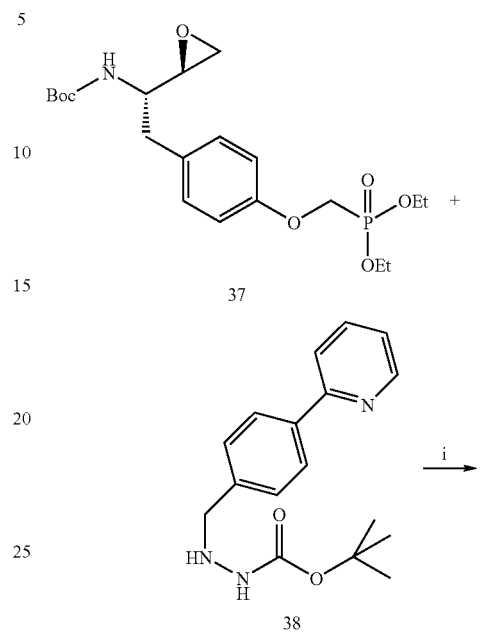

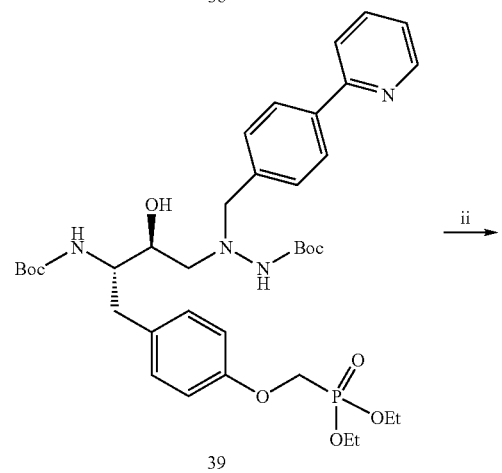

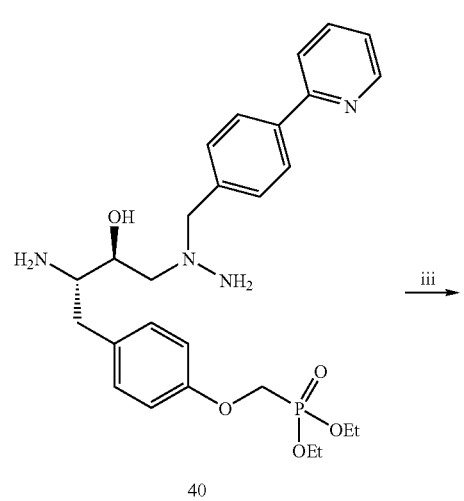

3.80 (m, 1H), 3.60 (m, 7H), 2.84 (m, 3H), 2.56 (m, 1H), 1.35 (dd, 6H), 0.82 (s, 9H), 0.78 (s, 9H). $^{31}$P NMR (300 MHz, CDCl$_3$): δ 19.543.

Preparation of Examples AC, AD, AE, and AF

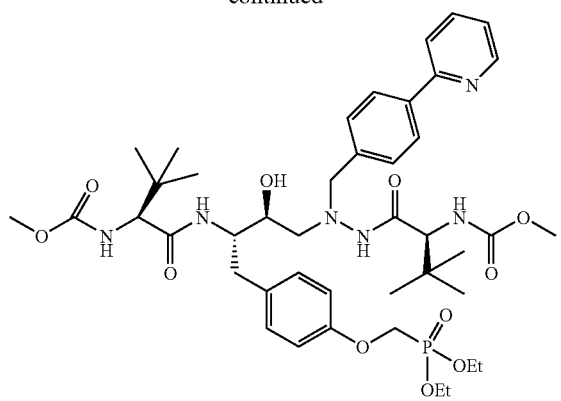

Example AB

Reagents and conditions: i. IPA, 80° C.; ii. TFA, DCM; iii. TPTU, DCM, DIEA, Compound 1

Compound 39

In a 50 mL round bottom flask, isopropanol (6 mL) was added to a mixture of Compound 37 (690 mg, 1.61 mmol, 1.0 eq.) and Compound 38 (481 mg, 1.1 eq.). The reaction mixture was refluxed at 80° C. for 15 hours. The reaction mixture was concentrated and purified by silica gel chromatography (40-100% EtOAc/hexane) to give Compound 39 as a white solid (916 mg, 78%). LC-MS shows 729.1 (M+H)$^+$.

Example 40

TFA (3.0 mL) was added to Compound 39 (916 mg, 1.25 mmol.) in 6 mL of anhydrous DCM at 0° C. The reaction mixture was stirred at 0° C. for 2 hours. After completion of the reaction, the reaction mixture was concentrated, extracted using EtOAc (3×)/saturated NaHCO$_3$ solution. The organic layers were combined, dried (Na$_2$SO$_4$), and concentrated to give Example 40 as a colorless oil (600 mg, 90%). LC-MS shows 529.1 (M+H)$^+$.

Example AB

TPTU (1.01 g, 3.4 mmol, 3.0 eq.) was added to Compound 1 (prepared following the procedure of *Journal of Medicinal Chemistry*, 1998, 41, 3399) (644 mg, 3.0 eq.) in 6 mL DCM at room temperature and stirred for 5 minutes. DIEA (1.19 mL, 3.0 eq.) was added to the mixture at 0° C. The mixture was stirred at 0° C. for 30 minutes. The reaction mixture was added to a solution of Compound 40 (600 mg, 1.135 mmol, 1.0 eq.) in 5 mL of DCM at 0° C. The reaction mixture was stirred at 0° C., and warmed to room temperature overnight. The reaction mixture was then extracted using DCM (3×)/saturated NaHCO$_3$ solution. The organic layer was dried (Na$_2$SO$_4$) and concentrated. The residue was purified using silica gel chromatography (4-8% MeOH/DCM) to give white solid (557 mg, 56%). LC-MS shows 871.1 (M+H)$^+$. $^1$H NMR (300 MHz, CDCl$_3$): δ 8.78 (d, 1H), 7.94 (d, 2H), 7.78 (m, 2H), 7.42 (d, 2H), 7.22 (m, 1H), 7.18 (d, 2H), 6.80 (d, 2H), 6.50 (d, 1H), 5.52 (d, 1H), 5.38 (d, 1H), 4.20 (m, 6H), 4.00 (m, 2H), Scheme 15

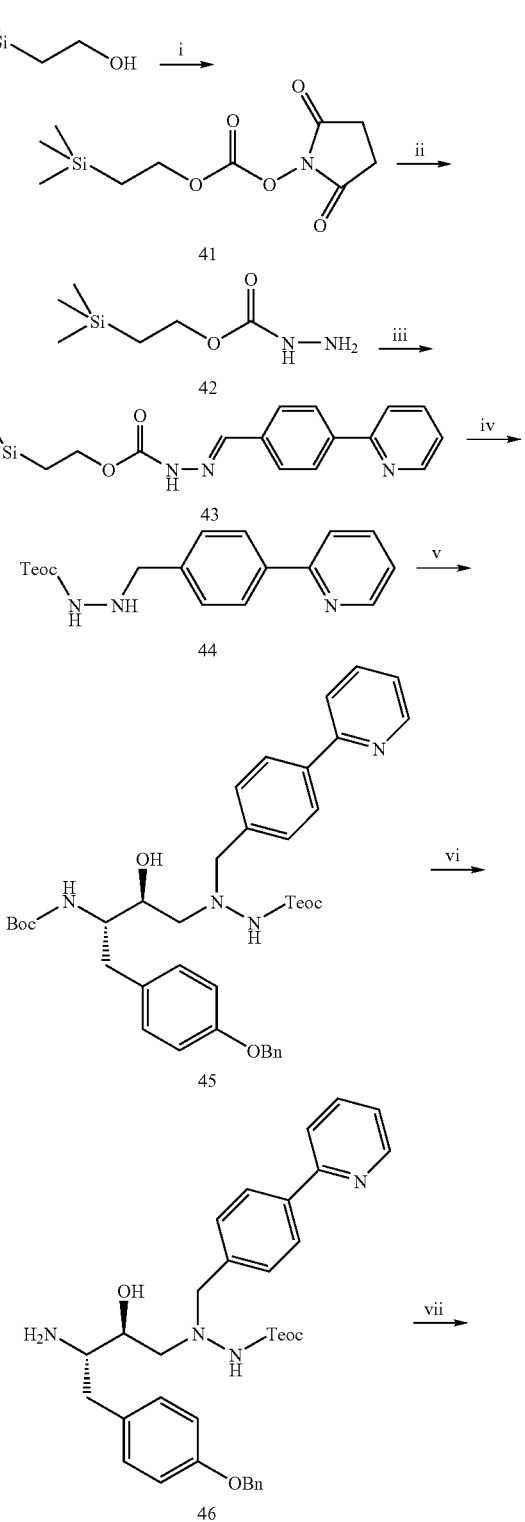

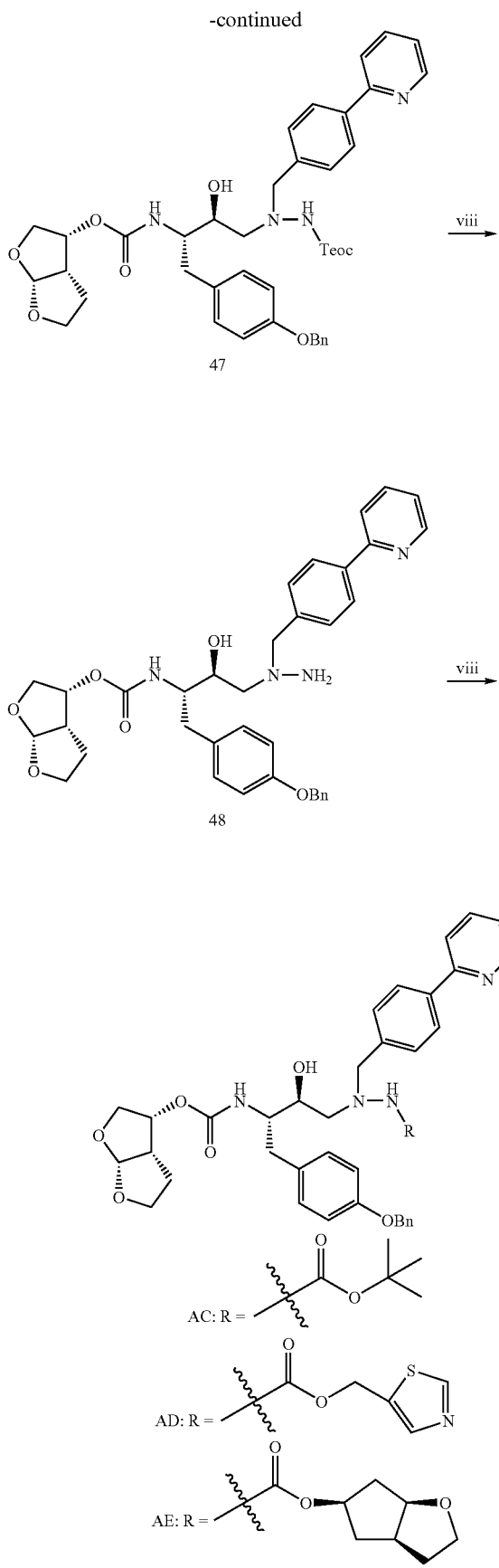

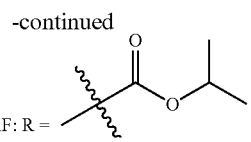

Reagents and conditions: i. Di-succinimidy carbonate, MeCn, TEA; ii. hydrazine, THF, 0° C.; iii. 4-pyridin-2-yl-benzaldehyde, EtOH; iv. a. sodium cyanoborohydride, THF, toluene-4-sulfonic acid; b. 1N NaOH, THF, MeOH; v. IPA, epoxide, 65° C.; vi. 1N HCl, 0° C.; vii. MeCN, DIEA, DMAP, Compound 70; viii. TFA, DCM, 0° C.; viiii. a(for AC). DMP, TEA, di-tert-butyl dicarbonate; b(for AD and AE). MeCN, DIEA, DMAP, carbonate; c (for AF). DCM, DIEA, acid chloride.

Compound 41

TEA (21.9 mL, 155.6 mmol, 3.0 eq.) was added to 2-trimethylsilanyl-ethanol (7.4 mL, 51.88 mmol, 1.0 eq.) in 260 mL MeCN, followed by di-succinimidyl carbonate (20 g, 1.5 eq.). The reaction mixture was stirred at room temperature for 3 hours. The reaction mixture was concentrated and extracted using EtOAc/saturated $NaHCO_3$. The organic layer was concentrated after dried over $Na_2SO_4$. Ether (100 mL) was added to the residue to form a precipitate. The precipitate was filtered and dried to give Compound 41 as a white solid (11.1 g, 84%). $^1$H NMR (300 MHz, $CDCl_3$): δ 4.42 (t, 3H), 2.82 (s, 4H), 1.16 (t, 2H), 0.1 (s, 9H).

Compound 42

Hydrazine monohydrate (5.73 mL, 115.6 mmol, 5.0 eq.) was added to Compound 41 (6 g, 23.13 mmol, 1.0 eq.) in 50 mL THF at 0° C. A precipitate formed. The reaction was monitored by $^1$H NMR. The reaction was complete after 2 hours. The reaction mixture was concentrated and extracted using EtOAc/saturated $NaHCO_3$ (1×) and brine (1×). The organic layer was concentrated and dried over $Na_2SO_4$ to give Compound 42 as a white solid (3.23 g, 79%). $^1$H NMR (300 MHz, $CDCl_3$): δ 5.84 (b, 1H), 4.20 (t, 2H), 1.00 (t, 2H), 0.1 (s, 9H).

Compound 43

4-Pyridin-2-yl-benzaldehyde (3.35 g, 18.3 mmol, 1.0 eq.) was added to Compound 42 (3.23 g, 18.3 mmol, 1.0 eq.) in 30 mL EtOH at room temperature. The reaction mixture was stirred at room temperature for 15 hours. The reaction mixture was concentrated and extracted using EtOAc/saturated $NaHCO_3$ (2×) and brine (1×). The organic layer was concentrated after dried over $Na_2SO_4$. The residue was re-crystallized (hexane/EtOAc) to give Compound 43 as a white solid (5.13 g, 82%). LC-MS shows 342.1 $(M+H)^+$.

Compound 44

Sodium cyanoborohydride (990 mg, 15.75 mmol, 1.05 eq.) was added to Compound 43 (5.13 g, 15.0 mmol, 1.0 eq.) in 30 mL THF at room temperature, followed by toluene-4-sulfonic acid monohydrate (2.85 g, 1.0 eq.). The reaction mixture was stirred at room temperature for 15 hours. The reaction mixture was concentrated. THF (20 mL) and MeOH (4 mL) mixture was added to the residue. 1N NaOH (82 mL, 5.5 eq.) was added to the above suspension at 0° C., dropwise. The reaction was stirred at 0° C. for 1 hour. The reaction mixture was extracted using EtOAc/brine (2×). The organic layer was concentrated and dried over $Na_2SO_4$. The residue was purified by silica gel chromatography (30-60% EtOAc/hexane) to give Compound 44 as a white solid (4.4 g, 86%). LC-MS shows 343.9 $(M+H)^+$.

Compound 45

Isopropanol (15 mL) was added to Compound 44 (1.96 g, 5.72 mmol, 1.0 eq.) and the epoxide ([2-(4-benzyloxy-phenyl)-1-oxiranyl-ethyl]-carbamic acid tert-butyl ester, purchased from Acme Bioscience) (2.11 g, 1.0 eq.). The reaction mixture was heated to 65° C. for 17 hours. The reaction mixture was concentrated and purified by silica gel chromatography (30-60% EtOAc/hexane) to give Compound 45 as a white solid (1.5 g, 47%). LC-MS shows 735.2 (M+Na)+.

Compound 46

1N HCl in MeCN (acetonitrile); 24 mL, excess) was added to Compound 45 (360 mg, 0.505 mmol) at 0° C. The reaction mixture was stirred at 0° C. for 2.5 hours. The reaction mixture was quenched by adding 22 mL 1N NaOH solution at 0° C. The reaction mixture was extracted using EtOAc/saturated NaHCO$_3$. The organic layer was concentrated and purified by silica gel chromatography (2-10% MeOH/DCM) to give Compound 46 as a white solid (285 mg, 92%). LC-MS shows 635.2 (M+Na)+.

Compound 47

DIEA (162 µL, 0.93 mmol, 2.0 eq.) was added to Compound 46 (285 mg, 0.465 mmol, 1.0 eq.) in 10 mL MeCN at 0° C., followed by bis-furan carbonate (carbonic acid hexahydro-furo[2,3-b]furan-3-yl ester 4-nitro-phenyl ester, prepared according to Miller et al Bioorg. Med. Chem. Lett. 2005, 15, 3496-3500) (144 mg, 1.05 eq.) and DMAP (11.5 mg, 0.2 eq.). The reaction mixture was stirred at 0° C. and warmed to room temperature overnight. The reaction mixture was extracted using EtOAc/saturated NaHCO$_3$ (3×). The organic layer was concentrated and purified by silica gel chromatography (20-80% EtOAc/hexane) to give Compound 47 as a white solid (276 mg, 77%). LC-MS shows 791.2 (M+Na)+.

Compound 48

TFA (3 mL) was added to Compound 47 (268 mg, 0.37 mmol) in 10 mL DCM at 0° C. The reaction mixture was stirred at 0° C. for 3 hours. The reaction mixture was concentrated and extracted using EtOAc/saturated NaHCO$_3$ (2×). The organic layer was concentrated to give Compound 48 as the white solid (211 mg, 89%). LC-MS shows 625.2 (M+H)+.

Example AC

TEA (14 µL, 0.10 mmol, 2.0 eq.) was added to Compound 48 (32 mg, 0.05 mmol) in 0.2 mL DMF at room temperature, followed by di-tert-butyl dicarbonate (17 mg, 1.5 eq.). The reaction mixture was stirred at room temperature for 2 hours. The reaction mixture was extracted using EtOAc/saturated NaHCO$_3$ (2×) and brine (1×). The organic layer was concentrated and purified by silica gel chromatography (2-10% MeOH/DCM) to give Example AC as a white solid (9.6 mg, 89%). LC-MS shows 725.2 (M+H)+. $^1$H NMR (300 MHz, CDCl$_3$): δ 8.70 (d, 1H), 8.0 (d, 2H), 7.78 (m, 2H), 7.40 (m, 7H), 7.24 (m, 1H), 7.15 (d, 2H), 6.84 (d, 2H), 5.62 (d, 1H), 5.36 (b, 2H), 5.02 (m, 4H), 3.65-4.16 (m, 8H), 2.84 (m, 1H), 2.57 (m, 2H), 1.68 (m, 2H), 1.38 (s, 9H).

Example AD

DIEA (12 µL, 0.07 mmol, 2.0 eq.) was added to Compound 48 (22 mg, 0.035 mmol) in 0.2 mL MeCN at 0° C., followed by carbonic acid 4-nitro-phenyl ester thiazol-5-ylmethyl ester (11 mg, 1.05 eq.) and DMAP (2 mg, 0.5 eq.). The reaction mixture was stirred at 0° C. and warmed up to room temperature overnight. The reaction mixture was extracted using EtOAc/saturated NaHCO$_3$ (2×) and brine (1×). The organic layer was concentrated and purified by silica gel chromatography (2-10% MeOH/DCM) to give Example AD as a white solid (4.0 mg, 15%). LC-MS shows 766.2 (M+H)+. $^1$H NMR (300 MHz, CDCl$_3$): δ 8.70 (m, 2H), 7.94 (d, 2H), 7.78 (m, 3H), 7.40 (m, 7H), 7.24 (m, 1H), 7.15 (d, 2H), 6.84 (d, 2H), 5.62 (d, 1H), 5.22 (s, 2H), 5.03 (m, 4H), 3.65-4.16 (m, 8H), 2.84 (m, 4H), 2.62 (m, 2H), 1.68 (m, 2H).

Example AE

DIEA (17 µL, 0.10 mmol, 2.0 eq.) was added to Compound 48 (31 mg, 0.05 mmol) in 0.2 mL MeCN at 0° C., followed by carbonic acid hexahydro-cyclopenta[b]furan-5-yl ester 4-nitro-phenyl ester (16 mg, 1.05 eq.), prepared according to WO03/078438A1, and DMAP (1.2 mg, 0.2 eq.). The reaction was stirred at 0° C., warmed up to room temperature overnight. The reaction mixture was extracted using EtOAc/saturated NaHCO3 (2×) and brine (1×). The organic layer was concentrated and purified by silica gel chromatography (2-10% MeOH/DCM) to give Example AE as a white solid (4.6 mg, 12%). LC-MS shows 779.2 (M+H)+. $^1$H NMR (300 MHz, CD$_3$OD): δ 8.78 (d, 2H), 8.40 (m, 1H), 8.23 (d, 1H), 7.94 (d, 2H), 7.80 (m, 1H), 7.63 (d, 2H), 7.40 (m, 5H), 7.18 (d, 2H), 6.84 (d, 2H), 5.62 (d, 1H), 5.06 (s, 2H), 4.95 (m, 2H), 4.40 (m, 1. H), 3.65-4.16 (m, 6H), 2.84 (m, 6H), 2.02 (m, 4H), 1.64 (m, 5H).

Example AF

DIEA (16 µL, 0.92 mmol, 2.0 eq.) was added to Compound 48 (29 mg, 0.046 mmol) in 0.6 mL DCM at 0° C., followed by isopropyl chloroformate (16 µL, 1.06 eq.). The reaction mixture was stirred at 0° C. for 4 hours. The reaction mixture was concentrated and purified by reverse phase HPLC (Phenomenex Synergi® column, 0.05% TFA in MeCN/water) to give Example AF as a white solid (2.3 mg, 7%). LC-MS shows 711.2 (M+H)+. $^1$H NMR (300 MHz, CD$_3$OD): δ 8.78 (d, 2H), 8.40 (m, 1H), 8.23 (d, 1H), 7.94 (d, 2H), 7.80 (m, 1H), 7.63 (d, 2H), 7.40 (m, 5H), 7.18 (d, 2H), 6.84 (d, 2H), 5.62 (d, 1H), 5.06 (s, 2H), 4.98 (m, 1H), 4.75 (m, 1H), 3.65-4.16 (m, 8H), 2.84 (m, 5H), 1.58 (m, 2H), 1.10 (m, 6H).

Preparation of Examples AG, AH, AI, AJ, AK, and AL

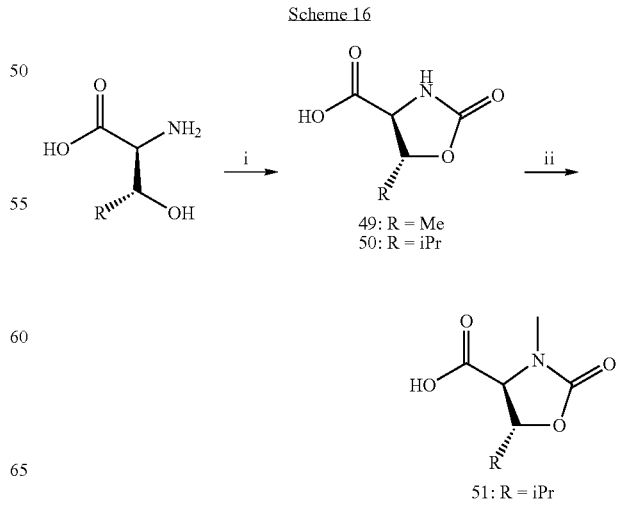

Scheme 16

49: R = Me
50: R = iPr

51: R = iPr

-continued

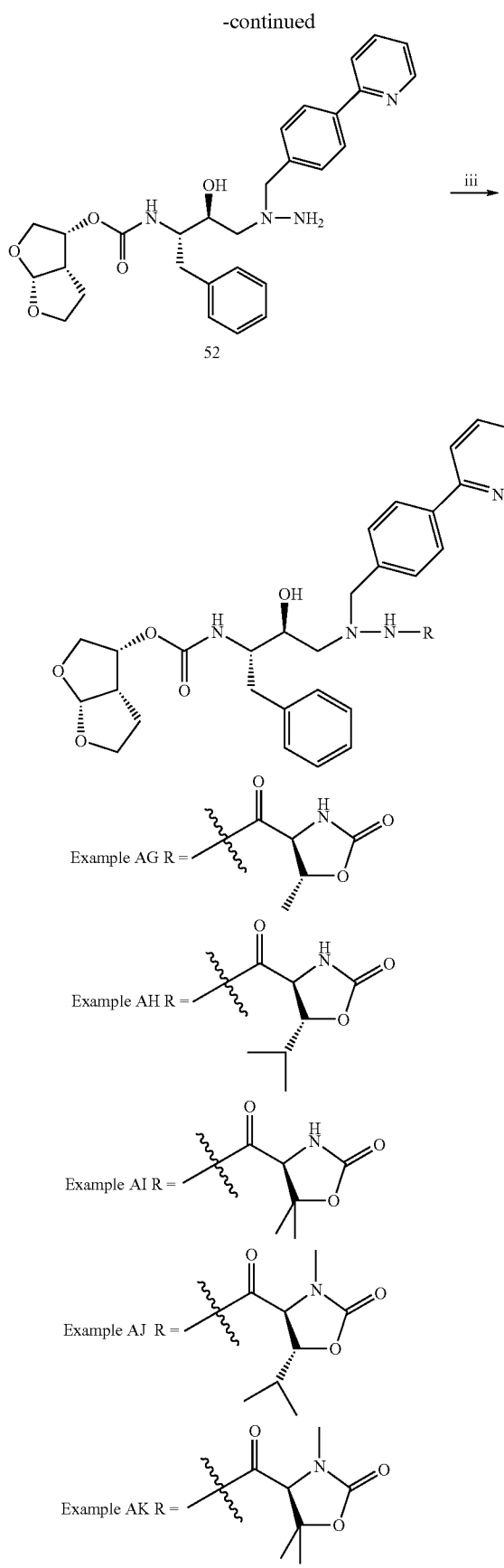

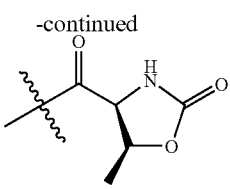

Example AL R =

Reagents and conditions: i. methyl chloroformate, 1 N NaOH, dioxane, 80° C. o/n; ii. a. MeI, Ag₂O, DMF; b. 1 N NaOH, MeOH; iii. DMF, DIEA, TPTU, carboxylic acid (described in the procedures).

Compound 49

1N NaOH Aqueous solution (24 mL, 4.0 eq.) was added to a suspension of L-threonine (705 mg, 5.92 mmol, 1.0 eq.) in anhydrous dioxane (2 mL) at room temperature, followed by methyl chloroformate (0.91 mL, 2.0 eq.), dropwise. The reaction mixture was heated to 80° C. overnight. The reaction mixture was acidified to pH 2. The mixture was extracted by EtOAc (2×). The organic layers were combined and concentrated to give Compound 49 as the colorless oil (460 mg, 54%). ¹H NMR (300 MHz, CD₃OD): δ 4.71 (tt, 1H), 4.04 (d, 1H), 1.50 (d, 3H).

Compound 50

Compound 50 was prepared using a procedure similar to that used to prepare Compound 49 using (2R,3S)-(−)-2-amino-3-hydroxy-4-methylpentanoic acid (260 mg, 1.77 mmol). Compound 50 was isolated as a colorless oil (304 mg, 99%). ¹H NMR (300 MHz, CD₃OD): δ 4.40 (dd, 1H), 4.32 (d, 1H), 2.00 (m, 1H), 1.02 (d, 6H).

Compound 51

MeI (265 μL, 8.0 eq.) was added to Compound 50 (92 mg, 0.531 mmol, 1.0 eq.) in DMF (1.5 mL) at room temperature, followed by silver oxide (492 mg, 4.0 eq.). The reaction mixture was stirred at room temperature for 5 hours. The reaction mixture was filtered through CELITE. Chloroform (100 mL) was added to the reaction mixture and was then extracted with water (2×). The organic layer was dried over Na₂SO₄ and concentrated to give a light yellow solid (91 mg, 85%). ¹H NMR (300 MHz, CD₃OD): δ 4.25 (m, 2H), 3.82 (s, 3H), 2.90 (s, 3H), 1.95 (m, 1H), 1.10 (d, 6H). The crude product was dissolved in 1 mL MeOH. 1 N NaOH (1 mL, 2.0 eq.) was added. The reaction mixture was stirred at room temperature for 1 hour. The reaction mixture was lyophilized to give Compound 51 as a white solid (141 mg, sodium salt). ¹H NMR (300 MHz, CD₃OD): δ 4.20 (t, 1H), 3.82 (d, 1H), 2.86 (s, 3H), 1.95 (m, 1H), 1.00 (dd, 6H).

Example AG

TPTU (21 mg, 1.2 eq.) was added to Compound 49 (10 mg, 1.2 eq.) in 0.5 mL DMF at 0° C. The mixture was stirred at 0° C. for 5 minutes. Compound 52 (28 mg, 0.054 mmol, 1.0 eq.) and DIEA (20 μL, 2.0 eq.) was added. The reaction mixture was stirred at 0° C. for 1 hour. The reaction mixture was purified by reverse phase HPLC (Phenomenex Synergi® column, 0.05% TFA in MeCN/water) and silica gel chromatography (2-8% MeOH/DCM) to give Example AG as a white solid (10.5 mg, 30%). LC-MS shows 646.2 (M+H)⁺. ¹H NMR (300 MHz, CD₃OD): δ 8.60 (d, 1H), 7.90 (m, 5H), 7.56

(d, 2H), 7.38 (m, 1H), 7.22 (m, 3H), 7.20 (m, 1H), 5.58 (d, 1H), 4.98 (m, 2H), 3.64-4.14 (m, 8H), 2.84 (m, 6H), 1.50 (m, 2H), 1.10 (d, 3H).

Example AH

Example AH was prepared using procedures similar to those used to prepare Compound AG, using Compound 52 (27 mg, 0.052 mmol, 1.0 eq.) and Compound 50 to give Example AH as a white solid (10.4 mg, 30%). LC-MS shows 674.2 (M+H)$^+$. $^1$H NMR (300 MHz, CD$_3$OD): δ 8.60 (d, 1H), 7.90 (m, 5H), 7.56 (d, 2H), 7.38 (m, 1H), 7.22 (m, 3H), 7.20 (m, 1H), 5.58 (d, 1H), 4.98 (m, 1H), 3.64-4.14 (m, 9H), 2.84 (m, 6H), 1.50 (m, 3H), 0.88 (dd, 6H).

Example AI

Example AI was prepared using procedures similar to those used to prepare Compound AG, using Compound 52 (25 mg, 0.048 mmol, 1.0 eq.) and 5,5-dimethyl-2-oxo-oxazolidine-4-carboxylic acid to give Example AI as a white solid (8.5 mg, 27%). LC-MS shows 660.2 (M+H)$^+$. $^1$H NMR (300 MHz, CD$_3$OD): δ 8.60 (d, 1H), 7.90 (m, 5H), 7.56 (d, 2H), 7.38 (m, 1H), 7.22 (m, 3H), 7.20 (m, 1H), 5.58 (d, 1H), 4.98 (m, 1H), 3.64-4.14 (m, 9H), 2.84 (m, 5H), 1.50 (m, 2H), 1.42 (s, 3H), 0.92 (s, 3H).

Example AJ

Example AJ was prepared using procedures similar to those used to prepare Compound AG, using Compound 52 (20 mg, 0.038 mmol, 1.0 eq.) and Compound 51 to give Example AJ as a white solid (12.5 mg, 47%). LC-MS shows 688.2 (M+H)$^+$. $^1$H NMR (300 MHz, CD$_3$OD): δ 8.60 (d, 1H), 7.90 (m, 5H), 7.56 (d, 2H), 7.38 (m, 1H), 7.22 (m, 3H), 7.20 (m, 1H), 5.58 (d, 1H), 4.98 (m, 1H), 3.64-4.14 (m, 9H), 2.84 (m, 9H), 1.50 (m, 3H), 0.88 (dd, 6H).

Example AK

Example AK was prepared using procedures similar to those used to prepare Compound AG, using Compound 52 (24 mg, 0.046 mmol, 1.0 eq.) and 3,5,5-trimethyl-2-oxo-oxazolidine-4-carboxylic acid (prepared in a manner similar to that used to prepare Compound 51) to give Example AK as a white solid (4.2 mg, 14%). LC-MS shows 674.2 (M+H)$^+$. $^1$H NMR (300 MHz, CD$_3$OD): δ 8.60 (d, 1H), 7.90 (m, 5H), 7.56 (d, 2H), 7.38 (m, 1H), 7.22 (m, 3H), 7.20 (m, 1H), 5.58 (d, 1H), 4.98 (m, 1H), 3.64-4.14 (m, 9H), 2.84 (m, 8H), 1.50 (m, 2H), 1.42 (s, 3H), 0.92 (s, 3H).

Example AL

Example AL was prepared using procedures similar to those used to prepare Compound AG, using Compound 52 (28 mg, 0.054 mmol, 1.0 eq.) and 5-methyl-2-oxo-oxazolidine-4-carboxylic acid (prepared using procedures similar to those used to prepare Compound 49, using L-allo-threonine) to give Example AL as a white solid (12 mg, 34%). LC-MS shows 646.2 (M+H)$^+$. $^1$H NMR (300 MHz, D$_6$-DMSO): δ 9.32 (s, 1H), 8.60 (d, 1H), 8.02 (d, 2H), 7.83 (m, 3H), 7.42 (d, 2H), 7.35 (m, 1H), 7.15 (d, 2H), 5.58 (d, 1H), 4.82 (m, 1H), 3.54-4.14 (m, 10H), 2.80 (m, 5H), 1.40 (m, 2H), 0.86 (dd, 3H).

Preparation of Examples AM and AN

Scheme 17

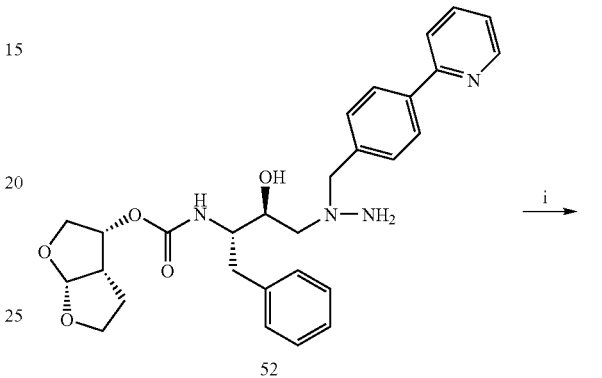

52

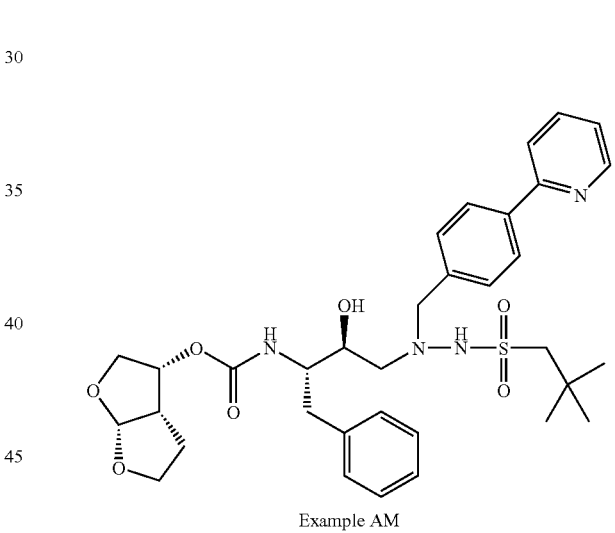

Example AM

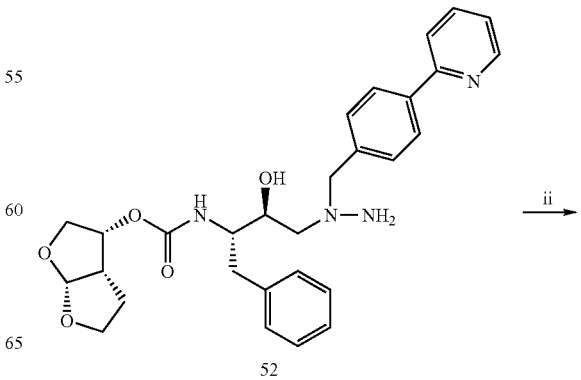

52

-continued

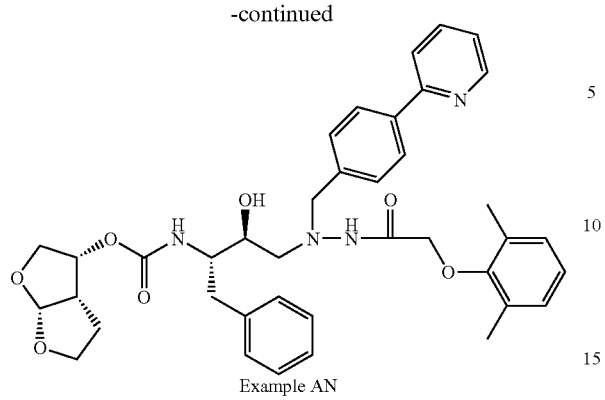

Example AN

Reagents and conditions: i. 2,2-Dimethyl-propane-1-sulfonyl chloride, THF, sat. NaHCO₃, r.t.; ii. DMF, DIEA, TPTU, acid.

Example AM 2,2-Dimethyl-propane-1-sulfonyl chloride was added to Compound 52 (23 mg, 0.044 mmol, 1.0 eq.) in a mixture of THF: saturated sodium bicarbonate aqueous solution (0.7 mL: 0.7 mL). The reaction mixture was stirred at room temperature overnight. The mixture was concentrated and extracted using EtOAc/sat. NaHCO₃. The organic layer was concentrated and purified by silica gel chromatography (2-8% MeOH/DCM) to give Example AM as a white solid (8 mg, 28%). LC-MS shows 653.1 (M+H)⁺. ¹H NMR (300 MHz, CD₃OD): δ 8.70 (d, 1H), 8.18 (m, 1H), 8.00 (m, 3H), 7.64 (d, 2H), 7.60 (m, 1H), 7.46 (m, 1H), 7.26 (m, 4H), 5.58 (d, 1H), 4.98 (m, 1H), 3.64-4.44 (m, 10H), 3.24 (m, 2H), 2.84 (m, 3H), 1.50 (m, 2H), 1.20 (s, 9H).

Example AN

TPTU (1.5 mg, 1.3 eq.) was added to (2,6-dimethyl-phenoxy)-acetic acid (9 mg, 1.3 eq.) in 0.5 mL DMF at 0° C. The mixture was stirred at 0° C. for 5 minutes. Compound 52 (20 mg, 0.038 mmol, 1.0 eq.) and DIEA (14 µL, 2.0 eq.) were added. The reaction mixture was stirred at 0° C. for 1 hour. The reaction mixture was purified by reverse phase HPLC (Phenomenex Synergi® column, 0.05% TFA in MeCN/water) and silica gel chromatography (2-8% MeOH/DCM) to give Example AN as a white solid (6 mg, 23%). LC-MS shows 681.2 (M+H)⁺. ¹H NMR (300 MHz, CD₃OD): δ 8.60 (d, 1H), 7.90 (m, 4H), 7.60 (d, 2H), 7.38 (m, 1H), 7.24 (m, 4H), 7.18 (m, 1H), 6.90 (m, 3H), 5.58 (d, 1H), 4.98 (m, 1H), 4.12 (m, 3H), 3.64-4.10 (m, 7H), 2.84 (m, 5H), 1.55 (m, 2H).

Preparation of Examples AO AP, and AQ

Scheme 18

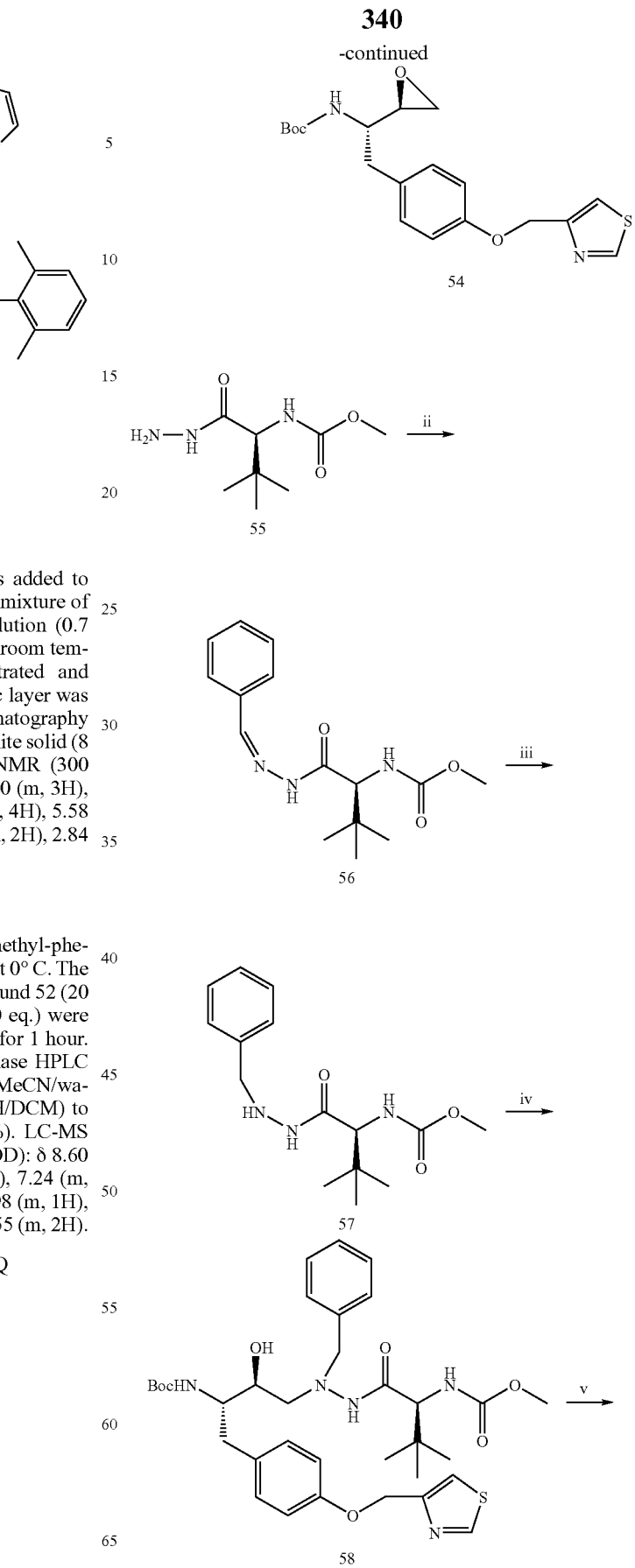

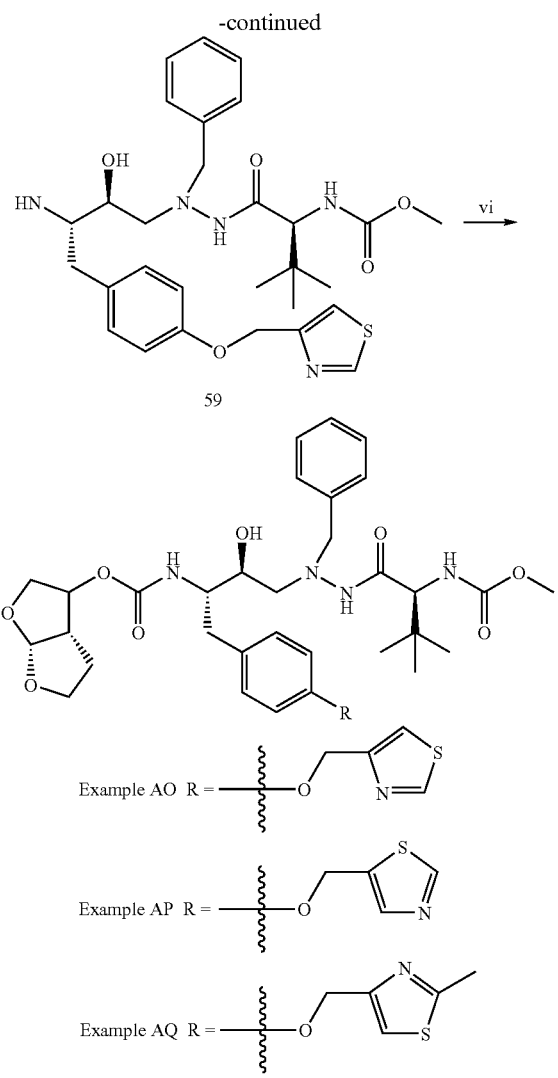

Reagents and conditions: i. Thiazol-4-ylmethanol, PPh3, DCM, di-tert-butyl azodicarboxylate; ii. PhCHO, IPA, 80° C.; iii.a. NaCNBH3, p-TsOH, THF; b, Na2B4O7, THF, water; iv. 54, IPA, 0.8 eq. HOAc; v. TFA, DCM; vi. Compound 70, DCM, DIEA, DMAP.

Compound 54

Di-tert-butyl azodicarboxylate (280 mg, 1.2 mmol, 2.0 eq.) was added to Compound 53, prepared by hydrogenation of (S)-t-butyl 2-(4-benzyloxyphenyl)-1-(R)-oxiran-2-yl)ethyl carbamate, purchased from Acme Bioscience, (170 mg, 0.6 mmol, 1.0 eq.) and thiazol-4-yl-methanol (140 mg, 2.0 eq.) in 4 mL DCM, followed by triphenyl-phosphane (320 mg, 2.0 eq.). The reaction mixture was stirred at room temperature overnight. The reaction mixture was concentrated. The residue was purified by silica gel chromatography (20-80% EtOAc/hexane) to give Compound 54 as a white solid (120 mg, 50%). $^1$H NMR (300 MHz, CDCl$_3$): δ 8.82 (s, 1H), 7.40 (s, 1H), 7.20 (d, 2H), 6.92 (d, 2H), 5.24 (s, 2H), 4.44 (m, 1H), 4.06 (m, 1H), 3.0 (m, 1H), 2.84 (m, 2H), 2.58 (m, 1H), 1.4 (s, 9H).

Compound 56

Benzylaldehyde (0.72 mL, 7.09 mmol, 1.0 eq.) was added to Compound 55 (prepared followed the procedure of *Journal of Medicinal Chemistry*, 1998, 41, 3399) (1.442 g, 7.09 mmol, 1.0 eq.) in 50 mL IPA. The reaction mixture was heated to 80° C. for 15 hours. The reaction mixture was cooled to room temperature and concentrated. The residue was re-crystallized (6 mL EtOAc, 15 mL hexane) to give Compound 56 as a white solid (1.67 g, 81%). LC-MS shows 292.2 (M+H)$^+$.

Compound 57

Sodium cyanoborohydride (1.47 g, 23.3 mmol, 3.0 eq.) was added to Compound 56 (2.26 g, 7.77 mmol, 1.0 eq.) in 250 mL of THF, followed by toluene-4-sulfonic acid monohydrate (4.43 g, 3.0 eq.) in 20 mL of THF, dropwise. The reaction mixture was stirred at room temperature for 15 hours. The reaction was filtered through a CELITE pad. The filtrate was extracted by EtOAc/sat. NaHCO$_3$ (1×) and brine (1×). The organic layer was concentrated. The residue was dissolved in a THF (100 mL) and water (100 mL) mixture. Sodium tetraborate decahydrate (3.63 g, 4.2 eq.) was added to the solution. The reaction mixture was stirred at room temperature overnight. The reaction mixture was extracted with EtOAc/sat. NaHCO$_3$ (2×) and brine (1×). The organic layer was concentrated and purified by silica gel chromatography (40-80% EtOAc/hexane) to give Compound 57 as a white solid (1.44 g, 63%). LC-MS shows 294.0 (M+H)$^+$.

Compound 58

Acetic acid (15 µL, 0.27 mmol, 0.8 eq.) was added to Compound 57 (99 g, 0.337 mmol, 1.0 eq.) and Compound 54 (127 mg, 1.0 eq.) in 2.5 mL IPA. The reaction mixture was heated to 80° C. for 22 hours. The reaction mixture was cooled to room temperature and concentrated. The residue was purified by silica gel chromatography (40-80% EtOAc/hexane) to give Compound 58 as a white solid (146 mg, 65%). LC-MS shows 670.7 (M+H)$^+$.

Compound 59

TFA (3 mL) was added to Compound 58 (146 mg, 0.218 mmol) in 10 mL DCM at 0° C. The reaction mixture was stirred at 0° C. for 90 minutes. The reaction mixture was concentrated and extracted with EtOAc/sat.NaHCO$_3$ (2×). The organic layer was dried over Na$_2$SO$_4$ and concentrated to give Compound 59 as a white solid (117 mg, 94%). LC-MS shows 570.7 (M+H)$^+$.

Example AO

DIEA (107 µL, 0.61 mmol, 3.0 eq.) was added to Compound 59 (117 mg, 0.205 mmol, 1.0 eq.) and Compound 70 (67 mg, 1.1 eq.) in 2.5 mL DCM, followed by DMAP (5 mg, 0.2 eq.). The reaction mixture was stirred at room temperature for 15 hours. The reaction mixture was concentrated and extracted with EtOAc/sat.NaHCO$_3$. The organic layer was concentrated and purified by silica gel chromatography (4-8% MeOH/DCM), followed by prep HPLC (Phenomenex Synergi® column, 0.5% TFA in MeCN/water) to give Example A$^o$ as a white solid (14 mg, 9%). LC-MS shows 726.2 (M+H)$^+$. $^1$H NMR (300 MHz, CDCl$_3$): δ 8.96 (s, 1H), 8.42 (s, 1H), 7.32 (m, 5H), 7.12 (d, 2H), 6.84 (d, 2H), 5.63 (d, 1H), 5.38 (d, 2H), 5.22 (s, 2H), 5.02 (m, 1H), 3.58-4.16 (m, 10H), 2.84 (m, 4H), 2.62 (m, 1H), 1.65 (m, 2H), 0.78 (s, 9H).

Example AP

Example AP was prepared using procedures similar to those used to prepare example AO, using thiazol-5-yl-methanol as a starting material. LC-MS of the product shows 726.1 (M+H)$^+$. $^1$H NMR (300 MHz, CDCl$_3$): δ 8.96 (s, 1H), 7.94 (s, 1H), 7.32 (m, 5H), 7.12 (d, 2H), 6.82 (d, 2H), 5.63 (d, 1H), 5.38 (m, 4H), 5.02 (m, 1H), 3.58-4.16 (m, 10H), 2.84 (m, 4H), 2.62 (m, 1H), 1.65 (m, 2H), 0.78 (s, 9H).

Example AQ
Example AQ was prepared using procedures similar to those used to prepare example AO, using (2-methyl-thiazol-4-yl)-methanol as a starting material. LC-MS of the product shows 740.2 (M+H)+. $^1$H NMR (300 MHz, CDCl$_3$): δ 7.32 (m, 5H), 7.20 (s, 1H), 7.12 (d, 2H), 6.82 (d, 2H), 5.63 (d, 1H), 5.34 (d, 2H), 5.16 (s, 2H), 5.02 (m, 1H), 3.58-4.16 (m, 10H), 2.84 (m, 4H), 2.75 (s, 3H), 2.62 (m, 1H), 1.65 (m, 2H), 0.78 (s, 9H).
Preparation of Examples AR, AS, AT, and AU
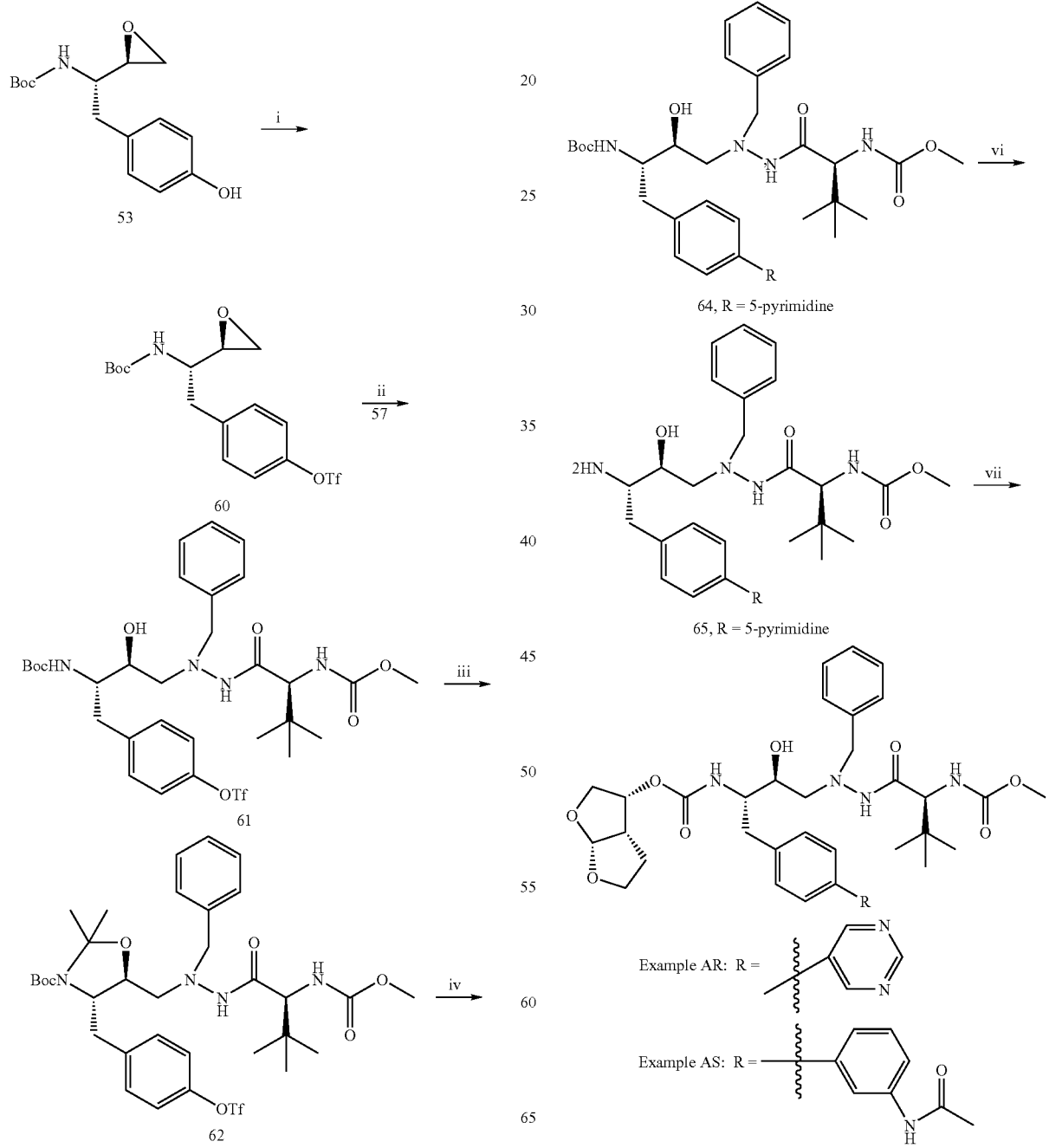

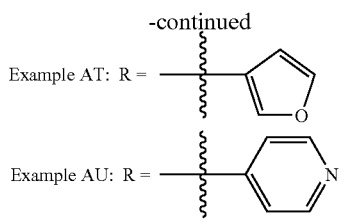

Example AT: R =

Example AU: R =

Reagents and conditions; i. Cs₂CO₃, DCM, N-phenyltrifluoromethanesulfonimde; ii. HOAc, IPA, 80° C.; iii. a. 2,2-dimethoxy propane, R-(-)-10-camphorsulfonic acid, acetone; iv. boronic acid, PdCl₂(dppf), DME, aq. Na₂CO₃; v. 1% TFA in MeCN/H₂O (1:1); vi TFA, DCM; vii. Compound 70, MeCN, DIEA, DMAP.

Compound 60

N-phenyltrifluoromethanesulfonimide (3.336 g, 9.337 mmol, 1.1 eq.) was added to Compound 53 (2.37 g, 8.488 mmol, 1.0 eq.) in 100 mL DCM, followed by Cs₂CO₃ (3.04 g, 1.1 eq.). The reaction mixture was stirred at room temperature for 12 hours. The reaction mixture was filtered through CELITE and concentrated. The residue was purified by silica gel chromatography (30-60% EtOAc/hexane) to give Compound 60 as the white solid (3.2 g, 92%). ¹H NMR (300 MHz, CDCl₃): δ 7.37 (d, 2H), 7.20 (d, 2H), 4.50 (m, 1H), 4.18 (m, 1H), 3.03 (m, 1H), 2.98 (m, 2H), 2.85 (m, 1H), 2.62 (m, 1H), 1.39 (s, 9H).

Compound 61

Acetic acid (0.23 mL, 4.6 mmol, 0.8 eq.) was added to Compound 60 (2.088 g, 5.075 mmol, 1.0 eq.) and Compound 57 (1.489 g, 1.0 eq.) in 45 mL IPA (isopropyl alcohol). The reaction mixture was heated to 80° C. for 22 hours. The reaction mixture was cooled to room temperature and concentrated. The residue was purified by silica gel chromatography (20-80% EtOAc/hexane) to give Compound 61 as a white solid (2.5 g, 70%). LC-MS shows 705.1 (M+H)⁺.

Compound 62

2,2-Dimethylpropane (0.265 mL, 2.15 mmol, 10 eq.) and R-(-)-10-camphorsulfonic acid (55 mg, 0.237 mmol) was added to Compound 61 (152 mg, 0.215 mmol) in 5 mL acetone. The reaction mixture was refluxed for 5 hours. The reaction mixture was cooled to room temperature and concentrated. The residue was purified by silica gel chromatography (20-80% EtOAc/hexane) to give Compound 62 as a white solid (102 mg, 77%). LC-MS shows 745.1 (M+H)⁺.

Compound 63

In a 0.5-2 mL microwave reaction tube, Compound 62 (43 mg, 0.057 mmol, 1.0 eq.), 5-pyrimidine boronic acid (18 mg, 2.5 eq.), Pd(dppf)₂Cl₂ (5 mg, 0.1 eq.), 0.144 mL 2 M Na₂CO₃ aqueous solution (5.0 eq.) and 0.7 mL DME was mixed and heated in microwave at 120° C. for 5 minutes. The reaction mixture was diluted with ethyl acetate and washed with saturated NaHCO₃ solution and brine. The organic layer was concentrated and purified by silica gel chromatography (40-80% EtOAc/hexane) to give Compound 63 as a brown colored solid (11 mg, 28%). LC-MS shows 675.4 (M+H)⁺.

Compound 64

2 mL 1% TFA in MeCN:water (1:1) was added to Compound 63 (11 mg, 0.0163 mmol) and stirred at room temperature for 4 hours. The reaction mixture was lyophilized to give Compound 64 as a light brown solid. LC-MS shows 635.4 (M+H)⁺.

Compound 65

1 mL TFA was added to Compound 64 (0.0163 mmol) in 2 mL DCM. The reaction mixture was stirred at room temperature for 1 hour. The reaction mixture was concentrated. The residue was dissolve in ethyl acetate and washed with saturated NaHCO₃ solution. The organic layer was dried over Na₂SO₄ and concentrated to give Compound 65 which was used without further purification in the next reaction. LC-MS shows 535.3 (M+H)⁺.

Example AR

DIEA (6.8 μL, 0.039 mmol, 3.0 eq.) was added to Compound 65 (7 mg, 0.013 mmol, 1.0 eq.) and bis-furan carbonate (5 mg, 1.3 eq.) in 0.6 mL MeCN, followed by DMAP (0.3 mg, 0.2 eq.). The reaction mixture was stirred at room temperature overnight. The reaction mixture concentrated and extracted with EtOAc/sat.NaHCO₃. The organic layer was concentrated and purified by silica gel chromatography (4-8% MeOH/DCM), followed by prep HPLC (Phenomenex Synergi® column, 0.5% TFA in MeCN/water) to give Example AR as a white solid (5 mg, 55%). LC-MS shows 691.3 (M+H)⁺. ¹H NMR (300 MHz, CD₃OD): δ 9.14 (s, 1H), 9.06 (s, 2H), 7.62 (d, 2H), 7.42 (m, 4H), 7.24 (m, 3H), 5.58 (m, 1H), 4.96 (m, 1H), 3.58-4.16 (m, 11H), 2.84 (m, 5H), 1.52 (m, 2H), 0.78 (s, 9H).

Example AS

Example AS was prepared using procedures similar to those used to prepare Example AR, using 3-acetamidophenylboronic acid in step iv. LC-MS of the product shows 747.8 (M+H)⁺. ¹H NMR (300 MHz, CD₃OD): δ 7.83 (s, 1H), 7.21-7.56 (m, 12H), 5.58 (m, 1H), 4.96 (m, 1H), 3.58-4.16 (m, 11H), 2.84 (m, 5H), 2.07 (s, 3H), 1.52 (m, 2H), 0.78 (s, 9H).

Example AT

Example AT was prepared using procedures similar to those used to prepare Example AR, using 3-furanboronic acid in step iv. LC-MS of the product shows 679.3 (M+H)⁺. ¹H NMR (300 MHz, CD₃OD): δ 7.84 (s, 1H), 7.57 (s, 1H), 7.40 (m, 4H), 7.24 (m, 5H), 6.77 (s, 1H), 5.58 (m, 1H), 4.96 (m, 1H), 3.58-4.16 (m, 11H), 2.84 (m, 5H), 1.52 (m, 2H), 0.78 (s, 9H).

Example AU

Example AU was prepared using procedures similar to those used to prepare Example AR, using 4-pyridineboronic acid in step iv. LC-MS of the product shows 690.3 (M+H)⁺. ¹H NMR (300 MHz, CD₃OD): δ 8.68 (d, 2H), 7.98 (d, 2H), 7.76 (d, 2H), 7.42 (m, 5H), 7.23 (m, 4H), 5.58 (m, 1H), 4.96 (m, 1H), 3.58-4.16 (m, 11H), 2.84 (m, 5H), 1.52 (m, 2H), 0.78 (s, 9H).

Preparation of Examples AV, AW, and AX

Scheme 20

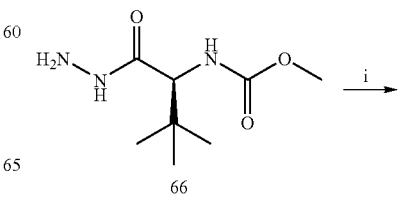

66

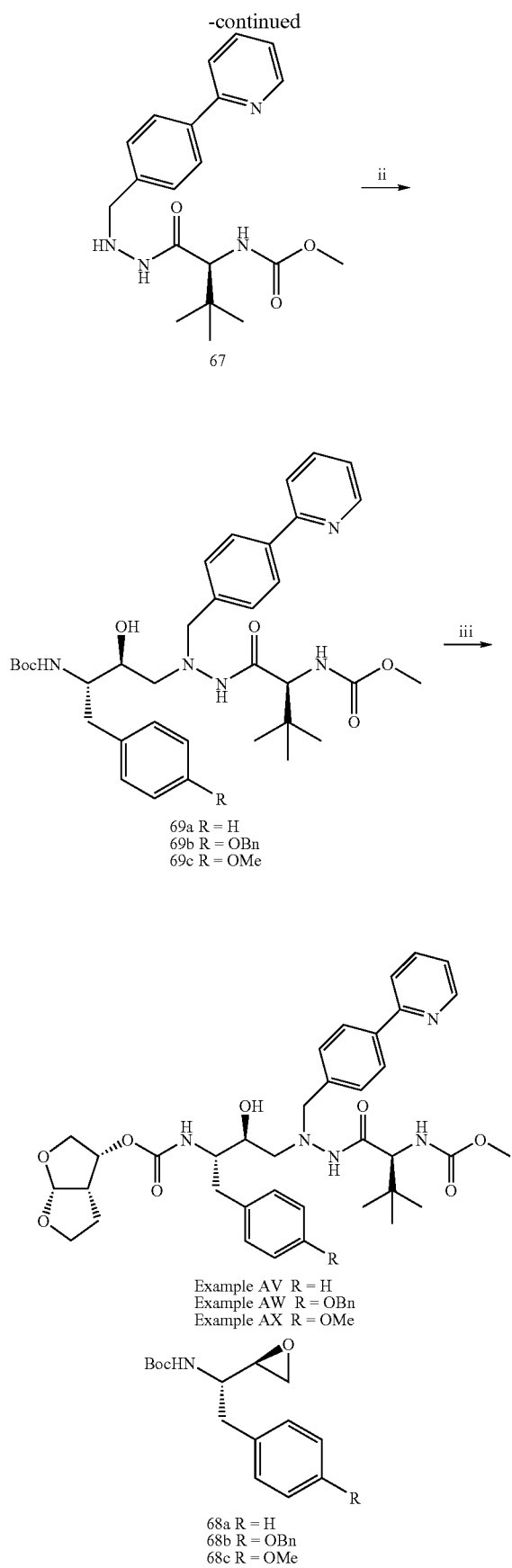
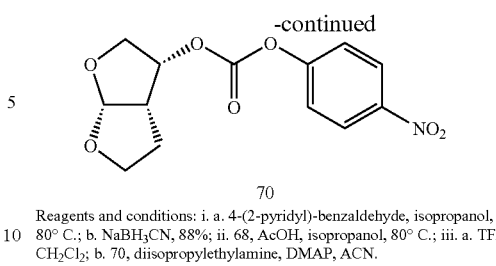

70

Reagents and conditions: i. a. 4-(2-pyridyl)-benzaldehyde, isopropanol, 80° C.; b. NaBH₃CN, 88%; ii. 68, AcOH, isopropanol, 80° C.; iii. a. TFA, CH₂Cl₂; b. 70, diisopropylethylamine, DMAP, ACN.

Compound 67

Compound 66 (7.18 g, 35.3 mmol), prepared according to Bold et al. *J. Med. Chem.* 1998, 41, 3387-3401, in isopropanol (106 mL) was treated with commercially available 4-(2-pyridyl)-benzaldehyde (4.96 g, 271 mmol) at 80° C. for 18 h. The reaction mixture was cooled to r.t., concentrated, and co-evaporated with ACN (acetonitrile) (2×) and diethyl ether (2×) gave an off-white solid (26.1 g). The solid was dissolved in THF (46 mL) and the solution was cooled to 0° C. Sodium cyanoborohydride (1.72 g, 27.4 mmol) was added, followed by dropwise addition of a solution of p-toluenesulfonic acid (5.06 g, 26.6 mmol) in THF (46 mL). The reaction mixture was warmed to r.t. overnight, then diluted with H₂O and extracted with EtOAc (3×). The combined organic layers were washed with saturated NaHCO₃ solution (2×), brine, dried (MgSO₄), and concentrated to give a yellow gum. The residue was dissolved in THF (100 mL) and H₂O (100 mL) and Na₂B₄O₇.10H₂O (21.6 g) was added. The reaction mixture was stirred overnight, diluted with EtOAc and washed with saturated NaHCO₃ solution. The aqueous layer was back-extracted with EtOAc (3×) and the combined organic layer was dried (MgSO₄), concentrated and purified (silica gel, 50 to 100% EtOAc/Hex) to give Compound 67 as a white foam (8.50 g, 22.9 mmol, 88%). Mass spectrum: 371.1 (M+H)⁺.

Compound 69a

To a solution of Compound 68a, purchased from Kaneka America Corporation, (1.20 g, 4.56 mmol) in isopropanol (5.0 mL) at 80° C. was added Compound 67 (0.563 g, 1.52 mmol) in two portions over 4 h. After stirring for 8 h at 80° C., reaction mixture was concentrated and purified (silica gel, 50 to 100% EtOAc/Hex) to give an impure product. Residue was dissolved in refluxing EtOAc and hexane was slowly added to give a cloudy solution. Allowed to cool to r.t. and product was collected by filtration to give Compound 69a as a white solid (0.340 g, 0.536 mmol, 35%). Mass spectrum: 634.3 (M+H)⁺.

Compound 69b

To a solution of Compound 68b, purchased from Acme Bioscience, Inc., (0.768 g, 2.08 mmol) in isopropanol (10.0 mL) at 80° C. was added Compound 67 (1.54 g, 4.16 mmol). After stirring for 5 h at 80° C., additional Compound 67 (0.58 g, 0.784 mmol) was added and reaction was continued for 3.5 h. The reaction mixture was cooled, concentrated and purified (silica gel chromatography, 50 to 100% EtOAc/Hex) to give Compound 69b as a white solid (0.800 g, 1.08 mmol, 52%). Mass spectrum: 740.1 (M+H)⁺.

Compound 68c

A mixture of commercially available [2-(4-Benzyloxy-phenyl)-1-oxiranyl-ethyl]-carbamic acid tert-butyl ester (0.99 g, 2.68 mmol) and 20 wt % palladium hydroxide (0.15 g) in EtOH/EtOAc (1:4, 25 mL) was stirred under a hydrogen atmosphere for 5 h. Mixture was filtered through a pad of CELITE, concentrated and purified by flash chromatography (silica gel, 25 to 60% EtOAc/Hex) to give a white solid (0.618 g, 2.21 mmol, 83%).

The above product (0.500 g, 1.79 mmol) was dissolved in acetonitrile (18 mL) and cooled to 0° C. Cesium carbonate (0.875 g, 2.685 mmol) and iodomethane (0.223 g, 3.58 mmol) was added and reaction mixture was warmed to r.t. overnight. The reaction mixture was concentrated, dissolved in EtOAc/H$_2$O and washed with brine. The organic layer was dried (MgSO$_4$), concentrated to give 68c as a while solid (0.589 g, 2.01 mmol, 83%).

Compound 69c

To a solution of Compound 68c (0.589 g, 1.486 mmol) in isopropanol (14.0 mL) at 80° C. was added Compound 67 (1.10 g, 2.97 mmol) in two portions over 2.5 h. After stirring for 2 h at 80° C., additional Compound 67 (0.30 g, 0.45 mmol) was added and reaction mixture was stirred for 2 h at 80° C., then overnight at r.t. Additional Compound 67 (0.30 g, 0.45 mmol) was added and reaction mixture was stirred for 2 h at 80° C., and then the reaction mixture was concentrated and purified (silica gel chromatography, 50 to 100% EtOAc/Hex) to give an impure product. The residue was dissolved in refluxing EtOAc and hexane was slowly added to give a cloudy solution. The solution was allowed to cool to r.t. and the product was collected by filtration to give Compound 69c as a white solid (0.659 g, 0.993 mmol, 67%). Mass spectrum: 664.3 (M+H)$^+$.

Example AV

To a solution of Compound 69a (0.340 g, 0.536 mmol) in CH$_2$Cl$_2$ (10 mL) cooled to 0° C. was added TFA (5.0 mL). The reaction mixture was stirred at 0° C. for 2 h, then concentrated and co-evaporated with CH$_2$Cl$_2$ (2×) and ACN (3×). The residue was lyophilized from ACN/H$_2$O to give a solid which was dissolved in ACN (5.4 mL) and cooled to 0° C. DMAP (6.6 mg, 0.054 mmol) and diisopropylethylamine (0.472 mL, 2.71 mmol) were added, followed by Compound 70 (0.160 g, 0.542 mmol). The reaction mixture was warmed to r.t. overnight, concentrated, dissolved in EtOAc and washed with H$_2$O (4×), 0.5M NaOH (2×), brine and dried (MgSO$_4$), then concentrated and purified (silica gel chromatography, 0 to 5% MeOH/CH$_2$Cl$_2$) to give an impure product. The residue was dissolved in refluxing EtOAc and hexane was slowly added to give a cloudy solution. The solution was allowed to cool to r.t. and the product was collected by filtration to give Example AV as a white solid (0.282 g, 0.409 mmol, 75%). $^1$H NMR (300 MHz, CD$_3$OD): δ 8.55 (d, J=4.2 Hz, 1H), 7.95-7.80 (m, 4H), 7.50 (d, J=8.1 Hz, 2H), 7.35-7.05 (m, 6H), 5.53 (d, J=5.4 Hz, 1H), 4.99-4.82 (m, 1H), 4.05-3.60 (m, 10H), 3.55 (s, 3H), 2.95-3.70 (m, 5H), 1.60-1.40 (m, 2H), 0.68 (s, 9H). Mass spectrum: 690.2 (M+H)$^+$.

Example AW

To a solution of Compound 69b (0.800 g, 1.08 mmol) in CH$_2$Cl$_2$ (20 mL) was added TFA (6.0 mL). The reaction mixture was stirred at r.t. for 1 h, then concentrated and co-evaporated with ACN (3×). The residue was dissolved in ACN (11.0 mL) and cooled to 0° C. DMAP (0.013 mg, 0.108 mmol) and diisopropylethylamine (1.764 mL, 10.1 mmol) were added, followed by Compound 70 (0.319 g, 0.108 mmol). The reaction mixture was warmed to r.t. overnight, concentrated, dissolved in EtOAc and washed with H$_2$O (4×), 0.5M NaOH (2×), brine and dried (MgSO$_4$), then concentrated and purified (silica gel chromatography, 50 to 100% EtOAc/Hex) to give Example AW as a white solid (0.664 g, 0.834 mmol, 77%). $^1$H NMR (300 MHz, CDCl$_3$): δ 8.64 (d, J=4.8 Hz, 1H), 7.90 (d, J=8.1 Hz, 2H), 7.80-7.60 (m, 2H), 7.50-7.2 (m, 7H), 7.08 (d, J=8.4 Hz, 2H), 6.82 (d, J=8.7 Hz, 2H), 6.64 (s, 1H), 5.61 (d, J=5.1 Hz, 1H), 5.28 (s, 1H), 5.25 (s, 1H), 5.03-4.90 (m, 3H), 4.80 (s, 1H), 4.15-3.55 (m, 12H), 2.95-3.60 (m, 5H), 1.60-1.40 (m, 2H), 0.69 (s, 9H). Mass spectrum: 796.2 (M+H)$^+$.

Example AX

To a solution of Compound 69c (0.250 g, 0.394 mmol) in CH$_2$Cl$_2$ (2.0 mL) was added TFA (1.0 mL). The reaction mixture was stirred at r.t. for 1 h, then concentrated and co-evaporated with ACN (3×). The residue was dissolved in ACN (5.4 mL) and cooled to 0° C. DMAP (0.005 g, 0.039 mmol) and diisopropylethylamine (0.34 mL, 1.97 mmol) were added, followed by Compound 70 (0.116 g, 0.394 mmol). The reaction mixture was warmed to r.t. overnight, concentrated, dissolved in EtOAc and washed with H$_2$O (3×), 0.5M NaOH (3×), brine and dried (MgSO$_4$), then concentrated and purified (silica gel chromatography, 50 to 100% EtOAc/Hex) to give an impure product. The residue was dissolved in refluxing EtOAc and hexane was slowly added to give a cloudy solution. The solution was allowed to cool to r.t. and the product was collected by filtration to give Example AX as a white solid (0.154 g, 0.214 mmol, 54%). $^1$H NMR (300 MHz, CD$_3$OD): δ 8.55 (d, J=4.8 Hz, 1H), 7.95-7.80 (m, 4H), 7.49 (d, J=8.4 Hz, 2H), 7.35-7.25 (m, 1H), 7.11 (d, J=8.7 Hz, 2H), 6.75 (d, J=8.4 Hz, 2H), 5.53 (d, J=5.4 Hz, 1H), 4.99-4.82 (m, 1H), 4.05-3.60 (m, 12H), 3.55 (s, 3H), 2.90-3.65 (m, 5H), 1.60-1.40 (m, 2H), 0.68 (s, 9H). Mass spectrum: 796.2 (M+H)$^+$.

Preparation of Examples AY and AZ

Scheme 21

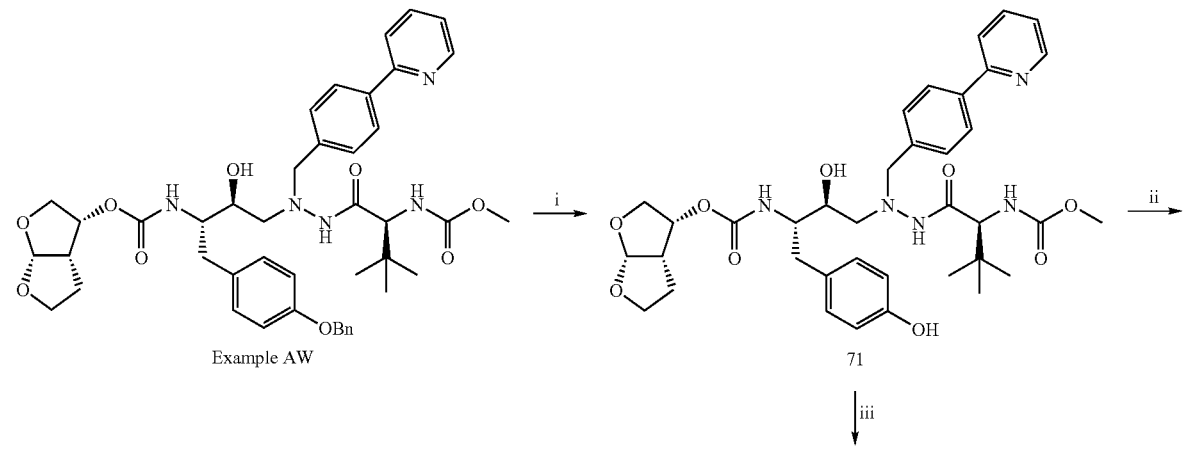

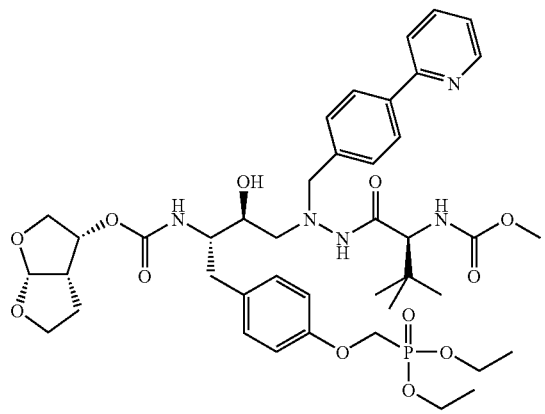

Example AY

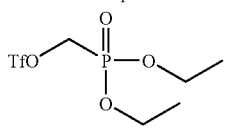

72

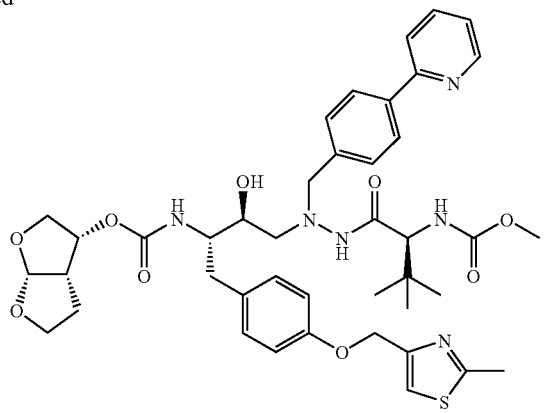

Example AZ

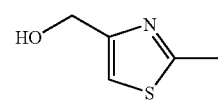

73

Reagents and conditions: i. H₂, Pd/C, AcOH, EtOH/EtOAc; 36%; ii. 72, Cs₂CO₃, ACN, 73%; iii. 73, di-tert-butyl azodicarboxylate, PPh₃, CH₂Cl₂, 52%.

Compound 71

A mixture of Example AW (0.664 g, 0.884 mmol) and 10% palladium/carbon (0.50 g) in EtOAc (15 mL) and EtOH (15 mL) was stirred under a hydrogen atmosphere for 24 h. The reaction mixture filtered through a pad of CELITE and concentrated. The residue was purified (silica gel chromatography, 80 to 100% EtOAc/Hex) to give Compound 71 as a white solid (0.2146 g, 0.304 mmol, 36%). $^1$H NMR (300 MHz, CD₃OD): δ 8.55 (d, J=5.1 Hz, 1H), 7.90-7.75 (m, 5H), 7.49 (d, 8.4 Hz, 2H), 7.35-7.30 (m, 1H), 7.00 (d, J=8.1Hz, 2H), 6.61 (d, 8.1 Hz, 2H), 5.32 (d, J=5.1 Hz, 1H), 4.97-4.87 (m, 1H), 4.15-3.55 (m, 12H), 2.95-2.60 (m, 5H), 1.60-1.40 (m, 2H), 0.68 (s, 9H). Mass spectrum: 706.2 (M+H)⁺.

Example AY

To a solution of Compound 71 (10 mg, 0.0142 mmol) in ACN (1.0 mL) at 0° C. (0.5 mL) was added cesium carbonate (9.3 mg, 0.0283 mmol), followed by a solution of Compound 72 (4.3 mg, 0.0142 mmol) in THF (0.5 mL). The reaction mixture was warmed to r.t. overnight, concentrated and purified by reversed phase HPLC (Phenomenex Synergi® column, 5 to 100% ACN/H₂O+0.1% TFA) to give Example AY as a white solid after lyophilization (10 mg, 0.0103 mmol, 73%). %). $^1$H NMR (300 MHz, CD₃OD): δ 8.73 (d, J=4.8 Hz, 1H), 8.55-8.425 (m, 1H), 8.24 (d, J=8.1 Hz, 1H), 7.90-7.850 (m, 1H), 7.85 (d, J=8.4 Hz, 2H), 7.68 (d, J=8.4 Hz, 2H), 7.15 (d, J=8.7 Hz, 2H), 6.86 (d, J=8.4 Hz, 2H), 5.53 (d, J=5.1 Hz, 1H), 4.97-4.87 (m, 1H), 4.30 (d, J=10.2 Hz, 2H), 4.20-3.60 (m, 14H), 3.54 (s, 3H), 2.95-2.60 (m, 5H), 1.60-1.40 (m, 2H), 1.31 (t, J=7.2 Hz, 6H), 0.68 (s, 9H). Mass spectrum: 856.2 (M+H)⁺.

Example AZ

To a solution of Compound 71 (22 mg, 0.031 mmol), Compound 73 (8.0 mg, 0.0623 mmol) and triphenylphosphine (16.0 mg, 0.0623 mmol) in CH₂Cl₂ (0.5 mL) was added di-tert-butyl azodicarboxylate (14 mg, 0.0623 mmol). The reaction mixture was stirred at r.t. for 2 h, then loaded directly onto a column and purified (silica gel chromatography, 60 to 100% EtOAc/Hex) to give an impure product. The impure product was purified again by reversed phase HPLC (Phenomenex Synergi® column, 5 to 100% ACN/H₂O+0.1% TFA) and product lyophilized to give Example AZ as a white powder (15.0 mg, 0.0161 mmol, 52%). $^1$H NMR (300 MHz, CD₃OD): δ 8.76 (d, J=5.7 Hz, 1H), 8.60-8.50 (m, 1H), 8.30 (d, J=8.1 Hz, 1H), 7.98-7.90 (m, 1H), 7.85 (d, J=8.4 Hz, 2H), 7.70 (d, J=8.1 Hz, 2H), 7.38 (s, 1H), 7.14 (d, J=8.4 Hz, 2H), 6.85 (d, J=8.4 Hz, 2H), 5.53 (d, J=5.1 Hz, 1H), 5.04 (s, 2H), 4.98-4.80 (m, 1H), 4.17-3.60 (m, 9H), 3.53 (s, 3H), 2.95-2.68 (m, 5H), 2.68 (s, 3H), 1.60-1.40 (m, 2H), 0.70 (s, 9H). Mass spectrum: 817.2 (M+H)⁺.

Preparation of Examples BA and BB

Scheme 22

74

353

-continued

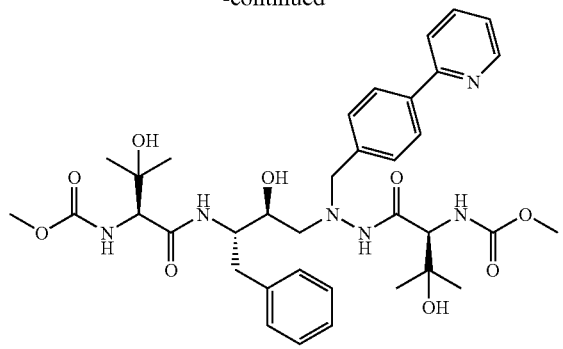

Example BA

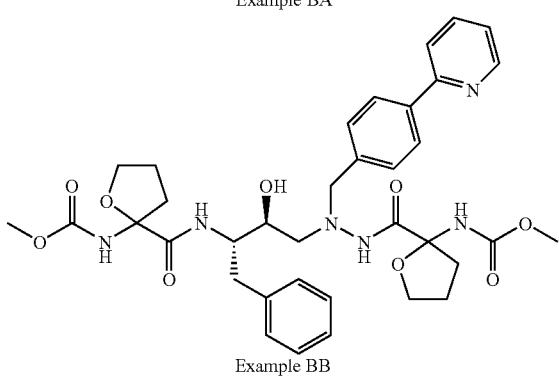

Example BB

Reagents and conditions: i. 70, diisopropylethylamine, DMAP, ACN, 19%; ii. carboxylic acid, TPTU, NMM, DMF.

Example BA

A solution of N-(methoxycarbonyl)-L-hydroxyvaline (39 mg, 0.204 mmol) and TPTU (60.6 mg, 0.204 mmol) in DMF (0.3 mL) was stirred for 10 min at r.t. Compound 74 (43 mg, 0.0927 mmol) and N-methylmorpholine (0.051 mL, 0.464 mmol) in DMF (0.3 mL) was added to the reaction mixture and stirred for 48 h at r.t. The reaction mixture was diluted with H$_2$O and extracted with CH$_2$Cl$_2$ (3×). The organic layer was dried (MgSO$_4$), concentrated and purified (silica gel chromatography 0 to 10% MeOH/CH$_2$Cl$_2$) to give an impure product, and purified again by reversed phase HPLC (Phenomenex Synergi® column, 5 to 100% ACN/H$_2$O+0.1% TFA) and lyophilized to give Example BA as a white powder (17.0 mg, 0.024 mmol, 26%). $^1$H NMR (300 MHz, CD$_3$OD): δ 8.74 (d, J=5.7 Hz, 1H), 8.60-8.50 (m, 1H), 8.25 (d, f=8.1 Hz, 1H), 7.90-7.85 (m, 1H), 7.83 (d, J=8.1 Hz, 2H), 7.65 (d, J=8.4 Hz, 2H), 7.30-7.05 (m, 5H), 4.25-3.65 (m, 10H), 3.60 (s, 3H), 3.55 (s, 3H), 2.95-2.68 (m, 4H), 1.06 (s, 3H), 1.03 (s, 3H), 0.95 (s, 3H), 0.90 (s, 3H). Mass spectrum: 709.2 (M+H)$^+$.

Example BB

A solution of N-2-methoxycarbonylamino-tetrahydro-furan-2-carboxylic acid (35 mg, 0.282 mmol) and TPTU (84 mg, 0.282 mmol) in DMF (0.3 mL) was stirred for 10 min at r.t. Compound 74 (60 mg, 0.128 mmol) and N-methylmorpholine (0.070 mL, 0.64 mmol) in DMF (0.4 mL) was added to the reaction mixture and stirred for 20 h at r.t. The reaction mixture was diluted with H$_2$O and extracted with CH$_2$Cl$_2$ (3×). The organic layer was dried (MgSO$_4$), concentrated and purified (silica gel chromatography 0 to 10% MeOH/CH$_2$Cl$_2$) to give an impure product, and purified again by reversed phase HPLC (Phenomenex Synergi® column, 5 to 100% ACN/H$_2$O+0.1% TFA) and lyophilized to give Example BB as a white powder (11.0 mg, 0.013 mmol, 11%). $^1$H NMR (300 MHz, CD$_3$OD): δ 8.74 (d, J=5.7 Hz, 1H), 8.60-8.45 (m, 1H), 8.26 (d, J=7.8 Hz, 1H), 7.92-7.80 (m, 3H), 7.65 (d, J=6.6 Hz, 2H), 7.40-7.05 (m, 5H), 4.25-3.45 (m, 18H), 2.95-2.68 (m, 5H), 2.10-1.70 (4H). Mass spectrum: 709.2 (M+H)$^+$.

Preparation of Example BC

Scheme 23

62 →$^{iv}$

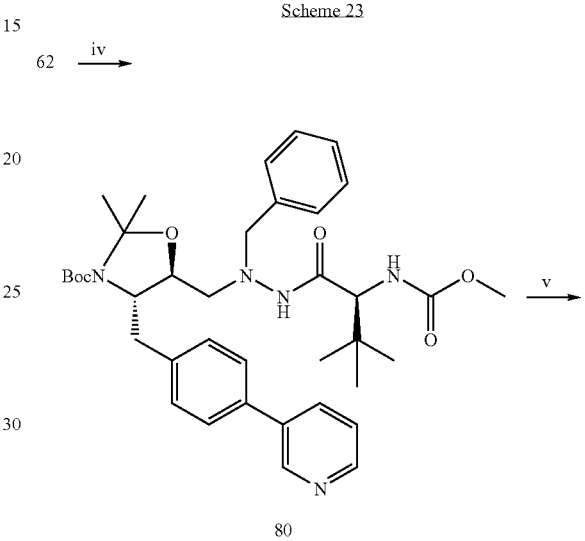

80 →$^v$

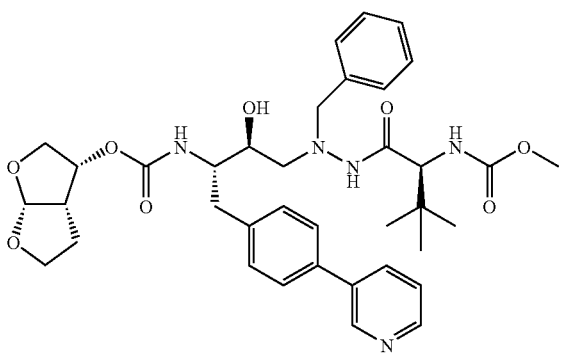

Example BC

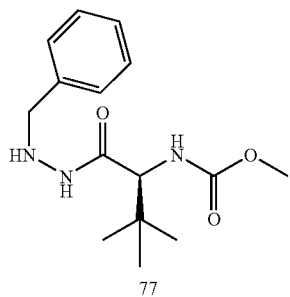

77

355

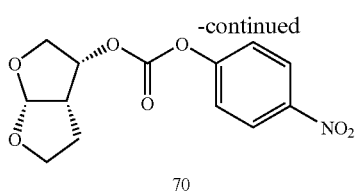

70

Reagents and conditions: i. N-phenyltrifluoromethanesulfonimide, Cs$_2$CO$_3$, CH$_2$Cl$_2$; ii. 77, AcOH, isopropanol, 80° C.; iii. camphorsulfonic acid, dimethoxypropane, acetone; iv. 3-pyridineboronic acid, PdCl$_2$(dppf), Na$_2$CO$_3$, DME; v.a. TFA, CH$_2$Cl$_2$; b. 70, diisopropylethylamine, DMAP, ACN.

Compound 80

To a Smith process vial were added Compound 62 (16 mg, 0.0215 mmol), 3-pyridineboronic acid (4.0 mg, 0.0322 mmol), PdCl$_2$(dppf) (1 mg), 2M Na$_2$CO$_3$ (0.2 mL) and DME (0.6 mL). The vial was sealed and heated at 120° C. for 25 min via microwave irradiation. The reaction mixture was diluted with EtOAc and washed with saturated NaHCO$_3$ solution, brine and dried (MgSO$_4$), concentrated and purified by reversed phase HPLC (Phenomenex Synergi® column, 5 to 100% ACN/H$_2$O+0.1% TFA) and concentrated to give Compound 80 as a brown oil (10.7 mg, 0.0136 mmol, 63%). Mass spectrum: 674.2 (M+H)$^+$.

Example BC

To a solution of Compound 80 (10.7 mg, 0.0136 mmol) in CH$_2$Cl$_2$ (0.6 mL) at r.t. was added TFA (0.3 mL) and the reaction mixture was stirred for 2.5 h. The reaction mixture was diluted with ACN and concentrated at 30° C. and co-evaporated with ACN (2×). The residue was dissolved in ACN (0.5 mL) and cooled to 0° C. Diisopropylethylamine (11 µL, 0.065 mmol) and DMAP (0.2 mg, 0.0013 mmol) were added, followed by Compound 70 (3.8 mg, 0.013 mmol). The reaction mixture was warmed to r.t. overnight and then diisopropylethylamine (11 µL, 0.065 mmol) was added and stirred for 3 h. The reaction mixture was diluted with EtOAc and washed with H$_2$O (3×), 1M NaOH (2×), brine and dried (MgSO$_4$), concentrated and purified by reversed phase HPLC (Phenomenex Synergi® column, 5 to 100% ACN/H$_2$O+0.1% TFA) to give Example BC as a white powder after lyophilization (8.0 mg, 0.010 mmol, 77%). $^1$H NMR (300 MHz, CD$_3$OD): δ 9.07 (s, 1H), 8.78-8.70 (m, 2H), 8.02 (dd, 18.1, 6.6 Hz, 1H), 7.67 (d, J=8.4 Hz, 2H), 7.45 (d, J=8.4 Hz, 2H), 7.36 (d, J=6.6 Hz, 2H), 7.27-7.15 (m, 3H), 5.52 (d, J=5.1 Hz, 1H), 4.97-4.80 (m, 1H), 4.01-3.55 (m, 12H), 2.97-2.78 (m, 5H), 1.58-1.40 (m, 2H), 0.67 (s, 9H). Mass spectrum: 690.2 (M+H)$^+$.

356

Preparation of Example BD

Scheme 24

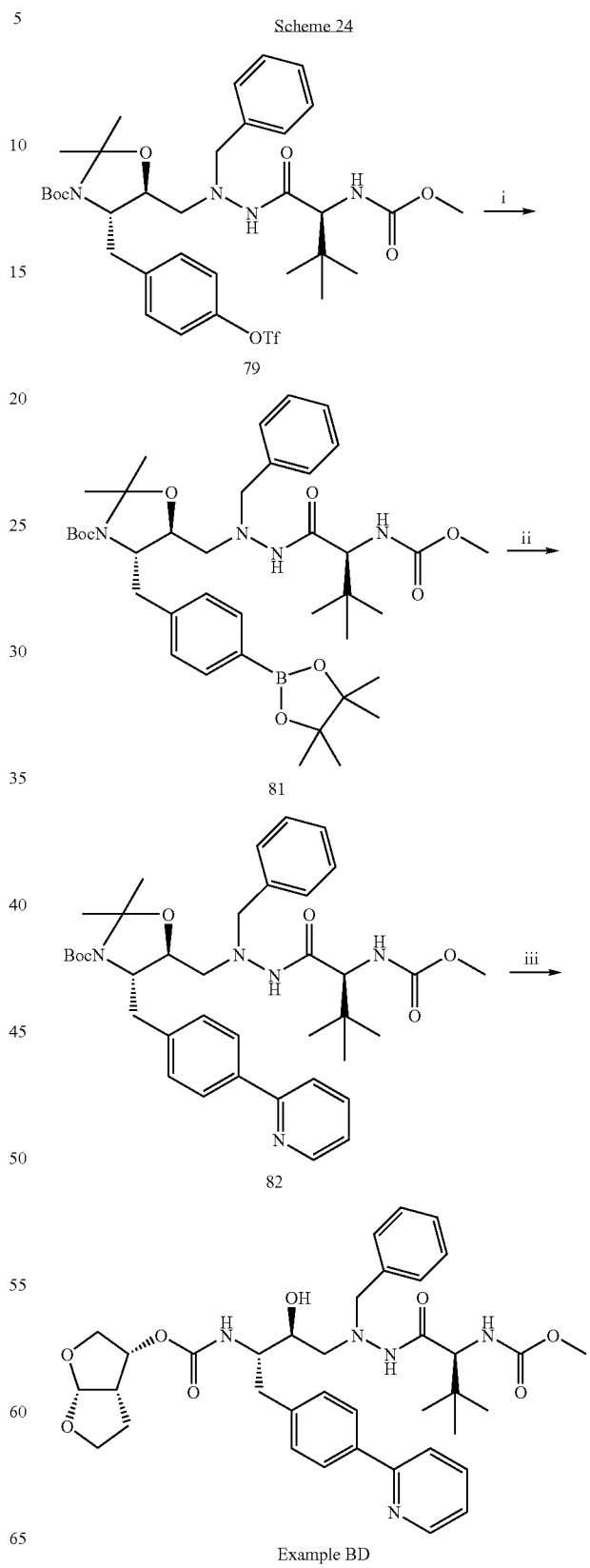

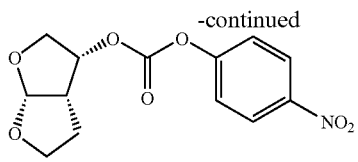

Reagents and conditions: i. 4,4,5,5-tetramethyl-1,3,2-dioxaborolane, PdCl$_2$(dppf), triethylamine, dioxane; ii. 2-bromopyridine, K$_3$PO$_4$, PdCl$_2$(dppf), dioxane; iii. a. TFA, CH$_2$Cl$_2$; b. 70, diisopropylethylamine, DMAP, ACN.

Compound 81

To an oven-dried flask charged with Compound 79 (73.7 mg, 0.0990 mmol) was distilled in dioxane (1.0 mL). To this solution was added PdCl$_2$(dppf) (4.9 mg, 0.00594 mmol), triethylamine (83 µL, 0.594 mmol) and 4,4,5,5-dioxaborolane (86 µL, 0.594 mmol). The reaction mixture was heated at 100° C. for 4.5 h under argon, cooled to r.t., diluted with EtOAc and washed with H$_2$O, brine and dried (MgSO$_4$), concentrated, purified (silica gel chromatography, 10 to 40% EtOAc/Hex) and purified again (silica gel chromatography, 10 to 40% EtOAc/Hex) to give Compound 81 as a white foam (48.1 mg, 0.067 mmol, 67%). Mass spectrum: 723.3 (M+H)$^+$.

Compound 82

An oven-dried flask was charged with Compound 81 (19 mg, 0.026 mmol), 2-bromopyridine (4 µL, 0.0384 mmol), potassium phosphate (28 mg, 0.130 mmol), H$_2$O (40 µL) and dioxane (0.6 mL). PdCl$_2$(dppf) (1 mg) was added and the reaction mixture was stirred at 65° C. 8 h. The reaction mixture was diluted with EtOAc and washed with H$_2$O, brine and dried (MgSO$_4$), concentrated and purified by reversed phase HPLC (Phenomenex Synergi® column, 5 to 100% ACN/H$_2$O+0.1% TFA) to give Compound 82 as a white powder after lyophilization (12.3 mg, 0.0156 mmol, 60%). Mass spectrum: 674.3 (M+H)$^+$.

Example BD

To a solution of Compound 82 (12.3 mg, 0.0156 mmol) in CH$_2$Cl$_2$ (0.6 mL) at r.t. was added TFA (0.3 mL) and the reaction mixture was stirred for 4 h. The reaction mixture was diluted with ACN and concentrated at 30° C. and co-evaporated with ACN (2×). The residue was dissolved in ACN (0.5 mL) and cooled to 0° C. Diisopropylethylamine (14 µL, 0.078 mmol) and DMAP (0.2 mg, 0.00156 mmol) were added, followed by Compound 70 (4.6 mg, 0.0156 mmol). The reaction mixture was warmed to r.t. over 8 h. The reaction mixture was concentrated and purified by reversed phase HPLC (Phenomenex Synergi® column, 5 to 100% ACN/H$_2$O+0.1% TFA) to give Example BD as a white powder after lyophilization (3.3 mg, 0.0041 mmol, 26%). $^1$H NMR (300 MHz, CD$_3$OD): δ 8.71 (d, J=5.4 Hz, 1H), 8.50-8.40 (m, 1H), 8.21 (d, J=8.1 Hz, 1H), 7.82 (d, J=8.4 Hz, 2H), 7.51 (d, J=8.4 Hz, 2H), 7.37 (d, J=6.6 Hz, 2H), 7.27-7.15 (m, 3H), 5.52 (d, J=5.4 Hz, 1H), 4.95-4.75 (m, 1H), 4.01-3.55 (m, 12H), 2.97-2.78 (m, 5H), 1.58-1.40 (m, 2H), 0.67 (s, 9H). Mass spectrum: 690.3 (M+H)$^+$.

Preparation of Examples BE and BF

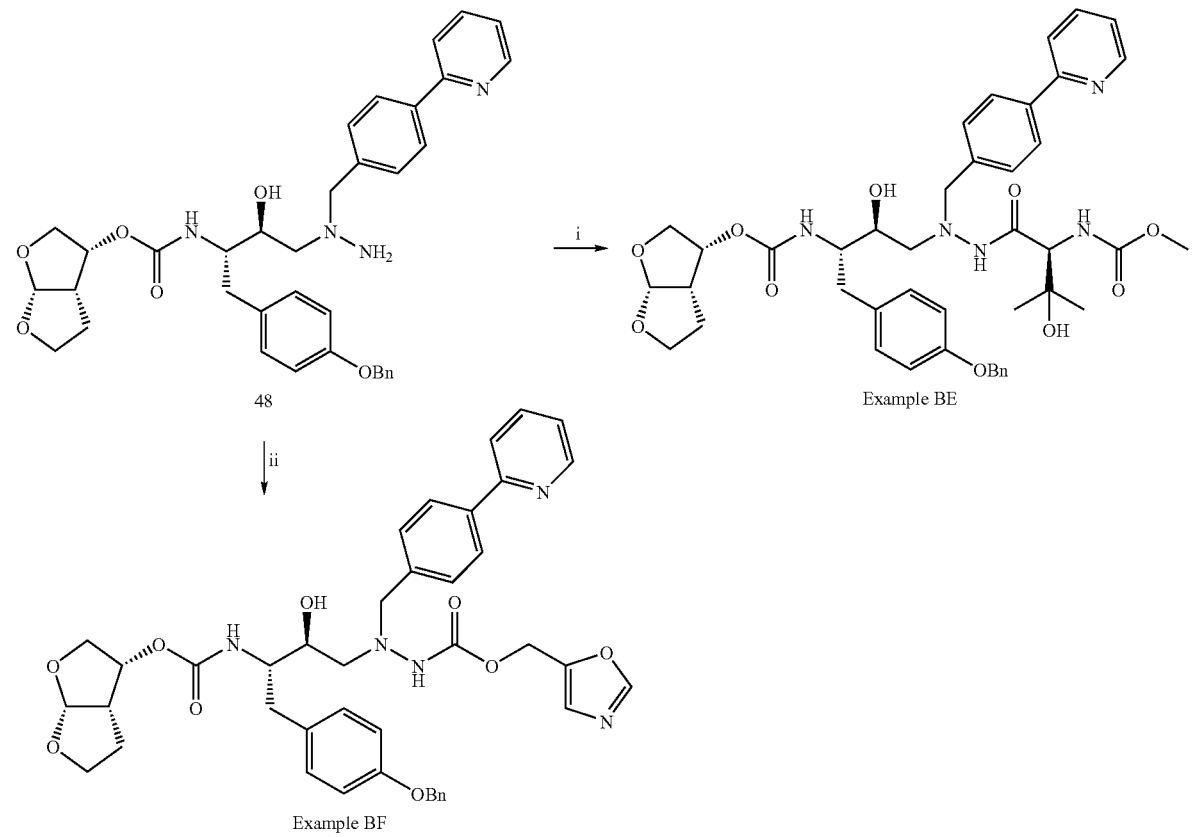

Scheme 25

-continued

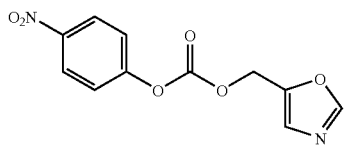

84

Reagents and conditions: i. carboxylic acid, TPTU, NMM, DMF; ii. 84, diisopropylethylamine, DMAP, ACN.

Example BE

A solution of 3-hydroxy-2-methoxycarbonylamino-3-methyl-butyric acid (20 mg, 0.106 mmol) and TPTU (32 mg, 0.106 mmol) in DMF (0.2 mL) was stirred for 20 min at r.t. Compound 48 (30 mg, 0.048 mmol) and N-methylmorpholine (16 μL, 0.144 mmol) in DMF (0.2 mL) was added to the reaction mixture and stirred for 1 h at r.t. The reaction mixture was diluted with H$_2$O and extracted with CH$_2$Cl$_2$ and dried (MgSO$_4$), concentrated and purified (2×) by reversed phase HPLC (Phenomenex Synergi® column, 5 to 100% ACN/H$_2$O+0.1% TFA) and lyophilized to give Example BE as a white powder (6 mg, 0.0066 mmol, 14%). $^1$H NMR (300 MHz, CD$_3$OD): δ 8.74 (d, J=6.0 Hz, 1H), 8.60-8.5 (m, 1H), 8.28 (d, J=8.4 Hz, 1H) 7.93-7.60 (m, 5H), 7.40-7.20 (m, 5H), 7.11 (d, J=8.4 Hz, 2H), 6.83 (d, J=8.7 Hz, 2H), 5.52 (d, J=5.1 Hz, 1H), 5.00 (s, 2H), 4.95-4.89 (m, 1H), 3.94-3.50 (m, 12H), 2.86-2.65 (m, 5H), 1.52-1.31 (m, 2H), 0.95 (d, J=14.4 Hz, 6H). Mass spectrum: 798.2 (M+H)$^+$.

Example BF

Compound 48 (31 mg, 0.0496 mmol) was dissolved in ACN (0.5 mL) and cooled to 0° C. Diisopropylethylamine (26 μL, 0.149 mmol) and DMAP (0.6 mg, 0.00496 mmol) were added, followed by Compound 84 (16 mg, 0.0546 mmol), prepared according to WO 9414436 A1. The reaction mixture was warmed to r.t. over 48 h. The reaction mixture was diluted with EtOAc and washed with H$_2$O (3×), 0.5M NaOH (3×), brine and dried, concentrated and purified (silica gel chromatography, 50 to 100% EtOAc/Hex), then by reversed phase HPLC (5 to 100% ACN/H$_2$O+0.1% TFA) to give Example BF as a white powder after lyophilization (5.5 mg, 0.0064 mmol, 13%). $^1$H NMR (300 MHz, CD$_3$OD): δ 8.75 (d, J=4.2 Hz, 1H), 8.57-8.5 (m, 1H), 8.27 (d, J=8.1 Hz, 1H), 8.05 (s, 1H), 7.93-7.89 (m, 1H), 7.82 (d, J=7.8 Hz, 2H), 7.63 (d, J=8.1 Hz, 2H), 7.40-7.06 (m, 7H), 6.96 (s, 1H), 6.83 (d, J=8.4 Hz, 2H), 5.52 (d, J=5.4 Hz, 1H), 5.00-4.87 (m, 5H), 4.10-3.55 (m, 7H), 2.86-2.65 (m, 5H), 1.52-1.31 (m, 2H). Mass spectrum: 750.1 (M+H)$^+$.

Preparation of Example BG

Scheme 26

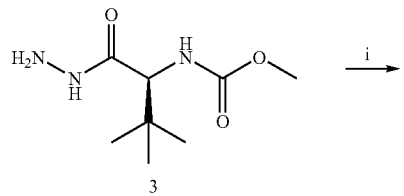

3

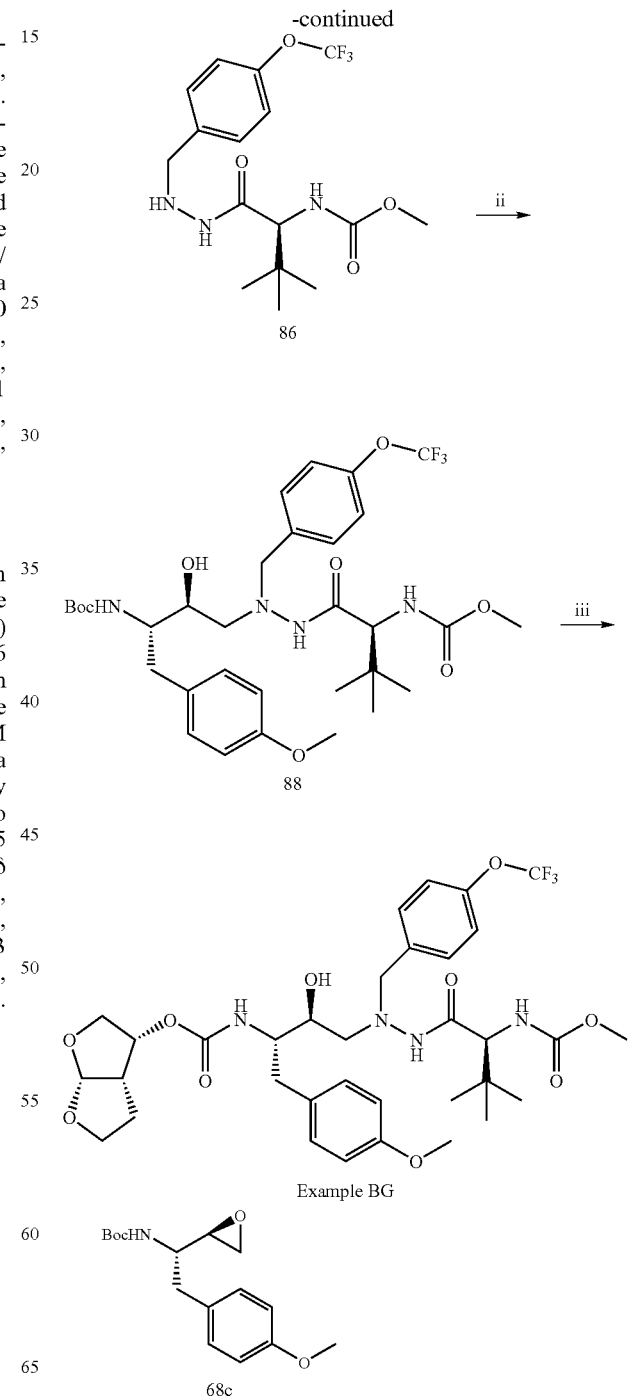

-continued

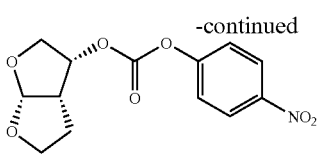

70

Reagents and conditions: i. a. 4-trifluoromethoxy-benzaldehyde, isopropanol, 80° C.; b. NaBH₃CN, 88%; ii. 68c, AcOH, isopropanol, 80° C.; iii. a. TFA, CH₂Cl₂; b. 70, diisopropylethylamine, DMAP, ACN.

Compound 86

Compound 3 (215 mg, 1.06 mmol), prepared according to Bold et al. *J. Med. Chem.* 1998, 41, 3387-3401, in isopropanol (10 mL) was treated with commercially available 4-trifluoromethoxy-benzaldehyde (151 µL, 1.06 mmol) at 80° C. for 18 h. The reaction mixture was cooled to r.t. and purified (silica gel chromatography, 0 to 100% EtOAc/Hex) to give a white solid (252 mg, 0.671 mmol, 63%). The solid was dissolved in THF (7 mL). Sodium cyanoborohydride (44.3 mg, 0.705 mmol) was added, followed by addition of p-toluenesulfonic acid (141 mg, 0.739 mmol). The reaction mixture was stirred for 5 hours, then partitioned with saturated NaHCO₃ solution and EtOAc, extracted with EtOAc (2×). The combined organic layer was dried over Na₂SO₄ and concentrated. The residue was dissolved in THF (2 mL) and MeOH (4 mL) and Na₂B₄O₇·10H₂O (4 eq) in H₂O was added. The reaction mixture was stirred overnight, then 10 drops of AcOH was added. The reaction mixture was stirred for an hour, then partitioned with saturated NaHCO₃ solution and EtOAc, extracted with EtOAc (2×), dried over Na₂SO₄ and purified (silica gel chromatography, 0 to 100% EtOAc/Hex) to give Compound 86 as a clear thick oil (173 mg, 0.460 mmol, 68%). Mass spectrum: 378.0 $(M+H)^+$.

Compound 88

To a solution of Compound 68c (53.9 mg, 0.184 mmol) in isopropanol (3.0 mL) were added Compound 86 (69.4 mg, 0.184 mmol) and AcOH (acetic acid) (8.8 mg). After stirring for 3 days at 80° C., reaction mixture was concentrated and purified (silica gel chromatography, 0 to 100% EtOAc/Hex and 0 to 8% MeOH/CH₂Cl₂) to give Compound 88 as a white solid (91.9 mg, 0.137 mmol, 75%). Mass spectrum: 671.1 $(M+H)^+$.

Example BG

To a solution of Compound 88 (91.9 mg, 0.137 mmol) in CH₂Cl₂ (1.6 mL) cooled to 0° C. was added TFA (0.4 mL). The reaction mixture was stirred at 0° C. for 15 min. and at r.t. for 1.5 hours. The mixture was co-evaporated with toluene (4 mL) and put under high-vacuum for 2 hours. The residue was dissolved in ACN (2 mL). DMAP (3.4 mg, 0.027 mmol) and diisopropylethylamine (0.072 mL, 0.412 mmol) were added, followed by Compound 70 (40.6 mg, 0.137 mmol). The reaction mixture was stirred for 2 hours then purified (prep-TLC, 4% MeOH/CH₂Cl₂) to give an Example BG as a white solid (48.3 mg, 0.066 mmol, 48%). ¹H NMR (300 MHz, CDCl₃): δ 7.41-7.39 (d), 7.27-7.11 (m), 6.80-6.77 (d), 6.69 (s), 5.66-5.65 (d), 5.37-5.30 (m), 5.05-5.00 (m), 4.81 (s), 4.13-4.07 (m), 3.97-3.94 (m), 3.85-3.47 (m), 2.93-2.86 (m), 2.69-2.67 (d), 1.96 (s), 1.66-1.60 (m), 1.28-1.23 (m), 0.88-0.85 (m), 0.65 (s). Mass spectrum: 727.2 $(M+H)^+$.

Preparation of Example BH

Scheme 27

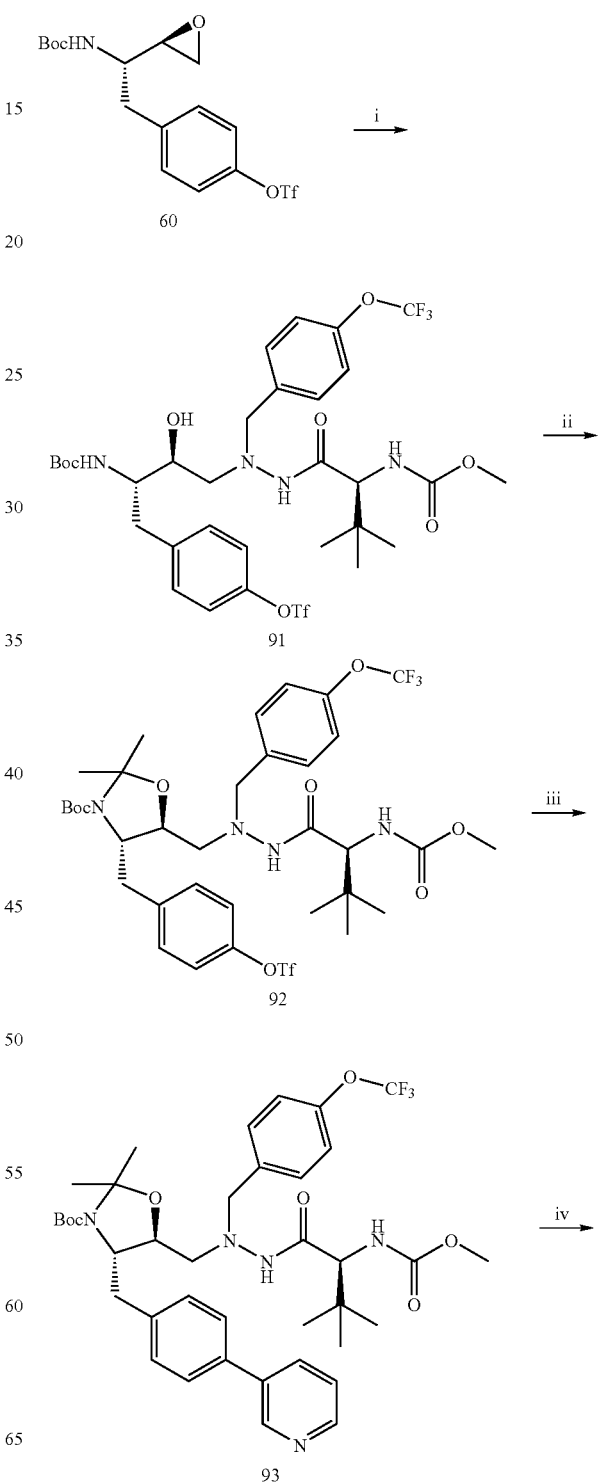

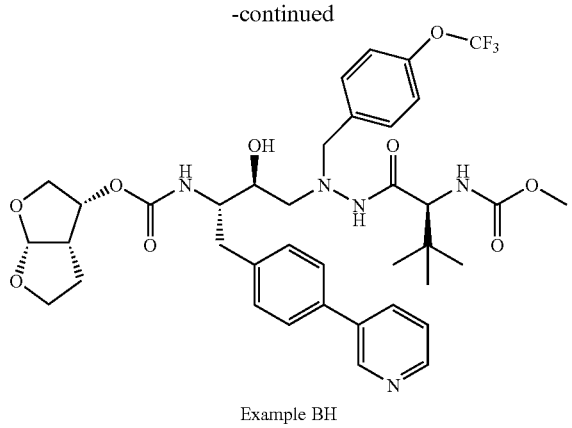

Example BH

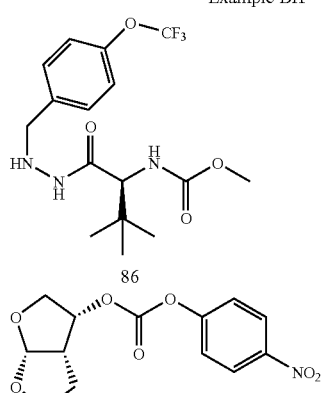

Reagents and conditions: i. 86, AcOH, isopropanol, 80° C.; ii. camphorsulfonic acid, dimethoxypropane, acetone; iii. 3-pyridineboronic acid, PdCl$_2$(dppf), Na$_2$CO$_3$, DME; iv. a. TFA, CH$_2$Cl$_2$; b. 70, diisopropylethylamine, DMAP, ACN.

Compound 91

To a solution of Compound 60 (113 mg, 0.276 mmol) in isopropanol (4.0 mL) were added Compound 86 (104 mg, 0.276 mmol) and AcOH (13.2 mg). After stirring for 3 days at 80° C., the reaction mixture was concentrated and purified (silica gel chromatography, 0 to 100% EtOAc/Hex and 0 to 8% MeOH/CH$_2$Cl$_2$) to give Compound 91 as a white solid (135 mg, 0.172 mmol, 62%). Mass spectrum: 789.0 (M+H)$^+$.

Compound 92

A solution of Compound 91 (135 mg, 0.172 mmol), camphorsulfonic acid (43.9 mg, 0.189 mmol) and dimethoxypropane (0.211 mL, 1.72 mmol) in acetone (3 mL) was heated at reflux for 4.5 h. The reaction mixture was cooled to r.t., partitioned with saturated NaHCO$_3$ solution and EtOAc, extracted with EtOAc (1×), washed with H$_2$O (1×) and dried over Na$_2$SO$_4$, concentrated and purified (silica gel chromatography, 0 to 100% EtOAc/Hex) to give Compound 92 as a clear film (72.0 mg, 0.087 mmol, 51%). Mass spectrum: 829.1 (M+H)$^+$.

Compound 93

To a Smith process vial were added Compound 92 (24 mg, 0.029 mmol), 3-pyridineboronic acid (8.9 mg, 0.072 mmol), PdCl$_2$(dppf) (3.3 mg, 0.003 mmol), 2M Na$_2$CO$_3$ (0.072 mL) and DME (0.6 mL). The vial was sealed and heated at 120° C. for 25 min via microwave irradiation. The reaction mixture was diluted with EtOAc and washed with saturated NaHCO$_3$ solution, H$_2$O and dried over Na$_2$SO$_4$, concentrated and purified (silica gel chromatography, 20 to 90% EtOAc/Hex) to give Compound 93 as a white solid (14.2 mg, 0.019 mmol, 65%). Mass spectrum: 758.2 (M+H)$^+$.

Example BH

To a solution of Compound 93 (14.2 mg, 0.019 mmol) in CH$_2$Cl$_2$ (1.5 mL) at r.t. was added TFA (1.5 mL) and the reaction mixture was stirred for overnight then concentrated, partitioned with saturated NaHCO$_3$ solution and EtOAc, extracted with EtOAc (1×), dried over Na$_2$SO$_4$ and concentrated. The residue was dissolved in ACN (1 mL). Diisopropylethylamine (6.5 μL, 0.037 mmol) and DMAP (0.5 mg, 0.004 mmol) were added, followed by Compound 70 (5.5 mg, 0.019 mmol). The reaction mixture was stirred for 4 h. then concentrated, purified with prep-TLC (silica gel plate, 6% MeOH/CH$_2$Cl$_2$) to give Example BH as a white solid (4.5 mg, 0.006 mmol, 31%). $^1$H NMR (300 MHz, CDCl$_3$): δ 8.83-8.82 (d), 8.59-8.57 (m), 7.87-7.84 (d), 7.52-7.49 (d), 7.44-7.33 (m), 7.19-7.16 (d), 6.36 (s), 5.66-5.64 (d), 5.33-5.31 (d), 5.25-5.21 (d), 5.07-5.00 (m), 4.84 (s), 4.17-4.12 (d), 4.01-3.96 (m), 3.89-3.52 (m), 3.02-2.89 (m), 2.71-2.67 (d), 1.63-1.59 (m), 1.32-1.26 (m), 0.66 (s). Mass spectrum: 774.2 (M+H)$^+$.

Preparation of Examples BI, BJ, BK, and BL

Scheme 28

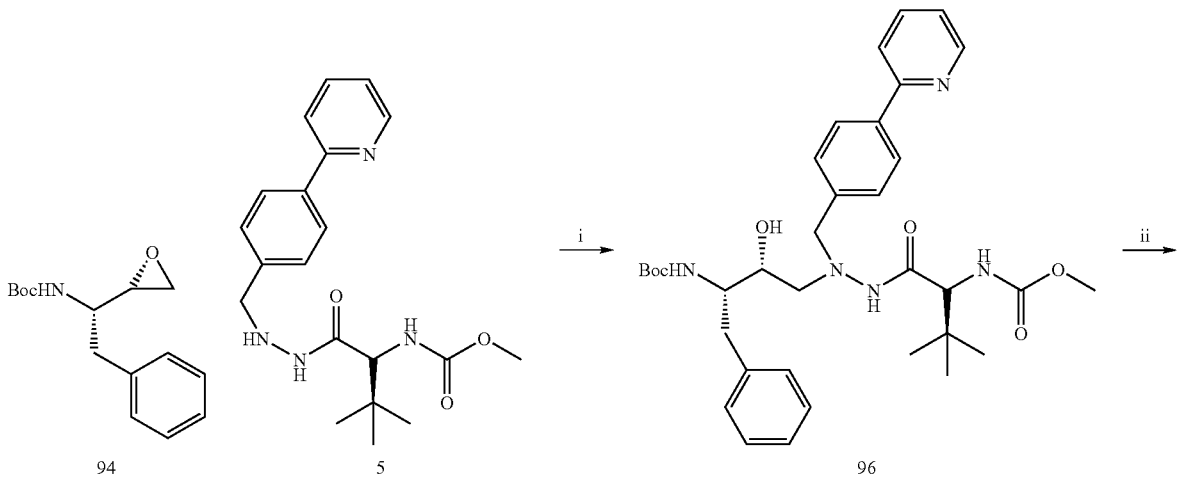

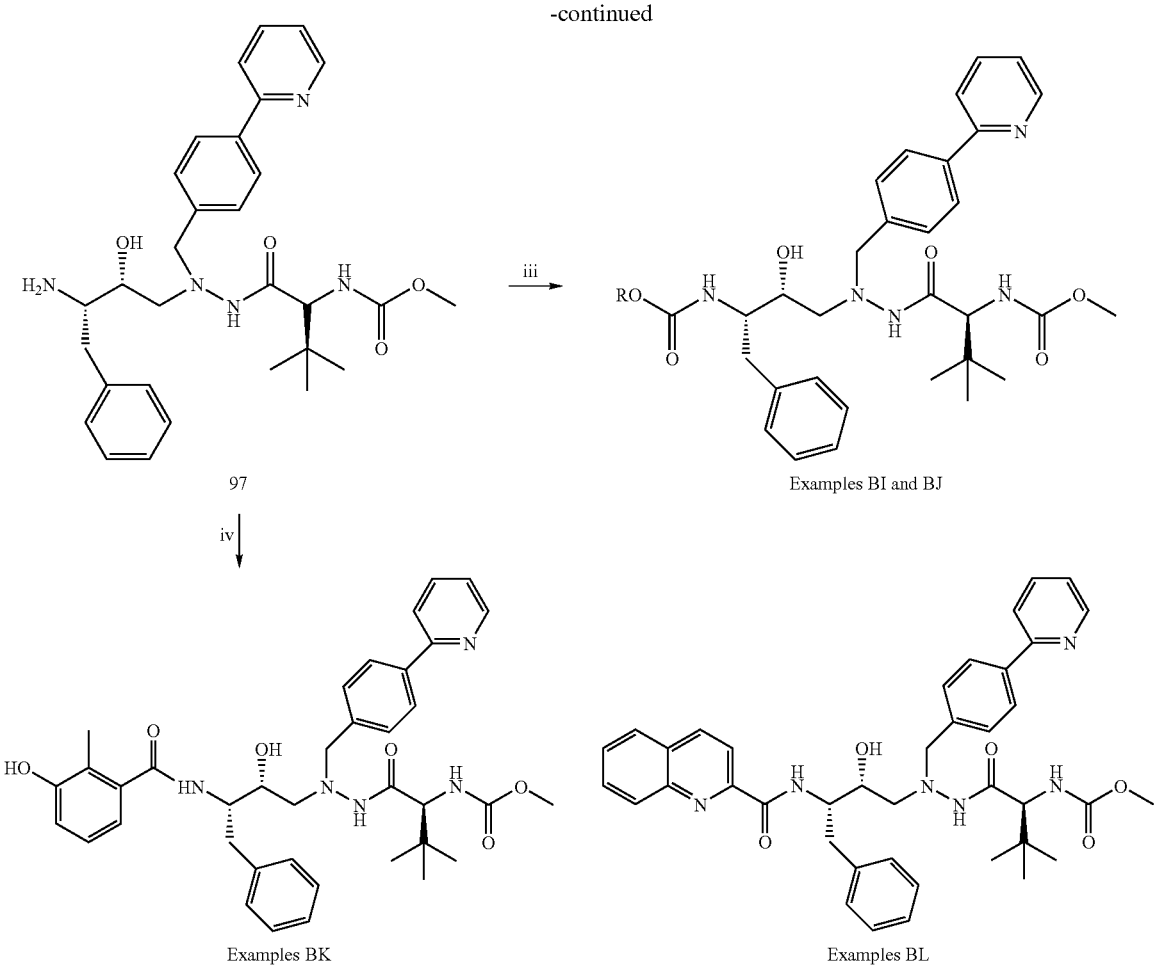

Examples BK                                   Examples BL

Reagents and Conditons: i. i-PrOH, 80° C.; ii. TFA, DCM; iii. DMAP, DIPEA, (R)-4-nitrophenyl bistetrahydrofuran-3-yl carbonate for BI, (R)-4-nitrophenyl tetrahydrofuran-3-yl carbonate for BJ CH₃CN.; iv. EDC, HOBt, NMM, DMF Compound 96

Epoxide 94, purchased from Kaneka Corporation, (527 mg, 2 mmol) and Compound 5 (741 mg, 2 mmol) were dissolved in isopropanol and heated to 80° C. The reaction mixture was allowed to stir for 18 h before it was cooled to r.t., concentrated, and purified on silica gel chromatography (ethyl acetate/hexane, 30-50%) to give Compound 96 (500 mg, 50%) Mass spectrum: $(M+Na)^+=656$ Example BI TFA (0.4 mL) was added to 96 (100 mg, 0.16 mmol) in DCM (1.6 mL) and the mixture was allowed to stir at r.t. for 1.5 h. The solution was concentrated and co-evaporated three times with DCM and three times with acetonitrile to obtain Compound 97. Compound 97 (28 mg, 0.052 mmol) was dissolved in anhydrous acetonitrile (0.5 mL) and cooled to 0° C. DMAP (1 mg, 0.008 mmol) was added followed by DIEA (35 μL, 0.2 mmol) until the solution reached pH 9. Compound 70 (16 mg, 0.052 mmol) was added. The reaction mixture was stirred for 2 h at 0° C. and for 16 h at r.t. The reaction mixture was concentrated and purified by reverse phase HPLC (Phenomenex Synergi® column, 25-100% acetonitrile/H₂O+ 0.1% TFA) to give Example BI (20 mg, 56%). ¹H NMR (300 MHz, CDCl₃): δ 9.04 (d, J=5.7 Hz, 1H), 8.36 (m, 1H), 8.03 (d, J=8.4 Hz, 1H), 7.86 (d, J=8.1 Hz, 2H), 7.79 (m, 1H), 7.61 (d, J=8.1 Hz, 2H), 7.21-7.18 (m, 5H), 5.66 (d, J=5.1 Hz, 1H), 5.33 (m, 2H), 5.00 (m, 1H), 4.09 (m, 2H), 4.05-3.63 (m, 10H), 3.58 (s, 3H), 3.08-2.98 (m, 5H), 1.72-1.58 (m, 2H), 0.83 (s, 9H). Mass spectrum: $(M+Na)^+=713$ Example BJ Compound 97 (53 mg, 0.1 mmol) was dissolved in anhydrous acetonitrile (1 mL) and cooled to 0° C. DMAP (1 mg, 0.008 mmol) was added followed by DIEA (70 μL, 0.4 mmol) until the solution reached pH 9. (R)-4-nitrophenyl tetrahydrofuran-3-yl carbonate (25 mg, 0.1 mmol) was added. The reaction mixture was stirred for 2 h at 0° C. and for 16 h at r.t. The reaction mixture was concentrated and purified by reverse phase HPLC (Phenomenex Synergi® column, 25-100% acetonitrile/H₂O+0.1% TFA) to give Example BJ (38 mg, 60%). ¹H NMR (300 MHz, CDCl₃): δ 9.05 (d, J=5.7 Hz, 1H), 8.31 (m, 1H), 7.98 (d, J=8.1 Hz, 1H), 7.85 (d, J=7.8 Hz, 2H), 7.74 (m, 1H), 7.59 (d, J=7.8 Hz, 2H), 7.27-7.20 (m, 5H), 5.12-4.88 (m, 4H), 4.09-3.61 (m, 10H), 3.54 (s, 3H), 2.95-2.88 (m, 4H), 2.18-1.92 (m, 2H), 0.84 (s, 9H). Mass spectrum: $(M+Na)^+=671$ Example BK A solution of 3-hydroxy-o-toluic acid, purchased from TCI, (15 mg, 0.1 mmol), EDC (21 mg, 0.11 mmol), HOBT (15 mg, 0.11 mmol), and 4-methylmorpholine (13 μL, 0.12 mmol) in DMF (0.5 mL) was allowed to stir for 45 min. Compound 97 (53 mg, 0.1 mmol) was dissolved in DMF (0.1 mL) and added to the reaction mixture. The resulting mixture was allowed to stir at r.t. for 24 h. The reaction solution was diluted with ethyl acetate, washed with saturated NaHCO$_3$, and brine. The combined aqueous layers were extracted with ethyl acetate and the combined organic layers were dried over Na$_2$SO$_4$ and concentrated. The resulting residue was purified by reverse phase HPLC (Phenomenex Synergi® column, 25-100% acetonitrile/H$_2$O+0.1% TFA) and yielded Example BK as a white solid (40 mg, 61%). $^1$H NMR (300 MHz, CD$_3$OD): δ 8.77 (d, J=5.4 Hz, 1H), 8.49 (m, 1H), 8.24 (d, J=8.1 Hz, 1H), 7.89-7.82 (m, 3H), 7.65 (d, J=8.1 Hz, 2H), 7.29-7.19 (m, 5H), 6.94 (m, 1H), 6.75 (d, J=7.8 Hz, 1H), 6.53 (d, J=7.8 Hz, 1H), 4.37 (m, 1H), 4.14 (s, 2H), 3.84 (m, 1H), 3.71 (m, 1H), 3.31 (s, 3H), 3.22-2.71 (m, 5H), 1.89 (s, 3H), 0.83 (s, 9H). Mass spectrum: (M+Na)$^+$=691

Example BL

Example BL was prepared from Compound 97 in a manner similar to that used to prepare Example BK, except that quinaldic acid, purchased from Aldrich, was used instead of 3-hydroxy-o-toluic acid to provide Example BL as a white powder (41 mg, 60%). $^1$H NMR (300 MHz, CDCl$_3$): δ 9.04 (d, J=5.7 Hz, 1H), 8.46 (d, J=9.3 Hz, 1H), 8.30-8.19 (m, 4H), 8.06-7.52 (m, 10H), 7.36-7.19 (m, 5H), 5.39 (m, 1H) 4.46 (m, 1H), 4.12-3.97 (m, 2H), 3.78-3.68 (m, 2H), 3.49 (s, 3H), 3.30-2.99 (m, 5H), 0.82 (s, 9H). Mass spectrum: (M+Na)$^+$= 712

Preparation of Examples BM and BN

Scheme 29

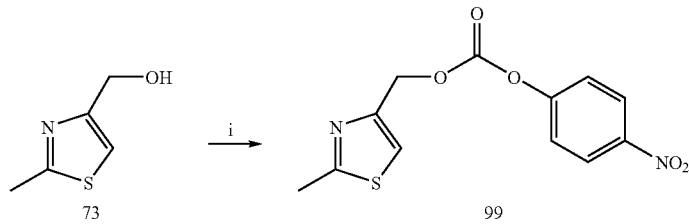

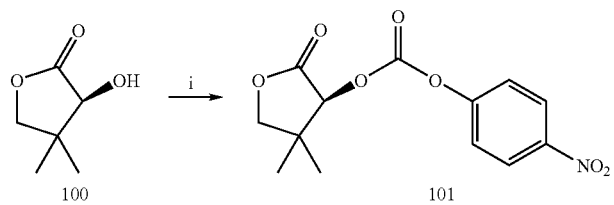

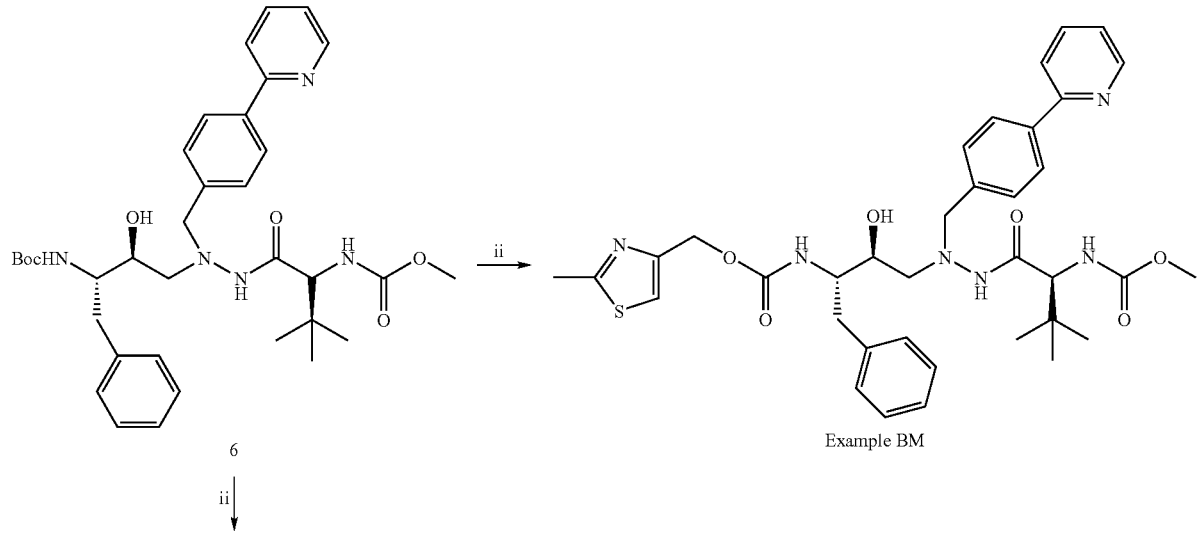

Example BM

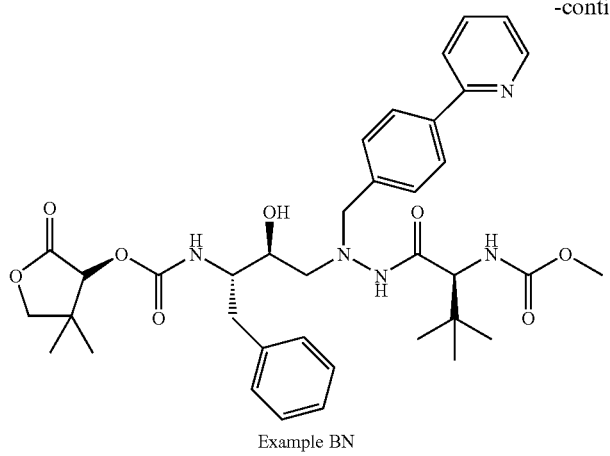

Example BN

Reagents and Conditions:
i. TEA, DCM, Bis(4-nitrophenyl)carbonate;
ii. a. TFA, DCM;
   b, DMAP, DIPEA, 99 for BM; and 101 for BN Compound 99

TEA (63 μL, 0.45 mmol) was added to a solution of Compound 73 (38 mg, 0.3 mmol) and Bis(4-nitrophenyl)carbonate (92 mg, 0.3 mmol) in DCM (1.2 mL) and the reaction mixture was allowed to stir at r.t. for 2 h. The reaction mixture was concentrated and then diluted with ethyl acetate, washed four times with an aqueous NaOH solution (1N), once with a solution of saturated NaHCO$_3$, and once with brine before it was dried over Na$_2$SO$_4$ and concentrated. The crude residue was purified on silica gel chromatography (10-30% ethyl acetate in hexane) to give Compound 99 (69 mg, 80%). Mass spectrum: (M+H)$^+$=295

Compound 101

TEA (209 μL, 1.5 mmol) was added to a solution of Compound 100 (S)-Pantolactone (130 mg, 1 mmol) and Bis(4-nitrophenyl)carbonate (304 mg, 1 mmol) in DCM (5 mL) and the reaction mixture was allowed to stir at r.t. for 2 h. The reaction mixture was concentrated and then diluted with ethyl acetate, washed four times with an aqueous NaOH solution (1N), once with a solution of saturated NaHCO$_3$, and once with brine before it was dried over Na$_2$SO$_4$ and concentrated. The crude residue was purified on silica gel (10-30% ethyl acetate in hexane) to give Compound 101 (240 mg, 81%). Mass spectrum: (M+H)$^+$=296

Example BM

TFA (0.3 mL) was added to Compound 6 (36 mg, 0.057 mmol) in DCM (1 mL) and the mixture was allowed to stir at r.t. for 2 h. The solution was concentrated and co-evaporated three times with DCM and three times with acetonitrile. The resulting residue was dissolved in anhydrous acetonitrile (0.6 mL) and cooled to 0° C. DMAP (1 mg, 0.08 mmol) was added followed by DIPEA (40 μL, 0.23 mmol) until pH 9 was reached. Addition of carbonate 99 (17 mg, 0.057 mmol) followed. The reaction mixture was stirred for 1 h at 0° C. and for 16 h at r.t. The reaction mixture was concentrated and dissolved in ethyl acetate. The organic layer was washed three times with H$_2$O, three times with NaOH (1N), and once with brine before it was dried over Na$_2$SO$_4$ and concentrated and purified by reverse phase HPLC (Phenomenex Synergi® column, 25-100% acetonitrile/H$_2$O+0.1% TFA) to give Example BM (23 mg, 60%). $^1$H NMR (300 MHz, CDCl$_3$): δ 9.05 (d, J=5.7 Hz, 1H), 8.28 (m, 1H), 7.95 (d, J=7.8 Hz, 1H), 7.85 (d, J=8.4 Hz, 2H), 7.72 (m, 1H), 7.58 (d, J=7.8 Hz, 2H), 7.21-7.17 (m, 4H), 6.97 (s, 1H), 5.45-5.10 (m, 4H), 4.18-3.86 (m, 7H), 3.61 (s, 3H), 3.57 (m, 1H), 2.93 (m, 4H), 2.74 (s, 3H), 0.71 (s, 9H). Mass spectrum: (M+Na)$^+$=712

Example BN

TFA (0.3 mL) was added to Compound 6 (33 mg, 0.06 mmol) in DCM (1 mL) and the mixture was allowed to stir at r.t. for 2 h. The solution was concentrated and co-evaporated three times with DCM and three times with acetonitrile. The resulting residue was dissolved in anhydrous acetonitrile (0.6 mL) and cooled to 0° C. DMAP (1 mg, 0.008 mmol) was added followed by DIPEA (42 μL, 0.24 mmol) until pH 9 was reached. Addition of carbonate 101 (18 mg, 0.06 mmol) followed. The reaction mixture was stirred for 1 h at 0° C. and for 16 h at r.t. The reaction mixture was concentrated and dissolved in ethyl acetate. The organic layer was washed three times with H$_2$O, three times with NaOH (1N), and once with brine before it was dried over Na$_2$SO$_4$ and concentrated and purified by reverse phase HPLC (Phenomenex Synergi® column, 25-100% acetonitrile/H$_2$O+0.1% TFA) to give Example BN (24 mg, 58%). $^1$H NMR (300 MHz, CDCl$_3$): δ 8.70 (d, J=4.5 Hz, 1H), 7.95 (d, J=7.8 Hz, 2H), 7.78-7.70 (m, 2H), 7.45 (m, 2H), 7.24-7.17 (m, 4H), 6.50 (s, 1H), 5.55-5.16 (m, 4H), 4.12-3.95 (m, 6H), 3.65 (s, 3H), 3.56 (m, 2H), 2.99-2.60 (m, 6H), 1.15 (s, 3H), 0.99 (s, 3H), 0.76 (s, 9H). Mass spectrum: (M+Na)$^+$=713

Preparation of Examples BO, BP, BQ, and BR
Scheme 30
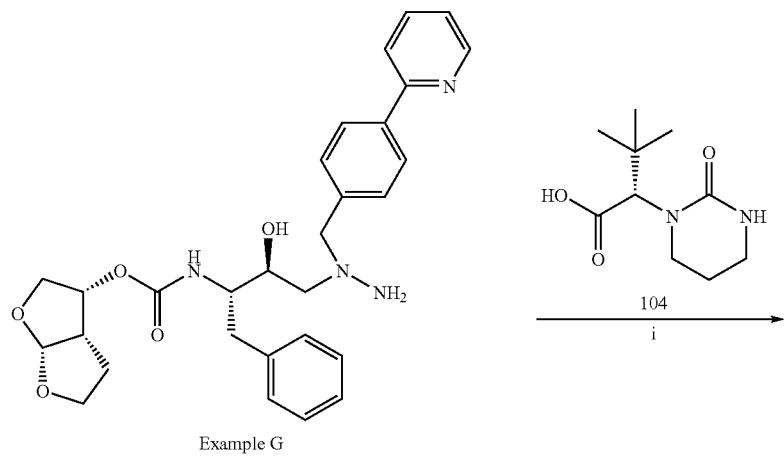
Example G
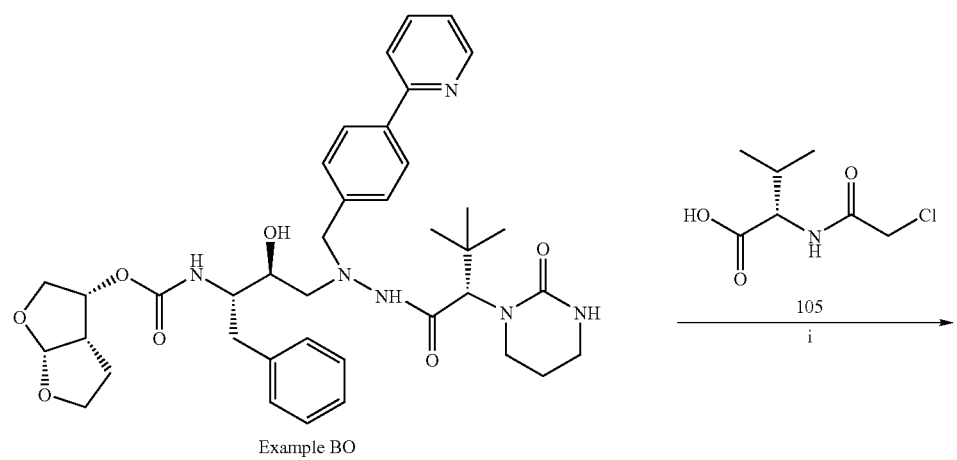
Example BO
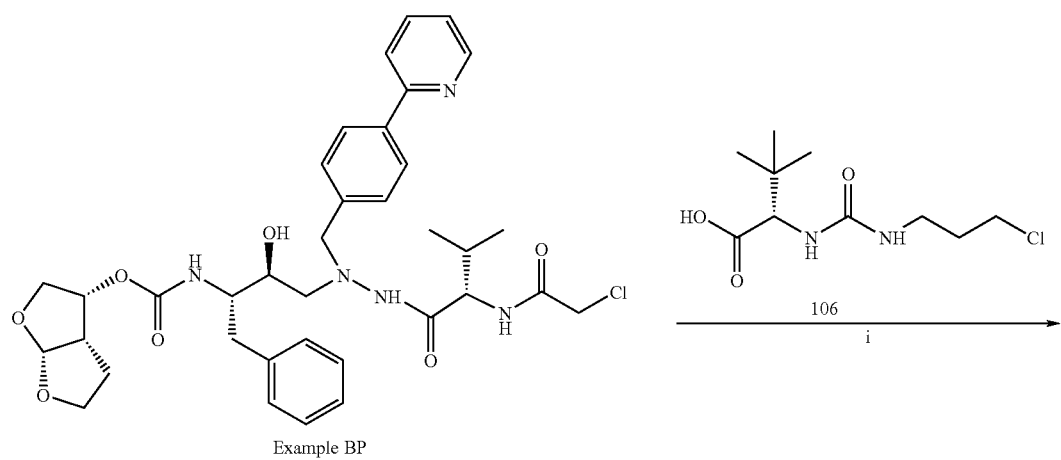
Example BP

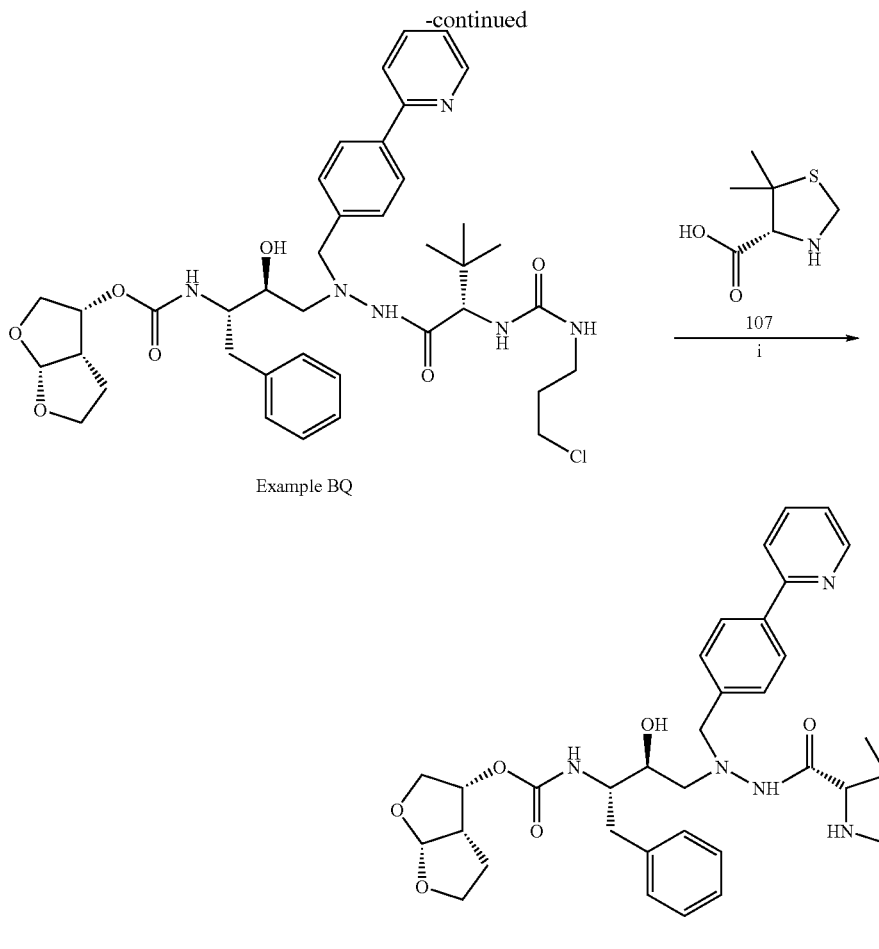

Reagents and conditions: i. TPTU, NMM, DMF

Example BO

Compound 104 (41 mg, 0.08 mmol) was dissolved in DMF (0.25 mL) at r.t. and TPTU (30 mg, 0.1 mmol) was added and the reaction mixture and was allowed to stir for 20 min. Example G (16 mg, 0.08 mmol) was dissolved in DMF (0.25 mL) and was added to the reaction flask followed by 4-methylmorpholine (16 μL, 0.14 mmol). The reaction mixture was allowed to stir at r.t. for 1 h and then the reaction mixture was diluted with $H_2O$ and extracted three times with DCM. The organic layer was dried over $Na_2SO_4$, and concentrated. Purification by reverse phase HPLC (Phenomenex Synergi® column, 25-100% acetonitrile/$H_2O$) yielded Example BO as a white solid (28 mg, 50%). $^1H$ NMR (300 MHz, $CDCl_3$): δ 8.68 (d, J=4.2 Hz, 1H), 7.93 (d, J=8.4 Hz, 2H), 7.76-7.70 (m, 2H), 7.45 (d, J=8.4 Hz, 2H), 7.27-7.18 (m, 6H), 5.66 (d, J=4.8 Hz, 1H), 5.31 (m, 1H), 5.03 (m, 1H), 4.68 (m, 1H), 4.06-3.60 (m, 10H), 3.20-2.93 (m, 8H), 1.79-1.60 (m, 6H), 0.85 (s, 9H). Mass spectrum: $(M+H)^+$=716.

Example BP

Compound 105 (41 mg, 0.08 mmol) was dissolved in DMF (0.25 mL) at r.t. and TPTU (48 mg, 0.16 mmol) was added and the reaction mixture and was allowed to stir for 20 min. Example G (31 mg, 0.16 mmol) was dissolved in DMF (0.25 mL) and was added to the reaction flask followed by 4-methylmorpholine (26 μL, 0.24 mmol). The reaction mixture was allowed to stir at r.t. for 1 h and then the reaction mixture was diluted with $H_2O$ and extracted three times with DCM. The organic layer was dried over $Na_2SO_4$, and concentrated. Purification by reverse phase HPLC (Phenomenex Synergi® column, 25-100% acetonitrile/$H_2O$) yielded Example BP as a white solid (37 mg, 68%). $^1H$ NMR (300 MHz, $CDCl_3$): δ 8.69 (d, J=4.5 Hz, 1H), 7.95 (d, J=8.1 Hz, 2H), 7.78-7.70 (m, 2H), 7.29-7.18 (m, 6H), 5.67 (d, J=5.1 Hz, 1H), 5.31-5.04 (m, 2H), 4.13 (m, 1H), 4.02-3.70 (m, 10H), 2.95 (m, 4H), 2.70 (m, 1H), 1.92-1.63 (m, 8H), 0.70 (d, J=6.7 Hz, 3H), 0.61 (d, J=6.7 Hz, 3H). Mass spectrum: $(M+H)^+$=695.

Example BQ

Compound 106 (41 mg, 0.08 mmol) was dissolved in DMF (0.25 mL) at r.t. and TPTU (48 mg, 0.16 mmol) was added and the reaction mixture and was allowed to stir for 20 min. Example G (40 mg, 0.16 mmol) was dissolved in DMF (0.25 mL) and was added to the reaction flask followed by 4-methylmorpholine (26 μL, 0.24 mmol). The reaction mixture was allowed to stir at r.t. for 1 h and then the reaction mixture was diluted with $H_2O$ and extracted three times with DCM.

The organic layer was dried over Na$_2$SO$_4$, and concentrated. Purification by reverse phase HPLC (Phenomenex Synergi® column, 25-100% acetonitrile/H$_2$O) yielded Example BQ as a white solid (35 mg, 60%). $^1$H NMR (300 MHz, DMSO): δ 9.23 (m, 1H), 8.64 (d, J=3.9 Hz, 1H), 7.97 (d, J=8.4 Hz, 2H), 7.89-7.81 (m, 2H), 7.45 (d, J=8.4 Hz, 2H), 7.34-7.15 (m, 5H), 6.21-6.01 (m, 1H), 5.49 (d, J=5.1 Hz, 1H), 4.99-4.91 (m, 2H), 4.03-3.48 (m, 10H), 3.07 (m, 2H), 2.75 (m, 7H), 1.75 (m, 3H), 1.39 (m, 3H), 0.61 (s, 9H). Mass spectrum: (M+H)$^+$=752.

Example BR

Compound 107 (52 mg, 0.1 mmol) was dissolved in DMF (0.25 mL) at r.t. and TPTU (60 mg, 0.2 mmol) was added and the reaction mixture and was allowed to stir for 20 min. Example G (32.2 mg, 0.2 mmol) was dissolved in DMF (0.25 mL) and was added to the reaction flask followed by 4-methylmorpholine (33 μL, 0.3 mmol). The reaction mixture was allowed to stir at r.t. for 1 h and then the reaction mixture was diluted with H$_2$O and extracted three times with DCM. The organic layer was dried over Na$_2$SO$_4$, and concentrated. Purification by reverse phase HPLC (Phenomenex Synergi® column, 25-100% acetonitrile/H$_2$O) yielded Example BR as a white solid (30 mg, 45%). $^1$H NMR (300 MHz, CDCl$_3$): δ 8.69 (d, J=5.1 Hz, 1H), 7.96 (d, J=8.1 Hz, 2H), 7.77-7.69 (m, 2H), 7.43 (d, J=8.1 Hz, 2H), 7.27-7.18 (m, 6H), 5.68 (d, J=5.1 Hz, 1H), 5.35 (d, J=5.1 Hz, 1H), 5.07-4.95 (m, 2H), 4.17-3.59 (m, 10H), 2.98-2.88 (m, 4H), 2.63 (m, 2H), 1.79-1.63 (m, 5H), 1.48 (s, 3H), 0.98 (s, 3H). Mass spectrum: (M+Na)$^+$=684.

Preparation of Examples BS, BT, BU, and BV

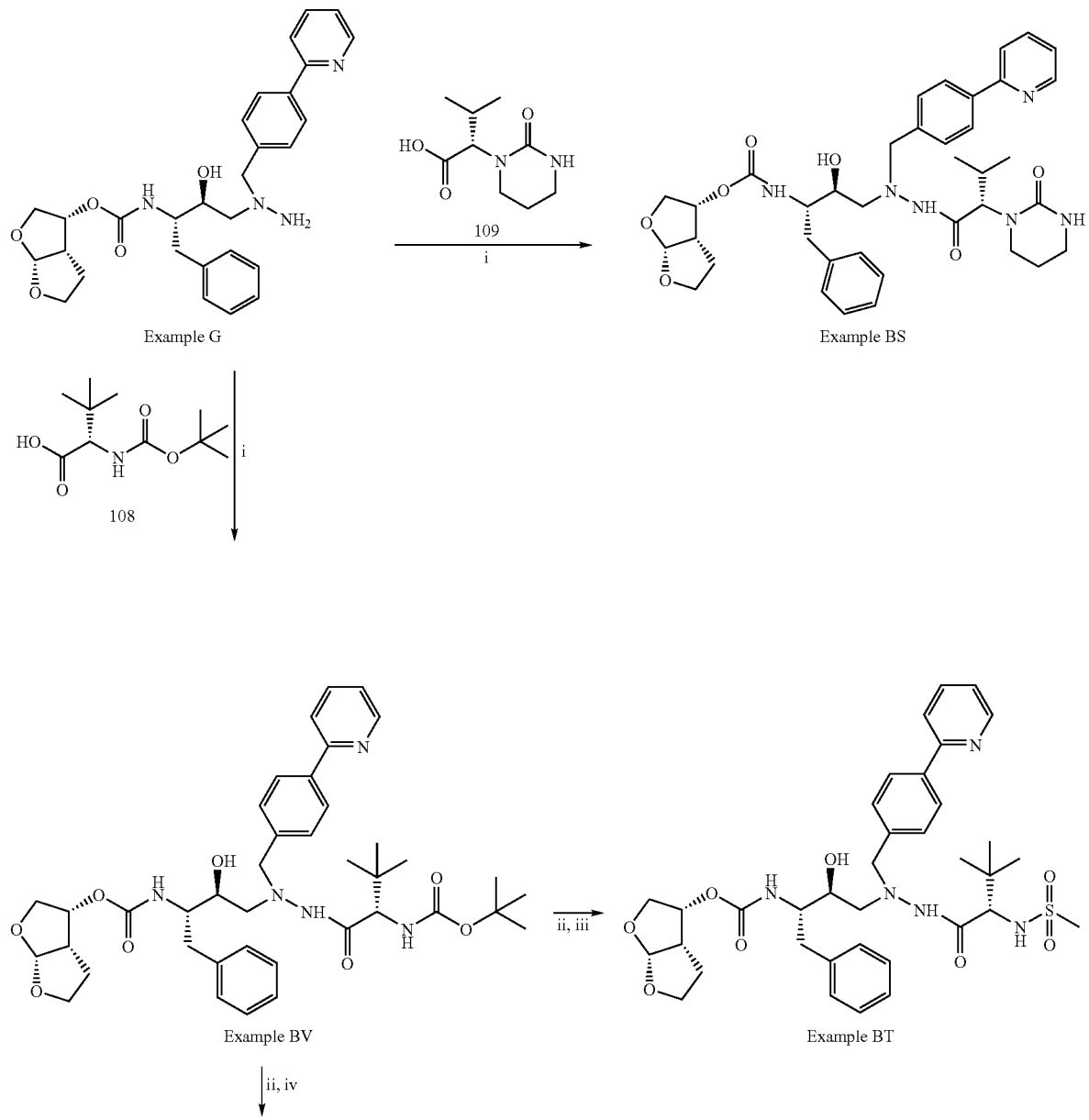

Scheme 31

-continued

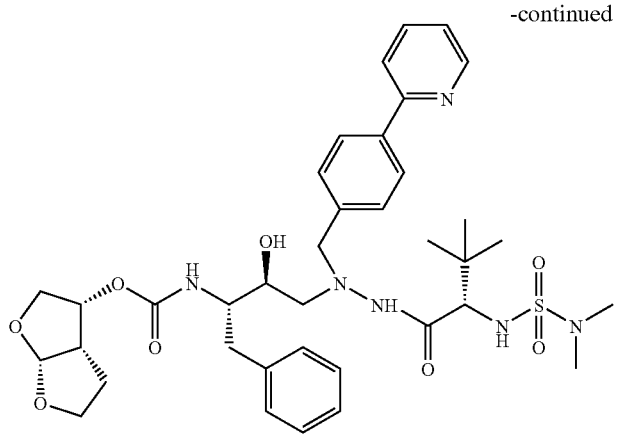

Example BU

Reagents and conditions: i. EDC, HOBt, NMM, DMF; ii. TFA, DCM; iii. Methanesulfonyl chloride, DIEA, DCM; iv. Dimethylsulfamoyl chloride, DIEA, DCM Example BV Boc-L-tert-leucine (46 mg, 0.2 mmol) was dissolved in DMF (0.25 mL) at r.t. EDC (38 mg, 0.2 mmol) and HOBT (27 mg, 0.2 mmol) were added and the reaction mixture was allowed to stir for 30 min. Example G (52 mg, 0.1 mmol) was dissolved in DMF (0.25 mL) and was added to the reaction flask after the addition of 4-methylmorpholine (26 µL, 0.24 mmol). The reaction mixture was allowed to stir at r.t. for 18 h and then the reaction mixture was diluted with ethyl acetate and washed with saturated $NaHCO_3$ and brine before it was dried over $Na_2SO_4$, and concentrated. Purification by reverse phase HPLC (Phenomenex Synergi® column, 25-100% acetonitrile/$H_2O$) yielded Example BV as a solid (47 mg, 65%). $^1$H NMR (300 MHz, $CDCl_3$): δ 9.06 (d, J=5.4 Hz, 1H), 8.34 (m, 1H), 8.00 (d, J=7.8 Hz, 1H), 7.86 (d, J=8.4 Hz, 2H), 7.75 (m, 1H), 7.63 (d, J=8.4 Hz, 2H), 7.25-7.18 (m, 5H), 5.64 (d, J=5.1 Hz, 1H), 5.29-4.99 (m, 3H), 4.16 (m, 1H), 4.03-3.53 (m, 10H), 2.92 (m, 7H), 1.42 (s, 9H), 0.73 (s, 9H), Mass spectrum: $(M+H)^+$=732.

Example BS

Carboxylic acid 109 (30 mg, 0.15 mmol) was dissolved in DMF (0.5 mL) at r.t. EDC (30 mg, 0.15 mmol) and HOBT (21 mg, 0.15 mmol) were added and the reaction mixture was allowed to stir for 30 min. Example G (78 mg, 0.15 mmol) was dissolved in DMF (0.5 mL) and was added to the reaction flask after the addition of 4-methylmorpholine (22 µL, 0.2 mmol). The reaction mixture was allowed to stir at r.t. for 18 h and then the reaction mixture was diluted with ethyl acetate and washed with saturated $NaHCO_3$ and brine before it was dried over $Na_2SO_4$, and concentrated. Purification by reverse phase HPLC (Phenomenex Synergi® column, 25-100% acetonitrile/$H_2O$) yielded Example BS as a solid (63 mg, 60%). $^1$H NMR (300 MHz, $CDCl_3$): δ 8.88 (d, J=4.5 Hz, 1H), 7.98 (m, 1H), 7.90 (d, J=8.4 Hz, 2H), 7.80 (d, J=8.1 Hz, 1H), 7.53 (d, J=8.4 Hz, 2H), 7.43 (m, 1H), 7.26-7.18 (m, 5H), 5.66 (d, J=5.1 Hz, 1H), 5.30-5.04 (m, 2H), 4.09 (m, 1H), 4.00-3.60 (m, 10H), 3.08-2.81 (m, 10H), 2.09 (m, 4H), 1.64 (m, 1H), 0.78 (d, J=6.3 Hz, 3H), 0.52 (d, J=6.3 Hz, 3H). Mass spectrum: $(M+H)^+$=702.

Example BT

DCM (1 mL) was used to dissolve Example BV (20 mg, 0.027 mmol) and TFA (0.2 mL) was added. The reaction mixture was allowed to stir at r.t. for 2 h then the reaction mixture was concentrated. The resulting residue was dissolved in anhydrous DCM (0.5 mL) and cooled to 0° C. DIPEA (14 µL, 0.08 mmol) was added followed by methanesulfonyl chloride (2.8 µL, 0.035 mmol) The reaction mixture was stirred for 1 h at 0° C. and for 16 h at r.t. The reaction mixture was concentrated and dissolved in ethyl acetate. The organic layer was washed three times with $H_2O$, three times with $NaHCO_3$ and once with brine before it was dried over $Na_2SO_4$ and concentrated and purified by reverse phase HPLC (Phenomenex Synergi® column, 25-100% acetonitrile/$H_2O$) to give Example BT (10 mg, 50%). $^1$H NMR (300 MHz, $CDCl_3$): δ 8.69 (d, J=4.2 Hz, 1H), 7.95 (d, J=8.4 Hz, 2H), 7.74 (m, 2H), 7.46 (d, J=8.4 Hz, 1H), 7.26-7.18 (m, 7H), 6.57 (m, 1H), 5.65 (d, J=5.4 Hz, 1H), 5.15-4.99 (m, 3H), 4.14 (m, 1H), 4.00-3.66 (m, 10H), 3.24 (m, 1H), 2.98-2.78 (m, 6H), 2.69 (s, 3H), 0.77 (s, 9H), Mass spectrum: $(M+H)^+$=711.

Example BU

DCM (1 mL) was used to dissolve Example BV (20 mg, 0.027 mmol) and TFA (0.2 mL) was added. The reaction mixture was allowed to stir at r.t. for 2 h then the reaction mixture was concentrated. The resulting residue was dissolved in anhydrous DCM (0.5 mL) and cooled to 0° C. DIPEA (42 µL, 0.24 mmol) was added followed by dimethanesulfamonyl chloride (3.8 µL, 0.035 mmol). The reaction mixture was stirred for 1 h at 0° C. and for 16 h at r.t. The reaction mixture was concentrated and dissolved in ethyl acetate. The organic layer was washed three times with $H_2O$, three times with $NaHCO_3$ and once with brine before it was dried over $Na_2SO_4$ and concentrated and purified by reverse phase HPLC (Phenomenex Synergi® column, 25-100% acetonitrile/$H_2O$) to give Example BU (9 mg, 45%). $^1$H NMR (300 MHz, $CDCl_3$): δ 8.98 (d, J=5.4 Hz, 1H), 8.19 (m, 1H), 7.90 (m, 3H), 7.62 (m, 3H), 7.26-7.18 (m, 5H), 5.63 (d, J=5.4

Hz, 1H), 5.26-4.94 (m, 3H), 4.20 (m, 1H), 4.03-3.66 (m, 10H), 3.19 (m, 1H), 2.98-2.83 (m, 6H), 2.78 (s, 6H), 0.74 (s, 9H), Mass spectrum: (M+H)$^+$=739.

Preparation of Examples BW and BX

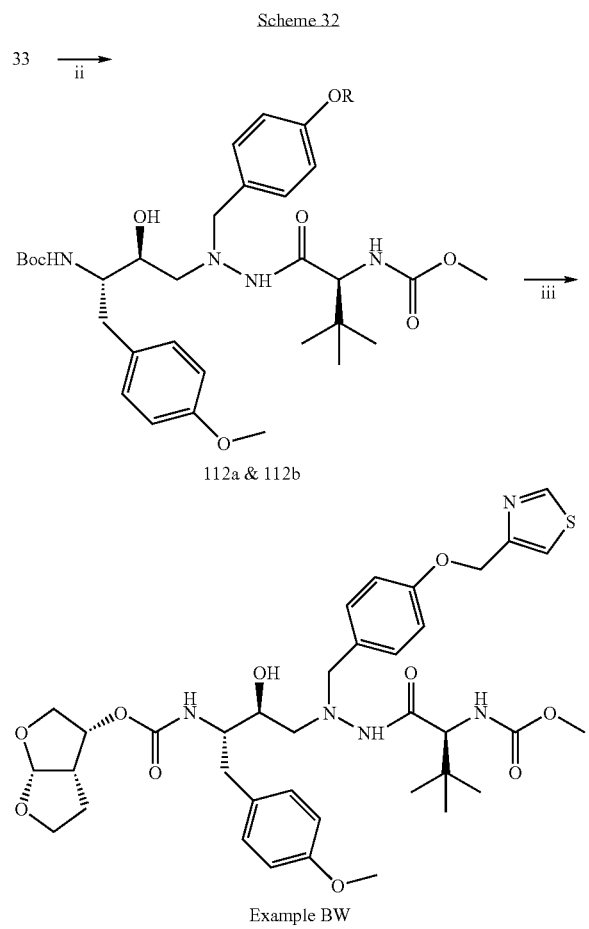

Reagents and conditions: i. TBAF, THF; ii. ROH, Ph$_3$P, DBAD, DCM; iii. TFA, DCM, DIEA, DMAP, Copound 70 MeCN Compounds 112a DCM (1.2 mL) was used to dissolve Compound 33 (36 mg, 0.06 mmol) and thiazol-4-yl methanol (0.12 mmol) was added at r.t. Follow by Ph$_3$P (31 mg, 0.12 mmol) and Di-tert-butylazodicarboxylate (28 mg, 0.12 mmol). The reaction mixture was allowed to stir at r.t. for 16 h, diluted with ethyl acetate (20 mL), and the organic layer was washed brine and dried over anhydrous Na$_2$SO$_4$ and concentrated and purified by silica gel chromatography to give Compounds 112a.

Compounds 112b

Compound 112b can be prepared following the procedure for Compound 112a, except using 3-hydroxymethylpyridine in place of thiazol-4-yl-methanol.

Example BW

DCM (1 mL) was used to dissolve Compound 112a (90 mg, 0.13 mmol) and TFA (0.2 mL) was added. The reaction mixture was allowed to stir at r.t. for 2 h then the reaction mixture was concentrated. The resulting residue was dissolved in anhydrous acetonitrile (0.5 mL) and cooled to 0° C. DIPEA (105 µL, 0.6 mmol) was added followed by Compound 70 (41 mg, 0.14 mmol) and DMAP (2 mg, 0.016 mmol). The reaction mixture was stirred for 1 h at 0° C. and for 16 h at r.t. The reaction mixture was concentrated and dissolved in ethyl acetate. The organic layer was washed three times with H$_2$O, three times with NaHCO$_3$ and once with brine before it was dried over Na$_2$SO$_4$ and concentrated and purified by reverse phase HPLC (Phenomenex Synergi® column, 25-100% acetonitrile/H$_2$O) to give Example BW (38 mg, 40%). $^1$H NMR (300 MHz, CDCl$_3$): δ 8.85 (d, J=1.8 Hz, 1H), 7.41 (m, 1H), 7.25 (d, J=8.4 Hz, 2H), 7.11 (d, J=8.4 Hz, 2H), 6.95 (d, J=8.4 Hz, 2H), 6.79 (d, J=8.4 Hz, 2H), 5.67 (d, J=5.4 Hz, 1H), 5.26-5.00 (m, 5H), 4.03-3.55 (m, 13H), 2.96-2.85 (m, 5H), 2.60 (m, 5H), 1.67 (m, 1H), 0.75 (s, 9H), Mass spectrum: (M+H)$^+$=757.

Example BX

DCM (0.5 mL) was used to dissolve Compound 112b (40 mg, 0.058 mmol) and TFA (0.1 mL) was added. The reaction mixture was allowed to stir at r.t. for 2 h then the reaction mixture was concentrated. The resulting residue was dissolved in anhydrous acetonitrile (0.5 mL) and cooled to 0° C. DIPEA (51 µL, 0.29 mmol) was added followed by Compound 70 (18 mg, 0.06 mmol) and DMAP (0.8 mg, 0.006 mmol). The reaction mixture was stirred for 1 h at 0° C. and for 16 h at r.t. The reaction mixture was concentrated and dissolved in ethyl acetate. The organic layer was washed three times with H$_2$O, three times with NaHCO$_3$ and once with brine before it was dried over Na$_2$SO$_4$ and concentrated and purified by reverse phase HPLC (Phenomenex Synergi® column, acetonitrile/H$_2$O+0.1% TFA) to give Example BX (20 mg, 45%). $^1$H NMR (300 MHz, CDCl$_3$): δ 9.02 (s, 1H), 8.84 (d, J=4.8 Hz, 1H), 8.45 (d, J=7.8 Hz, 1H), 7.91 (m, 1H), 7.31 (d, J=8.4 Hz, 2H), 7.10 (d, J=8.7 Hz, 2H), 6.93 (d, J=8.7 Hz, 2H), 6.79 (d, J=8.4 Hz, 2H), 5.66 (d, J=5.1 Hz, 1H), 5.34-5.01 (m, 5H), 4.07-3.61 (m, 16H), 2.92-2.66 (m, 6H), 1.68 (m, 2H), 0.79 (s, 9H), Mass spectrum: (M+H)$^+$=751.

Preparation of Example BY

Scheme 33

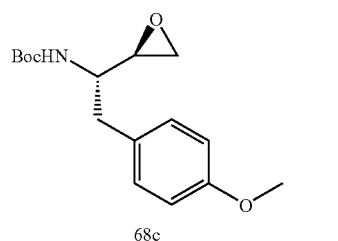

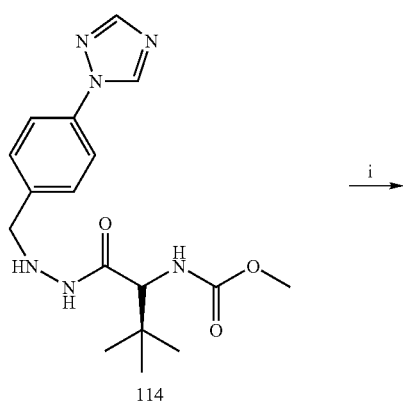

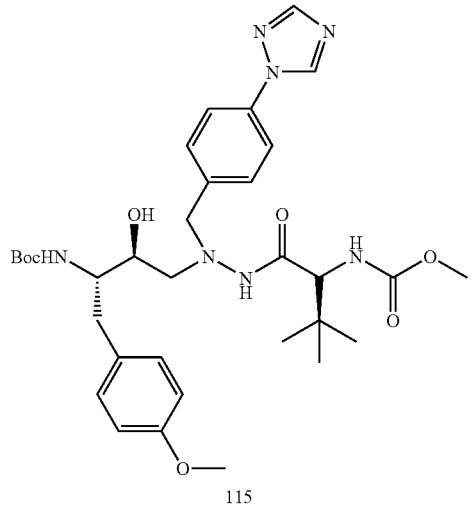

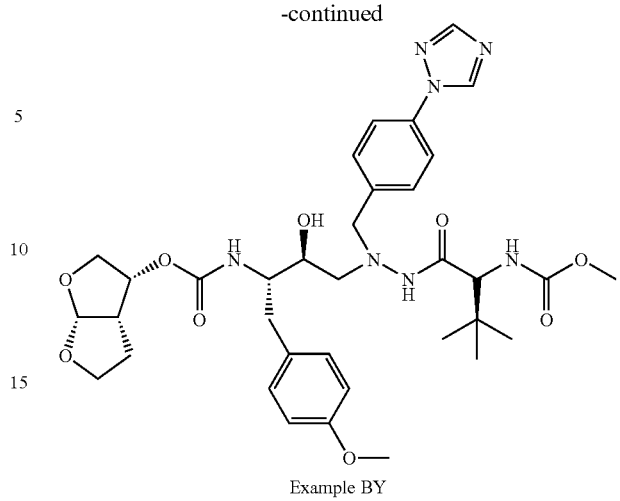

Reagents and Conditions: i. i-PrOH, 80° C.; ii. TFA, DCM; DMAP, DIPEA, Compound 70

Compound 115

Epoxide 68c (59 mg, 0.2 mmol) and 114 (76 mg, 0.21 mmol) were dissolved in isopropanol and heated to 80° C. The reaction mixture was allowed to stir for 18 h before it was cooled to r.t., concentrated, and purified on silica gel chromatography (ethyl acetate/hexane, 30-50%) to give Compound 115 (72 mg, 55%) Mass spectrum: $(M+H)^+=654$ Example BY TFA (0.05 mL) was added to 115 (50 mg, 0.075 mmol) in DCM (0.5 mL) and the mixture was allowed to stir at r.t. for 1.5 h. The solution was concentrated and co-evaporated three times with DCM and three times with acetonitrile. The residue was dissolved in anhydrous acetonitrile (1 mL) and cooled to 0° C. DMAP (1.5 mg, 0.01 mmol) was added followed by DIEA (52.5 μL, 0.3 mmol) until the solution reached pH 9. Compound 70 (23.5 mg, 0.08 mmol) was added. The reaction mixture was stirred for 2 h at 0° C. and for 16 h at r.t. The reaction mixture was concentrated and purified by reverse phase HPLC (Phenomenex Synergi® column, 25-100% acetonitrile/$H_2O$+0.1% TFA) to give Example BY (27 mg, 50%). $^1$H NMR (300 MHz, CDCl$_3$): 8.54 (s, 1H), 8.11 (s, 1H), 7.64 (d, J=8.7 Hz, 1H), 7.52 (d, J=8.7 Hz, 1H), 7.13 (d, J=8.4 Hz, 2H), 6.80 (d, J=8.4 Hz, 2H), 6.47 (m, 1H), 5.67 (d, J=5.1 Hz, 1H), 5.24 (m, 2H), 5.03 (m, 1H), 4.74 (m, 1H), 4.17-3.54 (m, 15H), 2.95-2.68 (m, 5H), 1.72-1.58 (m, 2H), 0.73 (s, 9H). Mass spectrum: $(M+H)^+=710$

Preparation of Examples BZ and CA

Scheme 34

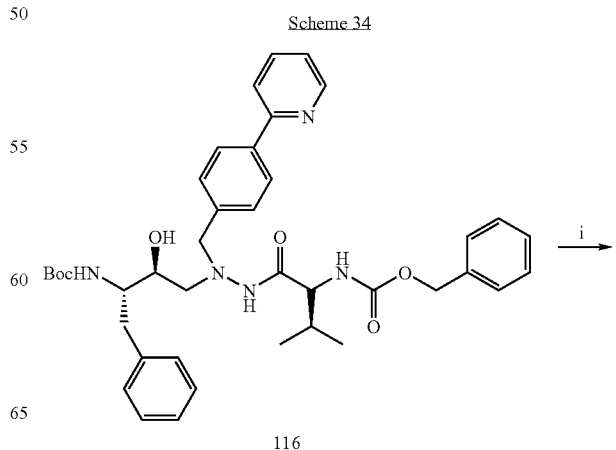

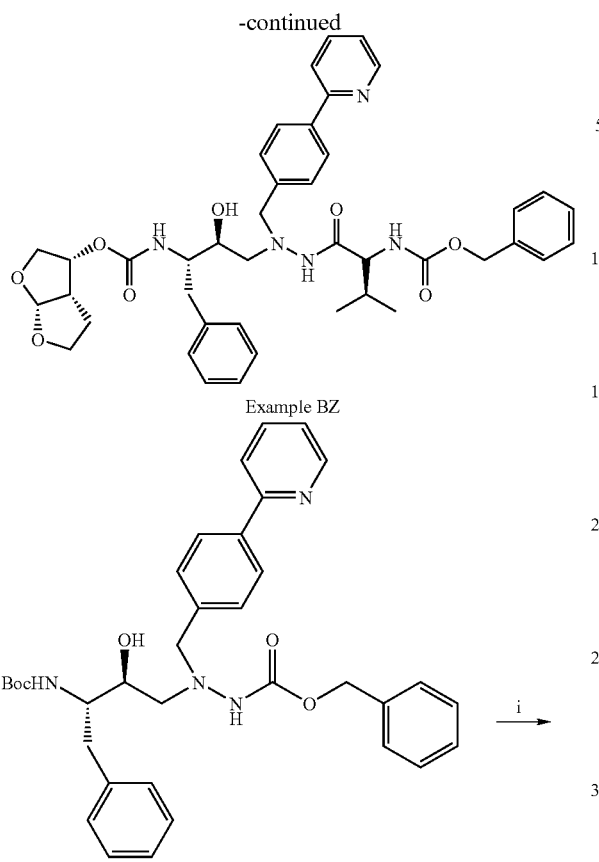

Example BZ

Example CA

Reagents and Conditions: i TFA, DCM; DMAP, DIPEA, Compound 70

Example BZ

TFA (0.03 mL) was added to 116 (28 mg, 0.052 mmol) in DCM (0.3 mL) and the mixture was allowed to stir at r.t. for 1.5 h. The solution was concentrated and co-evaporated three times with DCM and three times with acetonitrile. The residue was dissolved in anhydrous acetonitrile (0.5 mL) and cooled to 0° C. DMAP (1 mg, 0.008 mmol) was added followed by DIEA (35 μL, 0.2 mmol) until the solution reached pH 9. (R)-4-nitrophenyl bistetrahydrofuran-3-yl carbonate (16 mg, 0.052 mmol) was added. The reaction mixture was stirred for 2 h at 0° C. and for 16 h at r.t. The reaction mixture was concentrated and purified by reverse phase HPLC (Phenomenex Synergi® column, 25-100% acetonitrile/H$_2$O+ 0.1% TFA) to give Example BZ (15 mg, 50%). $^1$H NMR (300 MHz, CDCl$_3$): δ 8.99 (m, 1H), 8.25 (m, 1H), 8.12 (d, J=7.2 Hz, 2H), 7.91-7.15 (m, 12H), 6.88 (d, J=7.2 Hz, 2H) 5.66 (d, J=5.1 Hz, 1H), 5.48-5.03 (m, 10H), 4.11-3.59 (m, 6H), 2.95-2.68 (m, 4H), 1.92-1.63 (m, 4H), 0.65 (m, 6H). Mass spectrum: (M+H)$^+$=752

Example CA

TFA (0.03 mL) was added to 10 (31 mg, 0.052 mmol) in DCM (0.3 mL) and the mixture was allowed to stir at r.t. for 1.5 h. The solution was concentrated and co-evaporated three times with DCM and three times with acetonitrile. The residue was dissolved in anhydrous acetonitrile (0.5 mL) and cooled to 0° C. DMAP (1 mg, 0.008 mmol) was added followed by DIEA (35 μL, 0.2 mmol) until the solution reached pH 9. Compound 70 (16 mg, 0.052 mmol) was added. The reaction mixture was stirred for 2 h at 0° C. and for 16 h at r.t. The reaction mixture was concentrated and purified by reverse phase HPLC (Phenomenex Synergi® column, 25-100% acetonitrile/H$_2$O+0.1% TFA) to give Example CA (16 mg, 50%). $^1$H NMR (300 MHz, CDCl$_3$): δ 8.75 (m, 1H), 7.94 (d, J=7.5 Hz, 2H), 7.85-7.73 (m, 4H), 7.44-7.18 (m, 11H), 5.66 (d, J=5.1 Hz, 1H), 5.60 (m, 1H), 5.28-5.03 (m, 4H), 4.08-3.66 (m, 8H), 2.96-2.60 (m, 6H), 1.67 (m, 2H), Mass spectrum: (M+Na)$^+$=675

Preparation of Examples CB-CG

Scheme 35

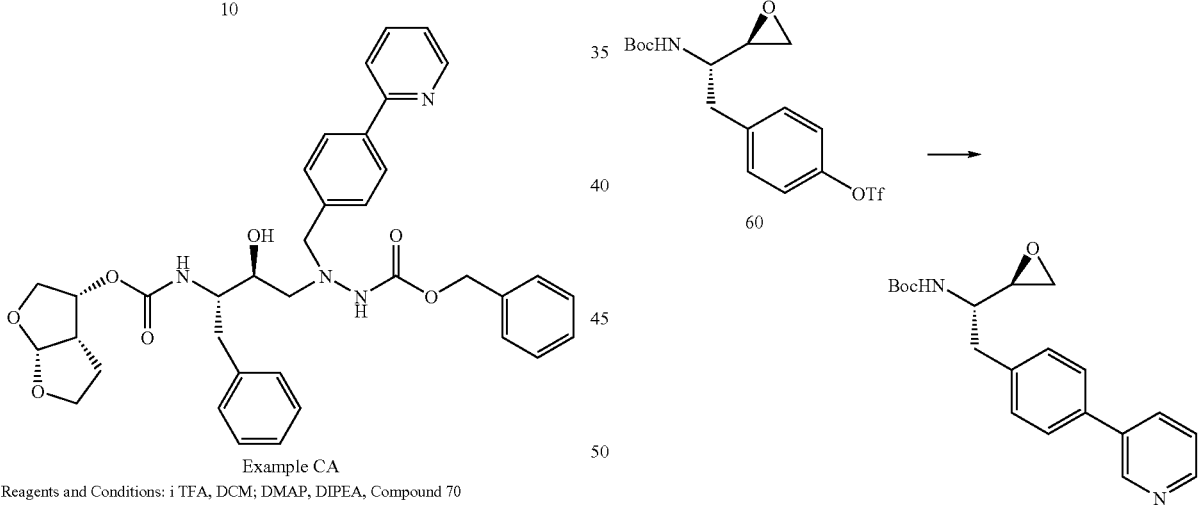

Reagents and Conditions: i. 3-pyridineboronic acid, PdCl$_2$(dppf), DME, aq. Na$_2$CO$_3$, 78%

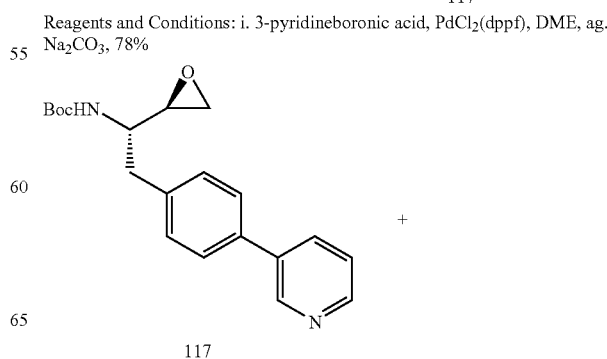

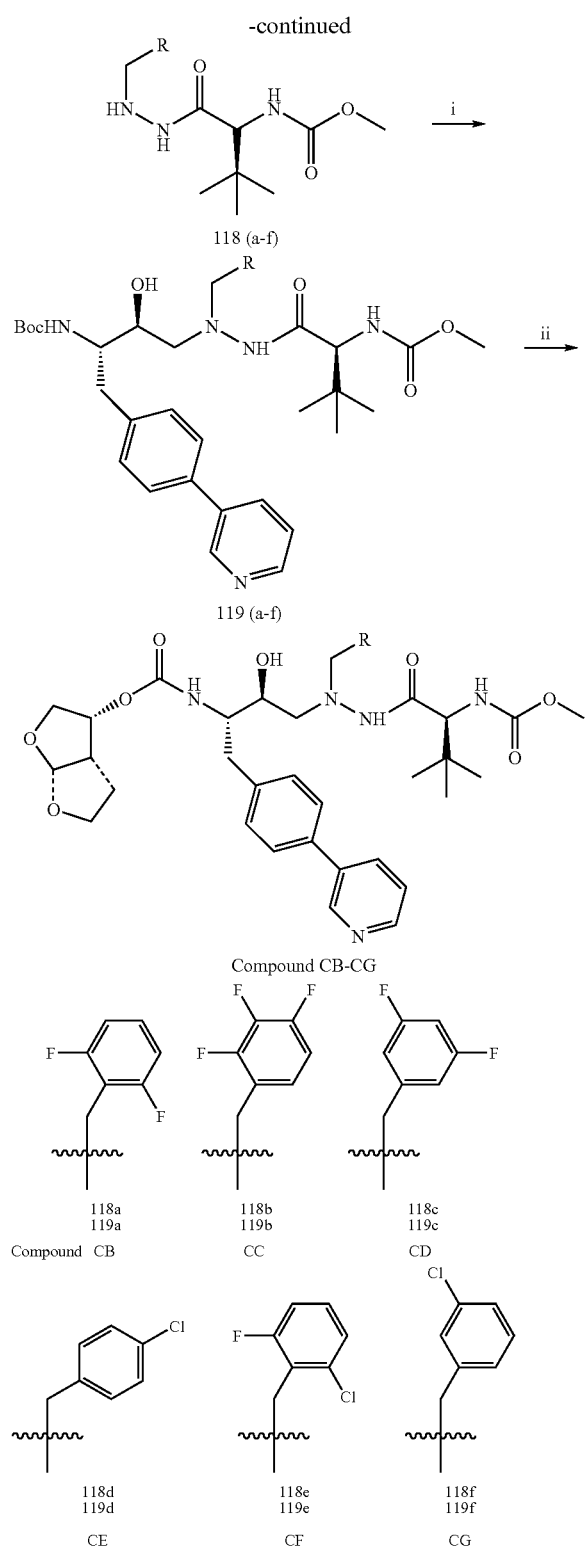

Reagents and Conditions: i. HOAc, i-PrOH, 80° C.; ii. TFA, DCM; DMAP, DIPEA, Bistetrahydrofuran-carbonate Compound 117

A round-bottom flask was charged with compound 60 (1.24 g, 3.01 mmol), 3-pyridineboronic acid (Aldrich, 0.741 g, 6.03 mmol), and $PdCl_2(dppf)$ (0.276 g, 0.301 mmol). A 2M aqueous sodium carbonate solution (7.5 mL, 15.05 mmol) and dimethoxyethane (30 mL) were added and the reaction mixture was stirred for 45 min at 80° C. The reaction mixture was diluted with ethyl acetate and washed with brine. The organic layer was dried ($MgSO_4$), concentrated to 10 mL and purified by flash chromatography (silica gel, 30 to 60% isopropanol/Hex) to give a white solid (0.7247 g, 70%). LC-MS shows 341.1 (M+1). $^1$H NMR (300 MHz, $CDCl_3$): δ 8.81 (s, 1H), 8.58 (m, 1H), 7.82 (m, 1H), 7.51 (m, 2H), 7.37 (m, 3H), 4.64 (m, 1H), 4.17 (m, 1H), 3.04 (m, 1H), 2.95 (m, 2H), 2.72 (t, 1H), 2.60 (s, 1H), 1.39 (s, 9H).

Compound 119a

Epoxide 117 (34 mg, 0.1 mmol) and 118a (100 mg, 0.3 mmol) were dissolved in isopropanol (1.5 mL), acetic acid (0.014 mL, 0.24 mmol) was added and the reaction mixture was heated to 80° C. The reaction was allowed to stir for 18 h before it was cooled to r.t., concentrated, and purified on silica gel (ethyl acetate/hexane, 30-50%) to give compound 119a (25 mg, 25%). Mass spectrum: $(M+Na)^+=693$ Example CB TFA (0.1 mL) was added to 119a (12 mg, 0.018 mmol) in DCM (0.5 mL) and the mixture was allowed to stir at r.t. for 2 h. The solution was concentrated and co-evaporated three times with DCM and three times with acetonitrile. The residue was dissolved in anhydrous acetonitrile (0.5 mL) and cooled to 0° C. DMAP (0.3 mg, 0.002 mmol) was added followed by DIEA (16 μL, 0.09 mmol) until the solution reached pH 9. The bistetrahydrofuran-carbonate (6 mg, 0.02 mmol) was added. The reaction was stirred for 2 h at 0° C. and for 16 h at r.t. The reaction mixture was concentrated and purified by reverse phase HPLC (25-100% acetonitrile/$H_2O$+ 0.1% TFA) to give Example CB (8 mg, 61%). $^1$H NMR (300 MHz, $CDCl_3$): δ 8.86 (s, 1H), 8.60 (m, 1H), 7.95 (d, 1H), 7.49 (d, 2H), 7.34 (d, 2H), 7.29 (m, 1H), 6.91 (d, 2H), 6.80 (s, 1H), 5.67 (d, 1H), 5.34 (m, 1H), 5.22 (m, 1H), 5.07 (m, 1H), 4.12 (m, 2H), 4.05-3.64 (m, 10H), 3.58 (s, 3H), 2.98-2.63 (m, 4H), 1.72 (m, 2H), 0.89 (s, 9H). Mass spectrum: $(M+H)^+=727$ Compound 119b Epoxide 117 (34 mg, 0.1 mmol) and 118b (97 mg, 0.28 mmol) were dissolved in isopropanol (1.5 mL), acetic acid (0.013 mL, 0.22 mmol) was added and the reaction mixture was heated to 80° C. The reaction was allowed to stir for 18 h before it was cooled to r.t., concentrated, and purified on silica gel (ethyl acetate/hexane, 30-50%) to give compound 119b (30 mg, 30%). Mass spectrum: $(M+Na)^+=711$ Example CC TFA (0.1 mL) was added to 119b (13 mg, 0.018 mmol) in DCM (0.5 mL) and the mixture was allowed to stir at r.t. for 2 h. The solution was concentrated and co-evaporated three times with DCM and three times with acetonitrile. The residue was dissolved in anhydrous acetonitrile (0.5 mL) and cooled to 0° C. DMAP (0.3 mg, 0.002 mmol) was added followed by DIEA (16 μL, 0.09 mmol) until the solution reached pH 9. The bistetrahydrofuran-carbonate (6 mg, 0.02 mmol) was added. The reaction mixture was stirred for 2 h at 0° C. and for 16 h at r.t. The reaction was concentrated and purified by reverse phase HPLC (25-100% acetonitrile/$H_2O$+ 0.1% TFA) to give Example CC (10 mg, 71%). $^1$H NMR (300 MHz, $CDCl_3$): δ 9.14 (s, 1H), 8.79 (d, 1H), 8.48 (d, 1H), 7.91 (m, 1H), 7.55 (d, 2H), 7.42 (d, 2H), 7.29 (m, 1H), 6.95 (m, 1H), 5.68 (d, 1H), 5.39 (m, 1H), 5.29 (m, 1H), 5.05 (m, 1H), 4.40 (m, 2H), 4.04-3.72 (m, 10H), 3.63 (s, 3H), 3.02-2.73 (m, 4H), 1.73 (m, 2H), 0.79 (s, 9H). Mass spectrum: (M+H)$^+$=745

Compound 119C

Epoxide 117 (34 mg, 0.1 mmol) and 118C (100 mg, 0.3 mmol) were dissolved in isopropanol (1.5 mL), acetic acid (0.014 mL, 0.24 mmol) was added and the reaction mixture was heated to 80° C. The reaction mixture was allowed to stir for 18 h before it was cooled to r.t., concentrated, and purified on silica gel (ethyl acetate/hexane, 30-50%) to give compound 119C (40 mg, 60%). Mass spectrum: (M+Na)$^+$=693

Example CD

TFA (0.1 mL) was added to 119C (36 mg, 0.054 mmol) in DCM (0.8 mL) and the mixture was allowed to stir at r.t. for 2 h. The solution was concentrated and co-evaporated three times with DCM and three times with acetonitrile. The residue was dissolved in anhydrous acetonitrile (1 mL) and cooled to 0° C. DMAP (0.5 mg, 0.004 mmol) was added followed by DIEA (47 μL, 0.27 mmol) until the solution reached pH 9. The bistetrahydrofuran-carbonate (16 mg, 0.055 mmol) was added. The reaction was stirred for 2 h at 0° C. and for 16 h at r.t. The reaction was concentrated and purified by reverse phase HPLC (25-100% acetonitrile/H$_2$O+ 0.1% TFA) to give Example CD (15 mg, 38%). $^1$H NMR (300 MHz, CDCl$_3$): δ 9.18 (s, 1H), 8.83 (m, 1H), 8.54 (m, 1H), 7.95 (m, 1H), 7.56 (d, 2H), 7.44 (d, 2H), 6.92 (d, 2H), 6.72 (m, 1H), 5.69 (d, 1H), 5.46 (m, 1H), 5.40 (m, 1H), 5.05 (m, 1H), 4.10-3.45 (m, 14H), 3.03-2.72 (m, 5H), 1.74 (m, 2H), 0.74 (s, 9H). Mass spectrum: (M+H)$^+$=727

Compound 119d

Epoxide 117 (136 mg, 0.4 mmol) and 118d (229 mg, 0.7 mmol) were dissolved in isopropanol (4 mL), acetic acid (0.032 mL, 0.56 mmol) was added and the reaction mixture was heated to 80° C. The reaction was allowed to stir for 18 h before it was cooled to r.t., concentrated, and purified on silica gel (ethyl acetate/hexane, 30-50%) to give compound 119d (64 mg, 24%). Mass spectrum: (M+Na)$^+$=691

Example CE

TFA (0.2 mL) was added to 119d (64 mg, 0.095 mmol) in DCM (1.0 mL) and the mixture was allowed to stir at r.t. for 2 h. The solution was concentrated and co-evaporated three times with DCM and three times with acetonitrile. The residue was dissolved in anhydrous acetonitrile (1.9 mL) and cooled to 0° C. DMAP (1.1 mg, 0.01 mmol) was added followed by DIEA (60 μL, 0.34 mmol) until the solution reached pH 9. The bistetrahydrofuran-carbonate (28 mg, 0.095 mmol) was added. The reaction was stirred for 2 h at 0° C. and for 16 h at r.t. The reaction was concentrated and purified by reverse phase HPLC (25-100% acetonitrile/H$_2$O+ 0.1% TFA) to give Example CE (32 mg, 40%). $^1$H NMR (300 MHz, CD$_3$OD): δ 9.09 (s, 1H), 8.76 (m, 2H), 8.05 (m, 1H), 7.67 (d, 2H), 7.45 (d, 2H), 7.35 (d, 2H), 7.21 (d, 2H), 5.52 (d, 1H), 4.91 (m, 1H), 3.99-3.57 (m, 16H), 2.94-2.81 (m, 5H), 1.47 (m, 2H), 0.70 (s, 9H). Mass spectrum: (M+H)$^+$=725

Compound 119e

Epoxide 117 (136 mg, 0.4 mmol) and 118e (242 mg, 0.7 mmol) were dissolved in isopropanol (4 mL), acetic acid (0.032 mL, 0.56 mmol) was added and the reaction mixture was heated to 80° C. The reaction mixture was allowed to stir for 18 h before it was cooled to r.t., concentrated, and purified on silica gel (ethyl acetate/hexane, 30-50%) to give compound 119e (51 mg, 19%). Mass spectrum: (M+Na)$^+$=709

Example CF

TFA (0.2 mL) was added to 119e (51 mg, 0.075 mmol) in DCM (1.0 mL) and the mixture was allowed to stir at r.t. for 2 h. The solution was concentrated and co-evaporated three times with DCM and three times with acetonitrile. The residue was dissolved in anhydrous acetonitrile (1.6 mL) and cooled to 0° C. DMAP (0.9 mg, 0.008 mmol) was added followed by DIEA (50 μL, 0.29 mmol) until the solution reached pH 9. The bistetrahydrofuran-carbonate (22 mg, 0.075 mmol) was added. The reaction was stirred for 2 h at 0° C. and for 16 h at r.t. The reaction was concentrated and purified by reverse phase HPLC (25-100% acetonitrile/H$_2$O+ 0.1% TFA) to give Example CF (17 mg, 26%). $^1$H NMR (300 MHz, CD$_3$OD): δ 9.07 (s, 1H), 8.73 (m, 2H), 8.02 (m, 1H), 7.67 (d, 2H), 7.43 (d, 2H), 7.22 (m, 2H), 7.00 (m, 1H), 5.52 (d, 1H), 4.90 (m, 1H), 4.22-3.60 (m, 16H), 2.91-2.84 (m, 5H), 1.50 (m, 2H), 0.82 (s, 9H). Mass spectrum: (M+H)$^+$=743

Compound 119f

Epoxide 117 (85 mg, 0.25 mmol) and 118f (164 mg, 0.5 mmol) were dissolved in isopropanol (2.5 mL), acetic acid (0.023 mL, 0.4 mmol) was added and the reaction mixture was heated to 80° C. The reaction mixture was allowed to stir for 18 h before it was cooled to r.t., concentrated, and purified on silica gel (ethyl acetate/hexane, 30-50%) to give compound 119f (46 mg, 27%). Mass spectrum: (M+Na)$^+$=691

Example CG

TFA (0.2 mL) was added to 119f (46 mg, 0.068 mmol) in DCM (1.0 mL) and the mixture was allowed to stir at r.t. for 2 h. The solution was concentrated and co-evaporated three times with DCM and three times with acetonitrile. The residue was dissolved in anhydrous acetonitrile (1.4 mL) and cooled to 0° C. DMAP (0.8 mg, 0.007 mmol) was added followed by DIEA (82 μL, 0.48 mmol) until the solution reached pH 9. The bistetrahydrofuran-carbonate (20 mg, 0.068 mmol) was added. The reaction was stirred for 2 h at 0° C. and for 16 h at r.t. The reaction was concentrated and purified by reverse phase HPLC (25-100% acetonitrile/H$_2$O+ 0.1% TFA) to give Example CG (19 mg, 34%). $^1$H NMR (300 MHz, CDCl$_3$): δ 9.11 (s, 1H), 8.76 (m, 1H), 8.45 (m, 1H), 7.88 (m, 1H), 7.50 (d, 2H), 7.40 (d, 2H), 7.32 (d, 2H), 7.22 (d, 2H), 5.64 (d, 1H), 5.34 (m, 2H), 5.01 (m, 2H), 4.58-3.56 (m, 15H), 2.98-2.89 (m, 4H), 1.69 (m, 1H), 0.68 (s, 9H). Mass spectrum: (M+H)$^+$=725

Preparation of Example CH

Scheme 36

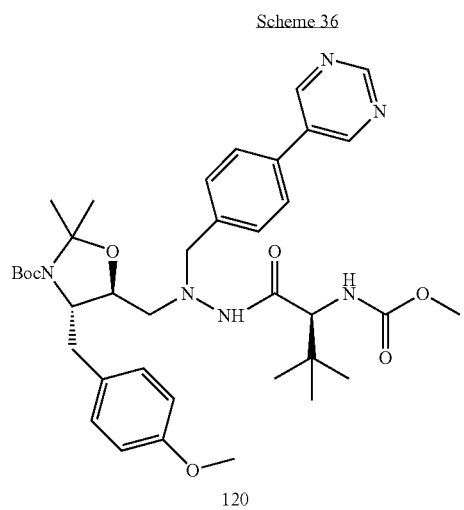

120

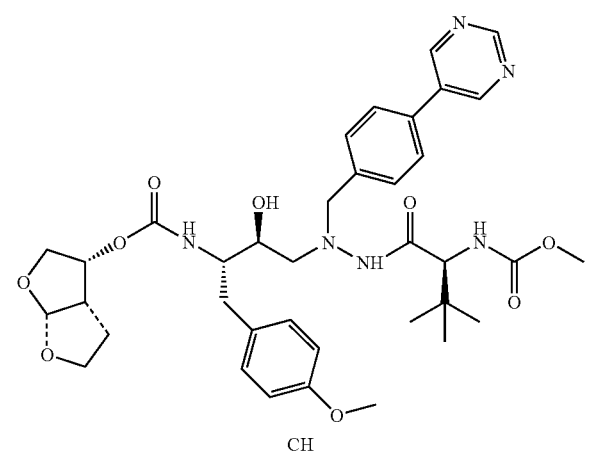

CH

Reagents and Conditions: i. TFA, DCM; DMAP, DIEA, Bistetrahydrofuran-carbonate

Example CH

TFA (0.15 mL) was added to 120 (18 mg, 0.026 mmol) in a 1:1 mixture of CH$_3$CN and H$_2$O (2.0 mL), and the mixture was allowed to stir at r.t. for 2 h. The solution was concentrated and co-evaporated three times with DCM and three times with acetonitrile. The residue was dissolved in anhydrous acetonitrile (0.4 mL) and cooled to 0° C. DMAP (0.3 mg, 0.002 mmol) was added followed by DIEA (20 μL, 0.12 mmol) until the solution reached pH 9. The bistetrahydrofuran-carbonate (7.6 mg, 0.026 mmol) was added. The reaction was stirred for 2 h at 0° C. and for 16 h at r.t. The reaction was concentrated and purified by reverse phase HPLC (25-100% acetonitrile/H$_2$O+0.1% TFA) to give Example CH (8 mg, 43%). $^1$H NMR (300 MHz, CDCl$_3$): δ 9.18 (s, 1H), 8.87 (s, 2H), 7.50 (s, 4H), 7.07 (d, 2H), 6.74 (d, 2H), 5.62 (d, 1H), 5.21

(m, 1H), 5.01 (m, 1H), 4.17 (m, 1H), 3.96-3.60 (m, 17H), 2.91-2.67 (m, 5H), 1.61 (m, 2H), 0.66 (s, 9H). Mass spectrum: (M+H)$^+$=722

Preparation of Example CI

Scheme 37

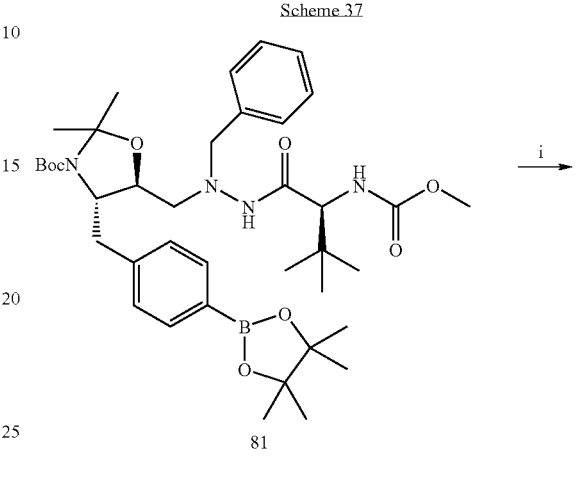

81

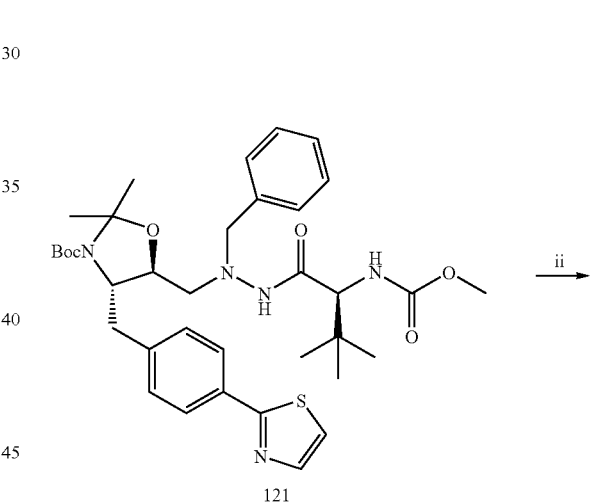

121

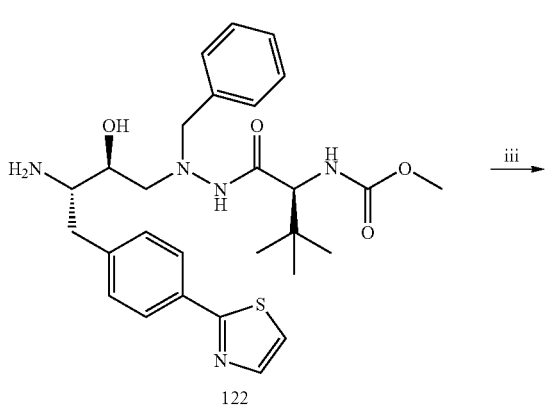

122

-continued

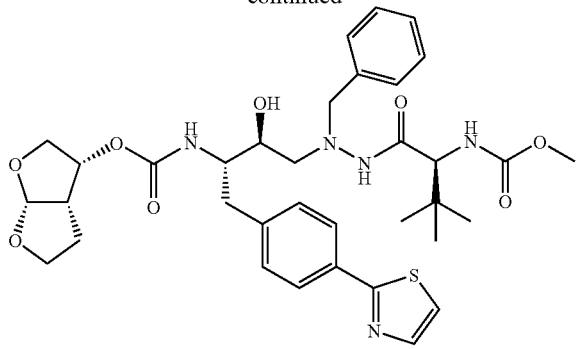

CI

Reagents and conditions: i. 2-bromo-thiazole, PdCl₂(dppf), DME, aq. Na₂CO₃; ii. a. 1% TFA in MeCN/H₂O (1:1); b. TFA, DCM; iii. 4-nitrophenyl (3R,3aS,6aR)-tetrahydro-2Hfuro[2,3-b]furan-3-yl carbonate, MeCN, DIEA, DMAP.

Compound 121

A 5 mL microwave reaction tube was charged with compound 81 (27 mg, 0.0373 mmol), 2-bromo-thiazole (5 μL, 0.056 mmol, 1.5 eq.), and PdCl₂(dppf) (0.6 mg, 0.0007 mmol, 0.02 eq.). A 2M aqueous sodium carbonate solution (0.093 mL, 0.186 mmol, 5 eq.) and dimethoxyethane (0.4 mL) were added. The reaction mixture was heated at 130° C. in the microwave reactor for 25 minutes. The reaction mixture was diluted with ethyl acetate and washed with brine. The organic layer was concentrated and purified by flash chromatography (silica gel, 30 to 90% ethyl acetate/Hexane) to give a light brown solid (7.6 mg, 30%). LC-MS shows: 680.2 (M+H)⁺.

Compound 122

1% TFA in acetonitrile/water (1:1) (2 mL) was added to compound 121 (7.6 mg, 0.011 mmol). The reaction mixture was stirred at room temperature for overnight. The crude reaction product was concentrated and dried under high vacuum. TFA (1 mL) was added to the above crude reaction product in 2 mL DCM. The reaction mixture was stirred at room temperature for 1 hour. The crude reaction product was concentrated and purified via reverse phase HPLC (0.5% TFA in MeCN/water) to give a white powder (7 mg, 90% for 2 steps). LC-MS shows: 540.2 (M+H)⁺. ¹H NMR (300 MHz, CD₃OD): δ 7.96 (d, 2H), 7.88 (d, 1H), 7.62 (d, 1H), 7.42 (d, 2H), 7.36 (m, 5H), 4.03 (m, 1H), 3.88-3.76 (m, 2H), 3.60 (s, 3H), 3.67-3.58 (m, 2H), 3.20-2.92 (m, 4H), 0.70 (s, 9H).

Example CI

DIEA (7 μL, 0.0.046 mmol, 3.0 eq.) was added to compound 122 (7 mg, 0.013 mmol, 1.0 eq.) and 4-nitrophenyl (3R,3aS,6aR)-tetrahydro-2Hfuro[2,3-b]furan-3-yl carbonate (4.6 mg, 0.016 mmol, 1.2 eq.) in 1.2 mL MeCN, followed by DMAP (0.3 mg, 0.2 eq.). The reaction mixture was stirred at room temperature for 12 hours. The crude reaction product was filtered and purified by prep HPLC (0.5% TFA in MeCN/water) to give a white powder (3.5 mg, 40%). LC-MS shows 696.2 (M+H)⁺. ¹H NMR (300 MHz, CD₃OD): δ 7.84 (m, 3H), 7.59 (d, 1H), 7.41 (m, 4H), 7.24 (m, 3H), 5.59 (d, 1H), 4.95 (m, 1H), 4.06-3.87 (m, 4H), 3.80 (m, 1H), 3.71 (m, 4H), 3.60 (s, 3H), 3.03-2.80 (m, 5H), 1.52 (m, 1H), 0.70 (s, 9H).

Preparation of Example CJ

Scheme 38

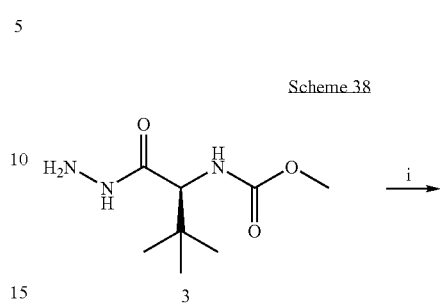

3

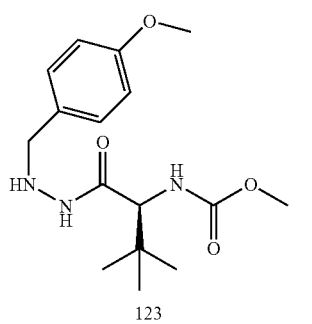

123

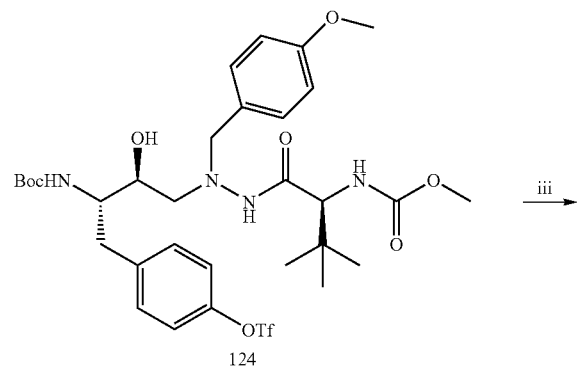

124

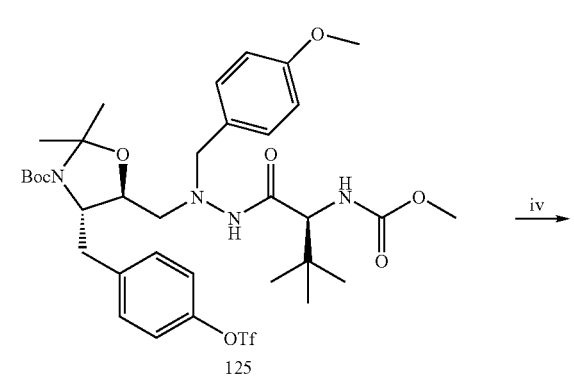

125

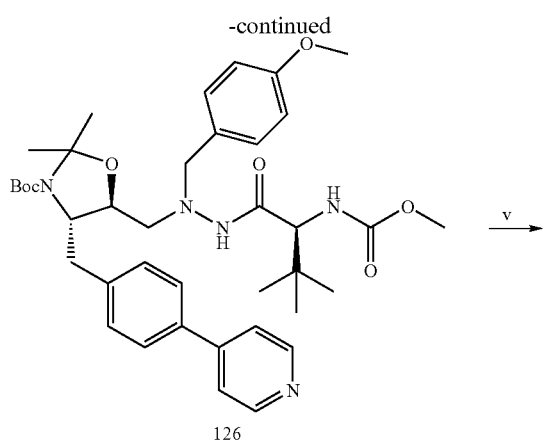

126

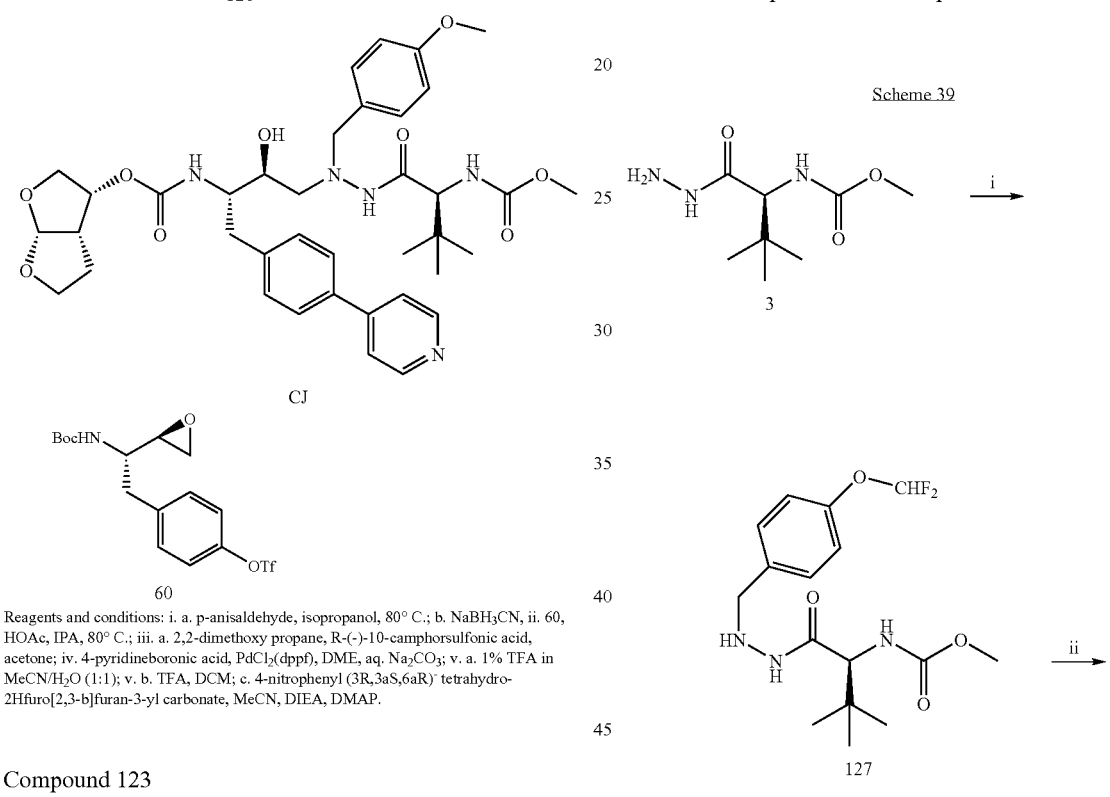

Reagents and conditions: i. a. p-anisaldehyde, isopropanol, 80° C.; b. NaBH₃CN, ii. 60, HOAc, IPA, 80° C.; iii. a. 2,2-dimethoxy propane, R-(-)-10-camphorsulfonic acid, acetone; iv. 4-pyridineboronic acid, PdCl₂(dppf), DME, aq. Na₂CO₃; v. a. 1% TFA in MeCN/H₂O (1:1); v. b. TFA, DCM; c. 4-nitrophenyl (3R,3aS,6aR)⁻tetrahydro-2Hfuro[2,3-b]furan-3-yl carbonate, MeCN, DIEA, DMAP.

Compound 123

Compound 123 was prepared in a manner similar to the procedure used to prepare compound 57 except p-anisaldehyde (1.01 mL, 8.36 mmol) was used instead of benzaldehyde; (1.66 g, 62%). Mass spectrum: 321.1 (M+H)⁺.

Compound 124

Compound 124 was prepared in a manner similar to the procedure used to prepare compound 61 except compound 123 (0.435 g, 1.056 mmol) was used instead of compound 57; 0.216 g, 27%. Mass spectrum: 734.3 (M+H)⁺.

Compound 125

Compound 125 was prepared in a manner similar to the procedure used to prepare compound 62 except compound 124 (0.216 g, 0.294 mmol) was used instead of compound 61; (0.156 g, 68%). Mass spectrum: 775.2 (M+H)⁺.

Compound 126

Compound 126 was prepared in a manner similar to the procedure used to prepare compound 63 except compound 125 (0.156 g, 0.202 mmol) was reacted with 4-pyridineboronic acid (Aldrich, 0.062 g, 0.505 mmol) to give compound 126; (0.1044 g, 73%). Mass spectrum: 704.4 (M+H)⁺.

Example CJ

Example CJ was prepared in a manner similar to the procedure used to prepare Example AR except compound 126 (0.021 g, 0.030 mmol) was used instead of compound 63; (0.0114 g, 53%). ¹H NMR (300 MHz, CD₃OD): δ 8.78 (d, J=6.9 Hz, 2H), 8.32 (d, J=6.9 Hz, 2H), 7.87 (d, J=8.1 Hz, 2H), 7.49 (d, J=8.4 Hz, 2H), 7.26 (d, J=8.7 Hz, 2H), 6.77 (d, J=8.7 Hz, 2H), 5.51 (d, J=4.64 Hz, 1H), 4.99-4.82 (m, 1H), 4.05-3.60 (m, 10H), 3.55 (s, 3H), 2.95-3.70 (m, 5H), 1.60-1.40 (m, 2H), 0.72 (s, 9H). Mass spectrum: 720.4 (M+H)⁺.

Preparation of Examples CK and CL

Scheme 39

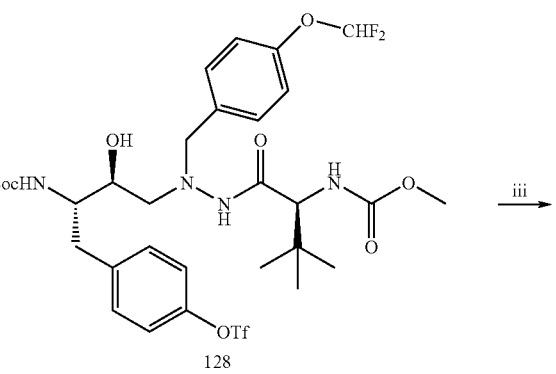

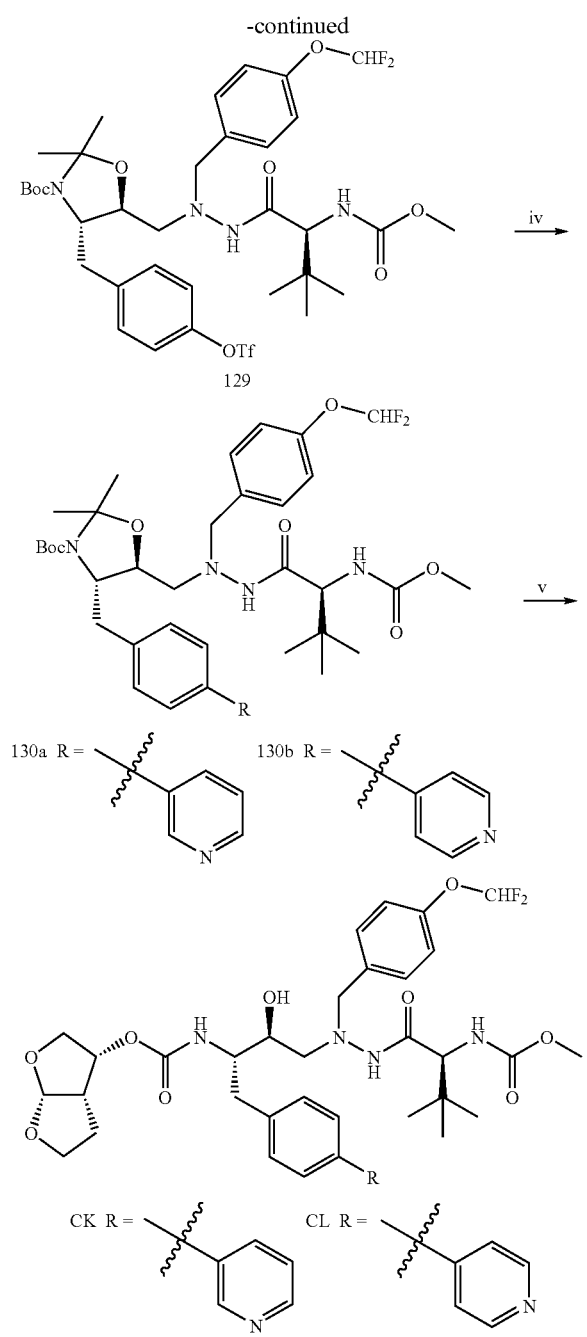

Reagents and conditions: i. a. 4-difluoromethoxy-benzaldehyde, isopropanol, 80° C.; b. Pd/C, H₂, EtOH; ii. 60, AcOH, isopropanol, 80° C.; iii. camphorsulfonic acid, dimethoxypropane, acetone; iv. pyridineboronic acid, PdCl₂(dppf), Na₂CO₃, DME; v. a. TFA, CH₂Cl₂; b. 70, diisopropylethylamine, DMAP, ACN.

Compound 127

Compound 3 (300 mg, 1.48 mmol), prepared according to Bold et al. J. Med. Chem. 1998, 41, 3387-3401, in isopropanol (10 mL) was treated with commercially available 4-difluoromethoxy-benzaldehyde (293 µL, 2.21 mmol) at 80° C. for 4.5 h. The reaction mixture was cooled to r.t. and purified (silica gel, 0 to 80% EtOAc/Hex) to give a white foam (449 mg, 1.26 mmol, 85%). To a solution of the above foam in ethanol (10 mL) was added 10% palladium/carbon (40 mg). The reaction mixture was stirred under a hydrogen atmosphere for 1.5 h, then filtered through a pad of Celite, concentrated and purified (silica gel, 20 to 100% EtOAc/Hexane) to give a white foam (256 mg, 0.713 mmol, 57%). Mass spectrum: 360.0 (M+H)⁺.

Compound 128

To a solution of compound 60 (258 mg, 0.628 mmol) in isopropanol (11 mL) were added compound 127 (205 mg, 0.571 mmol) and AcOH (27.4 mg). After stirring for 3 days at 80° C., reaction mixture was concentrated and purified (silica gel, 10 to 100% EtOAc/Hexane) to give compound 128 (286 mg, 0.371 mmol, 65%). Mass spectrum: 771.0 (M+H)⁺.

Compound 129

A solution of compound 128 (286 mg, 0.371 mmol), camphorsulfonic acid (94.8 mg, 0.408 mmol) and dimethoxypropane (0.455 mL, 3.71 mmol) in acetone (5 mL) was heated at reflux for 4.5 h. The reaction mixture was cooled to r.t., partitioned with saturated NaHCO₃ solution and EtOAc, extracted with EtOAc (1×), washed with H₂O (1×) and dried over Na₂SO₄. Concentrated and purified (silica gel, 0 to 100% EtOAc/Hex) to give a clear thick oil (211 mg, 0.260 mmol, 70%). Mass spectrum: 811.0 (M+H)⁺.

Compound 130a

To a Smith process vial were added compound 129 (70 mg, 0.088 mmol), 3-pyridineboronic acid (27 mg, 0.22 mmol), PdCl₂(dppf) (10 mg, 0.009 mmol), 2M Na₂CO₃ (0.22 mL), and DME (1.5 mL). The vial was sealed and heated at 120° C. for 25 min via microwave irradiation. The reaction mixture was diluted with EtOAc and washed with saturated NaHCO₃ solution, H₂O and dried over Na₂SO₄. Concentrated and purified (silica gel, 20 to 90% EtOAc/Hex) to give a white solid (49 mg, 0.067 mmol, 77%). Mass spectrum: 740.2 (M+H)⁺.

Compound 130b

To a Smith process vial were added compound 129 (53 mg, 0.064 mmol), 4-pyridineboronic acid (20 mg, 0.16 mmol), PdCl₂(dppf) (7.5 mg, 0.009 mmol), 2M Na₂CO₃ (0.16 mL) and DME (1.0 mL). The vial was sealed and heated at 120° C. for 25 min via microwave irradiation. The reaction mixture was diluted with EtOAc and washed with saturated NaHCO₃ solution, H₂O and dried over Na₂SO₄. Concentrated and purified (silica gel, 20 to 90% EtOAc/Hex) to give a white solid (35 mg, 0.067 mmol, 74%). Mass spectrum: 740.3 (M+H)⁺.

Example CK

To a solution of compound 130a (34.3 mg, 0.045 mmol) in MeCN/water (1 mL/1 mL) was added TFA (20 µL). The mixture was then stirred overnight and concentrated, redissolved in CH₂Cl₂ (1.6 mL), then TFA (0.4 mL) was added and the reaction mixture was stirred for 1 h, azeotroped with toluene and put under high vacuum for 1 hour. The residue was dissolved in acetonitrile (1.5 mL). Diisopropylethylamine (18 mg, 0.139 mmol) and DMAP (1.1 mg, 0.009 mmol) were added, followed by compound 70 (13.7 mg, 0.046 mmol). The reaction mixture was stirred for 4 h. then concentrated, and purified with prep-TLC (6% MeOH/CH₂Cl₂) to give a white solid (20 mg, 0.026 mmol, 57%). ¹H NMR (300 MHz, CDCl₃): δ 8.81 (s), 8.56 (m), 7.86-7.83 (d), 7.50-7.48 (d), 7.39-7.23 (m), 7.07-7.00 (m), 6.89 (s), 6.73 (s), 6.48 (s), 6.23 (s), 5.69 (d), 5.63 (d), 5.54-5.30 (m), 5.10-5.01 (m), 4.91 (s), 4.15-3.48 (m), 3.05-2.81 (m), 2.70-2.60 (m), 2.04-1.77 (m), 1.55 (m), 1.31-1.23 (m), 0.73-0.69 (d). Mass spectrum: 756.3 (M+H)⁺.

Example CL

To a solution of compound 130b (35.3 mg, 0.048 mmol) in MeCN/water (1 mL/1 mL) was added TFA (20 μL). The mixture was then stirred overnight and concentrated, redissolved in $CH_2Cl_2$ (1.6 mL), then TFA (0.4 mL) was added and the reaction mixture was stirred for 1 h, azeotroped with toluene and put under high vacuum for 1 hour. The residue was dissolved in acetonitrile (1.5 mL). Diisopropylethylamine (19 mg, 0.143 mmol) and DMAP (1.2 mg, 0.010 mmol) were added, followed by compound 70 (14.1 mg, 0.048 mmol). The reaction mixture was stirred for 4 h. then concentrated, and purified with prep-TLC (6% MeOH/$CH_2Cl_2$) to give a white solid (16.2 mg, 0.026 mmol, 45%). $^1H$ NMR (300 MHz, $CDCl_3$): δ 8.62-8.61 (m), 7.56-7.54 (d), 7.48-7.46 (d), 7.38-7.27 (m), 7.08-7.02 (m), 6.85 (s), 6.73 (s), 6.48 (s), 6.23 (s), 5.69 (d), 5.63 (d), 5.54-5.30 (m), 5.10-5.01 (m), 4.91 (s), 4.15-3.48 (m), 3.05-2.81 (m), 2.70-2.60 (m), 2.04-1.77 (m), 1.55 (m), 1.31-1.23 (m), 0.74-0.69 (d). Mass spectrum: 756.4 $(M+H)^+$.

Biological Assays Used for the Characterization of HIV Protease Inhibitors HIV-1 Protease Enzyme Assay (Ki)

The assay is based on the fluorimetric detection of synthetic hexapeptide substrate cleavage by HIV-1 protease in a defined reaction buffer as initially described by M. V. Toth and G. R. Marshall, Int. J. Peptide Protein Res. 36, 544 (1990)

Substrate: (2-aminobenzoyl)Thr-Ile-Nle-(p-nitro)Phe-Gln-Arg

Substrate supplied by Bachem California, Inc. (Torrance, Calif.; Cat. no. H-2992)

Enzyme: recombinant HIV-1 protease expressed in *E. Coli*
Enzyme supplied by Bachem California, Inc. (Torrance, Calif.; Cat. no. H-9040)

Reaction buffer: 100 mM ammonium acetate, pH 5.3
1 M sodium chloride
1 mM ethylendiaminetetraacetic acid
1 mM dithiothreitol
10% dimethylsulfoxide Assay Protocol for the Determination of Inhibition Constant Ki:
1. Prepare series of solutions containing identical amount of the enzyme (1 to 2.5 nM) and a tested inhibitor at different concentrations in the reaction buffer
2. Transfer the solutions (190 μL each) into a white 96-well plate
3. Preincubate for 15 min at 37° C.
4. Solubilize the substrate in 100% dimethylsulfoxide at a concentration of 800 μM. Start the reaction by adding 10 μL of 800 μM substrate into each well (final substrate concentration of 40 μM)
5. Measure the real-time reaction kinetics at 37° C. by using Gemini 96-well plate fluorimeter (Molecular Devices, Sunnyvale, Calif.) at λ(Ex)=330 nm and λ(Em)=420 nm
6. Determine initial velocities of the reactions with different inhibitor concentrations and calculate Ki (in picomolar concentration units) value by using EnzFitter program (Biosoft, Cambridge, U.K.) according to an algorithm for tight-binding competitive inhibition described by Ermolieff J., Lin X., and Tang J., Biochemistry 36, 12364 (1997)

Anti-HIV-1 Cell Culture Assay ($EC_{50}$)

The assay is based on quantification of the HIV-1-associated cytopathic effect by a calorimetric detection of the viability of virus-infected cells in the presence or absence of tested inhibitors. The HIV-1-induced cell death is determined using a metabolic substrate 2,3-bis(2-methoxy-4-nitro-5-sulfophenyl)-2H-tetrazolium-5-carboxanilide (XTT) which is converted only by intact cells into a product with specific absorption characterisitics as described by Weislow O S, Kiser R, Fine D L, Bader J, Shoemaker R H and Boyd M R, J. Natl. Cancer Inst. 81, 577 (1989).

Assay Protocol for Determination of $EC_{50}$:
1. Maintain MT2 cells in RPMI-1640 medium supplemented with 5% fetal bovine serum and antibiotics.
2. Infect the cells with the wild-type HIV-1 strain IIIB (Advanced Biotechnologies, Columbia, Md.) for 3 hours at 37° C. using the virus inoculum corresponding to a multiplicity of infection equal to 0.01.
3. Prepare a set of solutions containing various concentrations of the tested inhibitor by making 5-fold serial dilutions in 96-well plate (100 μL/well). Distribute the infected cells into the 96-well plate (20,000 cells in 100 μL/well). Include samples with untreated infected and untreated mock-infected control cells.
4. Incubate the cells for 5 days at 37° C.
5. Prepare XTT solution (6 mL per assay plate) at a concentration of 2 mg/mL in a phosphate-buffered saline pH 7.4. Heat the solution in water-bath for 5 min at 55° C. Add 50 μL of N-methylphenazonium methasulfate (5 μg/mL) per 6 mL of XTT solution.
6. Remove 100 μL media from each well on the assay plate.
7. Add 100 μL of the XTT substrate solution per well and incubate at 37° C. for 45 to 60 min in a $CO_2$ incubator.
8. Add 20 μL of 2% Triton X-100 per well to inactivate the virus.
9. Read the absorbance at 450 nm with subtracting off the background absorbance at 650 nm.
10. Plot the percentage absorbance relative to untreated control and estimate the $EC_{50}$ value as drug concentration resulting in a 50% protection of the infected cells.

Cytotoxicity Cell Culture Assay ($CC_{50}$);

The assay is based on the evaluation of cytotoxic effect of tested compounds using a metabolic substrate 2,3-bis(2-methoxy-4-nitro-5-sulfophenyl)-2H-tetrazolium-5-carboxanilide (XTT) as described by Weislow O S, Kiser R, Fine D L, Bader J, Shoemaker R H and Boyd M R, J. Natl. Cancer Inst. 81, 577 (1989).

Assay Protocol for Determination of $CC_{50}$:
1. Maintain MT-2 cells in RPMI-1640 medium supplemented with 5% fetal bovine serum and antibiotics.
2. Prepare a set of solutions containing various concentrations of the tested inhibitor by making 5-fold serial dilutions in 96-well plate (100 μL/well). Distribute cells into the 96-well plate (20,000 cells in 100 μL/well). Include samples with untreated cells as a control.
3. Incubate the cells for 5 days at 37° C.
4. Prepare XTT solution (6 mL per assay plate) in dark at a concentration of 2 mg/mL in a phosphate-buffered saline pH 7.4. Heat the solution in a water-bath at 55° C. for 5 min. Add 50 μL of N-methylphenazonium methasulfate (5 μg/mL) per 6 mL of XTT solution.
5. Remove 100 μL media from each well on the assay plate and add 100 μL of the XTT substrate solution per well. Incubate at 37° C. for 45 to 60 min in a $CO_2$ incubator.
6. Add 20 μl of 2% Triton X-100 per well to stop the metabolic conversion of XTT.
7. Read the absorbance at 450 nm with subtracting off the background at 650 nm.

Plot the percentage absorbance relative to untreated control and estimate the CC50 value as drug concentration resulting in a 50% inhibition of the cell growth. Consider the absorbance being directly proportional to the cell growth.

The compounds of the present invention have $K_i$ values (pM) in the range of about 1-1300, or about 1-1000, about 1-500, about 1-200, or less than about 30. For example, Examples C, J, M, N, Q, T, V, X, Z, AN, AQ, AS, AT, AX, and AY have $K_i$ values of less than about 30.

What is claimed:
1. A compound of Formula I

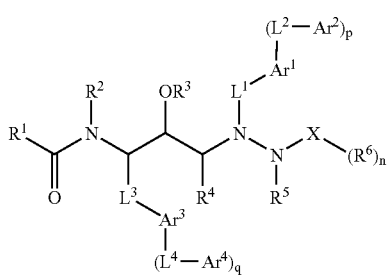

Formula I or a pharmaceutically acceptable salt, and/or ester thereof, wherein,

X is —C(O)—;

n is 1;

p and q are independently 0 or 1 with the proviso that p and q are not simultaneously zero;

$L^1$ and $L^3$ are alkylene;

$L^2$ and $L^4$ are independently selected from the group consisting of a covalent bond, —O—, —NH—, —O-alkylene-, and alkylene;

$Ar^1$, and $Ar^3$ are independently aryl, substituted aryl;

$Ar^2$, and $Ar^4$ are independently aryl, substituted aryl, heteroaryl, or substituted heteroaryl;

wherein said substituted aryl or said substituted heteroaryl of $Ar^1$, $Ar^2$, $Ar^3$ and $Ar^4$ is independently substituted by one to three substituents selected from the group consisting of alkyl, substituted alkyl, haloalkyl, halo, nitro, cyano, hydroxy, amino, alkoxy, haloalkoxy, —NH-alkyl, —NH-(alkyl)$_2$, —NH-acyl, —N(alkyl)-acyl, —NR$^a$S(O)$_2$R$^b$, —C(O)—R$^c$, —S(O)$_2$R$^b$, —S(O)$_2$NHR$^a$, —C(O)—NH—R$^a$, —NR$^a$C(O)OR$^b$, —NR$^a$S(O)$_2$NR$^a$R$^b$, —C(O)OR$^a$, and —Z$^1$-alkylene-R$^7$;

R$^a$ is H, alkyl, or substituted alkyl;

R$^b$ is alkyl, aryl, or substituted aryl;

R$^7$ is aryl, heterocyclyl, substituted aryl, substituted heterocyclyl, —Z$^2$-L$^5$-R$^{7b}$, or —O—PO$_3$R$^{7c}$R$^{7d}$;

L$^5$ is —C(O)—, —C(O)O—, —C(O)NR$^{7e}$, —S(O$_2$)—, —S(O)—, S(O$_2$)NR$^{7e}$, or —S(O)NR$^{7e}$—;

Z$^1$ and Z$^2$ are independently O or NR$^{7a}$;

R$^{7a}$, R$^{7c}$, R$^{7d}$, and R$^{7e}$ are independently H, alkyl, or substituted alkyl;

R$^{7b}$ is alkyl, substituted alkyl, heterocyclyl, or substituted heterocyclyl;

R$^1$ is —OR$^{1c}$;

R$^{1c}$ is

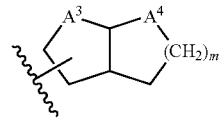

wherein $A^3$ and $A^4$ are O; m is 1;

R$^2$, R$^4$, and R$^5$ are each independently selected from the group consisting of H, alkyl, and substituted alkyl;

R$^3$ is H; and

R$^6$ is

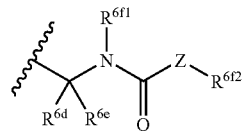

R$^{6d}$ and R$^{6e}$ are independently H, alkyl, haloalkyl, hydroxyalkyl, or alkoxy; or R$^{6d}$ and R$^{6e}$ are taken together to form a 5- or 6-membered non-aromatic tetrahydro heterocyclic ring;

Z is —NR$^{14}$— or —O—;

R$^{14}$ is H, alkyl, or substituted alkyl;

R$^{6f1}$ is H, alkyl, or substituted alkyl; and

R$^{6f2}$ is alkyl, haloalkyl, hydroxyalkyl, aryl-CH$_2$—, or alkoxy;

or R$^{6f2}$ is

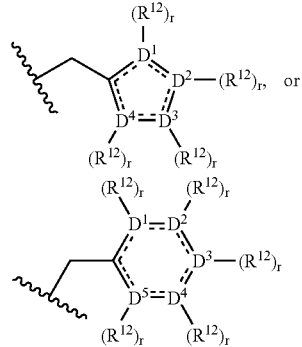

wherein D$^1$, D$^2$, D$^3$, D$^4$, and D$^5$ are independently selected from the group consisting of C, N, O, and S;

each R$^{12}$ is independently H, alkyl, or substituted alkyl, with the proviso that in each occurrence of (R$^{12}$)$_r$, r is 0, 1, or 2, whereby carbon is tetravalent, nitrogen is trivalent, and sulfur and oxygen are divalent; and ---- is a single or double bond;

or R$^6$ is

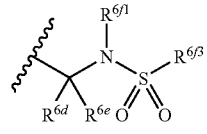

401
R^{6d} and R^{6e} are independently H, alkyl, haloalkyl, hydroxyalkyl, or alkoxy;
R^{6f1} is H, alkyl, or substituted alkyl; and
R^{6f3} is alkyl, substituted alkyl;
or R^6 is OR^{6a}, wherein R^{6a} is selected from the group consisting of alkyl and
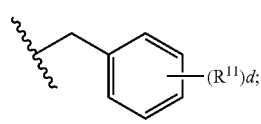
wherein d is 1, R^{11} is hydrogen or alkyl.
2. The compound of claim 1, selected from the group consisting of:
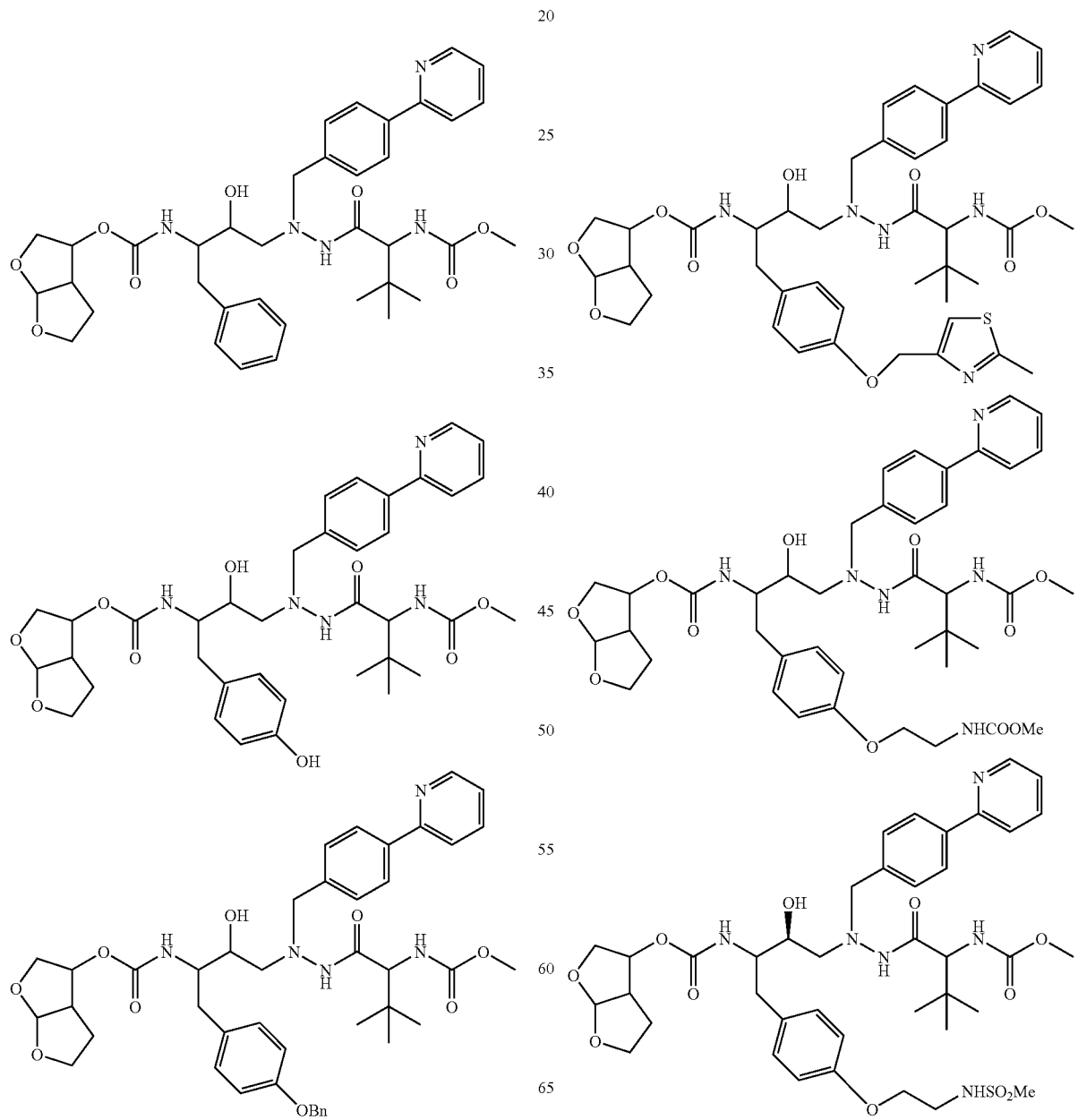

403
-continued
404
-continued
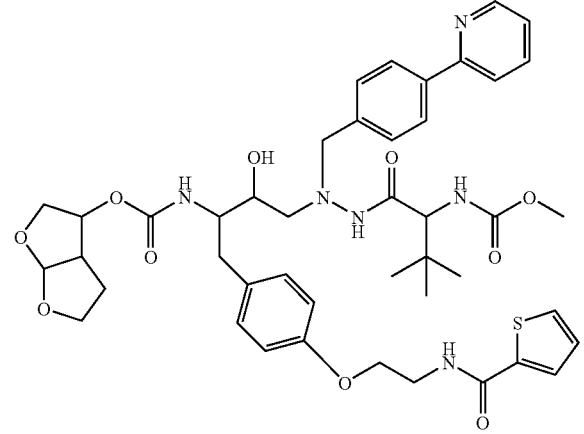
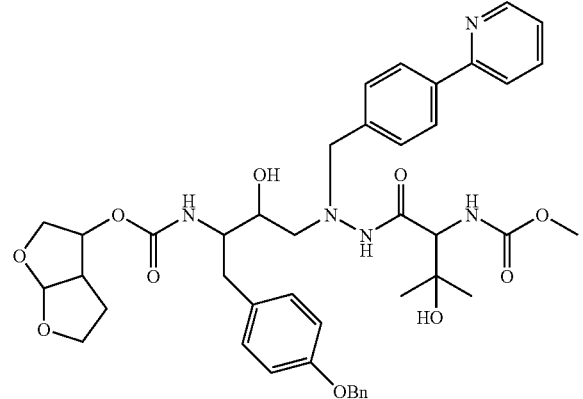

405
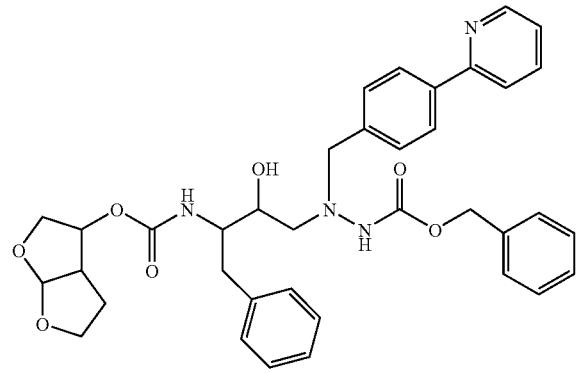
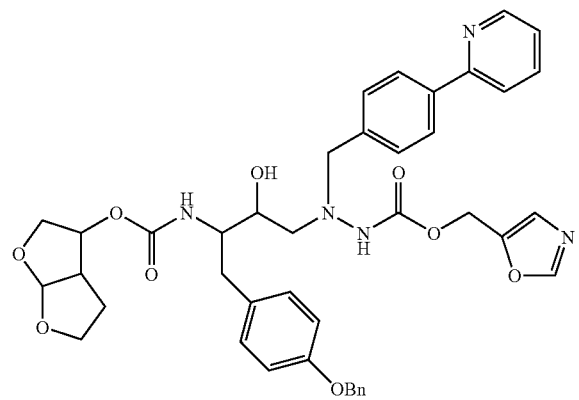
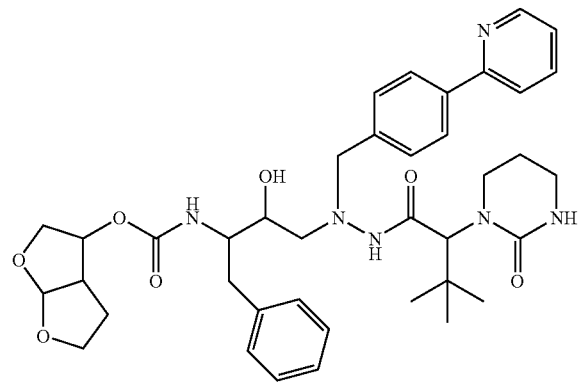
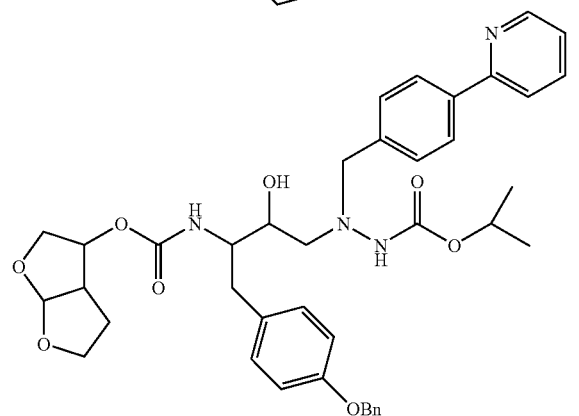
406
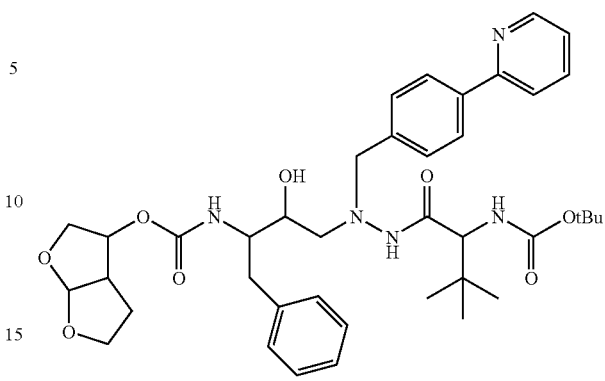
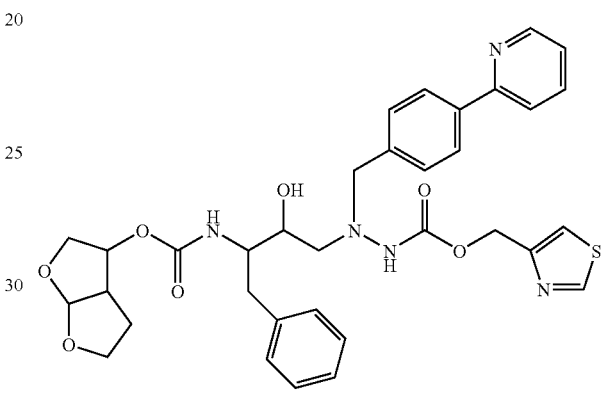
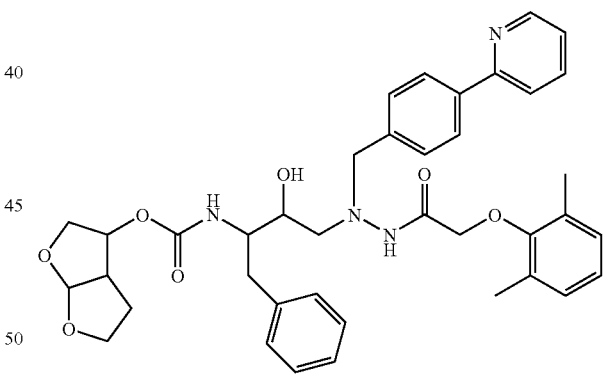
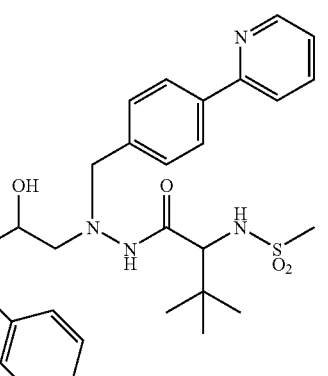

407
-continued
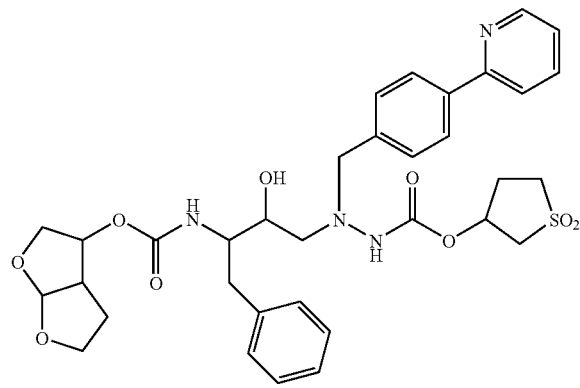
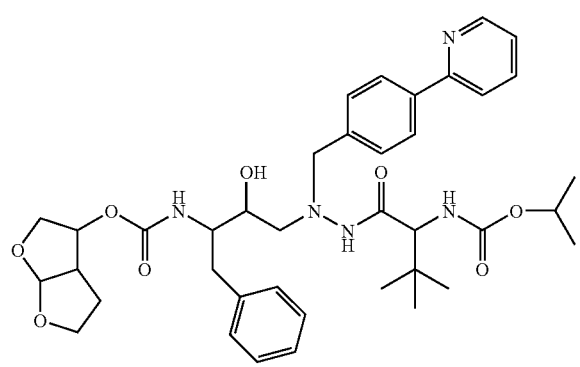
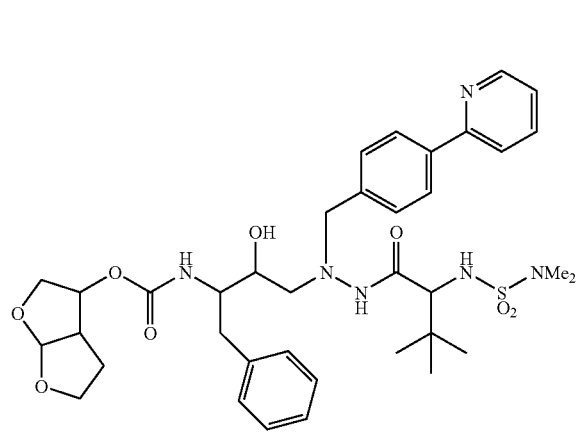
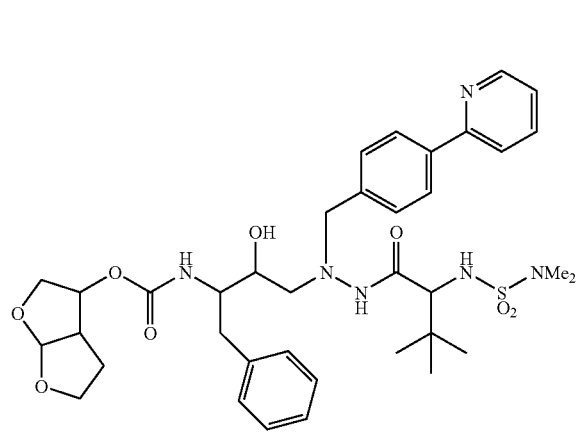
408
-continued
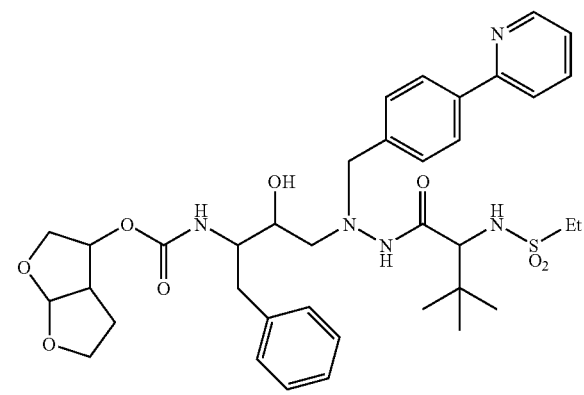
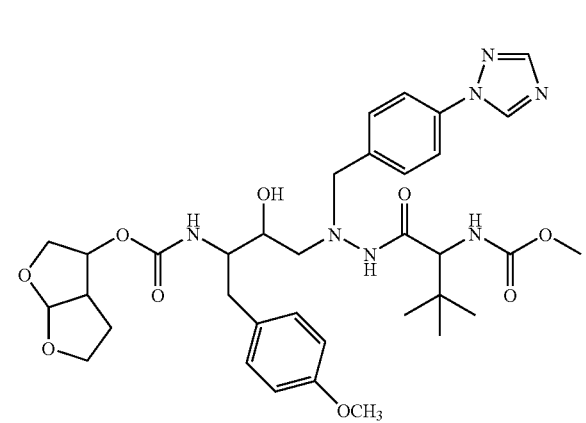
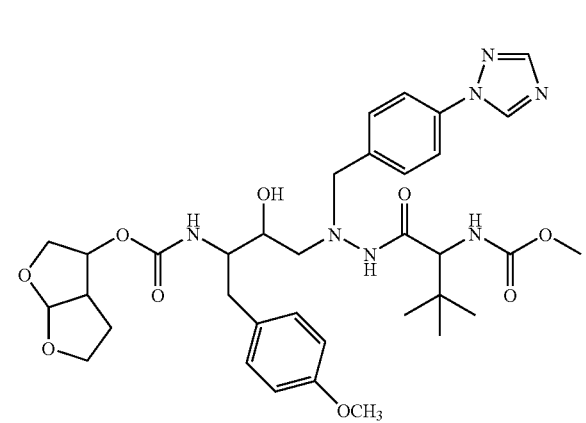
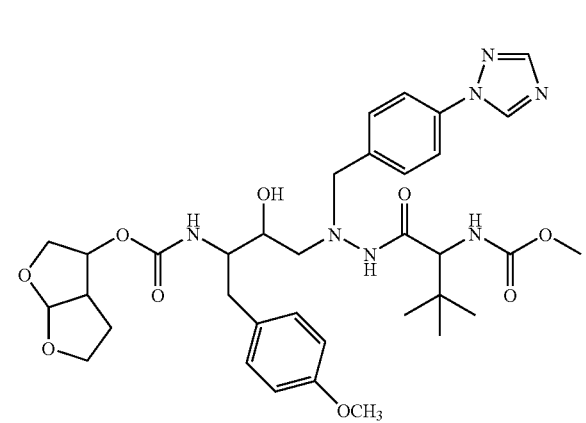

409                                          410
-continued                                   -continued
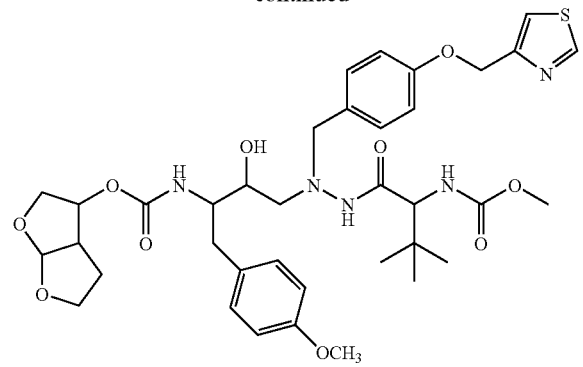
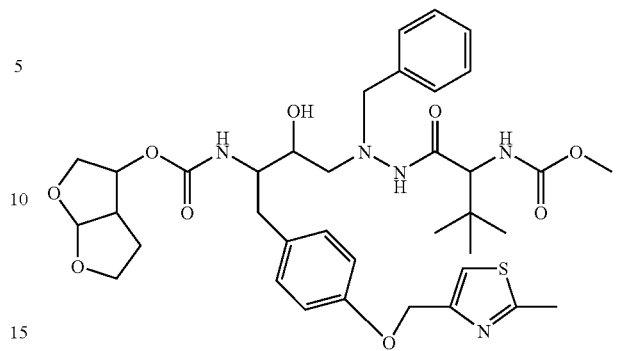
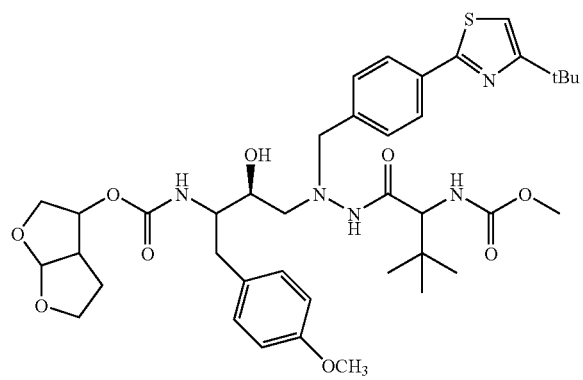
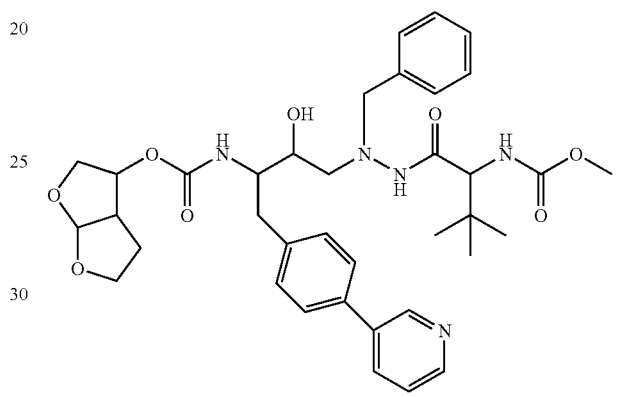
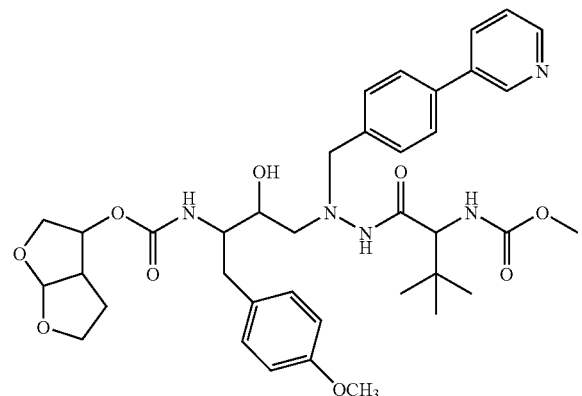
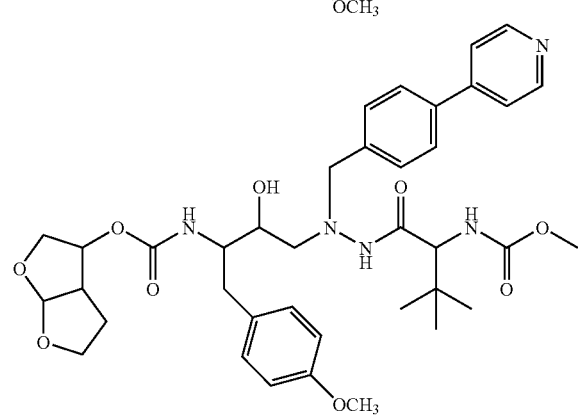

411
-continued
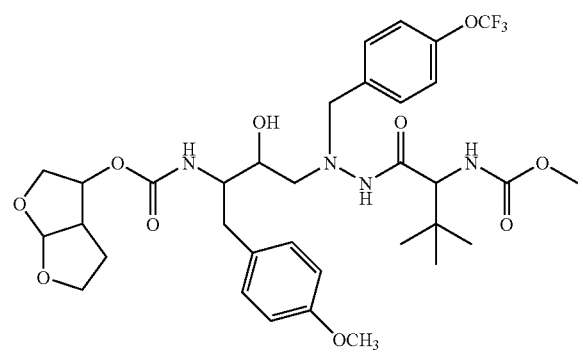
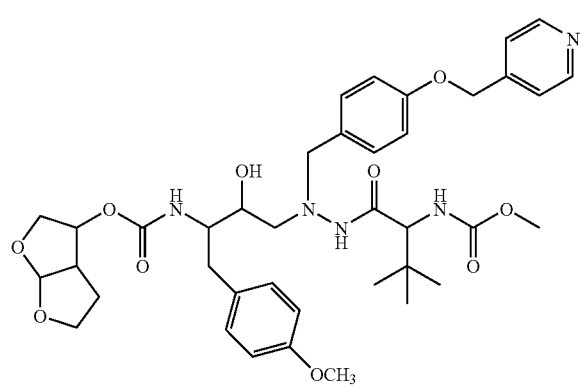
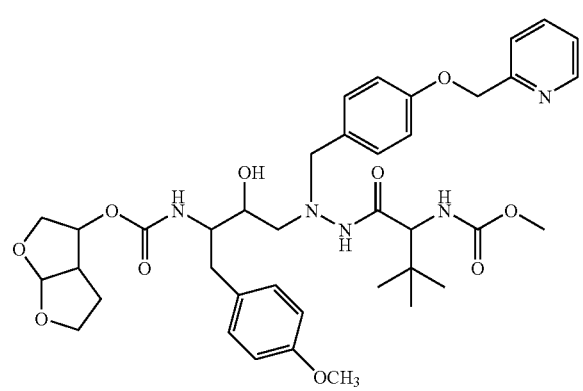
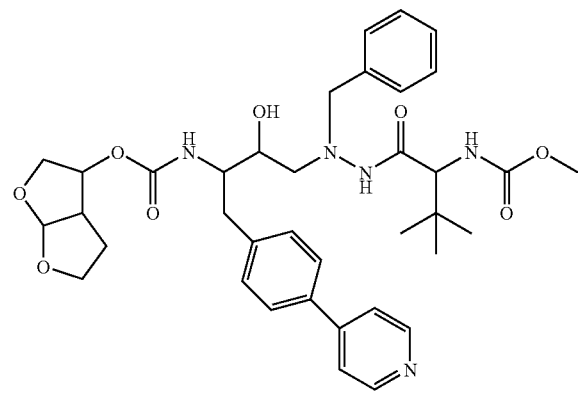
412
-continued
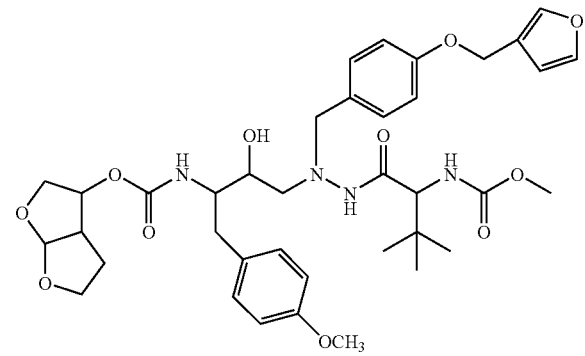
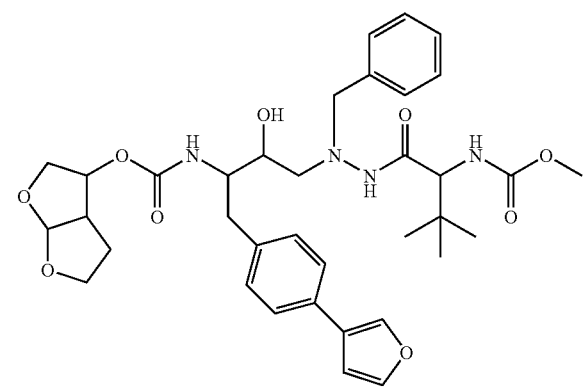
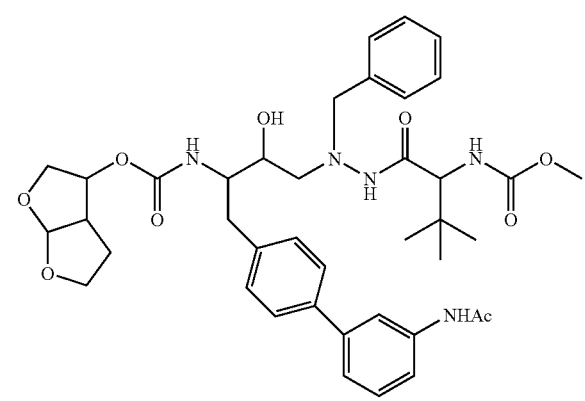
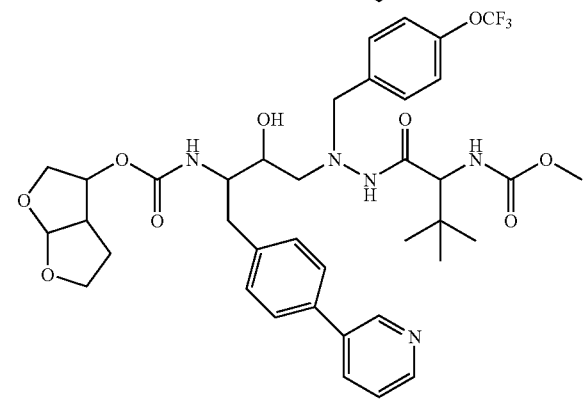

413
-continued
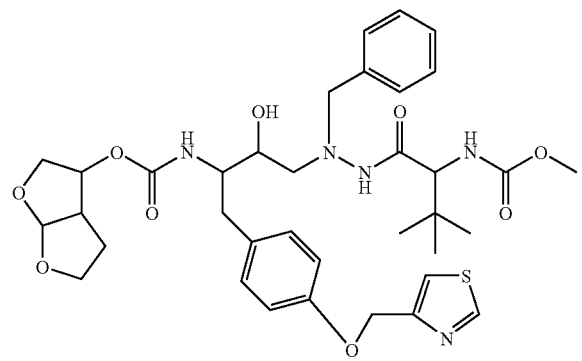
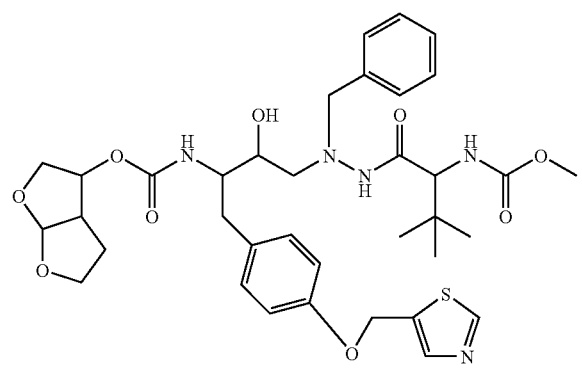
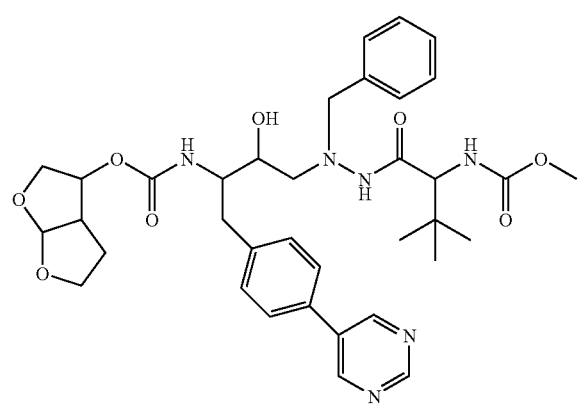
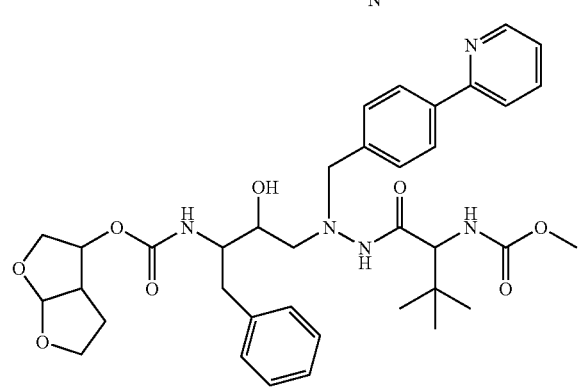
414
-continued
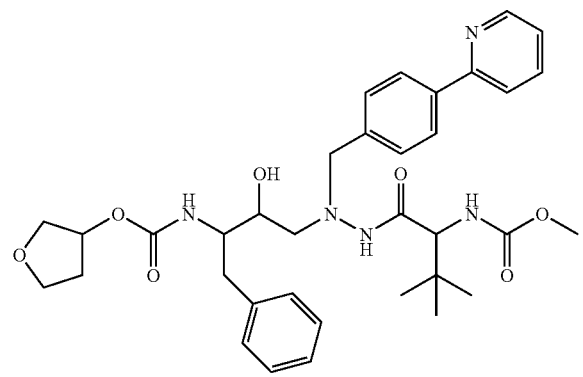
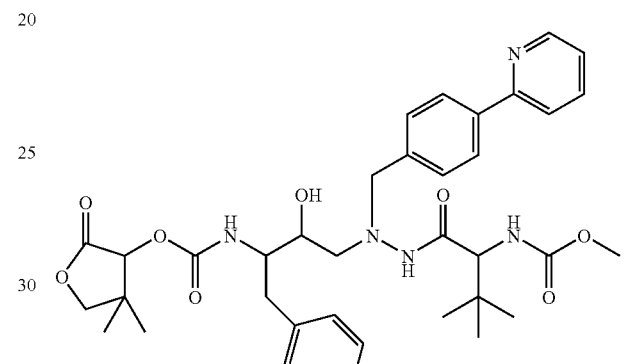
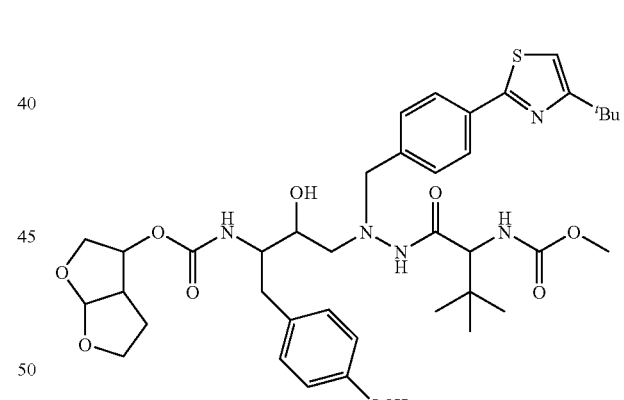
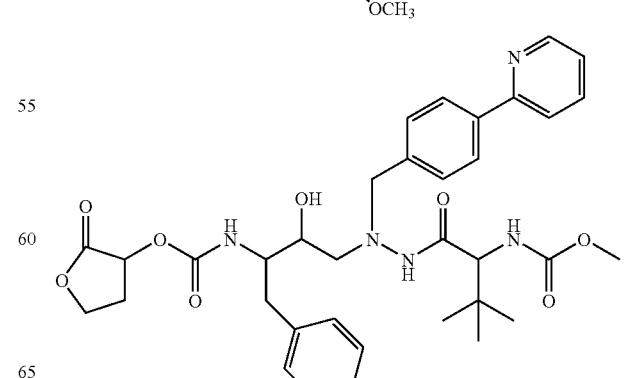

415
-continued
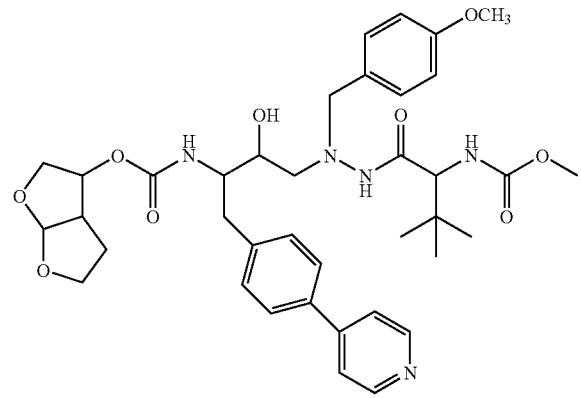
416
-continued
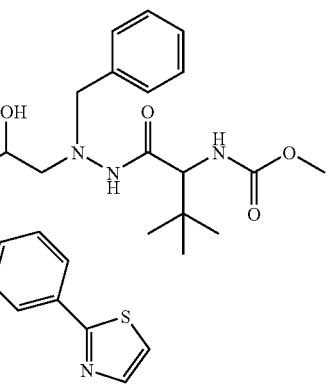

-continued

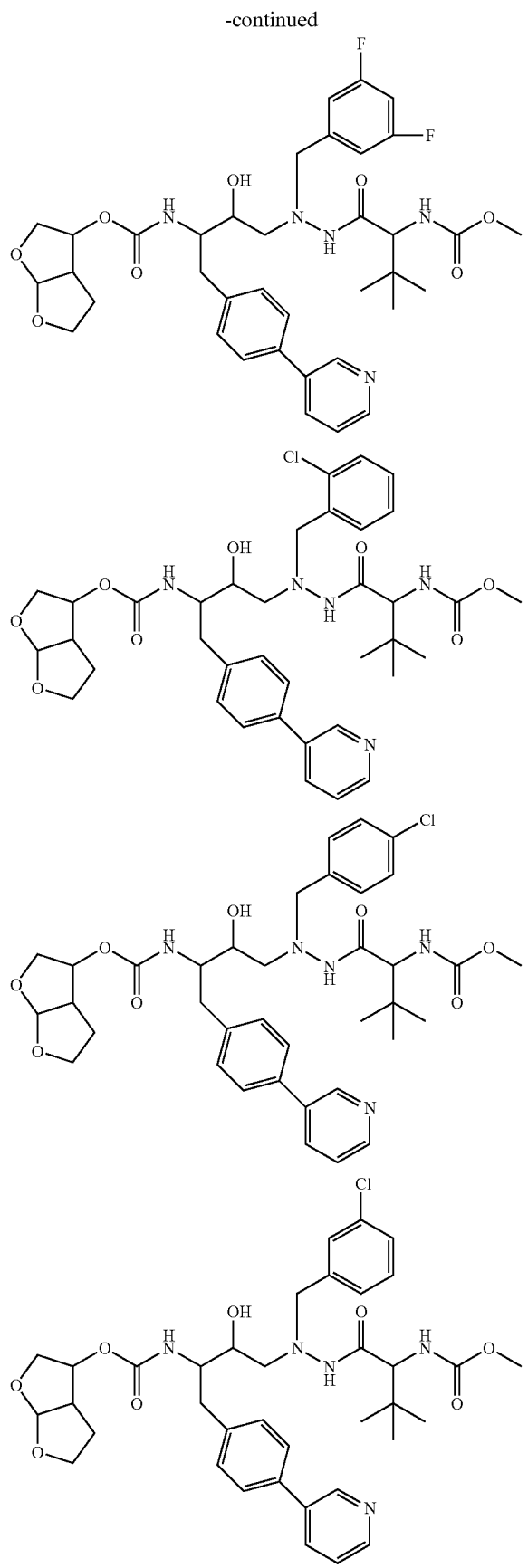

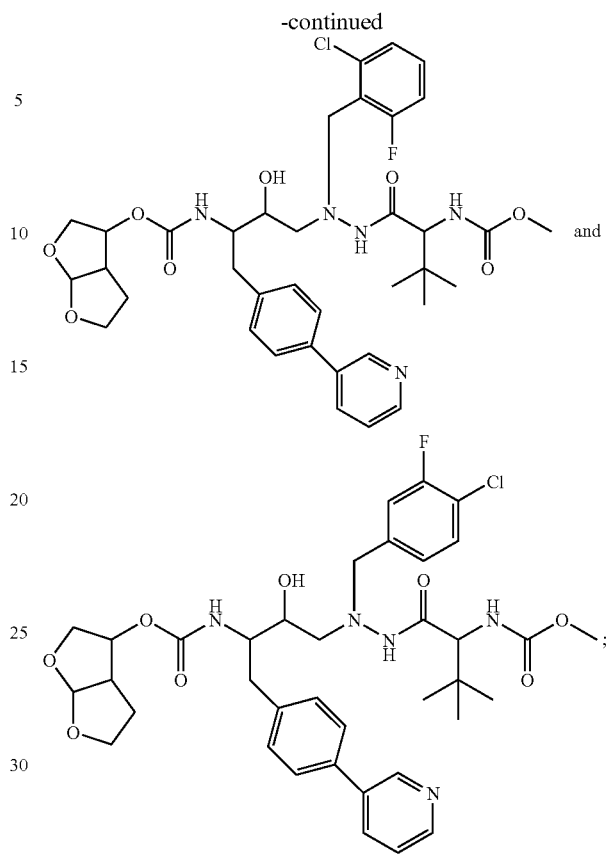

or a pharmaceutically acceptable salt, and/or ester thereof.

3. A pharmaceutical composition comprising:
    a therapeutically effective amount of at least one compound of claim 1, or a pharmaceutically acceptable salt, and/or ester thereof, and a pharmaceutically acceptable carrier or excipient.

4. The pharmaceutical composition of claim 3, further comprising:
    at least one additional active agent that is selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, entry inhibitors gp120 inhibitors, GGPD and NADH-oxidase inhibitors, CCR5 inhibitors, and mixtures thereof.

5. The compound of claim 1, wherein
    X is —C(O)—; n is 1;
    p is 1, q is 0;
    $L^1$ and $L^3$ are —$CH_2$—;
    $L^2$ is a bond, —$CH_2$—, or —O—$CH_2$—;
    $Ar^1$ is ($C_6$-$C_{12}$) aryl;
    $Ar^3$ is ($C_6$-$C_{12}$) aryl that is optionally substituted by one substituent selected from the group consisting of hydroxy, halo, nitro, amino, ($C_6$-$C_{12}$) aryl-$CH_2$—O—, ($C_1$-$C_6$) alkoxy, (5-membered) heterocyclyl-$CH_2$—O—, ($C_1$-$C_6$) alkyl-O—O(O)—NH—($CH_2$)$_2$—O—, alkyl-S($O_2$)—NH—($CH_2$)$_2$—O—, (5 membered) heterocyclyl-C(O)—NH—($CH_2$)—O—, and (($C_1$-$C_6$) alkyl)$_2$P($O_3$)—$CH^2$—O—;

Ar² is (5 to 6 membered) heteroaryl that is optionally substituted by one substituent selected from the group consisting of ($C_1$-$C_6$) alkyl, ($C_1$-$C_6$) alkoxy, ($C_1$-$C_6$) haloalkyl, ($C_1$-$C_6$) haloalkoxy, hydroxy, amino, and halo;

$R^2$, $R^3$, $R^4$ and $R^5$ are hydrogen;

$R^1$ is $R^{1c}$O—, $R^{1c}$ is

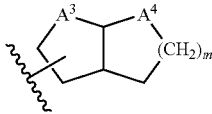

wherein $A^3$ and $A^4$ are O, m is 1;
$R^6$ is

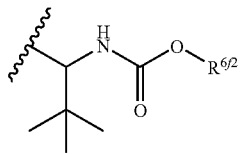

wherein $R^{6/2}$ is ($C_1$-$C_6$) alkyl, ($C_1$-$C_6$) alkoxy, ($C_1$-$C_6$) haloalkyl, and hydroxy-($C_1$-$C_6$) alkyl-.

6. The compound of claim 5, wherein X is —C(O)—; n is 1; p is 1, q is 0; $L^1$ and $L^3$ are —CH₂—; $L^2$ is a bond, —CH₂—, or —O—CH₂—; Ar¹ and Ar³ are phenyl; A² is pyridine; $R^2$, $R^3$, $R^4$ and $R^5$ are hydrogen; $R^1$ is $R^{1c}$O—, $R^{1c}$ is

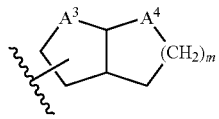

wherein $A^3$ and $A^4$ are O, m is 1; and
$R^6$ is

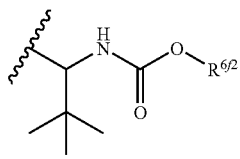

wherein $R^{6/2}$ is ($C_1$-$C_6$) alkyl.

7. The compound of claim 1, wherein
X is —C(O)—; n is 1;
p is 0, q is 1;

$L^1$ and $L^3$ are —CH₂—;
$L^4$ is a bond, —OH₂—, or O—OH₂—;
Ar¹ is ($C_6$-$C_{12}$) aryl that is optionally substituted by one to three substituents selected from the group consisting of ($C_1$-$C_6$) alkoxy, ($C_1$-$C_6$) haloalkoxy, halo and hydroxyl;
Ar³ is ($C_6$-$C_{12}$) aryl;
Ar⁴ is (5 to 6 membered) heteroaryl;
$R^2$, $R^3$, $R^4$ and $R^5$ are hydrogen;
$R^1$ is $R^{1c}$O—, $R^{1c}$ is

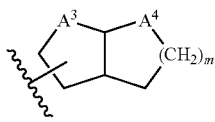

wherein $A^3$ and $A^4$ are O, m is 1; and
$R^6$ is

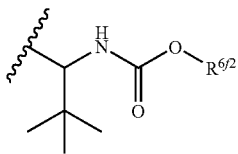

wherein $R^{6/2}$ is ($C_1$-$C_6$) alkyl, ($C_1$-$C_6$) alkoxy, ($C_1$-$C_6$) haloalkyl, and hydroxy-($C_1$-$C_6$) alkyl-.

8. The compound of claim 7, wherein X is —C(O)—; n is 1; p is 0, q is 1; $L^1$ and $L^3$ are —CH₂—; $L^4$ is a bond, —CH₂—, or —O—CH₂—; Ar¹ and Ar³ are phenyl; Ar⁴ is pyridine; $R^2$, $R^3$, $R^4$ and $R^5$ are hydrogen; $R^1$ is $R^{1c}$O—, $R^{1c}$ is

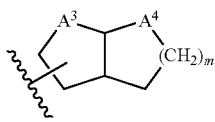

wherein $A^3$ and $A^4$ are O, m is 1; and
$R^6$ is

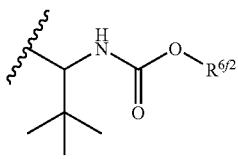

wherein $R^{6/2}$ is ($C_1$-$C_6$) alkyl.

* * * * *